US012703746B2

(12) United States Patent
Tuna et al.

(10) Patent No.: US 12,703,746 B2
(45) Date of Patent: Aug. 11, 2026

(54) ANTI-TCR DELTA VARIABLE 1 ANTIBODIES

(71) Applicant: Adaptate Biotherapeutics Ltd., London (GB)

(72) Inventors: Mihriban Tuna, London (GB); Oxana Polyakova, London (GB); Mark Uden, London (GB); Robert Good, London (GB); Joshua Freedman, London (GB); Shefali Bhumbra, London (GB); Natalie Mount, London (GB); Aoife McGinley, London (GB); Dan Foxler, London (GB)

(73) Assignee: Adaptate Biotherapeutics Ltd., London (GB)

( * ) Notice: Subject to any disclaimer, the term of this patent is extended or adjusted under 35 U.S.C. 154(b) by 130 days.

(21) Appl. No.: 17/674,129

(22) Filed: Feb. 17, 2022

(65) Prior Publication Data

US 2023/0028110 A1 Jan. 26, 2023

(30) Foreign Application Priority Data

Feb. 17, 2021 (GB) ..................................... 2102224
Aug. 14, 2021 (GB) ..................................... 2111685

(51) Int. Cl.

| | |
|---|---|
| ***C07K 16/28*** | (2006.01) |
| ***A61P 35/00*** | (2006.01) |
| ***C07K 16/18*** | (2006.01) |
| ***C07K 16/32*** | (2006.01) |
| ***C07K 16/40*** | (2006.01) |

(52) U.S. Cl.

CPC .......... *C07K 16/2809* (2013.01); *A61P 35/00* (2018.01); *C07K 16/18* (2013.01); *C07K 16/2803* (2013.01); *C07K 16/2818* (2013.01); *C07K 16/2863* (2013.01); *C07K 16/2878* (2013.01); *C07K 16/32* (2013.01); *C07K 16/40* (2013.01); *C07K 2317/21* (2013.01); *C07K 2317/31* (2013.01); *C07K 2317/34* (2013.01); *C07K 2317/565* (2013.01); *C07K 2317/732* (2013.01); *C07K 2317/734* (2013.01); *C07K 2317/74* (2013.01); *C07K 2317/76* (2013.01); *C07K 2317/92* (2013.01)

(58) Field of Classification Search

CPC ............ C07K 2317/31; C07K 16/2809; C07K 16/18; C07K 16/2803; C07K 16/2818; C07K 16/2863; C07K 16/2878; C07K 16/32; C07K 16/40; C07K 2317/21; C07K 2317/34; C07K 2317/565; C07K 2317/732; C07K 2317/734; C07K 2317/74; C07K 2317/76; C07K 2317/92; C07K 16/30; C07K 2317/73; A61P 35/00; Y02A 50/30

See application file for complete search history.

(56) References Cited

U.S. PATENT DOCUMENTS

| | | | |
|---|---|---|---|
| 9,334,331 | B2 | 5/2016 | Igawa et al. |
| 10,421,807 | B2 | 9/2019 | Gonzales et al. |
| 11,548,948 | B2 | 1/2023 | Tuna et al. |
| 11,629,193 | B2 | 4/2023 | Tuna et al. |
| 12,312,408 | B2 | 5/2025 | Tuna et al. |
| 2018/0228566 | A9 | 8/2018 | McAfee |
| 2019/0119634 | A1 | 4/2019 | Jakobovits et al. |
| 2022/0403025 | A1 | 12/2022 | Mount et al. |
| 2023/0090901 | A1 | 3/2023 | Polyakova et al. |
| 2024/0132599 | A1 | 4/2024 | Tuna et al. |
| 2024/0376215 | A1 | 11/2024 | Tuna et al. |

FOREIGN PATENT DOCUMENTS

| | | | | |
|---|---|---|---|---|
| CN | 101031641 | A | 9/2007 | |
| CN | 109414480 | A | 3/2019 | |
| JP | 2018-532383 | A | 11/2018 | |
| JP | 2019-519210 | A | 7/2019 | |
| WO | WO 03/080672 | A1 | 10/2003 | |
| WO | WO 2016/166544 | A1 | 10/2016 | |
| WO | WO 2016/198480 | A1 | 12/2016 | |
| WO | WO 2017/037707 | A1 | 3/2017 | |
| WO | WO 2017/197347 | A1 | 11/2017 | |
| WO | WO 2019/005637 | A2 | 1/2019 | |
| WO | WO 2019/147735 | A1 | 8/2019 | |
| WO | WO 2020/060406 | A1 | 3/2020 | |
| WO | WO 2020/154548 | A2 | 7/2020 | |
| WO | WO 2020/159368 | A1 | 8/2020 | |
| WO | WO 2020/210232 | A1 | 10/2020 | |
| WO | WO 2021/032951 | A1 | 2/2021 | |
| WO | WO 2021/032960 | A1 | 2/2021 | |
| WO | WO 2021/032961 | A1 | 2/2021 | |
| WO | WO 2021/032963 | A1 | 2/2021 | |
| WO | WO 2022/175414 | A1 | 8/2022 | |
| WO | WO-2022175413 | A1 * | 8/2022 | ............. A61P 35/00 |

OTHER PUBLICATIONS

Almagro et. al., Front. Immunol. 2018; 8:1751 (Year: 2018).*
Rudikoff et al., Proc. Nat'l Acad. Sci. USA, 79:1979-83 (1982) (Year: 1982).*

(Continued)

*Primary Examiner* — Meera Natarajan
*Assistant Examiner* — Francesca Edgingtongiordano
(74) *Attorney, Agent, or Firm* — Wolf, Greenfield & Sacks, P.C.

(57) ABSTRACT

The present invention provides high-affinity anti-TCR delta variable 1 (anti-Vδ1) antibodies and antibody fragments thereof. The present invention also provides compositions and pharmaceutical compositions comprising such antibodies, and method of making such antibodies. The present invention also provides methods of treatment and medical uses involving the antibodies.

21 Claims, 155 Drawing Sheets

Specification includes a Sequence Listing.

(56) References Cited

OTHER PUBLICATIONS

Brown et al., J. Immunol., 156(9):3285-91 (1996) (Year: 1996).*
Chiu et al., Antibodies, 8(55):1-80. (2019) (Year: 2019).*
Barros et. al. Cell. 167(1):203-218e17 (2016) (Year: 2016).*
International Search Report and Written Opinion for Application No. PCT/GB2020/051959, mailed Mar. 3, 2022.
International Preliminary Report on Patentability for Application No. PCT/GB2020/051959, mailed Oct. 30, 2020.
Davey et al., Clonal selection in the human Vδ1 T cell repertoire indicates γδ TCR-dependent adaptive immune surveillance. Nat Commun. Mar. 1, 2017;8:14760. doi: 10.1038/ncomms14760.
Deniger et al., Clinical applications of gamma delta T cells with multivalent immunity. Front Immunol. Dec. 11, 2014;5:636. doi: 10.3389/fimmu.2014.00636. eCollection 2014.
Fisher et al., Engineering Approaches in Human Gamma Delta T Cells for Cancer Immunotherapy. Front Immunol. Jun. 26, 2018;9:1409. doi: 10.3389/fimmu.2018.01409. eCollection 2018.
Oberg et al., Bispecific antibodies enhance tumor-infiltrating T cell cytotoxicity against autologous HER-2-expressing high-grade ovarian tumors. J Leukoc Biol. Jun. 2020;107(6):1081-1095. doi: 10.1002/JLB.5MA1119-265R. Epub Dec. 13, 2019.
Romagné et al., Structural analysis of γδ TCR using a novel set of TCR γ and δ chain-specific monoclonal antibodies generated against soluble γδ TCR: Evidence for a specific conformation adopted by the Jδ2 region and for a Vδ1 polymorphism. J Immunol Methods. Jan. 16, 1996;189(1):25-36. doi: 10.1016/0022-1759(95)00224-3.
Sebestyen et al., Translating gammadelta (γδ) T cells and their receptors into cancer cell therapies. Nat Rev Drug Discov. Mar. 2020;19(3):169-184. doi: 10.1038/s41573-019-0038-z. Epub Sep. 6, 2019.
Siegers et al., Cytotoxic and regulatory properties of circulating Vδ1+ γδ T cells: a new player on the cell therapy field? Mol Ther. Aug. 2014;22(8):1416-1422. doi: 10.1038/mt.2014.104. Epub Jun. 4, 2014.
U.S. Appl. No. 17/801,786, filed Aug. 23, 2022, Polyakova et al.
U.S. Appl. No. 18/277,708, filed Aug. 17, 2023, Tuna et al.
U.S. Appl. No. 18/451,047, filed Aug. 16, 2023, Tuna et al.
Invitation to Pay Additional Fees for Application No. PCT/GB2021/050459, mailed Jun. 7, 2021.
International Search Report and Written Opinion for Application No. PCT/GB2021/050459, mailed Jul. 28, 2021.
International Preliminary Report on Patentability for Application No. PCT/GB2021/050459, mailed Sep. 9, 2022.
International Search Report and Written Opinion for Application No. PCT/EP2022/054011, mailed May 30, 2022.
International Preliminary Report on Patentability for Application No. PCT/EP2022/054011, mailed Aug. 31, 2023.
International Search Report and Written Opinion for Application No. PCT/EP2022/054004, mailed May 24, 2022.
International Preliminary Report on Patentability for Application No. PCT/EP2022/054004, mailed Aug. 31, 2023.
Abeler-Dörner et al., Butyrophilins: an emerging family of immune regulators. Trends Immunol. Jan. 2012;33(1):34-41. doi: 10.1016/j.it.2011.09.007. Epub Oct. 24, 2011.
Almeida et al., Delta One T Cells for Immunotherapy of Chronic Lymphocytic Leukemia: Clinical-Grade Expansion/Differentiation and Preclinical Proof of Concept. Clin Cancer Res. Dec. 1, 2016;22(23):5795-5804. doi: 10.1158/1078-0432.CCR-16-0597. Epub Jun. 15, 2016.
Blink et al., γδ T cell subsets play opposing roles in regulating experimental autoimmune encephalomyelitis. Cell Immunol. Jul. 2014;290(1):39-51. doi: 10.1016/j.cellimm.2014.04.013. Epub May 10, 2014. Author Manuscript (29 pages).
Chitadze et al., The Ambiguous Role of γδ T Lymphocytes in Antitumor Immunity. Trends Immunol. Sep. 2017;38(9):668-678. doi: 10.1016/j.it.2017.06.004. Epub Jul. 11, 2017.
Cordova et al., Characterization of human γδ T lymphocytes infiltrating primary malignant melanomas. Plos ONE. 2012;7(11):e49878. doi: 10.1371/journal.pone.0049878. Epub Nov. 26, 2012.
Davodeau et al., Surface expression of two distinct functional antigen receptors on human gamma delta T cells. Science. Jun. 18, 1993;260(5115):1800-2. doi: 10.1126/science.8390096.
De Bruin et al., A bispecific nanobody approach to leverage the potent and widely applicable tumor cytolytic capacity of Vγ9Vδ2-T cells. Oncoimmunology. Oct. 20, 2017;7(1):e1375641. doi: 10.1080/2162402X.2017.1375641. eCollection 2017.
De Libero et al., Selection by two powerful antigens may account for the presence of the major population of human peripheral gamma/delta T cells. J Exp Med. Jun. 1, 1991;173(6):1311-22. doi: 10.1084/jem.173.6.1311.
De Weerdt et al., A Bispecific Single-Domain Antibody Boosts Autologous Vγ9Vδ2-T Cell Responses Toward CD1d in Chronic Lymphocytic Leukemia. Clin Cancer Res. Mar. 15, 2021;27(6):1744-1755. doi: 10.1158/1078-0432.CCR-20-4576. Epub Jan. 15, 2021.
Di Lorenzo et al., Broad Cytotoxic Targeting of Acute Myeloid Leukemia by Polyclonal Delta One T Cells. Cancer Immunol Res. Apr. 2019;7(4):552-558. doi: 10.1158/2326-6066.CIR-18-0647. Epub Mar. 20, 2019.
Dondelinger et al., Understanding the Significance and Implications of Antibody Numbering and Antigen-Binding Surface/Residue Definition. Front Immunol. Oct. 16, 2018:9:2278. doi: 10.3389/fimmu.2018.02278. eCollection 2018.
Dutta et al., Apoptosis Induced via Gamma Delta T Cell Antigen Receptor "Blocking" Antibodies: A Cautionary Tale. Front Immunol. Jun. 30, 2017:8:776. doi: 10.3389/fimmu.2017.00776. eCollection 2017.
Ferrarini et al., Killing of laminin receptor-positive human lung cancers by tumor-infiltrating lymphocytes bearing γδ+ T-cell receptors. J Natl Cancer Inst. Apr. 3, 1996;88(7):436-41. doi: 10.1093/jnci/88.7.436.
Fisher et al., Neuroblastoma killing properties of Vδ2 and Vδ2-negative γδT cells following expansion by artificial antigen-presenting cells. Clin Cancer Res. Nov. 15, 2014;20(22):5720-32. doi: 10.1158/1078-0432.CCR-13-3464. Epub Jun. 3, 2014.
Garber, γδ T cells bring unconventional cancer-targeting to the clinic—again. Nat Biotechnol. Apr. 2020;38(4):389-391. doi: 10.1038/s41587-020-0487-2.
Groh et al., Broad tumor-associated expression and recognition by tumor-derived gamma delta T cells of MICA and MICB. Proc Natl Acad Sci U S A. Jun. 8, 1999;96(12):6879-84. doi: 10.1073/pnas.96.12.6879.
Jefferis et al., Human immunoglobulin allotypes: possible implications for immunogenicity. Mabs. Jul.-Aug. 2009;1(4):332-8. doi: 10.4161/mabs.1.4.9122.
Khairallah et al., γδ T cells confer protection against murine cytomegalovirus (MCMV). PLoS Pathog. Mar. 6, 2015;11(3):e1004702. doi: 10.1371/journal.ppat.1004702. eCollection Mar. 2015.
Kitayama et al., Functional analysis of TCR gamma delta+ T cells in tumour-infiltrating lymphocytes (TIL) of human pancreatic cancer. Clin Exp Immunol. Sep. 1993;93(3):442-7. doi: 10.1111/j.1365-2249.1993.tb08198.x.
Knight et al., Human Vdelta1 gamma-delta T cells exert potent specific cytotoxicity against primary multiple myeloma cells. Cytotherapy. Oct. 2012;14(9):1110-8. doi: 10.3109/14653249.2012.700766. Epub Jul. 17, 2012.
Langerak et al., Immunophenotypic and immunogenotypic characteristics of TCRgammadelta+ T cell acute lymphoblastic leukemia. Leukemia. Feb. 1999;13(2):206-14. doi: 10.1038/sj.leu.2401276.
Luoma et al., Crystal structure of Vδ1 T cell receptor in complex with CD1d-sulfatide shows MHC-like recognition of a self-lipid by human γδ T cells. Immunity. Dec. 12, 2013;39(6):1032-42. doi: 10.1016/j.immuni.2013.11.001. Epub Nov. 14, 2013.
Maeurer et al., Human intestinal Vdelta1+ lymphocytes recognize tumor cells of epithelial origin. J Exp Med. Apr. 1, 1996;183(4):1681-96. doi: 10.1084/jem.183.4.1681.
Mahvi et al., Overexpression of 27-kDa heat-shock protein in MCF-7 breast cancer cells: effects on lymphocyte-mediated killing by natural killer and gamma delta T cells. Cancer Immunol Immunother. Aug. 1993;37(3):181-6. doi: 10.1007/BF01525433.
Mayassi et al., Chronic Inflammation Permanently Reshapes Tissue-Resident Immunity in Celiac Disease. Cell. Feb. 21, 2019;176(5):967-981.e19. doi: 10.1016/j.cell.2018.12.039. Epub Feb. 7, 2019.

(56) References Cited

OTHER PUBLICATIONS

Mikulak et al., NKp46-expressing human gut-resident intraepithelial Vδ1 T cell subpopulation exhibits high antitumor activity against colorectal cancer. JCI Insight. Dec. 19, 2019;4(24):e125884. doi: 10.1172/jci.insight.125884.
No Author Listed, Purified anti-mouse TCR V[gamma]4 Antibody Antigen. Biolegend. Version 1. Last revised: Aug. 10, 2020. Retrieved from the Internet: URL: https://www.biolegend.com/en-ie/global-elements/pdf-popup/purified-anti-mouse-tcr-vy4-antibody-19846?filename=Purified%20anti-mouse%20TCR%20Vgamma4%20Antibody.pdf&pdfgen=true. [retrieved on Sep. 29, 2022].
Oberg et al., Novel bispecific antibodies increase γδ T-cell cytotoxicity against pancreatic cancer cells. Cancer Res. Mar. 1, 2014;74(5):1349-60. doi: 10.1158/0008-5472.CAN-13-0675. Epub Jan. 21, 2014.
Sela-Culang et al., The structural basis of antibody-antigen recognition. Front Immunol. Oct. 8, 2013:4:302. doi: 10.3389/fimmu.2013.00302.
Tamura et al., Structural Correlates of an Anticarcinoma Antibody: Identification of Specificity-Determining Residues (SDRs) and Development of a Minimally Immunogenic Antibody Variant by Retention of SDRs Only. J Immunol. Feb. 1, 2000;164(3):1432-41. doi: 10.4049/jimmunol.164.3.1432.
Wu et al., Ex vivo expanded human circulating Vδ1 γδT cells exhibit favorable therapeutic potential for colon cancer. OncoImmunology. Jan. 22, 2015;4(3):e992749. doi: 10.4161/2162402X.2014.992749. eCollection Mar. 2015.
Xu et al., Crystal structure of a γδ T-cell receptor specific for the human MHC class I homolog MICA. Proc Natl Acad Sci U S A. Feb. 8, 2011;108(6):2414-9. doi: 10.1073/pnas.1015433108. Epub Jan. 24, 2011.
Yamashiro et al., Stimulation of human butyrophilin 3 molecules results in negative regulation of cellular immunity. J Leukoc Biol. Oct. 2010;88(4):757-67. doi: 10.1189/jlb.0309156. Epub Jul. 7, 2010.
U.S. Appl. No. 18/652,676, filed May 1, 2024, Tuna et al.
Al Qaraghuli et al., Antibody-protein binding and conformational changes: identifying allosteric signalling pathways to engineer a better effector response. Sci Rep. 2020; 10: 13696. Published online Aug. 13, 2020. doi: 10.1038/s41598-020-70680-0.
An et al., IgG2m4, an engineered antibody isotype with reduced Fc function. MAbs. Nov.-Dec. 2009;1(6):572-9. doi: 10.4161/mabs.1.6.10185.
Aruda et al., Impact of gd T cells on clinical outcome of hematopoietic stem cell transplantation: systematic review and meta-analysis. Blood Adv. 2019; 3 (21): 3436-3448. https://doi.org/10.1182/bloodadvances.2019000682.
Catellani et al., Expansion of Vdelta1 T lymphocytes producing IL-4 in low-grade non-Hodgkin lymphomas expressing UL-16-binding proteins. Blood. Mar. 1, 2007;109(5):2078-85. doi: 10.1182/blood-2006-06-028985. Epub Sep. 14, 2006.
Crescioli et al., IgG4 Characteristics and Functions in Cancer Immunity. Curr Allergy Asthma Rep. Jan. 2016;16(1):7. doi: 10.1007/s11882-015-0580-7.
Edwards et al., The remarkable flexibility of the human antibody repertoire; isolation of over one thousand different antibodies to a single protein, BLyS. J Mol Biol. Nov. 14, 2003;334(1):103-18. doi: 10.1016/j.jmb.2003.09.054.
Gentles et al., The prognostic landscape of genes and infiltrating immune cells across human cancers. Nat Med. Author manuscript; available in PMC May 2, 2016. Published in final edited form as: Nat Med. Aug. 2015; 21(8): 938-945. Published online Jul. 20, 2015. doi: 10.1038/nm.3909.
Godder et al., Long term disease-free survival in acute leukemia patients recovering with increased gammadelta T cells after partially mismatched related donor bone marrow transplantation. Bone Marrow Transplant. Jun. 2007;39(12):751-7. doi: 10.1038/sj.bmt.1705650. Epub Apr. 23, 2007.
Goel et al., Plasticity within the antigen-combining site may manifest as molecular mimicry in the humoral immune response. J Immunol. Dec. 15, 2004;173(12):7358-67. doi: 10.4049/jimmunol.173.12.7358.
Gonzales et al., Minimizing the Immunogenicity of Antibodies for Clinical Application. Tumour Biol. Jan.-Feb. 2005;26(1):31-43. doi: 10.1159/000084184.
Khan et al., Adjustable locks and flexible keys: plasticity of epitope-paratope interactions in germline antibodies. J Immunol. Jun. 1, 2014;192(11):5398-405. doi: 10.4049/jimmunol.1302143. Epub Apr. 30, 2014.
Kim et al., Spectrum of EGFR Gene Copy Number Changes and KRAS Gene Mutation Status in Korean Triple Negative Breast Cancer Patients. PLoS One. Oct. 30, 2013;8(10):e79014. doi: 10.1371/journal.pone.0079014. eCollection 2013.
Kontermann, Strategies to Extend Plasma Half-Lives of Recombinant Antibodies. BioDrugs. 2009;23(2):93-109. doi: 10.2165/00063030-200923020-00003.
Kunik et al., Structural Consensus among Antibodies Defines the Antigen Binding Site. PLoS Comput Biol. 2012;8(2):e1002388. doi: 10.1371/journal.pcbi.1002388. Epub Feb. 23, 2012.
Licitra et al., Evaluation of EGFR gene copy number as a predictive biomarker for the efficacy of cetuximab in combination with chemotherapy in the first-line treatment of recurrent and/or metastatic squamous cell carcinoma of the head and neck: Extreme study. Ann Oncol. May 2011;22(5):1078-1087. doi: 10.1093/annonc/mdq588. Epub Nov. 3, 2010.
Liu, Pharmacokinetics of monoclonal antibodies and Fc-fusion proteins. Protein Cell. Jan. 2018;9(1):15-32. doi: 10.1007/s13238-017-0408-4. Epub Apr. 19, 2017.
Lloyd et al., Modelling the human immune response: performance of a 1011 human antibody repertoire against a broad panel of therapeutically relevant antigens. Protein Eng Des Sel. Mar. 2009;22(3):159-68. doi: 10.1093/protein/gzn058. Epub Oct. 29, 2008.
Lucchese et al., How a single amino acid change may alter the immunological information of a peptide. Front Biosci (Elite Ed). Jan. 1, 2012;4(5):1843-52. doi: 10.2741/e506.
Mix et al., Immunoglobulins—Basic considerations. J Neurol. Sep. 2006:253 Suppl 5:V9-17. doi: 10.1007/s00415-006-5002-2.
Panka et al., Variable region framework differences result in decreased or increased affinity of variant anti-digoxin antibodies. Proc Natl Acad Sci U S A. May 1988;85(9):3080-4. doi: 10.1073/pnas.85.9.3080.
Poccia et al., Anti-severe acute respiratory syndrome coronavirus immune responses: the role played by V gamma 9V delta 2 T cells. J Infect Dis. May 1, 2006;193(9):1244-9. doi: 10.1086/502975. Epub Mar. 27, 2006.
Poosarla et al., Computational de novo design of antibodies binding to a peptide with high affinity. Biotechnol Bioeng. Jun. 2017;114(6):1331-1342. doi: 10.1002/bit.26244. Epub Feb. 2, 2017.
Strohl et al., Therapeutic antibody classes. Chapter 9 in: Therapeutic Antibody Engineering: Current and Future Advances Driving the Strongest Growth Area in the Pharmaceutical Industry. 1st edition. Woodhead Publishing Limited, eds. 2012; 197-223 and 459-595.
Ternant et al., Pharmacokinetics and concentration-effect relationships of therapeutic monoclonal antibodies and fusion proteins. Expert Opin Biol Ther. Sep. 2005:5 Suppl 1:S37-47. doi: 10.1517/14712598.5.1.s37.
Van Dorp et al., Therapeutic Potential of Gammadelta T-Cells in Controlling CMV After Allogeneic Stem Cell Transplantation. Biology of Blood and Marrow Transplantation. 2011; 17(2): S217.
Vidarsson et al., IgG subclasses and allotypes: from structure to effector functions. Front Immunol. Oct. 20, 2014:5:520. doi: 10.3389/fimmu.2014.00520. eCollection 2014.
Wark et al., Latest technologies for the enhancement of antibody affinityB. Adv Drug Deliv Rev. Aug. 7, 2006;58(5-6):657-70. doi: 10.1016/j.addr.2006.01.025. Epub May 22, 2006.
Wu et al., An innate-like Vδ1+ γδ T cell compartment in the human breast is associated with remission in triple-negative breast cancer. Sci Transl Med. Oct. 9, 2019;11(513):eaax9364. doi: 10.1126/scitranslmed.aax9364.

(56) References Cited

OTHER PUBLICATIONS

Wu et al., Humanization of a Murine Monoclonal Antibody by Simultaneous Optimization of Framework and CDR Residues. J Mol Biol. Nov. 19, 1999;294(1):151-62. doi: 10.1006/jmbi.1999.3141.
Xenaki et al., Antibody or Antibody Fragments: Implications for Molecular Imaging and Targeted Therapy of Solid Tumors. Front Immunol. Oct. 12, 2017:8:1287. doi: 10.3389/fimmu.2017.01287. eCollection 2017.
Zhang et al., Epidermal growth factor receptor expression and gene copy number analysis in gastric carcinoma samples from Chinese patients. Oncol Lett. Jan. 2016;11(1):173-181. doi: 10.3892/ol.2015.3875. Epub Nov. 5, 2015.
Zhao et al., Protective Role of γδ T Cells in Different Pathogen Infections and Its Potential Clinical Application. J Immunol Res. Jul. 10, 2018:2018:5081634. doi: 10.1155/2018/5081634. eCollection 2018.
Bruhns et al., Specificity and affinity of human Fcgamma receptors and their polymorphic variants for human IgG subclasses. Blood. Apr. 16, 2009;113(16):3716-25. doi: 10.1182/blood-2008-09-179754. Epub Nov. 18, 2008.
Chothia et al., Conformations of immunoglobulin hypervariable regions. Nature. Dec. 1989;342(6252):877-83. doi: 10.1038/342877a0.
He et al., Naturally activated V gamma 4 gamma delta T cells play a protective role in tumor immunity through expression of eomesodermin. J Immunol. Jul. 1, 2010;185(1):126-33. doi: 10.4049/jimmunol.0903767. Epub Jun. 4, 2010.
Kabat et al., Sequences of Proteins of Immunological Interest. vol. 1. Fifth Edition. U.S. Department of Health and Human Services. National Institutes of Health. 1991. NIH Publication No. 91-3242.
Ma et al., IL-17A produced by γδ T cells promotes tumor growth in hepatocellular carcinoma. Cancer Res. Apr. 1, 2014;74(7):1969-82. doi: 10.1158/0008-5472.CAN-13-2534. Epub Feb. 13, 2014.
Padlan, Anatomy of the antibody molecule. Mol Immunol. Feb. 1994;31(3):169-217. doi: 10.1016/0161-5890(94)90001-9.
Xu et al., In vitro characterization of five humanized OKT3 effector function variant antibodies. Cell Immunol. Feb. 25, 2000;200(1):16-26. doi: 10.1006/cimm.2000.1617.
Chen et al., Distribution and functions of γδ T cells infiltrated in the ovarian cancer microenvironment. J Transl Med. May 7, 2019;17(1):144. doi: 10.1186/s12967-019-1897-0.
Dahlén et al., Bispecific antibodies in cancer immunotherapy. Ther Adv Vaccines Immunother. Feb. 2018;6(1):3-17. doi: 10.1177/2515135518763280. Epub Mar. 28, 2018.
Daley et al., γδ T Cells Support Pancreatic Oncogenesis by Restraining αβ T Cell Activation. Cell. Sep. 8, 2016;166(6):1485-1499.e15. doi: 10.1016/j.cell.2016.07.046. Epub Aug. 25, 2016.
Declaration and Curriculum Vitae of Professor Frits Koning. Signed Mar. 11, 2025. 48 pages.
Deniger et al., Activating and propagating polyclonal gamma delta T cells with broad specificity for malignancies. Clin Cancer Res. Nov. 15, 2014;20(22):5708-19. doi: 10.1158/1078-0432.CCR-13-3451. Epub May 15, 2014.
Dopfer et al., The CD3 conformational change in the γδ T cell receptor is not triggered by antigens but can be enforced to enhance tumor killing. Cell Rep. Jun. 12, 2014;7(5):1704-1715. doi: 10.1016/j.celrep.2014.04.049. Epub May 22, 2014.
Einsele et al., The BiTE (bispecific T-cell engager) platform: Development and future potential of a targeted immuno-oncology therapy across tumor types. Cancer. Jul. 15, 2020;126(14):3192-3201. doi: 10.1002/cncr.32909. Epub May 13, 2020.
Gaspar et al., CD137/OX40 Bispecific Antibody Induces Potent Antitumor Activity that Is Dependent on Target Coengagement. Cancer Immunol Res. Jun. 2020;8(6):781-793. doi: 10.1158/2326-6066.CIR-19-0798. Epub Apr. 9, 2020.
Herrman et al., Bifunctional PD-1 × αCD3 × αCD33 fusion protein reverses adaptive immune escape in acute myeloid leukemia. Blood. Dec. 6, 2018;132(23):2484-2494. doi: 10.1182/blood-2018-05-849802. Epub Oct. 1, 2018.
Lejeune et al., Bispecific, T-Cell-Recruiting Antibodies in B-Cell Malignancies. Front Immunol. May 7, 2020:11:762. doi: 10.3389/fimmu.2020.00762. eCollection 2020.
Li et al., Membrane-Proximal Epitope Facilitates Efficient T Cell Synapse Formation by Anti-FcRH5/CD3 and Is a Requirement for Myeloma Cell Killing. Cancer Cell. Mar. 13, 2017;31(3):383-395. doi: 10.1016/j.ccell.2017.02.001. Epub Mar. 2, 2017.
Li et al., The Dual Roles of Human γδ T Cells: Anti-Tumor or Tumor-Promoting. Front Immunol. Feb. 16, 2021:11:619954. doi: 10.3389/fimmu.2020.619954. eCollection 2020.
Liu et al., The Role of Human γδ T Cells in Anti-Tumor Immunity and Their Potential for Cancer Immunotherapy. Cells. May 13, 2020;9(5):1206. doi: 10.3390/cells9051206.
Lum et al., Targeting T Cells with Bispecific Antibodies for Cancer Therapy. BioDrugs. Author manuscript; available in PMC: Oct. 8, 2013. Published in final edited form as: BioDrugs. Dec. 1, 2011;25(6):365-379. doi: 10.2165/11595950-000000000-00000.
Ma et al., A novel bispecific nanobody with PD-L1/TIGIT dual immune checkpoint blockade. Biochem Biophys Res Commun. Oct. 15, 2020;531(2):144-151. doi: 10.1016/j.bbrc.2020.07.072. Epub Aug. 8, 2020.
No Author Listed, Certified copy of priority document for Application No. GB1911799.3, filed Aug. 16, 2019. 82 pages.
No Author Listed, Certified copy of priority document for Application No. GB2010760.3, filed Jul. 13, 2020. 96 pages.
No Author Listed, Certified copy of priority document for Application No. GB2012172.9, filed Aug. 5, 2020. 131 pages.
No Author Listed, NCBI Gene ID: 2191; FAP fibroblast activation protein alpha [ *Homo sapiens* (human) ]. Last Updated: Jul. 5, 2025. Accessed at: https://www.ncbi.nlm.nih.gov/gene?Db=gene&Cmd=ShowDetailView&TermToSearch=2191 [last accessed Jul. 18, 2025].
No Author Listed, Sequence Listing for WO2021032960. GammaDelta Therapeutics Limited. 99 pages.
Oberg et al., Monitoring Circulating γδ T Cells in Cancer Patients to Optimize γδ T Cell-Based Immunotherapy. Front Immunol. Dec. 17, 2014:5:643. doi: 10.3389/fimmu.2014.00643. eCollection 2014.
Peng et al., Tumor-infiltrating gammadelta T cells suppress T and dendritic cell function via mechanisms controlled by a unique toll-like receptor signaling pathway. Immunity. Aug. 2007;27(2):334-48. doi: 10.1016/j.immuni.2007.05.020. Epub Jul. 26, 2007.
Qin et al., Novel immune checkpoint targets: moving beyond PD-1 and CTLA-4. Mol Cancer. Nov. 6, 2019;18(1):155. doi: 10.1186/s12943-019-1091-2.
Siegers et al., Human Vδ1 γδ T cells expanded from peripheral blood exhibit specific cytotoxicity against B-cell chronic lymphocytic leukemia-derived cells. Cytotherapy. Jul. 2011;13(6):753-64. doi: 10.3109/14653249.2011.553595. Epub Feb. 11, 2011.
Strohl et al., Bispecific T-Cell Redirection versus Chimeric Antigen Receptor (CAR)-T Cells as Approaches to Kill Cancer Cells. Antibodies (Basel). Jul. 3, 2019;8(3):41. doi: 10.3390/antib8030041.
Ye et al., Specific recruitment of γδ regulatory T cells in human breast cancer. Cancer Res. Oct. 15, 2013;73(20):6137-48. doi: 10.1158/0008-5472.CAN-13-0348. Epub Aug. 19, 2013.
Rabia et al., Understanding and overcoming trade-offs between antibody affinity, specificity, stability and solubility. Biochem Eng J. Sep. 15, 2018:137:365-374. doi: 10.1016/j.bej.2018.06.003. Epub Jun. 5, 2018.

* cited by examiner

| TNF alpha levels in supernatant (pg/ml) | | | | |
|---|---|---|---|---|
| clone | Donor1 | Donor2 | Average | STDEV |
| B07 | 612.369 | 652.9294 | 632.6492 | 28.68055 |
| E07 | 579.6175 | 497.477 | 538.5472 | 58.08211 |
| G04 | 760.3178 | 695.8256 | 728.0717 | 45.60288 |
| C08 | 512.5485 | 545.4042 | 528.9763 | 23.23252 |
| IgG1 (control) | <LOQ | <LOQ | <LOQ | <LOQ |

| IFN gamma levels in supernatant (pg/ml) | | | | |
|---|---|---|---|---|
| clone | Donor1 | Donor2 | Average | STDEV |
| B07 | 4916.846 | 5616.726 | 5266.786 | 494.89 |
| E07 | 4753.625 | 3875.864 | 4314.744 | 620.671 |
| G04 | 7279.766 | 7189.028 | 7234.397 | 64.16168 |
| C08 | 3713.296 | 4561.834 | 4137.565 | 600.0066 |
| IgG1 (control) | 469.6334 | 549.9306 | 509.782 | 56.77863 |

| % of GranToxiLux+ cells | | | | |
|---|---|---|---|---|
| | | | Average | STDVE |
| IgG1 | 25.1 | 27.8 | 26.45 | 1.909188 |
| B07 | 78.4 | 76.2 | 77.3 | 1.555635 |
| E07 | 68.6 | 68.7 | 68.65 | 0.070711 |
| G04 | 55.6 | 58.4 | 57 | 1.979899 |
| C08 | 50.7 | 36.6 | 43.65 | 9.970206 |

| | | | | | |
|---|---|---|---|---|---|
| CO8 | + | | | + | |
| OKT3 | | + | | | + |
| CK | | | + | + | + |

| | % improvement in EC50 |
|---|---|
| No mAb | 100% |
| D1.3 IgG1 | 109% |
| 1252_P01_C08 IgG1 | 337% |
| 1245_P02_G04 IgG | 383% |
| 1245_P01_E07 IgG | 159% |

FIG. 21C

| | EC50s | |
|---|---|---|
| | γδT-cell | T:E ratio |
| No mAb | 8729 | 0.11 |
| D1.3 IgG1 | 8019 | 0.12 |
| 1252_P01_C08 IgG1 | 2594 | 0.39 |
| 1245_P02_G04 IgG | 2278 | 0.44 |
| 1245_P01_E07 IgG | 5485 | 0.18 |

FIG. 21D

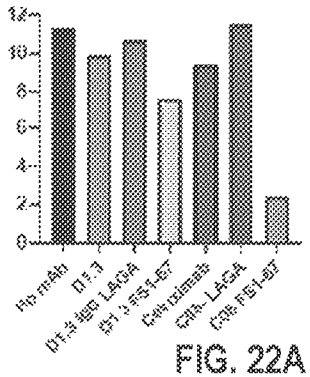
FIG. 22A
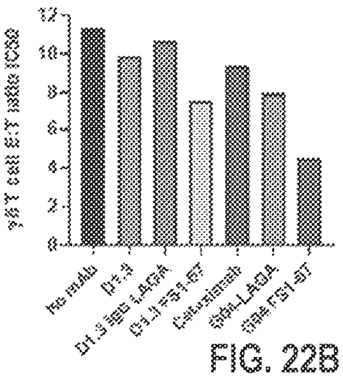
FIG. 22B
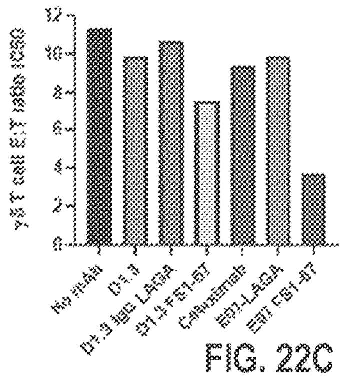
FIG. 22C
| | 5 hrs | 12 hrs | 24 hrs |
|---|---|---|---|
| No mAb | 100% | 100% | 100% |
| D1.3 | 114% | 99% | 112% |
| D1.3 IgG LAGA | 106% | 96% | 113% |
| D1.3 FS1-67 | 149% | 143% | 147% |
| Cetuximab | 121% | 110% | 126% |
| C08- LAGA | 99% | 84% | 101% |
| E07-LAGA | 115% | 117% | 127% |
| G04-LAGA | 141% | 128% | 163% |
| C08 FS1-67 | 467% | 424% | 371% |
| E07 FS1-67 | 303% | 292% | 259% |
| G04 FS1-67 | 254% | 232% | 212% |
FIG. 22D
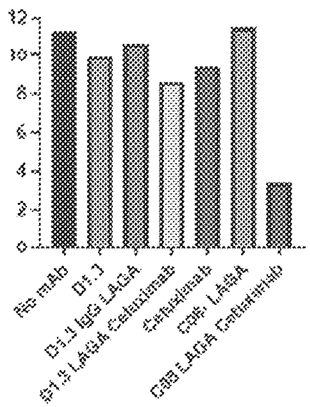
FIG. 22E
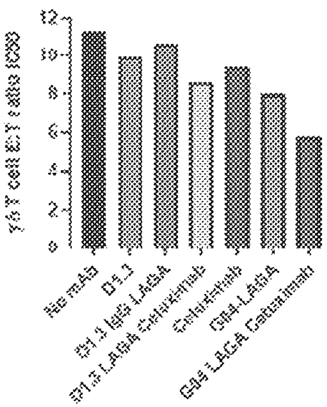
FIG. 22F
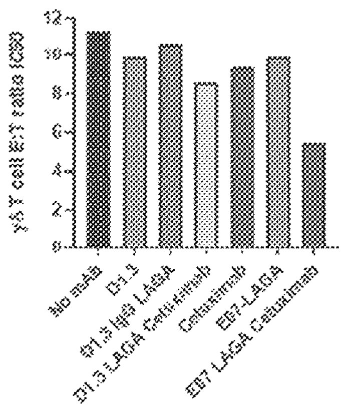
FIG. 22G
| | 5 hrs | 12 hrs | 24 hrs |
|---|---|---|---|
| No mAb | 100% | 100% | 100% |
| D1.3 | 114% | 99% | 112% |
| D1.3 IgG LAGA | 106% | 96% | 113% |
| D1.3 LAGA Cetuximab | 132% | 123% | 118% |
| Cetuximab | 121% | 110% | 126% |
| C08- LAGA | 99% | 84% | 101% |
| E07-LAGA | 115% | 117% | 127% |
| G04-LAGA | 141% | 128% | 163% |
| C08 LAGA Cetuximab | 334% | 313% | 245% |
| E07 LAGA Cetuximab | 208% | 216% | 187% |
| G04 LAGA Cetuximab | 197% | 210% | 158% |
FIG. 22H

| | EC50s | | |
|---|---|---|---|
| | γδT-cell | T:E ratio | % improvement |
| No mAb | 4102 | 0.24 | 100% |
| D1.3 IgG1 | 3651 | 0.27 | 112% |
| D1.3 IgG LAGA | 3640 | 0.27 | 113% |
| E07-LAGA | 3229 | 0.31 | 127% |
| D1.3 FS1-67 | 2794 | 0.36 | 147% |
| Cetuximab | 3246 | 0.31 | 126% |
| E07 FS1-67 | 1581 | 0.63 | 259% |

FIG. 22I

| | EC50s | | |
|---|---|---|---|
| | γδT-cell | T:E ratio | % improvement |
| RSV IgG | 1988 | 1.99 | 100% |
| G04 | 2128 | 2.13 | 93% |
| E07 | 1775 | 1.78 | 112% |
| D1.3 VHVL | 1143 | 1.14 | 174% |
| G04 VHVL | 470 | 0.47 | 423% |
| E07 VHVL | 828 | 0.83 | 240% |

FIG. 23A

| Antibody | huVδ1 [KD] | cynoVδ1 [KD] |
|---|---|---|
| ADT1-4 | 47nM | 397nM |
| ADT1-4 (S74L) | 3.5nM | 77nM |
| ADT1-4-2 | 0.34nM | 2.6nM |
| ADT1-4-2 (L74S) | 4nM | 61nM |

FIG. 26F

| Clone | Avg KD (M) | Fold-change |
|---|---|---|
| ADT1-4 | 1.49E-07 | 1.00 |
| ADT1-4-2 | 1.90E-10 | 784.21 |
| ADT1-4-19 | 1.77E-10 | 841.81 |
| ADT1-4-21 | 4.74E-10 | 314.35 |
| ADT1-4-31 | 4.42E-10 | 337.49 |
| ADT1-4-53 | 5.07E-10 | 294.18 |
| ADT1-4-86 | 7.16E-10 | 208.25 |
| ADT1-4-112 | 5.65E-10 | 263.95 |
| ADT1-4-143 | 4.24E-10 | 351.42 |
FIG. 32C
| Clone | Avg KD (M) | Fold-change |
|---|---|---|
| ADT1-7 | 3.81E-08 | 1.00 |
| ADT1-7-3 | 3.78E-09 | 10.07 |
| ADT1-7-20 | 4.99E-09 | 7.63 |
| ADT1-7-61 | 1.04E-09 | 36.62 |
FIG. 32D
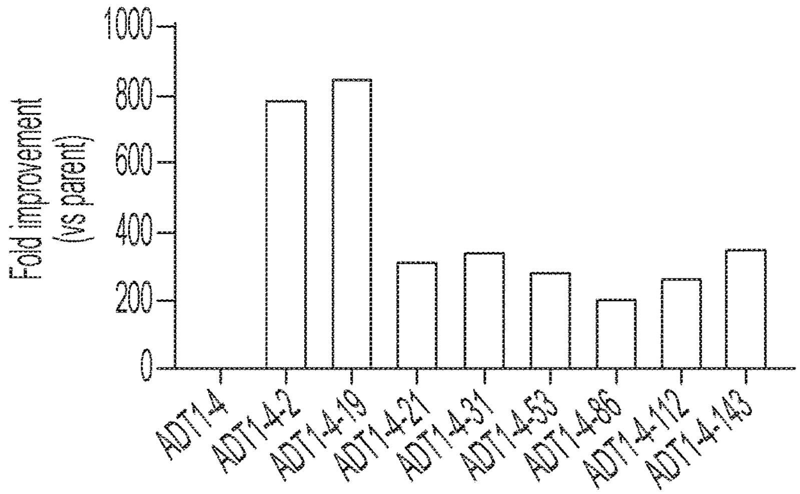
FIG. 32E
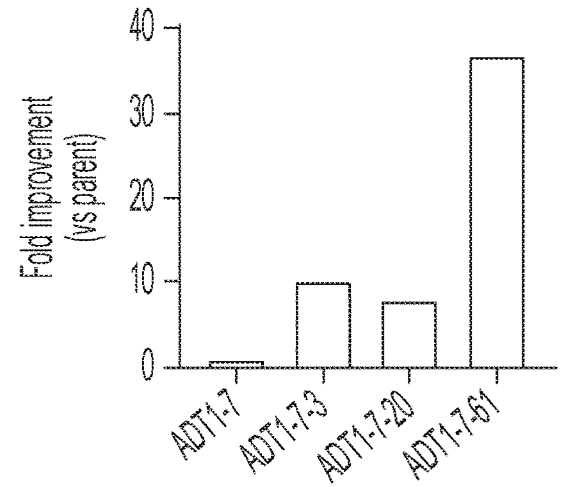
FIG. 32F

| Clone | Avg KD (M) |
|---|---|
| ADT1-4 | No binding |
| ADT1-4-2 | 1.92E-09 |
| ADT1-4-19 | 2.25E-09 |
| ADT1-4-21 | 4.38E-09 |
| ADT1-4-31 | 6.45E-09 |
| ADT1-4-53 | 4.01E-09 |
| ADT1-4-86 | 9.22E-09 |
| ADT1-4-112 | 8.27E-09 |
| ADT1-4-143 | 7.61E-09 |

| mAb | ATS006 IC50 | ATS006 % improvement in IC50 | TS164 IC50 | TS164 % improvement in IC50 |
|---|---|---|---|---|
| ADT1-4 | 107.7 | 0.00 | 575.9 | 0.00 |
| ADT1-4-2 | 2.164 | 4876.89 | 1.703 | 33716.79 |
| ADT1-4-19 | 2.375 | 4434.74 | 2.456 | 23348.70 |
| ADT1-4-21 | 2.536 | 4146.85 | 1.675 | 34282.09 |
| ADT1-4-31 | 3.33 | 3134.23 | 2.63 | 21797.34 |
| ADT1-4-53 | 2.228 | 4733.93 | 2.456 | 23348.70 |
| ADT1-4-86 | 5.357 | 1910.45 | 2.34 | 24511.11 |
| ADT1-4-112 | 2.621 | 4009.12 | 2.436 | 23541.22 |
| ADT1-4-143 | 2.819 | 3720.50 | 3.066 | 18683.43 |
| | ATS006 IC50 | ATS006 % improvement in IC50 | TS164 IC50 | TS164 % improvement in IC50 |
|---|---|---|---|---|
| ADT1-7 | *>100* | *0.00* | 225.6 | 0.00 |
| ADT1-7-3 | *5.153* | *N/A* | 0.9517 | 23604.95 |
| ADT1-7-20 | *37.22* | *N/A* | 2.684 | 8305.37 |
| ADT1-7-61 | *93.01* | *N/A* | 195.7 | 15.28 |
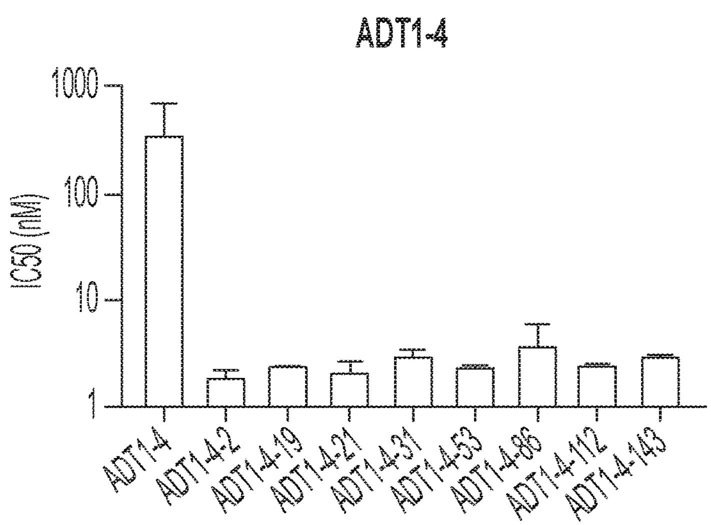
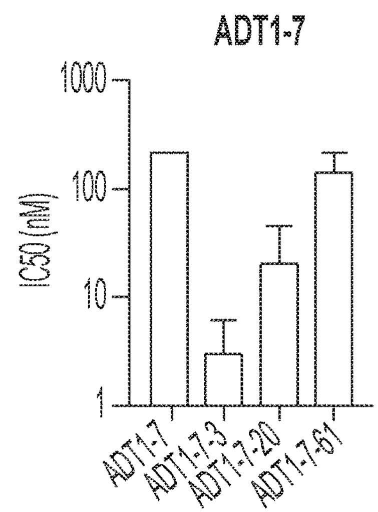
FIG. 34C

| mAb | IC50 (nM) | | | | | | | | |
|---|---|---|---|---|---|---|---|---|---|
| | Donor 1 (ATS006) | Donor 2 (TS164) | HEK293T | Raji | CD8 (PBMC) | CD4 (PBMC) | CD56 (PBMC) | CD19 (PBMC) | CD14 (PBMC) |
| ADT1-4 | 107.7 | 575.9 | No binding | No binding | No binding | No binding | No binding | No binding | No binding |
| ADT1-4-2 | 2.164 | 1.703 | No binding | No binding | No binding | No binding | No binding | No binding | No binding |
| ADT1-4-19 | 2.375 | 2.456 | No binding | No binding | No binding | No binding | No binding | No binding | No binding |
| ADT1-4-21 | 2.536 | 1.675 | No binding | No binding | No binding | No binding | No binding | No binding | No binding |
| ADT1-4-31 | 3.33 | 2.63 | No binding | No binding | No binding | No binding | No binding | No binding | No binding |
| ADT1-4-53 | 2.228 | 2.456 | No binding | No binding | No binding | No binding | No binding | No binding | No binding |
| ADT1-4-86 | 5.357 | 2.34 | No binding | No binding | No binding | No binding | No binding | No binding | No binding |
| ADT1-4-112 | 2.621 | 2.436 | No binding | No binding | No binding | No binding | No binding | No binding | No binding |
| ADT1-4-143 | 2.819 | 3.066 | No binding | No binding | No binding | No binding | No binding | No binding | No binding |

| mAb | IC50 (nM) | | | | | | | | |
|---|---|---|---|---|---|---|---|---|---|
| | Donor 1 (ATS006) | Donor 2 (TS164) | HEK293T | Raji | CD8 (PBMC) | CD4 (PBMC) | CD56 (PBMC) | CD19 (PBMC) | CD14 (PBMC) |
| ADT1-7 | >100 | 225.6 | No binding | No binding | No binding | No binding | No binding | No binding | No binding |
| ADT1-7-3 | 5.153 | 0.9517 | No binding | No binding | No binding | No binding | No binding | No binding | No binding |
| ADT1-7-20 | 37.22 | 2.684 | No binding | No binding | No binding | No binding | No binding | No binding | No binding |
| ADT1-7-61 | 93.01 | 195.7 | No binding | No binding | No binding | No binding | No binding | No binding | No binding |

| mAb | IC50 (nM) | | | | | |
|---|---|---|---|---|---|---|
| | Donor 1 (ATS006) | CD8 (PBMC) | CD4 (PBMC) | CD56 (PBMC) | CD19 (PBMC) | CD14 (PBMC) |
| OKT3 | 2.889 | 0.252 | 0.1906 | No binding | No binding | No binding |
| RSV (IgG control) | No binding | No binding | No binding | No binding | No binding | No binding |

FIG. 34D

| | IC50 | % improvement in IC50 |
|---|---|---|
| ADT1-4 | 38.28 | 100 |
| OKT3 | 19.43 | 197 |
| ADT1-4-2 | 0.31 | 12348 |
| ADT1-4-31 | 0.24 | 15630 |
| ADT1-4-21 | 0.27 | 14372 |
| ADT1-4-86 | 0.31 | 12472 |
| ADT1-4-143 | 0.31 | 12219 |
| ADT1-4-19 | 0.37 | 10420 |
| ADT1-4-53 | 0.25 | 15090 |
| ADT1-4-112 | 0.30 | 12964 |
| ADT1-4-1 | 0.36 | 6185 |
| ADT1-4-6 | 0.48 | 4648 |
| ADT1-4-138 | 8.38 | 266 |

| | IC50 | % improvement in IC50 |
|---|---|---|
| ADT1-7 | 22.42 | 100 |
| OKT3 | 19.43 | 115 |
| ADT1-7-3 | 0.16 | 13968 |
| ADT1-7-20 | 0.16 | 13697 |
| ADT1-7-61 | 6.26 | 358 |

FIG. 35F

| | IC50 | Fold improvement in IC50 |
|---|---|---|
| ADT1-4 | 38.28 | 1 |
| OKT3 | 19.43 | 2 |
| ADT1-4-1 | 0.36 | 62 |
| ADT1-4-2 | 0.31 | 123 |
| ADT1-4-6 | 0.48 | 46 |
| ADT1-4-19 | 0.37 | 104 |
| ADT1-4-21 | 0.27 | 144 |
| ADT1-4-31 | 0.24 | 156 |
| ADT1-4-53 | 0.25 | 151 |
| ADT1-4-86 | 0.31 | 125 |
| ADT1-4-112 | 0.30 | 130 |
| ADT1-4-138 | 8.38 | 3 |
| ADT1-4-143 | 0.31 | 122 |

| | IC50 | Fold improvement in IC50 |
|---|---|---|
| ADT1-7 | 22.42 | 1 |
| OKT3 | 19.43 | 1 |
| ADT1-7-3 | 0.16 | 140 |
| ADT1-7-20 | 0.16 | 137 |
| ADT1-7-61 | 6.26 | 4 |

FIG. 35G

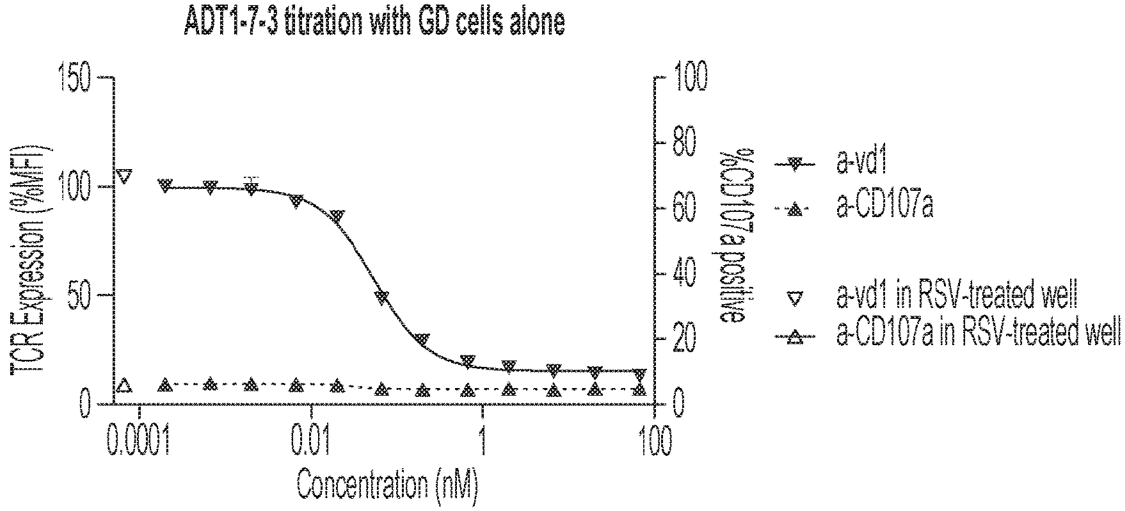
FIG. 36C
| | % increase in CD107a positive cells |
|---|---|
| ADT1-4-2 | 24.705 |
| ADT1-7-3 | 26.7 |
FIG. 36E
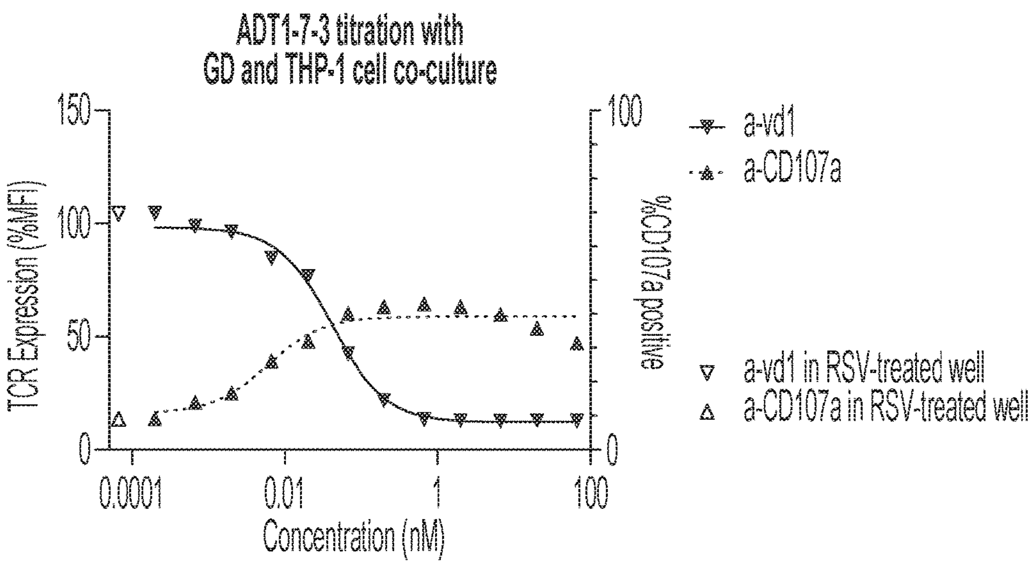
FIG. 36D
| Condition | mAb | % maximum increase in CD107a positive cells |
|---|---|---|
| GD | ADT1-4-2 | -3.73 |
| GD | ADT1-7-3 | -1.28 |
| GD + THP-1 | ADT1-4-2 | 19.53 |
| GD + THP-1 | ADT1-7-3 | 22.3 |
FIG. 36F

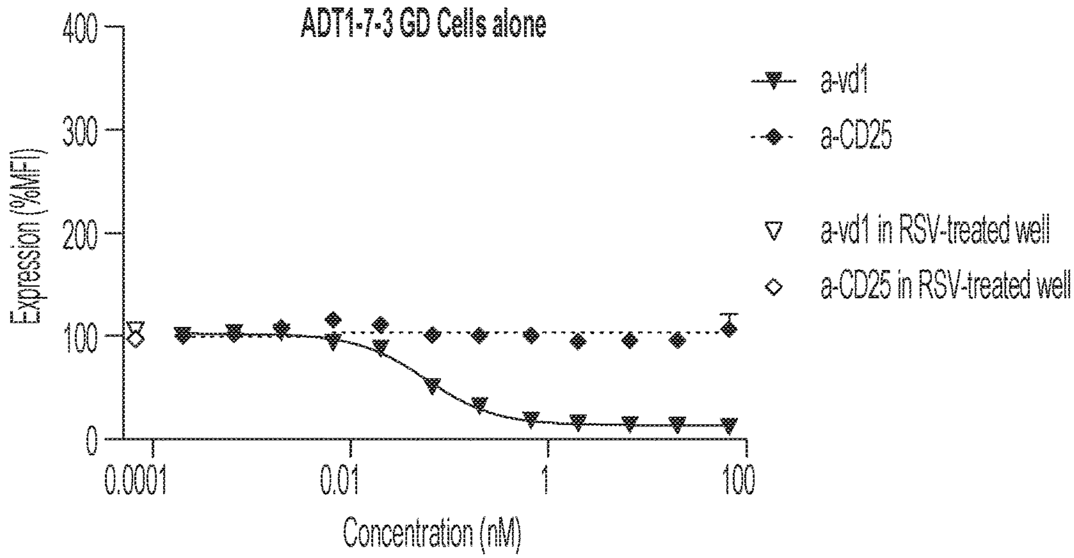
FIG. 37C
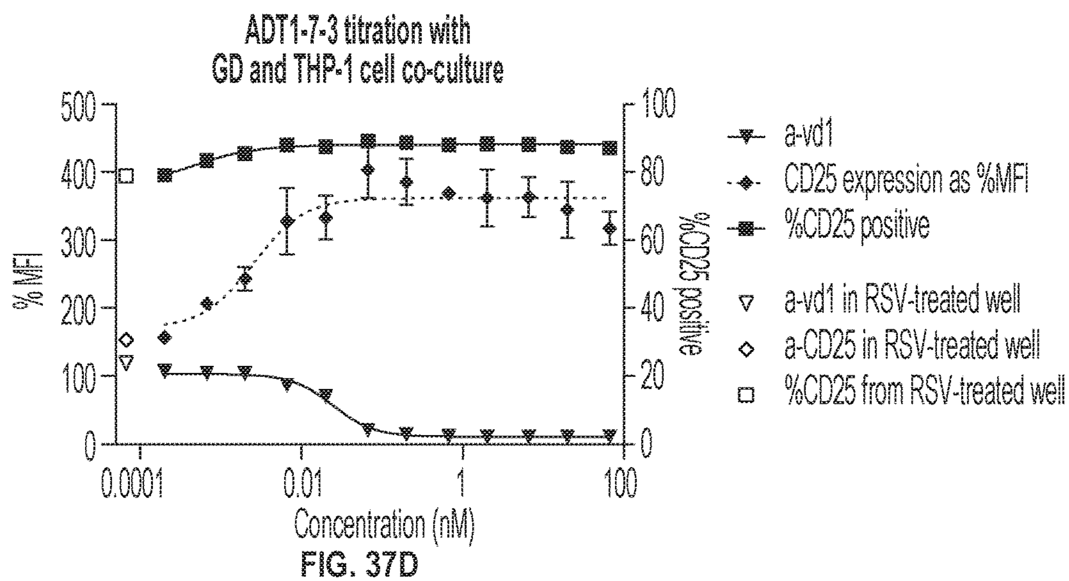
FIG. 37D
| | % increase in CD25 expression |
|---|---|
| ADT1-4-2 | 170.1 |
| ADT1-7-3 | 220.9 |
FIG. 37E
| Condition | mAb | % maximum increase in CD25 expression |
|---|---|---|
| GD | ADT1-4-2 | -15.23 |
| GD + THP-1 | ADT1-4-2 | 116.8 |
| GD | ADT1-7-3 | 3.84 |
| GD + THP-1 | ADT1-7-3 | 162.2 |
FIG. 37F

| Clone ID | THP-1 killing assay EC50 [pM] (average of ≥3 donors) | Standard deviation | Fold improvement | % improvement over parent |
|---|---|---|---|---|
| OKT3(anti-CD3) | 3.53 | 2.40 | | |
| ADT1-4 | 121.47 | 136.80 | 1.0 | 100% |
| ADT1-4-1 | 3.00 | 2.87 | 40.5 | 4049% |
| ADT1-4-2 | 6.33 | 3.67 | 19.2 | 1918% |
| ADT1-4-6 | 0.93 | 0.07 | 130.1 | 13014% |
| ADT1-4-19 | 8.33 | 6.13 | 14.6 | 1458% |
| ADT1-4-21 | 6.13 | 2.93 | 19.8 | 1980% |
| ADT1-4-31 | 10.93 | 4.73 | 11.1 | 1111% |
| ADT1-4-53 | 7.40 | 3.13 | 16.4 | 1641% |
| ADT1-4-86 | 7.60 | 2.87 | 16.0 | 1598% |
| ADT1-4-112 | 6.47 | 3.53 | 18.8 | 1878% |
| ADT1-6-138 | 2.53 | 0.73 | 47.9 | 4795% |
| ADT1-4-143 | 13.07 | 9.27 | 9.3 | 930% |
| ADT1-7 | 65.20 | 54.80 | 1.0 | 100% |
| ADT1-7-20 | 1.87 | 0.53 | 34.9 | 3493% |
| ADT1-7-3 | 1.33 | 0.87 | 48.9 | 4890% |
| ADT1-7-61 | 3.60 | 3.60 | 18.1 | 1811% |

FIG. 39D

ADT1-4-105 2499_01_D07

DIQMTQSPPALSASVGDRVTITCRASQDINDWLAWYQHKPGKAPKLLIYDASSLESGVPLRFSGSGSGTEFTLTISSLQPDDFATYYCQQKYSTPQITFGQGTRLEIK

ADT1-4-107 2499_01_F07

DIQMTQSPPALSASVGDRVTITCRASQDINDWLAWYQHKPGKAPKLLIYDASSLESGVPLRFSGSGSGTEFTLTISSLQPDDFATYYCQQRYSTPQITFGQGTRLEIK

ADT1-4-110 2499_02_A02

DIQMTQSPPALSASVGDRVTITCRASQDINDWLAWYQHKPGKAPKLLIYDASSLESGVPLRFSGSGSGTEFTLTISSLQPDDFATYYCQQKYSTPQVTFGAGTRLEIK

ADT1-4-112 2499_02_B04

DIQMTQSPPALSASVGDRVTITCRASQDINDWLAWYQHKPGKAPKLLIYDASSLESGVPLRFSGSGSGTEFTLTISSLQPDDFATYYCQQKYSQPQVTFGQGTRLEIK

ADT1-4-117 2499_02_F12

DIQMTQSPPALSASVGDRVTITCRASQDINDWLAWYQHKPGKAPKLLIYDASSLESGVPLRFSGSGSGTEFTLTISSLQPDDFATYYCQQRYSTPRVTFGQGTRLEIK

ADT1-4-19 2501_01_H01

DIQMTQSPPALSASVGDRVTITCRASQDINDWLAWYQHKPGKAPKLLIYDASSLESGVPLRFSGSGSGTEFTLTISSLQPDDFATYYCQQKYSTPKVTFGQGTRLEIK

ADT1-4-21 2501_02_A05

DIQMTQSPPALSASVGDRVTITCRASQDINDWLAWYQHKPGKAPKLLIYDASSLESGVPLRFSGSGSGTEFTLTISSLQPDDFATYYCQQKYSTPWVTFGQGTRLEIK

ADT1-4-31 2501_02_G09

DIQMTQSPPALSASVGDRVTITCRASQDINDWLAWYQHKPGKAPKLLIYDASSLESGVPLRFSGSGSGTEFTLTISSLQPDDFATYYCQQRYSTPPVTFGQGTRLEIK

ADT1-4-139 2502_01_C07

DIQMTQSPPALSASVGDRVTITCRASQDINDWLAWYQHKPGKAPKLLIYDASSLESGVPLRFSGSGSGTEFTLTISSLQPDDFATYYCQQGYSTPQLTFGQGTRLEIK

ADT1-4-4 2502_01_E01

DIQMTQSPPALSASVGDRVTITCRASQDINDWLAWYQHKPGKAPKLLIYDASSLESGVPLRFSGSGSGTEFTLTISSLQPDDFATYYCQQKYSTPWVTFGQGTRLEIK

ADT1-4-143 2502_01_E05

DIQMTQSPPALSASVGDRVTITCRASQDINDWLAWYQHKPGKAPKLLIYDASSLESGVPLRFSGSGSGTEFTLTISSLQPDDFATYYCQQRYSTHQVTFGQGTRLVIK

ADT1-4-53 2505_02_E12

DIQMTQSPPALSASVGDRVTITCRASQDINDWLAWYQHKPGKAPKLLIYDASSLESGVPLRFSGSGSGTEFTLTISSLQPDDFATYYCQQKYSTPQLTFGQGTRLEIK

FIG. 45A

ADT1-4-173 2505_02_G11

DIQMTQSPPALSASVGDRVTITCRASQDINDWLAWYQHKPGKAPKLLIYDASSLESGVPLRFSGSGSGTEFTLTISSLQPDDFATYYCQQKYSAPQVTFGQGTRLEIK

ADT1-4-2 2506_01_B10

DIQMTQSPPALSASVGDRVTITCRASQDINDWLAWYQHKPGKAPKLLIYDASSLESGVPLRFSGSGSGTEFTLTISSLQPDDFATYYCQQKYSAPQVTFGQGTRLEIK

ADT1-4-8 2506_01_B11

DIQMTQSPPALSASVGDRVTITCRASQDINDWLAWYQHKPGKAPKLLIYDASSLESGVPLRFSGSGSGTEFTLTISSLQPDDFATYYCQQKYSAPQVTFGQGTRLEIK

ADT1-4-82 2506_02_B09

DIQMTQSPPALSASVGDRVTITCRASQDINDWLAWYQHKPGKAPKLLIYDASSLESGVPLRFSGSGSGTEFTLTISSLQPDDFATYYCQQRYSTPQITFGQGTRLEIK

ADT1-4-83 2506_02_B10

DIQMTQSPPALSASVGDRVTITCRASQDINDWLAWYQHKPGKAPKLLIYDASSLESGVPLRFSGSGSGTEFTLTISSLQPDDFATYYCQQKYSEPQVTFGQGTRLEIK

ADT1-4-3 2506_02_C01

DIQMTQSPPALSASVGDRVTITCRASQDINDWLAWYQHKPGKAPKLLIYDASSLESGVPLRFSGSGSGTEFTLTISSLQPDDFATYYCQQKYSTPEVTFGQGTRLEIK

ADT1-4-84 2506_02_C02

DIQMTQSPPALSASVGDRVTITCRASQDINDWLAWYQHKPGKAPKLLIYDASSLESGVPLRFSGSGSGTEFTLTISSLQPDDFATYYCQQKYSDPQVTFGQGTRLEIK

ADT1-4-86 2506_02_C12

DIQMTQSPPALSASVGDRVTITCRASQDINDWLAWYQHKPGKAPKLLIYDASSLESGVPLRFSGSGSGTEFTLTISSLQPDDFATYYCQQKYSEPQVTFGQGTRLEIK

ADT1-4-95 2506_02_H04

DIQMTQSPPALSASVGDRVTITCRASQDINDWLAWYQHKPGKAPKLLIYDASSLESGVPLRFSGSGSGTEFTLTISSLQPDDFATYYCQQKYSTPQVTFGSGTRLEIK

ADT1-4-1 2501_01_C09

DIQMTQSPPALSASVGDRVTITCRASQDINDWLAWYQHKPGKAPKLLIYDASSLESGVPLRFSGSGSGTEFTLTISSLQPDDFATYYCQQRYSTPIVTFGQGTRLEIK

ADT1-4-6 2506_1_B06

DIQMTQSPPALSASVGDRVTITCRASQDINDWLAWYQHKPGKAPKLLIYDASSLESGVPLRFSGSGSGTEFTLTISSLQPDDFATYYCQQKYKTPQVTFGQGTRLEIK

ADT1-4-138 2502_01_B03

DIQMTQSPPALSASVGDRVTITCRASQDINDWLAWYQHKPGKAPKLLIYDASSLESGVPSRFSGSGSGTEFTLTISSLQPDDFATYYCQQRYSTDQVTFGQGTRLEIK

FIG. 45B

ADT1-4-105 2499_01_D07

EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARTWVGYVDVWGQGTLVTVSS

ADT1-4-107 2499_01_F07

EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARTWVGYADVWGQGTLVTVSS

ADT1-4-110 2499_02_A02

EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARTWVEYVDVWGQGTLVTVSS

ADT1-4-112 2499_02_B04

EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARTWVGYVDYWGQGTLVTVSS

ADT1-4-117 2499_02_F12

EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARTWVGYVDVWGQGTLVTVSS

ADT1-4-19 2501_01_H01

EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARTWVGYVDRWGQGTLVTVSS

ADT1-4-21 2501_02_A05

EVQLQQSGPGLVKPSQTLSLTCAISGDSVSSKSVAWNWIRQSPSRGLEWLGRTYYRSKWSTDYAASVKSRITINPDTSKNQLSLQLNSVTPEDTAVYYCARTWADYVDVWGQGTLVTVSS

ADT1-4-31 2501_02_G09

EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARTWVGYADVWGQGTLVTVSS

ADT1-4-139 2502_01_C07

EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARTWVGYVDYWGQGTLVTVSS

ADT1-4-4 2502_01_E01

EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARTWVGYADVWGQGTLVTVSS

ADT1-4-143 2502_01_E05

EVQLLQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARTWVGYADVWGQGTLVTVSS

ADT1-4-53 2505_02_E12

EVQLQQSGPGLVKPSQTLSLTCAISGDSVSSKSVAWNWIRQSPSRGLEWLGRTYYRSKWSTDYAASVKSRITINPDTSKNQLSLQLNSVTPEDTAVYYCARTWADYVDVWGQGTLVTVSS

FIG. 46A

ADT1-4-173 2505_02_G11

EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARTWAGYFDVWGQGTLVTVSS

ADT1-4-2 2506_01_B10

EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARTWVGYVDRWGQGTLVTVSS

ADT1-4-8 2506_01_B11

EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARTWVGYADVWGQGTLVTVSS

ADT1-4-82 2506_02_B09

EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARSWVGYVDVWGQGTLVTVSS

ADT1-4-83 2506_02_B10

EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARSWVGYVDVWGQGTLVTVSS

ADT1-4-3 2506_02_C01

EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARTWADYVDVWGQGTLVTVSS

ADT1-4-84 2506_02_C02

EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARTWVGYADVWGQGTLVTVSS

ADT1-4-86 2506_02_C12

EVQLQQSGPGLVKPSQTLSLTCAISGDSVSSKSVAWNWIRQSPSRGLEWLGRTYYRSKWSTDYAASVKSRITINPDTSKNQLSLQLNSVTPEDTAVYYCARTWLGNVDVWGQGTLVTVSS

ADT1-4-95 2506_02_H04

EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARTWVGYADVWGQGTLVTVSS

ADT1-4-1 2501_01_C09

EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARTWVGYADVWGQGTLVTVSS

ADT1-4-6 2506_1_B06

EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARTWAGYFDVWGQGTLVTVSS

ADT1-4-138 2502_01_B03

EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARTWADYVDVWGQGTLVTVSS

FIG. 46B

ADT1-7-10 2503_1_C12

DIQMTQSPSSLSASVGDRVTIACRAGQSIGTYLNWYQQKPGKAPKLLIYVASSLQSGVPSRFSGSGSGTEFTLTISSLQPEDFATYYCQQTASTLLTFGRGTKVEIK

ADT1-7-15 2503_1_F01

DIQMTQSPSSLSASVGDRVTIACRAGQSIGTYLNWYQQKPGKAPKLLIYVASSLQSGVPSRFSGSGSGTEFTLTISSLQPEDFATYYCQQSADTLLTFGRGTKVEIK

ADT1-7-17 2503_1_G05

DIQMTQSPSSLSASVGDRVTIACRAGQSIGTYLNWYQQKPGKAPKLLIYVASSLQSGVPSRFSGSGSGTEFTLTISSLQPEDFATYYCQQSGSELLTFGRGTKVEIK

ADT1-7-18 2503_1_G06

DIQMTQSPSSLSASVGDRVTIACRVGQSIGTYLNWYQQKPGKAPKLLIYVASSLQSGVPSRFSGSGSGTEFTLTISSLQPEDFATYYCQQSASELLTFGRGTKVEIK

ADT1-7-19 2503_1_G10

DIQMTQSPSSLSASVGDRVTIACRAGQSIGTYLNWYQQKPGKAPKLLIYVASSLQSGVPSRFSGSGSGTEFTLTISSLQPEDFATYYCQQSASELLTFGRGTKVEIK

ADT1-7-20 2503_1_H02

DIQMTQSPSSLSASVGDRVTIACRAGQSIGTYLNWYQQKPGKAPKLLIYVASSLQSGVPSRFSGSGSGTEFTLTISSLQPEDFATYYCQQSYSGLDTFGRGTKVEIK

ADT1-7-22 2503_2_A02

DIQMTQSPSSLSASVGDRVTIACRAGQSIGTYLNWYQQKPGKAPKLLIYVASSLQSGVPSRFSGSGSGTEFTLTISSLQPEDFATYYCQQSASELLTFGRGTKVEIK

ADT1-7-23 2503_2_A07

DIQMTQSPSSLSASVGDRVTIACRAGQSIGTYLNWYQQKPGKAPKLLIYVASSLQSGVPSRFSGSGSGTEFTLTISSLQPEDFATYYCQQSYSGLDTFGRGTKVEIK

ADT1-7-42 2503_2_H06

DIQMTQSPSSLSASVGDRVTIACRAGQSIGTYLNWYQQKPGKAPKLLIYVASSLQSGVPSRFSGSGSGTEFTLTISSLQPEDFATYYCQQSSSELLTFGRGTKVEIK

ADT1-7-3 2504_1_A01

DIQMTQSPSSLSASVGDRVTIACRAGQSIGTYLNWYQQKPGKAPKLLIYVASSLQSGVPSRFSGSGSGTEFTLTISSLQPEDFATYYCQQSYSGLDTFGRGTKVEIK

ADT1-7-61 2504_1_F02

DIQMTQSPSSLSASVGDRVTIACRAGQSIGTYLNWYQQKPGKAPKLLIYVASSLQSGVPSRFSGSGSGTEFTLTISSLQPEDFATYYCQQSASELLTFGRGTKVEIK

FIG. 47

ADT1-7-10 2503_1_C12

EVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCARDDYNDAFDIWGQGTLVTVSS

ADT1-7-15 2503_1_F01

EVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCARDDYNDAFDIWGQGTLVTVSS

ADT1-7-17 2503_1_G05

EVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCARIDYEDAFDIWGQGTLVTVSS

ADT1-7-18 2503_1_G06

EVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCARVSYDDAFDIWGQGTLVTVSS

ADT1-7-19 2503_1_G10

EVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCARIDYEDAFDIWGQGTLVTVSS

ADT1-7-20 2503_1_H02

EVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCARVDYQEAFDIWGQGTLVTVSS

ADT1-7-22 2503_2_A02

EVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCARDDYNDAFDIWGQGTLVTVSS

ADT1-7-23 2503_2_A07

EVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCARVDYNEAFDIWGQGTLVTVSS

ADT1-7-42 2503_2_H06

EVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCARDDYEDAFDIWGQGTLVTVSS

ADT1-7-3 2504_1_A01

EVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCARVSYAEAFDIWGQGTLVTVSS

ADT1-7-61 2504_1_F02

EVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCARDDYDDAFDIWGQGTLVTVSS

FIG. 48

Binding to
SK-BR-3 cells
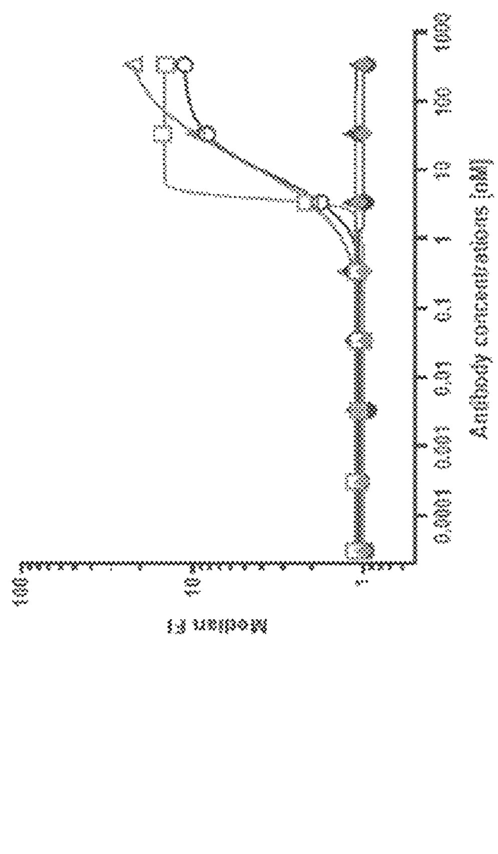
FIG. 51C
Binding to
BT-474 cells
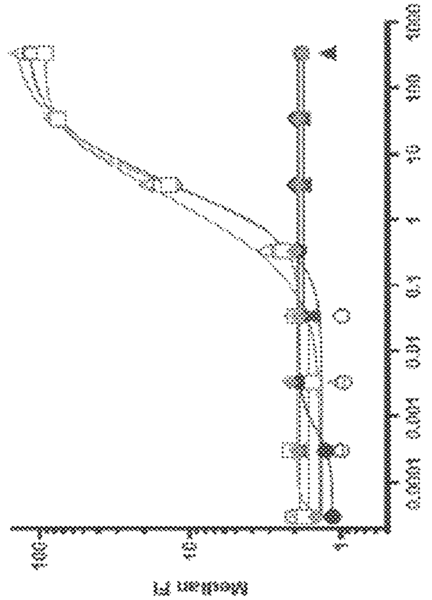
FIG. 51D
Binding to
MDA-MB-231 cells
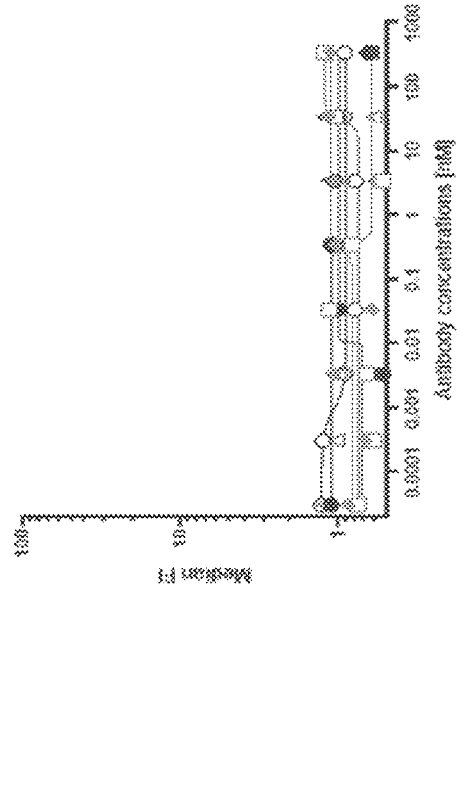
FIG. 51E
Binding to
VS1 γδT cells
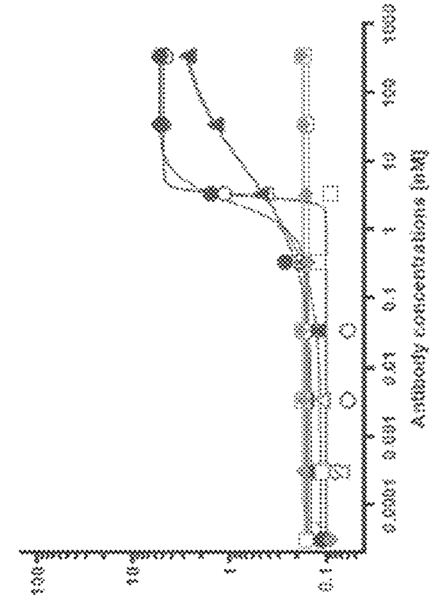
FIG. 51F

Anti-Vδ1

Anti-FAPα

Anti-Vδ1 x anti-FAPα

Anti-Vδ1
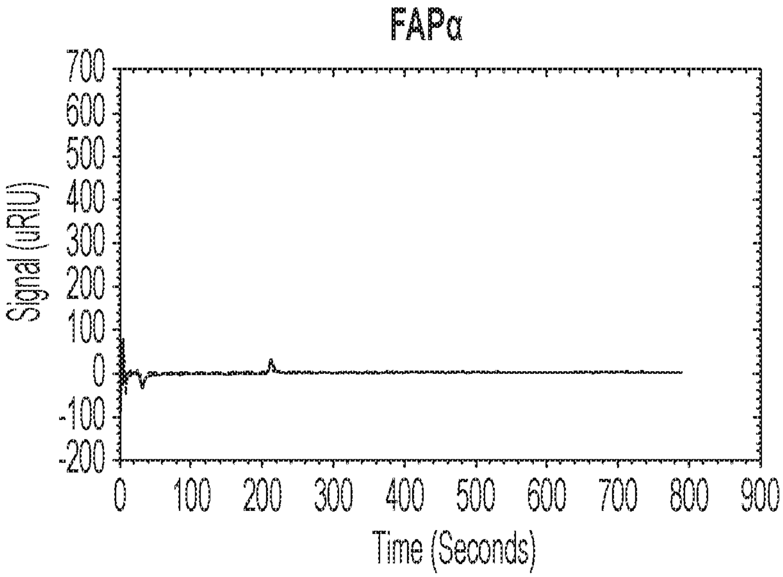
Anti-FAPα
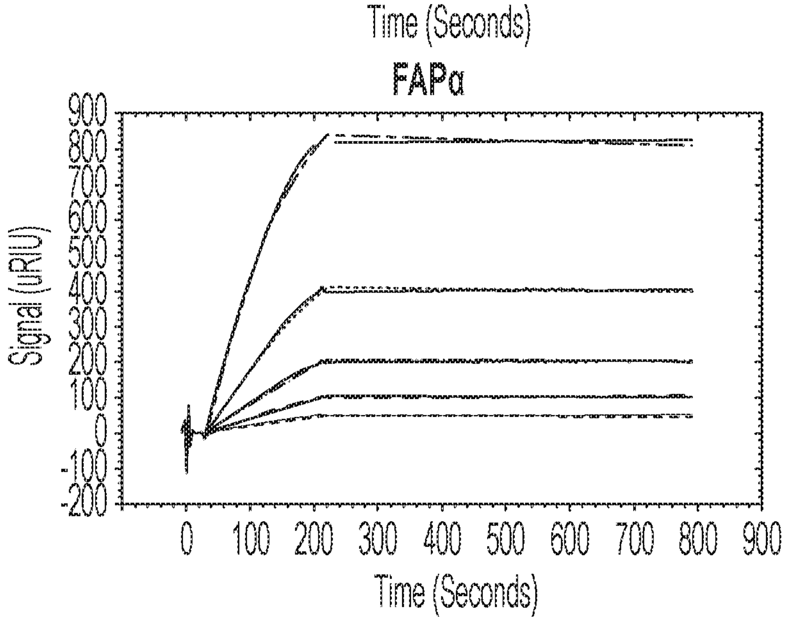
Anti-Vδ1 x anti-FAPα
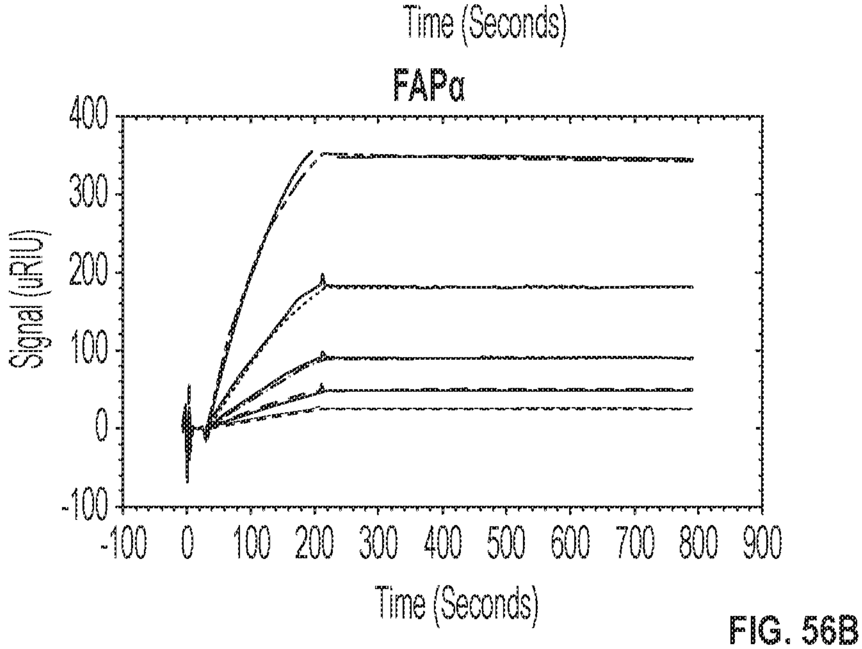
FIG. 56B

ANTI-TCR DELTA VARIABLE 1 ANTIBODIES

RELATED APPLICATIONS

Foreign priority benefits are claimed under 35 U.S.C. § 119 (a)-(d) or 35 U.S.C. § 365 (b) of British application number 2111685.0, filed Aug. 14, 2021 and British application number 2102224.9, filed Feb. 17, 2021. The entire contents of these applications are incorporated herein by reference in their entirety.

FIELD OF THE INVENTION

The present invention relates to antibodies and fragments and variants thereof that specifically bind the T cell receptor of gamma delta T cells.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on Jul. 22, 2022, is named T083370022US00-SUBSEQ-LGE and is 532,554 bytes in size.

BACKGROUND

The growing interest in T cell immunotherapy for cancer has focused on the evident capacity of subsets of CD8+ and CD4+ alpha beta (αβ) T cells to recognize cancer cells and to mediate host-protective functional potentials, particularly when de-repressed by clinically mediated antagonism of inhibitory pathways exerted by PD-1, CTLA-4, and other receptors. However, αβ T cells are MHC-restricted which can lead to graft versus host disease.

Gamma delta T cells (γδ T cells) represent a subset of T cells that express on their surface a distinct, defining γδ T-cell receptor (TCR). This TCR is made up of one gamma (γ) and one delta (δ) chain, each of which undergoes chain rearrangement but have a limited number of V genes as compared to αβ T cells. The main TRGV gene segments encoding Vγ are TRGV2, TRGV3, TRGV4, TRGV5, TRGV8, TRGV9 and TRGV11 and non-functional genes TRGV10, TRGV11, TRGVA and TRGVB. The most frequent TRDV gene segments encode V61, V62, and V63, plus several V segments that have both Vδ and Vα designation (Adams et al., 296:30-40 (2015) *Cell Immunol.*). Human γδ T cells can be broadly classified based on their TCR chains, as certain γ and δ types are found on cells more prevalently, though not exclusively, in one or more tissue types. For example, most blood-resident γδ T cells express a Vδ2 TCR, commonly Vγ9Vδ2, whereas this is less common among tissue-resident γδ T cells such as those in the skin, which more frequently use the Vδ1 TCR paired with gamma chains, for example often paired with Vγ4 in the gut.

γδ T cells play a critical role in immune surveillance, recognising malignant or transformed cells (such as cancer cells) through a pattern of stress markers and then exerting potent and selective cytotoxicity. γδ T cells can therefore act as orchestrators of an immune response. Modulation of these cells in situ provides the potential to increase immunogenicity even in tumours with low mutational load which have proven challenging with other immunotherapies. Recognition of tumours by γδ T cells is not dependent on any single tumour antigen and modulators of γδ T cells therefore have potential in a range of disease indications, including both haematological and solid malignancies. The recognition mechanism of γδ T cells is not MHC restricted.

The authors of WO2019147735 hypothesise that some γδ cells have pro-tumour activity or inhibit the anti-cancer immune response mediated by αβ T cells. The authors postulate that γδ T cells are immunosuppressants and therefore suggest they should be depleted, inhibited or blocked in a cancer setting with the aid of antibodies.

However, despite the prevailing view that that anti-γδ antibodies will negatively modulate γδ cell function by blocking or killing such cells, it has been found that a positive correlation between γδ T cell infiltration and prognosis and/or survival in patients exists.

Compared to αβ TCR receptor/ligand interactions, understanding of vδ1 TCR receptor/ligand interactions are limited. In the absence of such understanding, antibodies which recognize vδ1 TCRs to date are mainly exploratory tools to probe this interaction. Such tools are typically crude, blocking antibodies which suggest TCR receptor/ligand interactions results in blocking, suppression or ablation of vδ1+ cells. For example, tool antibodies TS8.2 and TS-1 are employed as anti-γδ blocking antibodies in studies which suggest said antibodies reduce the cytotoxicity of vδ1 cells. These studies, combined with others, suggest use of such anti-vδ1 antibodies to favourably modulate the cytotoxicity of vδ1 cells in an in situ disease setting is inconceivable and there is therefore the need for antibodies which increase, not reduce, vδ1 cytotoxicity.

To exploit γδ T cells for immunotherapy requires either a means to expand the cells in situ or to harvest them and expand them ex vivo prior to re-infusion. The latter approach has previously been described using the addition of exogenous cytokines, for example see WO2017/072367 and WO2018/212808. Methods for expanding a patients' own γδ T cells has been described using pharmacologically modified forms of hydroxy-methyl but-2-enyl pyrophosphate (HMBPP) or clinically-approved aminobisphosphonates. By these approaches, over 250 cancer patients have been treated, seemingly safely, but with only rare incidences of complete remission. However, there is still a need for activating agents that have the proven capacity to expand large numbers of γδ T cells.

Further, a binding or activating agent capable of preferentially targeting or binding or recognizing or specifically modulating or increasing the numbers of Vδ1+ cells in-situ may be highly desirable as a medicament.

However, whilst medicaments exist that do potentially modulate Vβ2+ cells inclusive of the aminobisphosphonates such as Zometa® (zoledronic acid), said medicines are primarily designed to slow bone reabsorption. And regardless of said Vβ2+ modulation, there is a need to develop medicines specifically designed to bind, target, modulate, activate, or increase the numbers of Vδ1+ cells. This is because, for example, repeat Vβ2+ modulation can result in long-lasting and a progressively exhausted phenotype.

Further, and given the predominate tissue-resident nature of Vδ1+ cells, an ideal medicament capable of modulating Vδ1+ would also exhibit fewer 'off-target' undesirable effects and rapid renal clearance. Typically, said undesirable effects can manifest when employing small-molecule chemicals. For example, the aforementioned aminobisphosphonates shown capable of modulating the separate class of Vβ2+ cells (as a secondary effect versus primary modulating effect on bone) are associated with renal toxicity which manifests as deterioration of renal function and potential renal failure (e.g. Markowitz et al. (2003) Kidney Int.

64(1):281-289). Additional undesirable effects as listed by the European Medicine Agency for Zometa include anemia, hypersensitivity reactions, hypertension, arterial fibrillation, myalgia, general pain, malaise, blood urea increase, vomiting, joint swelling, chest pain, etc.

Further consideration must also be given to the in situ milieu in which vδ1+ cells find themselves. For example, it has previously been shown that non-haematopoietic, tissue-resident γδ T cells showed a strong proliferative response when first separated from tissue but only if they were not in direct cellular contact with autologous fibroblasts. It is found that the non-haematopoietic tissue-resident T cells (γδ T cells) must be separated from the non-haematopoietic cells, (e.g. stromal cells, particularly fibroblasts) in order to function. This is because direct contact of the lymphocytes with stromal or epithelial cells appears to inhibit expansion of tissue-resident γδ T cells. The observation that the pre-activated cells in situ exist in a further suppressed state is another reason vδ1 cells have not been considered a promising therapeutic target to date, Indeed, until the discoveries described herein it has not been conceived how one could favourably and selectively modulate these cells in situ, where blood and tissue vδ1+ cells are typically considered 'resting', 'pre-activated' or 'non-activated'.

Various formats of bispecific and multispecific antibodies have been developed for a variety of therapeutic uses. Bi- and multispecific antibodies can be divided into separate, although overlapping, classes based on the types of biological targets and modes of action. For example, such multispecific antibodies can be divided into classes such as cytotoxic effector cell redirectors (also known as bispecific, T-cell-recruiting antibodies, bispecific T-cell engagers, TCEs, or BiTEs) and dual immunomodulators (DIs).

TCEs (T-cell engagers) are intended to enhance the patient's immune response to tumours by targeting T cells to tumour cells or vice versa, and work by targeting a first epitope of a T-cell receptor complex of a T-cell (usually CD3) and a second epitope, which is a cancer antigen or a cancer-associated antigen, such as a tumour associated antigen (TAA). Such antibodies colocalize tumour cells and T-cells to promote tumour cell killing. Examples of BiTEs include the CD3×CD19 bispecific antibody blinatumomab, the CD3×EpCAM bispecific antibody catumaxomab, and the CD3×HER2 bispecific antibody ertumaxomab. TCEs such as BiTEs are generally provided in an scFv format, although other formats have been provided. For example, BiKEs are similar to BiTEs, but they target CD16 on NK cells, rather than CD3.

The 'T-cell receptor has been described as the most intricate receptor structure of the mammalian immune system. It comprises a transmembrane multi-protein receptor complex comprises a T-cell receptor in close proximity to a number of CD3 chains. For example, in mammals, a typical such complex comprises a T-cell receptor, a CD3γ chain, a, CD3δ chain, and two CD3ε chains. These chains associate with the T-cell receptor (TCR) alongside ζ-chain (zeta-chain) which combined then generate typical activation signals in T lymphocytes. However alternative complexes have also been reported. For example, T-cell receptor complexes comprising a T-cell receptor and a zeta chain homodimer have been described. Additional co-receptors such as CD4 and CD8 can also aid TCR function.

Regardless of receptor complex composition, it is well established that said complexes translate cell surface binding events to intracellular phosphorylation signalling cascade. These phosphorylation events culminate in the activation of transcription factors such as NFAT and NFkB that lead to increased expression of cytokines and effector proteins such as granzymes and perforin.

However, whilst the use of such TCEs to treat cancer remain a compelling concept, to date and even after 30 years of concerted efforts to advance TCEs in early clinical development, many of such bispecific antibodies have exhibited lacklustre safety, efficacy and manufacturability profiles. Indeed, as of January 2020, blinatumomab remains the only approved TCE not then withdrawn. This TCE multispecific antibody fragment binds the T-cell receptor complex on a first binding arm and a CD19 target on a second binding arm.

Bispecific, T-cell-recruiting antibodies are discussed in Lejeune et al., 2020, Front Immunol., 11:762. However, the existing bispecific antibodies in this category, in particular those that recruit T-cells via CD3 binding, have significant off-target effects that result in severe adverse effects, given the potency of the CD3 antigen as signal transducer and its ubiquity in a patient's T-cell population. Hence for CD3 targeting bispecific examples such as Catumaxomab (now withdrawn), systemic delivery (e.g. intravenous) is not a realistic possibility. Instead, more contained delivery such as intra-operative, intra-peritoneal, intra-abdominal etc. is more often contemplated. This thereby limits optionality and use of said bispecifics as medicaments. Indeed, even for effector-attenuated anti-CD3 antibodies (i.e. a CD3 targeting T-cell complex engager but not a bispecific), the associated toxicity makes I.V. delivery challenging. For example, to limit exposure and reduce toxicity, the anti-CD3 antibody Foralumab is now most often being contemplated for oral delivery (e.g. in treatment of gut disease).

It is often stated that many of the current setbacks observed with such TCEs in early clinical trials are due to the high-affinity T-cell complex binding domains employed. Further, it has been proposed that this is because those designing these TCEs had not given due consideration to the low affinity of natural TCR-complex binding events they were hampered by severe dose-limiting toxicities resulting in prohibitively narrow therapeutic windows. Related to this it has been highlighted that many early TCE drug developers relied on three anti-CD3 T-cell complex binding domains derived from OKT3, SP34, and UCHT1. And these original binding domains all bind with a relatively high affinity in the single to low double-digit nM range equating to roughly to 1,000-fold higher affinity than a natural binding event. In turn it has been proposed that this can result in profoundly different (and often unfavourable) effects on the activation of T-cells compared to natural binding of the T-cell receptor complex. For example, TCE developers using platforms based on the higher affinity OKT3 may be confounded by the fact the OKT3 is apoptotic to T-cells in the presence of IL-2.

For these reasons it has become apparent that lower affinity T-cell complex binding is an important consideration for determining the design parameters of T-cell engaging bispecific antibody therapeutics.

Another issue when designing said TCEs, is the need to attenuate Fc function. Indeed, typically TCEs require the complete suppression of the Fc-mediated effector functions in order to maximize therapeutic efficacy and to minimize off-target toxicity because binding of Fc to Fc gamma receptor (FcγR) leads to activation of immune effector cells. In reality, the majority of the CD3-targeting bispecific antibodies currently in clinical practice have Fc domains with reduced binding activity to FcγR or are bispecific fragments intentionally without the Fc region. It would generally be expected that a TCE with unattenuated Fc function would induce an antibody-dependent cell-mediated cytotoxicity (ADCC) effect and thereby deplete the population of γδ T-cells recognized by the antibody. However, and again, by attenuating such functionality to avoid toxicity/safety complexities, one may also attenuate a potentially important efficacy angle too e.g. by engaging CD16+ or CD32+ or CD64+ immune cells, or by reducing half-life of the bispecific (e.g. if employing smaller bispecific antibody fragments such as BITEs). Methods of reducing the interaction of the FcγR and the TCE (such as using an IgG format designed to reduce said interaction) would be expected to reduce Fc-mediated immobilization of the TCE and reduce TCR clustering by cross-linking with the immobilized TCE.

To address some but not all of these complications, many companies such as Xencor (Pasadena, CA), Macrogenics (Gaithersburg, MD) and Genentech (San Francisco, CA) have more recently reported reducing the binding affinity of the T-cell receptor complex binding arms in their respective TCE platforms. However, reducing the affinities of said binding may result in less effective efficacy and less optionality in terms of TCE design and functionality. For example, it is now demonstrated that affinity of the binding domains in such TCEs drives distribution profile in vivo. Specifically, it is typically observed that TCE distribution is biased towards its highest affinity target. Hence, by reducing the affinity of a TCE binding domain to the T-cell complex, it is typical to then bias distribution away from T-cells; the very cells needed to drive efficacy of such TCEs. It is partly for such reasons that TCE therapeutic windows have been termed 'prohibitively narrow'.

Further, and in particular for solid-tumours, significant extra hurdles still exist for immunomodulatory therapeutics. For example, current state-of-the-art approaches include CD3-targeting bispecifics wherein a first domain binds CD3 and a second domain targets a TAA. However often these prove problematic. For example, Middelburg J, et al. Overcoming Challenges for CD3-Bispecific Antibody Therapy in Solid Tumors. Cancers. 2021; 13(2):287 summarize some of these hurdles in solid tumour space for such multispecific, T-cell engaging, immunomodulatory moieties inclusive of;

i. on-target, off-tumor toxicity issues—for example the authors highlight that solid tumor TAAs are often also expressed on tissues of healthy organs, which can in turn lead to immune pathology and organ failure with potential fatality, as shown in a preclinical mouse study using a CD3-bispecific.

ii. the availability of effector cells in the tumor microenvironment (TME)—for example, conventional CD3+ 'naïve' T-cells exist primarily in the blood and lymph system without any additional dendritic cell mediated activation.

iii. the quality of the tumour infiltrating lymphocytes (TILs) given these can include CD3+ Tregs and/or exhausted CD3+ cells—for example, CD3-targeting bispecifics may induce TIL apoptosis via activation-induced cell death, which hampers a strong anti-tumor response.

Hence there is need for improved multispecific immunomodulatory medicaments wherein at least one binding domain binds a T-cell and at least one second binding domain targets a TAA.

There is also a need for improved medicaments specifically designed to target Vδ1+ cells and for the treatment of infections, autoimmune conditions, and cancer. Specifically, there is a need for medicaments that can be administered to ameliorate signs and symptoms of disease by specifically binding Vδ1+ cells, targeting Vδ1+ cells, specifically activating Vδ1+ cells, specifically enhancing proliferation and/or cytotoxicity activity Vδ1+ cells, or specifically blocking activation of Vδ1+ cells.

SUMMARY OF THE INVENTION

The present invention provides high-affinity anti-TCR delta variable 1 (anti-Vδ1) antibodies and antibody fragments thereof. The antibodies of the present invention have an advantageous functional profile. In particular, unlike anti-Vδ1 antibodies of the prior art which focus on depletion of Vδ1 T-cells, the antibodies of the present invention are useful for the activation of Vδ1 T-cells. Although they may cause downregulation of the TCRs on T-cells to which they bind, they do not cause Vδ1 T-cell depletion, but rather they stimulate the T-cells and hence may be useful in therapeutic settings that would benefit from the activation of this compartment of T-cells. Activation of Vδ1 T-cells is evident through TCR downregulation, changes in activation markers such as CD25, Ki67, degranulation marker CD107a, NCRs (natural cytotoxicity receptors) and/or 4-1BB. Activation of Vδ1 T-cell in turn triggers release of inflammatory cytokines such as INFγ and TNFα to promote immune licensing. Surprisingly, antibodies having suitably high affinity for TRDV1 elicit increased Vδ1 T-cell killing and, unlike (for example) antibodies that target CD3, the provision of high affinity antibodies is possible without adverse effects associated with large-scale activation via CD3. In turn, the high affinity antibodies are able to induce strong immunostimulatory effects via tumour-infiltrating lymphocytes (TILs). This can be achieved with minimal exhaustion or killing of the Vδ1 cells. Therefore, the antibodies of the invention may be considered agonistic antibodies.

According to a first aspect of the invention, there is provided an anti-TCR delta variable 1 (anti-Vδ1) antibody or antigen-binding fragment thereof comprising:

a VHCDR3 comprising an amino acid sequence having at least 80% sequence identity to any one of SEQ ID NOs: 55 to 78; and/or a VLCDR3 comprising an amino acid sequence having at least 80% sequence identity to any one of SEQ ID NOs: 82 to 105 or comprising:

a VHCDR3 comprising an amino acid sequence having at least 80% sequence identity to any one of SEQ ID NOs: 133 to 143; and/or a VLCDR3 comprising an amino acid sequence having at least 80% sequence identity to any one of SEQ ID NOs: 147 to 157.

According to a second aspect of the invention, there is provided an anti-TCR delta variable 1 (anti-Vδ1) antibody or antigen-binding fragment thereof comprising:

an HCDR1 sequence comprising the sequence of GDSVSSKS$X_1$A (SEQ ID NO: 158);

an HCDR2 sequence comprising the sequence of SEQ ID NO: 53;

an HCDR3 sequence comprising the sequence of $X_2WX_3X_4X_5X_6DX_7$ (SEQ ID NO: 162), wherein the HCDR3 sequence is not SEQ ID NO: 54;

an LCDR1 sequence comprising the sequence of SEQ ID NO: 79;

an LCDR2 sequence comprising the sequence of SEQ ID NO: 80; and an LCDR3 sequence comprising the sequence of $QQX_8YX_9X_{10}X_{11}X_{12}X_{13}T$ (SEQ ID NO: 166), wherein the LCDR3 sequence is not SEQ ID NO: 81;

wherein each of $X_1$ to $X_{13}$ is a naturally occurring amino acid;

or an anti-TCR delta variable 1 (anti-Vδ1) antibody or antigen-binding fragment thereof comprising:

an HCDR1 sequence comprising the sequence of SEQ ID NO: 130 an HCDR2 sequence comprising the sequence of SEQ ID NO: 131 an HCDR3 sequence comprising the sequence of $X_1X_2YX_3X_4$AFDI (SEQ ID NO: 183), wherein the HCDR3 sequence is not SEQ ID NO: 132;

an LCDR1 sequence comprising the sequence of SEQ ID NO: 144;

an LCDR2 sequence comprising the sequence of SEQ ID NO: 145; and an LCDR3 sequence comprising the sequence of $QQX_5X_6X_7X_8LX_9T$ (SEQ ID NO: 186), wherein the LCDR3 sequence is not SEQ ID NO: 146;

wherein each of $X_1$ to $X_9$ is a naturally occurring amino acid.

In a third aspect of the invention there is provided an anti-TCR delta variable 1 (anti-Vδ1) antibody or antigen-binding fragment thereof, wherein the anti-Vδ1 antibody or antigen-binding fragment thereof is an affinity matured variant of a parent anti-Vδ1 antibody or antigen-binding fragment thereof, wherein the parent anti-Vδ1 antibody or antigen-binding fragment thereof comprises a VH comprising the amino acid sequence of SEQ ID NO: 1 and a VL sequence comprising the amino acid sequence of SEQ ID NO: 26, or wherein the parent anti-Vδ1 antibody or antigen-binding fragment thereof comprises a VH comprising the amino acid sequence of SEQ ID NO: 106 and a VL sequence comprising the amino acid sequence of SEQ ID NO: 118. Optionally, in any affinity matured variant, the first residue of the VH sequence may be Q or E. Optionally, in any affinity matured variant, the first two residues of the VL sequence may be absent in any affinity matured variant, compared to the parental sequence.

In a fourth aspect of the invention there is provided an anti-TCR delta variable 1 (anti-Vδ1) antibody or antigen-binding fragment thereof, wherein the anti-Vδ1 antibody or antigen-binding fragment thereof is an affinity matured variant of a parent anti-Vδ1 antibody or antigen-binding fragment thereof, wherein the parent anti-Vδ1 antibody or antigen-binding fragment thereof comprises:

a) a VH comprising the amino acid sequence of SEQ ID NO: 273 and a VL comprising the amino acid sequence of SEQ ID NO: 282;

b) a VH comprising the amino acid sequence of SEQ ID NO: 274 and a VL comprising the amino acid sequence of SEQ ID NO: 283;

c) a VH comprising the amino acid sequence of SEQ ID NO: 275 and a VL comprising the amino acid sequence of SEQ ID NO: 284;

d) a VH comprising the amino acid sequence of SEQ ID NO: 276 and a VL comprising the amino acid sequence of SEQ ID NO: 285;

e) a VH comprising the amino acid sequence of SEQ ID NO: 277 and a VL comprising the amino acid sequence of SEQ ID NO: 286;

f) a VH comprising the amino acid sequence of SEQ ID NO: 278 and a VL comprising the amino acid sequence of SEQ ID NO: 287;

g) a VH comprising the amino acid sequence of SEQ ID NO: 279 and a VL comprising the amino acid sequence of SEQ ID NO: 288;

h) a VH comprising the amino acid sequence of SEQ ID NO: 280 and a VL comprising the amino acid sequence of SEQ ID NO: 289;

i) a VH comprising the amino acid sequence of SEQ ID NO: 281 and a VL comprising the amino acid sequence of SEQ ID NO: 290; or j) a VH comprising the amino acid sequence of SEQ ID NO: 312 and a VL comprising the amino acid sequence of SEQ ID NO: 313.

In a fifth aspect of the invention there is provided an anti-TCR delta variable 1 (anti-Vδ1) antibody or antigen-binding fragment thereof comprising a kappa light chain variable sequence, in which the residue at position 74 of the kappa light chain variable sequence according to the IMGT numbering system is not serine. In some embodiments, the serine may be substituted with a non-human-germline amino acid at position 74. In some embodiments, the substitution may be a non-conservative mutation, for example to substitute the serine to a non-polar amino acid. In some embodiments, the serine may be substituted with a leucine.

In a sixth aspect of the invention there is provided an anti-TCR delta variable 1 (anti-Vδ1) antibody or antigen-binding fragment thereof that specifically binds to a variable delta 1 (Vδ1) chain of a γδ T cell receptor (TCR) and competes with binding to the variable delta 1 (Vδ1) chain of a γδ T cell receptor (TCR) with an antibody or antigen-binding fragment thereof of any of the first to fifth aspects of the invention.

In a seventh aspect of the invention, there is provided a polynucleotide sequence encoding an anti-Vδ1 antibody or antigen-binding fragment thereof of the invention. For example, there is provided a polynucleotide sequence encoding the anti-Vδ1 antibody or antibody binding fragment thereof comprising a sequence having at least 70% sequence identity with SEQ ID NO: 199 to 222, 224 to 247, 249 to 259 or 261 to 271.

In an eighth aspect of the invention, there is provided an expression vector comprising the polynucleotide sequence of the invention. There is also provided a host cell comprising a polynucleotide sequence of the invention or an expression vector of the invention. There is also provided a method for producing any antibody or antigen-binding fragment thereof of the invention, comprising culturing a host cell of the invention in a cell culture medium.

In a further aspect of the invention, there is provided a composition comprising an antibody or antibody binding fragment thereof of the invention. There is also provided a pharmaceutical composition comprising an antibody or antibody binding fragment thereof of the invention and a pharmaceutically acceptable diluent or carrier. Composition and pharmaceutical compositions may optionally further comprise one or more additional therapeutically active agents.

In a further aspect of the invention, there is provided a kit comprising an anti-Vδ1 antibody or antibody binding fragment of the invention or a pharmaceutical composition of the invention, optionally comprising instructions for use and/or an additional therapeutically active agent.

In a further aspect of the invention there is provided a method of treating a disease or disorder in a subject, comprising administering to the subject an anti-Vδ1 antibody or antibody binding fragment of the invention, or a pharmaceutical composition of the invention. There is also provided a method of modulating an immune response in a subject, comprising administering to the subject an anti-Vδ1 antibody or antibody binding fragment of the invention, or a pharmaceutical composition of the invention. Administration of antibodies to a subject may be administration in a therapeutically effective amount.

In a still further aspect of the invention, there is provided a method of mutating an antibody or antigen-binding fragment thereof, comprising providing an antibody comprising a kappa light chain having a serine at position 74 according to the IMGT numbering system, and substituting (e.g. mutating) the serine to a different amino acid. In some embodiments, the serine may be substituted with a non-human-germline amino acid at position 74. In some embodiments, the substitution may be a non-conservative mutation, for example to substitute the serine to a non-polar amino acid. In some embodiments, the serine may be substituted with a leucine.

In a further aspect of the invention there is provided a method of preparing a variant anti-TCR delta variable 1 (anti-Vδ1) antibody or antigen-binding fragment thereof comprising providing a parental antibody comprising:

a) a VH comprising the amino acid sequence of SEQ ID NO: 1 and a VL comprising the amino acid sequence of SEQ ID NO: 26;
b) a VH comprising the amino acid sequence of SEQ ID NO: 106 and a VL comprising the amino acid sequence of SEQ ID NO: 118;
c) a VH comprising the amino acid sequence of SEQ ID NO: 273 and a VL comprising the amino acid sequence of SEQ ID NO: 282;
d) a VH comprising the amino acid sequence of SEQ ID NO: 274 and a VL comprising the amino acid sequence of SEQ ID NO: 283;
e) a VH comprising the amino acid sequence of SEQ ID NO: 275 and a VL comprising the amino acid sequence of SEQ ID NO: 284;
f) a VH comprising the amino acid sequence of SEQ ID NO: 276 and a VL comprising the amino acid sequence of SEQ ID NO: 285;
g) a VH comprising the amino acid sequence of SEQ ID NO: 277 and a VL comprising the amino acid sequence of SEQ ID NO: 286;
h) a VH comprising the amino acid sequence of SEQ ID NO: 278 and a VL comprising the amino acid sequence of SEQ ID NO: 287;
i) a VH comprising the amino acid sequence of SEQ ID NO: 279 and a VL comprising the amino acid sequence of SEQ ID NO: 288;
j) a VH comprising the amino acid sequence of SEQ ID NO: 280 and a VL comprising the amino acid sequence of SEQ ID NO: 289;
k) a VH comprising the amino acid sequence of SEQ ID NO: 281 and a VL comprising the amino acid sequence of SEQ ID NO: 290; or
l) a VH comprising the amino acid sequence of SEQ ID NO: 312 and a VL comprising the amino acid sequence of SEQ ID NO: 313;

and subjecting the antibody to affinity maturation, wherein the antibody produced has a greater affinity to a variable delta 1 (Vδ1) chain of a γδ T cell receptor (TCR) than the parental antibody In a further aspect of the invention, there is provided a method of preparing a pharmaceutical composition comprising providing an antibody prepared according to a method of preparing a variant anti-TCR delta variable 1 (anti-Vδ1) antibody or antigen-binding fragment of the invention and co-formulating the antibody with at least one or more pharmaceutically acceptable diluents or carriers.

In a still further aspect of the invention, there is provided an anti-TCR delta variable 1 (anti-Vδ1) antibody or antigen-binding fragment thereof of the invention, or a pharmaceutical composition of the invention, or a kit of the invention, for use in medicine. There is also provided the use of an anti-TCR delta variable 1 (anti-Vδ1) antibody or antigen-binding fragment thereof of the invention in the manufacture of a medicament.

BRIEF DESCRIPTION OF THE FIGURES

(FIG. 2A) Heterodimer selections: heterodimeric LZ TCR format in round 1 and 2, with deselections on heterodimeric LZ TCR in both rounds. (FIG. 2B) Homodimer selections: round 1 performed using homodimeric Fc fusion TCR with deselection on human IgG1 Fc followed by round 2 on heterodimeric LZ TCR with deselection on heterodimeric LZ TCR. Each graph contains two bars for each target to represent selections from different libraries.

(FIG. 17A) The levels of TNF-alpha observed (FIG. 17B) The levels of IFN-gamma observed.

(FIG. 19A) The number of viable pan-γδ+ cells. (FIG. 19B) The number of viable Vδ1+ cells. (FIG. 19C) The percentage of viable, double-positive Vδ1+CD25+ cells.

(FIG. 20B) Total numbers of TIL Vδ1+ cells. (FIG. 20C) Example gating strategy (FIG. 20D) Comparative cell-surface phenotypic profile of TIL Vδ1+ cells. (FIG. 20E) Analysis of the TIL Vol-negative gated fraction.

FIGS. 21A-21D: Anti-Vδ1 antibody conferred enhancement of Vδ1+ mediated cytotoxicity, and diseased-cell-specific cytotoxicity. Cytotoxicity/potency-assays in model systems comprising a triculture of Vδ1+ effector cells, THP-1 monocytic cancer cells, and non-diseased, healthy primary monocytes. (FIG. 21A) Quantification of THP-1 and monocyte cell numbers in triple co-culture with γδ T-cells in the presence of anti-Vδ1 mAbs or controls. (FIG. 21B) A bar chart representation highlighting the window between diseased-cell specific killing and non-diseased healthy: Left-hand bar chart; fold-increase in killing of diseased-cells (THP-1) versus killing of non-diseased cells (primary human monocytes); Right-hand bar chart; same data but represented as percent-enhanced killing versus controls (FIG. 21C) Tabulated results summarizing the percent improvement in potency of Vδ1+ effector cell killing of THP-1 target cells+/−mAbs. (FIG. 21D) Tabulated results of EC50 values as calculated from Figure (FIG. 21A) represented as γδ T-cell numbers required to confer 50% THP-1 cell killing.

FIGS. 22A-22J: Multi-specific antibody conferred enhancement of Vδ1+ effector cell mediated cytotoxicity. The targeting of a tissue-centric disease associated antigen: (FIGS. 22A-22D) Example co-culture of Vδ1+ effector cells with A-431 cancer cells+/−multi-specific antibodies comprising anti-Vδ1×anti-TAA (EGFR) bispecific binding moieties wherein the anti-Vδ1 VL+VH binding domain (to the first target) is combined with the CH1-CH2-CH3 domain of an anti-EGFR binding moiety (to the second target). (FIGS. 22E-22H) Example co-culture of Vδ1+ effector cells with A-431 cancer cells+/−multi-specific antibodies comprising anti-Vδ1×anti-TAA (EGFR) bispecific binding moieties wherein the anti-Vδ1 binding domain (to the first target) comprises a full-length antibody (VH-CH1-CH2-CH3/VL-CL) then combined with an anti-EGFR cetuximab-derived scFv binding moiety (to the second target). (FIGS. 22I-22J) Alternative approach to representing the data: Percentage improvement conferred by multi-specific antibodies upon Vδ1+ effector cell cytotoxicity towards EGFR+ cells relative to component parts.

FIGS. 23A-23B: Multi-specific antibody conferred enhancement of Vδ1+ mediated cytotoxicity and diseased-cell-specific cytotoxicity. The targeting of a hemopoietic disease associated antigen (FIG. 23A) E:T ratios required to induce 50% Raji cell killing (FIG. 23B) Percentage improvement with addition of a Vδ1-CD19 multi-specific antibodies (FIG. 24A) Phage selections round 1 to 3 for the ADT1-7 library. (FIG. 24B) Phage selections Round 1 to 3 for the ADT1-4 library. (FIG. 24C) Phage selections Round 1 to 3 for the ADT1-4 library with a selection strategy for isolating cyno cross-reactive binders.

(FIG. 25A) Schematics of the flow sorting of ADT1-7 library. (FIG. 25B) Schematics of the flow sorting of ADT1-4 library 1 (human). (FIG. 25C) Schematics of the flow sorting of ADT1-4 library 2 (cyno).

FIGS. 26A-26F: Impact of kappa chain S74L change on affinity. (FIG. 26A) ADT1-4 Lineage Mammalian Display Outputs: Human Dissociation off-rate (SPR) vs Human Antigen binding (Delfia ELISA, 0.4 nM Human Antigen) with LC 74S (open circle) or 74L (filled circle) usage indicated. Results highlight good fit between improved affinity by SPR and by antigen binding by Delfia ELISA. These results also highlight the improved binding conferred by variable domain S74L modification. (FIG. 26B) ADT1-4 Lineage Mammalian Display Outputs: Cyno Dissociation Off-Rate (SPR) vs Cyno Antigen Binding (Delfia ELISA, 10 nM Cyno Antigen) with LC 74S (open circle) or 74L (filled circle) usage indicated. (FIG. 26C) ADT1-4 Lineage Mammalian Display Outputs: Correlation between Human Antigen Dissociation Off-Rate (SPR) improvements vs Cyno Antigen Dissociation Off-Rates (SPR) plus LC 74S (open circle) or 74L (filled circle) usage indicated. (FIGS. 26D-26F) Further confirmation of the effect of S74 versus L74 on ADT1-4 lineage affinity. The starting serine at kappa chain position 74 in the lower affinity parent ADT1-4 was mutated to a leucine to create kappa chain SEQ ID No: 504. This modified light chain was paired with starting ADT1-4 VH (SEQ ID NO:1) to create a new molecule "ADT1-4 (574L)" as indicated. The starting leucine at kappa chain position 74 of the high affinity ADT1-4-2 was reverted to serine to create kappa chain SEQ ID NO: 505. This was paired with ADT1-4-2 VH (SEQ ID NO: 15) to create a new molecule "ADT1-4-2 (L74S)". Affinity of these molecules (versus starting molecules ADT1-4 and ADT1-4-2 respectively) was determined by SPR analysis using a Reichert 4SPR instrument (Reichert Technologies). Antibodies (1.5 ug/mL) were coated onto a Planar Protein A Sensor Chip (Reichert Technologies) to give an increase on baseline of approximately 500 uRIU. Recombinant human or cynomolgus Vδ1 heterodimer was flown over the cell at a concentration of 100 nM, 50 nM, 25 nM, 12.5 nM, 6.25 nM with the following parameters: 180 s association, 480 s dissociation, flowrate 25 μL/min, running buffer PBS+0.05% Tween 20. All experiments were performed at room temperature: (D i FIGS. 26D-26E) Resulting SPR traces depicting affinity of the antibodies as indicated to human and cyno Vδ1 antigen (D ii FIG. 26F) A tabulated summary of the results.

(FIG. 27A) Example heavy chain and light chain cross-sharing between affinity matured antibodies in ADT1-4 (G04) lineage (0.4 nM Human TRDV1 ELISA results heat-map graded). This "heat map" demonstrates the cross-sharing of CDR3 sequences between different affinity matured antibodies in the ADT1-4 lineage, showing the affinity maturation process provided antibody sequences that do not have to be provided as specific heavy and light chain pairs. The results highlight the affinity matured antibodies can cross-share light chains and heavy chains and that differing LC/HC combinations generate equivalent or improved outcomes in a high-stringency antigen binding study. Also included in the figure is the ADT1-4 (G04) parent clone, (bottom left). (FIG. 27B) ADT1-4 Lineage Final Selection: CDR3 usage and cross-sharing+Cyno Antigen Binding 'Heat Map' versus starting parent ADT1-4 parent G04 mAb (bottom left). (FIG. 27C) ADT1-7 Lineage Final Selection: CDR3 usage and cross-sharing+Human Antigen Binding 'Heat Map' versus starting ADT1-7 parent E07 mAb (bottom left).

(FIG. 28A) Fold enhancement in recombinant human Vδ1 antigen binding. (FIG. 28B) Fold enhancement in recombinant cyno Vδ1 antigen binding. (FIG. 28C) Fold enhancement in primary Vδ1 MFI. (FIG. 28D) Fold enhancement in PEER Vδ1 cell line MFI.

(FIG. 29A). Fold enhancement in recombinant human Vδ1 antigen binding. (FIG. 29B). Fold enhancement in primary Vδ1 MFI. (FIG. 29C). Fold enhancement in PEER Vδ1 cell line MFI.

(FIG. 30A) Fold improvement in binding to human antigen. DELFIA ELISA signal of affinity matured clones vs parent ADT1-4 (G04), 0.4 nM of recombinant human L1 antigen (containing human Vδ1 TCR antigen). (FIG. 30B) Fold improvement in binding to cyno antigen (DV1/GV77 containing Cyno SEQ ID NO: 308 (mature, minus leader)). DELFIA ELISA signal of affinity matured clones vs parent ADT1-4 (G04), 0.4 nM of recombinant human L1 antigen. (FIG. 30C) Fold improvement in binding to human antigen. DELFIA ELISA signal of affinity matured clones vs parent ADT1-7 (E07), 0.4 nM of recombinant human L1 antigen.

(FIG. 31A) Fold improvement in human antigen KD for ADT1-4 (G04) lineage. (FIG. 31B) Fold improvement in cyno antigen KD for ADT1-4 (G04) lineage. (FIG. 31C) Fold improvement in human antigen KD for ADT1-7 (E07) lineage.

FIGS. 32A-32F. Binding affinity analysis (KD by SPR) to human Vδ1 antigen. (FIG. 32A) Surface plasmon resonance for ADT1-4 lineage. (FIG. 32B) Surface plasmon resonance for ADT1-7 lineage. (FIG. 32C) KD values and fold change against parental clone for ADT1-4 lineage. (FIG. 32D) KD values and fold change against parental clone for ADT1-7 lineage. (FIG. 32E) Fold change of KD against parental clone for ADT1-4 lineage. (FIG. 32F) Fold change of KD against parental clone for ADT1-7 lineage.

FIGS. 33A-33D. Binding affinity analysis (KD by SPR) to cyno antigen. (FIG. 33A-33C) Surface plasmon resonance for ADT1-4 lineage for cyno antigen. (FIG. 33D) KD values for ADT1-4 lineage for cyno antigen.

FIGS. 34A-34D. Binding Affinity to cell surface Vδ1 TCR (EC50 for binding to cell surface Vδ1). (FIGS. 34A-34B) The level of binding by the Vδ1 mAbs to two γδ T cell donors, ATS006 (FIG. 34A) and TS164 (FIG. 34B). (FIG. 34C) Bar chart representing the average 50% binding values from the ADT1-4 and ADT1-7 clones binding to Vδ1-positive γδ T cell, represented as the mean two donors, with these values provided in tables with % improvement. (FIG. 34D) Table summarizing the IC50s plotted in (FIG. 34A) & (FIG. 34B), and Vδ1-negative cell types including HEK293A, Raji cells and various leukocyte subsets with primary blood mononuclear cells. For Vδ1-positive γδ T cell, data is represented as the mean two donors.

FIGS. 35A-35G. TCR downregulation (with soluble antibodies). (FIGS. 35A-35B) ADT1-4 lineage (FIG. 35A) and ADT1-7 lineage (FIG. 35B). (FIG. 35C) Average TCR downregulation—IC50 results from two GD cell donors. (FIGS. 35D-35E) Fold TCR downregulation improved from the parental ADT1-4 clone (FIG. 35D) and the ADT1-7 clone (FIG. 35E). (FIG. 35F) 50% effect values from (C), with the percentage improvement calculated from the respective parents of ADT1-4 (upper) and ADT1-7 (lower). (FIG. 35G) 50% effect values from (FIG. 35C) with the fold improvement calculated from the respective parents of ADT1-4 (upper) and ADT1-7 (lower).

FIG. 36A-36F. Vδ1 monoclonal antibodies on γδ activation measured by CD107a expression. (FIGS. 36A-36B) ADT1-4-2 clone in cells GD cells alone (FIG. 36A) or with THP-1 cells (FIG. 36B). (FIGS. 36C-36D) ADT1-7-3 clone in cells GD cells alone (FIG. 36C) or with THP-1 cells (FIG. 36D). (FIG. 36E) Table representing the percentage increase in γδ CD107a expression from cocultured cells treated with the highest concentration of Vδ1 mAb compared to untreated non-cocultured γδ cells. (FIG. 36F) Table representing the percentage increase in γδ CD107a expression from cocultured cells treated with the highest concentration of Vδ1 mAb compared to untreated, co- and non-cocultured γδ cells.

FIGS. 37A-37F. Vδ1 monoclonal antibodies on γδ activation measured by CD25 expression. (FIGS. 37A-37B) ADT1-4-2 clone in cells GD cells alone (FIG. 37A) or with THP-1 cells (FIG. 37B). (FIGS. 37C-37D) ADT1-7-3 clone in cells GD cells alone (FIG. 37C) or with THP-1 cells (FIG. 37D). (FIG. 37E) Table representing the percentage increase in γδ CD25 expression from cocultured cells treated with the highest concentration of Vδ1 mAb compared to untreated non-cocultured γδ cells. (FIG. 37F) Table representing the percentage increase in γδ CD25 expression from cocultured cells treated with the highest concentration of Vδ1 mAb compared to untreated, co- and non-cocultured γδ cells.

(FIG. 38A) Comparison of ADT1-4-2 and ADT1-4 capability to engage and reduce the expression of VD1 on cynomolgus γδ-T cells. (FIG. 38B) Percentage of cell surface expression of VD1 upon treatment with ADT1-4-2. (FIG. 38C) individual EC50 value for the different donors combined with the mean and standard deviation. (FIGS. 38D-38H) Additional studies carried out with whole blood samples from cynomolgus macaques (n=5).

FIGS. 39A-39D. Quantification of live THP-1 cell numbers after 24 hours co-culture with γδ T-cells in the presence of Vδ1 mAbs or controls. (FIG. 39A) THP-1 cell killing assay for ADT1-4 clones. (FIG. 39B) THP-1 cell killing assay for ADT1-7 clones. (FIG. 39C) Mean EC50s in THP-1 killing assay for ADT1-4 and ADT1-7 clones. (FIG. 39D) Table summarizing the EC50s plotted in (FIG. 39C).

(FIGS. 43A-43B) Shows % decrease in Vδ1 TCR expression on total tumour infiltrating-γδ T cells following 48 (FIG. 43A) or 72 (FIG. 43B) hours mAb stimulation in two separate donors, confirming target engagement in each case. (FIG. 43C) Shows enhanced expression of both CD25 and Ki67 on Vδ1+ T cells following 48 hour stimulation with ADT1-4-2 compared with stimulation with IgG1 isotype control or ADT1-4. (FIG. 43D) Shows substantial fold increases in IFN-γ production by TILs stimulated with ADT1-4-2 or ADT1-7-3 for 72 hours in the presence of 50 ng/ml IL-15. (FIG. 43E) Shows that stimulation of TILs with ADT-1-4-2 or ADT1-7-3 did not enhance secretion of type 17-associated cytokines IL-6 or IL-17 at this timepoint. (FIGS. 43F-43G) Shows the % decrease in Vδ1 TCR expression on total tumour infiltrating-γδ T cells following mAb stimulation at 24 (FIG. 43F) or 72 (FIG. 43G) hours in two individual donors, confirming target engagement in TILs isolated by enzymatic digestion. (FIG. 43H) Shows dose-dependent enhanced expression of Ki67 on γδ T cells following 72 hours stimulation with ADT1-4-2. (FIGS. 43I-43J) Shows the fold increase in IFN-γ produced by TILs isolated from two individual donors by enzymatic digestion and stimulated with ADT1-4-2 at a concentration of 6.66 nM in the presence of 2 ng/ml IL-15 at 24 (FIG. 43I) or 72 (FIG. 43J) hours. In all cases, the concentration of the control anti-RSV and parent ADT1-4 are matched to highest concentration used in study (i.e. a conc. of 6.66 nM for A, C, F, G, H, I, J and a concentration of 66.6 nM for B and E).

(FIG. 44A) Shows enhanced expression of CD25 and Ki67 in γδ T cells stimulated for 10 days with ADT1-4-2. (FIG. 44B) Shows a substantial increase in Perforin+Granzyme B+γδ T cells following 10 days stimulation with ADT1-4-2. (FIG. 44C) Shows considerably enhanced expression of Granzyme B and Perforin by both CD8+ and $CD8^{-}$αβ T cells following 10 days stimulation of tumour-infiltrating Vδ1+ T cells with ADT1-4-2. (FIG. 44D) Shows markedly increased production of IFN-γ, and moderately increased production of IL-17 and IL-6 by lung tumour-derived TILs following stimulation with ADT1-4-2. FIG. 44E demonstrates enhanced production of the chemokines CCL2, CCL4 and CXCL10 by TILs following 10 days stimulation with ADT1-4-2. In all cases, control anti-RSV and parent ADT1-4 matched to same concentration as affinity matured ADT1-4-2.

FIGS. 45A-45B: Sequences of ADT1-4 lineage clones (light chains). (FIG. 45A) From top to bottom, SEQ ID NOs: 27, 28, 29, 30, 31, 32, 33, 34, 35, 36, 37, 38. (FIG. 45B) From top to bottom, SEQ ID NOs: 39, 40, 41, 42, 43, 44, 45, 46, 47, 48, 49, 50.

FIGS. 46A-46B: Sequences of ADT1-4 linage clones (heavy chains). (FIG. 46A) From top to bottom, SEQ ID NOs: 2, 3, 4, 5, 6, 7, 8, 9, 10, 11, 12, 13. (FIG. 46B) From top to bottom, SEQ ID NOs: 14, 15, 20, 17, 18, 19, 20, 21, 22, 23, 24, 25.

FIG. 47: Sequences of ADT1-7 lineage clones (light chains). From top to bottom, SEQ ID NOs: 119, 120, 121, 122, 123, 124, 125, 126, 127, 128, 129.

FIG. 48: Sequences of ADT1-7 lineage clones (heavy chains). From top to bottom, SEQ ID NOs: 107, 108, 109, 110, 111, 112, 113, 114, 115, 116, 117.

(FIG. 50A) Expression of CD19 on cancerous NALM-6, and Raji, and primary B-cells and Vδ1 γδT-cells determined by flow cytometry. (FIGS. 50B-50D) Effect of parental (ADT1-4) and affinity matured (ADT1-4-2) Vδ1-CD19 bispecific on NALM-6 cells (FIG. 50B), Raji cells (FIG. 50C) and B-cell cytotoxicity (FIG. 50D). Antibodies were titrated in the presence of 1:1 E:T ratio with Vδ1 γδT-cells for 12 hours. Percent live cells were calculated by high content confocal microscopy and normalized to live cell counts in the absence of Vδ1 γδT-cells. (FIG. 50E) Bar chart representing the percent number of live cells after 12 hours co-culture of Vδ1 γδT-cells either NALM-6, Raji or B-cells in the presence of Vδ1 bispecifics and controls as presented in (FIG. 50B), (FIG. 50C) and (FIG. 50D). (FIGS. 50F-50G) Effect of Vδ1-CD19 bispecifics on Vδ1 TCR surface expression in the presence of NALM-6 target cells (FIG. 50F) and healthy B-cells (FIG. 50G) as determined by flow cytometry after four hours co-culture. (FIG. 50H) Bar chart representing the maximum percent TCR downregulation as presented in (FIG. 50F) and (FIG. 50G) at the top concentrations (3 μg/ml). (FIGS. 501-50K) Effect of Vδ1-CD19 bispecifics on CD107a upregulation on Vδ1 cell surface in the presence of NALM-6 target cells (FIG. 50I) and healthy B-cells (FIG. 50J) as determined by flow cytometry after four hours co-culture. All data indicates mean±standard deviation and is representative of n=3. Blinatumomab (CD3-CD19 bispecific (BiTE)) was included as a control in all assays.

FIGS. 51A-51J: Affinity matured Vδ1 clones in a bispecific format bind to $Her2^{+}$ target cells and exhibit enhanced binding to Vδ1 γδT-cells, and enhanced cytotoxicity of $Her2^{+}$ target cells. (FIG. 51A) Cell surface expression of Her2 and Vδ1 on breast cancer cell lines and Vδ1 γδT-cells (FIG. 51B). (FIGS. 51C-51F) Binding of Vδ1-Her2 bispecific antibodies and Her2 mAb control (Trastuzumab) to Her2+ (SK-BR-3 (FIG. 51C), BT-474 (FIG. 51D)), $Her2^{-}$ (MDA-MD-231 (FIG. 51E)) and Vδ1+ cells (FIG. 51F). (FIGS. 51G-51I) Percent live cells remaining after 24 hours co-culture in a 1:1 E:T ratio with Vδ1 γδT-cells and SK-BR-3 cells (FIG. 51G), BT-474 (FIG. 51H), and MDA-MB-231 cells (FIG. 51I) in the presence of Vδ1-Her2 bispecific antibodies. (FIG. 51J) Bar chart representing the percent increase in cytotoxicity after 24 hours Vδ1 γδT-cells Vδ1-Her2 bispecific antibodies.

(FIGS. 52A-52F) Surface Plasmon Resonance (SPR) analysis was performed with Vδ1/EGFR bispecific variants to assess binding to human Vol (FIGS. 52A-52C) and human EGFR antigen (FIGS. 52D-52F). The parental mAbs, cetuximab and negative control mAbs were included for comparison purposes.

(FIGS. 53B-53C) The level of binding by the Vδ1/EGFR bispecific antibodies to A431 cell line or primary Vδ1 γδ T-cells. Target cells were stained with varying concentrations of antibody, followed by a fluorescent anti-human IgG detection antibody. All incubation steps were performed at 4° C. and mAb binding was determined using flow cytometry to measure the median level of fluorescence. Logarithmic four parameter dose-response curves were fitted using Graph Pad Prism 9.

(FIG. 54A) Cell surface expression of γδTCR on primary Vδ1 γδ T-cells following culture with bispecific antibodies for 24 hours in the presence or absence of A431 cells. (FIGS. 54B-54C) The number of viable A431 cells (FIG. 54B) and activation status of primary Vδ1 γδ T-cells (FIG. 54C) following co-culturing at 1:1 ratio alongside varying concentrations of antibody for 24 hours. Viability was measured by viability dye and activation status using a CD25 antibody. (FIG. 54D) Degranulation of primary Vδ1 γδ T-cells following co-culture with A431 cells at 1:1 ratio alongside varying concentrations of antibody for four hours. Degranulation was determined by adding fluorophore-conjugated anti-CD107a antibody directly into the cell-antibody mix at the start of the co-culture. (FIG. 54E) The number of viable A431 cells following 24-hours co-culture with 10 pM of antibody and varying quantity of primary Vδ1 γδ T-cells. (FIGS. 54A-54E) In all cases, fluorescence was determined using flow cytometry to measure the median level of fluorescence. Logarithmic four parameter dose-response curves were fitted using GraphPad Prism 9. Data is represented as mean±SD of two biological replicates (FIG. 55A) shows the vδ1 TCR MFI upon antibody stimulation as an indication of mAb target engagement on blood derived Vδ1 T cells. (FIG. 55B) shows the MFI of CD3 expression on positively gated blood derived vδ1 cells. Stimulation with the vδ1 antibody engaged vδ1 cells and resulted in down-regulation of both vδ1 and CD3 on vδ1 cells. (FIG. 55C, FIG. 55D, and FIG. 55E) shows conferred activation and non-depletion effects on tumour associated Vδ1 T cells with exemplar anti-Vδ1 antibodies of this invention.

FIGS. 56A-56I: Vδ1×FAPα bispecific antibodies enhance Vδ1 γδT-cell activation and lysis of FAPα$^+$ fibroblasts. (FIG. 56A-56B) shows binding kinetics of anti-Vδ1 (ADT-1-4-2), anti FAPα monoclonal (based on Sibrotuzumab) and anti-Vδ1×FAPα (ADT-1-4-2×Sibrotuzumab) bispecific antibodies for recombinant human Vδ1 and FAPα as determined by surface plasmon resonance (SPR). (FIGS. 56C-56D) Binding of anti-Vδ1 and anti FAPα antibodies to FAPα+ fibroblasts (FIG. 56C) and Vδ1 γδT-cells (FIG. 56D). (FIGS. 56E-56F) Effect of anti-Vδ1×FAPα bispecific antibodies and monoclonal controls, on Vδ1 TCR downregulation on Vδ1 γδT-cells in the absence (FIG. 56E) or presence of FAPα+ fibroblasts (FIG. 56F). (FIGS. 56G-56H) Effect of anti-Vδ1×FAPα bispecific antibodies and monoclonal controls, on CD107a upregulation on Vδ1 γδT-cells in the absence (FIG. 56G) or presence of FAPα+ fibroblasts (FIG. 56H). (FIG. 56I) Effect of anti-Vδ1×FAPα bispecific antibody and monoclonal controls on fibroblast lysis by Vδ1 NOT-cells after 24 hours co-culture. Percent live cells were calculated by high content confocal microscopy and normalized to live cell counts in the absence of Vδ1 γδT-cells.

(FIGS. 57A-57B) binding kinetics of anti-Vδ1 (ADT-1-4-2), anti-MSLN monoclonal (based on antibodies disclosed in US 2014/0004121) and anti-Vδ1×MSLN (ADT1-4-2×MSLN) bispecific antibodies for recombinant human Vδ1 and MSLN as determined by surface plasmon resonance (SPR). (FIGS. 57C-57D) Binding of anti-Vδ1 and anti-MSLN antibodies to MSLN+HeLa cells (FIG. 57C) and Vδ1 γδT-cells (FIG. 57D). (FIGS. 57E-57F) Effect of anti-Vδ1×MSLN bispecific and monoclonal antibodies, on Vδ1 TCR downregulation on Vδ1 γδT-cells in the absence (FIG. 57E) or presence of MSLN$^+$ OVCAR-3 cells (FIG. 57F). (FIGS. 57H-57I) Effect of anti-Vδ1×MSLN bispecific antibodies and monoclonal controls, on CD107a upregulation on Vδ1 γδT-cells in the absence (FIG. 57G) or presence of MSLN$^+$ OVCAR-3 cells (FIG. 57H). (FIG. 57I) Effect of anti-Vδ1×MSLN bispecific antibody and monoclonal controls on HeLa cell lysis by Vδ1 γδT-cells after 24 hours co-culture. Percent live cells were calculated by high content confocal microscopy and normalized to live cell counts in the absence of Vδ1 γδT-cells.

FIGS. 58A-58B) SPR analysis of anti-Vδ1 (ADT1-4-2), anti-PD-1 (based on pembrolizumab), anti-RSVIgGcontrol×anti-PD-1 and anti-Vδ1×anti-PD-1 (ADT1-4-2×pembrolizumab) bispecific antibodies binding to recombinant human Vδ1 and PD-1. FIG. 58C) Dual binding of anti-Vδ1 and anti-PD-1 bispecific antibodies to recombinant human PD-1 and Vδ1 as determined by SPR. FIG. 58D) Expression of PD-1 on CD4 and CD8 T-cells activated with anti-CD3/anti-CD28 dynabeads. FIG. 58E) Binding of anti-Vδ1 and anti-PD-1 antibodies to PD-1$^+$ activated CD4 and CD8 T-cells and Vδ1 γδT-cells. FIG. 58F) Effect of anti-Vδ1×PD-1 bispecific antibodies and monoclonal controls, on Vδ1 TCR downregulation on Vδ1 γδT-cells in the absence or presence of PD-1+CD4 T-cells. FIG. 58G) EC50 of anti-Vδ1×PD-1 bispecific antibodies on Vδ1 TCR downregulation on Vδ1 γδT-cells in the presence of absence of PD-1+CD4 T-cells. FIG. 58H) Effect of Vδ1 crosslinked anti-Vδ1×PD-1 bispecific antibody on PD-1+ T-cell activation.

FIGS. 59A-59D) SPR analysis of anti-Vδ1 (ADT1-4-2), anti-4-1BB (based on utomilumab), anti-RSVIgGcontrol×anti-4-1BB and anti-Vδ1×anti-4-1BB (ADT1-4-2×utomilumab) bispecific antibodies binding to recombinant human Vδ1 and 4-1BB. FIG. 59E) Dual binding of anti-Vδ1 and anti-4-1BB bispecific antibodies to recombinant human 4-1BB and Vδ1 as determined by SPR. FIG. 59E) Expression of 4-1 BB on CD4 and CD8 T-cells activated with anti-CD3/anti-CD28 dynabeads. FIG. 59F) Binding of anti-Vδ1 and anti-4-1BB antibodies to 4-1BB$^+$ activated CD8 T-cells and Vδ1 γδT-cells. FIG. 59G) Effect of anti-Vδ1×4-1BB bispecific antibodies and monoclonal controls, on Vδ1 TCR downregulation on Vδ1 γδT-cells in the absence (FIG. 59H) or presence of 4-1BB+CD8 T-cells (FIG. 59I). FIG. 59J) Effect of Vδ1 crosslinked anti-Vδ1×4-1BB bispecific antibody on 4-1BB+ T-cell activation.

FIGS. 60A-60B) SPR analysis of anti-Vδ1 (ADT1-4-2), anti-OX40 (based on pogalizumab), anti-RSVIgGcontrol× anti-OX40 and anti-Vδ1×anti-OX40 (ADT1-4-2×pogalizumab) bispecific antibodies binding to recombinant human Vδ1 and OX40. FIG. 60C) Dual binding of anti-Vδ1 and anti-OX40 bispecific antibodies to recombinant human OX40 and Vδ1 as determined by SPR. FIG. 60D) Expression of OX40 on CD4 and CD8 T-cells activated with anti-CD3/anti-CD28 dynabeads. FIG. 60E) Binding of anti-Vδ1 and anti-OX40 antibodies to OX40$^+$ activated CD4 T-cells and Vδ1 γδT-cells. E-F FIGS. 60G-60H) Effect of anti-Vδ1×OX40 bispecific antibodies and monoclonal controls, on Vδ1 TCR downregulation on Vδ1 NOT-cells in the absence (FIG. 60F) or presence of OX40+CD4 T-cells (FIG. 60G). FIG. 60H) Effect of Vδ1 crosslinked anti-Vδ1×OX40 bispecific antibody on OX40+ T-cell activation.

FIGS. 61A-61B) SPR analysis of anti-Vδ1 (ADT1-4-2), anti-TIGIT (based on tiragolumab), anti-RSVIgGcontrol×anti-TIGIT and anti-Vδ1×anti-TIGIT (ADT-1-4-2×tiragolumab) bispecific antibodies binding to recombinant human Vδ1 and TIGIT. FIG. 61C) Dual binding of anti-Vδ1 and anti-TIGIT bispecific antibodies to recombinant human TIGIT and Vδ1 as determined by SPR. FIG. 61D) Expression of TIGIT on CD4 and CD8 T-cells activated with anti-CD3/anti-CD28 dynabeads. FIG. 61E) Binding of anti-Vδ1 and anti-TIGIT antibodies to TIGIT$^+$ activated CD4 and CD8 T-cells and Vδ1 γδT-cells. FIG. 61F) Effect of anti-Vδ1×TIGIT bispecific antibodies and monoclonal controls, on Vδ1 TCR downregulation on Vδ1 γδT-cells in the absence or presence of TIGIT+CD8 T-cells. FIG. 61G) EC50 of anti-Vδ1×TIGIT bispecific antibodies on Vδ1 TCR downregulation on Vδ1 γδT-cells in the presence or absence of TIGIT+CD8 T-cells. FIG. 61H) Effect of Vδ1 crosslinked anti-Vδ1×TIGIT bispecific antibody on TIGIT+ T-cell activation.

FIGS. 63A-FIG. 63F) Effect of anti-Vδ1×CD19 and CD3×CD19 bispecific antibodies on γδ T-cell or αβ T-cell mediated lysis of Raji cells or healthy primary B-cells. Percent positive Raji or healthy primary B-cells were determined at 24 hours by confocal microscopy in tri-cultures of: Vδ1 γδT-cells with Raji cells (FIG. 63A) and primary healthy B-cells (FIG. 63B); tricultures of αβT-cells with Raji cells (FIG. 63C) and primary health B-cells (FIG. 63D); or quad cultures of Vδ1 NOT-cells and αβ T-cells, with Raji cells (FIG. 63E) and primary healthy B-cells (FIG. 63F). FIGS. 63*g*-FIG. 63I) Quantification of IL-17A secretion from γδT-cells or αβ T-cells 24 hours post stimulation by anti-Vδ1×CD19 and CD3×CD19 bispecific antibodies. Cell culture supernatants from co-cultures of Raji cells, primary B-cells and: γδT-cells (FIG. 63G); or αβ T-cells (FIG. 63H); or γδT-cells and αβ T-cells (FIG. 63I), were collected and IL-17A secretion determined by MSD. Dotted lines represent the lowest level of quantification.

(FIG. 64A) Enhanced expression of 4-1 BB by the addition of an exemplar high-affinity anti-Vδ1 antibody: Tissue-derived Vδ1+ T cells from 4 different human donors were incubated with indicated antibodies (1 μg/ml) in the presence of THP-1 cells (2:1 E:T). After 4 hours, expression of 4-1BB on the surface of Vδ1+ T cells was analyzed by flow cytometry. Cells stimulated with ADT1-4-2 had significantly increased expression of 4-1 BB at this timepoint, which was comparable to stimulation with OKT3 (*$p<0.05$, $p<0.01$ by Ordinary one-way ANOVA with Sidak's post test). (FIGS. 64B-FIG. 64C) Enhanced expression of 4-1BB; further studies: Tissue-derived Vδ1+ T cells were incubated with titrated quantities of ADT1-4-2 or anti-IgG1 isotype control as indicated in either (FIG. 64B) the presence of THP-1 cancer cells or (FIG. 64**C) healthy blood-derived monocytes at a 1:1 ratio. After 4 hours, expression of 4-1BB on the surface of Vδ1+ T cells was analyzed by flow cytometry. Stimulation with ADT1-4-2 increased expression of 4-1BB on the surface of Vδ1 T cells. Furthermore, even though activated Vδ1+ cell spare healthy cells (see elsewhere herein for further discussion) similar antibody-induced activation was observed when cross-linking was provided by tumour or healthy FcγR$^+$ cells.

(FIGS. 65B-65D) Anti-Vδ1 antibodies conferred enhanced expression of NCRs (NKp30, NKp44, NKp46) on detectable Vδ1+ cells: Alongside confirmation of target engagement for all anti-Vδ1 antibodies employed in this study, the fold-wise change in NCRs was also studied on the gated Vδ1+ cells. Specifically (FIG. 65B) presents fold-change in % double positive Vδ1+, NKp30+ relative to RSV control (RSV control normalized far right and represented as 1 -fold). (FIG. 65C) presents fold-change in % double-positive Vδ1+, NKp44+ relative to RSV control (RSV control normalized far right and represented as 1-fold). (FIG. 65D) presents fold-change in % double-positive Vδ1+, NKp46+ relative to RSV control (RSV control normalized far right and represented as 1-fold). These combined results highlight a consistent (donor-dependent) upregulation of NCRs in detectable Vδ1+ conferred by all affinity matured anti-Vδ1+ antibodies employed in this extended, 10-day primary PBMC culture system.

DETAILED DESCRIPTION OF THE INVENTION

Figure 1:
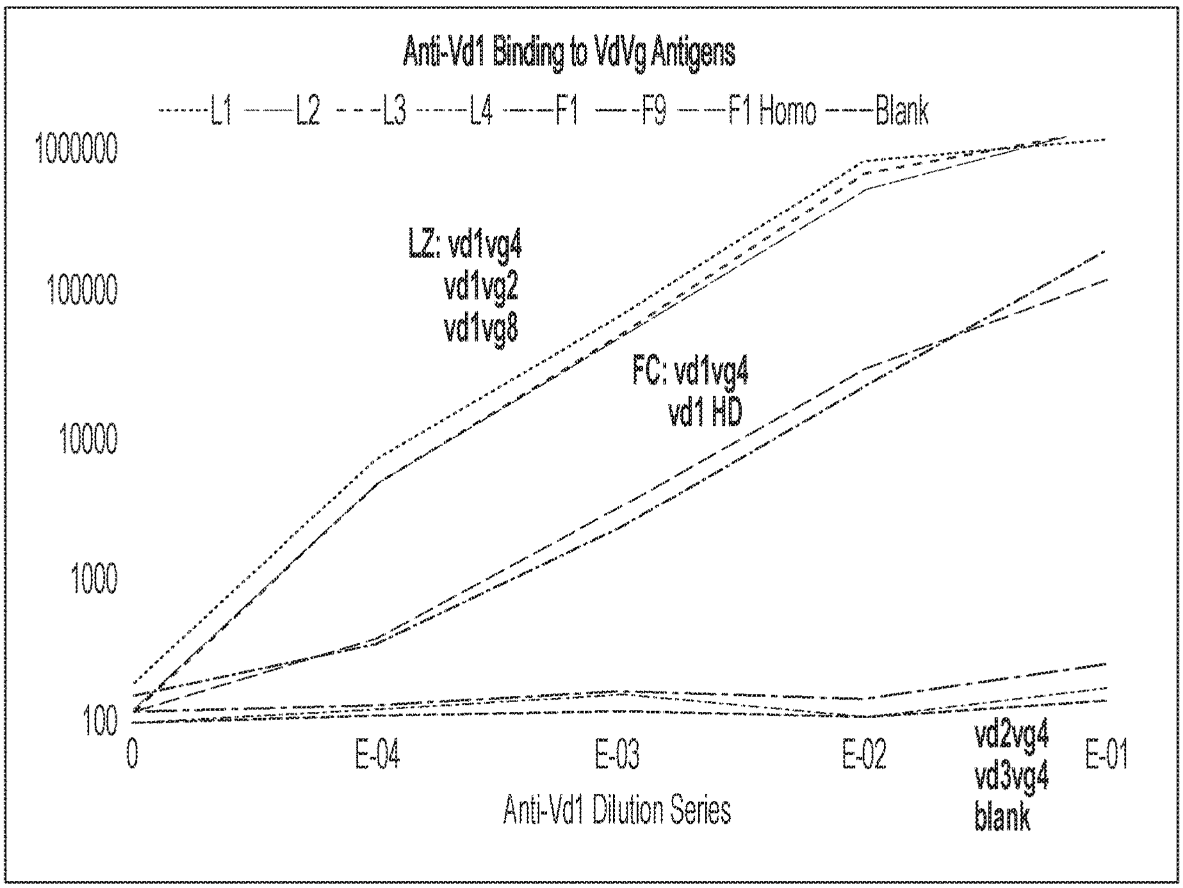
FIG. 1: ELISA Detection of Directly Coated Antigen with Anti-Vδ1Ab (REA173, Miltenyi Biotec). Detection was seen only with those antigens which contain the Vδ1 domain. Leucine zipper (LZ) format seems more potent than Fc format which is consistent with cell-based flow competition assay (data not shown).

The present invention provides high-affinity anti-TCR delta variable 1 (anti-Vδ1) antibodies, multispecific antibodies, and antibody fragments thereof. More specifically, the present invention relates to the provision and characterisation of optimised antibodies, for example antibodies prepared according to an optimised selection procedure beginning from parental anti-Vδ1 antibodies, such as the parental antibodies referred to herein as G04, E07, C08, B07, C05, E04, F07, G06, G09, B09, G10 and E01. The present invention relates in particular to optimised antibodies derived from G04 and E07.

Definitions

Unless defined otherwise, all technical and scientific terms used herein have the meaning commonly understood by a person skilled in the art to which this invention belongs. As used herein, the following terms have the meanings ascribed to them below.

Gamma delta (γδ) T cells represent a small subset of T cells that express on their surface a distinct, defining T Cell Receptor (TCR). This TCR is made up of one gamma (γ) and one delta (δ) chain. Each chain contains a variable (V) region, a constant (C) region, a transmembrane region and a cytoplasmic tail. The V region contains an antigen-binding site. There are two major sub-types of human γδ T cells: one that is dominant in the peripheral blood and one that is dominant in non-haematopoietic tissues. The two sub-types may be defined by the type of δ and/or γ present on the cells. For example, γδ T cells that are dominant in peripheral blood primarily express the delta variable 2 chain (Vβ2). γδ T cells that are dominant in non-haematopoietic tissues (i.e. are tissue-resident) primarily express the delta variable 1 chain. References to "Vδ1 T cells" or "Vδ1+ T cells" refer to γδ T cells with a Vδ1 chain, i.e. Vδ1+ cells.

References to "delta variable 1" may also referred to as Vδ1 or Vd1, while a nucleotide encoding a TCR chain containing this region or the TCR protein complex comprising this region may be referred to as "TRDV1". Antibodies or antigen-binding fragments thereof which interact with the Vδ1 chain of a γδ TCR, are all effectively antibodies or antigen-binding fragments thereof which bind to Vδ1 and may referred to as "anti-TCR delta variable 1 antibodies or antigen-binding fragments thereof" or "anti-Vδ1 antibodies or antigen-binding fragments thereof" or "anti-TRDV1 antibodies or antigen-binding fragments thereof".

Additional references are made herein to other delta chains such as the "delta variable 2" chain. These can be referred to in a similar manner. For example, delta variable 2 chains can be referred to as Vβ2, while a nucleotide encoding a TCR chain containing this region or the TCR protein complex comprising this region may be referred to as "TRDV2". In preferred embodiments antibodies or antigen-binding fragments thereof which interact with the Vδ1 chain of a γδ TCR, do not interact with other delta chains such as Vβ2. In the invention, the antibodies are specific to TRDV1 and do not bind to TRDV2 (SEQ ID NO: 310) or other antigens present on a gamma delta T-cell receptor, such as TRDV3 (SEQ ID NO: 311).

References to "gamma variable chains" are also made herein. These may be referred to as γ-chains or Vγ, while a nucleotide encoding a TCR chain containing this region or the TCR protein complex comprising this region may be referred to as TRGV. For example, TRGV4 refers to Vγ4 chain. In a preferred embodiments, antibodies or antigen-binding fragments thereof which interact with the Vδ1 chain of a γδ TCR, do not interact with gamma chains such as Vγ4 (e.g. SEQ ID NO: 309). The antibodies also do not bind or interact with other domains found within a γδ TCR, such as TRDJ, TRDC, TRGJ or TRGC The term "T-cell receptor complex" is the complex of proteins comprising the "T-cell receptor" (or "TCR") found on the surface of T-cells responsible for recognising a variety of antigens. The T-cell receptor complex comprises either the alpha and beta chains of the T-cell receptor, or in the case of gamma delta T cells, the gamma and delta chains of the T-cell receptor, and up to 6 additional chains or more, such as CD3δ, CD3γ, CD3ε and CD3ζ, although the precise makeup of T-cell receptor complexes can vary. The T-cell receptor complex mediates intracellular signalling in the T-cell, which may lead to T-cell activation.

The term "antibody" includes any antibody protein construct comprising at least one antibody variable domain comprising at least one antigen-binding site (ABS). Antibodies include, but are not limited to, immunoglobulins of types IgA, IgG, IgE, IgD, IgM (as well as subtypes thereof). The overall structure of Immunoglobulin G (IgG) antibodies assembled from two identical heavy (H)-chain and two identical light (L)-chain polypeptides is well established and highly conserved in mammals (Padlan (1994) *Mol. Immunol.* 31:169-217).

A conventional antibody or immunoglobulin (Ig) is a protein comprising four polypeptide chains: two heavy (H) chains and two light (L) chains. Each chain is divided into a constant region and a variable domain. The heavy (H) chain variable domains are abbreviated herein as VH, and the light (L) chain variable domains are abbreviated herein as VL. These domains, domains related thereto, and domains derived therefrom, may be referred to herein as immunoglobulin chain variable domains. The VH and VL domains (also referred to as VH and VL regions) can be further subdivided into regions, termed "complementarity determining regions" ("CDRs"), interspersed with regions that are more conserved, termed "framework regions" ("FRs"). The framework and complementarity determining regions have been precisely defined (Kabat et al. Sequences of Proteins of Immunological Interest, *Fifth Edition U.S. Department of Health and Human Services*, (1991) NIH Publication Number 91-3242). There are also alternative numbering conventions for CDR sequences, for example those set out in Chothia et al. (1989) Nature 342: 877-883 or as summarized by IMGT.org. In a conventional antibody, each VH and VL is composed of three CDRs and four FRs, arranged from amino-terminus to carboxy-terminus in the following order: FR1, CDR1, FR2, CDR2, FR3, CDR3, FR4. The conventional antibody tetramer of two heavy immunoglobulin chains and two light immunoglobulin chains is formed with the heavy and the light immunoglobulin chains inter-connected by e.g. disulphide bonds, and the heavy chains similarly connected. The heavy chain constant region includes three domains, CH1, CH2 and CH3. The light chain constant region is comprised of one domain, CL. The variable domain of the heavy chains and the variable domain of the light chains are binding domains that interact with an antigen. The constant regions of the antibodies typically mediate the binding of the antibody to host tissues or factors, including various cells of the immune system (e.g. effector cells) and the first component (C1q) of the classical complement system.

A "fragment" of the antibody (which may also referred to as "antibody fragment", "immunoglobulin fragment", "antigen-binding fragment" or "antigen-binding polypeptide") as used herein refers to a portion of an antibody (or constructs that contain said portion) that specifically binds to the target, the delta variable 1 (Vδ1) chain of a γδ T cell receptor (e.g. a molecule in which one or more immunoglobulin chains is not full length, but which specifically binds to the target). Examples of binding fragments encompassed within the term antibody fragment include:

(i) a Fab fragment (a monovalent fragment consisting of the VL, VH, CL and CH1 domains);
(ii) a F(ab')2 fragment (a bivalent fragment consisting of two Fab fragments linked by a disulphide bridge at the hinge region);
(iii) a Fd fragment (consisting of the VH and CH1 domains);
(iv) a Fv fragment (consisting of the VL and VH domains of a single arm of an antibody);
(v) a single chain variable fragment, scFv (consisting of VL and VH domains joined, using recombinant methods, by a synthetic linker that enables them to be made as a single protein chain in which the VL and VH regions pair to form monovalent molecules);
(vi) a VH (an immunoglobulin chain variable domain consisting of a VH domain);
(vii) a VL (an immunoglobulin chain variable domain consisting of a VL domain);
(viii) a domain antibody (dAb, consisting of either the VH or VL domain);
(ix) a minibody (consisting of a pair of scFv fragments which are linked via CH3 domains); and
(x) a diabody (consisting of a noncovalent dimer of scFv fragments that consist of a VH domain from one antibody connected by a small peptide linker a VL domain from another antibody).

"Human antibody" refers to antibodies having variable and constant regions derived from human germline immunoglobulin sequences. Human subjects administered with said human antibodies do not generate cross-species antibody responses (for example termed HAMA responses—human-anti-mouse antibody) to the primary amino acids contained within said antibodies. Said human antibodies may include amino acid residues not encoded by human germline immunoglobulin sequences (e.g. mutations introduced by random or site-specific mutagenesis or by somatic mutation), for example in the CDRs and in particular CDR3. However, the term is not intended to include antibodies in which CDR sequences derived from the germline of another mammalian species, such as a mouse, have been grafted onto human framework sequences. Human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g. a mouse) that is transgenic for human immunoglobulin genes or antibodies prepared, expressed, created or isolated by any other means that involves splicing of human immunoglobulin gene sequences to other DNA sequences, may also be referred to as "recombinant human antibodies".

Substituting at least one amino acid residue in the framework region of a non-human immunoglobulin variable domain with the corresponding residue from a human variable domain is referred to as "humanisation". Humanisation of a variable domain may reduce immunogenicity in humans.

"Specificity" refers to the number of different types of antigens or antigenic determinants to which a particular antibody or antigen-binding fragment thereof can bind. The specificity of an antibody is the ability of the antibody to recognise a particular antigen as a unique molecular entity and distinguish it from another. An antibody that "specifically binds" to an antigen or an epitope is a term well understood in the art. A molecule is said to exhibit "specific binding" if it reacts more frequently, more rapidly, with greater duration and/or with greater affinity with a particular target antigen or epitope, than it does with alternative targets. An antibody "specifically binds" to a target antigen or epitope if it binds with greater affinity, avidity, more readily, and/or with greater duration than it binds to other substances.

The antibodies of the present invention include monospecific antibodies (i.e., antibodies that only bind to one antigen) and multispecific antibodies. A "multispecific antibody" is an antibody that is capable of binding a plurality of different epitopes simultaneously or sequentially. Generally, the epitopes will not be on the same antigen. Hence a multispecific antibody has the capability to selectively bind to epitopes present on different antigens via a plurality of different binding domains. This contrasts with conventional monospecific antibodies which do not have this capability. Rather, a "monospecific antibody" only has binding specific for one antigen, although they may have multiple binding sites for that one antigen (e.g. the valency of a full human IgG antibody is 2, and the valency of other antibodies may be higher, but if the antibody only recognises one antigen, it is still classed as a monospecific antibody). Hence, the multispecific antibodies of the invention bind multiple different antigens simultaneously and/or sequentially.

In some embodiments of the invention, the antibodies are bispecific antibodies. A "bispecific antibody" is an antibody that is capable of binding two different epitopes simultaneously and/or sequentially. Generally, the epitopes will not be on the same antigen. Hence bispecific antibodies have the capability to selectively bind to two different epitopes present on two different antigens via two different binding domains. This contrasts with conventional monospecific antibodies which do not have this capability. Hence, the bispecific antibodies of the invention bind two different antigens simultaneously and/or sequentially.

"Affinity", represented by the equilibrium constant for the dissociation of an antigen with an antigen-binding polypeptide (KD), is a measure of the binding strength between an antigenic determinant and an antigen-binding site on the antibody (or antigen-binding fragment thereof): the lesser the value of the KD, the stronger the binding strength between an antigenic determinant and the antigen-binding polypeptide. Alternatively, the affinity can also be expressed as the affinity constant (KA), which is 1/KD. Affinity can be determined by known methods, depending on the specific antigen of interest. For example. KD may be determined by surface plasmon resonance.

Any KD value less than $10^{-6}$ is considered to indicate binding. Specific binding of an antibody, or antigen-binding fragment thereof, to an antigen or antigenic determinant can be determined in any suitable known manner, including, for example, Scatchard analysis and/or competitive binding assays, such as radioimmunoassays (RIA), enzyme immunoassays (EIA) and sandwich competition assays, equilibrium dialysis, equilibrium binding, gel filtration, ELISA, surface plasmon resonance, or spectroscopy (e.g. using a fluorescence assay) and the different variants thereof known in the art.

"Avidity" is the measure of the strength of binding between an antibody, or antigen-binding fragment thereof, and the pertinent antigen. Avidity is related to both the affinity between an antigenic determinant and its antigen-binding site on the antibody and the number of pertinent binding sites present on the antibody.

"In situ" means in the natural or original place, instead of being moved to another place. For example, an in situ Vδ1+ cell in a patient refers to a vδ1 cell in vivo, as opposed to an in vitro or ex vivo cell.

"Human tissue Vδ1+ cells," and "haemopoietic and blood Vδ1+ cells" and "tumour infiltrating lymphocyte (TIL) Vδ1+ cells," are defined as Vδ1+ cells contained in or derived from either human tissue or the haemopoietic blood system or human tumours respectively. All said cell types can be identified by their (i) location or from where they are derived and (ii) their expression of the Vδ1+TCR.

"Modulating antibodies" are antibodies that confer a measurable change including, but not limited to, a measurable change in cell cycle, and/or in cell number, and/or cell viability, and/or in one or more cell surface markers, and/or in the secretion of one or more secretory molecules (e.g., cytokines, chemokines, leukotrienes, etc.), and/or a function (such as cytotoxicity towards a target cell or diseased cell), upon contacting or binding to a cell expressing the target to which the antibody binds. A method of "modulating" a cell, or population thereof, refers to a method wherein in at least one measurable change in said cell or cells, or secretion therefrom, is triggered to generate one or more "modulated cells".

An "immune response" is a measurable change in at least one cell, or one cell-type, or one endocrine pathway, or one exocrine pathway, of the immune system (including but not limited to a cell-mediated response, a humoral response, a cytokine response, a chemokine response) upon addition of a modulating antibody.

An "immune cell" is defined as a cell of the immune system including, but not limited to, CD34+ cells, B-Cells, CD45+(lymphocyte common antigen) cells, Alpha-Beta T-cells, Cytotoxic T-cells, Helper T-cells, Plasma Cells, Neutrophils, Monocytes, Macrophages, Red Blood Cells, Platelets, Dendritic Cells, Phagocytes, Granulocytes, Innate lymphoid cells, Natural Killer (NK) cells and Gamma Delta T-cells. Typically, immune cells are classified with the aid of combinatorial cell surface molecule analysis (e.g., via flow cytometry) to identify or group or cluster to differentiate immune cells into sub-populations. These can be then still further sub-divided with additional analysis. For example, CD45+ lymphocytes can further sub-divided into vδ positive populations and vδ negative populations.

"Model systems" are biological models or biological representations designed to aid in the understanding of how a medicine such as an antibody or antigen-binding fragment thereof may function as a medicament in the amelioration of a sign or symptom of disease. Such models typically include the use of in vitro, ex vivo, and in vivo diseased cells, non-diseased cells, healthy cells, effector cells, and tissues etc., and in which the performance of said medicaments are studied and compared.

"Diseased cells" exhibit a phenotype associated with the progression of a disease such as a cancer, an infection such as a viral infection, or an inflammatory condition or inflammatory disease. For example, a diseased cell may be a tumour cell, an autoimmune tissue cell or a virally infected cell. Accordingly said diseased cells may be defined as tumorous, or virally infected, or inflammatory.

"Healthy cells" refers to normal cells that are not diseased. They may also be referred to as "normal" or "non-diseased" cells. Non-diseased cells include non-cancerous, or non-infected, or non-inflammatory cells. Said cells are often employed alongside relevant diseased cells to determine the diseased cell specificity conferred by a medicament and/or better understand the therapeutic index of a medicament.

"Diseased-cell-specificity" is a measure of how effective an effector cell or population thereof, (such as, for example, a population of Vδ1+ cells) is at distinguishing and killing diseased cells, such as cancer cells, whilst sparing non-diseased or healthy cells. This potential can be measured in model systems and may involve comparing the propensity of an effector cell, or a population of effector cells, to selectively kill or lyse diseased cells versus the potential of said effector cell/s to kill or lyse non-diseased or healthy cells. Said diseased-cell-specificity can inform the potential therapeutic index of a medicament.

"Enhanced diseased-cell specificity" describes a phenotype of an effector cell such as, for example, a Vδ1+ cell, or population thereof, which has been modulated to further increase its capacity to specifically kill diseased cells. This enhancement can be measured in a variety of ways inclusive of fold-change, or percentage increase, in diseased-cell killing specificity or selectivity.

"ADCC" or "antibody-dependent cell-mediated cytotoxicity" describes an immune response to cells coated with antibodies bound to the surface antigens of the cell. It is a cell-mediated process, whereby an immune effector cell (such as a NK cell, for example) recognise cell bound antibodies, triggering degranulation and lysis of the target cell. Typically, this is mediated via Fc-Fcγ interactions. The Fc region of the cell-bound antibody recruits effector cells expressing Fcγ receptors (e.g. NK cells), leading to effector cell degranulation and death of the target cell.

"Fc enabled" refers to an antibody that comprises a functional Fc region (fragment crystallizable region), i.e. a Fc region that has not been disabled by mutation or otherwise. Fc enabled antibodies demonstrate unattenuated Fc function. The Fc enabled antibody may comprise human IGHC heavy chain sequence as listed by IMGT that has not been modified or engineered or constructed to reduce binding to one or more Fc gamma receptors. For example, via IGHC hinge mutation or by construction of an antibody comprising heavy chain constant domains which are chimeric or hybrid for IgG1/IgG2A or IgG1/IgG4 IGHC sequences.

Suitably, the antibody or antigen-binding fragment thereof (i.e. polypeptide) of the invention is isolated. An "isolated" polypeptide is one that is removed from its original environment. The term "isolated" may be used to refer to an antibody that is substantially free of other antibodies having different antigenic specificities (e.g. an isolated antibody that specifically binds Vδ1, or a fragment thereof, is substantially free of antibodies that specifically bind antigens other than Vδ1). The term "isolated" may also be used to refer to preparations where the isolated antibody is sufficiently pure to be administered therapeutically when formulated as an active ingredient of a pharmaceutical composition, or at least 70-80% (w/w) pure, more preferably, at least 80-90% (w/w) pure, even more preferably, 90-95% pure; and, most preferably, at least 95%, 96%, 97%, 98%, 99%, or 100% (w/w) pure.

Suitably, the polynucleotides used in the present invention are isolated. An "isolated" polynucleotide is one that is removed from its original environment. For example, a naturally-occurring polynucleotide is isolated if it is separated from some or all of the coexisting materials in the natural system. A polynucleotide is considered to be isolated if, for example, it is cloned into a vector that is not a part of its natural environment or if it is comprised within cDNA.

The antibody or antigen-binding fragment thereof may be a "functionally active variant" which also includes naturally occurring allelic variants, as well as mutants or any other non-naturally occurring variants. As is known in the art, an allelic variant is an alternate form of a (poly)peptide that is characterized as having a substitution, deletion, or addition of one or more amino acids that does essentially not alter the biological function of the polypeptide. By way of non-limiting example, said functionally active variants may still function when the frameworks containing the CDRs are modified, when the CDRs themselves are modified, when said CDRs are grafted to alternate frameworks, or when N- or C-terminal extensions are incorporated. Further, CDR containing binding domains may be paired with differing partner chains such as those shared with another antibody. Upon sharing with so called 'common' light or 'common' heavy chains, said binding domains may still function. Further, said binding domains may function when multimerized. Further, 'antibodies or antigen-binding fragments thereof' may also comprise functional variants wherein the VH or VL or constant domains have been modified away or towards a different canonical sequence (for example as listed at IMGT.org) and which still function.

For the purposes of comparing two closely-related polypeptide sequences, the "% sequence identity" between a first polypeptide sequence and a second polypeptide sequence may be calculated using NCBI BLAST v2.0, using standard settings for polypeptide sequences (BLASTP). For the purposes of comparing two closely-related polynucleotide sequences, the "% sequence identity" between a first nucleotide sequence and a second nucleotide sequence may be calculated using NCBI BLAST v2.0, using standard settings for nucleotide sequences (BLASTN).

Polypeptide or polynucleotide sequences are said to be the same as or "identical" to other polypeptide or polynucleotide sequences, if they share 100% sequence identity over their entire length. Residues in sequences are numbered from left to right, i.e. from N- to C-terminus for polypeptides; from 5' to 3' terminus for polynucleotides.

In some embodiments, any specified % sequence identity of a sequence is calculated without the sequences of all 6 CDRs of the antibody. For example, the anti-Vδ1 antibody or antigen-binding fragment thereof may comprise a variable heavy chain region sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% to a specified variable heavy chain region sequence and/or a variable light chain region sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a specified variable light chain region sequence, wherein any amino acid variations occur only in the framework regions of the variable heavy and light chain region sequences. In such embodiments, the anti-Vδ1 antibody or antigen-binding fragment thereof having certain sequence identities retain the complete heavy and light chain CDR1, CDR2 and CDR3 sequences of the corresponding anti-Vδ1 antibody or antigen-binding fragment thereof. In a more specific example, although in no way limiting and only to further illustrate these embodiments of the invention, there is provided an anti-Vδ1 antibody or antigen-binding fragment thereof comprising a VH comprising or consisting of an amino acid sequence that is at least 90% identical to the amino acid sequence of SEQ ID NO: 15 and a VL comprising or consisting of an amino acid sequence that is at least 90% identical to the amino acid sequence of SEQ ID NO: 40, wherein any amino acid variations occur only in the framework regions of the variable heavy and light chain region sequences. The antibody of this specific example therefore further comprises a VHCDR1 comprising the amino acid sequence of SEQ ID NO: 51, a VHCDR2 comprising the amino acid sequence of SEQ ID NO: 53, a VHCDR3 comprising the amino acid sequence of SEQ ID NO: 68, a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 95.

Furthermore, antibodies and antigen-binding fragments thereof provided herein may comprise a kappa light chain variable sequence and retain an amino acid residue at position 74 according to the IMGT numbering system that is not serine, for example a non-polar and/or non-germline residue, for example they comprise a leucine residue at this position. For example, although in no way limiting and only to further illustrate these embodiments of the invention, there is provided an anti-Vδ1 antibody or antigen-binding fragment thereof comprising a VH comprising or consisting of an amino acid sequence that is at least 90% identical to the amino acid sequence of SEQ ID NO: 15 and a VL comprising or consisting of an amino acid sequence that is at least 90% identical to the amino acid sequence of SEQ ID NO: 40, wherein any amino acid variations occur only in the framework regions of the variable heavy and light chain region sequences, and wherein the antibody comprises a kappa light chain variable sequence comprising an amino acid residue at position 74 according to the IMGT numbering system that is non-germline and/or non-polar (for example a leucine residue at this position). The antibody of this specific example further comprises a VHCDR1 comprising the amino acid sequence of SEQ ID NO: 51, a VHCDR2 comprising the amino acid sequence of SEQ ID NO: 53, a VHCDR3 comprising the amino acid sequence of SEQ ID NO: 68, a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 95.

A "difference" between sequences refers to an insertion, deletion or substitution of a single amino acid residue in a position of the second sequence, compared to the first sequence. Two polypeptide sequences can contain one, two or more such amino acid differences. Insertions, deletions or substitutions in a second sequence which is otherwise identical (100% sequence identity) to a first sequence result in reduced % sequence identity. For example, if the identical sequences are 9 amino acid residues long, one substitution in the second sequence results in a sequence identity of 88.9%. If first and second polypeptide sequences are 9 amino acid residues long and share 6 identical residues, the first and second polypeptide sequences share greater than 66% identity (the first and second polypeptide sequences share 66.7% identity).

Alternatively, for the purposes of comparing a first, reference polypeptide sequence to a second, comparison polypeptide sequence, the number of additions, substitutions and/or deletions made to the first sequence to produce the second sequence may be ascertained. An "addition" is the addition of one amino acid residue into the sequence of the first polypeptide (including addition at either terminus of the first polypeptide). A "substitution" is the substitution of one amino acid residue in the sequence of the first polypeptide with one different amino acid residue. Said substitution may be conservative or non-conservative. A "deletion" is the deletion of one amino acid residue from the sequence of the first polypeptide (including deletion at either terminus of the first polypeptide).

Using the three letter and one letter codes the naturally occurring amino acids may be referred to as follows: glycine (G or Gly), alanine (A or Ala), valine (V or Val), leucine (L or Leu), isoleucine (I or Ile), proline (P or Pro), phenylalanine (F or Phe), tyrosine (Y or Tyr), tryptophan (W or Trp), lysine (K or Lys), arginine (R or Arg), histidine (H or His), aspartic acid (D or Asp), glutamic acid (E or Glu), asparagine (N or Asn), glutamine (Q or Gln), cysteine (C or Cys), methionine (M or Met), serine (S or Ser) and Threonine (T or Thr). Where a residue may be aspartic acid or asparagine, the symbols Asx or B may be used. Where a residue may be any amino acid the symbol Xaa or X may be used. Where a residue may be glutamic acid or glutamine, the symbols Glx or Z may be used. References to aspartic acid include aspartate, and glutamic acid include glutamate, unless the context specifies otherwise.

As used herein, numbering of polypeptide sequences and definitions of CDRs and FRs are as defined according to the EU and/or IMGT numbering system, as indicated in context. A "corresponding" amino acid residue between a first and second polypeptide sequence is an amino acid residue in a first sequence affinity which shares the same position according to the EU and/or IMGT numbering system, as indicated in context, with an amino acid residue in a second sequence, whilst the amino acid residue in the second sequence may differ in identity from the first. Suitably corresponding residues will share the same number (and letter) if the framework and CDRs are the same length according to EU or IMGT definition. Alignment can be achieved manually or by using, for example, a known computer algorithm for sequence alignment such as NCBI BLAST v2.0 (BLASTP or BLASTN) using standard settings.

References herein to an "epitope" refer to the portion of the target which is specifically bound by the antibody or antigen-binding fragment thereof. Epitopes may also be referred to as "antigenic determinants". An antibody binds "essentially the same epitope" as another antibody when they both recognize identical or sterically overlapping epitopes. Commonly used methods to determine whether two antibodies bind to identical or overlapping epitopes are competition assays, which can be configured in a number of different formats (e.g. well plates using radioactive or enzyme labels, or flow cytometry on antigen-expressing cells) using either labelled antigen or labelled antibody. An antibody binds "the same epitope" as another antibody when they both recognize identical epitopes (i.e. all contact points between the antigen and the antibody are the same).

Epitopes found on protein targets may be defined as "linear epitopes" or "conformational epitopes". Linear epitopes are formed by a continuous sequence of amino acids in a protein antigen. Conformational epitopes are formed of amino acids that are discontinuous in the protein sequence, but which are brought together upon folding of the protein into its three-dimensional structure.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g. bacterial vectors having a bacterial origin of replication and episomal mammalian and yeast vectors). Other vectors (e.g. non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g. replication defective retroviruses, adenoviruses and adeno-associated viruses), which serve equivalent functions, and also bacteriophage and phagemid systems. The term "recombinant host cell" (or simply "host cell"), as used herein, is intended to refer to a cell into which a recombinant expression vector has been introduced. Such terms are intended to refer not only to the particular subject cell but to the progeny of such a cell, for example, when said progeny are employed to make a cell line or cell bank which is then optionally stored, provided, sold, transferred, or employed to manufacture an antibody or antigen-binding fragment thereof as described herein.

References to "subject", "patient" or "individual" refer to a subject, in particular a mammalian subject, to be treated. Mammalian subjects include humans, non-human primates, farm animals (such as cows), sports animals, or pet animals, such as dogs, cats, guinea pigs, rabbits, rats or mice. In some embodiment, the subject is a human. In alternative embodiments, the subject is a non-human mammal, such as a mouse.

The term "sufficient amount" means an amount sufficient to produce a desired effect. The term "therapeutically effective amount" is an amount that is effective to ameliorate a symptom of a disease or disorder. A therapeutically effective amount can be a "prophylactically effective amount" as prophylaxis can be considered therapy.

A disease or disorder is "ameliorated" if the severity of a sign or symptom of the disease or disorder, the frequency with which such a sign or symptom is experienced by a subject, or both, is reduced (compared to an earlier point in time, for example, prior to administration of any antibody).

As used herein, "treating a disease or disorder" means reducing the frequency and/or severity of at least one sign or symptom of the disease or disorder experienced by a subject (compared to an earlier point in time, for example, prior to administration of any antibody).

"Cancer," as used herein, refers to the abnormal growth or division of cells. Generally, the growth and/or life span of a cancer cell exceeds, and is not coordinated with, that of the normal cells and tissues around it. Cancers may be benign, pre-malignant or malignant. Cancer occurs in a variety of cells and tissues, including the oral cavity (e.g., mouth, tongue, pharynx, etc.), digestive system (e.g., esophagus, stomach, small intestine, colon, rectum, liver, bile duct, gall bladder, pancreas, etc.), respiratory system (e.g., larynx, lung, bronchus, etc.), bones, joints, skin (e.g., basal cell, squamous cell, meningioma, etc.), breast, genital system, (e.g., uterus, ovary, prostate, testis, etc.), urinary system (e.g., bladder, kidney, ureter, etc.), eye, nervous system (e.g., brain, etc.), endocrine system (e.g., thyroid, etc.), and hematopoietic system (e.g., lymphoma, myeloma, leukemia, acute lymphocytic leukemia, chronic lymphocytic leukemia, acute myeloid leukemia, chronic myeloid leukemia, etc.).

As used herein, the term "about" when used herein includes up to and including 10% greater and up to and including 10% lower than the value specified, suitably up to and including κ% greater and up to and including 5% lower than the value specified, especially the value specified. The term "between", includes the values of the specified boundaries.

Antibodies and Antigen-Binding Fragments Thereof

Provided herein are antibodies or antigen-binding fragments thereof capable of specifically binding to the delta variable 1 chain (Vδ1) of a γδ T Cell Receptor (TCR). The invention relates to the use of said antibodies as medicaments for administration to a subject to be treated.

In one embodiment, the antibody or antigen-binding fragment thereof is an scFv, Fab, Fab', F(ab')2, Fv, variable domain (e.g. VH or VL), diabody, minibody or monoclonal antibody. In a further embodiment, the antibody or antigen-binding fragment thereof is an scFv.

Antibodies of the invention can be of any class, e.g. IgG, IgA, IgM, IgE, IgD, or isotypes thereof, and can comprise a kappa or lambda light chain. In one embodiment, the antibody is an IgG antibody, for example, at least one of isotypes, IgG1, IgG2, IgG3 or IgG4. In a further embodiment, the antibody may be in a format, such as an IgG format, that has been modified to confer desired properties, such as having the Fc mutated to reduce effector function, extend half-life, alter ADCC, or improve hinge stability. Such modifications are well known in the art.

In one embodiment, the antibody or antigen-binding fragment thereof is human. Thus, the antibody or antigen-binding fragment thereof may be derived from a human immunoglobulin (Ig) sequence. The CDR, framework and/or constant region of the antibody (or antigen-binding fragment thereof) may be derived from a human Ig sequence, in particular a human IgG sequence. The CDR, framework and/or constant region may be substantially identical for a human Ig sequence, in particular a human IgG sequence. An advantage of using human antibodies is that they are low or non-immunogenic in humans.

An antibody or antigen-binding fragment thereof can also be chimeric, for example a mouse-human antibody chimera.

Alternatively, the antibody or antigen-binding fragment thereof is derived from a non-human species, such as a mouse. Such non-human antibodies can be modified to increase their similarity to antibody variants produced naturally in humans, thus the antibody or antigen-binding fragment thereof can be partially or fully humanised. Therefore, in one embodiment, the antibody or antigen-binding fragment thereof is humanised.

Summary of Specific Antibodies Provided Herein

A summary of some of the specific antigen-binding molecules (i.e. antibodies) provided by the present invention is provided below, with identification of the assigned SEQ ID NO. in the accompanying sequence listing. Antigen-binding variants, derivatives and fragments thereof are also provided as part of the present invention. Sequences are provided in the attached sequence listing and the accompanying Figures. In the case of any discrepancy between the sequences in the sequence listing and those in FIGS. 45 to 48, the sequences in the Figures should prevail.

TABLE 1

Summary of antibodies derived from ADT1-4 (heavy chain) and the related SEQ ID NOs

| Antibody | VH | HFR1 | VHCDR1 | HFR2 | VHCDR2 | HFR3 | VHCDR3 | HFR4 |
|---|---|---|---|---|---|---|---|---|
| Parental ADT1-4 | 1 | 170 | 51 | 172 | 53 | 173 | 54 | 174 |
| ADT1-4-105 | 2 | 170 | 51 | 172 | 53 | 173 | 55 | 174 |
| ADT1-4-107 | 3 | 170 | 51 | 172 | 53 | 173 | 56 | 174 |
| ADT1-4-110 | 4 | 170 | 51 | 172 | 53 | 173 | 57 | 174 |
| ADT1-4-112 | 5 | 170 | 51 | 172 | 53 | 173 | 58 | 174 |
| ADT1-4-117 | 6 | 170 | 51 | 172 | 53 | 173 | 59 | 174 |
| ADT1-4-19 | 7 | 170 | 51 | 172 | 53 | 173 | 60 | 174 |
| ADT1-4-21 | 8 | 170 | 52 | 172 | 53 | 173 | 61 | 174 |
| ADT1-4-31 | 9 | 170 | 51 | 172 | 53 | 173 | 62 | 174 |
| ADT1-4-139 | 10 | 170 | 51 | 172 | 53 | 173 | 63 | 174 |
| ADT1-4-4 | 11 | 170 | 51 | 172 | 53 | 173 | 64 | 174 |
| ADT1-4-143 | 12 | 171 | 51 | 172 | 53 | 173 | 65 | 174 |
| ADT1-4-53 | 13 | 170 | 52 | 172 | 53 | 173 | 66 | 174 |
| ADT1-4-173 | 14 | 170 | 51 | 172 | 53 | 173 | 67 | 174 |
| ADT1-4-2 | 15 | 170 | 51 | 172 | 53 | 173 | 68 | 174 |
| ADT1-4-8 | 16 | 170 | 51 | 172 | 53 | 173 | 69 | 174 |
| ADT1-4-82 | 17 | 170 | 51 | 172 | 53 | 173 | 70 | 174 |
| ADT1-4-83 | 18 | 170 | 51 | 172 | 53 | 173 | 71 | 174 |
| ADT1-4-3 | 19 | 170 | 51 | 172 | 53 | 173 | 72 | 174 |
| ADT1-4-84 | 20 | 170 | 51 | 172 | 53 | 173 | 73 | 174 |
| ADT1-4-86 | 21 | 170 | 52 | 172 | 53 | 173 | 74 | 174 |
| ADT1-4-95 | 22 | 170 | 51 | 172 | 53 | 173 | 75 | 174 |
| ADT1-4-1 | 23 | 170 | 51 | 172 | 53 | 173 | 76 | 174 |
| ADT1-4-6 | 24 | 170 | 51 | 172 | 53 | 173 | 77 | 174 |
| ADT1-4-138 | 25 | 170 | 51 | 172 | 53 | 173 | 78 | 174 |

TABLE 2

Summary of antibodies derived from ADT1-4 (light chain) and the related SEQ ID NOs

| Antibody | VL | LFR1 | VLCDR1 | LFR2 | VLCDR2 | LFR3 | VLCDR3 | LFR4 |
|---|---|---|---|---|---|---|---|---|
| Parental ADT1-4 | 26 | 175 | 79 | 176 | 80 | 178 | 81 | 179 |
| ADT1-4-105 | 27 | 175 | 79 | 176 | 80 | 177 | 82 | 179 |
| ADT1-4-107 | 28 | 175 | 79 | 176 | 80 | 177 | 83 | 179 |
| ADT1-4-110 | 29 | 175 | 79 | 176 | 80 | 177 | 84 | 180 |
| ADT1-4-112 | 30 | 175 | 79 | 176 | 80 | 177 | 85 | 179 |
| ADT1-4-117 | 31 | 175 | 79 | 176 | 80 | 177 | 86 | 179 |
| ADT1-4-19 | 32 | 175 | 79 | 176 | 80 | 177 | 87 | 179 |
| ADT1-4-21 | 33 | 175 | 79 | 176 | 80 | 177 | 88 | 179 |
| ADT1-4-31 | 34 | 175 | 79 | 176 | 80 | 177 | 89 | 179 |
| ADT1-4-139 | 35 | 175 | 79 | 176 | 80 | 177 | 90 | 179 |
| ADT1-4-4 | 36 | 175 | 79 | 176 | 80 | 177 | 91 | 179 |
| ADT1-4-143 | 37 | 175 | 79 | 176 | 80 | 177 | 92 | 181 |
| ADT1-4-53 | 38 | 175 | 79 | 176 | 80 | 177 | 93 | 179 |
| ADT1-4-173 | 39 | 175 | 79 | 176 | 80 | 177 | 94 | 179 |
| ADT1-4-2 | 40 | 175 | 79 | 176 | 80 | 177 | 95 | 179 |
| ADT1-4-8 | 41 | 175 | 79 | 176 | 80 | 177 | 96 | 179 |
| ADT1-4-82 | 42 | 175 | 79 | 176 | 80 | 177 | 97 | 179 |
| ADT1-4-83 | 43 | 175 | 79 | 176 | 80 | 177 | 98 | 179 |
| ADT1-4-3 | 44 | 175 | 79 | 176 | 80 | 177 | 99 | 179 |
| ADT1-4-84 | 45 | 175 | 79 | 176 | 80 | 177 | 100 | 179 |
| ADT1-4-86 | 46 | 175 | 79 | 176 | 80 | 177 | 101 | 179 |
| ADT1-4-95 | 47 | 175 | 79 | 176 | 80 | 177 | 102 | 182 |
| ADT1-4-1 | 48 | 175 | 79 | 176 | 80 | 177 | 103 | 179 |
| ADT1-4-6 | 49 | 175 | 79 | 176 | 80 | 177 | 104 | 179 |
| ADT1-4-138 | 50 | 175 | 79 | 176 | 80 | 178 | 105 | 179 |

TABLE 3

Summary of antibodies derived from ADT1-7 (heavy chain) and the related SEQ ID NOs

| Antibody | VH | HFR1 | VHCDR1 | HFR2 | VHCDR2 | HFR3 | VHCDR3 | HFR4 |
|---|---|---|---|---|---|---|---|---|
| Parental ADT1-4 | 106 | 189 | 130 | 190 | 131 | 191 | 132 | 192 |
| ADT1-7-10 | 107 | 189 | 130 | 190 | 131 | 191 | 133 | 192 |
| ADT1-7-15 | 108 | 189 | 130 | 190 | 131 | 191 | 134 | 192 |
| ADT1-7-17 | 109 | 189 | 130 | 190 | 131 | 191 | 135 | 192 |
| ADT1-7-18 | 110 | 189 | 130 | 190 | 131 | 191 | 136 | 192 |
| ADT1-7-19 | 111 | 189 | 130 | 190 | 131 | 191 | 137 | 192 |
| ADT1-7-20 | 112 | 189 | 130 | 190 | 131 | 191 | 138 | 192 |
| ADT1-7-22 | 113 | 189 | 130 | 190 | 131 | 191 | 139 | 192 |
| ADT1-7-23 | 114 | 189 | 130 | 190 | 131 | 191 | 140 | 192 |
| ADT1-7-42 | 115 | 189 | 130 | 190 | 131 | 191 | 141 | 192 |
| ADT1-7-3 | 116 | 189 | 130 | 190 | 131 | 191 | 142 | 192 |
| ADT1-7-61 | 117 | 189 | 130 | 190 | 131 | 191 | 143 | 192 |

TABLE 4

Summary of antibodies derived from ADT1-7 (light chain) and the related SEQ ID NOs

| Antibody | VL | LFR1 | VLCDR1 | LFR2 | VLCDR2 | LFR3 | VLCDR3 | LFR4 |
|---|---|---|---|---|---|---|---|---|
| Parental ADT1-7 | 118 | 193 | 144 | 195 | 145 | 196 | 146 | 197 |
| ADT1-7-10 | 119 | 193 | 144 | 195 | 145 | 196 | 147 | 197 |
| ADT1-7-15 | 120 | 193 | 144 | 195 | 145 | 196 | 148 | 197 |
| ADT1-7-17 | 121 | 193 | 144 | 195 | 145 | 196 | 149 | 197 |
| ADT1-7-18 | 122 | 194 | 144 | 195 | 145 | 196 | 150 | 197 |
| ADT1-7-19 | 123 | 193 | 144 | 195 | 145 | 196 | 151 | 197 |
| ADT1-7-20 | 124 | 193 | 144 | 195 | 145 | 196 | 152 | 197 |
| ADT1-7-22 | 125 | 193 | 144 | 195 | 145 | 196 | 153 | 197 |
| ADT1-7-23 | 126 | 193 | 144 | 195 | 145 | 196 | 154 | 197 |
| ADT1-7-42 | 127 | 193 | 144 | 195 | 145 | 196 | 155 | 197 |
| ADT1-7-3 | 128 | 193 | 144 | 195 | 145 | 196 | 156 | 197 |
| ADT1-7-61 | 129 | 193 | 144 | 195 | 145 | 196 | 157 | 197 |

TABLE 5

Summary of other parental antibodies and the related SEQ ID NOs

| Parental Antibody | VH | VL |
|---|---|---|
| C08 | 273 | 282 |
| B07 | 274 | 283 |
| C05 | 275 | 284 |
| E04 | 276 | 285 |
| F07 | 277 | 286 |
| G06 | 278 | 287 |
| G09 | 279 | 288 |
| B09 | 280 | 289 |
| G10 | 281 | 290 |
| E01 | 312 | 313 |

ADT1-4- and ADT1-7-Derived Antibodies

The present invention provides antibodies derived from parental antibody ADT1-4 (having a variable heavy region sequence according to SEQ ID NO: 1 and a variable light region sequence according to SEQ ID NO: 26), and antibodies derived from parental antibody ADT1-7 (having a variable heavy region sequence according to SEQ ID NO: 106 and a variable light region sequence according to SEQ ID No: 118). ADT1-4 is also referred to herein as G04, and ADT1-4 and G04 are used interchangeably. ADT1-7 is also referred to herein as E07, and ADT1-7 and E07 are used interchangeably.

In some embodiments, the invention provides an anti-TCR delta variable 1 (anti-Vδ1) antibody or antigen-binding fragment thereof comprising:

- a heavy chain variable region comprising or consisting of a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of SEQ ID NOs: 55 to 78 and 133 to 143; and/or a light chain variable region comprising a VLCDR3 comprising or consisting of an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of SEQ ID NOs: 82 to 105 and 147 to 157. Certain amino acid substitutions may be made to provide one or more variant antibodies as described herein.

In some embodiments, the invention provides an anti-TCR delta variable 1 (anti-Vδ1) antibody or antigen-binding fragment thereof comprising:

- a heavy chain variable region comprising:
  - a VHCDR1 comprising or consisting of an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of: SEQ ID NOs: 51, 52 and 130;
  - a VHCDR2 comprising or consisting of an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of: SEQ ID NO: 53 and 131; and a VHCDR3 comprising or consisting of an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of: SEQ ID NOs: 55 to 78 and 133 to 143; and
- a light chain variable region comprising:
  - a VLCDR1 comprising or consisting of an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of: SEQ ID NO: 79 and 144;
  - a VLCDR2 comprising or consisting of an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of: SEQ ID NO: 80 and 145; and
  - a VLCDR3 comprising or consisting of an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of: SEQ ID NOs: 82 to 105 and 147 to 157.

Certain amino acid substitutions may be made to provide one or more variant antibodies as described herein.

In some embodiments, the invention provides an anti-TCR delta variable 1 (anti-Vδ1) antibody or antigen-binding fragment thereof comprising:

- a heavy chain variable region comprising or consisting of a sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of SEQ ID NOs: 2 to 25 and 107 to 117; and/or
- a light chain variable region comprising or consisting of a sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of SEQ ID NOs: 27 to 50 and 119 to 129.

ADT1-4-Derived Antibodies

The present invention provides antibodies derived from parental antibody ADT1-4 (having a variable heavy region sequence according to SEQ ID NO: 1 and a variable light region sequence according to SEQ ID NO: 26), for example as set out in the following. ADT1-4 is also referred to herein as G04, and ADT1-4 and G04 are used interchangeably.

Antibodies Comprising Particular CDR Sequences Derived from ADT1-4

The antibodies provided herein include the following antibodies having particular sequences derived from ADT1-4.

For example, in some embodiments, there is provided an anti-TCR delta variable 1 (anti-Vδ1) antibody or antigen-binding fragment thereof comprising a heavy chain variable region comprising a VHCDR3 comprising or consisting of an amino acid sequence selected from the group consisting of SEQ ID NOs: 55 to 78; and/or a light chain variable region comprising a VLCDR3 comprising or consisting of an amino acid sequence selected from the group consisting of SEQ ID NOs: 82 to 105. Certain amino acid substitutions may be made to provide one or more variant antibodies as described herein.

In some embodiments, there is provided an anti-TCR delta variable 1 (anti-Vδ1) antibody or antigen-binding fragment thereof comprising a heavy chain variable region comprising a VHCDR3 comprising or consisting of an amino acid sequence selected from the group consisting of SEQ ID NOs: 55 to 77; and/or a light chain variable region comprising a VLCDR3 comprising or consisting of an amino acid sequence selected from the group consisting of SEQ ID NOs: 82 to 104. Certain amino acid substitutions may be made to provide one or more variant antibodies as described herein.

In some embodiments, there is provided an anti-TCR delta variable 1 (anti-Vδ1) antibody or antigen-binding fragment thereof comprising a heavy chain variable region comprising a VHCDR3 comprising or consisting of an amino acid sequence selected from the group consisting of SEQ ID NOs: 58, 60, 61, 62, 65, 66, 68, 74, 76 and 77; and/or a light chain variable region comprising a VLCDR3 comprising or consisting of an amino acid sequence selected from the group consisting of SEQ ID NOs: 85, 87, 88, 89, 92, 93, 95, 101, 103 and 104. Certain amino acid substitutions may be made to provide one or more variant antibodies as described herein.

There is also provided an anti-TCR delta variable 1 (anti-Vδ1) antibody or antigen-binding fragment thereof comprising:

- a heavy chain variable region comprising:
  - a VHCDR1 comprising or consisting of an amino acid sequence selected from the group consisting of: SEQ ID NOs: 51 and 52;
  - a VHCDR2 comprising or consisting of the amino acid sequence of SEQ ID NO: 53; and
  - a VHCDR3 comprising or consisting of an amino acid sequence selected from the group consisting of: SEQ ID NOs: 55 to 78; and
- a light chain variable region comprising:
  - a VLCDR1 comprising or consisting of the amino acid sequence of SEQ ID NO: 79;
  - a VLCDR2 comprising or consisting of the amino acid sequence of SEQ ID NO: 80; and
  - a VLCDR3 comprising or consisting of an amino acid sequence selected from the group consisting of: SEQ ID NOs: 82 to 105.

Certain amino acid substitutions may be made to provide one or more variant antibodies as described herein.

There is also provided an anti-TCR delta variable 1 (anti-Vδ1) antibody or antigen-binding fragment thereof comprising:

- a heavy chain variable region comprising:
  - a VHCDR1 comprising or consisting of an amino acid sequence selected from the group consisting of: SEQ ID NOs: 51 and 52;
  - a VHCDR2 comprising or consisting of the amino acid sequence of SEQ ID NO: 53; and
  - a VHCDR3 comprising or consisting of an amino acid sequence selected from the group consisting of: SEQ ID NOs: 55 to 77; and
- a light chain variable region comprising:
  - a VLCDR1 comprising or consisting of the amino acid sequence of SEQ ID NO: 79;
  - a VLCDR2 comprising or consisting of the amino acid sequence of SEQ ID NO: 80; and
  - a VLCDR3 comprising or consisting of an amino acid sequence selected from the group consisting of: SEQ ID NOs: 82 to 104.

Certain amino acid substitutions may be made to provide one or more variant antibodies as described herein.

There is also provided an anti-TCR delta variable 1 (anti-Vδ1) antibody or antigen-binding fragment thereof comprising:

- a heavy chain variable region comprising:
  - a VHCDR1 comprising or consisting of an amino acid sequence selected from the group consisting of: SEQ ID NOs: 51 and 52;
  - a VHCDR2 comprising or consisting of the amino acid sequence of SEQ ID NO: 53; and
  - a VHCDR3 comprising or consisting of an amino acid sequence selected from the group consisting of: SEQ ID NOs: 58, 60, 61, 62, 65, 66, 68, 74, 76 and 77; and
- a light chain variable region comprising:
  - a VLCDR1 comprising or consisting of the amino acid sequence of SEQ ID NO: 79;
  - a VLCDR2 comprising or consisting of the amino acid sequence of SEQ ID NO: 80; and
  - a VLCDR3 comprising or consisting of an amino acid sequence selected from the group consisting of: SEQ ID NOs: 85, 87, 88, 89, 92, 93, 95, 101, 103 and 104.

Certain amino acid substitutions may be made to provide one or more variant antibodies as described herein.

There is also provided an anti-TCR delta variable 1 (anti-Vδ1) antibody or antigen-binding fragment thereof comprising a) a VHCDR1, a VHCDR2 and a VHCDR3 comprising or consisting of the amino acid sequences of SEQ ID NO: 51, 53 and 55, respectively, and a VLCDR1, a VLCDR2 and a VLCDR3 comprising or consisting of the amino acid sequences of SEQ ID NOs: 79, 80 and 82, respectively;

b) a VHCDR1, a VHCDR2 and a VHCDR3 comprising or consisting of the amino acid sequences of SEQ ID NO: 51, 53 and 56, respectively, and a VLCDR1, a VLCDR2 and a VLCDR3 comprising or consisting of the amino acid sequences of SEQ ID NOs: 79, 80 and 83, respectively;

c) a VHCDR1, a VHCDR2 and a VHCDR3 comprising or consisting of the amino acid sequences of SEQ ID NO: 51, 53 and 57, respectively, and a VLCDR1, a VLCDR2 and a VLCDR3 comprising or consisting of the amino acid sequences of SEQ ID NOs: 79, 80 and 84, respectively;

d) a VHCDR1, a VHCDR2 and a VHCDR3 comprising or consisting of the amino acid sequences of SEQ ID NO: 51, 53 and 58, respectively, and a VLCDR1, a VLCDR2 and a VLCDR3 comprising or consisting of the amino acid sequences of SEQ ID NOs: 79, 80 and 85, respectively;

e) a VHCDR1, a VHCDR2 and a VHCDR3 comprising or consisting of the amino acid sequences of SEQ ID NO: 51, 53 and 59, respectively, and a VLCDR1, a VLCDR2 and a VLCDR3 comprising or consisting of the amino acid sequences of SEQ ID NOs: 79, 80 and 86, respectively;

f) a VHCDR1, a VHCDR2 and a VHCDR3 comprising or consisting of the amino acid sequences of SEQ ID NO: 51, 53 and 60, respectively, and a VLCDR1, a VLCDR2 and a VLCDR3 comprising or consisting of the amino acid sequences of SEQ ID NOs: 79, 80 and 87, respectively;

g) a VHCDR1, a VHCDR2 and a VHCDR3 comprising or consisting of the amino acid sequences of SEQ ID NO: 52, 53 and 61, respectively, and a VLCDR1, a VLCDR2 and a VLCDR3 comprising or consisting of the amino acid sequences of SEQ ID NOs: 79, 80 and 88, respectively;

h) a VHCDR1, a VHCDR2 and a VHCDR3 comprising or consisting of the amino acid sequences of SEQ ID NO: 51, 53 and 62, respectively, and a VLCDR1, a VLCDR2 and a VLCDR3 comprising or consisting of the amino acid sequences of SEQ ID NOs: 79, 80 and 89, respectively;

i) a VHCDR1, a VHCDR2 and a VHCDR3 comprising or consisting of the amino acid sequences of SEQ ID NO: 51, 53 and 63, respectively, and a VLCDR1, a VLCDR2 and a VLCDR3 comprising or consisting of the amino acid sequences of SEQ ID NOs: 79, 80 and 90, respectively;

j) a VHCDR1, a VHCDR2 and a VHCDR3 comprising or consisting of the amino acid sequences of SEQ ID NO: 51, 53 and 64, respectively, and a VLCDR1, a VLCDR2 and a VLCDR3 comprising or consisting of the amino acid sequences of SEQ ID NOs: 79, 80 and 91, respectively;

k) a VHCDR1, a VHCDR2 and a VHCDR3 comprising or consisting of the amino acid sequences of SEQ ID NO: 51, 53 and 65, respectively, and a VLCDR1, a VLCDR2 and a VLCDR3 comprising or consisting of the amino acid sequences of SEQ ID NOs: 79, 80 and 92, respectively;

l) a VHCDR1, a VHCDR2 and a VHCDR3 comprising or consisting of the amino acid sequences of SEQ ID NO: 52, 53 and 66, respectively, and a VLCDR1, a VLCDR2 and a VLCDR3 comprising or consisting of the amino acid sequences of SEQ ID NOs: 79, 80 and 93, respectively;

m) a VHCDR1, a VHCDR2 and a VHCDR3 comprising or consisting of the amino acid sequences of SEQ ID NO: 51, 53 and 67, respectively, and a VLCDR1, a VLCDR2 and a VLCDR3 comprising or consisting of the amino acid sequences of SEQ ID NOs: 79, 80 and 94, respectively;

n) a VHCDR1, a VHCDR2 and a VHCDR3 comprising or consisting of the amino acid sequences of SEQ ID NO: 51, 53 and 68, respectively, and a VLCDR1, a VLCDR2 and a VLCDR3 comprising or consisting of the amino acid sequences of SEQ ID NOs: 79, 80 and 95, respectively;

o) a VHCDR1, a VHCDR2 and a VHCDR3 comprising or consisting of the amino acid sequences of SEQ ID NO: 51, 53 and 69, respectively, and a VLCDR1, a VLCDR2 and a VLCDR3 comprising or consisting of the amino acid sequences of SEQ ID NOs: 79, 80 and 96, respectively;

p) a VHCDR1, a VHCDR2 and a VHCDR3 comprising or consisting of the amino acid sequences of SEQ ID NO: 51, 53 and 70, respectively, and a VLCDR1, a VLCDR2 and a VLCDR3 comprising or consisting of the amino acid sequences of SEQ ID NOs: 79, 80 and 97, respectively;

q) a VHCDR1, a VHCDR2 and a VHCDR3 comprising or consisting of the amino acid sequences of SEQ ID NO: 51, 53 and 71, respectively, and a VLCDR1, a VLCDR2 and a VLCDR3 comprising or consisting of the amino acid sequences of SEQ ID NOs: 79, 80 and 98, respectively;

r) a VHCDR1, a VHCDR2 and a VHCDR3 comprising or consisting of the amino acid sequences of SEQ ID NO: 51, 53 and 72, respectively, and a VLCDR1, a VLCDR2 and a VLCDR3 comprising or consisting of the amino acid sequences of SEQ ID NOs: 79, 80 and 99, respectively;

s) a VHCDR1, a VHCDR2 and a VHCDR3 comprising or consisting of the amino acid sequences of SEQ ID NO: 51, 53 and 73, respectively, and a VLCDR1, a VLCDR2 and a VLCDR3 comprising or consisting of the amino acid sequences of SEQ ID NOs: 79, 80 and 100, respectively;

t) a VHCDR1, a VHCDR2 and a VHCDR3 comprising or consisting of the amino acid sequences of SEQ ID NO: 52, 53 and 74, respectively, and a VLCDR1, a VLCDR2 and a VLCDR3 comprising or consisting of the amino acid sequences of SEQ ID NOs: 79, 80 and 101, respectively;

u) a VHCDR1, a VHCDR2 and a VHCDR3 comprising or consisting of the amino acid sequences of SEQ ID NO: 51, 53 and 75, respectively, and a VLCDR1, a VLCDR2 and a VLCDR3 comprising or consisting of the amino acid sequences of SEQ ID NOs: 79, 80 and 102, respectively;

v) a VHCDR1, a VHCDR2 and a VHCDR3 comprising or consisting of the amino acid sequences of SEQ ID NO: 51, 53 and 76, respectively, and a VLCDR1, a VLCDR2 and a VLCDR3 comprising or consisting of the amino acid sequences of SEQ ID NOs: 79, 80 and 103, respectively;

w) a VHCDR1, a VHCDR2 and a VHCDR3 comprising or consisting of the amino acid sequences of SEQ ID NO: 51, 53 and 77, respectively, and a VLCDR1, a VLCDR2 and a VLCDR3 comprising or consisting of the amino acid sequences of SEQ ID NOs: 79, 80 and 104, respectively; or;

x) a VHCDR1, a VHCDR2 and a VHCDR3 comprising or consisting of the amino acid sequences of SEQ ID NO: 51, 53 and 78, respectively, and a VLCDR1, a VLCDR2 and a VLCDR3 comprising or consisting of the amino acid sequences of SEQ ID NOs: 79, 80 and 105, respectively.

The anti-Vδ1 antibodies or antigen-binding fragments thereof may comprise a kappa light chain variable sequence (or comprise a variable light chain that is derived from a kappa light chain variable sequence), wherein the residue at position 74 of the kappa light chain variable sequence according to the IMGT numbering system is not serine, for example a non-human-germline residue and/or a non-polar residue at position 74, for example the residue at position 74 is a leucine residue.

Further embodiments are provided below.

ADT1-4-105 and Fragments and Variants Thereof

Certain embodiments relate to the antibody ADT1-4-105 and fragments and variants thereof.

For example, in some embodiments, an antibody or antigen-binding fragment or variant thereof is provided comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 55 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 82. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 55 and/or a light chain variable region comprising a VLCDR3 comprising an amino acid sequence having at least 90% identity to the amino acid sequence of SEQ ID NO: 82. In one embodiment, an antibody or antigen-binding fragment or variant thereof is provided comprising a heavy chain variable region comprising a VHCDR3 comprising the amino acid sequence of SEQ ID NO: 55 and/or a light chain variable region comprising a VLCDR3 comprising the amino acid sequence of SEQ ID NO: 82.

Amino acid substitutions may be made to provide variant antibodies derived from ADT1-4-105, for example an antibody or antigen-binding fragment or variant thereof is provided comprising a heavy chain variable region comprising a VHCDR3 comprising the amino acid sequence of SEQ ID NO: 55, optionally comprising 1 or 2 amino acid substitutions, and/or a light chain variable region comprising a VLCDR3 comprising the amino acid sequence of SEQ ID NO: 82, optionally comprising 1 or 2 amino acid substitutions. The amino acid substitutions may be conservative amino acid substitutions.

In some embodiments, an antibody or antigen-binding fragment or variant thereof is provided comprising:

- a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 55; and/or
- a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 82.

In one embodiment, an antibody or antigen-binding fragment or variant thereof is provided comprising:

- a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 55; and/or
- a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 82.

In one embodiment, an antibody or antigen-binding fragment or variant thereof is provided comprising:

- a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 55; and
- a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 82.

Amino acid substitutions may be made to provide variant antibodies derived from ADT1-4-105, for example an antibody or antigen-binding fragment or variant thereof is provided comprising:

- a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 55 optionally comprising 1 or 2 amino acid substitutions; and/or
- a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 82 optionally comprising 1 or 2 amino acid substitutions. The amino acid substitutions may be conservative amino acid substitutions.

The antibodies may alternatively consist of the specified sequences (with or without amino acid substitutions).

ADT1-4-107 and Fragments and Variants Thereof

Certain embodiments relate to the antibody ADT1-4-107 and fragments and variants thereof.

For example, in some embodiments, an antibody or antigen-binding fragment or variant thereof is provided comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 56 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO:83. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 56 and/or a light chain variable region comprising a VLCDR3 comprising an amino acid sequence having at least 90% identity to the amino acid sequence of SEQ ID NO: 83. In one embodiment, an antibody or antigen-binding fragment or variant thereof is provided comprising a heavy chain variable region comprising a VHCDR3 comprising the amino acid sequence of SEQ ID NO: 56 and/or a light chain variable region comprising a VLCDR3 comprising the amino acid sequence of SEQ ID NO: 83.

Amino acid substitutions may be made to provide variant antibodies derived from ADT1-4-107, for example an antibody or antigen-binding fragment or variant thereof is provided comprising a heavy chain variable region comprising a VHCDR3 comprising the amino acid sequence of SEQ ID NO: 56, optionally comprising 1 or 2 amino acid substitutions, and/or a light chain variable region comprising a VLCDR3 comprising the amino acid sequence of SEQ ID NO: 83, optionally comprising 1 or 2 amino acid substitutions. The amino acid substitutions may be conservative amino acid substitutions.

In some embodiments, an antibody or antigen-binding fragment or variant thereof is provided comprising:

- a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 56; and/or
- a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 83.

In one embodiment, an antibody or antigen-binding fragment or variant thereof is provided comprising:

- a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 56; and/or
- a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 83.

In one embodiment, an antibody or antigen-binding fragment or variant thereof is provided comprising:

- a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 56; and
- a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 83.

Amino acid substitutions may be made to provide variant antibodies derived from ADT1-4-107, for example an antibody or antigen-binding fragment or variant thereof is provided comprising:

- a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 56 optionally comprising 1 or 2 amino acid substitutions; and/or
- a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 83 optionally comprising 1 or 2 amino acid substitutions. The amino acid substitutions may be conservative amino acid substitutions.

The antibodies may alternatively consist of the specified sequences (with or without amino acid substitutions).

ADT1-4-110 and Fragments and Variants Thereof

Certain embodiments relate to the antibody ADT1-4-110 and fragments and variants thereof.

For example, in some embodiments, an antibody or antigen-binding fragment or variant thereof is provided comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 57 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 84. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 57 and/or a light chain variable region comprising a VLCDR3 comprising an amino acid sequence having at least 90% identity to the amino acid sequence of SEQ ID NO: 84. In one embodiment, an antibody or antigen-binding fragment or variant thereof is provided comprising a heavy chain variable region comprising a VHCDR3 comprising the amino acid sequence of SEQ ID NO: 57 and/or a light chain variable region comprising a VLCDR3 comprising the amino acid sequence of SEQ ID NO: 84.

Amino acid substitutions may be made to provide variant antibodies derived from ADT1-4-110, for example an antibody or antigen-binding fragment or variant thereof is provided comprising a heavy chain variable region comprising a VHCDR3 comprising the amino acid sequence of SEQ ID NO: 57, optionally comprising 1 or 2 amino acid substitutions, and/or a light chain variable region comprising a VLCDR3 comprising the amino acid sequence of SEQ ID NO: 84, optionally comprising 1 or 2 amino acid substitutions. The amino acid substitutions may be conservative amino acid substitutions.

In some embodiments, an antibody or antigen-binding fragment or variant thereof is provided comprising:

- a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 57; and/or
- a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 84.

In one embodiment, an antibody or antigen-binding fragment or variant thereof is provided comprising:

- a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 57; and/or
- a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 84.

In one embodiment, an antibody or antigen-binding fragment or variant thereof is provided comprising:

- a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 57; and
- a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 84.

Amino acid substitutions may be made to provide variant antibodies derived from ADT1-4-110, for example an antibody or antigen-binding fragment or variant thereof is provided comprising:

- a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 57 optionally comprising 1 or 2 amino acid substitutions; and/or
- a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 84 optionally comprising 1 or 2 amino acid substitutions. The amino acid substitutions may be conservative amino acid substitutions.

The antibodies may alternatively consist of the specified sequences (with or without amino acid substitutions).

ADT1-4-112 and Fragments and Variants Thereof

Certain embodiments relate to the antibody ADT1-4-112 and fragments and variants thereof.

For example, in some embodiments, an antibody or antigen-binding fragment or variant thereof is provided comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 58 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 85. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 58 and/or a light chain variable region comprising a VLCDR3 comprising an amino acid sequence having at least 90% identity to the amino acid sequence of SEQ ID NO: 85. In one embodiment, an antibody or antigen-binding fragment or variant thereof is provided comprising a heavy chain variable region comprising a VHCDR3 comprising the amino acid sequence of SEQ ID NO: 58 and/or a light chain variable region comprising a VLCDR3 comprising the amino acid sequence of SEQ ID NO: 85.

Amino acid substitutions may be made to provide variant antibodies derived from ADT1-4-112, for example an antibody or antigen-binding fragment or variant thereof is provided comprising a heavy chain variable region comprising a VHCDR3 comprising the amino acid sequence of SEQ ID NO: 58, optionally comprising 1 or 2 amino acid substitutions, and/or a light chain variable region comprising a VLCDR3 comprising the amino acid sequence of SEQ ID NO: 85, optionally comprising 1 or 2 amino acid substitutions. The amino acid substitutions may be conservative amino acid substitutions.

In some embodiments, an antibody or antigen-binding fragment or variant thereof is provided comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 58; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 85.

In one embodiment, an antibody or antigen-binding fragment or variant thereof is provided comprising:

a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 58; and/or a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 85.

In one embodiment, an antibody or antigen-binding fragment or variant thereof is provided comprising:

a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 58; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 85.

Amino acid substitutions may be made to provide variant antibodies derived from ADT1-4-112, for example an antibody or antigen-binding fragment or variant thereof is provided comprising:

a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 58 optionally comprising 1 or 2 amino acid substitutions; and/or a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 85 optionally comprising 1 or 2 amino acid substitutions. The amino acid substitutions may be conservative amino acid substitutions.

The antibodies may alternatively consist of the specified sequences (with o-r without amino acid substitutions).

ADT1-4-117 and Fragments and Variants Thereof

Certain embodiments relate to the antibody ADT1-4-117 and fragments and variants thereof.

For example, in some embodiments, an antibody or antigen-binding fragment or variant thereof is provided comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 59 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 86. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 59 and/or a light chain variable region comprising a VLCDR3 comprising an amino acid sequence having at least 90% identity to the amino acid sequence of SEQ ID NO: 86. In one embodiment, an antibody or antigen-binding fragment or variant thereof is provided comprising a heavy chain variable region comprising a VHCDR3 comprising the amino acid sequence of SEQ ID NO: 59 and/or a light chain variable region comprising a VLCDR3 comprising the amino acid sequence of SEQ ID NO: 86.

Amino acid substitutions may be made to provide variant antibodies derived from ADT1-4-117, for example an antibody or antigen-binding fragment or variant thereof is provided comprising a heavy chain variable region comprising a VHCDR3 comprising the amino acid sequence of SEQ ID NO: 59, optionally comprising 1 or 2 amino acid substitutions, and/or a light chain variable region comprising a VLCDR3 comprising the amino acid sequence of SEQ ID NO: 86, optionally comprising 1 or 2 amino acid substitutions. The amino acid substitutions may be conservative amino acid substitutions.

In some embodiments, an antibody or antigen-binding fragment or variant thereof is provided comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 59; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 86.

In one embodiment, an antibody or antigen-binding fragment or variant thereof is provided comprising:

a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 59; and/or a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 86.

In one embodiment, an antibody or antigen-binding fragment or variant thereof is provided comprising:

a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 59; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 86.

Amino acid substitutions may be made to provide variant antibodies derived from ADT1-4-117, for example an antibody or antigen-binding fragment or variant thereof is provided comprising:

a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 59 optionally comprising 1 or 2 amino acid substitutions; and/or a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 86 optionally comprising 1 or 2 amino acid substitutions. The amino acid substitutions may be conservative amino acid substitutions.

The antibodies may alternatively consist of the specified sequences (with or without amino acid substitutions).

ADT1-4-19 and Fragments and Variants Thereof

Certain embodiments relate to the antibody ADT1-4-19 and fragments and variants thereof.

For example, in some embodiments, an antibody or antigen-binding fragment or variant thereof is provided comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 60 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 87. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 60 and/or a light chain variable region comprising a VLCDR3 comprising an amino acid sequence having at least 90% identity to the amino acid sequence of SEQ ID NO: 87. In one embodiment, an antibody or antigen-binding fragment or variant thereof is provided comprising a heavy chain variable region comprising a VHCDR3 comprising the amino acid sequence of SEQ ID NO: 60 and/or a light chain variable region comprising a VLCDR3 comprising the amino acid sequence of SEQ ID NO: 87.

Amino acid substitutions may be made to provide variant antibodies derived from ADT1-4-19, for example an antibody or antigen-binding fragment or variant thereof is provided comprising a heavy chain variable region comprising a VHCDR3 comprising the amino acid sequence of SEQ ID NO: 60, optionally comprising 1 or 2 amino acid substitutions, and/or a light chain variable region comprising a VLCDR3 comprising the amino acid sequence of SEQ ID NO: 87, optionally comprising 1 or 2 amino acid substitutions. The amino acid substitutions may be conservative amino acid substitutions.

In some embodiments, an antibody or antigen-binding fragment or variant thereof is provided comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 60; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 87.

In one embodiment, an antibody or antigen-binding fragment or variant thereof is provided comprising:

a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 60; and/or a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 87.

In one embodiment, an antibody or antigen-binding fragment or variant thereof is provided comprising:

a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 60; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 87.

Amino acid substitutions may be made to provide variant antibodies derived from ADT1-4-19, for example an antibody or antigen-binding fragment or variant thereof is provided comprising:

a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 60 optionally comprising 1 or 2 amino acid substitutions; and/or a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 87 optionally comprising 1 or 2 amino acid substitutions. The amino acid substitutions may be conservative amino acid substitutions.

The antibodies may alternatively consist of the specified sequences (with or without amino acid substitutions).

ADT1-4-21 and Fragments and Variants Thereof

Certain embodiments relate to the antibody ADT1-4-21 and fragments and variants thereof.

For example, in some embodiments, an antibody or antigen-binding fragment or variant thereof is provided comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 61 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 88. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 61 and/or a light chain variable region comprising a VLCDR3 comprising an amino acid sequence having at least 90% identity to the amino acid sequence of SEQ ID NO: 88. In one embodiment, an antibody or antigen-binding fragment or variant thereof is provided comprising a heavy chain variable region comprising a VHCDR3 comprising the amino acid sequence of SEQ ID NO: 61 and/or a light chain variable region comprising a VLCDR3 comprising the amino acid sequence of SEQ ID NO: 88.

Amino acid substitutions may be made to provide variant antibodies derived from ADT1-4-21, for example an antibody or antigen-binding fragment or variant thereof is provided comprising a heavy chain variable region comprising a VHCDR3 comprising the amino acid sequence of SEQ ID NO: 61, optionally comprising 1 or 2 amino acid substitutions, and/or a light chain variable region comprising a VLCDR3 comprising the amino acid sequence of SEQ ID NO: 88, optionally comprising 1 or 2 amino acid substitutions. The amino acid substitutions may be conservative amino acid substitutions.

In some embodiments, an antibody or antigen-binding fragment or variant thereof is provided comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 52, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 61; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 88.

In one embodiment, an antibody or antigen-binding fragment or variant thereof is provided comprising:

a heavy chain variable region comprising a VHCDR1 comprising at least 90% identity to the amino acid sequence of SEQ ID NO: 52, a VHCDR2 comprising at least 90% identity to the amino acid sequence of SEQ ID NO: 53 and a VHCDR3 comprising at least 90% identity to the amino acid sequence of SEQ ID NO: 61; and/or a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 88.

In one embodiment, an antibody or antigen-binding fragment or variant thereof is provided comprising:

a heavy chain variable region comprising a VHCDR1 comprising the amino acid sequence of SEQ ID NO: 52, a VHCDR2 comprising the amino acid sequence of SEQ ID NO: 53 and a VHCDR3 comprising the amino acid sequence of SEQ ID NO: 61; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 88.

Amino acid substitutions may be made to provide variant antibodies derived from ADT1-4-21, for example an antibody or antigen-binding fragment or variant thereof is provided comprising:

a heavy chain variable region comprising a VHCDR1 comprising the amino acid sequence of SEQ ID NO: 52 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 61 optionally comprising 1 or 2 amino acid substitutions; and/or a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 88 optionally comprising 1 or 2 amino acid substitutions. The amino acid substitutions may be conservative amino acid substitutions.

The antibodies may alternatively consist of the specified sequences (with or without amino acid substitutions).

ADT1-4-31 and Fragments and Variants Thereof

Certain embodiments relate to the antibody ADT1-4-31 and fragments and variants thereof.

For example, in some embodiments, an antibody or antigen-binding fragment or variant thereof is provided comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 62 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 89. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 62 and/or a light chain variable region comprising a VLCDR3 comprising an amino acid sequence having at least 90% identity to the amino acid sequence of SEQ ID NO: 89. In one embodiment, an antibody or antigen-binding fragment or variant thereof is provided comprising a heavy chain variable region comprising a VHCDR3 comprising the amino acid sequence of SEQ ID NO: 62 and/or a light chain variable region comprising a VLCDR3 comprising the amino acid sequence of SEQ ID NO: 89.

Amino acid substitutions may be made to provide variant antibodies derived from ADT1-4-31, for example an antibody or antigen-binding fragment or variant thereof is provided comprising a heavy chain variable region comprising a VHCDR3 comprising the amino acid sequence of SEQ ID NO: 62, optionally comprising 1 or 2 amino acid substitutions, and/or a light chain variable region comprising a VLCDR3 comprising the amino acid sequence of SEQ ID NO: 89, optionally comprising 1 or 2 amino acid substitutions. The amino acid substitutions may be conservative amino acid substitutions.

In some embodiments, an antibody or antigen-binding fragment or variant thereof is provided comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 62; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 89.

In one embodiment, an antibody or antigen-binding fragment or variant thereof is provided comprising:

a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 62; and/or a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 89.

In one embodiment, an antibody or antigen-binding fragment or variant thereof is provided comprising:

a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 62; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 89.

Amino acid substitutions may be made to provide variant antibodies derived from ADT1-4-31, for example an antibody or antigen-binding fragment or variant thereof is provided comprising:

a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 62 optionally comprising 1 or 2 amino acid substitutions; and/or a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 89 optionally comprising 1 or 2 amino acid substitutions. The amino acid substitutions may be conservative amino acid substitutions.

The antibodies may alternatively consist of the specified sequences (with or without amino acid substitutions).

ADT1-4-139 and Fragments and Variants Thereof

Certain embodiments relate to the antibody ADT1-4-139 and fragments and variants thereof.

For example, in some embodiments, an antibody or antigen-binding fragment or variant thereof is provided comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 63 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 90. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 63 and/or a light chain variable region comprising a VLCDR3 comprising an amino acid sequence having at least 90% identity to the amino acid sequence of SEQ ID NO: 90. In one embodiment, an antibody or antigen-binding fragment or variant thereof is provided comprising a heavy chain variable region comprising a VHCDR3 comprising the amino acid sequence of SEQ ID NO: 63 and/or a light chain variable region comprising a VLCDR3 comprising the amino acid sequence of SEQ ID NO: 90.

Amino acid substitutions may be made to provide variant antibodies derived from ADT1-4-139, for example an antibody or antigen-binding fragment or variant thereof is provided comprising a heavy chain variable region comprising a VHCDR3 comprising the amino acid sequence of SEQ ID NO: 63, optionally comprising 1 or 2 amino acid substitutions, and/or a light chain variable region comprising a VLCDR3 comprising the amino acid sequence of SEQ ID NO: 90, optionally comprising 1 or 2 amino acid substitutions. The amino acid substitutions may be conservative amino acid substitutions.

In some embodiments, an antibody or antigen-binding fragment or variant thereof is provided comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 63; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 90.

In one embodiment, an antibody or antigen-binding fragment or variant thereof is provided comprising:

a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 63; and/or a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 90.

In one embodiment, an antibody or antigen-binding fragment or variant thereof is provided comprising:

a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 63; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 90.

Amino acid substitutions may be made to provide variant antibodies derived from ADT1-4-139, for example an antibody or antigen-binding fragment or variant thereof is provided comprising:

a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 63 optionally comprising 1 or 2 amino acid substitutions; and/or a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 90 optionally comprising 1 or 2 amino acid substitutions. The amino acid substitutions may be conservative amino acid substitutions.

The antibodies may alternatively consist of the specified sequences (with or without amino acid substitutions).

ADT1-4-4 and Fragments and Variants Thereof

Certain embodiments relate to the antibody ADT1-4-4 and fragments and variants thereof.

For example, in some embodiments, an antibody or antigen-binding fragment or variant thereof is provided comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 64 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 91. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 64 and/or a light chain variable region comprising a VLCDR3 comprising an amino acid sequence having at least 90% identity to the amino acid sequence of SEQ ID NO: 91. In one embodiment, an antibody or antigen-binding fragment or variant thereof is provided comprising a heavy chain variable region comprising a VHCDR3 comprising the amino acid sequence of SEQ ID NO: 64 and/or a light chain variable region comprising a VLCDR3 comprising the amino acid sequence of SEQ ID NO: 91.

Amino acid substitutions may be made to provide variant antibodies derived from ADT1-4-4, for example an antibody or antigen-binding fragment or variant thereof is provided comprising a heavy chain variable region comprising a VHCDR3 comprising the amino acid sequence of SEQ ID NO: 64, optionally comprising 1 or 2 amino acid substitutions, and/or a light chain variable region comprising a VLCDR3 comprising the amino acid sequence of SEQ ID NO: 91, optionally comprising 1 or 2 amino acid substitutions. The amino acid substitutions may be conservative amino acid substitutions.

In some embodiments, an antibody or antigen-binding fragment or variant thereof is provided comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 64; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 91.

In one embodiment, an antibody or antigen-binding fragment or variant thereof is provided comprising:

a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 64; and/or a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 91.

In one embodiment, an antibody or antigen-binding fragment or variant thereof is provided comprising:

a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 64; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 91.

Amino acid substitutions may be made to provide variant antibodies derived from ADT1-4-4, for example an antibody or antigen-binding fragment or variant thereof is provided comprising:

a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 64 optionally comprising 1 or 2 amino acid substitutions; and/or a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 91 optionally comprising 1 or 2 amino acid substitutions. The amino acid substitutions may be conservative amino acid substitutions.

The antibodies may alternatively consist of the specified sequences (with or without amino acid substitutions).

ADT1-4-143 and Fragments and Variants Thereof

Certain embodiments relate to the antibody ADT1-4-143 and fragments and variants thereof.

For example, in some embodiments, an antibody or antigen-binding fragment or variant thereof is provided comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 65 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 92. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 65 and/or a light chain variable region comprising a VLCDR3 comprising an amino acid sequence having at least 90% identity to the amino acid sequence of SEQ ID NO: 92. In one embodiment, an antibody or antigen-binding fragment or variant thereof is provided comprising a heavy chain variable region comprising a VHCDR3 comprising the amino acid sequence of SEQ ID NO: 65 and/or a light chain variable region comprising a VLCDR3 comprising the amino acid sequence of SEQ ID NO: 92.

Amino acid substitutions may be made to provide variant antibodies derived from ADT1-4-143, for example an antibody or antigen-binding fragment or variant thereof is provided comprising a heavy chain variable region comprising a VHCDR3 comprising the amino acid sequence of SEQ ID NO: 65, optionally comprising 1 or 2 amino acid substitutions, and/or a light chain variable region comprising a VLCDR3 comprising the amino acid sequence of SEQ ID NO: 92, optionally comprising 1 or 2 amino acid substitutions. The amino acid substitutions may be conservative amino acid substitutions.

In some embodiments, an antibody or antigen-binding fragment or variant thereof is provided comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 65; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 92.

In one embodiment, an antibody or antigen-binding fragment or variant thereof is provided comprising:

a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 65; and/or a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 92.

In one embodiment, an antibody or antigen-binding fragment or variant thereof is provided comprising:

a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 65; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 92.

Amino acid substitutions may be made to provide variant antibodies derived from ADT1-4-143, for example an antibody or antigen-binding fragment or variant thereof is provided comprising:

a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 65 optionally comprising 1 or 2 amino acid substitutions; and/or a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 92 optionally comprising 1 or 2 amino acid substitutions. The amino acid substitutions may be conservative amino acid substitutions.

The antibodies may alternatively consist of the specified sequences (with or without amino acid substitutions).

ADT1-4-53 and Fragments and Variants Thereof

Certain embodiments relate to the antibody ADT1-4-53 and fragments and variants thereof.

For example, in some embodiments, an antibody or antigen-binding fragment or variant thereof is provided comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 66 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 93. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 66 and/or a light chain variable region comprising a VLCDR3 comprising an amino acid sequence having at least 90% identity to the amino acid sequence of SEQ ID NO: 93. In one embodiment, an antibody or antigen-binding fragment or variant thereof is provided comprising a heavy chain variable region comprising a VHCDR3 comprising the amino acid sequence of SEQ ID NO: 66 and/or a light chain variable region comprising a VLCDR3 comprising the amino acid sequence of SEQ ID NO: 93.

Amino acid substitutions may be made to provide variant antibodies derived from ADT1-4-53, for example an antibody or antigen-binding fragment or variant thereof is provided comprising a heavy chain variable region comprising a VHCDR3 comprising the amino acid sequence of SEQ ID NO: 66, optionally comprising 1 or 2 amino acid substitutions, and/or a light chain variable region comprising a VLCDR3 comprising the amino acid sequence of SEQ ID NO: 93, optionally comprising 1 or 2 amino acid substitutions. The amino acid substitutions may be conservative amino acid substitutions.

In some embodiments, an antibody or antigen-binding fragment or variant thereof is provided comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 52, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 66; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 93.

In one embodiment, an antibody or antigen-binding fragment or variant thereof is provided comprising:

a heavy chain variable region comprising a VHCDR1 comprising at least 90% identity to the amino acid sequence of SEQ ID NO: 52, a VHCDR2 comprising at least 90% identity to the amino acid sequence of SEQ ID NO: 53 and a VHCDR3 comprising at least 90% identity to the amino acid sequence of SEQ ID NO: 66; and/or a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 93.

In one embodiment, an antibody or antigen-binding fragment or variant thereof is provided comprising:

a heavy chain variable region comprising a VHCDR1 comprising the amino acid sequence of SEQ ID NO: 52, a VHCDR2 comprising the amino acid sequence of SEQ ID NO: 53 and a VHCDR3 comprising the amino acid sequence of SEQ ID NO: 66; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 93.

Amino acid substitutions may be made to provide variant antibodies derived from ADT1-4-53, for example an antibody or antigen-binding fragment or variant thereof is provided comprising:

a heavy chain variable region comprising a VHCDR1 comprising the amino acid sequence of SEQ ID NO: 52 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 66 optionally comprising 1 or 2 amino acid substitutions; and/or a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 93 optionally comprising 1 or 2 amino acid substitutions. The amino acid substitutions may be conservative amino acid substitutions.

The antibodies may alternatively consist of the specified sequences (with or without amino acid substitutions).

ADT1-4-173 and Fragments and Variants Thereof

Certain embodiments relate to the antibody ADT1-4-173 and fragments and variants thereof.

For example, in some embodiments, an antibody or antigen-binding fragment or variant thereof is provided comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 67 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 94. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 67 and/or a light chain variable region comprising a VLCDR3 comprising an amino acid sequence having at least 90% identity to the amino acid sequence of SEQ ID NO: 94. In one embodiment, an antibody or antigen-binding fragment or variant thereof is provided comprising a heavy chain variable region comprising a VHCDR3 comprising the amino acid sequence of SEQ ID NO: 67 and/or a light chain variable region comprising a VLCDR3 comprising the amino acid sequence of SEQ ID NO: 94.

Amino acid substitutions may be made to provide variant antibodies derived from ADT1-4-173, for example an antibody or antigen-binding fragment or variant thereof is provided comprising a heavy chain variable region comprising a VHCDR3 comprising the amino acid sequence of SEQ ID NO: 67, optionally comprising 1 or 2 amino acid substitutions, and/or a light chain variable region comprising a VLCDR3 comprising the amino acid sequence of SEQ ID NO: 94, optionally comprising 1 or 2 amino acid substitutions. The amino acid substitutions may be conservative amino acid substitutions.

In some embodiments, an antibody or antigen-binding fragment or variant thereof is provided comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 67; and/or

- a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 94.

In one embodiment, an antibody or antigen-binding fragment or variant thereof is provided comprising:

- a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 67; and/or
- a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 94.

In one embodiment, an antibody or antigen-binding fragment or variant thereof is provided comprising:

- a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 67; and
- a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 94.

Amino acid substitutions may be made to provide variant antibodies derived from ADT1-4-173, for example an antibody or antigen-binding fragment or variant thereof is provided comprising:

- a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 67 optionally comprising 1 or 2 amino acid substitutions; and/or
- a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 94 optionally comprising 1 or 2 amino acid substitutions. The amino acid substitutions may be conservative amino acid substitutions.

The antibodies may alternatively consist of the specified sequences (with or without amino acid substitutions).

ADT1-4-2 and Fragments and Variants Thereof

Certain embodiments relate to the antibody ADT1-4-2 and fragments and variants thereof.

For example, in some embodiments, an antibody or antigen-binding fragment or variant thereof is provided comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 68 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 95. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 68 and/or a light chain variable region comprising a VLCDR3 comprising an amino acid sequence having at least 90% identity to the amino acid sequence of SEQ ID NO: 95. In one embodiment, an antibody or antigen-binding fragment or variant thereof is provided comprising a heavy chain variable region comprising a VHCDR3 comprising the amino acid sequence of SEQ ID NO: 68 and/or a light chain variable region comprising a VLCDR3 comprising the amino acid sequence of SEQ ID NO: 95.

Amino acid substitutions may be made to provide variant antibodies derived from ADT1-4-2, for example an antibody or antigen-binding fragment or variant thereof is provided comprising a heavy chain variable region comprising a VHCDR3 comprising the amino acid sequence of SEQ ID NO: 68, optionally comprising 1 or 2 amino acid substitutions, and/or a light chain variable region comprising a VLCDR3 comprising the amino acid sequence of SEQ ID NO: 95, optionally comprising 1 or 2 amino acid substitutions. The amino acid substitutions may be conservative amino acid substitutions.

In some embodiments, an antibody or antigen-binding fragment or variant thereof is provided comprising:

- a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 68; and/or
- a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 95.

In one embodiment, an antibody or antigen-binding fragment or variant thereof is provided comprising:

a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 68; and/or a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 95.

In one embodiment, an antibody or antigen-binding fragment or variant thereof is provided comprising:

a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 68; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 95.

Amino acid substitutions may be made to provide variant antibodies derived from ADT1-4-2, for example an antibody or antigen-binding fragment or variant thereof is provided comprising:

a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 68 optionally comprising 1 or 2 amino acid substitutions; and/or a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 95 optionally comprising 1 or 2 amino acid substitutions. The amino acid substitutions may be conservative amino acid substitutions.

The antibodies may alternatively consist of the specified sequences (with or without amino acid substitutions).

ADT1-4-8 and Fragments and Variants Thereof

Certain embodiments relate to the antibody ADT1-4-8 and fragments and variants thereof.

For example, in some embodiments, an antibody or antigen-binding fragment or variant thereof is provided comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 69 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 96. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 69 and/or a light chain variable region comprising a VLCDR3 comprising an amino acid sequence having at least 90% identity to the amino acid sequence of SEQ ID NO: 96. In one embodiment, an antibody or antigen-binding fragment or variant thereof is provided comprising a heavy chain variable region comprising a VHCDR3 comprising the amino acid sequence of SEQ ID NO: 69 and/or a light chain variable region comprising a VLCDR3 comprising the amino acid sequence of SEQ ID NO: 96.

Amino acid substitutions may be made to provide variant antibodies derived from ADT1-4-8, for example an antibody or antigen-binding fragment or variant thereof is provided comprising a heavy chain variable region comprising a VHCDR3 comprising the amino acid sequence of SEQ ID NO: 69, optionally comprising 1 or 2 amino acid substitutions, and/or a light chain variable region comprising a VLCDR3 comprising the amino acid sequence of SEQ ID NO: 96, optionally comprising 1 or 2 amino acid substitutions. The amino acid substitutions may be conservative amino acid substitutions.

In some embodiments, an antibody or antigen-binding fragment or variant thereof is provided comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 69; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 96.

In one embodiment, an antibody or antigen-binding fragment or variant thereof is provided comprising:

a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 69; and/or a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 96.

In one embodiment, an antibody or antigen-binding fragment or variant thereof is provided comprising:

a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 69; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 96.

Amino acid substitutions may be made to provide variant antibodies derived from ADT1-4-8, for example an antibody or antigen-binding fragment or variant thereof is provided comprising:

a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 69 optionally comprising 1 or 2 amino acid substitutions; and/or a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 96 optionally comprising 1 or 2 amino acid substitutions. The amino acid substitutions may be conservative amino acid substitutions.

The antibodies may alternatively consist of the specified sequences (with or without amino acid substitutions).

ADT1-4-82 and Fragments and Variants Thereof

Certain embodiments relate to the antibody ADT1-4-82 and fragments and variants thereof.

For example, in some embodiments, an antibody or antigen-binding fragment or variant thereof is provided comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 70 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 97. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 70 and/or a light chain variable region comprising a VLCDR3 comprising an amino acid sequence having at least 90% identity to the amino acid sequence of SEQ ID NO: 97. In one embodiment, an antibody or antigen-binding fragment or variant thereof is provided comprising a heavy chain variable region comprising a VHCDR3 comprising the amino acid sequence of SEQ ID NO: 70 and/or a light chain variable region comprising a VLCDR3 comprising the amino acid sequence of SEQ ID NO: 97.

Amino acid substitutions may be made to provide variant antibodies derived from ADT1-4-82, for example an antibody or antigen-binding fragment or variant thereof is provided comprising a heavy chain variable region comprising a VHCDR3 comprising the amino acid sequence of SEQ ID NO: 70, optionally comprising 1 or 2 amino acid substitutions, and/or a light chain variable region comprising a VLCDR3 comprising the amino acid sequence of SEQ ID NO: 97, optionally comprising 1 or 2 amino acid substitutions. The amino acid substitutions may be conservative amino acid substitutions.

In some embodiments, an antibody or antigen-binding fragment or variant thereof is provided comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 70; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 97.

In one embodiment, an antibody or antigen-binding fragment or variant thereof is provided comprising:

a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 70; and/or a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 97.

In one embodiment, an antibody or antigen-binding fragment or variant thereof is provided comprising:

a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 70; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 97.

Amino acid substitutions may be made to provide variant antibodies derived from ADT1-4-82, for example an antibody or antigen-binding fragment or variant thereof is provided comprising:

a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 70 optionally comprising 1 or 2 amino acid substitutions; and/or a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 97 optionally comprising 1 or 2 amino acid substitutions. The amino acid substitutions may be conservative amino acid substitutions.

The antibodies may alternatively consist of the specified sequences (with or without amino acid substitutions).

ADT1-4-83 and Fragments and Variants Thereof

Certain embodiments relate to the antibody ADT1-4-83 and fragments and variants thereof.

For example, in some embodiments, an antibody or antigen-binding fragment or variant thereof is provided comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 71 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 98. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 71 and/or a light chain variable region comprising a VLCDR3 comprising an amino acid sequence having at least 90% identity to the amino acid sequence of SEQ ID NO: 98. In one embodiment, an antibody or antigen-binding fragment or variant thereof is provided comprising a heavy chain variable region comprising a VHCDR3 comprising the amino acid sequence of SEQ ID NO: 71 and/or a light chain variable region comprising a VLCDR3 comprising the amino acid sequence of SEQ ID NO: 98.

Amino acid substitutions may be made to provide variant antibodies derived from ADT1-4-83, for example an antibody or antigen-binding fragment or variant thereof is provided comprising a heavy chain variable region comprising a VHCDR3 comprising the amino acid sequence of SEQ ID NO: 71, optionally comprising 1 or 2 amino acid substitutions, and/or a light chain variable region comprising a VLCDR3 comprising the amino acid sequence of SEQ ID NO: 98, optionally comprising 1 or 2 amino acid substitutions. The amino acid substitutions may be conservative amino acid substitutions.

In some embodiments, an antibody or antigen-binding fragment or variant thereof is provided comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 71; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 98.

In one embodiment, an antibody or antigen-binding fragment or variant thereof is provided comprising:

a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 71; and/or a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 98.

In one embodiment, an antibody or antigen-binding fragment or variant thereof is provided comprising:

a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 71; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 98.

Amino acid substitutions may be made to provide variant antibodies derived from ADT1-4-83, for example an antibody or antigen-binding fragment or variant thereof is provided comprising:

a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 71 optionally comprising 1 or 2 amino acid substitutions; and/or a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 98 optionally comprising 1 or 2 amino acid substitutions. The amino acid substitutions may be conservative amino acid substitutions.

The antibodies may alternatively consist of the specified sequences (with or without amino acid substitutions).

ADT1-4-3 and Fragments and Variants Thereof

Certain embodiments relate to the antibody ADT1-4-3 and fragments and variants thereof.

For example, in some embodiments, an antibody or antigen-binding fragment or variant thereof is provided comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 72 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 99. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 72 and/or a light chain variable region comprising a VLCDR3 comprising an amino acid sequence having at least 90% identity to the amino acid sequence of SEQ ID NO: 99. In one embodiment, an antibody or antigen-binding fragment or variant thereof is provided comprising a heavy chain variable region comprising a VHCDR3 comprising the amino acid sequence of SEQ ID NO: 72 and/or a light chain variable region comprising a VLCDR3 comprising the amino acid sequence of SEQ ID NO: 99.

Amino acid substitutions may be made to provide variant antibodies derived from ADT1-4-3, for example an antibody or antigen-binding fragment or variant thereof is provided comprising a heavy chain variable region comprising a VHCDR3 comprising the amino acid sequence of SEQ ID NO: 72, optionally comprising 1 or 2 amino acid substitutions, and/or a light chain variable region comprising a VLCDR3 comprising the amino acid sequence of SEQ ID NO: 99, optionally comprising 1 or 2 amino acid substitutions. The amino acid substitutions may be conservative amino acid substitutions.

In some embodiments, an antibody or antigen-binding fragment or variant thereof is provided comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 72; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 99.

In one embodiment, an antibody or antigen-binding fragment or variant thereof is provided comprising:

a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 72; and/or a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 99.

In one embodiment, an antibody or antigen-binding fragment or variant thereof is provided comprising:

a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 72; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 99.

Amino acid substitutions may be made to provide variant antibodies derived from ADT1-4-3, for example an antibody or antigen-binding fragment or variant thereof is provided comprising:

a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 72 optionally comprising 1 or 2 amino acid substitutions; and/or a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 99 optionally comprising 1 or 2 amino acid substitutions. The amino acid substitutions may be conservative amino acid substitutions.

The antibodies may alternatively consist of the specified sequences (with or without amino acid substitutions).

ADT1-4-84 and Fragments and Variants Thereof

Certain embodiments relate to the antibody ADT1-4-84 and fragments and variants thereof.

For example, in some embodiments, an antibody or antigen-binding fragment or variant thereof is provided comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 73 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 100. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 73 and/or a light chain variable region comprising a VLCDR3 comprising an amino acid sequence having at least 90% identity to the amino acid sequence of SEQ ID NO: 100. In one embodiment, an antibody or antigen-binding fragment or variant thereof is provided comprising a heavy chain variable region comprising a VHCDR3 comprising the amino acid sequence of SEQ ID NO: 73 and/or a light chain variable region comprising a VLCDR3 comprising the amino acid sequence of SEQ ID NO: 100.

Amino acid substitutions may be made to provide variant antibodies derived from ADT1-4-84, for example an antibody or antigen-binding fragment or variant thereof is provided comprising a heavy chain variable region comprising a VHCDR3 comprising the amino acid sequence of SEQ ID NO: 73, optionally comprising 1 or 2 amino acid substitutions, and/or a light chain variable region comprising a VLCDR3 comprising the amino acid sequence of SEQ ID NO: 100, optionally comprising 1 or 2 amino acid substitutions. The amino acid substitutions may be conservative amino acid substitutions.

In some embodiments, an antibody or antigen-binding fragment or variant thereof is provided comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 73; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 100.

In one embodiment, an antibody or antigen-binding fragment or variant thereof is provided comprising:

a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 73; and/or a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 100.

In one embodiment, an antibody or antigen-binding fragment or variant thereof is provided comprising:

a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 73; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 100.

Amino acid substitutions may be made to provide variant antibodies derived from ADT1-4-84, for example an antibody or antigen-binding fragment or variant thereof is provided comprising:

a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 73 optionally comprising 1 or 2 amino acid substitutions; and/or a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 100 optionally comprising 1 or 2 amino acid substitutions. The amino acid substitutions may be conservative amino acid substitutions.

The antibodies may alternatively consist of the specified sequences (with or without amino acid substitutions).

ADT1-4-86 and Fragments and Variants Thereof

Certain embodiments relate to the antibody ADT1-4-86 and fragments and variants thereof.

For example, in some embodiments, an antibody or antigen-binding fragment or variant thereof is provided comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 74 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 101. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 74 and/or a light chain variable region comprising a VLCDR3 comprising an amino acid sequence having at least 90% identity to the amino acid sequence of SEQ ID NO: 101. In one embodiment, an antibody or antigen-binding fragment or variant thereof is provided comprising a heavy chain variable region comprising a VHCDR3 comprising the amino acid sequence of SEQ ID NO: 74 and/or a light chain variable region comprising a VLCDR3 comprising the amino acid sequence of SEQ ID NO: 101.

Amino acid substitutions may be made to provide variant antibodies derived from ADT1-4-86, for example an antibody or antigen-binding fragment or variant thereof is provided comprising a heavy chain variable region comprising a VHCDR3 comprising the amino acid sequence of SEQ ID NO: 74, optionally comprising 1 or 2 amino acid substitutions, and/or a light chain variable region comprising a VLCDR3 comprising the amino acid sequence of SEQ ID NO: 101, optionally comprising 1 or 2 amino acid substitutions. The amino acid substitutions may be conservative amino acid substitutions.

In some embodiments, an antibody or antigen-binding fragment or variant thereof is provided comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 52, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 74; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 101.

In one embodiment, an antibody or antigen-binding fragment or variant thereof is provided comprising:

a heavy chain variable region comprising a VHCDR1 comprising at least 90% identity to the amino acid sequence of SEQ ID NO: 52, a VHCDR2 comprising at least 90% identity to the amino acid sequence of SEQ ID NO: 53 and a VHCDR3 comprising at least 90% identity to the amino acid sequence of SEQ ID NO: 74; and/or a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 101.

In one embodiment, an antibody or antigen-binding fragment or variant thereof is provided comprising:

a heavy chain variable region comprising a VHCDR1 comprising the amino acid sequence of SEQ ID NO: 52, a VHCDR2 comprising the amino acid sequence of SEQ ID NO: 53 and a VHCDR3 comprising the amino acid sequence of SEQ ID NO: 74; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 101.

Amino acid substitutions may be made to provide variant antibodies derived from ADT1-4-86, for example an antibody or antigen-binding fragment or variant thereof is provided comprising:

a heavy chain variable region comprising a VHCDR1 comprising the amino acid sequence of SEQ ID NO: 52 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 74 optionally comprising 1 or 2 amino acid substitutions; and/or a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 101 optionally comprising 1 or 2 amino acid substitutions. The amino acid substitutions may be conservative amino acid substitutions.

The antibodies may alternatively consist of the specified sequences (with or without amino acid substitutions).

ADT1-4-95 and Fragments and Variants Thereof

Certain embodiments relate to the antibody ADT1-4-95 and fragments and variants thereof.

For example, in some embodiments, an antibody or antigen-binding fragment or variant thereof is provided comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 75 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 102. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 75 and/or a light chain variable region comprising a VLCDR3 comprising an amino acid sequence having at least 90% identity to the amino acid sequence of SEQ ID NO: 102. In one embodiment, an antibody or antigen-binding fragment or variant thereof is provided comprising a heavy chain variable region comprising a VHCDR3 comprising the amino acid sequence of SEQ ID NO: 75 and/or a light chain variable region comprising a VLCDR3 comprising the amino acid sequence of SEQ ID NO: 102.

Amino acid substitutions may be made to provide variant antibodies derived from ADT1-4-95, for example an antibody or antigen-binding fragment or variant thereof is provided comprising a heavy chain variable region comprising a VHCDR3 comprising the amino acid sequence of SEQ ID NO: 75, optionally comprising 1 or 2 amino acid substitutions, and/or a light chain variable region comprising a VLCDR3 comprising the amino acid sequence of SEQ ID NO: 102, optionally comprising 1 or 2 amino acid substitutions. The amino acid substitutions may be conservative amino acid substitutions.

In some embodiments, an antibody or antigen-binding fragment or variant thereof is provided comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 75; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 102.

In one embodiment, an antibody or antigen-binding fragment or variant thereof is provided comprising:

a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 75; and/or a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 102.

In one embodiment, an antibody or antigen-binding fragment or variant thereof is provided comprising:

a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 75; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 102.

Amino acid substitutions may be made to provide variant antibodies derived from ADT1-4-95, for example an antibody or antigen-binding fragment or variant thereof is provided comprising:

a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 75 optionally comprising 1 or 2 amino acid substitutions; and/or a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 102 optionally comprising 1 or 2 amino acid substitutions. The amino acid substitutions may be conservative amino acid substitutions.

The antibodies may alternatively consist of the specified sequences (with or without amino acid substitutions).

ADT1-4-1 and Fragments and Variants Thereof

Certain embodiments relate to the antibody ADT1-4-1 and fragments and variants thereof.

For example, in some embodiments, an antibody or antigen-binding fragment or variant thereof is provided comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 76 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 103. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 76 and/or a light chain variable region comprising a VLCDR3 comprising an amino acid sequence having at least 90% identity to the amino acid sequence of SEQ ID NO: 103. In one embodiment, an antibody or antigen-binding fragment or variant thereof is provided comprising a heavy chain variable region comprising a VHCDR3 comprising the amino acid sequence of SEQ ID NO: 76 and/or a light chain variable region comprising a VLCDR3 comprising the amino acid sequence of SEQ ID NO: 103.

Amino acid substitutions may be made to provide variant antibodies derived from ADT1-4-1, for example an antibody or antigen-binding fragment or variant thereof is provided comprising a heavy chain variable region comprising a VHCDR3 comprising the amino acid sequence of SEQ ID NO: 76, optionally comprising 1 or 2 amino acid substitutions, and/or a light chain variable region comprising a VLCDR3 comprising the amino acid sequence of SEQ ID NO: 103, optionally comprising 1 or 2 amino acid substitutions. The amino acid substitutions may be conservative amino acid substitutions.

In some embodiments, an antibody or antigen-binding fragment or variant thereof is provided comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 76; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 103.

In one embodiment, an antibody or antigen-binding fragment or variant thereof is provided comprising:

a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 76; and/or a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 103.

In one embodiment, an antibody or antigen-binding fragment or variant thereof is provided comprising:

a heavy chain variable region comprising a VHCDR1 comprising the amino acid sequence of SEQ ID NO:

51, a VHCDR2 comprising the amino acid sequence of SEQ ID NO: 53 and a VHCDR3 comprising the amino acid sequence of SEQ ID NO: 76; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 103.

Amino acid substitutions may be made to provide variant antibodies derived from ADT1-4-1, for example an antibody or antigen-binding fragment or variant thereof is provided comprising:

a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 76 optionally comprising 1 or 2 amino acid substitutions; and/or a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 103 optionally comprising 1 or 2 amino acid substitutions. The amino acid substitutions may be conservative amino acid substitutions.

The antibodies may alternatively consist of the specified sequences (with or without amino acid substitutions).

ADT1-4-6 and Fragments and Variants Thereof

Certain embodiments relate to the antibody ADT1-4-6 and fragments and variants thereof.

For example, in some embodiments, an antibody or antigen-binding fragment or variant thereof is provided comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 77 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 104. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 77 and/or a light chain variable region comprising a VLCDR3 comprising an amino acid sequence having at least 90% identity to the amino acid sequence of SEQ ID NO: 104. In one embodiment, an antibody or antigen-binding fragment or variant thereof is provided comprising a heavy chain variable region comprising a VHCDR3 comprising the amino acid sequence of SEQ ID NO: 77 and/or a light chain variable region comprising a VLCDR3 comprising the amino acid sequence of SEQ ID NO: 104.

Amino acid substitutions may be made to provide variant antibodies derived from ADT1-4-6, for example an antibody or antigen-binding fragment or variant thereof is provided comprising a heavy chain variable region comprising a VHCDR3 comprising the amino acid sequence of SEQ ID NO: 77, optionally comprising 1 or 2 amino acid substitutions, and/or a light chain variable region comprising a VLCDR3 comprising the amino acid sequence of SEQ ID NO: 104, optionally comprising 1 or 2 amino acid substitutions. The amino acid substitutions may be conservative amino acid substitutions.

In some embodiments, an antibody or antigen-binding fragment or variant thereof is provided comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 77; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 104.

In one embodiment, an antibody or antigen-binding fragment or variant thereof is provided comprising:

a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 77; and/or a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 104.

In one embodiment, an antibody or antigen-binding fragment or variant thereof is provided comprising:

a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 77; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 104.

Amino acid substitutions may be made to provide variant antibodies derived from ADT1-4-6, for example an antibody or antigen-binding fragment or variant thereof is provided comprising:

a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 77 optionally comprising 1 or 2 amino acid substitutions; and/or a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 104 optionally comprising 1 or 2 amino acid substitutions. The amino acid substitutions may be conservative amino acid substitutions.

The antibodies may alternatively consist of the specified sequences (with or without amino acid substitutions).

ADT1-4-138 and Fragments and Variants Thereof

Certain embodiments relate to the antibody ADT1-4-138 and fragments and variants thereof.

For example, in some embodiments, an antibody or antigen-binding fragment or variant thereof is provided comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 78 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 105. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 78 and/or a light chain variable region comprising a VLCDR3 comprising an amino acid sequence having at least 90% identity to the amino acid sequence of SEQ ID NO: 105. In one embodiment, an antibody or antigen-binding fragment or variant thereof is provided comprising a heavy chain variable region comprising a VHCDR3 comprising the amino acid sequence of SEQ ID NO: 78 and/or a light chain variable region comprising a VLCDR3 comprising the amino acid sequence of SEQ ID NO: 105.

Amino acid substitutions may be made to provide variant antibodies derived from ADT1-4-138, for example an antibody or antigen-binding fragment or variant thereof is provided comprising a heavy chain variable region comprising a VHCDR3 comprising the amino acid sequence of SEQ ID NO: 78, optionally comprising 1 or 2 amino acid substitutions, and/or a light chain variable region comprising a VLCDR3 comprising the amino acid sequence of SEQ ID NO: 105, optionally comprising 1 or 2 amino acid substitutions. The amino acid substitutions may be conservative amino acid substitutions.

In some embodiments, an antibody or antigen-binding fragment or variant thereof is provided comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 78; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 105.

In one embodiment, an antibody or antigen-binding fragment or variant thereof is provided comprising:

a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 78; and/or a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 105.

In one embodiment, an antibody or antigen-binding fragment or variant thereof is provided comprising:

a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 78; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 105.

Amino acid substitutions may be made to provide variant antibodies derived from ADT1-4-138, for example an antibody or antigen-binding fragment or variant thereof is provided comprising:

a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 78 optionally comprising 1 or 2 amino acid substitutions; and/or a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 105 optionally comprising 1 or 2 amino acid substitutions. The amino acid substitutions may be conservative amino acid substitutions.

The antibodies may alternatively consist of the specified sequences (with or without amino acid substitutions).

Antibodies Comprising Heavy and/or Light Chain Variable Regions Derived from ADT1-4

There is provided herein an anti-TCR delta variable 1 (anti-Vδ1) antibody or antigen-binding fragment thereof comprising:

a heavy chain variable region comprising or consisting of a sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of SEQ ID Nos: 2 to 25; and/or a light chain variable region comprising or consisting of a sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of SEQ ID Nos: 27 to 50.

There is also provided herein an anti-TCR delta variable 1 (anti-Vδ1) antibody or antigen-binding fragment thereof comprising:

a heavy chain variable region comprising or consisting of a sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of SEQ ID Nos: 2 to 25, wherein the heavy chain variable region sequence is not SEQ ID NO:1; and/or a light chain variable region comprising or consisting of a sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of SEQ ID Nos: 27 to 50, wherein the light chain variable region sequence is not SEQ ID NO: 26.

There is also provided an anti-TCR delta variable 1 (anti-Vδ1) antibody or antigen-binding fragment thereof comprising:

a heavy chain variable region comprising or consisting of a sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of SEQ ID Nos: 2 to 24; and/or a light chain variable region comprising or consisting of a sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of SEQ ID Nos: 27 to 49.

There is also provided an anti-TCR delta variable 1 (anti-Vδ1) antibody or antigen-binding fragment thereof comprising:

a heavy chain variable region comprising or consisting of a sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of SEQ ID Nos: 5, 7, 8, 9, 12, 13, 15, 21, 23 and 24; and/or a light chain variable region comprising or consisting of a sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of SEQ ID Nos: 30, 32, 33, 34, 37, 38, 40, 46, 48 and 49.

There is provided herein an anti-TCR delta variable 1 (anti-Vδ1) antibody or antigen-binding fragment thereof comprising:

a heavy chain variable region comprising or consisting of a sequence having at least 90% identity to a sequence selected from the group consisting of SEQ ID Nos: 2 to 25; and/or a light chain variable region comprising or consisting of a sequence having at least 90% identity to a sequence selected from the group consisting of SEQ ID Nos: 27 to 50.

There is also provided an anti-TCR delta variable 1 (anti-Vδ1) antibody or antigen-binding fragment thereof comprising:

a heavy chain variable region comprising or consisting of a sequence having at least 90% identity to a sequence selected from the group consisting of SEQ ID Nos: 2 to 24; and/or a light chain variable region comprising or consisting of a sequence having at least 90% identity to a sequence selected from the group consisting of SEQ ID Nos: 27 to 49.

There is also provided an anti-TCR delta variable 1 (anti-Vδ1) antibody or antigen-binding fragment thereof comprising:

a heavy chain variable region comprising or consisting of a sequence having at least 90% identity to a sequence selected from the group consisting of SEQ ID Nos: 5, 7, 8, 9, 12, 13, 15, 21, 23 and 24; and/or a light chain variable region comprising or consisting of a sequence having at least 90% identity to a sequence selected from the group consisting of SEQ ID Nos: 30, 32, 33, 34, 37, 38, 40, 46, 48 and 49.

Optionally the antibodies above retain the corresponding CDR sequences such that any variability in the VH and VL sequences occurs in the framework regions.

There is provided herein an anti-TCR delta variable 1 (anti-Vδ1) antibody or antigen-binding fragment thereof comprising:

a heavy chain variable region comprising or consisting of a sequence selected from the group consisting of SEQ ID Nos: 2 to 25; and/or a light chain variable region comprising or consisting of a sequence selected from the group consisting of SEQ ID Nos: 27 to 50.

There is also provided an anti-TCR delta variable 1 (anti-Vδ1) antibody or antigen-binding fragment thereof comprising:

a heavy chain variable region comprising or consisting of a sequence selected from the group consisting of SEQ ID Nos: 2 to 24; and/or a light chain variable region comprising or consisting of a sequence selected from the group consisting of SEQ ID Nos: 27 to 49.

There is also provided an anti-TCR delta variable 1 (anti-Vδ1) antibody or antigen-binding fragment thereof comprising:

a heavy chain variable region comprising or consisting of a sequence selected from the group consisting of SEQ ID Nos: 5, 7, 8, 9, 12, 13, 15, 21, 23 and 24; and/or a light chain variable region comprising or consisting of a sequence selected from the group consisting of SEQ ID Nos: 30, 32, 33, 34, 37, 38, 40, 46, 48 and 49.

In some embodiments, there is provided an anti-TCR delta variable 1 (anti-Vδ1) antibody or antigen-binding fragment thereof comprising:

a) a VH comprising or consisting of an amino acid sequence that is at least 90% identical to the amino acid sequence of SEQ ID NO: 2 and a VL comprising or consisting of an amino acid sequence that is at least 90% identical to the amino acid sequence of SEQ ID NO: 27;

b) a VH comprising or consisting of an amino acid sequence that is at least 90% identical to the amino acid sequence of SEQ ID NO: 3 and a VL comprising or consisting of an amino acid sequence that is at least 90% identical to the amino acid sequence of SEQ ID NO: 28;

c) a VH comprising or consisting of an amino acid sequence that is at least 90% identical to the amino acid sequence of SEQ ID NO: 4 and a VL comprising or consisting of an amino acid sequence that is at least 90% identical to the amino acid sequence of SEQ ID NO: 29;

d) a VH comprising or consisting of an amino acid sequence that is at least 90% identical to the amino acid sequence of SEQ ID NO: 5 and a VL comprising or consisting of an amino acid sequence that is at least 90% identical to the amino acid sequence of SEQ ID NO: 30;

e) a VH comprising or consisting of an amino acid sequence that is at least 90% identical to the amino acid sequence of SEQ ID NO: 6 and a VL comprising or consisting of an amino acid sequence that is at least 90% identical to the amino acid sequence of SEQ ID NO: 31;

f) a VH comprising or consisting of an amino acid sequence that is at least 90% identical to the amino acid sequence of SEQ ID NO: 7 and a VL comprising or consisting of an amino acid sequence that is at least 90% identical to the amino acid sequence of SEQ ID NO: 32;

g) a VH comprising or consisting of an amino acid sequence that is at least 90% identical to the amino acid sequence of SEQ ID NO: 8 and a VL comprising or consisting of an amino acid sequence that is at least 90% identical to the amino acid sequence of SEQ ID NO: 33;

h) a VH comprising or consisting of an amino acid sequence that is at least 90% identical to the amino acid sequence of SEQ ID NO: 9 and a VL comprising or consisting of an amino acid sequence that is at least 90% identical to the amino acid sequence of SEQ ID NO: 34;

i) a VH comprising or consisting of an amino acid sequence that is at least 90% identical to the amino acid sequence of SEQ ID NO: 10 and a VL comprising or consisting of an amino acid sequence that is at least 90% identical to the amino acid sequence of SEQ ID NO: 35;

j) a VH comprising or consisting of an amino acid sequence that is at least 90% identical to the amino acid sequence of SEQ ID NO: 11 and a VL comprising or consisting of an amino acid sequence that is at least 90% identical to the amino acid sequence of SEQ ID NO: 36;

k) a VH comprising or consisting of an amino acid sequence that is at least 90% identical to the amino acid sequence of SEQ ID NO: 12 and a VL comprising or consisting of an amino acid sequence that is at least 90% identical to the amino acid sequence of SEQ ID NO: 37;

l) a VH comprising or consisting of an amino acid sequence that is at least 90% identical to the amino acid sequence of SEQ ID NO: 13 and a VL comprising or consisting of an amino acid sequence that is at least 90% identical to the amino acid sequence of SEQ ID NO: 38;

m) a VH comprising or consisting of an amino acid sequence that is at least 90% identical to the amino acid sequence of SEQ ID NO: 14 and a VL comprising or consisting of an amino acid sequence that is at least 90% identical to the amino acid sequence of SEQ ID NO: 39;

n) a VH comprising or consisting of an amino acid sequence that is at least 90% identical to the amino acid sequence of SEQ ID NO: 15 and a VL comprising or consisting of an amino acid sequence that is at least 90% identical to the amino acid sequence of SEQ ID NO: 40;

o) a VH comprising or consisting of an amino acid sequence that is at least 90% identical to the amino acid sequence of SEQ ID NO: 16 and a VL comprising or consisting of an amino acid sequence that is at least 90% identical to the amino acid sequence of SEQ ID NO: 41;

p) a VH comprising or consisting of an amino acid sequence that is at least 90% identical to the amino acid sequence of SEQ ID NO: 17 and a VL comprising or consisting of an amino acid sequence that is at least 90% identical to the amino acid sequence of SEQ ID NO: 42;

q) a VH comprising or consisting of an amino acid sequence that is at least 90% identical to the amino acid sequence of SEQ ID NO: 18 and a VL comprising or consisting of an amino acid sequence that is at least 90% identical to the amino acid sequence of SEQ ID NO: 43;

r) a VH comprising or consisting of an amino acid sequence that is at least 90% identical to the amino acid sequence of SEQ ID NO: 19 and a VL comprising or consisting of an amino acid sequence that is at least 90% identical to the amino acid sequence of SEQ ID NO: 44;

s) a VH comprising or consisting of an amino acid sequence that is at least 90% identical to the amino acid sequence of SEQ ID NO: 20 and a VL comprising or consisting of an amino acid sequence that is at least 90% identical to the amino acid sequence of SEQ ID NO: 45;

t) a VH comprising or consisting of an amino acid sequence that is at least 90% identical to the amino acid sequence of SEQ ID NO: 21 and a VL comprising or consisting of an amino acid sequence that is at least 90% identical to the amino acid sequence of SEQ ID NO: 46;

u) a VH comprising or consisting of an amino acid sequence that is at least 90% identical to the amino acid sequence of SEQ ID NO: 22 and a VL comprising or consisting of an amino acid sequence that is at least 90% identical to the amino acid sequence of SEQ ID NO: 47;

v) a VH comprising or consisting of an amino acid sequence that is at least 90% identical to the amino acid sequence of SEQ ID NO: 23 and a VL comprising or consisting of an amino acid sequence that is at least 90% identical to the amino acid sequence of SEQ ID NO: 48;

w) a VH comprising or consisting of an amino acid sequence that is at least 90% identical to the amino acid sequence of SEQ ID NO: 24 and a VL comprising or consisting of an amino acid sequence that is at least 90% identical to the amino acid sequence of SEQ ID NO: 49; or x) a VH comprising or consisting of an amino acid sequence that is at least 90% identical to the amino acid sequence of SEQ ID NO: 25 and a VL comprising or consisting of an amino acid sequence that is at least 90% identical to the amino acid sequence of SEQ ID NO: 50.

Optionally the antibodies above retain the corresponding CDR sequences such that any variability in the VH and VL sequences occurs in the framework regions.

In some embodiments, there is provided an anti-TCR delta variable 1 (anti-Vδ1) antibody or antigen-binding fragment thereof comprising:

a) a VH comprising or consisting of an amino acid sequence that is at least 96% identical to the amino acid sequence of SEQ ID NO: 2 and a VL comprising or consisting of an amino acid sequence that is at least 96% identical to the amino acid sequence of SEQ ID NO: 27;

b) a VH comprising or consisting of an amino acid sequence that is at least 96% identical to the amino acid sequence of SEQ ID NO: 3 and a VL comprising or consisting of an amino acid sequence that is at least 96% identical to the amino acid sequence of SEQ ID NO: 28;

c) a VH comprising or consisting of an amino acid sequence that is at least 96% identical to the amino acid sequence of SEQ ID NO: 4 and a VL comprising or consisting of an amino acid sequence that is at least 96% identical to the amino acid sequence of SEQ ID NO: 29;

d) a VH comprising or consisting of an amino acid sequence that is at least 96% identical to the amino acid sequence of SEQ ID NO: 5 and a VL comprising or consisting of an amino acid sequence that is at least 96% identical to the amino acid sequence of SEQ ID NO: 30;

e) a VH comprising or consisting of an amino acid sequence that is at least 96% identical to the amino acid sequence of SEQ ID NO: 6 and a VL comprising or consisting of an amino acid sequence that is at least 96% identical to the amino acid sequence of SEQ ID NO: 31;

f) a VH comprising or consisting of an amino acid sequence that is at least 96% identical to the amino acid sequence of SEQ ID NO: 7 and a VL comprising or consisting of an amino acid sequence that is at least 96% identical to the amino acid sequence of SEQ ID NO: 32;

g) a VH comprising or consisting of an amino acid sequence that is at least 96% identical to the amino acid sequence of SEQ ID NO: 8 and a VL comprising or consisting of an amino acid sequence that is at least 96% identical to the amino acid sequence of SEQ ID NO: 33;

h) a VH comprising or consisting of an amino acid sequence that is at least 96% identical to the amino acid sequence of SEQ ID NO: 9 and a VL comprising or consisting of an amino acid sequence that is at least 96% identical to the amino acid sequence of SEQ ID NO: 34;

i) a VH comprising or consisting of an amino acid sequence that is at least 96% identical to the amino acid sequence of SEQ ID NO: 10 and a VL comprising or consisting of an amino acid sequence that is at least 96% identical to the amino acid sequence of SEQ ID NO: 35;

j) a VH comprising or consisting of an amino acid sequence that is at least 96% identical to the amino acid sequence of SEQ ID NO: 11 and a VL comprising or consisting of an amino acid sequence that is at least 96% identical to the amino acid sequence of SEQ ID NO: 36;

k) a VH comprising or consisting of an amino acid sequence that is at least 96% identical to the amino acid sequence of SEQ ID NO: 12 and a VL comprising or consisting of an amino acid sequence that is at least 96% identical to the amino acid sequence of SEQ ID NO: 37;

l) a VH comprising or consisting of an amino acid sequence that is at least 96% identical to the amino acid sequence of SEQ ID NO: 13 and a VL comprising or consisting of an amino acid sequence that is at least 96% identical to the amino acid sequence of SEQ ID NO: 38;

m) a VH comprising or consisting of an amino acid sequence that is at least 96% identical to the amino acid sequence of SEQ ID NO: 14 and a VL comprising or consisting of an amino acid sequence that is at least 96% identical to the amino acid sequence of SEQ ID NO: 39;

n) a VH comprising or consisting of an amino acid sequence that is at least 96% identical to the amino acid sequence of SEQ ID NO: 15 and a VL comprising or consisting of an amino acid sequence that is at least 96% identical to the amino acid sequence of SEQ ID NO: 40;

o) a VH comprising or consisting of an amino acid sequence that is at least 96% identical to the amino acid sequence of SEQ ID NO: 16 and a VL comprising or consisting of an amino acid sequence that is at least 96% identical to the amino acid sequence of SEQ ID NO: 41;

p) a VH comprising or consisting of an amino acid sequence that is at least 96% identical to the amino acid sequence of SEQ ID NO: 17 and a VL comprising or consisting of an amino acid sequence that is at least 96% identical to the amino acid sequence of SEQ ID NO: 42;

q) a VH comprising or consisting of an amino acid sequence that is at least 96% identical to the amino acid sequence of SEQ ID NO: 18 and a VL comprising or consisting of an amino acid sequence that is at least 96% identical to the amino acid sequence of SEQ ID NO: 43;

r) a VH comprising or consisting of an amino acid sequence that is at least 96% identical to the amino acid sequence of SEQ ID NO: 19 and a VL comprising or consisting of an amino acid sequence that is at least 96% identical to the amino acid sequence of SEQ ID NO: 44;

s) a VH comprising or consisting of an amino acid sequence that is at least 96% identical to the amino acid sequence of SEQ ID NO: 20 and a VL comprising or consisting of an amino acid sequence that is at least 96% identical to the amino acid sequence of SEQ ID NO: 45;

t) a VH comprising or consisting of an amino acid sequence that is at least 96% identical to the amino acid sequence of SEQ ID NO: 21 and a VL comprising or consisting of an amino acid sequence that is at least 96% identical to the amino acid sequence of SEQ ID NO: 46;

u) a VH comprising or consisting of an amino acid sequence that is at least 96% identical to the amino acid sequence of SEQ ID NO: 22 and a VL comprising or consisting of an amino acid sequence that is at least 96% identical to the amino acid sequence of SEQ ID NO: 47;

v) a VH comprising or consisting of an amino acid sequence that is at least 96% identical to the amino acid sequence of SEQ ID NO: 23 and a VL comprising or consisting of an amino acid sequence that is at least 96% identical to the amino acid sequence of SEQ ID NO: 48;

w) a VH comprising or consisting of an amino acid sequence that is at least 96% identical to the amino acid sequence of SEQ ID NO: 24 and a VL comprising or consisting of an amino acid sequence that is at least 96% identical to the amino acid sequence of SEQ ID NO: 49; or x) a VH comprising or consisting of an amino acid sequence that is at least 96% identical to the amino acid sequence of SEQ ID NO: 25 and a VL comprising or consisting of an amino acid sequence that is at least 96% identical to the amino acid sequence of SEQ ID NO: 50.

Optionally the antibodies above retain the corresponding CDR sequences such that any variability in the VH and VL sequences occurs in the framework regions.

In some embodiments, there is provided an anti-TCR delta variable 1 (anti-Vδ1) antibody or antigen-binding fragment thereof comprising:

a) a VH comprising or consisting of the amino acid sequence of SEQ ID NO: 2 and a VL comprising or consisting of the amino acid sequence of SEQ ID NO: 27 optionally comprising up to 5, up to 4, up to 3, up to 2 or 1 amino acid substitutions across both variable regions;

b) a VH comprising or consisting of the amino acid sequence of SEQ ID NO: 3 and a VL comprising or consisting of the amino acid sequence of SEQ ID NO: 28 optionally comprising up to 5, up to 4, up to 3, up to 2 or 1 amino acid substitutions across both variable regions;

c) a VH comprising or consisting of the amino acid sequence of SEQ ID NO: 4 and a VL comprising or consisting of the amino acid sequence of SEQ ID NO: 29 optionally comprising up to 5, up to 4, up to 3, up to 2 or 1 amino acid substitutions across both variable regions;

d) a VH comprising or consisting of the amino acid sequence of SEQ ID NO: 5 and a VL comprising or consisting of the amino acid sequence of SEQ ID NO: 30 optionally comprising up to 5, up to 4, up to 3, up to 2 or 1 amino acid substitutions across both variable regions;

e) a VH comprising or consisting of the amino acid sequence of SEQ ID NO: 6 and a VL comprising or consisting of the amino acid sequence of SEQ ID NO: 31 optionally comprising up to 5, up to 4, up to 3, up to 2 or 1 amino acid substitutions across both variable regions;

f) a VH comprising or consisting of the amino acid sequence of SEQ ID NO: 7 and a VL comprising or consisting of the amino acid sequence of SEQ ID NO: 32 optionally comprising up to 5, up to 4, up to 3, up to 2 or 1 amino acid substitutions across both variable regions;

g) a VH comprising or consisting of the amino acid sequence of SEQ ID NO: 8 and a VL comprising or consisting of the amino acid sequence of SEQ ID NO: 33 optionally comprising up to 5, up to 4, up to 3, up to 2 or 1 amino acid substitutions across both variable regions;

h) a VH comprising or consisting of the amino acid sequence of SEQ ID NO: 9 and a VL comprising or consisting of the amino acid sequence of SEQ ID NO: 34 optionally comprising up to 5, up to 4, up to 3, up to 2 or 1 amino acid substitutions across both variable regions;

i) a VH comprising or consisting of the amino acid sequence of SEQ ID NO: 10 and a VL comprising or consisting of the amino acid sequence of SEQ ID NO: 35 optionally comprising up to 5, up to 4, up to 3, up to 2 or 1 amino acid substitutions across both variable regions;

j) a VH comprising or consisting of the amino acid sequence of SEQ ID NO: 11 and a VL comprising or consisting of the amino acid sequence of SEQ ID NO: 36 optionally comprising up to 5, up to 4, up to 3, up to 2 or 1 amino acid substitutions across both variable regions;

k) a VH comprising or consisting of the amino acid sequence of SEQ ID NO: 12 and a VL comprising or consisting of the amino acid sequence of SEQ ID NO:

37 optionally comprising up to 5, up to 4, up to 3, up to 2 or 1 amino acid substitutions across both variable regions;

l) a VH comprising or consisting of the amino acid sequence of SEQ ID NO: 13 and a VL comprising or consisting of the amino acid sequence of SEQ ID NO: 38 optionally comprising up to 5, up to 4, up to 3, up to 2 or 1 amino acid substitutions across both variable regions;

m) a VH comprising or consisting of the amino acid sequence of SEQ ID NO: 14 and a VL comprising or consisting of the amino acid sequence of SEQ ID NO: 39 optionally comprising up to 5, up to 4, up to 3, up to 2 or 1 amino acid substitutions across both variable regions;

n) a VH comprising or consisting of the amino acid sequence of SEQ ID NO: 15 and a VL comprising or consisting of the amino acid sequence of SEQ ID NO: 40 optionally comprising up to 5, up to 4, up to 3, up to 2 or 1 amino acid substitutions across both variable regions;

o) a VH comprising or consisting of the amino acid sequence of SEQ ID NO: 16 and a VL comprising or consisting of the amino acid sequence of SEQ ID NO: 41 optionally comprising up to 5, up to 4, up to 3, up to 2 or 1 amino acid substitutions across both variable regions;

p) a VH comprising or consisting of the amino acid sequence of SEQ ID NO: 17 and a VL comprising or consisting of the amino acid sequence of SEQ ID NO: 42 optionally comprising up to 5, up to 4, up to 3, up to 2 or 1 amino acid substitutions across both variable regions;

q) a VH comprising or consisting of the amino acid sequence of SEQ ID NO: 18 and a VL comprising or consisting of the amino acid sequence of SEQ ID NO: 43 optionally comprising up to 5, up to 4, up to 3, up to 2 or 1 amino acid substitutions across both variable regions;

r) a VH comprising or consisting of the amino acid sequence of SEQ ID NO: 19 and a VL comprising or consisting of the amino acid sequence of SEQ ID NO: 44 optionally comprising up to 5, up to 4, up to 3, up to 2 or 1 amino acid substitutions across both variable regions;

s) a VH comprising or consisting of the amino acid sequence of SEQ ID NO: 20 and a VL comprising or consisting of the amino acid sequence of SEQ ID NO: 45 optionally comprising up to 5, up to 4, up to 3, up to 2 or 1 amino acid substitutions across both variable regions;

t) a VH comprising or consisting of the amino acid sequence of SEQ ID NO: 21 and a VL comprising or consisting of the amino acid sequence of SEQ ID NO: 46 optionally comprising up to 5, up to 4, up to 3, up to 2 or 1 amino acid substitutions across both variable regions;

u) a VH comprising or consisting of the amino acid sequence of SEQ ID NO: 22 and a VL comprising or consisting of the amino acid sequence of SEQ ID NO: 47 optionally comprising up to 5, up to 4, up to 3, up to 2 or 1 amino acid substitutions across both variable regions;

v) a VH comprising or consisting of the amino acid sequence of SEQ ID NO: 23 and a VL comprising or consisting of the amino acid sequence of SEQ ID NO: 48 optionally comprising up to 5, up to 4, up to 3, up to 2 or 1 amino acid substitutions across both variable regions;

w) a VH comprising or consisting of the amino acid sequence of SEQ ID NO: 24 and a VL comprising or consisting of the amino acid sequence of SEQ ID NO: 49 optionally comprising up to 5, up to 4, up to 3, up to 2 or 1 amino acid substitutions across both variable regions; or x) a VH comprising or consisting of the amino acid sequence of SEQ ID NO: 25 and a VL comprising or consisting of the amino acid sequence of SEQ ID NO: 50 optionally comprising up to 5, up to 4, up to 3, up to 2 or 1 amino acid substitutions across both variable regions, optionally wherein the VH sequence is not SEQ ID NO: 1 and/or the VL sequence is not SEQ ID NO: 26.

"Across both variable regions" means collectively, the antibody may comprise up to the specified number of substitutions in total when considering both the heavy and light chain variable regions. The amino acid substitutions may be conservative amino acid substitutions. In some embodiments, the substitutions (if present) may occur anywhere in the variable region sequences. In preferred embodiments, the substitutions (if present) may be limited to the framework regions. Accordingly, in some embodiments, the amino acid substitutions do not occur in a CDR sequence.

Optionally the antibodies above retain the corresponding CDR sequences such that any variability in the VH and VL sequences occurs in the framework regions.

In some embodiments, there is provided an anti-TCR delta variable 1 (anti-Vδ1) antibody or antigen-binding fragment thereof comprising:

a) a VH comprising or consisting of the amino acid sequence of SEQ ID NO: 2 and a VL comprising or consisting of the amino acid sequence of SEQ ID NO: 27;

b) a VH comprising or consisting of the amino acid sequence of SEQ ID NO: 3 and a VL comprising or consisting of the amino acid sequence of SEQ ID NO: 28;

c) a VH comprising or consisting of the amino acid sequence of SEQ ID NO: 4 and a VL comprising or consisting of the amino acid sequence of SEQ ID NO: 29;

d) a VH comprising or consisting of the amino acid sequence of SEQ ID NO: 5 and a VL comprising or consisting of the amino acid sequence of SEQ ID NO: 30;

e) a VH comprising or consisting of the amino acid sequence of SEQ ID NO: 6 and a VL comprising or consisting of the amino acid sequence of SEQ ID NO: 31;

f) a VH comprising or consisting of the amino acid sequence of SEQ ID NO: 7 and a VL comprising or consisting of the amino acid sequence of SEQ ID NO: 32;

g) a VH comprising or consisting of the amino acid sequence of SEQ ID NO: 8 and a VL comprising or consisting of the amino acid sequence of SEQ ID NO: 33;

h) a VH comprising or consisting of the amino acid sequence of SEQ ID NO: 9 and a VL comprising or consisting of the amino acid sequence of SEQ ID NO: 34;

i) a VH comprising or consisting of the amino acid sequence of SEQ ID NO: 10 and a VL comprising or consisting of the amino acid sequence of SEQ ID NO: 35;
j) a VH comprising or consisting of the amino acid sequence of SEQ ID NO: 11 and a VL comprising or consisting of the amino acid sequence of SEQ ID NO: 36;
k) a VH comprising or consisting of the amino acid sequence of SEQ ID NO: 12 and a VL comprising or consisting of the amino acid sequence of SEQ ID NO: 37;
l) a VH comprising or consisting of the amino acid sequence of SEQ ID NO: 13 and a VL comprising or consisting of the amino acid sequence of SEQ ID NO: 38;
m) a VH comprising or consisting of the amino acid sequence of SEQ ID NO: 14 and a VL comprising or consisting of the amino acid sequence of SEQ ID NO: 39;
n) a VH comprising or consisting of the amino acid sequence of SEQ ID NO: 15 and a VL comprising or consisting of the amino acid sequence of SEQ ID NO: 40;
o) a VH comprising or consisting of the amino acid sequence of SEQ ID NO: 16 and a VL comprising or consisting of the amino acid sequence of SEQ ID NO: 41;
p) a VH comprising or consisting of the amino acid sequence of SEQ ID NO: 17 and a VL comprising or consisting of the amino acid sequence of SEQ ID NO: 42;
q) a VH comprising or consisting of the amino acid sequence of SEQ ID NO: 18 and a VL comprising or consisting of the amino acid sequence of SEQ ID NO: 43;
r) a VH comprising or consisting of the amino acid sequence of SEQ ID NO: 19 and a VL comprising or consisting of the amino acid sequence of SEQ ID NO: 44;
s) a VH comprising or consisting of the amino acid sequence of SEQ ID NO: 20 and a VL comprising or consisting of the amino acid sequence of SEQ ID NO: 45;
t) a VH comprising or consisting of the amino acid sequence of SEQ ID NO: 21 and a VL comprising or consisting of the amino acid sequence of SEQ ID NO: 46;
u) a VH comprising or consisting of the amino acid sequence of SEQ ID NO: 22 and a VL comprising or consisting of the amino acid sequence of SEQ ID NO: 47;
v) a VH comprising or consisting of the amino acid sequence of SEQ ID NO: 23 and a VL comprising or consisting of the amino acid sequence of SEQ ID NO: 48;
w) a VH comprising or consisting of the amino acid sequence of SEQ ID NO: 24 and a VL comprising or consisting of the amino acid sequence of SEQ ID NO: 49; or
x) a VH comprising or consisting of the amino acid sequence of SEQ ID NO: 25 and a VL comprising or consisting of the amino acid sequence of SEQ ID NO: 50.

Certain amino acid substitutions may be made to provide one or more variant antibodies as described herein.

In any embodiments relating to defined VH and/or VL sequences (for example any VH and/or VL sequences defined as having certain percent identities and/or substitutions), preferably the VH sequence is not SEQ ID NO: 1 and the VL sequence is not SEQ ID NO: 26.

Other Antibodies Derived from ADT1-4

In one embodiment there is provided anti-TCR delta variable 1 (anti-Vδ1) antibody or antigen-binding fragment thereof comprising:

a) an HCDR1 sequence comprising or consisting of the sequence of GDSVSSKS$X_1$A (SEQ ID NO: 158);
b) an HCDR2 sequence comprising or consisting of the sequence of SEQ ID NO: 53
c) an HCDR3 sequence comprising or consisting of the sequence of $X_2$W$X_3X_4X_5X_6$D$X_7$ (SEQ ID NO: 162), wherein the HCDR3 sequence is not SEQ ID NO: 54;
d) an LCDR1 sequence comprising or consisting of the sequence of SEQ ID NO: 79;
e) an LCDR2 sequence comprising or consisting of the sequence of SEQ ID NO: 80; and
f) an LCDR3 sequence comprising or consisting of the sequence of QQ$X_8$Y$X_9X_{10}X_{11}X_{12}X_{13}$T (SEQ ID NO: 166), wherein the LCDR3 sequence is not SEQ ID NO: 81;

and wherein each of $X_1$ to $X_{13}$ is a naturally occurring amino acid.

In one embodiment there is provided anti-TCR delta variable 1 (anti-Vδ1) antibody or antigen-binding fragment thereof comprising:

a) an HCDR1 sequence comprising or consisting of the sequence of GDSVSSKS$X_1$A (SEQ ID NO: 159);
b) an HCDR2 sequence comprising or consisting of the sequence of SEQ ID NO: 53
c) an HCDR3 sequence comprising or consisting of the sequence of $X_2$W$X_3X_4X_5X_6$D$X_7$ (SEQ ID NO: 163), wherein the HCDR3 sequence is not SEQ ID NO: 54;
d) an LCDR1 sequence comprising or consisting of the sequence of SEQ ID NO: 79;
e) an LCDR2 sequence comprising or consisting of the sequence of SEQ ID NO: 80; and
f) an LCDR3 sequence comprising or consisting of the sequence of QQ$X_8$Y$X_9X_{10}X_{11}X_{12}X_{13}$T (SEQ ID NO: 167), wherein the LCDR3 sequence is not SEQ ID NO: 81;

and wherein: $X_1$ is selected from the group consisting of A and V; $X_2$ is selected from the group consisting of S and T; $X_3$ is selected from the group consisting of V, A and L; $X_4$ is selected from the group consisting of G, E, and D; $X_5$ is selected from the group consisting of Y and N; $X_6$ is selected from the group consisting of V, A and P; $X_7$ is selected from the group consisting of V, Y and R; $X_8$ is selected from the group consisting of K, R and G; $X_9$ is selected from the group consisting of S and K; $X_{10}$ is selected from the group consisting of T, Q, A, E and D; $X_{11}$ is selected from the group consisting of P, H and D; $X_{12}$ is selected from the group consisting of Q, R, K, W, P, E and I; and $X_{13}$ is selected from the group consisting of I, V and L. The antibody may further comprise an HFR1 sequence comprising the sequence of SEQ ID NO: 170 or 171; an HFR2 sequence comprising the sequence of SEQ ID NO: 172; an HFR3 sequence comprising the sequence of SEQ ID NO: 173; an HFR4 sequence comprising the sequence of SEQ ID NO: 174; an LFR1 sequence comprising the sequence of SEQ ID NO: 175; an LFR2 sequence comprising the sequence of SEQ ID NO: 176; an LFR3 sequence comprising the sequence of SEQ ID NO: 177 or 178; and an LFR4 sequence comprising the sequence of SEQ ID NO: 179, 180, 181 or 182.

In one embodiment there is provided anti-TCR delta variable 1 (anti-Vδ1) antibody or antigen-binding fragment thereof comprising:

a) an HCDR1 sequence comprising or consisting of the sequence of GDSVSSKS$X_1$A (SEQ ID NO: 160);
b) an HCDR2 sequence comprising or consisting of the sequence of SEQ ID NO: 53
c) an HCDR3 sequence comprising or consisting of the sequence of $X_2$W$X_3$$X_4$$X_5$$X_6$D$X_7$ (SEQ ID NO: 164), wherein the HCDR3 sequence is not SEQ ID NO: 54;
d) an LCDR1 sequence comprising or consisting of the sequence of SEQ ID NO: 79;
e) an LCDR2 sequence comprising or consisting of the sequence of SEQ ID NO: 80; and
f) an LCDR3 sequence comprising or consisting of the sequence of QQ$X_8$Y$X_9$$X_{10}$$X_{11}$$X_{12}$$X_{13}$T (SEQ ID NO: 168), wherein the LCDR3 sequence is not SEQ ID NO: 81;

and wherein $X_1$ is selected from the group consisting of A and V; $X_2$ is selected from the group consisting of S and T; $X_3$ is selected from the group consisting of V, A and L; $X_4$ is selected from the group consisting of G, E, and D; $X_5$ is selected from the group consisting of Y and N; $X_6$ is selected from the group consisting of V, A and P; $X_7$ is selected from the group consisting of V, Y and R; $X_8$ is selected from the group consisting of K, R and G; $X_9$ is selected from the group consisting of S and K; $X_{10}$ is selected from the group consisting of T, Q, A, E and D; $X_{11}$ is selected from the group consisting of P and H; $X_{12}$ is selected from the group consisting of Q, R, K, W, P, E and I; and $X_{13}$ is selected from the group consisting of I, V and L. The antibody may further comprise an HFR1 sequence comprising the sequence of SEQ ID NO: 170 or 171, an HFR2 sequence comprising the sequence of SEQ ID NO: 172, an HFR3 sequence comprising the sequence of SEQ ID NO: 173, an HFR4 sequence comprising the sequence of SEQ ID NO: 174, an LFR1 sequence comprising the sequence of SEQ ID NO: 175, an LFR2 sequence comprising the sequence of SEQ ID NO: 176, an LFR3 sequence comprising the sequence of SEQ ID NO: 177 and an LFR4 sequence comprising the sequence of SEQ ID NO: 179, 180, 181 or 182.

In one embodiment there is provided anti-TCR delta variable 1 (anti-Vδ1) antibody or antigen-binding fragment thereof comprising:

a) an HCDR1 sequence comprising or consisting of the sequence of GDSVSSKS$X_1$A (SEQ ID NO: 161);
b) an HCDR2 sequence comprising or consisting of the sequence of SEQ ID NO: 53
c) an HCDR3 sequence comprising or consisting of the sequence of $X_2$W$X_3$$X_4$$X_5$$X_6$D$X_7$ (SEQ ID NO: 165), wherein the HCDR3 sequence is not SEQ ID NO: 54;
d) an LCDR1 sequence comprising or consisting of the sequence of SEQ ID NO: 79;
e) an LCDR2 sequence comprising or consisting of the sequence of SEQ ID NO: 80; and
f) an LCDR3 sequence comprising or consisting of the sequence of QQ$X_8$Y$X_9$$X_{10}$$X_{11}$$X_{12}$$X_{13}$T (SEQ ID NO: 169), wherein the LCDR3 sequence is not SEQ ID NO: 81;

and wherein $X_1$ is selected from the group consisting of A and V; $X_2$ is selected from the group consisting of S and T; $X_3$ is selected from the group consisting of V, A and L; $X_4$ is selected from the group consisting of G and D; $X_5$ is selected from the group consisting of Y and N; $X_6$ is selected from the group consisting of V, A and P; $X_7$ is selected from the group consisting of V, Y and R; $X_8$ is selected from the group consisting of K and R; $X_9$ is selected from the group consisting of S and K; $X_{10}$ is selected from the group consisting of T, Q, A and E; $X_{11}$ is selected from the group consisting of P and H; $X_{12}$ is selected from the group consisting of Q, K, W, P and I; and $X_{13}$ is selected from the group consisting of V and L. The antibody may further comprise an HFR1 sequence comprising the sequence of SEQ ID NO: 170 or 171; an HFR2 sequence comprising the sequence of SEQ ID NO: 172; an HFR3 sequence comprising the sequence of SEQ ID NO: 173; an HFR4 sequence comprising the sequence of SEQ ID NO: 174; an LFR1 sequence comprising the sequence of SEQ ID NO: 175; an LFR2 sequence comprising the sequence of SEQ ID NO: 176; an LFR3 sequence comprising the sequence of SEQ ID NO: 177; and an LFR4 sequence comprising the sequence of SEQ ID NO: 179 or 181.

ADT1-7-Derived Antibodies

The present invention provides antibodies derived from parental antibody ADT1-7 (having a variable heavy region sequence according to SEQ ID NO: 106 and a variable light region sequence according to SEQ ID No: 118), for example as set out in the following. ADT1-7 is also referred to herein as E07, and ADT1-7 and E07 are used interchangeably.

Antibodies Comprising Particular CDR Sequences Derived from ADT1-7

The antibodies provided herein include the following antibodies having particular sequences derived from ADT1-7.

For example, in some embodiments, there is provided an anti-TCR delta variable 1 (anti-Vδ1) antibody or antigen-binding fragment thereof comprising a heavy chain variable region comprising a VHCDR3 comprising or consisting of an amino acid sequence selected from the group consisting of SEQ ID Nos: 133 to 143; and/or a light chain variable region comprising a VLCDR3 comprising or consisting of an amino acid sequence selected from the group consisting of SEQ ID Nos: 147 to 157. Certain amino acid substitutions may be made to provide one or more variant antibodies as described herein.

In some embodiments, there is provided an anti-TCR delta variable 1 (anti-Vδ1) antibody or antigen-binding fragment thereof comprising a heavy chain variable region comprising a VHCDR3 comprising or consisting of an amino acid sequence selected from the group consisting of SEQ ID Nos: 138, 142 and 143 and/or a light chain variable region comprising a VLCDR3 comprising or consisting of an amino acid sequence selected from the group consisting of SEQ ID Nos: 152, 156 and 157, Certain amino acid substitutions may be made to provide one or more variant antibodies as described herein.

There is also provided an anti-TCR delta variable 1 (anti-Vδ1) antibody or antigen-binding fragment thereof comprising:

- a heavy chain variable region comprising:
  - a VHCDR1 comprising or consisting of the amino acid sequence of SEQ ID NO: 130;
  - a VHCDR2 comprising or consisting of the amino acid sequence of SEQ ID NO: 131; and
  - a VHCDR3 comprising or consisting of an amino acid sequence selected from the group consisting of: SEQ ID Nos: 133 to 143; and
- a light chain variable region comprising:
  - a VLCDR1 comprising or consisting of the amino acid sequence of SEQ ID NO: 144;

a VLCDR2 comprising or consisting of the amino acid sequence of SEQ ID NO: 145; and a VLCDR3 comprising or consisting of an amino acid sequence selected from the group consisting of: SEQ ID Nos: 147 to 157.

Certain amino acid substitutions may be made to provide one or more variant antibodies as described herein.

There is also provided an anti-TCR delta variable 1 (anti-Vδ1) antibody or antigen-binding fragment thereof comprising:

a heavy chain variable region comprising:

a VHCDR1 comprising or consisting of the amino acid sequence of SEQ ID NO: 130;

a VHCDR2 comprising or consisting of the amino acid sequence of SEQ ID NO: 131; and a VHCDR3 comprising or consisting of an amino acid sequence selected from the group consisting of: SEQ ID Nos: 138, 142 and 143; and a light chain variable region comprising:

a VLCDR1 comprising or consisting of the amino acid sequence of SEQ ID NO: 144;

a VLCDR2 comprising or consisting of the amino acid sequence of SEQ ID NO: 145; and a VLCDR3 comprising or consisting of an amino acid sequence selected from the group consisting of: SEQ ID Nos: 152, 156 and 157.

Certain amino acid substitutions may be made to provide one or more variant antibodies as described herein.

Further embodiments are provided below.

ADT1-7-10 and Fragments and Variants Thereof

Certain embodiments relate to the antibody ADT1-7-10 and fragments and variants thereof.

For example, in some embodiments, an antibody or antigen-binding fragment or variant thereof is provided comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 133 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 147. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 133 and/or a light chain variable region comprising a VLCDR3 comprising an amino acid sequence having at least 90% identity to the amino acid sequence of SEQ ID NO: 147. In one embodiment, an antibody or antigen-binding fragment or variant thereof is provided comprising a heavy chain variable region comprising a VHCDR3 comprising the amino acid sequence of SEQ ID NO: 133 and/or a light chain variable region comprising a VLCDR3 comprising the amino acid sequence of SEQ ID NO: 147.

Amino acid substitutions may be made to provide variant antibodies derived from ADT1-7-10, for example an antibody or antigen-binding fragment or variant thereof is provided comprising a heavy chain variable region comprising a VHCDR3 comprising the amino acid sequence of SEQ ID NO: 133, optionally comprising 1 or 2 amino acid substitutions, and/or a light chain variable region comprising a VLCDR3 comprising the amino acid sequence of SEQ ID NO: 147, optionally comprising 1 or 2 amino acid substitutions. The amino acid substitutions may be conservative amino acid substitutions.

In some embodiments, an antibody or antigen-binding fragment or variant thereof is provided comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 130, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 131 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 133; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 144, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 145 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 147.

In one embodiment, an antibody or antigen-binding fragment or variant thereof is provided comprising:

a heavy chain variable region comprising a VHCDR1 comprising at least 90% identity to the amino acid sequence of SEQ ID NO: 130, a VHCDR2 comprising at least 90% identity to the amino acid sequence of SEQ ID NO: 131 and a VHCDR3 comprising at least 90% identity to the amino acid sequence of SEQ ID NO: 133; and/or a light chain variable region comprising a VLCDR1 comprising the at least 90% identity to the amino acid sequence of SEQ ID NO: 144, a VLCDR2 comprising at least 90% identity to the amino acid sequence of SEQ ID NO: 145 and a VLCDR3 comprising at least 90% identity to the amino acid sequence of SEQ ID NO: 147.

In one embodiment, an antibody or antigen-binding fragment or variant thereof is provided comprising:

a heavy chain variable region comprising a VHCDR1 comprising the amino acid sequence of SEQ ID NO: 130, a VHCDR2 comprising the amino acid sequence of SEQ ID NO: 131 and a VHCDR3 comprising the amino acid sequence of SEQ ID NO: 133; and a light chain variable region comprising a VLCDR1 comprising the amino acid sequence of SEQ ID NO: 144, a VLCDR2 comprising the amino acid sequence of SEQ ID NO: 145 and a VLCDR3 comprising the amino acid sequence of SEQ ID NO: 147.

Amino acid substitutions may be made to provide variant antibodies derived from ADT1-7-10, for example an antibody or antigen-binding fragment or variant thereof is provided comprising:

a heavy chain variable region comprising a VHCDR1 comprising the amino acid sequence of SEQ ID NO: 130 optionally comprising 1 or 2 amino acid substitutions, a VHCDR2 comprising the amino acid sequence of SEQ ID NO: 131 optionally comprising 1 or 2 amino acid substitutions, and a VHCDR3 comprising the amino acid sequence of SEQ ID NO: 133 optionally comprising 1 or 2 amino acid substitutions; and/or a light chain variable region comprising a VLCDR1 comprising the amino acid sequence of SEQ ID NO: 144 optionally comprising 1 or 2 amino acid substitutions, a VLCDR2 comprising the amino acid sequence of SEQ ID NO: 145 optionally comprising 1 or 2 amino acid substitutions and a VLCDR3 comprising the amino acid sequence of SEQ ID NO: 147 optionally comprising 1 or 2 amino acid substitutions. The amino acid substitutions may be conservative amino acid substitutions.

The antibodies may alternatively consist of the specified sequences (with or without amino acid substitutions).

ADT1-7-15 and Fragments and Variants Thereof

Certain embodiments relate to the antibody ADT1-7-15 and fragments and variants thereof.

For example, in some embodiments, an antibody or antigen-binding fragment or variant thereof is provided comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 134 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 148. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 134 and/or a light chain variable region comprising a VLCDR3 comprising an amino acid sequence having at least 90% identity to the amino acid sequence of SEQ ID NO: 148. In one embodiment, an antibody or antigen-binding fragment or variant thereof is provided comprising a heavy chain variable region comprising a VHCDR3 comprising the amino acid sequence of SEQ ID NO: 134 and/or a light chain variable region comprising a VLCDR3 comprising the amino acid sequence of SEQ ID NO: 148.

Amino acid substitutions may be made to provide variant antibodies derived from ADT1-7-15, for example an antibody or antigen-binding fragment or variant thereof is provided comprising a heavy chain variable region comprising a VHCDR3 comprising the amino acid sequence of SEQ ID NO: 134, optionally comprising 1 or 2 amino acid substitutions, and/or a light chain variable region comprising a VLCDR3 comprising the amino acid sequence of SEQ ID NO: 148, optionally comprising 1 or 2 amino acid substitutions. The amino acid substitutions may be conservative amino acid substitutions.

In some embodiments, an antibody or antigen-binding fragment or variant thereof is provided comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 130, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 131 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 134; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 144, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 145 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 148.

In one embodiment, an antibody or antigen-binding fragment or variant thereof is provided comprising:

a heavy chain variable region comprising a VHCDR1 comprising at least 90% identity to the amino acid sequence of SEQ ID NO: 130, a VHCDR2 comprising at least 90% identity to the amino acid sequence of SEQ ID NO: 131 and a VHCDR3 comprising at least 90% identity to the amino acid sequence of SEQ ID NO: 134; and/or a light chain variable region comprising a VLCDR1 comprising the at least 90% identity to the amino acid sequence of SEQ ID NO: 144, a VLCDR2 comprising at least 90% identity to the amino acid sequence of SEQ ID NO: 145 and a VLCDR3 comprising at least 90% identity to the amino acid sequence of SEQ ID NO: 148.

In one embodiment, an antibody or antigen-binding fragment or variant thereof is provided comprising:

a heavy chain variable region comprising a VHCDR1 comprising the amino acid sequence of SEQ ID NO: 130, a VHCDR2 comprising the amino acid sequence of SEQ ID NO: 131 and a VHCDR3 comprising the amino acid sequence of SEQ ID NO: 134; and a light chain variable region comprising a VLCDR1 comprising the amino acid sequence of SEQ ID NO: 144, a VLCDR2 comprising the amino acid sequence of SEQ ID NO: 145 and a VLCDR3 comprising the amino acid sequence of SEQ ID NO: 148.

Amino acid substitutions may be made to provide variant antibodies derived from ADT1-7-15, for example an antibody or antigen-binding fragment or variant thereof is provided comprising:

a heavy chain variable region comprising a VHCDR1 comprising the amino acid sequence of SEQ ID NO: 130 optionally comprising 1 or 2 amino acid substitutions, a VHCDR2 comprising the amino acid sequence of SEQ ID NO: 131 optionally comprising 1 or 2 amino acid substitutions, and a VHCDR3 comprising the amino acid sequence of SEQ ID NO: 134 optionally comprising 1 or 2 amino acid substitutions; and/or a light chain variable region comprising a VLCDR1 comprising the amino acid sequence of SEQ ID NO: 144 optionally comprising 1 or 2 amino acid substitutions, a VLCDR2 comprising the amino acid sequence of SEQ ID NO: 145 optionally comprising 1 or 2 amino acid substitutions and a VLCDR3 comprising the amino acid sequence of SEQ ID NO: 148 optionally comprising 1 or 2 amino acid substitutions. The amino acid substitutions may be conservative amino acid substitutions.

The antibodies may alternatively consist of the specified sequences (with or without amino acid substitutions).

ADT1-7-17 and Fragments and Variants Thereof

Certain embodiments relate to the antibody ADT1-7-17 and fragments and variants thereof.

For example, in some embodiments, an antibody or antigen-binding fragment or variant thereof is provided comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 135 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 149. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 135 and/or a light chain variable region comprising a VLCDR3 comprising an amino acid sequence having at least 90% identity to the amino acid sequence of SEQ ID NO: 149. In one embodiment, an antibody or antigen-binding fragment or variant thereof is provided comprising a heavy chain variable region comprising a VHCDR3 comprising the amino acid sequence of SEQ ID NO: 135 and/or a light chain variable region comprising a VLCDR3 comprising the amino acid sequence of SEQ ID NO: 149.

Amino acid substitutions may be made to provide variant antibodies derived from ADT1-7-17, for example an antibody or antigen-binding fragment or variant thereof is provided comprising a heavy chain variable region comprising a VHCDR3 comprising the amino acid sequence of SEQ ID NO: 135, optionally comprising 1 or 2 amino acid substitutions, and/or a light chain variable region comprising a VLCDR3 comprising the amino acid sequence of SEQ ID NO: 149, optionally comprising 1 or 2 amino acid substitutions. The amino acid substitutions may be conservative amino acid substitutions.

In some embodiments, an antibody or antigen-binding fragment or variant thereof is provided comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 130, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 131 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 135; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 144, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 145 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 149.

In one embodiment, an antibody or antigen-binding fragment or variant thereof is provided comprising:

a heavy chain variable region comprising a VHCDR1 comprising at least 90% identity to the amino acid sequence of SEQ ID NO: 130, a VHCDR2 comprising at least 90% identity to the amino acid sequence of SEQ ID NO: 131 and a VHCDR3 comprising at least 90% identity to the amino acid sequence of SEQ ID NO: 135; and/or a light chain variable region comprising a VLCDR1 comprising the at least 90% identity to the amino acid sequence of SEQ ID NO: 144, a VLCDR2 comprising at least 90% identity to the amino acid sequence of SEQ ID NO: 145 and a VLCDR3 comprising at least 90% identity to the amino acid sequence of SEQ ID NO: 149.

In one embodiment, an antibody or antigen-binding fragment or variant thereof is provided comprising:

a heavy chain variable region comprising a VHCDR1 comprising the amino acid sequence of SEQ ID NO: 130, a VHCDR2 comprising the amino acid sequence of SEQ ID NO: 131 and a VHCDR3 comprising the amino acid sequence of SEQ ID NO: 135; and a light chain variable region comprising a VLCDR1 comprising the amino acid sequence of SEQ ID NO: 144, a VLCDR2 comprising the amino acid sequence of SEQ ID NO: 145 and a VLCDR3 comprising the amino acid sequence of SEQ ID NO: 149.

Amino acid substitutions may be made to provide variant antibodies derived from ADT1-7-17, for example an antibody or antigen-binding fragment or variant thereof is provided comprising:

a heavy chain variable region comprising a VHCDR1 comprising the amino acid sequence of SEQ ID NO: 130 optionally comprising 1 or 2 amino acid substitutions, a VHCDR2 comprising the amino acid sequence of SEQ ID NO: 131 optionally comprising 1 or 2 amino acid substitutions, and a VHCDR3 comprising the amino acid sequence of SEQ ID NO: 135 optionally comprising 1 or 2 amino acid substitutions; and/or a light chain variable region comprising a VLCDR1 comprising the amino acid sequence of SEQ ID NO: 144 optionally comprising 1 or 2 amino acid substitutions, a VLCDR2 comprising the amino acid sequence of SEQ ID NO: 145 optionally comprising 1 or 2 amino acid substitutions and a VLCDR3 comprising the amino acid sequence of SEQ ID NO: 149 optionally comprising 1 or 2 amino acid substitutions. The amino acid substitutions may be conservative amino acid substitutions.

The antibodies may alternatively consist of the specified sequences (with or without amino acid substitutions).

ADT1-7-18 and Fragments and Variants Thereof

Certain embodiments relate to the antibody ADT1-7-18 and fragments and variants thereof.

For example, in some embodiments, an antibody or antigen-binding fragment or variant thereof is provided comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 136 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 150. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 136 and/or a light chain variable region comprising a VLCDR3 comprising an amino acid sequence having at least 90% identity to the amino acid sequence of SEQ ID NO: 150. In one embodiment, an antibody or antigen-binding fragment or variant thereof is provided comprising a heavy chain variable region comprising a VHCDR3 comprising the amino acid sequence of SEQ ID NO: 136 and/or a light chain variable region comprising a VLCDR3 comprising the amino acid sequence of SEQ ID NO: 150.

Amino acid substitutions may be made to provide variant antibodies derived from ADT1-7-18, for example an antibody or antigen-binding fragment or variant thereof is provided comprising a heavy chain variable region comprising a VHCDR3 comprising the amino acid sequence of SEQ ID NO: 136, optionally comprising 1 or 2 amino acid substitutions, and/or a light chain variable region comprising a VLCDR3 comprising the amino acid sequence of SEQ ID NO: 150, optionally comprising 1 or 2 amino acid substitutions. The amino acid substitutions may be conservative amino acid substitutions.

In some embodiments, an antibody or antigen-binding fragment or variant thereof is provided comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 130, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 131 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 136; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 144, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 145 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 150.

In one embodiment, an antibody or antigen-binding fragment or variant thereof is provided comprising:

a heavy chain variable region comprising a VHCDR1 comprising at least 90% identity to the amino acid sequence of SEQ ID NO: 130, a VHCDR2 comprising at least 90% identity to the amino acid sequence of SEQ ID NO: 131 and a VHCDR3 comprising at least 90% identity to the amino acid sequence of SEQ ID NO: 136; and/or a light chain variable region comprising a VLCDR1 comprising the at least 90% identity to the amino acid sequence of SEQ ID NO: 144, a VLCDR2 comprising at least 90% identity to the amino acid sequence of SEQ ID NO: 145 and a VLCDR3 comprising at least 90% identity to the amino acid sequence of SEQ ID NO: 150.

In one embodiment, an antibody or antigen-binding fragment or variant thereof is provided comprising:

a heavy chain variable region comprising a VHCDR1 comprising the amino acid sequence of SEQ ID NO: 130, a VHCDR2 comprising the amino acid sequence of SEQ ID NO: 131 and a VHCDR3 comprising the amino acid sequence of SEQ ID NO: 136; and a light chain variable region comprising a VLCDR1 comprising the amino acid sequence of SEQ ID NO: 144, a VLCDR2 comprising the amino acid sequence of SEQ ID NO: 145 and a VLCDR3 comprising the amino acid sequence of SEQ ID NO: 150.

Amino acid substitutions may be made to provide variant antibodies derived from ADT1-7-18, for example an antibody or antigen-binding fragment or variant thereof is provided comprising:

a heavy chain variable region comprising a VHCDR1 comprising the amino acid sequence of SEQ ID NO: 130 optionally comprising 1 or 2 amino acid substitutions, a VHCDR2 comprising the amino acid sequence of SEQ ID NO: 131 optionally comprising 1 or 2 amino acid substitutions, and a VHCDR3 comprising the amino acid sequence of SEQ ID NO: 136 optionally comprising 1 or 2 amino acid substitutions; and/or a light chain variable region comprising a VLCDR1 comprising the amino acid sequence of SEQ ID NO: 144 optionally comprising 1 or 2 amino acid substitutions, a VLCDR2 comprising the amino acid sequence of SEQ ID NO: 145 optionally comprising 1 or 2 amino acid substitutions and a VLCDR3 comprising the amino acid sequence of SEQ ID NO: 150 optionally comprising 1 or 2 amino acid substitutions. The amino acid substitutions may be conservative amino acid substitutions.

The antibodies may alternatively consist of the specified sequences (with or without amino acid substitutions).

ADT1-7-19 and Fragments and Variants Thereof

Certain embodiments relate to the antibody ADT1-7-19 and fragments and variants thereof.

For example, in some embodiments, an antibody or antigen-binding fragment or variant thereof is provided comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 137 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 151. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 137 and/or a light chain variable region comprising a VLCDR3 comprising an amino acid sequence having at least 90% identity to the amino acid sequence of SEQ ID NO: 151. In one embodiment, an antibody or antigen-binding fragment or variant thereof is provided comprising a heavy chain variable region comprising a VHCDR3 comprising the amino acid sequence of SEQ ID NO: 137 and/or a light chain variable region comprising a VLCDR3 comprising the amino acid sequence of SEQ ID NO: 151.

Amino acid substitutions may be made to provide variant antibodies derived from ADT1-7-19, for example an antibody or antigen-binding fragment or variant thereof is provided comprising a heavy chain variable region comprising a VHCDR3 comprising the amino acid sequence of SEQ ID NO: 137, optionally comprising 1 or 2 amino acid substitutions, and/or a light chain variable region comprising a VLCDR3 comprising the amino acid sequence of SEQ ID NO: 151, optionally comprising 1 or 2 amino acid substitutions. The amino acid substitutions may be conservative amino acid substitutions.

In some embodiments, an antibody or antigen-binding fragment or variant thereof is provided comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 130, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 131 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 137; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 144, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 145 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 151.

In one embodiment, an antibody or antigen-binding fragment or variant thereof is provided comprising:

a heavy chain variable region comprising a VHCDR1 comprising at least 90% identity to the amino acid sequence of SEQ ID NO: 130, a VHCDR2 comprising at least 90% identity to the amino acid sequence of SEQ ID NO: 131 and a VHCDR3 comprising at least 90% identity to the amino acid sequence of SEQ ID NO: 137; and/or a light chain variable region comprising a VLCDR1 comprising the at least 90% identity to the amino acid sequence of SEQ ID NO: 144, a VLCDR2 comprising at least 90% identity to the amino acid sequence of SEQ ID NO: 145 and a VLCDR3 comprising at least 90% identity to the amino acid sequence of SEQ ID NO: 151.

In one embodiment, an antibody or antigen-binding fragment or variant thereof is provided comprising:

a heavy chain variable region comprising a VHCDR1 comprising the amino acid sequence of SEQ ID NO: 130, a VHCDR2 comprising the amino acid sequence of SEQ ID NO: 131 and a VHCDR3 comprising the amino acid sequence of SEQ ID NO: 137; and a light chain variable region comprising a VLCDR1 comprising the amino acid sequence of SEQ ID NO: 144, a VLCDR2 comprising the amino acid sequence of SEQ ID NO: 145 and a VLCDR3 comprising the amino acid sequence of SEQ ID NO: 151.

Amino acid substitutions may be made to provide variant antibodies derived from ADT1-7-19, for example an antibody or antigen-binding fragment or variant thereof is provided comprising:

- a heavy chain variable region comprising a VHCDR1 comprising the amino acid sequence of SEQ ID NO: 130 optionally comprising 1 or 2 amino acid substitutions, a VHCDR2 comprising the amino acid sequence of SEQ ID NO: 131 optionally comprising 1 or 2 amino acid substitutions, and a VHCDR3 comprising the amino acid sequence of SEQ ID NO: 137 optionally comprising 1 or 2 amino acid substitutions; and/or
- a light chain variable region comprising a VLCDR1 comprising the amino acid sequence of SEQ ID NO: 144 optionally comprising 1 or 2 amino acid substitutions, a VLCDR2 comprising the amino acid sequence of SEQ ID NO: 145 optionally comprising 1 or 2 amino acid substitutions and a VLCDR3 comprising the amino acid sequence of SEQ ID NO: 151 optionally comprising 1 or 2 amino acid substitutions. The amino acid substitutions may be conservative amino acid substitutions.

The antibodies may alternatively consist of the specified sequences (with or without amino acid substitutions).

ADT1-7-20 and Fragments and Variants Thereof

Certain embodiments relate to the antibody ADT1-7-20 and fragments and variants thereof.

For example, in some embodiments, an antibody or antigen-binding fragment or variant thereof is provided comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 138 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 152. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 138 and/or a light chain variable region comprising a VLCDR3 comprising an amino acid sequence having at least 90% identity to the amino acid sequence of SEQ ID NO: 152. In one embodiment, an antibody or antigen-binding fragment or variant thereof is provided comprising a heavy chain variable region comprising a VHCDR3 comprising the amino acid sequence of SEQ ID NO: 138 and/or a light chain variable region comprising a VLCDR3 comprising the amino acid sequence of SEQ ID NO: 152.

Amino acid substitutions may be made to provide variant antibodies derived from ADT1-7-20, for example an antibody or antigen-binding fragment or variant thereof is provided comprising a heavy chain variable region comprising a VHCDR3 comprising the amino acid sequence of SEQ ID NO: 138, optionally comprising 1 or 2 amino acid substitutions, and/or a light chain variable region comprising a VLCDR3 comprising the amino acid sequence of SEQ ID NO: 152, optionally comprising 1 or 2 amino acid substitutions. The amino acid substitutions may be conservative amino acid substitutions.

In some embodiments, an antibody or antigen-binding fragment or variant thereof is provided comprising:

- a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 130, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 131 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 138; and/or
- a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 144, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 145 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 152.

In one embodiment, an antibody or antigen-binding fragment or variant thereof is provided comprising:

- a heavy chain variable region comprising a VHCDR1 comprising at least 90% identity to the amino acid sequence of SEQ ID NO: 130, a VHCDR2 comprising at least 90% identity to the amino acid sequence of SEQ ID NO: 131 and a VHCDR3 comprising at least 90% identity to the amino acid sequence of SEQ ID NO: 138; and/or
- a light chain variable region comprising a VLCDR1 comprising the at least 90% identity to the amino acid sequence of SEQ ID NO: 144, a VLCDR2 comprising at least 90% identity to the amino acid sequence of SEQ ID NO: 145 and a VLCDR3 comprising at least 90% identity to the amino acid sequence of SEQ ID NO: 152.

In one embodiment, an antibody or antigen-binding fragment or variant thereof is provided comprising:

- a heavy chain variable region comprising a VHCDR1 comprising the amino acid sequence of SEQ ID NO: 130, a VHCDR2 comprising the amino acid sequence of SEQ ID NO: 131 and a VHCDR3 comprising the amino acid sequence of SEQ ID NO: 138; and
- a light chain variable region comprising a VLCDR1 comprising the amino acid sequence of SEQ ID NO: 144, a VLCDR2 comprising the amino acid sequence of SEQ ID NO: 145 and a VLCDR3 comprising the amino acid sequence of SEQ ID NO: 152.

Amino acid substitutions may be made to provide variant antibodies derived from ADT1-7-20, for example an antibody or antigen-binding fragment or variant thereof is provided comprising:

a heavy chain variable region comprising a VHCDR1 comprising the amino acid sequence of SEQ ID NO: 130 optionally comprising 1 or 2 amino acid substitutions, a VHCDR2 comprising the amino acid sequence of SEQ ID NO: 131 optionally comprising 1 or 2 amino acid substitutions, and a VHCDR3 comprising the amino acid sequence of SEQ ID NO: 138 optionally comprising 1 or 2 amino acid substitutions; and/or a light chain variable region comprising a VLCDR1 comprising the amino acid sequence of SEQ ID NO: 144 optionally comprising 1 or 2 amino acid substitutions, a VLCDR2 comprising the amino acid sequence of SEQ ID NO: 145 optionally comprising 1 or 2 amino acid substitutions and a VLCDR3 comprising the amino acid sequence of SEQ ID NO: 152 optionally comprising 1 or 2 amino acid substitutions. The amino acid substitutions may be conservative amino acid substitutions.

The antibodies may alternatively consist of the specified sequences (with or without amino acid substitutions).

ADT1-7-22 and Fragments and Variants Thereof

Certain embodiments relate to the antibody ADT1-7-22 and fragments and variants thereof.

For example, in some embodiments, an antibody or antigen-binding fragment or variant thereof is provided comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 139 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 153. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 139 and/or a light chain variable region comprising a VLCDR3 comprising an amino acid sequence having at least 90% identity to the amino acid sequence of SEQ ID NO: 153. In one embodiment, an antibody or antigen-binding fragment or variant thereof is provided comprising a heavy chain variable region comprising a VHCDR3 comprising the amino acid sequence of SEQ ID NO: 139 and/or a light chain variable region comprising a VLCDR3 comprising the amino acid sequence of SEQ ID NO: 153.

Amino acid substitutions may be made to provide variant antibodies derived from ADT1-7-22, for example an antibody or antigen-binding fragment or variant thereof is provided comprising a heavy chain variable region comprising a VHCDR3 comprising the amino acid sequence of SEQ ID NO: 139, optionally comprising 1 or 2 amino acid substitutions, and/or a light chain variable region comprising a VLCDR3 comprising the amino acid sequence of SEQ ID NO: 153, optionally comprising 1 or 2 amino acid substitutions. The amino acid substitutions may be conservative amino acid substitutions.

In some embodiments, an antibody or antigen-binding fragment or variant thereof is provided comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 130, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 131 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 139; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 144, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 145 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 153.

In one embodiment, an antibody or antigen-binding fragment or variant thereof is provided comprising:

a heavy chain variable region comprising a VHCDR1 comprising at least 90% identity to the amino acid sequence of SEQ ID NO: 130, a VHCDR2 comprising at least 90% identity to the amino acid sequence of SEQ ID NO: 131 and a VHCDR3 comprising at least 90% identity to the amino acid sequence of SEQ ID NO: 139; and/or a light chain variable region comprising a VLCDR1 comprising the at least 90% identity to the amino acid sequence of SEQ ID NO: 144, a VLCDR2 comprising at least 90% identity to the amino acid sequence of SEQ ID NO: 145 and a VLCDR3 comprising at least 90% identity to the amino acid sequence of SEQ ID NO: 153.

In one embodiment, an antibody or antigen-binding fragment or variant thereof is provided comprising:

a heavy chain variable region comprising a VHCDR1 comprising the amino acid sequence of SEQ ID NO: 130, a VHCDR2 comprising the amino acid sequence of SEQ ID NO: 131 and a VHCDR3 comprising the amino acid sequence of SEQ ID NO: 139; and a light chain variable region comprising a VLCDR1 comprising the amino acid sequence of SEQ ID NO: 144, a VLCDR2 comprising the amino acid sequence of SEQ ID NO: 145 and a VLCDR3 comprising the amino acid sequence of SEQ ID NO: 153.

Amino acid substitutions may be made to provide variant antibodies derived from ADT1-7-22, for example an antibody or antigen-binding fragment or variant thereof is provided comprising:

a heavy chain variable region comprising a VHCDR1 comprising the amino acid sequence of SEQ ID NO: 130 optionally comprising 1 or 2 amino acid substitutions, a VHCDR2 comprising the amino acid sequence of SEQ ID NO: 131 optionally comprising 1 or 2 amino acid substitutions, and a VHCDR3 comprising the amino acid sequence of SEQ ID NO: 139 optionally comprising 1 or 2 amino acid substitutions; and/or a light chain variable region comprising a VLCDR1 comprising the amino acid sequence of SEQ ID NO: 144 optionally comprising 1 or 2 amino acid substitutions, a VLCDR2 comprising the amino acid sequence of SEQ ID NO: 145 optionally comprising 1 or 2 amino acid substitutions and a VLCDR3 comprising the amino acid sequence of SEQ ID NO: 153 optionally comprising 1 or 2 amino acid substitutions. The amino acid substitutions may be conservative amino acid substitutions.

The antibodies may alternatively consist of the specified sequences (with or without amino acid substitutions).

ADT1-7-23 and Fragments and Variants Thereof

Certain embodiments relate to the antibody ADT1-7-23 and fragments and variants thereof.

For example, in some embodiments, an antibody or antigen-binding fragment or variant thereof is provided comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 140 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 154. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 140 and/or a light chain variable region comprising a VLCDR3 comprising an amino acid sequence having at least 90% identity to the amino acid sequence of SEQ ID NO: 154. In one embodiment, an antibody or antigen-binding fragment or variant thereof is provided comprising a heavy chain variable region comprising a VHCDR3 comprising the amino acid sequence of SEQ ID NO: 140 and/or a light chain variable region comprising a VLCDR3 comprising the amino acid sequence of SEQ ID NO: 154.

Amino acid substitutions may be made to provide variant antibodies derived from ADT1-7-23, for example an antibody or antigen-binding fragment or variant thereof is provided comprising a heavy chain variable region comprising a VHCDR3 comprising the amino acid sequence of SEQ ID NO: 140, optionally comprising 1 or 2 amino acid substitutions, and/or a light chain variable region comprising a VLCDR3 comprising the amino acid sequence of SEQ ID NO: 154, optionally comprising 1 or 2 amino acid substitutions. The amino acid substitutions may be conservative amino acid substitutions.

In some embodiments, an antibody or antigen-binding fragment or variant thereof is provided comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 130, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 131 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 140; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 144, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 145 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 154.

In one embodiment, an antibody or antigen-binding fragment or variant thereof is provided comprising:

a heavy chain variable region comprising a VHCDR1 comprising at least 90% identity to the amino acid sequence of SEQ ID NO: 130, a VHCDR2 comprising at least 90% identity to the amino acid sequence of SEQ ID NO: 131 and a VHCDR3 comprising at least 90% identity to the amino acid sequence of SEQ ID NO: 140; and/or a light chain variable region comprising a VLCDR1 comprising the at least 90% identity to the amino acid sequence of SEQ ID NO: 144, a VLCDR2 comprising at least 90% identity to the amino acid sequence of SEQ ID NO: 145 and a VLCDR3 comprising at least 90% identity to the amino acid sequence of SEQ ID NO: 154.

In one embodiment, an antibody or antigen-binding fragment or variant thereof is provided comprising:

a heavy chain variable region comprising a VHCDR1 comprising the amino acid sequence of SEQ ID NO: 130, a VHCDR2 comprising the amino acid sequence of SEQ ID NO: 131 and a VHCDR3 comprising the amino acid sequence of SEQ ID NO: 140; and a light chain variable region comprising a VLCDR1 comprising the amino acid sequence of SEQ ID NO: 144, a VLCDR2 comprising the amino acid sequence of SEQ ID NO: 145 and a VLCDR3 comprising the amino acid sequence of SEQ ID NO: 154.

Amino acid substitutions may be made to provide variant antibodies derived from ADT1-7-23, for example an antibody or antigen-binding fragment or variant thereof is provided comprising:

a heavy chain variable region comprising a VHCDR1 comprising the amino acid sequence of SEQ ID NO: 130 optionally comprising 1 or 2 amino acid substitutions, a VHCDR2 comprising the amino acid sequence of SEQ ID NO: 131 optionally comprising 1 or 2 amino acid substitutions, and a VHCDR3 comprising the amino acid sequence of SEQ ID NO: 140 optionally comprising 1 or 2 amino acid substitutions; and/or a light chain variable region comprising a VLCDR1 comprising the amino acid sequence of SEQ ID NO: 144 optionally comprising 1 or 2 amino acid substitutions, a VLCDR2 comprising the amino acid sequence of SEQ ID NO: 145 optionally comprising 1 or 2 amino acid substitutions and a VLCDR3 comprising the amino acid sequence of SEQ ID NO: 154 optionally comprising 1 or 2 amino acid substitutions. The amino acid substitutions may be conservative amino acid substitutions.

The antibodies may alternatively consist of the specified sequences (with or without amino acid substitutions).

ADT1-7-42 and Fragments and Variants Thereof

Certain embodiments relate to the antibody ADT1-7-42 and fragments and variants thereof.

For example, in some embodiments, an antibody or antigen-binding fragment or variant thereof is provided comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 141 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 155. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 141 and/or a light chain variable region comprising a VLCDR3 comprising an amino acid sequence having at least 90% identity to the amino acid sequence of SEQ ID NO: 155. In one embodiment, an antibody or antigen-binding fragment or variant thereof is provided comprising a heavy chain variable region comprising a VHCDR3 comprising the amino acid sequence of SEQ ID NO: 141 and/or a light chain variable region comprising a VLCDR3 comprising the amino acid sequence of SEQ ID NO: 155.

Amino acid substitutions may be made to provide variant antibodies derived from ADT1-7-42, for example an antibody or antigen-binding fragment or variant thereof is provided comprising a heavy chain variable region comprising a VHCDR3 comprising the amino acid sequence of SEQ ID NO: 141, optionally comprising 1 or 2 amino acid substitutions, and/or a light chain variable region comprising a VLCDR3 comprising the amino acid sequence of SEQ ID NO: 155, optionally comprising 1 or 2 amino acid substitutions. The amino acid substitutions may be conservative amino acid substitutions.

In some embodiments, an antibody or antigen-binding fragment or variant thereof is provided comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 130, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 131 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 141; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 144, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 145 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 155.

In one embodiment, an antibody or antigen-binding fragment or variant thereof is provided comprising:

a heavy chain variable region comprising a VHCDR1 comprising at least 90% identity to the amino acid sequence of SEQ ID NO: 130, a VHCDR2 comprising at least 90% identity to the amino acid sequence of SEQ ID NO: 131 and a VHCDR3 comprising at least 90% identity to the amino acid sequence of SEQ ID NO: 141; and/or a light chain variable region comprising a VLCDR1 comprising the at least 90% identity to the amino acid sequence of SEQ ID NO: 144, a VLCDR2 comprising at least 90% identity to the amino acid sequence of SEQ ID NO: 145 and a VLCDR3 comprising at least 90% identity to the amino acid sequence of SEQ ID NO: 155.

In one embodiment, an antibody or antigen-binding fragment or variant thereof is provided comprising:

a heavy chain variable region comprising a VHCDR1 comprising the amino acid sequence of SEQ ID NO: 130, a VHCDR2 comprising the amino acid sequence of SEQ ID NO: 131 and a VHCDR3 comprising the amino acid sequence of SEQ ID NO: 141; and a light chain variable region comprising a VLCDR1 comprising the amino acid sequence of SEQ ID NO: 144, a VLCDR2 comprising the amino acid sequence of SEQ ID NO: 145 and a VLCDR3 comprising the amino acid sequence of SEQ ID NO: 155.

Amino acid substitutions may be made to provide variant antibodies derived from ADT1-7-42, for example an antibody or antigen-binding fragment or variant thereof is provided comprising:

a heavy chain variable region comprising a VHCDR1 comprising the amino acid sequence of SEQ ID NO: 130 optionally comprising 1 or 2 amino acid substitutions, a VHCDR2 comprising the amino acid sequence of SEQ ID NO: 131 optionally comprising 1 or 2 amino acid substitutions, and a VHCDR3 comprising the amino acid sequence of SEQ ID NO: 141 optionally comprising 1 or 2 amino acid substitutions; and/or a light chain variable region comprising a VLCDR1 comprising the amino acid sequence of SEQ ID NO: 144 optionally comprising 1 or 2 amino acid substitutions, a VLCDR2 comprising the amino acid sequence of SEQ ID NO: 145 optionally comprising 1 or 2 amino acid substitutions and a VLCDR3 comprising the amino acid sequence of SEQ ID NO: 155 optionally comprising 1 or 2 amino acid substitutions. The amino acid substitutions may be conservative amino acid substitutions.

The antibodies may alternatively consist of the specified sequences (with or without amino acid substitutions).

ADT1-7-3 and Fragments and Variants Thereof

Certain embodiments relate to the antibody ADT1-7-3 and fragments and variants thereof.

For example, in some embodiments, an antibody or antigen-binding fragment or variant thereof is provided comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 142 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 156. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 142 and/or a light chain variable region comprising a VLCDR3 comprising an amino acid sequence having at least 90% identity to the amino acid sequence of SEQ ID NO: 156. In one embodiment, an antibody or antigen-binding fragment or variant thereof is provided comprising a heavy chain variable region comprising a VHCDR3 comprising the amino acid sequence of SEQ ID NO: 142 and/or a light chain variable region comprising a VLCDR3 comprising the amino acid sequence of SEQ ID NO: 156.

Amino acid substitutions may be made to provide variant antibodies derived from ADT1-7-3, for example an antibody or antigen-binding fragment or variant thereof is provided comprising a heavy chain variable region comprising a VHCDR3 comprising the amino acid sequence of SEQ ID NO: 142, optionally comprising 1 or 2 amino acid substitutions, and/or a light chain variable region comprising a VLCDR3 comprising the amino acid sequence of SEQ ID NO: 156, optionally comprising 1 or 2 amino acid substitutions. The amino acid substitutions may be conservative amino acid substitutions.

In some embodiments, an antibody or antigen-binding fragment or variant thereof is provided comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 130, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 131 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 142; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 144, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 145 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 156.

In one embodiment, an antibody or antigen-binding fragment or variant thereof is provided comprising:

a heavy chain variable region comprising a VHCDR1 comprising at least 90% identity to the amino acid sequence of SEQ ID NO: 130, a VHCDR2 comprising at least 90% identity to the amino acid sequence of SEQ ID NO: 131 and a VHCDR3 comprising at least 90% identity to the amino acid sequence of SEQ ID NO: 142; and/or a light chain variable region comprising a VLCDR1 comprising the at least 90% identity to the amino acid sequence of SEQ ID NO: 144, a VLCDR2 comprising at least 90% identity to the amino acid sequence of SEQ ID NO: 145 and a VLCDR3 comprising at least 90% identity to the amino acid sequence of SEQ ID NO: 156.

In one embodiment, an antibody or antigen-binding fragment or variant thereof is provided comprising:

a heavy chain variable region comprising a VHCDR1 comprising the amino acid sequence of SEQ ID NO: 130, a VHCDR2 comprising the amino acid sequence of SEQ ID NO: 131 and a VHCDR3 comprising the amino acid sequence of SEQ ID NO: 142; and a light chain variable region comprising a VLCDR1 comprising the amino acid sequence of SEQ ID NO: 144, a VLCDR2 comprising the amino acid sequence of SEQ ID NO: 145 and a VLCDR3 comprising the amino acid sequence of SEQ ID NO: 156.

Amino acid substitutions may be made to provide variant antibodies derived from ADT1-7-3, for example an antibody or antigen-binding fragment or variant thereof is provided comprising:

a heavy chain variable region comprising a VHCDR1 comprising the amino acid sequence of SEQ ID NO: 130 optionally comprising 1 or 2 amino acid substitutions, a VHCDR2 comprising the amino acid sequence of SEQ ID NO: 131 optionally comprising 1 or 2 amino acid substitutions, and a VHCDR3 comprising the amino acid sequence of SEQ ID NO: 142 optionally comprising 1 or 2 amino acid substitutions; and/or a light chain variable region comprising a VLCDR1 comprising the amino acid sequence of SEQ ID NO: 144 optionally comprising 1 or 2 amino acid substitutions, a VLCDR2 comprising the amino acid sequence of SEQ ID NO: 145 optionally comprising 1 or 2 amino acid substitutions and a VLCDR3 comprising the amino acid sequence of SEQ ID NO: 156 optionally comprising 1 or 2 amino acid substitutions. The amino acid substitutions may be conservative amino acid substitutions.

The antibodies may alternatively consist of the specified sequences (with or without amino acid substitutions).

ADT1-7-61 and Fragments and Variants Thereof

Certain embodiments relate to the antibody ADT1-7-61 and fragments and variants thereof.

For example, in some embodiments, an antibody or antigen-binding fragment or variant thereof is provided comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 143 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 157. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 143 and/or a light chain variable region comprising a VLCDR3 comprising an amino acid sequence having at least 90% identity to the amino acid sequence of SEQ ID NO: 157. In one embodiment, an antibody or antigen-binding fragment or variant thereof is provided comprising a heavy chain variable region comprising a VHCDR3 comprising the amino acid sequence of SEQ ID NO: 143 and/or a light chain variable region comprising a VLCDR3 comprising the amino acid sequence of SEQ ID NO: 157.

Amino acid substitutions may be made to provide variant antibodies derived from ADT1-7-61, for example an antibody or antigen-binding fragment or variant thereof is provided comprising a heavy chain variable region comprising a VHCDR3 comprising the amino acid sequence of SEQ ID NO: 143, optionally comprising 1 or 2 amino acid substitutions, and/or a light chain variable region comprising a VLCDR3 comprising the amino acid sequence of SEQ ID NO: 157, optionally comprising 1 or 2 amino acid substitutions. The amino acid substitutions may be conservative amino acid substitutions.

In some embodiments, an antibody or antigen-binding fragment or variant thereof is provided comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 130, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 131 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 143; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 144, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 145 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 157.

In one embodiment, an antibody or antigen-binding fragment or variant thereof is provided comprising:

a heavy chain variable region comprising a VHCDR1 comprising at least 90% identity to the amino acid sequence of SEQ ID NO: 130, a VHCDR2 comprising at least 90% identity to the amino acid sequence of SEQ ID NO: 131 and a VHCDR3 comprising at least 90% identity to the amino acid sequence of SEQ ID NO: 143; and/or a light chain variable region comprising a VLCDR1 comprising the at least 90% identity to the amino acid sequence of SEQ ID NO: 144, a VLCDR2 comprising at least 90% identity to the amino acid sequence of SEQ ID NO: 145 and a VLCDR3 comprising at least 90% identity to the amino acid sequence of SEQ ID NO: 157.

In one embodiment, an antibody or antigen-binding fragment or variant thereof is provided comprising:

a heavy chain variable region comprising a VHCDR1 comprising the amino acid sequence of SEQ ID NO: 130, a VHCDR2 comprising the amino acid sequence of SEQ ID NO: 131 and a VHCDR3 comprising the amino acid sequence of SEQ ID NO: 143; and a light chain variable region comprising a VLCDR1 comprising the amino acid sequence of SEQ ID NO: 144, a VLCDR2 comprising the amino acid sequence of SEQ ID NO: 145 and a VLCDR3 comprising the amino acid sequence of SEQ ID NO: 157.

Amino acid substitutions may be made to provide variant antibodies derived from ADT1-7-61, for example an antibody or antigen-binding fragment or variant thereof is provided comprising:

a heavy chain variable region comprising a VHCDR1 comprising the amino acid sequence of SEQ ID NO: 130 optionally comprising 1 or 2 amino acid substitutions, a VHCDR2 comprising the amino acid sequence of SEQ ID NO: 131 optionally comprising 1 or 2 amino acid substitutions, and a VHCDR3 comprising the amino acid sequence of SEQ ID NO: 143 optionally comprising 1 or 2 amino acid substitutions; and/or a light chain variable region comprising a VLCDR1 comprising the amino acid sequence of SEQ ID NO: 144 optionally comprising 1 or 2 amino acid substitutions, a VLCDR2 comprising the amino acid sequence of SEQ ID NO: 145 optionally comprising 1 or 2 amino acid substitutions and a VLCDR3 comprising the amino acid sequence of SEQ ID NO: 157 optionally comprising 1 or 2 amino acid substitutions. The amino acid substitutions may be conservative amino acid substitutions.

The antibodies may alternatively consist of the specified sequences (with or without amino acid substitutions).

Antibodies Comprising Heavy and/or Light Chain Variable Regions Derived from ADT1-7

There is provided herein an anti-TCR delta variable 1 (anti-Vδ1) antibody or antigen-binding fragment thereof comprising:

a heavy chain variable region comprising or consisting of a sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of SEQ ID Nos: 107 to 117; and/or a light chain variable region comprising or consisting of a sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of SEQ ID Nos: 119 to 129.

There is also provided herein an anti-TCR delta variable 1 (anti-Vδ1) antibody or antigen-binding fragment thereof comprising:

a heavy chain variable region comprising or consisting of a sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of SEQ ID Nos: 107 to 117, wherein the heavy chain variable region sequence is not SEQ ID NO: 106; and/or a light chain variable region comprising or consisting of a sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of SEQ ID Nos: 119 to 129, wherein the light chain variable region sequence is not SEQ ID NO: 118.

There is also provided an anti-TCR delta variable 1 (anti-Vδ1) antibody or antigen-binding fragment thereof comprising:

a heavy chain variable region comprising or consisting of a sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of SEQ ID Nos: 112, 116 and 117; and/or a light chain variable region comprising or consisting of a sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of SEQ ID Nos: 124, 128 and 129.

There is provided herein an anti-TCR delta variable 1 (anti-Vδ1) antibody or antigen-binding fragment thereof comprising:

a heavy chain variable region comprising or consisting of a sequence having at least 90% identity to a sequence selected from the group consisting of SEQ ID Nos: 107 to 117; and/or a light chain variable region comprising or consisting of a sequence having at least 90% identity to a sequence selected from the group consisting of SEQ ID Nos: 119 to 129.

There is also provided an anti-TCR delta variable 1 (anti-Vδ1) antibody or antigen-binding fragment thereof comprising:

a heavy chain variable region comprising or consisting of a sequence having at least 90% identity to a sequence selected from the group consisting of SEQ ID Nos: 112, 116 and 117; and/or a light chain variable region comprising or consisting of a sequence having at least 90% identity to a sequence selected from the group consisting of SEQ ID Nos: 124, 128 and 129.

Optionally the antibodies above retain the corresponding CDR sequences such that any variability in the VH and VL sequences occurs in the framework regions.

There is provided herein an anti-TCR delta variable 1 (anti-Vδ1) antibody or antigen-binding fragment thereof comprising:

a heavy chain variable region comprising or consisting of a sequence selected from the group consisting of SEQ ID Nos: 107 to 117; and/or a light chain variable region comprising or consisting of a sequence selected from the group consisting of SEQ ID Nos: 119 to 129.

There is also provided an anti-TCR delta variable 1 (anti-Vδ1) antibody or antigen-binding fragment thereof comprising:

a heavy chain variable region comprising or consisting of a sequence selected from the group consisting of SEQ ID Nos: 112, 116 and 117; and/or a light chain variable region comprising or consisting of a sequence selected from the group consisting of SEQ ID Nos: 124, 128 and 129.

In some embodiments, there is provided an anti-TCR delta variable 1 (anti-Vδ1) antibody or antigen-binding fragment thereof comprising:

a) a VH comprising or consisting of an amino acid sequence that is at least 90% identical to the amino acid sequence of SEQ ID NO: 107 and a VL comprising or consisting of an amino acid sequence that is at least 90% identical to the amino acid sequence of SEQ ID NO: 119;

b) a VH comprising or consisting of an amino acid sequence that is at least 90% identical to the amino acid sequence of SEQ ID NO: 108 and a VL comprising or consisting of an amino acid sequence that is at least 90% identical to the amino acid sequence of SEQ ID NO: 120;

c) a VH comprising or consisting of an amino acid sequence that is at least 90% identical to the amino acid sequence of SEQ ID NO: 109 and a VL comprising or consisting of an amino acid sequence that is at least 90% identical to the amino acid sequence of SEQ ID NO: 121;

d) a VH comprising or consisting of an amino acid sequence that is at least 90% identical to the amino acid sequence of SEQ ID NO: 110 and a VL comprising or consisting of an amino acid sequence that is at least 90% identical to the amino acid sequence of SEQ ID NO: 122;

e) a VH comprising or consisting of an amino acid sequence that is at least 90% identical to the amino acid sequence of SEQ ID NO: 111 and a VL comprising or consisting of an amino acid sequence that is at least 90% identical to the amino acid sequence of SEQ ID NO: 123;

f) a VH comprising or consisting of an amino acid sequence that is at least 90% identical to the amino acid sequence of SEQ ID NO: 112 and a VL comprising or consisting of an amino acid sequence that is at least 90% identical to the amino acid sequence of SEQ ID NO: 124;

g) a VH comprising or consisting of an amino acid sequence that is at least 90% identical to the amino acid sequence of SEQ ID NO: 113 and a VL comprising or consisting of an amino acid sequence that is at least 90% identical to the amino acid sequence of SEQ ID NO: 125;

h) a VH comprising or consisting of an amino acid sequence that is at least 90% identical to the amino acid sequence of SEQ ID NO: 114 and a VL comprising or consisting of an amino acid sequence that is at least 90% identical to the amino acid sequence of SEQ ID NO: 126;

i) a VH comprising or consisting of an amino acid sequence that is at least 90% identical to the amino acid sequence of SEQ ID NO: 115 and a VL comprising or consisting of an amino acid sequence that is at least 90% identical to the amino acid sequence of SEQ ID NO: 127;

j) a VH comprising or consisting of an amino acid sequence that is at least 90% identical to the amino acid sequence of SEQ ID NO: 116 and a VL comprising or consisting of an amino acid sequence that is at least 90% identical to the amino acid sequence of SEQ ID NO: 128; or k) a VH comprising or consisting of an amino acid sequence that is at least 90% identical to the amino acid sequence of SEQ ID NO: 117 and a VL comprising or consisting of an amino acid sequence that is at least 90% identical to the amino acid sequence of SEQ ID NO: 129, optionally wherein the VH sequence is not SEQ ID NO: 106 and/or the VL sequence is not SEQ ID NO: 118.

Optionally the antibodies above retain the corresponding CDR sequences such that any variability in the VH and VL sequences occurs in the framework regions.

In some embodiments, there is provided an anti-TCR delta variable 1 (anti-Vδ1) antibody or antigen-binding fragment thereof comprising:

a) a VH comprising or consisting of the amino acid sequence of SEQ ID NO: 107 and a VL comprising or consisting of the amino acid sequence of SEQ ID NO: 119 optionally comprising up to 5, up to 4, up to 3, up to 2 or 1 amino acid substitutions across both variable regions;

b) a VH comprising or consisting of the amino acid sequence of SEQ ID NO: 108 and a VL comprising or consisting of the amino acid sequence of SEQ ID NO: 120 optionally comprising up to 5, up to 4, up to 3, up to 2 or 1 amino acid substitutions across both variable regions;

c) a VH comprising or consisting of the amino acid sequence of SEQ ID NO: 109 and a VL comprising or consisting of the amino acid sequence of SEQ ID NO: 121 optionally comprising up to 5, up to 4, up to 3, up to 2 or 1 amino acid substitutions across both variable regions;

d) a VH comprising or consisting of the amino acid sequence of SEQ ID NO: 110 and a VL comprising or consisting of the amino acid sequence of SEQ ID NO: 122 optionally comprising up to 5, up to 4, up to 3, up to 2 or 1 amino acid substitutions across both variable regions;

e) a VH comprising or consisting of the amino acid sequence of SEQ ID NO: 111 and a VL comprising or consisting of the amino acid sequence of SEQ ID NO: 123 optionally comprising up to 5, up to 4, up to 3, up to 2 or 1 amino acid substitutions across both variable regions;

f) a VH comprising or consisting of the amino acid sequence of SEQ ID NO: 112 and a VL comprising or consisting of the amino acid sequence of SEQ ID NO: 124 optionally comprising up to 5, up to 4, up to 3, up to 2 or 1 amino acid substitutions across both variable regions;

g) a VH comprising or consisting of the amino acid sequence of SEQ ID NO: 113 and a VL comprising or consisting of the amino acid sequence of SEQ ID NO: 125 optionally comprising up to 5, up to 4, up to 3, up to 2 or 1 amino acid substitutions across both variable regions;

h) a VH comprising or consisting of the amino acid sequence of SEQ ID NO: 114 and a VL comprising or consisting of the amino acid sequence of SEQ ID NO: 126 optionally comprising up to 5, up to 4, up to 3, up to 2 or 1 amino acid substitutions across both variable regions;

i) a VH comprising or consisting of the amino acid sequence of SEQ ID NO: 115 and a VL comprising or consisting of the amino acid sequence of SEQ ID NO: 127 optionally comprising up to 5, up to 4, up to 3, up to 2 or 1 amino acid substitutions across both variable regions;

j) a VH comprising or consisting of the amino acid sequence of SEQ ID NO: 116 and a VL comprising or consisting of the amino acid sequence of SEQ ID NO: 128 optionally comprising up to 5, up to 4, up to 3, up to 2 or 1 amino acid substitutions across both variable regions; or k) a VH comprising or consisting of the amino acid sequence of SEQ ID NO: 117 and a VL comprising or consisting of the amino acid sequence of SEQ ID NO:

129 optionally comprising up to 5, up to 4, up to 3, up to 2 or 1 amino acid substitutions across both variable regions.

"Across both variable regions" means collectively, the antibody may comprise up to the specified number of substitutions in total when considering both the heavy and light chain variable regions. The amino acid substitutions may be conservative amino acid substitutions. In some embodiments, the substitutions (if present) may occur anywhere in the variable region sequences. In preferred embodiments, the substitutions (if present) may be limited to the framework regions. Accordingly in some embodiments, the amino acid substitutions do not occur in a CDR sequence.

Optionally the antibodies above retain the corresponding CDR sequences such that any variability in the VH and VL sequences occurs in the framework regions.

In some embodiments, there is provided an anti-TCR delta variable 1 (anti-Vδ1) antibody or antigen-binding fragment thereof comprising:

a) a VH comprising or consisting of the amino acid sequence of SEQ ID NO: 107 and a VL comprising or consisting of the amino acid sequence of SEQ ID NO: 119;
b) a VH comprising or consisting of the amino acid sequence of SEQ ID NO: 108 and a VL comprising or consisting of the amino acid sequence of SEQ ID NO: 120;
c) a VH comprising or consisting of the amino acid sequence of SEQ ID NO: 109 and a VL comprising or consisting of the amino acid sequence of SEQ ID NO: 121;
d) a VH comprising or consisting of the amino acid sequence of SEQ ID NO: 110 and a VL comprising or consisting of the amino acid sequence of SEQ ID NO: 122;
e) a VH comprising or consisting of the amino acid sequence of SEQ ID NO: 111 and a VL comprising or consisting of the amino acid sequence of SEQ ID NO: 123;
f) a VH comprising or consisting of the amino acid sequence of SEQ ID NO: 112 and a VL comprising or consisting of the amino acid sequence of SEQ ID NO: 124;
g) a VH comprising or consisting of the amino acid sequence of SEQ ID NO: 113 and a VL comprising or consisting of the amino acid sequence of SEQ ID NO: 125;
h) a VH comprising or consisting of the amino acid sequence of SEQ ID NO: 114 and a VL comprising or consisting of the amino acid sequence of SEQ ID NO: 126;
i) a VH comprising or consisting of the amino acid sequence of SEQ ID NO: 115 and a VL comprising or consisting of the amino acid sequence of SEQ ID NO: 127;
j) a VH comprising or consisting of the amino acid sequence of SEQ ID NO: 116 and a VL comprising or consisting of the amino acid sequence of SEQ ID NO: 128; or
k) a VH comprising or consisting of the amino acid sequence of SEQ ID NO: 117 and a VL comprising or consisting of the amino acid sequence of SEQ ID NO: 129.

Certain amino acid substitutions may be made to provide one or more variant antibodies as described herein.

In any embodiments relating to defined VH and/or VL sequences (for example any VH and/or VL sequences defined as having certain percent identities and/or substitutions), preferably the VH sequence is not SEQ ID NO: 106 and the VL sequence is not SEQ ID NO: 118.

Other Antibodies Derived from ADT1-7

In one embodiment there is provided anti-TCR delta variable 1 (anti-Vδ1) antibody or antigen-binding fragment thereof comprising:

a) an HCDR1 sequence comprising or consisting of the sequence of SEQ ID NO: 130;
b) an HCDR2 sequence comprising or consisting of the sequence of SEQ ID NO: 131;
c) an HCDR3 sequence comprising or consisting of the sequence of $X_1X_2YX_3X_4$AFDI (SEQ ID NO: 183), wherein the HCDR3 sequence is not SEQ ID NO: 132;
d) an LCDR1 sequence comprising or consisting of the sequence of SEQ ID NO: 144;
e) an LCDR2 sequence comprising or consisting of the sequence of SEQ ID NO: 145; and
f) an LCDR3 sequence comprising or consisting of the sequence of $QQX_5X_6X_7X_8LX_9T$ (SEQ ID NO: 186), wherein the LCDR3 sequence is no SEQ ID NO: 146;

wherein each of $X_1$ to $X_9$ is a naturally occurring amino acid.

In one embodiment there is provided anti-TCR delta variable 1 (anti-Vδ1) antibody or antigen-binding fragment thereof comprising:

a) an HCDR1 sequence comprising or consisting of the sequence of SEQ ID NO: 130;
b) an HCDR2 sequence comprising or consisting of the sequence of SEQ ID NO: 131;
c) an HCDR3 sequence comprising or consisting of the sequence of $X_1X_2YX_3X_4$AFDI (SEQ ID NO: 184), wherein the HCDR3 sequence is not SEQ ID NO: 132;
d) an LCDR1 sequence comprising or consisting of the sequence of SEQ ID NO: 144;
e) an LCDR2 sequence comprising or consisting of the sequence of SEQ ID NO: 145; and
f) an LCDR3 sequence comprising or consisting of the sequence of $QQX_5X_6X_7X_8LX_9T$ (SEQ ID NO: 187), wherein the LCDR3 sequence is no SEQ ID NO: 146;

wherein $X_1$ is selected from the group consisting of D, I and V; $X_2$ is selected from the group consisting of D and S; $X_3$ is selected from the group consisting of N, E, D, Q and A; $X_4$ is selected from the group consisting of D and E; $X_5$ is selected from the group consisting of T and S; $X_6$ is selected from the group consisting of A, G, Y and S; $X_7$ is selected from the group consisting of S and D; $X_8$ is selected from the group consisting of T, E and G; and $X_9$ is selected from the group consisting of L and D. The antibody may further comprise an HFR1 sequence comprising the sequence of SEQ ID NO: 189; an HFR2 sequence comprising the sequence of SEQ ID NO: 190; an HFR3 sequence comprising the sequence of SEQ ID NO: 191; an HFR4 sequence comprising the sequence of SEQ ID NO: 192; an LFR1 sequence comprising the sequence of SEQ ID NO: 193 and 194; an LFR2 sequence comprising the sequence of SEQ ID NO: 195; an LFR3 sequence comprising the sequence of SEQ ID NO: 196; and an LFR4 sequence comprising the sequence of SEQ ID NO: 197.

In one embodiment there is provided anti-TCR delta variable 1 (anti-Vδ1) antibody or antigen-binding fragment thereof comprising:

a) an HCDR1 sequence comprising or consisting of the sequence of SEQ ID NO: 130;
b) an HCDR2 sequence comprising or consisting of the sequence of SEQ ID NO: 131;

c) an HCDR3 sequence comprising or consisting of the sequence of $X_1X_2YX_3X_4$AFDI (SEQ ID NO: 185), wherein the HCDR3 sequence is not SEQ ID NO: 132;

d) an LCDR1 sequence comprising or consisting of the sequence of SEQ ID NO: 144;

e) an LCDR2 sequence comprising or consisting of the sequence of SEQ ID NO: 145; and f) an LCDR3 sequence comprising or consisting of the sequence of $QQX_5X_6X_7X_8LX_9T$ (SEQ ID NO: 188), wherein the LCDR3 sequence is no SEQ ID NO: 146;

wherein $X_1$ is selected from the group consisting of D and V; $X_2$ is selected from the group consisting of D and S; $X_3$ is selected from the group consisting of D, Q and A; $X_4$ is selected from the group consisting of D and E; $X_5$ is S; $X_6$ is selected from the group consisting of A and Y; $X_7$ is 5, $X_8$ is selected from the group consisting of E and G; and $X_9$ is selected from the group consisting of L and D. The antibody may further comprise an HFR1 sequence comprising the sequence of SEQ ID NO: 189; an HFR2 sequence comprising the sequence of SEQ ID NO: 190; an HFR3 sequence comprising the sequence of SEQ ID NO: 191; an HFR4 sequence comprising the sequence of SEQ ID NO: 192; an LFR1 sequence comprising the sequence of SEQ ID NO: 193; an LFR2 sequence comprising the sequence of SEQ ID NO: 195; an LFR3 sequence comprising the sequence of SEQ ID NO: 196; and an LFR4 sequence comprising the sequence of SEQ ID NO: 197.

Antibodies Having Sequence Substitutions

The skilled person is aware that various amino acids have similar properties. One or more such amino acids of a substance can often be substituted by one or more other such amino acids without eliminating a desired activity of that substance.

Thus, the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains).

A "conservative" amino acid substitution is an amino acid substitution in which an amino acid residue is replaced with another amino acid residue of similar chemical structure and which is expected to have little influence on the function, activity or other biological properties of the polypeptide. Such conservative substitutions suitably are substitutions in which one amino acid within the following groups is substituted by another amino acid residue from within the same group:

| Group | Amino acid residue |
|---|---|
| Non-polar aliphatic | Glycine<br>Alanine<br>Valine<br>Methionine<br>Leucine<br>Isoleucine |

-continued

| Group | Amino acid residue |
|---|---|
| Aromatic | Phenylalanine<br>Tyrosine<br>Tryptophan |
| Polar uncharged | Serine<br>Threonine<br>Cysteine<br>Proline<br>Asparagine<br>Glutamine |
| Negatively charged | Aspartate<br>Glutamate |
| Positively charged | Lysine<br>Arginine<br>Histidine |

Suitably, a hydrophobic amino acid residue is a non-polar amino acid. More suitably, a hydrophobic amino acid residue is selected from V, I, L, M, F, W or C. In some embodiments, a hydrophobic amino acid residue is selected from glycine, alanine, valine, methionine, leucine, isoleucine, phenylalanine, tyrosine, or tryptophan.

Therefore, references to "conservative" amino acid substitutions refer to amino acid substitutions in which one or more of the amino acids in the sequence of the antibody (e.g. in the CDRs or in the VH or VL sequences) is substituted with another amino acid in the same class as indicated above. Conservative amino acid substitutions may be preferred in the CDR regions to minimise adverse effects on the function of the antibody. However, conservative amino acid substitutions may also occur in the framework regions. Therefore in some embodiments, any substitutions in the CDRs may be conservative substitutions, whereas substitutions in the framework regions may by substitutions of naturally occurring amino acids with another other naturally occurring amino acids.

Amino acid deletions or insertions can also be made relative to the amino acid sequences provided for the antibodies described herein. Thus, for example, amino acids which do not have a substantial effect on the activity of the polypeptide, or at least which do not eliminate such activity, can be deleted. Such deletions can be advantageous since the overall length and the molecular weight of a polypeptide can be reduced whilst still retaining activity. This can enable the amount of polypeptide required for a particular purpose to be reduced—for example, dosage levels can be reduced.

Amino acid changes relative to the sequences provided herein can be made using any suitable technique e.g. by using site-directed mutagenesis or solid-state synthesis.

It should be appreciated that amino acid substitutions or insertions within the scope of the present invention can be made using naturally occurring or non-naturally occurring amino acids, although naturally occurring amino acids may be preferred. Whether or not natural or synthetic amino acids are used, it may be preferred that only L-amino acids are present.

Various embodiments comprising optional amino acid substitutions the provided sequences are provided herein. In addition, in one embodiment of the invention there is provided an antibody, or antigen-binding fragment thereof, of the invention comprising up to 10, suitably up to 5, or suitably up to 2 amino acid substitutions in the antibody binding domain or antigen-binding domains. For example, in one embodiment of the invention, there is provided an Vδ1 antibody or antigen-binding fragment thereof, wherein the antibody or antigen-binding fragment thereof comprises the 6 CDR regions of an antibody selected from the group consisting of ADT1-4-105, ADT1-4-107, ADT1-4-110, ADT1-4-112, ADT1-4-117, ADT1-4-19, ADT1-4-21, ADT1-4-31, ADT1-4-139, ADT1-4-4, ADT1-4-143, ADT1-4-53, ADT1-4-173, ADT1-4-2, ADT1-4-8, ADT1-4-82, ADT1-4-83, ADT1-4-3, ADT1-4-84, ADT1-4-86, ADT1-4-95, ADT1-4-1, ADT1-4-6, ADT1-4-138, ADT1-7-10, ADT1-7-15, ADT1-7-17, ADT1-7-18, ADT1-7-19, ADT1-7-20, ADT1-7-22, ADT1-7-23, ADT1-7-42, ADT1-7-3 and ADT1-7-61, wherein the antibody or antigen-binding fragment thereof has up to 10 amino acid substitutions across all of its CDR regions, suitably up to 5 amino acid substitutions or up to 2 amino acid substitutions. In a further embodiment of the invention, there is provided an anti-Vδ1 antibody or antigen-binding fragment thereof, wherein the antibody or antigen-binding fragment thereof comprises the VH and VL sequences of an antibody selected from the group consisting of ADT1-4-105, ADT1-4-107, ADT1-4-110, ADT1-4-112, ADT1-4-117, ADT1-4-19, ADT1-4-21, ADT1-4-31, ADT1-4- 139, ADT1-4-4, ADT1-4-143, ADT1-4-53, ADT1-4-173, ADT1-4-2, ADT1-4-8, ADT1-4-82, ADT1-4-83, ADT1-4-3, ADT1-4-84, ADT1-4-86, ADT1-4-95, ADT1-4-1, ADT1-4-6, ADT1-4-138, ADT1-7-10, ADT1-7-15, ADT1-7- 17, ADT1-7-18, ADT1-7-19, ADT1-7-20, ADT1-7-22, ADT1-7-23, ADT1-7-42, ADT1-7-3 and ADT1-7-61, wherein the antibody has up to 10 amino acid substitutions across its VH and VL sequences, suitably up to 5 amino acid substitutions or up to 2 amino acid substitutions. In a still further embodiment of the invention, there is provided an anti-Vδ1 antibody or antigen-binding fragment thereof, wherein the antibody or antigen-binding fragment thereof is an antibody selected from the group consisting of ADT1-4-105, ADT1-4-107, ADT1-4-110, ADT1-4-112, ADT1-4-117, ADT1-4-19, ADT1-4-21, ADT1-4-31, ADT1-4- 139, ADT1-4-4, ADT1-4-143, ADT1-4-53, ADT1-4-173, ADT1-4-2, ADT1-4-8, ADT1-4-82, ADT1-4-83, ADT1-4-3, ADT1-4-84, ADT1-4-86, ADT1-4-95, ADT1-4-1, ADT1-4-6, ADT1-4-138, ADT1-7-10, ADT1-7-15, ADT1-7- 17, ADT1-7-18, ADT1-7-19, ADT1-7-20, ADT1-7-22, ADT1-7-23, ADT1-7-42, ADT1-7-3 and ADT1-7-61, wherein the antibody has up to amino acid substitutions, suitably up to 5 amino acid substitutions or up to 2 amino acid substitutions. Substitutions are of course substitutions with reference to the original CDR or variable chain sequences of the starting antibody.

In some embodiments, the one or more amino acid substitutions are in the CDR region or regions. In other embodiments, the one or more amino acid substitutions are in the framework regions, i.e. in the variable heavy and light chains but not in the CDR region or regions. In other embodiments, the one or more amino acid substitutions may be at any position in the variable heavy and/or variable light regions. In some embodiments, the amino acid substitutions do not occur in a CDR sequence.

In some embodiments, the amino acid substitutions do not adversely affect the binding specificity and/or affinity of the antibody. Accordingly, the variant antibody may have the same (or substantially the same) or a superior functional profile as the antibody from which is it derived.

In some embodiments, amino acid substitutions may be made to increase the binding affinity of the antibody to a particular antigen. For example, in embodiments of the invention relating to the mutagenesis of the serine at position 74 of the (variable region of the) light chain, a substitution may be made to increase the cross reactivity of the antibody for a the cyno homolog of the human antigen against which the antibody was prepared. Unlike other substitutions described above, this substitution may preferably be non-conservative. In some embodiments, the substitution may be a substitution of the serine at position 74 to a non-polar amino acid (for example to an amino acid selected from the group consisting of glycine, alanine, valine, methionine, leucine and isoleucine). Alternatively, the serine may be substituted with a non-human-germline amino acid (for example to an amino acid selected from the group consisting of arginine, cysteine, glutamine, glutamic acid, glycine, histidine, isoleucine, leucine, lysine, methionine, phenylalanine, threonine, tryptophan, tyrosine and valine) at position 74. In some embodiments, the serine may be substituted with an amino acid that is both non-germline and non-polar, i.e. an amino acid selected from the group consisting of glycine, valine, methionine, leucine and isoleucine. In some embodiments, the serine may be substituted with a leucine.

Epitopes

Provided herein are antibodies (or antigen-binding fragments thereof) which bind to an epitope of the Vol chain of a γδ TCR. Such binding may optionally have an effect on γδ TCR activity, such as activation. The antibodies of the invention are specific for the Vδ1 chain of a γδ TCR, and do not bind epitopes of other antigens, such as the Vβ2 chain of a γδ TCR or the V03 chain of a γδ TCR. The antibodies of the present invention may be considered agonistic antibodies, at least with respect to the agonistic effect conferred upon Vδ1 cells upon binding.

In one embodiment, the epitope may be an activating epitope of a γδ T cell. An "activating" epitope can include, for example, stimulating a TCR function, such as cell degranulation, TCR downregulation, cytotoxicity, proliferation, mobilisation, increased survival or resistance to exhaustion, intracellular signalling, cytokine or growth factor secretion, phenotypic change, or a change in gene expression. For example, the binding of the activating epitope may stimulate expansion (i.e. proliferation) of the γδ T cell population, preferably the Vδ1+ T cell population. Accordingly, these antibodies can be used to modulate γδ T cell activation, and, thereby, to modulate the immune response. Therefore, in one embodiment, binding of the activating epitope downregulates the γδ TCR. In an additional or alternative embodiment, binding of the activating epitope activates degranulation of the γδ T cell. In a further additional or alternative embodiment, binding of the activating epitope promotes γδ T cell mediated killing.

In some embodiments, an activating epitope of TRDV1 is one that, upon being bound by an antibody, results in down-regulation of the receptor and optionally activates the Vδ1 cell. In some embodiments, the activating epitope is one that upregulates expression of activatory markers on the Vδ1 cell, for example CD107a, CD25, CD69 and/or Ki67. In some embodiments, the activating epitope is one that upregulates expression of activatory markers on the Vδ1 cell, for example CD107 and CD25, and optionally CD69 and/or Ki67. In some embodiments, upregulation of the one or more activatory markers (such as CD107a) may be upregulation in the presence of cancer cells. In preferred embodiments of the invention, the antibodies bind activating epitopes of TRDV1, in particular via the TRDV1-binding domain.

As T-cell receptors are often complexed with other proteins, downregulation of the T-cell receptor via Vδ1 antibody binding may cause downregulation of other proteins associated with the T-cell receptor (i.e. the binding of the Vδ1 antibody causes down regulation of the T-cell receptor complex). For example, in some embodiments, an activating epitope of TRDV1 is one that upon binding, down-regulates the TCR/CD3 receptor complex. In this way, the antibodies of the invention may cause indirect downregulation of cell surface proteins that are not bound by the antibody, but are complexed to the T-cell receptor. Given T-cells expressing gamma delta 1 chains (i.e. Vδ1 cells) represent only a small number of the total T-cell population, the antibodies of the invention can be used to selectively (and indirectly) down-regulate proteins in the TCR complex, such as CD3, by only downregulating them in Vδ1 cells.

In some embodiments, a T-cell receptor complex activating epitope is one that upon activation, downregulates the T-cell receptor complex, whilst not downregulating CD3 molecules not associated with said TRDV1 TCR complex.

The epitope is preferably comprised of at least one extracellular, soluble, hydrophilic or external portion of the Vδ1 chain of a γδ TCR.

In particular, the epitope does not comprise an epitope found in a hypervariable region of the Vδ1 chain of the γδ TCR, in particular CDR3 of the Vδ1 chain. In a preferred embodiment, the epitope is within the non-variable region of the Vδ1 chain of the γδ TCR. It will be appreciated that such binding allows for the unique recognition of the Vδ1 chain without the restriction to the sequences of the TCR which are highly variable (in particular CDR3). Various γδ TCR complexes which recognise antigen may be recognised in this way, solely by presence of the Vδ1 chain. As such, it will be appreciated that any Vδ1 chain-comprising γδ TCR may be recognised using the antibodies or antigen-binding fragments thereof as defined herein, irrespective of the specificity of the γδ TCR. In one embodiment, the epitope comprises one or more amino acid residues within amino acid regions 1-24 and/or 35-90 of SEQ ID NO: 272, e.g. the portions of the Vδ1 chain which are not part of the CDR1 and/or CDR3 sequences. In one embodiment, the epitope does not comprise amino acid residues within amino acid region 91-105 (CDR3) of SEQ ID NO: 272.

In some embodiments the epitope comprises amino acids in the TRDV-1 CDR2 sequence.

In a similar manner to the well characterised αβ T cells, γδ T cells utilize a distinct set of somatically rearranged variable (V), diversity (D), joining (J), and constant (C) genes, although γδ T cells contain fewer V, D, and J segments than αβ T cells. In one embodiment, the epitope bound by the antibodies (or antigen-binding fragments thereof) does not comprise an epitope found in the J region of the Vδ1 chain (e.g. one of the four J regions encoded in the human delta one chain germline: SEQ ID NO: 301 (J1*0) or 302 (J2*0) or 303 (J3*0) or 304 (J4*0)) or in the C-region of the Vδ1 chain (e.g. SEQ ID NO: 305 (C1*0) which contains the C-terminal juxtamembrane/transmembrane regions). In one embodiment, the epitope bound by the antibodies (or antigen-binding fragments thereof) does not comprise an epitope found in the N-terminal leader sequence of the Vδ1 chain (e.g. SEQ ID NO: 299). The antibody or fragment may therefore only bind in the V region of the Vδ1 chain (e.g. SEQ ID NO: 300). Thus, in one embodiment, the epitope consists of an epitope in the V region of the γδ TCR (e.g. amino acid residues 1-90 of SEQ ID NO: 272).

Reference to the epitope are made in relation to the Vδ1 sequence derived from the sequence described in Luoma et al. (2013) *Immunity* 39: 1032-1042, and RCSB Protein Data Bank entries: 3OMZ, shown as SEQ ID NO: 272:

(SEQ ID NO: 272)

AQKVTQAQSSVSMPVRKAVTLNCLYETSWWSYYIFWYKQLPSKEMIFLIR

QGSDEQNAKSGRYSVNFKKAAKSVALTISALQLEDSAKYFCALGESLTRA

DKLIFGKGTRVTVEPNIQNPDPAVYQLRDSKSSDKSVCLFTDFDSQTNVS

QSKDSDVYITDKTVLDMRSMDFKSNSAVAWSNKSDFACANAFNNSIIPED

TFFPSPESS

SEQ ID NO: 272 represents a soluble TCR comprising a V region (also referred to as the variable domain), a D region, a J region and a TCR constant region. The V region comprises amino acid residues 1-90, the D region comprises amino acid residues 91-104, the J region comprises amino acid residues 105-115 and the constant region (derived from T-cell receptor alpha) comprises amino acid residues 116-209. Within the V region, CDR1 is defined as amino acid residues 25-34 of SEQ ID NO: 272, CDR2 is defined as amino acid residues 50-54 of SEQ ID NO: 272, and CDR3 is defined as amino acid residues 93-104 of SEQ ID NO: 272 (Xu et al., PNAS USA 108(6):2414-2419 (2011)).

Therefore, according to an aspect of the invention, there is provided an isolated antibody or antigen-binding fragment thereof, which binds to an epitope of a variable delta 1 (Vδ1) chain of a γδ T cell receptor (TCR) comprising one or more amino acid residues within amino acid regions:

(i) 3-20 of SEQ ID NO: 272; and/or (ii) 37-77 of SEQ ID NO: 272.

In any aspect of the invention, there is provided an isolated antibody or antigen-binding fragment thereof, which binds to an epitope of a variable delta 1 (Vδ1) chain of a γδ T cell receptor (TCR) consisting of one or more amino acid residues within amino acid regions:

(i) 3-20 of SEQ ID NO: 272; and/or (ii) 37-77 of SEQ ID NO: 272.

In a further embodiment, antibodies or antigen-binding fragments thereof additionally recognize the polymorphic V region comprising or consisting of amino acid residues 1-90 epitope of SEQ ID NO: 306. Hence, amino acids 1-90 of SEQ ID NO: 272 and the polymorphic germline variant sequence (amino acids 1-90 SEQ ID NO: 306) may be considered interchangeable when defining epitopes described herein. Studies presented herein have demonstrated antibodies of the invention can recognize both variants of this germline sequence. By way of example, where it is stated that antibodies or antigen-binding fragments thereof as defined herein recognize epitopes comprising or consisting of one or more amino acid residues within amino acid regions 1-24 and/or 35-90 of SEQ ID NO: 272, they additionally recognise equivalent epitopes (i.e. at the same position) in SEQ ID NO: 306.

In one embodiment, antibodies or antigen-binding fragments thereof recognize one or more amino acid residues within amino acid regions 1-90 of SEQ ID NO: 272. More specifically, in one embodiment antibodies or antigen-binding fragments thereof as defined herein recognize a human germline epitope wherein said germline encodes either an alanine (A) or valine (V) at position 71 of SEQ ID NO: 272.

In one embodiment, the epitope comprises or consists of one or more, such as two, three, four, five, six, seven, eight, nine, ten or more amino acid residues within the described regions.

In a further embodiment, the epitope comprises or consists of one or more (such as 5 or more, such as 10 or more) amino acid residues within amino acid region 3-20 of SEQ ID NO: 272. In an alternative embodiment, the epitope comprises or consists of one or more (such as 5 or more, such as 10 or more) amino acid residues within amino acid region 37-77 of SEQ ID NO: 272 (such as amino acid region 50-54). In a yet further embodiment, the epitope comprises or consists of one or more (such as 5 or more, such as 10 or more) amino acid residues within amino acid region 3-20 (such as 5-20 or 3-17) and one or more (such as 5 or more, such as 10 or more) amino acid residues within amino acid region 37-77 (such as 62-77 or 62-69) of SEQ ID NO: 272.

It will be further understood that said antibody (or antigen-binding fragment thereof) does not need to bind to all amino acids within the defined range. Such epitopes may be referred to as linear epitopes. For example, an antibody which binds to an epitope comprising or consisting of amino acid residues within amino acid region 5-20 of SEQ ID NO: 272 may only bind with one or more of the amino acid residues in said range, e.g. the amino acid residues at each end of the range (i.e. amino acids 5 and 20), optionally including amino acids within the range (i.e. amino acids 5, 9, 16 and 20).

In one embodiment, the epitope comprises or consists of at least one of amino acid residues 3, 5, 9, 10, 12, 16, 17, 20, 37, 42, 50, 53, 59, 62, 64, 68, 69, 72 or 77 of SEQ ID NO: 272. In further embodiments, the epitope comprises or consists of one, two, three, four, five, six, seven, eight, nine, ten, eleven or twelve amino acids selected from amino acid residues 3, 5, 9, 10, 12, 16, 17, 20, 37, 42, 50, 53, 59, 62, 64, 68, 69, 72 or 77 of SEQ ID NO: 272.

In one embodiment, the epitope comprises or consists of one or more amino acid residues within the following amino acid regions of SEQ ID NO: 272:

(i) 3-17;
(ii) 5-20;
(iii) 37-53;
(iv) 50-64;
(v) 59-72;
(vi) 59-77;
(vii) 62-69; and/or
(viii) 62-77.

In further embodiments, the epitope comprises or consists of one or more amino acid residues within amino acid regions: 5-20 and 62-77 (for example, although not limited to, embodiments relating to antibodies derived from the parental clone E07, such as affinity matured variants thereof); 50-64 (for example, although not limited to, embodiments relating to antibodies derived from the parental clone C08, such as affinity matured variants thereof); 37-53 and 59-72 (for example, although not limited to, embodiments relating to antibodies derived from the parental clone G04, such as affinity matured variants thereof); 59-77 (for example, although not limited to, embodiments relating to antibodies derived from the parental clone C05, such as affinity matured variants thereof); or 3-17 and 62-69 (for example, although not limited to, embodiments relating to antibodies derived from the parental clone E01, such as affinity matured variants thereof), of SEQ ID NO: 272. In a further embodiment, the epitope consists of one or more amino acid residues within amino acid regions: 5-20 and 62-77; 50-64; 37-53 and 59-72; 59-77; or 3-17 and 62-69, of SEQ ID NO: 272.

In a further embodiment, the epitope comprises or consists of amino acid residues: 3, 5, 9, 10, 12, 16, 17, 62, 64, 68 and 69 of SEQ ID NO: 272, or suitably consists of amino acid residues: 3, 5, 9, 10, 12, 16, 17, 62, 64, 68 and 69 of SEQ ID NO: 272 (for example, although not limited to, embodiments relating to antibodies derived from the parental clone E01, such as affinity matured variants thereof). In a further embodiment, the epitope comprises or consists of amino acid residues: 5, 9, 16, 20, 62, 64, 72 and 77 of SEQ ID NO: 272, or suitably consists of amino acid residues: 5, 9, 16, 20, 62, 64, 72 and 77 of SEQ ID NO: 272 (for example, although not limited to, embodiments relating to antibodies derived from the parental clone E07, such as affinity matured variants thereof). In yet further embodiment, the epitope comprises or consists of the amino acid residues: 37, 42, 50, 53, 59, 64, 68, 69, 72, 73 and 77 of SEQ ID NO: 272, or suitably consists of amino acid residues: 37, 42, 50, 53, 59, 64, 68, 69, 72, 73 and 77 of SEQ ID NO: 272 (for example, although not limited to, embodiments relating to antibodies derived from the parental clone G04, such as affinity matured variants thereof). In a further embodiment, the epitope comprises or consists of the amino acid residues: 50, 53, 59, 62 and 64 of SEQ ID NO: 272, or suitably consists of amino acid residues: 50, 53, 59, 62 and 64 of SEQ ID NO: 272 (for example, although not limited to, embodiments relating to antibodies derived from the parental clone C08, such as affinity matured variants thereof). In a further embodiment, the epitope comprises or consists of amino acid residues: 59, 60, 68 and 72 of SEQ ID NO: 272, or suitably consists of amino acid residues: 59, 60, 68 and 72 of SEQ ID NO: 272 (for example, although not limited to, embodiments relating to antibodies derived from the parental clone C05, such as affinity matured variants thereof).

In one embodiment, the epitope comprises or consists of one or more amino acid residues within amino acid regions 37-53 and/or 59-77 of SEQ ID NO: 272. In a further embodiment, the epitope consists of one or more amino acid residues within amino acid regions 37-53 and 59-77 of SEQ ID NO: 272. In an alternative further embodiment, the epitope comprises or consists of one or more amino acid residues within amino acid regions 37-53 or 59-77 of SEQ ID NO: 272. Antibodies or antigen-binding fragments thereof having such epitopes may have some or all of the sequences of G04, or such antibodies or antigen-binding fragments thereof may be derived from G04. For example, antibodies or antigen-binding fragments thereof having one or more CDR sequences of G04 or one or both of the VH and VL sequences of G04 may bind such epitopes.

In one embodiment, the epitope comprises or consists of one or more amino acid residues within amino acid regions 5-20 and/or 62-77 of SEQ ID NO: 272. In a further embodiment, the epitope consists of one or more amino acid residues within amino acid regions 5-20 and 62-77 of SEQ ID NO: 272. In an alternative further embodiment, the epitope comprises or consists of one or more amino acid residues within amino acid regions 5-20 or 62-77 of SEQ ID NO: 272. Antibodies or antigen-binding fragments thereof having such epitopes may have some or all of the sequences of E07, or such antibodies or antigen-binding fragments thereof may be derived from E07. For example, antibodies or antigen-binding fragments thereof having one or more CDR sequences of E07 or one or both of the VH and VL sequences of E07 may bind such epitopes.

In one embodiment, the epitope comprises or consists of one or more amino acid residues within amino acid region 50-64 of SEQ ID NO: 272. In a further embodiment, the epitope consists of one or more amino acid residues within amino acid region 50-64 of SEQ ID NO: 272. Antibodies or antigen-binding fragments thereof having such epitopes may have some or all of the sequences of C08, or such antibodies or antigen-binding fragments thereof may be derived from C08. For example, antibodies or antigen-binding fragments thereof having one or more CDR sequences of C08 or one or both of the VH and VL sequences of C08 may bind such epitopes.

In one embodiment, the epitope comprises or consists of one or more amino acid residues within amino acid region 59-72 of SEQ ID NO: 272. In a further embodiment, the epitope consists of one or more amino acid residues within amino acid region 59-72 of SEQ ID NO: 272. Antibodies or antigen-binding fragments thereof having such epitopes may have some or all of the sequences of C05, or such antibodies or antigen-binding fragments thereof may be derived from C05. For example, antibodies or antigen-binding fragments thereof having one or more CDR sequences of C05 or one or both of the VH and VL sequences of C05 may bind such epitopes.

In one embodiment, the epitope does not comprise or consist of amino acid residues within amino acid region 11-21 of SEQ ID NO: 272. In one embodiment, the epitope does not comprise or consist of amino acid residues within amino acid region 21-28 of SEQ ID NO: 272. In one embodiment, the epitope does not comprise or consist of amino acid residues within amino acid region 59 and 60 of SEQ ID NO: 272. In one embodiment, the epitope does not comprise or consist of amino acid residues within amino acid region 67-82 of SEQ ID NO: 272.

The epitopes of affinity matured antibodies will generally be the same as the epitopes identified herein for the parental clone. For those epitopes on cyno TRDV1, the positions of the epitopes of the affinity matured antibodies will generally the same positions as the epitopes identified for the corresponding parental clone. The reference to "positions" is necessary since the skilled person would appreciate the identity of some of the amino acids in the epitopes differ from human TRDV1. Despite these variations between human and cyno TRDV1, such antibodies are still able to specifically bind to both antigens.

In one embodiment, the epitope is not the same epitope bound by a commercially available anti-Vol antibody, such as TS-1 or TS8.2. As described in WO2017197347, binding of TS-1 and TS8.2 to soluble TCRs was detected when the δ1 chain included Vδ1 J1 and Vδ1 J2 sequences but not to the Vδ1 J3 chain, indicating that the binding of TS-1 and TS8.2 involved critical residues in the delta J1 and delta J2 region.

References to "within" herein include the extremities of the define range. For example, "within amino acid regions 5-20" refers to all of amino acid resides from and including residue 5 up to and including residue 20.

Various techniques are known in the art to establish which epitope is bound by an antibody. Exemplary techniques include, for example, routine cross-blocking assays, alanine scanning mutational analysis, peptide blot analysis, peptide cleavage analysis crystallographic studies and NMR analysis. In addition, methods such as epitope excision, epitope extraction and chemical modification of antigens can be employed. Another method that can be used to identify the amino acids within a polypeptide with which an antibody interacts is hydrogen/deuterium exchange detected by mass spectrometry (as described in Example 9). In general terms, the hydrogen/deuterium exchange method involves deuterium-labelling the protein of interest, followed by binding the antibody to the deuterium-labelled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labelled residues which correspond to the specific amino acids with which the antibody interacts.

The antibodies and antigen-binding fragments therefor suitably specifically bind to both human TRDV1 (SEQ ID NO: 272 and the polymorphic variant of SEQ ID NO: 306) as well as an ortholog in cynomolgus monkey, cyno TRDV1 (SEQ ID NO: 308 see also UniProtKB—G7P9S6 (G7P9S6_MACFA)). In some embodiments, the antibodies or antigen-binding fragments thereof are G04-derived antibodies that specifically bind to both human and cyno TRDV1. It is hypothesised the epitopes bound by the antibodies of the invention (for example although not limited to those binding in a region within amino acid resides 37 to 77 of any of SEQ ID NOs: 272, 306 or 308) may be particularly advantageous, since it allows the provision of anti-Vδ1 antibodies that are specific to Vδ1 (i.e. do not bind similar antigens, such as Vβ2 or V03) but also provide cross-reactivity to polymorphic variants of Vδ1 (i.e. TRDV1 SEQ ID NO: 272 and TRDV1 SEQ ID NO: 306, despite the polymorphism at residue position 20 and this being identified as a possible contact residue or close to an identified contact residue for some antibodies) and provides cross-reactivity between human and cyno Vδ1 (despite all of residues 42, 50, 54, 59, 60, 68, 73, 75 and 76 occurring within the region of amino acid resides 37 to 77 of SEQ ID NOs: 272 and 308 being different between human and cyno TRDV1 sequences).

Epitopes of ADT1-4-Derived Antibodies

The ADT1-4-derived antibodies bind the same or substantially the same epitope as the ADT1-4 parental antibody. Accordingly, in some embodiments, in particular those relating to antibodies derived from or related to the ADT1-4 parental antibody, the anti-Vδ1 antibody or antigen-binding fragment binds an epitope comprising or consisting of one or more amino acid residues within amino acid region 37 to 77, for example within amino acid regions 37-53 and/or 59-77, of SEQ ID NO: 272 (or SEQ ID NO: 306). In some embodiments, the epitope comprises or consists of amino acid residues 37, 42, 50, 53, 59, 64, 68, 69, 72, 73 and 77 of SEQ ID NO: 272 (or SEQ ID NO: 306). In some embodiments, the epitope consists of amino acid residues 37, 42, 50, 53, 59, 64, 68, 69, 72, 73 and 77 of SEQ ID NO: 272 (or SEQ ID NO: 306).

The ADT1-4-derived antibodies also bind to epitope of the cyno variable delta 1 (Vδ1) chain of a γδ T cell receptor (TCR), aka cyno TRDV1 (SEQ ID NO: 308). Hence, in some embodiments, in particular those relating to antibodies derived from or related to the G04 parental antibody, the anti-Vδ1 antibody or antigen-binding fragment binds an epitope comprising or consisting of one or more amino acid residues within amino acid region 37 to 77, for example within amino acid regions 37-53 and/or 59-77, of SEQ ID NO: 308. In some embodiments, the epitope comprises or consists of amino acid residues 37, 42, 50, 53, 59, 64, 68, 69, 72, 73 and 77 of SEQ ID NO: 308. In some embodiments, the epitope consists of amino acid residues 37, 42, 50, 53, 59, 64, 68, 69, 72, 73 and 77 of SEQ ID NO: 308.

Given the cross-reactivity of the ADT1-4-derived antibodies in particular, and the ability of the antibodies disclosed herein to bind to the polymorphic variant of TRDV1, in some embodiments, in particular those relating to antibodies derived from or related to the G04 parental antibody, the anti-Vδ1 antibody or antigen-binding fragment binds an epitope comprising or consisting of one or more amino acid residues within amino acid region 37 to 77, for example within amino acid regions 37-53 and/or 59-77, of SEQ ID NOs: 272, 306 and 308. In some embodiments, the epitope comprises or consists of amino acid residues 37, 42, 50, 53, 59, 64, 68, 69, 72, 73 and 77 of SEQ ID NO: 272, 306 and 308. In some embodiments, the epitope consists of amino acid residues 37, 42, 50, 53, 59, 64, 68, 69, 72, 73 and 77 of SEQ ID NOs: 272, 306 and 308.

The provision of antibodies that comprise or consist of such epitopes as those described above yet providing cross-reactivity between human and cyno TRDV1 sequences is surprising, given the location of the amino acid variants between these sequences from the two species.

Epitopes of ADT1-7-Derived Antibodies

The ADT1-7-derived antibodies bind the same or substantially the same epitope as the ADT1-7 parental antibody. Accordingly, in some embodiments, in particular those relating to antibodies derived from or related to the ADT1-7 parental antibody, the anti-Vδ1 antibody or antigen-binding fragment binds an epitope comprising or consisting of one or more amino acid residues within amino acid regions 5-20 and/or 62-77 of SEQ ID NO: 272 (or SEQ ID NO: 306). In some embodiment, the epitope comprises or consists of amino acid residues 5, 9, 16, 20, 62, 64, 72 and 77 of SEQ ID NO: 272 (or SEQ ID NO: 306). In some embodiments, the epitope consists of amino acid residues 5, 9, 16, 20, 62, 64, 72 and 77 of SEQ ID NO: 272 (or SEQ ID NO: 306).

Framework and Other Sequences

Suitably the VH and VL regions of the antibodies or antigen-binding fragments of the invention each comprise four framework regions (FR1-FR4). In one embodiment, the antibody or antigen-binding fragment thereof comprises a framework region (e.g. FR1, FR2, FR3 and/or FR4) comprising a sequence having at least 80% sequence identity with the framework region in any one of SEQ ID NOs: 2 to 25 (for example in the case of light chain variable sequences derived from G04), SEQ ID NOs: 27 to 50 (for example in the case of heavy chain variable sequences derived from G04), SEQ ID NOs: 107 to 117 (for example in the case of light chain variable sequence derived from E07) or SEQ ID NOs: 119 to 129 (for example in the case of light chain variable sequence derived from E07). In one embodiment, the antibody or antigen-binding fragment thereof comprises a framework region (e.g. FR1, FR2, FR3 and/or FR4) comprising a sequence having at least 90%, such as at least 95%, 97% or 99% sequence identity with the framework region in any one of SEQ ID NOs: 2 to 25 (for example in the case of light chain variable sequences derived from G04), SEQ ID NOs: 27 to 50 (for example in the case of heavy chain variable sequences derived from G04), SEQ ID NOs: 107 to 117 (for example in the case of light chain variable sequence derived from E07) or SEQ ID NOs: 119 to 129 (for example in the case of light chain variable sequence derived from E07). In one embodiment, the antibody or antigen-binding fragment thereof comprises a framework region (e.g. FR1, FR2, FR3 and/or FR4) comprising a sequence in any one of SEQ ID NOs: 2 to 25 (for example in the case of light chain variable sequences derived from G04), SEQ ID NOs: 27 to 50 (for example in the case of heavy chain variable sequences derived from G04), SEQ ID NOs: 107 to 117 (for example in the case of light chain variable sequence derived from E07) or SEQ ID NOs: 119 to 129 (for example in the case of light chain variable sequence derived from E07). In one embodiment, the antibody or antigen-binding fragment thereof comprises a framework region (e.g. FR1, FR2, FR3 and/or FR4) consisting of a sequence in any one of SEQ ID NOs: 2 to 25 (for example in the case of light chain variable sequences derived from G04), SEQ ID NOs: 27 to 50 (for example in the case of heavy chain variable sequences derived from G04), SEQ ID NOs: 107 to 117 (for example in the case of light chain variable sequence derived from E07) or SEQ ID NOs: 119 to 129 (for example in the case of light chain variable sequence derived from E07).

In some embodiments, the anti-Vδ1 antibody or antigen-binding fragment thereof may comprise an HFR1 (i.e. heavy framework 1 region) sequence comprising or consisting of the sequence of SEQ ID NO: 170 or 171; an HFR2 sequence comprising or consisting of the sequence of SEQ ID NO: 172; an HFR3 sequence comprising or consisting of the sequence of SEQ ID NO: 173; an HFR4 sequence comprising or consisting of the sequence of SEQ ID NO: 174; an LFR1 sequence comprising or consisting of the sequence of SEQ ID NO: 175; an LFR2 sequence comprising or consisting of the sequence of SEQ ID NO: 176; an LFR3 sequence comprising or consisting of the sequence of SEQ ID NO: 177 or 178; and/or an LFR4 sequence comprising or consisting of the sequence of SEQ ID NO: 179, 180, 181 or 182.

In some embodiments, the anti-Vδ1 antibody or antigen-binding fragment thereof may comprise an HFR1 (i.e. heavy framework 1 region) sequence comprising or consisting of the sequence of SEQ ID NO: 170 or 171; an HFR2 sequence comprising or consisting of the sequence of SEQ ID NO: 172; an HFR3 sequence comprising or consisting of the sequence of SEQ ID NO: 173; an HFR4 sequence comprising or consisting of the sequence of SEQ ID NO: 174; an LFR1 sequence comprising or consisting of the sequence of SEQ ID NO: 175; an LFR2 sequence comprising or consisting of the sequence of SEQ ID NO: 176; an LFR3 sequence comprising or consisting of the sequence of SEQ ID NO: 177; and/or an LFR4 sequence comprising or consisting of the sequence of SEQ ID NO: 179, 180, 181 or 182.

In some embodiments, the anti-Vδ1 antibody or antigen-binding fragment thereof may comprise an HFR1 (i.e. heavy framework 1 region) sequence comprising or consisting of the sequence of SEQ ID NO: 170 or 171; an HFR2 sequence comprising or consisting of the sequence of SEQ ID NO: 172; an HFR3 sequence comprising or consisting of the sequence of SEQ ID NO: 173; an HFR4 sequence comprising or consisting of the sequence of SEQ ID NO: 174; an LFR1 sequence comprising or consisting of the sequence of SEQ ID NO: 175; an LFR2 sequence comprising or consisting of the sequence of SEQ ID NO: 176; an LFR3 sequence comprising or consisting of the sequence of SEQ ID NO: 177; and/or an LFR4 sequence comprising or consisting of the sequence of SEQ ID NO: 179 or 181.

In some embodiments, the anti-Vδ1 antibody or antigen-binding fragment thereof may comprise an HFR1 sequence comprising or consisting of the sequence of SEQ ID NO: 189; an HFR2 sequence comprising or consisting of the sequence of SEQ ID NO: 190; an HFR3 sequence comprising or consisting of the sequence of SEQ ID NO: 191; an HFR4 sequence comprising or consisting of the sequence of SEQ ID NO: 192; an LFR1 sequence comprising or consisting of the sequence of SEQ ID NO: 193 and 194; an LFR2 sequence comprising or consisting of the sequence of SEQ ID NO: 195; an LFR3 sequence comprising or consisting of the sequence of SEQ ID NO: 196; and an LFR4 sequence comprising or consisting of the sequence of SEQ ID NO: 197.

In some embodiments, the anti-Vδ1 antibody or antigen-binding fragment thereof may comprise an HFR1 sequence comprising or consisting of the sequence of SEQ ID NO: 189; an HFR2 sequence comprising or consisting of the sequence of SEQ ID NO: 190; an HFR3 sequence comprising or consisting of the sequence of SEQ ID NO: 191; an HFR4 sequence comprising or consisting of the sequence of SEQ ID NO: 192; an LFR1 sequence comprising or consisting of the sequence of SEQ ID NO: 193; an LFR2 sequence comprising or consisting of the sequence of SEQ ID NO: 195; an LFR3 sequence comprising or consisting of the sequence of SEQ ID NO: 196; and an LFR4 sequence comprising or consisting of the sequence of SEQ ID NO: 197.

For fragments comprising both the VH and VL regions, these may be associated either covalently (e.g. via disulphide bonds or a linker) or non-covalently. The antibody fragment described herein may comprise an scFv, i.e. a fragment comprising a VH region and a VL region joined by a linker. In one embodiment, the VH and VL region are joined by a (e.g. synthetic) polypeptide linker. The polypeptide linker may comprise a $(Gly_4Ser)_n$ linker, where n=from 1 to 8, e.g. 2, 3, 4, 5 or 7. The polypeptide linker may comprise a $[(Gly_4Ser)_n(Gly_3AlaSer)_m]_p$ linker, where n=from 1 to 8, e.g. 2, 3, 4, 5 or 7, m=from 1 to 8, e.g. 0, 1, 2 or 3, and p=from 1 to 8, e.g. 1, 2 or 3. In a further embodiment, the linker comprises SEQ ID NO: 291. In a further embodiment, the linker consists of SEQ ID NO: 291.

It will be understood by a person skilled in the art that scFv constructs may be designed and made inclusive of N-terminal and C-terminal modifications to aid with translation, purification and detection. For example, at the N-terminus of an scFv sequence, an additional methionine and/or alanine amino acid residue may be included ahead of the canonical VH sequences (e.g. starting QVQ or EVQ). At the C-terminus (i.e. C-terminal to the canonical mature VL domain sequence ending as per the IMGT definition), additional sequences may be included such as (i) a partial sequence of the constant domain and/or (ii) additional synthetic sequences inclusive of tags, such as His-tags and Flag-tags, to aid with purification and detection (for example the tags of any of SEQ ID NOs: 292 to 295).

As described herein, the antibodies may be in any format. In a preferred embodiment, the antibody is in an IgG1 (e.g. human IgG1) format (i.e. the antibody is a human IgG1 antibody).

In some embodiments, the antibody or antigen-binding fragment thereof comprises a light chain constant region comprising the sequence of SEQ ID NO: 296 or SEQ ID NO: 307 (or a sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity with SEQ ID NO: 296 or SEQ ID NO: 307) and/or a heavy chain constant region comprising the sequence of SEQ ID NO: 297 or SEQ ID NO: 298 (or a sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity with SEQ ID NO: 297 or SEQ ID NO: 298). In some embodiments, effector function of the heavy chain constant region may be reduced or disabled (effector function disabling mutations). Suitable mutations to attenuate the effector functions are known to the skilled person. For example, the L235A and/or G237A mutations ("LAGA") or the L234A and/or L235A mutations ("LALA") according to the EU numbering. For example, in one embodiment, the antibody or antigen-binding fragment thereof comprises a light chain constant region comprising the sequence of SEQ ID NO: 296 and/or a heavy chain constant region comprising the sequence of SEQ ID NO: 297 or SEQ ID NO: 298.

Competing Antibodies

In one embodiment, the antibody binds to the same, or essentially the same, epitope as, or competes with, an antibody or antigen-binding fragment thereof as defined herein. One can easily determine whether an antibody binds to the same epitope as, or competes for binding with, a reference anti-Vδ1 antibody by using routine methods known in the art. For example, to determine if a test antibody binds to the same epitope as a reference anti-Vδ1 antibody of the invention, the reference antibody is allowed to bind to a Vδ1 protein or peptide under saturating conditions. Next, the ability of a test antibody to bind to the Vδ1 chain is assessed. If the test antibody is able to bind to Vδ1 following saturation binding with the reference anti-Vδ1 antibody, it can be concluded that the test antibody binds to a different epitope than the reference anti-Vδ1 antibody. On the other hand, if the test antibody is not able to bind to the Vδ1 chain following saturation binding with the reference anti-Vδ1 antibody, then the test antibody may bind to the same epitope as the epitope bound by the reference anti-Vδ1 antibody of the invention.

The present invention also includes anti-Vδ1 antibodies that compete for binding to Vδ1 with an antibody or antigen-binding fragment thereof as defined herein, or an antibody having the CDR sequences of any of the exemplary antibodies described herein. For example, competitive assays can be performed with the antibody of the present invention in order to determine what proteins, antibodies, and other antagonists compete for binding to the Vδ1 chain with the antibody of the present invention and/or share the epitope. These assays are readily known to those of skill in the art; they evaluate competition between antagonists or ligands for a limited number of binding sites on a protein, e.g. Vδ1. The antibody (or antigen-binding fragment thereof) is immobilized or insolubilized before or after the competition and the sample bound to the Vδ1 chain is separated from the unbound sample, for example, by decanting (where the antibody was pre-insolubilized) or by centrifuging (where the antibody was precipitated after the competitive reaction). Also, the competitive binding may be determined by whether the function is altered by the binding or lack of binding of the antibody to the protein, e.g. whether the antibody molecule inhibits or potentiates the enzymatic activity of, for example, a label. ELISA and other functional assays may be used, as known in the art and described herein.

Two antibodies bind to the same or overlapping epitope if each competitively inhibits (blocks) binding of the other to the target antigen. That is, a 1-, 5-, 10-, 20- or 100-fold excess of one antibody inhibits binding of the other by at least 50% but preferably 75%, 90% or even 99% as measured in a competitive binding assay. Alternatively, two antibodies have the same epitope if essentially all amino acid mutations in the target antigen that reduce or eliminate binding of one antibody reduce or eliminate binding of the other.

Additional routine experimentation (e.g. peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Antibody Binding and Pharmacological Properties of the Antibodies

The antibodies of the invention may have favourable binding and/or pharmacological properties, for example as described below.

Binding Affinity ($K_D$)

Generally speaking, the affinity matured clones will have an affinity for their antigen(s) that is higher than the parental clones. For example, the affinity for human TRDV1 (SEQ ID NOs 272 or 306) will be at least 20%, at least 30%, at least 40%, at least 50%, at least 100% or at least 500% greater affinity than the parental antibody.

The antibodies or antigen-binding fragments thereof of the invention may bind to human TRDV1 (SEQ ID NOs 272 or 306) with a binding affinity ($K_D$, for example as measured by surface plasmon resonance) of less than about 100 nM, preferably less than about 50 nM.

The antibodies or antigen-binding fragments thereof may further be defined as binding to human TRDV1 (SEQ ID NOs 272 or 306) with a binding affinity ($K_D$, for example as measured by surface plasmon resonance) of less than about 10 nM, preferably less than about 5 nM.

In some embodiments, for example antibodies or antigen-binding fragments thereof relating to or derived from the ADT1-4 lineage, the antibodies or antigen-binding fragments thereof of the invention may bind to human TRDV1 with $K_D$ of less than about 100 nM, preferably less than about 50 nM.

In some embodiments, for example antibodies or antigen-binding fragments thereof relating to or derived from the ADT1-4 lineage (but excluding ADT1-4-138), the antibodies or antigen-binding fragments thereof of the invention may bind to human TRDV1 with $K_D$ of less than about 10 nM, preferably less than about 5 nM.

In some embodiments, for example antibodies or antigen-binding fragments thereof relating to or derived from the ADT1-4 lineage members ADT1-4-19, ADT1-4-21, ADT1-4-31, ADT1-4-53, ADT1-4-2, ADT1-4-86, ADT1-4-112, ADT1-4-143 and/or ADT1-4-1, the antibodies or antigen-binding fragments thereof of the invention may bind to human TRDV1 with $K_D$ of less than about 10 nM, preferably less than about 1 nM.

The antibodies or antigen-binding fragments thereof of the invention may bind to cyno TRDV1 (SEQ ID NO 308) with a binding affinity ($K_D$, for example as measured by surface plasmon resonance) of less than about 100 nM, preferably less than about 50 nM.

In some embodiments, for example antibodies or antigen-binding fragments thereof relating to or derived from the ADT1-4 lineage, the antibodies or antigen-binding fragments thereof of the invention may bind to cyno TRDV1 with $K_D$ of less than about 100 nM, preferably less than about 50 nM.

In some embodiments, for example antibodies or antigen-binding fragments thereof relating to or derived from the ADT1-4 lineage members ADT1-4-19, ADT1-4-21, ADT1-4-31, ADT1-4-53, ADT1-4-2, ADT1-4-86, ADT1-4-112, ADT1-4-143 and/or ADT1-4-1, the antibodies or antigen-binding fragments thereof of the invention may bind to cyno TRDV1 with $K_D$ of less than about 50 nM.

In some embodiments, for example those relating to or derived from the ADT1-4 lineage, the antibodies or antigen-binding fragments thereof of the invention may bind to human TRDV1 with $K_D$ of less than about 100 nM, preferably less than about 50 nM and bind to cyno TRDV1 with a binding affinity ($K_D$, for example as measured by surface plasmon resonance) of less than about 100 nM, preferably less than about 50 nM.

In some embodiments, for example antibodies or antigen-binding fragments thereof relating to or derived from the ADT1-4 lineage (but excluding ADT1-4-138), the antibodies or antigen-binding fragments thereof of the invention may bind to human TRDV1 with $K_D$ of less than about 10 nM and bind to cyno TRDV1 with a binding affinity ($K_D$, for example as measured by surface plasmon resonance) of less than about 100 nM. Preferably in this embodiment, the antibodies or antigen-binding fragments thereof of the invention may bind to human TRDV1 with $K_D$ of less than about 5 nM and bind to cyno TRDV1 with a binding affinity ($K_D$, for example as measured by surface plasmon resonance) of less than about 50 nM.

In some embodiments, for example antibodies or antigen-binding fragments thereof relating to or derived from the ADT1-4 lineage members ADT1-4-19, ADT1-4-21, ADT1-4-31, ADT1-4-53, ADT1-4-2, ADT1-4-86, ADT1-4-112, ADT1-4-143 and/or ADT1-4-1, the antibodies or antigen-binding fragments thereof of the invention may bind to human TRDV1 with $K_D$ of less than about 10 nM and bind to human TRDV1 with $K_D$ of less than 50 nM. Preferably in this embodiment, the antibodies or antigen-binding fragments thereof of the invention may bind to human TRDV1 with $K_D$ of less than about 1 nM and bind to cyno TRDV1 with a binding affinity ($K_D$, for example as measured by surface plasmon resonance) of less than about 50 nM.

In some embodiments, for example antibodies or antigen-binding fragments thereof relating to or derived from the ADT1-7 lineage, the antibodies or antigen-binding fragments thereof of the invention may bind to human TRDV1 with $K_D$ of less than about 10 nM, preferably less than about 5 nM.

In some embodiments, the binding affinity of the antibody or antigen-binding fragment thereof is established by coating the antibody or antigen-binding fragment thereof directly or indirectly (e.g. by capture with an anti-human IgG Fc) onto the surface of a sensor (e.g. an amine high capacity chip or equivalent), wherein the target bound by the antibody or antigen-binding fragment thereof (i.e. the Vδ1 chain of a γδ TCR) is flowed over the chip to detect binding. Suitably, a MASS-2 instrument (which may also be referred to as Sierra SPR-32) is used at 25° C. in PBS+0.02% Tween 20 running buffer at 30 μl/min.

Described herein are other assays which may be used to define antibody function. For example, the antibody or antigen-binding fragment thereof described herein may be assessed by γδ TCR engagement, e.g. measuring downregulation of the γδ TCR upon antibody binding. Surface expression of the γδ TCR following application of the antibody or antigen-binding fragment thereof (optionally presented on the surface of a cell) can be measured, e.g. by flow cytometry. The antibody or antigen-binding fragment thereof described herein may also be assessed by measuring γδ T cell degranulation. For example, expression of CD107a, a marker for cell degranulation, can be measured following application of the antibody or antigen-binding fragment thereof (optionally presented on the surface of a cell) to γδ T cells, e.g. by flow cytometry. The antibody or antigen-binding fragment thereof described herein may also be assessed by measuring γδ T cell mediated killing activity (to test if the antibody has an effect on the killing activity of the γδ T cell). For example, target cells may be incubated with γδ T cells in the presence of the antibody or antigen-binding fragment thereof (optionally presented on the surface of a cell). Following incubation, the culture may be stained with a cell viability dye to distinguish between live and dead target cells. The proportion of dead cells can then be measured, e.g. by flow cytometry.

Inhibition Concentrations (IC50 and IC90)

TCR Downregulation

TCR down regulation may be measured according to the assays described herein. For example, the antibody to be tested may be incubated at different concentration with a culture of γδ T cells and the downregulation measured. If measuring cell killing (for example THP-1 cell killing), the γδ T cells are co-cultured with a suitable cell line, for example THP-1 cells. TCR down regulation may be measured by flow cytometry. Cell killing may be achieved by any suitable means, for example by flow cytometry. For the initial TCR downregulation studies with the parental antibodies (e.g. ADT1-7 and ADT1-4), the TCR downregulation assay involved 'loading' the antibody onto Fc gamma receptor +ve THP-1 cells (see Example 1, Example 6 and Table 5). As such, the antibodies in this instance are presented on a cell surface ahead of co-incubation with γδ T cells. Such loading thereby affords maximum opportunity to exploit cross-linking effects upon TCR engagement. Aside loading antibodies onto Fc receptor +ve cells, alternate similar approaches to presenting the antibody on sold-surfaces may include pre-incubating the antibody on a plate (so-called plate-bound), or the use of carrier beads to present the antibody. In all such assays, and once presented on a solid surface, it is then typical to investigate and measure the technical effect conferred by the antibody upon engagement of the target receptor (in this instance a γδ T cell receptor), Presenting antibodies in this way is commonplace, particularly when exploring the effects of antibody engagement of immune cell receptor targets and complexes such as antibody engagement of targets such as CD3, CD28 etc.

In contrast, for affinity matured antibodies of the invention as described herein, the inventors wanted to dissect and compare the impact of affinity maturation to its fullest and hence the inventors explored the capabilities of these antibodies in more 'soluble' TCR downregulation assay formats. Assessing the effect in solution may also be more physiologically relevant. For these reasons, and unless otherwise indicated, in all TCR downregulation cell-based experiments wherein the effects of affinity-matured antibodies, multispecific antibodies, or fragments thereof, are measured or characterized and compared to parent antibodies (e.g. see FIG. 35), a soluble assay format is explored. The IC50 difference of employing this more stringent soluble assay is summarized below wherein the TCR downregulation of EC50 values for an example parent molecule (ADT1-4) is summarised via both approaches.

TCR Downregulation: 'Presented' versus 'Soluble' Assay Format:

ADT1-4 IC50 (loaded on THP-1 cells): 0.01-0.05 ug/ml=0.065 nM to 0.325 nM (See Example 1, Example 6, and Table 5)

Vs.

Figure 35A:
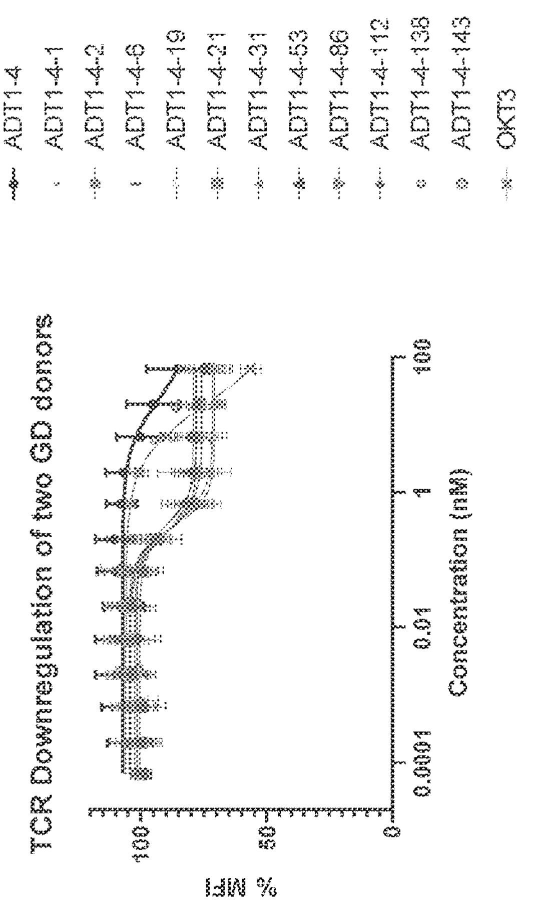
Figure 35B:
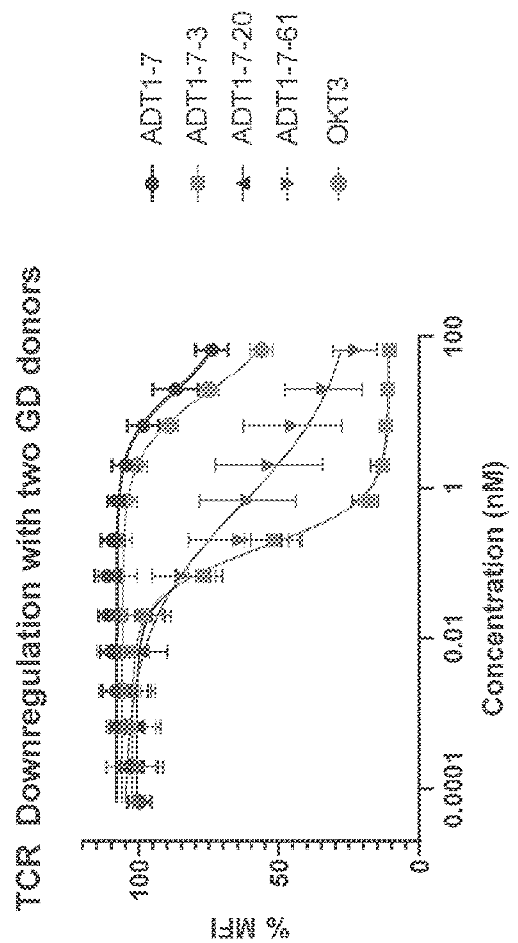
Figure 35C:
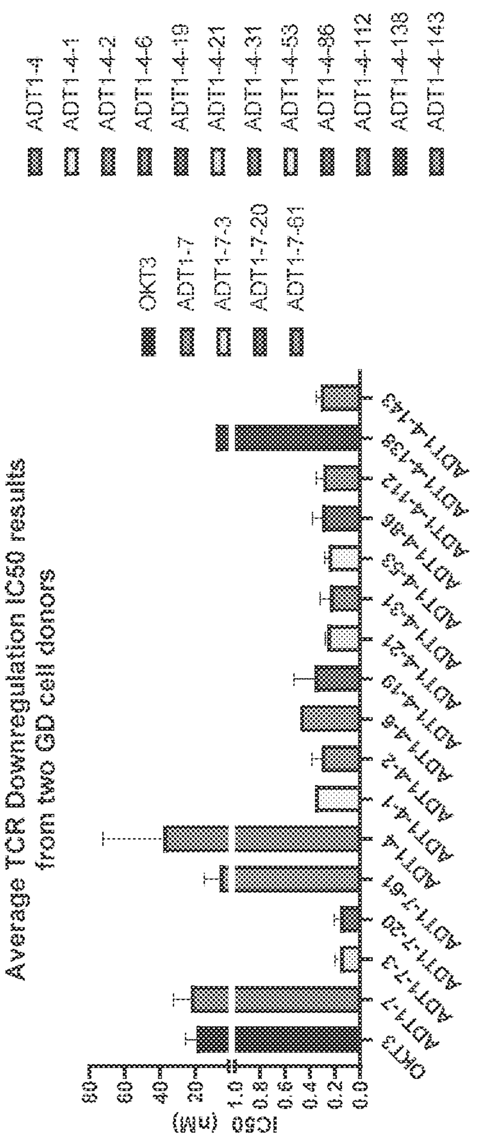
Figure 35D:
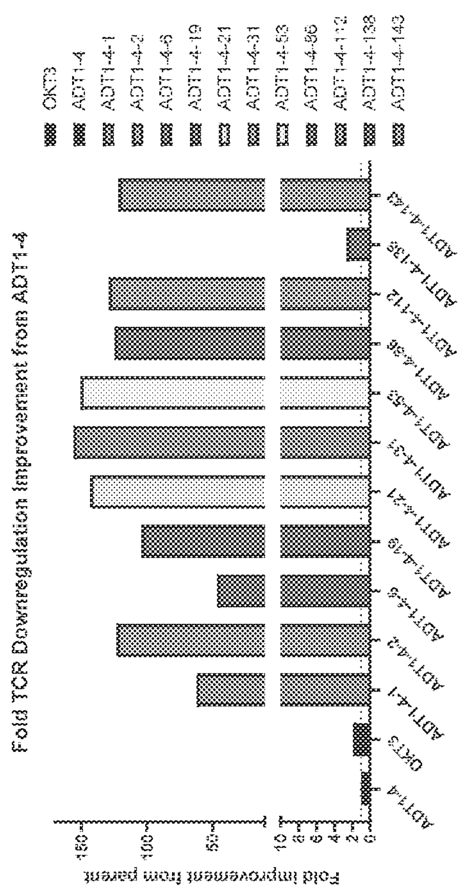
Figure 35E:
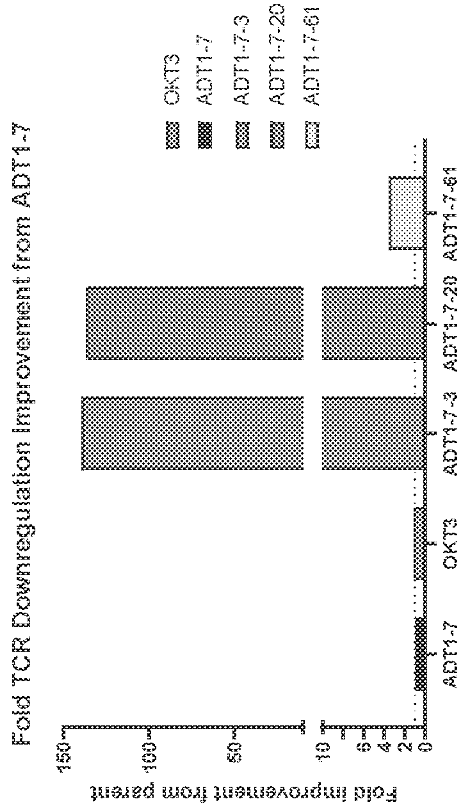

ADT1-4 IC50 (soluble assay, added in solution)=38.28 nM (See FIG. 35F)

The antibodies or antigen-binding fragments thereof of the invention may have an IC50 for TCR downregulation of less than about 50 nM. Preferably the IC50 is less than about 10 nM.

In some embodiments, for example antibodies or antigen-binding fragments thereof relating to or derived from the ADT1-4 lineage, the antibodies or antigen-binding fragments thereof of the invention may have an IC50 for TCR downregulation of less than about 50 nM and/or an IC90 for TCR downregulation of less than about 100 nM. Preferably the IC50 is less than about 10 nM and the IC90 is less than about 50 nM.

In some embodiments, for example antibodies or antigen-binding fragments thereof relating to or derived from the ADT1-4 lineage (but excluding ADT1-4-138), the antibodies or antigen-binding fragments thereof of the invention may have an IC50 for TCR downregulation of less than about 1 nM and/or an IC90 for TCR downregulation of less than about 10 nM. Preferably the IC50 is less than about 0.5 nM and the IC90 is less than about 5 nM.

In some embodiments, for example antibodies or antigen-binding fragments thereof relating to or derived from the ADT1-4 lineage members ADT1-4-19, ADT1-4-21, ADT1-4-31, ADT1-4-53, ADT1-4-2, ADT1-4-86, ADT1-4-112, ADT1-4-143 and/or ADT1-4-1, the antibodies or antigen-binding fragments thereof of the invention may have an IC50 for TCR downregulation of less than about 1 nM and/or an IC90 for TCR downregulation of less than about 10 nM. Preferably the IC50 is less than about 0.5 nM and the IC90 is less than about 5 nM.

In some embodiments, for example antibodies or antigen-binding fragments thereof relating to or derived from the ADT1-7 lineage, the antibodies or antigen-binding fragments thereof of the invention may have an IC50 for TCR downregulation of less than about 50 nM. Preferably the IC50 is less than about 10 nM.

In some embodiments, for example antibodies or antigen-binding fragments thereof relating to or derived from the ADT1-7 lineage members ADT1-7-20 or ADT1-7-3, the antibodies or antigen-binding fragments thereof of the invention may have an IC50 for TCR downregulation of less than about 5 nM and/or an IC90 for TCR downregulation of less than about 10 nM. Preferably the IC50 is less than about 10 nM and the IC90 is less than about 5 nM.

THP-1 Cell Killing

Cell killing may be measured according to the assays described herein. For example, the antibody to be tested may be incubated at different concentration with a co-culture of γδ T cells and tumour cells (for example THP-1 cells). Cell killing may be measured by any suitable means, for example by flow cytometry.

The antibodies or antigen-binding fragments thereof of the invention may have an IC50 for THP-1 cell killing of less than about 10 nM and/or an IC90 for THP-1 cell killing of less than about 50 nM. Preferably the IC50 is less than about 5 nM and the IC90 is less than about 50 nM.

In some embodiments, for example antibodies or antigen-binding fragments thereof relating to or derived from the ADT1-4 lineage, the antibodies or antigen-binding fragments thereof of the invention may have an IC50 for THP-1 cell killing of less than about 10 nM and/or an IC90 for THP-1 cell killing of less than about 50 nM. Preferably the IC50 is less than about 5 nM and the IC90 is less than about 50 nM.

In some embodiments, for example antibodies or antigen-binding fragments thereof relating to or derived from the ADT1-7 lineage, the antibodies or antigen-binding fragments thereof of the invention may have an IC50 for THP-1 cell killing of less than about 5 nM and/or an IC90 for THP-1 cell killing of less than about 50 nM. Preferably the IC50 is less than about 1 nM and the IC90 is less than about 50 nM.

In some embodiments, for example antibodies or antigen-binding fragments thereof relating to or derived from the ADT1-7 lineage members ADT1-7-20 or ADT1-7-3, the antibodies or antigen-binding fragments thereof of the invention may have an IC50 for THP-1 cell killing of less than about 5 nM and/or an IC90 for THP-1 cell killing of less than about 10 nM. Preferably the IC50 is less than about 1 nM and the IC90 is less than about 5 nM.

Of course, the advantageous pharmacological profiles of the antibodies can be combined such that the antibodies exhibit an advantageous $K_D$ and advantageous IC50 and/or IC90 values for the various tested properties.

For example, in some embodiments, the antibodies or antigen-binding fragments thereof of the invention may:

- bind to human TRDV1 (SEQ ID NOs 272 or 306) with a binding affinity ($K_D$, for example as measured by surface plasmon resonance) of less than about 100 nM (preferably less than about 50 nM);
- optionally bind to cyno TRDV1 (SEQ ID NO 308) with a binding affinity ($K_D$, for example as measured by surface plasmon resonance) of less than about 100 nM (preferably less than about 50 nM);
- have an IC50 for TCR downregulation of less than about 50 nM (preferably less than about 10 nM);
- have an IC50 for THP-1 cell killing of less than about 10 nM (preferably less than about 5 nM) and
- have an IC90 for THP-1 cell killing of less than about 50 nM.

In some embodiments, in particular those relating to the ADT1-4 lineage, the antibodies or antigen-binding fragments thereof may:

- bind to human TRDV1 with a $K_D$ of less than about 100 nM (preferably less than about 50 nM);
- bind to cyno TRDV1 with a $K_D$ of less than about 100 nM (preferably less than about 50 nM);
- have an IC50 for TCR downregulation of less than about 50 nM (preferably less than about 10 nM) and an IC90 for TCR downregulation of less than about 100 nM (less than about 50 nM);
- have an IC50 for THP-1 cell killing of less than about 10 nM (preferably less than about 5 nM)
- have an IC90 for THP-1 cell killing of less than about 50 nM.

In some embodiments, for example antibodies or antigen-binding fragments thereof relating to or derived from the ADT1-4 lineage (but excluding ADT1-4-138), the antibodies or antigen-binding fragments thereof of the invention may:

- bind to human TRDV1 with a $K_D$ of less than about 10 nM (preferably less than about 5 nM);
- bind to cyno TRDV1 with a $K_D$ of less than about 100 nM (preferably less than about 50 nM);
- have an IC50 for TCR downregulation of less than about 1 nM (preferably less than about 0.5 nM) and an IC90 for TCR downregulation of less than about 10 nM (less than about 5 nM);
- have an IC50 for THP-1 cell killing of less than about 10 nM (preferably less than about 5 nM)
- have an IC90 for THP-1 cell killing of less than about 50 nM.

In some embodiments, for example antibodies or antigen-binding fragments thereof relating to or derived from the ADT1-4 lineage members ADT1-4-19, ADT1-4-21, ADT1-4-31, ADT1-4-53, ADT1-4-2, ADT1-4-86, ADT1-4-112, ADT1-4-143 and/or ADT1-4-1, the antibodies or antigen-binding fragments thereof of the invention may:

- bind to human TRDV1 with a $K_D$ of less than about 10 nM (preferably less than about 1 nM);
- bind to cyno TRDV1 with a $K_D$ of less than about 50 nM;
- have an IC50 for TCR downregulation of less than about 1 nM (preferably less than about 0.5 nM) and an IC90 for TCR downregulation of less than about 10 nM (less than about 5 nM);
- have an IC50 for THP-1 cell killing of less than about 10 nM (preferably less than about 5 nM)
- have an IC90 for THP-1 cell killing of less than about 50 nM.

In some embodiments, in particular those relating to the ADT1-7 lineage, the antibodies or antigen-binding fragments thereof may:

- bind to human TRDV1 with a $K_D$ of less than about 10 nM (preferably less than about 5 nM);
- have an IC50 for TCR downregulation of less than about 50 nM (preferably less than about 10 nM);
- have an IC50 for THP-1 cell killing of less than about 5 nM (preferably less than about 1 nM)
- have an IC90 for THP-1 cell killing of less than about 50 nM.

In some embodiments, in particular those relating to the ADT1-7 lineages ADT1-7-20 or ADT1-7-3, the antibodies or antigen-binding fragments thereof may:

- bind to human TRDV1 with a $K_D$ of less than about 10 nM (preferably less than about 5 nM);
- have an IC50 for TCR downregulation of less than about 5 nM (preferably less than about 1 nM);
- have an IC90 for TCR downregulation of less than about 10 nM (preferably less than about 5 nM);
- have an IC50 for THP-1 cell killing of less than about 5 nM (preferably less than about 1 nM)
- have an IC90 for THP-1 cell killing of less than about 10 nM (preferably less than about 5 nM).

Pharmacological Properties of Antibodies of the ADT1-4 Lineage

Antibodies of or derived from ADT1-4-105 (for example fragments thereof, variants having one or more amino acid substitutions or having certain percent identity thereto) may have a $K_D$ for human TRDV1 of less than about 10 nM (preferably less than about 1 nM) and/or a $K_D$ for cyno TRDV1 of less than about 50 nM.

Antibodies of or derived from ADT1-4-107 (for example fragments thereof, variants having one or more amino acid substitutions or having certain percent identity thereto) may have a $K_D$ for human TRDV1 of less than about 10 nM (preferably less than about 1 nM) and/or a $K_D$ for cyno TRDV1 of less than about 50 nM.

Antibodies of or derived from ADT1-4-110 (for example fragments thereof, variants having one or more amino acid substitutions or having certain percent identity thereto) may have a $K_D$ for human TRDV1 of less than about 10 nM (preferably less than about 1 nM) and/or a $K_D$ for cyno TRDV1 of less than about 50 nM.

Antibodies of or derived from ADT1-4-112 (for example fragments thereof, variants having one or more amino acid substitutions or having certain percent identity thereto) may have a $K_D$ for human TRDV1 of less than about 10 nM (preferably less than about 1 nM) and/or a $K_D$ for cyno TRDV1 of less than about 50 nM. Such antibodies may alternatively or additionally have an IC50 for TCR down regulation of less than about 1 nM (preferably less than about 0.5 nM) and/or an IC90 for TCR down regulation of less than about 10 nM (preferably less than about 5 nM). Such antibodies may alternatively or additional have an IC50 for THP-1 cell killing of less than about 10 nM (preferably less than about 5 nM) and/or an IC90 for THP-1 cell killing of less than about 50 nM (preferably less than about 10 nM).

Antibodies of or derived from ADT1-4-117 (for example fragments thereof, variants having one or more amino acid substitutions or having certain percent identity thereto) may have a $K_D$ for human TRDV1 of less than about 10 nM (preferably less than about 1 nM) and/or a $K_D$ for cyno TRDV1 of less than about 50 nM.

Antibodies of or derived from ADT1-4-19 (for example fragments thereof, variants having one or more amino acid substitutions or having certain percent identity thereto) may have a $K_D$ for human TRDV1 of less than about 1 nM (preferably less than about 0.5 nM) and/or a $K_D$ for cyno TRDV1 of less than about 10 nM (preferably less than about 5 nM). Such antibodies may alternatively or additionally have an IC50 for TCR down regulation of less than about 1 nM (preferably less than about 0.5 nM) and/or an IC90 for TCR down regulation of less than about 10 nM (preferably less than about 5 nM). Such antibodies may alternatively or additional have an IC50 for THP-1 cell killing of less than about 10 nM (preferably less than about 5 nM) and/or an IC90 for THP-1 cell killing of less than about 50 nM (preferably less than about 10 nM).

Antibodies of or derived from ADT1-4-21 (for example fragments thereof, variants having one or more amino acid substitutions or having certain percent identity thereto) may have a $K_D$ for human TRDV1 of less than about 10 nM (preferably less than about 1 nM) and/or a $K_D$ for cyno TRDV1 of less than about 50 nM (preferably less than about 10 nM). Such antibodies may alternatively or additionally have an IC50 for TCR down regulation of less than about 1 nM (preferably less than about 0.5 nM) and/or an IC90 for TCR down regulation of less than about 10 nM (preferably less than about 5 nM). Such antibodies may alternatively or additional have an IC50 for THP-1 cell killing of less than about 10 nM (preferably less than about 5 nM) and/or an IC90 for THP-1 cell killing of less than about 50 nM (preferably less than about 10 nM).

Antibodies of or derived from ADT1-4-31 (for example fragments thereof, variants having one or more amino acid substitutions or having certain percent identity thereto) may have a $K_D$ for human TRDV1 of less than about 10 nM (preferably less than about 1 nM) and/or a $K_D$ for cyno TRDV1 of less than about 50 nM (preferably less than about 10 nM). Such antibodies may alternatively or additionally have an IC50 for TCR down regulation of less than about 1 nM (preferably less than about 0.5 nM) and/or an IC90 for TCR down regulation of less than about 10 nM (preferably less than about 5 nM). Such antibodies may alternatively or additional have an IC50 for THP-1 cell killing of less than about 10 nM (preferably less than about 5 nM) and/or an IC90 for THP-1 cell killing of less than about 50 nM.

Antibodies of or derived from ADT1-4-139 (for example fragments thereof, variants having one or more amino acid substitutions or having certain percent identity thereto) may have a $K_D$ for human TRDV1 of less than about 10 nM (preferably less than about 1 nM) and/or a $K_D$ for cyno TRDV1 of less than about 50 nM.

Antibodies of or derived from ADT1-4-4 (for example fragments thereof, variants having one or more amino acid substitutions or having certain percent identity thereto) may have a $K_D$ for human TRDV1 of less than about 10 nM (preferably less than about 1 nM) and/or a $K_D$ for cyno TRDV1 of less than about 50 nM.

Antibodies of or derived from ADT1-4-143 (for example fragments thereof, variants having one or more amino acid substitutions or having certain percent identity thereto) may have a $K_D$ for human TRDV1 of less than about 10 nM (preferably less than about 1 nM) and/or a $K_D$ for cyno TRDV1 of less than about 50 nM (preferably less than about 10 nM). Such antibodies may alternatively or additionally have an IC50 for TCR down regulation of less than about 1 nM (preferably less than about 0.5 nM) and/or an IC90 for TCR down regulation of less than about 10 nM (preferably less than about 5 nM). Such antibodies may alternatively or additional have an IC50 for THP-1 cell killing of less than about 10 nM (preferably less than about 5 nM) and/or an IC90 for THP-1 cell killing of less than about 50 nM.

Antibodies of or derived from ADT1-4-53 (for example fragments thereof, variants having one or more amino acid substitutions or having certain percent identity thereto) may have a $K_D$ for human TRDV1 of less than about 10 nM (preferably less than about 1 nM) and/or a $K_D$ for cyno TRDV1 of less than about 50 nM (preferably less than about 10 nM). Such antibodies may alternatively or additionally have an IC50 for TCR down regulation of less than about 1 nM (preferably less than about 0.5 nM) and/or an IC90 for TCR down regulation of less than about 10 nM (preferably less than about 5 nM). Such antibodies may alternatively or additional have an IC50 for THP-1 cell killing of less than about 10 nM (preferably less than about 5 nM) and/or an IC90 for THP-1 cell killing of less than about 50 nM (preferably less than about 10 nM).

Antibodies of or derived from ADT1-4-173 (for example fragments thereof, variants having one or more amino acid substitutions or having certain percent identity thereto) may have a $K_D$ for human TRDV1 of less than about 10 nM (preferably less than about 1 nM) and/or a $K_D$ for cyno TRDV1 of less than about 50 nM.

Antibodies of or derived from ADT1-4-2 (for example fragments thereof, variants having one or more amino acid substitutions or having certain percent identity thereto) may have a $K_D$ for human TRDV1 of less than about 1 nM (preferably less than about 0.5 nM) and/or a $K_D$ for cyno TRDV1 of less than about 10 nM (preferably less than about 5 nM). Such antibodies may alternatively or additionally have an IC50 for TCR down regulation of less than about 1 nM (preferably less than about 0.5 nM) and/or an IC90 for TCR down regulation of less than about 10 nM (preferably less than about 5 nM). Such antibodies may alternatively or additional have an IC50 for THP-1 cell killing of less than about 10 nM (preferably less than about 5 nM) and/or an IC90 for THP-1 cell killing of less than about 50 nM (preferably less than about 10 nM)

Antibodies of or derived from ADT1-4-8 (for example fragments thereof, variants having one or more amino acid substitutions or having certain percent identity thereto) may have a $K_D$ for human TRDV1 of less than about 10 nM (preferably less than about 1 nM) and/or a $K_D$ for cyno TRDV1 of less than about 50 nM.

Antibodies of or derived from ADT1-4-82 (for example fragments thereof, variants having one or more amino acid substitutions or having certain percent identity thereto) may have a $K_D$ for human TRDV1 of less than about 10 nM (preferably less than about 1 nM) and/or a $K_D$ for cyno TRDV1 of less than about 50 nM.

Antibodies of or derived from ADT1-4-83 (for example fragments thereof, variants having one or more amino acid substitutions or having certain percent identity thereto) may have a $K_D$ for human TRDV1 of less than about 10 nM (preferably less than about 1 nM) and/or a $K_D$ for cyno TRDV1 of less than about 50 nM.

Antibodies of or derived from ADT1-4-3 (for example fragments thereof, variants having one or more amino acid substitutions or having certain percent identity thereto) may have a $K_D$ for human TRDV1 of less than about 10 nM (preferably less than about 1 nM) and/or a $K_D$ for cyno TRDV1 of less than about 50 nM.

Antibodies of or derived from ADT1-4-84 (for example fragments thereof, variants having one or more amino acid substitutions or having certain percent identity thereto) may have a $K_D$ for human TRDV1 of less than about 10 nM (preferably less than about 1 nM) and/or a $K_D$ for cyno TRDV1 of less than about 50 nM.

Antibodies of or derived from ADT1-4-86 (for example fragments thereof, variants having one or more amino acid substitutions or having certain percent identity thereto) may have a $K_D$ for human TRDV1 of less than about 10 nM (preferably less than about 1 nM) and/or a $K_D$ for cyno TRDV1 of less than about 50 nM (preferably less than about 10 nM). Such antibodies may alternatively or additionally have an IC50 for TCR down regulation of less than about 1 nM (preferably less than about 0.5 nM) and/or an IC90 for TCR down regulation of less than about 10 nM (preferably less than about 5 nM). Such antibodies may alternatively or additional have an IC50 for THP-1 cell killing of less than about 10 nM (preferably less than about 5 nM) and/or an IC90 for THP-1 cell killing of less than about 50 nM (preferably less than about 10 nM).

Antibodies of or derived from ADT1-4-95 (for example fragments thereof, variants having one or more amino acid substitutions or having certain percent identity thereto) may have a $K_D$ for human TRDV1 of less than about 10 nM (preferably less than about 1 nM) and/or a $K_D$ for cyno TRDV1 of less than about 50 nM.

Antibodies of or derived from ADT1-4-1 (for example fragments thereof, variants having one or more amino acid substitutions or having certain percent identity thereto) may have a $K_D$ for human TRDV1 of less than about 1 nM (preferably less than about 0.5 nM) and/or a $K_D$ for cyno TRDV1 of less than about 10 nM (preferably less than about 1 nM). Such antibodies may alternatively or additionally have an IC50 for TCR down regulation of less than about 1 nM (preferably less than about 0.5 nM) and/or an IC90 for TCR down regulation of less than about 10 nM (preferably less than about 1 nM). Such antibodies may alternatively or additional have an IC50 for THP-1 cell killing of less than about 10 nM (preferably less than about 1 nM) and/or an IC90 for THP-1 cell killing of less than about 10 nM (preferably less than about 5 nM).

Antibodies of or derived from ADT1-4-6 (for example fragments thereof, variants having one or more amino acid substitutions or having certain percent identity thereto) may have a $K_D$ for human TRDV1 of less than about 10 nM (preferably less than about 5 nM) and/or a $K_D$ for cyno TRDV1 of less than about 10 nM (preferably less than about 1 nM). Such antibodies may alternatively or additionally have an IC50 for TCR down regulation of less than about 1 nM (preferably less than about 0.5 nM) and/or an IC90 for TCR down regulation of less than about 10 nM (preferably less than about 5 nM). Such antibodies may alternatively or additional have an IC50 for THP-1 cell killing of less than about 10 nM (preferably less than about 1 nM) and/or an IC90 for THP-1 cell killing of less than about 10 nM (preferably less than about 1 nM).

Antibodies of or derived from ADT1-4-138 (for example fragments thereof, variants having one or more amino acid substitutions or having certain percent identity thereto) may have a $K_D$ for human TRDV1 of less than about 100 nM (preferably less than about 50 nM) and/or a $K_D$ for cyno TRDV1 of less than about 100 nM (preferably less than about 50 nM). Such antibodies may alternatively or additionally have an IC50 for TCR down regulation of less than about 50 nM (preferably less than about 10 nM) and/or an IC90 for TCR down regulation of less than about 100 nM (preferably less than about 50 nM). Such antibodies may alternatively or additional have an IC50 for THP-1 cell killing of less than about 10 nM (preferably less than about 1 nM) and/or an IC90 for THP-1 cell killing of less than about 50 nM (preferably less than about 10 nM).

Pharmacological Properties of Antibodies of the ADT1-7 Lineage

Antibodies of or derived from ADT1-7-10 (for example fragments thereof, variants having one or more amino acid substitutions or having certain percent identity thereto) may have a $K_D$ for human TRDV1 of less than about 10 nM (preferably less than about 5 nM).

Antibodies of or derived from ADT1-7-15 (for example fragments thereof, variants having one or more amino acid substitutions or having certain percent identity thereto) may have a $K_D$ for human TRDV1 of less than about 10 nM (preferably less than about 5 nM).

Antibodies of or derived from ADT1-7-17 (for example fragments thereof, variants having one or more amino acid substitutions or having certain percent identity thereto) may have a $K_D$ for human TRDV1 of less than about 10 nM (preferably less than about 5 nM).

Antibodies of or derived from ADT1-7-18 (for example fragments thereof, variants having one or more amino acid substitutions or having certain percent identity thereto) may have a $K_D$ for human TRDV1 of less than about 10 nM (preferably less than about 5 nM).

Antibodies of or derived from ADT1-7-19 (for example fragments thereof, variants having one or more amino acid substitutions or having certain percent identity thereto) may have a $K_D$ for human TRDV1 of less than about 10 nM (preferably less than about 5 nM).

Antibodies of or derived from ADT1-7-20 (for example fragments thereof, variants having one or more amino acid substitutions or having certain percent identity thereto) may have a $K_D$ for human TRDV1 of less than about 10 nM (preferably less than about 5 nM). Such antibodies may alternatively or additionally have an IC50 for TCR down regulation of less than about 5 nM (preferably less than about 1 nM) and/or an IC90 for TCR down regulation of less than about 10 nM (preferably less than about 5 nM). Such antibodies may alternatively or additional have an IC50 for THP-1 cell killing of less than about 5 nM (preferably less than about 1 nM) and/or an IC90 for THP-1 cell killing of less than about 10 nM (preferably less than about 5 nM).

Antibodies of or derived from ADT1-7-22 (for example fragments thereof, variants having one or more amino acid substitutions or having certain percent identity thereto) may have a $K_D$ for human TRDV1 of less than about 10 nM (preferably less than about 5 nM).

Antibodies of or derived from ADT1-7-23 (for example fragments thereof, variants having one or more amino acid substitutions or having certain percent identity thereto) may have a $K_D$ for human TRDV1 of less than about 10 nM (preferably less than about 5 nM).

Antibodies of or derived from ADT1-7-42 (for example fragments thereof, variants having one or more amino acid substitutions or having certain percent identity thereto) may have a $K_D$ for human TRDV1 of less than about 10 nM (preferably less than about 5 nM).

Antibodies of or derived from ADT1-7-3 (for example fragments thereof, variants having one or more amino acid substitutions or having certain percent identity thereto) may have a $K_D$ for human TRDV1 of less than about 10 nM (preferably less than about 1 nM). Such antibodies may alternatively or additionally have an IC50 for TCR down regulation of less than about 5 nM (preferably less than about 1 nM) and/or an IC90 for TCR down regulation of less than about 10 nM (preferably less than about 1 nM). Such antibodies may alternatively or additional have an IC50 for THP-1 cell killing of less than about 5 nM (preferably less than about 1 nM) and/or an IC90 for THP-1 cell killing of less than about 10 nM (preferably less than about 5 nM).

Antibodies of or derived from ADT1-7-61 (for example fragments thereof, variants having one or more amino acid substitutions or having certain percent identity thereto) may have a $K_D$ for human TRDV1 of less than about 10 nM (preferably less than about 1 nM). Such antibodies may alternatively or additionally have an IC50 for TCR down regulation of less than about 50 nM (preferably less than about 10 nM). Such antibodies may alternatively or additional have an IC50 for THP-1 cell killing of less than about 5 nM (preferably less than about 1 nM) and/or an IC90 for THP-1 cell killing of less than about 50.

Other Functional Properties of the Antibodies

The antibodies of the present invention have an advantageous functional profile. In particular, unlike anti-Vol antibodies of the prior art which focus on depletion of Vδ1 T-cells, the antibodies of the present invention are useful for the activation of Vδ1 T-cells. Although they may cause downregulation of the TCRs on T-cells to which they bind, they do not cause Vδ1 T-cell depletion, but rather they stimulate the T-cells and hence may be useful in therapeutic settings that would benefit from the activation of this compartment of T-cells. Activation of Vδ1 T-cells is evident through TCR downregulation, changes in activation markers such as CD25 and Ki67 and degranulation marker CD107a. Activation of Vδ1 T-cell in turn triggers release of inflammatory cytokines such as INFγ and TNFα to promote immune licensing. Surprisingly, antibodies having suitably high affinity for TRDV1 elicit increased Vδ1 T-cell killing and, unlike (for example) antibodies that target CD3, the provision of high affinity antibodies is possible without adverse effects associated with large-scale activation via CD3. In turn, the high affinity antibodies are able to induce strong immunostimulatory effects via tumour-infiltrating lymphocytes (TILs). This can be achieved with minimal exhaustion or killing of the Vδ1 cells. Therefore, the antibodies of the present invention may be considered agonistic antibodies.

In one embodiment of the invention, there is provided an anti-Vδ1 antibody or antigen-binding fragment thereof, characterised in that it:

a) causes downregulation of TCRs on Vδ1 T-cells;

b) does not exhibit CDC or ADCC; and c) does not deplete Vδ1 T-cells.

In some embodiments, the anti-Vδ1 antibody or antigen-binding fragments also stimulate Vδ1 T-cell proliferation.

The antibodies or antigen-binding fragments thereof may further be defined as binding to human TRDV1 (SEQ ID NOs 272 or 306) with a binding affinity ($K_D$, for example as measured by surface plasmon resonance) of less than about 10 nM, preferably less than about 5 nM.

The antibodies or antigen-binding fragments thereof may further be defined as having the advantageous $K_D$, IC50 and/or IC90 values as discussed above.

T-cell depletion is the process of T cell death removal or reduction. References to the antibodies or antigen binding fragments not depleting the Vδ1 T cells refers to a depletion of less than about 30% or less than about 20% (preferably less than about 10%) of the viable Vδ1 T+ cell population when incubated by one or more of the antibodies of the invention as described herein (for example when the antibodies is provided as an IgG1 antibody), and as measured by any via suitable means in a controlled study (for example via controlled flow cytometry methodology or via other established controlled assays such as described in FIG. 41 and FIG. 55).

ADCC and CDC are mechanisms by which T-cell depletion may occur. Reference to the antibodies or antigen binding fragments herein not causing ADCC or CDC refers to a depletion of less than about 30% or less than about 20% (preferably less than about 10%) of the viable Vδ1 T+ cell population via ADCC and/or CDC when incubated by one or more of the antibodies of the invention as described herein (for example when the antibodies is provided as an IgG1 antibody), as measured by any via suitable means (for example via controlled flow cytometry methodology or via other established controlled assays such as described in FIG. 41).

In one embodiment, there is provided an anti-Vδ1 antibody or antigen-binding fragment thereof, characterised in that it does not induce secretion of IL-17A. IL-17A (Interleukin-17A) is a pro-tumorigenic cytokine which is produced by activated T-cells. IL-17A can enhance tumour growth and dampen the anti-cancer immune response. As shown in FIG. 63, G to I, anti-vδ1 antibodies do not induce secretion of IL-17A when added to a population of cells comprising human lymphocytes that include Vδ1+ve cells whereas comparator anti-CD3 antibodies such as OKT 3 do induce IL17A in such circumstances. Hence, reference to the antibodies or antigen binding fragments herein not inducing secretion of IL-17A refers to inducing less than about 30%, or less than about 20%, or less than about 10% of the IL-17A secretion induced by a comparator anti-CD3 antibodies in such circumstances (as typified by OKT 3; the anti-CD3 comparator employed in FIG. 63 G to I).

Antibody Modifications

The antibodies and fragments thereof may be modified in other ways using known methods. Sequence modifications to antibody molecules described herein can be readily incorporate by those skilled in the art. The following examples are non-limiting.

During antibody discovery and sequence recovery from phage libraries, desired antibody variable domains may be re-formatted into full length IgG by sub-cloning. To accelerate the process, variable domains are often transferred using restriction enzymes. These unique restriction sites may introduce additional/alternate amino acids and away from the canonical sequence (such canonical sequences may be found, for example, in the international ImMunoGeneTics [IMGT] information system, see http://www.imgt.org). These may be introduced as kappa or lambda light chain sequence modifications.

Light Chain Modifications

The variable light chain variable sequences may be cloned using restriction sites (e.g. Nhe1-Not1) during re-formatting into full length IgG. More specifically, at the light chain N-terminus, an additional Ala-Ser sequence was introduced in the parental (non-affinity matured) antibodies to support cloning. Preferably, this additional AS sequence is then removed during further development such to generate the canonical N-terminal sequence. Hence, in some embodiments, light chain containing antibodies described herein do not contain an AS sequence at their N-termini, i.e. SEQ ID NOs: 26, 118, 282 to 290 or 313 do not comprise the initial AS sequence. The N-termini of the light chain sequences of the affinity-matured antibodies already do not comprise this AS motif.

Additional amino acid changes may be made to support cloning. For example, for the parental antibodies described herein having kappa light chains (i.e. B07, C05, E04, F07, G06, G09, B09, G10, G04 and E07), at the kappa light-chain variable-domain/constant domain border a valine-to-alanine change was introduced to support cloning when preparing full-length sequences. This resulted in a kappa constant domain modification. Specifically, this results in the constant domain beginning RTAAAPS (from a NotI restriction site). Preferably, such sequences can be modified during further development to generate the canonical kappa light-chain constant regions which start with RTVAAPS. Such modifications do not change the functional properties of the antibodies. Hence, in some embodiments, kappa light chain containing antibodies described herein contain a constant domain starting with the sequence RTV (for example as in SEQ ID NO: 296).

As another example, for the antibodies described herein (specifically E01 and C08) at the lambda light-chain variable-domain/constant domain border a lysine-to-alanine sequence change was introduced to support cloning. This resulted in a lambda constant domain modification. Specifically, this results in the constant domain beginning with GQPAAAPS (from a Not1 restriction site). Preferably, this sequence can be modified during further development such to generate the canonical lambda light constant region which starts GQPKAAPS. Hence, in some embodiments, lambda light chain containing antibodies described herein contain a constant domain starting with the sequence GQPK.

Heavy Chain Modifications

Typically, human variable heavy chain sequences start with either the basic glutamine (Q) or acidic glutamate (E). However, both such sequences are then known to convert to the acidic amino acid residue, pyro-glutamate (pE). The Q to pE conversion results in a charge change to the antibody, whilst an E to pE conversion does not change the charge of the antibody. Hence to avoid a variable charge-change over time one option is to modify a starting heavy chain sequence from Q to E in the first instance. Hence, in one embodiment, the heavy chain of antibody described herein having a Q residue at the N-terminus of the heavy chain may contain a Q to E modification at the N-terminus. In particular, the initial residue of any of SEQ ID NOs: 1, 106, 276 to 279 or 312 may be modified from Q to E. It will be understood that this embodiment also applies to any embodiment incorporating these sequences, for example into full-length antibodies or antigen-binding fragments thereof. In some embodiments, it may be advantageous to substitute an E residue at the N-terminus of the heavy chain to an E residue. Accordingly, in some embodiments, the E residue at the N-terminus of any one SEQ ID NOs: 2 to 25, 107 to 117, 273 to 275, 280 or 281 may be substituted with a Q residue.

Furthermore, the C-terminus of the IgG1 constant domain ends with PGK. However, the terminal basic lysine (K, EU position 447) is then often cleaved during expression (e.g. in CHO cells). This in turn results in charge change to the antibody through varied loss of the C-terminal lysine residue. Therefore, one option is to remove the lysine in the first instance resulting in a uniform and consistent heavy chain C-terminus sequence ending in PG. An alternative option is to also remove the terminal G (EU position 446). Hence, in one embodiment, the heavy chain of an antibody described herein has the terminal K, or the terminal GK, removed from its C-terminus.

In some embodiments, the antibody or antigen-binding fragment thereof contains a modified effector function through alteration to the sugars linked to Asn 297 (EU numbering scheme). In a further said modification, Asn 297 is not fucosylated or exhibits reduced fucosylation (i.e., a defucosylated antibody or a non-fucosylated antibody). Fucosylation includes the addition of the sugar fucose to a molecule, for example, the attachment of fucose to N-glycans, 0-glycans and glycolipids. Accordingly, in a defucosylated antibody, fucose is not attached to the carbohydrate chains of the constant region. The antibody may be modified to prevent or inhibit fucosylation of the antibody. Typically, glycosylation modifications involve expressing said antibody or antigen-binding fragment thereof in a host cell containing alternate glycosylation processing capabilities either through targeted engineering or through targeted or serendipitous host or clone selection (e.g. see Example 13). These and other effector modifications are discussed further in recent reviews such as by Xinhua Wang et al. (2018) Protein & Cell 9: 63-73 and by Pereira et al. (2018) mAbs 10(5): 693-711 and which are hereby incorporated.

Optional Allotype Modifications

During antibody discovery, specific human allotypes may be employed. Optionally, the antibodies can be switched to differing human allotypes during development. By way of non-limiting example, for the kappa chain there are three human allotypes designated Km1, Km1,2 and Km3 which define three Km alleles (using allotype numbering): Km1 correlates with valine 153 (IMGT V45.1) and leucine 191 (IMGT L101); Km1,2 correlates with alanine 153 (IMGT A45.1) and leucine 191 (IMGT L101); and Km3 correlates with alanine 153 (IMGT A45.1) and valine 191 (IMGT V101). Optionally, one can therefore modify a sequence from one allotype to another by standard cloning approaches. For example, a L191V (IMGT L101V) change will convert a Km1,2 allotype to a Km3 allotype. For further reference on such allotypes see Jefferis and Lefranc (2009) MAbs 1(4):332-8, which is herein incorporated by reference.

Hence in one embodiment an antibody described herein contains amino acid substitutions derived from another human allotype of the same gene. In a further embodiment, the antibody contains a L191V (IMGT L101V) substitution to the kappa chain to convert the c-domain from a km1,2 to a km3 allotype.

Multispecific Antibodies

The antibodies of the present invention may be monospecific. In some embodiments, the antibodies are not multispecific antibodies. In some embodiments, the antibodies are not bispecific antibodies. However, the present invention also provides multispecific antibodies. Therefore, the antibodies may bind additional targets and may therefore be bispecific or multispecific. Multispecific antibodies may be specific for different epitopes of one target polypeptide or may be specific for more than one target polypeptide. Therefore, in one embodiment, the antibody or antigen-binding fragment thereof comprises a first binding specificity to Vol and a second binding specificity for a second target epitope or antigen.

In particular, the present invention provides a new class of multispecific antibodies that target a variable delta 1 (Vδ1)

chain of a γδ T cell receptor (TCR) and a second antigen. The second antigen may be, for example, a cancer antigen or a cancer-associated antigen (such as a TAA) hence thus the antibody may be referred to as a T-cell engager (TCE). Alternatively, the second antigen may be, for example, an immunomodulatory antigen, and thus the antibody may be a dual immunomodulatory antibody. Thus, multispecific antibodies of the present invention can be divided into two classes. The first are multispecific antibodies that are T-cell engagers. The second are multispecific antibodies that are dual immunomodulators (Dis).

The TCEs of the present invention provide several advantages over the TCEs of the prior art. In particular, the TCEs may overcome many of the challenges associated with TCEs of the prior art by targeting the T-cell receptor complex via an entirely novel and discrete mechanism. Indeed, by specifically targeting (and activating) the T-cell receptor complex solely via binding to an epitope on the TRDV1 domain, a number of advantages are realized including:

- Engaging only a sub-set of T-cells rather than all T-cells (e.g. engagement of T-regs in a cancer setting may be undesirable);
- Engaging only a sub-set of T-cells (TRDV1+ T-cells) that are predominantly 'tissue-resident' and whose presence often positively correlates with good prognosis in a cancer/tumour setting;
- Activating the T-cell receptor complex via TRDV1 engagement thereby affording more optionality (e.g. increasing affinity of this binding domain, as in the antibodies of the present invention). For example, by developing recombinant TCEs which engage a T-Cell Receptor complex solely via the TRDV1 domain rather than via CD3, increased affinity may drive more favourable functionality. For example, high-affinity TRDV1-binding TCEs may activate but not exhaust T-cells; and/or
- Engaging the TCE complex via said novel means and via recombinant TRDV1 binding domains may result in less deleterious effects and so reduce the need to attenuate Fc functionality in said TCE moieties. It would generally be expected that a TCE with unattenuated Fc function would induce an antibody-dependent cell-mediated cytotoxicity (ADCC) effect and thereby deplete the population of γδ T-cells recognized by the antibody. However, and again, by attenuating such functionality to avoid toxicity/safety complexities, one may also attenuate a potentially important efficacy angles too e.g. by engaging CD16+ or CD32+ or CD64+ immune cells, or by reducing half-life of the bispecific (e.g. if employing smaller bispecific antibody fragments such as BITEs). Methods of reducing the interaction of the FcγR and the TCE (such as using an IgG format designed to reduce said interaction) would be expected to reduce Fc-mediated immobilization of the TCE and reduce TCR clustering by cross-linking with the immobilized TCE. Reducing the need to attenuate Fc functionality in said TCE moieties then may afford additional optionality, for example by allowing TRDV1 TCEs to engage TRDV1+ cells via one binding domain, engaging a second cell type (such as a cancerous cell) by a second binding arm, and engaging other effector cells such as CD16+ or CD32+ or CD64+ immune cells via a functioning Fc domain.
- Activate the vδ1 TCR without depleting vδ1+ T cells. The antibodies described herein can therefore engage and activate the CD3/γδ TCR complex and confer its down-regulation and loss of surface expression, without unwanted depletion of vδ1 T cells (see FIG. 55). This enables the antibodies described herein to be employed as medicaments to treat a disease or disorder such to ameliorate at least one sign or symptom of a disease or disorder through a mechanism involving the activation of blood, tissue and tumour resident Vδ1+ T cells.

Hence through the discoveries as described herein, the present inventors have generated a novel class of recombinant TCEs. Specifically, the present inventors have discovered a new class of TCEs which engage the T-cell receptor via a TRDV1 domain rather than other domains in said T-cell receptor signalling complexes. More specifically the present inventors have discovered a new class of TCEs which engage this complex via an activating epitope on TRDV1 and which may be bound at higher affinities without potentially conferring some of the previously reported deleterious effects high-affinity T-cell receptor complex engagement. Further this new class of TCEs may engage in such a way which may allow for wild-type Fc functionality too, thereby affording additional efficacy potential too.

The DIs of the present invention provide a completely novel method of dual immunomodulatory target engagement that is entirely unique, providing a huge possible range of novel therapies requiring immunomodulation, such as cancer. The DI platform of the present invention provides a new class of therapeutics that may provide an important alternative or improvement to the existing DI approaches. Previously it has not be contemplated that a TRDV1-specific binding function as described herein could be incorporated into a DI format.

The multispecific antibodies of the invention may also display improved properties compared to equivalent monospecific antibodies. For example, the multispecific antibodies of the invention may also display improved properties compared to monospecific antibodies having the same antigen binding domains as the component parts of the multispecific antibodies. In some embodiments, for example, the recombinant multispecific antibody confers increased gamma delta T-cell mediated cytotoxicity towards a diseased cell expressing the second epitope compared to the cytotoxicity conferred by an equivalent amount of said first monospecific antibody. The multispecific antibodies of the invention may also display improved cytotoxicity towards diseased cells whilst still sparing healthy cells.

The identity of the second antigen determines if the antibody is in one of two categories, as discussed herein: a T-cell engager (TCE) antibody or a dual immunomodulator (DI) antibody.

In embodiments relating to TCEs, the second antigen is a cancer antigen or a cancer-associated antigen. In such embodiments, the antibodies specifically bind a first target epitope, wherein the first target epitope is an epitope of the variable delta 1 (Vδ1) chain of a γδ T cell receptor (TCR); and a second target epitope, wherein the second target epitope is an epitope of a cancer antigen or cancer-associated antigen. The identities of specific possible second antigens in this category are discussed herein. However, the second antigen can be any antigen expressed by a cancer cell that promotes the Vδ1-T cell mediated killing of said cancer cell (e.g. direct killing or via immune licensing effect of signalling to other immune cells upon tumour cell binding). Such Vδ1-cell mediated cancer cell killing is promoted by colocalizing the Vδ1-T cells and cancer cells, and activation of the Vδ1-T cells via binding of the multispecific antibody, in particular to an activating epitope of the Vδ1-T cell. The present invention exemplifies a completely novel platform for TCE-type antibodies.

In some embodiments, the second antigen is not an antigen of an ovarian carcinoma. In some embodiments, the second antigen is not an antigen of a Mov19+ ovarian carcinoma. In some embodiments, the multispecific (suitably bispecific) antibody does not specifically bind to Mov19+ ovarian carcinoma cells. In some embodiments, the multispecific (suitably bispecific) antibody does not specifically bind to alpha-folate receptor (alpha-FR). Alpha-FR is also known as folate receptor 1, FOLR1, folate receptor alpha, or FRα. It is encoded by the FOLR1 gene (UniProt accession no. P15328) and has the sequence of SEQ ID NO: 390. In some embodiments, the multispecific (suitably bispecific) antibody does not specifically bind to an epitope bound by the scFv MOV19.

In some embodiments, the antibody or antigen-binding fragment thereof is a bispecific antibody, wherein the second antigen is not alpha-folate receptor.

In some embodiments the multispecific antibody is a human recombinant antibody encoded by a recombinant nucleic acid open reading frame or frames expressed from a recombinant host cell. In some embodiments the multispecific antibody is not a rodent or other non-human antibody derived from B-cell fusion hybridoma technologies. In some embodiments the multispecific antibody does not comprise non-human IgG constant domain sequence found only in non-human animal species, such as sequence found in rodent-derived hybridomas.

In embodiments relating to DIs, the second antigen is an immunomodulatory antigen. In such embodiments, the antibodies specifically bind a first target epitope, wherein the first target epitope is an epitope of the variable delta 1 (Vδ1) chain of a γδ T cell receptor (TCR); and a second target epitope, wherein the second target epitope is an immunomodulatory antigen. An "immunomodulatory antigen" is an antigen that modulates (for example promotes) antibody- and/or cell-mediated immunity. An immunomodulatory antigen is one that is present on the cell surface of a T-cell. In embodiments of the invention in which the second antigen is an immunomodulatory antigen, the second antigen is not the T-cell receptor or a component of the T-cell receptor complexes. For example, in embodiments of the invention in which the second epitope is an epitope of an immunomodulatory antigen, the second epitope is not an epitope of TRDV1. In preferred embodiments of the invention in which the second epitope is an epitope of an immunomodulatory antigen, the second epitope is not an epitope of the T-cell receptor complex. For example, in some embodiments, the second epitope is not an epitope of CD3. Hence the antibodies of these embodiments are "dual immunomodulators" as they specifically bind to T-cells via TRDV1, and may additionally bind to T-cells via a second, different, epitope, wherein the epitope is not an epitope of the T-cell receptor complex. Example second antigens include, for example, the immune checkpoint inhibitors PD-L1, PD-1, OX40, CTLA-4, LAG-3, TIM-3, TIGIT and VISTA. For example, solid tumors recruit immunosuppressive cells such as myeloid derived suppressor cells (MDSCs), tumor-associated macrophages (TAMs), and regulatory T-cells (Tregs), all of which inhibit the activity of cytotoxic T-cells. Therefore, the most effective use of DIs in solid tumors will likely require the use of multispecific moieties to target T-cell modulating pathways in combination to help to overcome the immunosuppressive TME and render an immune excluded or immune desert "cold" tumor into an inflamed "hot" one. However, the present invention is not limited to specific second immunomodulatory antigens, since it presents a completely novel platform for DI-type antibodies.

In preferred embodiments, the multispecific antibodies (suitably bispecific antibodies) of the invention, do not specifically bind (or directly interact with) CD3. In preferred embodiments, the second antigen is not CD3.

In some embodiments, the second antigen is not CD3 or alpha-folate receptor.

In some embodiments, the second target epitope is on an antigen expressed by a Vδ1+ T-cell (in particular an antigen expressed on the surface of a Vδ1+ T-cell). In other embodiments, the second target epitope is on an antigen expressed by another cell, i.e. a cell that is not Vδ1+ T-cell (in particular an antigen expressed on the surface of a cell that is not Vδ1+ T-cell). For example, the second antigen may be expressed by a cancer cell.

References herein to an antigen being "on" a cell refer to antigens that are expressed on the cell surface membrane or are associated with the (extracellular side of) the cell surface membrane of such cells.

In various embodiments, the second target epitope is an epitope of a cancer antigen or a cancer-associated antigen. In various embodiments, the cancer antigen or cancer-associated antigen is one selected from AFP, AKAP-4, ALK, alpha-fetoprotein, Androgen receptor, B7H3, BAGE, BCA225, BCAA, Bcr-abl, beta-Catenin, beta-HCG, beta-human chorionic gonadotropin, BORIS, BTAA, CA 125, CA 15-3, CA 195, CA 19-9, CA 242, CA 27.29, CA 72-4, CA-50, CAM 17.1, CAM43, Carbonic anhydrase IX, carcinoembryonic antigen, CD22, CD33/IL3Ra, CD68\P1, CDK4, CEA, chondroitin sulfate proteoglycan 4 (CSPG4), c-Met, CO-029, CSPG4, Cyclin B1, cyclophilin C-associated protein, CYP1 B1, E2A-PRL, EGFR, EGFRvIII, ELF2M, EpCAM, EphA2, EphrinB2, Epstein Barr virus antigens EBVA, ERG (TMPRSS2ETS fusion gene), ETV6-AML, FAP, FGF-5, Fos-related antigen 1, Fucosyl GM1, G250, Ga733\EpCAM, GAGE-1, GAGE-2, GD2, GD3, glioma-associated antigen, GloboH, Glycolipid F77, GM3, GP 100, GP 100 (Pmel 17), H4-RET, HER-2/neu, HER-2/Neu/ErbB-2, high-molecular-weight melanoma-associated antigen (HMW-MAA), HPV E6, HPV E7, hTERT, HTgp-175, human telomerase reverse transcriptase, Idiotype, IGF-I receptor, IGF-II, IGH-IGK, insulin growth factor (IGF)-I, intestinal carboxyl esterase, K-ras, LAGE-1a, LCK, lectin-reactive AFP, Legumain, LMP2, M344, MA-50, Mac-2 binding protein, MAD-CT-1, MAD-CT-2, MAGE, MAGE A1, MAGE A3, MAGE-1, MAGE-3, MAGE-4, MAGE-5, MAGE-6, MART-1, MART-1/MelanA, M-CSF, melanoma-associated chondroitin sulfate proteoglycan (MCSP), Mesothelin, MG7-Ag, ML-IAP, MN-CA IX, MOV18, MUC1, Mum-1, hsp70-2, MYCN, MYL-RAR, NA17, NB/70K, neuron-glial antigen 2 (NG2), neutrophil elastase, nm-23H1, NuMa, NY-BR-1, NY-CO-1, NY-ESO, NY-ESO-1, NY-ESO-1, OY-TES1, p15, p16, p180erbB3, p185erbB2, p53, p53 mutant, Page4, PAX3, PAX5, PDGFR-beta, PLAC1, Polysialic Acid, prostate-carcinoma tumor antigen-1 (PCTA-1), prostate-specific antigen, prostatic acid phosphatase (PAP), Proteinase3 (PR1), PSA, PSCA, PSMA, RAGE-1, Ras, Ras-mutant, RCAS1, RGS5, RhoC, ROR1, RU1, RU2 (AS), SART3, SDCCAG16, sLe(a), Sperm protein 17, SSX2, STn, Survivin, TA-90, TAAL6, a TAG-72, telomerase, thyroglobulin, Tie 2, TLP, Tn, TPS, TRP-1, TRP-2, TRP-2, TSP-180, Tyrosinase, VEGF, VEGFR2, VISTA, WT1, XAGE 1, 43-9F, 5T4, and 791Tgp72.

In some embodiments, the second target epitope is in the ErbB subfamily. Erb-B1 (EGFR), Erb-B2 (HER2) are members of subclass I of the superfamily of receptor tyrosine kinases (RTKs). In some embodiments the second target epitope is an RTK. RTKs share a similar protein structure comprised of an extracellular ligand binding domain and a single transmembrane helix. They are then predominantly sub-divided further into separate sub-classes via the nature of their intracellular tyrosine kinase domain (TKD) and a carboxyl (C-) terminal tail. The extracellular domain regions of RTKs exhibits a variety of conserved elements including immunoglobulin (Ig)-like or epidermal growth factor (EGF)-like domains. In some embodiments the second epitope is an epitope of a receptor tyrosine kinase. Examples of the RTK family include VEGFR2, EGFR, c-MET, IGF-1 receptor, PDGFR-beta, CD115, CD117, CD140A, CD140B, CD167a, CD167b, CD172g, CD220, CD246, CD303 CD331, CD332, CD333 and CD340.

For example, in some embodiments the second target epitope is HER2 (human epidermal growth factor receptor 2). HER2 (also known as ErbB-2 or CD340) is a cancer-associated antigen and is an example of a receptor tyrosine kinase, in the ErbB subfamily. HER2 expression is low in healthy tissues, with up to 40-100 fold increases in expression in Her2+ cancers compared to normal tissues. Her2 overexpression is associated with many breast cancers, gastric cancers, espohageal cancers, ovarian cancers, endometrial cancers, NSCLCs and colorectal cancers. In many cancers, HER2 dimerises with other ErbB receptors and results in activation of various downstream signalling pathways, in turn leading to uncontrolled proliferation and apoptosis resistance. Overexpression of HER2 correlates with lower survival rates, and it is therefore a target to improve prognosis, as well as a tumour marker. Monoclonal antibodies that specifically bind to epitopes of HER2 are well known in the art. For example, trastuzumab is a monoclonal antibody which binds specifically to an epitope of HER2.

In some embodiments, the second target epitope is EGFR. EGFR (epidermal growth factor receptor) is a cancer-associated antigen and is an example of a receptor tyrosine kinase, in the ErbB subfamily. EGFR is expressed in multiple organs and plays an important role in initiating signaling that directs the behaviour of epithelial cells and tumours of epithelial origin. EGFR-mediated signaling is also involved in controlling cell proliferation, migration, survival, and metastasis by regulating diverse cellular pathways. As with other receptor tyrosine kinases, mutations affecting EGFR activity or leading to EGFR upregulation are associated with many cancers. In fact, genetic alterations in EGFR are observed in up to 30% of solid tumours and are typically associated with poor prognosis. Disruption of EGFR signalling, by inhibiting binding of EGF to the extracellular domain or by inhibiting the intracellular tyrosine kinase activity can limit EGFR-expressing tumour growth. EGFR inhibitors can therefore be anti-cancer agents. Indeed, certain tumour cells are dependent on EGFR signaling and thus possess an “Oncogene addiction”, which makes this receptor an attractive target for therapy. Monoclonal antibodies that specifically bind to epitopes of EGFR are well known in the art. For example, cetuximab is a monoclonal antibody which binds specifically to an epitope of EGFR.

In some embodiments, the second target epitope is an epitope of a B-lymphocyte antigen. Examples of antigens notably expressed on B-cells include CD1d, CD5, CD10, CD11 b, CD19, CD20, CD21, CD22, CD23, CD24, CD32A, CD32B CD37, CD39, CD40, CD45, CD52, CD72, CD79a, CD79b, CD138, CD166, CD179A, CD179B, CD180, CD185, CD150, CD213a1, CD213a2, CD217, CD244, CD255, CD229, CD232, CD267, CD268, CD269, CD274, CD277, CD279, CD290, CD300A, CD300C, CD305, CD307a, CD307b, CD307c, CD307d, CD307e, CD316, CD319, CD327, CD352, and CD361. For example, in some embodiments the second target epitope is CD19. CD19 (cluster of differentiation 19) is a cancer-associated antigen. CD19 is also an example of a Type I transmembrane glycoprotein in the immunoglobulin superfamily. In some embodiments the second target is an epitope present on a member of the immunoglobulin superfamily (IgSF). Examples of this family include, CD2, CD3, CD4, CD7, CD8, CD19, CD79A, CD79B, CD28, CD48, CD58, CD80, CD86, CD90, CD96, CD147, CD150, CD155, CD229, CD244, CD273, CD274, CD276. CD19 is widely expressed on B cells throughout their development, with the surface density of CD19 increasing as B cells mature. CD19 is involved in recruiting signalling proteins from the cytoplasm. CD19 is also involved in B cell receptor signalling pathways and is essential to the functioning of the B cell receptor. Its expression on B cells makes it a useful target against leukaemia and neoplastic lymphocytes, as well as a diagnostic biomarker for cancers arising from B cells. CD19 mutations can lead to reduced production of antibodies and immunodeficiency, therefore CD19 can also be targeted for autoimmune disease treatments. Monoclonal antibodies that specifically bind to epitopes of CD19 are well known in the art. For example, blinatumomab is a monoclonal antibody which binds specifically to an epitope of CD19.

In some embodiments, the second target epitope is present on a tumour stromal antigen. Examples of tumour stromal antigens include FAP alpha, CD29, CD44, CD73, CD105 and CD166. For example, in some embodiments the second target epitope is FAPα (Fibroblast activation protein α). FAPα is a cancer-associated antigen also known as seprase or prolyl endopeptidase FAP. It is selectively expressed in the stroma of a range of epithelial carcinomas. FAPα is an example of a cell surface serine protease in the dipeptidyl peptidase family. FAPα is expressed by cancer associated fibroblasts (CAFs), which play an important role in the tumour microenvironment. Other molecules selectively expressed on CAFs include CD10, CD90, CD140A, and CD140B. In some embodiments the second epitope is an epitope present on a molecule selectively expressed on CAFs. Over 90% of epithelial cancers (breast, CRC skin and pancreatic cancers) are found to express FAPα on the surface of CAFs in the surrounding stroma. CAFs secrete the chemokine CXCL12 that binds to CXCR4 on T-cells and is immunosuppressive. FAPα is found to be expressed in aggressive melanoma cell lines and is significantly increased in patients with poor outcome and survival in breast cancer. FAPα has both collagenase and dipeptidase activities and promotes tumour growth, migration, invasion, metastasis and ECM degradation. Normal healthy adult tissues have no detectable FAPα expression outside areas of tissue remodelling or wound healing and therefore FAPα is a promising anti-cancer target due to its nearly exclusive expression in tumour stroma and the direct role of FAPα in various aspects of cancer progression. Monoclonal antibodies that specifically bind to epitopes of FAPα are well known in the art. For example, sibrotuzumab is a monoclonal antibody which binds specifically to an epitope of FAPα.

In some embodiments, the bi- or multi-specific antibody comprises a FAPα-binding component comprising a heavy chain variable region comprising a VHCDR1 comprising the amino acid sequence of SEQ ID NO: 458, a VHCDR2 comprising the amino acid sequence of SEQ ID NO: 459 and a VHCDR3 comprising the amino acid sequence of SEQ ID NO: 460; and a light chain variable region comprising a VLCDR1 comprising the amino acid sequence of SEQ ID NO: 461, a VLCDR2 comprising the amino acid sequence of SEQ ID NO: 462 and a VLCDR3 comprising the amino acid sequence of SEQ ID NO: 463. In some embodiments, the bi- or multi-specific antibody comprises an FAPα-binding component comprising a VH comprising or consisting of the amino acid sequence of SEQ ID NO: 456 and a VL comprising or consisting of the amino acid sequence of SEQ ID NO: 457. In some embodiments, the bi- or multi-specific antibody specifically binds to FAPα and comprises SEQ ID NO: 402.

Such sequences may be combined with any suitable anti-TRDV1 binding sequences. For example, in some embodiments, the bi- or multi-specific antibody specifically binds to TRDV1 and FAPα and comprises:

- a TRDV1 binding component comprising a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 68; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 95; and
- a FAPα binding component comprising a heavy chain variable region comprising a VHCDR1 comprising the amino acid sequence of SEQ ID NO: 458, a VHCDR2 comprising the amino acid sequence of SEQ ID NO: 459 and a VHCDR3 comprising the amino acid sequence of SEQ ID NO: 460; and a light chain variable region comprising a VLCDR1 comprising the amino acid sequence of SEQ ID NO: 461, a VLCDR2 comprising the amino acid sequence of SEQ ID NO: 462 and a VLCDR3 comprising the amino acid sequence of SEQ ID NO: 463.

In some embodiments, the bi- or multi-specific antibody specifically binds to TRDV1 and FAPα and comprises:

- a TRDV1 binding component comprising a VH comprising or consisting of the amino acid sequence of SEQ ID NO: 15 and a VL comprising or consisting of the amino acid sequence of SEQ ID NO: 40; and
- a FAPα binding component comprising a VH comprising or consisting of the amino acid sequence of SEQ ID NO: 456 and a VL comprising or consisting of the amino acid sequence of SEQ ID NO: 457.

In some embodiments, the bi- or multi-specific antibody specifically binds to TRDV1 and FAPα and comprises:

- a TRDV1 binding component comprising a VH comprising or consisting of the amino acid sequence of SEQ ID NO: 15 and a VL comprising or consisting of the amino acid sequence of SEQ ID NO: 40; and
- a FAPα binding component comprising SEQ ID NO: 402.

In some embodiments, the bi- or multi-specific antibody specifically binds to TRDV1 and FAPα and comprises SEQ ID NO: 414 and SEQ ID NO: 415. In some embodiments the antibody specifically binds to TRDV1 and FAPα and comprises SEQ ID NO: 504 and SEQ ID NO: 415. In some embodiments the antibody specifically binds to TRDV1 and FAPα and comprises SEQ ID NO: 505 and SEQ ID NO: 415.

In some embodiments, the second target epitope is present on a cell-surface glycoprotein. Protein glycosylation is an important and common post-translational modification. More than 50% of human proteins are believed to be glycosylated to modulate the functionality of proteins. Aberrant glycosylation has been correlated to several diseases, such as inflammatory skin diseases, diabetes mellitus, cardiovascular disorders, rheumatoid arthritis, Alzheimer's and prion diseases, and cancer Examples of cell-surface glycoproteins include CD1a, CD1b, CD1c, CD1d, CD1e, CD3d, CD3e, CD3g, CD8a, CD8b, CD11a, CD21, CD36, CD42a, CD42b, CD42c, CD42d, CD43, CD66a, CD66f, CD177, CD235a, CD235b, CD236, CD238, CD243, CD227 and CD301. For example, in some embodiments the second target epitope is mesothelin (MSLN). MSLN is a cancer-associated antigen and is an example of a cell-surface glycoprotein. MSLN has limited expression in healthy cells (mesothelial cells lining the pleura, peritoneum, and pericardium) but is also expressed on a number of cancers (malignant mesothelioma and pancreatic, cholangiocarcinoma, ovarian and lung adenocarcinomas, malignant mesothelioma, pancreatic cancer, ovarian cancer, endometrial cancer, biliary cancer, gastric cancer, and paediatric acute myeloid leukaemia). MSLN is an example of a tumour-differentiation antigen. The physiological function of MSLN is unclear, but MSLN is a useful target for localisation of therapies to MSLN+ tumours, or can be exploited as a tumour marker. Monoclonal antibodies that specifically bind to epitopes of MSLN are well known in the art. For example, anetumab is a monoclonal antibody which binds specifically to an epitope of MSLN.

In some embodiments, the bi- or multi-specific antibody comprises a MSLN-binding component comprising a heavy chain variable region comprising a VHCDR1 comprising the amino acid sequence of SEQ ID NO: 466, a VHCDR2 comprising the amino acid sequence of SEQ ID NO: 467 and a VHCDR3 comprising the amino acid sequence of SEQ ID NO: 468; and a light chain variable region comprising a VLCDR1 comprising the amino acid sequence of SEQ ID NO: 469, a VLCDR2 comprising the amino acid sequence of SEQ ID NO: 470 and a VLCDR3 comprising the amino acid sequence of SEQ ID NO: 471. In some embodiments, the bi- or multi-specific antibody comprises an MSLN-binding component comprising a VH comprising or consisting of the amino acid sequence of SEQ ID NO: 464 and a VL comprising or consisting of the amino acid sequence of SEQ ID NO: 465. In some embodiments, the bi- or multi-specific antibody specifically binds to MSLN and comprises SEQ ID NO: 404.

Such sequences may be combined with any suitable anti-TRDV1 binding sequences. For example, in some embodiments, the bi- or multi-specific antibody specifically binds to TRDV1 and MSLN and comprises:

- a TRDV1 binding component comprising a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 68; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 95; and
- a MSLN binding component comprising a heavy chain variable region comprising a VHCDR1 comprising the amino acid sequence of SEQ ID NO: 466, a VHCDR2 comprising the amino acid sequence of SEQ ID NO: 467 and a VHCDR3 comprising the amino acid sequence of SEQ ID NO: 468; and a light chain variable region comprising a VLCDR1 comprising the amino acid sequence of SEQ ID NO: 469, a VLCDR2 comprising the amino acid sequence of SEQ ID NO: 470 and a VLCDR3 comprising the amino acid sequence of SEQ ID NO: 471.

In some embodiments, the bi- or multi-specific antibody specifically binds to TRDV1 and MSLN and comprises:

a TRDV1 binding component comprising a VH comprising or consisting of the amino acid sequence of SEQ ID NO: 15 and a VL comprising or consisting of the amino acid sequence of SEQ ID NO: 40; and a MSLN binding component comprising a VH comprising or consisting of the amino acid sequence of SEQ ID NO: 464 and a VL comprising or consisting of the amino acid sequence of SEQ ID NO: 465.

In some embodiments, the bi- or multi-specific antibody specifically binds to TRDV1 and MSLN and comprises:

a TRDV1 binding component comprising a VH comprising or consisting of the amino acid sequence of SEQ ID NO: 15 and a VL comprising or consisting of the amino acid sequence of SEQ ID NO: 40; and a MSLN binding component comprising SEQ ID NO: 404

In some embodiments, the bi- or multi-specific antibody specifically binds to TRDV1 and MSLN and comprises SEQ ID NO: 414 and SEQ ID NO: 416. In some embodiments the antibody specifically binds to TRDV1 and MSLN and comprises SEQ ID NO: 504 and SEQ ID NO: 416. In some embodiments the antibody specifically binds to TRDV1 and MSLN and comprises SEQ ID NO: 505 and SEQ ID NO: 416.

In various embodiments, the second target epitope is an epitope of a immunomodulator antigen. Immunomodulator antigens are antigens that modulate (activate or suppress) the immune system. In some embodiments, the immunomodulator antigen is a cell-surface protein (i.e. an antigen expressed on the surface of a cell, in particular an antigen expressed on the surface of an immune cell, such as lymphocytes, neutrophils, monocytes or macrophages). The immunomodulator antigen may be expressed on a Vδ1+ T-cell or may be expressed by a different cell, for example a CD4+ cell, a CD8+ cell, or a different immune cell. The immunomodulatory antigen may be selected from the group consisting of B7-1 (CD80), B7-2 (CD86), B7-DC (CD273), B7-H1 (CD274), B7-H2 (CD275), B7-H3 (CD276), B7-H4 (VTCN1), B7-H5 (VISTA), BTLA (CD272), 4-1BB (CD137), CD137L, CD24, CD27, CD28, CD38, CD40, CD40L (CD154), CD54, CD59, CD70, CTLA4 (CD152), CXCL9, GITR (CD357), HVEM (CD270), ICAM-1 (CD54), ICOS (CD278), LAG-3 (CD223), OX40 (CD134), OX40L (CD252), PD-1 (CD279), PD-L1 (CD274), TIGIT, CD314, CD334, CD335, CD337, and TIM-3 (CD366).

In some embodiments, the second target epitope is an epitope of a stimulatory immune checkpoint molecule. For example, in some embodiments the second target epitope is OX40 (CD134). OX40 is an immunomodulator antigen and an example of a member of the TNFR superfamily (TNFRSF). In some embodiments the second target epitope is an epitope present on a TNFRSF molecule. These proteins are a superfamily of cytokine receptors characterized by the ability to bind tumor necrosis factors (TNFs) via an extracellular cysteine-rich domain. Examples include CD18, CD27, CD30, CD40, CD95, CD120a, CD120b, CD134, CD137, CD265, CD268, CD269, CD270, CD271, CD357 and CD358. One such example OX40 (CD134) is a late-co-stimulatory immune checkpoint receptor expressed on CD4+ and CD8+ T-cells. OX40 is more highly expressed on CD4+ T cells and is not constitutively expressed on naïve T-cells as expression of OX40 is dependent on full activation of the T-cell. When activated (e.g. by OX40L). OX40 promotes CD4+/CD8+ T-cell activation, survival and expansion of effector and memory T-cells, as well as supressing Treg activity. This supresses immune evasion by the tumour. As OX40 is a stimulatory target, therapies which target OX40 activate OX40 expressing immune cells to stimulate immune response (e.g. a CD48+ T-cell response) against the tumour. Monoclonal antibodies that specifically bind to epitopes of OX40 are well known in the art. For example, pogalizumab is a monoclonal antibody which binds specifically to an epitope of OX40.

In some embodiments, the bi- or multi-specific antibody comprises a OX40-binding component comprising a heavy chain variable region comprising a VHCDR1 comprising the amino acid sequence of SEQ ID NO: 490, a VHCDR2 comprising the amino acid sequence of SEQ ID NO: 491 and a VHCDR3 comprising the amino acid sequence of SEQ ID NO: 492; and a light chain variable region comprising a VLCDR1 comprising the amino acid sequence of SEQ ID NO: 493, a VLCDR2 comprising the amino acid sequence of SEQ ID NO: 494 and a VLCDR3 comprising the amino acid sequence of SEQ ID NO: 495. In some embodiments, the bi- or multi-specific antibody comprises an OX40-binding component comprising a VH comprising or consisting of the amino acid sequence of SEQ ID NO: 488 and a VL comprising or consisting of the amino acid sequence of SEQ ID NO: 489. In some embodiments, the bi- or multi-specific antibody specifically binds to OX40 and comprises SEQ ID NO: 410.

Such sequences may be combined with any suitable anti-TRDV1 binding sequences. For example, in some embodiments, the bi- or multi-specific antibody specifically binds to TRDV1 and OX40 and comprises:

a TRDV1 binding component comprising a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 68; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 95; and an OX40 binding component comprising a heavy chain variable region comprising a VHCDR1 comprising the amino acid sequence of SEQ ID NO: 490, a VHCDR2 comprising the amino acid sequence of SEQ ID NO: 491 and a VHCDR3 comprising the amino acid sequence of SEQ ID NO: 492; and a light chain variable region comprising a VLCDR1 comprising the amino acid sequence of SEQ ID NO: 493, a VLCDR2 comprising the amino acid sequence of SEQ ID NO: 494 and a VLCDR3 comprising the amino acid sequence of SEQ ID NO: 495.

In some embodiments, the bi- or multi-specific antibody specifically binds to TRDV1 and OX40 and comprises:

a TRDV1 binding component comprising a VH comprising or consisting of the amino acid sequence of SEQ ID NO: 15 and a VL comprising or consisting of the amino acid sequence of SEQ ID NO: 40; and an OX40 binding component comprising a VH comprising or consisting of the amino acid sequence of SEQ ID NO: 488 and a VL comprising or consisting of the amino acid sequence of SEQ ID NO: 489.

In some embodiments, the bi- or multi-specific antibody specifically binds to TRDV1 and OX40 and comprises:

a TRDV1 binding component comprising a VH comprising or consisting of the amino acid sequence of SEQ ID NO: 15 and a VL comprising or consisting of the amino acid sequence of SEQ ID NO: 40; and an OX40 binding component comprising SEQ ID NO: 410.

In some embodiments, the bi- or multi-specific antibody specifically binds to TRDV1 and OX40 and comprises SEQ ID NO: 414 and SEQ ID NO: 419. In some embodiments the antibody specifically binds to TRDV1 and OX40 and comprises SEQ ID NO: 504 and SEQ ID NO: 419. In some embodiments the antibody specifically binds to TRDV1 and OX40 and comprises SEQ ID NO: 505 and SEQ ID NO: 419.

In some embodiments, the second target epitope is an epitope present on a TNF superfamily member. For example, in some embodiments the second target epitope is an epitope of 4-1BB (CD137). 4-1BB is an immunomodulator antigen and also an example of a member of the TNF superfamily. This is a protein superfamily of type II transmembrane proteins containing TNF homology domain which includes CD70, CD137, CD153, CD154, CD252, CD253, CD254, CD256, CD257, and CD258. 4-1BB (CD137) is an inducible, co-stimulatory immune checkpoint receptor expressed on T-cells, as well as NK cells, dendritic cells (DC), monocytes, neutrophils and B-cells. 4-1 BB is a stimulatory antigen and is particularly expressed on activated CD8+ T-cells. In vitro 4-1BB stimulates expansion of CD4+ T-cells, CD8+ T-cells, macrophages and DCs as well as cytokine production. In vivo 4-1BB is biased towards CD8+ T-cell activation and demonstrates strong anti-tumour activity, as crosslinking of 4-1 BB is shown to enhance T-cell proliferation, IL-2 secretion, survival and cytolytic activity. As 4-1 BB is a stimulatory target, therapies which target 4-1BB activate 4-1BB expressing immune cells to stimulate immune response (e.g. a cytolytic CD8+ T-cell response) against the tumour. Monoclonal antibodies that specifically bind to epitopes of 4-1BB are well known in the art. For example, utomilumab is a monoclonal antibody which binds specifically to an epitope of 4-1BB.

In some embodiments, the bi- or multi-specific antibody comprises a 4-1 BB-binding component comprising a heavy chain variable region comprising a VHCDR1 comprising the amino acid sequence of SEQ ID NO: 482, a VHCDR2 comprising the amino acid sequence of SEQ ID NO: 483 and a VHCDR3 comprising the amino acid sequence of SEQ ID NO: 484; and a light chain variable region comprising a VLCDR1 comprising the amino acid sequence of SEQ ID NO: 485, a VLCDR2 comprising the amino acid sequence of SEQ ID NO: 486 and a VLCDR3 comprising the amino acid sequence of SEQ ID NO: 487. In some embodiments, the bi- or multi-specific antibody comprises an 4-1BB-binding component comprising a VH comprising or consisting of the amino acid sequence of SEQ ID NO: 480 and a VL comprising or consisting of the amino acid sequence of SEQ ID NO: 481. In some embodiments, the bi- or multi-specific antibody specifically binds to 4-1BB and comprises SEQ ID NO: 408.

Such sequences may be combined with any suitable anti-TRDV1 binding sequences. For example, in some embodiments, the bi- or multi-specific antibody specifically binds to TRDV1 and 4-1BB and comprises:

a TRDV1 binding component comprising a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 68; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 95; and a 4-1BB binding component comprising a heavy chain variable region comprising a VHCDR1 comprising the amino acid sequence of SEQ ID NO: 482, a VHCDR2 comprising the amino acid sequence of SEQ ID NO: 483 and a VHCDR3 comprising the amino acid sequence of SEQ ID NO: 484; and a light chain variable region comprising a VLCDR1 comprising the amino acid sequence of SEQ ID NO: 485, a VLCDR2 comprising the amino acid sequence of SEQ ID NO: 486 and a VLCDR3 comprising the amino acid sequence of SEQ ID NO: 487.

In some embodiments, the bi- or multi-specific antibody specifically binds to TRDV1 and 4-1BB and comprises:

a TRDV1 binding component comprising a VH comprising or consisting of the amino acid sequence of SEQ ID NO: 15 and a VL comprising or consisting of the amino acid sequence of SEQ ID NO: 40; and a 4-1BB binding component comprising a VH comprising or consisting of the amino acid sequence of SEQ ID NO: 480 and a VL comprising or consisting of the amino acid sequence of SEQ ID NO: 481.

In some embodiments, the bi- or multi-specific antibody specifically binds to TRDV1 and 4-1BB and comprises:

a TRDV1 binding component comprising a VH comprising or consisting of the amino acid sequence of SEQ ID NO: 15 and a VL comprising or consisting of the amino acid sequence of SEQ ID NO: 40; and a 4-1BB binding component comprising SEQ ID NO: 408

In some embodiments, the bi- or multi-specific antibody specifically binds to TRDV1 and 4-1BB and comprises SEQ ID NO: 414 and SEQ ID NO: 418. In some embodiments the antibody specifically binds to TRDV1 and 4-1BB and comprises SEQ ID NO: 504 and SEQ ID NO: 418. In some embodiments the antibody specifically binds to TRDV1 and 4-1BB and comprises SEQ ID NO: 505 and SEQ ID NO: 418.

In some embodiments, the second target epitope is an immune checkpoint inhibitor molecule. For example, in some embodiments the second target epitope is TIGIT (T cell immunoreceptor with Ig and ITIM domains). TIGIT is an immunomodulator antigen and is an example of an immune checkpoint inhibitor expressed on T-cells, including γδ T cells, and NK cells. TIGIT plays a role in immune homeostasis and preventing autoimmunity by binding to its ligand (PVR/CD155) resulting in T-cell suppression. TIGIT is overexpressed on tumor infiltrated lymphocytes. Therapeutic blockade of TIGIT is desirable because it increases T-cell proliferation, cytokine productions and degranulation. Monoclonal antibodies that specifically bind to epitopes of TIGIT are well known in the art. For example, tiragolumab is a monoclonal antibody which binds specifically to an epitope of TIGIT.

In some embodiments, the bi- or multi-specific antibody comprises a TIGIT-binding component comprising a heavy chain variable region comprising a VHCDR1 comprising the amino acid sequence of SEQ ID NO: 498, a VHCDR2 comprising the amino acid sequence of SEQ ID NO: 499 and a VHCDR3 comprising the amino acid sequence of SEQ ID NO: 500; and a light chain variable region comprising a VLCDR1 comprising the amino acid sequence of SEQ ID NO: 501, a VLCDR2 comprising the amino acid sequence of SEQ ID NO: 502 and a VLCDR3 comprising the amino acid sequence of SEQ ID NO: 503. In some embodiments, the bi- or multi-specific antibody comprises an TIGIT-binding component comprising a VH comprising or consisting of the amino acid sequence of SEQ ID NO: 496 and a VL comprising or consisting of the amino acid sequence of SEQ ID NO: 497. In some embodiments, the bi- or multi-specific antibody specifically binds to TIGIT and comprises SEQ ID NO: 412.

Such sequences may be combined with any suitable anti-TRDV1 binding sequences. For example, in some embodiments, the bi- or multi-specific antibody specifically binds to TRDV1 and TIGIT and comprises:

a TRDV1 binding component comprising a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 68; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 95; and a TIGIT binding component comprising a heavy chain variable region comprising a VHCDR1 comprising the amino acid sequence of SEQ ID NO: 498, a VHCDR2 comprising the amino acid sequence of SEQ ID NO: 499 and a VHCDR3 comprising the amino acid sequence of SEQ ID NO: 500; and a light chain variable region comprising a VLCDR1 comprising the amino acid sequence of SEQ ID NO: 501, a VLCDR2 comprising the amino acid sequence of SEQ ID NO: 502 and a VLCDR3 comprising the amino acid sequence of SEQ ID NO: 503.

In some embodiments, the bi- or multi-specific antibody specifically binds to TRDV1 and TIGIT and comprises:

a TRDV1 binding component comprising a VH comprising or consisting of the amino acid sequence of SEQ ID NO: 15 and a VL comprising or consisting of the amino acid sequence of SEQ ID NO: 40; and a TIGIT binding component comprising a VH comprising or consisting of the amino acid sequence of SEQ ID NO: 496 and a VL comprising or consisting of the amino acid sequence of SEQ ID NO: 497.

In some embodiments, the bi- or multi-specific antibody specifically binds to TRDV1 and TIGIT and comprises:

a TRDV1 binding component comprising a VH comprising or consisting of the amino acid sequence of SEQ ID NO: 15 and a VL comprising or consisting of the amino acid sequence of SEQ ID NO: 40; and a TIGIT binding component comprising SEQ ID NO: 412

In some embodiments, the bi- or multi-specific antibody specifically binds to TRDV1 and TIGIT and comprises SEQ ID NO: 439 and SEQ ID NO: 420.

In some embodiments, the second target epitope is an immune checkpoint inhibitor molecule. For example, in some embodiments the second target epitope is PD-1 (programmed cell death protein 1). PD-1 is an immunomodulator antigen and an example of a cell surface receptor member of the immunoglobulin superfamily. PD-1 is an example of an immune checkpoint inhibitor expressed on activated CD4+/CD8+ T-cells, as well as other types of immune cells such as γδ T cells, B cells and macrophage. The binding of PD-1 to its ligands results in inhibition of T-cell activation. Under normal circumstances this plays a role in immune homeostasis—protecting against autoimmunity by decreasing apoptosis in Tregs and increase apoptosis of antigen-specific T-cells. In cancer settings this results in immune escape for tumor cells by inactivating cytolytic CD8+ T-cells. Blockade of PD-1 is therefore a promising therapeutic target. Monoclonal antibodies that specifically bind to epitopes of PD-1 are well known in the art. For example, pembrolizumab is a monoclonal antibody which binds specifically to an epitope of PD-1.

In some embodiments, the bi- or multi-specific antibody comprises a PD-1-binding component comprising a heavy chain variable region comprising a VHCDR1 comprising the amino acid sequence of SEQ ID NO: 474, a VHCDR2 comprising the amino acid sequence of SEQ ID NO: 475 and a VHCDR3 comprising the amino acid sequence of SEQ ID NO: 476; and a light chain variable region comprising a VLCDR1 comprising the amino acid sequence of SEQ ID NO: 477, a VLCDR2 comprising the amino acid sequence of SEQ ID NO: 478 and a VLCDR3 comprising the amino acid sequence of SEQ ID NO: 479. In some embodiments, the bi- or multi-specific antibody comprises an PD-1-binding component comprising a VH comprising or consisting of the amino acid sequence of SEQ ID NO: 472 and a VL comprising or consisting of the amino acid sequence of SEQ ID NO: 473. In some embodiments, the bi- or multi-specific antibody specifically binds to PD-1 and comprises SEQ ID NO: 406.

Such sequences may be combined with any suitable anti-TRDV1 binding sequences. For example, in some embodiments, the bi- or multi-specific antibody specifically binds to TRDV1 and PD-1 and comprises:

a TRDV1 binding component comprising a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 68; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 95; and a PD-1 binding component comprising a heavy chain variable region comprising a VHCDR1 comprising the amino acid sequence of SEQ ID NO: 474, a VHCDR2 comprising the amino acid sequence of SEQ ID NO: 475 and a VHCDR3 comprising the amino acid sequence of SEQ ID NO: 476; and a light chain variable region comprising a VLCDR1 comprising the amino acid sequence of SEQ ID NO: 477, a VLCDR2 comprising the amino acid sequence of SEQ ID NO: 478 and a VLCDR3 comprising the amino acid sequence of SEQ ID NO: 479.

In some embodiments, the bi- or multi-specific antibody specifically binds to TRDV1 and PD-1 and comprises:

a TRDV1 binding component comprising a VH comprising or consisting of the amino acid sequence of SEQ ID NO: 15 and a VL comprising or consisting of the amino acid sequence of SEQ ID NO: 40; and a PD-1 binding component comprising a VH comprising or consisting of the amino acid sequence of SEQ ID NO: 472 and a VL comprising or consisting of the amino acid sequence of SEQ ID NO: 473.

In some embodiments, the bi- or multi-specific antibody specifically binds to TRDV1 and PD-1 and comprises:

a TRDV1 binding component comprising a VH comprising or consisting of the amino acid sequence of SEQ ID NO: 15 and a VL comprising or consisting of the amino acid sequence of SEQ ID NO: 40; and a PD-1 binding component comprising SEQ ID NO: 406.

In some embodiments, the bi- or multi-specific antibody specifically binds to TRDV1 and PD-1 and comprises SEQ ID NO: 438 and SEQ ID NO: 417.

In some embodiments, the second target epitope is a stimulatory immune checkpoint molecule. Stimulatory immune checkpoint molecules include, for example, OX40, OX40L, 4-1BB (CD137), CD137L, CD27, CD70, CD28, GITR, ICOS, CD40 and CD40L. In some embodiments, the second target epitope is one or more selected from OX40, OX40L, 4-1BB (CD137), CD137L, CD27, CD70, CD28, GITR, ICOS, CD40 and CD40L. In some embodiments, the second target epitope is one or more selected from OX40 and 4-1BB.

In some embodiments, the second target epitope is an immune checkpoint inhibitor molecule. Immune checkpoint inhibitor molecules include, for example, TIGIT, CD155, PD-1, PD-L1, CTLA-4, B7-H3, B7-H4, BTLA, LAG-3, VISTA and TIM-3. In some embodiments, the second target epitope is one or more selected from TIGIT, CD155, PD-1, PD-L1, CTLA-4, B7-H3, B7-H4, BTLA, LAG-3, VISTA and TIM-3. In some embodiments, the second target epitope is one or more selected from TIGIT and PD-1.

References herein to an antigen being "on" a cell refer to antigens that are expressed on the cell surface membrane or are associated with the (extracellular side of) the cell surface membrane of such cells.

In various embodiments, the second target epitope is an epitope of a cluster of differentiation CD antigen. The cluster of differentiation (CD) nomenclature is a unifying system by which cell surface molecules are identified and named. Typically, cell surface proteins are not assigned a CD number until at least two monoclonal antibodies have been raised against said cell surface proteins. As such this system ensures all cell surface proteins assigned a CD number are tractable to being recognized and bound by specific monoclonal antibodies or fragment thereof. In various embodiments, the CD antigen is one selected from CD1a, CD1b, CD1c, CD1d, CD1e, CD2, CD3, CD3d, CD3e, CD3g, CD4, CD5, CD6, CD7, CD8, CD8a, CD8b, CD9, CD10, CD11 a, CD11 b, CD11c, CD11d, CD13, CD14, CD15, CD16, CD16a, CD16b, CD17, CD18, CD19, CD20, CD21, CD22, CD23, CD24, CD25, CD26, CD27, CD28, CD29, CD30, CD31, CD32A, CD32B, CD33, CD34, CD35, CD36, CD37, CD38, CD39, CD40, CD41, CD42, CD42a, CD42b, CD42c, CD42d, CD43, CD44, CD45, CD46, CD47, CD48, CD49a, CD49b, CD49c, CD49d, CD49e, CD49f, CD50, CD51, CD52, CD53, CD54, CD55, CD56, CD57, CD58, CD59, CD60a, CD60b, CD60c, CD61, CD62E, CD62L, CD62P, CD63, CD64a, CD65, CD65s, CD66a, CD66b, CD66c, CD66d, CD66e, CD66f, CD68, CD69, CD70, CD71, CD72, CD73, CD74, CD75, CD75s, CD77, CD79A, CD79B, CD80, CD81, CD82, CD83, CD84, CD85A, CD85B, CD85C, CD85D, CD85F, CD85G, CD85H, CD85I, CD85J, CD85K, CD85M, CD86, CD87, CD88, CD89, CD90, CD91, CD92, CD93, CD94, CD95, CD96, CD97, CD98, CD99, CD100, CD101, CD102, CD103, CD104, CD105, CD106, CD107, CD107a, CD107b, CD108, CD109, CD110, CD111, CD112, CD113, CD114, CD115, CD116, CD117, CD118, CD119, CD120, CD120a, CD120b, CD121a, CD121b, CD122, CD123, CD124, CD125, CD126, CD127, CD129, CD130, CD131, CD132, CD133, CD134, CD135, CD136, CD137, CD138, CD139, CD140A, CD140B, CD141, CD142, CD143, CD144, CDw145, CD146, CD147, CD148, CD150, CD151, CD152, CD153, CD154, CD155, CD156, CD156a, CD156b, CD156c, CD157, CD158, CD158A, CD158B1, CD158B2, CD158C, CD158D, CD158E1, CD158E2, CD158F1, CD158F2, CD158G, CD158H, CD158I, CD158J, CD158K, CD159a, CD159c, CD160, CD161, CD162, CD163, CD164, CD165, CD166, CD167a, CD167b, CD168, CD169, CD170, CD171, CD172a, CD172b, CD172g, CD173, CD174, CD175, CD175s, CD176, CD177, CD178, CD179a, CD179b, CD180, CD181, CD182, CD183, CD184, CD185, CD186, CD187, CD188, CD189, CD190, CD191, CD192, CD193, CD194, CD195, CD196, CD197, CDw198, CDw199, CD200, CD201, CD202b, CD203c, CD204, CD205, CD206, CD207, CD208, CD209, CD210, CDw210a, CDw210b, CD211, CD212, CD213a1, CD213a2, CD214, CD215, CD216, CD217, CD218a, CD218b, CD219, CD220, CD221, CD222, CD223, CD224, CD225, CD226, CD227, CD228, CD229, CD230, CD231, CD232, CD233, CD234, CD235a, CD235b, CD236, CD237, CD238, CD239, CD240CE, CD240D, CD241, CD242, CD243, CD244, CD245, CD246, CD247, CD248, CD249, CD250, CD251, CD252, CD253, CD254, CD255, CD256, CD257, CD258, CD259, CD260, CD261, CD262, CD263, CD264, CD265, CD266, CD267, CD268, CD269, CD270, CD271, CD272, CD273, CD274, CD275, CD276, CD277, CD278, CD279, CD280, CD281, CD282, CD283, CD284, CD285, CD286, CD287, CD288, CD289, CD290, CD291, CD292, CDw293, CD294, CD295, CD296, CD297, CD298, CD299, CD300A, CD300C, CD301, CD302, CD303, CD304, CD305, CD306, CD307, CD307a, CD307b, CD307c, CD307d, CD307e, CD308, CD309, CD310, CD311, CD312, CD313, CD314, CD315, CD316, CD317, CD318, CD319, CD320, CD321, CD322, CD323, CD324, CD325, CD326, CD327, CD328, CD329, CD330, CD331, CD332, CD333, CD334, CD335, CD336, CD337, CD338, CD339, CD340, CD344, CD349, CD351, CD352, CD353, CD354, CD355, CD357, CD358, CD360, CD361, CD362, CD363, CD364, CD365, CD366, CD367, CD368, CD369, CD370, and CD371.

Healthy Cell Sparing

While the mechanisms by which γδ T-cells recognize antigens and distinguish between healthy and diseased cells are not fully understood (Ming Heng and Madalene Heng, Antigen Recognition by γδ T-Cells. Madame Curie Bioscience Database [Internet], Austin (Tex.): Landes Bioscience; 2000-2013), the fact that γδ T-cells are able to distinguish between healthy cells and diseased cells and exhibit remarkable diseased cell polycytotoxicity (see non-limiting example cell types in Table 6) this means that they can be leveraged to provide improved medicaments with improved therapeutic windows. Further, by leveraging such γδ T-cell capabilities, there is provided an opportunity to treat disease while sparing healthy cells, by colocalizing γδ T-cells with diseased cells even when a particular cancer antigen, inflammatory antigen, or pathogen antigen is either not known, or is also present on healthy cells, in a particular patient.

TABLE 6

| Example cancer cells killed by polycytotoxic human Vδ1+ cells | |
|---|---|
| Breast Cancer | |
| M-CSF7, T47D, MDA-MB-231 | Mahvi et al (1993) Cancer Imm. Immunother. (1993) 37: 181-186<br>Dutta I et al (2017). Front. Immunol. 8: 776 |

TABLE 6-continued

| Example cancer cells killed by polycytotoxic human Vδ1+ cells | |
|---|---|
| Lung Cancer | |
| GLC1, N592 | Ferrarini et al (1996) Jn of Nat. Cancer Inst., Volume 88 (7) pp 436-441 |
| Pancreas Cancer | |
| panc89, QGP-1, PANC-1 | Maeurer et al (1996) JEM 183 (4) 1681-1696 Kitayama 1993 Clin Exp Imm 93 (3) 442-7 |
| Gastrointestinal Cancer | |
| HT29, HCT116, Y, SKCO1, Caco2, HCT116, Lovo, DLD-1, SW480 | Wu, et al. (2015), OncoImmunology, 4: 3, e992749 Mikulak, et al (2019) JCI Insight. 4(24): e125884 Groh et al (1999) PNAS 96 (12) 6879-6884 |
| Neuroblastoma | |
| LAN1, KELLY | Fisher et al (2014) Clin Cancer Res; 20(22); 5720-32 |
| Melanoma | |
| A375 | Cordova (2012) Plos ONE 7 (11) e49878 |
| Ovarian Cancer | |
| OV-1063, SW626 | Groh et al (1999) PNAS 96 (12) 6879-6884 |
| Liver Cancer | |
| HepG2 | Groh et al (1999) PNAS 96 (12) 6879-6884 |
| Cervical Cancer | |
| HeLa | Groh et al (1999) PNAS 96 (12) 6879-6884 |
| Prostate Cancer | |
| DV145, PC-3 | Groh et al (1999) PNAS 96 (12) 6879-6884 |
| Multiple Myeloma | |
| ARH77, U266 | Knight et al (2012) Cytotherapy, 14: 9, 1110-1118, |
| AML | |
| KG-1, KASUMI-1, OCI-AML3, U937, HL60, MV4 11, AML193, HEL, THP-1 | Lorenzo et al (2019) Canc Imm Res 7 (4) |
| CLL | |
| MEC-1 | Almeida et al (2016) Clin Can Res 22 (23) |

By way of one non-limiting example, recent studies with CD3×HER2 multi-specifics highlight the challenges of current or conventional approaches. Specifically, use of such conventional approaches can result in less favorable toxicity profiles. This is because like many other tumour associated antigens (TAAs), the HER2 antigen is not only expressed in cancers such as breast cancer but is also expressed on healthy tissues such as heart cells. Hence use of CD3×HER2 medicaments which engage and co-localize all T-cells with HER2 positive cells can result in less favorable therapy windows or therapeutic indices. This is because such medicaments will engage all T-cells of which the vast majority in circulation will be αβ T-cells (CD4+ positive, CD8+ positive etc.). And once αβ T-cells are co-localized with HER2 positive cells, such conventional αβ T-cells exhibit limited capabilities to spare HER2+ healthy cells and limited capabilities to kill only diseased HER2+ diseased cells. Consequently, and by way of this example, in cynomolgus studies whereby such CD3×HER2 bispecifics were administered, early euthanasia (even on the day of dosing) was required in some situations. Further, during this example study (see Staflin et al. (2020) JCI Insight 5(7): e133757) it was concluded that retargeting T cells to kill HER2-expressing cells may induce adverse effects on HER2-expressing tissues. It was noted that with exception of the liver, all affected or damaged tissues expressed HER2.

In a further non-limiting example, a second binding specificity may be to a tumour associated moiety also involved in controlling or regulating immune cell function. For example, the second specificity may be designed to target a so-called "checkpoint inhibitor" such as PD-L1 (CD274) or CD155. Once again, neither PDL-1 and CD155 are 100% disease specific. Both proteins can also be expressed on healthy cells. However, multi-specific antibodies designed to specifically co-localize Vδ1+ cells to either PD-L1 positive cells or CD155 positive cells may result in the selective killing PD-L1 or CD155 positive diseased or cancerous cells. Further targeting diseased-associated checkpoint inhibitors present on diseased cells such as cancer cells will not only co-localize Vδ1+ cells to such tumours but may also confer additional favourable effects, for example by modulating or dampening PD-1/PD-L1 or TIGIT/CD155 signalling which otherwise may negatively regulate T cell-mediated immune responses to the disease.

Hence instead of employing such conventional approaches, provided herein are multi-specific antibodies wherein at least one first binding domain is able to specifically bind Vδ1+ cells and at least one second binding domain is able to specifically bind targets present on diseased tissues and cells. The use of such multi-specific antibodies in this way may thereby result in the co-localization of Vδ1+ cells to diseased cells expressing the second target. Further, and given such disease associated targets are not often 100% disease specific, this approach of targeting and co-localizing Vδ1+ effector cells specifically, may be more preferred over conventional approaches. This is because Vδ1+ effector cells may be capable of recognizing stress patterns in diseased or infected cells and so able to selectively kill diseased cells whilst sparing healthy cells also expressing the same target.

The multispecific antibodies presented herein are therefore able to engage on the TCR of vδ1 cells but full activation does not occur unless tumour cells are also present. Full engagement of the presently presented antibodies on the TCR leads to partial downregulation and it is believed the vδ1 cells bound by the presently presented antibodies only become fully activated and become cytotoxic when in the presence of stressed cells such as tumour cells. This is shown, for example, in FIG. 50, I, J, K and FIG. 63A-F). This represents another vital safety advantage for the approach presented herein, since off target cytotoxicity is reduced and the full potency of the multispecific antibodies to activate vδ1 cells is only unleashed in the presence of tumour cells, meaning healthy cells (even healthy cells expressing the second target antigen of the multispecific antibody) are spared.

One mechanism behind γδ T cells being able to detect stress signals on tumour cells is believed to be due to the NCRs (natural cytotoxicity receptors) they express. The NCRs are able to engage NCR ligands on tumour cells. A dual mechanism of activation may therefore be employed, wherein the γδ T cells are activated via TCR stimulation, including via NCRs, which can sense the tumour cells to enable full activation and cytotoxicity.

This contrasts with stimulation of αß T cells via CD3, for example, wherein all stimulation is via the TCR. Such cells are therefore almost indiscriminate between healthy or transformed cells because they do not have mechanisms such as antigen presentation independent sensing of tumour cells, for example via NCRs. Therefore, if CD3 antibodies are Fc enabled they will attract other immune cells which can trigger a cascade of unpredictable and desirable events such as cytokine storms, exhaustion and even overactivation of immune cells leading to, for example, NK cells killing T cells etc. In the present approach, stimulation of γδ T cells with the presently presented multispecific antibodies do not lead to such concerns because γδ T cells are able to distinguish between healthy cells and tumour cells, including via their NCR sensing mechanism and therefore selectively kill stressed cells such as cancer cells or virally infected cells due to this diseased cell specificity In a further non-limiting example, a patient may have liver cancer, where no liver cancer specific antigen is known in the patient. In this instance, the second specificity of the multi-specific antibody can be to an epitope present on many or all liver cells, such as, for example, asialoglycoprotein receptor 1. This will then colocalize the γδ T-cells to the liver, where the γδ T-cells can kill the liver cancer cells, while sparing the healthy liver cells. This is shown, for example, in FIG. 50, I, J, K and FIG. 63, A-F. By way of a third non-limiting example, in a patient that has lung cancer, where no lung cancer antigen is known in the patient, the second specificity of the multi-specific antibody can be to an epitope on a normal lung cell, such as, for example, SP-1. This will colocalize the γδ T-cells to the lung, where the γδ T-cells can kill the lung cancer cells, while sparing the healthy lung cells. By way of a fourth non-limiting example, in a patient that has B cell lymphoma, where no B cell lymphoma antigen is known in the patient, the second specificity of the multi-specific antibody can be to an epitope on normal B cells, such as, for example, CD19. This will colocalize the γδ T-cells to B cells, where the γδ T-cells can kill the lymphoma cells, while sparing healthy B cells. Cell-specific antigens, cell-associated antigens, tissue-specific antigens, and tissue-associated antigens are well known in the art and any such antigen can be targeted by the second specificity of the multi-specific antibodies of the invention.

The second binding specificity may target an antigen on the same cell as Vδ1 or on a different cell of the same tissue type or of a different tissue type. In certain embodiments, the target epitope may be on a different cell including a different T-cell, a B-cell, a tumour cell, an autoimmune tissue cell or a virally infected cell. Alternatively, the target epitope may be on the same cell.

The multi-specific antibodies, or antigen-binding fragments thereof, can be made in any format, so long as the antibody, or antigen-binding fragment thereof, has multiple specificities. Examples of multi-specific antibody formats include, but are not limited to, CrossMab, DAF (two-in-one), DAF (four-in-one), DutaMab, DT-IgG, Knobs-in-holes (KIH), Knobs-in-holes (common light chain), Charge pair, Fab-arm exchange, SEEDbody, Triomab, LUZ-Y, Fcab, KA-body, orthogonal Fab, DVD-IgG, IgG(H)-scFv, scFv-(H)IgG, IgG(L)-scFv, scFv-(L)IgG, IgG(L,H)-Fv, IgG (H)-V, V(H)—IgG, IgG(L)-V, V(L)-IgG, KIH IgG-scFab, 2scFv-IgG, IgG-2scFv, scFv4-Ig, Zybody, DVI-IgG(four-in-one), Nanobody, Nanoby-HAS, BiTE, Diabody, DART, TandAb, scDiabody, scDiabody-CH3, Diabody-CH3, Triple Body, Morrison formats, Miniantibody, Minibody, TriBi minibody, scFv-CH3 KIH, Fab-scFv, scFv-CH-CL-scFv, F(ab')2, F(ab)2-scFv2, scFv-KIH, Fab-scFv-Fc, Tetravalent HCAb, scDiabody-Fc, Diabody-Fc, Tandem scFv-Fc, Intrabody, Dock and Lock, ImmTAC, HSAbody, scDiabody-HAS, Tandem scFv-Toxin, IgG-IgG, ov-X-Body, duobody, $mab^2$ and scFv1-PEG-scFv2 (see Spiess et al. (2015) Molecular Immunology 67:95-106).

An antibody or antigen-binding fragment thereof as described herein may also be assessed by measuring its capacity for enhanced functionality in a multi-specific format such as a bispecific or trispecific format. Surprisingly through such studies it is possible to identify yet further functional improvements in the performance of the antibodies or antigen-binding fragments thereof as described herein.

Various antibody-derived multi-specific formats have been described previously and are typically built empirically from the component binding parts. Typically, once constructed, the performance of such multi-specific or multi-target binding formats as described herein may be measured in one or more of the aforementioned model systems (cell killing, cell proliferation, healthy cell sparing/diseased cell specific models etc). Optionally they are also compared to said component parts and other comparator molecules.

Whilst not being limited by this approach, in general when constructing antibodies as multi-specific antibodies, the binding domain modules to each target (first, second, third etc) are optional built from scFv, Fab, Fab', F(ab')2, Fv, variable domain (e.g. VH or VL), diabody, minibody or full length antibodies. For example, each said binding domain or module is created in one or more of the following non-limiting formats wherein binding domains comprising variable domains, and/or full length antibodies, and/or antibody fragments, are operatively linked in series to generate multi-specific antibodies.

Remarkably, multi-specific antibodies comprising at least one (first) binding domain targeting the Vδ1 chain of a γδ TCR as described herein are further enhanced when said first binding domain is formatted with a multi-specific antibody format comprising at least one second binding domain against either tissue ("solid") and haemopoietic ("liquid") disease or cell-type associated targets.

Multi-Specific Antibodies—Non-Limiting Examples:

To outline the applicability of the approach a series of non-limiting example multi-specific antibodies were constructed. These multi-specific antibodies comprised at least one (first) binding domain targeting the Vol chain of a γδ TCR and at least one (second) binding domain targeting a disease associated target:

A First Example; Vδ1-EGFR Multi-Specific Antibody

For this example, one binding domain (to the first target) comprised intact antibody moieties; specifically, VH-CH1-CH2-CH3 and cognate VL-CL partners, whilst the second binding domain (to the second target) comprised an antibody fragment; specifically, a scFv format. The two binding modules were then fused with aid of a linker. The resulting bispecific format is sometimes termed a 'Morrison format'. In this instance a first binding domain targets the Vδ1 chain of a γδ TCR and a second binding domain targets EGFR (see Example 20).

A Second Example; Vδ1-EGFR Multi-Specific Antibody

For this example, one binding domain (to the first target) comprised an antibody variable domain (specifically comprising a VH and cognate VL domain) whilst the second binding domain (to the second target) comprises a binding domain within a heavy chain constant domain (CH1-CH2-CH3) (see also EP2546268 A1 Table 1/EP3487885 A1). The resulting bispecific comprises a first binding domain targeting the Vδ1 chain of a γδ TCR and a second binding domain targeting EGF receptor (see Example 20).

A Third Example; Vδ1-CD19 Multi-Specific Antibody

For this example, one binding domain (to the first target) comprised intact antibody moieties specifically, VH-CH1-

CH2-CH3 and cognate VL-CL partners, whilst the second binding domain (to the second target) comprised an antibody fragment; specifically, a scFv format. The two binding modules were then fused with aid of a linker. For this example, the resulting bispecific comprised a first binding domain targeting the Vδ1 chain of a γδ TCR and a second binding domain targeting CD19 (see Example 21).

A Fourth Example; a Further Vδ1-CD19 Multi-Specific Antibody

For this example, an additional multi-specific antibody specifically binding to both TRDV1 and CD19 was prepared and tested for antigen binding (including both human and cyno-TRDV1), Vδ1-cell activation and Vδ1-cell cytotoxicity. The example was prepared based on ADT1-4-2, see Examples 26 and 27.

A Fifth Example; a Vδ1-Her2 Multi-Specific Antibody

For this example, a multi-specific antibody specifically binding to both TRDV1 and Her2 was prepared and tested for antigen binding, Vδ1-cell activation and Vδ1-cell cytotoxicity. The example was prepared based on ADT1-4-2, see Example 28.

A Sixth Example; a Further Vδ1-EGFR Multi-Specific Antibody

For this example, an additional multi-specific antibody specifically binding to both TRDV1 and EGFR was prepared and tested for antigen binding, Vδ1-cell activation and Vδ1-cell cytotoxicity. The example was prepared based on ADT1-4-2, see Examples 29 and 30.

A Seventh Example; a Vδ1-FAPα Multi-Specific Antibody

For this example, one binding domain (to the first target) comprised intact antibody moieties specifically, VH-CH1-CH2-CH3 and cognate VL-CL partners, whilst the second binding domain (to the second target) comprised an antibody fragment; specifically, a scFv format. The two binding modules were then fused with aid of a linker. For this example, the resulting bispecific comprised a first binding domain targeting the Vol chain of a γδ TCR and a second binding domain targeting FAPα (see Example 33).

An Eighth Example; a Vδ1-Mesothelin Multi-Specific Antibody

For this example, one binding domain (to the first target) comprised intact antibody moieties specifically, VH-CH1-CH2-CH3 and cognate VL-CL partners, whilst the second binding domain (to the second target) comprised an antibody fragment; specifically, a scFv format. The two binding modules were then fused with aid of a linker. For this example, the resulting bispecific comprised a first binding domain targeting the Vol chain of a γδ TCR and a second binding domain targeting mesothelin (see Example 34).

A Ninth Example; a Vδ1-PD-1 Multi-Specific Antibody

For this example, one binding domain (to the second target) comprised intact antibody moieties specifically, VH-CH1-CH2-CH3 and cognate VL-CL partners, whilst the second binding domain (to the first target) comprised an antibody fragment; specifically, a scFv format. The two binding modules were then fused with aid of a linker. For this example, the resulting bispecific comprised a first binding domain targeting PD-1 and a second binding domain targeting the Vδ1 chain of a γδ TCR (see Example 35).

A Tenth Example; a Vδ1-4-1BB Multi-Specific Antibody

For this example, one binding domain (to the first target) comprised intact antibody moieties specifically, VH-CH1-CH2-CH3 and cognate VL-CL partners, whilst the second binding domain (to the second target) comprised an antibody fragment; specifically, a scFv format. The two binding modules were then fused with aid of a linker. For this example, the resulting bispecific comprised a first binding domain targeting the Vδ1 chain of a γδ TCR and a second binding domain targeting 4-1BB (see Example 36).

An Eleventh Example; a Vδ1-OX40 Multi-Specific Antibody

For this example, one binding domain (to the first target) comprised intact antibody moieties specifically, VH-CH1-CH2-CH3 and cognate VL-CL partners, whilst the second binding domain (to the second target) comprised an antibody fragment; specifically, a scFv format. The two binding modules were then fused with aid of a linker. For this example, the resulting bispecific comprised a first binding domain targeting the Vδ1 chain of a γδ TCR and a second binding domain targeting OX40 (see Example 34).

A Twelfth Example; a Vδ1-TIGIT Multi-Specific Antibody

For this example, one binding domain (to the second target) comprised intact antibody moieties specifically, VH-CH1-CH2-CH3 and cognate VL-CL partners, whilst the second binding domain (to the first target) comprised an antibody fragment; specifically, a scFv format. The two binding modules were then fused with aid of a linker. For this example, the resulting bispecific comprised a first binding domain targeting TIGIT and a second binding domain targeting the Vδ1 chain of a γδ TCR (see Example 38).

Remarkably in all said examples comprising at least one (first) binding domain targeting the Vδ1 chain of a γδ TCR at least one second domain targeting a second epitope enhanced functionality was observed versus the controls and component parts (see Examples 20, 21 and 26 to 38 herein).

Collectively, these non-limiting examples highlight the flexibility of the multispecific antibodies or antigen-binding fragments thereof as described herein. These non-limiting examples outline that multi-specific antibody approach wherein antibodies of fragments thereof targeting the germline Vδ1 chain (amino acids 1-90 of e.g. SEQ ID NO: 272) may be further enhanced by combining with second binding domains to form multi-specific antibodies. By way of non-limiting examples, multi-specific antibodies are provided herein with enhanced functionality and which contain binding domains comprising intact antibodies (VH-CH1-CH2-CH3 and VL-CL), and/or variable domains (VH and cognate VL or VH-CH1 and cognate VL-CL), and/or antibody fragments (scFv).

In one embodiment multi-specific antibody binding domains which target Vδ1 chain of a γδ TCR (the first target)

may comprise (i) one or two or more antibody binding domains each comprising a heavy chain (VH-CH1-CH2-CH3) and a cognate light chain partner (VL-CL) and/or (ii) one or two or more antibody binding domains each comprising a heavy chain variable domain (VH, or VH-CH1) and a cognate light chain variable domain partner (VL, or VL-VC) and/or (iii) one or two or more antibody binding domains each comprising a CDR-containing antibody fragment.

In one embodiment there is provided a multi-specific antibody comprising at least one first antibody-derived binding domain targeting the Vδ1 chain of a γδ TCR and which is operatively linked to at least one second antibody binding domain targeting a second epitope. Optionally, said binding domains comprise at least one or more VH and cognate VL binding domain, or one or more VH-CH1-CH2-CH3 and cognate VL-CL binding domain, or one or more antibody fragment binding domains. Optionally, said second binding domain targets a second epitope associated with, or expressed on, the cell surface of a cell. Optionally, said second epitope is located on a cell surface polypeptide associated with a diseased cell or tumour cell or a virally infected cell or an autoimmune tissue cell. Optionally, said second epitope or epitopes are located on the disease and cell-type associated CD19, EGFR Her2, FAPα, mesothelin, PD-1, 4-1BB, OX40 or TIGIT antigens. Optionally, said multi-specific antibody comprising at least one first antibody-derived binding domain targeting the Vδ1 chain of a γδ TCR is operatively linked to a second binding domain binding the EGF receptor and comprising one or more of the following heavy chain modifications in accordance with EU numbering; L358T and/or T359D and/or K360D and/or N361G and/or Q362P and/or N384T and/or G385Y and/or Q386G and/or D413S and/or K414Y and/or S415W and/or Q418Y and or Q419K.

Optionally, a multi-specific antibody comprising at least one first antibody-derived binding domain targeting the Vδ1 chain of a γδ TCR is operatively linked to a second binding domain comprising SEQ ID NO: 385 or SEQ ID NO: 386 or SEQ ID NO: 387 or SEQ ID NO: 314 or SEQ ID or SEQ ID NO: 394 or SEQ ID NO: 395 or SEQ ID NO: 397 or SEQ ID NO: 402 or SEQ ID NO: 404 or SEQ ID NO: 406 or SEQ ID NO: 408 or SEQ ID NO: 410 or SEQ ID NO: 412 or functionally equivalent binding variants thereof and which target EGFR, CD19 Her2, FAPα, mesothelin, PD-1, 4-1 BB, OX40 or TIGIT. Optionally, multi-specific antibodies comprise SEQ ID NO: 388; or SEQ ID; or SEQ ID NO: 315; or SEQ ID NO: 316; or SEQ ID NO: 378; or SEQ ID NO: 379; or SEQ ID NO: 380; or SEQ ID NO: 382; or SEQ ID NO: 383; or SEQ ID NO: 384; or SEQ ID NO: 393; or SEQ ID NO: 396; or SEQ ID NO: 398; or SEQ ID NO: 399; or SEQ ID NO: 401; or SEQ ID NO: 403; or SEQ ID NO: 405; or SEQ ID NO: 407; or SEQ ID NO: 409; or SEQ ID NO: 411; or SEQ ID NO: 414 and SEQ ID NO: 415; or SEQ ID NO: 414 and SEQ ID NO: 416; or SEQ ID NO: 414 and SEQ ID NO: 419; or SEQ ID NO: 414 and SEQ ID NO: 418; or SEQ ID NO: 504 and SEQ ID NO: 415; or SEQ ID NO: 504 and SEQ ID NO: 416; or SEQ ID NO: 504 and SEQ ID NO: 419; or SEQ ID NO: 504 and SEQ ID NO: 418; or SEQ ID NO: 505 and SEQ ID NO: 415; or SEQ ID NO: 505 and SEQ ID NO: 416; or SEQ ID NO: 505 and SEQ ID NO: 419; or SEQ ID NO: 505 and SEQ ID NO: 418; or SEQ ID NO: 421 and SEQ ID NO: 422; or SEQ ID NO: 504 and SEQ ID NO: 422; or SEQ ID NO: 423 and SEQ ID NO: 424; or SEQ ID NO: 425 and SEQ ID NO: 426; or SEQ ID NO: 421 and SEQ ID NO: 437; or SEQ ID NO: 504 and SEQ ID NO: 437; or SEQ ID NO: 423 and SEQ ID NO: 427; or SEQ ID NO: 425 and SEQ ID NO: 428; or SEQ ID NO: 421 and SEQ ID NO: 429; or SEQ ID NO: 504 and SEQ ID NO: 429; or SEQ ID NO: 423 and SEQ ID NO: 430; or SEQ ID NO: 414 and SEQ ID NO: 431; or SEQ ID NO: 414 and SEQ ID NO: 433; or SEQ ID NO: 414 and SEQ ID NO: 434; or SEQ ID NO: 414 and SEQ ID NO: 435; or SEQ ID NO: 504 and SEQ ID NO: 431; or SEQ ID NO: 504 and SEQ ID NO: 433; or SEQ ID NO: 504 and SEQ ID NO: 434; or SEQ ID NO: 504 and SEQ ID NO: 435; or SEQ ID NO: 505 and SEQ ID NO: 431; or SEQ ID NO: 505 and SEQ ID NO: 433; or SEQ ID NO: 505 and SEQ ID NO: 434; or SEQ ID NO: 505 and SEQ ID NO: 435; or SEQ ID NO: 438 and SEQ ID NO: 417; or SEQ ID NO: 439 and SEQ ID NO: 420.

TABLE A

Summary of bispecific sequences

| SEQ ID NO: | Description |
|---|---|
| 314 | scFv anti-CD19 binding module |
| 315 | G04x Anti-CD19 multispecific (full length) |
| 316 | E07 × Anti-CD19 multispecific (full length) |
| 377 | Anti-Chick Lysozyme × FS1-67 Fcab (EGFR binding domain) |
| 378 | Parent C08 × FS1-67 (LAGA) |
| 379 | Parent G04 × FS1-67 (LAGA) |
| 380 | Parent E07 × FS1-67 (LAGA) |
| 381 | Anti-Chick Lysozyme × Cetuximab scFV |
| 382 | Parent C08 × Cetuximab scFV |
| 383 | Parent G04 × Cetuximab scFV |
| 384 | Parent E07 × Cetuximab scFV |
| 385 | IgG1 CH1-CH2-CH3 FS-167 Fcab |
| 386 | IgG1 CH1-CH2-CH3 FS-167 Fcab (LAGA) |
| 387 | scFV Cetuximab |
| 388 | ADT1-4-2 × FS1-67 EGFR (LAGA) |
| 390 | Folate receptor alpha |
| | ) |
| 393 | ADT1-4-2 HER2 (LAGA) |
| 394 | HER2 Binding module (LAGA) |
| 395 | HER2 Binding module (Ig WT) |
| 396 | ADT1-4-2xCD19 |
| 397 | CD19 Binding Module |
| 398 | ADT1-4-2 HER2 (wt IgG1) |
| 399 | ADT1-4-2 × FS1-67 EGFR (wt) |
| 401 | ADT1-4-2 × FAP alpha |
| 402 | anti-FAP alpha scFv binding module |
| 403 | ADT1-4-2 × MSLN |
| 404 | anti-MSLN scFv binding module |

TABLE A-continued

| Summary of bispecific sequences | |
|---|---|
| SEQ ID NO: | Description |
| 405 | PD-1xADT1-4-2 |
| 406 | Example anti-PD-1 binding module as scFV |
| 407 | ADT1-4-2x 4-1BB |
| 408 | anti-41 BB scFv binding module LC |
| 409 | ADT1-4-2xOX40 |
| 410 | anti-OX40 scFv binding module |
| 411 | TIGIT × ADT1-4-2 |
| 412 | Example anti-TIGIT scFv binding module as scFV |
| 413 | anti-VD1 scFv binding module |
| 414 | ADT1-4-2 LC |
| 415 | ADT1-4-2 HC + FAPa scFv |
| 416 | ADT1-4-2 HC + MSLN scFv |
| 417 | PD-1 HC + scFV ADT1-4-2 |
| 418 | ADT1-4-2 HC + 4-1 BB scFv |
| 419 | ADT1-4-2 HC + OX40 scFv |
| 420 | TIGIT HC + scFV ADT1-4-2 |
| 421 | G04 LC |
| 422 | G04 HC + CD19 scFv |
| 423 | E07 LC |
| 424 | E07 HC + CD19 scFv |
| 425 | C08 LC |
| 426 | C08 HC (LAGA) EGFR FS1-67 |
| 427 | E07 HC (LAGA) EGFR FS1-67 |
| 428 | C08 HC + EGFR scFv |
| 429 | G04 HC + EGFR scFv |
| 430 | E07 HC + EGFR scFv |
| 431 | ADT1-4-2 HC (LAGA) EGFR FS1-67 |
| 433 | ADT1-4-2 HC (LAGA) HER2 Fcab |
| 434 | ADT1-4-2 HC (wt) HER2 Fcab |
| 435 | ADT1-4-2 HC (wt) EGFR FS1-67 |
| 437 | G04 HC (LAGA) EGFR FS1-67 |
| 438 | PD-1 LC |
| 439 | TIGIT LC |
| 504 | ADT1-4 modified light chain (S74L) |
| 505 | ADT1-4-2 reverted light chain (L74S) |

In one aspect of the invention multi-specific antibodies of the invention can be used in therapeutically effective amounts to treat a disease or disorder such to ameliorate at least one sign or symptom of a disease or disorder.

In one embodiment, there is provided a method of selecting or characterizing or comparing antibodies or antigen-binding fragment thereof as described herein which bind to the Vδ1 chain of a γδ TCR in a multi-specific antibody format wherein said multi-specific antibody is applied to Vδ1+ cells in order to measure the conferred effect by said multi-specific entity Vδ1+ cells (e.g. upon said Vδ1+ phenotype and/or cytotoxicity and/or diseased-cell specificity and/or enhancement thereof).

Combinatorial Therapies

The anti-Vδ1 antibodies or antigen-binding fragments thereof of the invention may be used in certain combination therapies. In some embodiments, the anti-Vδ1 antibodies or antigen-binding fragments thereof may be combined with a modulator of a cancer antigen or a cancer-associated antigen, for example a modulator for a cancer antigen or a cancer-associated antigen listed above as possible candidates for multi-specific antibodies incorporating the anti-Vδ1 antibodies or antigen-binding fragments thereof of the invention. In some embodiments, the anti-Vδ1 antibodies or antigen-binding fragments thereof may be combined with a modulator of a cluster of differentiation CD antigen, for example a modulator of a CD antigen listed above as possible candidates for multi-specific antibodies incorporating the anti-Vδ1 antibodies or antigen-binding fragments thereof of the invention. In some embodiments, the modulators may be antagonistic or agonistic. Suitable modulators include antibodies, fusion proteins or small molecules.

Immunoconjugates

The antibodies or antigen-binding fragments thereof of the present invention may be conjugated to a therapeutic moiety, such as a cytotoxin or a chemotherapeutic agent. Such conjugates may be referred to as immunoconjugates. As used herein, the term "immunoconjugate" refers to an antibody which is chemically or biologically linked to another moiety, such as a cytotoxin, a radioactive agent, a cytokine, an interferon, a target or reporter moiety, an enzyme, a toxin, a peptide or protein or a therapeutic agent. The antibody may be linked to the cytotoxin, radioactive agent, cytokine, interferon, target or reporter moiety, enzyme, toxin, peptide or therapeutic agent at any location along the molecule so long as it is able to bind its target. Examples of immunoconjugates include antibody drug conjugates and antibody-toxin fusion proteins. In one embodiment, the agent may be a second different antibody to Vδ1. In certain embodiments, the antibody may be conjugated to an agent specific for a tumor cell or a virally infected cell. The type of therapeutic moiety that may be conjugated to the anti-Vδ1 antibody and will take into account the condition to be treated and the desired therapeutic effect to be achieved. In one embodiment, the agent may be a second antibody, or antigen-binding fragment thereof, that binds to a molecule other than Vδ1.

Methods of Affinity Maturation and Related Antibodies

The present invention also provides affinity matured anti-TCR delta variable 1 (anti-Vδ1) antibodies or antigen-binding fragments thereof.

For example, there is provided an anti-TCR delta variable 1 (anti-Vδ1) antibody or antigen-binding fragment thereof, wherein the anti-Vδ1 antibody or antigen-binding fragment thereof is an affinity matured variant of a parent anti-Vδ1 antibody or antigen-binding fragment thereof, wherein the parent anti-Vδ1 antibody or antigen-binding fragment thereof comprises a VH comprising the amino acid sequence of SEQ ID NO: 1 and a VL sequence comprising the amino acid sequence of SEQ ID NO: 26. In another embodiment, there is provided an anti-TCR delta variable 1 (anti-Vδ1) antibody or antigen-binding fragment thereof, wherein the anti-Vδ1 antibody or antigen-binding fragment thereof is an affinity matured variant of a parent anti-Vδ1 antibody or antigen-binding fragment thereof, wherein the parent anti-Vδ1 antibody or antigen-binding fragment thereof comprises a VH comprising the amino acid sequence of SEQ ID NO: 106 and a VL sequence comprising the amino acid sequence of SEQ ID NO: 118. There is also provided anti-TCR delta variable 1 (anti-Vδ1) antibody or antigen-binding fragment thereof, wherein the anti-Vδ1 antibody or antigen-binding fragment thereof is an affinity matured variant of a parent anti-Vδ1 antibody or antigen-binding fragment thereof, wherein the parent anti-Vδ1 antibody or antigen-binding fragment thereof comprises:

- a VH comprising the amino acid sequence of SEQ ID NO: 273 and a VL comprising the amino acid sequence of SEQ ID NO: 282;
- a VH comprising the amino acid sequence of SEQ ID NO: 274 and a VL comprising the amino acid sequence of SEQ ID NO: 283;
- a VH comprising the amino acid sequence of SEQ ID NO: 275 and a VL comprising the amino acid sequence of SEQ ID NO: 284;
- a VH comprising the amino acid sequence of SEQ ID NO: 276 and a VL comprising the amino acid sequence of SEQ ID NO: 285;
- a VH comprising the amino acid sequence of SEQ ID NO: 277 and a VL comprising the amino acid sequence of SEQ ID NO: 286;
- a VH comprising the amino acid sequence of SEQ ID NO: 278 and a VL comprising the amino acid sequence of SEQ ID NO: 287;
- a VH comprising the amino acid sequence of SEQ ID NO: 279 and a VL comprising the amino acid sequence of SEQ ID NO: 288;
- a VH comprising the amino acid sequence of SEQ ID NO: 280 and a VL comprising the amino acid sequence of SEQ ID NO: 289;
- a VH comprising the amino acid sequence of SEQ ID NO: 281 and a VL comprising the amino acid sequence of SEQ ID NO: 290; or
- a VH comprising the amino acid sequence of SEQ ID NO: 312 and a VL comprising the amino acid sequence of SEQ ID NO: 313.

Any known methods can be used to increase the affinity of the antibodies of the invention to generate affinity-matured antibodies or humanised affinity-matured antibodies with an increased affinity for Vol antibodies.

Suitably, the affinity matured variants bind to a variable delta 1 (Vδ1) chain of a γδ T cell receptor (TCR) with at least 20%, at least 30%, at least 40%, more preferably at least 50% greater affinity than the parental antibody, for example as measured by Kd.

In some embodiments the invention provides a method of preparing antibodies of the invention (or antigen-binding fragments thereof) comprising providing a parental antibody disclosed herein, and subjecting the antibody to affinity maturation, wherein the antibody produced binds to a variable delta 1 (Vδ1) chain of a γδ T cell receptor (TCR) with greater affinity than the parental antibody. Suitably the produced antibody binds to a variable delta 1 (Vδ1) chain of a γδ T cell receptor (TCR) with at least 20%, at least 30%, at least 40%, at least 50%, at least 100%, at least 500% or more preferably at least about 1000% greater affinity than the parental antibody binds to a variable delta 1 (Vδ1) chain of a γδ T cell receptor (TCR), for example as measured by the Kd. Methods for measuring affinity are known in the art and described in the Examples below. The affinity matured antibodies produced by such methods can be formulated and used as described herein for the other anti-Vδ1 antibodies and antigen-binding fragments of the invention.

Affinity maturation may be carried out according to any suitable method known to the skilled person. For example, in vitro antibody display systems are widely used for the generation of specific antibodies with high affinity. In these systems, the phenotype (i.e., the antibody fragment) is coupled to the genotype (i.e., the antibody gene) allowing the direct determination of the sequence of the antibody. Several systems have been developed to achieve display of antibody repertoires to allow subsequent selection of binders and by increasing the stringency of selection allows for the selection of higher and higher affinity variants. The antibody fragments can be expressed in yeast, ribosomes, phage display particles or by direct coupling to DNA.

Current antibody affinity maturation methods belong to two mutagenesis categories: stochastic and non-stochastic. Error-prone polymerase chain reaction (PCR), mutator bacterial strains, and saturation mutagenesis are typical examples of stochastic mutagenesis methods. Non-stochastic techniques often use alanine-scanning or site-directed mutagenesis to generate limited collections of specific variants. In addition, shuffling approaches to obtain shuffled variants of the parent antibody can also be used to improve antibodies' affinity further.

Accordingly, in one embodiment of the invention, the method of affinity maturation is selected from the group consisting of stochastic mutagenesis (for example error-prone polymerase chain reaction (PCR), mutator bacterial strains, or saturation mutagenesis), non-stochastic mutagenesis (for example alanine-scanning or site-directed mutagenesis), shuffling (for example DNA shuffling, chain shuffling or CDR shuffling) and the use of the CRISPR-Cas9 system to introduce modifications.

Affinity maturation methods are described in, for example, Rajpal et al., Proc Natl Acad Sci USA, 2005, 102(24):8466-71, Steinwand et al., MAbs, 2014, 6(1):204-18, as well as in Handbook of Therapeutic Antibodies, Wiley, 2014, Chapter 6, Antibody Affinity (pages 115-140).

In some embodiments there is provided a method of preparing a pharmaceutical composition comprising providing an antibody prepared according to a method above, (i.e. for producing an antibody by affinity maturation) and co-formulating the antibody with at least one or more pharmaceutically acceptable excipients. The antibody used in the preparation of the pharmaceutical composition can be an affinity matured variant of G04, E07, C08, B07, C05, E04, F07, G06, G09, B09, G10 or E01, including any and all ADT1-4 and ADT1-7 lineage antibodies and antigen-binding fragments and variants thereof. The pharmaceutical compositions produced by such methods can be used in the methods of treatment of the present invention as described herein for the other anti-Vδ1 antibodies.

There are therefore provided anti-Vδ1 antibodies and antigen-binding fragments thereof that are affinity matured mutants or variants of the antibodies disclosed herein. For example, in one embodiment there is provided an affinity-matured variant of an antibody selected from the group consisting of G04, E07, C08, B07, C05, E04, F07, G06, G09, B09, G10 and E01. Generally, the affinity matured mutants have a higher affinity for a variable delta 1 (Vδ1) chain of a γδ T cell receptor (TCR) than the parent antibody (the antibody from which the mutant is derived). Also provided by the present invention are antibodies and antigen-binding fragments thereof obtainable or obtained by affinity maturation of an antibody or antigen-binding fragment thereof of the invention.

Methods of affinity maturation may introduce advantageous mutations preferentially to particular parts of the parental sequence. For example, the in some embodiments, the affinity matured variants retain certain regions of the parental antibody (or the methods of the invention do not introduce mutations to certain regions of the parental antibody). For example, in some embodiments, the affinity matured variants retain:

a) the HCDR2, LCDR1 and LCDR2 sequences (for example, although not limited to, antibodies derived from G04)
b) the HCDR1, HCDR2, LCDR1 and LCDR2 sequences (for example, although not limited to, antibodies derived from E07)
c) the HFR2, HFR3, HFR4, LFR1 and LFR2 sequences (for example, although not limited to, antibodies derived from G04)
d) the HFR1, HFR2, HFR3, HFR4, LFR2, LFR3 and LFR4 sequences (for example, although not limited to, antibodies derived from E07)
e) the HFR2, HCDR2, HFR3, HFR4, LFR1, LCDR1, LFR2 and LCDR2 sequences (for example, although not limited to, antibodies derived from G04); or
f) the HFR1, HCDR1, HFR2, HCDR2, HFR3, HFR4, LCDR1, LFR2, LCDR2, LFR3 and LFR4 sequences (for example, although not limited to, antibodies derived from E07).

In some embodiments, the affinity matured antibodies comprises a kappa light chain variable sequence but comprise a residue at position 74 according to the IMGT numbering system of the light chain variable sequence is not serine. Generally, the amino acid at this residue will be a naturally occurring amino acid.

In some embodiments, the residue at this position is a non-polar residue (for example any amino acid selected from the group consisting of glycine, alanine, valine, methionine, leucine and isoleucine) and/or is a non-human germline residue at that position (for example any amino acid selected from the group consisting of arginine, cysteine, glutamine, glutamic acid, glycine, histidine, isoleucine, leucine, lysine, methionine, phenylalanine, threonine, tryptophan, tyrosine and valine). In some embodiments, the amino acid residue at position 74 is leucine.

In some embodiments, the affinity matured antibodies retain the HFR2, HCDR2, HFR3, HFR4, LFR1, LCDR1, LFR2, LCDR2 and HFR3 sequences of the parental antibody (for example, although not limited to, antibodies derived from G04) with the exception of position 74 in the LFR3 region being mutated to an amino acid other than serine (for example a non-polar and/or non-human-germline residue at that position, such as a leucine residue).

In some embodiments, the affinity matured antibodies retain the HFR1, HCDR1, HFR2, HCDR2, HFR3, HFR4, LCDR1, LFR2, LCDR2, LFR3 and LFR4 sequences of the parental antibody (for example, although not limited to, antibodies derived from E07) with the exception of position 74 in the LFR3 region being mutated to a residue that is not serine (for example a nonhuman-germline and/or non-polar residue at position 74, for example a leucine residue).

In some embodiments, the affinity matured antibodies retain a certain percent identity compared to the parental sequence. For example, in some embodiments, the affinity matured antibodies comprise VH and VL sequences that are at least 80%, at least 90%, at least 95% or at least 96% identical to the corresponding parental VH and VL sequences.

In some embodiments, the affinity matured variants retain:

a) the HCDR2, LCDR1 and LCDR2 sequences (for example, although not limited to, antibodies derived from G04) and comprise VH and VL sequences that are at least 80%, at least 90%, or at least 95%, or at least 96% identical to the corresponding parental VH and VL sequences;
b) the HCDR1, HCDR2, LCDR1 and LCDR2 sequences (for example, although not limited to, antibodies derived from E07) and comprise VH and VL sequences that are at least 80%, at least 90%, or at least 95%, or at least 96% identical to the corresponding parental VH and VL sequences;
c) the HFR2, HFR3, HFR4, LFR1 and LFR2 sequences (for example, although not limited to, antibodies derived from G04) and comprise VH and VL sequences that are at least 80%, at least 90%, or at least 95%, or at least 96% identical to the corresponding parental VH and VL sequences;
d) the HFR1, HFR2, HFR3, HFR4, LFR2, LFR3 and LFR4 sequences (for example, although not limited to, antibodies derived from E07) and comprise VH and VL sequences that are at least 80%, at least 90%, or at least 95%, or at least 96% identical to the corresponding parental VH and VL sequences;
e) the HFR2, HCDR2, HFR3, HFR4, LFR1, LCDR1, LFR2 and LCDR2 sequences (for example, although not limited to, antibodies derived from G04); and comprise VH and VL sequences that are at least 80%, at least 90%, or at least 95%, or at least 96% identical to the corresponding parental VH and VL sequences; or
f) the HFR1, HCDR1, HFR2, HCDR2, HFR3, HFR4, LCDR1, LFR2, LCDR2 LFR3 and LFR4 sequences (for example, although not limited to, antibodies derived from E07) and comprise VH and VL sequences that are at least 80%, at least 90%, or at least 95%, or at least 96% identical to the corresponding parental VH and VL sequences.

In some embodiments, the affinity matured antibodies retain the HFR2, HCDR2, HFR3, HFR4, LFR1, LCDR1, LFR2, LCDR2 and HFR3 sequences of the parental antibody (for example, although not limited to, antibodies derived from G04) with the exception of position 74 in the LFR3 region being mutated to a residue that is not serine (for example a non-human-germline and/or non-polar residue at position 74, for example a leucine residue), and the antibodies and comprise VH and VL sequences that are at least 80%, at least 90%, or at least 95%, or at least 96% identical to the corresponding parental VH and VL sequences.

In some embodiments, the affinity matured antibodies retain the HFR1, HCDR1, HFR2, HCDR2, HFR3, HFR4, LCDR1, LFR2, LCDR2, LFR3 and LFR4 sequences of the parental antibody (for example, although not limited to, antibodies derived from E07) with the exception of position 74 in the LFR3 region being mutated to a residue that is not serine (for example a non-human-germline and/or non-polar residue at position 74, for example a leucine residue), and the antibodies and comprise VH and VL sequences that are at least 80%, at least 90%, or at least 95%, or at least 96% identical to the corresponding parental VH and VL sequences.

In some embodiments, the affinity matured antibodies comprise up to 20, for example up to 15, for example up to 10 amino acid substitutions compared to the parental antibody sequences.

Specific methods may be used to prepare affinity matured antibodies. For example, the affinity matured antibodies of the present invention where prepared according to a specific triaging protocol, to help provide affinity matured antibodies with particular favourable characteristics. Specifically, all anti Vd1 mAb were analysed for binding to the native target, γδTCR expressed by primary γδ T cells. The binding of antibodies to γδ T cells was tested by incubating a fixed concentration of purified antibodies with 3×10^5 skin derived γδT cells. This incubation was performed under blocking conditions to prevent unspecific binding of antibodies via the Fc receptor. Detection was performed by addition of a secondary, fluorescent dye-conjugated antibody against human IgG1. For negative controls, cells were prepared with a) an isotype antibody only (recombinant human IgG), b) the fluorescent dye-conjugated anti-human IgG antibody only. As positive controls the parental clones were included and commercial anti Vd1 mAB clone TS8.2. Most affinity matured antibodies demonstrated improved binding to native target as was indicated by increase in amplitude of signal (MFI) and % of Vδ1 cell detected in the heterogeneous population of skin derived γδT cells ii comparison to commercial anti Vδ1 tool Ab.

To further triage anti Vδ1 mAb, 12 antibodies from each library, with the best improved off rate parameter over parent clones were taken forward to full KD determination by SPR with human and cyno antigen for ADT1-4 lineage and human antigen only for ADT1-7 lineage. 8 clones of ADT1-4 lineage (ADT1-4-19, ADT1-4-21, ADT1-4-31, ADT1-4-53, ADT1-4-2, ADT1-4-86, ADT1-4-112 and ADT1-4- 143) and 3 clones of ADT1-7 clones (ADT1-7-20, ADT1-7-3, ADT1-7-61) were then taken forward to functional characterisation. These clones (and also ADT1-4-1, ADT1-4-6 and ADT1-4-138) were characterised in TCR downregulation assay to confirm improvement in target engagement over parent clones. The improvement of affinity matured antibodies in activation of Vδ1 cells were tested in the CD107a upregulation assay in the imaging based killing assay for their ability to increase cytotoxicity of skin derived Vδ1 γδ T cells towards cancer cells.

Accordingly, in some embodiments, methods of preparing affinity matured anti-Vδ1 antibodies may comprise the following steps:

a) providing a parental anti-Vδ1 antibody having a VH region sequence and a VL region sequence;

b) providing a panel of one or more anti-Vδ1 antibody variants derived from the parental antibody, wherein the VH region of each of the one or more antibody variants comprises a sequence that is at least about a 96% identical the VH region of the parental antibody and the VL region of each of the one or more antibody variants comprises a sequence that is at least about a 96% identical the VL region of the parental antibody;

c) screening the panel of antibody variants to identify antibody variants having an affinity for human and/or cyno TRDV1 that is greater than the affinity of the parental anti-Vδ1 antibody to provide a sub-panel of antibody variants having greater affinity for human and/or cyno TRDV1 than the parental antibody. Such a screening step may be performed by testing the binding of the panel of antibody variants to γδTCR expressed by primary γδ T cells. Such a screening step may additionally or alternatively comprise determining the $K_D$ value of the one or more antibody variants in the panel, for example by surface plasmon resonance. In some embodiments, antibody variants may be selected for the sub-panel when they have an affinity that is at least 20%, at least 30%, at least 40%, at least 50% greater, at least 100%, at least 500% or at least about 1000% greater affinity than the parental antibody for human and/or cyno TRVD1.

The variations in sequence between the parental antibody and the one or more antibody variants in the first panel may occur anywhere in the variable region sequences. In some embodiments, the variations in sequence between the parental antibody and the one or more antibody variants in the first panel may occur in the CDR regions.

The method may further comprise:

d) functionally screening the sub-panel of antibody variants.

Functionally screening the sub-panel of antibody variants may comprise screening the antibody variants for causing:

i. TCR downregulation in Vδ1 cells;

ii. Increase in NCR expression in Vδ1 cells;

iii. Increase in 4-1 BB expression in Vδ1 cells;

iv. CD107a upregulation in Vδ1 cells; and/or v. Vδ1-cell mediated cancer cell killing; and optionally vi. Vδ1-cell depletion.

The method may further comprise:

e) Selecting one or more antibody variants from the sub-panel of antibody variants to provide the one or more affinity matured anti-vd2 antibodies.

The selection criteria may be:

i. causing TCR downregulation in Vδ1 cells;

ii. causing an increase in NCR expression in Vδ1 cells;

iii. causing an increase in 4-1 BB expression in Vδ1 cells;

iv. causing CD107a upregulation in Vδ1 cells; and/or v. causing Vδ1-cell mediated cancer cell killing; and optionally vi. not causing Vδ1-cell depletion.

In some embodiments, the method may be a method of providing one or more affinity matured anti-Vδ1 antibodies, comprising:

a) providing a parental anti-Vδ1 antibody having a VH region sequence and a VL region sequence;

b) providing a panel of one or more anti-Vδ1 antibody variants derived from the parental antibody, wherein the VH region of each of the one or more antibody variants comprises a sequence that is at least about a 96% identical the VH region of the parental antibody and the VL region of each of the one or more antibody variants comprises a sequence that is at least about a 96% identical the VL region of the parental antibody;

c) screening the panel of antibody variants to identify antibody variants having an affinity for human TRDV1 that is at least 500% greater than the affinity of the parental anti-Vδ1 antibody to provide a sub-panel of antibody variants.

d) functionally screening the sub-panel of antibody variants to identify antibody variants in the sub-panel that:

i. cause TCR downregulation in Vδ1 cells;

ii. cause an increase in NCR expression in Vδ1 cells;

iii. cause an increase in 4-1 BB expression in Vδ1 cells;

iv. cause CD107a upregulation in Vδ1 cells; and/or v. cause Vδ1-cell mediated cancer cell killing e) selecting one or more antibody variants from the sub-panel of antibody variants to provide the one or more affinity matured anti-Vδ1 antibodies, wherein the one or more affinity matured anti-Vδ1 antibodies:

i. cause TCR downregulation in Vδ1 cells;
ii. cause an increase in NCR expression in Vδ1 cells;
iii. cause an increase in 4-1 BB expression in Vδ1 cells;
iv. cause CD107a upregulation in Vδ1 cells; and/or
v. cause Vδ1-cell mediated cancer cell killing In some embodiments, the method may be a method of providing one or more affinity matured anti-Vδ1 antibodies, comprising:

a) providing a parental anti-Vδ1 antibody having a VH region sequence and a VL region sequence;
b) providing a panel of one or more anti-Vδ1 antibody variants derived from the parental antibody, wherein the VH region of each of the one or more antibody variants comprises a sequence that is at least about a 96% identical the VH region of the parental antibody and the VL region of each of the one or more antibody variants comprises a sequence that is at least about a 96% identical the VL region of the parental antibody;
c) screening the panel of antibody variants to identify antibody variants having an affinity for human TRDV1 that is at least 500% greater than the affinity of the parental anti-Vδ1 antibody;
d) screening the panel of antibody variants to identify antibody variants having an affinity for cyno TRDV1 that is at least 500% greater than the affinity of the parental anti-Vδ1 antibody;
e) providing a sub-panel of anti-Vδ1 antibody variants, wherein the sub-panel of anti-Vδ1 antibody variants comprises anti-Vδ1 antibody variants that bind to both human and cyno TRDV1 with an affinity that is at least 500% greater than the affinity of the parental anti-Vδ1 antibody for human and cyno TRDV1;
f) functionally screening the sub-panel of antibody variants to identify antibody variants in the sub-panel that:
   i. cause TCR downregulation in Vδ1 cells;
   ii. cause an increase in NCR expression in Vδ1 cells;
   iii. cause an increase in 4-1 BB expression in Vδ1 cells;
   iv. cause CD107a upregulation in Vδ1 cells; and/or
   v. cause Vδ1-cell mediated cancer cell killing
g) selecting one or more antibody variants from the sub-panel of antibody variants to provide the one or more affinity matured anti-Vδ1 antibodies, wherein the one or more affinity matured anti-Vδ1 antibodies:
   i. cause TCR downregulation in Vδ1 cells;
   ii. cause an increase in NCR expression in Vδ1 cells;
   iii. cause an increase in 4-1 BB expression in Vδ1 cells;
   iv. cause CD107a upregulation in Vδ1 cells; and/or
   v. cause Vδ1-cell mediated cancer cell killing.

Cyno-Cross Reactivity

Suitably, the anti-Vδ1 antibodies and antigen-binding fragments thereof exhibit cross-reactivity to both human TRDV1 SEQ ID NO: 272 (including the polymorphic variant i.e. SEQ ID NO: 306) and cyno TRDV1 (SEQ ID NO: 308). Cross reactivity is clearly useful in providing antibodies that can be used in in vivo animal studies during pre-clinical evaluation.

The present inventors have surprisingly identified a framework mutation that can confer increased binding of antibodies, for example anti-Vδ1 antibodies and antigen-binding fragments thereof, to cynomolgus antigens. The framework mutation does not adversely affect the affinity of the antibody or antigen-binding fragment thereof to the corresponding human version of the antigen. The mutation is the mutation of the serine residue to position 74 according to the IMGT numbering system of a kappa light chain variable sequence to a residue that is not serine (for example a non-human-germline and/or non-polar residue at position 74). Non-polar amino acids may be selected from the group consisting of glycine, alanine, valine, methionine, leucine and isoleucine. Non-germline amino acids may be selected from the group consisting of arginine, cysteine, glutamine, glutamic acid, glycine, histidine, isoleucine, leucine, lysine, methionine, phenylalanine, threonine, tryptophan, tyrosine and valine. Non-polar and non-germline amino acids (i.e. amino acids that are both non-polar and non-germline) may be selected from the group consisting of glycine, valine, methionine, leucine and isoleucine). In some embodiments, the mutation is the mutation of the serine residue to position 74 according to the IMGT numbering system of a kappa light chain variable sequence to a leucine residue. The mutation is a direct substitution such the overall length of the chain does not change. Therefore, the serine a position 74 according to the IMGT numbering system is removed and directly replaced with another amino acid (such as a non-human-germline and/or non-polar amino acid at position 74, such as a leucine). The substitution may be achieved according to any suitable method known to the skilled person.

This is demonstrated by FIG. 26 for example. FIG. 26 demonstrates the remarkable effects conferred by mutating kappa chain serine 74 to leucine. Across kappa germlines, position 74 is only partially conserved and interestingly a number of differing polar/non-polar/charged amino acids are present in differing kappa chain germline sub-classes (see IMGT.org). However, to the best of our knowledge, this is the first example of any kappa chain with a leucine at position 74. Regardless, this research conclusively demonstrates that by mutating this single amino acid position, one can enhance affinity of ADT1-4 parent molecule for human and cyno Vδ1 TCR by approximately 13-fold and 5-fold respectively. To further validate this finding, the reversion of leucine 74 back to starting germline serine was undertaken for a high affinity example daughter molecule (ADT1-4-2). Reciprocally, this demonstrated that by reversion back to germline serine, one can reduce the affinity for human and cyno Vδ1 by approximately 11-fold and 23-fold respectively (see FIG. 26D (i) and (ii)). These results dissect the importance of the additive, ratcheting contributions of CDR3 modifications combined with kappa light chain position 74 modifications when enhancing the affinity of ADT1-4 to both human and cyno Vδ1 TCR by up to a most desired 100-fold or more. These findings are non-exhaustive examples of how to (i) enhance the affinity of the parent ADT1-4 molecule or (ii) dial down the affinity of high affinity daughter molecules (as exemplified by ADT1-4-2 in this instance). Accordingly, these discoveries highlight that one can dial up and down affinity of this class of molecule as desired by targeted combinatorial changes to heavy and light chain CDR3 in concert with the selection of specific amino acids at kappa chain position 74.

References herein to antibodies comprising a kappa light chain variable sequence comprising a residue at position 74 according to the IMGT numbering that is not serine may alternatively be defined as antibodies comprising a light chain variable sequence comprising a LFR1 region, a LCDR1 region, a LFR2 region, a LCDR2 region, a LFR3 region, a LCDR3 region and a LFR4 region, wherein the LFR3 region comprises a residue at position 74 according to the IMGT numbering that is not serine (for example a non-human-germline and/or non-polar amino acid at position 74, such as a leucine residue). Such an alternative definition is applicable to all antibodies disclosed herein comprising a kappa light chain variable sequence comprising a residue at position 74 according to the IMGT numbering that is not serine (for example a non-human-germline and/or non-polar amino acid, such as a leucine residue).

Accordingly, the present invention provides anti-TCR delta variable 1 (anti-Vδ1) antibodies or antigen-binding fragments thereof comprising a kappa light chain variable sequence, in which the residue at position 74 according to the IMGT numbering system of the light chain variable sequence is a non-serine (for example a non-human-germline and/or non-polar amino acid at position 74, such as a leucine residue). In some embodiments, the residue at position 74 according to the IMGT numbering system of the light chain variable sequence is a leucine. Suitably, the antibody may be an IgG antibody. For example, the antibody may be IgG1 antibody.

The anti-Vδ1 antibodies and antigen-binding fragments thereof provided herein may be provided with the substitution at position 74 (according to the IMGT numbering system) of the light chain variable sequence. For example, the anti-Vδ1 antibodies and antigen-binding fragments and variants thereof described herein may comprise a kappa light chain variable sequence comprising a residue other than serine at position 74 according to the IMGT numbering system (for example a non-human-germline and/or non-polar amino acid at position 74, such as a leucine residue). In some embodiments, the anti-Vδ1 antibodies and antigen-binding fragments and variants thereof described herein may comprise a kappa light chain variable sequence comprising a leucine residue at position 74 according to the IMGT numbering system. Embodiments comprising a mutation at position 74 according to the IMGT numbering system of a kappa light chain may be particularly relevant to antibodies derived from ADT1-4, although the mutation may be equally applicable to other antibodies. For example, it is observed that light chain position 74 is not highly conserved across the different kappa/lambda light chain germlines. Further it is noted that differing light chain germlines contain differently polarising and/or charged amino acids at this position ranging from non-polar (e.g. alanine) to polar neutral (e.g. serine) to negatively or positively charged (e.g. aspartate or asparagine respectively). It is well understood that amino acid polarity/charge at any given position may impact protein structure. For example, it is well understood that a change in polarity and charge can impact hydrophobicity and tendency for an amino acid to be more surface exposed or more buried. Regardless, this remarkable finding highlights that non-conservative amino acid changes at light chain position 74 can modify affinity to a selected target by greater than 10-fold. Hence aside improving affinity as outlined herein, use of this knowledge may offer a new approach to dialling up or down affinity more broadly. For example, a method comprising changing the residue at position 74 from more polar to non-polar, or for example non-polar to more charged, may be more preferable to complex/cumbersome mutagenesis methods such as saturation mutagenesis etc when one desires to dial up or dial down affinity for any given antibody.

In a further embodiment of the invention there is also provided a method of mutating an antibody or antigen-binding fragment thereof, comprising providing an antibody comprising a kappa light chain having a serine at position 74 of the light chain variable sequence according to the IMGT numbering system, and mutating the serine to a different residue, for example a non-human-germline and/or non-polar amino acid, such as a leucine. In some embodiments, the antibody is an anti-TCR delta variable 1 (anti-Vδ1) antibody or antigen-binding fragment thereof. In some embodiments, the antibody is an antibody having a VH comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 1 and a VL comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 26 both before and after the mutation at position 74 of the light chain variable sequence is introduced.

In some embodiments, the antibody is an antibody having a VH comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 106 and a VL comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 118 both before and after the mutation at position 74 of the light chain variable sequence is introduced.

In some embodiments, the antibody is an antibody comprising:

- a VH comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 273 and a VL comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 282 both before and after the mutation is introduced;
- a VH comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 274 and a VL comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 283 both before and after the mutation is introduced;
- a VH comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 275 and a VL comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 284 both before and after the mutation is introduced;
- a VH comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 276 and a VL comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 285 both before and after the mutation is introduced;

a VH comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 277 and a VL comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 286 both before and after the mutation is introduced;

a VH comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 278 and a VL comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 287 both before and after the mutation is introduced;

a VH comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 279 and a VL comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 288 both before and after the mutation is introduced;

a VH comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 280 and a VL comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 289 both before and after the mutation is introduced;

a VH comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 281 and a VL comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 290 both before and after the mutation is introduced; or a VH comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 312 and a VL comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 313 both before and after the mutation is introduced.

In some embodiments, the antibody is an antibody comprising:

a VH comprising the amino acid sequence of SEQ ID NO: 273 and a VL comprising the amino acid sequence of SEQ ID NO: 282;

a VH comprising the amino acid sequence of SEQ ID NO: 274 and a VL comprising the amino acid sequence of SEQ ID NO: 283;

a VH comprising the amino acid sequence of SEQ ID NO: 275 and a VL comprising the amino acid sequence of SEQ ID NO: 284;

a VH comprising the amino acid sequence of SEQ ID NO: 276 and a VL comprising the amino acid sequence of SEQ ID NO: 285;

a VH comprising the amino acid sequence of SEQ ID NO: 277 and a VL comprising the amino acid sequence of SEQ ID NO: 286;

a VH comprising the amino acid sequence of SEQ ID NO: 278 and a VL comprising the amino acid sequence of SEQ ID NO: 287;

a VH comprising the amino acid sequence of SEQ ID NO: 279 and a VL comprising the amino acid sequence of SEQ ID NO: 288;

a VH comprising the amino acid sequence of SEQ ID NO: 280 and a VL comprising the amino acid sequence of SEQ ID NO: 289;

a VH comprising the amino acid sequence of SEQ ID NO: 281 and a VL comprising the amino acid sequence of SEQ ID NO: 290; or a VH comprising the amino acid sequence of SEQ ID NO: 312 and a VL comprising the amino acid sequence of SEQ ID NO: 313.

The antibody produced by such methods has 100% identity to the specified VH and VL sequences, with the exception of the mutation at position 74.

In some embodiments, the mutation at position 74 increases the affinity of the antibody or antigen-binding fragment thereof for a homologous cynomolgus (cyno) monkey antigen. The increase of the affinity of the antibody or antigen-binding fragment thereof is relative to the affinity of the antibody or antigen-binding fragment thereof before the mutation was introduced (when measured under the same or substantially the same conditions). In some embodiments, the antibody or antigen-binding fragment thereof is an anti-TCR delta variable 1 (anti-Vδ1) antibody or antigen-binding fragment thereof that binds to a human variable delta 1 (Vδ1) chain of a γδ T cell receptor (TCR) (for example SEQ ID NO: 272 and/or 306) before and after the mutation is introduced, and the antibody has increased affinity for a cynomolgus monkey variable delta 1 (Vδ1) chain of a γδ T cell receptor (TCR) (for example SEQ ID NO: 308) after the mutation is introduced.

In any embodiment, in the amino acid at position 74 (according to the IMGT numbering system) of the light chain variable sequence may preferably be leucine.

Polynucleotide Sequences and Expression Vectors

In one aspect of the invention there is provided a polynucleotide encoding the anti-Vδ1 antibody or multi-specific antibody or fragment of the invention. In one embodiment, the polynucleotide comprises or consists of a sequence having at least 70%, such as at least 80%, such as at least 90%, such as at least 95%, such as at least 99% sequence identity with any one of SEQ ID NOs: 199 to 222, 224 to 247, 249 to 259 or 261 to 271. In a further embodiment the polynucleotide comprises or consists of any one of SEQ ID NOs: 199 to 222, 224 to 247, 249 to 259 or 261 to 271. In a further aspect there is provided a cDNA comprising said polynucleotide.

In one aspect of the invention there is provided a polynucleotide comprising or consisting of a sequence having at least 70%, such as at least 80%, such as at least 90%, such as at least 95%, such as at least 99% sequence identity with any one of the portions SEQ ID NOs: 199 to 222, 224 to 247, 249 to 259 or 261 to 271 which encodes CDR1, CDR2 and/or CDR3 of the encoded immunoglobulin chain variable domain.

In one aspect of the invention there is provided a polynucleotide comprising or consisting of a sequence having at least 70%, such as at least 80%, such as at least 90%, such as at least 95%, such as at least 99% sequence identity with any one of the portions of SEQ ID NOs: 199 to 222, 224 to 247, 249 to 259 or 261 to 271 which encodes FR1, FR2, FR3 and/or FR4 of the encoded immunoglobulin chain variable domain.

The present invention also provides expression vectors and plasmids comprising the polynucleotide sequences of the invention. In some embodiments, the expression vectors comprise a sequence having at least 70%, such as at least 80%, such as at least 90%, such as at least 95%, such as at least 99% sequence identity or 100% identity with any one of SEQ ID NOs: 199 to 222 or 249 to 259 (encoding variable heavy regions). In some embodiments, the expression vectors comprise a sequence having at least 70%, such as at least 80%, such as at least 90%, such as at least 95%, such as at least 99% sequence identity or 100% identity with any one of SEQ ID NOs: 224 to 247 or 261 to 271 (encoding variable light regions). Such expression vectors may be used in pairs, suitable pairing the heavy and light chain variable sequences according to the pairing of various amino acid sequences providing the antibodies of the invention disclosed herein. In some embodiments, the expression vectors comprise a sequence having at least 70%, such as at least 80%, such as at least 90%, such as at least 95%, such as at least 99% sequence identity or 100% identity with any one of SEQ ID NOs: 199 to 222 or 249 to 259 (encoding a variable heavy region) and further comprises a sequence having at least 70%, such as at least 80%, such as at least 90%, such as at least 95%, such as at least 99% sequence identity or 100% identity with any one of SEQ ID NOs: 224 to 247 or 261 to 271 (encoding a variable light region). Again, the sequences may be provided in specific pairs as described herein to encode the antibodies of the invention.

The present invention also provides polynucleotide sequences and expression vectors and plasmids encoding all of the antibody sequences disclosed herein, including any variant antibody sequences disclosed herein optionally comprising one or more amino acid substitutions.

The polynucleotides and expression vectors of the invention may also be described in reference to the amino acid sequence encoded. Therefore, in one embodiment, the polynucleotide comprises or consists of a sequence encoding the amino acid sequence of any one of SEQ ID NOs: 1 to 505.

To express the antibodies, or antigen-binding fragments thereof, polynucleotides encoding partial or full-length light and heavy chains, as described herein, are inserted into expression vectors such that the genes are operatively linked to transcriptional and translational control sequences. Therefore, in one aspect of the invention there is provided an expression vector comprising the polynucleotide sequence as defined herein. In one embodiment, the expression vector comprises the VH region of any one of SEQ ID NOs: 199 to 222 or 249 to 259. In another embodiment, the expression vector comprises the VL region of any one of SEQ ID NOs: 224 to 247 or 261 to 271.

It will be understood that the nucleotide sequences described herein may comprise additional sequences encoding amino acid residues to aid with translation, purification and detection, however alternative sequences may be used depending upon the expression system used. These optional sequences can be removed, modified or substituted if alternate design, translation, purification or detection strategies are adopted.

Mutations can be made to the DNA or cDNA that encode polypeptides which are silent as to the amino acid sequence of the polypeptide, but which provide preferred codons for translation in a particular host. The preferred codons for translation of a nucleic acid in, e.g. *E. coli* and *S. cerevisiae*, as well as mammalian, specifically human, are known.

Mutation of polypeptides can be achieved for example by substitutions, additions or deletions to a nucleic acid encoding the polypeptide. The substitutions, additions or deletions to a nucleic acid encoding the polypeptide can be introduced by many methods, including for example error-prone PCR, shuffling, oligonucleotide-directed mutagenesis, assembly PCR, PCR mutagenesis, in vivo mutagenesis, cassette mutagenesis, recursive ensemble mutagenesis, exponential ensemble mutagenesis, site-specific mutagenesis, gene reassembly, artificial gene synthesis, Gene Site Saturation Mutagenesis (GSSM), synthetic ligation reassembly (SLR) or a combination of these methods. The modifications, additions or deletions to a nucleic acid can also be introduced by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, ensemble mutagenesis, chimeric nucleic acid multimer creation, or a combination thereof.

In particular, artificial gene synthesis may be used. A gene encoding a polypeptide of the invention can be synthetically produced by, for example, solid-phase DNA synthesis. Entire genes may be synthesized de novo, without the need for precursor template DNA. To obtain the desired oligonucleotide, the building blocks are sequentially coupled to the growing oligonucleotide chain in the order required by the sequence of the product. Upon the completion of the chain assembly, the product is released from the solid phase to solution, deprotected, and collected. Products can be isolated by high-performance liquid chromatography (HPLC) to obtain the desired oligonucleotides in high purity.

Expression vectors include, for example, plasmids, retroviruses, cosmids, yeast artificial chromosomes (YACs) and Epstein-Barr virus (EBV) derived episomes. The polynucleotide is ligated into a vector such that transcriptional and translational control sequences within the vector serve their intended function of regulating the transcription and translation of the polynucleotide. Expression and/or control sequences can include promoters, enhancers, transcription terminators, a start codon ATG) 5' to the coding sequence, splicing signals for introns and stop codons. The expression vector and expression control sequences are chosen to be compatible with the expression host cell used. For example, the sequences may comprise nucleotide sequences encoding single chain variable fragments versions of the antibodies invention, comprising a VH region and a VL region joined by a synthetic linker (e.g. encoding SEQ ID NO: 291). It will be understood that polynucleotides or expression vectors of the invention may comprise the VH region, the VL region or both (optionally including the linker). Therefore, polynucleotides encoding the VH and VL regions can be inserted into separate vectors, alternatively sequences encoding both regions are inserted into the same expression vector. The polynucleotide(s) are inserted into the expression vector by standard methods (e.g. ligation of complementary restriction sites on the polynucleotide and vector, or blunt end ligation if no restriction sites are present).

A convenient vector is one that encodes a functionally complete human CH or CL immunoglobulin sequence, with appropriate restriction sites engineered so that any VH or VL sequence can be easily inserted and expressed, as described herein. The expression vector can also encode a signal peptide that facilitates secretion of the antibody (or antigen-binding fragment thereof) from a host cell. The polynucleotide may be cloned into the vector such that the signal peptide is linked in-frame to the amino terminus of the antibody. The signal peptide can be an immunoglobulin signal peptide or a heterologous signal peptide (i.e. a signal peptide from a non-immunoglobulin protein).

In one aspect of the invention there is provided a cell (e.g. a host cell, such as a recombinant host cell) comprising the polynucleotide or expression vector as defined herein. It will be understood that the cell may comprise a first vector encoding the light chain of the antibody or antigen-binding fragment thereof, and a second vector encoding the heavy chain of the antibody or antigen-binding fragment thereof. Alternatively, the heavy and light chains both encoded on the same expression vector introduced into the cell.

In one embodiment, the polynucleotide or expression vector encodes a membrane anchor or transmembrane domain fused to the antibody or antigen-binding fragment thereof, wherein the antibody or antigen-binding fragment thereof is presented on an extracellular surface of the cell.

Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, biolistic injection and direct microinjection of the DNA into nuclei. In addition, nucleic acid molecules may be introduced into mammalian cells by viral vectors.

Mammalian cell lines available as hosts for expression are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g. Hep G2), A549 cells, 3T3 cells, and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9 cells, amphibian cells, bacterial cells, plant cells and fungal cells. Antigen-binding fragments of antibodies such as the scFv and Fv fragments can be isolated and expressed in *E. coli* using methods known in the art.

The antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Antibodies (or fragments) of the invention can be obtained and manipulated using the techniques disclosed for example in Green and Sambrook, *Molecular Cloning: A Laboratory Manual* (2012) 4th Edition Cold Spring Harbour Laboratory Press.

Monoclonal antibodies can be produced using hybridoma technology, by fusing a specific antibody-producing B cell with a myeloma (B cell cancer) cell that is selected for its ability to grow in tissue culture and for an absence of antibody chain synthesis.

A monoclonal antibody directed against a determined antigen can, for example, be obtained by:

a) immortalizing lymphocytes obtained from the peripheral blood of an animal previously immunized with a determined antigen, with an immortal cell and preferably with myeloma cells, in order to form a hybridoma,
b) culturing the immortalized cells (hybridoma) formed and recovering the cells producing the antibodies having the desired specificity.

Alternatively, the use of a hybridoma cell is not required. Antibodies capable of binding to the target antigens as described herein may be isolated from a suitable antibody library via routine practice, for example, using the phage display, yeast display, ribosomal display, or mammalian display technology known in the art. Accordingly, monoclonal antibodies can be obtained, for example, by a process comprising the steps of:

a) cloning into vectors, especially into phage and more particularly filamentous bacteriophages, DNA or cDNA sequences obtained from lymphocytes especially peripheral blood lymphocytes of an animal (suitably previously immunized with determined antigens),
b) transforming prokaryotic cells with the above vectors in conditions allowing the production of the antibodies,
c) selecting the antibodies by subjecting them to antigen-affinity selection,
d) recovering the antibodies having the desired specificity.

Optionally, isolated polynucleotide encoding antibodies or antigen-binding fragment thereof as described herein and which bind to the Vδ1 chain of a γδ can also be readily manufactured to make sufficient quantities to be employed as a medicament to ameliorate the signs or symptoms of disease. When employed as a medicament in this manner, typically the polynucleotides of interest are first operatively linked to an expression vector or expression cassette designed to express said antibodies or antigen-binding fragment thereof in a subject or patient. Such expression cassettes and methods of delivery of polynucleotides or what are sometime termed 'nucleic-based' medicaments are well known in the art. For recent review see Hollevoet and Declerck (2017) J. Transl. Med. 15(1): 131.

Also provided is a method for the production of an anti-Vδ1 antibody or antigen-binding fragment or variant thereof, comprising culturing a host cell of the invention in a cell culture medium under conditions to express the encoding nucleic acid sequence of the plasmid or vector inside the cell. The method may further comprise obtaining the anti-Vδ1 antibody or antigen-binding fragment or variant thereof from the cell culture supernatant. The obtained antibodies may then be formulated into a pharmaceutical composition. Further, there is provided a method of producing cell that expresses an anti-Vδ1 antibody or antigen-binding fragment or variant thereof, comprising transfecting said cell with a plasmid or vector of the invention. Said cells can then be cultured for the production of the anti-Vδ1 antibody or antigen-binding fragment or variant thereof.

Pharmaceutical Compositions

According to a further aspect of the invention, there is provided a composition comprising the antibody or antigen-binding fragment thereof as defined herein. In such embodiments, the composition may comprise the antibody, optionally in combination with other excipients. Also included are compositions comprising one or more additional active agents (e.g. active agents suitable for treating the diseases mentioned herein).

According to a further aspect of the invention, there is provided a pharmaceutical composition comprising the antibody or antigen-binding fragment thereof as defined herein, together with a pharmaceutically acceptable diluent or carrier. The antibodies of the invention can be incorporated into pharmaceutical compositions suitable for administration to a subject. Typically, the pharmaceutical composition comprises an antibody of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, salts, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable substances such as wetting or minor amounts of auxiliary substances such as wetting or emulsifying agents, preservatives or buffers, which enhance the shelf life or effectiveness of the antibody or antigen-binding fragment thereof.

The compositions of this invention may be in a variety of forms. These include, for example, liquid, semi-solid and solid dosage forms, such as liquid solutions (e.g. injectable and infusible solutions), dispersions or suspensions, tablets, pills, powders, liposomes and suppositories. The preferred form depends on the intended mode of administration and therapeutic application. Typical preferred compositions are in the form of injectable or infusible solutions.

The preferred mode of administration is parenteral (e.g. intravenous, subcutaneous, intraperitoneal, intramuscular, intrathecal). In a preferred embodiment, the antibody is administered by intravenous infusion or injection. In another preferred embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration.

It is within the scope of the invention to use the pharmaceutical composition of the invention in therapeutic methods for the treatment of diseases as described herein as an adjunct to, or in conjunction with, other established therapies normally used in the treatment of such diseases.

In a further aspect of the invention, the antibody, composition or pharmaceutical composition is administered sequentially, simultaneously or separately with at least one active agent.

Treatment Methods

According to a further aspect of the invention, there is provided an isolated anti-Vδ1 antibody or antigen-binding fragment thereof as defined herein for use as a medicament. References herein to an antibody or antigen-binding fragment thereof "for use" as a medicament or in therapy are limited to administration of the antibody or antigen-binding fragment thereof to a subject.

In one embodiment, the anti-Vδ1 antibody or antigen-binding fragment thereof is for use in the treatment of cancer, an infectious disease or an inflammatory disease. In one embodiment, the invention is a method of treating a disease or disorder in a subject in need thereof, comprising the step of administering an anti-Vδ1 antibody or antigen-binding fragment thereof to the subject. In various embodiments, the disease or disorder is cancer, an infectious disease or an inflammatory disease. In one embodiment, the anti-Vδ1 antibody or antigen-binding fragment thereof is for use in the treatment of cancer, an infectious disease or an inflammatory disease, leads to the death of diseased cells while sparing healthy cells. In a further embodiment, the antibody or antigen-binding fragment thereof is for use in the treatment of cancer.

In one embodiment, the antibody or antigen-binding fragment thereof is for use in the treatment of cancer, an infectious disease or an inflammatory disease. In a further embodiment, the antibody or antigen-binding fragment thereof is for use in the treatment of cancer.

According to a further aspect of the invention, there is provided the pharmaceutical composition as defined herein for use as a medicament. In one embodiment, the pharmaceutical composition is for use in the treatment of cancer, an infectious disease or an inflammatory disease. In a further embodiment, the pharmaceutical composition is for use in the treatment of cancer.

According to a further aspect of the invention, there is provided a method of modulating an immune response in a subject in need thereof comprising administering a therapeutically effective amount of the isolated anti-Vδ1 antibody or antigen-binding fragment thereof as defined herein. In various embodiments, modulating an immune response in a subject comprises binding or targeting γδ T cells, activating γδ T cells, causing or increasing proliferation of γδ T cells, causing or increasing expansion of γδ T cells, causing or increasing γδ T cell degranulation, causing or increasing γδ T cell mediated killing activity, causing or increasing γδ T cell mediated killing activity while sparing healthy cells, causing or increasing γδ T cytotoxicity, causing or increasing γδ T cytotoxicity while sparing healthy cells, causing or increasing γδ T cell mobilization, increasing survival of γδ T cells, or increasing resistance to exhaustion of γδ T cells. Modulating the immune response in a subject may further comprise binding or targeting the second antigen. For example, in some embodiments, binding of the second antigen, in particular when it is an immunomodulatory antigen, may stimulate immunomodulation via the second antigen in addition to immunomodulation via binding of the multispecific antibody to TRDV1. Hence the modulation of the immune response may comprise modulation via two different signalling pathways, a first signalling pathway modulated via TRDV1 antigen engagement and a second signalling pathway modulated via engagement of a second immunomodulatory antigen.

According to a further aspect of the invention, there is provided method of treating a cancer, an infectious disease or an inflammatory disease in a subject in need thereof, comprising administering a therapeutically effective amount of the isolated anti-Vδ1 antibody or antigen-binding fragment thereof as defined herein. Alternatively, a therapeutically effective amount of the pharmaceutical composition is administered.

According to further aspects of the invention, there is provided the use of an antibody or antigen-binding fragment thereof as defined herein for the manufacture of a medicament, for example in the treatment of cancer, an infectious disease or an inflammatory disease.

In one embodiment, the antibody or antigen-binding fragment thereof is administered to a subject, wherein the subject has cancer, an infectious disease or an inflammatory disease.

According to a further aspect of the invention, there is provided the pharmaceutical composition as defined herein for use as a medicament. In one embodiment, the pharmaceutical composition is administered to a subject, wherein the subject has cancer, an infectious disease or an inflammatory disease.

According to a further aspect of the invention, there is provided a method of administering a therapeutically effective amount of the isolated anti-Vδ1 antibody or antigen-binding fragment thereof as defined herein to a subject, wherein the subject has cancer, an infectious disease or an inflammatory disease. Alternatively, a therapeutically effective amount of the pharmaceutical composition is administered.

According to further aspects of the invention, there is provided the use of an antibody or antigen-binding fragment thereof as defined herein for the manufacture of a medicament, for example for the administration to a subject, wherein the subject has cancer, an infectious disease or an inflammatory disease.

In various embodiments, the cancer that can be treated by the disclosed methods and compositions include, but are not limited to acute lymphoblastic, acute myeloid leukemia, adrenocortical carcinoma, appendix cancer, basal cell carcinoma, bile duct cancer, bladder cancer, bone cancer, osteosarcoma and malignant fibrous histiocytoma, brain stem glioma, brain tumor, brain tumor, brain stem glioma, central nervous system atypical teratoid/rhabdoid tumor, central nervous system embryonal tumors, cerebellar astrocytoma, cerebral astrocytoma/malignant glioma, craniopharyngioma, ependymoblastoma, ependymoma, medulloblastoma, medulloepithelioma, pineal parenchymal tumors of intermediate differentiation, supratentorial primitive neuroectodermal tumors and pineoblastoma, visual pathway and hypothalamic glioma, brain and spinal cord tumors, breast cancer, bronchial tumors, Burkitt lymphoma, carcinoid tumor, gastrointestinal carcinoid tumor, central nervous system atypical teratoid/rhabdoid tumor, central nervous system embryonal tumors, central nervous system lymphoma, cerebellar astrocytoma cerebral astrocytoma/malignant glioma, cervical cancer, chordoma, chronic lymphocytic leukemia, chronic myelogenous leukemia, chronic myeloproliferative disorders, colon cancer, colorectal cancer, craniopharyngioma, cutaneous T-cell lymphoma, esophageal cancer, Ewing family of tumors, extragonadal germ cell tumor, extrahepatic bile duct cancer, intraocular melanoma, retinoblastoma, gallbladder cancer, gastric (stomach) cancer, gastrointestinal carcinoid tumor, gastrointestinal stromal tumor (gist), germ cell tumor, gestational trophoblastic tumor, glioma, glioma brain stem, glioma cerebral astrocytoma, glioma visual pathway and hypothalamic, hairy cell leukemia, head and neck cancer, hepatocellular (liver) cancer, Langerhans cell histiocytosis, Hodgkin lymphoma, hypopharyngeal cancer, hypothalamic and visual pathway glioma, intraocular melanoma, islet cell tumors, kidney (renal cell) cancer, Langerhans cell histiocytosis, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, non-small cell lung cancer, small cell lung cancer, aids-related lymphoma, Burkitt lymphoma, cutaneous T-cell lymphoma, non-Hodgkin lymphoma, primary central nervous system lymphoma, Waldenstrom macroglobulinemia, malignant fibrous histiocytoma of bone and osteosarcoma, medulloblastoma, melanoma, Merkel cell carcinoma, mesothelioma, metastatic squamous neck cancer with occult primary, mouth cancer, multiple endocrine neoplasia syndrome, multiple myeloma/plasma cell neoplasm, mycosis, fungoides, myelodysplastic syndromes, myelodysplastic/myeloproliferative diseases, myelogenous leukemia, myeloid leukemia, myeloid leukemia acute, multiple myeloma, myeloproliferative disorders, nasal cavity and paranasal sinus cancer, nasopharyngeal cancer, neuroblastoma, non-small cell lung cancer, oral cancer, oral cavity cancer, oropharyngeal cancer, osteosarcoma and malignant fibrous histiocytoma of bone, ovarian cancer, ovarian epithelial cancer, ovarian germ cell tumor, ovarian low malignant potential tumor, pancreatic cancer, pancreatic cancer, papillomatosis, parathyroid cancer, penile cancer, pharyngeal cancer, pheochromocytoma, pineal parenchymal tumors of intermediate differentiation, pineoblastoma and supratentorial primitive neuroectodermal tumors, pituitary tumor, plasma celt neoplasm/multiple myeloma, pleuropulmonary blastoma, primary central nervous system lymphoma, prostate cancer, rectal cancer, renal cell (kidney) cancer, renal pelvis and ureter, respiratory tract carcinoma involving the nut gene on chromosome 15, retinoblastoma, rhabdomyosarcoma, salivary gland cancer, sarcoma, Ewing family of tumors, Kaposi sarcoma, soft tissue sarcoma, uterine sarcoma, Sezary syndrome, skin cancer (nonmelanoma), skin cancer (melanoma), Merkel cell skin carcinoma, small cell lung cancer, small intestine cancer, soft tissue sarcoma, squamous cell carcinoma, squamous neck cancer, stomach (gastric) cancer, supratentorial primitive neuroectodermal tumors, T-cell lymphoma, testicular cancer, throat cancer, thymoma and thymic carcinoma, thyroid cancer, transitional cell cancer of the renal pelvis and ureter, gestational trophoblastic tumor, urethral cancer, uterine cancer, uterine sarcoma, vaginal cancer, vulvar cancer, Waldenstrom macroglobulinemia, and Wilms tumor. In various embodiments, the cancer that can be treated by the disclosed methods and compositions is treated while healthy cells are spared, In various embodiments, the inflammatory diseases that can be treated by the disclosed methods and compositions include, but are not limited to Achalasia, Acute disseminated encephalomyelitis (ADEM), Acute motor axonal neuropathy, Acute respiratory distress syndrome (ARDS), Addison's disease, Adiposis dolorosa, Adult Still's disease, Adult-onset Still's disease, Agammaglobulinemia, Alopecia Areata, Amyloidosis, Amyotrophic lateral sclerosis, Ankylosing spondylitis, Anti-GBM/Anti-TBM nephritis, Anti-N-Methyl-D-Aspartate (Anti-NMDA) Receptor Encephalitis, Antiphospholipid syndrome, Antiphospholipid syndrome (APS, APLS), Antisynthetase syndrome, Anti-tubular basement membrane nephritis, Aplastic anemia, Atopic allergy, Atopic dermatitis, Autoimmune angioedema, Autoimmune comorbidities, Autoimmune dysautonomia, Autoimmune encephalomyelitis, Autoimmune enteropathy, Autoimmune hemolytic anemia, Autoimmune hepatitis, Autoimmune inner ear disease (AIED), Autoimmune lymphoproliferative syndrome, Autoimmune myocarditis, Autoimmune neutropenia, Autoimmune oophoritis, Autoimmune orchitis, Autoimmune pancreatitis (AIP), Autoimmune peripheral neuropathy, Autoimmune polyendocrine syndrome (APS) type 1, Autoimmune polyendocrine syndrome (APS) type 2, Autoimmune polyendocrine syndrome (APS) type 3, Autoimmune retinopathy, Autoimmune thrombocytopenic purpura, Autoimmune thyroiditis, Autoimmune urticaria, Autoimmune uveitis, Autoimmune vasculitis, Axonal & neuronal neuropathy (AMAN), Balo concentric sclerosis, Baló disease, Behcet's disease, Benign mucosal pemphigoid, Bickerstaff's encephalitis, Blau syndrome, Bullous pemphigoid, Castleman disease (CD), Celiac disease, Chagas disease, Chronic fatigue syndrome, Chronic inflammatory demyelinating polyneuropathy (CIDP), Chronic obstructive pulmonary disease, Chronic recurrent multifocal osteomyelitis (CRMO), Churg-Strauss Syndrome (CSS) or Eosinophilic Granulomatosis (EGPA), Cicatricial pemphigoid, Cogan syndrome, Cold agglutinin disease, Complement component 2 deficiency, Complex regional pain syndrome, Congenital heart block, Connective tissue, systemic, and multi-organ, Contact dermatitis, Coxsackie myocarditis, CREST syndrome, Crohn's disease, Cushing's syndrome, Cutaneous leukocytoclastic angiitis, Dego's disease, Dermatitis herpetiformis, Dermatomyositis, Devic's Disease (neuromyelitis optica), Diabetes mellitus type 1, Digestive system, Discoid lupus, Dressler's syndrome, Drug-induced lupus, Eczema, Endometriosis, Enthesitis-related arthritis, Eosinophilic esophagitis (EoE), Eosinophilic fasciitis, Eosinophilic gastroenteritis, Eosinophilic granulomatosis with polyangiitis (EGPA), Eosinophilic pneumonia, Epidermolysis bullosa acquisita, Erythema nodosum, Erythroblastosis fetalis, Esophageal achalasia, Essential mixed cryoglobulinemia, Evans syndrome, Exocrine, Felty syndrome, Fibrodysplasia ossificans progressiva, Fibromyalgia, Fibrosing alveolitis, Gastritis, Gastrointestinal pemphigoid, Giant cell arteritis (temporal arteritis), Giant cell myocarditis, Glomerulonephritis, Goodpasture's syndrome, Granulomatosis with Polyangiitis, Graves' ophthalmopathy, Graves' disease, Guillain-Barre syndrome, Hashimoto's thyroiditis, Hashimoto's encephalopathy, Hemolytic anemia, Henoch-Schonlein purpura (HSP), Herpes gestationis or pemphigoid gestationis (PG), Hidradenitis Suppurativa (HS) (Acne Inversa), Hypogammaglobulinemia, Idiopathic giant-cell myocarditis, Idiopathic inflammatory demyelinating diseases, Idiopathic pulmonary fibrosis, IgA Nephropathy, IgA vasculitis (IgAV), IgG4-related disease, IgG4-related sclerosing disease, Immune thrombocytopenic purpura (ITP), Inclusion body myositis (IBM), Inflammatory Bowel Disease, Intermediate uveitis, Interstitial cystitis (IC), Interstitial lung disease, IPEX syndrome, Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lupus nephritis, Lupus vasculitis, Lyme disease chronic, Majeed syndrome, Meniere's disease, Microscopic polyangiitis (MPA), Mixed connective tissue disease (MCTD), Mooren's ulcer, Morphea, Mucha-Habermann disease, MultifocalMotor Neuropathy (MMN) orMMNCB, Multiple sclerosis, Myasthenia gravis, Myocarditis, Myositis, Narcolepsy, Neonatal Lupus, Nervous system, Neuromyelitis optica, Neuromyotonia, Neutropenia, Ocular cicatricial pemphigoid, Opsoclonus myoclonus syndrome, Optic neuritis, Ord's thyroiditis, Oshtoran syndrome, Palindromic rheumatism (PR), Paraneoplastic cerebellar degeneration (PCD), Paroxysmal nocturnal hemoglobinuria (PNH), Parry-Romberg syndrome, Parsonage-Turner syndrome, ParsPlanitis (peripheral uveitis), Pediatric Autoimmune Neuropsychiatric Disorder Associated with *Streptococcus* (PANDAS), Pelvic Inflammatory Disease (PID), Pemphigus, Pemphigus vulgaris, Peripheral neuropathy, Perivenous encephalomyelitis, Pernicious anemia (PA), *Pityriasis* lichenoides et varioliformis *acuta*, POEMS syndrome, Polyarteritis nodosa, Polyglandular syndromes type I, II, III, Polymyalgia rheumatica, Polymyositis, Postmyocardial infarction syndrome, Postpericardiotomy syndrome, Primary biliary cholangitis (PBC), Primary biliary cirrhosis, Primary immunodeficiency, Primary sclerosing cholangitis, Progesterone dermatitis, Progressive inflammatory neuropathy, Psoriasis, Psoriatic arthritis, Pure red cell aplasia (PRCA), Pyoderma gangrenosum, Rasmussen's encephalitis, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Rheumatoid vasculitis, Sarcoidosis, Schizophrenia, Schmidt syndrome, Schnitzler syndrome, Scleritis, Scleroderma, Serum sickness, Sjögren's Syndrome, Sperm & testicular autoimmunity, Spondyloarthropathy, Stiff person syndrome (SPS), Subacute bacterial endocarditis (SBE), Susac's Syndrome, Sweet's syndrome, Sydenham's chorea, Sympathetic ophthalmia (SO), Systemic lupus erythematosus (SLE), Takayasu's arteritis, Temporal arteritis/Giant cell arteritis, Thrombocytopenia, Thrombocytopenic purpura (TTP), Thyroid gland, Tolosa-Hunt syndrome (THS), Transverse myelitis, Type 1 diabetes, Ulcerativecolitis(UC), Undifferentiated connective tissue disease (UCTD), Undifferentiated spondyloarthropathy, Urticarial vasculitis, Uticaria, Uveitis, Vasculitis, Vitiligo, and Vogt-Koyanagi-HaradaDisease. In various embodiments, the inflammatory disease that can be treated by the disclosed methods and compositions is treated, while healthy cells are spared.

In various embodiments, the infectious disease that can be treated by the disclosed methods and compositions include, but are not limited to *Acinetobacter* infection, Actinomycosis, Acute Flaccid Myelitis (AFM), African sleeping sickness (African trypanosomiasis), AIDS (acquired immunodeficiency syndrome), Ameba infection, Amebiasis, *Anaplasma phagocytophilum* infection, Anaplasmosis, Angiostrongyliasis, Anisakiasis, Anthrax, Arboviral diseases, neuroinvasive and non-neuroinvasive, Arcanobacterium *haemolyticum* infection, Argentine hemorrhagic fever, Ascariasis, Aspergillosis, Astrovirus infection, Avian Influenza, Babesiosis, *Bacillus cereus* infection, Bacterial infection, Bacterial meningitis, Bacterial pneumonia, Bacterial vaginosis, *Bacteroides* infection, Balantidiasis, Bartonellosis, *Baylisascaris* infection, BK virus infection, Black piedra, Blastocystosis, Bolivian hemorrhagic fever, Botulism, Botulism (foodborne), Botulism (infant), Botulism (other), Botulism (wound), Brazilian hemorrhagic fever, Brucellosis, Bubonic plague, *Burkholderia* infection, Buruli ulcer, Calicivirus infection (Norovirus and Sapovirus), California serogroup virus diseases, *Campylobacter, Campylobacteriosis, Candida auris*, clinical, Candidiasis (Moniliasis; Thrush), Capillariasis, Carbapenemase Producing Carbapenem-Resistant Enterobacteriaceae (CP-CRE), Carbapenem-resistant Infection (CRE/CRPA), Carrion's disease, Cat-scratch disease, Cellulitis, Chagas disease (trypanosomiasis), Chancroid, Chickenpox, Chikungunya Virus Infection (Chikungunya), *Chlamydia, Chlamydia tra-*

*chomatis, Chlamydophila pneumoniae* infection, Cholera, Chromoblastomycosis, Chytridiomycosis, Ciguatera, Clonorchiasis, *Clostridium difficile* colitis, *Clostridium Difficile* Infection, *Clostridium perfringens*, Coccidioidomycosis fungal infection (Valley fever), Colorado tick fever (CTF), Common cold (Acute viral rhinopharyngitis; Acute coryza), Congenital syphilis, Conjunctivitis, COVID-19 (Coronavirus Disease 2019), CP-CRE, *Enterobacter* spp., CP-CRE, *Escherichia coli* (*E. coli*), CP-CRE, *Klebsiella* spp., Creutzfeldt-Jacob Disease, transmissible spongiform encephalopathy (CJD), Creutzfeldt—Jakob disease (CJD), Crimean-Congo hemorrhagic fever (CCHF), Crusted Scabies, Cryptococcosis, Cryptosporidiosis (Crypto), Cutaneous larva migrans (CLM), *Cyclospora*, Cyclosporiasis, Cysticercosis, Cytomegalovirus infection, Dengue virus infections, Dengue, 1,2,3,4 (Dengue Fever), Dengue-like illness, Desmodesmus infection, Diarrheal Illness, Dientamoebiasis, Diphtheria, Diphyllobothriasis, Dracunculiasis, *E. coli, E. coli* infection, Shiga toxin-producing (STEC), Eastern equine encephalitis virus disease, Ebola Hemorrhagic Fever (Ebola), Echinococcosis, *Ehrlichia chaffeensis* infection, *Ehrlichia ewingii* infection, Ehrlichiosis, Anaplasmosis, Encephalitis, Arboviral or parainfectious, Enterobiasis (Pinworm infection), *Enterococcus* infection, Enterovirus Infection, D68 (EV-D68), Enterovirus Infection, Non-Polio (Non-Polio Enterovirus), Epidemic typhus, Epstein-Barr virus infectious mononucleosis (Mono), Erythema infectiosum (Fifth disease), Exanthem subitum (Sixth disease), Fasciolasis, Fasciolopsiasis, Fatal familial insomnia (FFI), Fifth Disease, Filariasis, Flu (Seasonal), Food Poisoning, Food poisoning by *Clostridium perfringens*, Free-living amebic infection, Fungal infection, *Fusobacterium* infection, Gas gangrene (Clostridial myonecrosis), Genital Herpes, Genital Warts, Geotrichosis, German Measles, Gerstmann-Sträussler-Scheinker syndrome (GSS), Giardiasis, Glanders, Gnathostomiasis, Gonorrhea, Granuloma inguinale, Granuloma inguinale (Donovanosis), Group A streptococcal infection, Group A *Streptococcus*, Group B streptococcal infection, Guanarito virus, *Haemophilus* Influenza disease, Type B (Hib or H-flu), *Haemophilus influenzae* infection, Hand, foot and mouth disease (HFMD), Hansen's Disease, Hantavirus infection, Hantavirus Pulmonary Syndrome (HPS), Heartland virus disease, *Helicobacter pylori* infection, Hemolytic Uremic Syndrome (HUS), Hemorrhagic fever with renal syndrome (HFRS), Hendra virus infection, Hepatitis A (Hep A), Hepatitis B (Hep B), Hepatitis C (Hep C), Hepatitis D (Hep D), Hepatitis E (Hep E), Herpes, Herpes B Virus, Herpes simplex, Herpes Zoster, zoster VZV (Shingles), Hib Disease, Histoplasmosis infection (Histoplasmosis), Hookworm infection, HPV (Human Papillomavirus), Human bocavirus infection, Human *ewingii* ehrlichiosis, Human granulocytic anaplasmosis (HGA), Human Immunodeficiency Virus/AIDS (HIV/AIDS), Human metapneumovirus infection, Human monocytic ehrlichiosis, Human papillomavirus (HPV) infection, Human parainfluenza virus infection, Hymenolepiasis, Impetigo, Influenza (flu), Influenza (Seasonal), Invasive pneumococcal disease, Isosporiasis, Junin virus-Kawasaki Syndrome, Keratitis, Kingella kingae infection, Kuru, Lassa fever, Lassa virus, Legionellosis (Legionnaires' disease), Leishmaniasis, Leprosy (Hansens Disease), Leptospirosis, Listeriosis (*Listeria*), Lujo virus, Lyme disease, Lymphatic filariasis (Elephantiasis), Lymphocytic Choriomeningitis (LCMV), Lymphogranuloma venereum infection (LGV), Machupo virus, Malaria, Marburg virus infection, Measles, Melioidosis (Whitmore's disease), Meningitis, Meningitis-Bacterial, Meningitis-Viral, Meningococcal disease, Metagonimiasis, Microsporidiosis, Middle East respiratory syndrome (MERS), Molluscum contagiosum (MC), Monkeypox, Mononucleosis, Mosquito-borne Illness, MRSA, Mumps-Murine typhus (Endemic typhus), Mycetoma, *Mycoplasma genitalium* infection, *Mycoplasma* pneumonia, Myiasis, *Neisseria meningitidis*, Neonatal conjunctivitis (Ophthalmia neonatorum), Nipah virus infection, Nocardiosis, Norovirus, Onchocerciasis (River blindness), Opisthorchiasis, Orf Virus (Sore Mouth), Paracoccidioidomycosis (South American blastomycosis), Paragonimiasis, Paralytic Shellfish Poisoning (Paralytic Shellfish Poisoning, Ciguatera), Pasteurellosis, PEP, Parasitic infection, Pertussis (whooping cough), Pink Eye, Pneumococcal Disease, Pneumococcal infection, *Pneumocystis* pneumonia (PCP), Pneumonia, Pneumonic Plague, Poliomyelitis (Polio), Poliomyelitis, paralytic, Poliovirus infection, Pontiac fever, Powassan virus disease, *Prevotella* infection, Primary amoebic meningoencephalitis (PAM), Progressive multifocal leukoencephalopathy, Protozoan infection, Psittacosis (Parrot Fever), Pustular Rash diseases (Small pox, monkeypox, cowpox), Rabies, Raccoon Roundworm, Rat Bite Fever, Recreational Water Illnesses, Relapsing fever, Respiratory syncytial virus infection, Reye's Syndrome, Rhinosporidiosis, Rh inovirus infection, Rickettsial infection, Rickettsiosis (Rocky Mountain Spotted Fever), Rift Valley fever (RVF), Ringworm, Rotavirus infection, Rubella, Sabia virus, *Salmonella, Salmonella* Paratyphi infection, *Salmonella Typhi* infection, *Salmonellosis*, SARS (severe acute respiratory syndrome), Scabies, Scarlet fever, Schistosomiasis, Scombroid, Sepsis, Septic Shock, Septicemic Plague, Severe Acute Respiratory Syndrome (SARS), Shiga toxin-producing *Escherichia coli, Shigella*, Shigellosis, Shingles, Shingles (Herpes zoster), Smallpox, Sore Mouth (Orf Virus), Sporotrichosis, Spotted fever rickettsiosis, St. Louis encephalitis virus disease, Staphyloccal Infection, Staphyloccal Infection (Methicillin-resistant (MRSA)), Staphylococcal food poisoning, Staphylococcal Infection (Vancomycin Intermediate (VISA)), Strep Throat, Streptococcal Disease, Group A (invasive) (Strep A (invasive)), Streptococcal Disease, Group B (Strep-B), Streptococcal toxic shock syndrome, Strongyloidiasis, Subacute sclerosing panencephalitis, Syphilis, Taeniasis, Tetanus Infection, Tick-borne Diseases, Tinea barbae, Tinea capitis, Tinea corporis, Tinea cruris, Tinea manum, Tinea nigra, Tinea pedis, Tinea unguium, Tinea *versicolor*, Toxic shock syndrome, Toxocariasis (ocular larva migrans (OLM)), Toxocariasis (visceral larva migrans (VLM)), Toxoplasmosis, Trachoma, Trichinellosis, Trichomoniasis, Trichonosis Infection (Trichinosis), Trichuriasis (whipworm infection), Tuberculosis (TB), Tularemia (Rabbit fever), Typhoid fever, Typhoid Fever, Group D, Typhus, Typhus fever, *Ureaplasma urealyticum* infection, Vaginosis, Valley fever, Variant Creutzfeldt-Jakob disease (vCJD, nvCJD), Varicella (Chickenpox), Venezuelan equine encephalitis, Venezuelan hemorrhagic fever, *Vibrio cholerae* (Cholera), *Vibrio parahaemolyticus* enteritis, *Vibrio vulnificus* infection, Vibriosis, Viral infection, Viral hemorrhagic fever, Viral Hemorrhagic Fever (Ebola, Lassa, Marburg), Viral Hemorrhagic Fevers (VHF), Viral pneumonia, West Nile virus disease, Western equine encephalitis virus disease, White *piedra* (tinea blanca), Whooping Cough, Yellow Fever, Yersenia (*Yersinia*), *Yersinia pseudotuberculosis* infection, Yersiniosis, Zeaspora, Zika fever, Zika Virus, Zika virus disease, congenital, Zika virus disease, non-congenital, Zika Virus Infection (Zika), Zika virus infection, congenital, Zika virus infection, non-congenital, and Zygomycosis. In various embodiments, the infectious disease that can be treated by the disclosed methods and compositions is treated, while healthy cells are spared.

In one embodiment, the invention is a method of activating at least one γδ T cell in a subject, comprising the step of administering an anti-Vδ1 antibody or antigen-binding fragment thereof as defined herein.

In one embodiment, the invention is a method of causing or increasing proliferation of γδ T cells in a subject, comprising the step of administering to the subject an anti-Vδ1 antibody or antigen-binding fragment thereof as defined herein.

In one embodiment, the invention is a method of causing or increasing γδ T cell degranulation in a subject, comprising the step of administering to the subject an anti-Vδ1 antibody or antigen-binding fragment thereof as defined herein.

In one embodiment, the invention is a method of causing or increasing γδ T cell killing activity (e.g. T cell mediated killing activity) in a subject, comprising the step of administering to the subject an anti-Vδ1 antibody or antigen-binding fragment thereof as defined herein. In one embodiment, the invention is a method of causing or increasing γδ T cell killing activity (e.g. T cell mediated killing activity) in a subject, while sparing healthy cells, comprising the step of administering to the subject an anti-Vδ1 antibody or antigen-binding fragment thereof as defined herein.

In one embodiment, the invention is a method of causing or increasing γδ T cytotoxicity in a subject, comprising the step of administering to the subject an anti-Vδ1 antibody or antigen-binding fragment thereof as defined herein. In one embodiment, the invention is a method of causing or increasing γδ T cytotoxicity in a subject, while sparing healthy cells, comprising the step of administering to the subject an anti-Vδ1 antibody or antigen-binding fragment thereof as defined herein.

In one embodiment, the invention is a method of causing or increasing γδ T cell mobilization in a subject, comprising the step of administering to the subject an anti-Vδ1 antibody or antigen-binding fragment thereof as defined herein.

In one embodiment, the invention is a method of increasing survival of γδ T cells in a subject, comprising the step of administering to the subject an anti-Vδ1 antibody or antigen-binding fragment thereof as defined herein.

In one embodiment, the invention is a method of or increasing resistance to exhaustion of γδ T cells in a subject, comprising the step of administering to the subject an anti-Vδ1 antibody or antigen-binding fragment thereof as defined herein.

According to a further aspect of the invention, there is provided a method of stimulating an immune response in a subject, the method comprising administration to the subject an anti-Vδ1 antibody or antigen-binding fragment thereof in an amount effective at stimulating an immune response.

Uses of Antibodies or Antigen-Binding Fragments Thereof

According to a further aspect of the invention, there is provided the use of an anti-Vδ1 antibody or antigen-binding fragment thereof as described herein to study antigen recognition, activation, signal transduction or function of γδ T cells (in particular Vδ1 T cells). As described herein, the antibodies have been shown to be active in assays which can be used to investigate γδ T cell function. Such antibodies may also be useful for inducing the proliferation of γδ T cells, therefore may be used in methods of expanding γδ T cells (such as Vδ1 T cells).

Antibodies which bind to the Vδ1 chain can be used to detect γδ T cells. For example, the antibody may be labelled with a detectable label or reporter molecule or used as a capture ligand to selectively detect and/or isolate Vδ1 T cells in a sample. Labelled antibodies find use in many methods known in the art, for example immunohistochemistry and ELISA.

The detectable label or reporter molecule can be a radioisotope, such as $^{3}H$, $^{14}C$, $^{32}P$, $^{35}S$, or $^{125}I$; a fluorescent or chemiluminescent moiety such as fluorescein isothiocyanate, or rhodamine; or an enzyme such as alkaline phosphatase, β-galactosidase, horseradish peroxidase, or luciferase. Fluorescent labels applied to antibodies of the invention may then be used in fluorescence-activated cell sorting (FACS) methods.

Thus in various embodiments, the invention includes in vivo methods of modulating γδ T cells, methods of binding γδ T cells, methods of targeting γδ T cells, methods of activating γδ T cells, methods of proliferating γδ T cells, methods of expanding γδ T cells, methods of detecting γδ T cells, methods of causing γδ T cell degranulation, methods of causing γδ T cell mediated killing activity, methods of selecting antibodies or antigen-binding fragments thereof, the methods comprising the step of administering an anti-γδ antibody or antigen-binding fragment thereof to a subject as described herein.

Medicaments for Modulating Gamma Delta T Cells

The anti-vδ1 antibodies or antigen-binding fragments thereof as described herein may be used to modulate or useful for modulating delta variable 1 chain (Vδ1) T cells in a patient in situ (i.e. in vivo). The antibodies or antigen-binding fragments thereof may be comprised in medicaments for such purposes.

Modulation of Vδ1 T cells may include:

- expansion of the Vδ1 T cells, e.g. by selectively increasing the number of Vδ1 T cells or promotion of survival of Vδ1 T cells;
- stimulation of the Vδ1 T cells, e.g. by increasing Vδ1 T cell potency, i.e. increasing target cell killing;
- prevention of Vδ1 T cell exhaustion, e.g. by increasing persistence of the Vδ1 T cells;
- degranulation of Vδ1 T cells;
- increase in NCR expression;
- increase 4-1BB expression
- immunomodulation of the Vδ1 T cells, e.g. by downregulation of Vδ1 TCR cell surface expression, i.e. by causing Vδ1 TCR internalisation or reduced expression of Vδ1 TCR protein, or blocking the Vδ1 TCR from binding; and/or
- downregulation of a TCR/CD3 complex.

Unlike anti-Vδ1 antibodies of the prior art which focus on depletion of Vδ1 T-cells, the antibodies of the present invention are useful for the activation of Vδ1 T-cells via the TRDV1-binding domain. Although they may cause downregulation of the TCRs on T-cells to which they bind, they do not cause Vδ1 T-cell depletion, but rather they stimulate the T-cells and hence may be useful in therapeutic settings that would benefit from the activation of this compartment of T-cells. Activation of Vδ1 T-cells is evident through TCR downregulation, CD3 downregulation, changes in activation markers such as CD25 and Ki67 and degranulation marker CD107a. Activation of Vδ1 T-cell in turn triggers release of inflammatory cytokines such as INFγ and TNFα to promote immune licensing.

Medicaments that Modulate Immune Cell Markers on Vδ1+ Cells

The antibody or antigen-binding fragment thereof may modulate immune cell markers of Vδ1+ cells upon administration to a patient.

An antibody or antigen-binding fragment thereof described herein may also be assessed for its suitability for its therapeutic use by measuring γδ T modulation. For example, by measuring a change in the levels of CD25 or CD69 or CD107a present on a Vδ1+ T-cell or cells in a model system. Such markers are often used as markers of lymphocyte modulation (e.g. proliferation or degranulation) and can be measured following application of an antibody or antigen-binding fragment thereof as described herein, e.g. by flow cytometry. Surprisingly, during such assessments (e.g. see e.g. Examples 7, 17, 18) it was observed that antibodies as described herein conferred measurably higher levels of CD25 or CD69 or CD107a levels on target Vδ1+ T-cells. Optionally, the change in phenotype of a Vδ1+ cell or population thereof tested in the model system can then be compared to the change in phenotype when an alternative comparator antibody is applied (e.g. OKT-3, TS8.2, etc.) to said equivalent γδ T cells.

Hence in one aspect of the invention, there is provided a method of assessing an antibody or antigen-binding fragment thereof which binds to the Vδ1 chain of a γδ TCR for therapeutic use comprising administering the antibody or antigen-binding fragment thereof to a cell population comprising Vδ1+ cells and determining the effect on the level of CD25 and/or CD69 and/or CD107a on the surface of the Vδ1+ cells. The effect on the level of CD25, CD69 and/or CD107a may be determined/measured over a period of time. It will be understood that the effect can be measured in comparison to the level of CD25 and/or CD69 and/or CD107a on the surface of the Vδ1+ cell when said antibody is not applied to said cell over the same period of time. In a further aspect of the invention there is provided a method of selecting or characterizing or comparing the antibodies or antigen-binding fragments thereof as described herein which bind to the Vδ1 chain of a γδ TCR by adding said antibodies to a cell population comprising Vδ1+ cells and then measuring the level (or expression) of CD25 or CD69 or CD107a on the surface of said Vδ1+ cells.

Medicaments that Modulate Growth Properties or Numbers of Vδ1+ Cells

The antibody or antigen-binding fragment thereof may modulate the growth properties of Vδ1+ cells upon administration to a patient. For example, the antibody or antigen-binding fragment thereof may expand Vδ1+ cells.

An alternate approach to measuring γδ T proliferation may include measuring the change in relative number of Vδ1+ cells over time when applying an antibody or antigen-binding fragment thereof as described herein to model systems containing said cells. Surprisingly, during such assessments it was observed that antibodies as described herein where able to measurably increase the number of said Vδ1+ T-cells (e.g. see e.g. Example 10, 17 and 18), Optionally this change in number can then be compared to the change in number observed when an alternative comparator antibody is applied (e.g. anti-OKT3) to said model systems.

Hence in another aspect of the invention, there is provided a method of assessing an antibody or antigen-binding fragment thereof which binds to the Vδ1 chain of a γδ TCR comprising administering the antibody or antigen-binding fragment thereof to a cell population comprising Vδ1+ cells and determining the effect on the number of Vδ1+ cells in the population. The effect on cell number can be determined/measured over a period of time. It will be understood that the effect can be measured in comparison to the effect on cell numbers observed when said antibody is not applied to the cell population for the same period of time. In a further aspect of the invention there is provided a method of selecting or characterizing or comparing antibodies or antigen-binding fragment thereof as described herein which bind to the Vδ1 chain of a γδ TCR by applying said antibodies to a cell population comprising Vδ1+ cells and then measuring the number of said cells over time.

Medicaments that Modulate the Proliferative Capacity and Numbers of Vδ1+ Cells

An ideal therapeutic antibody or antigen-binding fragment thereof as described herein which binds to the Vδ1 chain of a γδ TCR may be one that is capable of enhancing the proliferation of Vδ1+ cells in vivo. Such antibodies can then be employed as medicaments designed to specifically increase the Vδ1+ cell number in a subject or patient. For example:

Cancer:

Relative increases in the numbers of Vδ1+ cells have been reported as a positive prognostic indicator associated with improved outcomes for many cancer (for example see Gentles et al (2015) Nature Immunology 21: 938-945; Wu et al. (2019) Sci. Trans. Med. 11(513): eaax9364; Catellani et al. (2007) Blood 109(5): 2078-2085). In one embodiment, presented herein is a medicament capable of increasing the relative or absolute numbers of Vδ1+ cells in situ within in a cancer patient.

Pathogenic/Parasitic/Viral Infections:

Vδ1+ cell enrichment is observed during host defense against numerous acquired pathogenic/parasitic/viral infections. For recent general review see Zhao et al. (2018) Immunol. Res. 2018:5081634. Furthermore, increased numbers Vδ1+ are also considered protective against a variety of DNA and RNA viral infections. For example, increased numbers are also considered protective during CMV infections associated with allogeneic transplants (see van Dorp et al. (2011) Biology of Blood and Marrow Transplantation 17(2): S217). Additionally, Vδ+ cell numbers increase in patients with coronavirus infection (Poccia et al. (2006) J. Infect. Dis. 193(9): 1244-1249).

In another embodiment, presented herein is a medicament capable of increasing the relative or absolute numbers of Vδ1+ cells in a subject or patient harboring a pathogenic infection.

Stem Cell Transplant:

Increased numbers of Vδ1+ cells have also been associated with less disease relapse, fewer viral infections, higher overall and disease-free survival and favorable clinical outcomes in general during hematopoietic stem cell transplant (for example see Aruda et al. (2019) Blood 3(21): 3436-3448 and see Godder et al. (2007) Bone Marrow Transplantation 39: 751-757). Hence another embodiment, presented herein is a medicament capable of increasing the relative or absolute numbers of Vδ1+ cells in a subject as part of a treatment regimen supporting a stem cell transplant.

Consequently, a medicament capable of preferentially or specifically increasing the numbers of Vδ1+ cells in-situ is highly desirable.

Medicaments that Maintain or Induce or Increase Vδ1+ Cell Cytokine Secretion

Cytokines are a large group of proteins, peptides or glycoproteins that are secreted by specific cells of immune system. They are a category of signaling molecules that mediate and regulate immunity, inflammation, and hematopoiesis. A number of cytokines have been implicated in ameliorating signs and symptoms of disease through either direct or indirect modulation of the tumour and cellular microenvironment, autoimmune tissue and associated microenvironment, or virally infected tissue or cellular environment. Exemplar pro-inflammatory cytokines include tumour necrosis factor-alpha (TNFα) and Interferon-gamma (IFNγ).

However, many such cytokines exhibit unfavourable toxicity when dosed systemically. For example, whilst TNFα can induce the haemorrhagic necrosis of transplanted tumours, and has been reported to exert synergic anti-tumour effects when combined with other chemotherapeutic drugs, various clinical trials with systemic recombinant human TNFα (rhTNFα) have highlighted significant dose limiting side effects inclusive of hypotension, rigors, phlebitis, thrombocytopenia, leucopenia and hepatotoxicity, fever, fatigue, nausea/vomiting, malaise and weakness, headache, chest tightness, low back pain, diarrhoea and shortness of breath.

Use of recombinant IFNγ also faces similar systemic toxicity challenges. For example, whilst in a cancer setting IFNγ can exert favorable pleiotropic effects including MHC class I and II upregulation to stimulate anti-tumour immunity, increasing T-cell infiltration, conferring anti-angiogenesis effects, inducing chemokine/cytokine secretion, and exerting direct cancer cell anti-proliferative effects, adverse side-effects are also observed. These include fever, headache, chills, fatigue, diarrhoea, nausea, vomiting, anorexia, transient increases in hepatic transaminase, and transient decreases in granulocyte and leucocyte counts.

For a recent review on both the potential and limitation of systemic recombinant TNFα and IFNγ see Shen et al. (2018) Cell Prolif. 51(4): e12441.

Hence there is a need for more in situ controlled, more localized, more tissue or cell specific production of such cytokines. For example, more controlled expression or induction of pro-inflammatory cytokines is proposed as one approach whereby “cold” tumours can be turned “hot”. Hot tumours are also sometimes termed “T-cell-inflamed” because of an increase in the number or density of CD45+ T-cells also observed. See Bonaventura et al. (2019) Front. Immunol. 10: 168 for a recent review.

For such reasons, an ideal therapeutic antibody or antigen-binding fragment thereof as described herein which binds to the Vδ1 chain of a γδ TCR may be one that can maintain or enhance or induce the secretion of cytokines in Vδ1+ cells in vivo. Such antibodies can then be employed as medicaments designed to specifically increase or induce cytokines in a subject or patient and in a more localized, less systemic manner and one which better correlates with the distribution of Vδ1+ cells in said subject or patient.

Remarkably, when antibodies as described herein which bind to the Vδ1 chain of a γδ TCR are applied to Vδ1+ cells, a significantly higher level of secreted cytokines are observed. More specifically, and as a non-limiting example, a significant higher level of TNFα and IFNγ is observed. See e.g. Example 15.

Hence in another aspect of the invention, there is provided a method of assessing an antibody or antigen-binding fragment thereof which binds to the Vδ1 chain of a γδ TCR comprising administering the antibody or antigen-binding fragment thereof to a cell population comprising Vδ1+ cells and determining the amount of at least one cytokine produced by the cell population. The amount of cytokine produced can be determined/measured over a period of time and optionally compared to the amount observed when said antibody is not applied to the cell population for the same period of time. In one embodiment, the observed level of cytokine produced when the antibody is administered to the cell population is more than about 10%, more than about 20%, more than about 30%, more than about 50%, more than about 100%, more than about 150%, more than about 200%, more than about 250%, more than about 300%, more than about 350%, more than about 400%, more than about 450%, more than about 500%, more than about 1000%, relative to the level of cytokine produced when the antibody is not applied. In a further aspect of the invention, the cytokine is a pro-Inflammatory cytokine. In a further aspect of the invention, the cytokine is the TNF-α cytokine. In a further aspect of the invention, is IFN-γ cytokine.

In a further aspect of the invention there is provided a method of selecting or characterizing or comparing antibodies or antigen-binding fragment thereof as described herein which bind to the Vδ1 chain of a γδ TCR by applying said antibodies to a cell population comprising Vδ1+ cells and then measuring the level of at least one cytokine generated. In a further aspect of the invention the cytokine measured is TNF-α cytokine and/or IFN-γ cytokine.

In a further aspect of the invention, there is provided a method of assessing an antibody or antigen-binding fragment thereof which binds to the Vδ1 chain of a γδ TCR by applying said antibody or antigen-binding fragment thereof to a cell population comprising Vδ1+ cells and measuring the effect of the antibody on modulating a colder or cold tumour to become a hotter or hot tumour by determining the quantity of proinflammatory cytokines produced and/or the number or density of CD45+ T-cells present in the tumour or tumour microenvironment.

Medicaments that Maintain or Induce or Increase Vδ1+ Cell Granzyme B Activity

Granzyme B is a serine protease commonly found in the granules of natural killer cells (NK cells) and cytotoxic T cells. It is secreted by these cells along with the pore forming protein perforin to mediate apoptosis in target cells, such as diseased cells.

When Vδ1+ cells are incubated in co-cultures with target diseased cells (such as cancer cells) in model systems, levels of Granzyme B levels and activity can be measured in the target diseased cells ahead of lysis. Remarkably when an antibody or antigen-binding fragment thereof as described herein which binds to the Vδ1 chain of a γδ TCR is then applied to such co-cultures of Vδ1+ cells and cancer cells in such model systems, higher Granzyme B levels and activity are then observed in the diseased cancer cells ahead of cell death (see e.g. Example 16).

Hence in another aspect of the invention, there is provided a method for assessing an antibody or antigen-binding fragment thereof which binds to the Vδ1 chain of a γδ TCR comprising administering the antibody or antigen-binding fragment thereof to a co-culture comprising Vδ1+ cells and diseased cells (such as cancer cells) and measuring the effect on the amount of Granzyme B produced by the diseased cells in the co-culture. The amount of cytokine produced can be determined/measured over a period of time and optionally compared to the amount observed when said antibody is not applied to said co-cultures for the same period of time. In one embodiment, the level of Granzyme B measured when said antibody is applied to said co-culture is more than about 10%, more than about 20%, more than about 30%, more than about 40%, more than about 50%, more than about 70%, more than about 80%, more than about 90%, more than about 100%, more than about 200%, relative to the Granzyme B level observed when said antibody is not applied.

In a further aspect of the invention there is provided a method of selecting or characterizing or comparing antibodies or antigen-binding fragment thereof as described herein which bind to the Vδ1 chain of a γδ TCR by applying said antibodies to a co-culture comprising Vδ1+ cells and diseased cells and then measuring the quantity or activity of Granzyme B in the diseased cell.

Figure 64A:
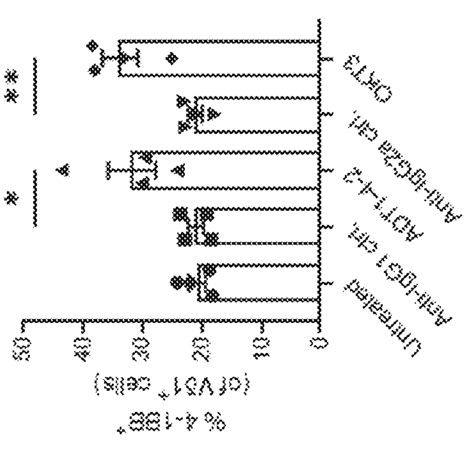
FIGS. 64A-64C: Stimulation with a high-affinity anti-Vδ1+ antibody enhances expression of 4-1BB on Vδ1 γδ T cells.
Figure 64B:
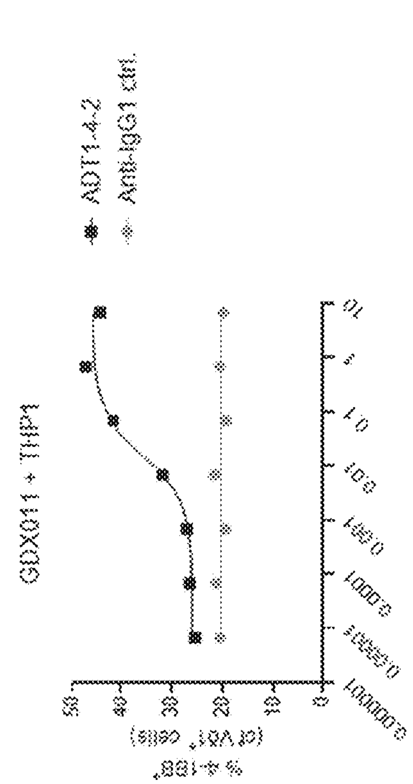
Figure 64C:
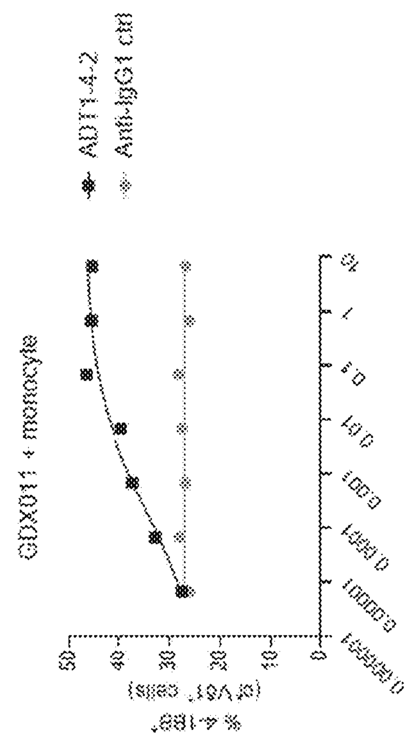
Figure 65A:
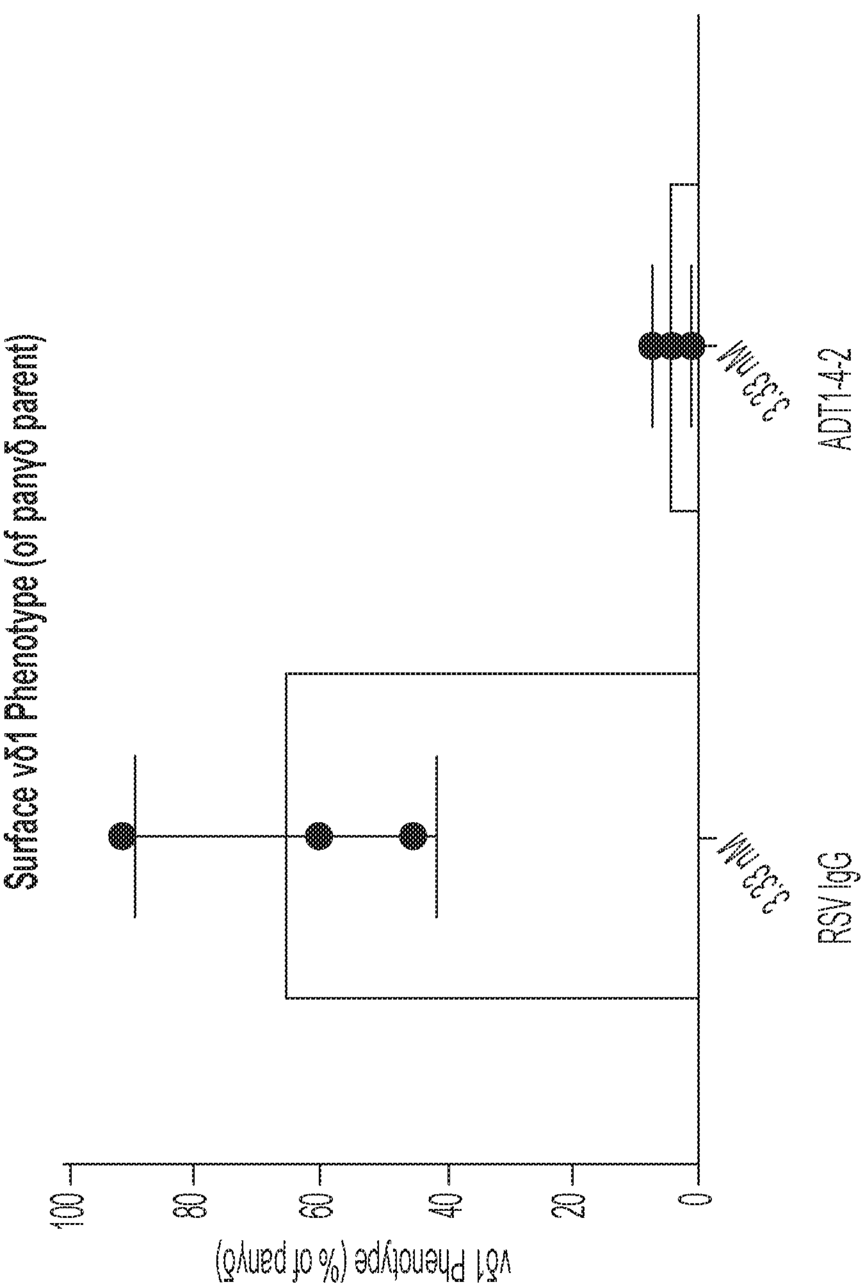
FIGS. 65A-65D: Upregulation of Natural Cytotoxicity Receptors (NCRs) on Vδ1+ T cells in primary PBMCs (FIG. 65A) Experimental culture set-up inclusive of confirmatory TCR downregulation analysis: Human PBMC cultures from three different donors were incubated with 3.33 nM of exemplar affinity-matured ADT1-4 and ADT1-7 anti-Vδ1 antibodies clones as indicated (see also FIG. 65B, FIG. 65C, and FIG. 65D) or anti-RSV controls for 10-days. Cultures were also supplemented with 4 ng/ml IL-2 and 10 ng/ml IL-15 (Miltenyi, 130-097-746 and Peprotech, 200-15-500 ug respectively). After 10 days in culture, % Vδ1+ T cells were analyzed by flow cytometry. All cultures incubated with the anti-Vδ1 antibodies exhibited marked reduction in detectable Vδ1+ cells (as % pan-Gamma) relative to the anti-RSV control cultures. A representative and typical result is shown here for one such antibody. Through such analysis, it is possible to confirm that all affinity-matured anti-Vδ1 antibodies included in this study exhibited marked target engagement and conferred TCR downregulation.
Figure 65B:
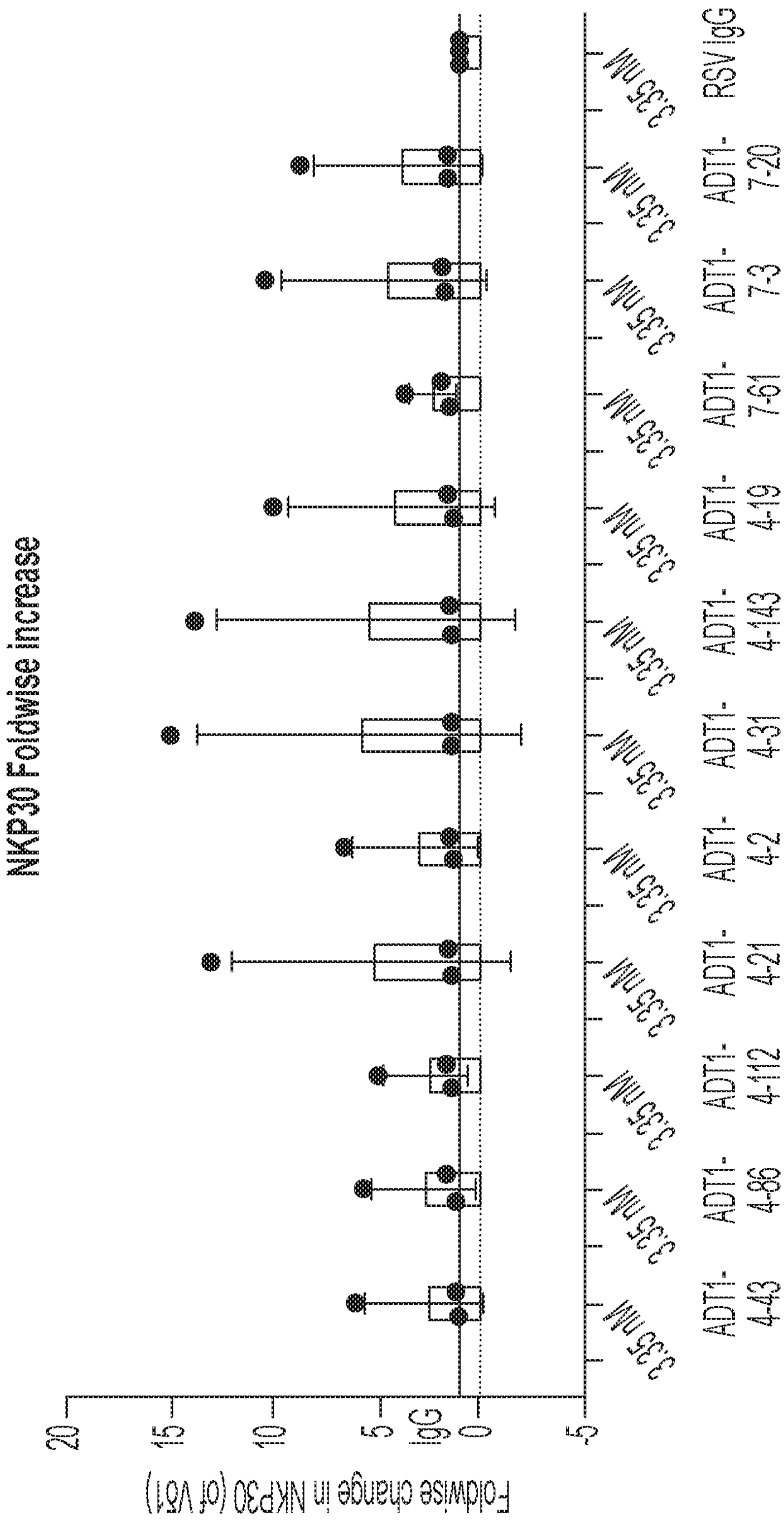
Figure 65C:
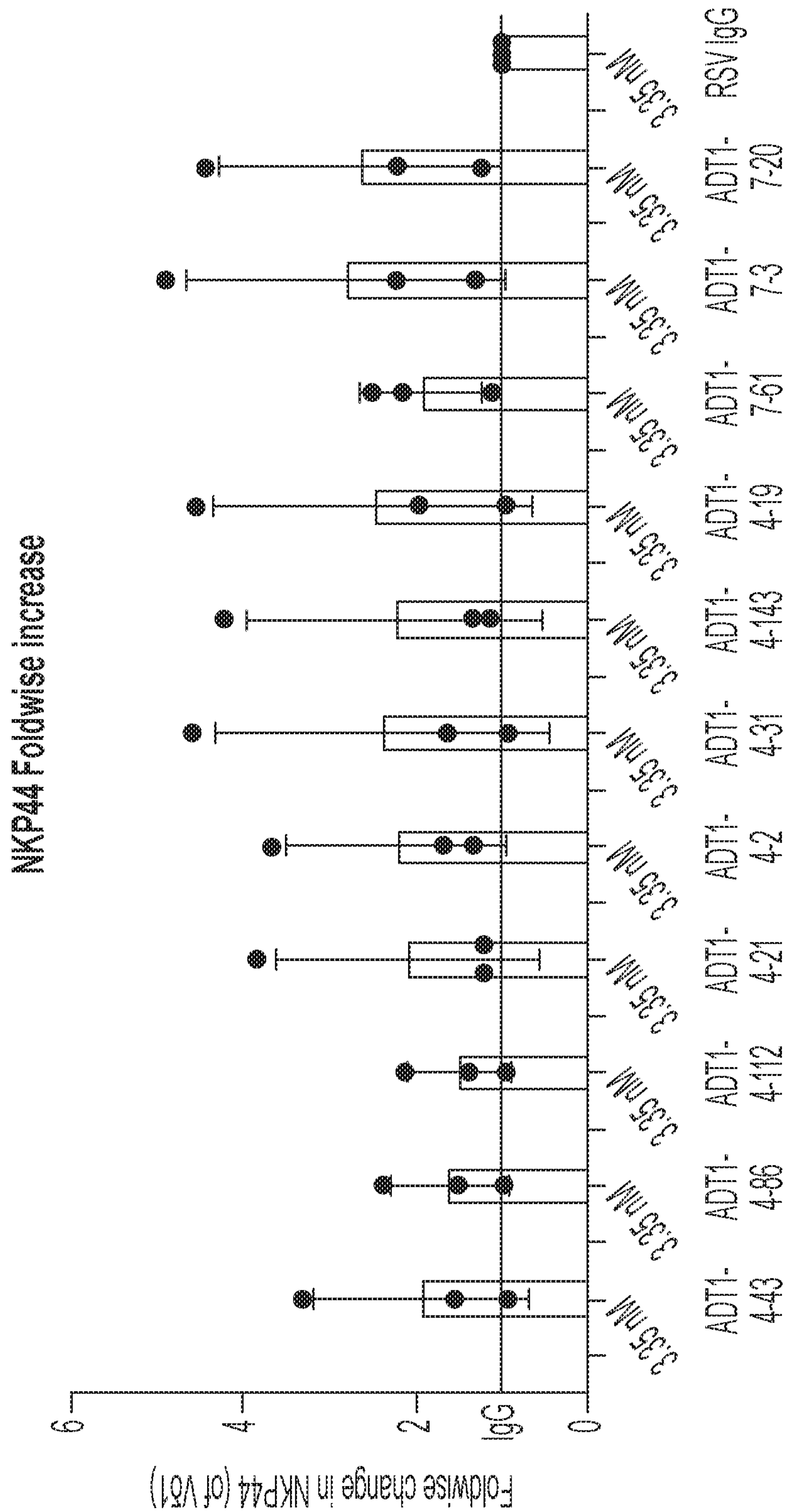
Figure 65D:
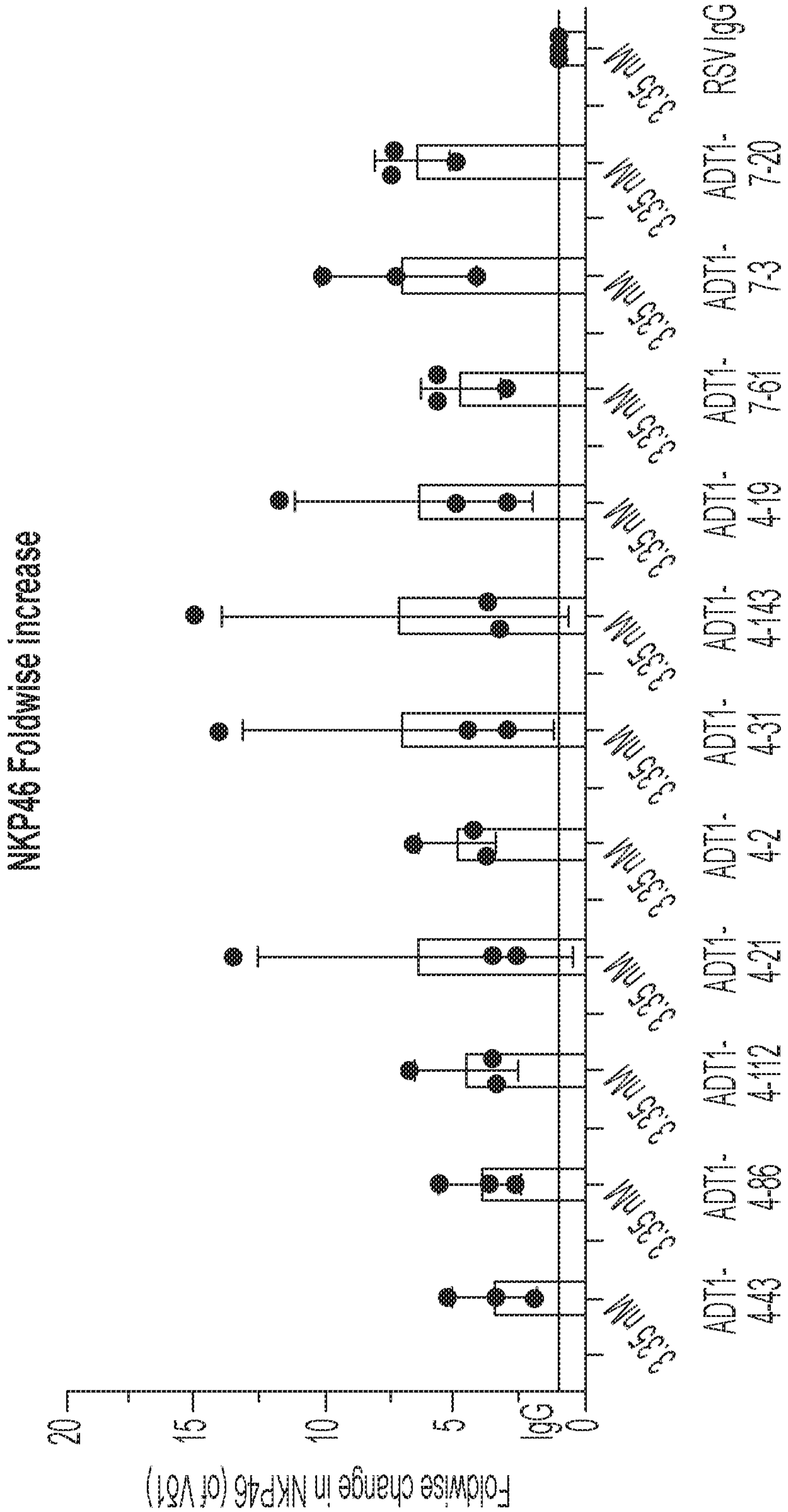

Medicaments that Upregulate the Expression of 4-1 BB (CD137) Specifically on Vδ1+ T Cells 4-1BB (CD137), a member of the TNFR superfamily, is an inducible T-cell costimulatory molecule. With few exceptions, expression of 4-1BB is activation dependent. Typically, 4-1BB is less detectable on conventional (a) resting T cells or associated T-cell lines. However, 4-1BB is stably upregulated when conventional T cells are activated by a variety of agonists such as plate-bound anti-CD3, concanavalin A, phytohemagglutinin, interleukin (IL)-2, IL-4, and CD28, as well as phorbol myristic acetate and ionomycin, either in isolation or in combination with APCs. However, whilst it is known such agents can universally upregulate T-cells, there remains a need for a less sledgehammer-like, more targeted approach to avoid overstimulation often conferred by anti-CD3 medicaments and the like. Furthermore, and although the role and function of 4-1BB in 'conventional' αβ T cells have been well studied, its role in γδ T cells has been less explored. Nevertheless, in at least one report, Lee at al 2013 (https://doi.org/10.1002/eji.201242842) demonstrated that whilst 4-1BB is not normally expressed on resting human peripheral blood human γδ T cells (sub-type not fully defined, likely Vγ9Vδ2 predominant), 4-1 BB upregulation can be achieved in the presence of IPP/IL-2 cytokine for 7-days. Further, the authors then demonstrated that the resulting γδ T cells are more effective at preventing *Listeria* infection in an adoptive mouse model. More recently, Park and Lee 2021 (https://doi.org/10.1038/s12276-021-00576-0) have concurred with these observations, at least for peripheral blood dominant cell types, wherein they state that 4-1BB is known to enhance Vγ9Vδ2 T cells (whilst also conceding that the role and mechanism remain unclear). Therefore, there is a need for medicaments that specifically enhance the expression 4-1BB on γδ T cells to treat a disease or disorder such to ameliorate at least one sign or symptom of a disease or disorder. This is particularly the case for in situ scenarios where, and as discussed elsewhere herein, such cells include tissue resident Vδ1+ T cells often considered 'resting'. Hence in a further embodiment there is presented herein a class of high affinity human anti-Vδ1 antibodies capable of significantly increasing levels of 4-1BB in Vδ1+ T-cells (see FIG. 64). And in a still further embodiment, presented herein are a class of class of high affinity human anti-Vδ1 antibodies capable of significantly increasing levels of 4-1BB in tissue-derived Vδ1+ T-cells. A significant increase could, for example, be $p<0.05$ by Ordinary one-way ANOVA with Sidak's post test.

Medicaments that Upregulate the Expression of Natural Cytotoxicity Receptors (NCRs) on Vδ1$^+$ T Cells As discussed elsewhere herein, a desired medicament may be one which specifically targets and activates a most desired subset of T cells; specifically, one which targets and activates Vδ1+ T cells. Given the capacity of such Vδ1+ T cells to recognize and distinguish stressed or dysregulated 'self' signatures (such as those signatures found on infected cells or cancerous cells) with the aid of sensing mechanism inclusive of engagement via Natural Cytotoxicity Receptors (NCRs), then an ideal medicament might be one which is capable of upregulating NCRs on Vδ1+ T cells. In studies presented herein (see FIG. 65), all affinity matured anti-Vδ1+ antibodies studied conferred NCR upregulation upon Vδ1+ T cells in extended PBMC culture models.

Medicaments that Expand Polyclonal Vδ1+ Cell Populations

An ideal antibody medicament may also be one designed to ensure the expanding Vδ1+ cells do not become too clonally focused at the hypervariable CDR3 sequence level. Hence an ideal antibody medicament may be designed such to avoid inducing proliferation Vδ1+ cells by binding to specific or 'private' 61+ CDR3 sequence paratopes. Rather, the antibody may bind via conserved germline sequences present on all Vδ1+ T cell receptors and in a gamma-chain independent manner, rather than bind to sequences presented only a sub-set of Vδ1+ cells.

Hence an ideal antibody medicament may stimulate the expansion Vδ1+ cells to generate a plurality of Vδ1+ cells containing a mixture of CDR3 sequences. This in turn would result in an in vivo expanded heterogenous polyclonal population of Vδ1+ cells displaying different CDR3 sequences on delta variable 1 chains. Remarkably, during analysis of expanded Vδ1+ cell populations generated by a method of adding an antibody or antigen-binding fragment thereof as described herein to a starting population of immune cells containing Vδ1+ cells, extensive polyclonality is observed by RNAseq based methodologies designed to sequence through the CDR3 hypervariable regions of RNA extracted (see e.g. Example 10).

Accordingly in one aspect, there is provided a method of assessing an antibody or antigen-binding fragment thereof which binds to the Vδ1 chain of a γδ TCR comprising administering the antibody or antigen-binding fragment thereof to a cell population comprising Vδ1+ cells and determining the polyclonality of the expanded Vδ1+ cells. It is desirable for an antibody medicament to generate an expanded polyclonal population containing a plurality of Vδ1+ CDR3 sequences. Polyclonality can be determined using methods known in the art, such as by nucleic acid sequencing approaches capable of analysing the Vδ1 chain hypervariable CDR3 content of said Vδ1+ cells.

Medicaments that Expand Polyclonal Vδ1+ Cells for Extended Periods of Time

An ideal antibody medicament may be able to enhance or promote or stimulate the proliferation of primary Vδ1+ cells without exhausting such cells in vivo. For example, and by way of comparison, anti-CD3 medicaments such as OKT3 (e.g. Muronomab), whilst capable of expanding CD3 positive T-cells may also exhaust or induce anergy. To assess the capacity of antibodies as described herein and which bind to the Vδ1 chain of a γδ TCR to drive continued cell division of viable Vδ1+ cells, longer term proliferation studies were undertaken. Remarkably these studies revealed that antibodies as described herein and which bind to the Vδ1 chain of a γδ TCR are capable of driving cell division/proliferation of viable and still functionally cytotoxic Vδ1+ cells for over 40 days (see e.g. Example 10).

In one embodiment, there is provided a method of assessing an antibody or antigen-binding fragment thereof which binds to the Vδ1 chain of a γδ TCR comprising applying the antibody or antigen-binding fragment thereof to a cell population and monitoring the length of time Vδ1+ cell division occurs. Ideally, the antibody is capable of stimulating Vδ1+ cell division for a period of 5 to 60 days, such as at least 7 to 45 days, 7 to 21 days, or 7 to 18 days.

In a further embodiment, there provided an antibody or antigen-binding fragment thereof as described herein which binds to the Vδ1 chain of a γδ TCR and which when administered to a patient is capable of stimulating Vδ1+ cell division to increase the number by at least 2-fold in number, at least 5-fold in number, at least 10-fold in number, at least 25-fold in number, at least 50-fold in number, at least 60-fold in number, at least 70-fold in number, at least 80-fold in number, at least 90-fold in number, at least 100-fold in number, at least 200-fold in number, at least 300-fold in number, at least 400-fold in number, at least 500-fold in number, at 600-fold in number, or at least 1,000-fold in number.

In a further aspect of the invention there is provided a method of selecting or characterizing or comparing antibodies or antigen-binding fragment thereof as described herein which bind to the Vδ1 chain of a γδ TCR by applying said antibodies to Vδ1+ cells or mixed cell population containing Vδ1+ cells and then measuring Vδ1+ cell numbers over time.

Medicaments that Modulate Non-Vδ1+ Immune Cells Through Targeting Vδ1+ Immune Cells An antibody or antigen-binding fragment thereof as described herein may also be assessed by measuring Vδ1+ cell mediated modulation of other immune cells. For example, a change observed in a non-γδ T cell 'fraction' can be measured following application of an antibody or antigen-binding fragment thereof as described herein to a model system comprising mixed population of immune cells such as one comprising human tissue αβ cells and γδ T cells. Further, the effect on non-γδ cell types in said models can be measured by flow cytometry. For example, by measuring the relative change in numbers of CD8+ αβ T cells upon addition of an antibody or antigen-binding fragment thereof as described herein to mixed cultures comprising γδ T cells and non-γδ T cells. Optionally, the observed change in number or phenotype of a non-γδ T-cell CD8+ lymphocyte population can then be compared to the change in number when an alternative comparator antibody is applied (e.g. OKT-3) to said mixed population.

Hence in another aspect of the invention, there is provided a method of assessing an antibody or antigen-binding fragment thereof which binds to the Vδ1 chain of a γδ TCR comprising administering the antibody or antigen-binding fragment thereof to a mixed population of immune cells or tissues comprising Vδ1+ cells and Vol-negative immune cells and measuring the effect on the Vol-negative immune cells. The effect can be determined/measured over a period of time and optionally compared to the effect observed in Vδ1-negative cells when said antibody is not applied for the same period of time. The effect may be measured as a change in the number of Vol-negative immune cells. For example, the antibody may increase the number Vδ1-negative immune cells by more than about 10%, more than about 20%, more than about 30%, more than about 40%, more than about 50%, more than about 70%, more than about 80%, more than about 90%, more than about 100%, more than about 500%, relative to the levels observed when said antibody is not applied.

In a further aspect of the invention the modulated Vδ1-negative cell is a CD45+ cell. In a further aspect of the invention the modulated cell is a αβ T-cell. In a further aspect of the invention the modulated αβ+ cell is CD8+ lymphocyte. In a further aspect of the invention the modulated αβ T-cell, or population thereof, exhibits evidence of enhanced cell division. In a further aspect of the invention there is provided a method of selecting or characterizing or comparing antibodies or antigen-binding fragment thereof as described herein which bind to the Vδ1 chain of a γδ TCR by administering said antibodies to a population of mixed immune cells comprising Vδ1+ cells and Vδ1-negative immune cells and then measuring an effect conferred on the Vδ1-negative cell population by Vδ1+ cells modulated by said antibodies or antigen-binding fragments thereof.

Optionally, and during "Vδ1+ cell mediated immune system modulation" as conferred by an antibody or antigen-binding fragment thereof as described herein, a concomitant increase in Vδ1+ cell number is also observed. And whilst not being bound by this theory, it is possible that said increase in Vδ1+ cell number may be causal in driving the concomitant expansion of co-present Vδ1-negative immune cells, such as αβ T-cells. An alternate hypothesis may be that antibody-induced cytokine secretions from the Vδ1+ T cells stimulate the expansion of Vδ1-negative immune cells.

In a further aspect of the invention the observed increase in αβ+CD8+ lymphocyte population is compared to a comparator antibody such as OKT3 antibody or alternate anti-Vδ1 antibody. In a further aspect of the invention there is provided a method of selecting or characterizing or comparing antibodies or antigen-binding fragment thereof as described herein which bind to the Vδ1 chain of a γδ TCR by applying said antibodies to a population of mixed immune cells comprising Vδ1+ T-cells and αβ T-cells and then measuring the numbers of CD8+αβ+ T-cells lymphocytes over time.

Medicaments that Modulate Tumour Infiltrating Lymphocytes (TILs)

An antibody or antigen-binding fragment thereof as described herein may also be assessed by measuring the effect conferred on tumour-infiltrating populations (TILs) in model systems. Surprisingly (see e.g. Example 18) during such assessments antibodies as described herein measurably modulated TIL populations in human tumours. For example, a change in either the number or phenotype of γδ+ lymphocyte TIL population or the non-γδ lymphocyte TIL population is measured following application of an antibody or antigen-binding fragment thereof as described herein to a human tumour such as a human renal cell carcinoma. Optionally, the observed change in number or phenotype of either the γδ+ lymphocyte TIL population or non-γδ lymphocyte TIL population can then be compared to the change observed when an alternative comparator antibody is applied (e.g. OKT-3) to said model system.

Hence in another aspect of the invention, there is provided a method of assessing an antibody or antigen-binding fragment thereof which binds to the Vδ1 chain of a γδ TCR comprising administering the antibody or antigen-binding fragment thereof to TILs located in, or derived from, a human tumour and determining the effect on the number of TILs. The effect can be determined/measured over a period of time and optionally compared to the TIL number observed when said antibody is not applied over the same period of time. The effect may be an increase in the number of TILs. For example, the antibody may increase the number of TILs more than about 10%, more than about 20%, more than about 30%, more than about 40%, more than about 50%, more than about 70%, more than about 80%, more than about 90%, more than about 100% relative to the number of TILs observed when said antibody is not applied. In a further aspect, the TILs in which the number observed are γδ+ lymphocyte TIL cells and/or non-γδ lymphocyte TIL cells.

In a further aspect of the invention there is provided a method of selecting or characterizing or comparing antibodies or antigen-binding fragment thereof as described herein which bind to the Vδ1 chain of a γδ TCR cells antibodies by applying said antibodies to TIL or TILs located in or derived from a human tumour and then measuring the change in number of TIL or TILs cells over a period of time.

Medicaments that Modulate Human Vδ1+ Cytotoxicity

An antibody or antigen-binding fragment thereof as described herein may also be assessed by measuring the conferred effect on Vδ1+ mediated cell cytotoxicity. Surprisingly, during such assessments of antibodies as described herein (e.g. see e.g. Examples 19 and 27) measurably enhanced Vδ1+ mediated cell cytotoxicity was observed. For example, a reduction in the number of cancer cells or an increase in the number of killed cancer cells is observed following application of an antibody or antigen-binding fragment thereof to a model system comprising a mixed culture comprising Vδ1+ cells and said cancer cells. Optionally, the reduction in the number of cancer cells or the increase in the number of killed cancer cells can then be compared to the outcome when an alternative comparator antibody is applied (e.g. OKT-3) to said model systems.

Hence in another aspect of the invention, there is provided a method of assessing an antibody or antigen-binding fragment thereof which binds to the Vδ1 chain of a γδ TCR comprising applying the antibody or antigen-binding fragment thereof to a mixed population of cells comprising Vδ1+ cells and cancer cells and measuring the cytotoxicity of the Vδ1+ cells towards the cancer cells. The cytotoxicity may be measured by an increase in the number of dead cancer cells over a period of time, optionally compared to the number of dead cancer cells observed when said antibody is not applied to the mixed population of cells over the same period of time. For example, the observed increase in dead cells when said antibody is applied may be more than about 10%, by more than about 20%, by more than about 30%, by more than about 40%, by more than about 50%, more than about 70%, more than about 80%, more than about 90%, more than about 100%, more than about 200%, more than about 500%, relative to the number of dead cells observed when said antibody is not applied.

In a further aspect of the invention there is provided a method of selecting or characterizing or comparing antibodies or antigen-binding fragment thereof as described herein which bind to the Vδ1 chain of a γδ TCR cells by adding said antibodies to said population of mixed immune cells comprising human Vδ1+ cells and cancer cells and then measuring an increase in dead cancer cells overtime.

Medicaments that Modulate Vδ1+ Cell Target-to-Effector Cell Ratios (T:E Ratios)

An antibody or antigen-binding fragment thereof as described herein may also be assessed by measuring how said antibodies enhance Vδ1+ mediated cancer cell cytotoxicity by determining the target cell to effector cell ratio wherein the 50% of the target cells (EC50) are killed in a model system to assess said antibodies as potential medicaments. For example, mixed cultures comprising target cancer cells with human Vδ1+ effector cells. Surprisingly, during such assessments (e.g. see e.g. Example 19) antibodies as described herein favourably modify the EC50 T:E ratio in model systems. Such modifications can be measured as numbers of Vδ1+ cells required to observe 50% killing of cancer cells over a set time. This can also be reported as change or as fold-improvements or as percent-improvements in cytotoxicity towards said cancer cells. Optionally, the T:E ratio conferred by antibodies of this invention can then be compared to the T:E ratios when an alternative comparator antibody is applied (e.g. OKT-3) to said model systems. In some scenarios, the multispecific antibodies of the invention present opportunities for improved cancer cell cytotoxicity even at lower E:T ratios, compared to monospecific antibodies.

Hence in another aspect of the invention, there is provided a method of assessing an antibody or antigen-binding fragment thereof which binds to the Vδ1 chain of a γδ TCR comprising applying the antibody or antigen-binding fragment thereof to a mixed population of cells comprising human Vδ1+ cells and cancer cells and measuring the number of Vδ1+ cells required to kill 50% of the cancer cells. This may be measured relative to the number Vδ1+ cells required to kill 50% of cancer cells without application of said antibody, optionally over the same period of time. For example, the reduction in the number of Vδ1+ cells required to kill 50% of the cancer cells when said antibody is applied may be greater than about 10%, greater than about 20%, greater than about 30%, greater than about 40%, greater than about 50%, greater than about 70%, greater than about 80%, greater than about 90%, greater than about 100%, greater about 200%, greater than about 500%, relative to the number of Vδ1+ cells required to kill 50% of the cancer cells when said antibody is not applied.

In a further aspect of the invention there is provided a method of selecting or characterizing or comparing antibodies or antigen-binding fragment thereof as described herein which bind to the Vδ1 chain by adding said antibodies to said population of cells comprising Vδ1+ cells plus cancer cells and then measuring the numbers of Vδ1+ cells required to kill 50% of the cancer cells.

Medicaments which Enhance Vδ1+ Cell EC50 Cytotoxicity

An alternate way to measure the observed enhanced cytotoxicity of human Vδ1+ cells or population thereof is to measure the number of cells required to kill 50% of the cancer cells over a set period of time in condition A (such as starting control) and compare this to the number of cells required to kill 50% of the cancer cells over a set period of time in condition B (such as upon application of antibody of the invention as described herein).

Whilst it is recognized that there are a variety of ways to measure such parameters, to aid in understanding, the following non-limiting hypothetical example will be outlined:

Hypothetically, effector cell cytotoxicity enhancement can be measured as follows:—In condition A (control treatment) it is observed that 1000 Vδ1+ cells are required to kill 50% of the cancer cells over a set period of time (e.g. 5 hours). In condition B (e.g. application of antibody of the invention described herein) it is observed that 500 Vδ1+ cells were required to kill 50% of the cancer cell over the same period of time. Hence in this example, the application of an antibody has enhanced the cytotoxicity of the Vδ1+ cell population by 200%:

$$(1000/500)\times 100=200\%$$

For example (see e.g. Examples 19 to 21), surprisingly such percentage enhancements have been observed for antibodies of the invention as described herein.

In a further aspect of the invention there is provided a method of selecting or characterizing or comparing antibodies or antigen-binding fragment thereof as described herein which bind to the Vδ1 chain of a γδ TCR by adding said antibodies to said population of mixed immune cells comprising Vδ1+ cells and cancer cells and determining the relative or percent-change in cytotoxicity versus an equivalent or control experiment wherein there is no application of said antibody to said mixture of cells.

Medicaments which Enhance Vδ1+ Cells Diseased-Cell Specificity Whilst Sparing Healthy Cells Another approach to assess antibodies or antigen-binding fragments thereof as described herein is to measure how said antibodies modulate diseased-cell specific cytotoxicity. Surprisingly during such studies, it was discovered such antibodies can specifically enhance the Vδ1+ cell specific killing of diseased-cells such as cancer cells (e.g. see Examples 19 and 27) whilst sparing healthy or non-diseased cells. Ideal antibody medicaments administered to a patient to ameliorate a symptom of cancer will confer enhanced cytotoxicity specifically towards diseased cells whilst sparing healthy cells. And medicaments which enhance effector cell cytotoxicity specifically towards diseased cells, such as cancer cells, can be said to exhibit an enhanced therapeutic index (TI) over medicaments which do not selectively enhance effector cell cytotoxicity specifically towards said diseased cells. The therapeutic index is also referred to as therapeutic ratio and is a quantitative measurement of the relative safety of a drug. It is a comparison of the amount of a therapeutic agent that causes the therapeutic effect to the amount that causes toxicity e.g. by conferring undesirable death in related or relevant healthy cell populations. An antibody or antigen-binding fragment thereof as described herein may be assessed by measuring its ability to change or to enhance or to fold-improve Vδ1+ cell capacity to selectivity kill diseased cells over and above healthy cells in model systems. For example, said model systems may comprise Vδ1+ effector cells, cancer cells, and control cells (such as healthy cells). Optionally, the fold-improvement in selective diseased-cell killing conferred by antibodies of the invention can then be compared to the fold-improvement observed when an alternative comparator antibody is applied (e.g. OKT-3) to said model systems.

The diseased-cell specificity and diseased-cell specificity-enhancement of Vδ1+ cells can be measured in cultures comprising Vδ1+ cells, diseased cells, and healthy cells. For example, Vδ1+ specificity towards diseased cells can be measured by observing the number of cancer cells killed by the Vδ1+ cells and then comparing the number of healthy cells killed by the Vδ1+ cells. Such comparisons can be controlled by including equivalent numbers of diseased cells and healthy cells in a model system also containing Vδ1+ cells e.g. "tricultures". Alternative comparison methodology can also be considered—for example when analytical or equipment limitations reduce the ability to distinguish and track all three cell types or more in parallel in a single assay (inclusive of Vδ1+ cells, diseased cells, and non-diseased cells). In said instances, comparing Vδ1+ cell cytotoxicity towards diseased cells in one experiment and then comparing Vδ1+ cell cytotoxicity towards healthy cells in a separate equivalent experiment offers an alternate approach to such studies.

In another aspect of the invention, there is provided a method of assessing an antibody or antigen-binding fragment thereof which binds to the Vδ1 chain of a γδ TCR comprising administering the antibody or antigen-binding fragment thereof to a cell population comprising Vδ1+ cells and target cells and measuring the cell cytotoxic specificity towards the target cells. In one embodiment, the cell cytotoxicity specificity to a first target cell type can be compared to the cytotoxicity observed towards a second target cell type, therefore the method may be repeated using different target cell types. In a further aspect of the invention the first target cell type is a diseased cell and the second target cell type is a control cell such as a healthy cell or a cell with a different disease to the first target cell type.

In a further aspect of the invention there is provided a method for selecting or characterizing or comparing antibodies or antigen-binding fragment thereof as described herein which bind to the Vδ1 chain of a γδ TCR wherein the effect conferred by said antibody on Vδ1+ cell cytotoxicity towards (i) a first cell type and (ii) a second cell type is measured and compared. In a further aspect of the invention an antibody is thereby selected which enhances the specific cytotoxicity towards the first cell type more so than towards the second cell type. In a further aspect of the invention the first cell type is a diseased-cell and the second cell type is a healthy cell.

As described herein, the antibodies or antigen-binding fragments thereof used in the assays may be presented on a surface, for example the surface of a cell, such as a cell comprising an Fc receptor. For example, the antibodies or antigen-binding fragments thereof may be presented on the surface of THP-1 cells, such as TIB-202™ cells (available from American Type Culture Collection (ATCC)). Alternatively, the antibodies or antigen-binding fragments thereof may be used directly in the assays.

In such functional assays, output may be measured by calculating the half maximal concentration, also referred to as "EC50" or "effective concentration at 50 percent". The term "IC50" refers to the inhibitory concentration. Both EC50 and IC50 may be measured using methods known in the art, such as flow cytometry methods. In some instances, EC50 and IC50 are the same value or can be considered equivalent. For example, the effective concentration (EC) of effector cells required to inhibit (e.g. kill) 50% of a certain cell type may also be considered the 50% inhibitory concentration (IC). For the avoidance of doubt, the values of EC50 in the present application are provided using IgG1 formatted antibody when referring to an antibody. Such values can be easily converted based on the molecular weight of the antibody format for equivalent values as follows:

$$(\mu g/ml)/(MW \text{ in kDa}) = \mu M$$

The EC50 for downregulation of the γδ TCR upon antibody (or fragment) binding for the parental clones described herein may be less than 0.50 μg/ml, such as less than 0.40 μg/ml, 0.30 μg/ml, 0.20 μg/ml, 0.15 μg/ml, 0.10 μg/ml, 0.06 μg/ml or 0.05 μg/ml. In a preferred embodiment, the EC50 for downregulation of the γδ TCR upon antibody (or fragment) binding is less than 0.10 μg/ml. In particular, the EC50 for downregulation of the γδ TCR upon antibody (or fragment) binding may be less than 0.06 μg/ml, such as less than 0.05 μg/ml, 0.04 μg/ml or 0.03 μg/ml. In particular, said EC50 values are when the antibody is measured in an IgG1 format. For example, the EC50 γδ TCR downregulation value can be measured using flow cytometry (e.g. as described in the assay of e.g. Examples 6 and 27).

The EC50 for γδ T cell degranulation upon antibody (or fragment) binding may be less than 0.050 μg/ml, such as less than 0.040 μg/ml, 0.030 μg/ml, 0.020 μg/ml, 0.015 μg/ml, 0.010 μg/ml or 0.008 μg/ml. In particular, the EC50 for γδ T cell degranulation upon antibody (or fragment) binding may be less than 0.005 μg/ml, such as less than 0.002 μg/ml. In a preferred embodiment, the EC50 for γδ T cell degranulation upon antibody (or fragment) binding is less than 0.007 μg/ml. In particular, said EC50 values are when the antibody is measured in an IgG1 format. For example, the γδ T cell degranulation EC50 value can be measured by detecting CD107a expression (i.e. a marker of cell degranulation) using flow cytometry (e.g. as described in the assay of Example 7). In one embodiment, CD107a expression is measured using an anti-CD107a antibody, such as anti-human CD107a BV421 (clone H4A3) (BD Biosciences).

The EC50 for γδ T cell killing upon the antibody (or fragment) binding may be less than 0.50 μg/ml, such as less than 0.40 μg/ml, 0.30 μg/ml, 0.20 μg/ml, 0.15 μg/ml, 0.10

μg/ml or 0.07 μg/ml. In a preferred embodiment, the EC50 for γδ T cell killing upon the antibody (or fragment) binding is less than 0.10 μg/ml. In particular, the EC50 for γδ T cell killing upon the antibody (or fragment) binding may be less than 0.060 μg/ml, such as less than 0.055 μg/ml, in particular less than 0.020 μg/ml. In particular, said EC50 values are when the antibody is measured in an IgG1 format. For example, the EC50 γδ T cell killing value can be measured by detecting proportion of dead cells (i.e. using a cell viability dye) using flow cytometry following incubation of the antibody, γδ T cell and target cells (e.g. as described in the assay of Example 8). In one embodiment, death of the target cell is measured using a cell viability dye is Viability Dye eFluor™ 520 (ThermoFisher).

In the assays described in these aspects, the antibody or antigen-binding fragment thereof may be presented on the surface of a cell, such as a THP-1 cell, for example TIB-202™ (ATCC). The THP-1 cells are optionally labelled with a dye, such as CellTracker™ Orange CMTMR (ThermoFisher).

Medicaments that Downregulate CD3 Molecules Associated with a Vδ1 TCR.

Presented herein are antibodies which engage the T-cell/CD3 complex differently. Specifically, these antibodies can engage via the TRDV1 domain of Vδ1 TCRs expressed only on Vδ1+ cells. In doing so such medicaments function differently. In turn this engagement event can downregulate TCR-associated CD3 molecule complexes. Such CD3 downregulation can be synonymous with T-cell activation. However, by engaging the T-cell/CD3 complex via the TRDV1 domain in this way, only CDR3 molecules associated with the Vδ1 TCR are then downregulated. This mechanism is clearly shown in FIG. 55.

Hence in one embodiment there is provided a method of downregulating a TRDV1-containing Vδ1 TCR and the associated CD3 molecule complex on the surface of a cell with an antibody, and the use of such antibodies for this purpose.

In some embodiments, also presented herein are multispecific TCEs capable of engaging the T-cell/CD3 complex via the TRDV1 domain. Current multispecific TCE-formatted medicaments typically engage and activate a T-Cell via CD3 binding events. This can result in downregulation of CD3 molecule complexes from the surface of a T-cell. However, it also well understood that TCEs can also overstimulate T-cells via such engagement and downregulation. CD3 molecule complexes are not specific to one class of T-cell and are therefore not a precise target to aim for. Stimulating all T-cells (mainly αß subtype) via CD3 can in turn can result in overproduction of cytokines, leading to acute cytokine flares (so-called cytokine storms). Additionally, in non-targeted approaches which engage and activate all T-cells via CD3, paradoxically the T-cells can become overactivated which leads to chronic T-cell exhaustion and/or T-cell death. Indeed, this non-specific pan T cell activation leads to activation of both effector and regulatory T cells whereas the presently presented approach interacts specifically with an effector population. This 'sledge-hammer' approach is therefore far from ideal when one may wish to upregulate selective T-cells only.

By contrast, presented herein are multispecific antibodies, in particular T-cell engagers, which engage the T-cell/CD3 complex differently. Specifically, these TCEs can engage via the TRDV1 domain of Vδ1 TCRs expressed only on Vδ1+ cells. In doing so such TCE-based medicaments function differently. First, these TCEs are able to down-regulate a TCR via engaging a TRDV-1 epitope. In turn this engagement event downregulates TCR-associated CD3 molecule complexes. Such CD3 downregulation can be synonymous with T-cell activation. However, by engaging the T-cell/CD3 complex via the TRDV1 domain in this way, only CDR3 molecules associated with the Vδ1 TCR are then downregulated. This approach of specifically targeting and activating Vδ1 cells allows many of the above issues (cytokine storms, T-cell exhaustion/depletion and ADCC, for example) to be avoided. Again, this mechanism is clearly shown in FIG. 55.

Stimulation of T-cells via the CD3 'sledge-hammer' approach can also contribute to depletion of T-cells via Fc gamma receptor driven mechanisms, such as ADCC. Therefore, the majority of the CD3-targeting bispecific antibodies currently in clinical practice have Fc domains with reduced binding activity to FcγR or are bispecific fragments intentionally without the Fc region. CD3-targeting therapies may also have reduced binding affinity of the T-cell receptor complex binding arms.

This reduction in affinity may result in reduced efficacy and less optionality in terms of TCE design and functionality. For example, affinity of the binding domains in such TCEs is known to drive distribution profile in vivo. Specifically, it is typically observed that TCE distribution is biased towards its highest affinity target. Hence, by reducing the affinity of a TCE binding domain to the T-cell complex, it is typical to then bias distribution away from T-cells; the very cells needed to drive efficacy of such TCEs. It is partly for such reasons that TCE therapeutic windows have been termed 'prohibitively narrow'.

The approach presented here specifically targets and activates vδ1 cells, avoiding the need to ablate Fc function or reduce affinity.

Additionally, in the approach presented here, the antibodies engage on the TCR of vδ1 cells but full activation does not occur unless tumour cells are also present. Full engagement of the presently presented antibodies on the TCR leads to partial downregulation and the vδ1 cells bound by the presently presented antibodies only become fully activated and become cytotoxic in the tumour microenvironment. This represents another vital safety advantage for the present approach, since off target cytotoxicity is reduced and the full potency of the present antibodies to activate vδ1 cells is only unleashed in the presence of tumour cells.

One mechanism behind γδ T cells being able to detect stress signals on tumour cells is believed to be due to the NCRs (natural cytotoxicity receptors) they express. The NCRs are able to engage NCR ligands on tumour cells. A dual mechanism of activation is therefore employed, wherein the γδ T cells are activated via TCR stimulation and the NCRs sense the tumour cells to enable full activation and cytotoxicity.

This is in contrast to stimulation of αß T cells via CD3, wherein all stimulation is via the TCR. Such cells are therefore almost indiscriminate between healthy or transformed cells because they may not have this antigen presentation independent sensing of tumour cells via NCRs. Therefore, if CD3 antibodies are Fc enabled they will attract other immune cells which can trigger a cascade of unpredictable and desirable events such as cytokine storms, exhaustion and even overactivation of immune cells leading to, for example, NK cells killing T cells etc. In the present approach, stimulation of γδ T cells with the presently presented antibodies does not lead to such concerns because both γδ T cells (and other immune cells such as NK cells) are able to distinguish between healthy cells and tumour cells including via their NCR sensing mechanism and therefore selectively kill stressed cells such as cancer cells or vi-ally infected cells due to this diseased cell specificity For example, in initial cynomolgus studies with the anti-vδ1 Fc-enabled multispecific antibody presented herein, with specificity to both human and cyno vδ1 antigen (eg SEQ ID NO: 272 and SEQ D NO: 308 respectively), was found to be safe and well tolerated, in dose-escalating, repeat dose in-vivo studies by all parameters measured. None of the side effects typically associated with T cell activation, such as cytokine release or weight loss were observed.

These findings also highlight another advantage of the approach described herein. Specifically, and unlike TCEs typified by CD3 engagers and the like, TCE bispecifics of the invention can optionally be designed as full-length antibody, for example comprising heavy chains with a VH-CH1-CH2-CH3 format with cognate light chains with a VL-CL format. Unlike smaller bispecific formats (e.g. less than 70 KDa), such full-length bispecific format can exhibit longer half-lives in-vivo and thereby require less frequent dosing regimens. The longer half-lives observed by such formats are for a variety of reasons inclusive of increased size (>70 KDa) which means such formats are not filtered by kidneys (glomerulus pore size cut-off 60-70 KDa). In one embodiment, the multispecific antibodies may be larger than about 70 KDa, and may comprise human IGHC sequence (e.g. IGHA, IGHD, IGHD, IGHM, IGHG sequence) as listed by IMGT. Such IgG1 formats can also be re-cycled by FcRn mechanism. The clear downside of such full-length antibody formats for TCE bispecifics in particular is that such format exhibit unfavorable safety profiles due to the reduce clearance rate, increased and more chronic exposures.

Therefore, the present approach allows the possibility of Fc functionality without any concern of off-target effects, such as NK cells killing γδ T cells or vice versa. The present approach is therefore superior to CD3 directed approaches which are stunted by the necessity of workarounds such as reducing CD3 affinity, eliminating Fc function etc. to limit collateral damage outside the tumour environment. The multispecific antibodies, in particular T-cell engagers, presented here are able to bind to vδ1 cells without any damage potential and the full activation and cytotoxicity enhancement is only engaged when the vδ1 cells are in close contact with tumour cells.

Hence in one embodiment there is provided a method of downregulating a TRDV1-containing Vδ1 TCR and the associated CD3 molecule complex on the surface of a cell with a TCE multispecific antibody, and the use of such multispecific antibodies for this purpose.

Other features and advantages of the present invention will be apparent from the description provided herein. It should be understood, however, that the description and the specific examples while indicating preferred embodiments of the invention are given by way of illustration only, since various changes and modifications will become apparent to those skilled in the art. The invention will now be described using the following, non-limiting examples:

EXAMPLES

Example 1. Materials and Methods

Human Antibody Discovery

Human phage display was employed to generate the human anti-human variable Vδ1+ domain antibodies as described herein. The library was constructed as described in Schofield et al (*Genome biology* 2007, 8(11): R254) and comprised a single chain fragment variable (scFv) displaying library of ~40 billion human clones. This library was screened using antigens, methods, selections, deselection, screening, and characterization strategies as described herein.

Antigen Preparation

The design of the soluble γδ TCR heterodimers comprising the TCRα and TCRβ constant regions used in the below Examples were generated according to Xu et al. (2011) *PNAS* 108: 2414-2419. Vγ or Vδ domains were fused in-frame to a TCRα or TCRβ constant region lacking the transmembrane domain, followed by a leucine zipper sequence or an Fc sequence, and a histidine tag/linker.

The expression construct was transiently transfected in mammalian EXPI HEK293 suspension cells (either as single or co-transfections for heterodimer). Secreted recombinant proteins were recovered and purified from culture supernatant by affinity chromatography. To ensure good recovery of monomer antigen, samples were further purified using preparative size exclusion chromatography (SEC). Purified antigens were analysed for purity by SDS-PAGE and aggregation state by analytical SEC.

Antigen Functional Validation

The specificity of the antigens containing delta variable 1 (Vδ1) chain was confirmed in DELFIA immunoassay (Perkin Elmer) and in flow-based assay in competition with γδ T cells using REA173-Miltenyi Biotec anti-Vδ1 antibody.

Dissociation-Enhanced Lanthanide Fluorescence Immunoassay (DELFIA)

For the confirmation of antigen's specificity, DELFIA immunoassay was performed with the antigen directly coated to the plate (3 μg/mL of antigen in 50 μL PBS at 4° C. overnight (Nunc #437111) and serial dilution of primary antibodies starting at 300 nM. For detection DELFIA Eu-N1 Anti-Human IgG (Perkin Elmer #1244-330) was used as secondary antibody at 1/500 dilution in 50 μL of 3% of MPBS (PBS+3% (w/V) skimmed milk powder). Development was with 50 μL of DELFIA enhancement solution (Perkin Elmer #4001-0010).

Affinity ranking of antibody of interest were performed using DELFIA immunoassay in which antibodies were captured via protein G coated on the plate and soluble biotinylated L1 (DV1-GV4) antigen was added at 5 nM in 50 μL (3MPBS). For detection 50 μL of streptavidin-Eu (1:500 in assay buffer, Perkin Elmer) was used and signal was developed with DELFIA enhancement solution. D1.3 hIgG1 (described in England et al. (1999) *J. Immunol.* 162: 2129-2136) was used as a negative control.

Phage display selection outputs were subcloned into the scFv expression vector pSANG10 (Martin et al. (2006) *BMC Biotechnol.* 6: 46). Soluble scFv were expressed and screened for binding in DELFIA on directly immobilised targets. Hits were defined as a DELFIA signal above 3000 fluorescence units.

Antibody Preparation

Selected scFvs were subcloned into IgG1 frameworks using commercially available plasmids. expi293F suspension cells were transfected with said plasmids for antibody expression. For convenience, unless otherwise noted, the antibodies characterised in these Examples refer to IgG1 formatted antibodies selected from phage display as scFv. However, the antibodies of the invention may be in any antibody format as previously discussed.

Antibody Purification

IgG antibodies were batch purified from supernatants using protein A chromatography. Concentrated protein A eluates were then purified using Size Exclusion Chromatography (SEC). Quality of purified IgG was analysed using ELISA, SDS-PAGE and SEC-HPLC.

γδ T Cell Preparation

Populations of enriched γδ T cells were prepared according to the methods described in WO2016/198480 (i.e. blood-derived γδ T cells) or WO2020/095059 (i.e. skin-derived γδ T cells). Briefly, for blood-derived γδ T cells PBMCs were obtained from blood and subjected to magnetic depletion of αβ T cells. The αβ-depleted PBMCs were then cultured in CTS OpTmiser media (ThermoFisher) in the presence of OKT-3 (or respective anti-Vδ1 antibody), IL-4, IFN-γ, IL-21 and IL-$1_R$ for 7 days. At day 7 of culture, the media was supplemented with OKT-3 (or respective anti-Vδ1 antibody), IL-21 and IL-15 for a further 4 days. At day 11 of culture, the media was supplemented with OKT-3 (or respective anti-Vδ1 antibody) and IL-15 for a further 3 days. At day 14 of culture, half of the media was replaced with fresh complete OpTmiser and supplemented with OKT-3 (or respective anti-Vδ1 antibody), IL-15 and IFN-γ. From day 17 of culture onwards, the culture was supplemented with OKT-3 (or respective anti-Vδ1 antibody) and IL-15 every 3 to 4 days; half of the media was replaced with fresh media every 7 days.

For skin-derived γδ T cells, skin samples are prepared by removing subcutaneous fat and a 3 mm biopsy punch is used to make multiple punches. Punches are placed on carbon matrix grids and placed in the well of a G-REX6 (Wilson Wolf). Each well is filled with complete isolation medium containing AIM-V media (Gibco, Life Technologies), CTS Immune Serum Replacement (Life Technologies), IL-2 and IL-15. For the first 7 days of culture, complete isolation medium containing Amphotericin B (Life Technologies) was used ("+AMP"). Media was changed every 7 days by gently aspirating the upper media and replacing with 2× complete isolation medium (without AMP), trying not to disturb the cells at the bottom of the plate or bioreactor. Beyond three weeks in culture, the resulting egressed cells are then passaged into fresh tissue culture vessels and fresh media (e.g. AIM-V media or TexMAX media (Miltenyi)) plus recombinant IL-2, IL-4, IL-15 and IL-21 before harvest. Optionally, αβ T cells also present within the culture are then removed with aid of αβ T cell depletion kits and associated protocols, such as those provided by Miltenyi. For further reference see WO2020/095059.

γδ T Cell Binding Assay

The binding of antibodies to γδ T cells was tested by incubating a fixed concentration of purified antibodies with 250000 γδ T cells. This incubation was performed under blocking conditions to prevent unspecific binding of antibodies via the Fc receptor. Detection was performed by addition of a secondary, fluorescent dye-conjugated antibody against human IgG1. For negative controls, cells were prepared with a) an isotype antibody only (recombinant human IgG), b) the fluorescent dye-conjugated anti-human IgG antibody only and c) a combination of a) and b). A control well of completely unstained cells was also prepared and analysed. As positive controls, a purified murine monoclonal IgG2 anti-human CD3 antibody and a purified murine monoclonal IgG1 anti-human TCR Vδ1 antibody were used in two different concentrations and stained with a fluorescent dye-conjugated goat anti-mouse secondary antibody. The assay was accepted if the lower concentration positive controls' mean fluorescence intensity in the FITC channel was at least tenfold as high as the highest negative control.

SPR Analysis

A MASS-2 instrument with an amine high capacity chip (both from Sierra Sensors, Germany) was used to perform SPR analysis. 15 nM IgG were captured via protein G to an amine high capacity chip (100 nM for TS8.2). L1 (DV1-GV4) antigen was flown over the cell at a 1:2 dilution series from 2000 nM to 15.625 nM with the following parameters: 180 s association, 600 s dissociation, flowrate 30 μL/min, running buffer PBS+0.02% Tween 20. All experiments were performed at room temperature on MASS-2 instrument. Steady state fitting was determined according to Langmuir 1:1 binding using software Sierra Analyzer 3.2.

Comparator Antibodies

Antibodies of the invention were compared to commercially available antibodies in test assays as described.

| Antibody | Source | Catalogue No. |
|---|---|---|
| Ultra-LEAF ™ Purified anti-human CD3 Antibody (OKT3), functional | Biolegend | 317326 |
| Ultra-LEAF ™ Purified anti-human IgG2a Antibody (isotype control for OKT3) | Biolegend | 400264 |
| Human TCR Vδ1 purified mAb (functional TS8.2) | ThermoFisher | TCR1730 |
| Ultra-LEAF ™ Purified Mouse IgG1, κ Isotype Ctrl Antibody for TS8.2 | Biolegend | 400166 |
| Anti-human CD107a BV421 (clone H4A3) | BD Biosciences | 562623 |
| BV421 Mouse IgG1, k Isotype Control Clone X40 (RUO) | BD Biosciences | 562438 |
| Anti-TCR Vδ1-PE-Vio770, human (flow, discontinued) | Miltenyi | 130-100-540 |
| Cetuximab | In-house | — |
| D1.3 HEL (anti-chicken lysozyme; mouse VH-VL + Human IgG1 Fc). | In-house | — |
| Anti-RSV (aka Motavizumab) | In-house | — |

γδ TCR Downregulation and Degranulation Assay

THP-1 (TIB-202™, ATCC) target cells loaded or not with test antibodies were labelled with CellTracker™ Orange CMTMR (ThermoFisher, C2927) and incubated with γδ T cells at 2:1 ratio in the presence of CD107a antibody (Anti-human CD107a BV421 (clone H4A3) BD Biosciences 562623). After 2 hours of incubation, the surface expression of γδ TCR (to measure TCR downregulation) and expression of CD107a (to measure degranulation) on γδ T cells was evaluated using flow cytometry.

Figure 6A:
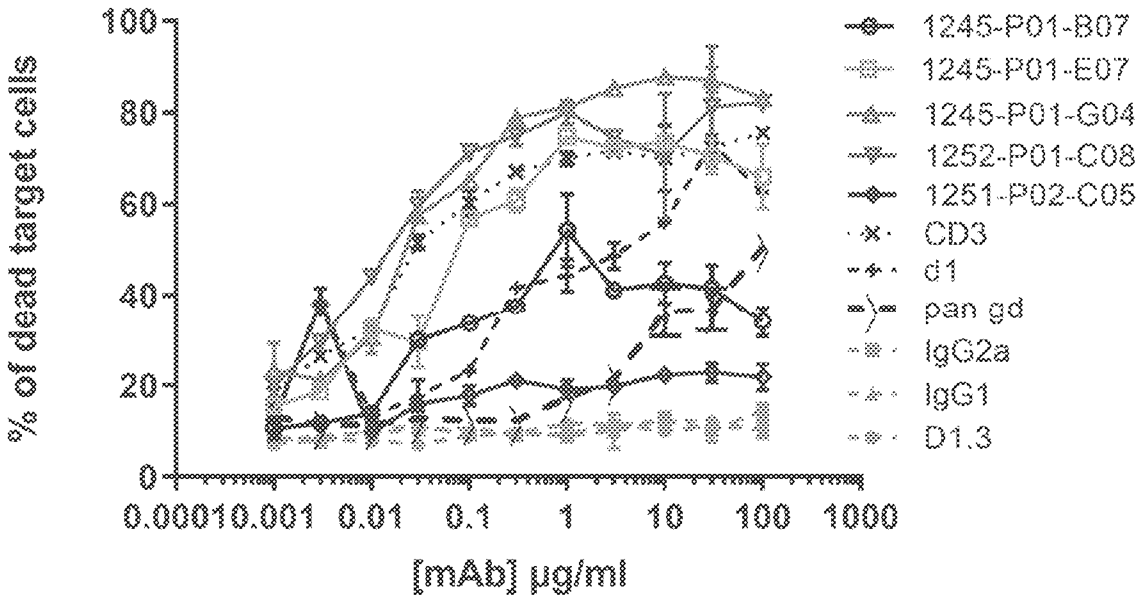
FIGS. 6A-6B: Results of Killing Assay (THP-1 flow-based assay) for clones 1245_P01_E07, 1252_P01_C08, 1245_P02_G04, 1245_P01_B07 and 1251_P02_C05 (FIG. 6A) or clones 1139_P01_E04, 1245_P02_F07, 1245_P01_G06, 1245_P01_G09, 1138_P01_B09 and 1251_P02_G10 (FIG. 6B).
Figure 6B:
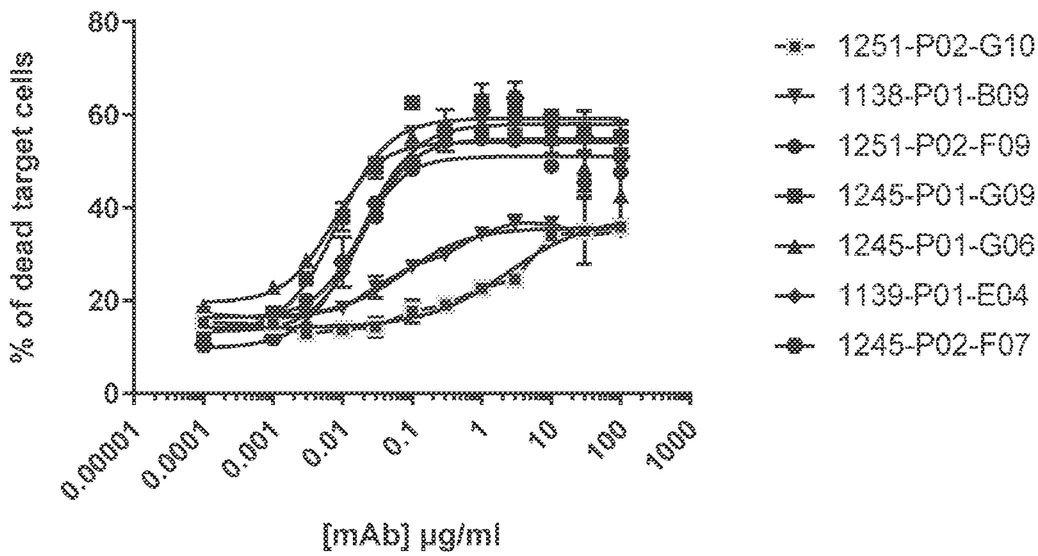

Killing Assay (e.g. for FIG. 6)

Gamma delta T cell killing activity and effect of test antibodies on the killing activity of γδ T cells was accessed by flow cytometry. After 4 hours of in vitro co-culture at 20:1 ratio of γδ T cells and CellTracker™ Orange CMTMR (ThermoFisher, C2927) labelled THP-1 cells (loaded or not with the antibody) were stained with Viability Dye eFluor™ 520 (ThermoFisher, 520 65-0867-14) to distinguish between live and dead target THP-1 cells. During sample acquisition, target cells were gated on the CellTracker™ Orange CMTMR positivity and examined for cell death based on the uptake of Viability Dye. CMTMR and eFluor™ 520 double positive cells were recognized as the dead target cells. The killing activity of γδ T cells was presented as a % of the dead target cells.

Epitope Mapping

All protein samples (antigen L1 (DV1-GV4) and antibodies 1245_P01_E07, 1245_P02_G04, 1252_P01_C08, 1251_P02_C05 and 1141_P01_E01) used for epitope mapping were analyzed for protein integrity and aggregation level using a high-mass MALDI.

In order to determine the epitope of L1 (DV1-GV4)/1245_P01_E07, L1(DV1-GV4)/1245_P02_G04, L1(DV1-GV4)/1252_P01_C08, L1(DV1-GV4)/1251_P02_C05, and L1(DV1-GV4)/1141_P01_E01 complexes with high resolution, the protein complexes were incubated with deuterated cross-linkers and subjected to multi-enzymatic proteolysis using trypsin, chymotrypsin, Asp-N, elastase and thermolysin. After enrichment of the cross-linked peptides, the samples were analyzed by high resolution mass spectrometry (nLC-LTQ-Orbitrap MS) and the data generated were analyzed using XQuest and Stavrox software.

SYTOX-Flow Killing Assay

The SYTOX assay allows the quantification of T cell mediated cytolysis of target cells using flow cytometry. Dead/dying cells are detected by a dead cell stain (SYTOX® AADvanced™, Life Technologies, S10274) which only penetrates into cells with compromised plasma membranes but cannot not cross intact cell membranes of healthy cells. NALM-6 target cells were labelled with CTV dye (Cell Trace Violet™, Life Technologies, C34557) and were thus distinguishable from the unlabelled effector T cells. Dead/dying target cells are identified through double staining of the dead cell dye and the cell trace dye.

After 16 hours in vitro co-culture of effector and CTV labelled target cells at indicated Effector-to-Target ratios (E:T, 1:1 or 10:1) the cells were stained with SYTOX® AADvanced™ and acquired on a FACSLyric™ (BD). The killing results are presented as % target cell reduction which is calculated by taking into account the number of live target cells (sample counts) in the test samples over the live target cells in the control wells without added effector cells (maximum counts):

% target reduction=100−((sample counts/maximum counts)×100)

Example 2. Antigen Design

Gamma delta (γδ) T cells are polyclonal with CDR3 polyclonality. In order to avoid a situation where generated antibodies would be selected against the CDR3 sequence (as the CDR3 sequence will differ from TCR clone to TCR clone), the antigen design involved maintaining a consistent CDR3 in different formats. This design aimed to generate antibodies recognising a sequence within the variable domain, which is germline encoded and therefore the same in all clones, thus providing antibodies which recognise a wider subset of γδ T cells.

Another important aspect of the antigen preparation process was to design antigens which are suitable for expression as a protein. The γδ TCR is a complex protein involving a heterodimer with inter-chain and intra-chain disulphide bonds. A leucine zipper (LZ) format and Fc format were used to generate soluble TCR antigens to be used in the phage display selections. Both the LZ and Fc formats expressed well and successfully displayed the TCR (particularly heterodimeric TCRs, e.g. Vδ1 Vγ4).

It was found that the CDR3 sequence from a public database entry for the γδ TCR expressed well as proteins (RCSB Protein Data Bank entries: 3OMZ). This was therefore selected for antigen preparation.

Antigens containing the delta variable 1 chain were expressed in LZ formats as a heterodimer (i.e. in combination with different gamma variable chains—“L1”, “L2”, “L3”) and in Fc format either as a heterodimer (“F1”, “F2”, “F3”) or as a homodimer (i.e. in combination with another delta variable 1 chain—“Fc1/1”). All delta variable 1 chains of the antigens contained the 3OMZ CDR3. Another series of γδ TCR antigens using similar formats were designed containing different delta variable chains (such as delta variable 2 and delta variable 3) and used to deselect antibodies with non-specific or off target binding (“L4”, “F9”, “Fc4/4”, “Fc8/8”). These antigens were also designed to include the 3OMZ CDR3 to ensure that antibodies binding in the CDR3 region were also deselected.

Antigen functional validation was performed to confirm that the designed antigens would be suitable to generate anti-TRDV1 (TCR delta variable 1) antibodies. Detection was seen only with antigens containing the δ1 domain (FIG. 1).

Example 3. Phage Display

Phage display selections were performed against libraries of human scFvs using either heterodimeric LZ TCR format in round 1 and 2, with deselections on heterodimeric LZ TCR in both rounds. Or round 1 was performed using homodimeric Fc fusion TCR with deselection on human IgG1 Fc followed by round 2 on heterodimeric LZ TCR with deselection on heterodimeric LZ TCR (see Table 7).

TABLE 7

Overview phage display selections

| Target | Round 1 selection | Round 1 deselection | Round 2 selection | Round 2 deselection |
|---|---|---|---|---|
| DV1 | bt-L1 (DV1-GV4) | L4 (DV2-GV4) | bt-L3 (DV1-GV8) | L4 (DV2-GV4) |
| DV1 | bt-Fc1/1 (DV1-DV1) | Fc | bt-L1 (DV1-GV4) | L4 (DV2-GV4) |

bt = biotin.

Selections were performed in solution phase using 100 nM biotinylated proteins. Deselections were performed using 1 μM non-biotinylated proteins.

Figure 2A:
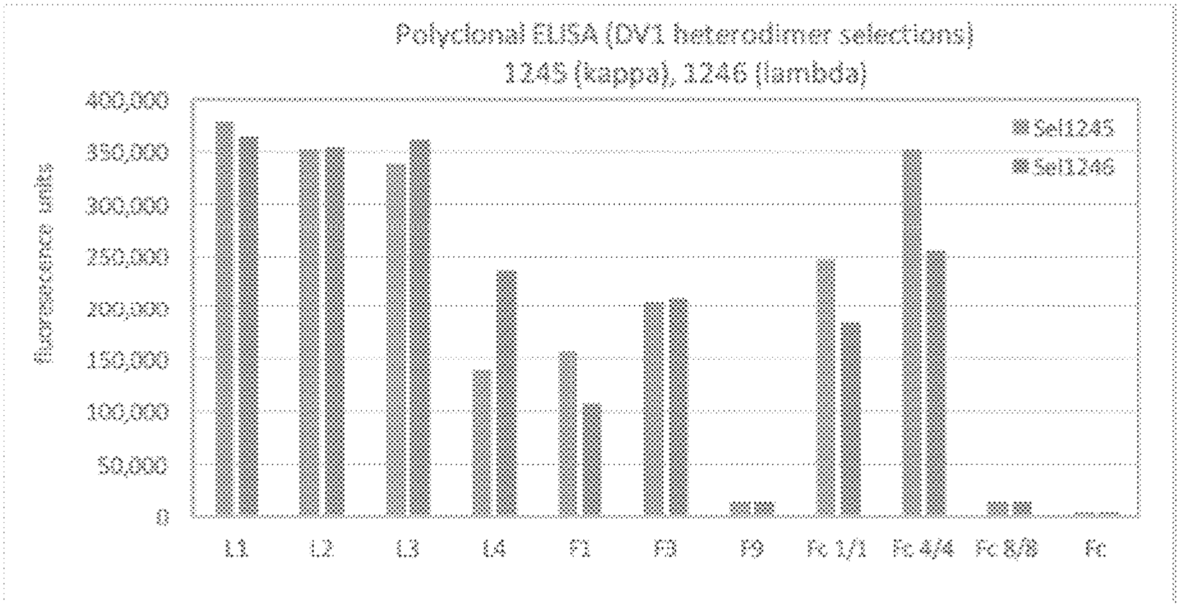
FIGS. 2A-2B: Polyclonal phage DELFIA data for DV1 selections.
Figure 2B:
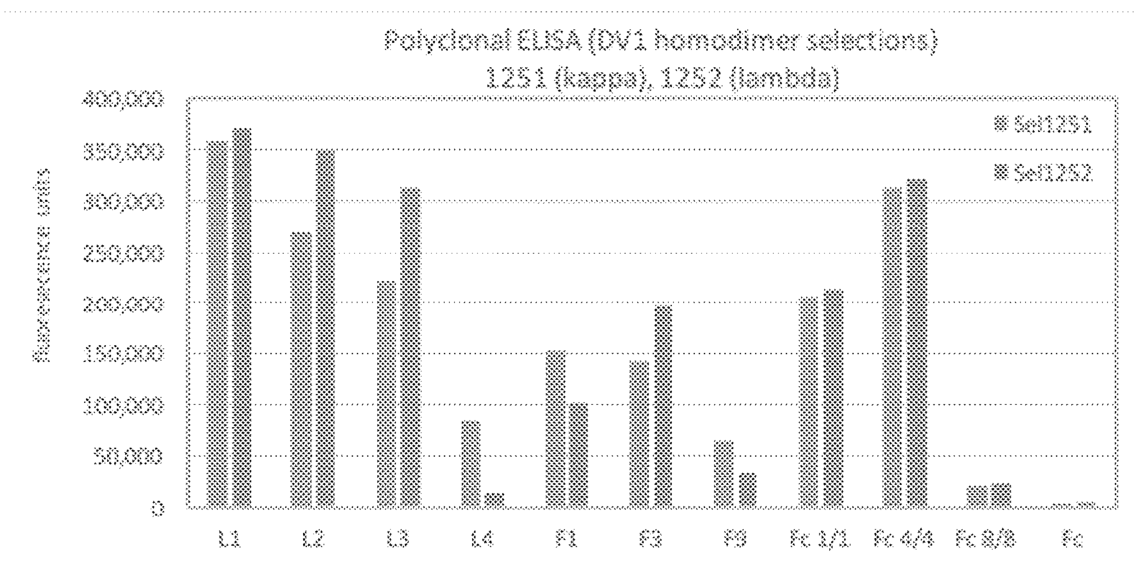

Success of the phage display selections was analysed by polyclonal phage ELISA (DELFIA). All DV1 selection outputs showed the desired binding to the targets Fc 1/1, L1, L2, L3, F1 and F3. Varying degrees of binding to non-targets L4, F9, Fc 4/4, Fc 8/8 and Fc were detected (see FIGS. 2A and B).

Example 4. Antibody Selection

Hits obtained in Example 3 were sequenced (using standard methods known in the art). 130 unique clones were identified, which showed a unique combination of VH and VL CDR3. Of these 130 unique clones, 125 showed a unique VH CDR3 and 109 showed a unique VL CDR3.

Unique clones were re-arrayed and specificity was analysed by ELISA (DELFIA). A panel of 94 unique human scFv binders which bind TRDV1 (L1, L2, L3, F1, F2, F3) but not TRDV2 (L4), were identified from the selections.

Affinity ranking of the selected binders was included to aid the choice of clones going forward. A large number of binders showed affinities in the nanomolar range, reacting with 25 to 100 nM biotinylated antigen. A handful of binders showed a strong reaction with 5 nM antigen, indicating possible single digit nanomolar affinities. Some binders showed no reaction with 100 nM antigen, indicating affinities in the micromolar range.

For the selection of clones to proceed with to IgG conversion, the aim was to include as many germline lineages and as many different CDR3s as possible. Further, sequence liabilities like glycosylation, integrin binding sites, CD11c/CD18 binding sites, unpaired cysteines were avoided. In addition, a variety of affinities was included.

Selected clones were screened for binding to natural, cell-surface expressed γδTCR using skin derived γδ T cells obtained from different donors. The clones chosen to be converted to IgG are shown in Table 8.

TABLE 8

DV1 binders for IgG conversion

| Clone ID | Heavy CDR1 | SEQ ID NO. | Heavy CDR2 | SEQ ID NO. | Heavy CDR3 | SEQ ID NO. | Light CDR1 | SEQ ID NO. | Light CDR2 | SEQ | Light CDR3 | SEQ ID NO. | 100 nM L1 |
|---|---|---|---|---|---|---|---|---|---|---|---|---|---|
| 1245_P02_G04 | GDSVSSKSAA | 51 | TYYRSKWST | 53 | TWSGYVDV | 54 | QDINDW | 79 | DAS | 80 | QQSYSTPQVT | 81 | 5896 |
| 1245_P01_E07 | GFTFSDYY | 130 | ISSSGSTI | 131 | VDYADAFDI | 132 | QSIGTY | 144 | VAS | 145 | QQSYSTLLT | 146 | 162591 |
| 1252_P01_C08 | GFTVSSNY | 317 | IYSGGST | 318 | PIELGAFDI | 319 | NIGSQS | 347 | YDS | 348 | QVWDSSSDHVV | 349 | 1977 |
| 1245_P01_B07 | GFTFSDYY | 320 | ISSSGSTI | 321 | ENYLNAFDI | 322 | QSLSNY | 350 | AAS | 351 | QQSYSTPLT | 352 | 64271 |
| 1251_P02_C05 | GFTFSSYA | 323 | ISGGGGTT | 324 | DSGVAFDI | 325 | QNIRTW | 353 | DAS | 354 | QQFKRYPPT | 355 | 65269 |
| 1139_P01_E04 | GDSVSSNSAA | 326 | TYYRSKWYN | 327 | SWNDAFDI | 328 | QSISTW | 356 | DAS | 357 | QQSYSTPLT | 358 | 23786 |
| 1245_P02_F07 | GDSVSSNSAA | 329 | TYYRSKWYN | 330 | DYYYSMDV | 331 | QSISSW | 359 | DAS | 360 | QQSHSHPPT | 361 | 10450 |
| 1245_P01_G06 | GFTFSDYY | 332 | ISSSGSTI | 333 | HSWNDAFDV | 334 | QSISSY | 362 | AAS | 363 | QQSYSTPDT | 364 | 22474 |
| 1245_P01_G09 | GDSVSSNSAA | 335 | TYYGSKWYN | 336 | DYYYSMDV | 337 | QSISTW | 365 | DAS | 366 | QQSYSTPVT | 367 | 18430 |
| 1138_P01_B09 | GFTFSDYY | 338 | ISSSGSTI | 339 | HSWSDAFDI | 340 | QDISNY | 368 | DAS | 369 | QQSYSTPLT | 370 | 29193 |
| 1251_P02_G10 | GFTFSDYY | 341 | ISSSGSTI | 342 | HSWNDAFDI | 343 | QSISSH | 371 | AAS | 372 | QQSYSTLLT | 373 | 17053 |
| 1141_P01_E01 | GYSFTSYW | 344 | IYPGDSDT | 345 | HQVDTRTADY | 346 | RSDVGGYNY | 374 | EVS | 375 | SSYTSTSTLV | 376 | 136780 |

Example 5. Antibody SPR Analysis

Figure 3A:
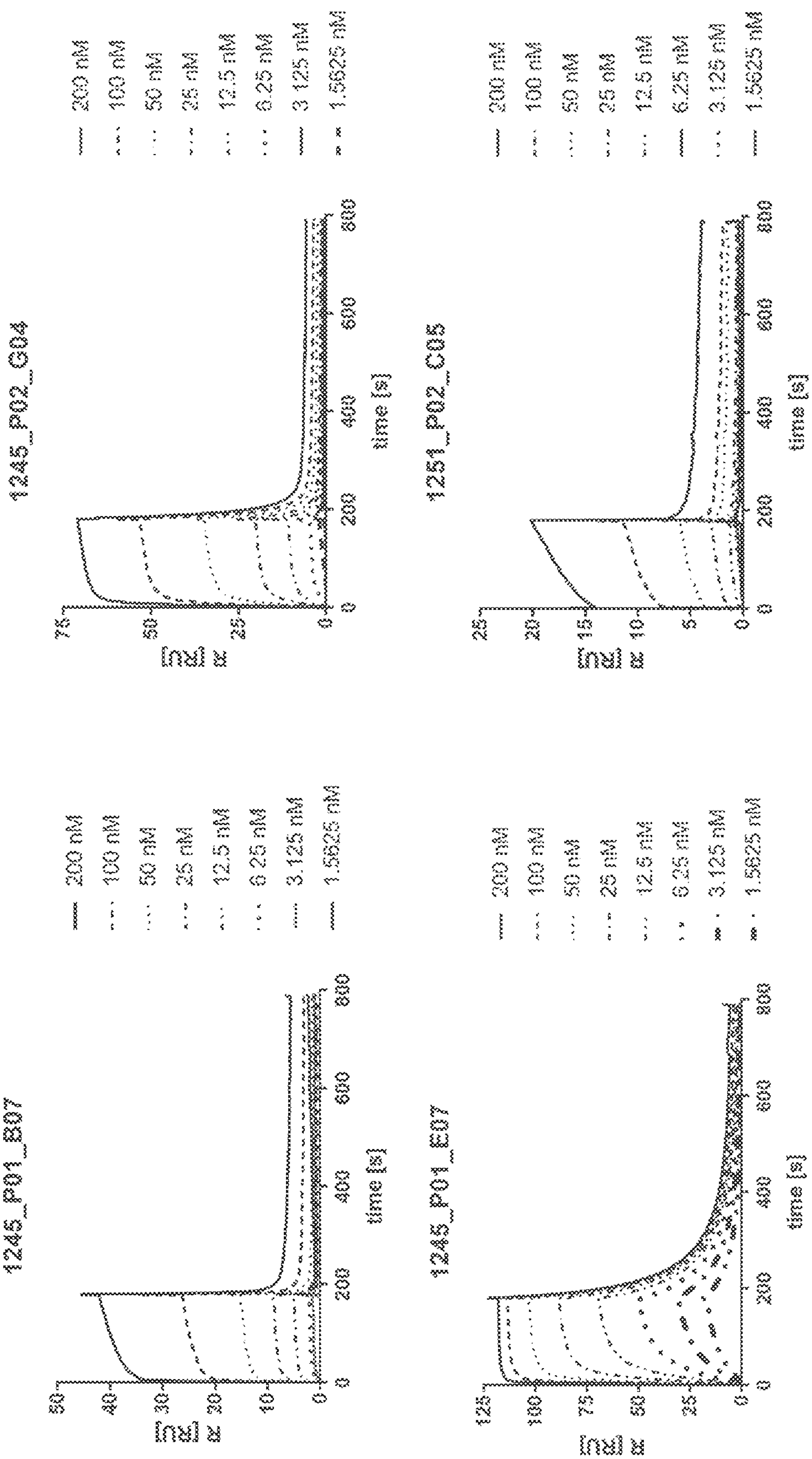
FIGS. 3A-3B: IgG capture: left) Sensorgrams of interaction of anti-L1 IgG with L1, right) steady state fits, if available. All experiments were performed at room temperature on MASS-2 instrument. Steady state fitting according to Langmuir 1:1 binding.
Figure 3B:
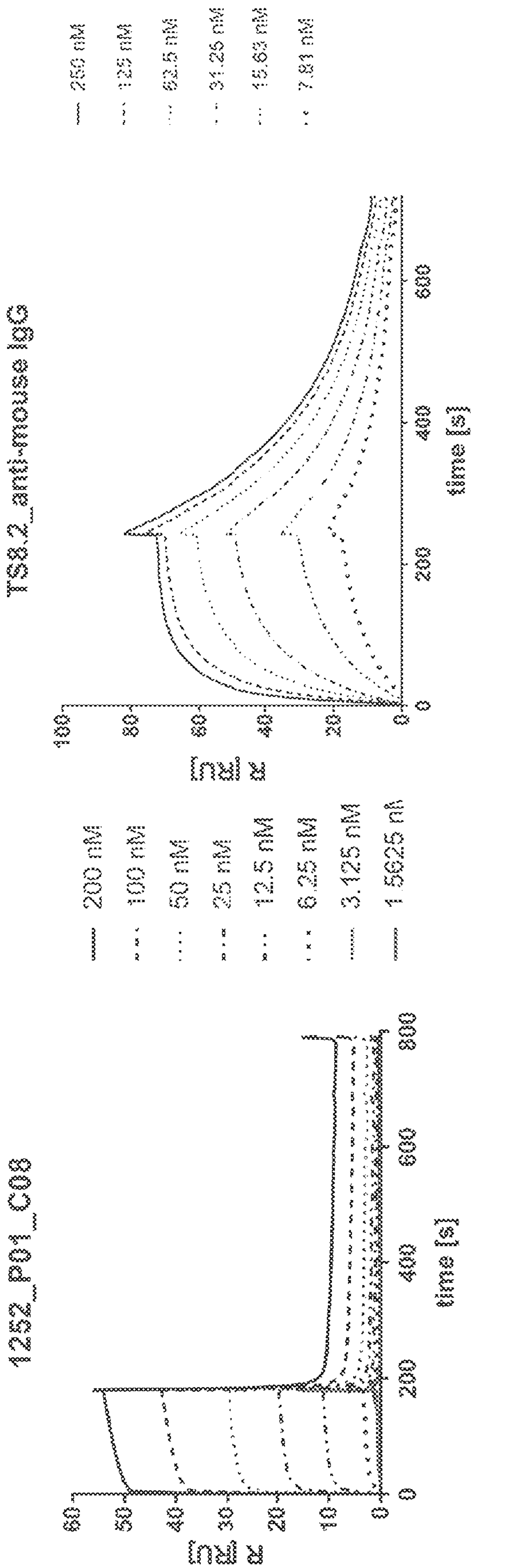

Prepared IgG antibodies where passed through a γδ cell binding assay, and 5 were selected for further functional and biophysical characterization. SPR analysis was performed to determine the equilibrium dissociation constants ($K_D$). Sensorgrams of the interaction of the tested antibody with the analyte, along with steady state fits (if available), are presented in FIG. 3. No binding was detected for TS8.2 with 80 RU of IgG captured on the chip. Results are summarised in Table 9.

TABLE 9

Results of IgG capture

| Analyte | Clone ID | $K_D$ (nM) | $K_D$ (M) |
|---|---|---|---|
| L1 (DV1-GV4) | 1245_P01_E07 | 12.4 | 1.24e-08 |
| L1 (DV1-GV4) | 1252_P01_C08 | 100 | 1.00e-07 |
| L1 (DV1-GV4) | 1245_P02_G04 | 126 | 1.26e-07 |
| L1 (DV1-GV4) | 1245_P01_B07 | 341 | 3.41e-07 |
| L1 (DV1-GV4) | 1251_P02_C05 | 1967* | 1.97e-06 |
| L1 (DV1-GV4) | 1139_P01_E04 | 251 | 2.51e-07 |
| L1 (DV1-GV4) | 1245_P02_F07 | 193 | 1.93e-07 |
| L1 (DV1-GV4) | 1245_P01_G06 | 264 | 2.64e-07 |
| L1 (DV1-GV4) | 1245_P01_G09 | 208 | 2.08e-07 |
| L1 (DV1-GV4) | 1138_P01_B09 | 290 | 2.90e-07 |
| L1 (DV1-GV4) | 1251_P02_G10 | 829 | 8.29e-07 |
| L1 (DV1-GV4) | TS8.2 (commercial anti-Vδ1 antibody) | 44 | 4.40e-08 |

*Binding of 1252_P02_C05 did not reach saturation, therefore data was extrapolated

Example 6. TCR Engagement Assay

The inventors designed several assays to be used for functional characterization of the selected antibodies. The first assay assessed γδ TCR engagement by measuring downregulation of the γδ TCR upon antibody binding. Selected antibodies were tested against commercial anti-CD3 and anti-Vδ1 antibodies which were used as positive controls or against 1252_P01_C08 as a positive control (for 1139_P01_E04, 1245_P02_F07, 1245_P01_G06 and 1245_P01_G09). Commercial anti-panγδ was used as a negative control because it is a panγδ antibody, recognising all γδ T cells irrespective of variable chain, and therefore is likely to have a different mode of action.

Figure 4A:
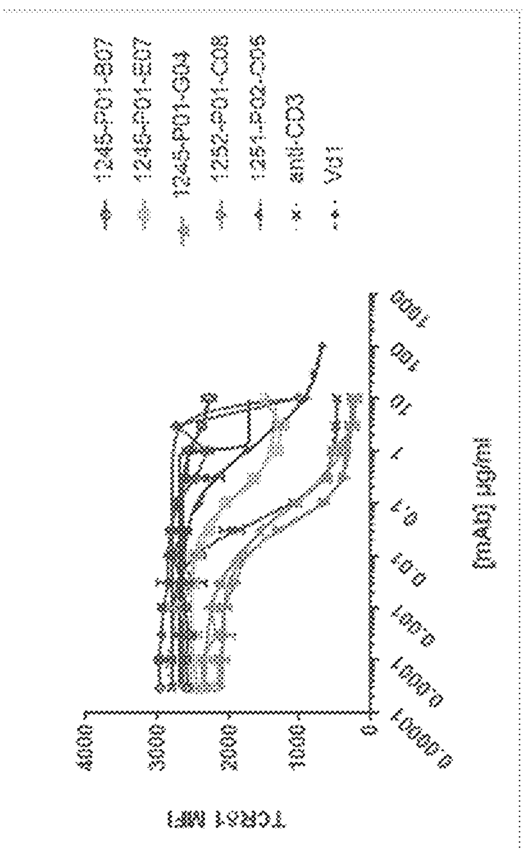
FIGS. 4A-4B: Results of TCR Downregulation Assay (with THP-1 pre-loaded antibodies) for clones 1245_P01_E07, 1252_P01_C08, 1245_P02_G04, 1245_P01_B07 and 1251_P02_C05 (FIG. 4A) or clones 1139_P01_E04, 1245_P02_F07, 1245_P01_G06 1245_P01_G09, 1138_P01_B09, 1251_P02_G10 and 1252_P01_C08 (FIG. 4B)
Figure 4B:
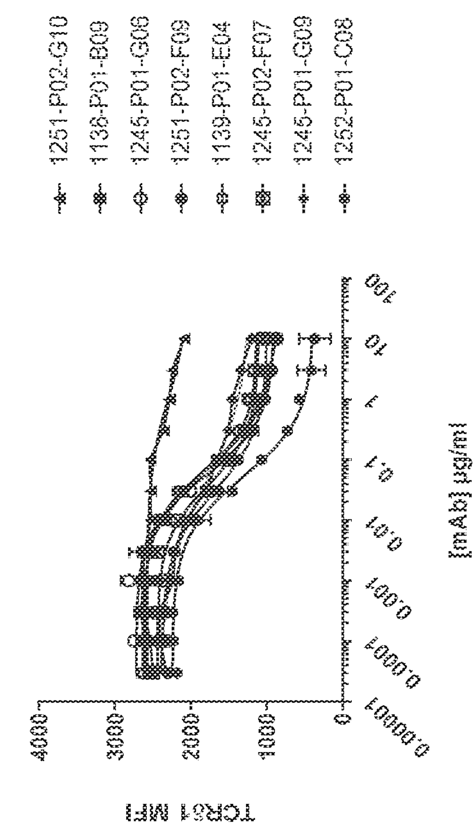

The assay was performed using skin-derived γδ T cells obtained from three different donor samples (samples with 94%, 80% and 57% purity). Results are shown in FIG. 4. EC50 values are summarised in Table 10, below.

Example 7. T Cell Degranulation Assay

A second assay assessed the degranulation of γδ T cells. It is thought γδ T cells may mediate target cell killing by perforin-granzyme-mediated activation of apoptosis. Lytic granules within the cytoplasm of the γδ T cell may be released toward the target cell upon T cell activation. Therefore, labelling target cells with antibodies to CD107a and measuring the expression by flow cytometry can be used to identify degranulating γδ T cells.

Figure 5A:
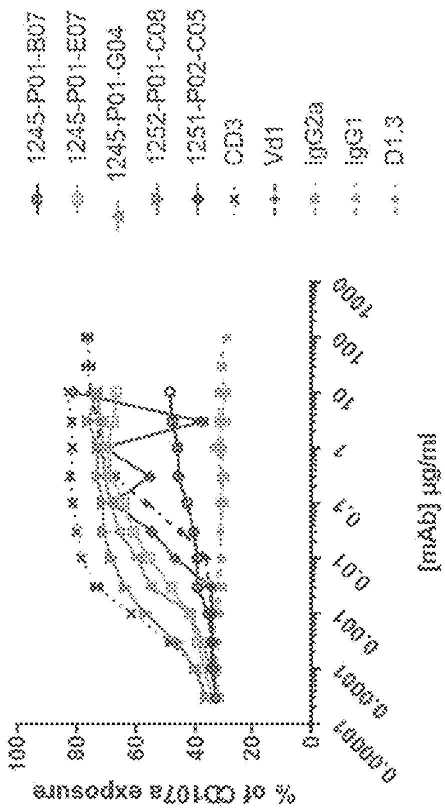
FIGS. 5A-5B: Results of T cell degranulation Assay for clones 1245_P01_E07, 1252_P01_C08, 1245_P02_G04, 1245_P01_B07 and 1251_P02_C05 (FIG. 5A) or clones 1139_P01_E04, 1245_P02_F07, 1245_P01_G06, 1245_P01_G09, 1138_P01_B09, and 1251_P02_G10 (FIG. 5B).
Figure 5B:
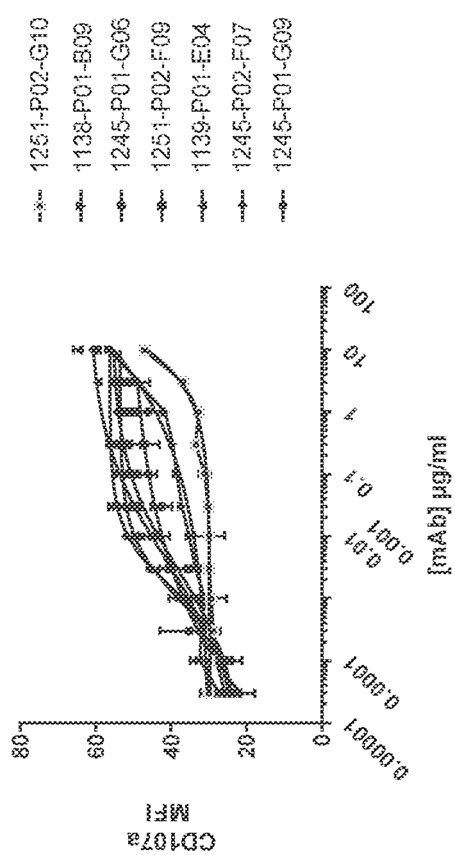

As for Example 6, selected antibodies were tested against commercial anti-CD3 and anti-Vδ1 antibodies as positive controls or against 1252_P01_C08 as a positive control (for 1139_P01_E04, 1245_P02_F07, 1245_P01_G06 and 1245_P01_G09). IgG2a, IgG1 and D1.3 antibodies were used as negative controls. The assay was performed using skin-derived γδ T cells obtained from three different donor samples (samples with 94%, 80% and 57% purity). Results are shown in FIG. 5. EC50 values are summarised in Table 10, below.

Example 8. Killing Assay

A third assay assessed the ability of γδ T cells activated with the selected antibodies to kill target cells.

As for Example 6, selected antibodies were tested against commercial anti-CD3 and anti-Vδ1 antibodies as positive controls or against 1252_P01_C08 as a positive control (for 1139_P01_E04, 1245_P02_F07, 1245_P01_G06 and 1245_P01_G09) and anti-panγδ as a negative control. IgG2a, IgG1 and D1.3 antibodies were also used as isotype controls. The assay was performed using skin-derived γδ T cells obtained from two donors (94% and 80% purity) and the results are shown in FIG. 6.

Results from the three functional assays tested in Examples 6-8 are summarised in Table 5.

TABLE 10

Summary of results obtained from functional assays

| Clone ID | TCR downregulation (EC50 μg/ml-3 donors) | T cell degranulation (EC50 μg/ml-3 donors) | Killing assay (EC50 μg/ml-2 or 3 donors) |
|---|---|---|---|
| 1245_P01_E07 | 0.04-0.11 | 0.007-0.004 | 0.06 |
| 1252_P01_C08 | 0.02-0.03 | 0.001-0.0006 | 0.02 |
| 1245_P02_G04 | 0.01-0.05 | 0.002 | 0.10 |
| 1245_P01_B07 | Positive; 0.35 (1 donor only) | Positive; 0.1 (1 donor only) | 0.13 |
| 1251_P02_C05 | Positive; N/D | Positive; N/D | N/D* |
| 1139_P01_E04 | 0.027-0.057 | 0.005 | 0.005-0.019 |
| 1245_P02_F07 | 0.032-0.043 | 0.001-0.002 | 0.006-0.018 |
| 1245_P01_G06 | 0.042-0.055 | 0.001 | 0.007-0.051 |
| 1245_P01_G09 | 0.029-0.040 | 0.001 | 0.003-0.008 |
| 1138_P01_B09 | 0.078-0.130 | N/D | 0.055-0.199 |
| 1251_P02_G10 | 0.849; N/D | N/D | N/D** |
| OKT3 (anti-CD3 antibody) | 0.03-0.04 | 0.001-0.008 | 0.05 |
| TS8.2 (anti-Vδ1 antibody) | 0.48-0.8 | 0.07-0.16 | N/D* |

N/D: could not be determined; N/D*: could not be determined, titration curve did not reach plateau; N/D**: Reduced killing profile, EC50 not established Example 9. Epitope Mapping In order to determine the epitope of antigen/antibody complexes with high resolution, the protein complexes were incubated with deuterated cross-linkers and subjected to multi-enzymatic cleavage. After enrichment of the cross-linked peptides, the samples were analysed by high resolution mass spectrometry (nLC-LTQ-Orbitrap MS) and the data generated were analysed using XQuest (version 2.0) and Stavrox (version 3.6) software.

After trypsin, chymotrypsin, Asp-N, elastase and thermolysin proteolysis of the protein complex L1(DV1-GV4)/1245_P01_E07 with deuterated d0d12, the nLC-orbitrap MS/MS analysis detected 13 cross-linked peptides between L1(DV1-GV4) and the antibody 1245_P01_E07.

After trypsin, chymotrypsin, Asp-N, elastase and thermolysin proteolysis of the protein complex L1(DV1-GV4)/1252_P01_C08 with deuterated d0d12, the nLC-orbitrap MS/MS analysis detected 5 cross-linked peptides between L1(DV1-GV4) and the antibody 1252_P01_C08.

After trypsin, chymotrypsin, Asp-N, elastase and thermolysin proteolysis of the protein complex L1(DV1-GV4)/1245_P02_G04 with deuterated d0d12, the nLC-orbitrap MS/MS analysis detected 20 cross-linked peptides between L1(DV1-GV4) and the antibody 1245_P02_G04.

After trypsin, chymotrypsin, Asp-N, elastase and thermolysin proteolysis of the protein complex L1(DV1-GV4)/1251_P02_CO5 with deuterated d0d12, the nLC-orbitrap MS/MS analysis detected 5 cross-linked peptides between L1(DV1-GV4) and the antibody 1251_P02_C05.

Epitope binding with another antibody, Clone ID 1141_P01_E01, was also tested. After trypsin, chymotrypsin, Asp-N, elastase and thermolysin proteolysis of the protein complex L1(DV1-GV4)/1141_P01_E01 with deuterated d0d12, the nLC-orbitrap MS/MS analysis detected 20 cross-linked peptides between L1(DV1-GV4) and the antibody 1141_P01_E01.

A summary of the epitope mapping results is presented in Table 11.

TABLE 11

| Results of epitope mapping for antigen/antibody complexes | |
|---|---|
| Clone ID | Epitope mapping, amino acid numbering of SEQ ID NO: 272 |
| 1245_P01_E07 | 5, 9, 16, 20, 62, 64, 72, 77 |
| 1252_P01_C08 | 50, 53, 59, 62, 64 |
| 1245_P02_G04 | 37, 42, 50, 53, 59, 64, 68, 69, 72, 73, 77 |
| 1251_P02_C05 | 59, 60, 68, 72 |
| 1141_P01_E01 | 3, 5, 9, 10, 12, 16, 17, 62, 64, 68, 69 |

Example 10. Expansion of Vδ1 T Cells

Expansion of isolated γδ T cells was investigated in the presence of selected antibodies and comparator antibodies. Comparator antibodies were selected from: OKT3 anti-CD3 antibody as a positive control, no antibody as a negative control or IgG1 antibody as an isotype control. Commercially available anti-Vδ1 antibodies, TS-1 and TS8.2 were also tested for comparison.

Experiment 1

An initial investigation was conducted by seeding 70,000 cells/well with Complete Optimizer and cytokines as described in the "γδ T cell preparation" for blood-derived γδ T cells of Example 1. Selected and comparator antibodies were tested at various concentrations ranging from 4.2 ng/ml to 420 ng/ml. This experiment was conducted using tissue culture plates which allow the binding/immobilisation of the antibodies to the plastic.

Figure 7A:
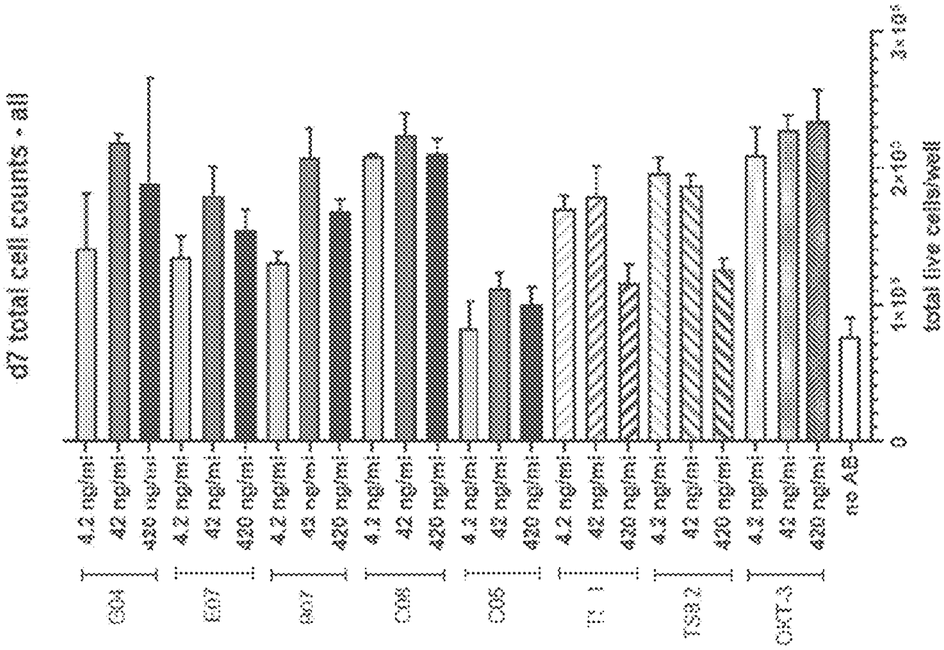
FIGS. 7A-7C: Total cell counts during Experiment 1 of Example 10. Samples were cultured with varying concentration of anti-Vδ1 antibodies described herein and compared to samples cultured with comparator antibodies or controls. Graphs show total cell counts at (FIG. 7A) day 7, (FIG. 7B) day 14 and (FIG. 7C) day 18.
Figure 7B:
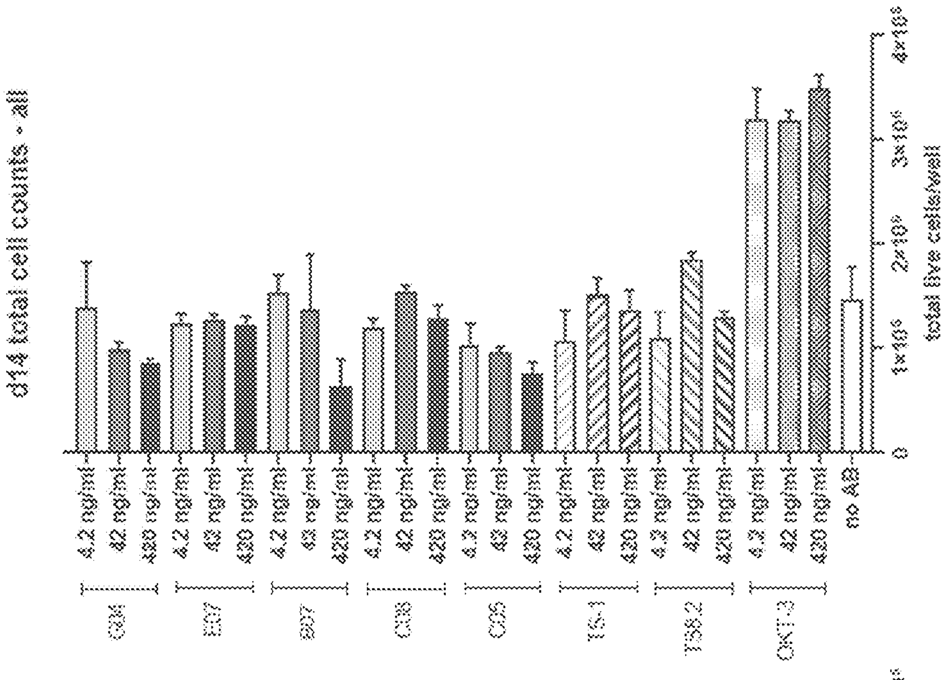
Figure 7C:
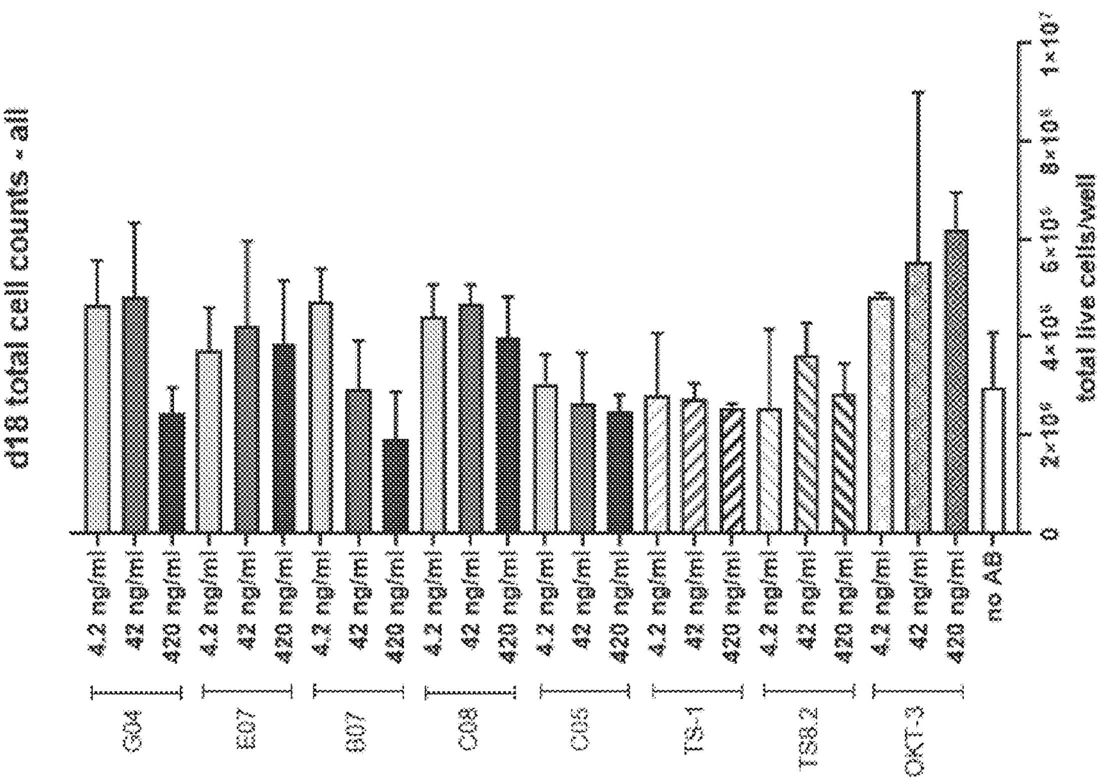
Figure 8B:
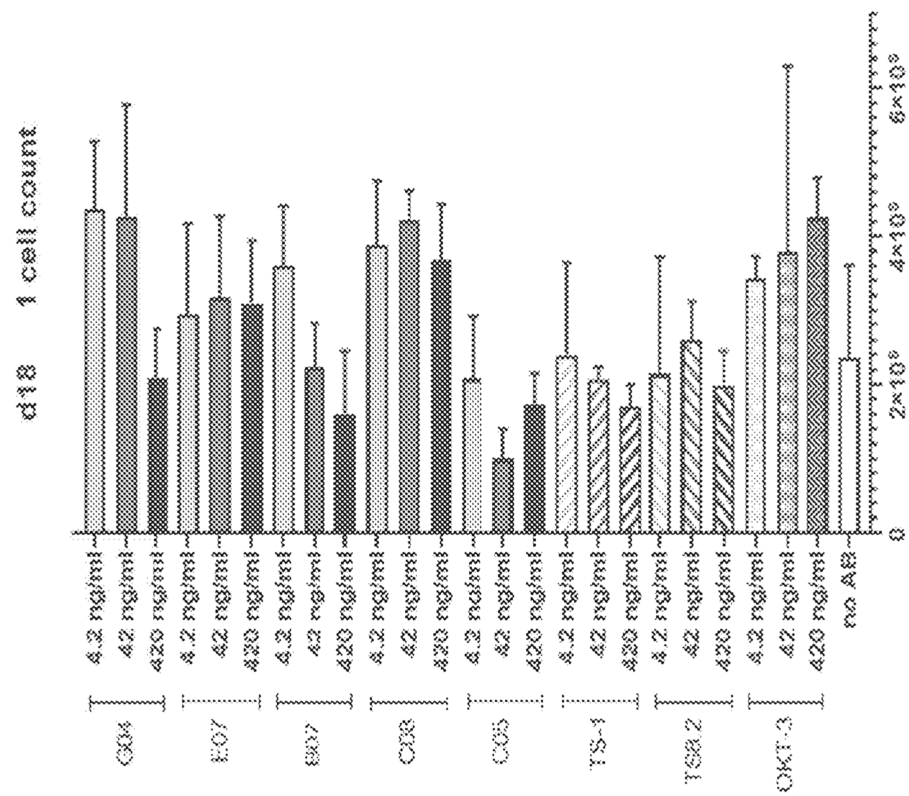
FIGS. 8A-8C: Analysis of Vδ1 T cells during Experiment 1 of Example 10. Graphs show (FIG. 8A) percentage of Vδ1 T cells, (FIG. 8B) Vδ1 T cell count and (FIG. 8C) Vδ1 fold change in the samples at day 18.
Figure 8A:
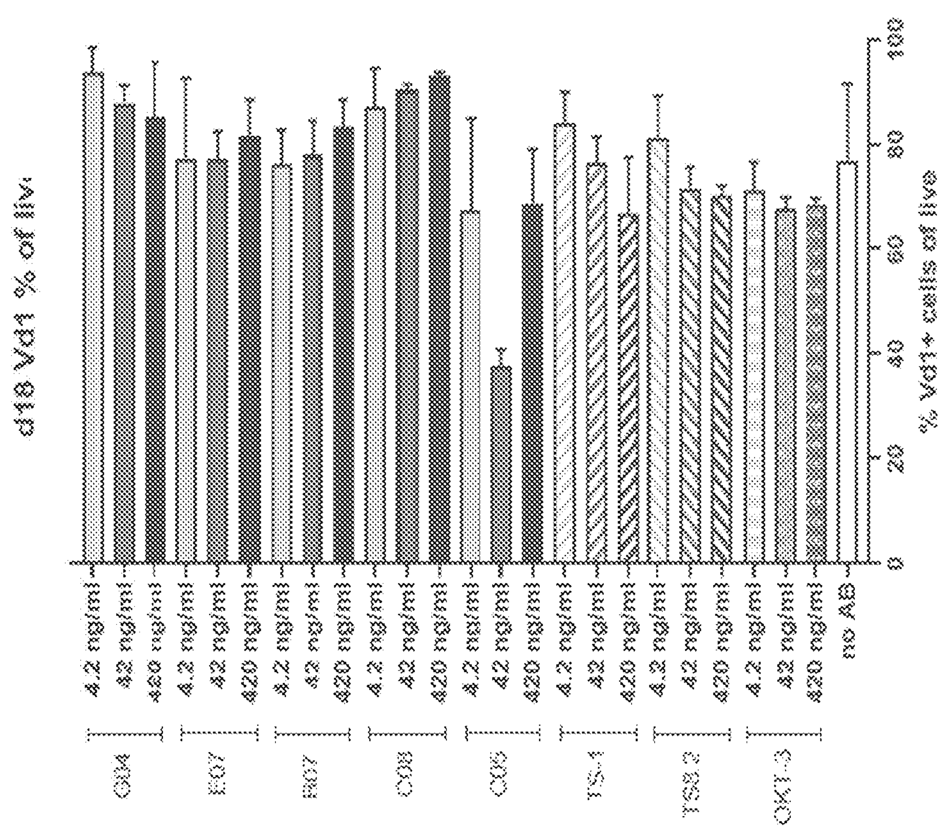
Figure 8C:
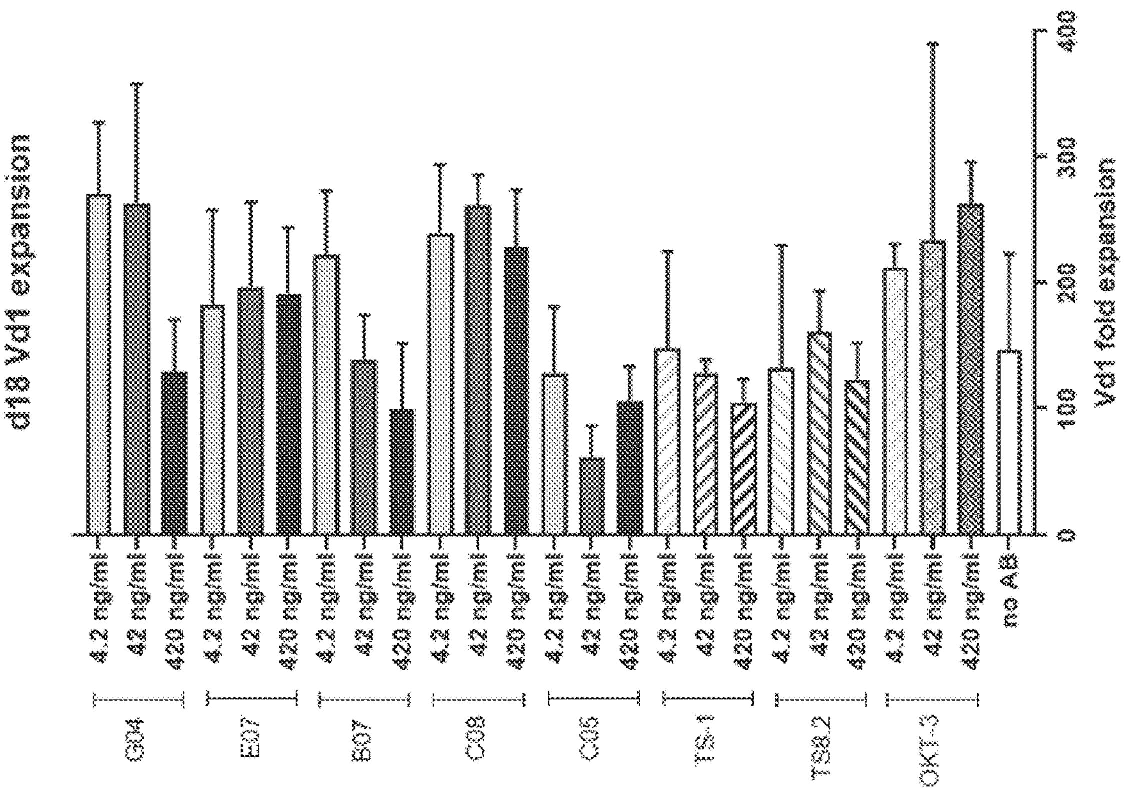
Figure 9B:
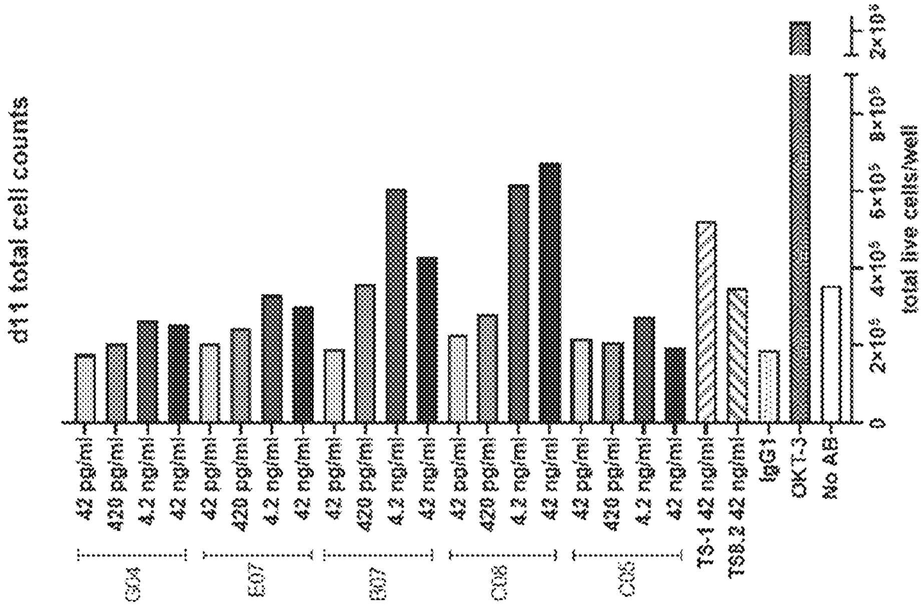
FIGS. 9A-9D: Total cell counts during Experiment 2 of Example 10. Samples were cultured with varying concentration of anti-Vδ1 antibodies described herein and compared to samples cultured with comparator antibodies or controls. Graphs show total cell counts at (FIG. 9A) day 7, (FIG. 9B) day 11, (FIG. 9C) day 14 and (FIG. 9D) day 17.
Figure 9A:
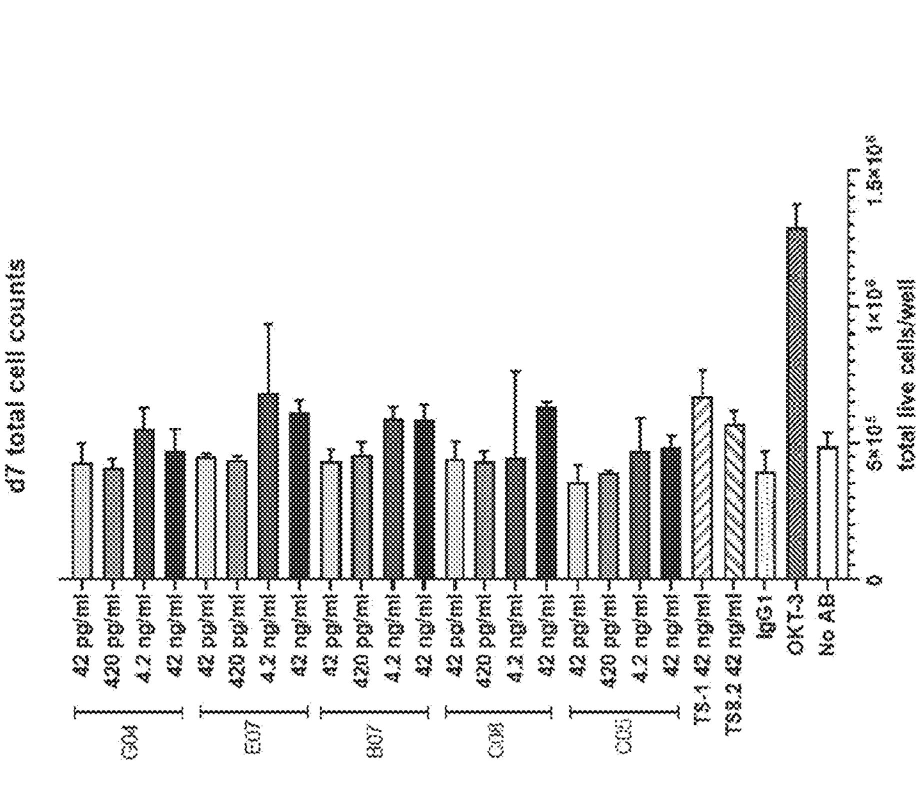
Figure 9D:
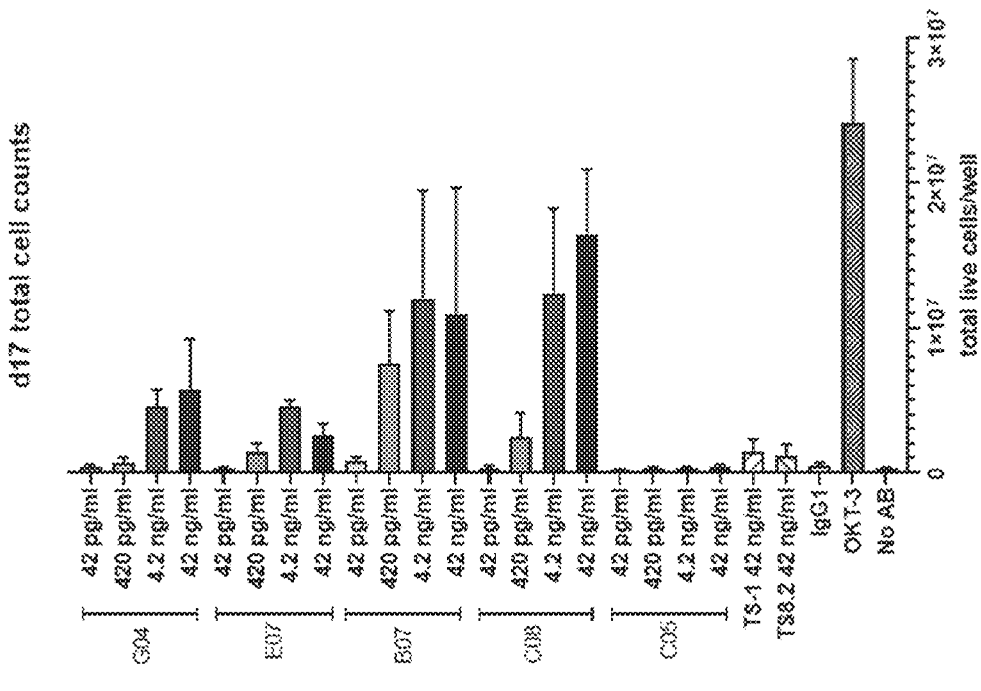
Figure 9C:
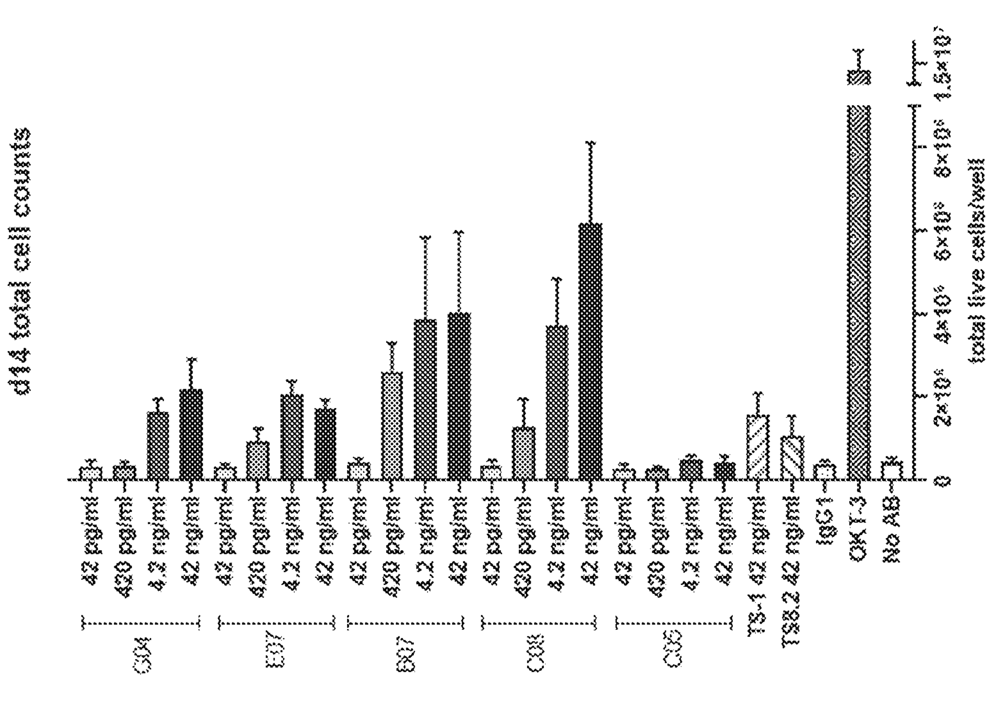

Cells were harvested on days 7, 14 and 18 and the total cell count was determined using a cell counter (NC250, ChemoMetec). The results are shown in FIG. 7. Cell viability of Vδ1 T cells was also measured on each harvest and all antibodies were shown to maintain cell viability throughout the experiments (data not shown). On day 18, the percentage, cell count and fold change of Vδ1 T cells was also analysed. The results are shown in FIG. 8.

As can be seen in FIG. 7, the total number of cells produced in cultures with antibodies increased steadily throughout the culture and were comparable or better than the commercial anti-Vδ1 antibodies. At day 18, the proportion of Vδ1 positive cells in the presence of 1245_P02_G04 ("G04"), 1245_P01_E07 ("E07"), 1245_P01 B07 ("B07") and 1252_P01_C08 ("C08") antibodies at most concentrations tested was greater than in cultures where OKT3, TS-1 or TS8.2 control antibodies were present (see FIG. 8A).

Experiment 2

A subsequent experiment was performed on isolated cells in a culture vessel with cytokines as described in the "γδ T cell preparation" of Example 1. Compared to Experiment 1, a different culture vessel was used whose surface does not facilitate antibody binding/immobilisation. Selected and comparator antibodies were tested at various concentrations ranging from 42 μg/ml to 42 ng/ml. During Experiment 2, results were obtained from experiments run in triplicates.

Figure 10B:
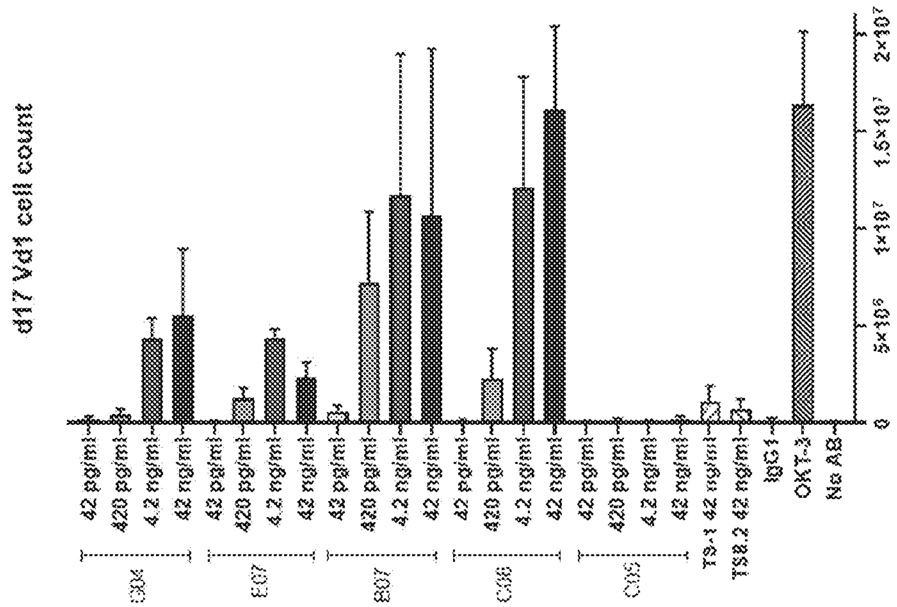
FIGS. 10A-10C: Analysis of Vδ1 T cells during Experiment 2 of Example 10. Graphs show (FIG. 10A) percentage of Vδ1 T cells, (FIG. 10B) Vδ1 T cell count and (FIG. 10C) Vδ1 fold change in the samples at day 17.
Figure 10A:
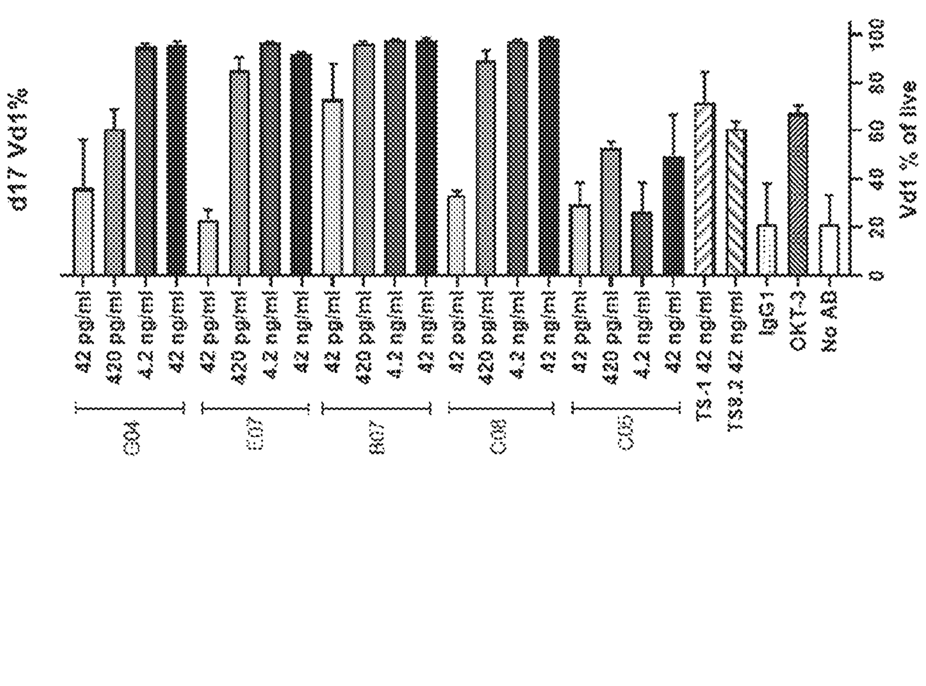
Figure 10C:
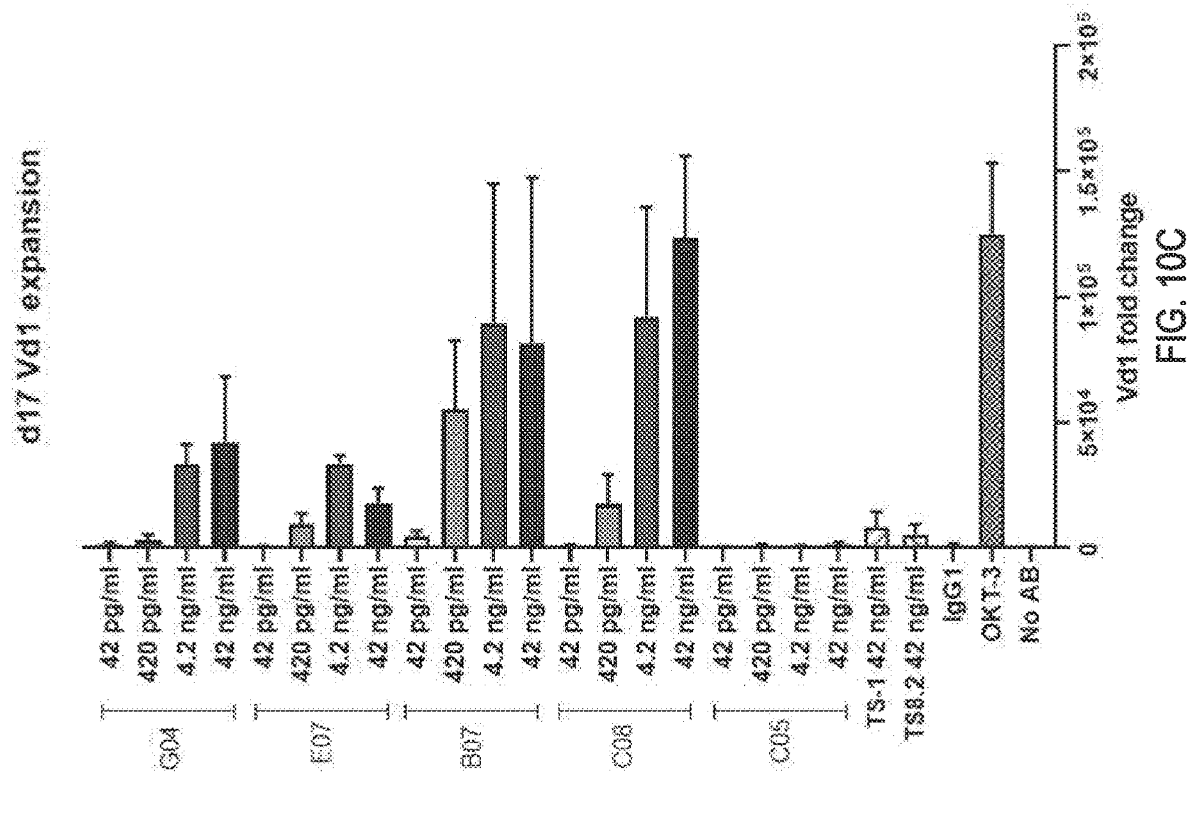

Cells were harvested on days 7, 11, 14 and 17 and the total cell count was determined using a cell counter as before. The results are shown in FIG. 9. On day 17, the percentage, cell count and fold change of Vol T cells was also analysed. The results are shown in FIG. 10.

Figure 11:
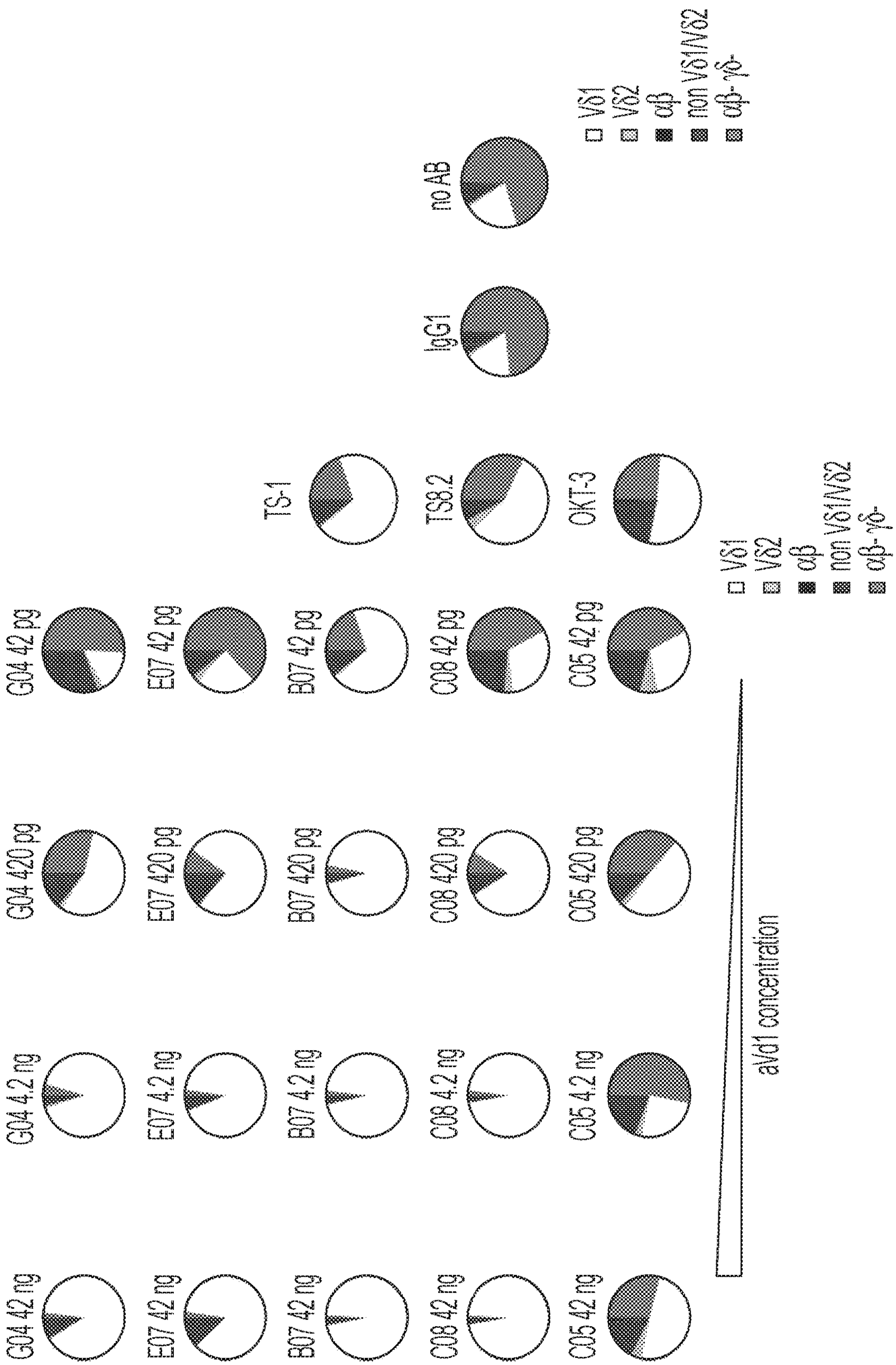
FIG. 11: Cell composition analysis. The cell types present in the samples (including non-Vδ1 cells) were measured on day 17 of Experiment 2. Cells were harvested and analysed by flow cytometry for surface expression of Vδ1, Vδ2 and αβTCR. The percentage values are also provided in Table 12.

The cell composition, including non-Vδ1 cells, were also measured during Experiment 2. Day 17 cells were harvested and analysed by flow cytometry for surface expression of Vδ1, Vβ2 and αβTCR. The proportions of each cell type in each culture are shown graphically in FIG. 11 and the percentage values are provided in Table 12.

TABLE 12

Cell composition at day 17-Percentage of live cells of each subset

| | αβ- γ- | Vδ1 | Vδ2 | non Vδ1/ Vδ2 | αβ |
|---|---|---|---|---|---|
| no AB | 63.00 | 18.17 | 0.86 | 7.10 | 0.37 |
| OKT-3 | 25.63 | 50.43 | 0.25 | 20.13 | 1.13 |
| IgG1 | 65.77 | 15.59 | 1.11 | 6.91 | 0.42 |
| TS8.2 42 ng/ml | 30.60 | 53.57 | 3.59 | 7.46 | 0.14 |
| TS-1 42 ng/ml | 18.77 | 65.90 | 0.91 | 9.51 | 0.12 |
| C08 42 ng/ml | 0.79 | 96.43 | 0.08 | 2.51 | 0.05 |
| C08 4.2 ng/ml | 1.91 | 94.67 | 0.18 | 2.63 | 0.05 |
| C08 420 pg/ml | 8.47 | 80.57 | 0.28 | 8.42 | 0.04 |
| C08 42 pg/ml | 35.97 | 25.93 | 3.04 | 19.50 | 0.31 |
| B07 42 ng/ml | 0.94 | 95.57 | 0.46 | 2.73 | 0.05 |
| B07 4.2 ng/ml | 1.79 | 94.10 | 0.40 | 3.28 | 0.01 |
| B07 420 pg/ml | 3.08 | 91.80 | 0.29 | 3.94 | 0.02 |
| B07 42 pg/ml | 17.93 | 62.90 | 0.85 | 9.16 | 0.07 |
| E07 42 ng/ml | 2.29 | 85.13 | 0.19 | 11.65 | 0.04 |
| E07 4.2 ng/ml | 2.15 | 91.23 | 0.13 | 5.77 | 0.04 |
| E07 420 pg/ml | 9.25 | 73.90 | 0.42 | 13.05 | 0.02 |
| E07 42 pg/ml | 49.23 | 18.67 | 2.17 | 7.70 | 0.43 |
| G04 42 ng/ml | 1.90 | 88.53 | 0.47 | 8.09 | 0.05 |
| G04 4.2 ng/ml | 4.25 | 89.67 | 0.93 | 3.98 | 0.02 |
| G04 420 pg/ml | 25.97 | 50.60 | 1.45 | 12.72 | 0.11 |
| G04 42 pg/ml | 44.00 | 13.77 | 2.33 | 26.30 | 0.32 |
| CO5 42 ng/ml | 25.00 | 42.03 | 3.75 | 13.67 | 1.32 |
| CO5 4.2 ng/ml | 46.87 | 22.03 | 2.58 | 16.46 | 0.38 |
| C05 420 pg/ml | 33.53 | 44.60 | 2.23 | 11.13 | 0.22 |
| C05 42 pg/ml | 36.83 | 25.23 | 6.16 | 18.00 | 0.30 |

As can be seen from these results, the proportion of Vδ1 positive cells is greater in cultures with B07, C08, E07 and G04 present compared to OKT3, TS-1 or TS8.2 controls. Therefore, the tested antibodies produce and expand Vδ1 positive cells more efficiently than commercially available antibodies, even when present at low concentrations in culture.

Cells from day 17 of Experiment 2 were also analysed for additional cell markers, including CD3-CD56+ to identify the presence of Natural Killer (NK) cells and Vδ1 T cells which express CD27 (i.e. CD27+). The results are summarised in Table 13.

TABLE 13

Cell composition at day 17-Percentage of NK and CD27+ cells

| | % CD56+ CD3− | | % CD27+ of Vδ1 | |
|---|---|---|---|---|
| | Mean | SEM | Mean | SEM |
| no AB | 66.33 | 8.49 | 92.43 | 1.58 |
| OKT-3 | 7.90 | 1.04 | 99.03 | 0.14 |
| IgG1 | 70.67 | 6.41 | 87.87 | 0.81 |
| TS8.2 42 ng/ml | 31.63 | 1.99 | 66.73 | 5.55 |
| TS-1 42 ng/ml | 22.97 | 1.75 | 94.40 | 1.14 |
| C08 42 ng/ml | 1.00 | 0.15 | 98.17 | 0.31 |
| C08 4.2 ng/ml | 2.06 | 0.07 | 95.07 | 1.23 |
| C08 420 pg/ml | 8.63 | 1.64 | 88.43 | 3.65 |
| C08 42 pg/ml | 45.10 | 3.44 | 91.50 | 2.50 |
| B07 42 ng/ml | 1.40 | 0.39 | 95.47 | 1.37 |
| B07 4.2 ng/ml | 1.70 | 0.16 | 96.70 | 0.43 |
| B07 420 pg/ml | 3.47 | 0.38 | 95.17 | 0.86 |
| B07 42 pg/ml | 22.03 | 4.66 | 88.03 | 3.00 |
| E07 42 ng/ml | 2.59 | 0.93 | 92.27 | 2.10 |
| E07 4.2 ng/ml | 1.98 | 0.09 | 95.77 | 0.52 |

TABLE 13-continued

| Cell composition at day 17-Percentage of NK and CD27+ cells | | | | |
|---|---|---|---|---|
| | % CD56+ CD3− | | % CD27+ of Vδ1 | |
| | Mean | SEM | Mean | SEM |
| E07 420 pg/ml | 8.72 | 1.33 | 92.43 | 0.14 |
| E07 42 pg/ml | 67.73 | 1.23 | 93.60 | 1.16 |
| G04 42 ng/ml | 2.20 | 0.32 | 93.80 | 0.36 |
| G04 4.2 ng/ml | 3.53 | 0.51 | 91.63 | 1.80 |
| G04 420 pg/ml | 30.53 | 5.00 | 81.37 | 3.11 |
| G04 42 pg/ml | 51.13 | 8.90 | 94.20 | 0.93 |
| C05 42 ng/ml | 37.17 | 6.53 | 93.80 | 0.87 |
| C05 4.2 ng/ml | 52.27 | 8.16 | 85.40 | 4.46 |
| C05 420 pg/ml | 37.93 | 1.57 | 90.83 | 2.01 |
| C05 42 pg/ml | 43.40 | 8.64 | 92.17 | 2.02 |

SEM: Standard error of the mean

Example 11. Functionality of Vδ1 T Cells

Figure 12A:
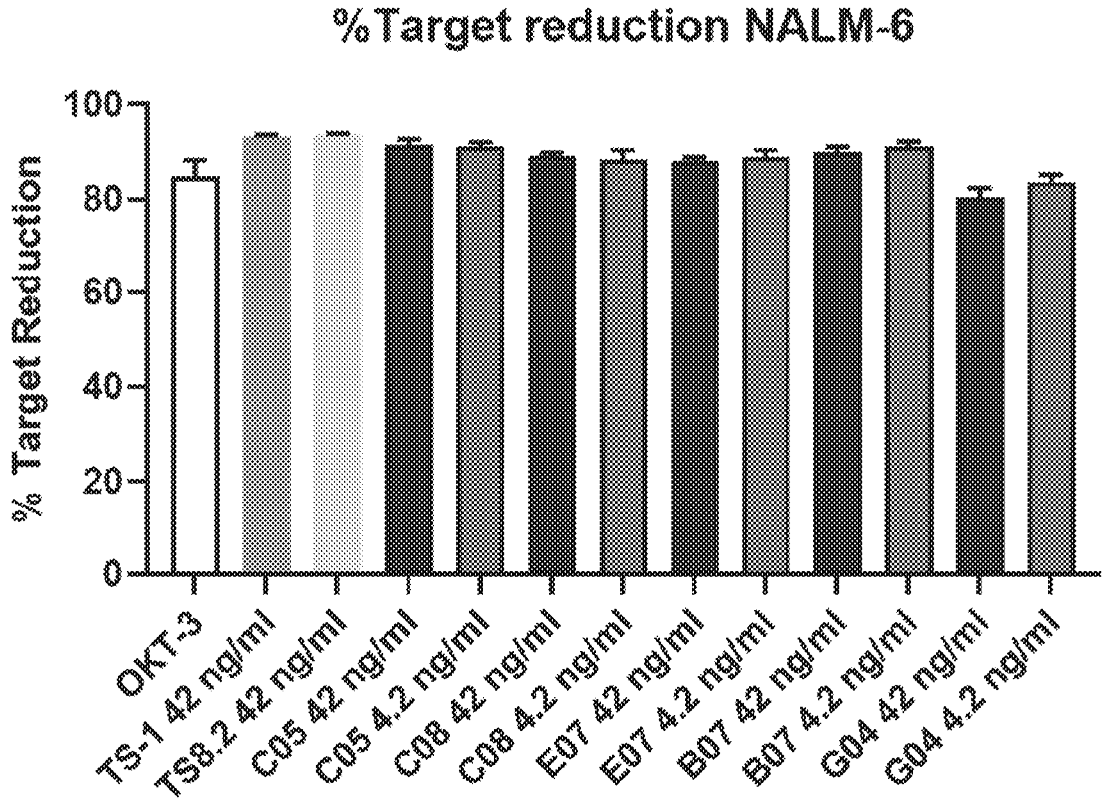
FIGS. 12A-12B: SYTOX-flow killing assay results. Cell functionality was tested using the SYTOX-flow killing assay and results are presented for (FIG. 12A) Experiment 1 at day 14 using cells in a 10:1 Effector-to-Target (E:T) ratio, and (FIG. 12B) Experiment 2 at day 17 (post freeze-thaw) using cells at a 1:1 and 10:1 E:T ratio.
Figure 12B:
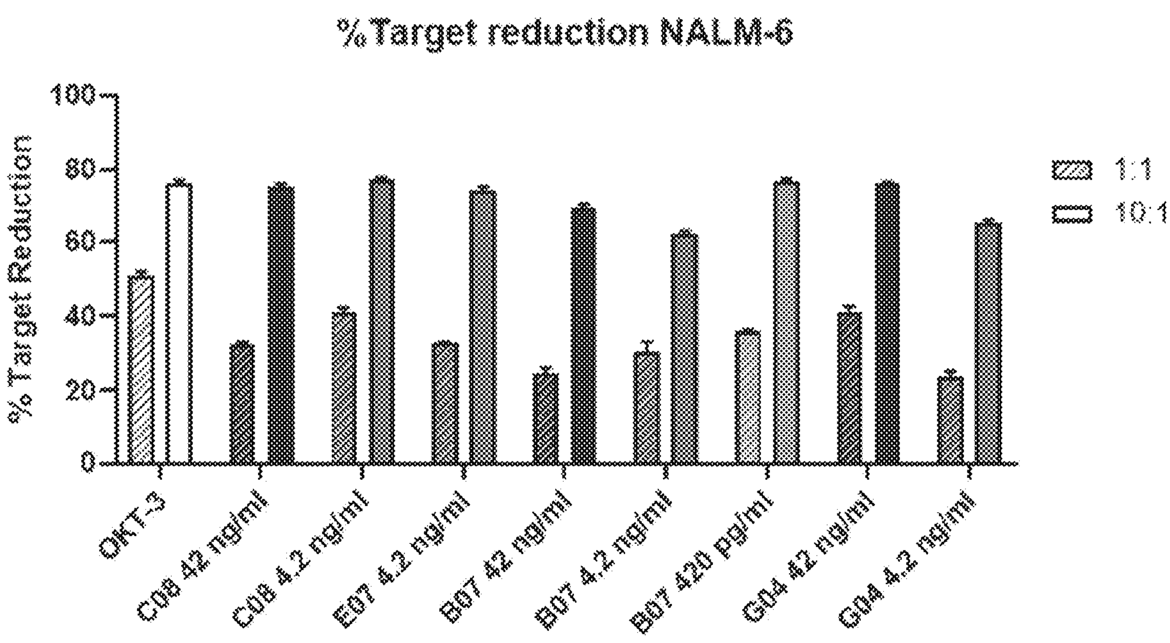

Vδ1 T cells expanded in the presence of the selected antibodies retained a polyclonal repertoire of CDR3 regions and were also tested for functionality using the SYTOX-flow killing assay. The results are presented for cells obtained during Experiment 1 at day 14 using cells in a 10:1 Effector-to-Target (E:T) ratio (FIG. 12A) and for cells obtained during Experiment 2 at day 17 (post freeze-thaw) using cells at a 1:1 and 10:1 E:T ratio (FIG. 12B).

As can be seen in FIG. 12, Vδ1 positive cells expanded in the presence of all antibodies effectively lysed target cells, indicating that they are functional even after freezing and thawing the cells.

Example 12. Functionality of Cells after Storage

Figure 14:
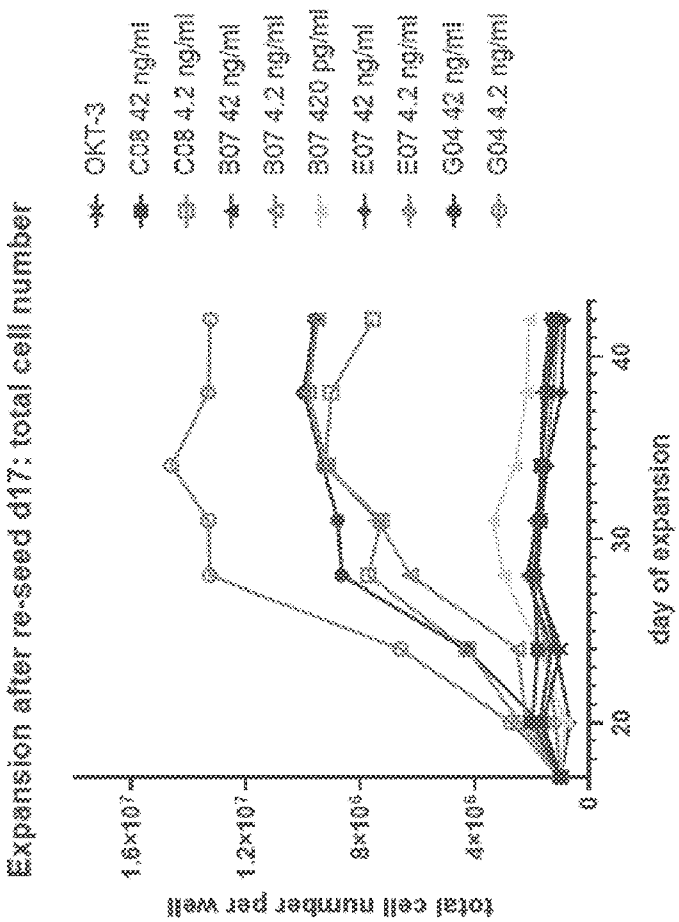
FIG. 14: Monitoring cell expansion. Total cell counts were monitored until day 42 for cells cultured post freeze-thaw.
Figure 13:
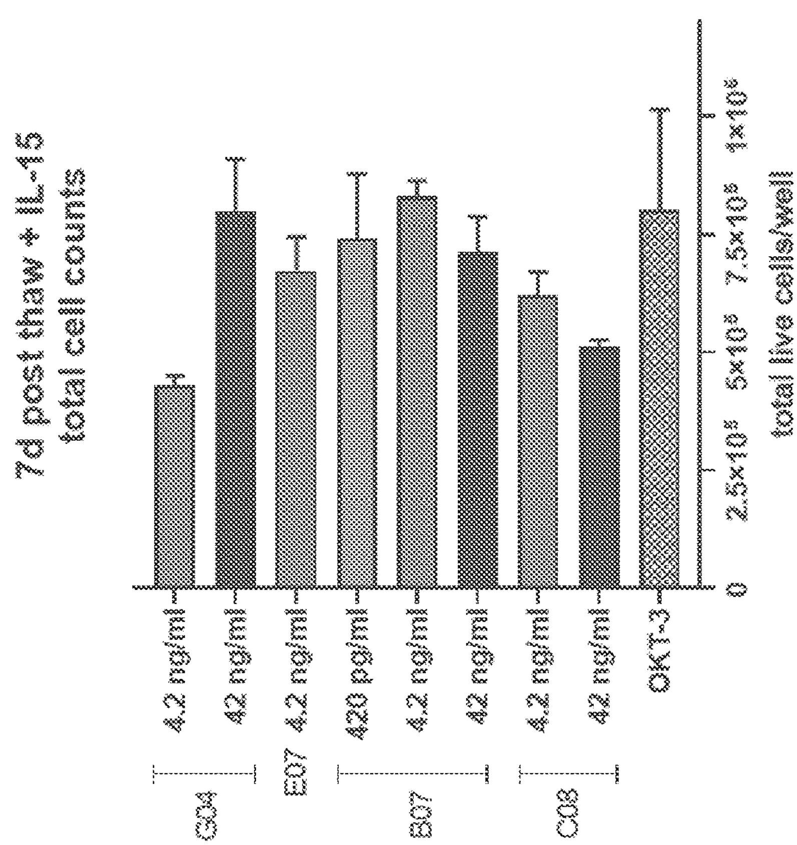
FIG. 13: Total cell count post freeze-thaw. Graph shows the total cell counts after 7 days of culturing cells post freeze-thaw for cultures contacted with B07, C08, E07, G04 or OKT-3 antibodies prior to freezing.

The functionality of cells after a storage step of freezing and then thawing was also investigated. A portion of cells was removed from culture at day 17 of Experiment 2 and frozen. Cells were then thawed and further expanded in culture with IL-15. FIG. 13 shows the total cell counts after 7 days of culturing cells post freeze-thaw for cultures contacted with B07, C08, E07, G04 or OKT-3 antibodies prior to freezing. All cultures showed the ability to proliferate after storage. Culturing was continued until day 42 and total cell counts were monitored during this period (results shown in FIG. 14). Total cell numbers were maintained or increased in the cultures previously exposed to selected antibodies.

Example 13. Binding Equivalence Studies on Modified Anti-Vδ1 Antibodies

An ELISA-based antigen titration binding study was undertaken to compare the 1245_P02_G04 antibody manufactured in HEK to sequence and glycosylation variants thereof manufactured in CHO. Specifically, modifications to framework, to allotype, to hinge-mediated effector functionality, to Asn 297 glycosylation, and/or method of manufacture were undertaken and then included in this study. The assay ELISA set-up was as follows: Antigen comprised Antigen L1 (TRDV1/TRGV4); blocking buffer—2% Marvel/PBS; mAbs diluted in a 1/2 dilution series starting at 5 μg/ml; Antigen-antibody incubation in ELISA plates—1 hour; Wash to remove non-specific binding—3×PBS-Tween, then 3×PBS; Secondary antibody employed—DELFIA Eu labelled anti-human IgG (PerkinElmer; Cat #: 1244-330; 50 μg/ml) at 1/500 dilution; thereafter 1 hr incubation prior to addition of DELFIA Enhancement Solution (PerkinElmer, used as per instruction); measurement by time-resolved fluorometry (TRF). For the antibodies made in CHO, standard expression vectors containing heavy and light chain cassettes were prepared under low-endotoxin conditions based on anion exchange chromatography. DNA concentration was determined by measuring the absorption at a wavelength of 260 nm. Sequences were verified with Sanger sequencing (with up to two sequencing reactions per plasmid depending on the size of the cDNA.) Suspension-adapted CHO K1 cells (originally from ATCC and adapted to serum-free growth in suspension culture) were employed for manufacture. The seed cells were grown in a chemically defined, animal-component free, serum-free medium. Cells were then transfected with vectors and transfection reagent, and cells were grown further. Supernatant was harvested by centrifugation and subsequent filtration (0.2 μm filter) and the antibody was purified using MabSelect™ SuRe™ prior to formulation. To generate the example defucosylated antibody, protocols first described by von Horsten H H et al. (2010) Glycobiology 20(12):1607-18 were introduced into the CHO expression platform described above and ahead of expression and purification. Once manufactured and purified, mAb defucosylation was confirmed by MS-based analysis.

Figure 15:
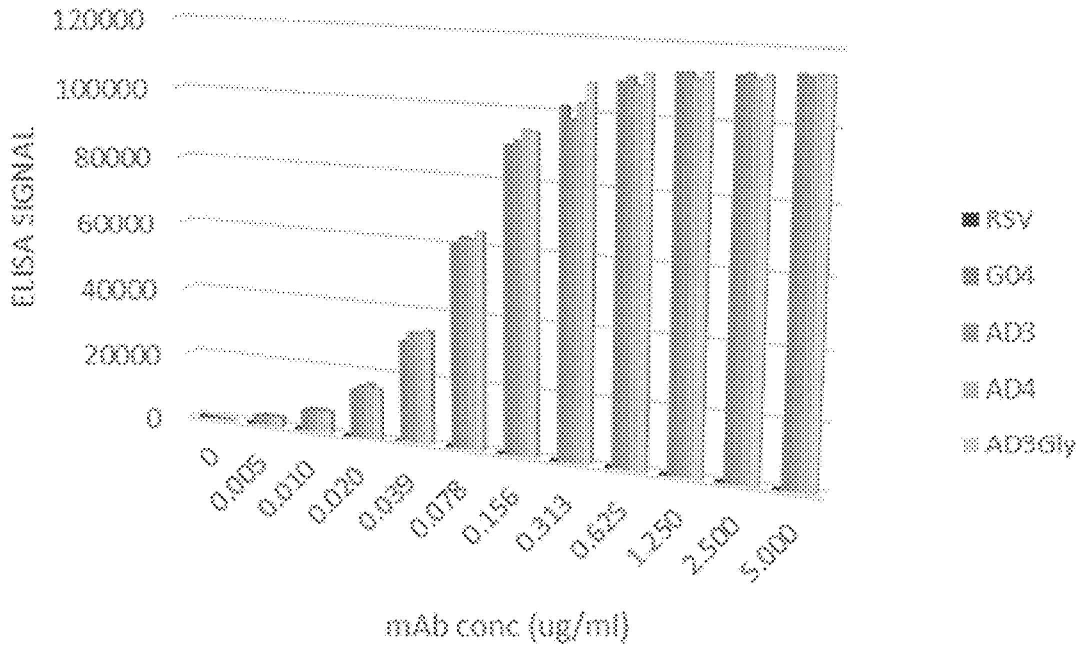
FIG. 15: Binding equivalence studies on modified anti-Vδ1 antibodies.

The results of this study are summarised in FIG. 15. Therein the y-axis indicates ELISA signal and the x-axis indicates Vδ1 antigen concentrations (ug/ml) employed. Antibodies included in this titration study are outlined and for further detail, RSV=anti-RSV control mAb control (made in CHO). G04=1245_P02_G04 (made in HEK). AD3=variant G04 (made in CHO). AD4=hinge modified AD3 (made in CHO). AD3gly=defucosylated AD3 made in engineered CHO. Under all titrations, equivalent antigen binding was observed for all variants.

Figure 16:
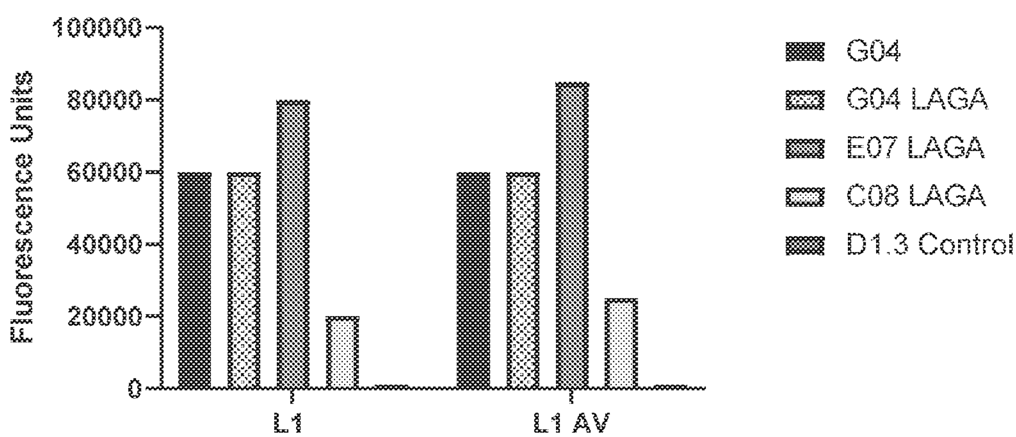
FIG. 16: Anti-Vδ1 antibody binding equivalence studies on human germline Vδ1 antigen and a polymorphic variant thereof.

Example 14. Anti-Vδ1 Antibody Binding Equivalence Studies on Human Germline Vδ1 Antigen and a Polymorphic Variant Thereof An ELISA-based binding study comparison was undertaken to study anti-Vδ1 antibody binding to human germline Vδ1 antigen as per IMGT database (see SEQ ID NO: 272) versus binding to polymorphic human germline Vδ1 antigen (SEQ ID NO: 306). Specifically, a comparison of antibody binding and cross-reactivity with Antigen L1 (containing canonical TRDV1/TRGV4 germline sequence) and L1AV (variant TRDV1/TRGV4 comprising said TRDV1 germline polymorphism) was performed. The results are presented in FIG. 16. Antibodies indicated as follows: G04=1245_P02_G04; G04 LAGA=G04 with Hinge Fc modification (L235A, G237A EU numbering). E07 LAGA=1245_P01_E07 with L235A, G237A. C08 LAGA=1252_P01_C08 with L235A, G237A, D1.3=control. A serial dilution of each antibody to said antigens was performed and at all dilutions, for each antibody variant, equivalent binding to both antigens was observed. Shown is the equivalent binding observed for one example dilution (1 nM antibody) in said series.

Figure 17A:
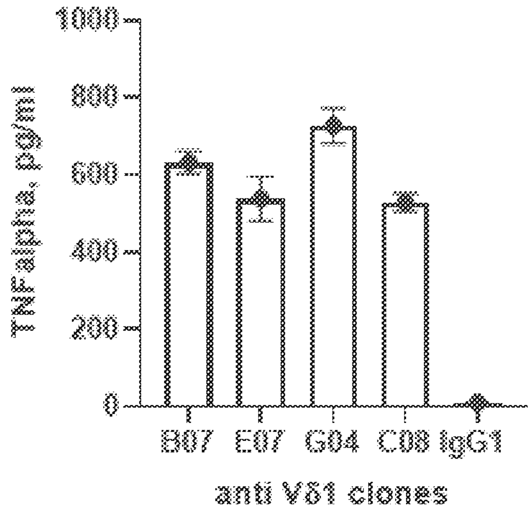
FIGS. 17A-17B: Anti-Vδ1 antibody conferred increases in Vδ1+ cell cytokine secretion levels. Tissue-derived γδ T cells incubated with the antibodies as indicated.
Figure 17B:
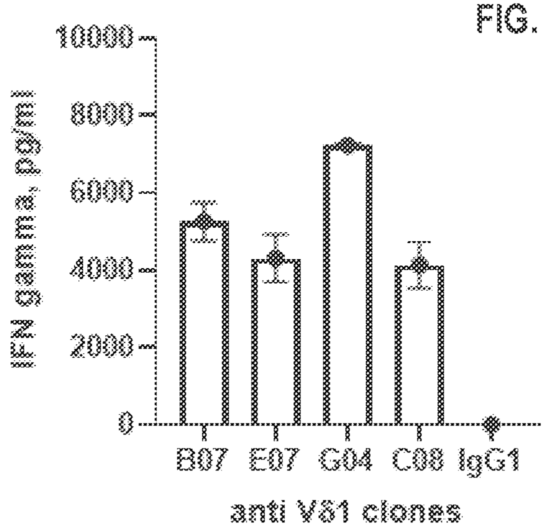
Figure 18:
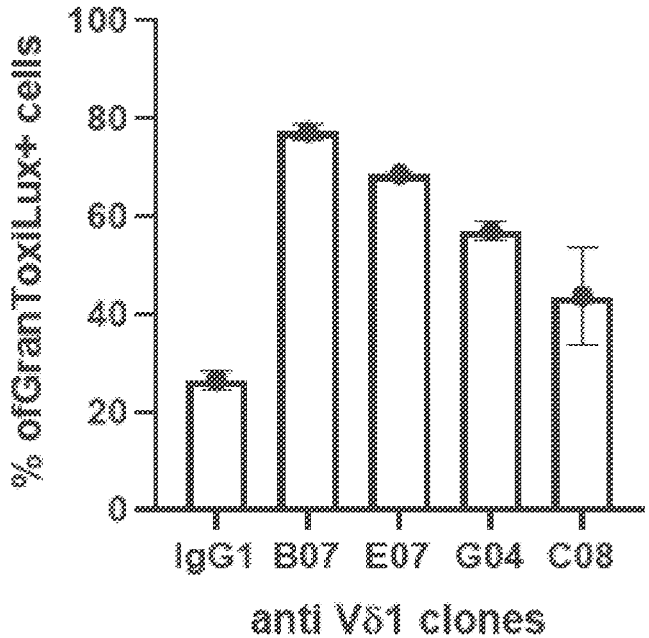
FIG. 18: Anti-Vδ1 antibody conferred increases in Vδ1+ cell Granzyme B levels/activity Cancer cells co-cultured with tissue-derived γδ T cells for one hour at a set 1:20 T:E ratio and with the antibodies as indicated. Results highlight the quantities of Granzyme B detected in the cancer cells at the end of co-culture.

Example 15. Anti-Vδ1 Antibody Binding Conferred Increase in Vδ1+ Cell Cytokine Secretion In brief, all antibodies were diluted to 10 μg/ml and incubated overnight to bind the antibodies to the plate, before washing. Skin-derived γδ T cells from two different skin donations were prepared as outlined elsewhere herein (see Example 1; specifically, the section on skin-derived γδ T cell preparation). These skin cells were then added to tissue culture plates (100,000 cells per well) containing the bound antibodies as indicated. Cells were then left for one day prior to harvest of the supernatant and storage at −80° C. For cytokine analysis of the supernatants, an MSD U-PLEX Human Assay: K151TTK-1, K151UCK-1 was employed (Mesoscale Diagnostics, Maryland). Antibodies employed in this study included IgG1 (non-Vδ1-binding control), B07 (1245_P01_B07), E07 (1245_P01_E07), G04 (1245_P02_G04; 1245), and C08 (1252_P01_C08). The results of this study are presented in FIG. 17. Specifically, FIGS. 17 (A) and (B) respectively outline the quantities of TNF-alpha and IFN-gamma detected in the supernatant when skin-derived γδ T cells and the higher levels observed when anti-Vδ1 antibodies as indicated are applied Example 16. Anti-Vδ1 Antibody Conferred Increase in Vδ1+ Cell Granzyme B Levels/Activity Skin-derived γδ T cells were prepared as outlined elsewhere herein (see Example 1; the section on skin-derived γδ T cell preparation). THP-1 cells were first loaded with GranToxiLux probe (a cell permeable, fluorogenic substrate is designed to detect Granzyme B activity in the target cells) and in accordance with manufacturer's instructions (Oncolmmunin, Inc. Gaithersburg, US). The THP-1 cells were then pulsed with the antibodies as indicated in FIG. 18 at 10 μg/ml prior to mixing with the skin-derived γδ T at a target/effector ratio of 1:20. The co-cultures were then briefly centrifuged to ensure rapid conjugate formation prior to co-culture for 1 hour and subsequent flow analysis in accordance with GranToxiLux protocols. Antibodies employed in this study included IgG1 (non-Vδ1-binding control), B07 (1245_P01_B07), E07 (1245_P01_E07), G04 (1245_P02_G04; 1245), and C08 (1252_P01_C08). The results are presented in FIG. 18 and highlight higher levels of Granzyme B in the target cancer cells observed when anti-Vδ1 antibodies as indicated are applied to this Vδ1+/THP-1 co-culture model system.

Figure 19A:
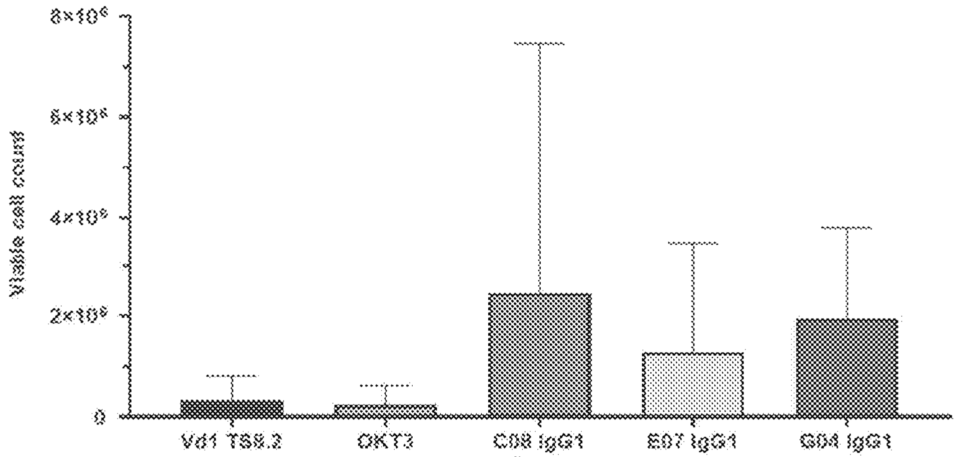
FIGS. 19A-19C: Anti-Vδ1 antibody conferred modulation and proliferation of immune cells in human tissue. Human skin punch-biopsies (from five different donors) incubated for 21-days in culture with the antibodies as indicated.
Figure 19B:
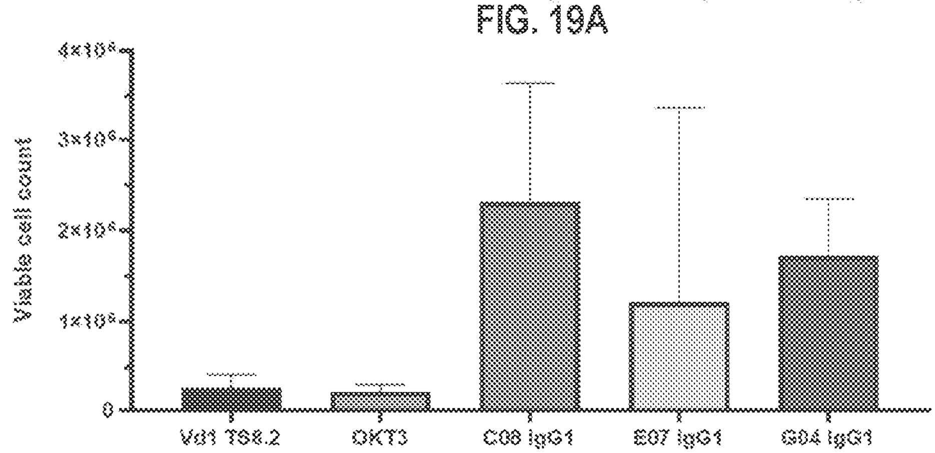
Figure 19C:
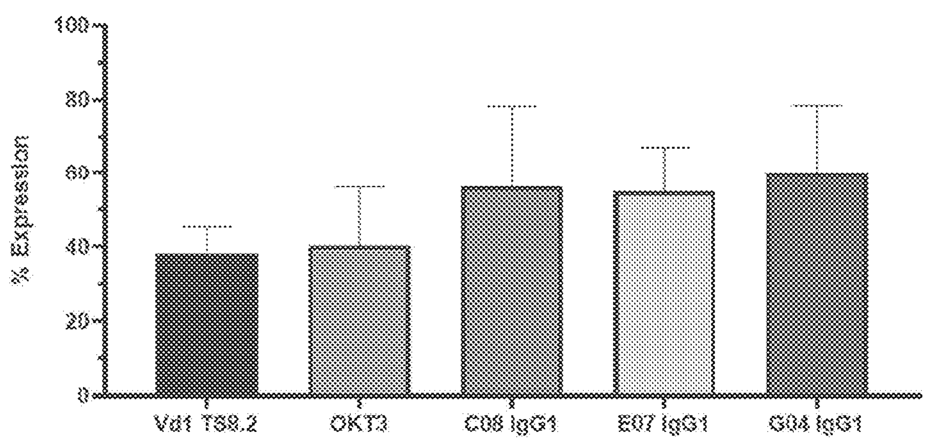
Figure 20A:
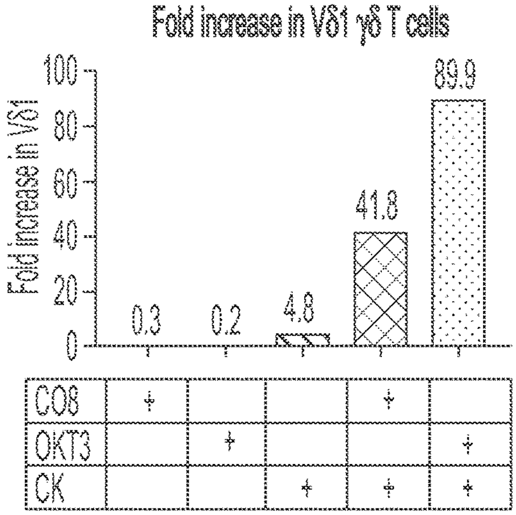
FIG. 20A-20E: Anti-Vδ1 antibody conferred modulation and proliferation of tumour-infiltrating-lymphocyte (TILs) in human tumours. Studies on renal cell carcinoma (RCC)+/−antibodies (FIG. 20A) Fold-increase in TIL Vδ1+ cells.
Figure 20B:
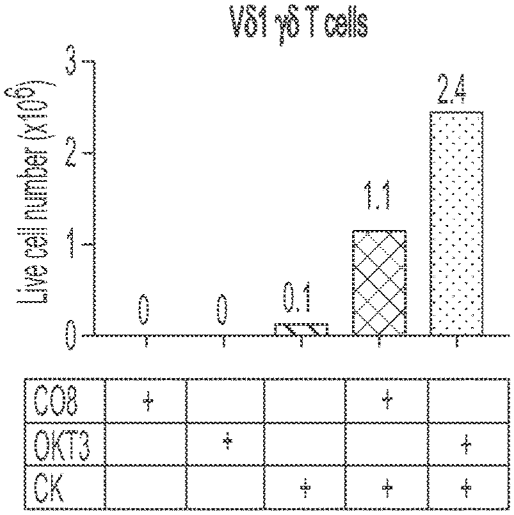
Figure 20C:
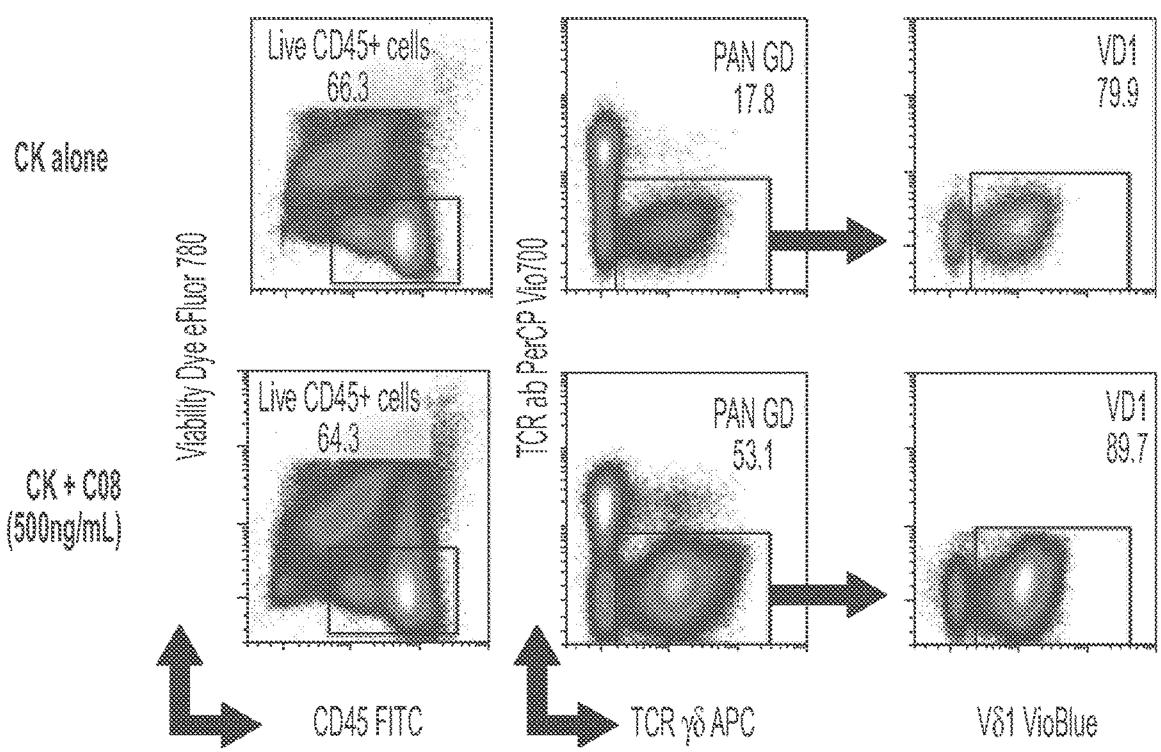
Figure 20D:
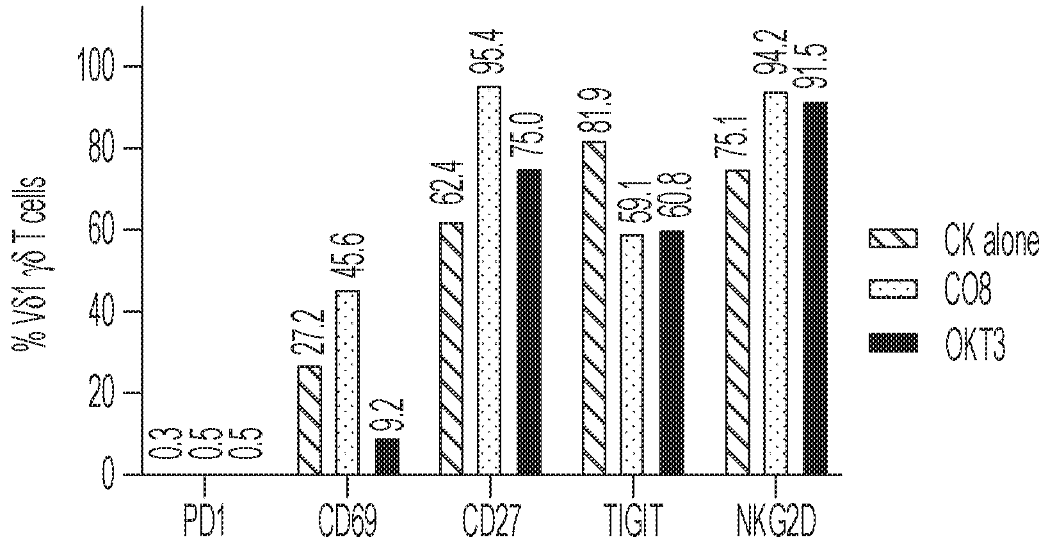
Figure 20E:
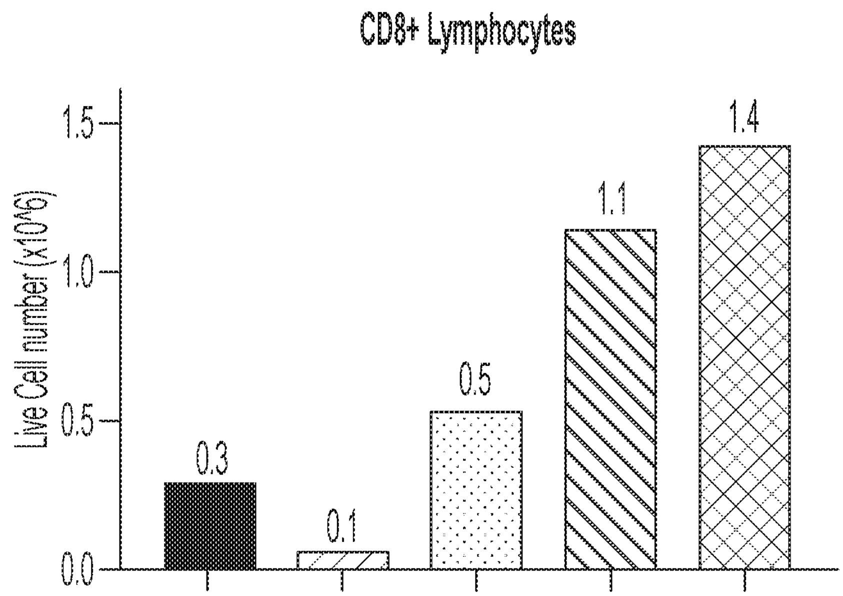

Example 17. Anti-Vδ1 Antibody Conferred Modulation and Proliferation of Immune Cells in Human Tissue Human skin punch-biopsies (from five different donors) were incubated for 21-days in culture with the antibodies as indicated. Skin samples were prepared by removing subcutaneous fat etc. as described elsewhere herein (see Example 1; the section on skin-derived γδ T cell preparation). Replicate punches from each donation were then placed on carbon matrix grids which were then placed in the well of a G-REX6 (Wilson Wolf). Each well was filled with complete medium as also described elsewhere herein. To investigate and compare the effect of differing antibodies, these were added on day 0, 7, 14 to a working concentration of 100 ng/ml. After 21 days in culture cells were harvested and analysed by flow cytometry. The results of said study are presented in FIG. 19 and specifically highlight marked differences in modulatory effect of the differing antibodies: Order from left to right: Vd1 TS8.2=TS8.2 (Thermo Fisher); OKT-3 (Biolegend); C08 IgG1=1252_P01_C08; E07=1245_P01_E07; G04=1245_P02 G04. FIG. 19 (A) highlights the mean quantity of viable pan-γδ TCR positive cells observed at end of culture; results presented as a gated fraction (percent mean+Std Dev) of the total live cell population as analysed by flow cytometry. For pan-γδ content analysis flow gating strategy as follows: Singlets>Live cells>Pan-γδ antibody (Miltenyi, 130-113-508). FIG. 19 (B) highlights the mean quantity of viable Vδ1+TCR positive cells observed at end of culture; results presented as a gated percent fraction (percent mean+Std Dev) of the total live cell population as analysed by flow cytometry. For Vδ1+ cell content analysis, flow gating strategy as follows: Singlets>Live cells>Panγδ (Miltenyi, 130-113-508)>Vδ1 (Miltenyi, 130-100-553). FIG. 19 (C) highlights the number of viable double positive Vδ1+CD25+ cells observed at end of culture; results presented as a gated fraction (percent mean+Std Dev) of the total live cell population. For CD25+ Vδ1+ cell content analysis, Flow gating strategy as follows: Singlets>Live cells>Panγδ (Miltenyi, 130-113-508)>Vδ1 (Miltenyi, 130-100-553)>CD25 (Miltenyi, 130-113-286. The combined results of this study summarise the differential effect of the antibodies of the invention as described herein relative to comparator antibodies TS8.2 and OKT3. And whilst not being bound by this theory, one possibility for the less favourable effects conferred on Vδ1+ cells by TS8.2 or OKT3 may be due to the deleterious effect conferred by these comparator molecules on immune cell function over time in this model system.

Example 18. Anti-Vδ1 Antibody Conferred Modulation and Proliferation of Immune Cells in TILs Studies were undertaken to explore anti-Vδ1 antibody conferred modulation and proliferation of human tumour infiltrating lymphocytes (TILs). For these studies, human renal cell carcinoma (RCC) tumour biopsies were shipped fresh and processed upon receipt. Specifically, the tissue was chopped into −2 $mm^2$. Up to 1 g of tissue was placed into each Miltenyi C tube along with 4.7 mL RPMI and enzymes from Miltenyi's Tumour Dissociation Kit at concentrations recommended by the manufacturer aside from Enzyme R which was used at 0.2× concentration to prevent cleavage of pertinent cell surface molecules. C-Tubes were placed on the gentleMACS™ Octo Dissociator with Heaters. Program 37C_h_TDK_1 for the dissociation of soft tumours was selected. The digest was then filtered through a 70 mM filter to generate a single cell suspension. RPMI containing 10% FBS was added to the digest to quench enzymatic activity. The cells are washed 2× with RPMI/10% FBS and resuspended for counting. Derived cells were then seeded in TC wells (24-well G-REX, Wilson Wolf) at 2.5×10e6 per well. Cells were then incubated without or without cytokines and with or without antibodies for 18 days. Antibodies included in the study are outlined in FIG. 20. These include OKT3 (to 50 ng/ml) and 1252_P01_C08 aka "C08" herein (to 500 ng/ml). When included, bolus additions of these antibodies were added on day 0, 7, 11 and 14. During said incubation, media was replaced with fresh media on days 11 and day 14. Flow cytometry analysis was performed on day 0 and day 18 to determine the lymphocyte phenotype as well as fold change in cell number. Cells were first gated on live CD45+ cells and then as indicated. In arms where recombinant cytokines were included these were added as follows. Day 0: IL-4, IFN-γ, IL-21, IL-1β. Additional IL-15 was included on day 7, 11, 14. Additional IL-21 and IFN-γ were included on day 7 and day 14 respectively. FIG. 20 (A) shows the fold-increase in TIL Vδ1+ cells following 18 days culture in the presence of C08 or OKT3 with and without cytokine support (CK) where indicated. These results show substantial fold increases in TIL Vδ1+ cells with the application of either the C08 or comparator OKT3 antibody in the presence of cytokines, as compared to antibody or cytokines alone. FIG. 20 (B) shows increases in total Vδ1 cell number at harvest following. These results show substantial increases in TIL Vδ1+ cell number following culture with C08 or comparator OKT3 antibody in the presence of cytokines, as compared to antibody or cytokines alone. FIG. 20 (C) presents an example gating strategy used in the flow cytometric analysis of the cells. From the live CD45+ cell population cells were gated on lymphocytes based on their forward and side scatter properties (not shown), γδ T cells were then separated from αβ T cells by staining for the T cell receptors. Finally, the proportion of Vδ1 cells within the total γδ T cell population was determined. Example data for day 18 is shown for 2 conditions as indicated (+/−1252_P01_C08): 64.3% cells were CD45+, of those CD45% cells, 53.1% were γδ+, and of the γδ cells, 89.7% were Vδ1+. FIG. 20 (D) presents a cell-surface phenotypic profile of TIL Vδ1+ cells at harvest. Higher levels of CD69 were observed following culture with the C08 antibody. FIG. 20 (E) presents analysis of the TIL γδ-negative, CD8-positive lymphocyte fraction within the live CD45-positive gate at harvest. In summary, the combined results highlight the modulatory effects conferred by anti-Vδ1 antibody of the invention described herein on TIL populations.

Figure 21A:
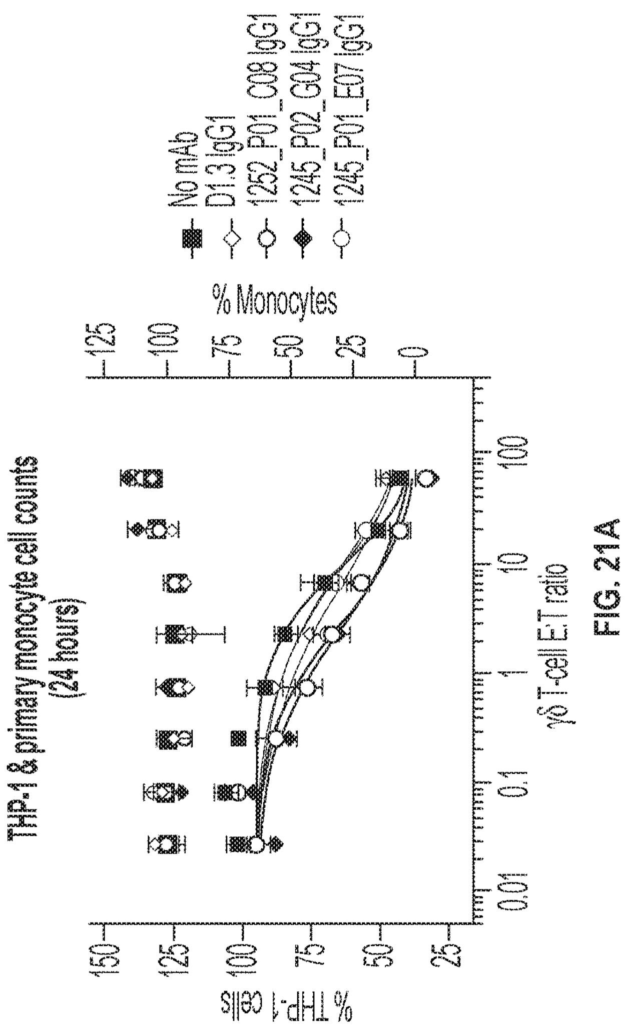
Figure 21B:
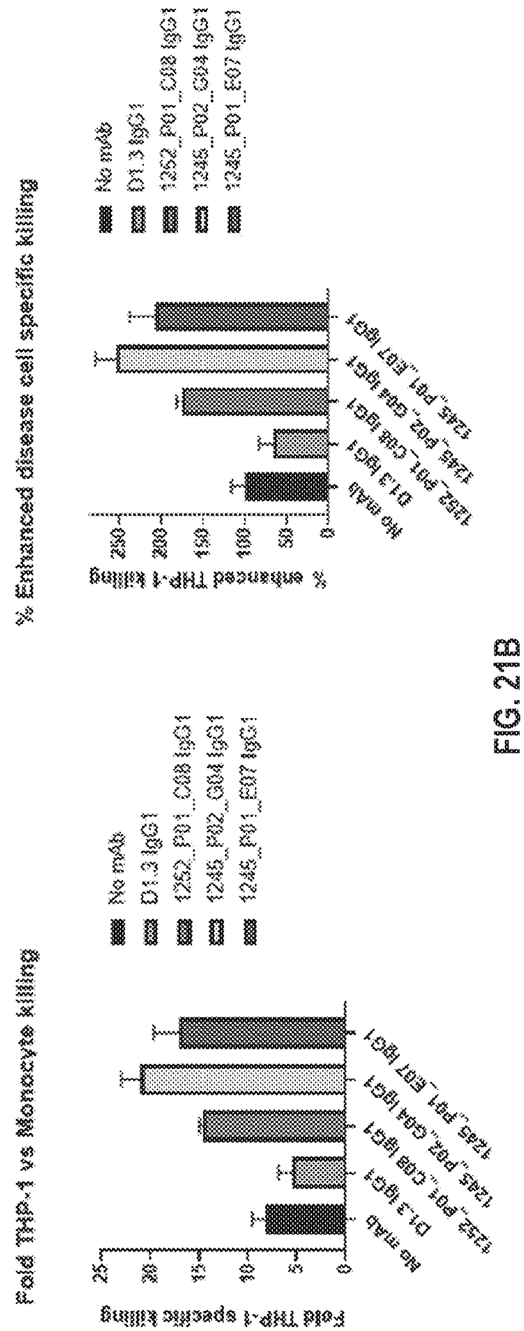

Example 19. Anti-Vδ1 Antibody Conferred Enhancement of Vδ1+ Cell Mediated Cytotoxicity and Diseased-Cell-Specific Cytotoxicity Cytotoxicity/potency-assays and studies were undertaken in model systems comprising a triculture of Vδ1+ effector cells, THP-1 monocytic cancer cells, and healthy primary monocytes+/−anti-Vδ1 antibodies (1245_P02_G04; 1245_P01_E07; 1252_P01_C08) as described herein and inclusive of controls (no mAb or D1.3) as indicated in FIG. 21. In brief, all antibodies were diluted to 10 μg/ml in PBS and incubated overnight at 4° C. in 384-well ultra imaging assay plates (Perkin Elmer) to bind antibodies to the plate, before washing with PBS. Healthy control monocytes were isolated from peripheral blood mononuclear cells (PBMCs; Lonza) by negative selection using magnetic activated cell sorting (MACS; Miltenyi Biotec). Monocytes and cultured THP-1 cells (ATCC) were stained with [0.5 μM] CellTrace Violet and CellTrace CFSE live cell dyes respectively for 20 minutes before mixing in a 1:1 ratio. Expanded skin derived Vδ1 γδ T-cells were detached from tissue culture flasks and serial diluted to generate a range of effector to target ratios (E:T) before adding to THP1:monocyte cell suspensions. Cell suspensions were seeding into 384-well assay plates to give a final cell seeding density of 1,000 THP-1 cells per well, 1,000 Monocytes per well, and a range of γδ T-cells (top E:T ratio of 60:1). To determine the numbers of live THP-1 and healthy control monocytes after 24 hours, confocal images were acquired using an Opera Phenix high content platform capturing nine fields of view at 10× magnification. Live cell counts were quantified based on size, morphology, texture and intensity of live cell stains. Results are presented in FIG. 21. FIG. 21 (A) presents THP-1 and monocyte cell numbers after 24 hours in triple co-culture with γδ T-cells in the presence of plate-bound mAbs or controls as indicated. Cell numbers were calculated using high content confocal microscopy using live cell imaging. FIG. 21 (B) presents a bar chart representation designed to highlight the window between diseased-cell specific killing and non-diseased healthy cell sparing at the top E:T ratio (60:1) after 24 hours co-culture: Left-hand bar chart; fold-increase in killing of diseased-cells (THP-1) versus killing of non-diseased cells (primary human monocytes). Right-hand bar chart; same data but represented as percent enhanced killing versus control. FIG. 21 (C) presents tabulated results summarizing the percent improvement in potency of Vδ1 γδ T-cells killing THP-1 target cells in the presence of Vδ1 mAbs compared to no mAb control as calculated from figure (A). FIG. 21 (D) presents tabulated results of EC50 values as calculated from Figure (A) represented as γδ T-cell numbers required to confer 50% THP-1 cell killing. The combined results and discoveries as outlined in FIG. 21 highlight the ability of antibodies described herein to enhance cytotoxicity and diseased-cell specificity of Vδ1+ cells.

Example 20. Multi-Specific Antibody Conferred Enhancement of Vδ1+ Effector Cell Mediated Cytotoxicity; Targeting a Tissue-Centric Disease Associated Antigen Cytotoxicity/potency-assay studies were undertaken to explore the effect of multi-specific antibodies on co-cultures of Vδ1+ effector cells and A-431 cancer cells. A-431 ($EGFR^{++}$; ATCC) target cells were seeded in a 384-well imaging plate (Perkin Elmer) at 1,000 cells/well and incubated at 37° C. overnight in DMEM (10% FCS). Antibodies and multi-specific antibodies as indicated were diluted to 10 μg/ml and added assay plate (2 μg/ml final assay concentration). Expanded skin-derived Vδ1 γδ T-cells were detached from tissue culture flasks and serial diluted to give a range of E:T ratios (top E:T ratio of 60:1) before adding to assay plate. A-431 cells were incubated with Vδ1 γδ T-cells in the presence of antibodies or controls at 30° C., 5% CO2. After 24 hours incubation, Hoechst 33342 (ThermoFisher) was added to stain cells (2 μM final). To determine the numbers of live A-431 cells, confocal images were acquired using an Opera Phenix high content platform capturing nine fields of view at 10× magnification. Live cell counts were quantified base on size, morphology, texture, and intensity of live cell stains. Effector/Target (E:T) time course studies to determine the ET ratio wherein 50% of target cells are killed in model systems+/−the controls, comparators, antibodies and multi-specific antibodies as indicated. Results are presented in FIG. 22.

Figure 22J:
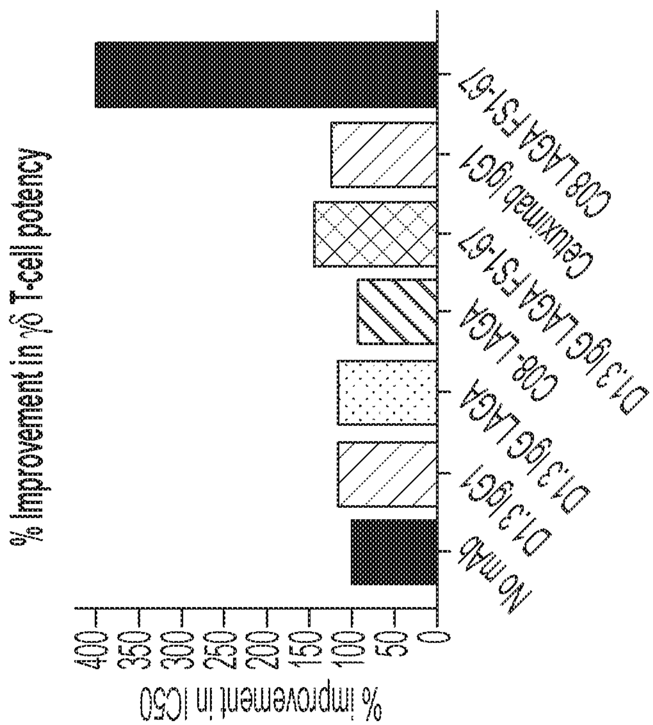

First, FIG. 22 (A-D) present example co-culture results wherein Vδ1+/A-431 co-cultures were studies+/−multi-specific antibodies comprising anti-Vδ1× anti-TAA (EGFR) bispecific binding moieties wherein the anti-Vδ1 VL+VH binding domain (to the first target) is combined with the CH1-CH2-CH3 domain of an anti-EGFR binding moiety (to the second target). Controls and comparators employed as indicated; from left to right: No mAb=no antibody added; D1.3=D1.3 control; D1.3 IgG LAGA=D1.3+L235A, G237A; D1.3 FS1-67=D1.3 variable domain with EGFR binding constant domain plus L235A, G237A; Cetuximab (in-house generated). More specifically, FIG. 22 (A) presents the results for five-hour co-cultures with aforementioned controls, comparators, and the following test articles: C08-LAGA=1252_P01_C08 with L235A,G237A; C08 FS1−67=1252_P01_C08 combined with EGFR binding domain containing a L235A,G237A. FIG. 22 (B) presents equivalent data of five-hour co-cultures with aforementioned controls, comparators, and the following test articles: G04-LAGA=1245_P02_G04 with L235A,G237A; G04 FS1−67=1245_P02_G04 combined with EGFR binding domain containing L235A,G237A. FIG. 22 (C) presents equivalent data of five-hour co-cultures with controls, comparators, and the following test articles: E07-

LAGA=1245_P01_E07 with L235A,G237A; E07 FS1-67=1245_P01_E07 combined with EGFR binding domain containing L235A,G237A. FIG. 22 (D) presents a Table summarizing the percent improvement in cytotoxicity of Vδ1 γδ T-cells in the presence of controls, comparators, and test articles over 5, 12 and 24 hours. A greater than 450% enhancement can be observed when antibodies or antigen-binding fragment thereof as described herein are presented in a multi-specific format.

Second, FIG. 22 (E-H) present example results wherein Vδ1+/A-431 co-cultures were studied+/−multi-specific antibodies comprising anti-Vδ1× anti-TAA (EGFR) bispecific binding moieties wherein the anti-Vδ1 binding domain (to the first target) comprises a full-length antibody (VH-CH1-CH2-CH3/VL-CL) then combined with an anti-EGFR scFv binding moiety (to the second target). Controls and comparators employed as indicated; from left to right: No mAb=no antibody added; D1.3=Control; D1.3 IgG LAGA=D1.3+L235A,G237A; D1.3 LAGA Cetuximab=D1.3 with L235A, G237A plus a C-term Cetuximab-derived scFv; Cetuximab (in-house generated). More specifically, FIG. 22 (E) presents five-hour co-cultures with aforementioned controls, comparators, and the following test articles: C08-LAGA=1252_P01_C08 with L235A, G237A; C08 LAGA Cetuximab=1252_P01_C08 with L235A,G237A and with C-term Cetuximab-derived scFv. FIG. 22 (F) presents five-hour culture with aforementioned controls, comparators, and the following test articles: G04-LAGA=1245_P02_G04 with L235A,G237A; G04 LAGA Cetuximab=1245_P02_G04 with L235A,G237A and with C-term Cetuximab-derived scFv. FIG. 22 (G) presents five-hour culture with controls, comparators, and the following test articles: E07-LAGA=1245_P01_E07 with L235A, G237A; E07 LAGA Cetuximab=1245_P01_E07 with L235A,G237A and with C-term Cetuximab-derived scFv. FIG. 22 (H) presents a Table summarizing the percent improvement in potency of Vδ1 γδ T-cells in the presence of controls, comparators, and test articles over 5, 12 and 24 hours. A greater than 300% enhancement can be observed when antibodies or antigen-binding fragment thereof as described herein are presented in a multi-specific format.

Third, FIG. 22 (I and J) outline an example alternative approach to representing the data. Specifically shown is percentage improvement conferred by multi-specific antibody E07 FS1-67 (I) or C08 FS1-67 (J) upon Vδ1+ effector cell cytotoxicity towards EGFR+ cells relative at the 24-hour time point relative to all component parts and comparators as indicated.

Figure 23B:
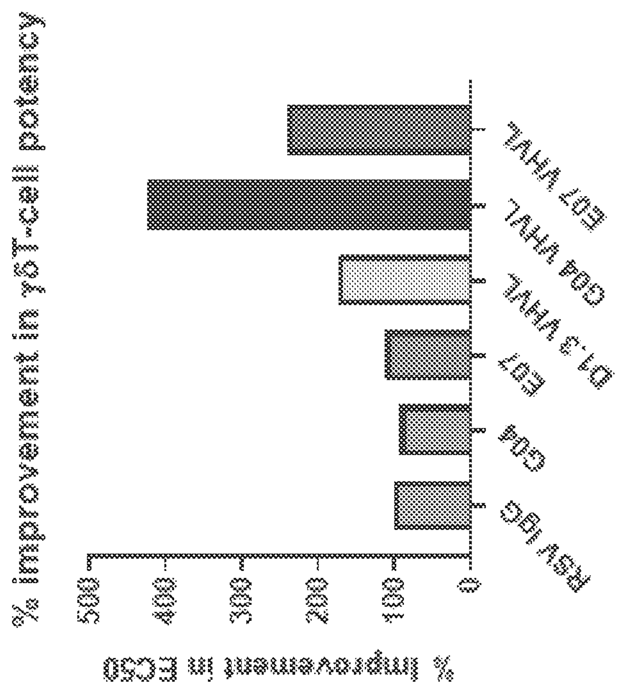

Example 21. Multi-Specific Antibody Conferred Enhancement of Vδ1+ Mediated Cytotoxicity and Diseased-Cell-Specific Cytotoxicity; Targeting a Hemopoietic-Centric Disease Associated Antigen Cytotoxicity/potency-assays and studies were undertaken in model systems comprising a triculture Vδ1+ effector cells, and Raji cancer cells, and healthy primary monocytes+/−multi-specific antibodies comprising anti-Vδ1× anti-TAA (CD19) multi-specific antibody in order to determine whether tumour associated antigen (TAA) linked Vδ1 monoclonal antibodies in a bispecific format can enhance Vδ1 γδ T-cell killing of specific target cells. Specifically, Raji cells (CD19++; ATCC) were incubated with Vδ1 γδ T-cells in the presence of Vδ1×CD19 multi-specific antibodies. All antibodies were diluted to 4 μg/ml (final assay concentration 1 μg/ml) and added to a 384-well imaging plate (Perkin Elmer). Expanded skin derived Vδ1 γδ T-cells were detached from tissue culture flasks and serial diluted to give a range of effector to target ratios (E:T). Raji cells were stained with [0.5 μM] CellTrace Far Red before mixing in a 1:1 ratio with titrated Vδ1 γδ T-cells. Cell suspensions were seeding into 384-well assay plates to give a final cell seeding density of 1,000 Raji cells per well, and a range of γδ T-cells (top E:T ratio of 30:1). To determine the numbers of live Raji after 24 hours, confocal images were acquired using an Opera Phenix high content platform capturing nine fields of view at 10× magnification. Live cell counts were quantified base on size, morphology, texture and intensity of live cell stains. Results are captured in FIG. 23. Antibodies and comparators employed therein are as indicated. Specifically, RSV IgG=Motavizumab non-binding control, G04=1245_P02_G04; E07=1245_P01_E07; D1.3 VHVL=D1.3 HEL with heavy-chain C-terminal anti-CD19 scFv (see SEQ ID NO: 314 for scFv binding module employed); G04 VHVL=1245_P02_G04 LAGA with heavy chain C-terminal anti-CD19 scFv (SEQ ID NO: 315, or SEQ ID NO: 421 and SEQ ID NO: 422); E07 VHVL=1245_P01_E07 LAGA with heavy chain C-terminal anti-CD19 scFv (SEQ ID NO: 316, SEQ ID NO: 423 and SEQ ID NO: 424). FIG. 23 (A) Table summarizing (i) the calculated EC50s represented as γδ T-cell numbers or E:T ratios required to induce 50% Raji cell killing, and (ii) percentage improvement in EC50s compared to no mAb control. FIG. 23 (B) Bar chart representing the percentage improvement in ability of γδ T-cells to lyse 50% of Raji target cells in the presence of Vδ1-CD19 multi-specific antibodies.

Example 22. Mammalian Display

Two clones were selected for affinity maturation. The preparation and characterisation of affinity matured clones derived from clone ADT1-4 (G04) and clone ADT1-7 (E07) will now be presented.

Affinity Maturation of Human Anti-Vδ1 Monoclonal Antibodies

Phage display employed to generate parental antiVδ1 monoclonal antibodies yielded antibodies with the affinity ranging from 12 nM-1 μM, as described above. Parental antibodies clone ADT1-4 (G04) and clone ADT1-7 (E07) were then affinity matured in vitro to surprisingly attain 100 fold improved affinity for superior target engagement. In vitro affinity maturation of parental antibodies was achieved via two-step process: diversification of the parental antibody sequence using targeted CDR3 mutagenesis and then selective enrichment of affinity improved antibodies using phage and mammalian display platforms. VH and VL CDR3 2-mer libraries for the clones ADT1-4 and ADT1-7 were created using Kunkel mutagenesis (Kunkel et al., 1987; Sidhu and Weiss, 2004) and RCA amplification. Combinations of all single and double amino acid substitutions at specified positions in the VH and VL CDR3s were incorporated using Agilent primer synthesis technology. The number of different amino acids to be incorporated at a particular position were specified. Cysteine and methionine were omitted. The changes made in the CDRs of the clones are summarised below in Table 14.

TABLE 14

| CDR3 positions and specified residue changes | | | | |
|---|---|---|---|---|
| | POS | AMINOACID(S) | POS | AMINOACID(S) |
| E07 | V | A, D, E, F, G, H, I, K, L, N, P, Q, R, S, T, W, Y | Q | A, D, E, F, G, H, I, K, L, N, P, R, S, T, V, W, Y |
| (V3-11/Vκ1-39) | D | A, E, F, G, H, I, K, L, N, P, Q, R, S, T, V, W, Y | S | A, D, E, F, G, H, I, K, L, N, P, Q, R, T, V, W, Y |
| | Y | A, D, E, F, G, H, I, K, L, N, P, Q, R, S, T, V, W | Y | A, D, E, F, G, H, I, K, L, N, P, Q, R, S, T, V, W |
| | A | D, E, F, G, H, I, K, L, N, P, Q, R, S, T, V, W, Y | S | A, D, E, F, G, H, I, K, L, N, P, Q, R, T, V, W, Y |
| | D | A, E, F, G, H, I, K, L, N, P, Q, R, S, T, V, W, Y | T | A, D, E, F, G, H, I, K, L, N, P, Q, R, S, V, W, Y |
| | A | D, E, F, G, H, I, K, L, N, P, Q, R, S, T, V, W, Y | L | A, D, E, F, G, H, I, K, N, P, Q, R, S, T, V, W, Y |
| | F | A, G, H, I, L, N, S, T, V, Y | L | A, D, E, F, G, H, I, K, N, P, Q, R, S, T, V, W, Y |
| | D | A, G, N, S, T | R | A, G, Q, S, T, V |
| | I | G, S, V, Y | | |
| G04 | T | A, D, E, F, G, H, I, K, L, N, P, Q, R, S, V, W, Y | S | A, D, E, F, G, H, I, K, L, N, P, Q, R, T, V, W, Y |
| (VH6-1/Vκ1-5) | W | A, D, E, F, G, H, I, K, L, N, P, Q, R, S, T, V, Y | Y | A, D, E, F, G, H, I, K, L, N, P, Q, R, S, T, V, W |
| | S | A, D, E, F, G, H, I, K, L, N, P, Q, R, T, V, W, Y | S | A, D, E, F, G, H, I, K, L, N, P, Q, R, T, V, W, Y |
| | G | A, D, E, F, G, H, I, K, L, N, P, Q, R, S, T, V, W, Y | T | A, D, E, F, G, H, I, K, L, N, P, Q, R, S, V, W, Y |
| | Y | A, D, E, F, G, H, I, K, L, N, P, Q, R, S, T, V, W | P | A, D, E, F, G, H, I, K, L, N, P, Q, R, S, T, V, W, Y |
| | V | A, D, E, F, G, H, I, L, N, P, S, T, Y | Q | A, D, E, F, G, H, I, K, L, N, P, R, S, T, V, W, Y |
| | D | A, G, N, S, T | V | A, D, E, F, G, H, I, K, L, N, P, Q, R, S, T, W, Y |
| | V | G, I, S, Y | Q | A, G, R, S, T, V |

The size of each library is shown in Table 15.

TABLE 15

| Library Size | |
|---|---|
| ADT1-7 | $5.4 \times 10^9$ |
| ADT1-4 | $5.5 \times 10^9$ |

Generation of Mutagenized VH and VL CDR3 Libraries

Figure 24A:
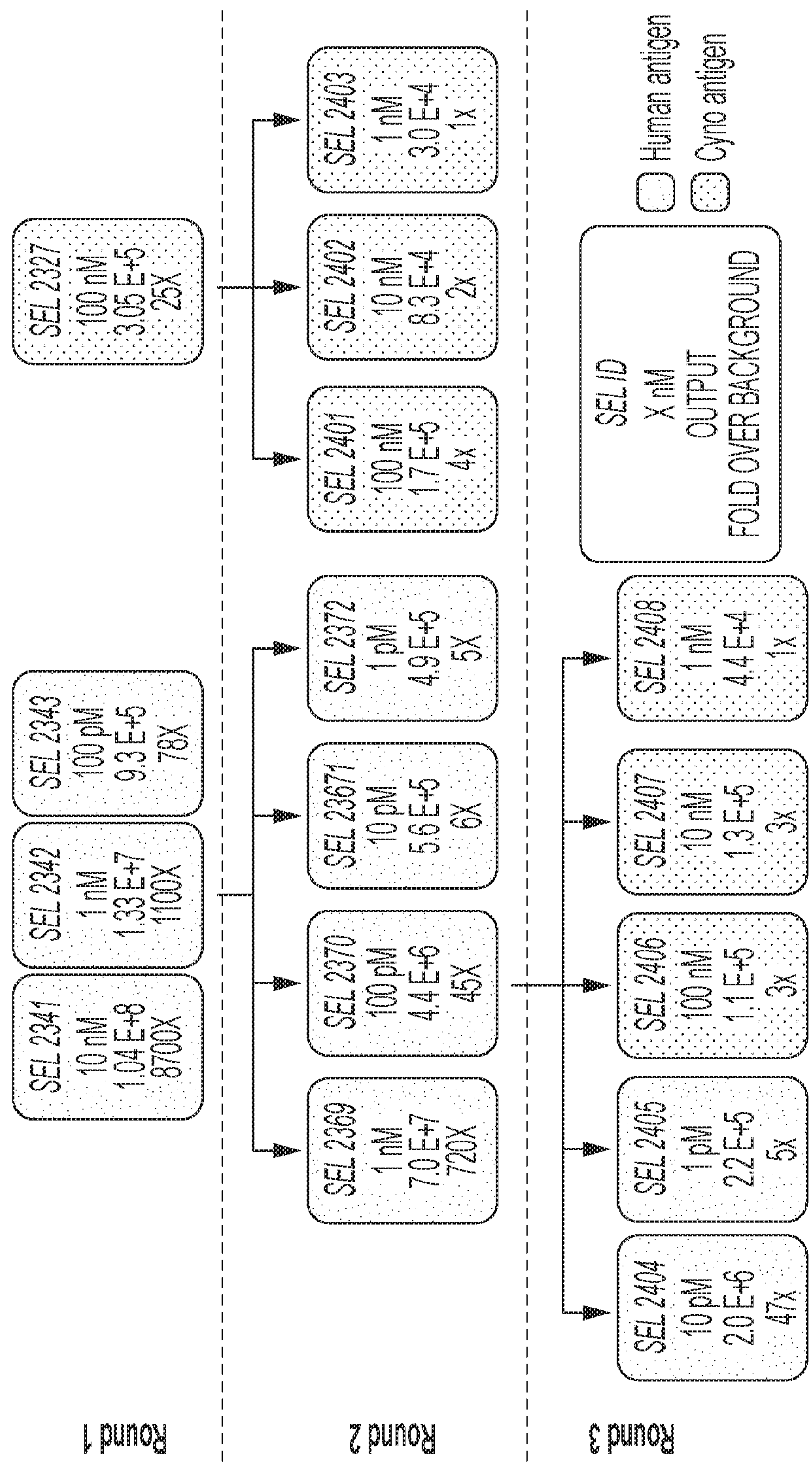
FIGS. 24A-24C: Phage selection rounds.
Figure 24B:
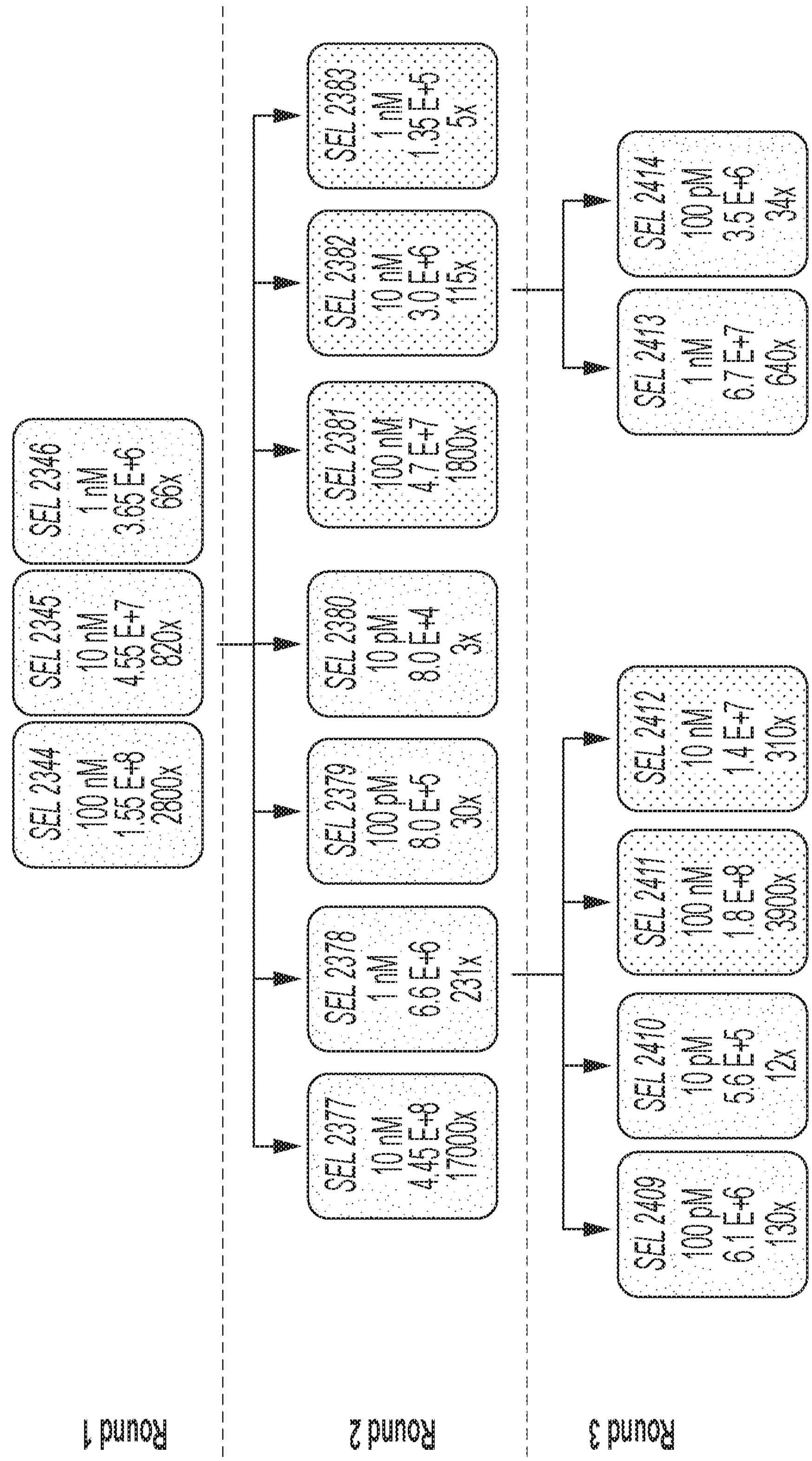
Figure 24C:
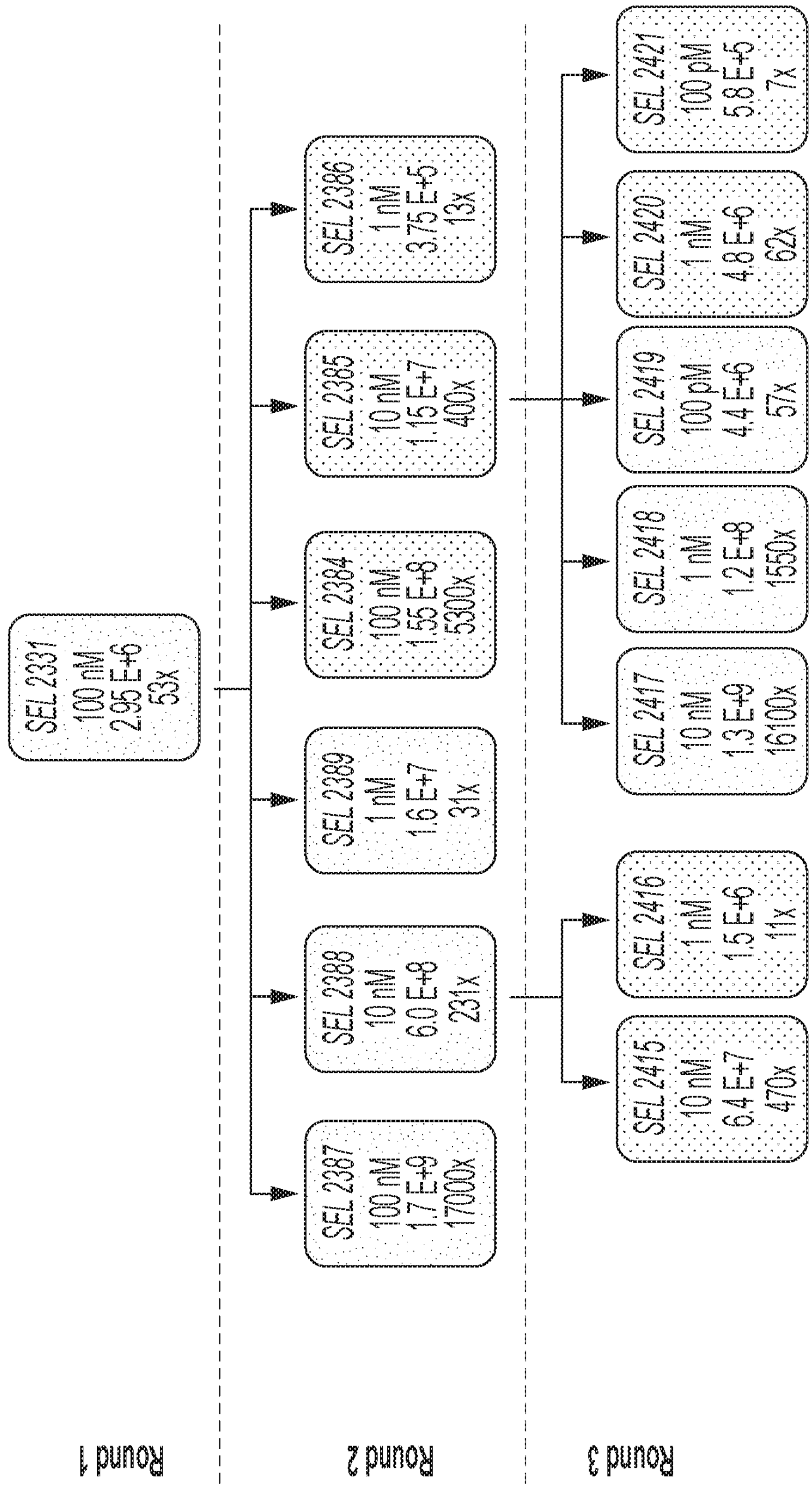

Mutagenised libraries were prepared from suitable culture volumes covering an appropriate excess of library members. Affinity maturation was performed using phage display technology as described in Schofield et al. (2007) using solution phase selection. Selections were performed in the solutions using human and cyno antigen (human antigen including human TRDV1 sequence, cyno antigen includes SEQ ID NO: 308 minus leader). To isolate binders from a mutant library with higher affinities antigen concentration was controlled to give a series of increasingly stringent selections. Several rounds of phage display selections with human and with cyno antigen were performed for each clone as presented in the FIG. 24. For ADT1-4 lineage the antigen concentration used in the selection was ranging from 100 nm-10 μM for human and 100 nM and 10 nM for cyno antigen. For ADT1-7 lineage the human antigen was used at concentration from 10 nM to 1 μM and for cyno from 100 nM to 100 μM. FIG. 24 shows the phage selection rounds for the ADT1-7 library (iA), the ADT1-4 library (iB) and the ADT1-7 library with a selection strategy for isolating cyno cross-reactive binders (iC).

Polyclonal phage ELISA was used to evaluate the progress of the selections. Human antigen (DV1/GV4) and Cyno antigen (DV1/GV76) were coated overnight at 150 ng/well, 50 μL/well. Cyno antigen DV2/GV76 (which does not contain SEQ ID: 308) and HSA were used as controls. Only the outputs from the ADT4-1 library were both cross reactive to human and cyno DV1 antigen. The output from ADT1-7 were only reactive to human antigen. Selected outputs were characterised further by monoclonal phage ELISA and the summary is presented in Table 16. The boxes indicate the selection was carried out with either human or cyno antigen. The arrows provide an indication as to the percentage of clones that are classified as binders to human or cyno DV1 (pointing up being high and pointing down being low).

TABLE 16

| Monoclonal phage ELISA summary | | | | | |
|---|---|---|---|---|---|
| | Phage rounds | | | Binding | |
| | #1 | #2 | #3 | huDVl | cyDVl |
| G04 selection | | | | | |
| 2378 | 10 nM (human antigen) | 1 nM (human antigen) | | ⇑ 79% (cyno binder) | ⇛ 25% (human binder) |
| 2409 | | | 100 pM (human antigen) | ⇑ 75% (cyno binder) | ⇑ 100% (cyno binder) |
| 2412 | | | 10 nM (cyno antigen) | ⇗ 72% (human binder) | ⇑ 100% (cyno binder) |
| 2413 | | 10 nM (cyno antigen) | 1 nM (human antigen) | ⇑ 84% (cyno binder) | ⇑ 100% (cyno binder) |
| 2385 | 100 nM (cyno antigen) | 10 nM (cyno antigen) | | ⇗ 71% (human binder) | ⇑ 75% (cyno binder) |
| 2418 | | | 1 nM (human antigen) | ⇑ 100% (cyno binder) | ⇑ 94% (cyno binder) |
| 2420 | | | 1 nM (cyno antigen) | ⇑ 94% (cyno binder) | ⇑ 94% (cyno binder) |

TABLE 16-continued

| Monoclonal phage ELISA summary | | | | | |
|---|---|---|---|---|---|
| | Phage rounds | | | Binding | |
| | #1 | #2 | #3 | huDV1 | cyDV1 |
| 2415 | | 10 nM (human antigen) | 10 nM (cyno antigen) | ↑ 100% (cyno binder) | ↑ 94% (cyno binder) |
| E07 selection | | | | | |
| 2370 | 1 nM (cyno antigen) | 100 pM (cyno antigen) | | ↑ 96% (cyno binder) | ↑ 0% (cyno binder) |
| 2404 | | | 10 pM | ↑ 83% (cyno binder) | ↑ 0% (cyno binder) |

The sequence diversity is summarised in Table 17. The boxes indicate the selection was carried out with either human or cyno antigen. The arrows provide an indication as to the level of diversity (pointing up being high and pointing down being low.

Pools were then advanced to mammalian display. Single chain variable fragment antibodies (scFvs) populations were converted en masse into the IgG format, maintaining the original variable heavy (VH) and variable light (VL) chain pairing. The IgG formatted antibodies were then cloned into a mammalian display donor vector which was co-transfected with plasmids encoding a TALE nuclease pair to enable nuclease directed antibody gene integration at a single chromosomal locus. A mammalian display antibody library covering the phage output diversity (>$10^6$ clones) was created in HEK293 cells. Stable populations of cells expressing antibodies on the cell surface were selected by blasticidin addition 2 days post transfection (dpt). Cells expressing

TABLE 17

| Monoclonal phage sequencing summary | | | | | | |
|---|---|---|---|---|---|---|
| | Phage rounds | | | Diversity | | |
| | #1 | #2 | #3 | Heavy CDR3 | Light CDR3 | Heavy-light CDR3 |
| G04 selection | | | | | | |
| 2378 | 10 nM (human antigen) | 1 nM (human antigen) | | ↑ 83% (cyno binder) | ↑ 96% (cyno binder) | ↑ 100% (cyno binder) |
| 2409 | | | 100 pM (human antigen) | ↘ 50% (cyno binder) | ↘ 53% (human binder) | ↗ 72% (human binder) |
| 2412 | | | 10 nM (cyno antigen) | ↘ 63% (human binder) | ↑ 97% (cyno binder) | ↑ 97% (cyno binder) |
| 2413 | | 10 nM (cyno antigen) | 1 nM (cyno antigen) | ↗ 71% (human binder) | ↑ 97% (cyno binder) | ↑ 100% (cyno binder) |
| 2385 | 100 nM (cyno antigen) | 10 nM (cyno antigen) | | ↑ 83% (cyno binder) | ↑ 88% (cyno binder) | ↑ 100% (cyno binder) |
| 2418 | | | 1 nM (human antigen) | ↗ 66% (human binder) | ↗ 81% (human binder) | ↑ 88% (cyno binder) |
| 2420 | | | 1 nM (cyno antigen) | ↘ 63% (human binder) | ↗ 73% (human binder) | ↗ 80% (human binder) |
| 2415 | | 10 nM (human antigen) | 10 nM (cyno antigen) | ↘ 63% (human binder) | ↗ 78% (human binder) | ↑ 88% (cyno binder) |
| E07 selection | | | | | | |
| 2370 | 1 nM (human antigen) | 100 pM (human antigen) | | ↑ 88% (cyno binder) | ↑ 96% (cyno binder) | ↑ 100% (cyno binder) |
| 2404 | | | 10 pM (human antigen) | ↗ 75% (human binder) | ↗ 67% (human binder) | ↑ 96% (human binder) |

Generation of IgG Mammalian Display Libraries

To form final libraries for mammalian display the following ADT1-4 selections were pooled:—

SEL2409, 2412 and 2413 to create ADT1-4 library 1 (human)—

SEL 2418, 2420 and 2415 to create ADT1-4 library 2 (cyno)—

SEL2370 and 2404 to create ADT1-7 library.

antibodies on the cell surface were enriched by magnetic-activated cell sorting (MACS) sorting (7 dpt); the cells were labelled with anti-Fc-PE followed by anti-PE microbeads and sorted using Midi MACS magnet (Miltenyi Biotec) and LS columns. These populations of cells were advanced to selections.

Selection of Matured Antibodies by Mammalian Display

Figure 25A:
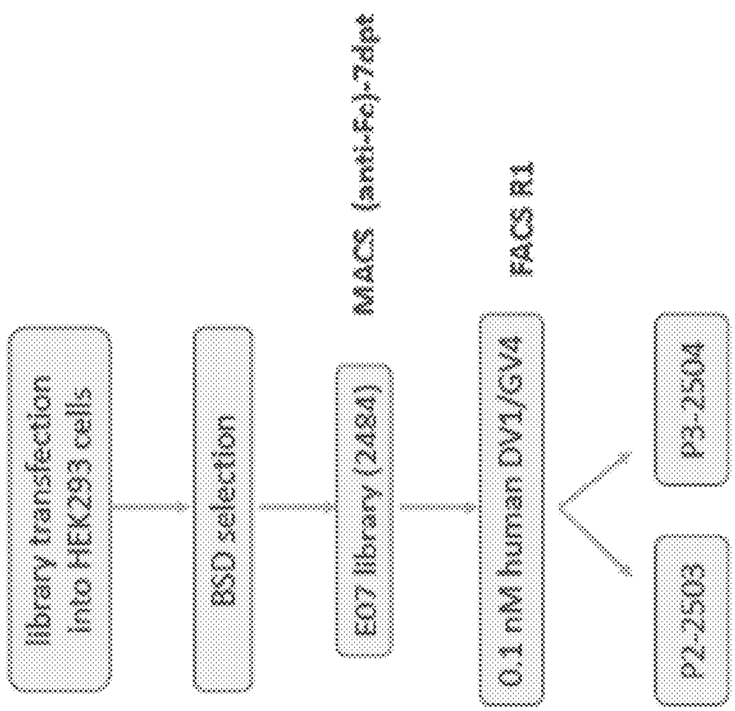
FIGS. 25A-25C:A schematic overview of selection of matured antibodies by mammalian display.
Figure 25B:
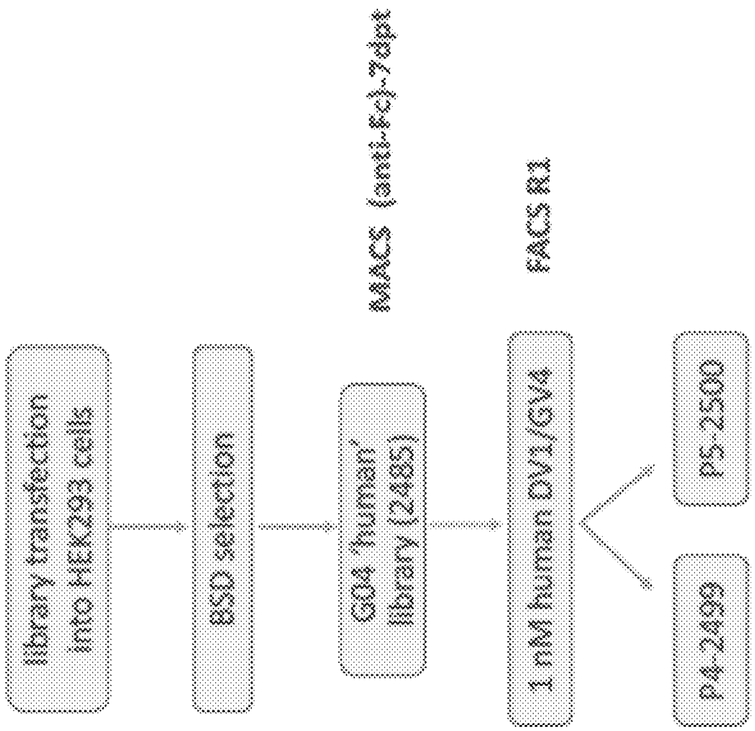
Figure 25C:
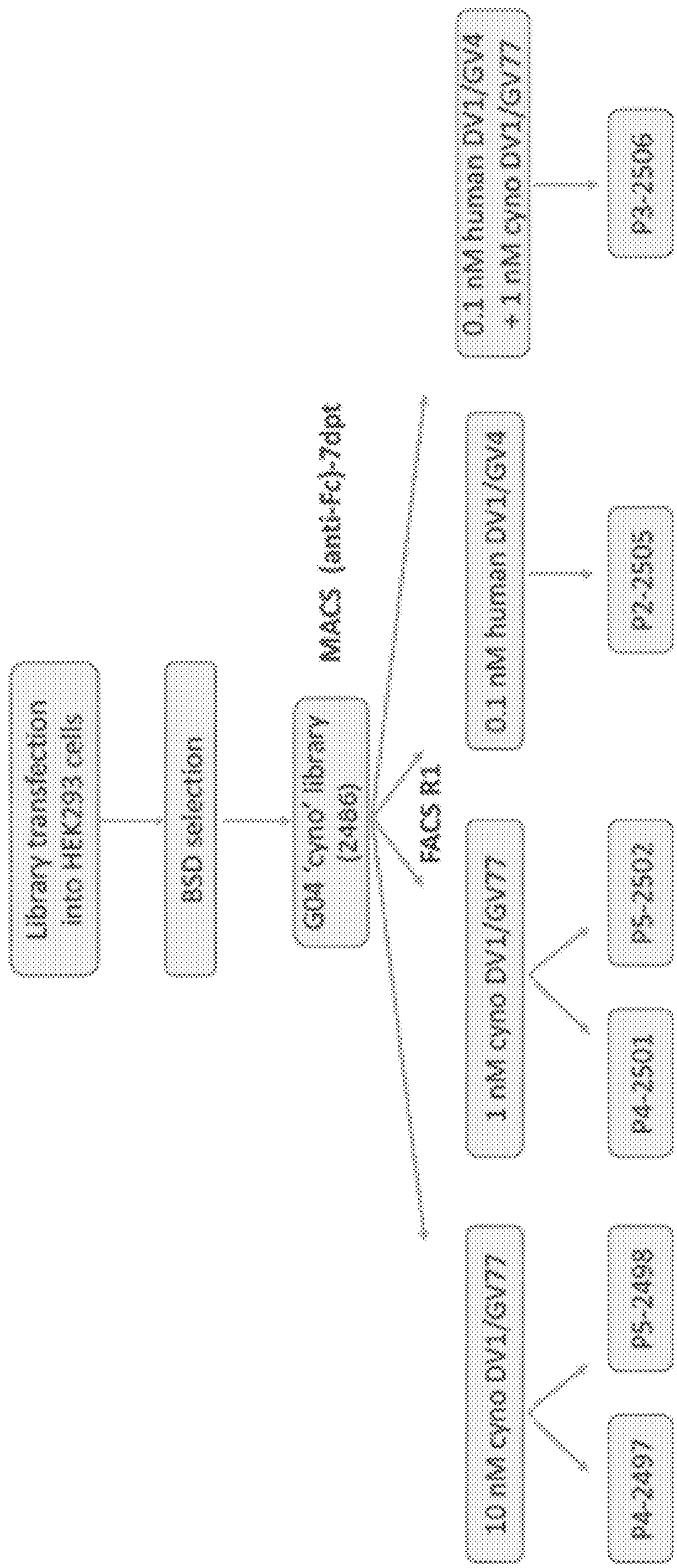
Figure 26A:
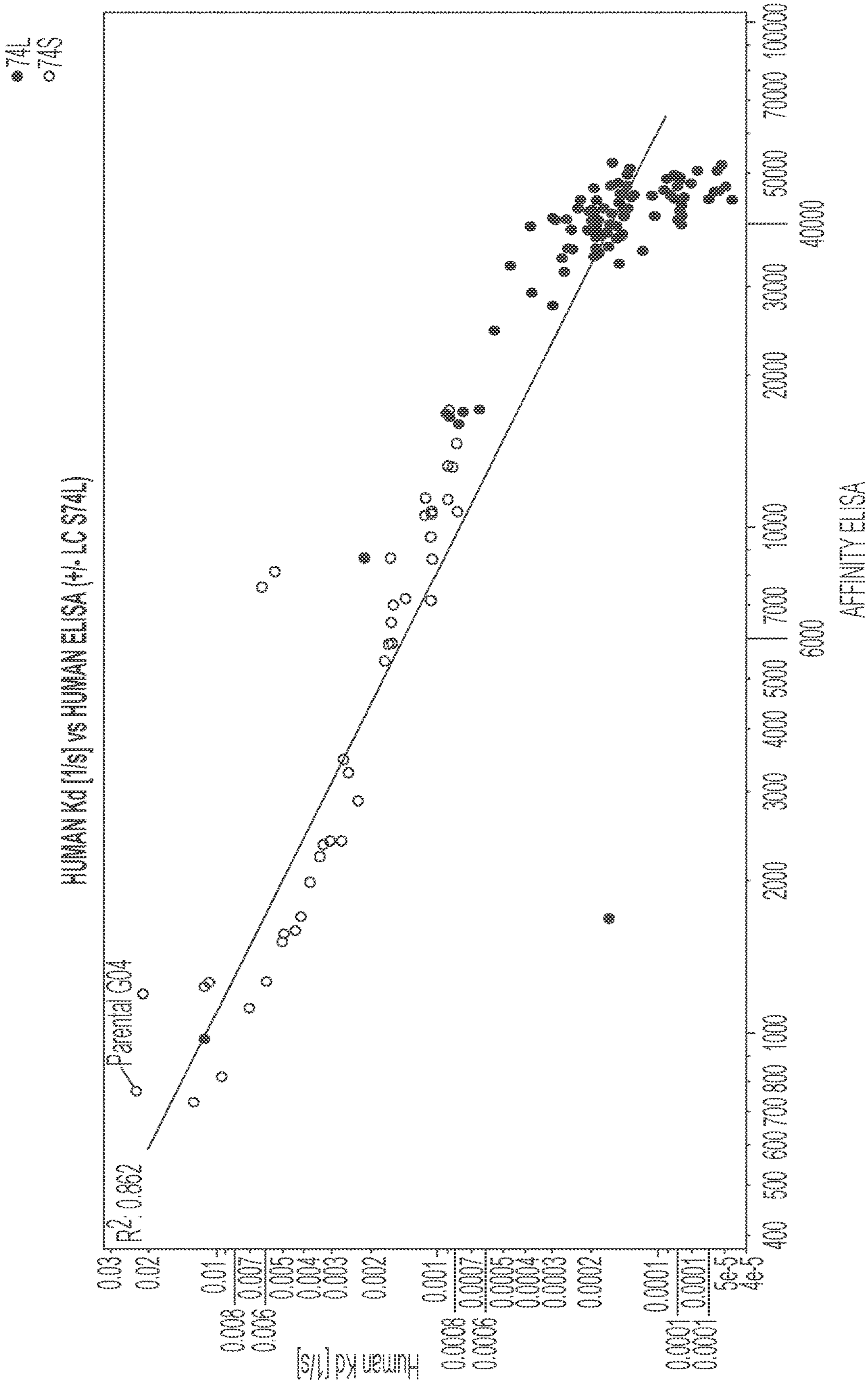
Figure 26B:
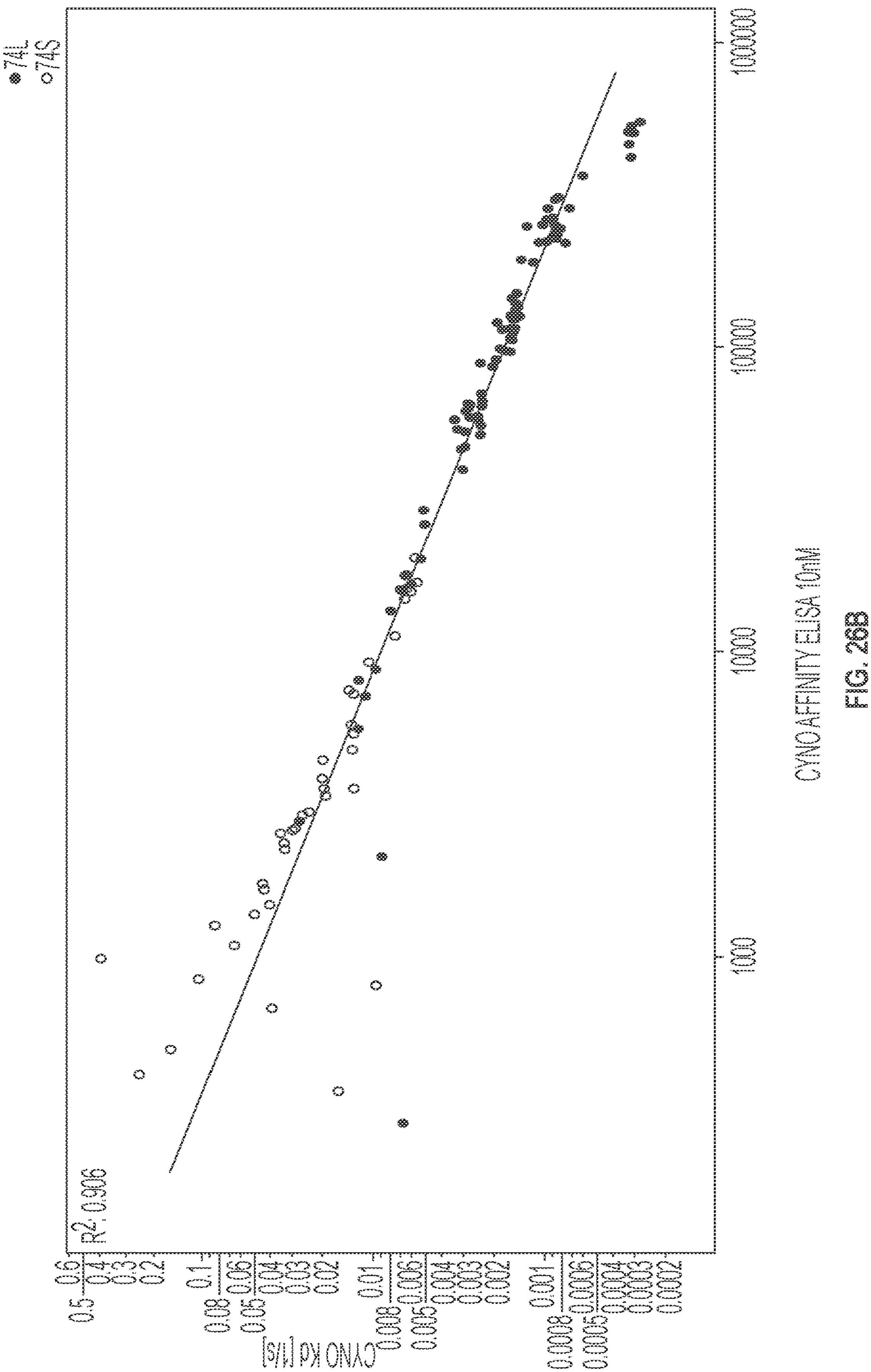
Figure 26C:
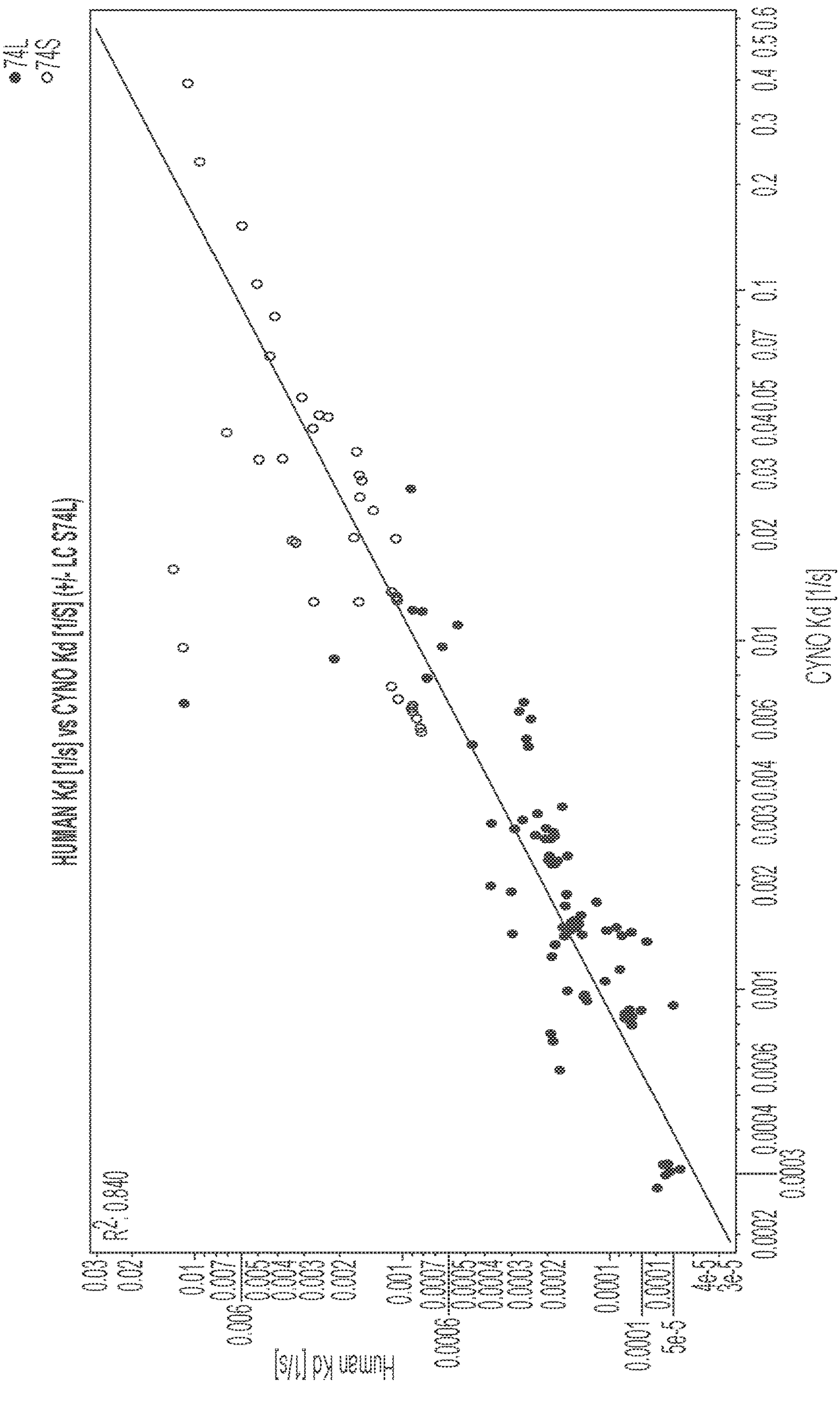

Following MACS to enrich antibody expressing cells, two strategies were adopted to identify TRDV1 binders. The main strategy involved dual colour fluorescence sorting based on Fc expression and antigen binding. The other involved dual colour fluorescence sorting based on the binding of both cyno and human antigens to maximise the chances of isolating high affinity cross-reactive binders. A schematic overview of the process is presented in FIG. 25.

Sequence, Specificity, Affinity Ranking and Characterisation

Genomic DNA was extracted from eight different sorted populations. DNA encoding the selected IgGs were amplified and cloned into the soluble IgG1 expression vector. A total of 1472 clones from the 8 different selections were chosen. The pDNA was transfected into Expi293 cells. Supernatants were harvested 5 days after transfection and the expressed antibodies affinity ranked for human and cyno TRDV1 binding in a capture ELISA. A total of 93 anti-DV1 antibodies from each selections strand were chosen for sequence and SPR off-rate analysis. In addition, these clones were checked by direct ELISA for binding to: human TRDV1, polymorphic human TRDV1 (A->V), human TRDV2, cyno TRDV1 and BSA.

Example 23. Binding Affinity to Human and Cyno Antigens

Binding to Recombinant Antigen and vδ1 TCR Expressed on Cells: ADT1-4 Lineage

Figure 28D:
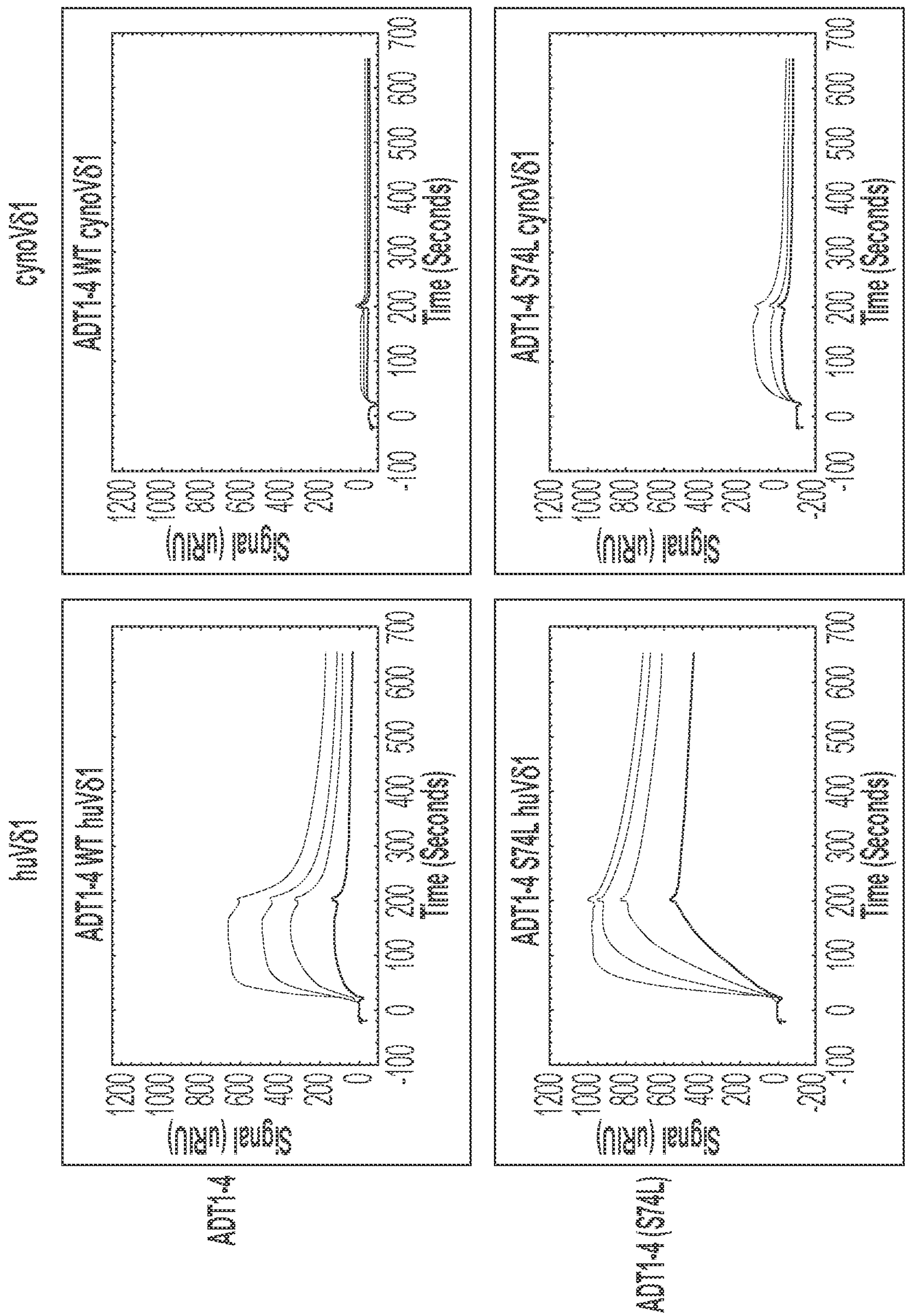
FIGS. 28A-28D: Fold enhancement in binding for ADT1-4 linage compared to ADT1-4 parental G04).
Figure 26E:
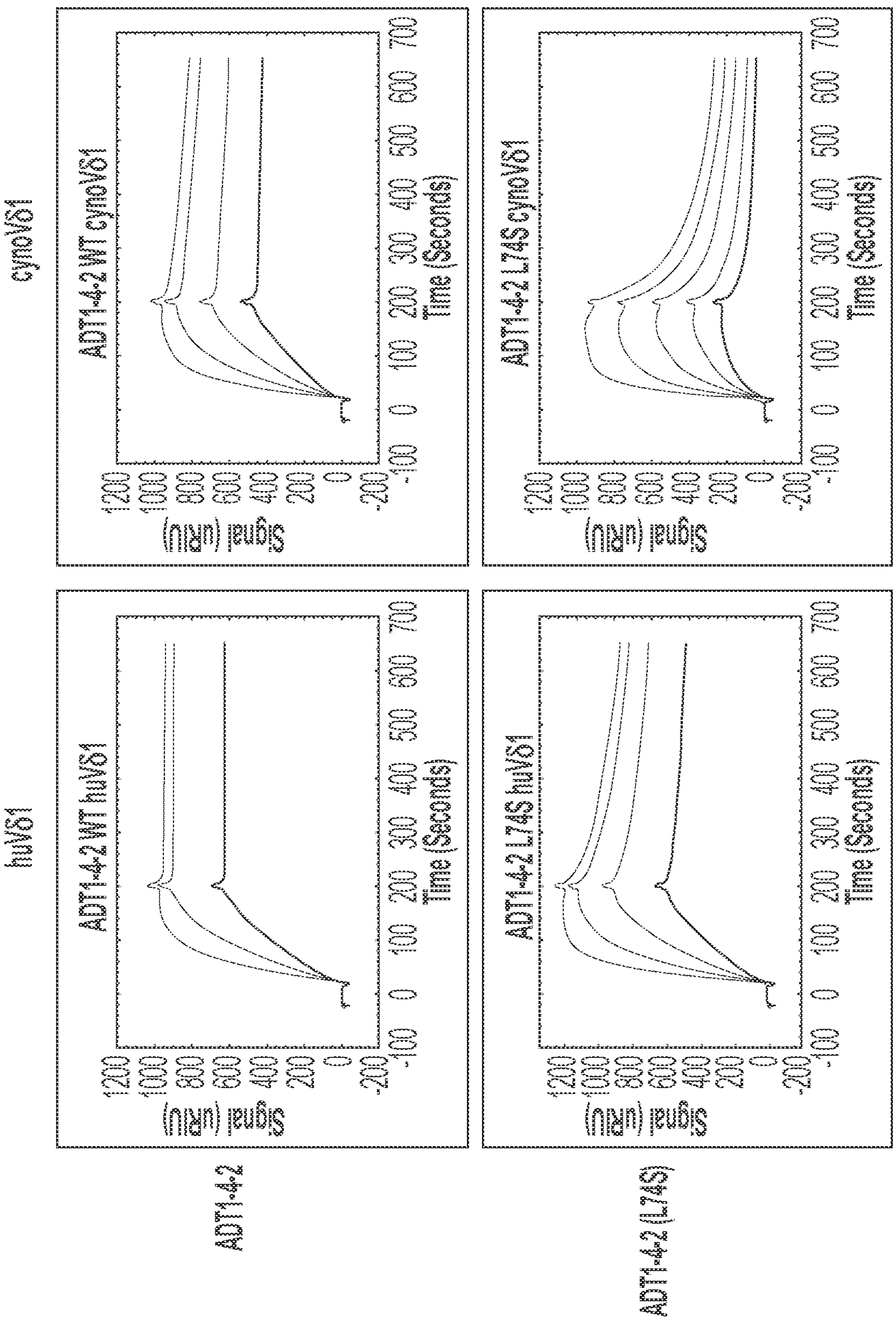
Figure 27A:
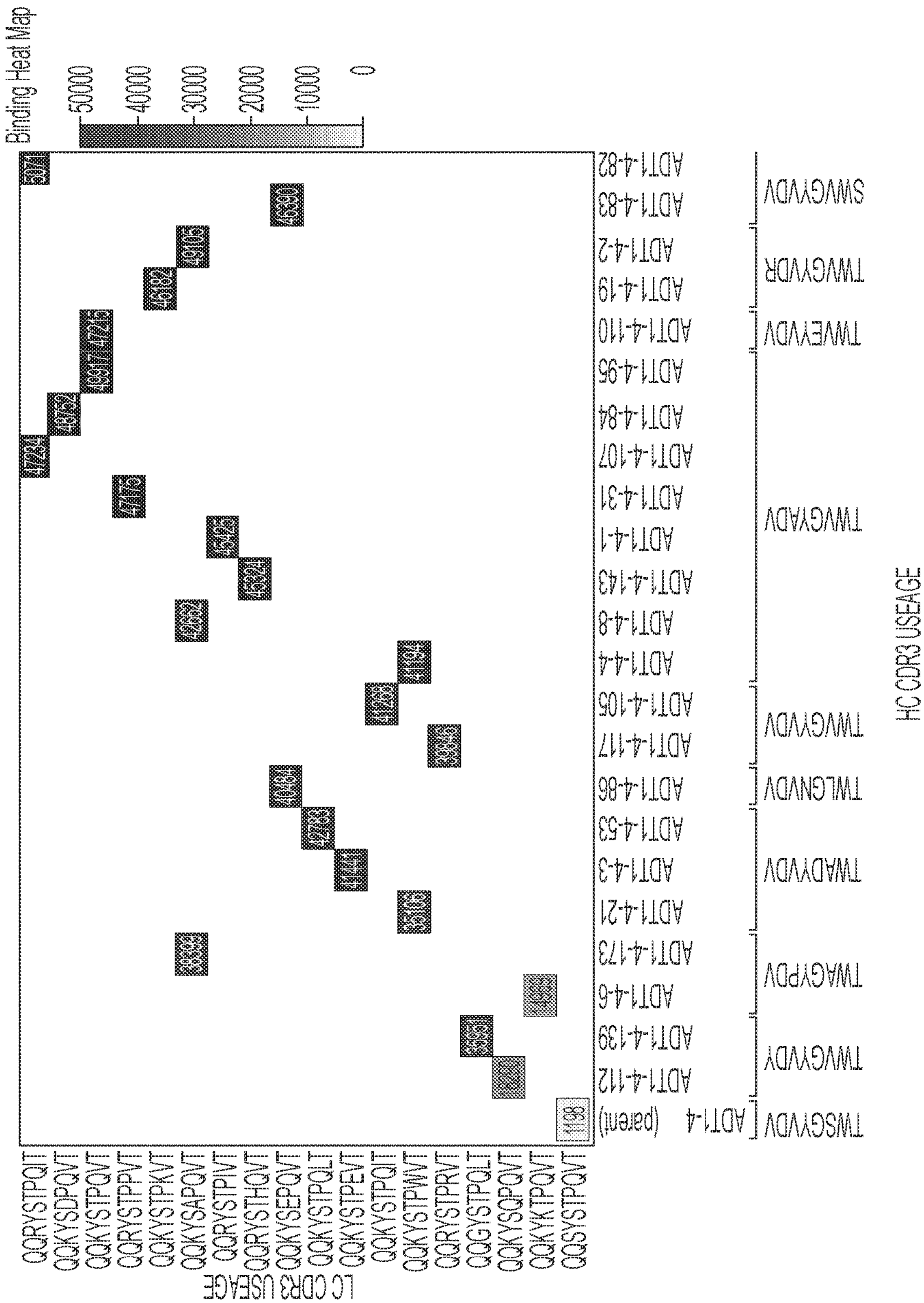
FIG. 27A-27C: CDR3 usage and cross-sharing.
Figure 27B:
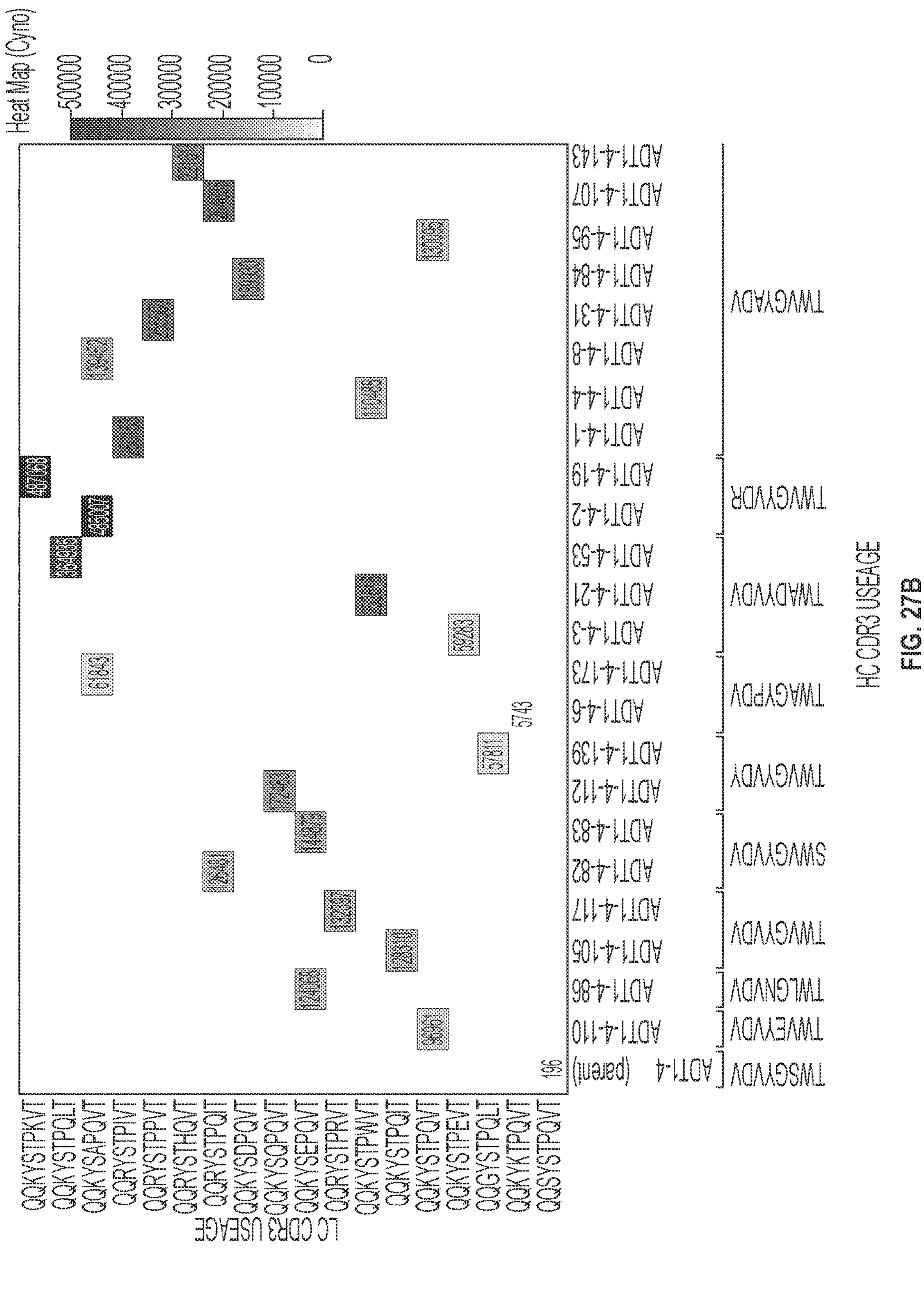
Figure 27C:
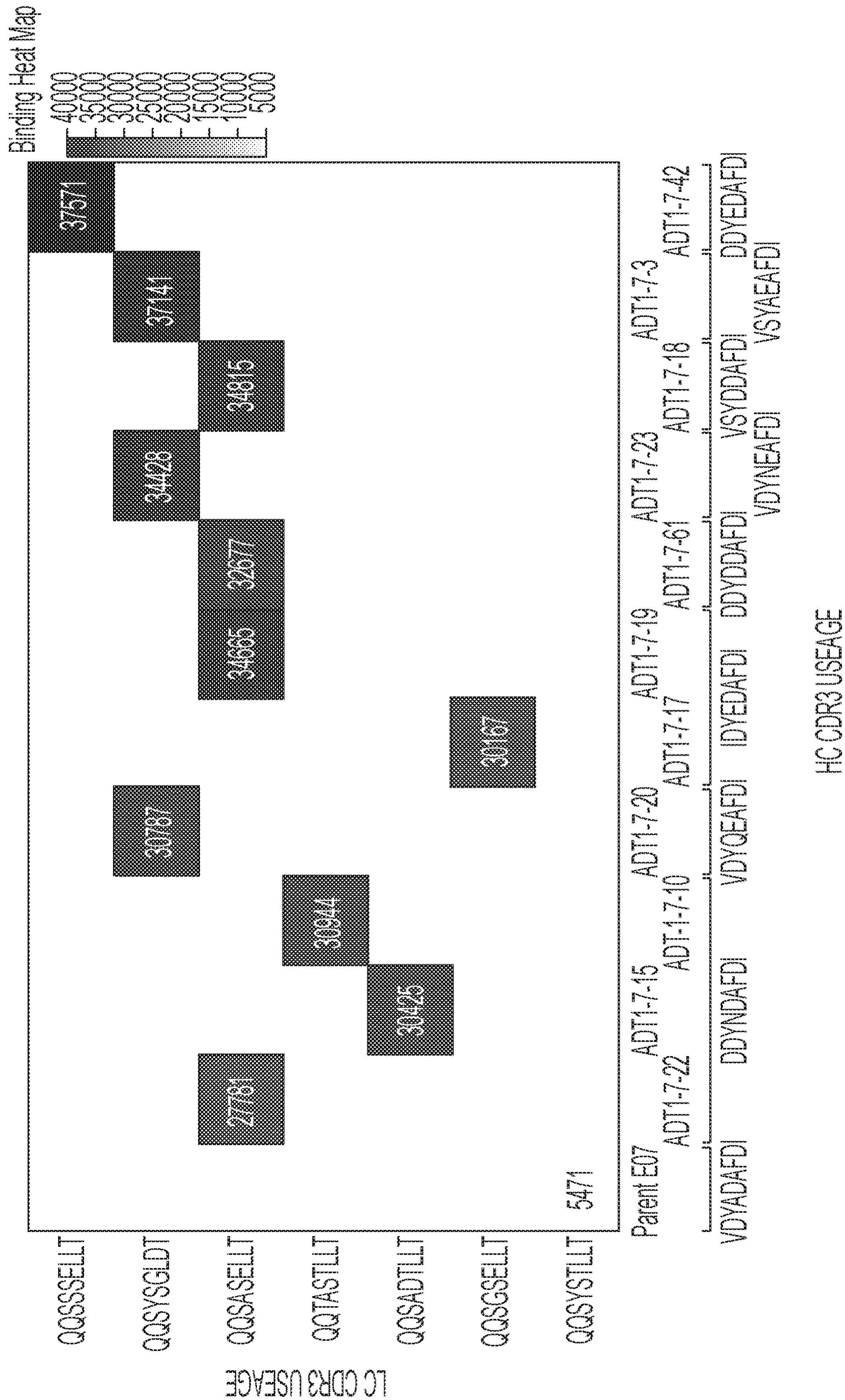
Figure 28A:
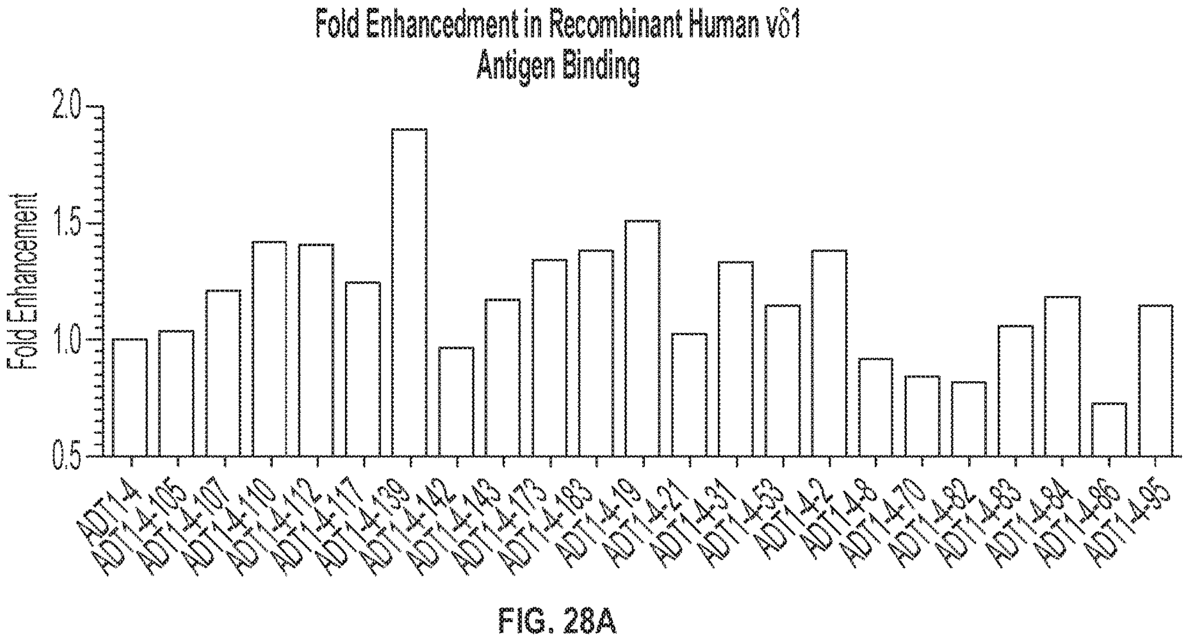
Figure 28B:
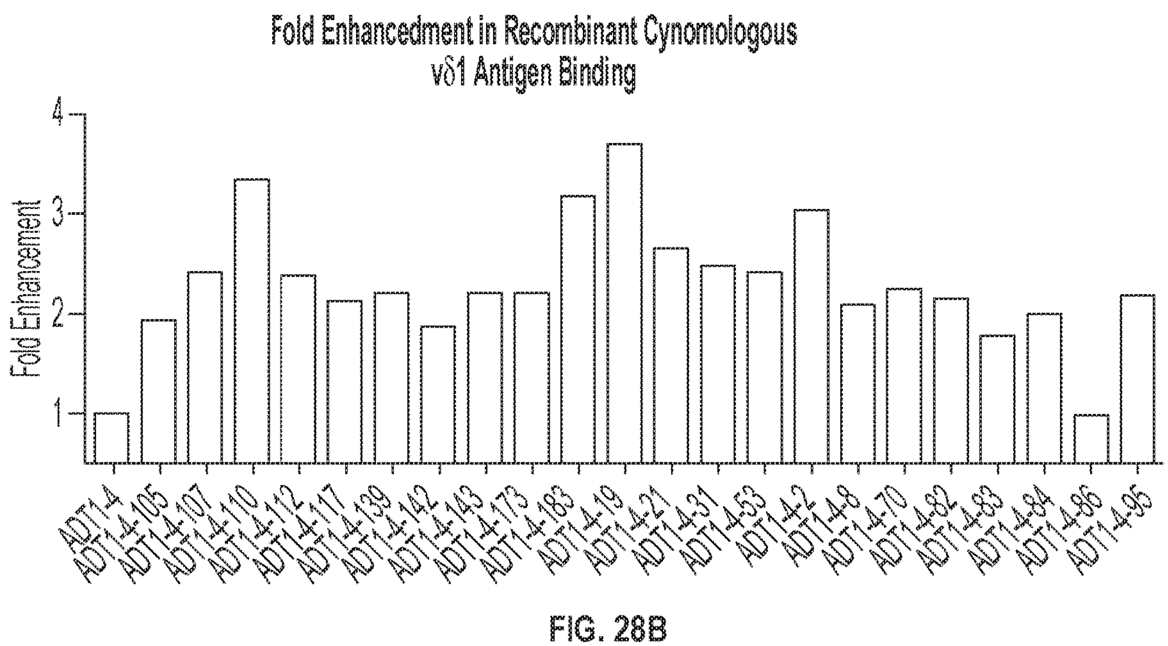
Figure 28C:
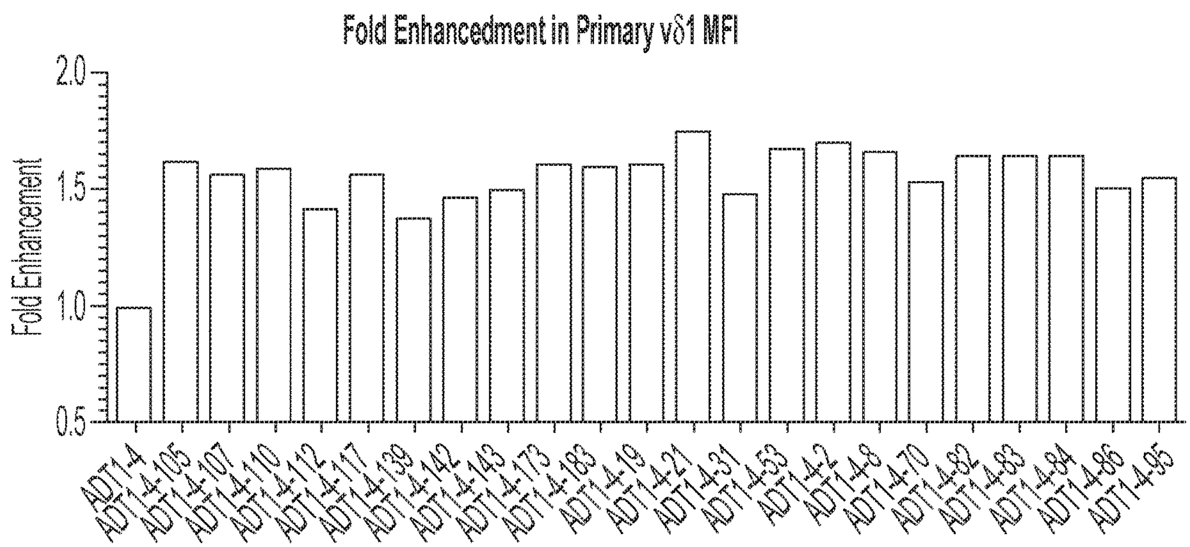
Figure 28D:
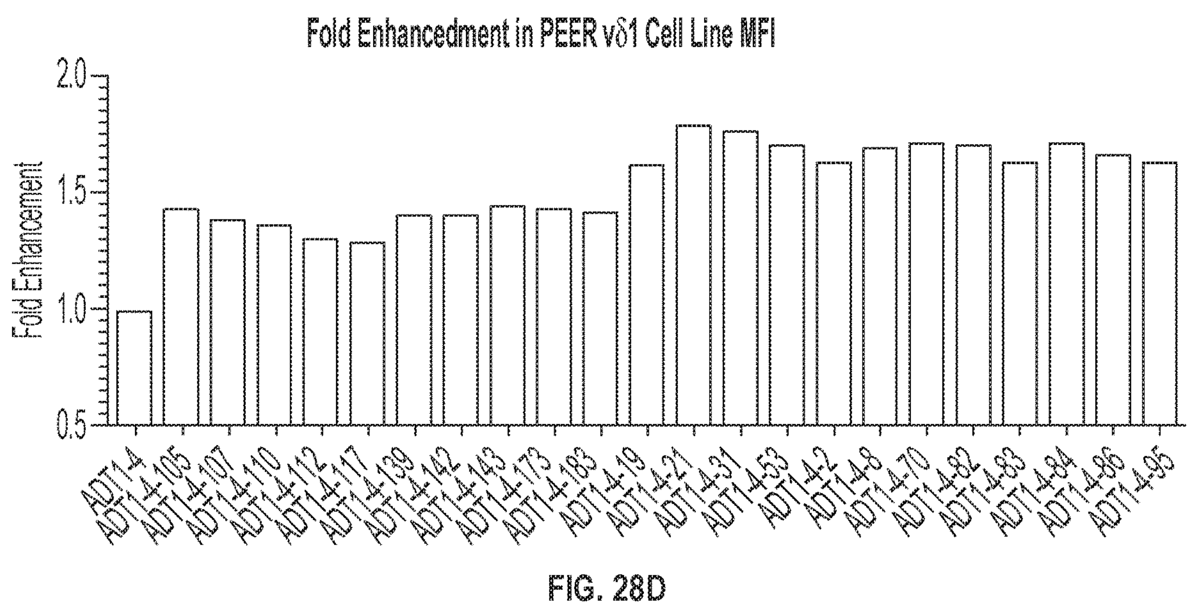

Studies were undertaken to explore the binding of anti-vδ1 antibodies to their target antigens. The binding of anti-Vδ1 mAbs to Vδ1 TCR antigen was tested by ELISA. 1 ug of human antigen or 1 ug of cynomolgus antigen was immobilized per well onto 96 well Immunoassay plates (SLS #475904) and then blocked with BSA to prevent non-specific binding. 1.3 pmol (20 ng) of each mAb were added and incubated for 1 hour at room temperature. mAb binding to antigen was detected using ProteinA-HRP (Abcam #Ab7456) along with TMB substrate (Fisher #12750000) and Stop solution (Biolegend #423001) by measuring absorbance at 450 nM. Parental controls were included as positive controls for both the assay and inter-plate variability. Hits were identified as those mAbs giving absorbance readings above those of the parental mAbs. FIG. 28A shows the fold increase in absorbance for matured ADT1-4 clones compared to parental ADT1-4 binding absorbance when 1.3 pmol of antibody was bound to human vδ1 antigen. FIG. 28B shows the fold increase in absorbance for matured ADT1-4 clones compared to parental ADT1-4 binding absorbance when 1.3 pmol of antibody was bound to cynomolgus Vδ1 antigen.

mAb binding to endogenous Vδ1 TCR was tested using flow cytometry. Skin Vδ1 cells (donor ATS006; ADT expanded E0000113) or the PEER Vδ1 cell line were seeded at 3×10^5 cells/well into 96 well round bottom plates and resuspended in 50 ul of FACS buffer (v/v: 2% FCS, 0.1% NaAzide and 1 mM EDTA in PBS) containing 3 ug/ml of test mAb for 15 min at 4° C. Cells were pelleted and secondary anti-hmIgG-APC antibody (Miltenyi #130-119-772) was added at 1/100 in FACS buffer and incubated for a further 20 min at 4° C. Cells were washed and fixed in CellFix (BD #340181) and analysed by flow cytometry. The % Vδ1 phenotype and Mean Fluorescence Intensity was calculated (Inivai Technologies, Flowlogicv7.2). As a positive control the parental antibody was included. FIG. 28C shows the fold increase in mean fluorescence intensity for matured ADT1-4 clones compared to parental ADT1-4 binding primary skin derived human Vδ1 cells. FIG. 28D shows the fold increase in mean fluorescence intensity for matured ADT1-4 clones compared to parental ADT1-4 binding the transformed PEER Vδ1 cell line.

Figure 29A:
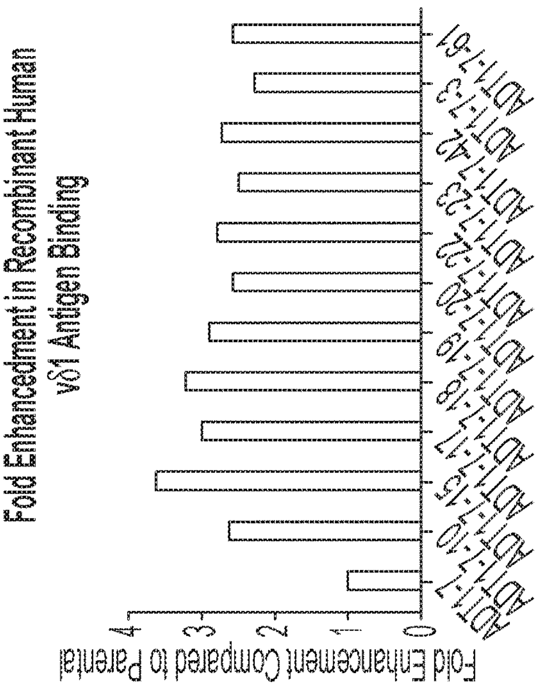
FIGS. 29A-29C: Fold enhancement in binding for ADT1-7 linage compared to ADT1-7 parental E07).
Figure 29B:
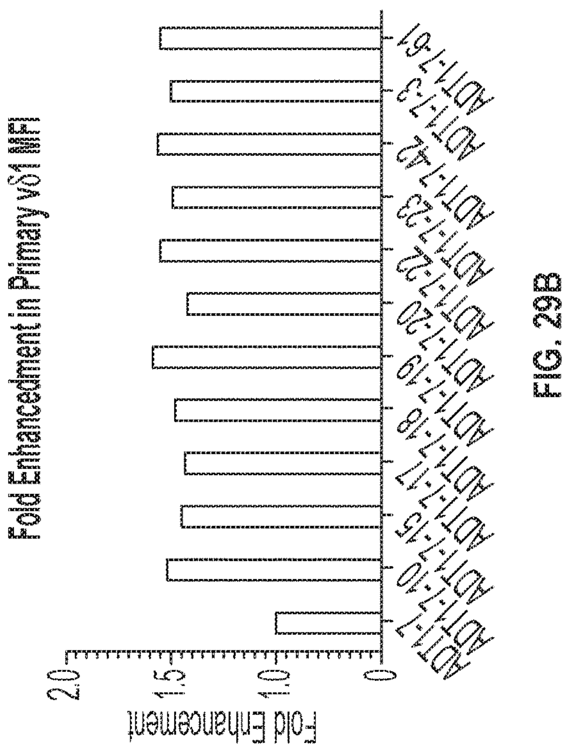
Figure 29C:
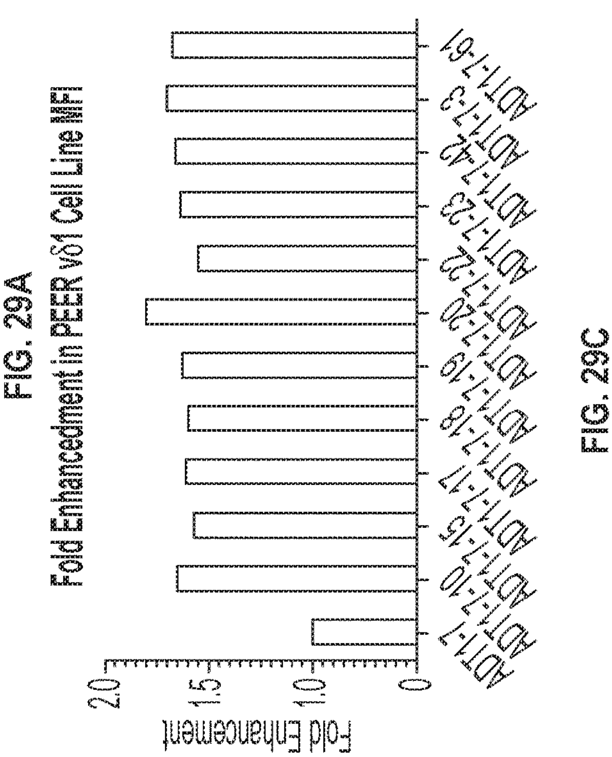

Binding to Recombinant Antigen and vδ1 TCR Expressed on Cells: ADT1-7 Lineage:

Studies were undertaken to explore the binding of ADT1-7 matured anti-vδ1 antibodies to their target antigens. The binding of anti-Vδ1 mAbs to Vδ1 TCR antigen was tested by ELISA. 1 ug of antigen was immobilized per well onto 96 well Immunoassay plates (SLS #475904) and then blocked with BSA to prevent non-specific binding. A titration of 6.7 pmol (100 ng), 1.3 pmol (20 ng) and 0.27 pmol (4 ng) of mAb were added and incubated for 1 hour at room temperature. mAb binding to antigen was detected using ProteinA-HRP (Abcam #Ab7456) along with TMB substrate (Fisher #12750000) and Stop solution (Biologend #423001) by measuring absorbance at 450 nM. Parental controls were included as positive controls for both the assay and inter-plate variability. Hits were identified as those mAbs giving absorbance readings above those of the parental mAbs. FIG. 29A shows the fold increase in absorbance for matured ADT1-4 clones compared to parental ADT1-4 binding absorbance when 1.3 pmol of antibody was bound to human Vδ1 antigen.

mAb binding to endogenous Vδ1 TCR was tested using flow cytometry. Skin Vδ1 cells (donor ATS006; ADT expanded E0000113) or the PEER Vδ1 cell line were seeded at 3×10^5 cells/well into 96 well round bottom plates and resuspended in 50 ul of FACS buffer (v/v: 2% FCS, 0.1% NaAzide and 1 mM EDTA in PBS) containing 3 ug/ml of test mAb for 15 min at 4° C. Cells were pelleted and secondary anti-hmIgG-APC antibody (Miltenyi #130-119-772) was added at 1/100 in FACS buffer and incubated for a further 20 min at 4° C. Cells were washed and fixed in CellFix (BD #340181) and analysed by flow cytometry. The % Vδ1 phenotype and Mean Fluorescence Intensity was calculated (Inivai Technologies, Flowlogicv7.2). As a positive control the parental antibody was included. FIG. 29B shows the fold increase in mean fluorescence intensity for matured ADT1-4 clones compared to parental ADT1-4 binding primary skin derived human Vδ1 cells. FIG. 29C shows the fold increase in mean fluorescence intensity for matured ADT1-7 clones compared to parental ADT1-7 binding the transformed PEER Vδ1 cell line.

Fold Improvements Over Parental Clones

Dissociation-Enhanced Lanthanide Fluorescence Immunoassay (DELFIA)

For the confirmation of improvement in binding of affinity matures mAb to human and cyno antigen's, DELFIA immunoassay was performed with the antigen directly coated to the plate (3 μg/mL of antigen in 50 μL PBS at 4° C. overnight (Nunc #437111). For detection DELFIA Eu-N1 Anti-Human IgG (Perkin Elmer #1244-330) was used as secondary antibody at 1/500 dilution in 50 μL of 3% of MPBS (PBS+3% (w/V) skimmed milk powder). Development was with 50 μL of DELFIA enhancement solution (Perkin Elmer #4001-0010).

Figure 30A:
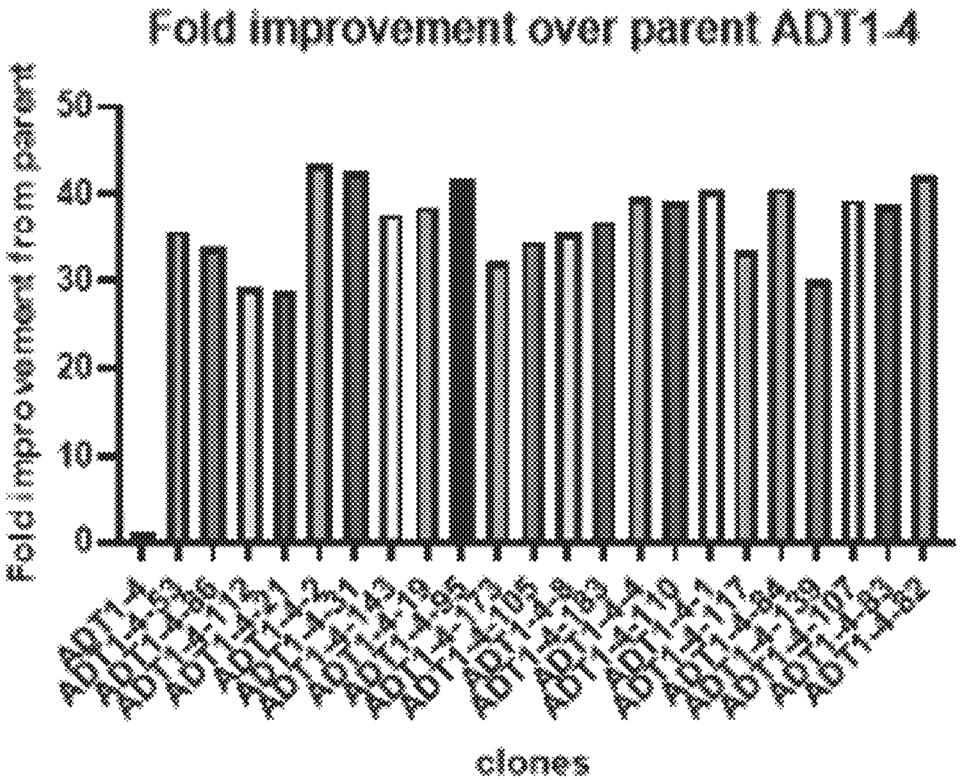
FIGS. 30A-30C. Fold improvements in human (and cyno) antigen binding over parental clones.
Figure 30B:
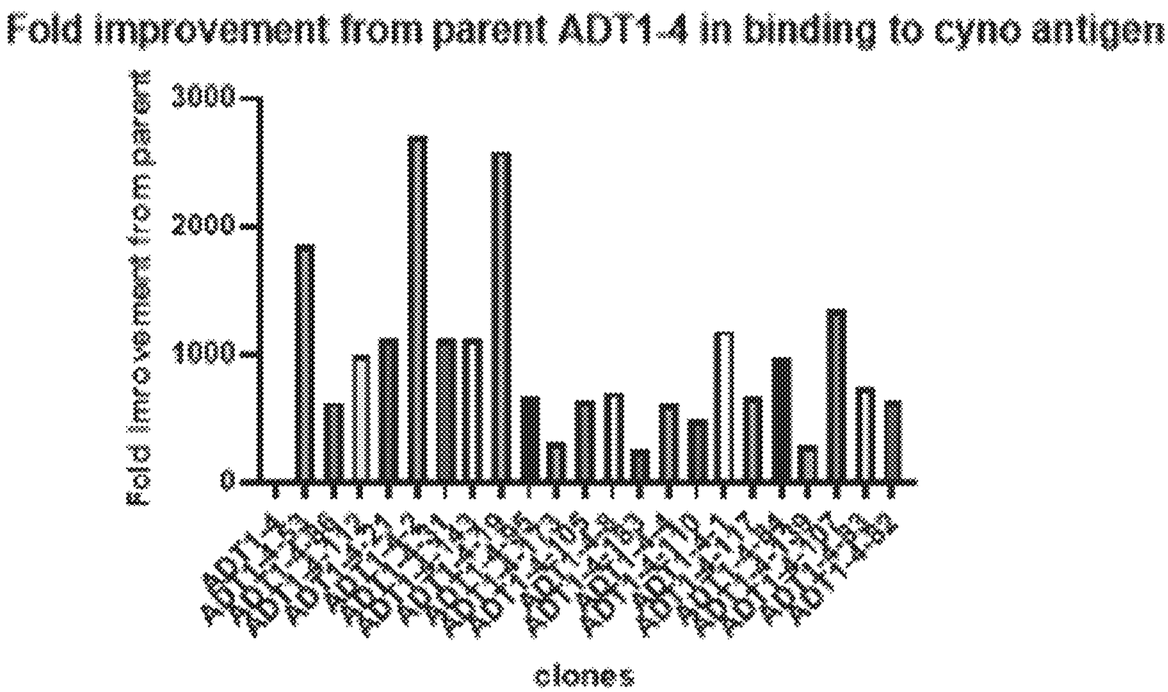
Figure 30C:
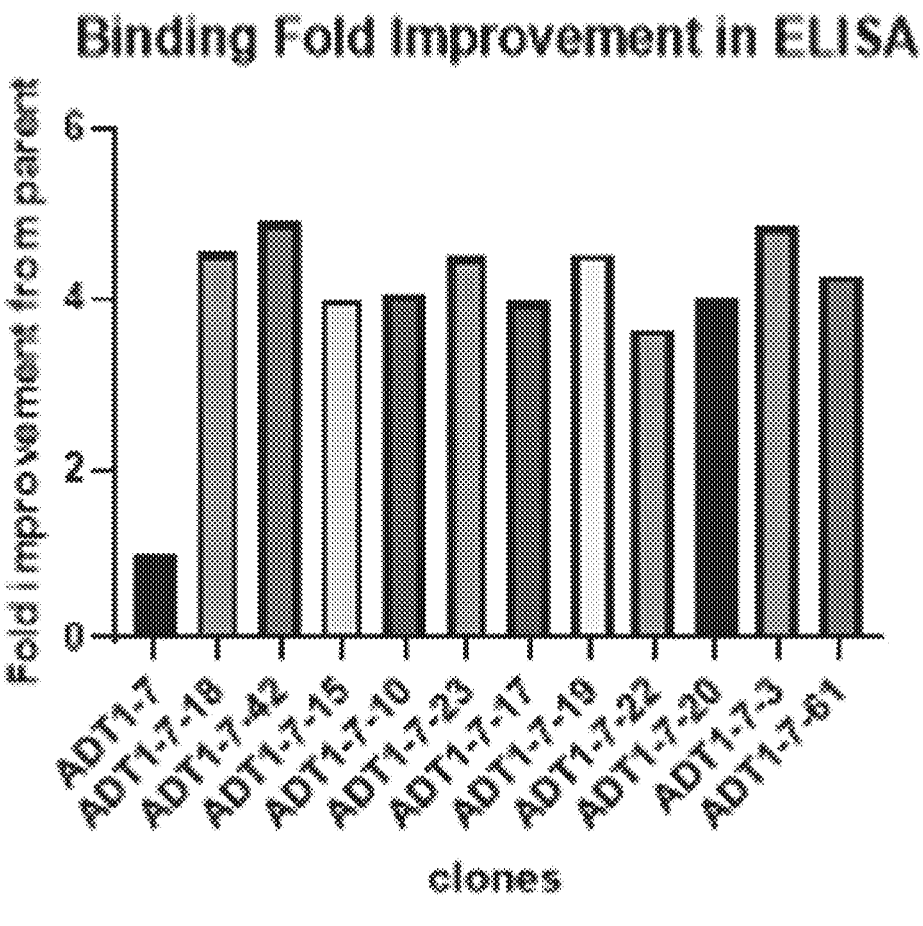

Affinity ranking of antibody of interest were performed using DELFIA immunoassay in which antibodies were captured via protein G coated on the plate and human soluble biotinylated L1 (DV1-GV4) antigen was added at 0.4 nM and cyno antigen DV1/GV77 at 10 nM (3MPBS). For detection 50 μL of streptavidin-Eu (1:500 in assay buffer, Perkin Elmer) was used and signal was developed with DELFIA enhancement solution. D1.3 hIgG1 (described in England et al. (1999) *J. Immunol.* 162: 2129-2136) was used as a negative control. The results are provided in FIGS. 30A to C.

SPR Analysis—IgG Capture

Figure 31A:
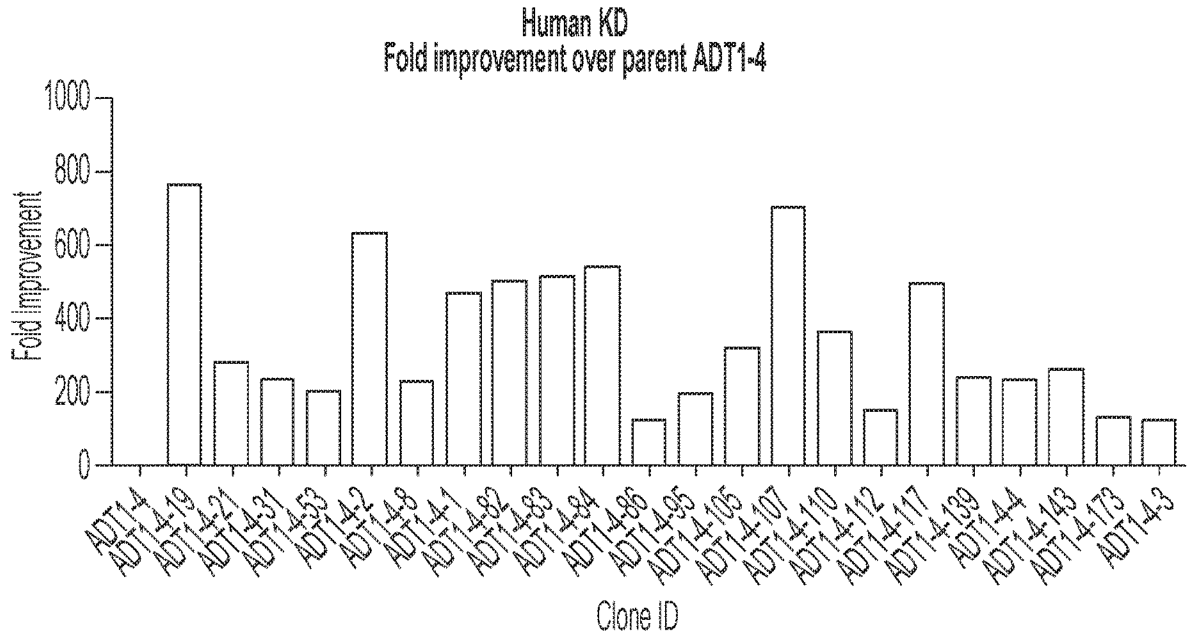
FIGS. 31A-31C. Fold improvements in KD for human (and cyno) antigen over parental clones.
Figure 31B:
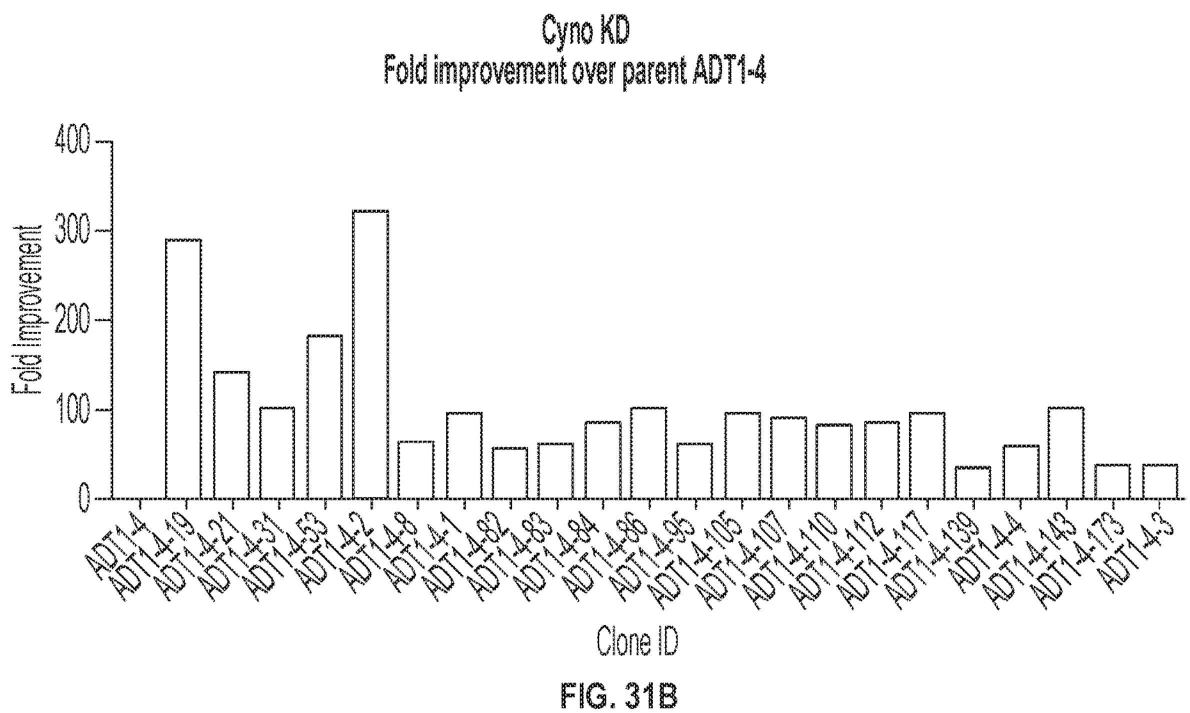
Figure 31C:
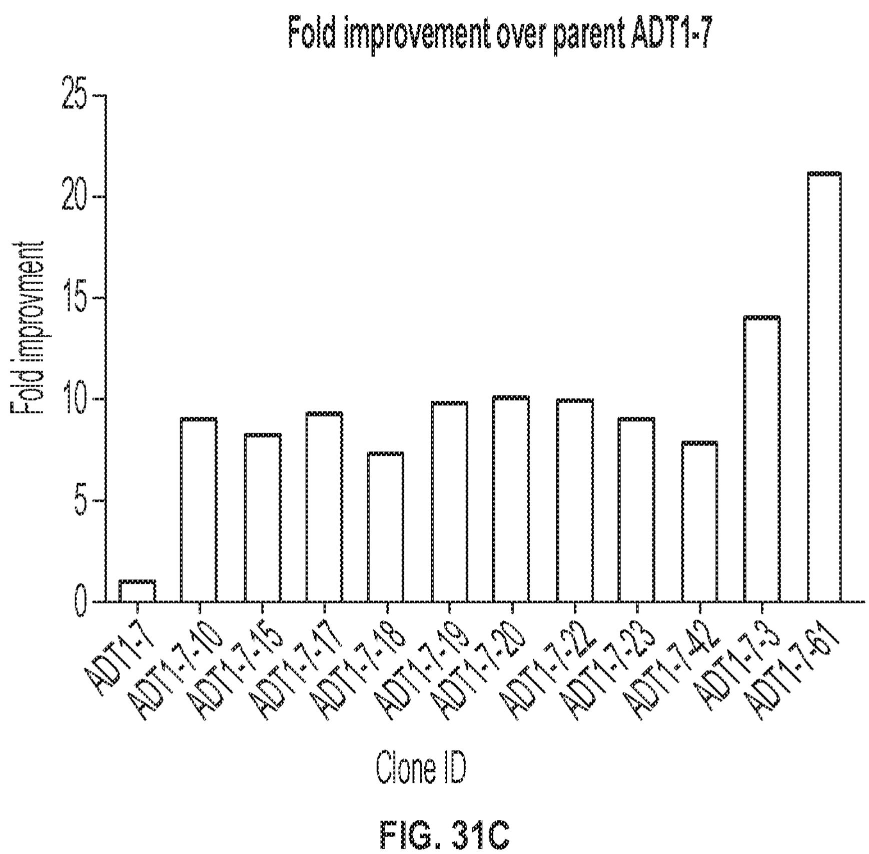

SPR analysis was used to compare $K_D$ values for the affinity matured clones compared to the parental clones. Instrument used: MASS-2 (Sierra Sensors); Chip: amine high capacity (Sierra Sensors); running buffer PBS+0.02% Tween 20. Experiments were performed at room temperature or 37° C., protein G was coupled to the chip. Antigen was flown over the cell in a dilution series ranging from 50 nM to 0.2 nM for human DV1-GV4 and from 100 nM to 1 nM for Cyno DV1-77. 120 sec association, 600 sec dissociation, 50 μL/min flowrate, regeneration with 10 mM glycine pH 1.5 kinetic fit according to Langmuir 1:1 binding using software Sierra Analyzer. The results are shown in FIGS. 31A to C.

Binding Affinity Analysis ($K_D$ by SPR)

Vδ1 Monoclonal Antibody Binding Affinity to Vδ1 Antigen

The binding affinity of the antibodies to target (i.e. the Vδ1 chain of a γδ TCR) is established by SPR analysis using a Reichert 4SPR instrument (Reichert Technologies). Antibody (1.5 ug/mL) is coated onto a Planar Protein A Sensor Chip (Reichert Technologies) to give an increase on baseline of approximately 500 uRIU. Antigen (e.g. L1 (DV1-GV4) was flown over the cell at a 1:3 dilution series from 300 nM to 3.7 nM with the following parameters: 180 s association, 600 s dissociation, flowrate 25 μL/min, running buffer PBS+0.05% Tween 20. All experiments were performed at room temperature. Steady state fitting was determined according to Langmuir 1:1 binding using software TraceDrawer (Reichert Technologies).

Human Antigen

Figure 32A:
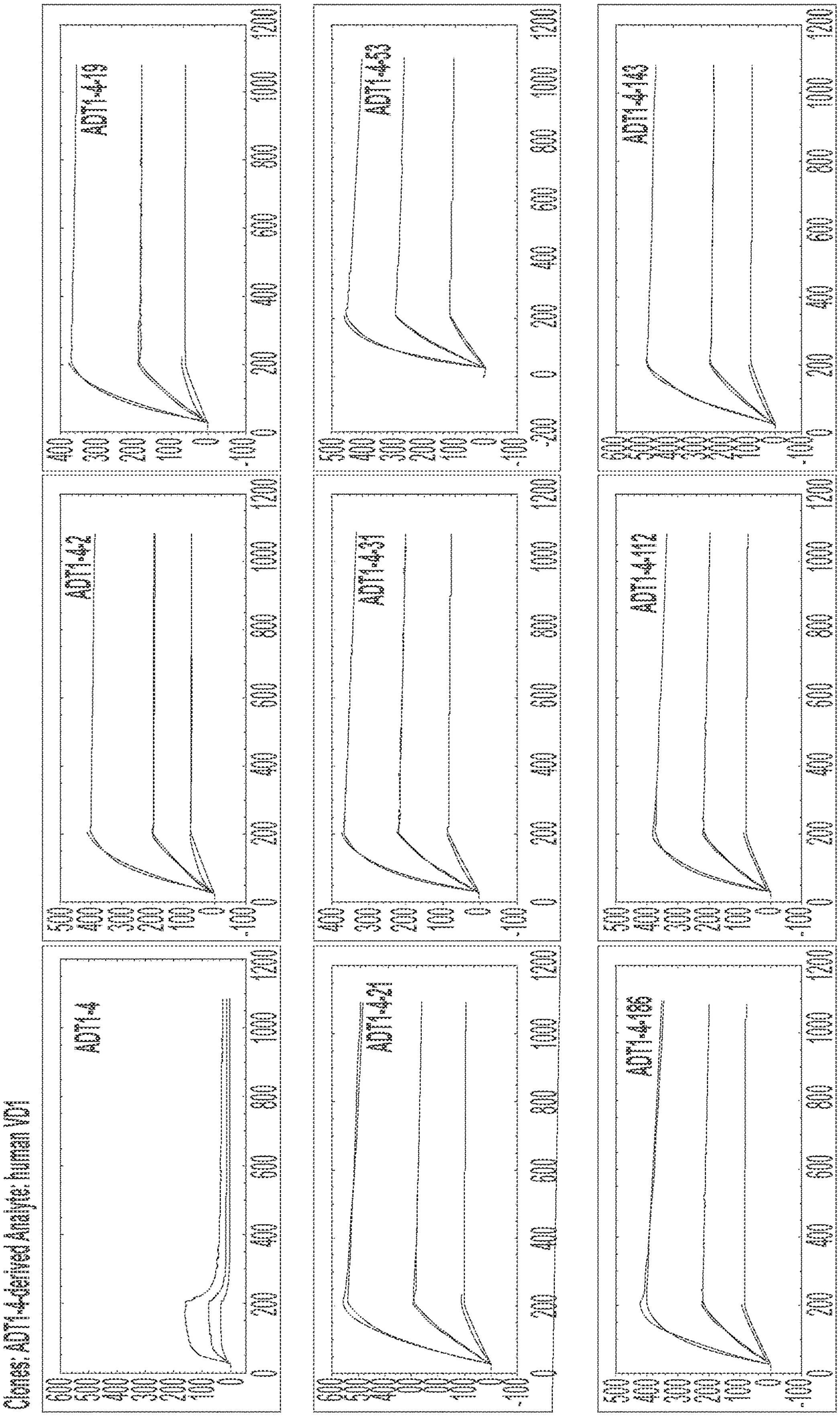
Figure 32B:
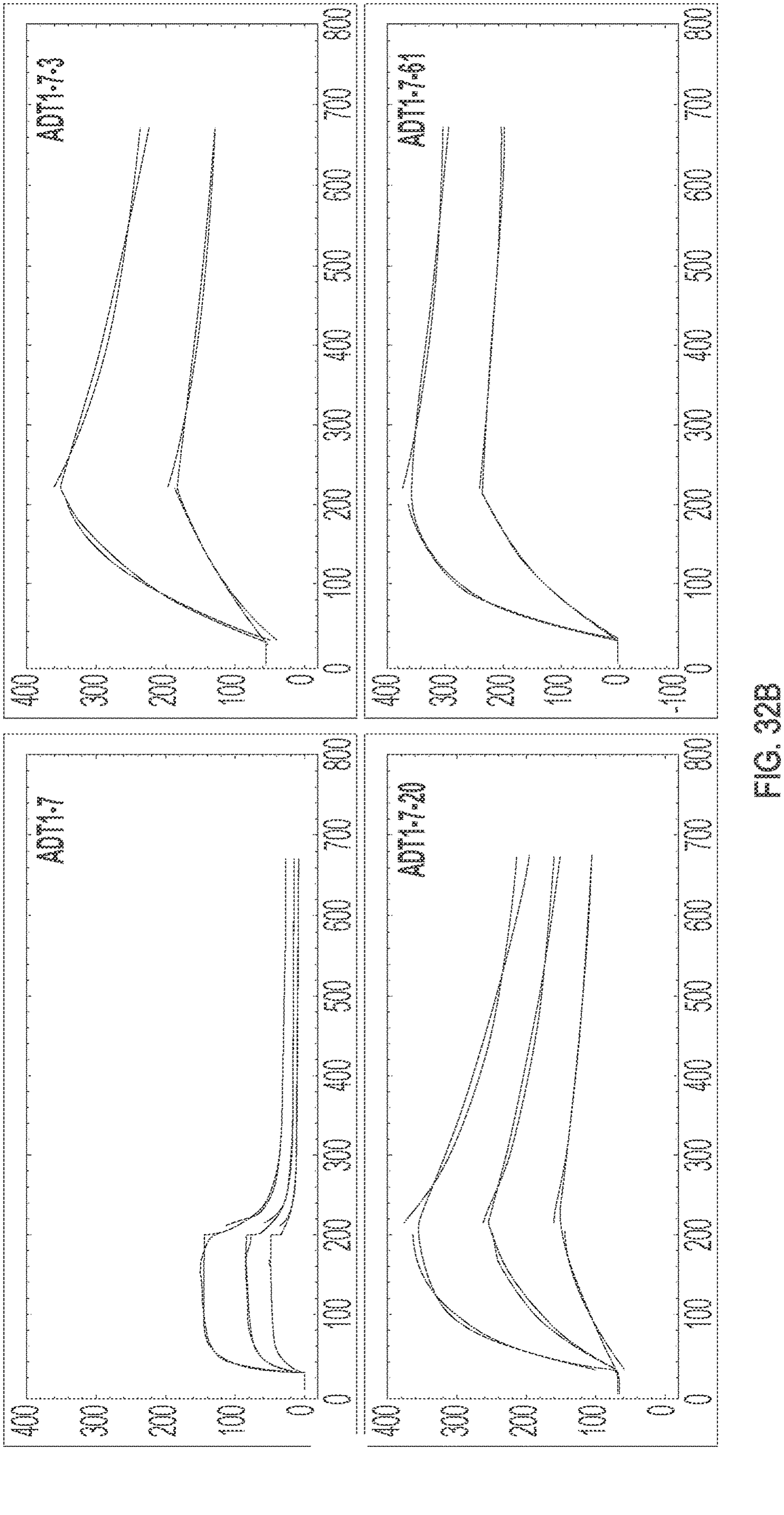

Affinity-matured Vδ1 mAbs exhibit greatly enhanced affinity to human Vδ1 antigen that either parent as determine by surface plasmon resonance (SPR) analysis (FIG. 32). (A, B) Surface Plasmon Resonance (SPR) analysis was performed with ADT1-4 (A) or ADT1-7 (B) parent mAbs and their affinity-matured derivatives to determine the binding affinity to human Vδ1 antigen. The binding interaction of Vδ1 and the affinity-matured mAbs were modelled according to Langmuir 1:1 binding. (C,D) Tables summarizing the equilibrium dissociation constant ($K_D$) of Vδ1-targeted antibodies, as derived from the sensograms illustrated in (A) and (B). The data is represented as the mean of two replicates performed on two different SPR instruments. (E,F) Bar charts representing the fold increase in equilibrium dissociation constant ($K_D$) of the affinity-matured derivative to Vδ1 antigen, as compared to their parent, ADT1-4 or ADT1-7.

Conclusions: This data demonstrates that the affinity-matured derivatives of ADT1-4 and ADT1-7 demonstrate significantly higher affinity to human Vδ1 antigen than the parent antibodies.

Cyno Antigen

Figure 33A:
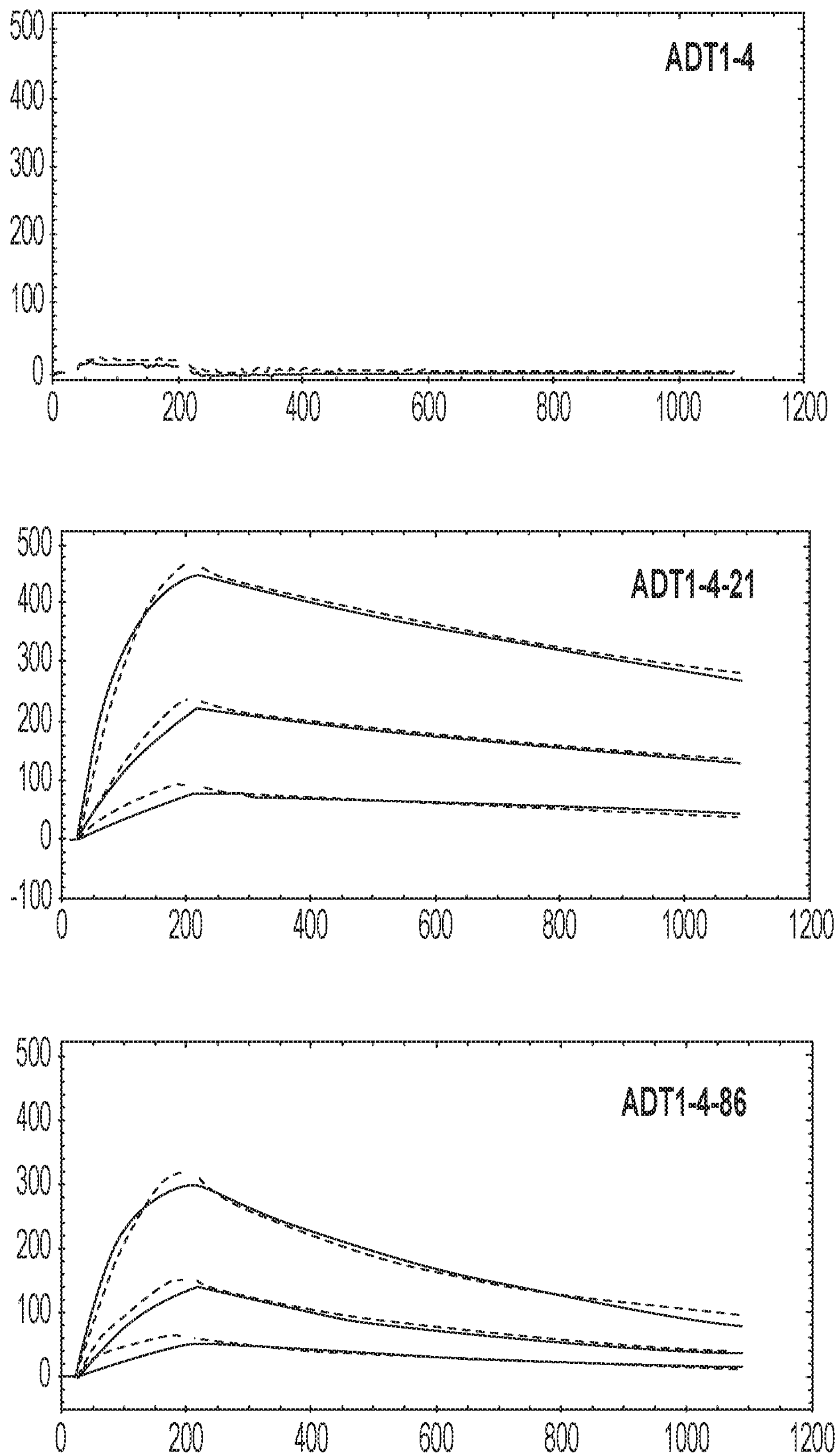
Figure 33B:
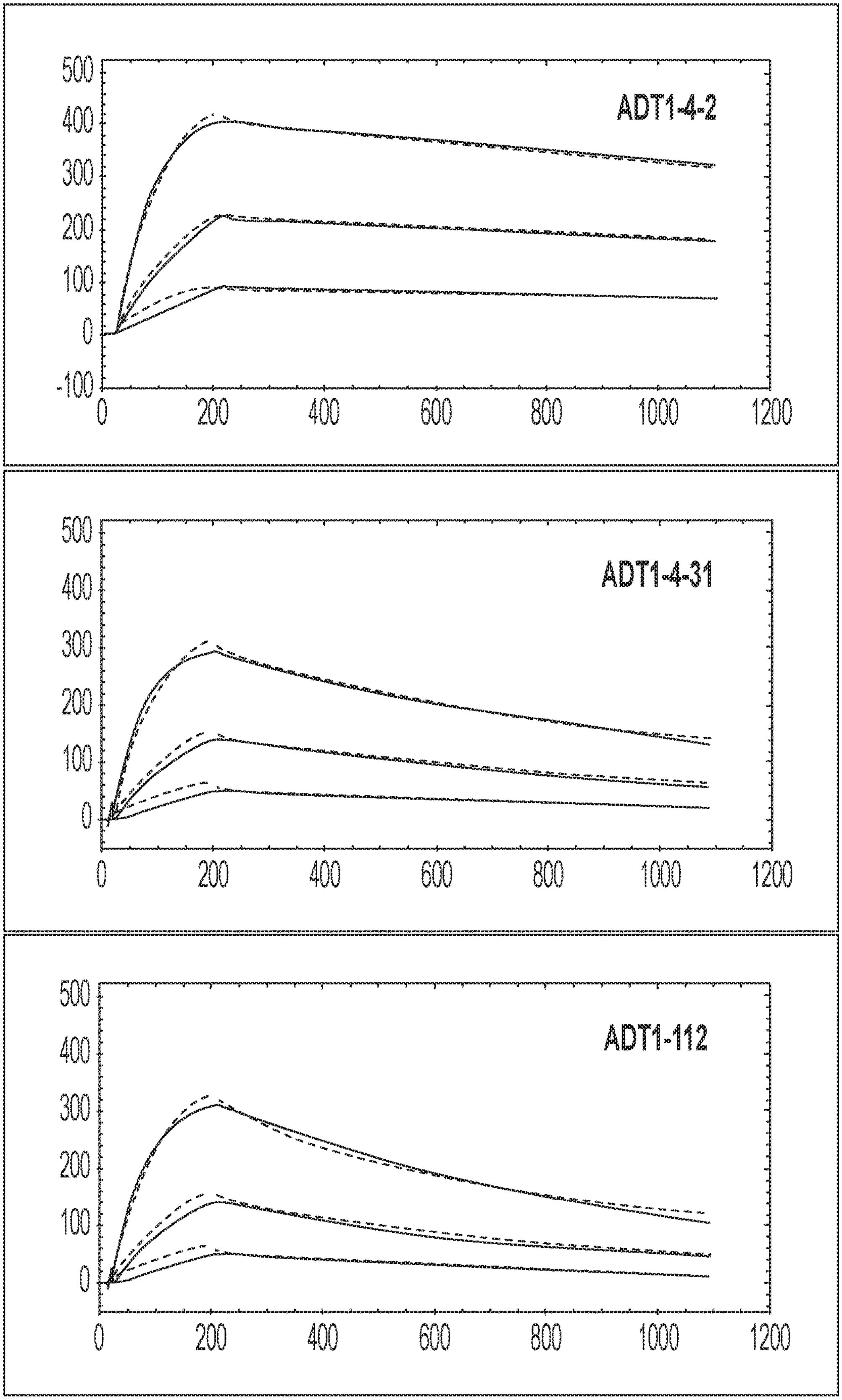
Figure 33C:
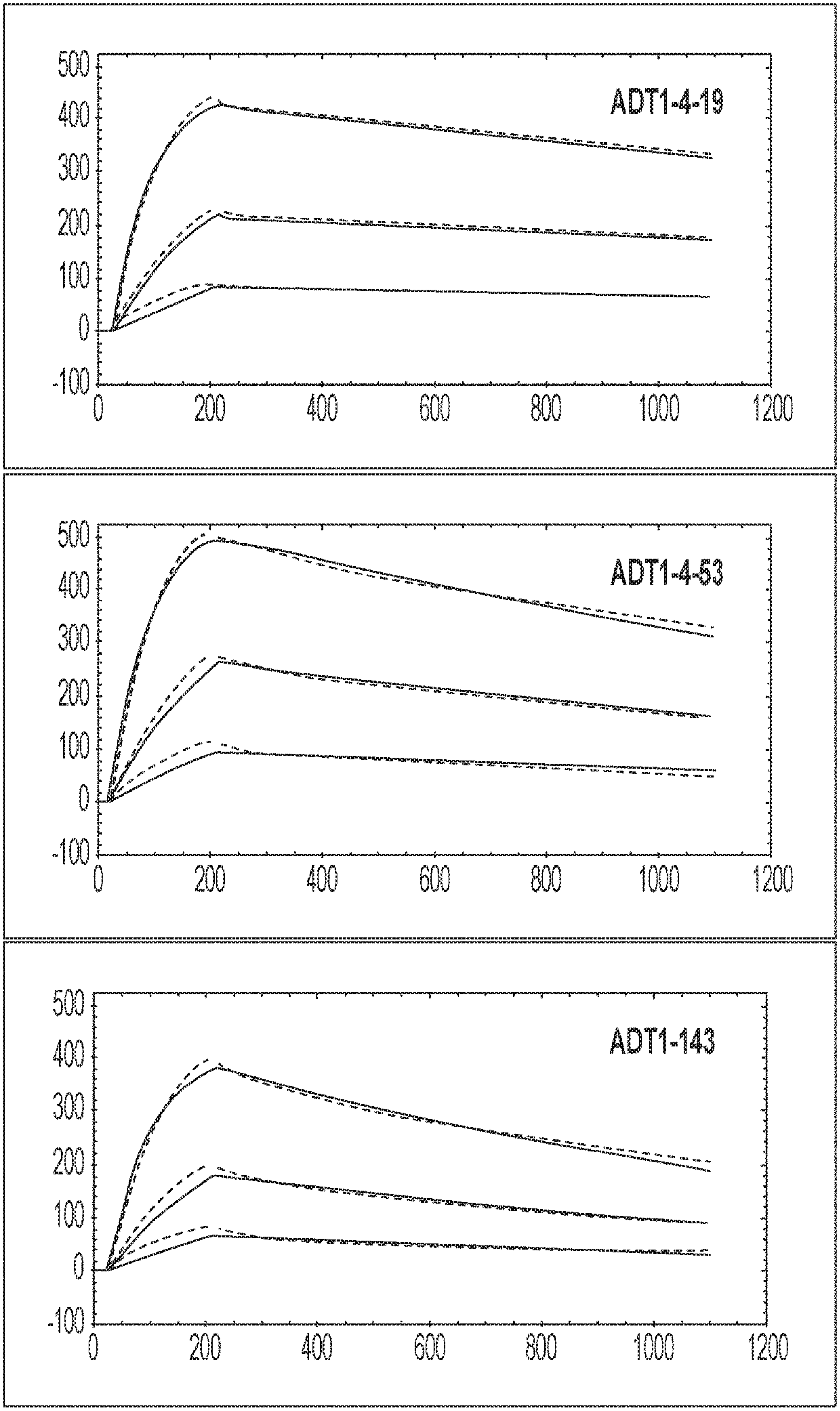
Figure 34A:
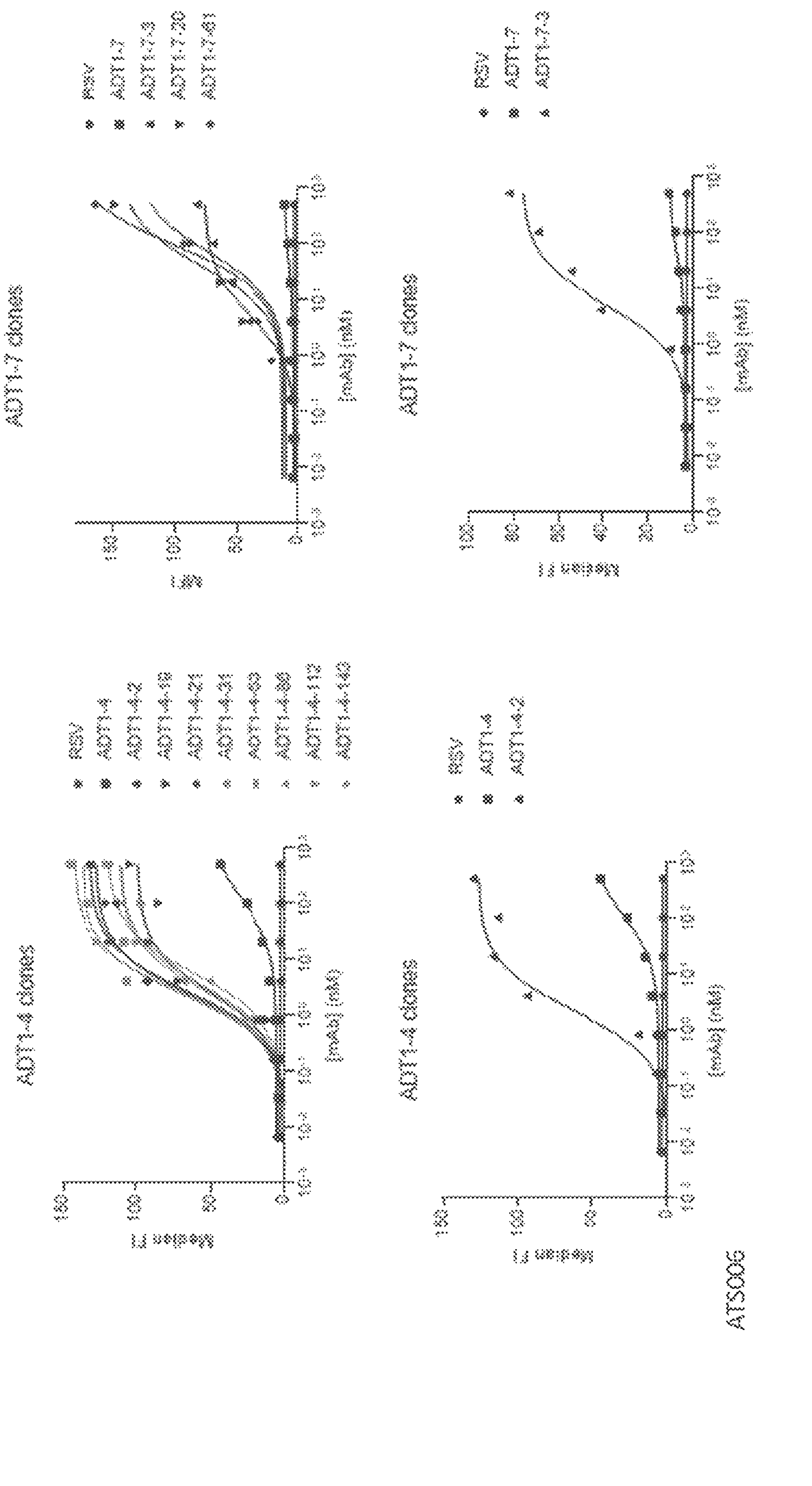
Figure 34B:
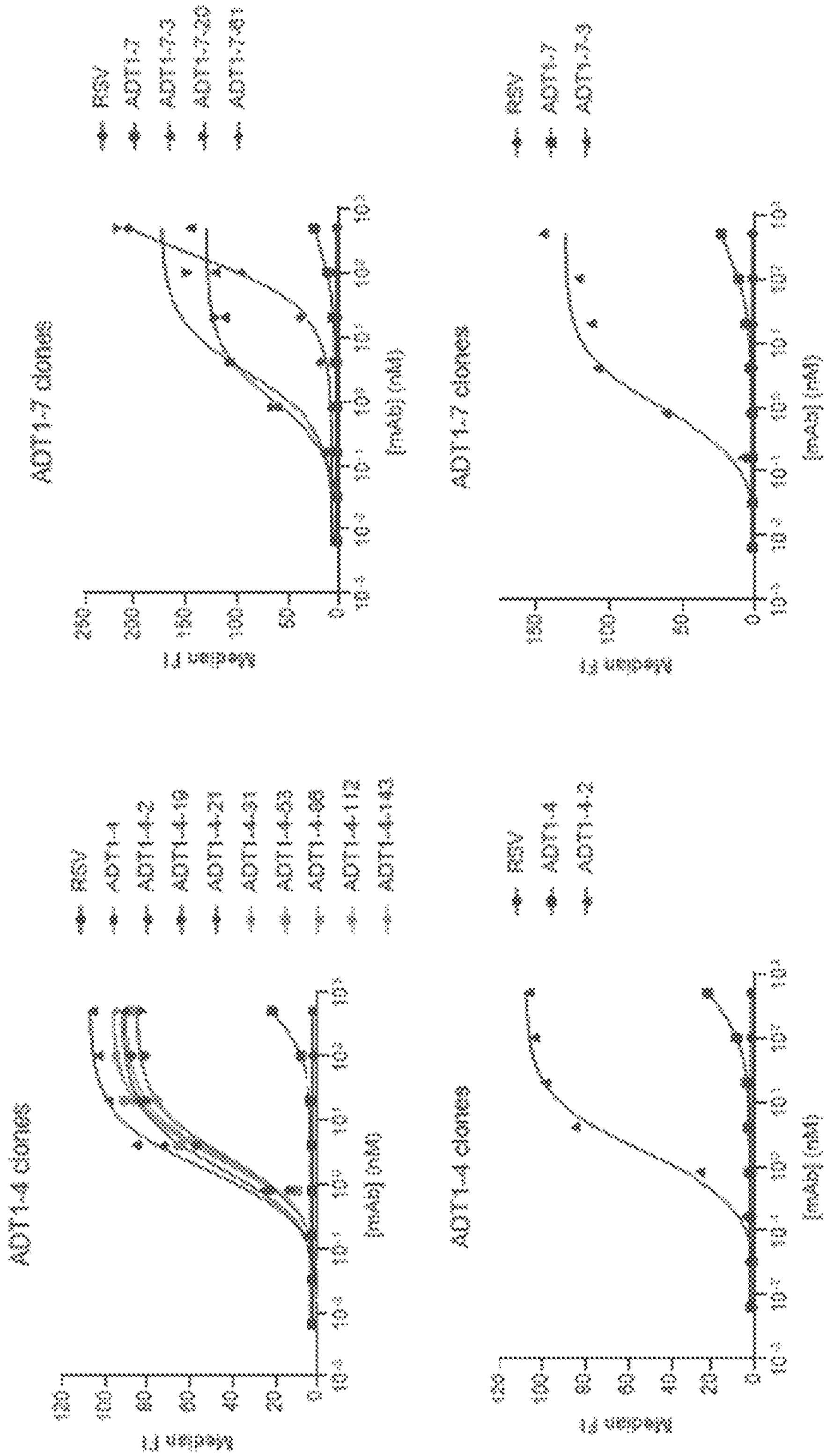

Surface plasmon resonance analysis demonstrates that the affinity-matured Vδ1 mAbs of the ADT1-4 lineage show a greatly enhanced affinity to cynomolgus Vδ1 antigen than the parent antibody (FIG. 33). (A-C) Surface Plasmon Resonance (SPR) analysis was performed with ADT1-4 parent antibody and the affinity-matured derivatives to determine the binding affinity to cynomolgus Vδ1 antigen. The binding interaction of Vδ1 and the affinity-matured mAbs were modelled according to Langmuir 1:1 binding. (D) Table summarizing the equilibrium dissociation constant ($K_D$) of Vδ1-targeted antibodies, as derived from the sensograms illustrated in (A-C). The data is represented as the mean of two replicates performed on two different SPR instruments. The results are shown in FIGS. 33A through 33D.

Conclusions: This data demonstrates that the affinity-matured derivatives of ADT1-4 demonstrate significantly higher affinity to cynomolgus Vδ1 antigen than the parent antibody.

Binding Affinity to Cell Surface Vδ1 TCR (EC50 for Binding to Cell Surface Vδ1)

Affinity matured Vδ1 mAbs exhibit greatly enhanced affinity to Vδ1-positive γδT cells, with no demonstrable binding to cells lacking Vδ1, as show in FIGS. 34A to D. (A, B) The level of binding by the Vδ1 mAbs to two γδ T cell donors, ATS006 (A) and TS164 (B). γδ T cells were stained with varying concentrations of Vol mAbs, followed by a fluorescent anti-human IgG detection antibody (xxx). All incubation steps were performed at 4° C. and mAb binding was determined using flow cytometry to measure the median level of fluorescence. Logarithmic four parameter dose-response curves were fitted using GraphPad Prism 9. (C) Bar chart representing the average EC50s from the ADT1-4 and ADT1-7 clones binding to Vδ1-positive γδ T cell, represented as the mean two donors. (D) Table summarizing the EC50s plotted in (A) & (B), and Vol-negative cell types including HEK293A, Raji cells and various leukocyte subsets with primary blood mononuclear cells. For Vδ1-positive γδ T cell, data is represented as the mean two donors.

Conclusions: This data demonstrates that the affinity-matured derivatives of ADT1-4 and ADT1-7 demonstrate significantly higher affinity to Vδ1-positive γδ T cells than their parent mAbs, whilst showing no binding to Vδ1-negative cells HEK293T, Raji, or CD8, CD4, NK, CD19 or monocytic cells within PBMCs.

Target Cell Binding of Vδ1 Monoclonal Antibodies

A range of target cells were assayed to determine the specificity and affinity of Vδ1 mAb binding. This included expanded skin-derived Vδ1 γδ T-cells, HEK293T cells, Raji cells, and multiple leukocyte subsets within human primary blood mononuclear cells. Adherent or semi-adherent cells (skin-derived Vδ1 γδ T-cells, HEK293T) were detached from tissue culture flask and resuspended in PBS. Similarly, non-adherent cell types (Raji, PBMC), were harvested and resuspended in PBS. Cells were seeded at a final density of 100,000 cells per well in v-bottom 96-well plates. Cells underwent centrifugation and the cell pellets were resuspended in FcR blocking reagent according to the manufacturer's instructions, and incubated for 20 minutes at 4C prior to a further wash. Vδ1 mAbs, anti-RSV IgG control and anti-CD3 OKT3 were diluted to 500 nM in PBS and serially diluted 1:5 in PBS to 6.4 μM, and added to the cells, followed by a 20-minute incubation at 4C. To determine the quantity of mAb bound to the cell surface, the cells were then stained with a murine anti-human IgG secondary antibody, conjugated to APC (dilution: 1:100). For Vδ1 γδ T-cells, HEK293T and Raji, the cells were also stained solely with a viability dye. For PBMC, conjugated antibodies against CD4, CD8, CD56, CD11 b and CD19 (all at 1:100) were also included, allowing the discrimination of αβ subsets, NK cells, B cell and monocytic cells. Following 20-minute incubation at 4C, the cells were washed twice, and fluorescence measured using the MACSQuant. IC50s are shown in FIG. 34D.

Summary of $K_D$ Values for ADT1-4 Lineage (Human and Cyno)

The table below provides the $K_D$ values for the 24 clones in the ADT1-4 lineage and the ADT1-4 parent clone (G04) (for binding to human TRDV1 and cyno TRDV1):

| Clone ID | HUMAN $K_D$ [M] | HUMAN $K_D$ (nM) | CYNO $K_D$ [M] | CYNO $K_D$ (nM) |
|---|---|---|---|---|
| ADT1-4 | 1.26E−07 | 126 nM | N/A | N/A |
| ADT1-4-19 | 1.63E−10 | 0.163 nM | 3.40E−09 | 3.40 nM |
| ADT1-4-21 | 4.41E−10 | 0.441 nM | 6.79E−09 | 6.79 nM |
| ADT1-4-31 | 5.22E−10 | 0.522 nM | 9.43E−09 | 9.43 nM |
| ADT1-4-53 | 6.08E−10 | 0.608 nM | 5.34E−09 | 5.34 nM |
| ADT1-4-2 | 1.95E−10 | 0.195 nM | 3.08E−09 | 3.08 nM |
| ADT1-4-8 | 5.41E−10 | 0.541 nM | 1.51E−08 | 15.1 nM |
| ADT1-4-82 | 2.49E−10 | 0.249 nM | 1.67E−08 | 16.7 nM |
| ADT1-4-83 | 2.41E−10 | 0.241 nM | 1.58E−08 | 15.8 nM |
| ADT1-4-84 | 2.27E−10 | 0.227 nM | 1.16E−08 | 11.6 nM |
| ADT1-4-86 | 9.39E−10 | 0.939 nM | 9.49E−09 | 9.49 nM |
| ADT1-4-95 | 6.42E−10 | 0.642 nM | 1.50E−08 | 15.0 nM |
| ADT1-4-105 | 3.81E−10 | 0.381 nM | 1.01E−08 | 10.1 nM |
| ADT1-4-107 | 1.77E−10 | 0.177 nM | 1.05E−08 | 10.5 nM |
| ADT1-4-110 | 3.33E−10 | 0.333 nM | 1.19E−08 | 11.9 nM |
| ADT1-4-112 | 7.84E−10 | 0.784 nM | 1.11 E−08 | 11.1 nM |
| ADT1-4-117 | 2.45E−10 | 0.245 nM | 1.01E−08 | 10.1 nM |
| ADT1-4-139 | 4.99E−10 | 0.499 nM | 2.69E−08 | 26.9 nM |
| ADT1-4-4 | 5.19E−10 | 0.519 nM | 1.62E−08 | 16.2 nM |
| ADT1-4-143 | 4.63E−10 | 0.463 nM | 9.39E−09 | 9.39 nM |
| ADT1-4-173 | 9.07E−10 | 0.907 nM | 2.40E−08 | 24.0 nM |
| ADT1-4-3 | 9.35E−10 | 0.935 nM | 2.85E−08 | 28.5 nM |
| ADT1-4-1 | 8.00E−11 | 0.08 nM | 4.1E−10 | 0.41 nM |

-continued

| Clone ID | HUMAN $K_D$ [M] | HUMAN $K_D$ (nM) | CYNO $K_D$ [M] | CYNO $K_D$ (nM) |
|---|---|---|---|---|
| ADT1-4-6 | 1.06E−9 | 1.06 nM | 1.01E−9 | 1.01 nM |
| ADT1-4-138 | 4.38E−8 | 43.8 nM | 3.47E−8 | 34.7 nM |

Summary of $K_D$ Values for ADT1-7 Lineage (Human Only)

The table below provides the $K_D$ values for the 11 clones in the ADT1-7 lineage and the ADT1-7 parental clone (E07) (for binding to human TRDV1 only):

| Clone ID | $K_D$ [M] | $K_D$ (nM) |
|---|---|---|
| ADT1-7 | 1.24E−08 | 12.4 nM |
| ADT1-7-10 | 1.30E−09 | 1.30 nM |
| ADT1-7-15 | 1.42E−09 | 1.42 nM |
| ADT1-7-17 | 1.26E−09 | 1.26 nM |
| ADT1-7-18 | 1.61E−09 | 1.61 nM |
| ADT1-7-19 | 1.19E−09 | 1.19 nM |
| ADT1-7-20 | 1.17E−09 | 1.17 nM |
| ADT1-7-22 | 1.18E−09 | 1.18 nM |
| ADT1-7-23 | 1.29E−09 | 1.29 nM |
| ADT1-7-42 | 1.51E−09 | 1.51 nM |
| ADT1-7-3 | 8.31E−10 | 0.831 nM |
| ADT1-7-61 | 5.57E−10 | 0.557 nM |

Summary of Pharmacological Data for the Preferred Members of the ADT1-4 Lineage

| Clone ID | HUMAN K_D [M] | HUMAN K_D (nM) | CYNO K_D [M] | CYNO K_D (nM) | IC50 TCR DR (no THP-1) | IC90 TCR DR (noTHP-1) | IC50 Killing | IC90 Killing |
|---|---|---|---|---|---|---|---|---|
| ADT1-4 | 1.26E−07 | 126 nM | N/A | N/A | 38.2* | 72.4* | 2.603E−08 (26.03 nM) | 7.048E−08 |
| ADT1-4-19 | 1.63E−10 | 0.163 nM | 3.40E−09 | 3.40 nM | 3.67E−10 (0.367 nM) | 1.583E−9 (1.583 nM) | 1.12E−09 (1.12 nM) | 8.38E−09 (8.38 nM) |
| ADT1-4-21 | 4.41E−10 | 0.441 nM | 6.79E−09 | 6.79 nM | 2.66E−10 (0.266 nM) | 8.92E−10 (0.892 nM) | 9.4E−10 (0.94 mM) | 5.88E−09 (5.88 nM) |
| ADT1-4-31 | 5.22E−10 | 0.522 nM | 9.43E−09 | 9.43 nM | 2.45E−10 (0.245 nM) | 1.091E−9 (1.091 nM) | 1.63E−09 (1.63 nM) | 1.658E−08 (16.58 nM) |
| ADT1-4-53 | 6.08E−10 | 0.608 nM | 5.34E−09 | 5.34 nM | 2.54E−10 (0.254 nM) | 6.98E−10 (0.698 nM) | 1.05E−09 (1.05 nM) | 4.23E−09 (4.23 nM) |
| ADT1-4-2 | 1.95E−10 | 0.195 nM | 3.08E−09 | 3.08 nM | 3.1E−10 (0.31 nM) | 8.34E−10 (0.834 nM) | 8.7E−10 (0.87 nM) | 3.12E−09 (3.12 nM) |
| ADT1-4-86 | 9.39E−10 | 0.939 nM | 9.49E−09 | 9.49 nM | 3.07E−10 (0.307 nM) | 1.001E−9 (1.001 nM) | 1.05E−09 (1.05 nM) | 4.3E−09 (4.3 nM) |
| ADT1-4-112 | 7.84E−10 | 0.784 nM | 1.11E−08 | 11.1 nM | 2.95E−10 (0.295 nM) | 1.093E−9 (1.093 nM) | 9E−10 (0.9 nM) | 3.8E−09 (3.8 nM) |
| ADT1-4-143 | 4.63E−10 | 0.463 nM | 9.39E−09 | 9.39 nM | 3.13E−10 (0.313 nM) | 8.53E−10 (0.853 nM) | 1.78E−09 (1.78 nM) | 1.42E−08 (14.2 nM) |
| ADT1-4-1 | 8.00E−11 | 0.08 | 4.1E−10 | 0.41 | 3.604E−10 (0.3604 nM) | 6.702E−10 (0.6702 nM) | 1.4E−10 (0.14 nM) | 2.8E−10 (0.28 nM) |
| ADT1-4-6 | 1.06E−9 | 1.06 | 1.01E−9 | 1.01 | 4.796E−10 (0.4796 nM) | 1.911E−9 (1.911 nM) | 1.4E−10 (0.14 nM) | 2E−10 (0.2 nM) |
| ADT1-4-138 | 4.38E−8 | 43.8 | 3.47E−8 | 34.7 | 8.384E−9 (8.384 nM) | 3.83E−8 (38.3 nM) | 3.8E−10 (0.38 nM) | 6.44E−09 (6.44 nM) |

*ADT1-4 results did not reach full saturation in this assay, therefore data was extrapolated Summary of Pharmacological Data for the Preferred Members of the ADT1-7 Lineage

| Clone ID | K_D [M] | K_D (nM) | IC50 TCR DR (no THP-1) | IC90 TCR DR (noTHP-1) | IC50 Killing | IC90 Killing |
|---|---|---|---|---|---|---|
| ADT1-7 | 1.24E−08 | 12.4 nM | 22.4 nM** | 139.2 nM** | 5.53E−09 (5.53 nM) | 7.48E−08 (74.8 nM) |
| ADT1-7-20 | 1.17E−09 | 1.17 nM | 1.64E−10 (0.164 nM) | 1.036E−9 (1.036 nM) | 2.80E−10 (0.28 nM) | 2.47E−09 (2.47 nM) |
| ADT1-7-3 | 8.31E−10 | 0.831 nM | 1.61E−10 (0.161 nM) | 7.90E−10 (0.79 nM) | 1.60E−10 (0.16 nM) | 1.06E−09 (1.06 nM) |
| ADT1-7-61 | 5.57E−10 | 0.557 nM | 1.73E−10* (0.173 nM) | 3.668E−9* (3.67 nM) | 4.20E−10 (0.42 nM) | 1.66E−08 (16.6 nM) |

*Assay result for ADT1 -7-61 representative of one donor only

**ADT1-7 results did not reach full saturation in this assay, therefore data was extrapolated

Example 24. Functional Characterisation

Vδ1 monoclonal antibodies on TCR Downregulation The capacity of ADT mAb to engage with and resultantly downregulate γδ T-cell receptors is evaluated by measuring TCR expression. Skin γδ T-cells (from donor ATS006 and TS164) were seeded into a 96 well round bottom plate at 3×10^5 cells/ml in γδ media with increasing concentration of the test mAbs (range from 0.00067 to 67 nM) or the highest concentration (67 nM) of the corresponding isotype control (hIgG1, RSV), diluted in PBS. The cells were incubated for 2 hours in a humidified CO2 chamber at 37° C. The cells were washed and stained for dead cells (Thermo Fisher #15580607) and their VD1 TCRs (Miltenyi #130-117-697) for 30 minutes at 4° C. The cells were washed in FACS buffer and resuspended in Cell Fix (BD sciences #340181) before incubating overnight at 4° C. in the dark. The VD1 TCR expression level, determined by median fluorescence intensity (MFI), was measured by flow cytometry the following day using the MACS Quant Analyzer 16.

The results are shown in FIG. 35, which shows affinity matured Vδ1 mAbs bind and downregulate Vδ1 TCR more effectively than their parental clone and OKT3 in soluble assay format (A and B). This remarkable finding highlights that the approach taken herein involving use of high affinity Vδ1 mAbs to downregulate/activate TCR/CD3 complexes containing a Vδ1 receptor is not only far more selective, but also far more effective, relative to conventional CD3 targeting approaches. Quantification of γδ TCR expression after 2 hours incubation of γδ cells with Vδ1 mAbs and OKT3 before staining of the Vδ1 TCR with a-Vδ1 TCR-PE-Vio770. MFI of a-Vδ1 staining was acquired using flow cytometry and calculated from the TCR positive gate before calculating % MFI from the MFI of TCR positive, untreated γδ cells. The upper graph represents data from the ADT1-4 lineage and the lower graph represents data from the ADT1-7 lineage. (C) Bar chart representing the IC50 values calculated from (A). (D and E). Bar chart representing the IC50 values in (B) presented as fold improvement from the parent ADT1-4 (left) and ADT1-7 (right). (F) Table representing IC50 values (in nM) from (B) with the percentage improvement calculated from the respective parents of ADT1-4 (upper) and ADT1-7 (lower). (G) Table representing IC50 values from (B) with the fold improvement calculated from the respective parents of ADT1-4 (upper) and ADT1-7 (lower).

Vδ1 Monoclonal Antibodies on vδ Activation Measured by CD107a Expression

The capacity of ADT mAb to engage with and activate VD1 γδ cells is evaluated by measuring CD107a expression. Skin γδ T-cells (from donor ATS006) were seeded into a 96 well round bottom plate at 6×10^5 cells/ml in γδ media with THP-1 cells (ATCC-TIB-202) at 1.2×10^6 cells/ml and increasing concentration of the test mAbs (range from 0.00067 to 67 nM) or the highest concentration (67 nM) of the corresponding isotype control (hIgG1, RSV), diluted in PBS. The cells were incubated for 2 hours in a humidified CO2 chamber at 37° C. The cells were washed and stained for dead cells (Thermo Fisher #15580607), VD1 TCRs (Miltenyi #130-117-697) and aCD107a (Miltenyi #130-112-610) for 30 minutes at 4° C. The cells were washed in FACS buffer before incubating overnight at 4° C. in the dark. The VD1 TCR and CD107a expression level, determined by median fluorescence intensity (MFI), was measured by flow cytometry the following day using the MACS Quant Analyzer 16.

Figure 36A:
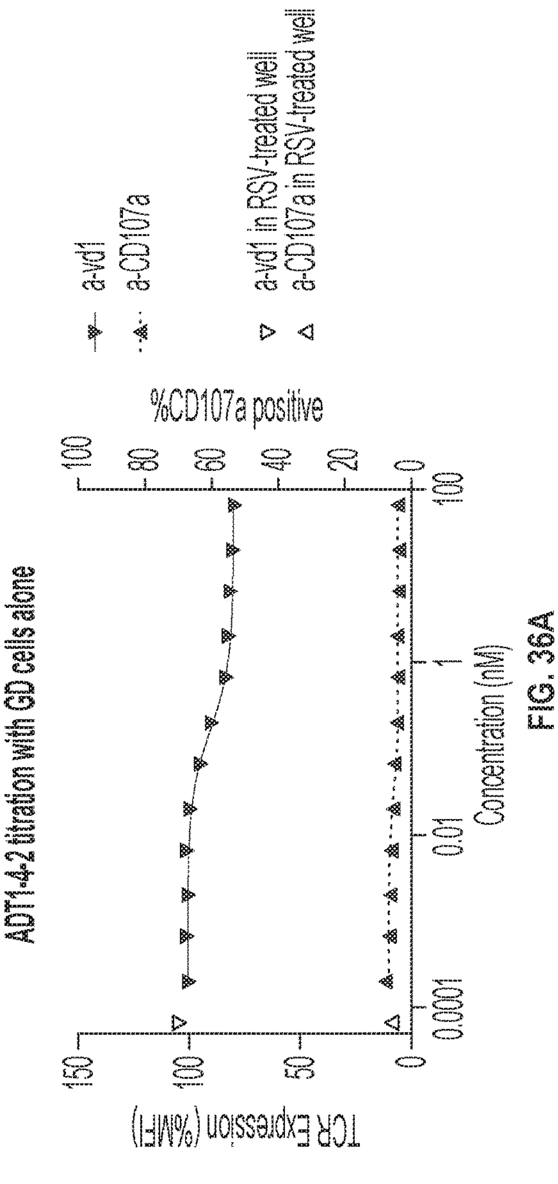
Figure 36B:
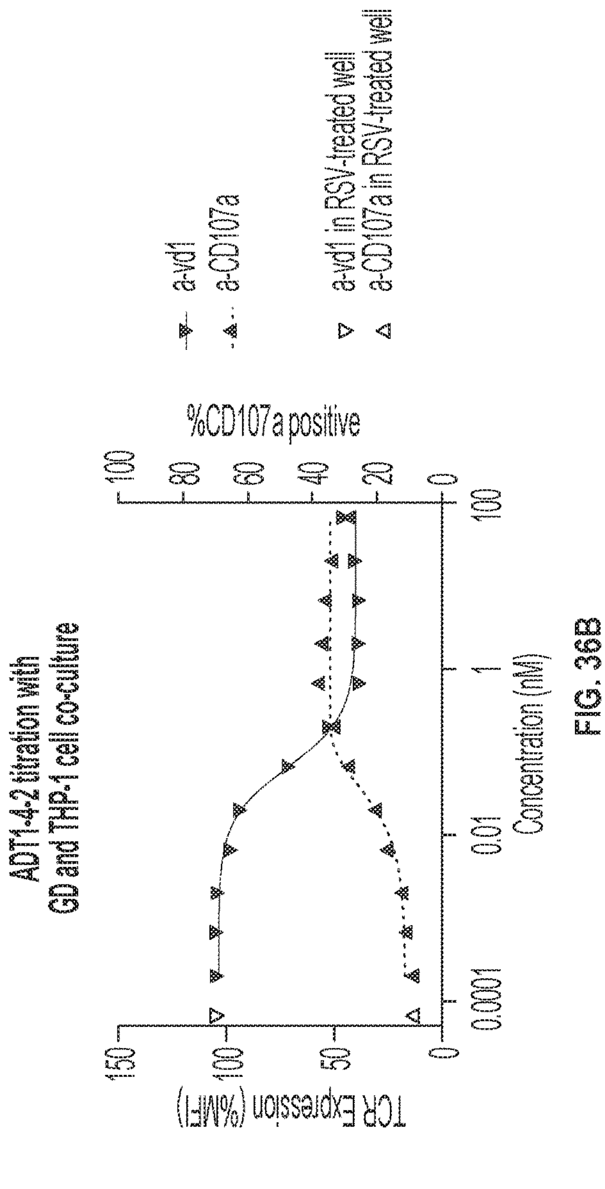

The results are shown in FIG. 36, which shows affinity matured Vδ1 mAbs induce activation only when in the presence of target cells. (A and B) Quantification of γδ TCR expression (black) and CD107a expression (grey) after 2 hours incubation of γδ cells with ADT1-4-2 alone (upper) and with THP-1 cells (lower) at a 1:2 target-to-effector ratio before staining of the Vδ1 TCR and CD107a with a-Vδ1 TCR-PE-Vio770 and a-CD107a-VioBlue respectively. MFI of Vδ1 staining was acquired using flow cytometry and calculated from the TCR positive gate before calculating % MFI from the MFI of TCR positive, untreated and non-cocultured γδ cells. MFI of CD107a staining was acquired using flow cytometry and calculated from the 'NOT THP-1' gate before calculating % MFI from the CD107a MFI of untreated non-cocultured γδ cells. (C and D) Quantification of γδ TCR expression (black) and CD107a expression (grey) after 2 hours incubation of γδ cells with ADT1-7-3 alone (upper) and with THP-1 cells (lower) at a 1:2 target-to-effector ratio before staining of the Vδ1 TCR and CD107a with a-Vδ1 TCR-PE-Vio770 and a-CD107a-VioBlue respectively. MFI of Vδ1 staining was acquired using flow cytometry and calculated from the TCR positive gate before calculating % MFI from the MFI of TCR positive, untreated and non-cocultured γδ cells. MFI of CD107a staining was acquired using flow cytometry and calculated from the 'NOT THP-1' gate before calculating % MFI from the CD107a MFI of untreated non-cocultured γδ cells. (E) Table representing the percentage increase in γδ CD107a expression from cocultured cells treated with the highest concentration of Vδ1 mAb compared to untreated non-cocultured γδ cells. (F) Table representing the percentage increase in γδ CD107a expression from cocultured cells treated with the highest concentration of Vδ1 mAb compared to untreated, co- and non-cocultured γδ cells.

Vδ1 Monoclonal Antibodies on vδ Activation Measured by CD25 Expression

The capacity of ADT mAb to engage with and activate VD1 γδ cells is evaluated by measuring CD25 expression. Skin γδ T-cells (from donor ATS006) were seeded into a 96 well round bottom plate at 6×10^5 cells/ml in γδ media with THP-1 cells (ATCC-TIB-202) at 1.2×10^6 cells/ml and increasing concentration of the test mAbs (range from 0.00067 to 67 nM) or the highest concentration (67 nM) of the corresponding isotype control (hIgG1, RSV), diluted in PBS. The cells were incubated for 24 hours in a humidified CO2 chamber at 37° C. The cells were washed and stained for dead cells (Thermo Fisher #15580607), VD1 TCRs (Miltenyi #130-117-697) and CD25 (Miltenyi #130-113-280) for 30 minutes at 4° C. The cells were washed in FACS buffer before incubating overnight at 4° C. in the dark. The VD1 TCR and CD107a expression level, determined by median fluorescence intensity (MFI), was measured by flow cytometry the following day using the MACS Quant Analyzer 16.

Figure 37A:
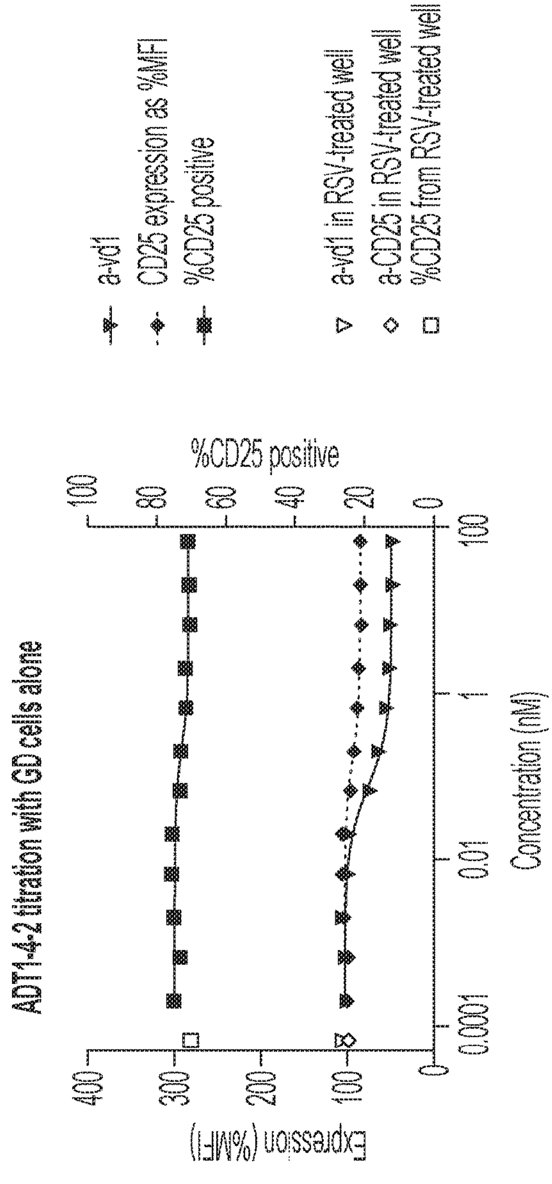
Figure 37B:
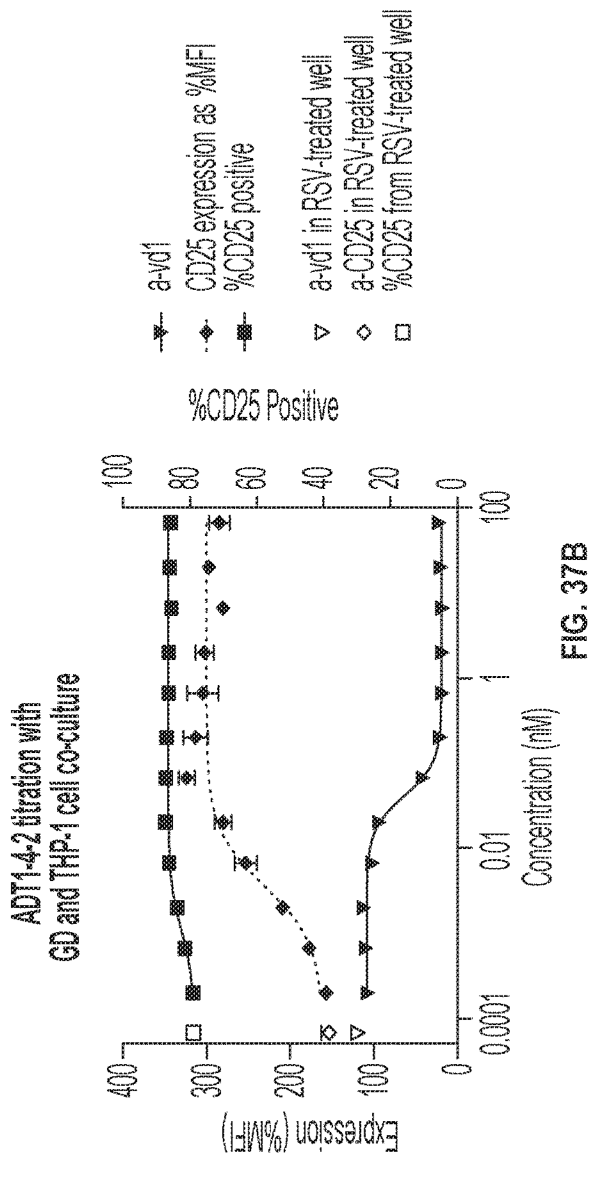
Figure 38A:
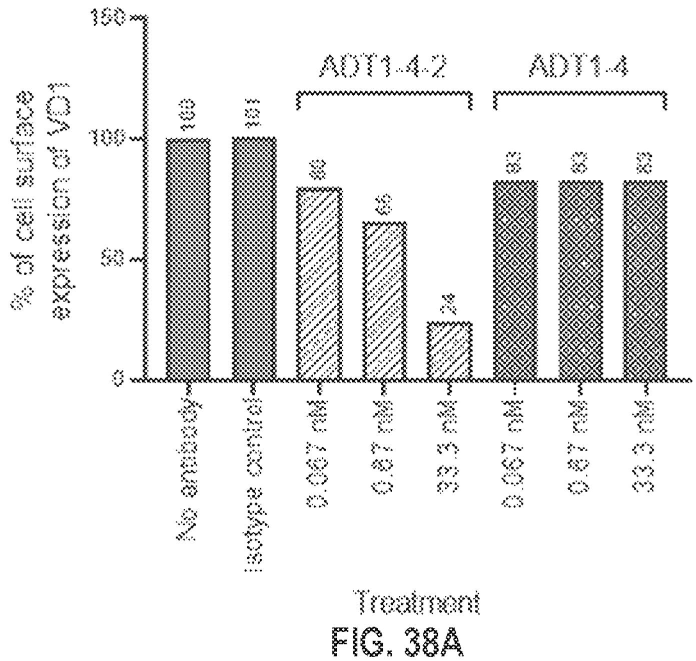
FIGS. 38A-38H. Cyno TCR Downregulation (with soluble antibodies).
Figure 38B:
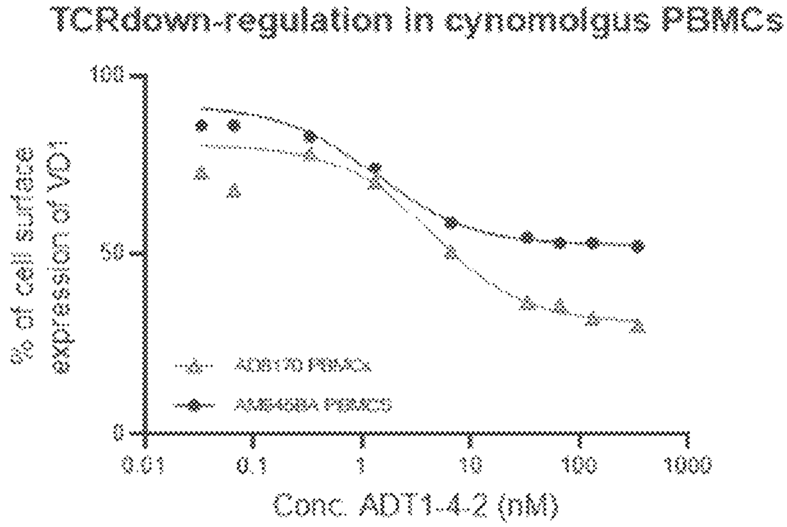
Figure 38C:
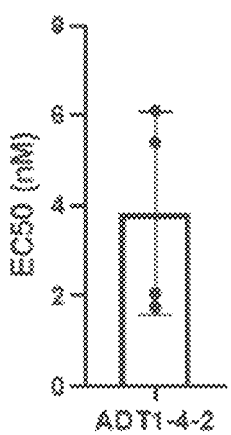
Figure 38D:
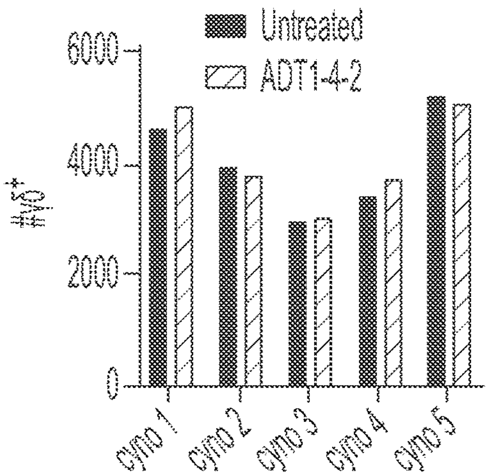
Figure 38E:
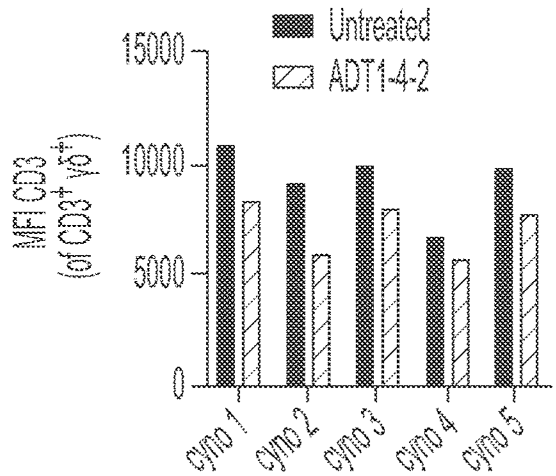
Figure 38F:
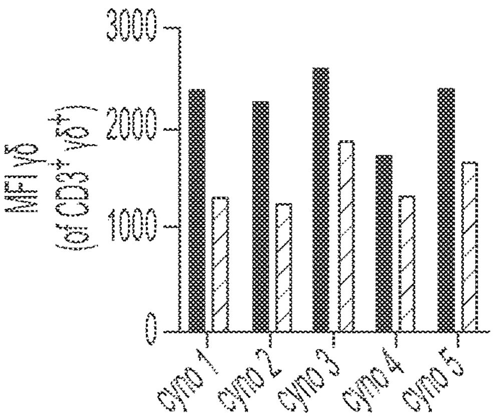
Figure 38G:
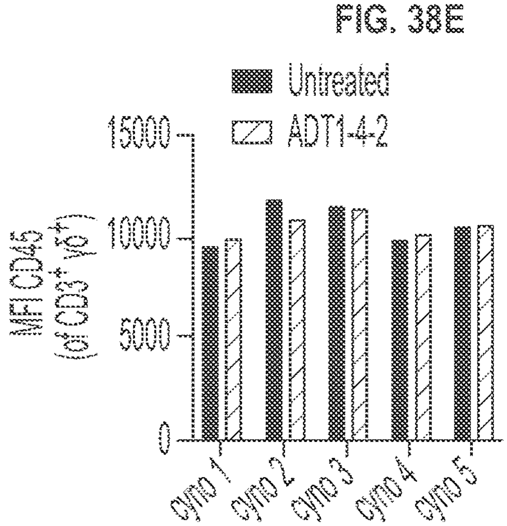
Figure 38H:
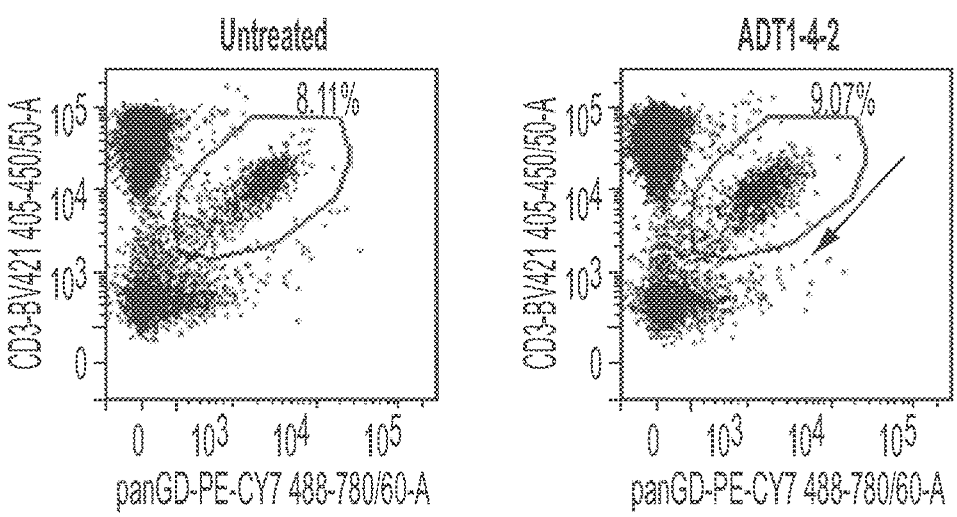

The results are shown in FIG. 37, which shows affinity matured Vδ1 mAbs induce activation only when in the presence of target cells. (A and B) Quantification of γδ TCR expression (black) and CD25 expression (grey) after 24 hours incubation of γδ cells with RSV (added at 67 nM) and ADT1-4-2 alone (upper) and with THP-1 cells (lower) at a 1:2 target-to-effector ratio before staining of the Vδ1 TCR and CD25 with a-Vδ1 TCR-PE-Vio770 and a-CD25-VioBlue respectively. MFI of Vδ1 staining was acquired using flow cytometry and calculated from the TCR positive gate before calculating % MFI from the MFI of TCR positive, untreated and non-cocultured γδ cells. MFI of CD25 staining was acquired using flow cytometry and calculated from the 'NOT THP-1' gate before calculating % MFI from the CD25 MFI of untreated non-cocultured γδ cells. (C and D) Quantification of γδ TCR expression (black) and CD25 expression (grey) after 2 hours incubation of γδ cells with RSV (added at 67 nM) and ADT1-7-3 alone (upper) and with THP-1 cells (lower) at a 1:2 target-to-effector ratio before staining of the Vδ1 TCR and CD25 with a-Vδ1 TCR-PE-Vio770 and a-CD25-VioBlue respectively. MFI of Vδ1 staining was acquired using flow cytometry and calculated from the TCR positive gate before calculating % MFI from the MFI of TCR positive, untreated and non-cocultured γδ cells. MFI of CD25 staining was acquired using flow cytometry and calculated from the 'NOT THP-1' gate before calculating % MFI from the CD25 MFI of untreated non-cocultured γδ cells. (E) Table representing the percentage increase in γδ CD25 expression from cocultured cells treated with the highest concentration of Vol mAb compared to untreated non-cocultured γδ cells. (F) Table representing the percentage increase in γδ CD25 expression from cocultured cells treated with the highest concentration of Vδ1 mAb compared to untreated, co- and non-cocultured γδ cells.

Cyno TCR Downregulation

Studies were undertaken to explore the capability of ADT1-4-2 to bind to cynomolgus vδ1 gamma delta T cells and to induce its TCR down-regulation. For these studies, cynomolgus monkeys PBMCs were collected from fresh blood and put into culture for 14 days to expand γδ-T cells. Alternatively, a8-T cells were depleted from the total PBMCs population using magnetic beads coated with an anti-0 antibody(Clone R73) before to be expanded in vitro. Expansion was as followed, 250,000 cells were added per well of a U-bottom 96-well plate in RPMI-1640 media containing 10% of FCS, antibiotics (P/S) and a cocktail of cytokines (IFNγ, IL21, IL4, IL1β and IL15). Seven days later, cells were spiked with 10 μl of fresh media containing 10% of FCS, antibiotics (P/S) and the cytokines IL21 and IL15. It was followed by the replacement of 100 μl of media by fresh media containing 10% of FCS, antibiotics (P/S) and IL15 at day 11. At day 14, cells were collected and subjected to the TCR down-regulation assay. This assay consists of mixing the cells with various concentrations of antibodies for 2 hours. After the incubation time, cells were stained for flow cytometry analysis for the following markers: CD3, TCR-αδ, TCR-γδ and VD1. A live/death cell dye was also included to discriminate the live population of cells. Flow cytometry analysis was performed by gating on the CD3+, TCR-γδ+ and VD1+ cell population and VD1 mean florescence intensity was measured inside the VD1+ gate. Isotype control (anti-RSV) or no antibodies were use as negative control at the highest concentration only. Data were normalized to the control without any antibody. FIG. 38 (A) shows the comparison of ADT1-4-2 and ADT1-4 capability to engage and reduce the expression of VD1 on cynomolgus γδ-T cells. Results shows a dose response reduction of VD1 expression upon treatment with ADT1-4-2 (up to 76% at 33.3 nM) but not ADT1-4 antibody. In that particular assay, γδ-T cells were expanded from an a8-T cell depleted population. A 500 time fold range of concentration was used. FIG. 38 (B) shows the percentage of cell surface expression of VD1 upon treatment with ADT1-4-2. In this assay, expansion of γδ-T cells was from the all PBMCs population. A 10,000 fold range of concentration was used. Data shows a dose response reduction of VD1 cellular expression in 2 different donors (AD8170 and AM945BA) as an example. A total of 4 donors was tested and EC50 was extracted individually using GraphPad Prism nonlinear fit curve function. FIG. 38 (C) shows the individual EC50 value for the different donors combined with the mean and standard deviation. The mean is 3.83±2.23 nM. Antibodies:

CD3-AF700 (BD Bioscience, clone SP34-2, ref:557917)
TCR-αβ-AF647 (BioLegend, clone R73, ref: 201116)
TCR-γδ-BV421 (BioLegend, clone B1, ref: 331218
VD1-PE (eBioscience, clone TS8.2, ref: 12-5679-42)

Additional studies were carried out with whole blood samples from cynomolgus macaques (n=5) (see FIG. 38 (D-G)). These were stimulated for 20 hours with ADT1-4-2 (0.052 mg/ml—cyno donors 1-2, or 1 mg/ml—cyno donor 3-5). Untreated whole blood samples from each animal were used as a control. Live, single, CD45+ mononuclear cells were analysed by flow cytometry post stimulation. For the flow analysis in FIG. 38 D-G, the labelled analytical antibodies employed included: anti-CD3, BV421, SP34-2 BD Biosciences (cat no 562877), anti-CD45, Vδ00, D058-1283 BD Biosciences (561489), anti-panGD PE-Cy7 B1 BioLegend (cat no 331222). Results first show in (D) that absolute numbers of total live γδ+ cells remain unchanged following stimulation with ADT1-4-2 compared with untreated control. Despite the absolute numbers of γδ T cells remaining consistent, (E) then shows that compared with unstimulated controls, the surface expression of both CD3 (Ei) and pan γδ TCR (Eii) is downregulated on γδ T cells following stimulation with ADT1-4-2, measured via a reduction in median fluorescent intensity (MFI). Representative flow plots from cyno donor 1 are then shown in (F) wherein γδ T cells shift diagonally towards the bottom left of the plot as surface expression of CD3 and pan γδ is downregulated following stimulation with ADT1-4-2, whilst the overall % pan γδ+ remains similar in both conditions. Finally, and in contrast, (G) shows that surface expression of CD45, a molecule not involved in TCR signalling, is unchanged on γδ T cells following stimulation with ADT1-4-2. These are critical data exemplifying pharmacological activity of the cyno cross reactive, affinity matured, anti-Vδ1 antibodies as described herein on γδ T cells from cynomolgus macaques.

Enhanced Cytotoxicity of Affinity Matured Clones

Affinity maturation of both ADT1-4 and ADT1-7 Vδ1 clones significantly enhances the cytotoxic effect of Vol γδ T-cells in the in vitro THP-1 killing assay THP-1 Cell Killing Assay Vδ1 mAbs and anti-RSV IgG control were diluted to 1 μg/ml in PBS and serially diluted 1:10 in PBS before adding to 384-well ultra imaging assay plates (Perkin Elmer). THP-1 cells (ATCC) cultured in RPMI, 10% FCS (Invitrogen) were stained with [0.5 μM] CellTrace CFSE live cell dye for 20 minutes. Expanded skin derived Vδ1 γδ T-cells were detached from tissue culture flasks and re-suspended in basal growth media before mixing 1:1 with THP-1 cells in suspension. Cell suspensions were seeding into 384-well assay plates to give a final cell seeding density of 1,000 THP-1 cells per well and 2,000 Vδ1 γδ T-cells per well. mAbs were diluted in the final assay volumes to concentrations ranging from 200 ng/ml to 0.2 μg/ml. THP-1 and Vol γδ T-cells were cultured in the presence of Vδ1 mAbs at 37° C., 5% CO2 for 24 hours. To determine the numbers of live THP-1 cells after 24 hours, confocal images were acquired using an Opera Phenix high content platform capturing nine fields of view at 10× magnification. Live cell counts were quantified base on size, morphology, texture and intensity of live cell stains.

Figure 39B:
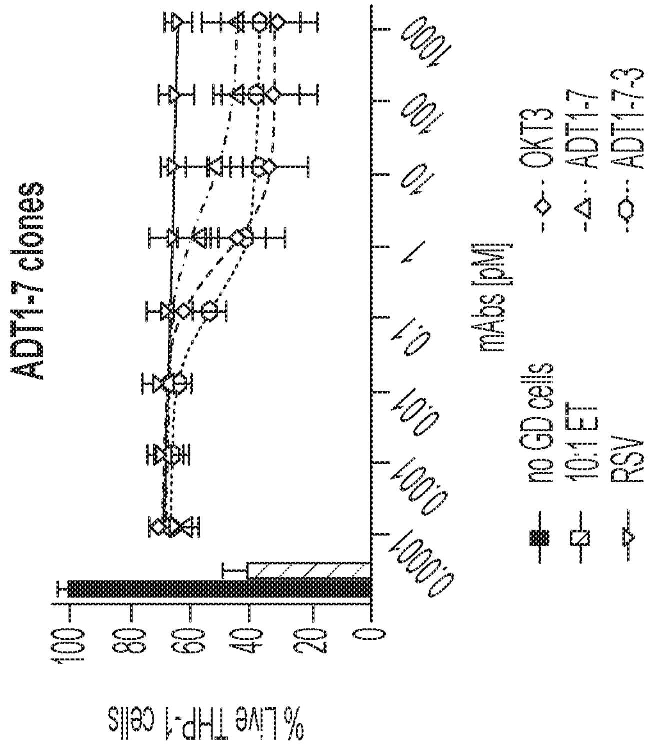
Figure 39A:
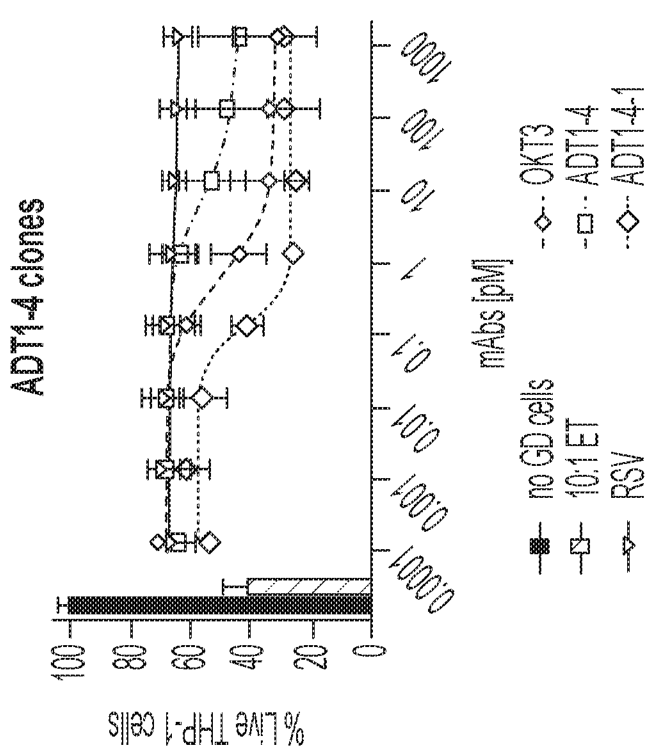
Figure 39C:
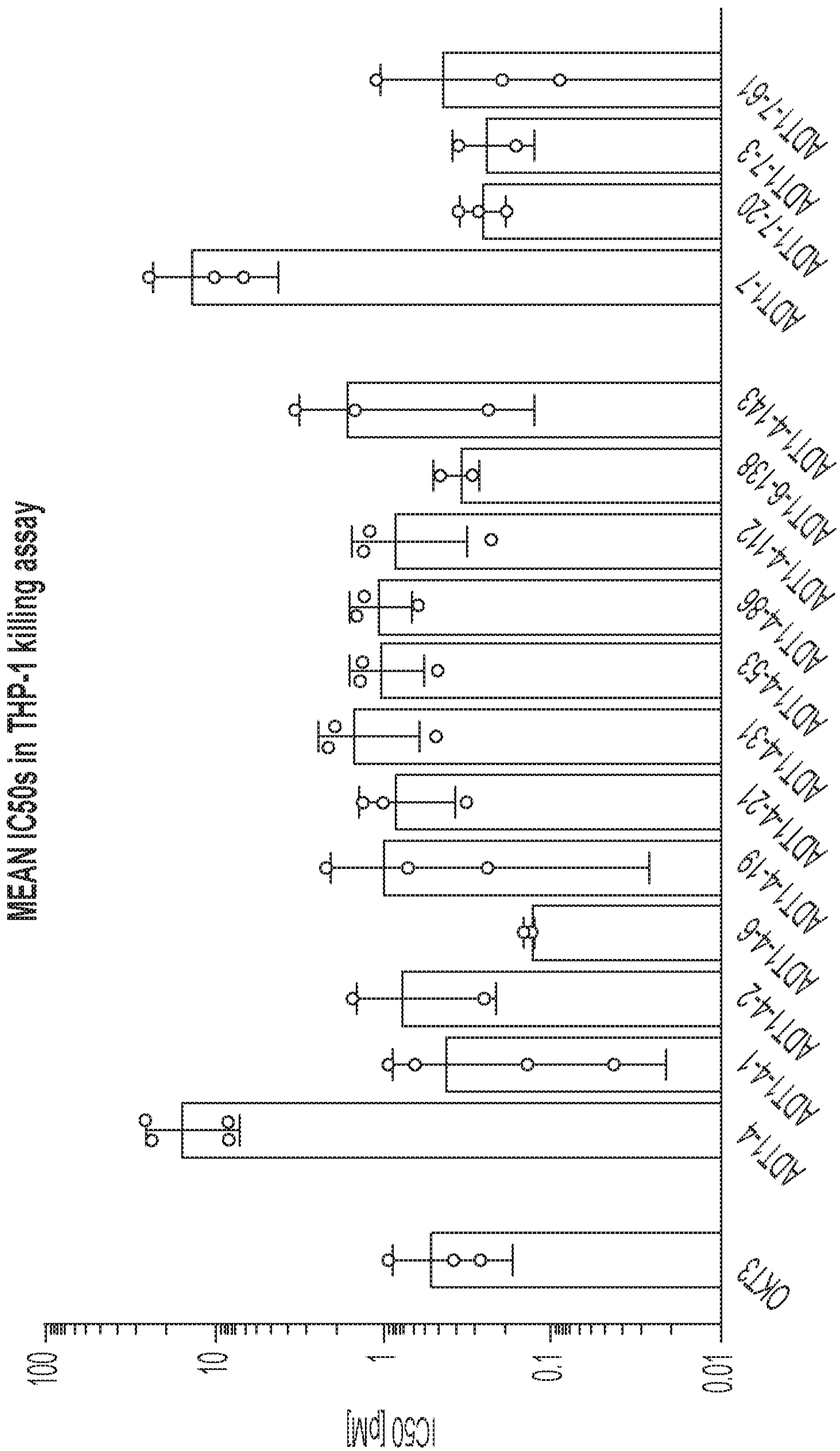

FIG. 39 shows the affinity matured Vδ1 mAbs exhibit enhanced potency in a THP-1 high content cytotoxicity assay compared to parental clones. (A&B) Quantification of live THP-1 cell numbers after 24 hours co-culture with γδ T-cells in the presence of Vδ1 mAbs or controls [Effector: Target ratio 2:1]. Cell numbers were normalized as a percentage of the no γδ T-cell control (100%). OKT3 (anti-CD3 antibody) and an anti-RSV isotype control were included as assay controls. Cell numbers were calculated using high content confocal microscopy on live cells. Graphs are representative of parental ADT1-4 (A) and ADT1-7 (B) clones. (C) Bar chart representing the average EC50s from OKT3 control, and the ADT1-4 and ADT1-7 clones. Data is represented as Mean±standard deviation of n=3 biological replicates. (D) Table summarizing the EC50s plotted in (C). Data is represented as Mean, Standard deviation, fold change and percentage improvement compared to ADT1-4 and ADT1-7 parental clones.

Vδ1 Monoclonal Antibodies on Antibody-Dependent Cellular Cytotoxicity (ADCC)

Expanded skin-derived Vδ1 γδ T-cells from three donors were detached from tissue culture flasks and re-suspended in basal growth media and seeded at a final density of 20,000 cells per well in white 96-well plates. Raji cells were similarly seeded at 20,000 per well, to be used as a positive control for ADCC induced by the CD20-targeted antibody Rituximab. mAbs were diluted and added to each well in final concentrations ranging from 1 to 100 nM. FcγRIIIa+ ADD Bioassay effector cells were thawed, and 62,500 cells were added to each well followed by incubation at 37° C., 5% CO2 for 4.5 hours. Luciferin-containing Bio-Glo reagent was added to each well, followed by a further 10-minute incubation, and luminescence measured using a plate reader.

Figure 40A:
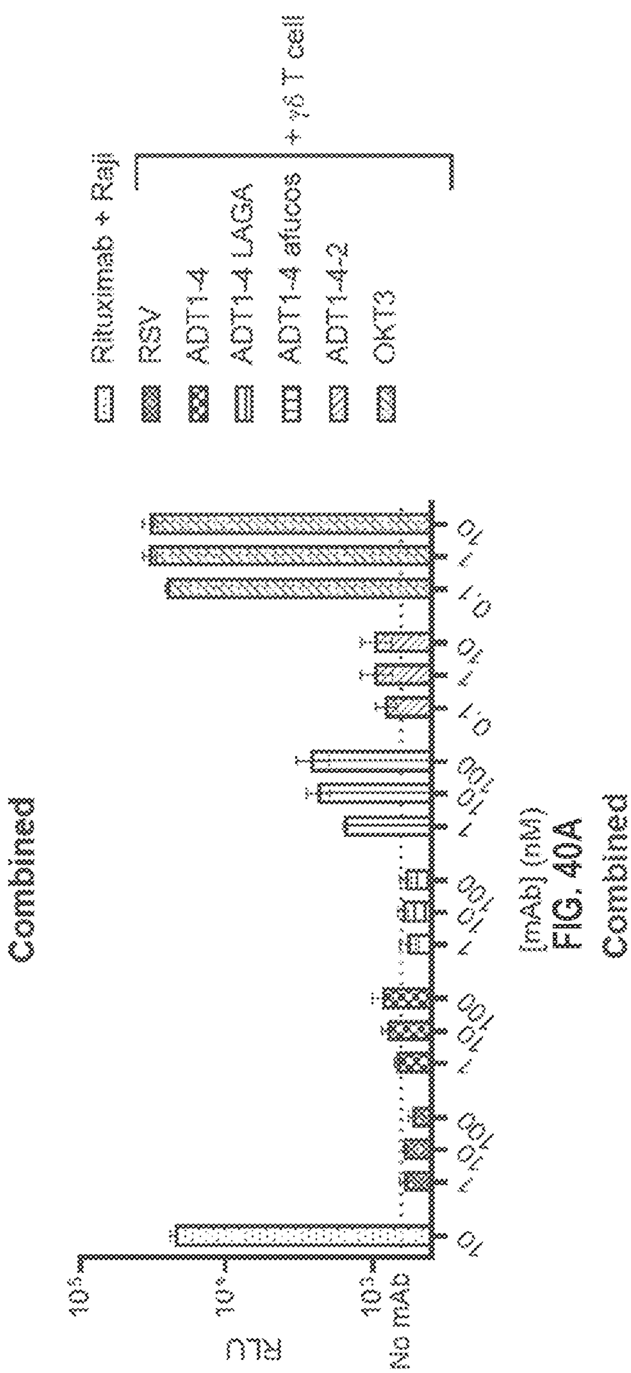
FIGS. 40A-40B. Vδ1 monoclonal antibodies on antibody-dependent cellular cytotoxicity (ADCC).
Figure 40B:
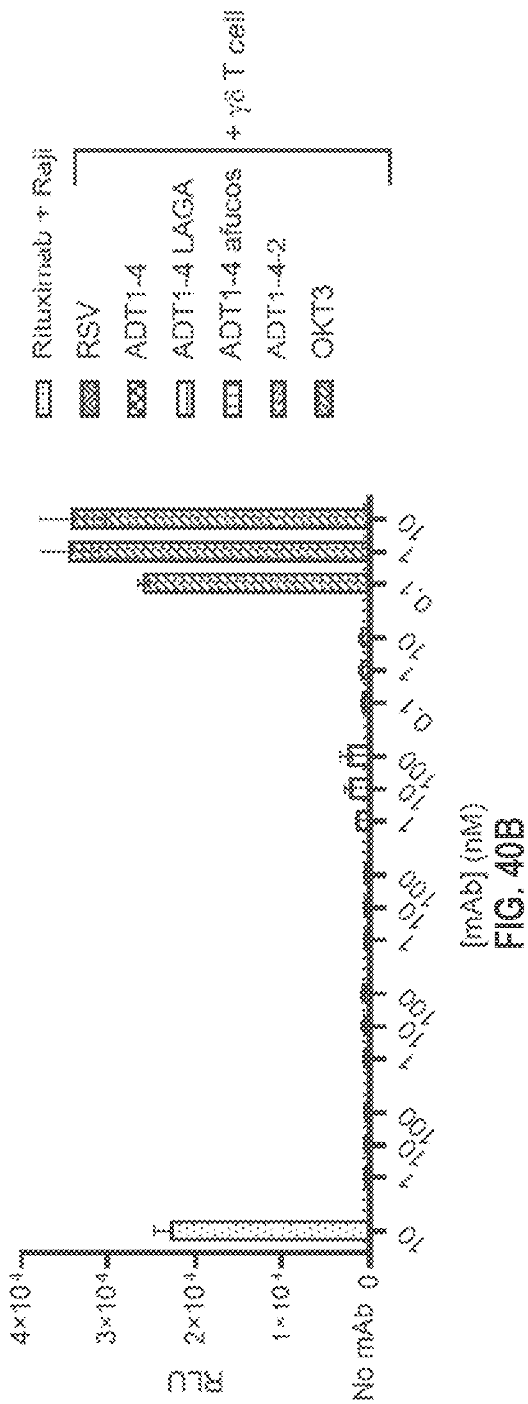

FIG. 40 shows the Vδ1-targeted mAbs induce negligible antibody-dependent cellular cytotoxicity (ADCC). ADCC, as measured using a surrogate reporter assay in which downstream NFAT signalling is measured by induction of luciferase activity within FcγRIIIa+ effector cells. The effector cells were co-cultured with three γδ T-cell donors (Effector:Target ratio 3) and varying concentrations of monoclonal antibody. $CD20^+$ Raji cells and Rituximab were included as a positive control. Bioluminescence was measured after 4.5 hours of co-culture. Data is represented as mean±SD of three biological replicates (three γδ T-cell donors).

Conclusions: This data demonstrates that ADT1-4 parent and the affinity matured derivative ADT1-4-2 does not induce ADCC, demonstrated via a FcγRIIIa+ effector reporter cell line in which NFAT signalling induces luciferase activity. OKT3, however, appears to induce high levels of ADCC-specific signalling.

Vδ1 Monoclonal Antibodies on Complement-Dependent Cytotoxicity (CDC)

Expanded skin-derived Vδ1 γδ T-cells were detached from tissue culture flasks and re-suspended in basal growth media and seeded at a final density of 75,000 cells per well in white 96-well plates. Raji cells were similarly seeded at 75,000 per well, to be used as a positive control for CDC induced by the CD20-targeted antibody Rituximab. mAbs were diluted and added to each well in final concentrations ranging from 1 to 100 nM. Human serum, either fresh or heat-inactivated, was added to a final concentration of 40%. Heat-inactivation was performed by warming the serum in a water-bath at 56C for 30 minutes, followed by cooling on ice. The cultures were then incubated at 37° C., 5% CO2 for 24 hours. To determine the numbers of live cells after 24 hours, the cells were harvested and stained with xx viability dye at a 1:1000 dilution for 20 minutes. Fluorescence was measured using the MACSQuant and live cell counts were quantified based on negative staining for the viability dye.

Figure 41:
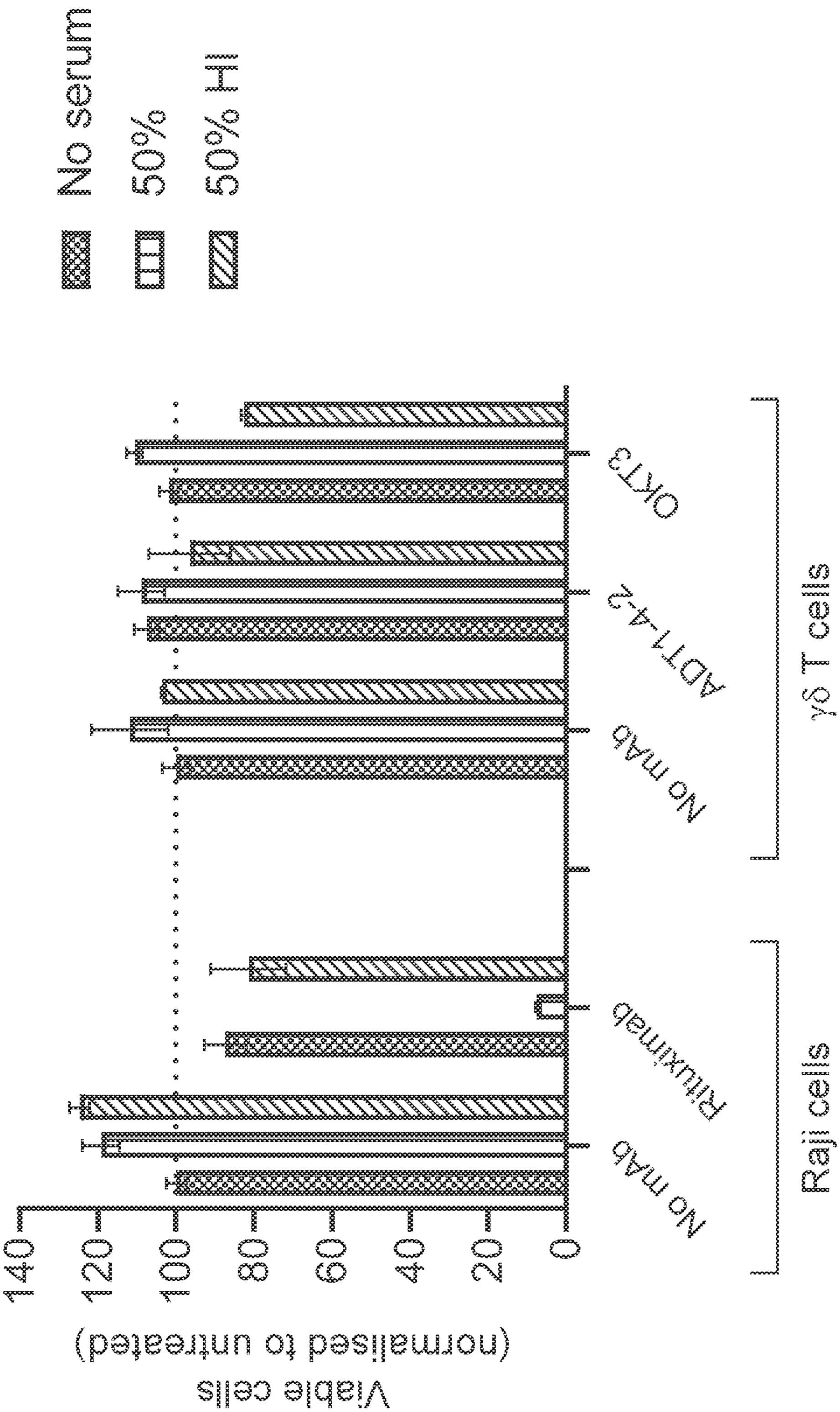
FIG. 41. Vδ1 monoclonal antibodies on complement-dependent cytotoxicity (CDC).

The results are shown in FIG. 41, which demonstrates Vδ1-targeted mAbs do not induce complement-dependent cytotoxicity (CDC). The number of viable γδ T cells following culture with 40% human serum and 50 nM anti-CD3 OKT3 or anti-Vδ1 ADT1-4-2. and varying concentrations of monoclonal antibody. Serum was used fresh or underwent prior heat-inactivation. $CD20^+$ Raji cells and Rituximab were included as a positive control. Viability was measured after 24 hours of co-culture via viability dye. Data is represented as mean±SD of three biological replicates.

Conclusions: This data demonstrates that ADT1-4-2 does not induce complement-dependent cytotoxicity (CDC), with no increase in cytotoxicity of Vδ1-positive cells in the presence of complement-containing serum. Rituximab, however, shows strong CDC stimulation against CD20-positive Raji cells.

Healthy Cell Sparing

Studies were undertaken to explore the effect of stimulating/activating vδ1 cells with anti-vδ1 antibody with respect to cytotoxicity towards healthy cells. This was tested by incubating the anti-vδ1 clone ADT1-4-2 with PBMC and then assessing monocyte cytotoxicity and apoptosis.

Cryopreserved human peripheral blood mononuclear cells (PBMC) were commercially sourced from 3 healthy donors. PBMC were seeded into round bottom 96-well tissue culture plates at 250,000 cells/well in 250 ul of complete media (RPMI supplemented with 10% FCS, pen/strep, non-essential amino acids, sodium pyruvate and HEPES) with 10 ng/ml IL15. A titration vδ1 antibody ADT1-4-2 was added to a final concentration of 6.6 nM. RSV IgG, IgG2a and OKT3 antibodies were included as controls. Stimulations were performed for 20 hours. Flow cytometry analysis was performed at the end-point to determine the monocyte phenotype in each condition and apoptotic monocytes. on vδ1 cells. Cells were gated firstly on live singlets, followed by CD14 (Miltenyi 130-110-523) to identify monocytes.

Apoptotic monocytes were then identified through positive ApoTracker Green staining (Biolegend 427402).

Figure 42:
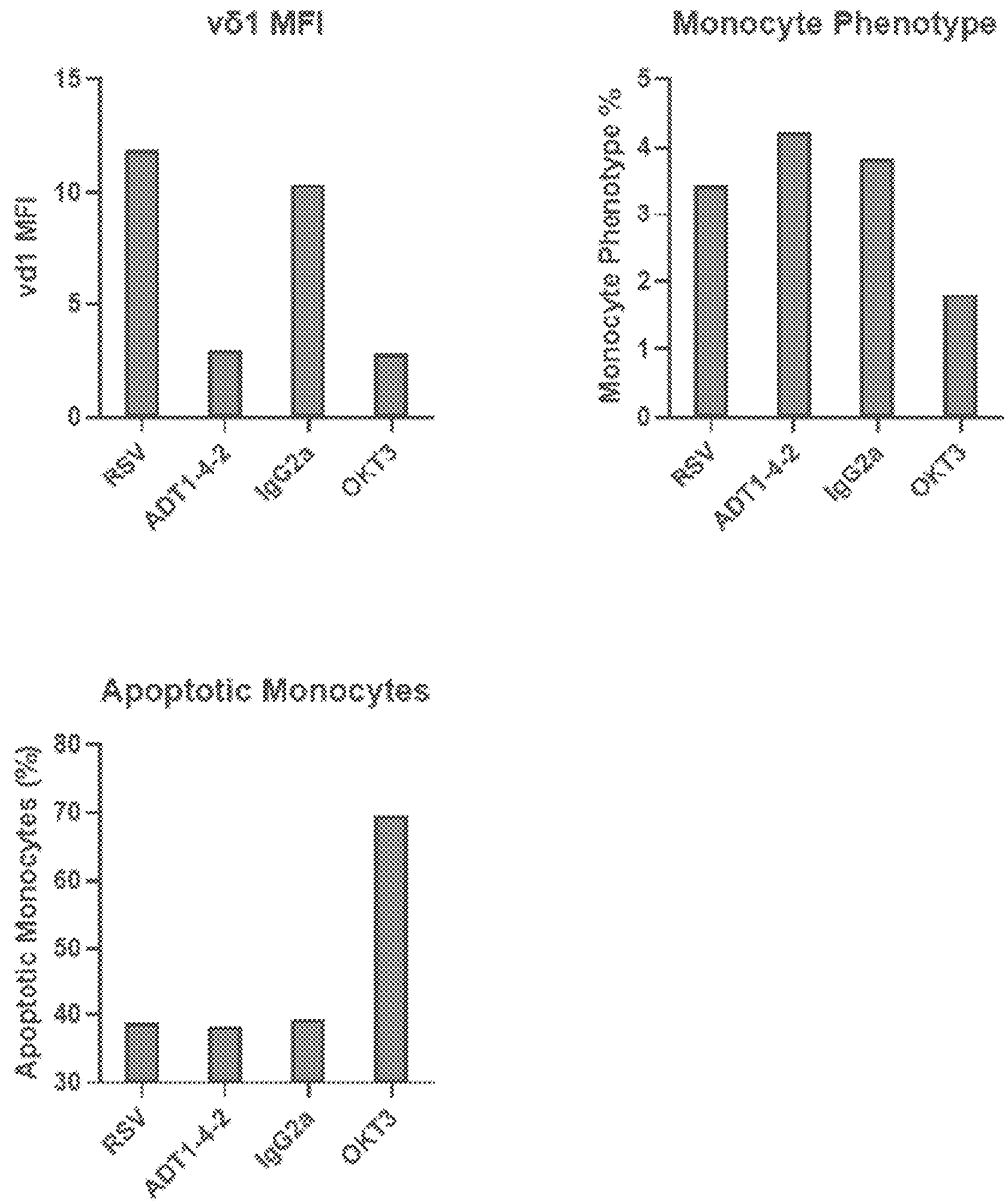
FIG. 42. Healthy cell sparing of clone ADT1-4-2.
Figures 43A, 43B, 43C, 43D:
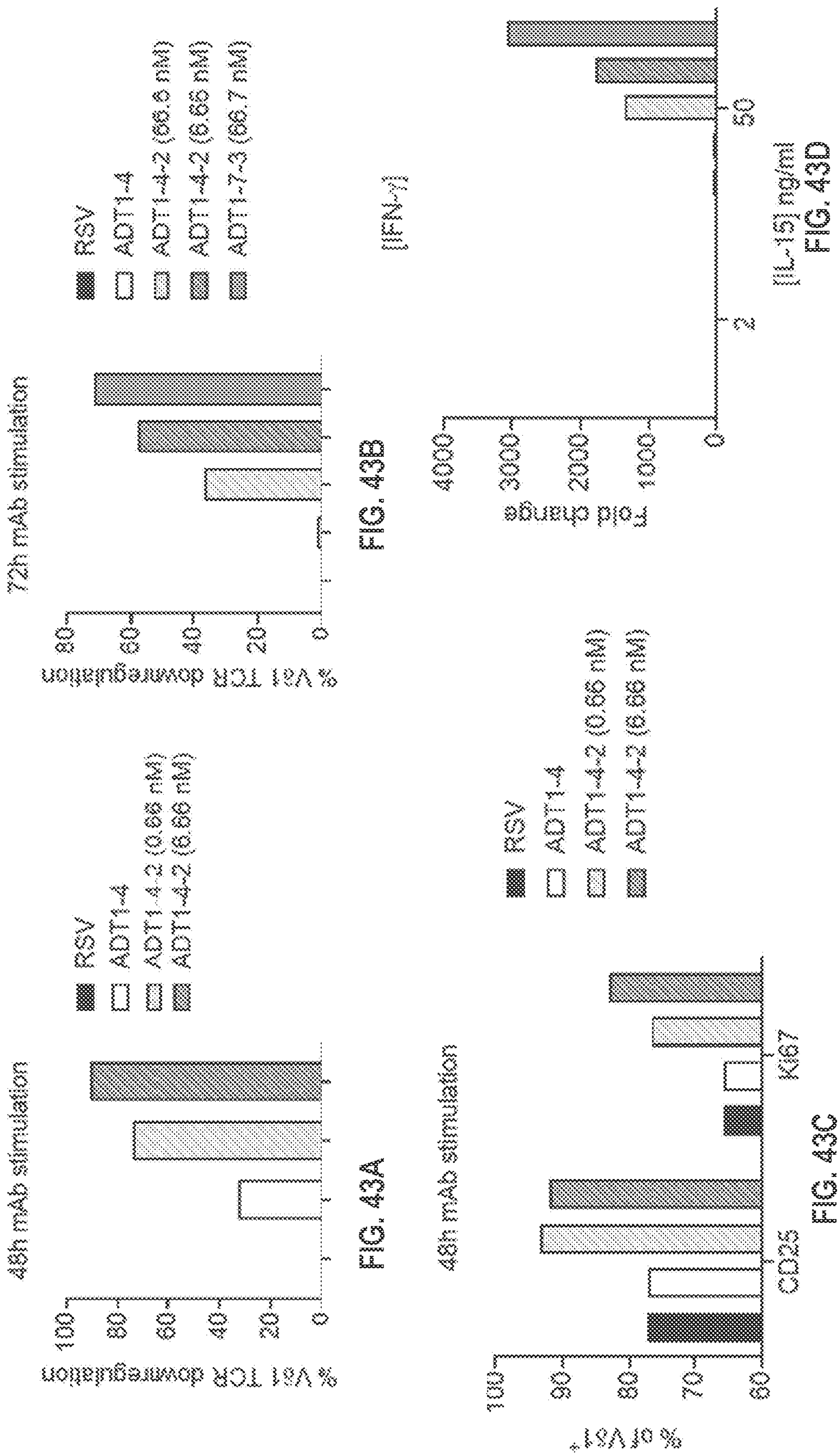
FIGS. 43A-43J. Effect of anti-Vδ1 antibodies on TIL populations from primary tumour biopsies.
Figure 43E:
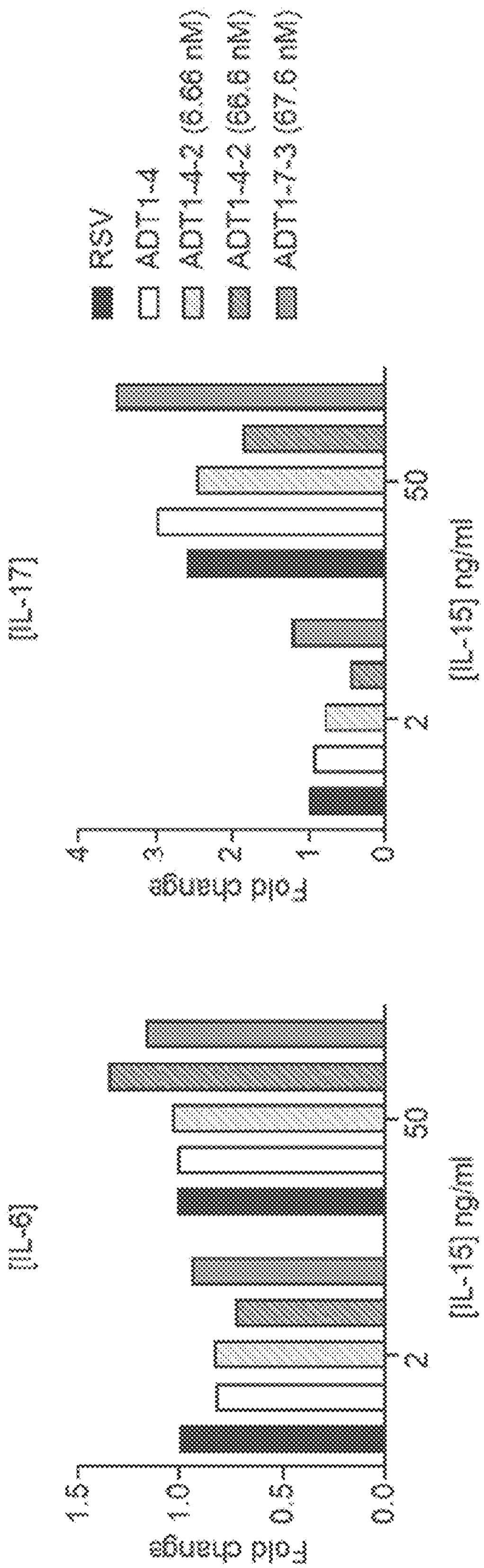
Figure 43F:
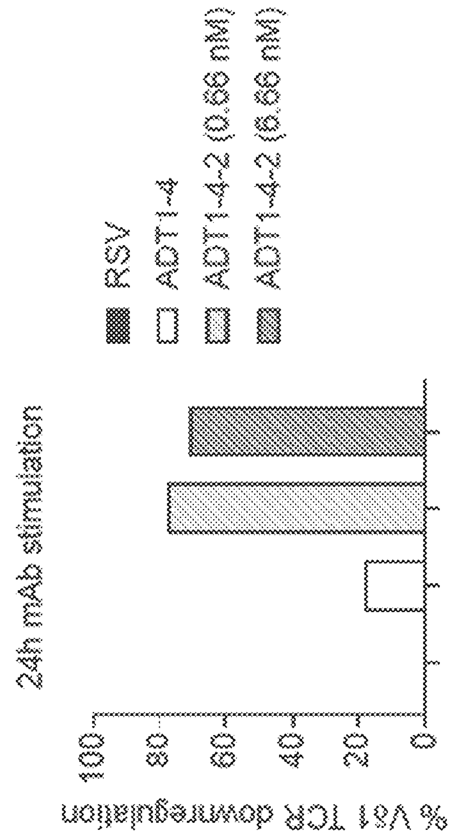
Figure 43G:
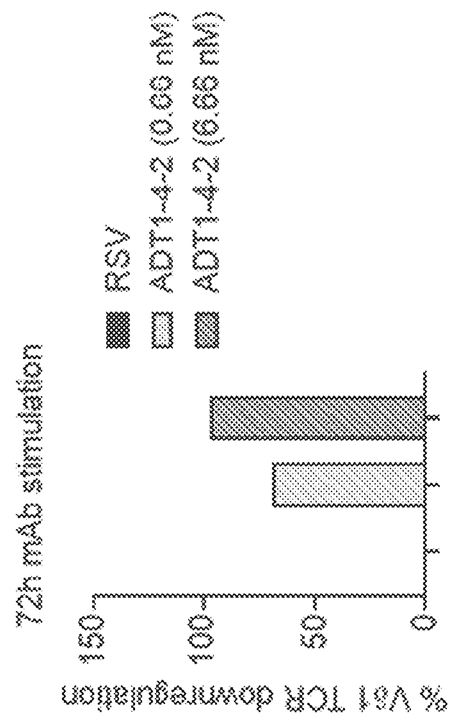
Figure 43H:
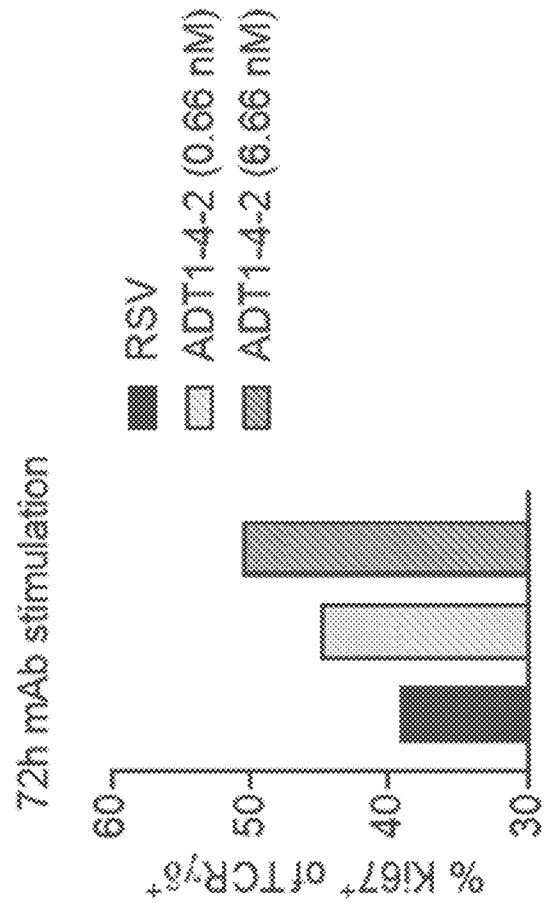
Figure 43J:
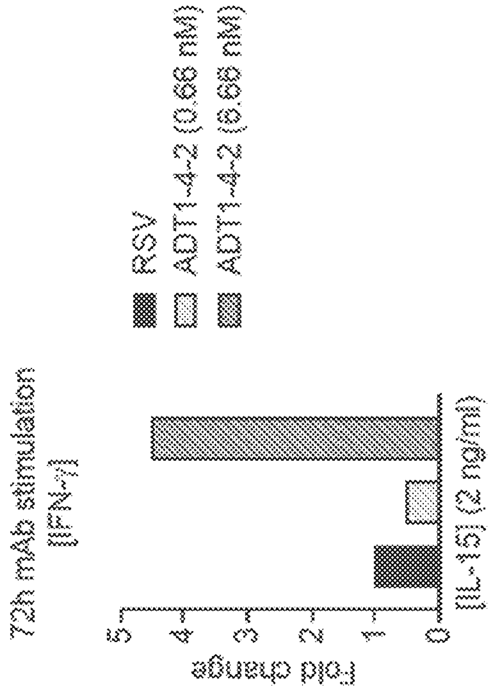
Figure 43I:
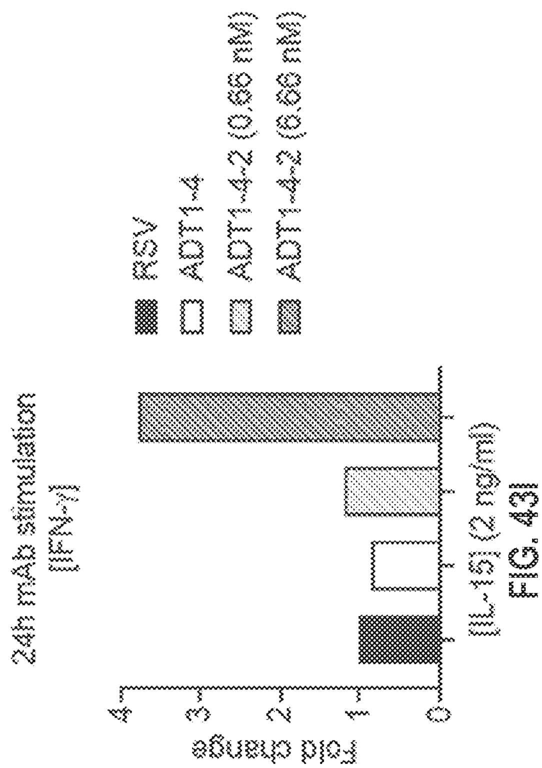
Figure 44A:
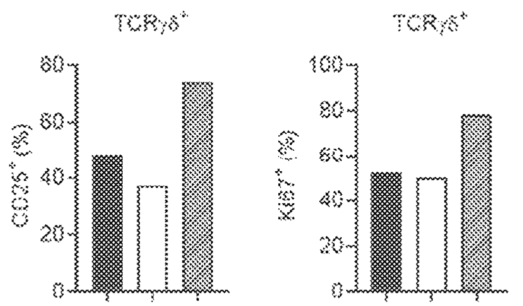
FIGS. 44A-44E. Effect of anti-Vδ1 antibodies on TIL populations from primary tumour biopsies.
Figure 44B:
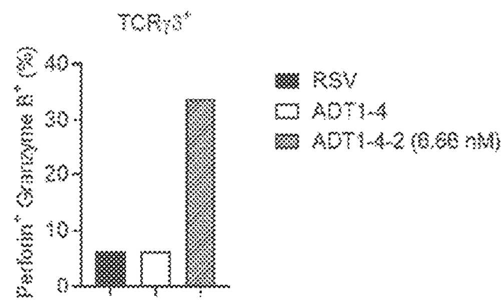
Figure 44C:
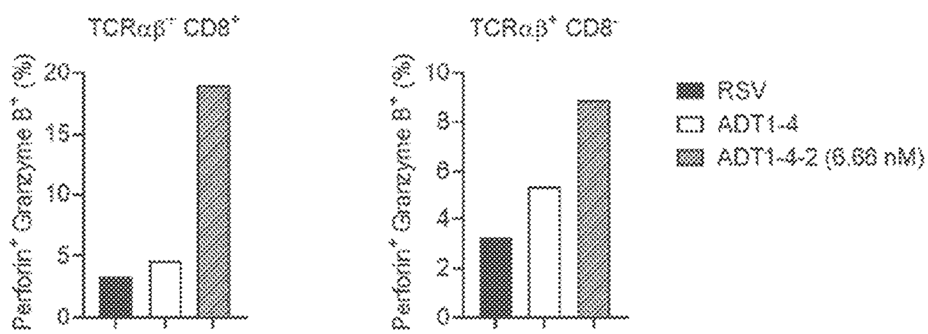
Figure 44D:
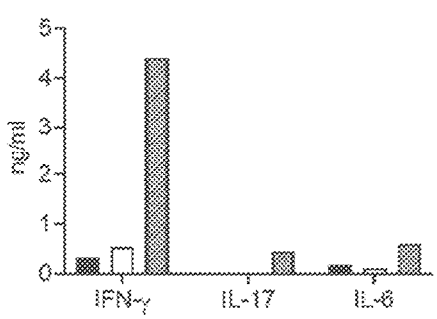
Figure 44E:
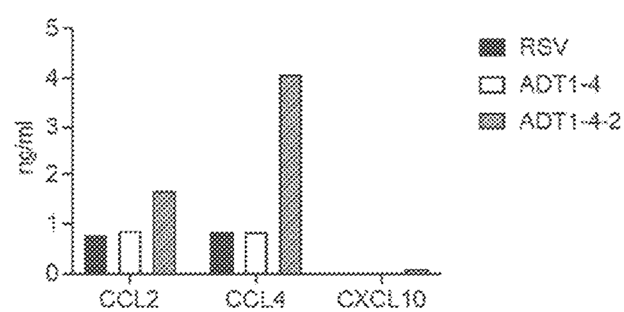

FIG. 42A (upper left panel) shows the vδ1 TCR staining MFI upon antibody stimulation as an indication of target engagement. FIG. 42B (upper right panel) and xixC (lower panel) shows the endpoint monocyte phenotype and apoptotic monocytes (respectively) following antibody stimulation. Stimulation with the vδ1 antibody clone ADT1-4-2 engaged Vδ1 cells but did not causes healthy monocyte cytotoxicity.

Example 25. Effect of Anti-vδ1 Antibody on Til Populations from Primary Tumour Biopsies Anti-Vδ1 Antibody Promoted Activation, Proliferation, and Cytotoxicity in Tumour-Infiltrating Lymphocytes.

Studies were undertaken to explore anti-Vδ1 antibody-conferred modulation of human tumour-infiltrating lymphocytes (TILs). For these studies, human renal cell carcinoma (RCC) tumour biopsies were shipped fresh and processed upon receipt. Biopsies were cut into pieces measuring −2 $mm^2$ and TILs were obtained using an adaptation of the method originally described by Kupper and Clarke (Clarke et al, 2006). Specifically, up to four 2 $mm^2$ biopsies were placed on 9 mm×9 mm×1.5 mm Cellfoam matrices, and one matrix was placed per well on a 24-well plate. Biopsies were then cultured in 2 ml Iscove's Modified Dulbecco's Medium (IMDM) supplemented with 4% human plasma, β-mercaptoethanol (50 μM), penicillin (100 U/ml), streptomycin (100 μg/ml), amphotericin B (2.5 μg/ml), HEPES (10 mM), Na Pyruvate (1 mM), MEM Non-Essential Amino Acids Solution (1×) and IL-15 (2 ng/ml, Miltenyi Biotech). 1 ml of medium was aspirated every 3-4 days and replaced with 1 ml complete medium containing 2× concentrated IL-15. TILs were harvested 10 or 11 days later, passed through a 70 μM nylon cell strainer, centrifuged at 300×g for 5 minutes and resuspended in complete medium for counting. 400,000 cells were then plated per well in 96-well plates prior to stimulation with anti-Vδ1 antibodies. TILs were stimulated with ADT1-4, ADT1-4-2, ADT1-7-3, or RSV IgG1 isotype control antibodies in the presence of IL-15 at a concentration of 2 or 50 ng/ml.

FIG. 43 (A and B) show the % decrease in Vδ1 TCR expression on total tumour infiltrating-γδ T cells following 48 (A) or 72 (B) hours mAb stimulation in two separate donors, confirming target engagement in each case. Tumour-infiltrating Vδ1+ cells were analysed for expression of CD25 and Ki67. FIG. 43 (C) shows enhanced expression of both CD25 and Ki67 on Vδ1+ T cells following 48 hour stimulation with ADT1-4-2 compared with stimulation with IgG1 isotype control or ADT1-4. Supernatants from cultures of mAb-stimulated TILs were analysed for cytokine production by MSD. FIG. 43 (D) shows substantial fold increases in IFN-γ production by TILs stimulated with ADT1-4-2 or ADT1-7-3 for 72 hours in the presence of 50 ng/ml IL-15. FIG. 43 (E) shows that stimulation of TILs with ADT-1-4-2 or ADT1-7-3 did not enhance secretion of type 17-associated cytokines IL-6 or IL-17 at this timepoint.

Alternatively, biopsies from different donors were digested enzymatically upon receipt to obtain a single cell suspension. Specifically, up to 1 g of tissue was placed into a Miltenyi C tube along with 4.7 ml RPMI supplemented with enzymes from Miltenyi's Tumour Dissociation Kit at concentrations recommended by the manufacturer aside from Enzyme R which was used at 0.2× concentration to prevent cleavage of pertinent cell surface molecules. C-Tubes were placed on the gentleMACS™ Octo Dissociator with heating blocks attached. Program 37C_h_TDK_1 for the dissociation of small tumours was selected. After 1 hour the digest was filtered through a 70 μM filter and complete IMDM containing 4% human plasma was added to quench enzymatic activity. Cells were then washed twice and resuspended in complete IMDM for counting. Depending on cell numbers, $2\times10^6$ or $4\times10^6$ cells were plated per well in 48-well plates and were stimulated with ADT1-4, ADT1-4-2, or RSV IgG1 isotype control antibodies in the presence of IL-15 at a concentration of 2 ng/ml. TILs isolated by enzymatic digestion were analysed by flow cytometry 24-72 hours post mAb stimulation. FIG. 43 (F and G) show the % decrease in Vδ1 TCR expression on total tumour infiltrating-γδ T cells following mAb stimulation at 24 (F) or 72 (G) hours in two individual donors, confirming target engagement in TILs isolated by enzymatic digestion. FIG. 43 (H) shows dose-dependent enhanced expression of Ki67 on γδ T cells following 72 hours stimulation with ADT1-4-2. Supernatants from cultures of mAb-stimulated TILs were analysed for cytokine production by MSD. FIG. 43 (I and J) show the fold increase in IFN-γ produced by TILs isolated from two individual donors by enzymatic digestion and stimulated with ADT1-4-2 at a concentration of 6.66 nM in the presence of 2 ng/ml IL-15 at two time points, 24 hours (I) and 72 hours (J). In summary, these combined results highlight the ability of affinity matured anti-Vδ1 antibody to drive activation, proliferation and anti-tumourigenic cytokine production by tumour-infiltrating γδ T cells within 72 hours of stimulation.

In another experiment, lung tumour-derived TILs were isolated on grid matrices and stimulated with ADT1-4, ADT1-4-2 or IgG1 isotype control for 10 days in the presence of 2 ng/ml IL-15. FIG. 44 (A) shows enhanced expression of CD25 and Ki67 in γδ T cells stimulated for 10 days with ADT1-4-2. FIG. 44 (B) shows a substantial increase in $Perforin^+$ Granzyme B+γδ T cells following 10 days stimulation with ADT1-4-2. Stimulation with mAbs over a longer time period allowed for the analysis of immune licensing of a6 T cells via anti-Vδ1 antibody-stimulated Vδ1+ T cells. FIG. 44 (C) shows considerably enhanced expression of Granzyme B and Perforin by both CD8+ and $CD8^-$αβ T cells following 10 days stimulation of tumour-infiltrating Vδ1+ T cells with ADT1-4-2. Supernatants from TILs cultured for 10 days with mAbs were analysed by MSD. FIG. 44 (D) shows markedly increased production of IFN-γ, and moderately increased production of IL-17 and IL-6 by lung tumour-derived TILs following stimulation with ADT1-4-2. FIG. 44 (E) demonstrates enhanced production of the chemokines CCL2, CCL4 and CXCL10 by TILs following 10 days stimulation with ADT1-4-2. In summary, these results highlight the ability of anti-Vδ1 antibody to drive activation and cytotoxicity in tumour-infiltrating γδ T cells, which can then promote cytotoxicity in tumour-infiltrating αβ T cells.

Example 26. Vδ1-CD19 Bispecific Antibody Binding Affinity to Human and Cyno Vδ1

Figure 49:
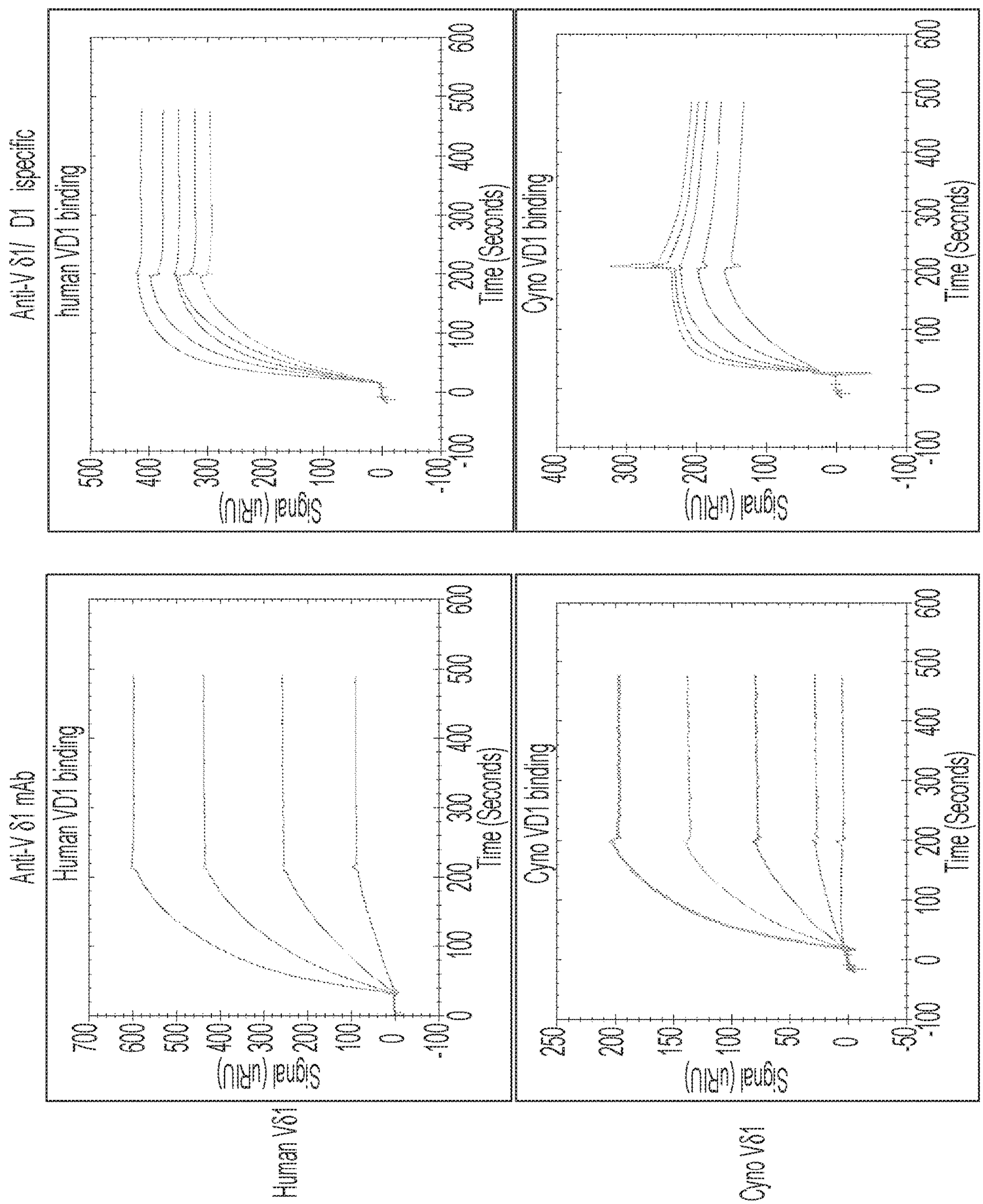
FIG. 49: Anti-Vδ1/CD19 bispecific antibodies exhibit high affinity binding to human Vδ1 and cyno Vδ1, comparable to the parental monoclonal Vδ1 mAb. Surface Plasmon Resonance (SPR) analysis was performed with ADT1-4-2/CD19 bispecific to assess binding to human Vδ1 and CD19 antigen. The bispecific antibody binds both human and cyno Vδ1, with only a small reduction in affinity for both antigens.

The binding affinity of the antibodies to target (i.e. the Vδ1 chain of a γδ TCR, both human and cyno antigens) is established by SPR analysis using a Reichert 4SPR instrument (Reichert Technologies). Antibody is coated onto a Planar Protein A Sensor Chip (Reichert Technologies) to give an increase on baseline of approximately 500 uRIU. Recombinant human Vδ1 heterodimer or cyno Vδ1 heterodimer was flown over the cell. All experiments were performed at room temperature. The results are shown in FIG. 49.

These data demonstrate the bispecific antibody binds both human and cyno Vδ1.

Figure 50A:
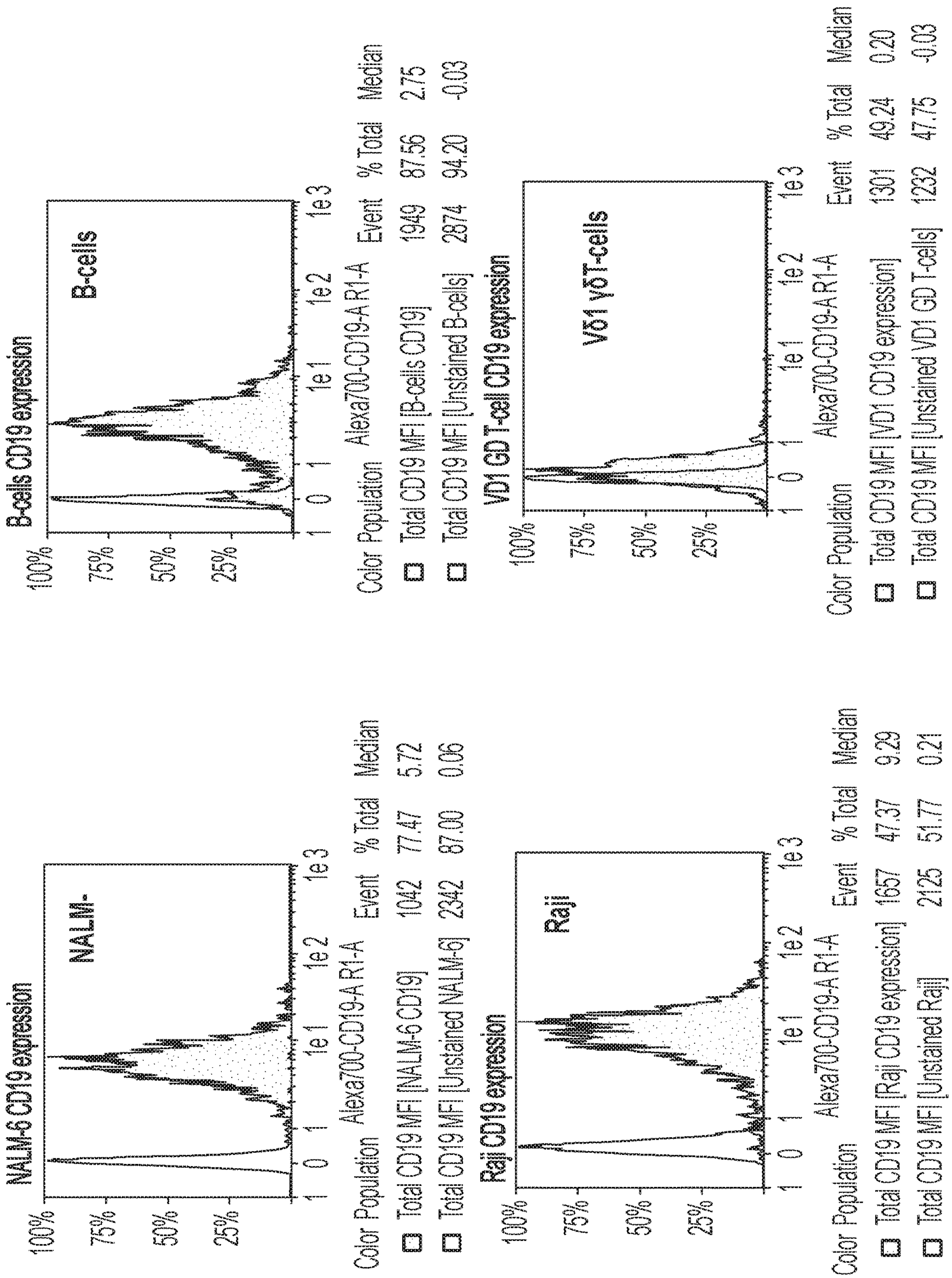
FIGS. 50A-50K: Vδ1-CD19 Bispecific T cell Engagers enhance $CD19^{+}$ target cell cytotoxicity and γδT-cell activation while sparing healthy $CD19^{+}$ B-cells.
Figure 50B:
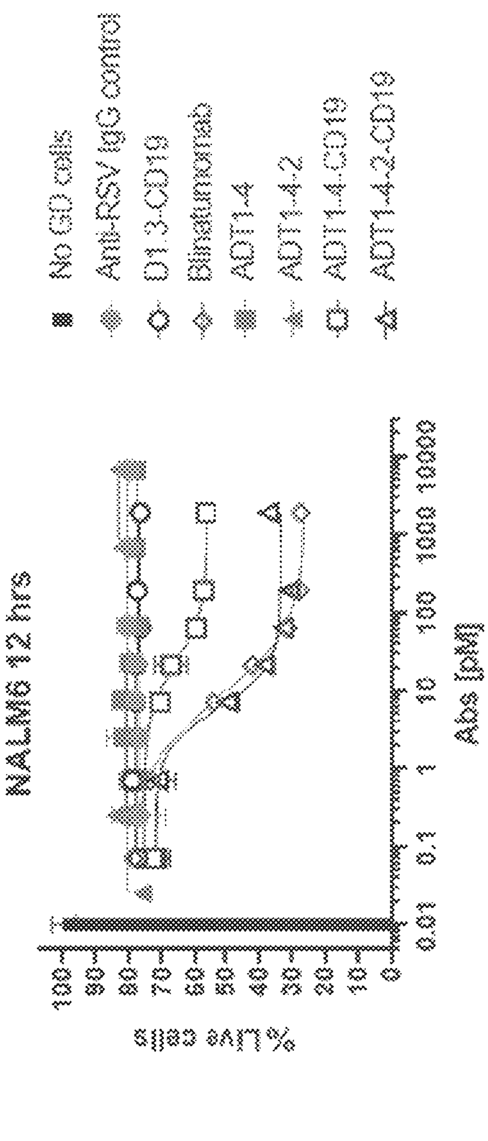
Figure 50C:
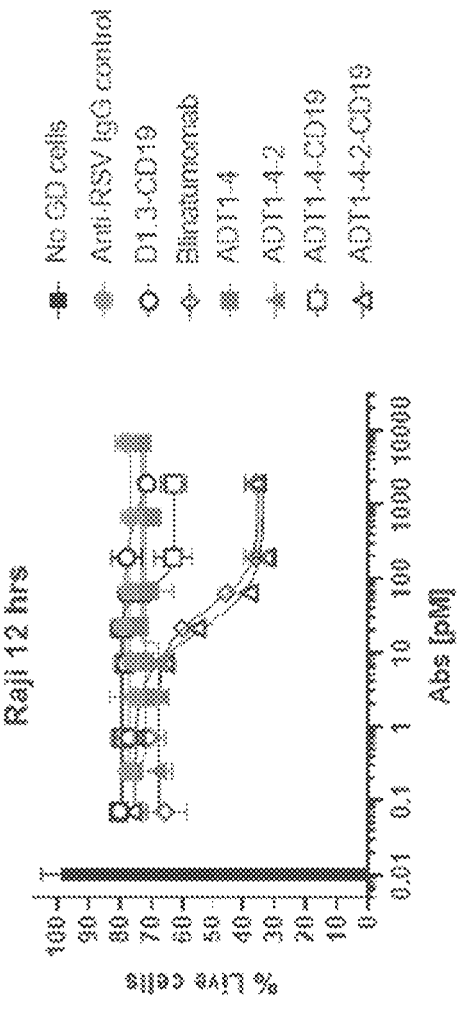
Figure 50D:
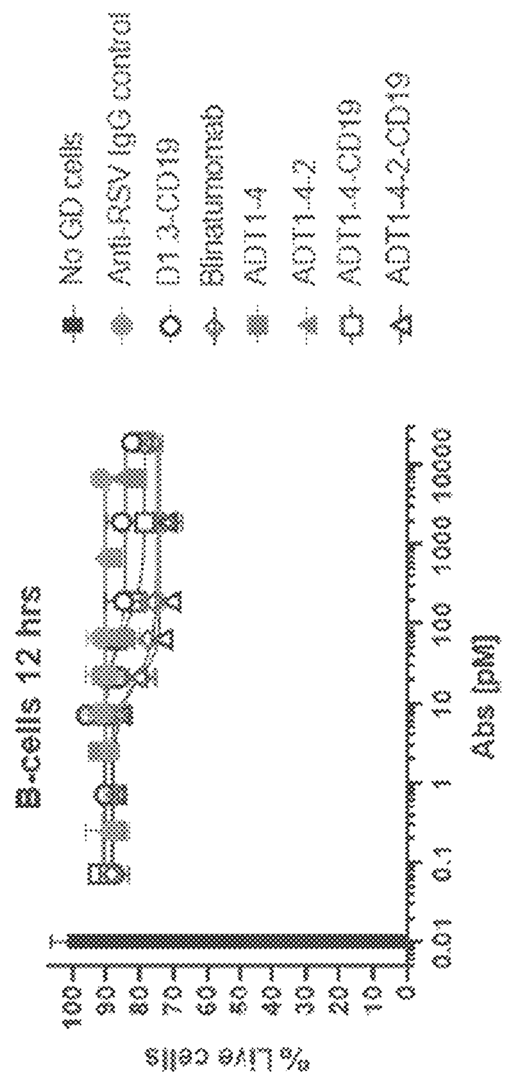
Figure 50E:
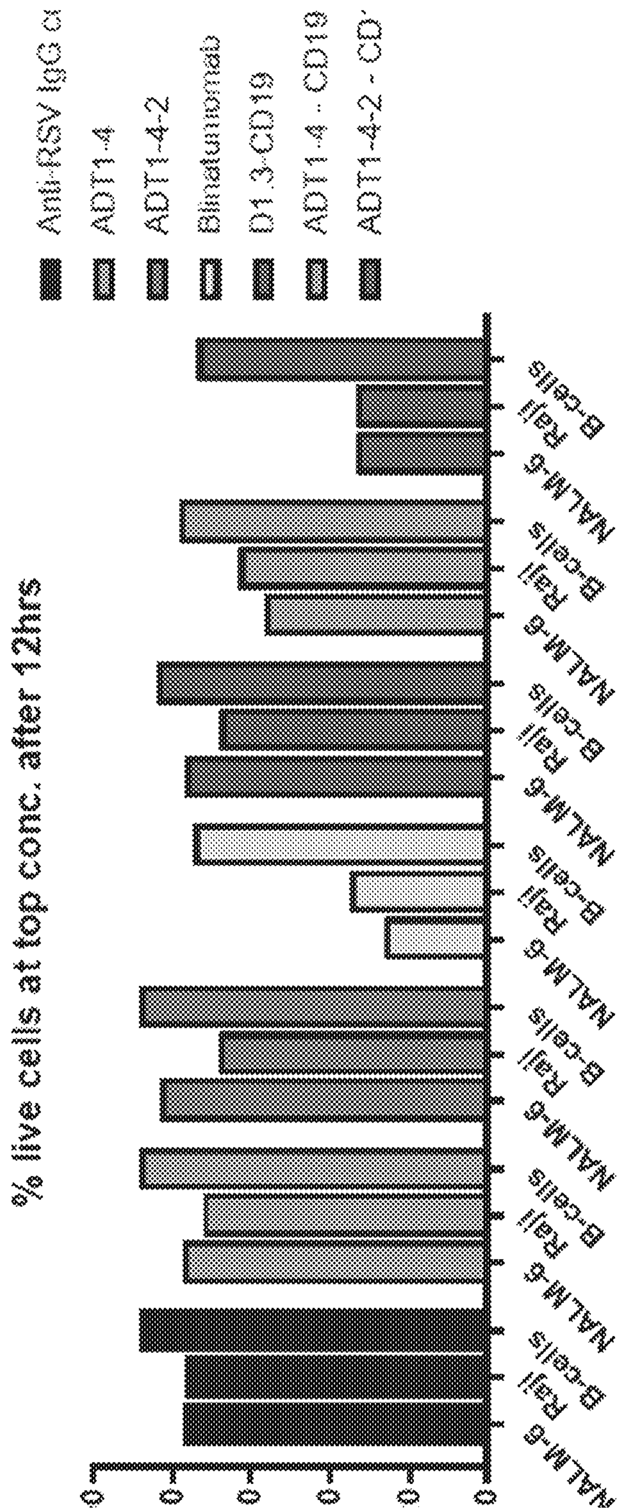
Figure 50F:
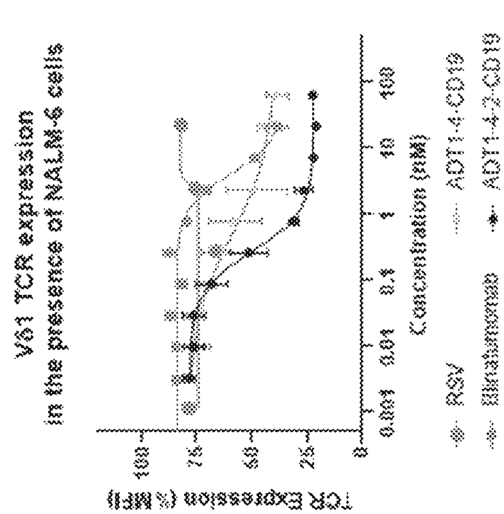
Figure 50G:
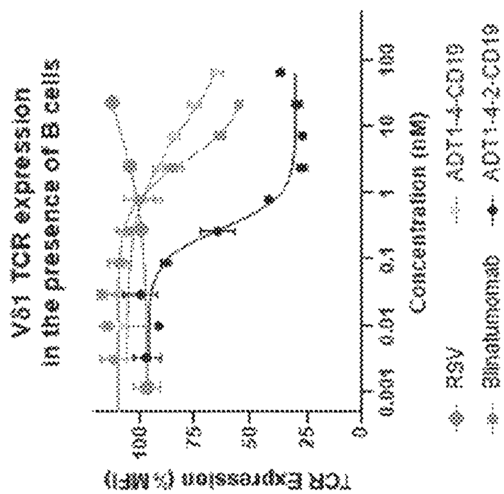
Figure 50H:
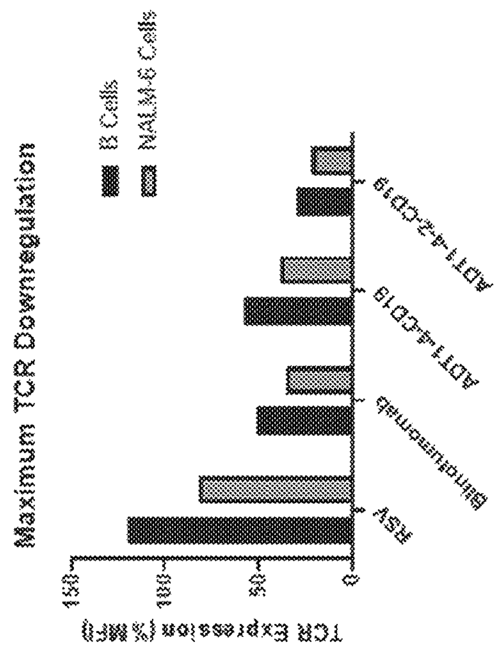
Figure 50I:
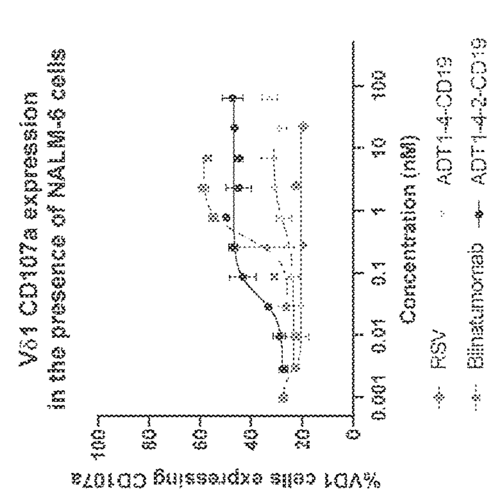
Figure 50J:
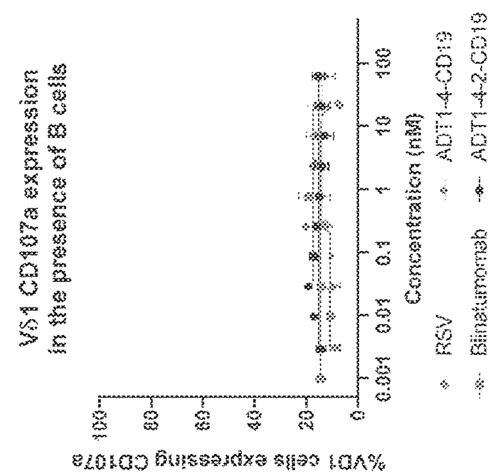
Figure 50K:
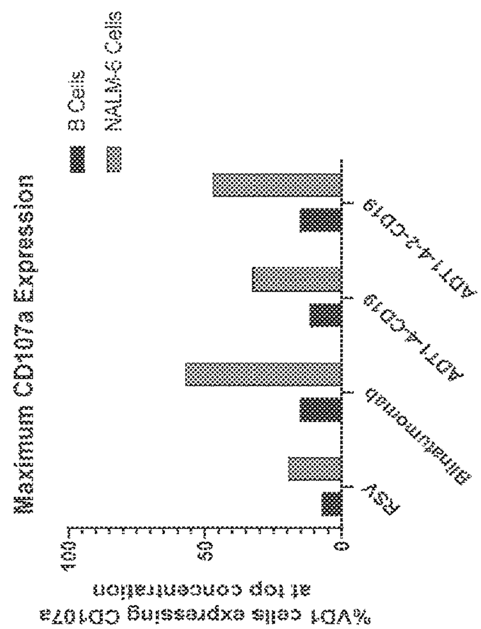

Example 27A. Vol-CD19 Bispecific Antibodies in Vδ1 γδT-Cells Activation and Cytotoxicity Assays Healthy B-cells were isolated from PBMCs (Lonza), using negative magnetic activated cell sorting (MACS; MiltenyiBiotec). Expression of CD19 on cancerous NALM-6 cells (ATCC), Raji cells (ATCC) and healthy isolated B-cells was determined. Briefly, 5×10ˆ4 cells were incubated with CD19 antibodies (Biolegend) for 15 minutes at 4° C. before washing and fixing. Expression of CD19 was determined by flow cytometry (MACSQuant10, MiltenyiBiotec). The results are shown in FIG. 50A.

The effect of CD19-Vδ1 bispecific antibodies on $CD19^+$ target cell cytotoxicity and CD19+ healthy cell sparing was determined using high content confocal imaging in the Opera Phenix (Perkin Elmer). NALM-6, Raji and B-cells were stained with [0.5 μM] CellTrace CFSE live cell dye for 20 minutes. Bispecific antibodies and controls were serially diluted into PBS before adding to 384-well imaging assay plates (Perkin Elmer). Expanded skin derived Vδ1 γδ T-cells were detached from tissue culture flasks and re-suspended in basal growth media before mixing 1:1 with either NALM-6, Raji or B-cells in suspension. Cell suspensions were seeding into 384-well assay plates to give a final cell seeding density of 2,000 NALM-6, Raji or B-cells per well and 2,000 Vδ1 γδ T-cells per well. Final assay antibody concentrations ranged between 6.6 nM to 66 μM. Cells were co-cultured for 24 hours before staining with DRAQ7 (1:300 final, Abcam). To determine the numbers of live target cells, confocal images were acquired using an Opera Phenix high content platform capturing nine fields of view at 10× magnification. Live cell counts were quantified base on size, morphology, texture and intensity of CFSE staining and the absence of DRAQ7 staining. The results are shown in FIG. 50, B to D.

To determine the effect of CD19-Vδ1 bispecific antibodies on Vδ1 γδ T-cell activation and degranulation, Vδ1 TCR downregulation and CD107a upregulation was quantified in the presence of $CD19^+$ target cells and CD19+ healthy cells. Briefly, antibodies were serially diluted in PBS before adding to U-bottomed 96-well plates. NALM-6 and isolated B-cells were stained with [0.5 μM] CellTrace CFSE live cell dye for 20 minutes. Skin derived Vδ1 γδ T-cells were detached from culture flasks and cell suspensions were mixed 0.5:1 with NALM-6 or B-cells. Cell suspensions were seeded into assay plates at 2.5×10ˆ4 Vδ1 γδ T-cells per well to 5×10ˆ4 NALM-6 or B-cells per well. Final assay antibody concentrations range from 60 nM to 3 μM. The cells were incubated for 4 hours at 37° C., 5% CO2. Cells were washed and stained for dead cells (eFlour 520, Invitrogen), Vδ1 TCR (MiltenyiBiotec) and aCD107a (Miltenyi) surface expression for 30 minutes at 4° C. The cells were washed in FACS buffer and resuspended in Cell Fix (BD sciences) before incubating overnight at 4° C. in the dark. The VD1 TCR expression level was measured by flow cytometry the following day using the MACS Quant Analyzer 16. The results are shown in in FIG. 50, F to K.

Conclusion: Vδ1-CD19 bispecifics enhance γδT-cell mediated cytotoxicity of $CD19^+$ target cells while sparing healthy CD19+ cells. Affinity maturation of Vδ1 antibodies enhances cytotoxicity compared to parental clones in a monovalent format.

Example 27B. Vδ1-CD19 Bispecific Antibodies Selectively Enhance the Cytotoxic Effect of Vδ1 γδT-Cells on Cancer Cells while Sparing Healthy Cells The effect of CD19-Vδ1 bispecific antibodies on $CD19^+$ target cell cytotoxicity and CD19+ healthy cell sparing was determined using high content confocal imaging in the Opera Phenix (Perkin Elmer). Healthy B-cells were isolated from PBMCs (Lonza), using negative magnetic activated cell sorting (MACS; MiltenyiBiotec). Raji cells and healthy primary B-cells were stained with CellTrace dyes. Expanded skin derived Vδ1 γδ T-cells and donor matched αβT-cells were removed from culture, washed and resuspended in culture media before mixing 1:1 with Raji cells and B-cells. Bispecific antibodies and controls were serially diluted in PBS before adding to 384-well imaging assay plates (Perkin Elmer). Cell suspensions of either γδ T-cells, Raji cells, and B-cells, or αβT-cells, Raji cells, and B-cells, or Vδ1 γδ T-cells, αβT-cells Raji cells, and B-cells were added to 384-well imaging assay plate to achieve 2,000 of each cell type per well and final antibody assay concentrations ranging between 6.6 nM to 66 μM. To determine the numbers of live target cells, confocal images were acquired using an Opera Phenix high content platform capturing nine fields of view at 10× magnification. Live cell counts were quantified base on size, morphology, texture and intensity of CFSE staining at 24 hours. The results are shown in FIG. 63, A to F.

To determine whether activation of Vδ1 γδ T-cells or αβT-cells resulted in elevated production of the pro-tumorigenic cytokine IL-17, supernatants were collected from imaging plates after images were acquired at 24 hours. Supernatants were run on the U-Plex 10-plex Meso Scale Discovery (MSD) to quantify IL-17A levels. Results are shown in FIG. 63, G to I.

IL-17A (Interleukin-17A) is a pro-tumorigenic cytokine which is produced by activated T-cells. IL-17A can enhance tumour growth and dampen the anti-cancer immune response. As shown in FIG. 63, G to I, anti-vδ1 antibodies do not induce secretion of IL-17A, whereas anti-CD3 antibodies do.

Conclusion: Vδ1-CD19 bispecific antibodies enhance γδT-cell mediated cytotoxicity of $CD19^+$ target cells while sparing healthy CD19+ cells. In contrast, anti-CD3×CD19 bispecifics enhanced both γδT-cell and 4T-cell mediated lysis of $CD19^+$ target cells, however activation of 4T-cells also enhanced the lysis of healthy primary $CD19^+$ B-cells, as well as the secretion of the pro-tumorigenic cytokine IL-17A.

Figure 51A:
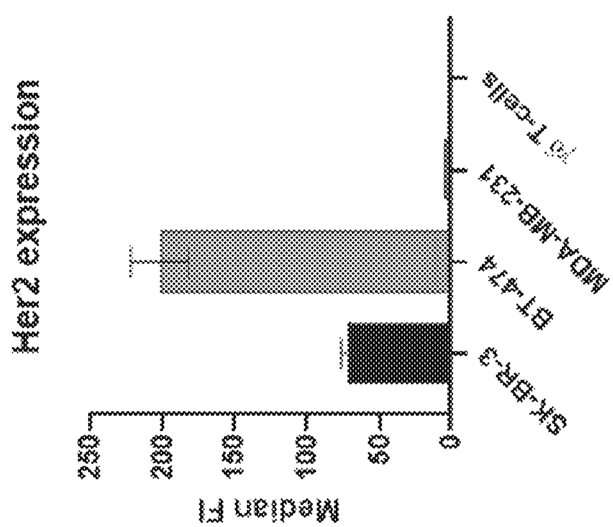
Figure 51B:
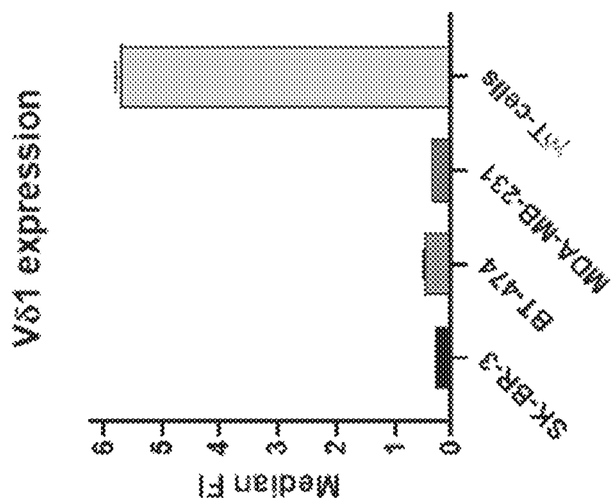
Figure 51G:
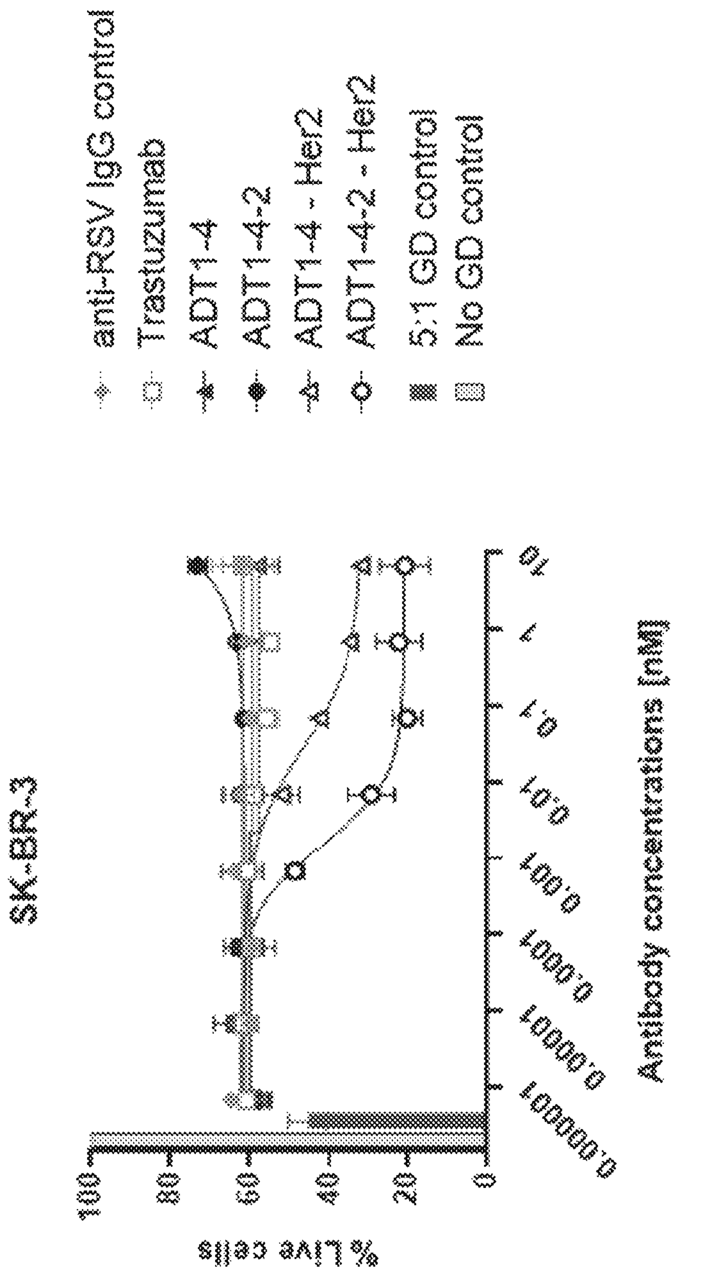
Figure 51H:
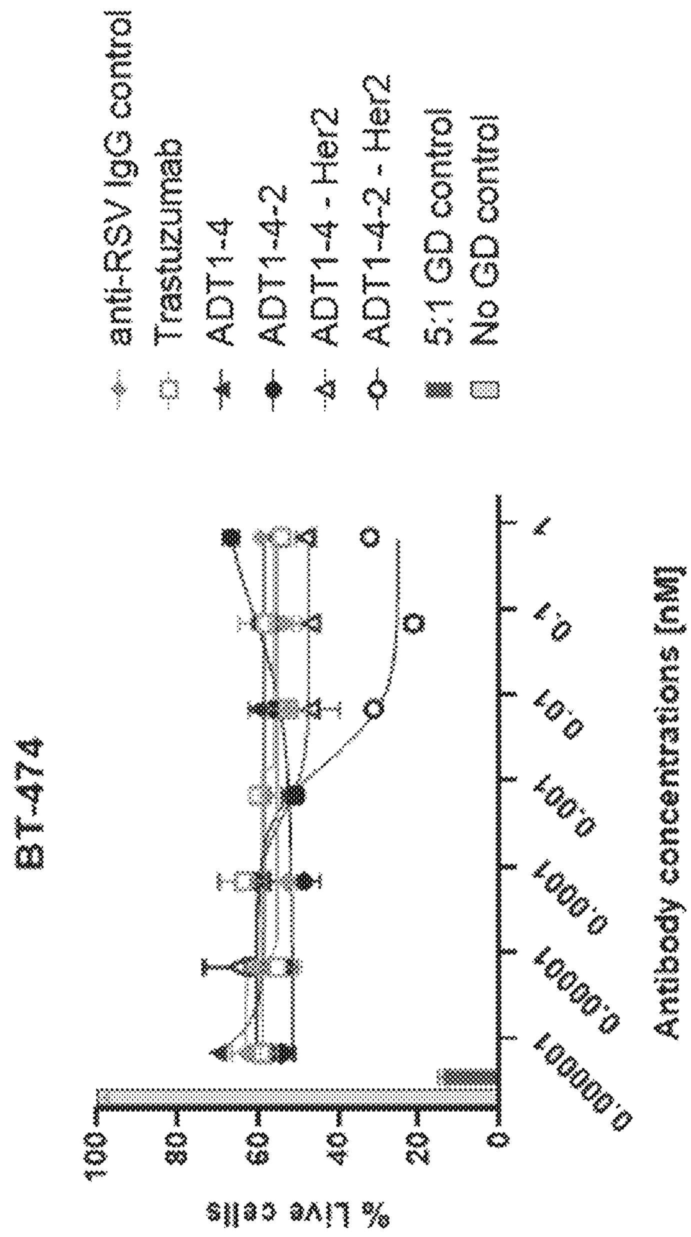
Figure 51I:
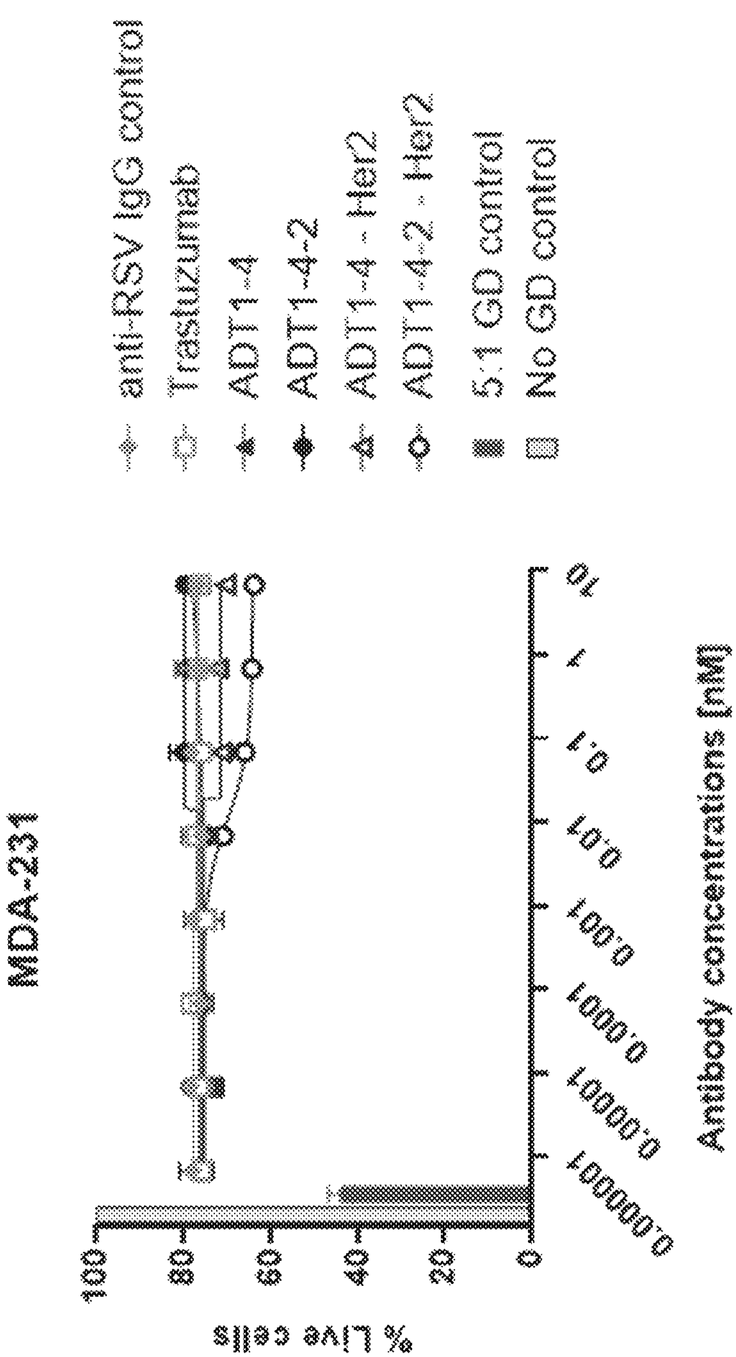
Figure 51J:
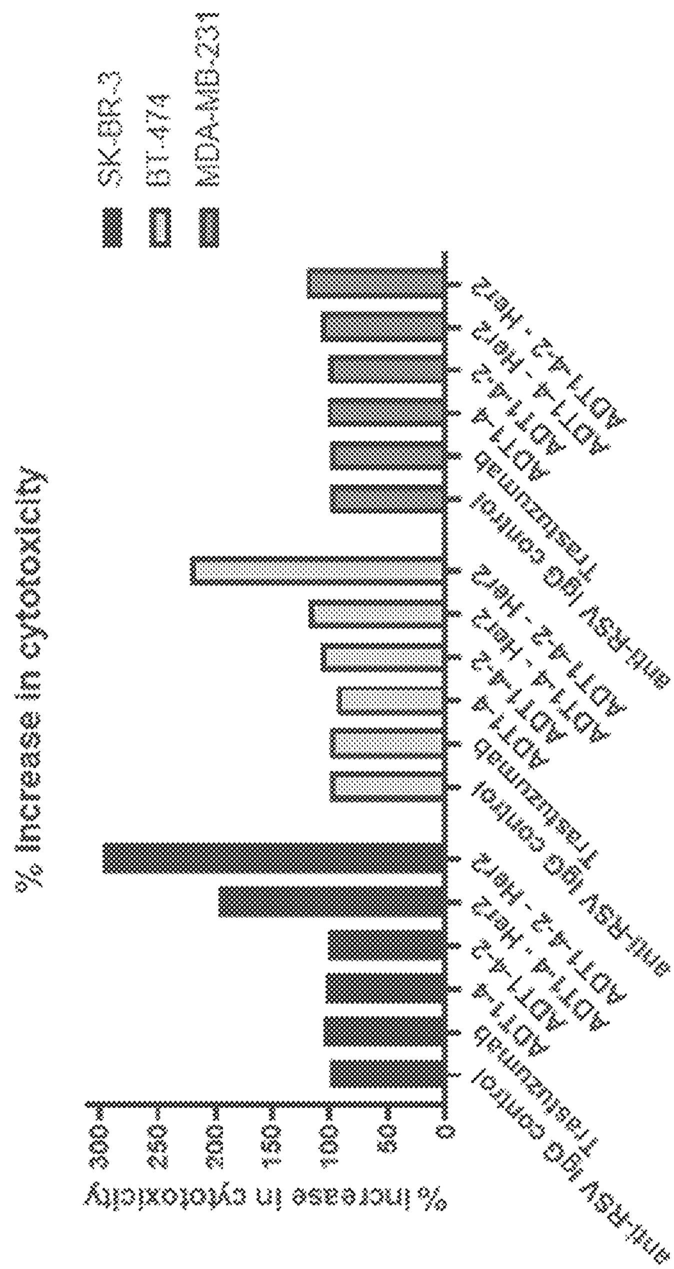

Example 28. Vδ1-Her2 Bispecific Antibodies in Binding and High Content Cytotoxicity Assays Her2 and Vδ1 expression was determined on SK-BR-3 cells (Caltag-Medsystems Ltd), BT-474 cells (ATCC), MDA-MB-231-Luc cells (Creative Biogene Biotechnology) and Vδ1 γδT-cells. Briefly, 5×10ˆ4 cells were incubated with Her2 and Vδ1 antibodies (MiltenyiBiotec) for 15 minutes at 4° C. before washing and fixing. Expression of Her2 and Vδ1 was determined by flow cytometry (MACSQuant10, MiltenyiBiotec). The results are shown in FIGS. 51A and 51B. Binding of Her2-Vδ1 bispecific antibodies was determined by incubating target cells with a range of concentrations of ADT1-4 or ADT1-4-2 mAbs or Vδ1 bispecific antibodies, or controls (IgG control or Trastuzumab) for 15 minutes. After washing, cells were incubated for a further 15 minutes with anti-human IgG secondary antibodies before washing and fixing. The amount of antibody bound to each cell type was determined by flow cytometry. The results are shown in FIG. 51, C to F.

The effect of Her2-Vδ1 bispecific antibodies on Her2+/Her2− target cell cytotoxicity was determined using high content confocal imaging in the Opera Phenix (Perkin Elmer). Briefly, SK-BR-3, BT-474 and MDA-MB-231 cells were seeded into 384-well imaging plates (Perkin Elmer) to give a final seeding density of 2,000 target cells per well before incubating overnight at 37° C., 5% CO2. Antibodies were diluted into PBS and serially diluted 1:10 before adding to the assay plates to give a final assay concentrations of 333 nM to 0.33 μM. Expanded skin derived Vδ1 γδ T-cells were detached from tissue culture flasks and re-suspended in basal growth media before adding to the assay plate at 2,000 cells per well at a 1:1 Effector:Target ratio. Cells were co-cultured for 24 hours before staining with Hoechst (1:1000 final, Invitrogen) and DRAQ7 (1:300 final, Abcam). To determine the numbers of live target cells, confocal images were acquired using an Opera Phenix high content platform capturing nine fields of view at 10× magnification. Live cell counts were quantified base on size, morphology, texture and intensity of live cell stains and the absence of DRAQ7 staining. The results are shown in FIG. 51, G to J.

Conclusion: Vδ1-Her2 bispecific antibodies enhance γδT-cell mediated cytotoxicity of $Her2^+$ target cells while sparing $Her2^-$ cells. Affinity maturation of Vδ1 antibodies (ADT1-4-2) enhances cytotoxicity compared to parental clones (ADT4-1).

Figure 52A:
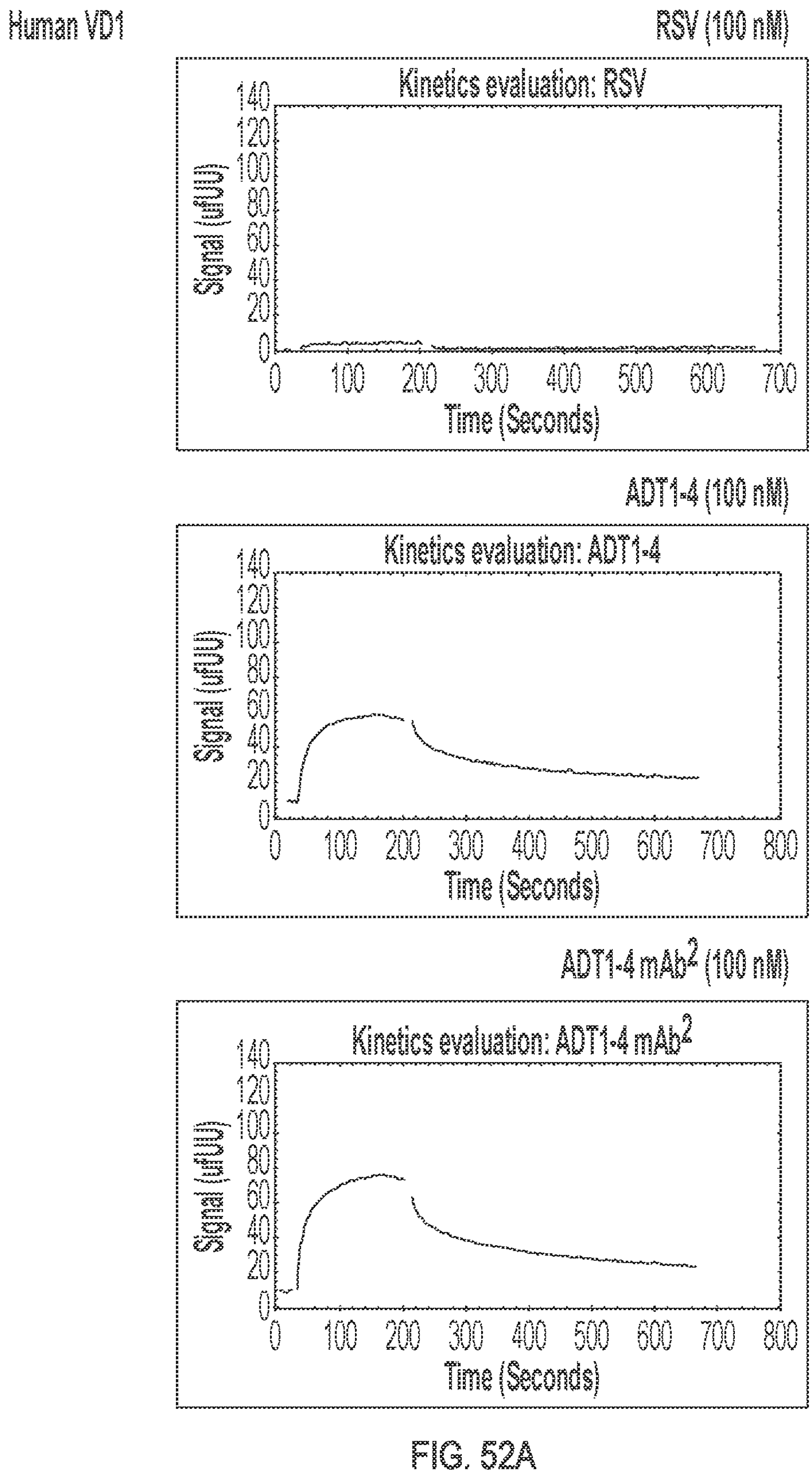
FIGS. 52A-52F: Vδ1/EGFR bispecific antibodies exhibit high affinity binding to human EGFR and a human Vol-binding affinity comparable to their parental mAbs.
Figure 52B:
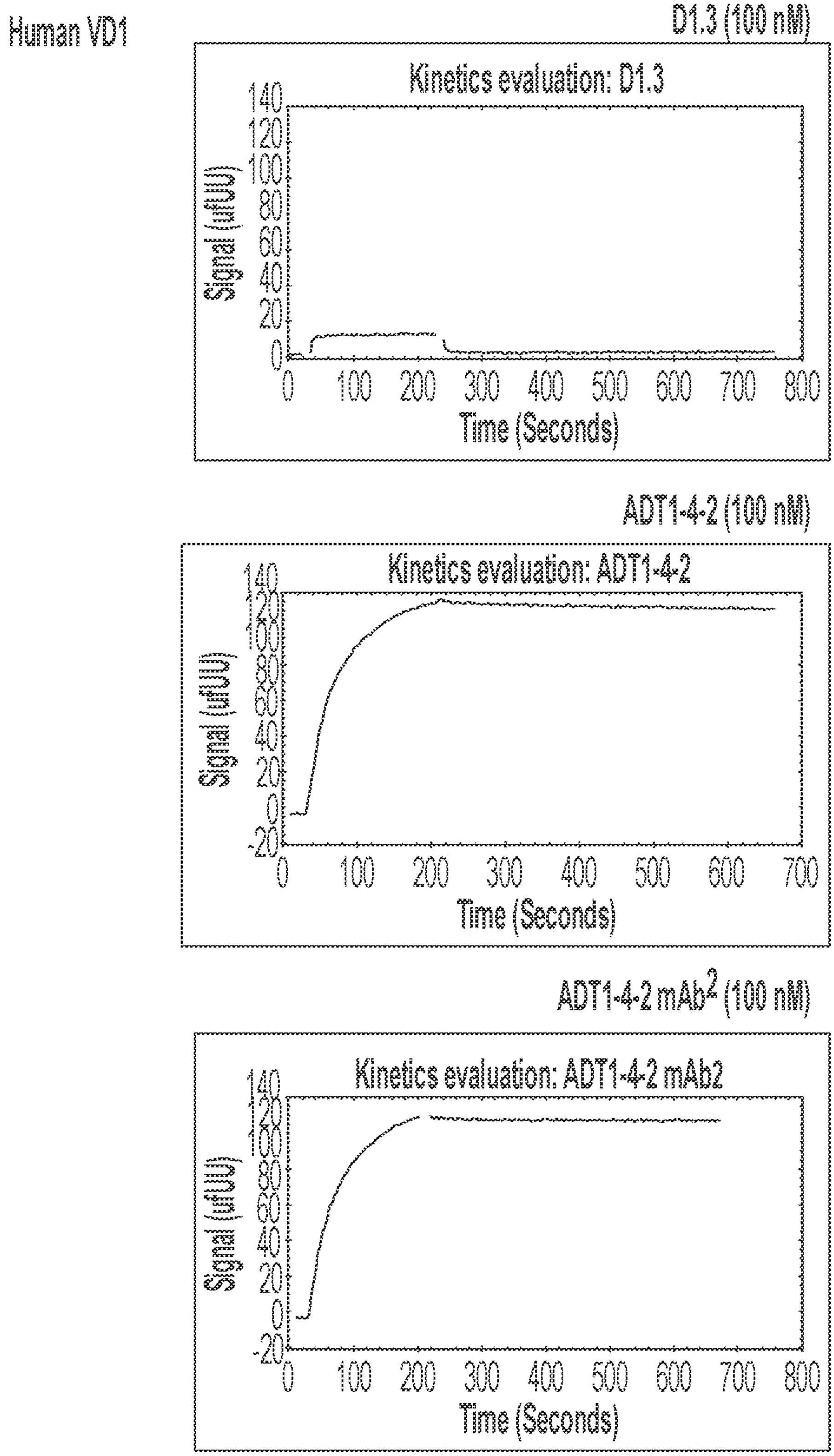
Figure 52C:
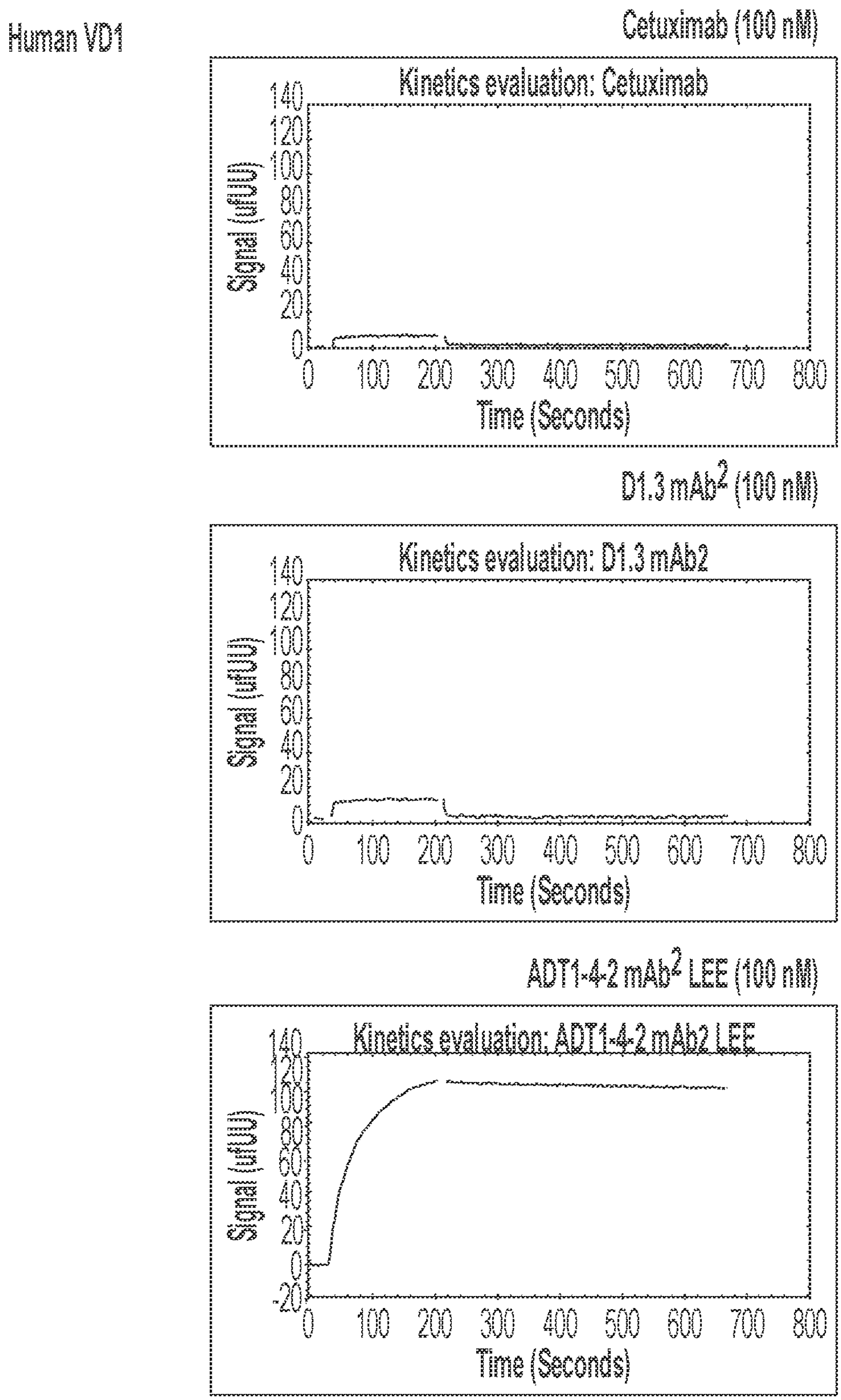
Figure 52D:
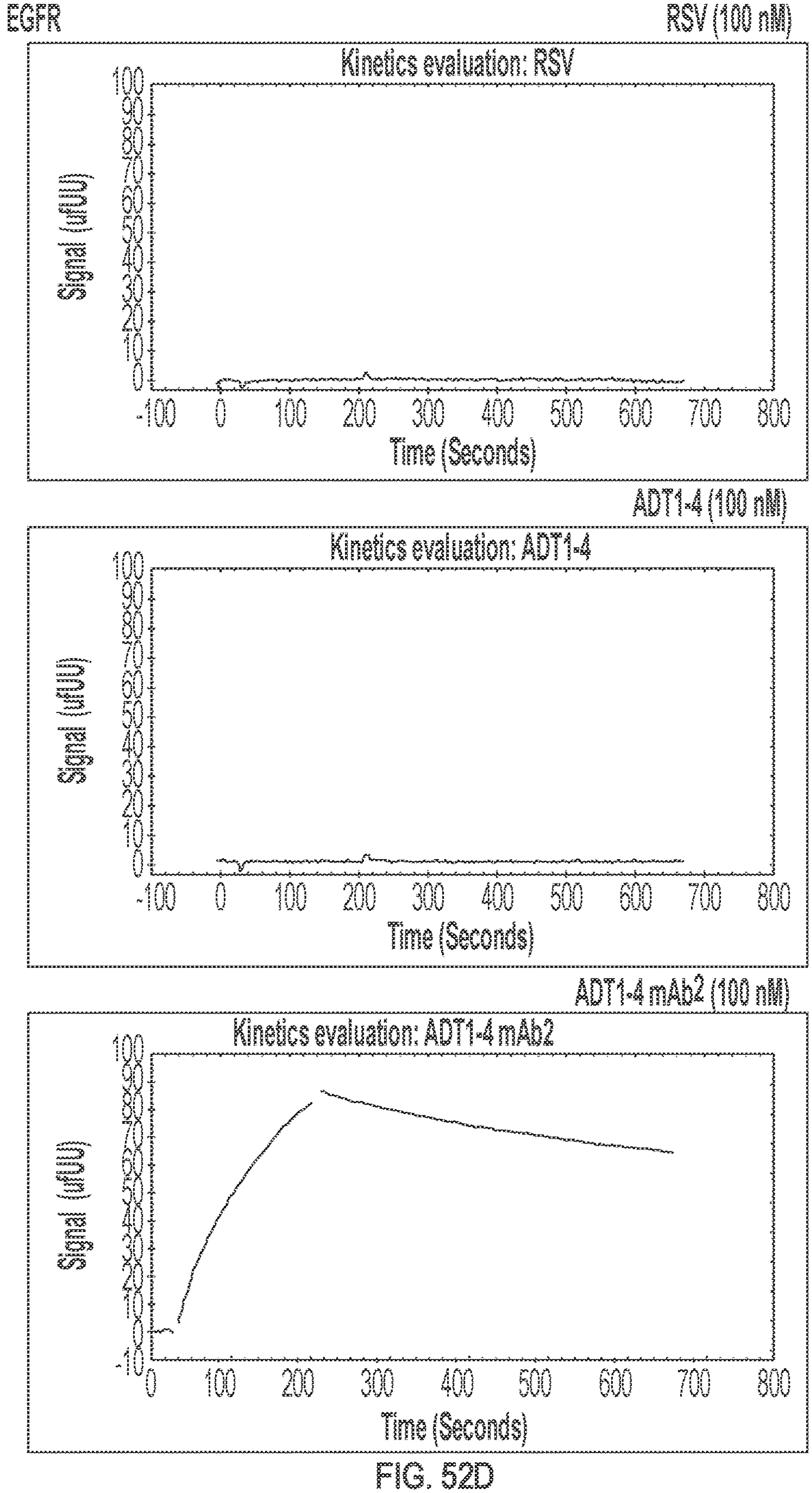
Figure 52E:
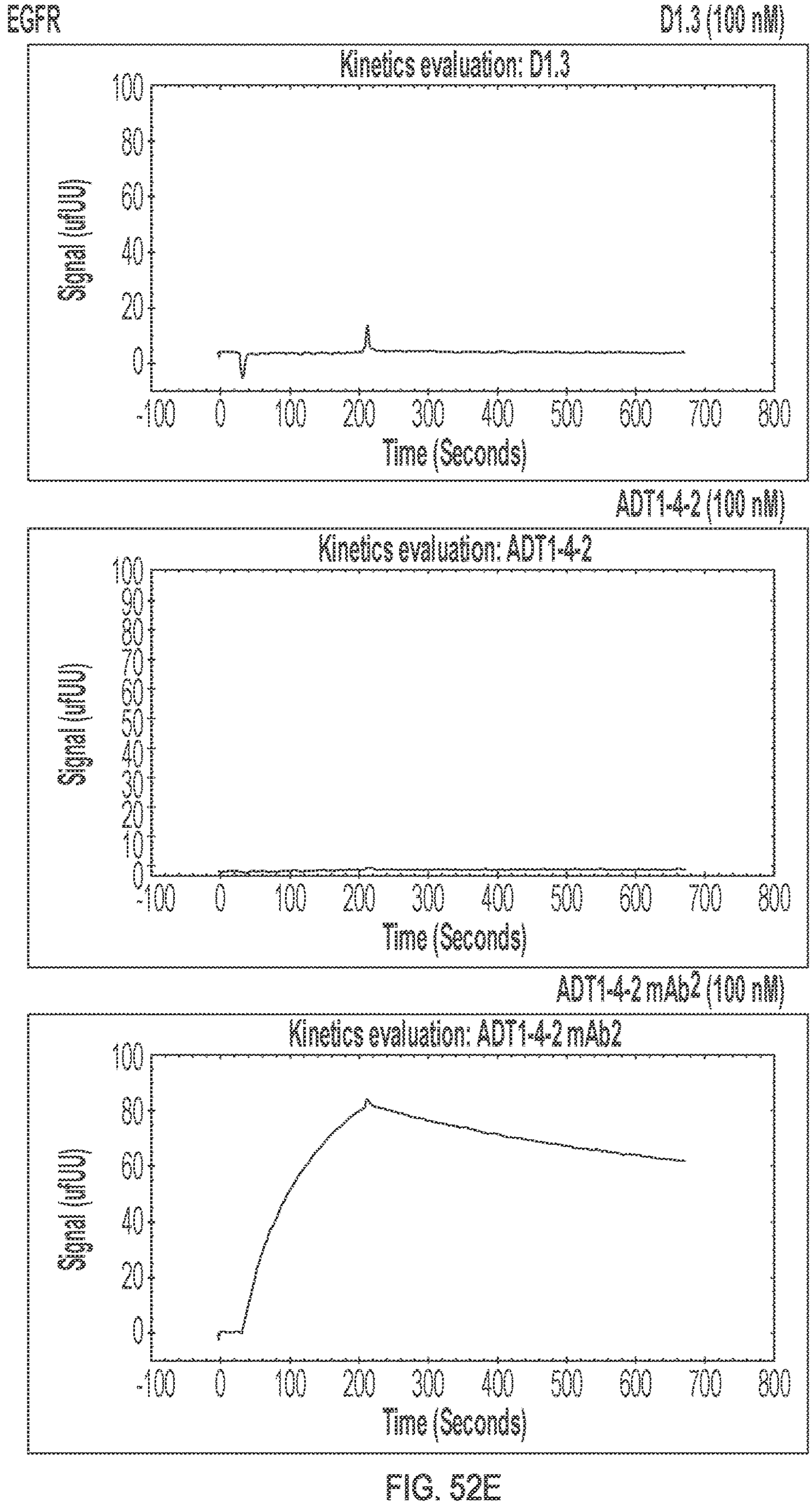
Figure 52F:
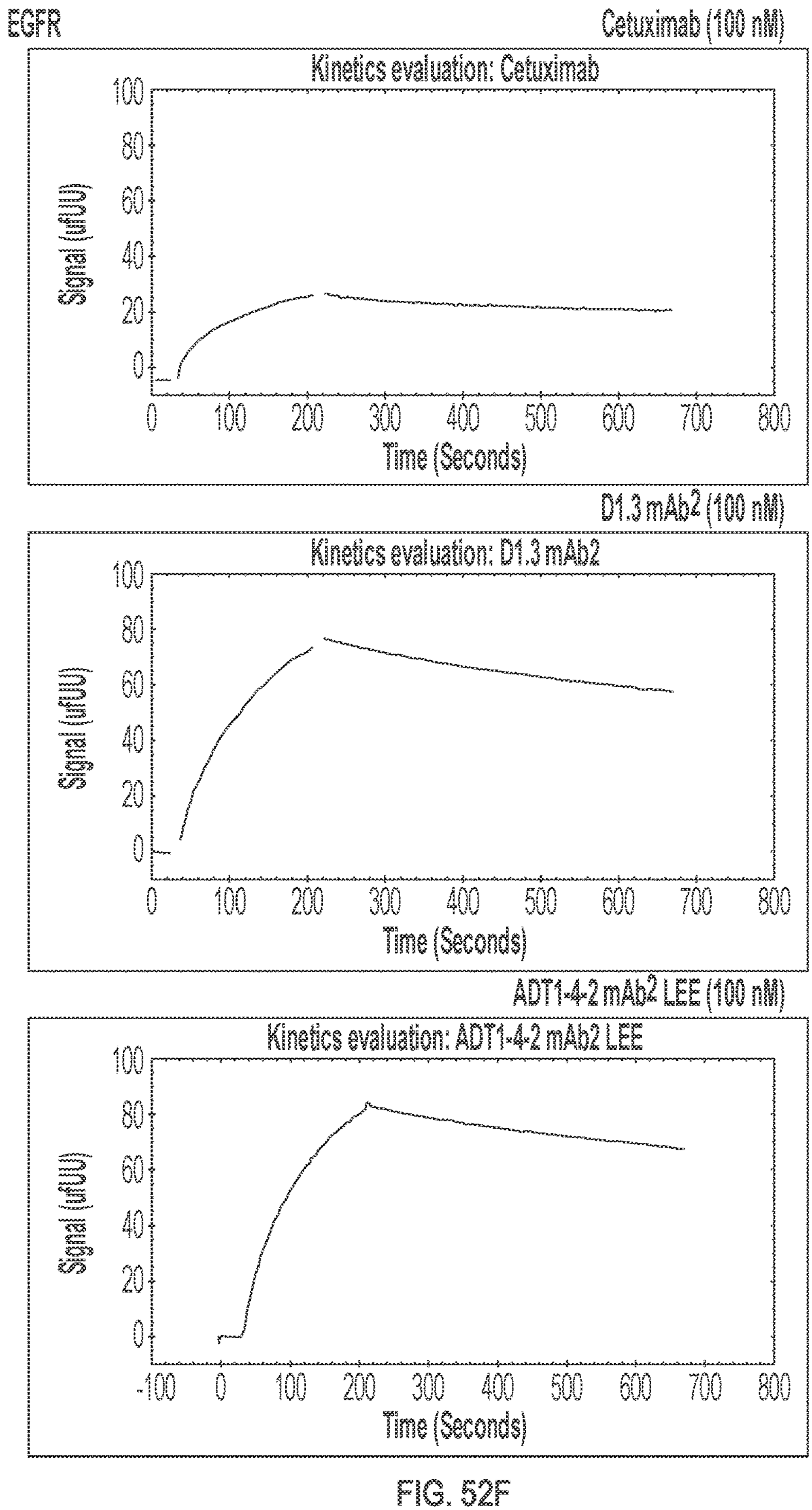

Example 29. Vδ1-EGFR Bispecific Antibody Binding Affinity to Human Vδ1 and Human EGFR Antigen The binding affinity of the antibodies to target (i.e. the Vδ1 chain of a γδ TCR and EGFR) is established by SPR analysis using a Reichert 4SPR instrument (Reichert Technologies). Antibody (1.5 ug/mL) is coated onto a Planar Protein A Sensor Chip (Reichert Technologies) to give an increase on baseline of approximately 500 uRIU. Recombinant human Vδ1 heterodimer or human EGFR was flown over the cell at a concentration of 100 nM with the following parameters: 180 s association, 480 s dissociation, flowrate 25 μL/min, running buffer PBS+0.05% Tween 20. All experiments were performed at room temperature. The results are shown in FIGS. 52A and 52B.

Conclusions: This data demonstrates that the Vδ1/EGFR bispecific antibodies demonstrate binding to human Vδ1 that is comparable to that of the monospecific anti-Vδ1 antibodies used in their preparation, notwithstanding the introduction of human EGFR binding capability.

Example 30. Target Cell Binding of Vδ1-EGFR Bispecific Antibodies

Figure 53A:
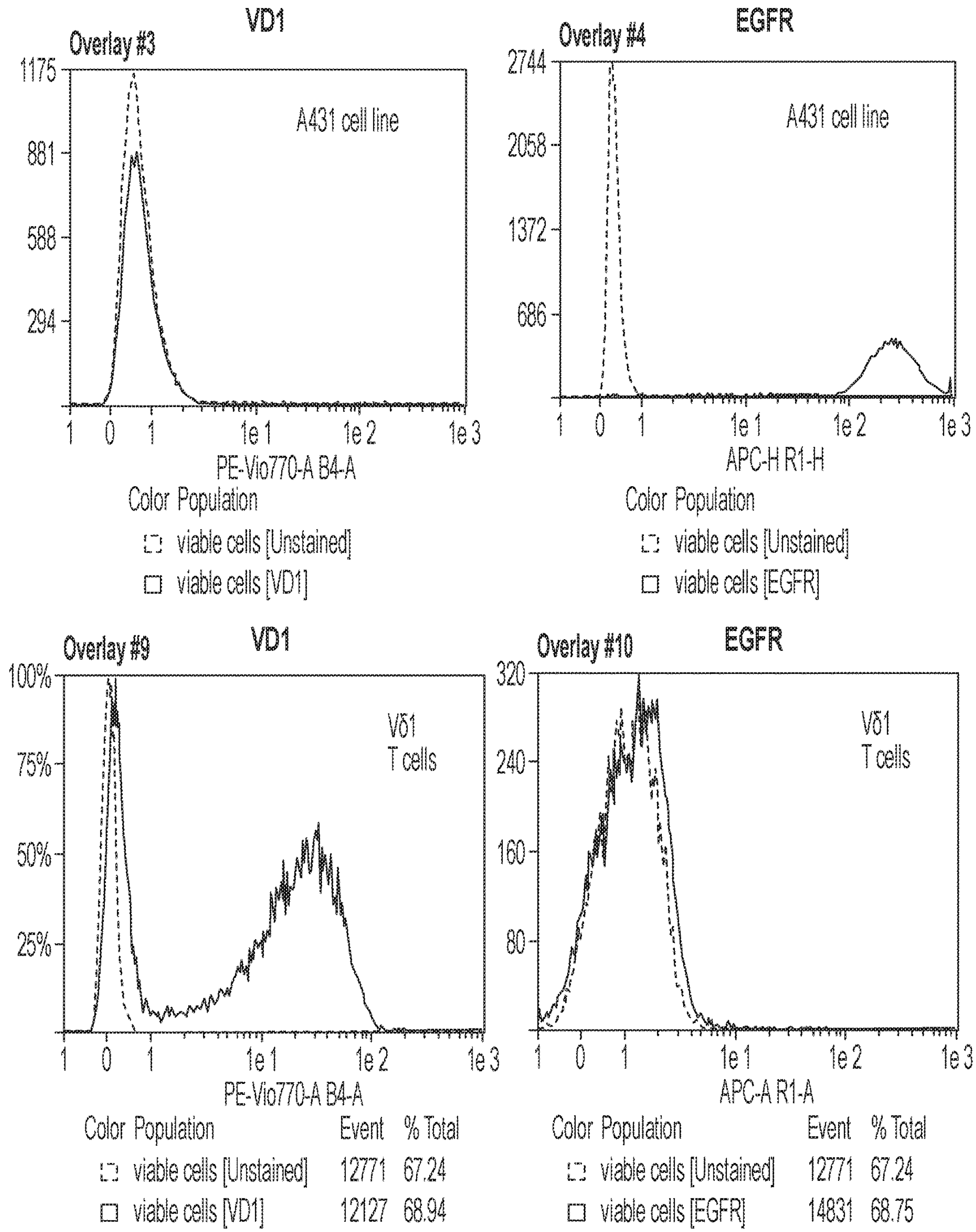
FIGS. 53A-53C: Vδ1/EGFR bispecific antibody binds to EGFR+A431 target cells and Vδ1 γδ T-cells (FIG. 53A) Cell surface expression of EGFR and Vδ1 on A431 cell line and primary Vδ1 γδT-cells.
Figure 53B:
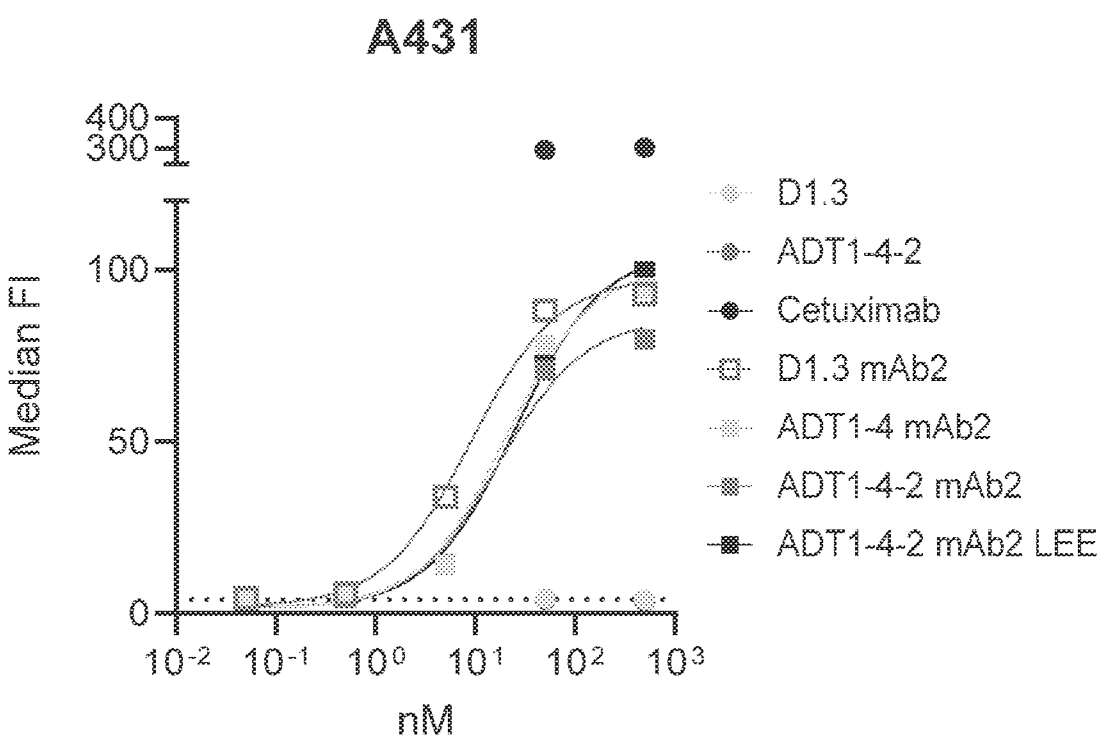
Figure 53C:
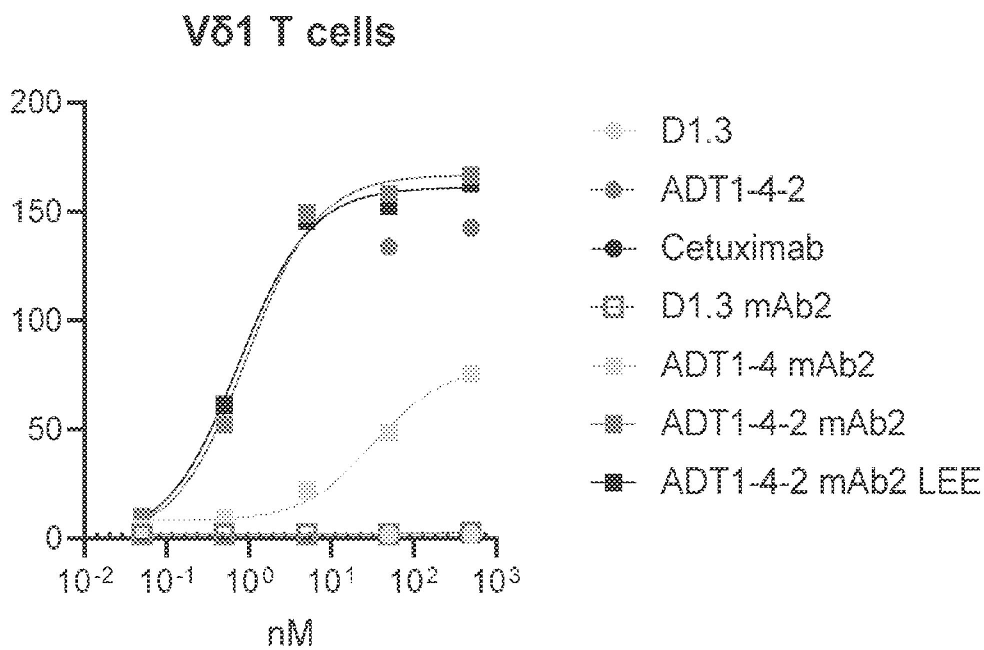
Figure 54A:
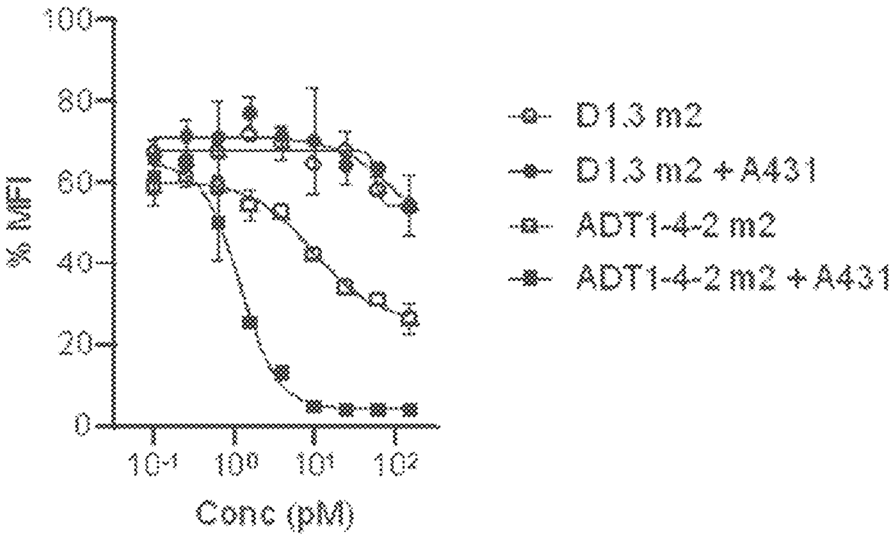
FIGS. 54A-54E: Vδ1/EGFR bispecific antibodies induces EGFR-specific T cell activation and degranulation leading to increased γδ T cell-mediated cytotoxicity of A431 target cells.
Figure 54B:
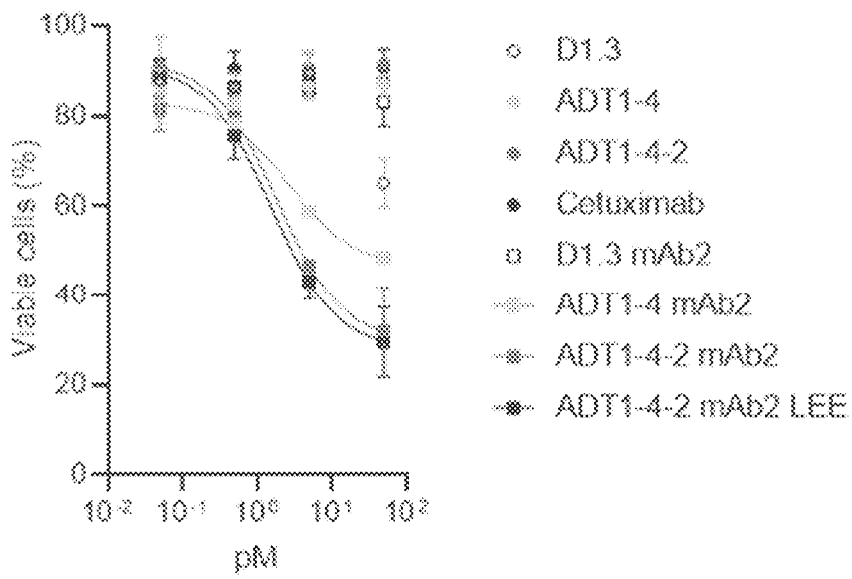
Figure 54C:
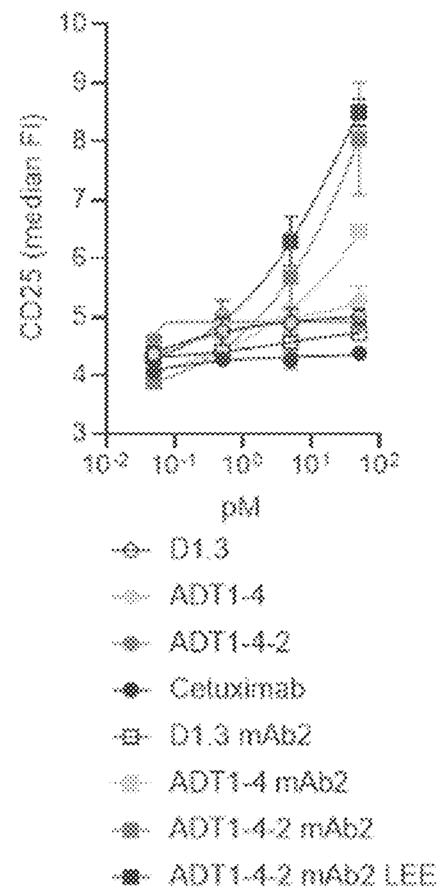
Figure 54D:
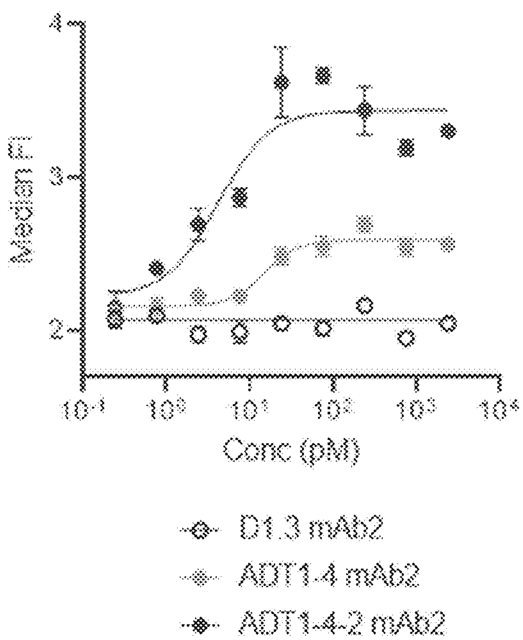
Figure 54E:
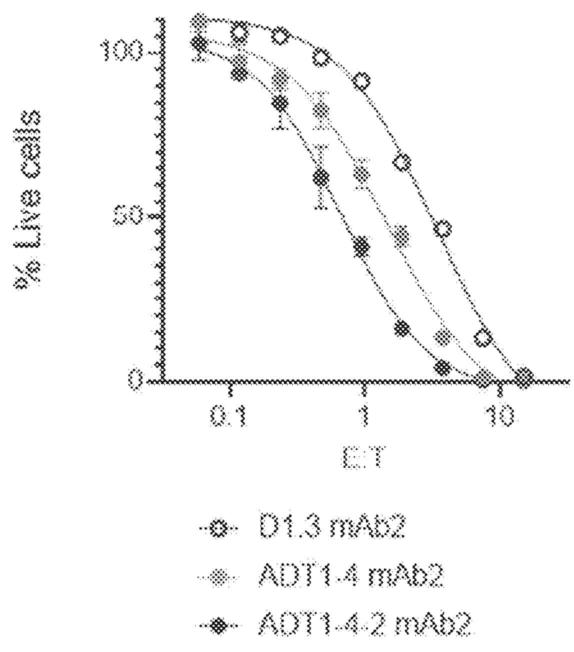

EGFR-positive A431 and Vδ1-positive primary γδT-cells were assayed to determine the specificity and affinity of EGFR/Vδ1 bispecific antibody binding. Target cells were detached from tissue culture flask, resuspended in PBS and seeded at a final density of 100,000 cells per well in v-bottom 96-well plates. Cells underwent centrifugation and the cell pellets were resuspended in FcR blocking reagent according to the manufacturer's instructions, and incubated for 20 minutes at 4C prior to a further wash. Antibodies were diluted to 500 nM in PBS and serially diluted 1:10 in PBS to 50 μM, and added to the cells, followed by a 20-minute incubation at 4C. To determine the quantity of mAb bound to the cell surface, the cells were then stained with a murine anti-human IgG secondary antibody, conjugated to APC, dilution: 1:100) in addition to a viability dye. Following 20-minute incubation at 4C, the cells were washed twice, and fluorescence measured using the MACSQuant. The results are shown in FIG. 53.

Conclusions: This data demonstrates that the Vδ1/EGFR bispecific antibodies demonstrate binding to Vδ1-positive γδT-cells that is comparable to that of the monospecific anti-Vδ1 antibodies used in their preparation, notwithstanding the introduction of binding to the EGFR-positive A431 cell line.

Example 31. Assessing γδ T Cell Activation and Target Cell Cytotoxicity In Vitro Expanded skin-derived Vδ1 γδ T-cells and A431 cells were detached from tissue culture flasks and re-suspended in basal growth media and seeded in 96-well plates at the relevant cell dilutions dependent on the desired effector: target ratio. mAbs were diluted and added to each well at the specified concentration. The cultures were then incubated at 37° C., 5% CO2 for 4 (D) or 24 hours (A-C, E). To determine the numbers of live cells, the cells were harvested and stained with viability dye at a 1:1000 dilution for 20 minutes. To determine CD25 status, cells were surface stained with an anti-CD25 antibody following cell harvest. To measure degranulation, a fluorophore-conjugated anti-CD107a antibody was added directly into the cell-antibody mix at the start of the co-culture. Following, two washes and cell fixation, fluorescence was measured using the MACSQuant and live cell counts and median fluorescence intensity determined. The results are shown in FIG. 54.

Conclusions: This data demonstrates that the Vδ1/EGFR bispecific antibodies induce activation and degranulation of primary Vol-positive γδ T-cells leading to increased cell-mediated lysis of EGFR-positive A431 cell line.

Example 32. Further Assessing γδ T Cell Activation and Non-Depletion Effects Conferred by Antibodies of this Invention For Studies with Blood-Derived vδ1+ Cells (FIG. 55A,B):

Studies were undertaken to explore the effect of stimulating/activating vδ1 cells with anti-vδ1 antibody with respect to down-regulation of CD3 on vδ1 cells. This was tested by incubating the anti-vδ1 clone ADT1-4-2 with PBMC and then analysing the TCR by phenotyping.

Cryopreserved human peripheral blood mononuclear cells (PBMC) were commercially sourced and seeded into round bottom 96-well tissue culture plates at 250,000 cells/well in 250 ul of complete media (RPMI supplemented with 10% FCS, pen/strep, non-essential amino acids, sodium pyruvate and HEPES) with 10 ng/ml IL15. A titration vδ1 antibody ADT1-4-2 was added to a final concentration of 1 ug/ml (6.67 nM), 0.01 ug/ml (0.067 nM) or 0.0001 ug/ml (0.00067 nM). RSV IgG antibody was included as a control at matched concentration. Cultures were incubated for 14 days, with media and antibody replenished every 3 days. Flow cytometry analysis was performed at the end-point to phenotype the vδ1 cells and TCR expression in each condition.

Cells were gated firstly on live singlets, followed by panγδ (Miltenyi REA592; 130-113-508), which was the parent gate for vδ1 (Miltenyi REA173; 130-100-553), which was itself the parent gate for CD3 (Miltenyi REA613; 130-113-142). Cell populations were identified through positive staining, and then the relative level of expression of each marker between samples through the MFI.

For Studies on Tumour-Resident vδ1+ Cells (FIG. 55 C,D, E):

For FIGS. 55 C, D and E, Solid tumour biopsies (resected from renal cell carcinoma (RCC) patients) were shipped fresh and processed upon receipt to obtain a single cell suspension. Specifically, the tissue was chopped in pieces measuring ~2 mm2 and up to 1 g of tissue was placed into a Miltenyi C tube along with 4.7 ml RPMI with enzymes from Miltenyi's Tumour Dissociation Kit at concentrations recommended by the manufacturer aside from Enzyme R which was used at 0.2× concentration to prevent cleavage of pertinent cell surface molecules. C-Tubes were placed on the gentleMACS™ Octo Dissociator with heating blocks attached. Program 37C_h_TDK_1 for the dissociation of soft tumours was selected. After 1 hour the digest was filtered through a 70 μM filter and complete IMDM containing 4% human plasma was added to quench enzymatic activity. Cells were then washed twice and resuspended in complete IMDM for counting. At this point, cells were plated for stimulation. 2.5×106 cells were plated per well in a 24-well plate and were stimulated with ADT-1-4-2 or anti-IgG1 isotype control antibodies in the presence of IL-15 at a concentration of 2 ng/ml. Live, single CD45+ tumour-infiltrating lymphocytes (TILs) were analysed by flow cytometry 24 hours post mAb stimulation.

Figure 55A:
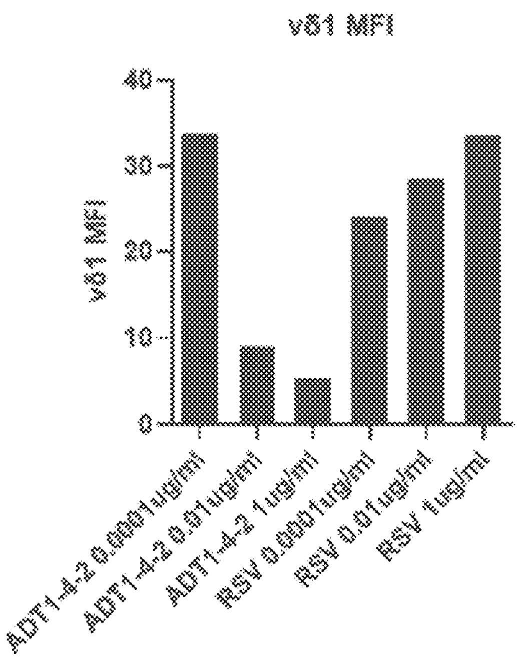
FIGS. 55A-55E: Further evidence of non-depletion and CD3 downregulation in both blood-derived and tumour-associated Vδ1 T cells.
Figure 55B:
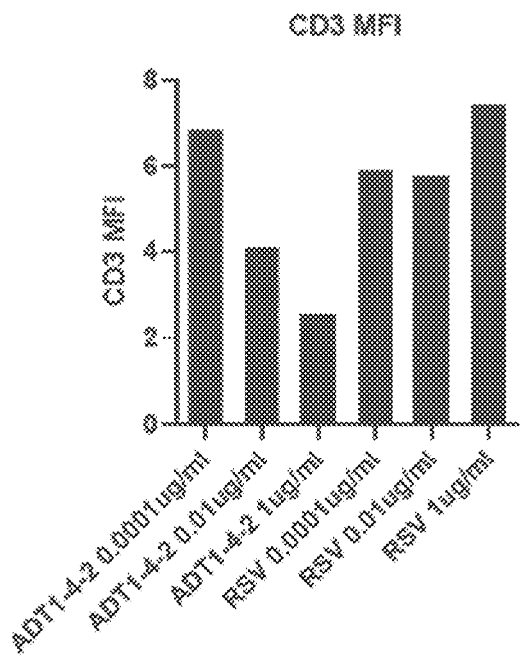
Figure 55C:
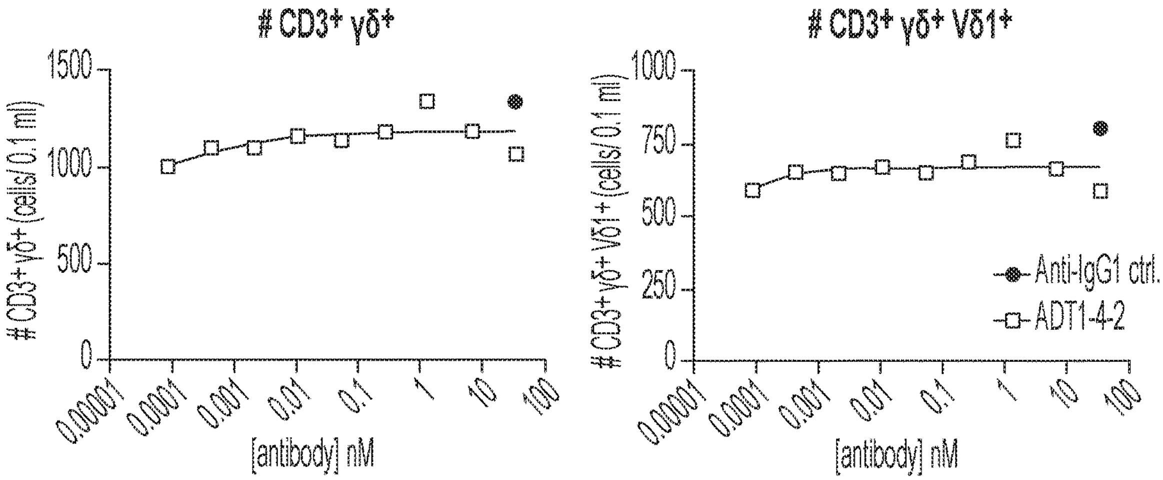
Figure 55D:
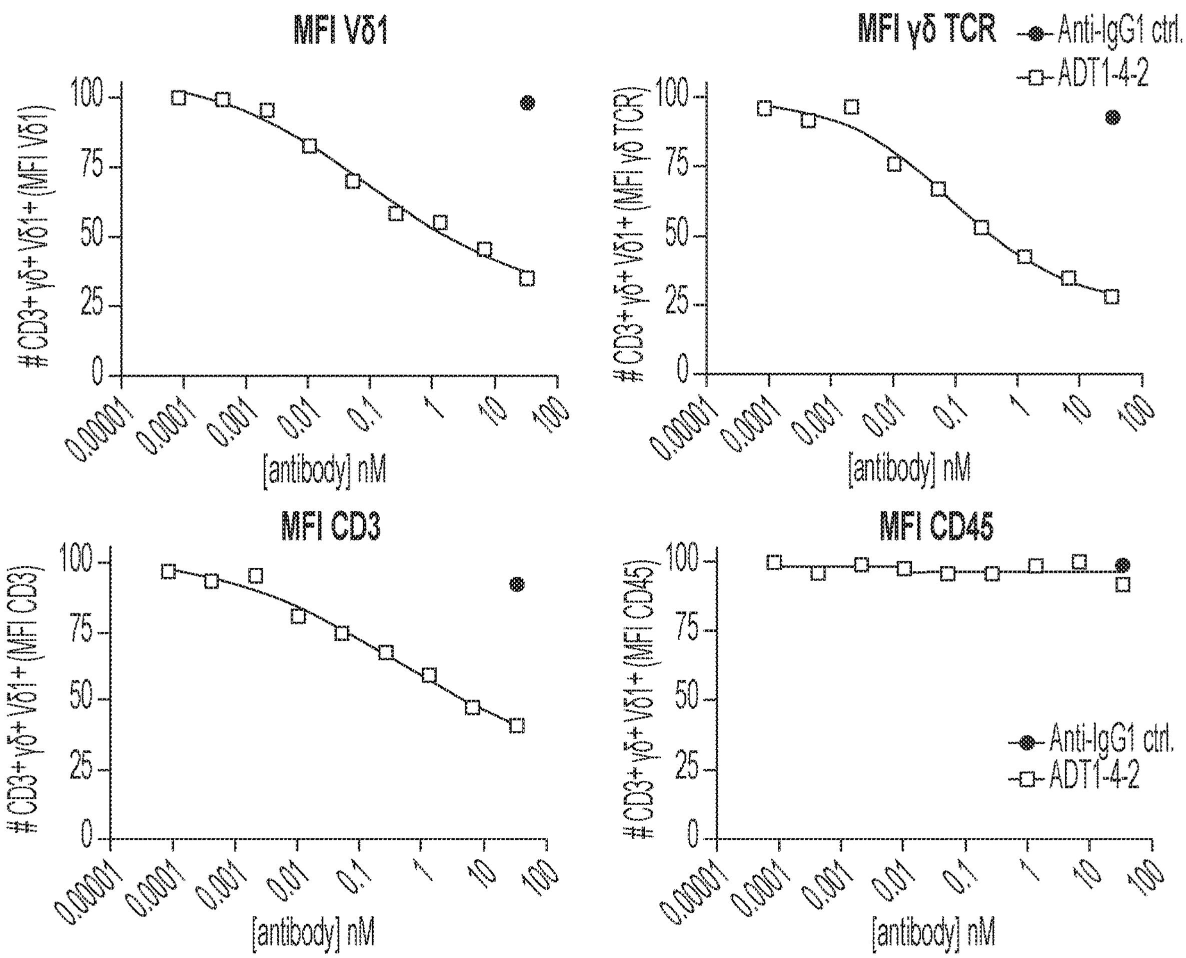
Figure 55E:
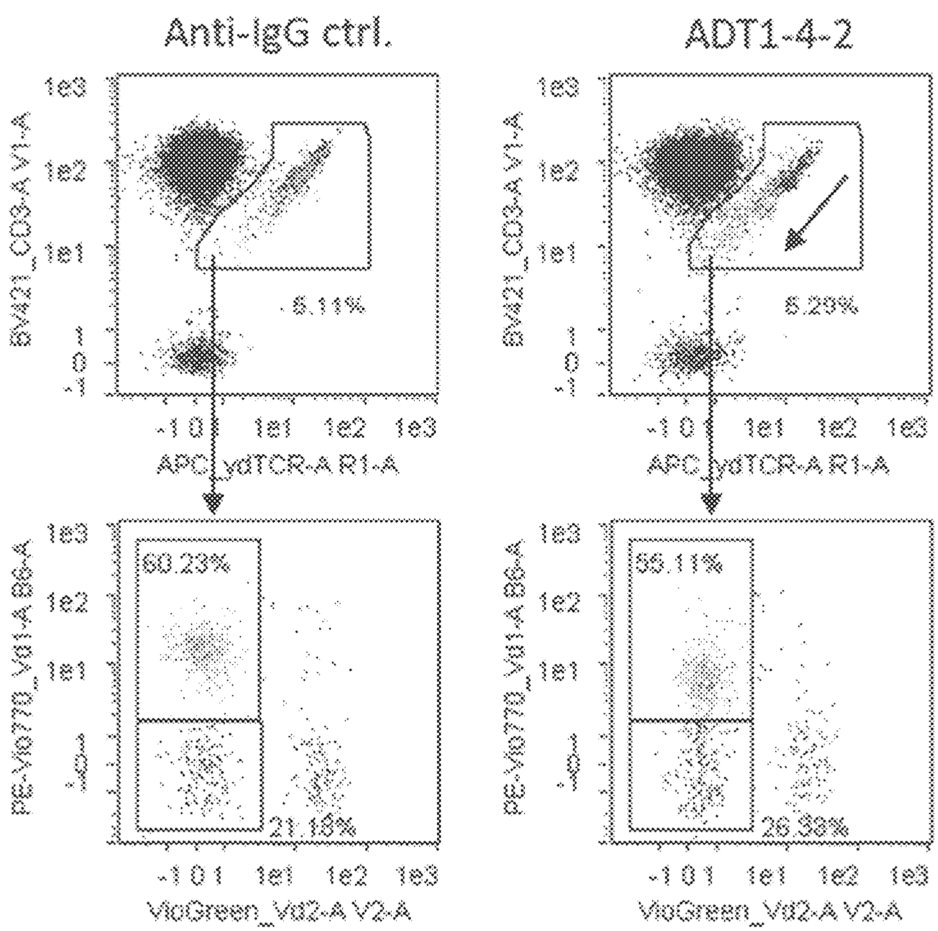
Figure 56A:
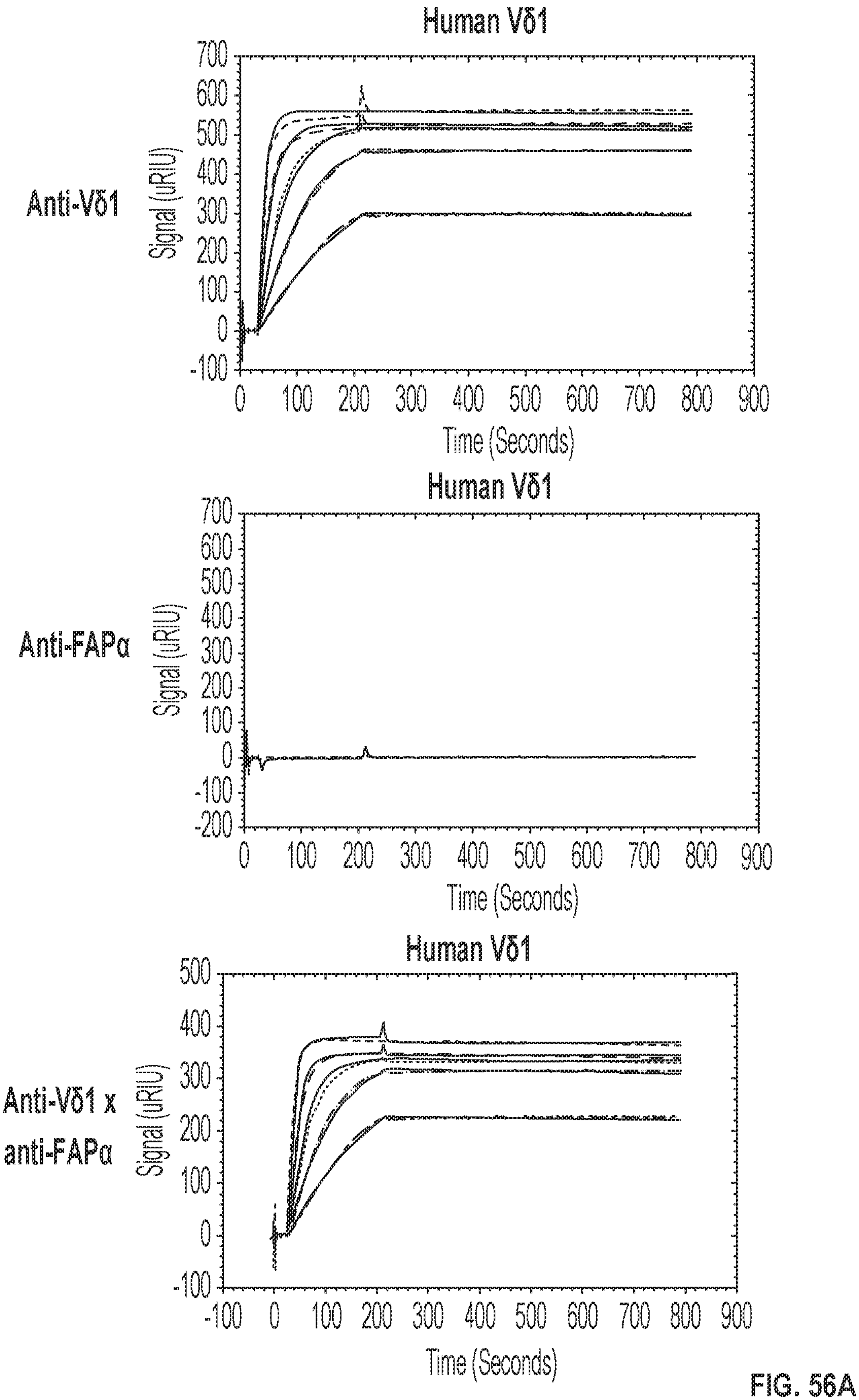
Figure 56C:
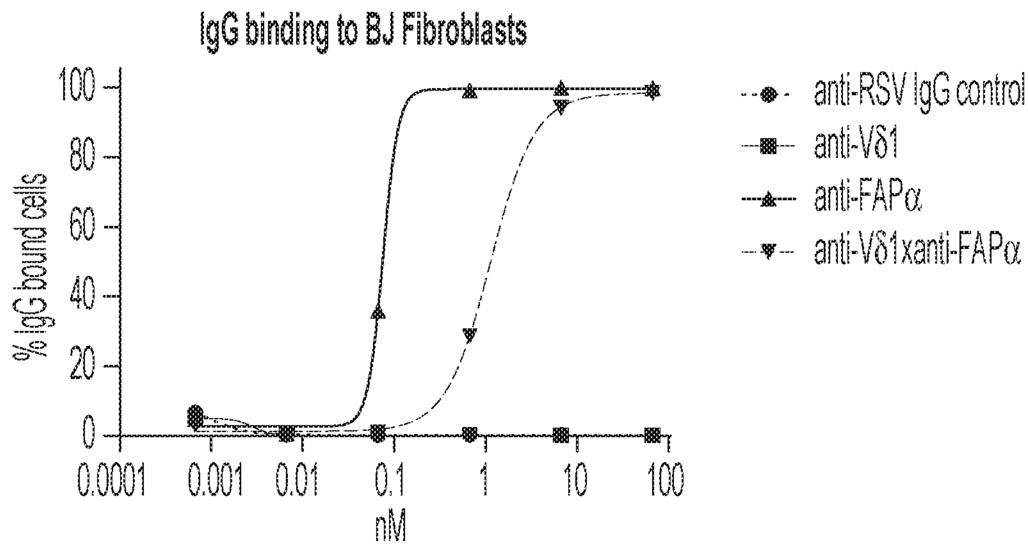
Figure 56D:
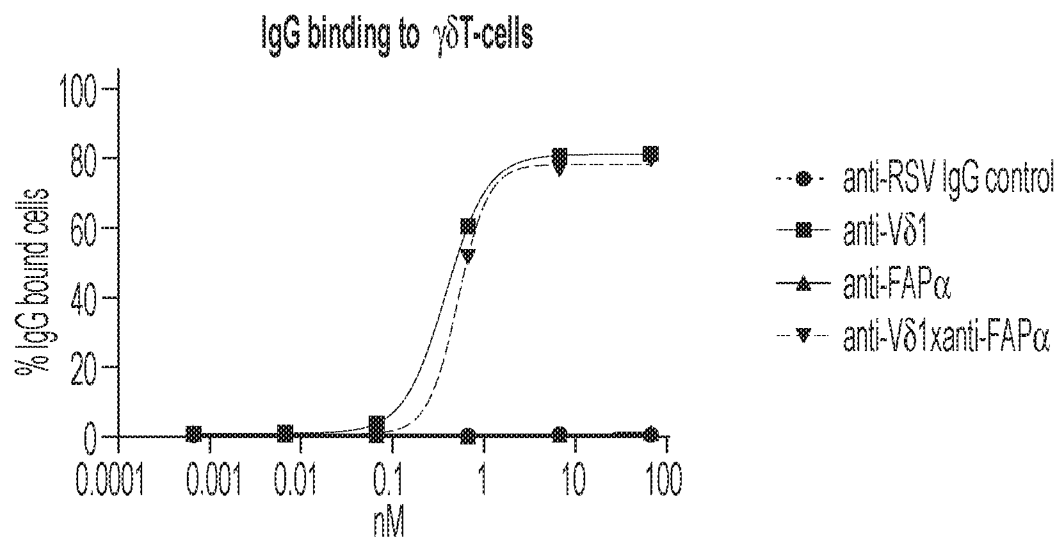
Figure 56E:
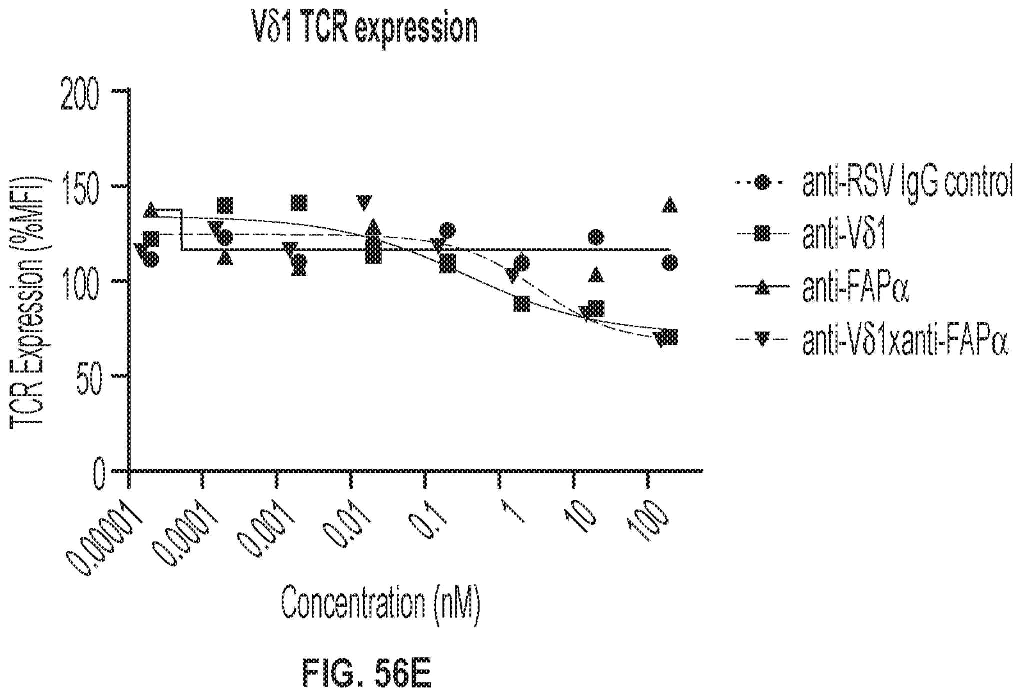
Figure 56F:
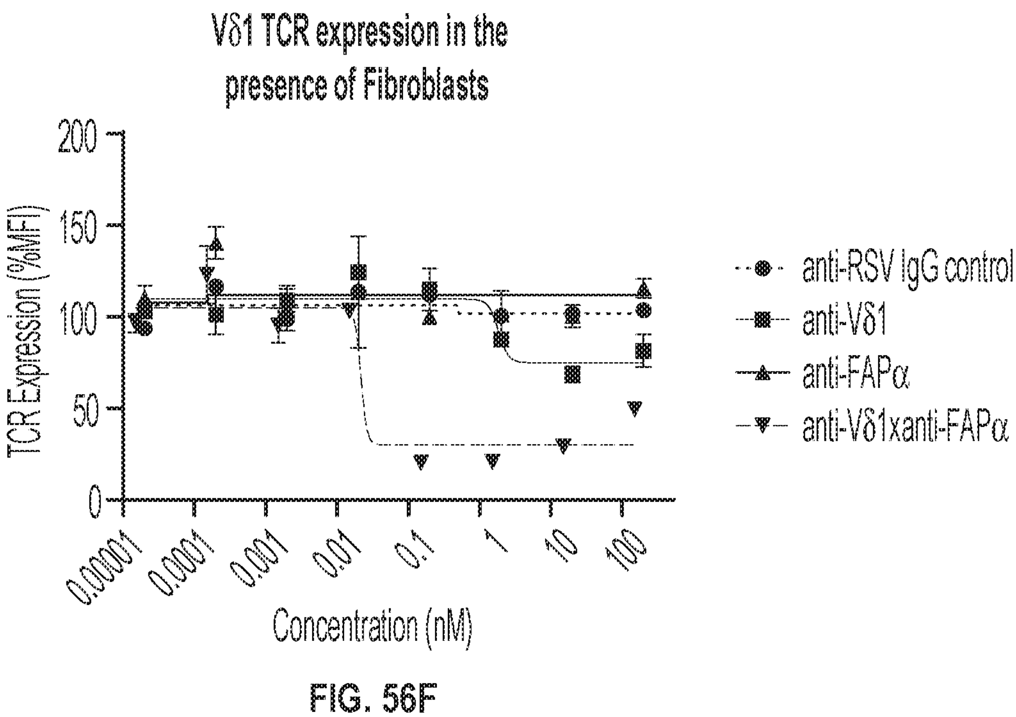
Figure 56G:
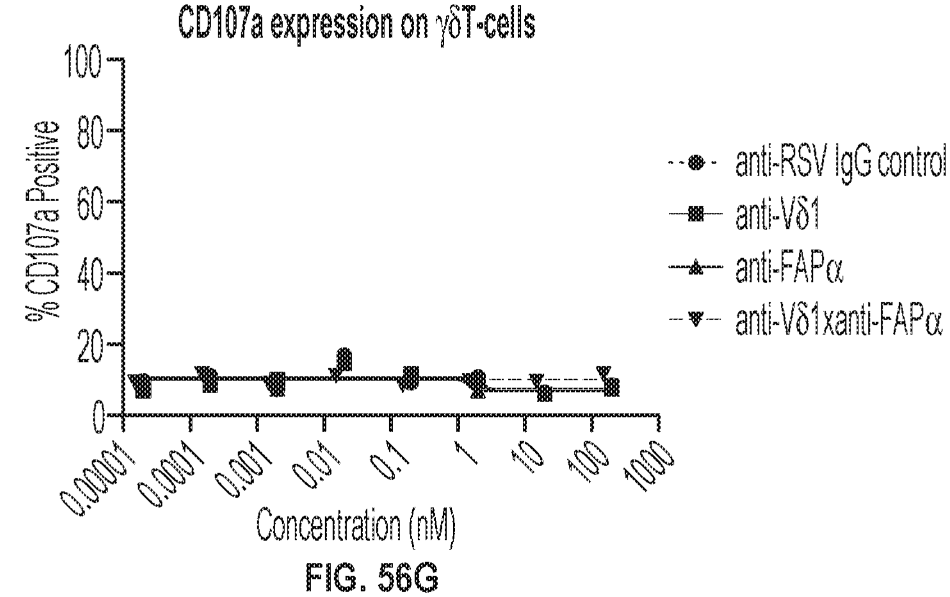
Figure 56H:
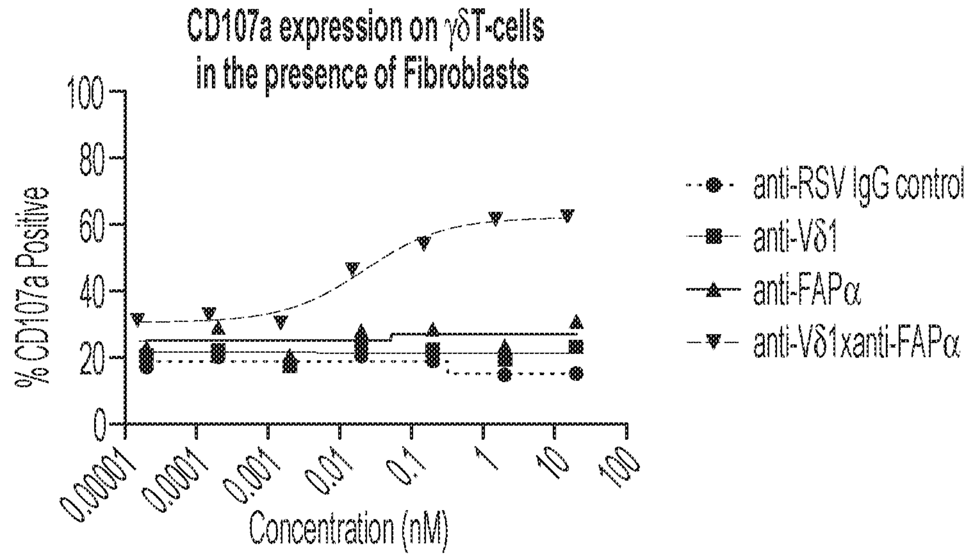
Figure 56I:
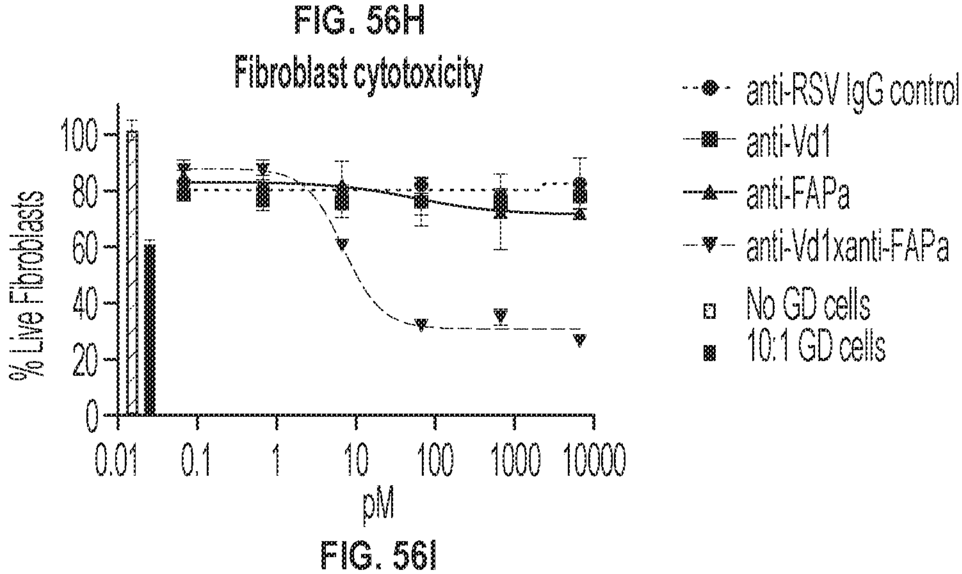
Figure 57A:
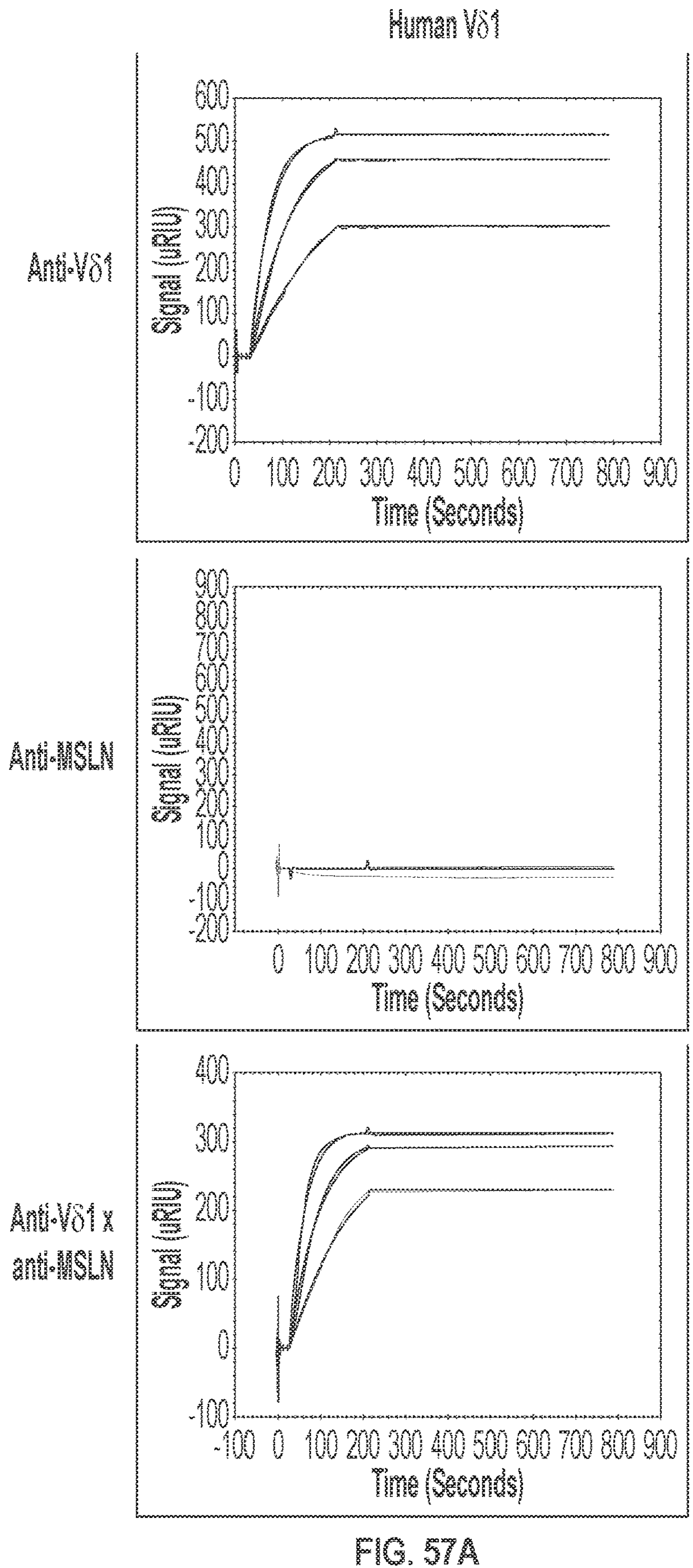
FIGS. 57A-57I: Vδ1×MSLN bispecific antibodies enhance Vδ1 γδT-cell activation and lysis of MSLN$^+$ target cells.
Figure 57B:
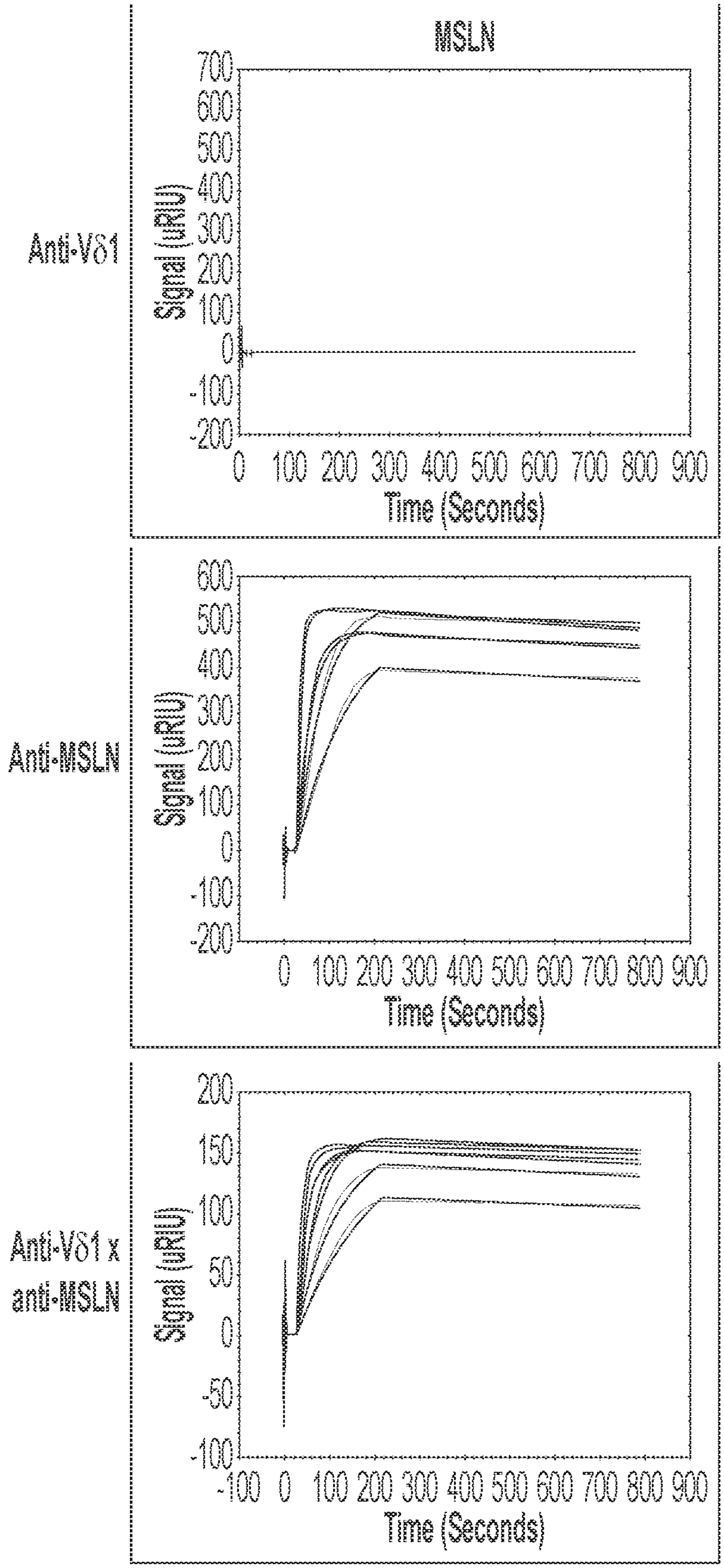
Figure 57C:
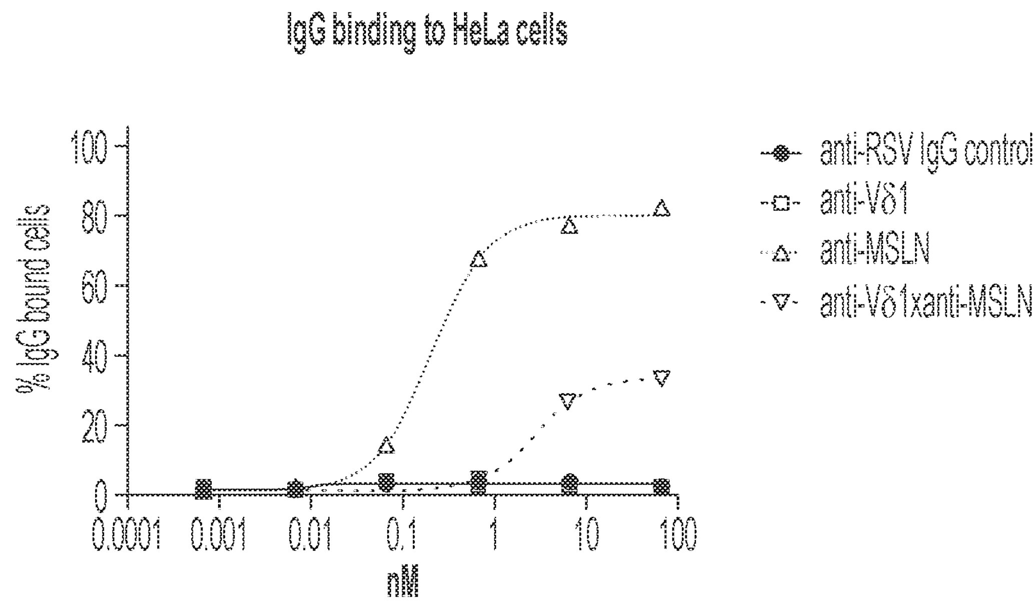
Figure 57D:
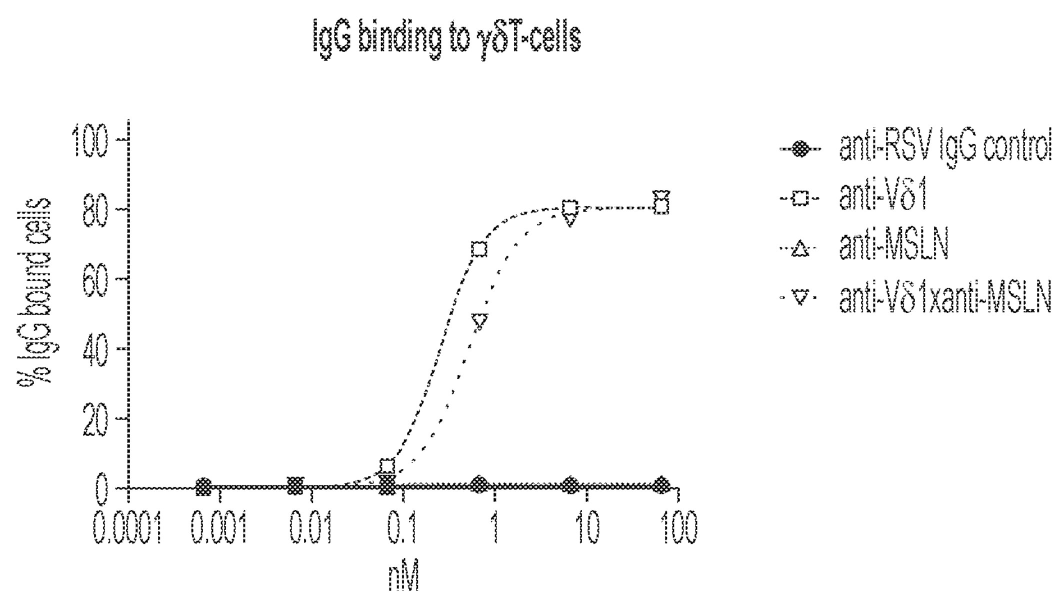
Figure 57E:
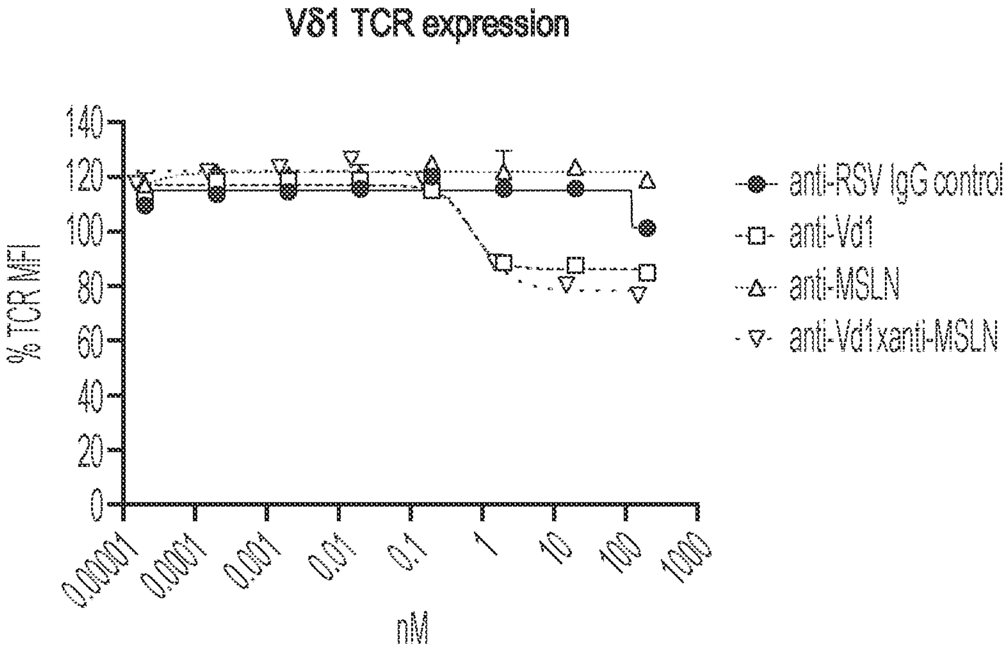
Figure 57F:
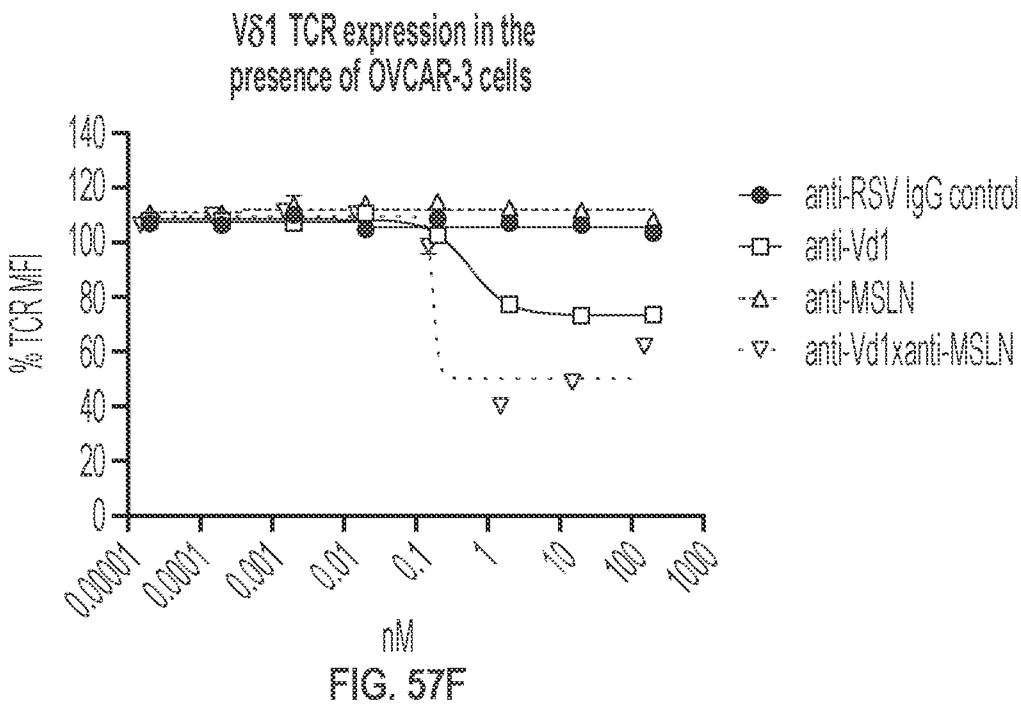
Figure 57G:
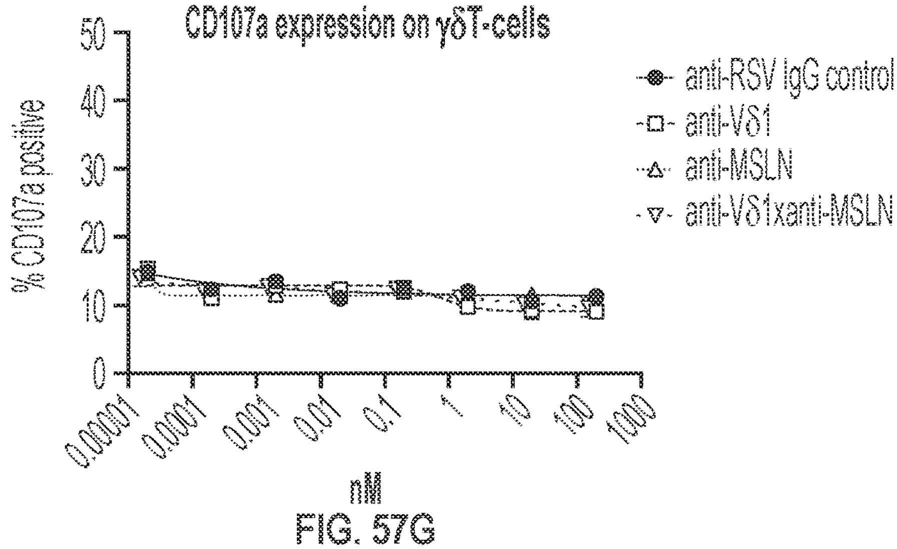
Figure 57H:
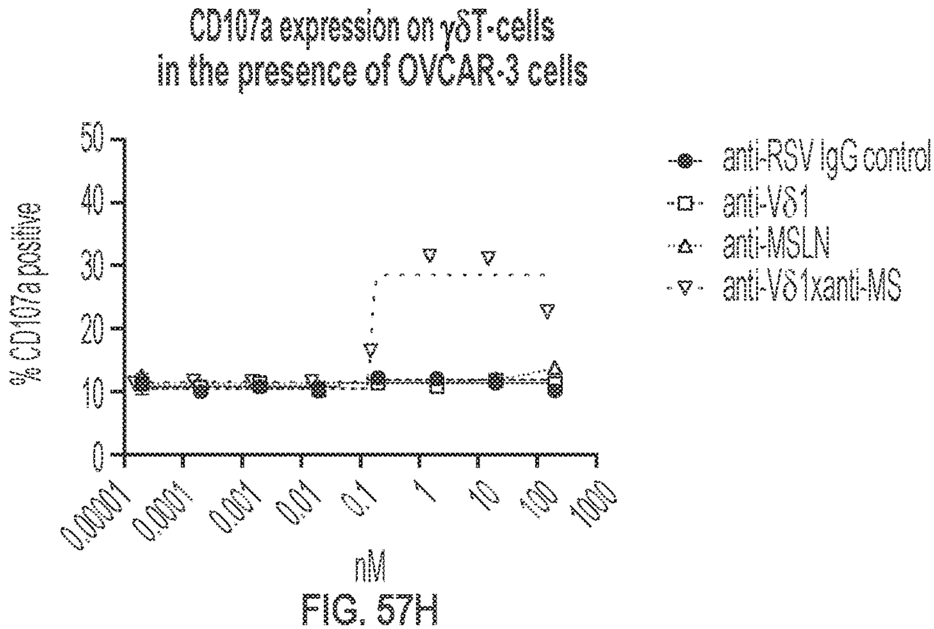
Figure 57I:
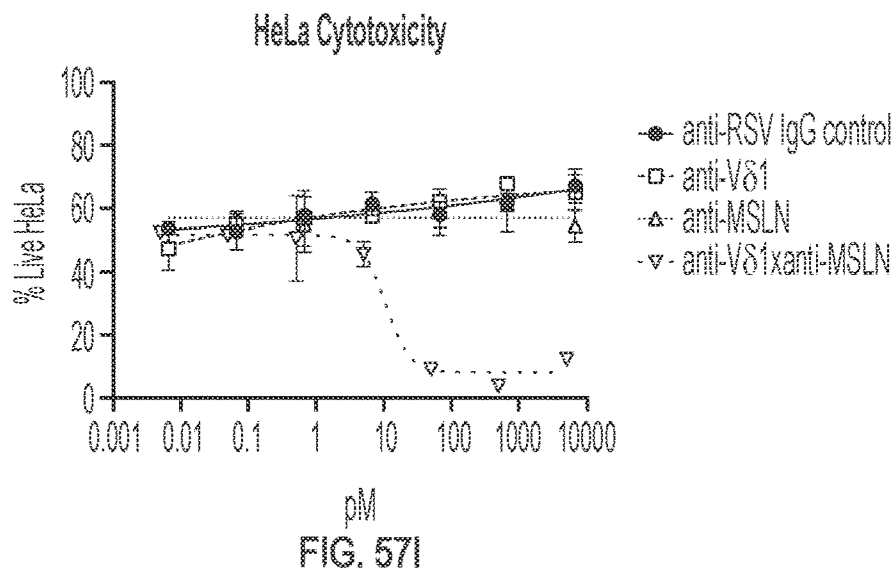

FIG. 55A shows the vδ1 TCR MFI upon antibody stimulation as an indication of mAb target engagement. FIG. 55B shows the MFI of CD3 expression on positively gated vδ1 cells. Stimulation with the vδ1 antibody clone ADT1-4-2 engaged vδ1 cells and resulted in down-regulation of both vδ1 and CD3 on vδ1 cells. Combined, FIGS. 55C, D and E show that activation of tumour-associated Vδ1 T cells with exemplar anti-Vδ1 antibodies as described herein does not deplete Vδ1+ T cells, but does engage and activate the CD3/γδ TCR complex and confer its downregulation and loss of surface expression. Specifically, FIG. 55C shows that absolute numbers of total γδ+ and γδ+Vδ1+ cells per well remains constant following stimulation with ADT-1-4-2 or anti-IgG1 isotype control. Despite the absolute numbers of Vδ1 T cells remaining consistent, FIG. 55D shows that the surface expression of Vδ1 TCR, pan γδ TCR and CD3 is downregulated on Vδ1 T cells following stimulation with ADT-1-4-2, but not with anti-IgG1 isotype control. In contrast, surface expression of CD45, a molecule not involved in TCR signalling, is unchanged following stimulation with ADT-1-4-2. FIG. 55E shows FACS plots representative of the data in FIG. 55D (mAb concentration 33.3 nM), with Vδ1 T cells labelled in grey. Here Vδ1+ T cells shift diagonally towards the bottom left of the plot as surface expression of CD3 and pan γδ is downregulated following stimulation with ADT-1-4-2 but not isotype controls (top panels as indicated), however the overall % pan γδ+ of CD45+ remains similar in both conditions. Further gating on Vδ1 expression (bottom panels) specifically shows reduced Vδ1 MFI following stimulation and to the point that a small fraction (~5%) moves from the established Vδ1 TCR positive gate and to the Vδ1 'negative' gate (with a concomitant ~5% increase in the 'negative' gate observed). Combined, these are critical data which exemplify that the activation of Vδ1 TCR with antibodies as described herein do not deplete Vδ1+ T cells. From such discoveries and the like it can be conceived that antibodies of this invention could be employed as medicaments to treat a disease or disorder such to ameliorate at least one sign or symptom of a disease or disorder through a mechanism involving the activation of blood, tissue and tumour resident Vδ1+ T cells.

Example 33. Vδ1-FAPα Bispecific Antibodies Enhance Vδ1 vδT-Cell Activation and Lysis of FAPα+ Fibroblasts The binding kinetics of the binding of anti-Vδ1 (ADT1-4-2), anti-FAPα (based on sibrotuzumab) and anti-Vδ1×FAPα (ADT1-4× sibrotuzumab) (SEQ ID NO: 401 or SEQ ID NO: 414 and SEQ ID NO: 415) antibodies to their targets (i.e. the Vδ1 chain of a γδ TCR and FAPα) are established by SPR analysis using a Reichert 4SPR instrument (Reichert Technologies). Antibody (1.5 ug/mL) is coated onto a Planar Protein A Sensor Chip (Reichert Technologies) to give an increase on baseline of approximately 500 uRIU. Recombinant human Vδ1 heterodimer or human FAPα was flown over the cell at a concentration of 100 nM with the following parameters: 180 s association, 480 s dissociation, flowrate 25 μL/min, running buffer PBS+0.05% Tween 20. All experiments were performed at room temperature. The results are shown in FIG. 56, A to B. The KD values are as follows:

| Antibody | KD Vδ1 [nM] | KD FAPα [nM] |
|---|---|---|
| Anti-Vδ1 (ADT1-4-2) | 0.14 nM | n/a |
| Anti-FAPα (based on sibrotuzumab) | n/a | 3.9 nM |
| Anti-Vδ1xFAPα (ADT1-4-2x sibrotuzumab) | 0.26 nM | 1.4 nM |

Binding of Vδ1-FAPα bispecific antibodies was determined by incubating FAPα+ target cells or Vδ1+ effector cells with a range of concentrations of anti-Vδ1 antibody or Vδ1 bispecific antibodies, or controls (IgG control or anti-FAPα) for 15 minutes. After washing, cells were incubated for a further 15 minutes with anti-human Fc secondary antibodies before washing and fixing. The amount of antibody bound to each cell type was determined by flow cytometry. The results are shown in FIG. 56, C to D.

To determine the effect of Vδ1-FAPα bispecific antibodies on Vδ1 γδ T-cell activation and degranulation, Vol TCR downregulation and CD107a upregulation was quantified in the presence of $FAP\alpha^+$ target cells. Briefly, anti-Vδ1, anti-FAPα and anti-Vδ1×FAPα bispecific antibodies were serially diluted in PBS before adding to U-bottomed 96-well plates. $FAP\alpha^+$ target cells (BJ fibroblasts or human dermal fibroblasts) were stained with [0.5 μM] CellTrace CFSE live cell dye for 20 minutes. Skin derived Vδ1 γδ T-cells were detached from culture flasks and cell suspensions were mixed 1:1 with $FAP\alpha^+$ target cells or diluted 1:1 with media. Cell suspensions were seeded into assay plates at 2.5×10^4 Vδ1 γδ T-cells per well in the presence or absence of 2.5×10^4 $FAP\alpha^+$ target cells per well. Final assay antibody concentrations range from 200 nM to 2 μM. The cells were incubated for 4 hours at 37° C., 5% CO2 before washing and staining for dead cells (eFlour 520, Invitrogen), Vδ1 TCR (MiltenyiBiotec) and aCD107a (Miltenyi) surface expression for 30 minutes at 4° C. The cells were washed in FACS buffer and resuspended in Cell Fix (BD sciences) before incubating overnight at 4° C. in the dark. The VD1 TCR and CD107a expression level, determined by median fluorescence intensity (MFI), was measured by flow cytometry the following day using the MACS Quant Analyzer 16. The results are shown in FIG. 56 E-H.

Moderate Vδ1 TCR downregulation is observed in the absence of FAPα+ fibroblasts (FIG. 56, E). However, in the presence of FAPα+ fibroblasts, anti-FAPα-Vδ1 bispecific antibodies greatly enhance TCR downregulation (FIG. 56, F). This shows the effect of anti-FAPα-Vδ1 bispecific antibodies on Vδ1 TCR downregulation on Vδ1 γδT-cells is enhanced by via binding to a tumour specific antigen such as FAPα, on adjacent cells.

In the presence of anti-Vδ1×FAPα bispecific antibodies and FAPα+ fibroblasts, CD107a (a marker of degranulation) is upregulated on Vδ1 γδT-cells compared to monoclonal controls (FIG. 56, H), When the FAPα+ fibroblasts are not present, CD107a is not upregulated on Vδ1 γδT-cells compared to monoclonal controls (FIG. 56, G), This shows the effect of anti-FAPα-Vδ1 bispecific antibodies on CD107a upregulation on Vδ1 γδ T-cells is specific and the anti-FAPα-Vδ1 bispecific antibodies enhance the degranulation and activation of Vδ1 γδT-cells in the presence of FAPα+ cells.

The effect of FAPα-Vδ1 bispecific antibodies on FAPα$^+$ target cell cytotoxicity was determined using high content confocal imaging in the Opera Phenix (Perkin Elmer). FAPα$^+$ target cells (BJ fibroblasts, human dermal fibroblasts) were seeded into 384-well imaging plates (Perkin Elmer) and incubated for 24 hours. Bispecific antibodies and controls were serially diluted into PBS before adding to assay plates. Expanded skin derived Vδ1 γδ T-cells were detached from tissue culture flasks and re-suspended in basal growth media before adding to assay plates for an Effector: Target ratio of 1:1. Final assay antibody concentrations ranged between 6.6 nM to 66 fM. Cells were co-cultured for 24 hours before staining with DRAQ7 (1:300 final, Abcam) and Hoechst (1:1,000, Invitrogen). To determine the numbers of live target cells, confocal images were acquired using an Opera Phenix high content platform capturing nine fields of view at 10× magnification. Live cell counts were quantified base on size, morphology, texture and intensity of Hoechst staining and the absence of DRAQ7 staining. The results are shown in FIG. 56, I. In the presence of anti-FAPα-Vδ1 bispecific antibodies, a marked increase in fibroblast cytotoxicity was observed compared to anti-Vδ1 and anti-FAPα controls (FIG. 56, I). This demonstrates that directly bridging Vδ1 γδ T-cells with target cells can specifically enhance the activation and cytotoxic effect of Vδ1 γδ T-cells.

Conclusions: Anti-Vδ1-FAPα bispecific antibodies bind specifically to Vδ1+γδ T-cells and FAPα$^+$ target cells resulting in enhanced activation of Vδ1 γδ T-cells in the presence of FAPα+ cells, indicated by elevated Vol TCR downregulation, CD107a upregulation, and lysis of FAPα+ fibroblasts.

Example 34. Vδ1-MSLN Bispecific Antibodies Enhance Vδ1 γδT-Cell Activation and Lysis of MSLN$^+$ Target Cells The binding kinetics of the binding of anti-Vδ1 (ADT1-4-2), anti-MSLN (Mesothelin) (based on antibodies disclosed in US 2014/0004121) and anti-Vδ1×MSLN (ADT1-4-2×MSLN) (SEQ ID NO: 403 or SEQ ID NO: 414 and SEQ ID NO: 416) antibodies to their targets (i.e. the Vδ1 chain of a γδ TCR and MSLN) is established by SPR analysis using a Reichert 4SPR instrument (Reichert Technologies). Antibody (1.5 ug/mL) is coated onto a Planar Protein A Sensor Chip (Reichert Technologies) to give an increase on baseline of approximately 500 uRIU. Recombinant human Vδ1 heterodimer or human MSLN was flown over the cell at a top concentration of 100 nM with the following parameters: 180 s association, 480 s dissociation, flowrate 25 μL/min, running buffer PBS+0.05% Tween 20. All experiments were performed at room temperature. The results are shown in FIG. 57, A. The KD values are as follows:

| Antibody | KD Vδ1 [nM] | KD FAPα [nM] |
|---|---|---|
| Anti-Vδ1 (ADT1-4-2) | 0.01 nM | n/a |
| Anti-MSLN (based on antibodies disclosed in US 2014/0004121) | n/a | 0.52 nM |
| Anti-Vδ1xMSLN (ADT1-4-2xMSLN) | 0.026 nM | 0.87 nM |

Binding of MSLN-Vδ1 bispecific antibodies was determined by incubating MSLN$^+$ target cells or Vδ1+ effector cells with a range of concentrations of anti-Vδ1 antibody or Vδ1 bispecific antibodies, or controls (IgG control or anti-MSLN) for 15 minutes. After washing, cells were incubated for a further 15 minutes with anti-human IgG secondary antibodies before washing and fixing. The amount of antibody bound to each cell type was determined by flow cytometry. The results are shown in FIG. 57, B to C.

To determine the effect of MSLN-Vδ1 bispecific antibodies on Vδ1 γδ T-cell activation and degranulation, Vol TCR downregulation and CD107a upregulation was quantified in the presence of MSLN$^+$ target cells. Briefly, anti-Vol, anti-MSLN and anti-Vδ1×MSLN bispecific antibodies were serially diluted in PBS before adding to U-bottomed 96-well plates. MSLN$^+$ target cells (OVCAR-3 or HeLa) were stained with [0.5 μM] CellTrace CFSE live cell dye for 20 minutes. Skin derived Vδ1 γδ T-cells were detached from culture flasks and cell suspensions were mixed 1:1 with MSLN$^+$ target cells or diluted 1:1 with media. Cell suspensions were seeded into assay plates at 2.5×10^4 Vδ1 γδ T-cells per well in the presence or absence of 2.5×10^4 MSLN$^+$ target cells per well. Final assay antibody concentrations range from 200 nM to 2 μM. The cells were incubated for 4 hours at 37° C., 5% CO2 before washing and stained for dead cells (eFlour 520, Invitrogen), Vδ1 TCR (MiltenyiBiotec) and aCD107a (Miltenyi) surface expression for 30 minutes at 4° C. The cells were washed in FACS buffer and resuspended in Cell Fix (BD sciences) before incubating overnight at 4° C. in the dark. The VD1 TCR and CD107a expression level, determined by median fluorescence intensity (MFI), was measured by flow cytometry the following day using the MACS Quant Analyzer 16. The results are shown in FIG. 57 D-G.

Moderate Vδ1 TCR downregulation is observed in the absence of MSLN$^+$ target cells (FIG. 57, D). However in the presence of MSLN$^+$ OVCAR-3 cells, anti-MSLN-Vδ1 bispecific antibodies greatly enhance TCR downregulation (FIG. 57, E). This shows the effect of anti-MSLN-Vδ1 bispecific antibodies on Vδ1 TCR downregulation on Vδ1 γδ T-cells is enhanced by via binding to a tumour specific antigen such as MSLN, on adjacent cells.

In the presence of anti-Vδ1×MSLN bispecific antibodies and MSLN$^+$ OVCAR-3 cells, CD107a (a marker of degranulation) is upregulated on Vδ1 γδT-cells compared to monoclonal controls (FIG. 57, G), When the MSLN$^+$ OVCAR-3 cells are not present, CD107a is not upregulated on Vδ1

γδT-cells compared to monoclonal controls (FIG. 57, F), This shows the effect of anti-MSLN-Vδ1 bispecific antibodies on CD107a upregulation on Vδ1 γδ T-cells is specific and the anti-MSLN-Vδ1 bispecific antibodies enhance the degranulation and activation of Vδ1 γδT-cells in the presence of MSLN+ cells.

The effect of MSLN-Vδ1 bispecific antibodies on $MSLN^+$ target cell cytotoxicity was determined using high content confocal imaging in the Opera Phenix (Perkin Elmer). $MSLN^+$ target cells (HeLa or OVCAR-2) were seeded into 384-well imaging plates (Perkin Elmer) and incubated for 24 hours. Bispecific antibodies and controls were serially diluted into PBS before adding to assay plates. Expanded skin derived Vδ1 γδ T-cells were detached from tissue culture flasks and re-suspended in basal growth media before adding to assay plates for an Effector:Target ratio of 1:1. Final assay antibody concentrations ranged between 6.6 nM to 66 fM. Cells were co-cultured for 24 hours before staining with DRAQ7 (1:300 final, Abcam) and Hoechst (1:1,000, Invitrogen). To determine the numbers of live target cells, confocal images were acquired using an Opera Phenix high content platform capturing nine fields of view at 10× magnification. Live cell counts were quantified base on size, morphology, texture and intensity of Hoechst staining and the absence of DRAQ7 staining. The results are shown in FIG. 57, H. In the presence of anti-MSLN-Vδ1 bispecific antibodies, a marked increase in target cell cytotoxicity was observed compared to anti-Vδ1 and anti-MSLN controls (FIG. 57, H). This demonstrates that directly bridging Vδ1 γδ T-cells with target cells can specifically enhance the activation and cytotoxic effect of Vδ1 γδ T-cells.

Conclusions: Anti-Vδ1×MSLN bispecific antibodies bind specifically to Vδ1+γδ T-cells and $MSLN^+$ target cells resulting in enhanced activation of Vδ1 γδT-cells in the presence of MSLN+ cells, indicated by elevated Vol TCR downregulation, CD107a upregulation, and lysis of $MSLN^+$ target cells.

Figure 58A:
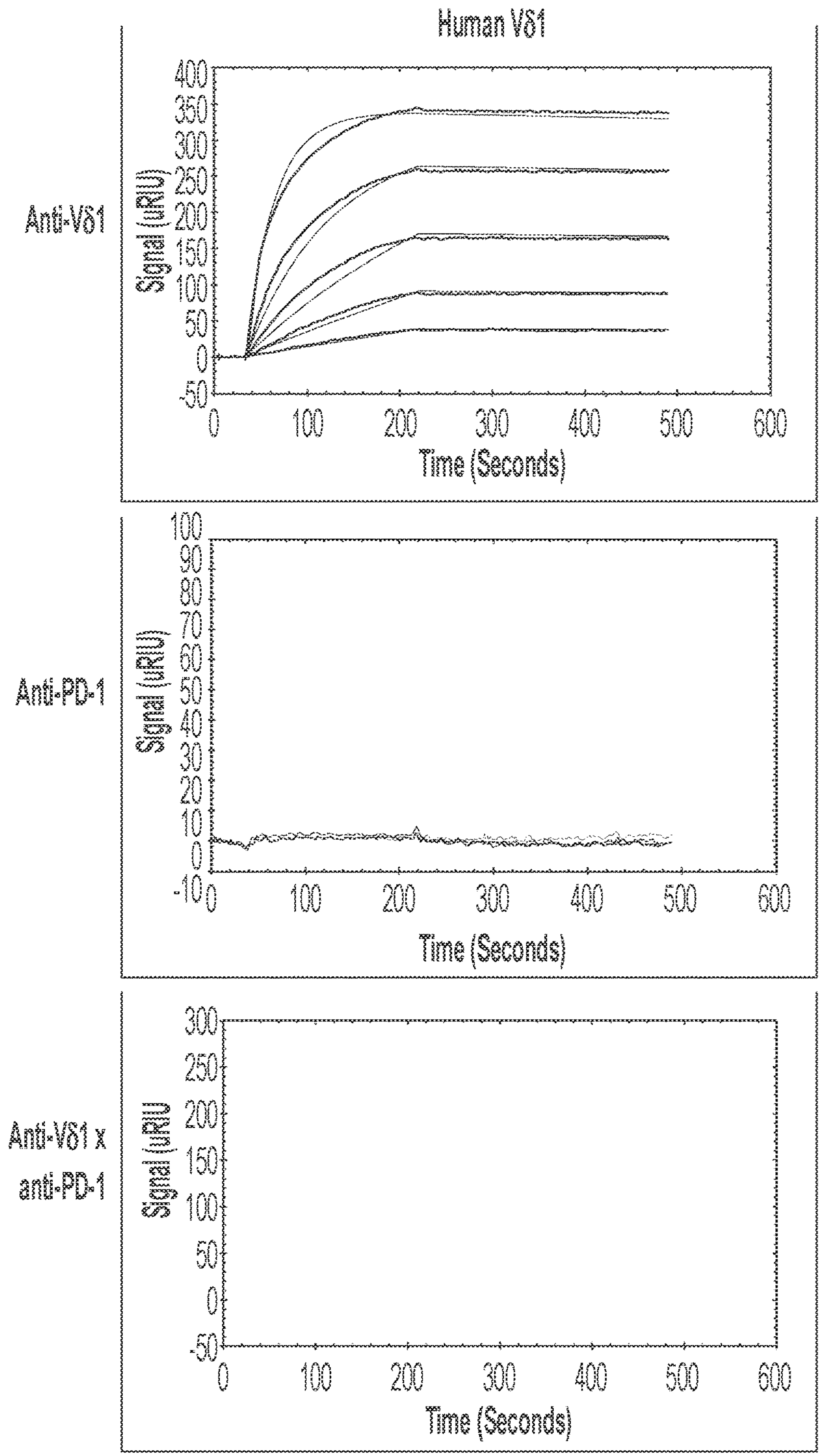
FIGS. 58A-58H: Vδ1×PD-1 bispecific antibodies enhance activation of Vδ1 γδT-cells and inhibit checkpoint blockade of PD-1+ T-cells.
Figure 58B:
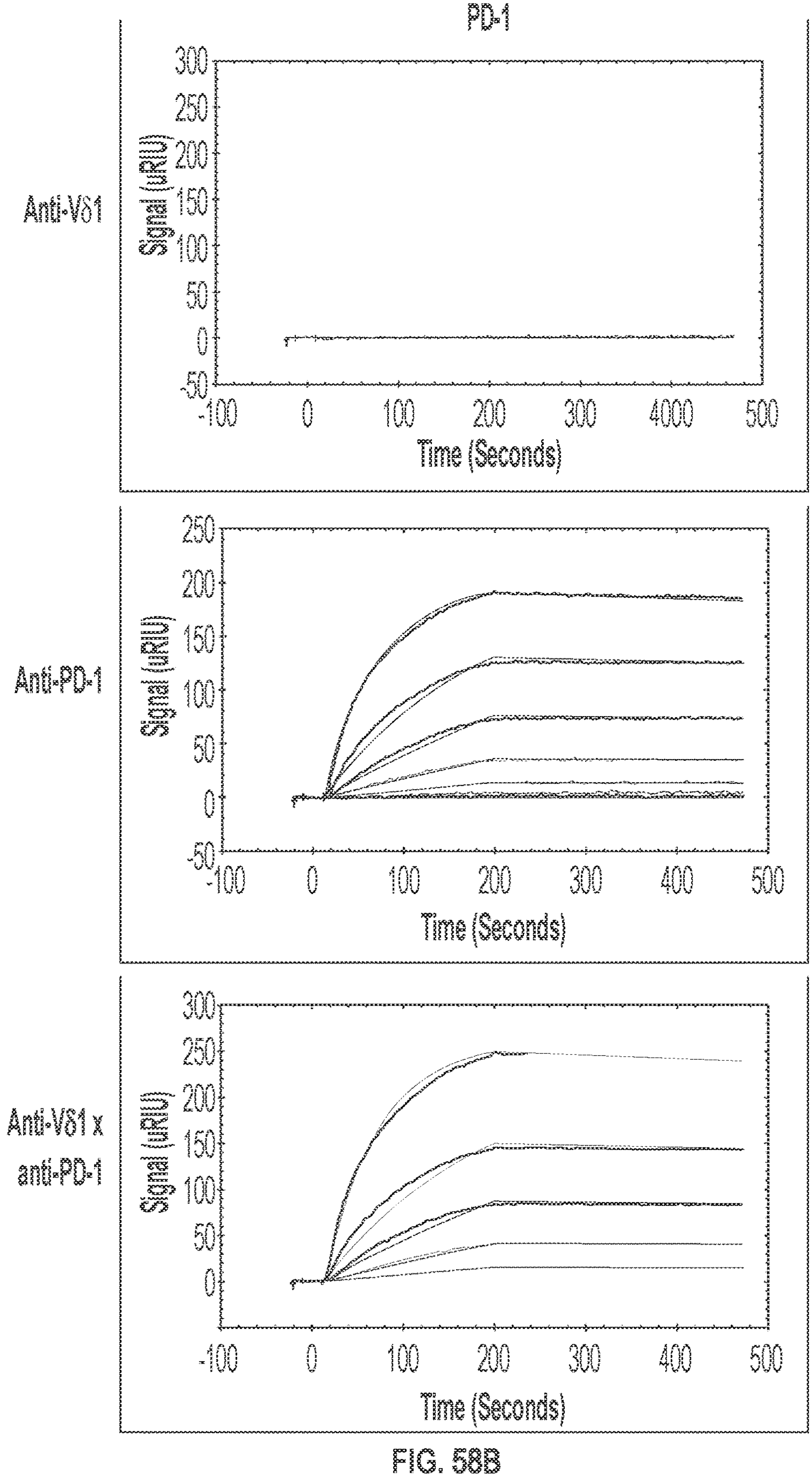
Figure 58C:
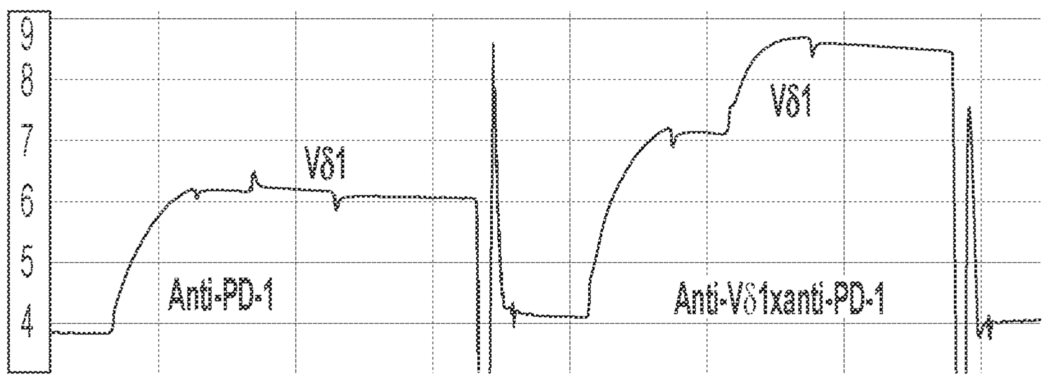
Figure 58D:
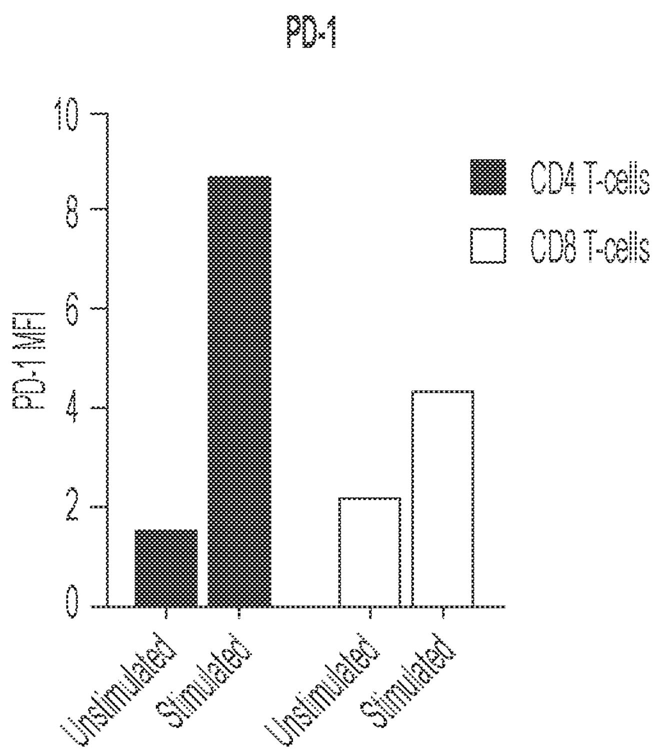
Figure 58E:
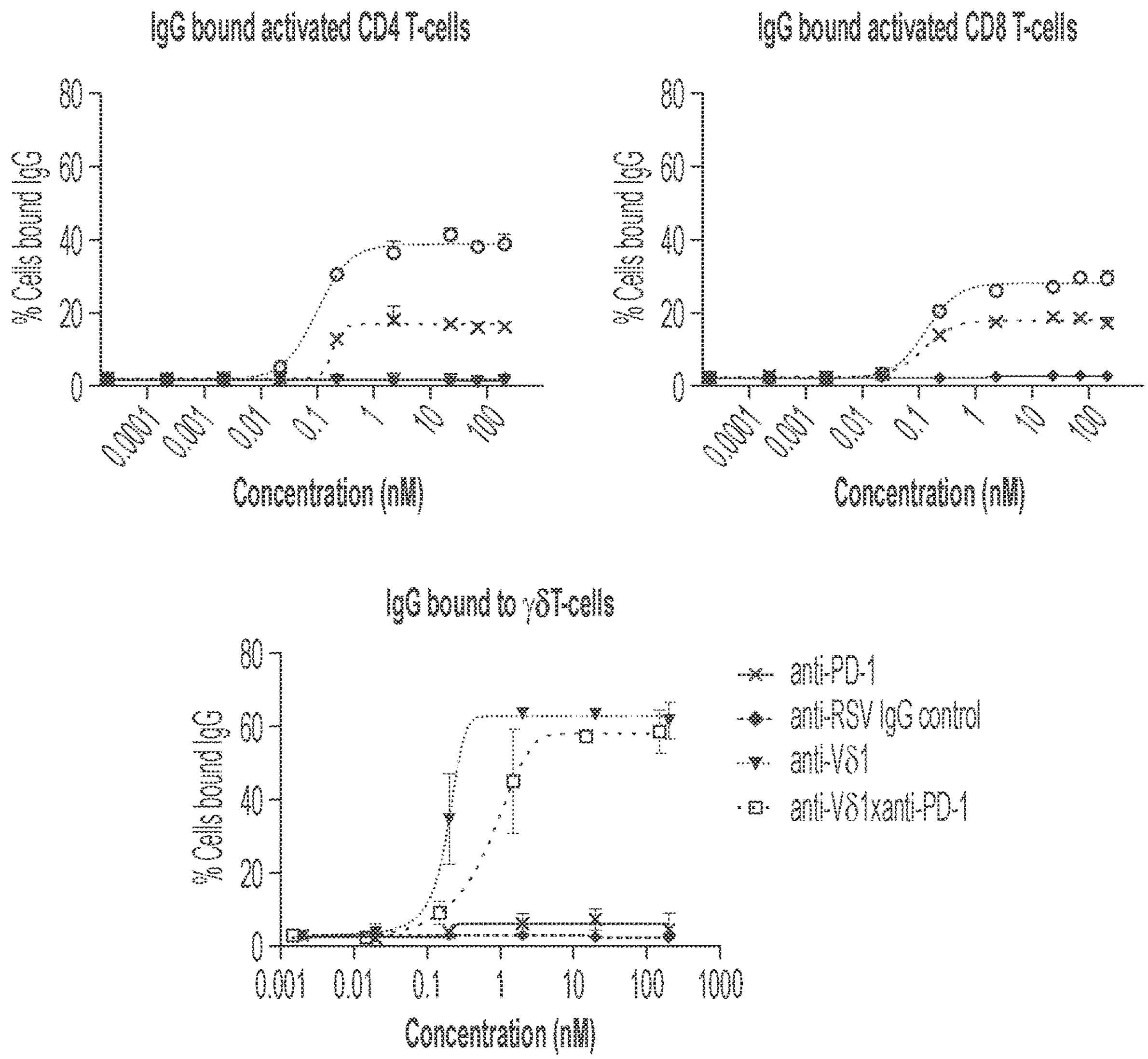
Figure 58F:
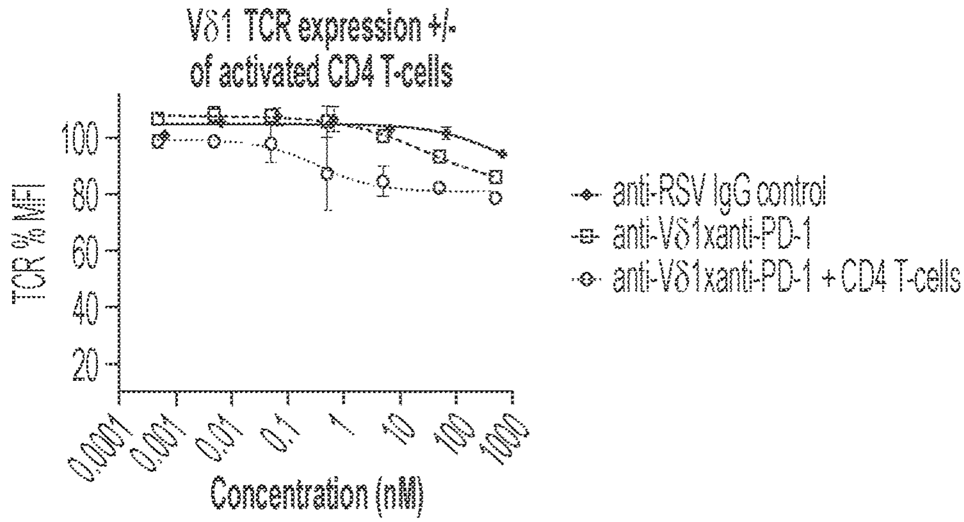
Figure 58G:
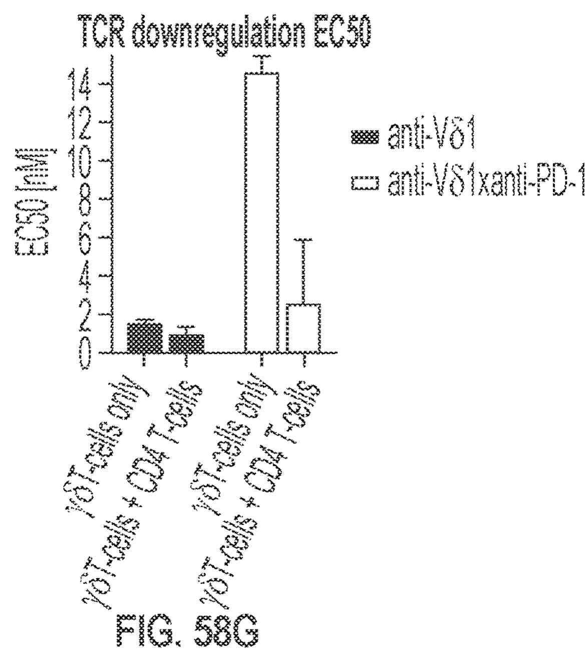
Figure 58H:
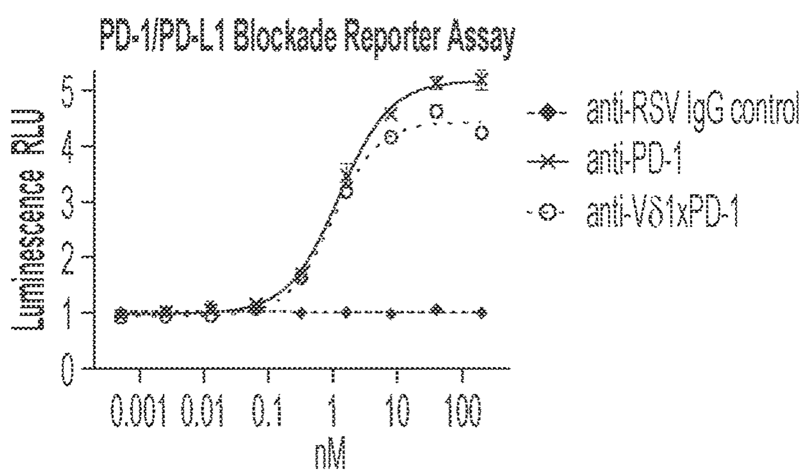

Example 35. Vol-PD-1 Bispecific Antibodies Enhance Vδ1 γδT-Cell Activation and Block PD-1/PD-L1 Checkpoint Inhibition The binding kinetics of the binding of anti-Vδ1 (ADT1-4-2), anti-PD-1 (based on pembrolizumab) and anti-Vδ1×PD-1 (ADT1-4-2× pembrolizumab) (SEQ ID NO: 405 or SEQ ID NO: 438 and SEQ ID NO: 417) antibodies to bind (i.e. the Vδ1 chain of a γδ TCR and PD-1) is established by SPR analysis using a Reichert 4SPR instrument (Reichert Technologies). Antibody (1.5 ug/mL) is coated onto a Planar Protein A Sensor Chip (Reichert Technologies) to give an increase on baseline of approximately 500 uRIU. Recombinant human Vδ1 heterodimer or human PD-1 was flown over the cell at a top concentration of 100 nM. The results are shown in FIG. 58A. The $K_D$ values are as follows:

| | VD1 KD [nM] | TIGIT KD [nM] |
|---|---|---|
| Anti-Vδ1 (ADT1-4-2) | 0.29 | n/a |
| Anti-PD-1 (based on pembrolizumab) | n/a | 0.95 |
| Anti-Vδ1xAnti-PD-1 (ADT1-4-2xpembrolizumab) | 1.5 | 0.9 |

To assess the dual binding of bispecific antibodies to both target ligands, recombinant PD-1 was first immobilised on a Carboxymethyl Dextran Sensor Chip (Reichert Technologies) at 10 ug/ml before flowing over the bispecific antibodies at 100 nM. The ability to subsequently bind to the Vδ1 γδ TCR was then assessed by flowing over recombinant human Vδ1 heterodimer at 100 nM. All experiments were performed at room temperature. The results are shown in FIG. 58 B.

Binding of anti-Vδ1×PD-1 bispecific antibodies to Vδ1 γδ T-cells and PD-1+ immune cells was assessed by flow cytometry. Initially CD4 and CD8 T-cells were negatively selected by magnetic sorting from PBMC buffy coats extracted from whole blood. Following activation by anti-CD3/anti-CD28 antibodies conjugated to Dynabeads (Invitrogen), cell surface expression of PD-1 was detected on CD4 and CD8 T-cells. Activated T-cells and Vδ1 γδ T-cells were incubated with a range of concentrations of anti-Vδ1×PD-1 bispecific antibodies or controls (IgG control or anti-PD-1) for 15 minutes. After washing, cells were incubated for a further 15 minutes with anti-human IgG secondary antibodies before washing and fixing. The amount of antibody bound to each cell type was determined by flow cytometry. The results are shown in FIG. 58 C, D.

To determine the effect of anti-Vδ1×PD-1 bispecific antibodies on Vδ1 γδ T-cell activation, Vδ1 TCR downregulation was quantified in the presence of PD-1+ T-cells. Briefly, anti-Vδ1, anti-PD-1 and anti-Vδ1×PD-1 bispecific antibodies were serially diluted in PBS before adding to assay plates. PD-1+ T-cells were stained with CellTrace CFSE live cell dye and mixed 1:1 with skin derived Vδ1 γδ T-cells or diluted 1:1 with media. Cell suspensions were seeded into assay plates at 2.5×10^4 Vδ1 γδ T-cells per well in the presence or absence of 2.5×10^4 PD-1+ T-cells per well. Final assay antibody concentrations range from 200 nM to 2 μM. Cells were incubated for 4 hours at 37° C., 5% CO2 before washing and stained for dead cells (eFlour 520, Invitrogen) and Vδ1 TCR (MiltenyiBiotec). Cells were washed and resuspended in Cell Fix (BD sciences). VD1 TCR expression level was determined by median fluorescence intensity (MFI), measured by flow cytometry using the MACS Quant Analyzer 16. The results are shown in FIG. 58 E, F.

To assess the effect of anti-Vδ1×PD-1 bispecific antibodies on the activation of PD-1+ T-cells, $PD-1^+$ NFAT Jurkat cells (Promega, JA2191) were incubated with anti-Vδ1×PD-1 bispecific antibodies or controls (PD-1 monoclonal antibody or anti-RSVIgG×anti-PD-1) for 5 hours at 37° C., 5% CO2. The assay was performed in the presence or absence of recombinant Vδ1 protein pre-coated at 1 μg/well in opaque, white 96-well plates. After 5 hours, Bio-Glo Luciferase reagent (Promega) was added to cells in a 1:1 ratio. After incubating for 5 minutes at room temperature the luminescence signal was detected on a BioTek Synergy plate reader. Raw luminescence signal was converted to fold relative luminesence units (RLU). The results are shown in FIG. 58 G.

Conclusions: anti-Vδ1×PD-1 bispecific antibodies enhance the activation of Vδ1 γδ T-cells, for example by crosslinking via PD-1+CD4 or CD8 T-cells, as well as blocking the PD-1/PD-L1 immune checkpoint inhibition in CD4 or CD8 T-cells.

Figure 59A:
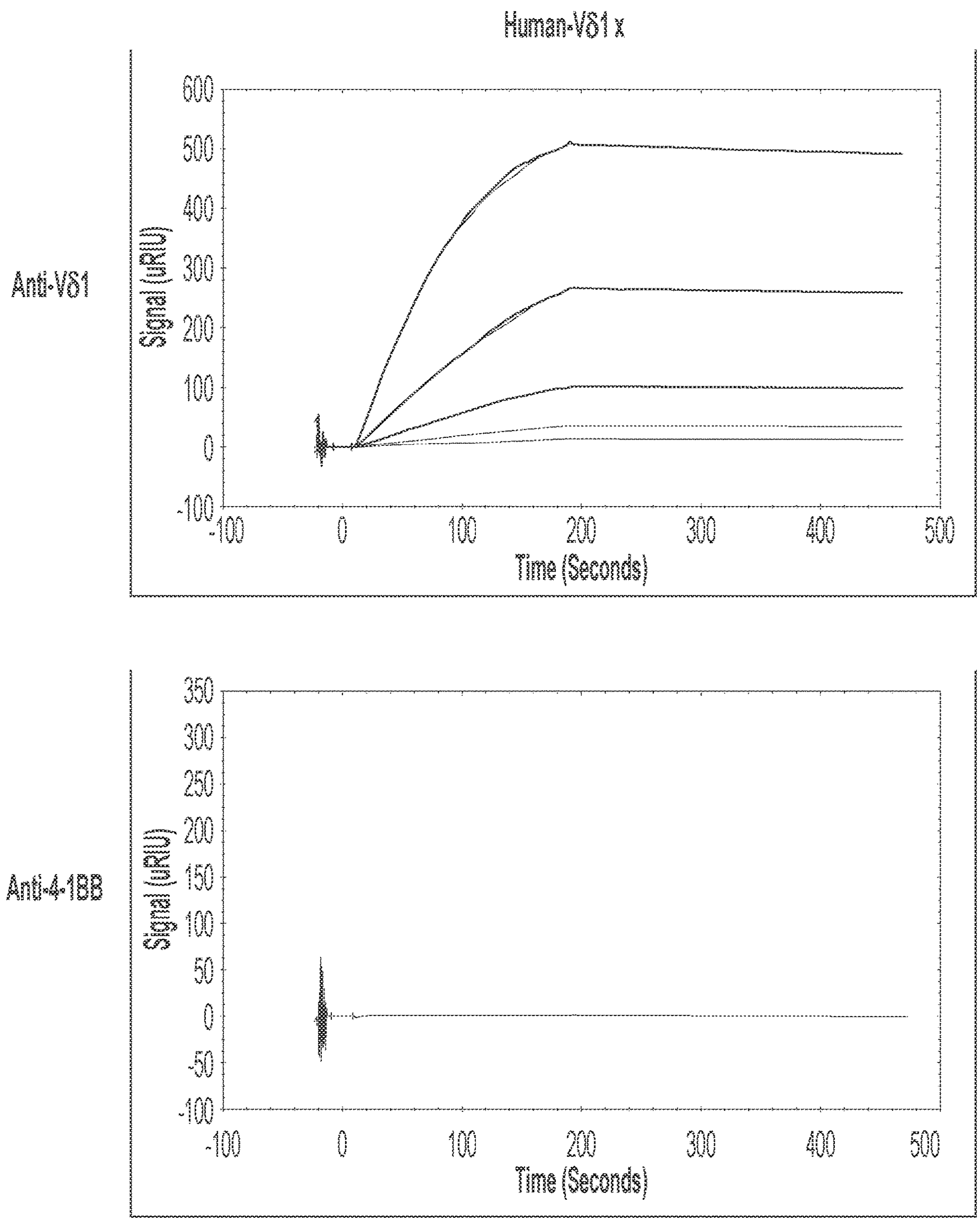
FIGS. 59A-59J: Vδ1×4-1BB bispecific antibodies enhance activation of Vδ1 γδT-cells and 4-16B+ T-cells.
Figure 59B:
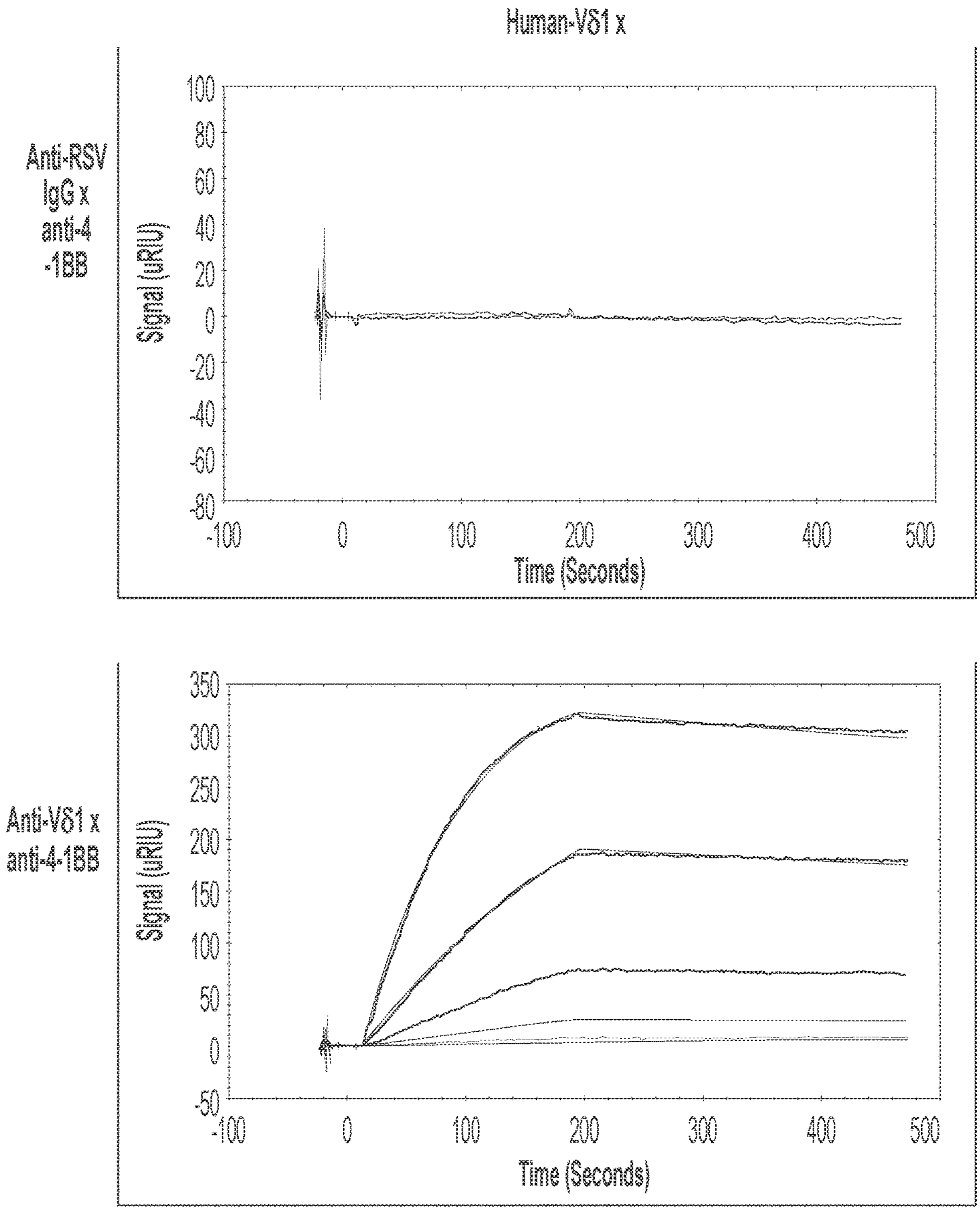
Figure 59C:
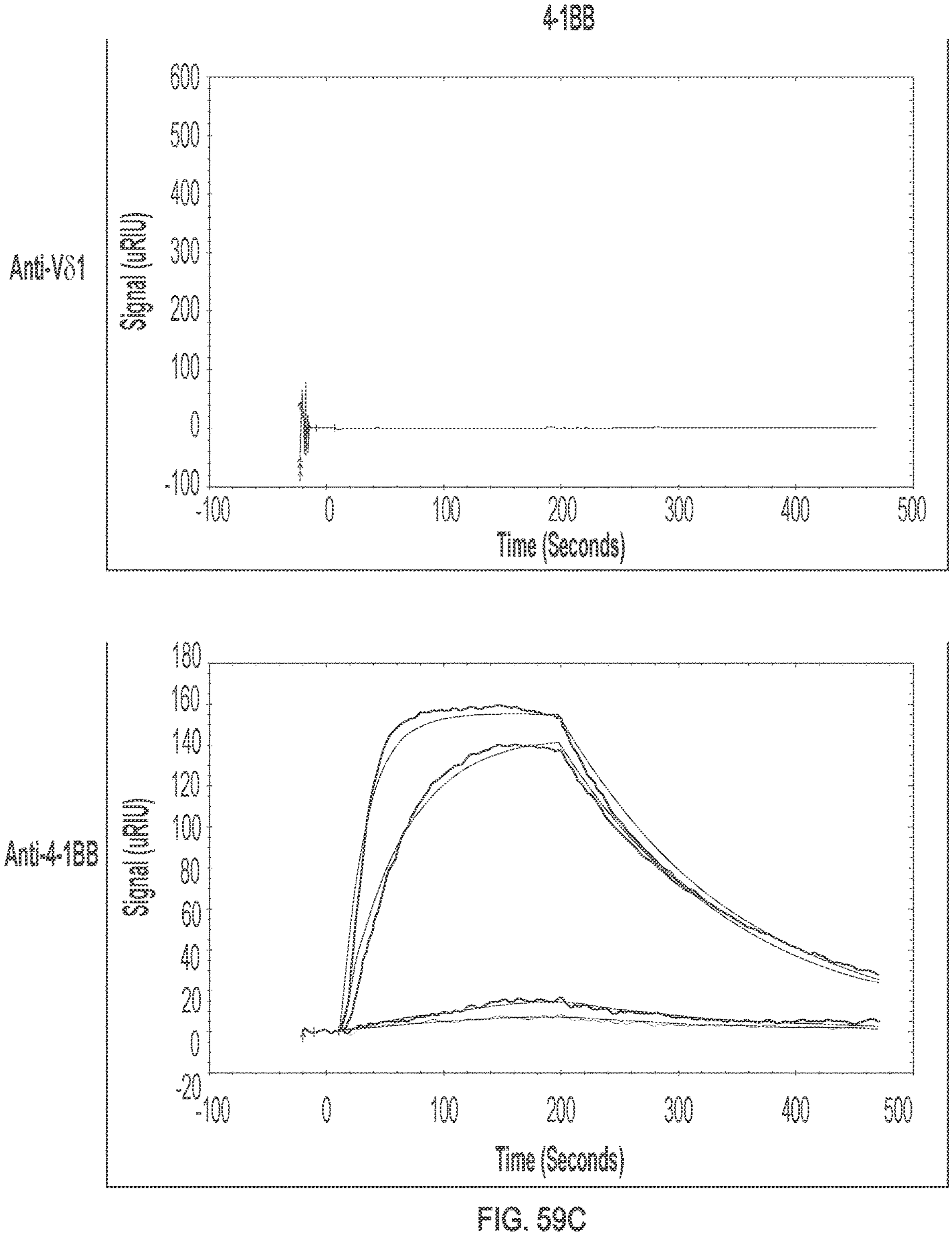
Figure 59D:
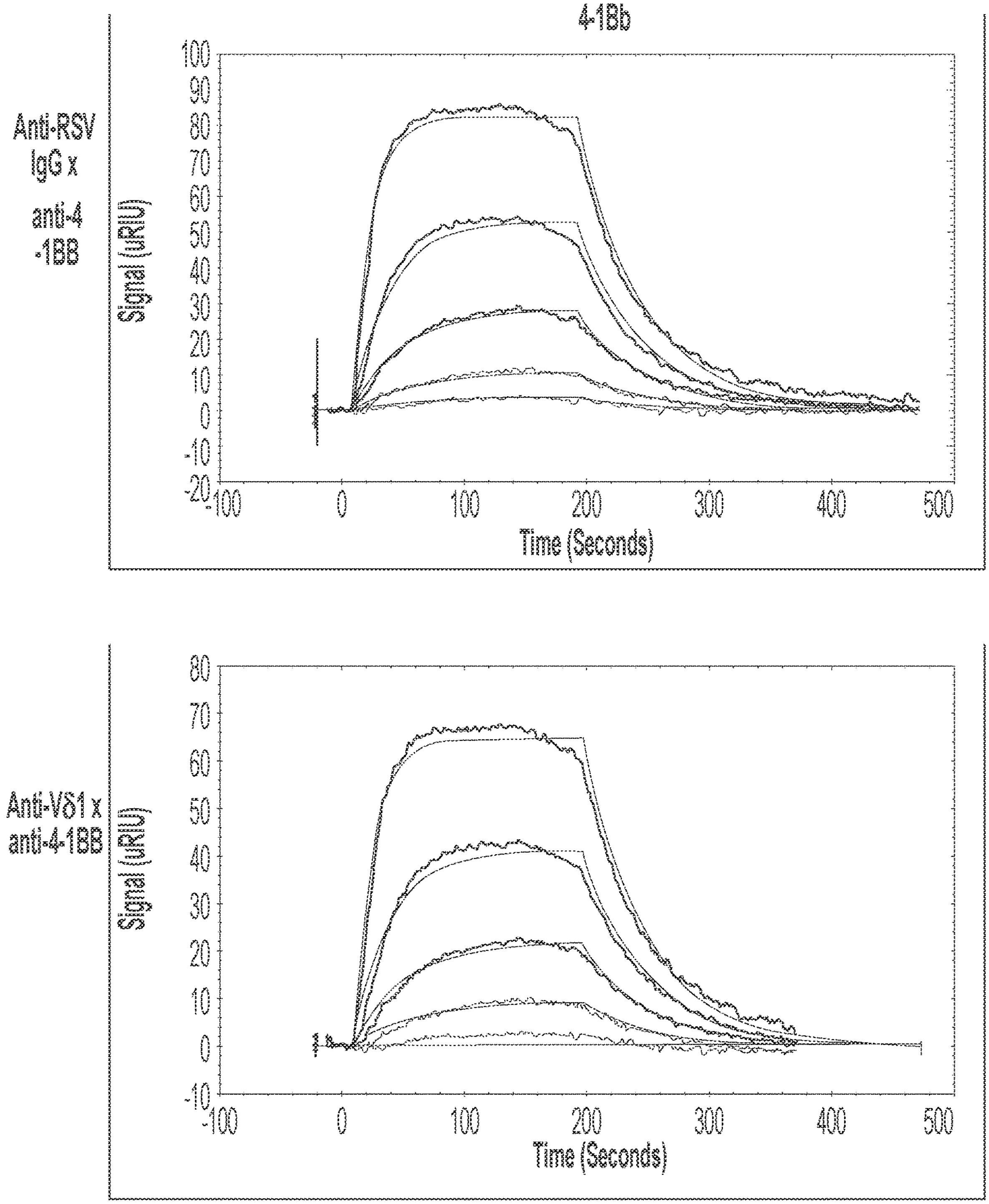
Figure 59E:
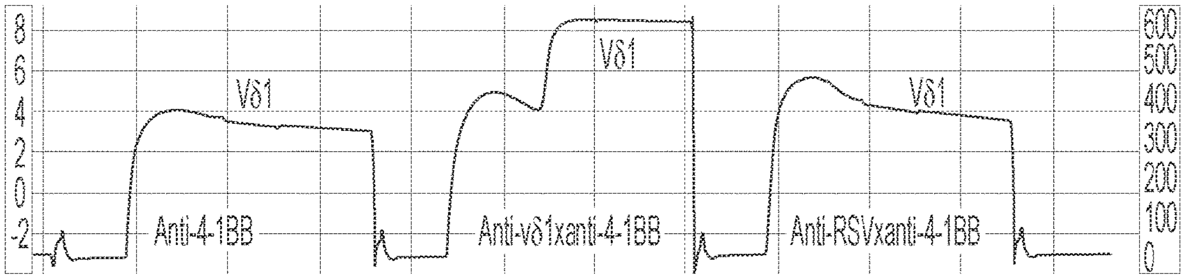
Figure 59F:
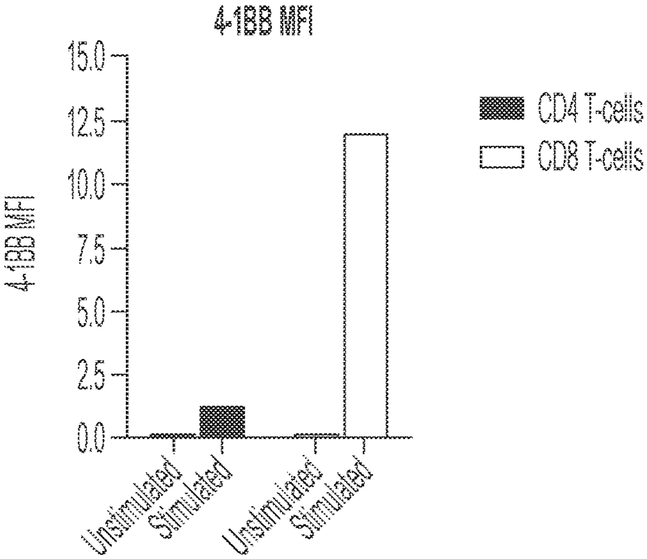
Figure 59G:
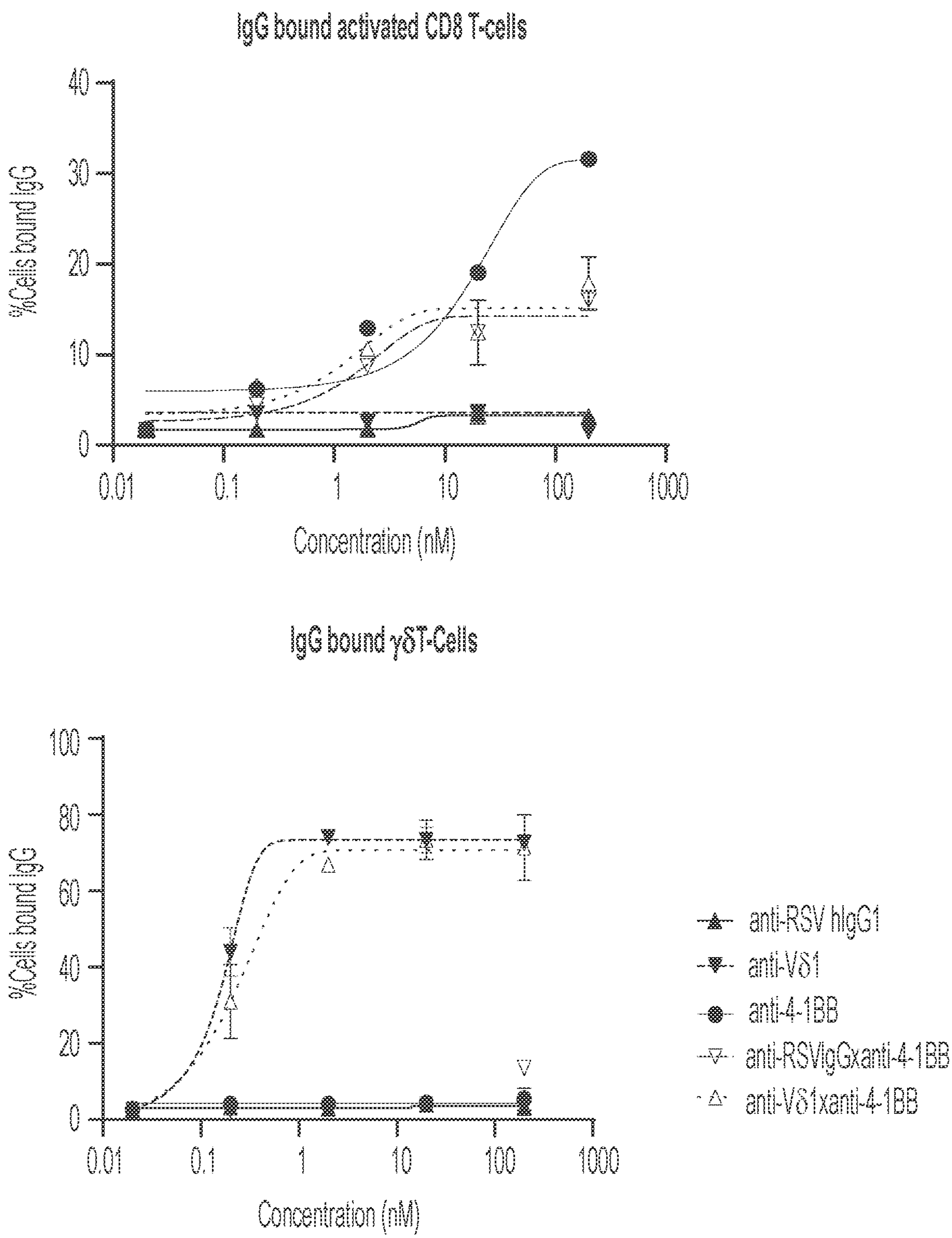
Figure 59H:
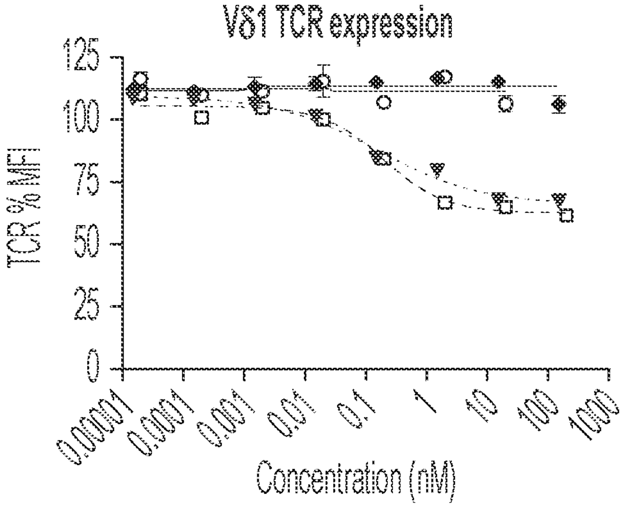
Figure 59I:
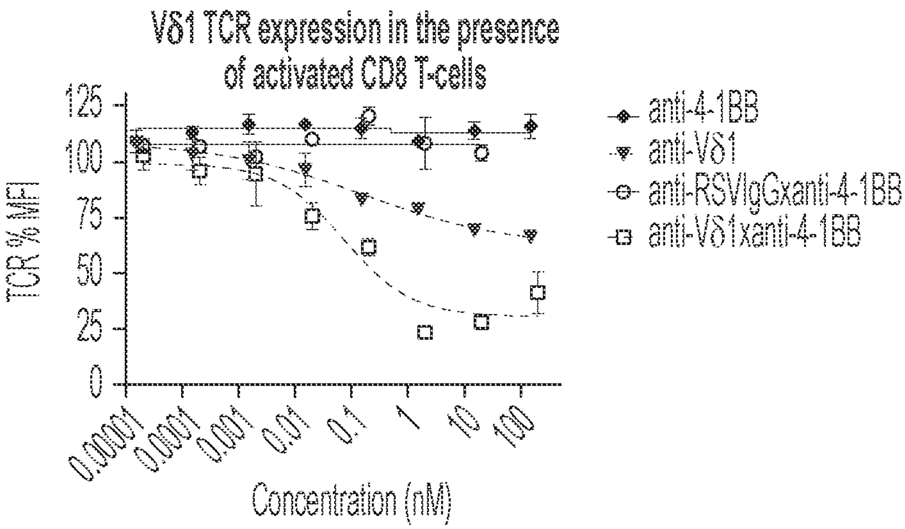
Figure 59J:
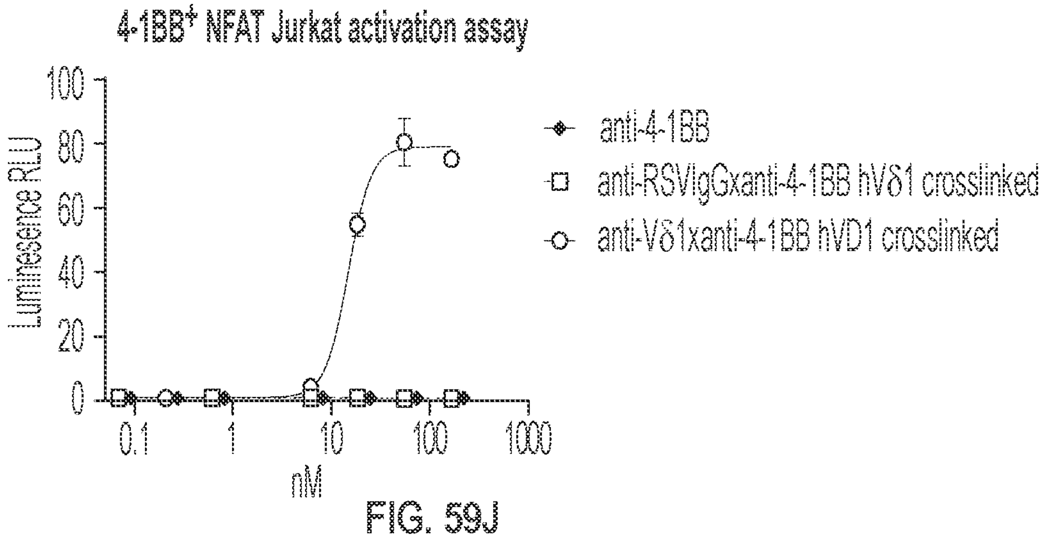
Figure 60A:
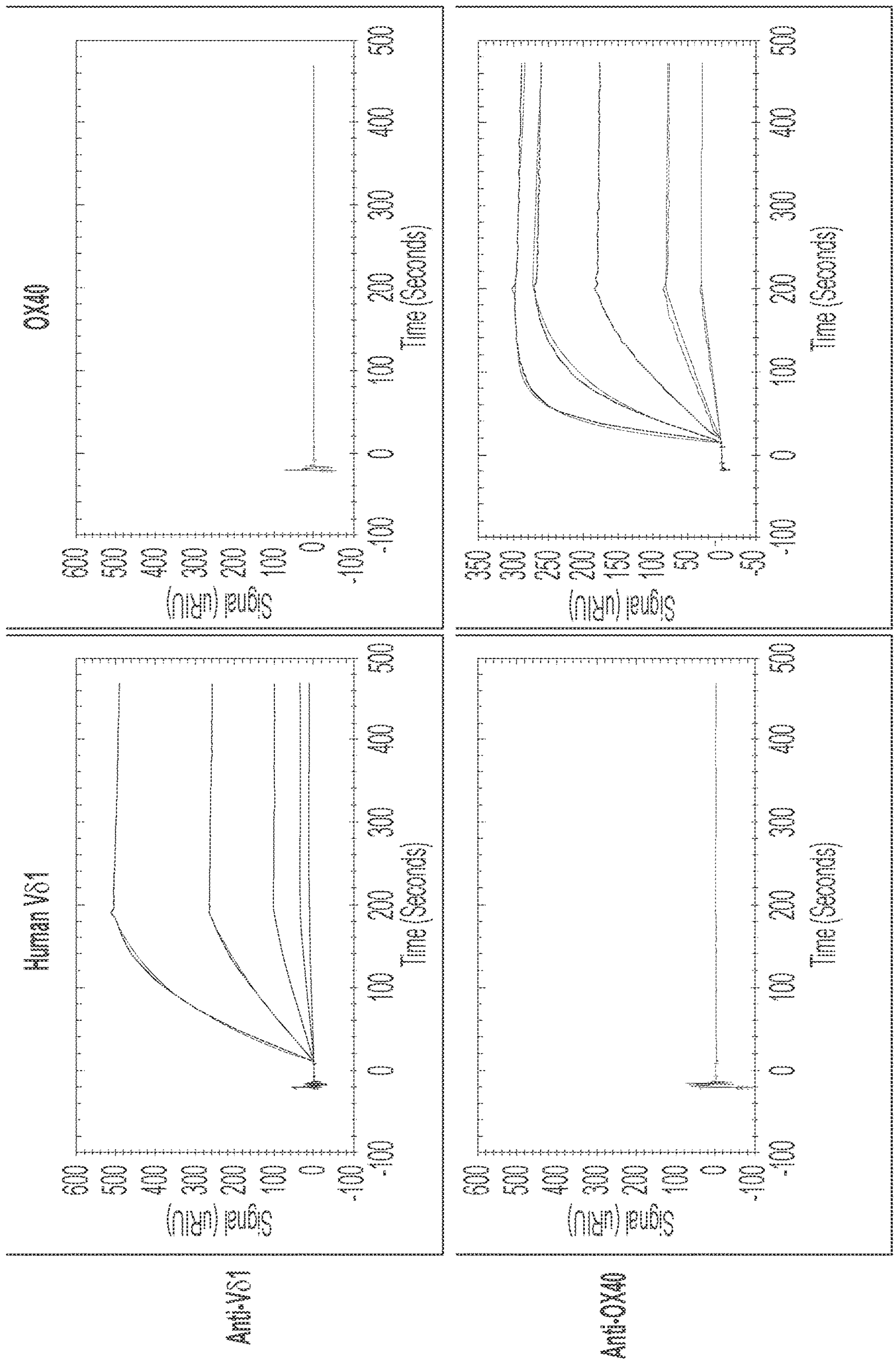
FIGS. 60A-60H: Vδ1×OX40 bispecific antibodies enhance activation of Vδ1 γδT-cells and OX40+ T-cells.
Figure 60B:
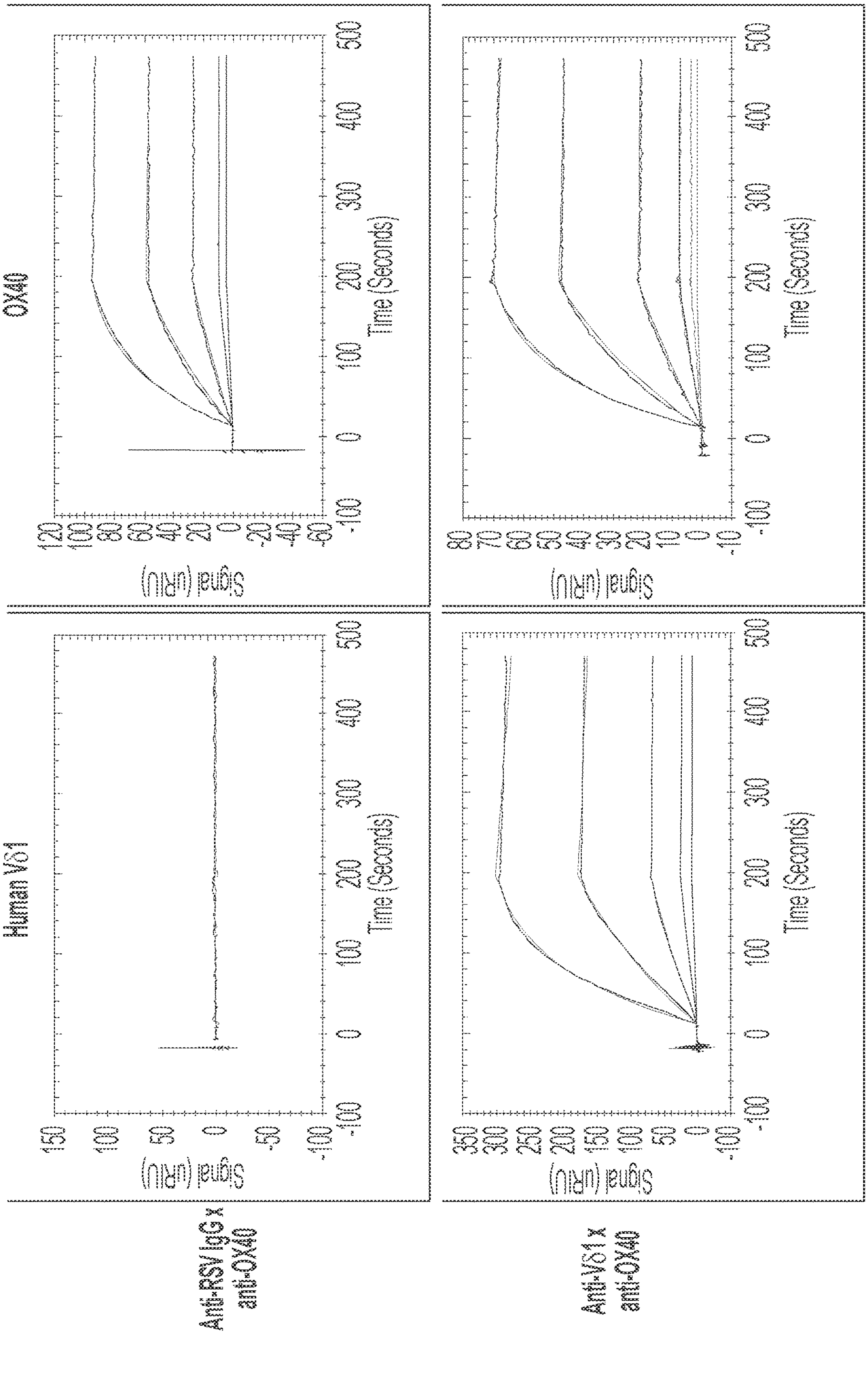
Figure 60C:
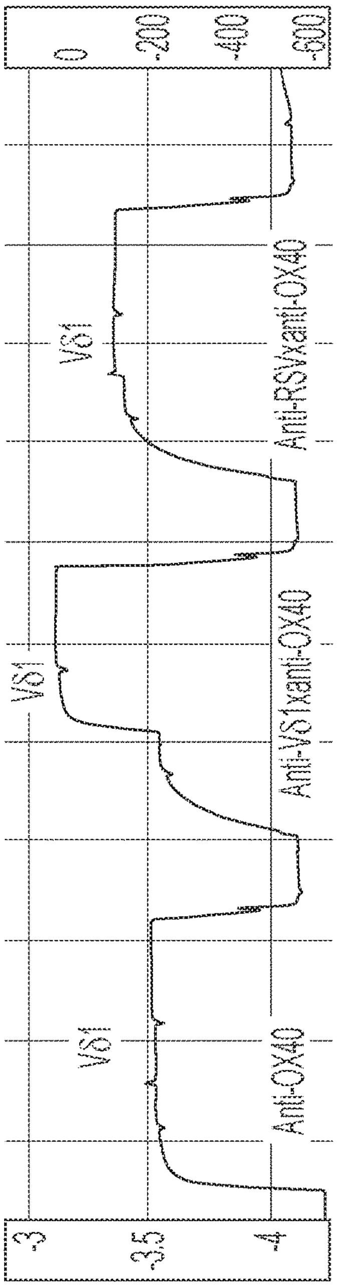
Figure 60D:
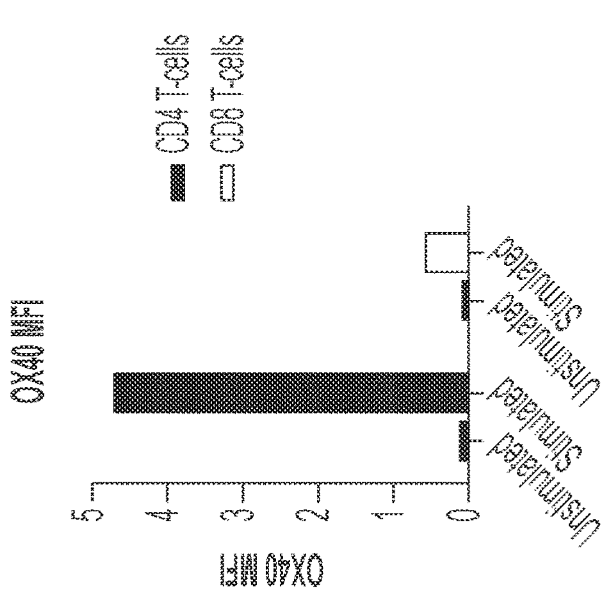
Figure 60F:
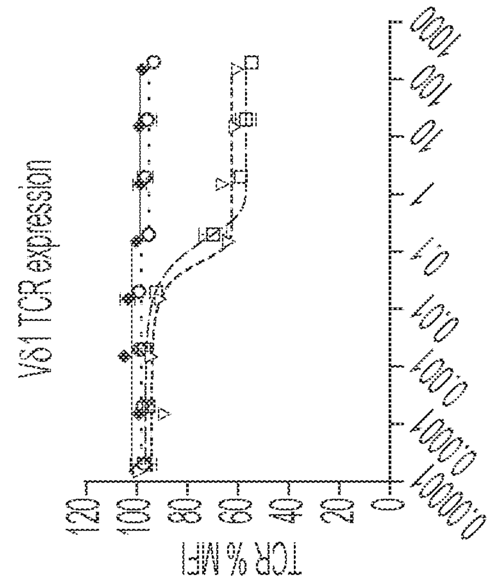
Figure 60E:
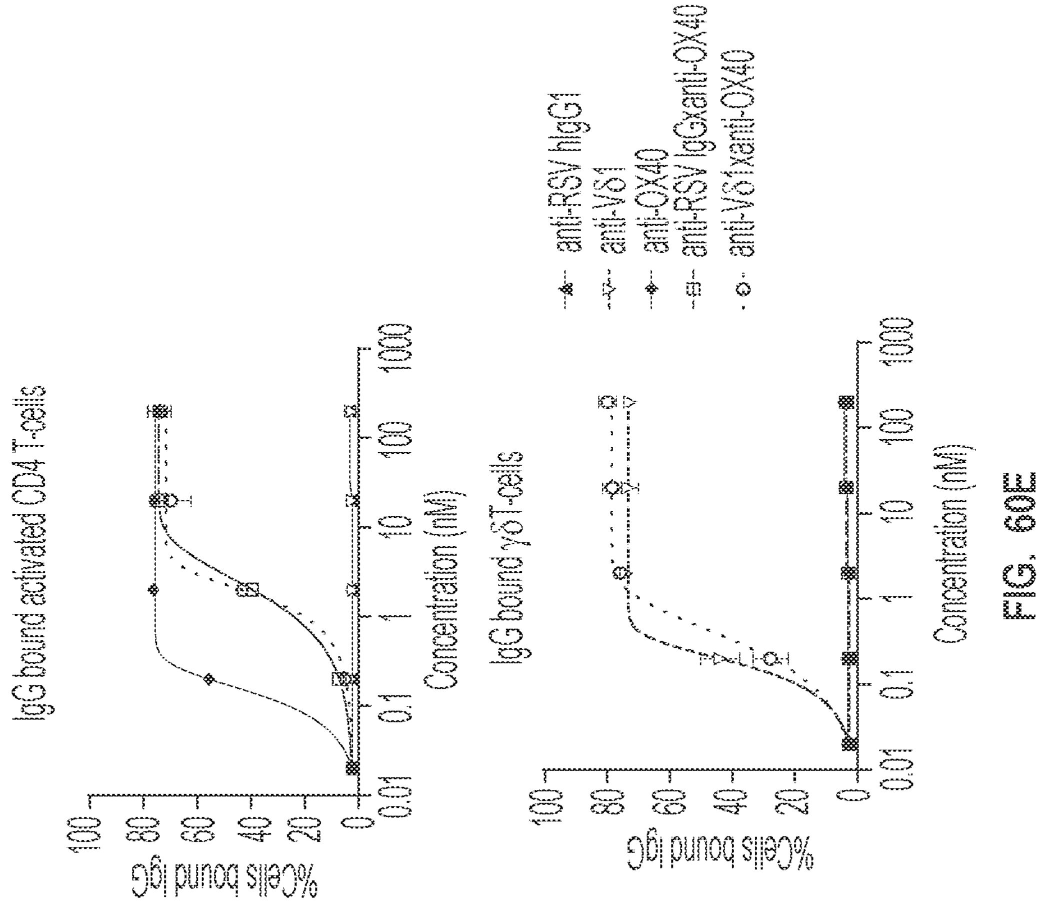
Figure 60G:
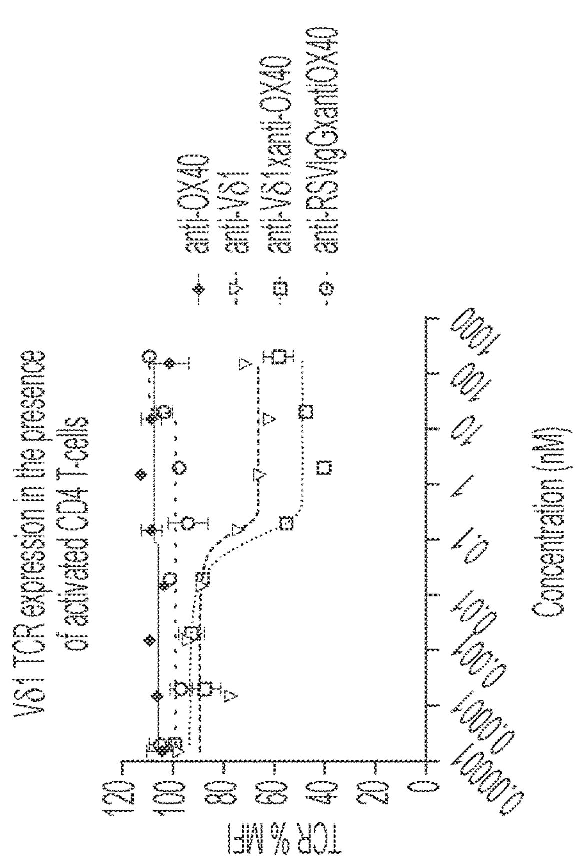
Figure 60H:
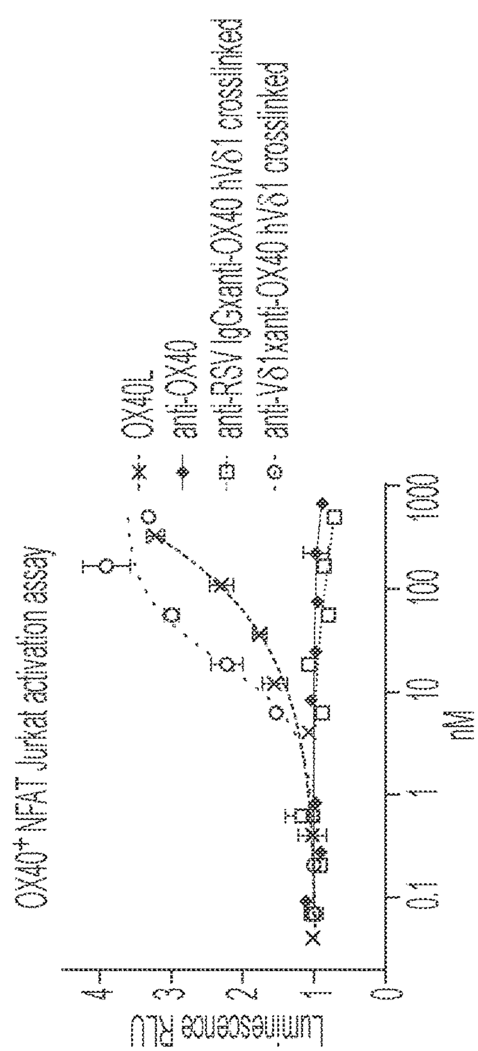
Figure 61A:
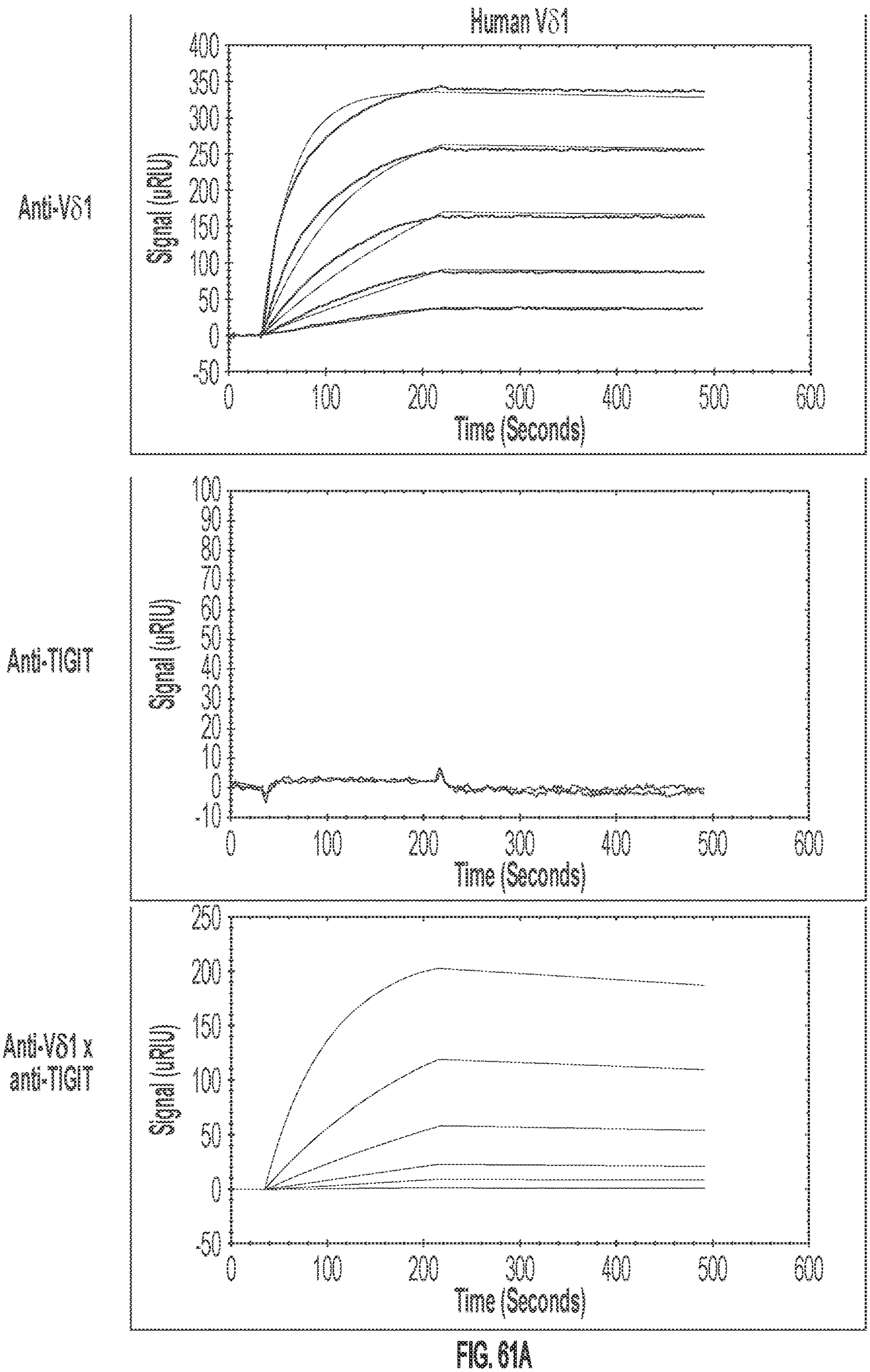
FIGS. 61A-61H: Vδ1×TIGIT bispecific antibodies enhance activation of Vδ1 γδT-cells and inhibit checkpoint blockade of TIGIT+ T-cells.
Figure 61B:
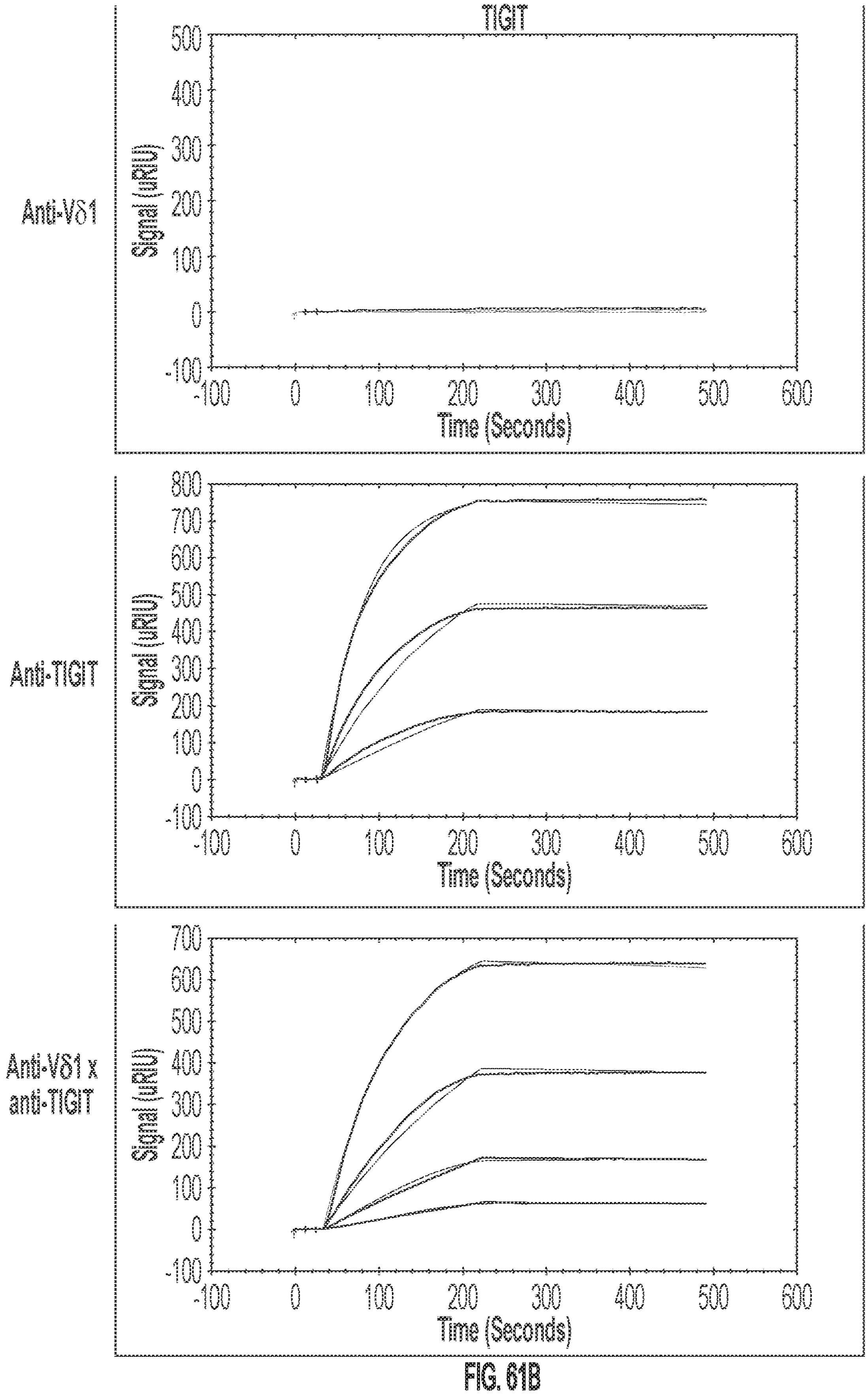
Figure 61C:
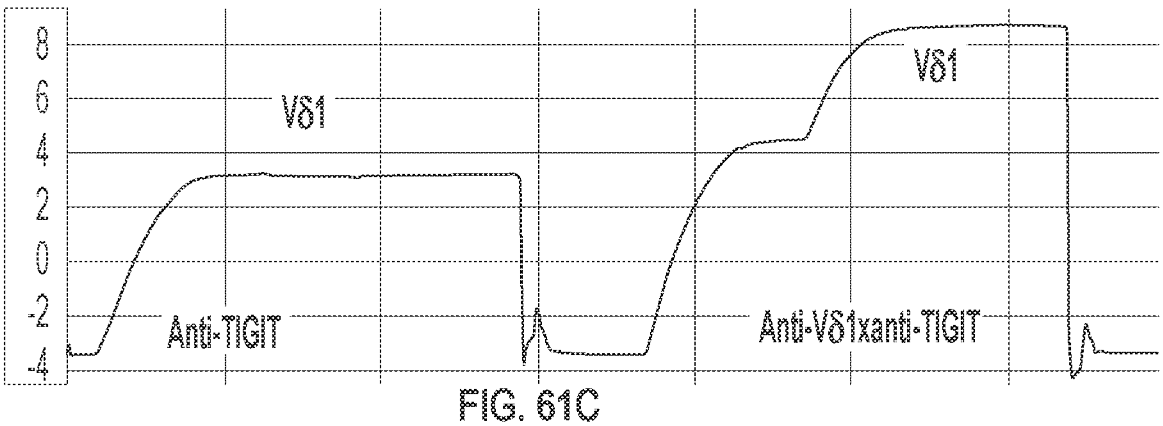
Figure 61D:
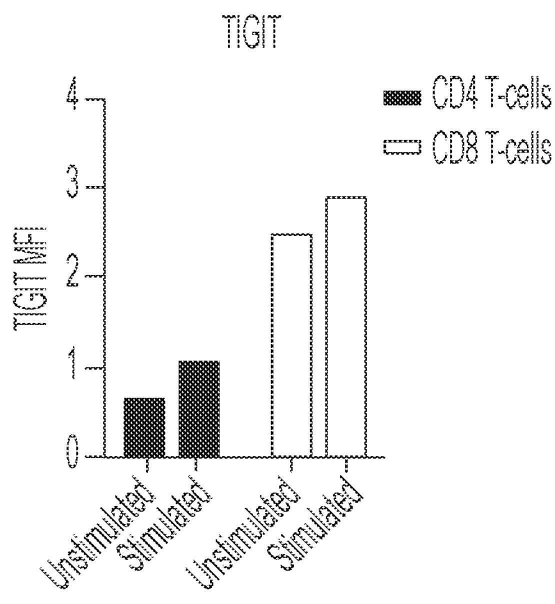
Figure 61E:
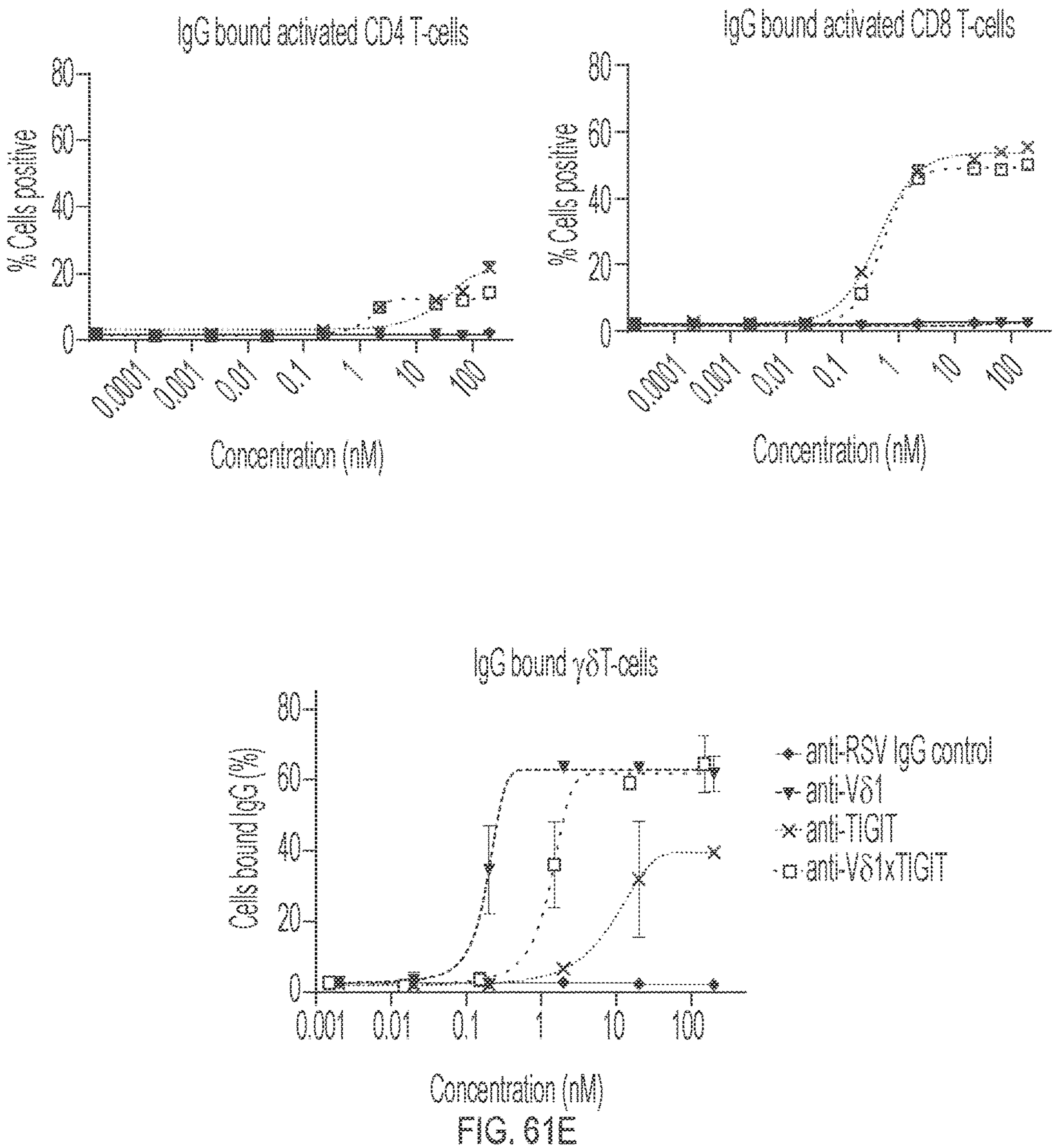
Figure 61F:
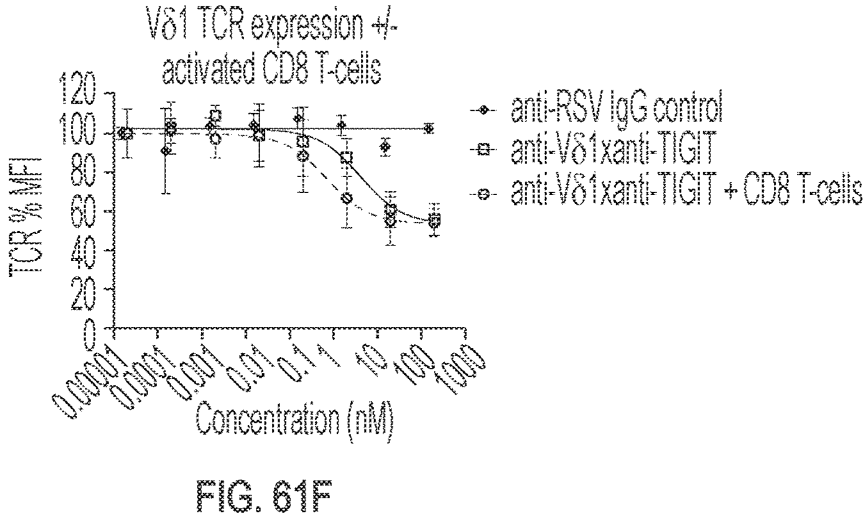
Figure 61G:
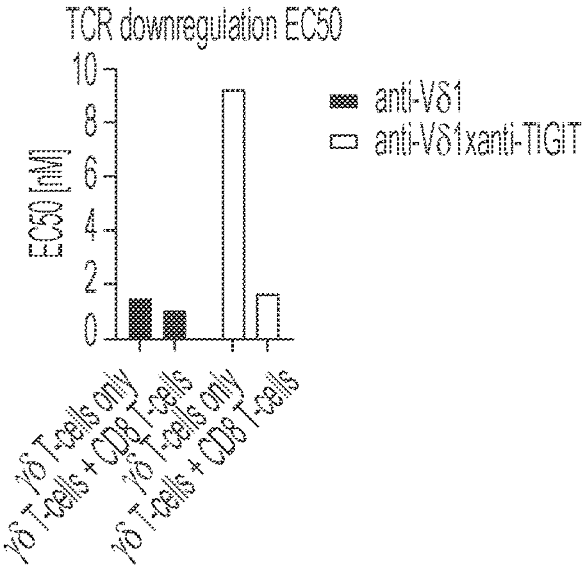
Figure 61H:
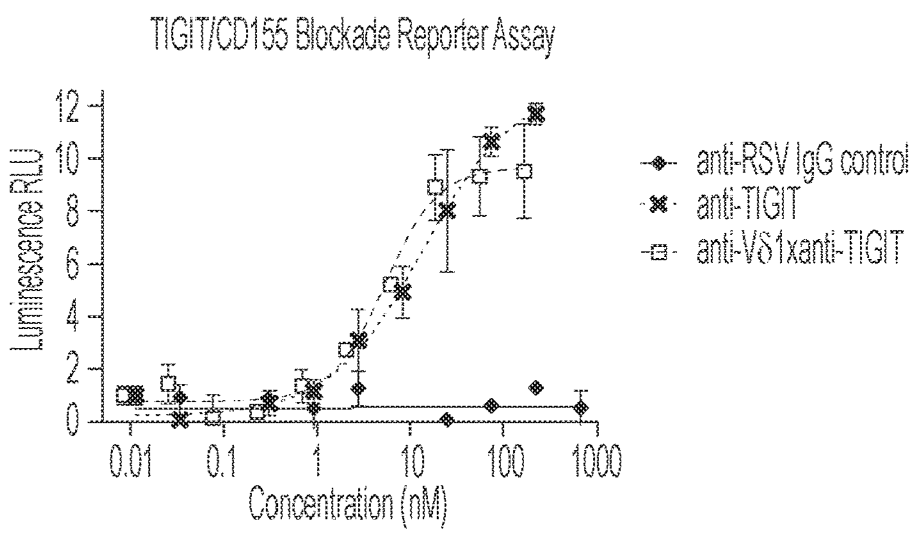

Example 36. Vδ1-4-1BB Bispecific Antibodies Enhance Vδ1 vδT-Cell and CD8 T-Cell Activation The binding kinetics of the binding of anti-Vδ1 (ADT1-4-2), anti-4-1BB (based on utomilumab) and anti-Vδ1×4-1 BB (ADT1-4-2× utomilumab) (SEQ ID NO: 407 or SEQ ID NO: 414 and SEQ ID NO: 418) antibodies to their targets (i.e. the Vδ1 chain of a γδ TCR and 4-1BB) is established by SPR analysis using a Reichert 4SPR instrument (Reichert Technologies). Antibody (1.5 ug/mL) is coated onto a Planar Protein A Sensor Chip (Reichert Technologies) to give an increase on baseline of approximately 500 uRIU. Recombinant human Vδ1 heterodimer or human 4-1BB was flown over the cell at a top concentration of 100 nM. The results are shown in FIG. 59A. The $K_D$ values are as follows:

| Antibody | KD VD1 [nM] | KD 4-1BB [nM] |
|---|---|---|
| Anti-Vδ1 (ADT1-4-2) | 1.25 nM | n/a |
| Anti-4-1BB (based on utomilumab) | n/a | 32 nM |
| Anti-RSVxAnti-4-1BB | n/a | 86 nM |
| Anti-Vδ1xanti-4-1BB (ADT1-4-2xutomilumab) | 1.2 nM | 91 nM |

To assess the dual binding of bispecific antibodies to both target ligands, recombinant 4-1 BB was first immobilised on a Carboxymethyl Dextran Sensor Chip (Reichert Technologies) at 10 ug/ml before flowing over the bispecific antibodies at 100 nM. The ability to subsequently bind to the Vδ1 γδ TCR was then assessed by flowing over recombinant human Vδ1 heterodimer at 100 nM. All experiments were performed at room temperature. The results are shown in FIG. 59 B.

Binding of anti-Vδ1×4-1BB bispecific antibodies to Vδ1 γδ T-cells and 4-1BB+ immune cells was assessed by flow cytometry. Initially CD8+ T-cells were negatively selected by magnetic sorting from PBMC buffy coats extracted from whole blood. Following activation by anti-CD3/anti-CD28 antibodies conjugated to Dynabeads (Invitrogen), cell surface expression of 4-1BB was elevated on CD8 T-cells. Activated 4-1BB+CD8 T-cells and Vδ1 γδ T-cells were incubated with a range of concentrations of anti-Vδ1×4-1BB bispecific antibodies or controls (IgG control or anti-4-1BB) for 15 minutes. After washing, cells were incubated for a further 15 minutes with anti-human IgG secondary antibodies before washing and fixing. The amount of antibody bound to each cell type was determined by flow cytometry. The results are shown in FIG. 59 C, D.

To determine the effect of anti-Vδ1×4-1BB bispecific antibodies on Vδ1 γδ T-cell activation, Vδ1 TCR downregulation was quantified in the presence of 4-1BB+ T-cells. Briefly, anti-Vδ1, anti-4-1BB and anti-Vδ1×4-1BB bispecific antibodies were serially diluted in PBS before adding to assay plates. 4-1BB+CD8 T-cells were stained with CellTrace CFSE live cell dye and mixed 1:1 with skin derived Vδ1 γδ T-cells or diluted 1:1 with media. Cell suspensions were seeded into assay plates at 2.5×10^4 Vδ1 γδ T-cells per well in the presence or absence of 2.5×10^4 4-1 BB+CD8 T-cells per well. Final assay antibody concentrations range from 200 nM to 2 μM. Cells were incubated for 4 hours at 37° C., 5% CO2 before washing and stained for dead cells (eFlour 520, Invitrogen) and Vδ1 TCR (MiltenyiBiotec). Cells were washed and resuspended in Cell Fix (BD sciences). VD1 TCR expression level was determined by median fluorescence intensity (MFI), measured by flow cytometry using the MACS Quant Analyzer 16. The results are shown in FIG. 59 E, F.

To assess the effect of anti-Vδ1×4-1BB bispecific antibodies on the activation of 4-1BB+ T-cells, 4-1BB$^+$ NFAT Jurkat cells (Promega, JA2191) were incubated with anti-Vδ1×4-1BB bispecific antibodies or controls (anti-4-1BB monoclonal antibodies or anti-RSVIgG×anti-4-1BB) for 5 hours at 37° C., 5% CO2. Assay was performed in the presence or absence of recombinant Vδ1 protein pre-coated at 1 μg/well in opaque, white 96-well plates. After 5 hours, Bio-Glo Luciferase reagent (Promega) was added to cells in a 1:1 ratio. After incubating for 5 minutes at room temperature the luminescence signal was detected on a BioTek Synergy plate reader. Raw luminescence signal was converted to fold relative luminesence units (RLU). The results are shown in FIG. 59 G.

Conclusions: anti-Vδ1×4-1BB bispecific antibodies enhance the activation of Vδ1 γδ T-cells, for example by crosslinking to 4-1BB+CD8 T-cells, as well as activating 4-1 BB+ T-cells.

Example 37. Vδ1-OX40 Bispecific Antibodies Enhance Vδ1 vδT-Cell and CD4 T-Cell Activation The binding kinetics of the binding of anti-Vδ1 (ADT1-4-2), anti-OX40 (based on pogalizumab) and anti-Vδ1×OX40 (ADT1-4-2× pogalizumab) (SEQ ID NO: 409 or SEQ ID NO: 414 and SEQ ID NO: 419) antibodies to their targets (i.e. the Vδ1 chain of a γδ TCR and OX40) is established by SPR analysis using a Reichert 4SPR instrument (Reichert Technologies). Antibody (1.5 ug/mL) is coated onto a Planar Protein A Sensor Chip (Reichert Technologies) to give an increase on baseline of approximately 500 uRIU. Recombinant human Vδ1 heterodimer or human OX40 was flown over the cell at a top concentration of 100 nM. The results are shown in FIG. 60, A. The $K_D$ values are as follows:

| Antibody | KD Vδ1 [nM] | KD OX40 [nM] |
|---|---|---|
| Anti-Vδ1 (ADT1-4-2) | 1.25 nM | n/a |
| Anti-OX40 (based on pogalizumab) | n/a | 0.82 nM |
| Anti-RSVxAnti-OX40 | n/a | 1.84 nM |
| Anti-Vδ1xanti-OX40 (ADT1-4-2xpogalizumab) | 1.2 nM | 1.63 nM |

To assess the dual binding of bispecific antibodies to both target ligands, recombinant OX40 was first immobilised on a Carboxymethyl Dextran Sensor Chip (Reichert Technologies) at 10 ug/ml before flowing over the bispecific antibodies at 100 nM. The ability to subsequently bind to the Vδ1 γδ TCR was then assessed by flowing over recombinant human Vδ1 heterodimer at 100 nM. All experiments were performed at room temperature. The results are shown in FIG. 60, B.

Binding of anti-Vδ1×OX40 bispecific antibodies to Vδ1 γδ T-cells and OX40$^+$ immune cells was assessed by flow cytometry. Initially CD4+ T-cells were negatively selected by magnetic sorting from PBMC buffy coats extracted from whole blood. Following activation by anti-CD3/anti-CD28 antibodies conjugated to Dynabeads (Invitrogen), cell surface expression of OX40 was elevated on CD4 T-cells. Activated OX40+CD4 T-cells and Vδ1 γδ T-cells were incubated with a range of concentrations of anti-Vδ1×OX40 bispecific antibodies or controls (IgG control or anti-OX40) for 15 minutes. After washing, cells were incubated for a further 15 minutes with anti-human IgG secondary antibodies before washing and fixing. The amount of antibody bound to each cell type was determined by flow cytometry. The results are shown in FIG. 60, C, D.

To determine the effect of anti-Vδ1×OX40 bispecific antibodies on Vδ1 γδ T-cell activation, Vδ1 TCR downregulation was quantified in the presence of OX40+ T-cells. Briefly, anti-Vδ1, anti-OX40 and anti-Vδ1×OX40 bispecific antibodies were serially diluted in PBS before adding to assay plates. OX40+CD4 T-cells were stained with CellTrace CFSE live cell dye and mixed 1:1 with skin derived Vδ1 γδ T-cells or diluted 1:1 with media. Cell suspensions were seeded into assay plates at 2.5×10^4 Vδ1 γδ T-cells per well in the presence or absence of 2.5×10^4 $OX_{40}$+CD4 T-cells per well. Final assay antibody concentrations range from 200 nM to 2 μM. Cells were incubated for 4 hours at 37° C., 5% CO2 before washing and stained for dead cells (eFlour 520, Invitrogen) and Vδ1 TCR (MiltenyiBiotec). Cells were washed and resuspended in Cell Fix (BD sciences). VD1 TCR expression level was determined by median fluorescence intensity (MFI), measured by flow cytometry using the MACS Quant Analyzer 16. The results are shown in FIG. 60, E, F.

To assess the effect of anti-Vδ1×OX40 bispecific antibodies on the activation of OX40+ T-cells, $OX40^+$ NFAT Jurkat cells (Promega, JA2191) were incubated with anti-Vδ1×OX40 bispecific antibodies or controls (OX40L (OX40 Ligand), anti-OX40 or anti-RSVIgG×anti-OX40) for 5 hours at 37° C., 5% CO2. Assay was performed in the presence or absence of recombinant Vδ1 protein pre-coated at 1 μg/well in opaque, white 96-well plates. After 5 hours, Bio-Glo Luciferase reagent (Promega) was added to cells in a 1:1 ratio. After incubating for 5 minutes at room temperature the luminescence signal was detected on a BioTek Synergy plate reader. Raw luminescence signal was converted to fold relative luminesence units (RLU). The results are shown in FIG. 60, G.

Conclusions: anti-Vδ1×OX40 bispecific antibodies enhance the activation of Vδ1 γδ T-cells, for example by crosslinking to OX40+CD4 T-cells, as well as activating OX40+ T-cells.

Example 38. Vδ1-TIGIT Bispecific Antibodies Enhance Vδ1 γδT-Cell Activation and Block TIGIT/PVR(CD155) Checkpoint Inhibition The binding kinetics of the binding of anti-Vδ1 (ADT1-4-2), anti-TIGIT (based on tiragolumab) and anti-Vδ1× TIGIT (ADT1-4-2× tiragolumab) (SEQ ID NO: 411 or SEQ ID NO: 439 and SEQ ID NO: 420) antibodies to their targets (i.e. the Vδ1 chain of a γδ TCR and TIGIT) is established by SPR analysis using a Reichert 4SPR instrument (Reichert Technologies). Antibody (1.5 ug/mL) is coated onto a Planar Protein A Sensor Chip (Reichert Technologies) to give an increase on baseline of approximately 500 uRIU. Recombinant human Vδ1 heterodimer or human TIGIT was flown over the cell at a top concentration of 100 nM. The results are shown in FIG. 61, A. The KD values are as follows:

| Antibody | VD1 KD [nM] | TIGIT KD [nM] |
|---|---|---|
| Anti-Vδ1 (ADT1-4-2) | 0.29 | n/a |
| Anti-TIGIT (based on tiragolumab) | n/a | 0.3 |
| Anti-Vδ1xAnti-TIGIT (ADT1-4-2xtiragolumab) | 1.9 | 0.3 |

To assess the dual binding of bispecific antibodies to both target ligands, recombinant TIGIT was first immobilised on a Carboxymethyl Dextran Sensor Chip (Reichert Technologies) at 10 ug/ml before flowing over the bispecific antibodies at 100 nM. The ability to subsequently bind to the Vδ1 γδ TCR was then assessed by flowing over recombinant human Vδ1 heterodimer at 100 nM. All experiments were performed at room temperature. The results are shown in FIG. 61, B.

Binding of anti-Vδ1×TIGIT bispecific antibodies to Vδ1 γδ T-cells and TIGIT+ immune cells was assessed by flow cytometry. Initially CD4 and CD8 T-cells were negatively selected by magnetic sorting from PBMC buffy coats extracted from whole blood. Following activation by anti-CD3/anti-CD28 antibodies conjugated to Dynabeads (Invitrogen), cell surface expression of 4-1BB was detected on CD4 and CD8 T-cells. Activated T-cells and Vδ1 γδ T-cells were incubated with a range of concentrations of anti-Vδ1× 4-1BB bispecific antibodies or controls (IgG control or anti-4-1BB) for 15 minutes. After washing, cells were incubated for a further 15 minutes with anti-human IgG secondary antibodies before washing and fixing. The amount of antibody bound to each cell type was determined by flow cytometry. The results are shown in FIG. 61, C, D.

To determine the effect of anti-Vδ1×TIGIT bispecific antibodies on Vδ1 γδ T-cell activation, Vδ1 TCR downregulation was quantified in the presence of TIGIT+ T-cells. Briefly, anti-Vδ1, anti-TIGIT and anti-Vδ1×TIGIT bispecific antibodies were serially diluted in PBS before adding to assay plates. TIGIT+CD8 T-cells were stained with CellTrace CFSE live cell dye and mixed 1:1 with skin derived Vδ1 γδ T-cells or diluted 1:1 with media. Cell suspensions were seeded into assay plates at 2.5×10^4 Vδ1 γδ T-cells per well in the presence or absence of 2.5×10^4 TIGIT+CD8 T-cells per well. Final assay antibody concentrations range from 200 nM to 2 μM. Cells were incubated for 4 hours at 37° C., 5% CO2 before washing and stained for dead cells (eFlour 520, Invitrogen) and Vδ1 TCR (MiltenyiBiotec). Cells were washed and resuspended in Cell Fix (BD sciences). VD1 TCR expression level was determined by median fluorescence intensity (MFI), measured by flow cytometry using the MACS Quant Analyzer 16. The results are shown in FIG. 61, E, F.

To assess the effect of anti-Vδ1×TIGIT bispecific antibodies on the activation of TIGIT+ T-cells, $TIGIT^+$ NFAT Jurkat cells (Promega, JA2191) were incubated with anti-Vδ1×TIGIT bispecific antibodies or controls (anti-TIGIT monoclonal antibody or anti-RSVIgG×anti-TIGIT) for 5 hours at 37° C., 5% CO2. Assay was performed in the presence or absence of recombinant Vδ1 protein pre-coated at 1 μg/well in opaque, white 96-well plates. After 5 hours, Bio-Glo Luciferase reagent (Promega) was added to cells in a 1:1 ratio. After incubating for 5 minutes at room temperature the luminescence signal was detected on a BioTek Synergy plate reader. Raw luminescence signal was converted to fold relative luminesence units (RLU). The results are shown in FIG. 61, G.

Conclusions: anti-Vδ1×TIGIT bispecific antibodies enhance the activation of Vδ1 γδ T-cells by crosslinking via TIGIT+CD8 T-cells, as well as blocking the TIGIT/CD155 immune checkpoint inhibition in CD8 T-cells.

Example 39. Anti-vδ1 Antibodies do not Induce ADCC

An ADCC Reporter Bioassay (Promega) was used to assess the level of ADCC (antibody dependent cell-mediated cytotoxicity) induced by anti-vδ1 antibodies compared to control antibodies.

ADCC refers to the biological phenomenon whereby effector cells kill target cells that are tagged by antibodies. The effector cells bind to the antibodies through their Fcγ receptors and subsequently kill the target cell. The ADCC reporter bioassay presented here uncovers potential ADCC mechanisms of action of antibodies that are tested within the assay, by detecting the early initiation of ADCC via activation of gene transcription through the NFAT (nuclear factor of activated T-cells) pathway. The reporter assay is an engineered system that utilizes effector cells (Jurkats) that express high affinity FcγRIIIa receptor linked to the NFAT pathway which is further engineered in order to, upon its activation, induce further activation of the firefly luciferase enzyme. Luciferase activity is quantified with a luminescence readout which can correlate to levels of ADCC taking place.

This assay was utilized to understand whether anti-vδ1 antibodies, or suitably the anti-vδ1 arm of multispecific antibodies, would drive an ADCC reaction. The target cells utilized were γδ cells which bind to the anti-vδ1 antibody through the vδ1 γδ TCR. If an ADCC mechanism of action exists, the anti-vδ1 antibody would bind the Fcγ receptors on the assay effector cells and generate a luminescence signal; if no signal is generated, this would suggest that ADCC is not taking place.

The ADCC Reporter Bioassay Kit (Promega) was utilised for this assay. One bottle of Bio-Glo Luciferase Assay Buffer was thawed and transferred to the substrate bottle. The mixture was kept at room temperature for 4-6 hours. A dilution plate was prepared with antibody concentrations (at 3× concentration) ranging from 10 nM to 0.01 nM (final concentration) for the following antibodies: anti-vδ1 antibody (ADT1-4-2), same anti-vδ1 antibody but Fc disabled (L235A, G237A) (ADT1-4-2 LAGA), Rituximab, RSV and OKT3. The target cells (γδ cells) were seeded into the 2 assay plates at 25 μl per well. Then 25 μl of the appropriate antibody solution from the antibody dilution plate were transferred to the appropriate well. The effector cells (engineered Jurkat cells) were thawed into warm assay buffer, resuspended into 4 ml of the assay buffer, and 25 μl of the effector cell solution was pipetted into each well. The plates were then incubated at 37° C. for 4.5 hours. Following the incubation period, the plates were allowed to equilibrate to room temperature, after which 75 μl Bio-Glo Luciferase Assay reagent was added to each well and the plates were incubated for 10 mins at room temperature. The plates were then read using a Biotek H4 plate reader which collected the luminescence signals (as relative light units RLU) from the plates. Fold induction was calculated using the following equation: Fold of Induction=RLU (induced−background)/RLU (no antibody control−background).

As a positive control, OKT3 (anti-CD3 antibody) was used. As an additional positive control, Raji cells were seeded instead of γδ cells in the control wells. Raji cells are a commonly accepted cell line used to demonstrate a strong ADCC reaction when utilised with the anti-CD20 antibody, Rituximab. As an internal control and in order to understand whether anti-vδ1 antibodies drive ADCC in the absence of vδ1 binding on γδ cells, anti-vδ1 antibodies of this invention and the same anti-vδ1 antibodies but Fc-disabled, L235A, G237A) were also added with the effector cells alone.

Figure 62:
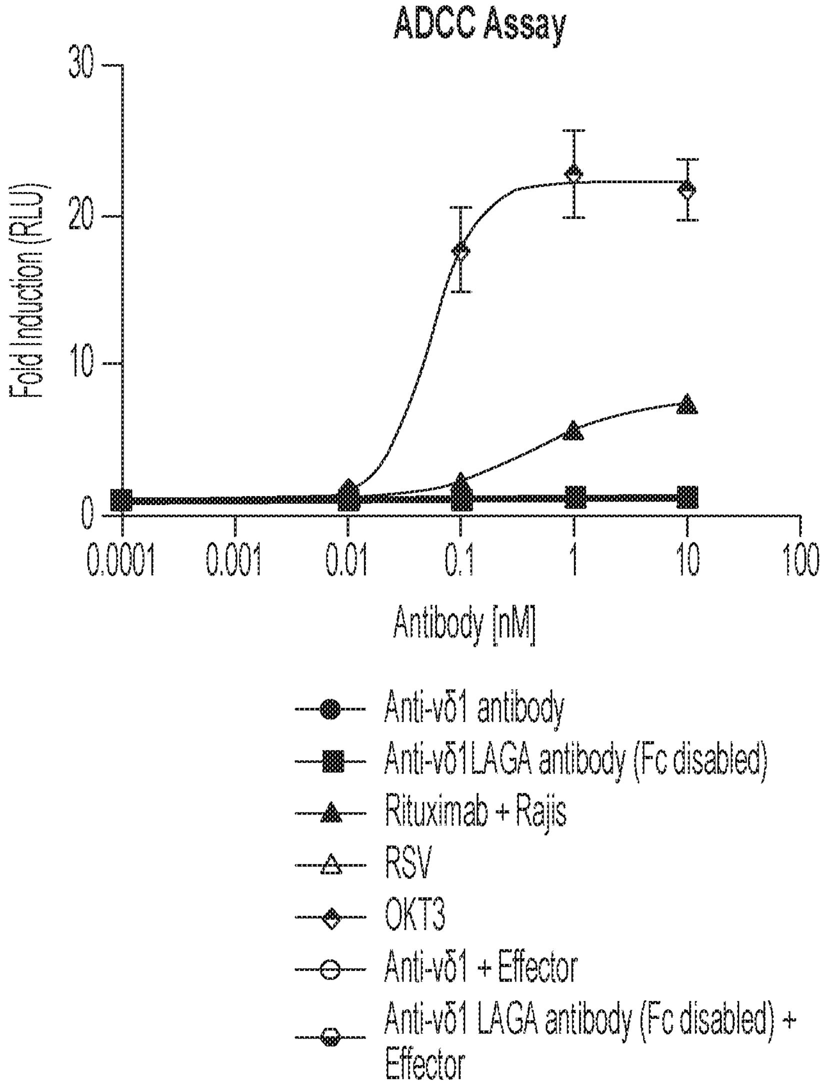
FIG. 62: ADCC reporter bioassay shows no ADCC as a result of the anti-vδ1 antibodies. Target cells, i.e. γδ cells, were incubated with the ADCC bioassay effector cells in presence of anti-vδ1 antibodies, anti-vδ1 LAGA antibodies (Fc disabled), and RSV Isotype control. Luminescence signal was recorded as relative light units (RLU) and fold induction was calculated as described in the methods. N=2 γδ donors (performed in technical duplicates) for "anti-vδ1 antibody", "anti-vδ1 LAGA antibody", "RSV", "OKT3". N=1 Raji cell lines for the "Rituximab+Rajis" condition (in technical duplicates) and n=1 γδ donors for the "anti-vδ1 antibody+Effector" and "anti-vδ1 LAGA antibody+Effector" conditions (performed in technical duplicate and singlicate, respectively). Effector:target ratio at 3:1.
Figure 63A:
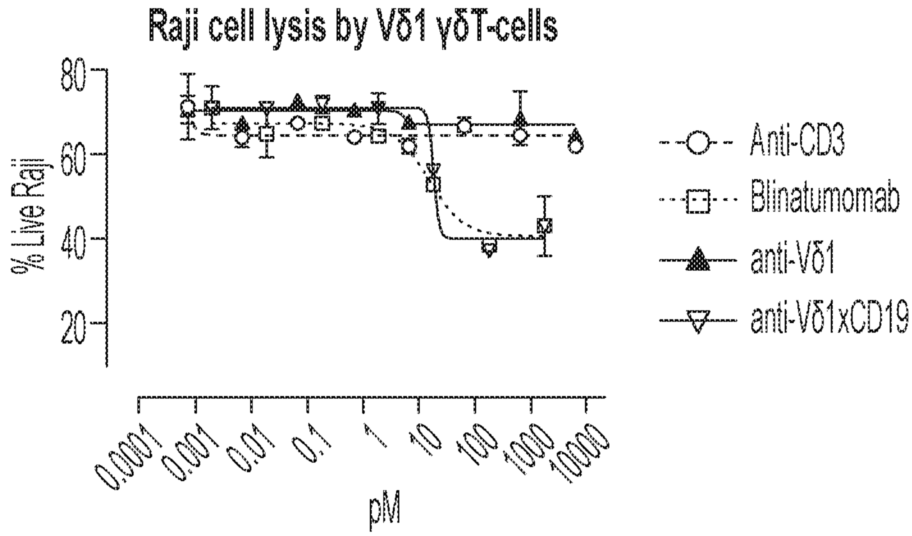
FIGS. 63A-63I: Vδ1-CD19 Bispecific T cell Engagers enhance CD19$^+$ target cell cytotoxicity and γδT-cell activation while sparing healthy CD19$^+$ B-cells.
Figure 63B:
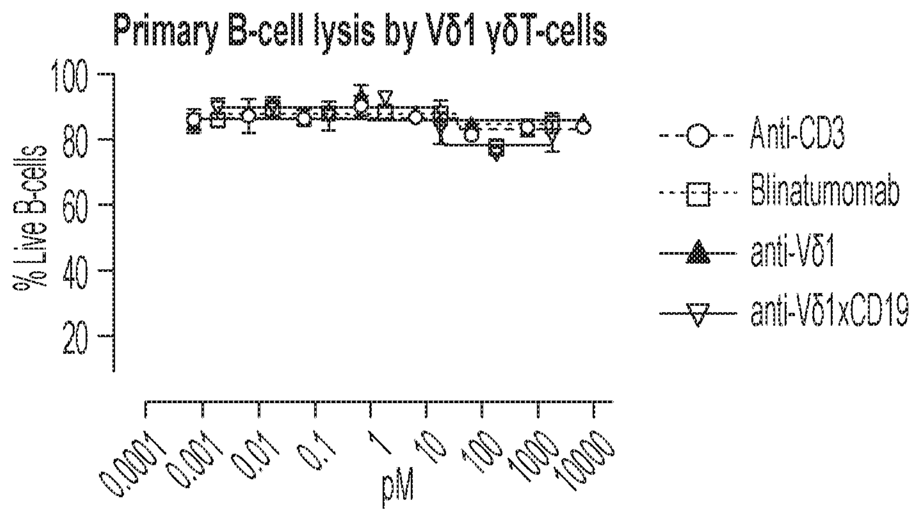
Figure 63C:
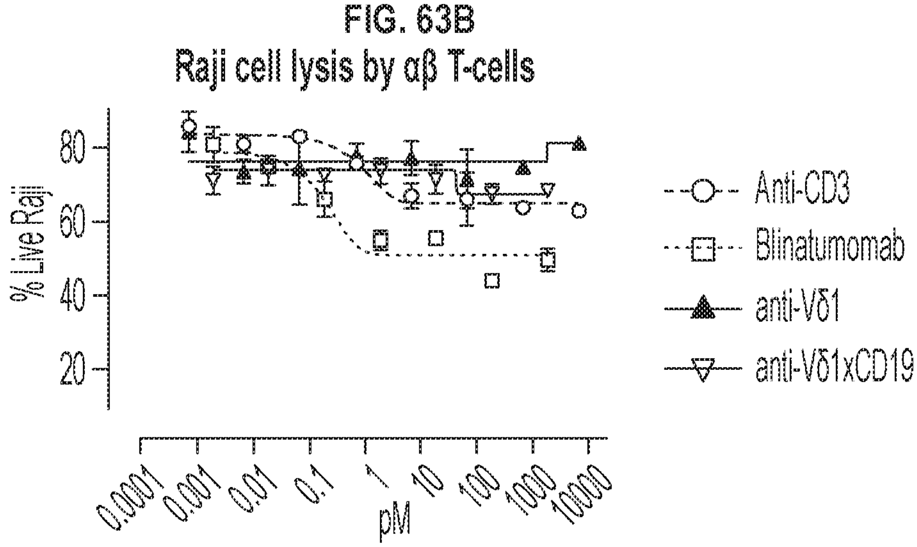
Figure 63D:
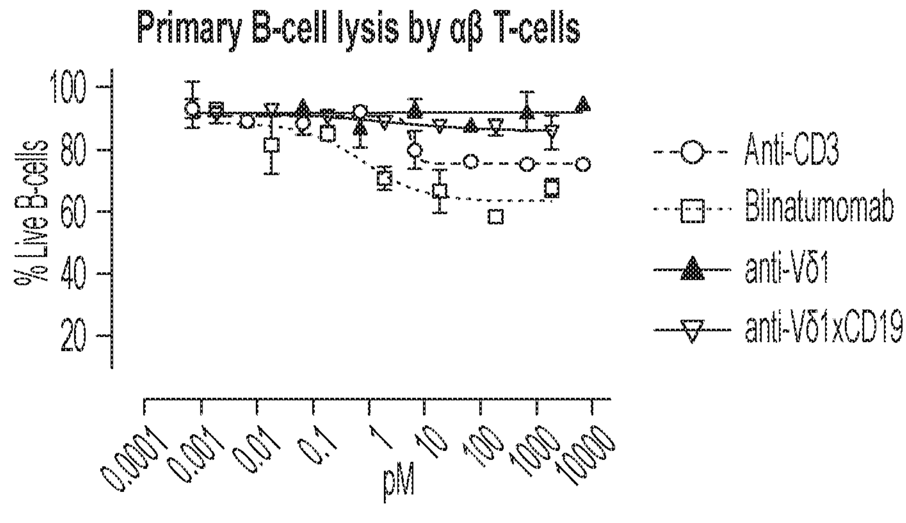
Figure 63E:
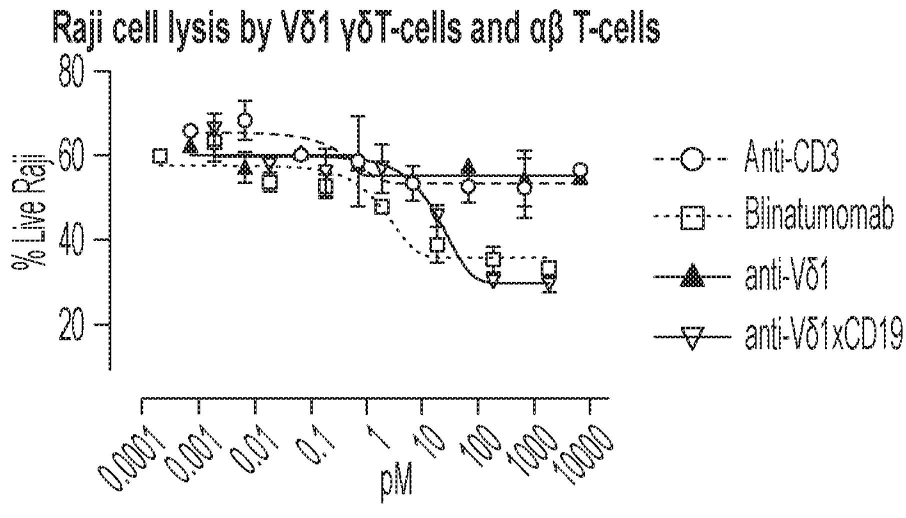
Figure 63F:
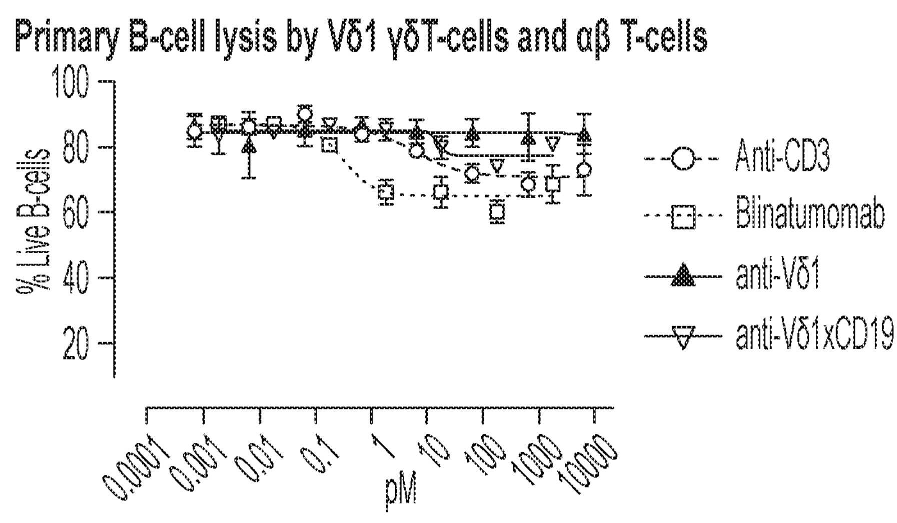
Figure 63G:
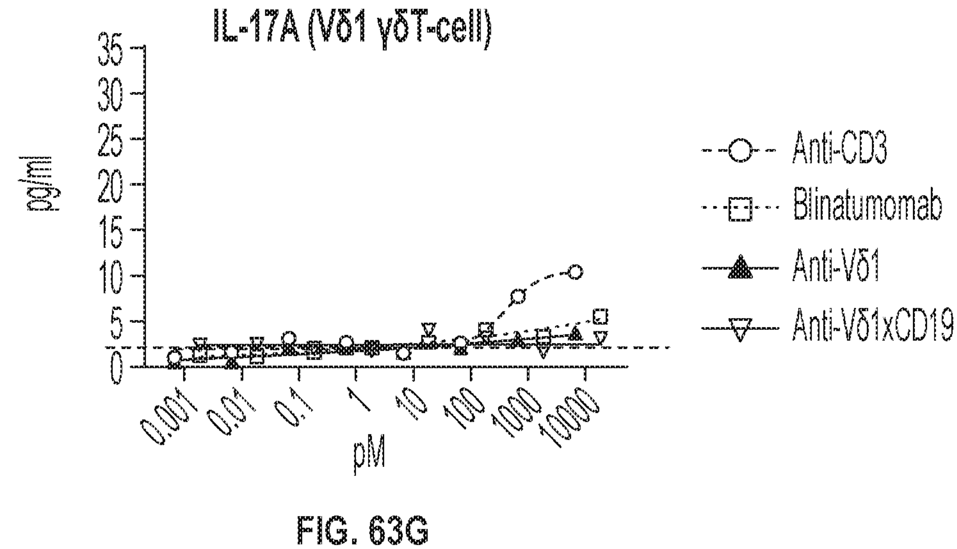
Figure 63H:
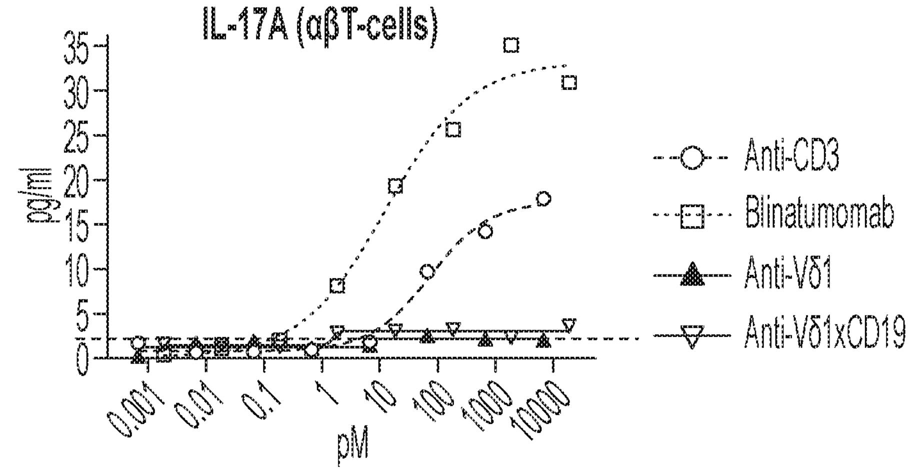
Figure 63I:
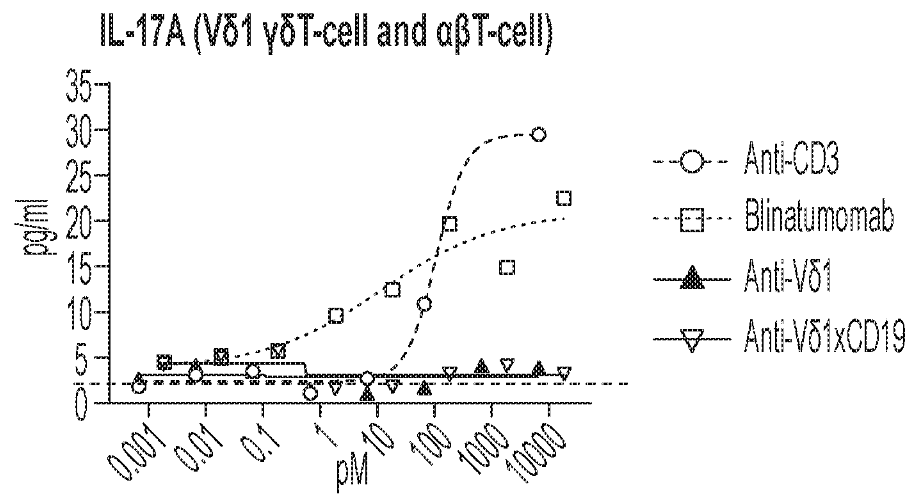

The results are shown in FIG. 62.

Conclusions: A strong ADCC reaction was shown in the positive control using Rituximab with Raji cells and an even stronger ADCC reaction was demonstrated with OKT3 against γδ cells. Contrastingly, no ADCC reaction was detected in either conditions using the anti-vδ1 antibodies of this invention, the same anti-vδ1 antibodies but also Fc disabled L235A, G237A, or RSV negative control. This demonstrates that in this system, antibodies of this invention that bind to vδ1 (such as anti-vδ1 mAbs or anti-vδ1 multispecific antibodies) do not show evidence of an ADCC mechanism of action. Remarkably, even Fc-enabled anti-Vδ1 antibodies do not deplete γδ T cells, which provides the option of maintaining Fc function in the anti-Vδ1 antibodies presented herein, adding functionality, for example in high Fcγ tumour environments. This further highlights the suitability of such anti-Vδ1 antibodies for inclusion in bispecific antibody formats as described herein.

Suitably, the functional properties of the antibodies when provided in a monospecific format are shared by the multispecific antibodies of the invention that additionally specifically bind to a second antigen.

EMBODIMENTS

The present invention includes at least the following numbered embodiments:

1. An anti-TCR delta variable 1 (anti-Vδ1) antibody or antigen-binding fragment thereof comprising:
   - a heavy chain variable region comprising a VHCDR3 comprising or consisting of an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of SEQ ID NOs: 55 to 78 and 133 to 143; and/or
   - a light chain variable region comprising a VLCDR3 comprising or consisting of an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of SEQ ID NOs: 82 to 105 and 147 to 157.
2. The anti-TCR delta variable 1 (anti-Vδ1) antibody or antigen-binding fragment thereof of embodiment 1, comprising:
   - a heavy chain variable region comprising:
     - a VHCDR1 comprising or consisting of an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of: SEQ ID NOs: 51, 52 and 130;
     - a VHCDR2 comprising or consisting of an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of: SEQ ID NO: 53 and 131; and
     - a VHCDR3 comprising or consisting of an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of: SEQ ID NOs: 55 to 78 and 133 to 143; and/or a light chain variable region comprising:

a VLCDR1 comprising or consisting of an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of: SEQ ID NO: 79 and 144;

a VLCDR2 comprising or consisting of an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of: SEQ ID NO: 80 and 145; and a VLCDR3 comprising or consisting of an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of: SEQ ID NOs: 82 to 105 and 147 to 157.

3. The anti-TCR delta variable 1 (anti-Vδ1) antibody or antigen-binding fragment thereof of embodiment 1 or embodiment 2, comprising:

a heavy chain variable region comprising or consisting of a sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of SEQ ID NOs: 2 to 25 and 107 to 117; and/or a light chain variable region comprising or consisting of a sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of SEQ ID NOs: 27 to 50 and 119 to 129.

4. An anti-TCR delta variable 1 (anti-Vδ1) antibody or antigen-binding fragment thereof comprising:

a. a VHCDR3 comprising or consisting of an amino acid sequence having at least 90% sequence identity to any one of SEQ ID NOs: 55 to 78; and/or b. a VLCDR3 comprising or consisting of an amino acid sequence having at least 90% sequence identity to any one of SEQ ID NOs: 82 to 105.

5. The anti-Vδ1 antibody or antigen-binding fragment thereof of any preceding embodiment, comprising:

a. a VHCDR3 comprising or consisting of the amino acid sequence of any one of SEQ ID NOs: 55 to 78; and/or b. a VLCDR3 comprising or consisting of the amino acid sequence of any one of SEQ ID NOs: 82 to 105

6. The anti-Vδ1 antibody or antigen-binding fragment thereof of any preceding embodiment, further comprising:

a. a VHCDR1 comprising or consisting of an amino acid sequence having at least 90% sequence identity to SEQ ID NO: 51 or SEQ ID NO: 52;

b. a VHCDR2 comprising or consisting of an amino acid sequence having at least 90% sequence identity to SEQ ID NO: 53;

c. a VLCDR1 comprising or consisting of an amino acid sequence having at least 90% sequence identity to SEQ ID NO: 79; and/or d. a VLCDR2 comprising or consisting of an amino acid sequence having at least 90% sequence identity to SEQ ID NO: 80.

7. The anti-Vδ1 antibody or antigen-binding fragment thereof of any preceding embodiment, further comprising:

a. a VHCDR1 comprising or consisting of the amino acid sequence of SEQ ID NO: 51 or SEQ ID NO: 52;

b. a VHCDR2 comprising or consisting of the amino acid sequence of SEQ ID NO: 53;

c. a VLCDR1 comprising or consisting of the amino acid sequence of SEQ ID NO: 79; and/or d. a VLCDR2 comprising or consisting of the amino acid sequence of SEQ ID NO: 80.

8. The anti-Vδ1 antibody or antigen-binding fragment thereof of any preceding embodiment, comprising:

a. a VHCDR1, a VHCDR2 and a VHCDR3 comprising or consisting of the amino acid sequences of SEQ ID NO: 51, 53 and 55, respectively, and a VLCDR1, a VLCDR2 and a VLCDR3 comprising or consisting of the amino acid sequences of SEQ ID NOs: 79, 80 and 82, respectively;

b. a VHCDR1, a VHCDR2 and a VHCDR3 comprising or consisting of the amino acid sequences of SEQ ID NO: 51, 53 and 56, respectively, and a VLCDR1, a VLCDR2 and a VLCDR3 comprising or consisting of the amino acid sequences of SEQ ID NOs: 79, 80 and 83, respectively;

c. a VHCDR1, a VHCDR2 and a VHCDR3 comprising or consisting of the amino acid sequences of SEQ ID NO: 51, 53 and 57, respectively, and a VLCDR1, a VLCDR2 and a VLCDR3 comprising or consisting of the amino acid sequences of SEQ ID NOs: 79, 80 and 84, respectively;

d. a VHCDR1, a VHCDR2 and a VHCDR3 comprising or consisting of the amino acid sequences of SEQ ID NO: 51, 53 and 58, respectively, and a VLCDR1, a VLCDR2 and a VLCDR3 comprising or consisting of the amino acid sequences of SEQ ID NOs: 79, 80 and 85, respectively;

e. a VHCDR1, a VHCDR2 and a VHCDR3 comprising or consisting of the amino acid sequences of SEQ ID NO: 51, 53 and 59, respectively, and a VLCDR1, a VLCDR2 and a VLCDR3 comprising or consisting of the amino acid sequences of SEQ ID NOs: 79, 80 and 86, respectively;

f. a VHCDR1, a VHCDR2 and a VHCDR3 comprising or consisting of the amino acid sequences of SEQ ID NO: 51, 53 and 60, respectively, and a VLCDR1, a VLCDR2 and a VLCDR3 comprising or consisting of the amino acid sequences of SEQ ID NOs: 79, 80 and 87, respectively;

g. a VHCDR1, a VHCDR2 and a VHCDR3 comprising or consisting of the amino acid sequences of SEQ ID NO: 52, 53 and 61, respectively, and a VLCDR1, a VLCDR2 and a VLCDR3 comprising or consisting of the amino acid sequences of SEQ ID NOs: 79, 80 and 88, respectively;

h. a VHCDR1, a VHCDR2 and a VHCDR3 comprising or consisting of the amino acid sequences of SEQ ID NO: 51, 53 and 62, respectively, and a VLCDR1, a VLCDR2 and a VLCDR3 comprising or consisting of the amino acid sequences of SEQ ID NOs: 79, 80 and 89, respectively;

i. a VHCDR1, a VHCDR2 and a VHCDR3 comprising or consisting of the amino acid sequences of SEQ ID NO: 51, 53 and 63, respectively, and a VLCDR1, a VLCDR2 and a VLCDR3 comprising or consisting of the amino acid sequences of SEQ ID NOs: 79, 80 and 90, respectively;

j. a VHCDR1, a VHCDR2 and a VHCDR3 comprising or consisting of the amino acid sequences of SEQ ID NO: 51, 53 and 64, respectively, and a VLCDR1, a VLCDR2 and a VLCDR3 comprising or consisting of the amino acid sequences of SEQ ID NOs: 79, 80 and 91, respectively;

k. a VHCDR1, a VHCDR2 and a VHCDR3 comprising or consisting of the amino acid sequences of SEQ ID NO: 51, 53 and 65, respectively, and a VLCDR1, a VLCDR2 and a VLCDR3 comprising or consisting of the amino acid sequences of SEQ ID NOs: 79, 80 and 92, respectively;

l. a VHCDR1, a VHCDR2 and a VHCDR3 comprising or consisting of the amino acid sequences of SEQ ID NO: 52, 53 and 66, respectively, and a VLCDR1, a VLCDR2 and a VLCDR3 comprising or consisting of the amino acid sequences of SEQ ID NOs: 79, 80 and 93, respectively;

m. a VHCDR1, a VHCDR2 and a VHCDR3 comprising or consisting of the amino acid sequences of SEQ ID NO: 51, 53 and 67, respectively, and a VLCDR1, a VLCDR2 and a VLCDR3 comprising or consisting of the amino acid sequences of SEQ ID NOs: 79, 80 and 94, respectively;

n. a VHCDR1, a VHCDR2 and a VHCDR3 comprising or consisting of the amino acid sequences of SEQ ID NO: 51, 53 and 68, respectively, and a VLCDR1, a VLCDR2 and a VLCDR3 comprising or consisting of the amino acid sequences of SEQ ID NOs: 79, 80 and 95, respectively;

o. a VHCDR1, a VHCDR2 and a VHCDR3 comprising or consisting of the amino acid sequences of SEQ ID NO: 51, 53 and 69, respectively, and a VLCDR1, a VLCDR2 and a VLCDR3 comprising or consisting of the amino acid sequences of SEQ ID NOs: 79, 80 and 96, respectively;

p. a VHCDR1, a VHCDR2 and a VHCDR3 comprising or consisting of the amino acid sequences of SEQ ID NO: 51, 53 and 70, respectively, and a VLCDR1, a VLCDR2 and a VLCDR3 comprising or consisting of the amino acid sequences of SEQ ID NOs: 79, 80 and 97, respectively;

q. a VHCDR1, a VHCDR2 and a VHCDR3 comprising or consisting of the amino acid sequences of SEQ ID NO: 51, 53 and 71, respectively, and a VLCDR1, a VLCDR2 and a VLCDR3 comprising or consisting of the amino acid sequences of SEQ ID NOs: 79, 80 and 98, respectively;

r. a VHCDR1, a VHCDR2 and a VHCDR3 comprising or consisting of the amino acid sequences of SEQ ID NO: 51, 53 and 72, respectively, and a VLCDR1, a VLCDR2 and a VLCDR3 comprising or consisting of the amino acid sequences of SEQ ID NOs: 79, 80 and 99, respectively;

s. a VHCDR1, a VHCDR2 and a VHCDR3 comprising or consisting of the amino acid sequences of SEQ ID NO: 51, 53 and 73, respectively, and a VLCDR1, a VLCDR2 and a VLCDR3 comprising or consisting of the amino acid sequences of SEQ ID NOs: 79, 80 and 100, respectively;

t. a VHCDR1, a VHCDR2 and a VHCDR3 comprising or consisting of the amino acid sequences of SEQ ID NO: 52, 53 and 74, respectively, and a VLCDR1, a VLCDR2 and a VLCDR3 comprising or consisting of the amino acid sequences of SEQ ID NOs: 79, 80 and 101, respectively;

u. a VHCDR1, a VHCDR2 and a VHCDR3 comprising or consisting of the amino acid sequences of SEQ ID NO: 51, 53 and 75, respectively, and a VLCDR1, a VLCDR2 and a VLCDR3 comprising or consisting of the amino acid sequences of SEQ ID NOs: 79, 80 and 102, respectively;

v. a VHCDR1, a VHCDR2 and a VHCDR3 comprising or consisting of the amino acid sequences of SEQ ID NO: 51, 53 and 76, respectively, and a VLCDR1, a VLCDR2 and a VLCDR3 comprising or consisting of the amino acid sequences of SEQ ID NOs: 79, 80 and 103, respectively;

w. a VHCDR1, a VHCDR2 and a VHCDR3 comprising or consisting of the amino acid sequences of SEQ ID NO: 51, 53 and 77, respectively, and a VLCDR1, a VLCDR2 and a VLCDR3 comprising or consisting of the amino acid sequences of SEQ ID NOs: 79, 80 and 104, respectively; or x. a VHCDR1, a VHCDR2 and a VHCDR3 comprising or consisting of the amino acid sequences of SEQ ID NO: 51, 53 and 78, respectively, and a VLCDR1, a VLCDR2 and a VLCDR3 comprising or consisting of the amino acid sequences of SEQ ID NOs: 79, 80 and 105, respectively.

9. The anti-Vδ1 antibody or antigen-binding fragment thereof of any preceding embodiment, comprising
   a. a VH comprising an amino acid sequence having at least 90% sequence identity to any one of SEQ ID NOs: 2 to 25; and/or
   b. a VL comprising or consisting of an amino acid sequence having at least 90% identity to any one of SEQ ID NOs: 27 to 50.

10. The anti-Vδ1 antibody or antigen-binding fragment thereof of any preceding embodiment, comprising:
   a. a VH comprising or consisting of the amino acid sequence of any one of SEQ ID NOs: 2 to 25; and/or
   b. a VL comprising or consisting of the amino acid sequence of any one of SEQ ID NOs: 27 to 50.

11. The anti-Vδ1 antibody or antigen-binding fragment thereof of any preceding embodiment, comprising:
   a. a VH comprising or consisting of an amino acid sequence having at least 90% sequence identity to SEQ ID NO: 2 and a VL comprising or consisting of an amino acid sequence having at least 90% sequence identity to SEQ ID NO: 27;
   b. a VH comprising or consisting of an amino acid sequence having at least 90% sequence identity to SEQ ID NO: 3 and a VL comprising or consisting of an amino acid sequence having at least 90% sequence identity to SEQ ID NO: 28;
   c. a VH comprising or consisting of an amino acid sequence having at least 90% sequence identity to SEQ ID NO: 4 and a VL comprising or consisting of an amino acid sequence having at least 90% sequence identity to SEQ ID NO: 29;
   d. a VH comprising or consisting of an amino acid sequence having at least 90% sequence identity to SEQ ID NO: 5 and a VL comprising or consisting of an amino acid sequence having at least 90% sequence identity to SEQ ID NO: 30;

e. a VH comprising or consisting of an amino acid sequence having at least 90% sequence identity to SEQ ID NO: 6 and a VL comprising or consisting of an amino acid sequence having at least 90% sequence identity to SEQ ID NO: 31;

f. a VH comprising or consisting of an amino acid sequence having at least 90% sequence identity to SEQ ID NO: 7 and a VL comprising or consisting of an amino acid sequence having at least 90% sequence identity to SEQ ID NO: 32;

g. a VH comprising or consisting of an amino acid sequence having at least 90% sequence identity to SEQ ID NO: 8 and a VL comprising or consisting of an amino acid sequence having at least 90% sequence identity to SEQ ID NO: 33;

h. a VH comprising or consisting of an amino acid sequence having at least 90% sequence identity to SEQ ID NO: 9 and a VL comprising or consisting of an amino acid sequence having at least 90% sequence identity to SEQ ID NO: 34;

i. a VH comprising or consisting of an amino acid sequence having at least 90% sequence identity to SEQ ID NO: 10 and a VL comprising or consisting of an amino acid sequence having at least 90% sequence identity to SEQ ID NO: 35;

j. a VH comprising or consisting of an amino acid sequence having at least 90% sequence identity to SEQ ID NO: 11 and a VL comprising or consisting of an amino acid sequence having at least 90% sequence identity to SEQ ID NO: 36;

k. a VH comprising or consisting of an amino acid sequence having at least 90% sequence identity to SEQ ID NO: 12 and a VL comprising or consisting of an amino acid sequence having at least 90% sequence identity to SEQ ID NO: 37;

l. a VH comprising or consisting of an amino acid sequence having at least 90% sequence identity to SEQ ID NO: 13 and a VL comprising or consisting of an amino acid sequence having at least 90% sequence identity to SEQ ID NO: 38;

m. a VH comprising or consisting of an amino acid sequence having at least 90% sequence identity to SEQ ID NO: 14 and a VL comprising or consisting of an amino acid sequence having at least 90% sequence identity to SEQ ID NO: 39;

n. a VH comprising or consisting of an amino acid sequence having at least 90% sequence identity to SEQ ID NO: 15 and a VL comprising or consisting of an amino acid sequence having at least 90% sequence identity to SEQ ID NO: 40;

o. a VH comprising or consisting of an amino acid sequence having at least 90% sequence identity to SEQ ID NO: 16 and a VL comprising or consisting of an amino acid sequence having at least 90% sequence identity to SEQ ID NO: 41;

p. a VH comprising or consisting of an amino acid sequence having at least 90% sequence identity to SEQ ID NO: 17 and a VL comprising or consisting of an amino acid sequence having at least 90% sequence identity to SEQ ID NO: 42;

q. a VH comprising or consisting of an amino acid sequence having at least 90% sequence identity to SEQ ID NO: 18 and a VL comprising or consisting of an amino acid sequence having at least 90% sequence identity to SEQ ID NO: 43;

r. a VH comprising or consisting of an amino acid sequence having at least 90% sequence identity to SEQ ID NO: 19 and a VL comprising or consisting of an amino acid sequence having at least 90% sequence identity to SEQ ID NO: 44;

s. a VH comprising or consisting of an amino acid sequence having at least 90% sequence identity to SEQ ID NO: 20 and a VL comprising or consisting of an amino acid sequence having at least 90% sequence identity to SEQ ID NO: 45;

t. a VH comprising or consisting of an amino acid sequence having at least 90% sequence identity to SEQ ID NO: 21 and a VL comprising or consisting of an amino acid sequence having at least 90% sequence identity to SEQ ID NO: 46;

u. a VH comprising or consisting of an amino acid sequence having at least 90% sequence identity to SEQ ID NO: 22 and a VL comprising or consisting of an amino acid sequence having at least 90% sequence identity to SEQ ID NO: 47;

v. a VH comprising or consisting of an amino acid sequence having at least 90% sequence identity to SEQ ID NO: 23 and a VL comprising or consisting of an amino acid sequence having at least 90% sequence identity to SEQ ID NO: 48;

w. a VH comprising or consisting of an amino acid sequence having at least 90% sequence identity to SEQ ID NO: 24 and a VL comprising or consisting of an amino acid sequence having at least 90% sequence identity to SEQ ID NO: 49; or x. a VH comprising or consisting of an amino acid sequence having at least 90% sequence identity to SEQ ID NO: 25 and a VL comprising or consisting of an amino acid sequence having at least 80% sequence identity to SEQ ID NO: 50.

12. The anti-Vδ1 antibody or antigen-binding fragment thereof of any preceding embodiment, comprising:

a. a VH comprising or consisting of the amino acid sequence of SEQ ID NO: 2 and a VL comprising or consisting of the amino acid sequence of SEQ ID NO: 27;

b. a VH comprising or consisting of the amino acid sequence of SEQ ID NO: 3 and a VL comprising or consisting of the amino acid sequence of SEQ ID NO: 28;

c. a VH comprising or consisting of the amino acid sequence of SEQ ID NO: 4 and a VL comprising or consisting of the amino acid sequence of SEQ ID NO: 29;

d. a VH comprising or consisting of the amino acid sequence of SEQ ID NO: 5 and a VL comprising or consisting of the amino acid sequence of SEQ ID NO: 30;

e. a VH comprising or consisting of the amino acid sequence of SEQ ID NO: 6 and a VL comprising or consisting of the amino acid sequence of SEQ ID NO: 31;

f. a VH comprising or consisting of the amino acid sequence of SEQ ID NO: 7 and a VL comprising or consisting of the amino acid sequence of SEQ ID NO: 32;

g. a VH comprising or consisting of the amino acid sequence of SEQ ID NO: 8 and a VL comprising or consisting of the amino acid sequence of SEQ ID NO: 33;

h. a VH comprising or consisting of the amino acid sequence of SEQ ID NO: 9 and a VL comprising or consisting of the amino acid sequence of SEQ ID NO: 34;
i. a VH comprising or consisting of the amino acid sequence of SEQ ID NO: 10 and a VL comprising or consisting of the amino acid sequence of SEQ ID NO: 35;
j. a VH comprising or consisting of the amino acid sequence of SEQ ID NO: 11 and a VL comprising or consisting of the amino acid sequence of SEQ ID NO: 36;
k. a VH comprising or consisting of the amino acid sequence of SEQ ID NO: 12 and a VL comprising or consisting of the amino acid sequence of SEQ ID NO: 37;
l. a VH comprising or consisting of the amino acid sequence of SEQ ID NO: 13 and a VL comprising or consisting of the amino acid sequence of SEQ ID NO: 38;
m. a VH comprising or consisting of the amino acid sequence of SEQ ID NO: 14 and a VL comprising or consisting of the amino acid sequence of SEQ ID NO: 39;
n. a VH comprising or consisting of the amino acid sequence of SEQ ID NO: 15 and a VL comprising or consisting of the amino acid sequence of SEQ ID NO: 40;
o. a VH comprising or consisting of the amino acid sequence of SEQ ID NO: 16 and a VL comprising or consisting of the amino acid sequence of SEQ ID NO: 41;
p. a VH comprising or consisting of the amino acid sequence of SEQ ID NO: 17 and a VL comprising or consisting of the amino acid sequence of SEQ ID NO: 42;
q. a VH comprising or consisting of the amino acid sequence of SEQ ID NO: 18 and a VL comprising or consisting of the amino acid sequence of SEQ ID NO: 43;
r. a VH comprising or consisting of the amino acid sequence of SEQ ID NO: 19 and a VL comprising or consisting of the amino acid sequence of SEQ ID NO: 44;
s. a VH comprising or consisting of the amino acid sequence of SEQ ID NO: 20 and a VL comprising or consisting of the amino acid sequence of SEQ ID NO: 45;
t. a VH comprising or consisting of the amino acid sequence of SEQ ID NO: 21 and a VL comprising or consisting of the amino acid sequence of SEQ ID NO: 46;
u. a VH comprising or consisting of the amino acid sequence of SEQ ID NO: 22 and a VL comprising or consisting of the amino acid sequence of SEQ ID NO: 47;
v. a VH comprising or consisting of the amino acid sequence of SEQ ID NO: 23 and a VL comprising or consisting of the amino acid sequence of SEQ ID NO: 48;
w. a VH comprising or consisting of the amino acid sequence of SEQ ID NO: 24 and a VL
comprising or consisting of the amino acid sequence of SEQ ID NO: 49; or
x. a VH comprising or consisting of the amino acid sequence of SEQ ID NO: 25 and a VL comprising or consisting of the amino acid sequence of SEQ ID NO: 50.

13. The anti-Vδ1 antibody or antigen-binding fragment thereof of any preceding embodiment, wherein the antibody or antigen-binding fragment thereof comprises an amino acid residue other than serine at position 74 according to the IMGT kappa light chain variable sequence numbering system.
14. The anti-Vδ1 antibody or antigen-binding fragment thereof of embodiment 13, wherein the residue at position 74 according to the IMGT numbering system is an amino acid selected from the group consisting of glycine, alanine, valine, methionine, leucine and isoleucine.
15. The anti-Vδ1 antibody or antigen-binding fragment thereof of embodiment 13, wherein the residue at position 74 according to the IMGT numbering system is an amino acid selected from the group consisting of arginine, cysteine, glutamine, glutamic acid, glycine, histidine, isoleucine, leucine, lysine, methionine, phenylalanine, threonine, tryptophan, tyrosine and valine.
16. The anti-Vδ1 antibody or antigen-binding fragment thereof of embodiment 13, wherein the residue at position 74 according to the IMGT kappa light chain variable sequence numbering system is an amino acid selected from the group consisting of glycine, valine, methionine, leucine and isoleucine.
17. The anti-Vδ1 antibody or antigen-binding fragment thereof of embodiment 13, wherein the residue at position 74 according to the IMGT numbering system is a leucine residue.
18. The anti-Vδ1 antibody or antigen-binding fragment thereof of any preceding embodiment, wherein the anti-Vδ1 antibody or antigen-binding fragment thereof is an antibody selected from the group consisting of ADT1-4-105, ADT1-4-107, ADT1-4-110, ADT1-4-112, ADT1-4-117, ADT1-4-19, ADT1-4-21, ADT1-4-31, ADT1-4-139, ADT1-4-4, ADT1-4-143, ADT1-4-53, ADT1-4-173, ADT1-4-2, ADT1-4-8, ADT1-4-82, ADT1-4-83, ADT1-4-3, ADT1-4-84, ADT1-4-86, ADT1-4-95, ADT1-4-1, ADT1-4-6 and ADT1-4-138.
19. The anti-Vδ1 antibody or antigen-binding fragment thereof of embodiment 18, wherein the antibody comprises from 1 to 10, from 1 to 5 or from 1 to 2 amino acid substitutions across all 6 CDR regions.
20. The anti-Vδ1 antibody or antigen-binding fragment thereof of embodiment 18 or embodiment 19, wherein the antibody comprises up to 2 or up to 1 amino acid substitution across all 6 CDR regions.
21. The anti-Vδ1 antibody or antigen-binding fragment thereof of any one of embodiments 18 to 20, wherein the antibody comprises 1 or 2 amino acid substitution across all 6 CDR regions.
22. The anti-Vδ1 antibody or antigen-binding fragment thereof of any one of embodiments 18 to 21, wherein the antibody comprises 1 to 10, 1 to 5 or 1 to 2 amino acid substitutions in one or more framework regions.
23. The anti-Vδ1 antibody or antigen-binding fragment thereof of any one of embodiments 18 to 22, wherein the antibody comprises up to 2 or up to 1 amino acid substitutions in one or more framework regions.
24. The anti-Vδ1 antibody or antigen-binding fragment thereof of any one of embodiments 18 to 23, wherein the antibody comprises 1 or 2 amino acid substitutions in one or more framework regions.

25. The anti-Vδ1 antibody or antigen-binding fragment thereof of any one of embodiments 18 to 24, wherein the amino acid substitutions are conservative amino acid substitutions.

26. An anti-TCR delta variable 1 (anti-Vδ1) antibody or antigen-binding fragment thereof comprising:
   a. an HCDR1 sequence comprising or consisting of the sequence of GDSVSSKS$X_1$A;
   b. an HCDR2 sequence comprising or consisting of the sequence of SEQ ID NO: 53
   c. an HCDR3 sequence comprising or consisting of the sequence of $X_2$W$X_3$$X_4$$X_5$$X_6$D$X_7$, wherein the HCDR3 sequence is not SEQ ID NO: 54;
   d. an LCDR1 sequence comprising or consisting of the sequence of SEQ ID NO: 79;
   e. an LCDR2 sequence comprising or consisting of the sequence of SEQ ID NO: 80; and
   f. an LCDR3 sequence comprising or consisting of the sequence of QQ$X_8$Y$X_9$$X_{10}$$X_{11}$$X_{12}$$X_{13}$T, wherein the LCDR3 sequence is not SEQ ID NO: 81;
   wherein each of $X_1$ to $X_{13}$ is a naturally occurring amino acid.

27. The anti-Vδ1 antibody or antigen-binding fragment thereof of embodiment 26, wherein:
   a. $X_1$ is selected from the group consisting of A and V;
   b. $X_2$ is selected from the group consisting of S and T;
   c. $X_3$ is selected from the group consisting of V, A and L;
   d. $X_4$ is selected from the group consisting of G, E, and D;
   e. $X_5$ is selected from the group consisting of Y and N;
   f. $X_6$ is selected from the group consisting of V, A and P;
   g. $X_7$ is selected from the group consisting of V, Y and R;
   h. $X_8$ is selected from the group consisting of K, R and G;
   i. $X_9$ is selected from the group consisting of S and K;
   j. $X_{10}$ is selected from the group consisting of T, Q, A, E and D;
   k. $X_{11}$ is selected from the group consisting of P, H and D;
   l. $X_{12}$ is selected from the group consisting of Q, R, K, W, P, E and I; and
   m. $X_{13}$ is selected from the group consisting of I, V and L.

28. The anti-Vδ1 antibody or antigen-binding fragment thereof of embodiment 26 or embodiment 27, wherein the antibody further comprises:
   a. an HFR1 sequence comprising or consisting of the sequence of SEQ ID NO: 170 or 171;
   b. an HFR2 sequence comprising or consisting of the sequence of SEQ ID NO: 172;
   c. an HFR3 sequence comprising or consisting of the sequence of SEQ ID NO: 173;
   d. an HFR4 sequence comprising or consisting of the sequence of SEQ ID NO: 174;
   e. an LFR1 sequence comprising or consisting of the sequence of SEQ ID NO: 175;
   f. an LFR2 sequence comprising or consisting of the sequence of SEQ ID NO: 176;
   g. an LFR3 sequence comprising or consisting of the sequence of SEQ ID NO: 177 or 178; and
   h. an LFR4 sequence comprising or consisting of the sequence of SEQ ID NO: 179, 180, 181 or 182.

29. The anti-Vδ1 antibody or antigen-binding fragment thereof of any preceding embodiment, wherein the antibody or antigen-binding fragment thereof:
   a. binds to human TRDV1 (SEQ ID NOs 272 or 306) with a binding affinity ($K_D$, for example as measured by surface plasmon resonance) of less than about 100 nM (preferably less than about 50 nM);
   b. optionally binds to cyno TRDV1 (SEQ ID NO 308) with a binding affinity ($K_D$, for example as measured by surface plasmon resonance) of less than about 100 nM (preferably less than about 50 nM);
   c. has an IC50 for TCR downregulation of less than about 50 nM (preferably less than about 10 nM);
   d. has an IC50 for THP-1 cell killing of less than about 10 nM (preferably less than about 5 nM); and/or
   e. has an IC90 for THP-1 cell killing of less than about 50 nM.

30. The anti-Vδ1 antibody or antigen-binding fragment thereof of any preceding embodiment, wherein the antibody or antigen-binding fragment thereof:
   a. binds to human TRDV1 with a KD of less than about 100 nM (preferably less than about 50 nM);
   b. binds to cyno TRDV1 with a KD of less than about 100 nM (preferably less than about 50 nM);
   c. has an IC50 for TCR downregulation of less than about 50 nM (preferably less than about 10 nM) and an IC90 for TCR downregulation of less than about 100 nM (less than about 50 nM);
   d. has an IC50 for THP-1 cell killing of less than about 10 nM (preferably less than about 5 nM)
   e. has an IC90 for THP-1 cell killing of less than about 50 nM.

31. The anti-Vδ1 antibody or antigen-binding fragment thereof of embodiment 26, wherein:
   a. $X_1$ is selected from the group consisting of A and V;
   b. $X_2$ is selected from the group consisting of S and T;
   c. $X_3$ is selected from the group consisting of V, A and L;
   d. $X_4$ is selected from the group consisting of G, E, and D;
   e. $X_5$ is selected from the group consisting of Y and N;
   f. $X_6$ is selected from the group consisting of V, A and P;
   g. $X_7$ is selected from the group consisting of V, Y and R;
   h. $X_8$ is selected from the group consisting of K, R and G;
   i. $X_9$ is selected from the group consisting of S and K;
   j. $X_{10}$ is selected from the group consisting of T, Q, A, E and D;
   k. $X_{11}$ is selected from the group consisting of P and H;
   l. $X_{12}$ is selected from the group consisting of Q, R, K, W, P, E and I; and
   m. $X_{13}$ is selected from the group consisting of I, V and L.

32. The anti-Vδ1 antibody or antigen-binding fragment thereof of embodiment 31, wherein the antibody further comprises:
   a. an HFR1 sequence comprising or consisting of the sequence of SEQ ID NO: 170 or 171;
   b. an HFR2 sequence comprising or consisting of the sequence of SEQ ID NO: 172;
   c. an HFR3 sequence comprising or consisting of the sequence of SEQ ID NO: 173;
   d. an HFR4 sequence comprising or consisting of the sequence of SEQ ID NO: 174;

e. an LFR1 sequence comprising or consisting of the sequence of SEQ ID NO: 175;
f. an LFR2 sequence comprising or consisting of the sequence of SEQ ID NO: 176;
g. an LFR3 sequence comprising or consisting of the sequence of SEQ ID NO: 177; and
h. an LFR4 sequence comprising or consisting of the sequence of SEQ ID NO: 179, 180, 181 or 182.

33. The anti-Vδ1 antibody or antigen-binding fragment thereof of any preceding embodiment, wherein the antibody or antigen-binding fragment thereof:
a. binds to human TRDV1 with a $K_D$ of less than about 10 nM (preferably less than about 5 nM);
b. binds to cyno TRDV1 with a $K_D$ of less than about 100 nM (preferably less than about 50 nM);
c. has an IC50 for TCR downregulation of less than about 1 nM (preferably less than about 0.5 nM) and an IC90 for TCR downregulation of less than about 10 nM (less than about 5 nM);
d. has an IC50 for THP-1 cell killing of less than about 10 nM (preferably less than about 5 nM); and/or
e. has an IC90 for THP-1 cell killing of less than about 50 nM.

34. The anti-Vδ1 antibody or antigen-binding fragment thereof of embodiment 26, wherein:
a. $X_1$ is selected from the group consisting of A and V;
b. $X_2$ is selected from the group consisting of S and T;
c. $X_3$ is selected from the group consisting of V, A and L;
d. $X_4$ is selected from the group consisting of G and D;
e. $X_5$ is selected from the group consisting of Y and N;
f. $X_6$ is selected from the group consisting of V, A and P;
g. $X_7$ is selected from the group consisting of V, Y and R;
h. $X_8$ is selected from the group consisting of K and R;
i. $X_9$ is selected from the group consisting of S and K;
j. $X_{10}$ is selected from the group consisting of T, Q, A and E;
k. $X_{11}$ is selected from the group consisting of P and H;
l. $X_{12}$ is selected from the group consisting of Q, K, W, P and I; and
m. $X_{13}$ is selected from the group consisting of V and L.

35. The anti-Vδ1 antibody or antigen-binding fragment thereof of embodiment 34, wherein the antibody further comprises:
a. an HFR1 sequence comprising or consisting of the sequence of SEQ ID NO: 170 or 171;
b. an HFR2 sequence comprising or consisting of the sequence of SEQ ID NO: 172;
c. an HFR3 sequence comprising or consisting of the sequence of SEQ ID NO: 173;
d. an HFR4 sequence comprising or consisting of the sequence of SEQ ID NO: 174;
e. an LFR1 sequence comprising or consisting of the sequence of SEQ ID NO: 175;
f. an LFR2 sequence comprising or consisting of the sequence of SEQ ID NO: 176;
g. an LFR3 sequence comprising or consisting of the sequence of SEQ ID NO: 177; and
h. an LFR4 sequence comprising or consisting of the sequence of SEQ ID NO: 179 or 181.

36. The anti-Vδ1 antibody or antigen-binding fragment thereof of any preceding embodiment, wherein the antibody or antigen-binding fragment thereof:
a. binds to human TRDV1 with a $K_D$ of less than about 10 nM (preferably less than about 1 nM);
b. binds to cyno TRDV1 with a $K_D$ of less than about 50 nM;
c. has an IC50 for TCR downregulation of less than about 1 nM (preferably less than about 0.5 nM) and an IC90 for TCR downregulation of less than about 10 nM (less than about 5 nM);
d. gas an IC50 for THP-1 cell killing of less than about 10 nM (preferably less than about 5 nM); and/or
e. gas an IC90 for THP-1 cell killing of less than about 50 nM.

37. The anti-Vδ1 antibody or antigen-binding fragment thereof of any preceding embodiment, wherein the epitope bound by the antibody or antigen-binding fragment thereof comprises one or more amino acid residues within amino acid regions 37-53 and/or 59-77 of SEQ ID NO: 272.

38. The anti-Vδ1 antibody or antigen-binding fragment thereof of any preceding embodiment, wherein the epitope bound by the antibody or antigen-binding fragment thereof comprises amino acid residues 37, 42, 50, 53, 59, 64, 68, 69, 72, 73 and 77 of SEQ ID NO: 272.

39. The anti-Vδ1 antibody or antigen-binding fragment thereof of any preceding embodiment, wherein the epitope bound by the antibody or antigen-binding fragment thereof consists of amino acid residues 37, 42, 50, 53, 59, 64, 68, 69, 72, 73 and 77 of SEQ ID NO: 272.

40. An anti-TCR delta variable 1 (anti-Vδ1) antibody or antigen-binding fragment thereof comprising:
a. a VHCDR3 comprising or consisting of an amino acid sequence having at least 90% sequence identity to any one of SEQ ID NOs: 133 to 143; and/or
b. a VLCDR3 comprising or consisting of an amino acid sequence having at least 90% sequence identity to any one of SEQ ID NOs: 147 to 157.

41. The anti-Vδ1 antibody or antigen-binding fragment thereof of embodiment 40, comprising:
a. a VHCDR3 comprising or consisting of the amino acid sequence of any one of SEQ ID NOs: 133 to 143; and/or
b. a VLCDR3 comprising or consisting of the amino acid sequence of any one of SEQ ID NOs: 147 to 157.

42. The anti-Vδ1 antibody or antigen-binding fragment thereof of any one of embodiments 40 to 41, further comprising:
a. a VHCDR1 comprising or consisting of an amino acid sequence having at least 90% sequence identity to SEQ ID NO: 130;
b. a VHCDR2 comprising or consisting of an amino acid sequence having at least 90% sequence identity to SEQ ID NO: 131;
c. a VLCDR1 comprising or consisting of an amino acid sequence having at least 90% sequence identity to SEQ ID NO: 144; and/or
d. a VLCDR2 comprising or consisting of an amino acid sequence having at least 90% sequence identity to SEQ ID NO: 145.

43. The anti-Vδ1 antibody or antigen-binding fragment thereof of any one of embodiments 40 to 42, further comprising:
a. a VHCDR1 comprising or consisting of the amino acid sequence of SEQ ID NO: 130;
b. a VHCDR2 comprising or consisting of the amino acid sequence of SEQ ID NO: 131;

c. a VLCDR1 comprising or consisting of the amino acid sequence of SEQ ID NO: 144; and/or d. a VLCDR2 comprising or consisting of the amino acid sequence of SEQ ID NO: 145.

44. The anti-Vδ1 antibody or antigen-binding fragment thereof of any one of embodiments 40 to 43, comprising:

a. a VHCDR1, a VHCDR2 and a VHCDR3 comprising or consisting of the amino acid sequences of SEQ ID NO: 130, 131 and 133, respectively, and a VLCDR1, a VLCDR2 and a VLCDR3 comprising or consisting of the amino acid sequences of SEQ ID NOs: 144, 145 and 147, respectively;

b. a VHCDR1, a VHCDR2 and a VHCDR3 comprising or consisting of the amino acid sequences of SEQ ID NO: 130, 131 and 134, respectively, and a VLCDR1, a VLCDR2 and a VLCDR3 comprising or consisting of the amino acid sequences of SEQ ID NOs: 144, 145 and 148, respectively;

c. a VHCDR1, a VHCDR2 and a VHCDR3 comprising or consisting of the amino acid sequences of SEQ ID NO: 130, 131 and 135, respectively, and a VLCDR1, a VLCDR2 and a VLCDR3 comprising or consisting of the amino acid sequences of SEQ ID NOs: 144, 145 and 149, respectively;

d. a VHCDR1, a VHCDR2 and a VHCDR3 comprising or consisting of the amino acid sequences of SEQ ID NO: 130, 131 and 136, respectively, and a VLCDR1, a VLCDR2 and a VLCDR3 comprising or consisting of the amino acid sequences of SEQ ID NOs: 144, 145 and 150, respectively;

e. a VHCDR1, a VHCDR2 and a VHCDR3 comprising or consisting of the amino acid sequences of SEQ ID NO: 130, 131 and 137, respectively, and a VLCDR1, a VLCDR2 and a VLCDR3 comprising or consisting of the amino acid sequences of SEQ ID NOs: 144, 145 and 151, respectively;

f. a VHCDR1, a VHCDR2 and a VHCDR3 comprising or consisting of the amino acid sequences of SEQ ID NO: 130, 131 and 138, respectively, and a VLCDR1, a VLCDR2 and a VLCDR3 comprising or consisting of the amino acid sequences of SEQ ID NOs: 144, 145 and 152, respectively;

g. a VHCDR1, a VHCDR2 and a VHCDR3 comprising or consisting of the amino acid sequences of SEQ ID NO: 130, 131 and 139, respectively, and a VLCDR1, a VLCDR2 and a VLCDR3 comprising or consisting of the amino acid sequences of SEQ ID NOs: 144, 145 and 153, respectively;

h. a VHCDR1, a VHCDR2 and a VHCDR3 comprising or consisting of the amino acid sequences of SEQ ID NO: 130, 131 and 140, respectively, and a VLCDR1, a VLCDR2 and a VLCDR3 comprising or consisting of the amino acid sequences of SEQ ID NOs: 144, 145 and 154, respectively;

i. a VHCDR1, a VHCDR2 and a VHCDR3 comprising or consisting of the amino acid sequences of SEQ ID NO: 130, 131 and 141, respectively, and a VLCDR1, a VLCDR2 and a VLCDR3 comprising or consisting of the amino acid sequences of SEQ ID NOs: 144, 145 and 155, respectively;

j. a VHCDR1, a VHCDR2 and a VHCDR3 comprising or consisting of the amino acid sequences of SEQ ID NO: 130, 131 and 142, respectively, and a VLCDR1, a VLCDR2 and a VLCDR3 comprising or consisting of the amino acid sequences of SEQ ID NOs: 144, 145 and 156, respectively; or k. a VHCDR1, a VHCDR2 and a VHCDR3 comprising or consisting of the amino acid sequences of SEQ ID NO: 130, 131 and 143, respectively, and a VLCDR1, a VLCDR2 and a VLCDR3 comprising or consisting of the amino acid sequences of SEQ ID NOs: 144, 145 and 157, respectively.

45. The anti-Vδ1 antibody or antigen-binding fragment thereof of any one of embodiments 40 to 44, comprising a. a VH comprising or consisting of an amino acid sequence having at least 90% sequence identity to any one of SEQ ID NOs: 107 to 117; and/or b. a VL comprising or consisting of an amino acid sequence having at least 90% sequence identity to any one of SEQ ID NOs: 119 to 129.

46. The anti-Vδ1 antibody or antigen-binding fragment thereof of any one of embodiments 40 to 45, comprising:

a. a VH comprising or consisting of the amino acid sequence of any one of SEQ ID NOs: 107 to 117; and/or b. a VL comprising or consisting of the amino acid sequence of any one of SEQ ID NOs: 119 to 129.

47. The anti-Vδ1 antibody or antigen-binding fragment thereof of any of embodiments 40 to 46, comprising:

a. a VH comprising or consisting of an amino acid sequence having at least 90% sequence identity to SEQ ID NO: 107 and a VL comprising or consisting of an amino acid sequence having at least 90% sequence identity to SEQ ID NO: 119;

b. a VH comprising or consisting of an amino acid sequence having at least 90% sequence identity to SEQ ID NO: 108 and a VL comprising or consisting of an amino acid sequence having at least 90% sequence identity to SEQ ID NO: 120;

c. a VH comprising or consisting of an amino acid sequence having at least 90% sequence identity to SEQ ID NO: 109 and a VL comprising or consisting of an amino acid sequence having at least 90% sequence identity to SEQ ID NO: 121;

d. a VH comprising or consisting of an amino acid sequence having at least 90% sequence identity to SEQ ID NO: 110 and a VL comprising or consisting of an amino acid sequence having at least 90% sequence identity to SEQ ID NO: 122;

e. a VH comprising or consisting of an amino acid sequence having at least 90% sequence identity to SEQ ID NO: 111 and a VL comprising or consisting of an amino acid sequence having at least 90% sequence identity to SEQ ID NO: 123;

f. a VH comprising or consisting of an amino acid sequence having at least 90% sequence identity to SEQ ID NO: 112 and a VL comprising or consisting of an amino acid sequence having at least 90% sequence identity to SEQ ID NO: 124;

g. a VH comprising or consisting of an amino acid sequence having at least 90% sequence identity to SEQ ID NO: 113 and a VL comprising or consisting of an amino acid sequence having at least 90% sequence identity to SEQ ID NO: 125;

h. a VH comprising or consisting of an amino acid sequence having at least 90% sequence identity to SEQ ID NO: 114 and a VL comprising or consisting of an amino acid sequence having at least 90% sequence identity to SEQ ID NO: 126;

i. a VH comprising or consisting of an amino acid sequence having at least 90% sequence identity to SEQ ID NO: 115 and a VL comprising or consisting of an amino acid sequence having at least 90% sequence identity to SEQ ID NO: 127;

j. a VH comprising or consisting of an amino acid sequence having at least 90% sequence identity to SEQ ID NO: 116 and a VL comprising or consisting of an amino acid sequence having at least 90% sequence identity to SEQ ID NO: 128; or k. a VH comprising or consisting of an amino acid sequence having at least 90% sequence identity to SEQ ID NO: 117 and a VL comprising or consisting of an amino acid sequence having at least 90% sequence identity to SEQ ID NO: 129.

48. The anti-Vδ1 antibody or antigen-binding fragment thereof of any one of embodiments 40 to 47, comprising a. a VH comprising or consisting of the amino acid sequence of SEQ ID NO: 107 and a VL comprising or consisting of the amino acid sequence of SEQ ID NO: 119;

b. a VH comprising or consisting of the amino acid sequence of SEQ ID NO: 108 and a VL comprising or consisting of the amino acid sequence of SEQ ID NO: 120;

c. a VH comprising or consisting of the amino acid sequence of SEQ ID NO: 109 and a VL comprising or consisting of the amino acid sequence of SEQ ID NO: 121;

d. a VH comprising or consisting of the amino acid sequence of SEQ ID NO: 110 and a VL comprising or consisting of the amino acid sequence of SEQ ID NO: 122;

e. a VH comprising or consisting of the amino acid sequence of SEQ ID NO: 111 and a VL comprising or consisting of the amino acid sequence of SEQ ID NO: 123;

f. a VH comprising or consisting of the amino acid sequence of SEQ ID NO: 112 and a VL comprising or consisting of the amino acid sequence of SEQ ID NO: 124;

g. a VH comprising or consisting of the amino acid sequence of SEQ ID NO: 113 and a VL comprising or consisting of the amino acid sequence of SEQ ID NO: 125;

h. a VH comprising or consisting of the amino acid sequence of SEQ ID NO: 114 and a VL comprising or consisting of the amino acid sequence of SEQ ID NO: 126;

i. a VH comprising or consisting of the amino acid sequence of SEQ ID NO: 115 and a VL comprising or consisting of the amino acid sequence of SEQ ID NO: 127;

j. a VH comprising or consisting of the amino acid sequence of SEQ ID NO: 116 and a VL comprising or consisting of the amino acid sequence of SEQ ID NO: 128; or k. a VH comprising or consisting of the amino acid sequence of SEQ ID NO: 117 and a VL comprising or consisting of the amino acid sequence of SEQ ID NO: 129.

49. The anti-Vδ1 antibody or antigen-binding fragment thereof of any one of embodiments 40 to 48, wherein the antibody or antigen-binding fragment thereof comprises a kappa light chain variable sequence having an amino acid residue other than serine at position 74 according to the IMGT numbering system.

50. The anti-Vδ1 antibody or antigen-binding fragment thereof of embodiment 49, wherein the residue at position 74 according to the IMGT numbering system of the light chain variable sequence is an amino acid selected from the group consisting of glycine, alanine, valine, methionine, leucine and isoleucine.

51. The anti-Vδ1 antibody or antigen-binding fragment thereof of embodiment 49, wherein the residue at position 74 according to the IMGT numbering system of the light chain variable sequence is an amino acid selected from the group consisting of arginine, cysteine, glutamine, glutamic acid, glycine, histidine, isoleucine, leucine, lysine, methionine, phenylalanine, threonine, tryptophan, tyrosine and valine.

52. The anti-Vδ1 antibody or antigen-binding fragment thereof of embodiment 49, wherein the residue at position 74 according to the IMGT numbering system of the light chain variable sequence is an amino acid selected from the group consisting of glycine, valine, methionine, leucine and isoleucine.

53. The anti-Vδ1 antibody or antigen-binding fragment thereof of embodiment 49, wherein the residue at position 74 according to the IMGT numbering system of the light chain variable sequence is a leucine residue.

54. The anti-Vδ1 antibody or antigen-binding fragment thereof of any one of embodiments 40 to 53, wherein the anti-Vδ1 antibody or antigen-binding fragment thereof is an antibody selected from the group consisting of ADT1-7-10, ADT1-7-15, ADT1-7-17, ADT1-7-18, ADT1-7-19, ADT1-7-20, ADT1-7-22 ADT1-7-23, ADT1-7-42, ADT1-7-3 and ADT1-7-61.

55. The anti-Vδ1 antibody or antigen-binding fragment thereof of embodiment 54, wherein the antibody comprises from 1 to 10, from 1 to 5 or from 1 to 2 amino acid substitutions across all 6 CDR regions.

56. The anti-Vδ1 antibody or antigen-binding fragment thereof of embodiment 54 or 55, wherein the antibody comprises up to 2 or up to 1 amino acid substitution across all 6 CDR regions.

57. The anti-Vδ1 antibody or antigen-binding fragment thereof of any one of embodiments 54 to 56, wherein the antibody comprises 1 or 2 amino acid substitution across all 6 CDR regions.

58. The anti-Vδ1 antibody or antigen-binding fragment thereof of any one of embodiments 54 to 57, wherein the antibody comprises 1 to 10, 1 to 5 or 1 to 2 amino acid substitutions in one or more framework regions.

59. The anti-Vδ1 antibody or antigen-binding fragment thereof of any one of embodiments 54 to 55, wherein the antibody comprises up to 2 or up to 1 amino acid substitutions in one or more framework regions.

60. The anti-Vδ1 antibody or antigen-binding fragment thereof of any one of embodiments 54 to 59, wherein the antibody comprises 1 or 2 amino acid substitutions in one or more framework regions.

61. The anti-Vδ1 antibody or antigen-binding fragment thereof of any one of embodiments 55 to 60, wherein the amino acid substitutions are conservative amino acid substitutions.

62. An anti-TCR delta variable 1 (anti-Vδ1) antibody or antigen-binding fragment thereof comprising:

a. an HCDR1 sequence comprising or consisting of the sequence of SEQ ID NO: 130 b. an HCDR2 sequence comprising or consisting of the sequence of SEQ ID NO: 131 c. an HCDR3 sequence comprising or consisting of the sequence of $X_1X_2YX_3X_4$AFDI, wherein the HCDR3 sequence is not SEQ ID NO: 132;
d. an LCDR1 sequence comprising or consisting of the sequence of SEQ ID NO: 144;
e. an LCDR2 sequence comprising or consisting of the sequence of SEQ ID NO: 145; and
f. an LCDR3 sequence comprising or consisting of the sequence of $QQX_5X_6X_7X_8LX_9T$,
wherein the LCDR3 sequence is no SEQ ID NO: 146;
wherein each of $X_1$ to $X_9$ is a naturally occurring amino acid.

63. The anti-Vδ1 antibody or antigen-binding fragment thereof of embodiment 62, wherein:
a. $X_1$ is selected from the group consisting of D, I and V;
b. $X_2$ is selected from the group consisting of D and S;
c. $X_3$ is selected from the group consisting of N, E, D, Q and A;
d. $X_4$ is selected from the group consisting of D and E;
e. $X_5$ is selected from the group consisting of T and S;
f. $X_6$ is selected from the group consisting of A, G, Y and S;
g. $X_7$ is selected from the group consisting of S and D;
h. $X_8$ is selected from the group consisting of T, E and G; and
i. $X_9$ is selected from the group consisting of L and D.

64. The anti-Vδ1 antibody or antigen-binding fragment thereof of embodiment 62 or embodiment 63, wherein the antibody further comprises:
a. an HFR1 sequence comprising or consisting of the sequence of SEQ ID NO: 189;
b. an HFR2 sequence comprising or consisting of the sequence of SEQ ID NO: 190;
c. an HFR3 sequence comprising or consisting of the sequence of SEQ ID NO: 191;
d. an HFR4 sequence comprising or consisting of the sequence of SEQ ID NO: 192;
e. an LFR1 sequence comprising or consisting of the sequence of SEQ ID NO: 193 and 194;
f. an LFR2 sequence comprising or consisting of the sequence of SEQ ID NO: 195;
g. an LFR3 sequence comprising or consisting of the sequence of SEQ ID NO: 196; and
h. an LFR4 sequence comprising or consisting of the sequence of SEQ ID NO: 197.

65. The anti-Vδ1 antibody or antigen-binding fragment thereof of any one of embodiments 40 to 64, wherein the antibody or antigen-binding fragment thereof:
a. binds to human TRDV1 with a $K_D$ of less than about 10 nM (preferably less than about 5 nM);
b. has an IC50 for TCR downregulation of less than about 50 nM (preferably less than about 10 nM);
c. has an IC50 for THP-1 cell killing of less than about 5 nM (preferably less than about 1 nM)
d. has an IC90 for THP-1 cell killing of less than about 50 nM.

66. The anti-Vδ1 antibody or antigen-binding fragment thereof of embodiment 62, wherein:
a. $X_1$ is selected from the group consisting of D and V;
b. $X_2$ is selected from the group consisting of D and S;
c. $X_3$ is selected from the group consisting of D, Q and A;
d. $X_4$ is selected from the group consisting of D and E;
e. $X_5$ is S;
f. $X_6$ is selected from the group consisting of A and Y;
g. $X_7$ is S;
h. $X_8$ is selected from the group consisting of E and G; and
i. $X_9$ is selected from the group consisting of L and D.

67. The anti-Vδ1 antibody or antigen-binding fragment thereof of embodiment 66, wherein the antibody further comprises:
a. an HFR1 sequence comprising or consisting of the sequence of SEQ ID NO: 189;
b. an HFR2 sequence comprising or consisting of the sequence of SEQ ID NO: 190;
c. an HFR3 sequence comprising or consisting of the sequence of SEQ ID NO: 191;
d. an HFR4 sequence comprising or consisting of the sequence of SEQ ID NO: 192;
e. an LFR1 sequence comprising or consisting of the sequence of SEQ ID NO: 193;
f. an LFR2 sequence comprising or consisting of the sequence of SEQ ID NO: 195;
g. an LFR3 sequence comprising or consisting of the sequence of SEQ ID NO: 196; and
h. an LFR4 sequence comprising or consisting of the sequence of SEQ ID NO: 197.

68. The anti-Vδ1 antibody or antigen-binding fragment thereof of any one of embodiments 40 to 67, wherein the antibody or antigen-binding fragment thereof:
a. binds to human TRDV1 with a $K_D$ of less than about 10 nM (preferably less than about 5 nM);
b. has an IC50 for TCR downregulation of less than about 5 nM (preferably less than about 1 nM);
c. has an IC90 for TCR downregulation of less than about 10 nM (preferably less than about 5 nM);
d. has an IC50 for THP-1 cell killing of less than about 5 nM (preferably less than about 1 nM)
e. has an IC90 for THP-1 cell killing of less than about 10 nM (preferably less than about 5 nM).

69. The anti-Vδ1 antibody or antigen-binding fragment thereof of any one of embodiments 40 to 68, wherein the epitope bound by the antibody or antigen-binding fragment thereof comprises one or more amino acid residues within amino acid regions 5-20 and/or 62-77 of SEQ ID NO: 271.

70. The anti-Vδ1 antibody or antigen-binding fragment thereof of any one of embodiments 40 to 69, wherein the epitope bound by the antibody or antigen-binding fragment thereof comprises amino acid residues 5, 9, 16, 20, 62, 64, 72 and 77 of SEQ ID NO: 272.

71. The anti-Vδ1 antibody or antigen-binding fragment thereof of any one of embodiments 40 to 70, wherein the epitope bound by the antibody or antigen-binding fragment thereof consists of amino acid residues 5, 9, 16, 20, 62, 64, 72 and 77 of SEQ ID NO: 272.

72. An anti-TCR delta variable 1 (anti-Vδ1) antibody or antigen-binding fragment thereof, wherein the anti-Vδ1 antibody or antigen-binding fragment thereof is an affinity matured variant of a parent anti-Vδ1 antibody or antigen-binding fragment thereof, wherein the parent anti-Vδ1 antibody or antigen-binding fragment thereof comprises a VH comprising the amino acid sequence of SEQ ID NO: 1 and a VL sequence comprising the amino acid sequence of SEQ ID NO: 26.

73. The anti-Vδ1 antibody or antigen-binding fragment thereof of embodiment 72, wherein the antibody is an antibody as defined in any one of embodiments 4 to 40.

74. The anti-Vδ1 antibody or antigen-binding fragment thereof of any one of embodiments 4 to 40, 72 or 73, wherein the antibody or antigen-binding fragment thereof:

a. binds to human TRDV1 with a $K_D$ of less than about 100 nM (preferably less than about 50 nM);
b. binds to cyno TRDV1 with a $K_D$ of less than about 100 nM (preferably less than about 50 nM);
c. has an IC50 for TCR downregulation of less than about 50 nM (preferably less than about 10 nM) and an IC90 for TCR downregulation of less than about 100 nM (less than about 50 nM);
d. has an IC50 for THP-1 cell killing of less than about 10 nM (preferably less than about 5 nM); and/or
e. has an IC90 for THP-1 cell killing of less than about 50 nM.

75. The anti-Vδ1 antibody or antigen-binding fragment thereof of any one of embodiments 4 to 40, 72 or 73, wherein the antibody or antigen-binding fragment thereof:
a. binds to human TRDV1 with a $K_D$ of less than about 10 nM (preferably less than about 5 nM);
b. binds to cyno TRDV1 with a $K_D$ of less than about 100 nM (preferably less than about 50 nM);
c. has an IC50 for TCR downregulation of less than about 1 nM (preferably less than about 0.5 nM) and an IC90 for TCR downregulation of less than about 10 nM (less than about 5 nM);
d. has an IC50 for THP-1 cell killing of less than about 10 nM (preferably less than about 5 nM); and/or
e. has an IC90 for THP-1 cell killing of less than about 50 nM.

76. The anti-Vδ1 antibody or antigen-binding fragment thereof of any one of embodiments 4 to 40, 72 or 73, wherein the antibody or antigen-binding fragment thereof:
a. binds to human TRDV1 with a $K_D$ of less than about 10 nM (preferably less than about 1 nM),
b. binds to cyno TRDV1 with a $K_D$ of less than about 50 nM;
c. has an IC50 for TCR downregulation of less than about 1 nM (preferably less than about 0.5 nM) and an IC90 for TCR downregulation of less than about 10 nM (less than about 5 nM);
d. gas an IC50 for THP-1 cell killing of less than about 10 nM (preferably less than about 5 nM) and/or
e. gas an IC90 for THP-1 cell killing of less than about 50 nM.

77. An anti-TCR delta variable 1 (anti-Vδ1) antibody or antigen-binding fragment thereof, wherein the anti-Vδ1 antibody or antigen-binding fragment thereof is an affinity matured variant of a parent anti-Vδ1 antibody or antigen-binding fragment thereof, wherein the parent anti-Vδ1 antibody or antigen-binding fragment thereof comprises a VH comprising the amino acid sequence of SEQ ID NO: 106 and a VL sequence comprising the amino acid sequence of SEQ ID NO: 118.

78. The anti-Vδ1 antibody or antigen-binding fragment thereof of embodiment 77, wherein the antibody is an antibody as defined in any one of embodiments 41 to 71.

79. The anti-Vδ1 antibody or antigen-binding fragment thereof of any one of embodiments 41 to 71, 77 or 78, wherein the antibody or antigen-binding fragment thereof:
a. binds to human TRDV1 with a $K_D$ of less than about 10 nM (preferably less than about 5 nM);
b. has an IC50 for TCR downregulation of less than about 50 nM (preferably less than about 10 nM);
c. has an IC50 for THP-1 cell killing of less than about 5 nM (preferably less than about 1 nM); and/or
d. has an IC90 for THP-1 cell killing of less than about 50 nM.

80. The anti-Vδ1 antibody or antigen-binding fragment thereof of any one of embodiments 41 to 71, 77 or 78, wherein the antibody or antigen-binding fragment thereof:
a. binds to human TRDV1 with a $K_D$ of less than about 10 nM (preferably less than about 5 nM);
b. has an IC50 for TCR downregulation of less than about 5 nM (preferably less than about 1 nM);
c. has an IC90 for TCR downregulation of less than about 10 nM (preferably less than about 5 nM);
d. has an IC50 for THP-1 cell killing of less than about 5 nM (preferably less than about 1 nM); and/or
e. has an IC90 for THP-1 cell killing of less than about 10 nM (preferably less than about 5 nM).

81. An anti-TCR delta variable 1 (anti-Vδ1) antibody or antigen-binding fragment thereof, wherein the anti-Vδ1 antibody or antigen-binding fragment thereof is an affinity matured variant of a parent anti-Vδ1 antibody or antigen-binding fragment thereof, wherein the parent anti-Vδ1 antibody or antigen-binding fragment thereof comprises:
a. a VH comprising or consisting of the amino acid sequence of SEQ ID NO: 273 and a VL comprising or consisting of the amino acid sequence of SEQ ID NO: 282;
b. a VH comprising or consisting of the amino acid sequence of SEQ ID NO: 274 and a VL comprising or consisting of the amino acid sequence of SEQ ID NO: 283;
c. a VH comprising or consisting of the amino acid sequence of SEQ ID NO: 275 and a VL comprising or consisting of the amino acid sequence of SEQ ID NO: 284;
d. a VH comprising or consisting of the amino acid sequence of SEQ ID NO: 276 and a VL comprising or consisting of the amino acid sequence of SEQ ID NO: 285;
e. a VH comprising or consisting of the amino acid sequence of SEQ ID NO: 277 and a VL comprising or consisting of the amino acid sequence of SEQ ID NO: 286;
f. a VH comprising or consisting of the amino acid sequence of SEQ ID NO: 278 and a VL comprising or consisting of the amino acid sequence of SEQ ID NO: 287;
g. a VH comprising or consisting of the amino acid sequence of SEQ ID NO: 279 and a VL comprising or consisting of the amino acid sequence of SEQ ID NO: 288;
h. a VH comprising or consisting of the amino acid sequence of SEQ ID NO: 280 and a VL comprising or consisting of the amino acid sequence of SEQ ID NO: 289;
i. a VH comprising or consisting of the amino acid sequence of SEQ ID NO: 281 and a VL comprising or consisting of the amino acid sequence of SEQ ID NO: 290; or
j. a VH comprising or consisting of the amino acid sequence of SEQ ID NO: 312 and a VL comprising or consisting of the amino acid sequence of SEQ ID NO: 313.

82. The anti-Vδ1 antibody or antigen-binding fragment thereof of any one of embodiments 72 to 81, wherein the affinity matured antibody has at least 20%, at least 30%, at least 40%, at least 50%, at least 100%, at least 500% or more preferably at least about 1000% greater affinity than the parental antibody for binding to a variable delta 1 (Vδ1) chain of a γδ T cell receptor (TCR), for example as measured by the Kd.

83. The anti-Vδ1 antibody or antigen-binding fragment thereof of any one of embodiments 72 to 82, wherein the affinity matured anti-Vδ1 antibody or antigen-binding fragment thereof comprises VH and VL sequences that are at least 80%, at least 90%, at least 95% or at least 96% identical to the corresponding parental VH and VL sequences.

84. The anti-Vδ1 antibody or antigen-binding fragment thereof of any one of embodiments 72 to 82, wherein the affinity matured anti-Vδ1 antibody or antigen-binding fragment comprises up to 20, for example up to 15, for example up to 10 amino acid substitutions compared to the parental antibody sequences.

85. The anti-Vδ1 antibody or antigen-binding fragment thereof of any preceding embodiment, wherein the antibody does not comprise an VHCDR3 having SEQ ID NO: 54 and a VLCDR3 having SEQ ID NO: 81, and/or wherein the antibody not comprise an VHCDR3 having SEQ ID NO: 132 and a VLCDR3 having SEQ ID NO: 146.

86. The anti-Vδ1 antibody or antigen-binding fragment thereof of any preceding embodiment, wherein the antibody does not comprise a VH region having SEQ ID NO: 1 and a VL region having SEQ ID NO: 26, and/or wherein the antibody does not comprise a VH region having SEQ ID NO: 106 and a VL region having SEQ ID NO: 118.

87. An anti-TCR delta variable 1 (anti-Vδ1) antibody or antigen-binding fragment thereof comprising a kappa light chain variable sequence, in which the residue at position 74 according to the IMGT numbering system is not a serine reside.

88. The anti-Vδ1 antibody or antigen-binding fragment thereof of embodiment 85, wherein the residue at position 74 according to the IMGT numbering system is an amino acid selected from the group consisting of glycine, alanine, valine, methionine, leucine and isoleucine.

89. The anti-Vδ1 antibody or antigen-binding fragment thereof of embodiment 88, wherein the residue at position 74 according to the IMGT numbering system is an amino acid selected from the group consisting of arginine, cysteine, glutamine, glutamic acid, glycine, histidine, isoleucine, leucine, lysine, methionine, phenylalanine, threonine, tryptophan, tyrosine and valine.

90. The anti-Vδ1 antibody or antigen-binding fragment thereof of embodiment 88, wherein the residue at position 74 according to the IMGT numbering system is an amino acid selected from the group consisting of glycine, valine, methionine, leucine and isoleucine.

91. The anti-Vδ1 antibody or antigen-binding fragment thereof of embodiment 88, wherein the residue at position 74 according to the IMGT numbering system is a leucine residue.

92. The anti-Vδ1 antibody or antigen-binding fragment thereof of any preceding embodiment, wherein the antibody is an IgG antibody.

93. The anti-Vδ1 antibody or antigen-binding fragment thereof of any preceding embodiment, wherein the antibody is an IgG1 antibody.

94. The anti-Vδ1 antibody or antigen-binding fragment thereof of any preceding embodiment, wherein the antibody is an antibody as defined in any one of embodiments 4 to 40 or 72 to 76.

95. An anti-Vδ1 antibody or antigen-binding fragment, wherein the antibody is a multispecific antibody that specifically binds:
   a. a first target epitope, wherein the first target epitope is an epitope of the variable delta 1 (Vδ1) chain of a γδ T cell receptor (TCR); and
   b. a second target epitope.

96. An anti-Vδ1 antibody or antigen-binding fragment, wherein the antibody is a multispecific antibody that specifically binds:
   a. a first target epitope, wherein the first target epitope is an epitope of the variable delta 1 (Vδ1) chain of a γδ T cell receptor (TCR); and
   b. a second target epitope;

wherein the multispecific antibody comprises SEQ ID NO: 385; SEQ ID NO: 386; SEQ ID NO: 387; SEQ ID NO: 314; SEQ ID NO: 393; SEQ ID NO: 394; SEQ ID NO: 395; SEQ ID NO: 397; SEQ ID NO: 388; SEQ ID NO: 315; SEQ ID NO: 316; SEQ ID NO: 378; SEQ ID NO: 379; SEQ ID NO: 380; SEQ ID NO: 382; SEQ ID NO: 383; SEQ ID NO: 384; SEQ ID NO: 393; SEQ ID NO: 396; SEQ ID NO: 398; SEQ ID NO: 399; SEQ ID NO: 401; SEQ ID NO: 402; SEQ ID NO: 403; SEQ ID NO: 404; SEQ ID NO: 405; SEQ ID NO: 406; SEQ ID NO: 407; SEQ ID NO: 408; SEQ ID NO: 409; SEQ ID NO: 410; SEQ ID NO: 411; SEQ ID NO: 412; SEQ ID NO: 413; SEQ ID NO: 414 and SEQ ID NO: 415; SEQ ID NO: 414 and SEQ ID NO: 416; SEQ ID NO: 414 and SEQ ID NO: 419; SEQ ID NO: 414 and SEQ ID NO: 418; SEQ ID NO: 504 and SEQ ID NO: 415; SEQ ID NO: 504 and SEQ ID NO: 416; SEQ ID NO: 504 and SEQ ID NO: 419; SEQ ID NO: 504 and SEQ ID NO: 418; SEQ ID NO: 505 and SEQ ID NO: 415; SEQ ID NO: 505 and SEQ ID NO: 416; SEQ ID NO: 505 and SEQ ID NO: 419; SEQ ID NO: 505 and SEQ ID NO: 418; SEQ ID NO: 421 and SEQ ID NO: 422; SEQ ID NO: 504 and SEQ ID NO: 422; SEQ ID NO: 423 and SEQ ID NO: 424; SEQ ID NO: 425 and SEQ ID NO: 426; SEQ ID NO: 421 and SEQ ID NO: 437; SEQ ID NO: 504 and SEQ ID NO: 437; SEQ ID NO: 423 and SEQ ID NO: 427; SEQ ID NO: 425 and SEQ ID NO: 428; SEQ ID NO: 421 and SEQ ID NO: 429; SEQ ID NO: 504 and SEQ ID NO: 429; SEQ ID NO: 423 and SEQ ID NO: 430; SEQ ID NO: 414 and SEQ ID NO: 431; SEQ ID NO: 414 and SEQ ID NO: 433; SEQ ID NO: 414 and SEQ ID NO: 434; SEQ ID NO: 414 and SEQ ID NO: 435; SEQ ID NO: 504 and SEQ ID NO: 431; SEQ ID NO: 504 and SEQ ID NO: 433; SEQ ID NO: 504 and SEQ ID NO: 434; SEQ ID NO: 504 and SEQ ID NO: 435; SEQ ID NO: 505 and SEQ ID NO: 431; SEQ ID NO: 505 and SEQ ID NO: 433; SEQ ID NO: 505 and SEQ ID NO: 434; SEQ ID NO: 505 and SEQ ID NO: 435; SEQ ID NO: 438 and SEQ ID NO: 417; or SEQ ID NO: 439 and SEQ ID NO: 420.

97. The anti-Vδ1 antibody or antigen-binding fragment of any one of embodiments 1 to 95, wherein the antibody is a multispecific antibody that specifically binds:
   a. a first target epitope, wherein the first target epitope is an epitope of the variable delta 1 (Vδ1) chain of a γδ T cell receptor (TCR); and
   b. a second target epitope;

wherein the multispecific antibody comprises SEQ ID NO: 385; SEQ ID NO: 386; SEQ ID NO: 387; SEQ ID NO: 314; SEQ ID NO: 393; SEQ ID NO: 394; SEQ ID NO: 395; SEQ ID NO: 397; SEQ ID NO: 388; SEQ ID NO: 315; SEQ ID NO: 316; SEQ ID NO: 378; SEQ ID NO: 379; SEQ ID NO: 380; SEQ ID NO: 382; SEQ ID NO: 383; SEQ ID NO: 384; SEQ ID NO: 393; SEQ ID NO: 396; SEQ ID NO: 398; SEQ ID NO: 399; SEQ ID NO: 401; SEQ ID NO: 402; SEQ ID NO: 403; SEQ ID NO: 404; SEQ ID NO: 405; SEQ ID NO: 406; SEQ ID NO: 407; SEQ ID NO: 408; SEQ ID NO: 409; SEQ ID NO: 410; SEQ ID NO: 411; SEQ ID NO: 412; SEQ ID NO: 414 and SEQ ID NO: 415; SEQ ID NO: 414 and SEQ ID NO: 416; SEQ ID NO: 414 and SEQ ID NO: 419; SEQ ID NO: 414 and SEQ ID NO: 418; SEQ ID NO: 504 and SEQ ID NO: 415; SEQ ID NO: 504 and SEQ ID NO: 416; SEQ ID NO: 504 and SEQ ID NO: 419; SEQ ID NO: 504 and SEQ ID NO: 418; SEQ ID NO: 505 and SEQ ID NO: 415; SEQ ID NO: 505 and SEQ ID NO: 416; SEQ ID NO: 505 and SEQ ID NO: 419; SEQ ID NO: 505 and SEQ ID NO: 418; SEQ ID NO: 421 and SEQ ID NO: 422; SEQ ID NO: 504 and SEQ ID NO: 422; SEQ ID NO: 423 and SEQ ID NO: 424; SEQ ID NO: 425 and SEQ ID NO: 426; SEQ ID NO: 421 and SEQ ID NO: 437; SEQ ID NO: 504 and SEQ ID NO: 437; SEQ ID NO: 423 and SEQ ID NO: 427; SEQ ID NO: 425 and SEQ ID NO: 428; SEQ ID NO: 421 and SEQ ID NO: 429; SEQ ID NO: 504 and SEQ ID NO: 429; SEQ ID NO: 423 and SEQ ID NO: 430; SEQ ID NO: 414 and SEQ ID NO: 431; SEQ ID NO: 414 and SEQ ID NO: 433; SEQ ID NO: 414 and SEQ ID NO: 434; SEQ ID NO: 414 and SEQ ID NO: 435; SEQ ID NO: 504 and SEQ ID NO: 431; SEQ ID NO: 504 and SEQ ID NO: 433; SEQ ID NO: 504 and SEQ ID NO: 434; SEQ ID NO: 504 and SEQ ID NO: 435; SEQ ID NO: 505 and SEQ ID NO: 431; SEQ ID NO: 505 and SEQ ID NO: 433; SEQ ID NO: 505 and SEQ ID NO: 434; SEQ ID NO: 505 and SEQ ID NO: 435; SEQ ID NO: 438 and SEQ ID NO: 417; or SEQ ID NO: 439 and SEQ ID NO: 420.

98. The anti-Vδ1 antibody or antigen-binding fragment of embodiment 94 or embodiment 95, wherein the multispecific antibody comprises SEQ ID NO: 388; SEQ ID NO: 393; SEQ ID NO: 394; SEQ ID NO: 395; SEQ ID NO: 396; SEQ ID NO: 397; SEQ ID NO: 398; SEQ ID NO: 399; SEQ ID NO: 401; SEQ ID NO: 402; SEQ ID NO: 403; SEQ ID NO: 404; SEQ ID NO: 405; SEQ ID NO: 406; SEQ ID NO: 407; SEQ ID NO: 408; SEQ ID NO: 409; SEQ ID NO: 410; SEQ ID NO: 411; SEQ ID NO: 412; SEQ ID NO: 414 and SEQ ID NO: 415; SEQ ID NO: 414 and SEQ ID NO: 416; SEQ ID NO: 414 and SEQ ID NO: 419; SEQ ID NO: 414 and SEQ ID NO: 418; SEQ ID NO: 504 and SEQ ID NO: 415; SEQ ID NO: 504 and SEQ ID NO: 416; SEQ ID NO: 504 and SEQ ID NO: 419; SEQ ID NO: 504 and SEQ ID NO: 418; SEQ ID NO: 505 and SEQ ID NO: 415; SEQ ID NO: 505 and SEQ ID NO: 416; SEQ ID NO: 505 and SEQ ID NO: 419; SEQ ID NO: 505 and SEQ ID NO: 418; SEQ ID NO: 414 and SEQ ID NO: 431; SEQ ID NO: 414 and SEQ ID NO: 433; SEQ ID NO: 414 and SEQ ID NO: 434; SEQ ID NO: 414 and SEQ ID NO: 434; SEQ ID NO: 504 and SEQ ID NO: 431; SEQ ID NO: 504 and SEQ ID NO: 433; SEQ ID NO: 504 and SEQ ID NO: 434; SEQ ID NO: 504 and SEQ ID NO: 435; SEQ ID NO: 505 and SEQ ID NO: 431; SEQ ID NO: 505 and SEQ ID NO: 433; SEQ ID NO: 505 and SEQ ID NO: 434; SEQ ID NO: 438 and SEQ ID NO: 417; or SEQ ID NO: 439 and SEQ ID NO: 420.

99. The anti-Vδ1 antibody or antigen-binding fragment of any one of embodiments 96 to 98, wherein the first target epitope is an epitope as defined in any one of embodiments 37 to 39 or 69 to 71.

100. An anti-TCR delta variable 1 (anti-Vδ1) antibody or antigen-binding fragment thereof that specifically binds to a variable delta 1 (Vδ1) chain of a γδ T cell receptor (TCR) and competes with binding to the variable delta 1 (Vδ1) chain of a γδ T cell receptor (TCR) with an antibody or antigen-binding fragment thereof of any preceding embodiment.

101. The anti-Vδ1 antibody or antigen-binding fragment of any previous embodiment, wherein the antibody is Fc-enabled.

102. An anti-TCR delta variable 1 (anti-Vδ1) antibody or antigen-binding fragment thereof, characterised in that it:

a. causes downregulation of TCRs on Vδ1 T-cells to which it binds;

b. does not exhibit CDC or ADCC; and c. does not deplete Vδ1 T-cells.

103. The anti-TCR delta variable 1 (anti-Vδ1) antibody or antigen-binding fragment thereof of embodiment 102, wherein the antibody_causes a depletion of less than about 30%, or less than about 20%, or less than about 10% of the viable Vδ1 T+ cell population via ADCC and/or CDC.

104. The anti-TCR delta variable 1 (anti-Vδ1) antibody or antigen-binding fragment thereof of embodiment 102, wherein the antibody does not induce secretion of IL-17A.

105. The anti-TCR delta variable 1 (anti-Vδ1) antibody or antigen-binding fragment thereof of embodiment 102, wherein the antibody induces less than about 30%, or less than about 20%, or less than about 10% of the IL-17A secretion induced by equivalent CD3 antibodies.

106. The anti-TCR delta variable 1 (anti-Vδ1) antibody or antigen-binding fragment thereof of any one of embodiments 102 to 105, wherein the antibody or antigen-binding fragment thereof binds to human TRVD1 with a KD of less than about 10 nM.

107. The anti-TCR delta variable 1 (anti-Vδ1) antibody or antigen-binding fragment thereof of any one of embodiments 102 to 106, wherein the antibody or antigen-binding fragment thereof binds to human TRVD1 with a KD of less than about 5 nM.

108. The anti-Vδ1 antibody or antigen-binding fragment thereof of any one of embodiments 102 to 107, wherein the antibody or antigen-binding fragment thereof binds to cyno TRVD1 with a KD of less than about 100 nM.

109. The anti-Vδ1 antibody or antigen-binding fragment thereof of any one of embodiment 108, wherein the antibody or antigen-binding fragment thereof binds to cyno TRVD1 with a KD of less than about 50 nM.

110. An anti-TCR delta variable 1 (anti-Vδ1) antibody or antigen-binding fragment thereof that specifically binds to a human variable delta 1 (Vδ1) chain of a γδ T cell receptor (TCR) with a KD of less than about 10 nM.

111. The anti-Vδ1 antibody or antigen-binding fragment thereof of embodiment 110, wherein the anti-Vδ1 antibody or antigen-binding fragment thereof is an antibody or antigen-binding fragment thereof as defined in any one of embodiments 1 to 109.

112. The anti-Vδ1 antibody or antigen-binding fragment thereof of any preceding embodiment, wherein the anti-Vδ1 antibody or antigen-binding fragment thereof binds to a cyno variable delta 1 (Vδ1) chain of a γδ T cell receptor (TCR) with a KD of less than about 100 nM or less than about 50 nM.

113. The anti-Vδ1 antibody or antigen-binding fragment thereof of any preceding embodiment, wherein the antibody or antigen-binding fragment thereof has an IC50 for TCR downregulation of less than about 50 nM, preferably less than about 10 nM.

114. The anti-Vδ1 antibody or antigen-binding fragment thereof of any preceding embodiment, wherein the antibody or antigen-binding fragment thereof has an IC90 for TCR downregulation of less than about 100 nM, preferably less than about 50 nM.

115. The anti-Vδ1 antibody or antigen-binding fragment thereof of any preceding embodiment, wherein the antibody or antigen-binding fragment thereof has an IC50 for THP-1 cell killing of less than about 10 nM, preferably less than about 5 nM.

116. The anti-Vδ1 antibody or antigen-binding fragment thereof of any preceding embodiment, wherein the antibody or antigen-binding fragment thereof has an IC90 for THP-1 cell killing of less than about 50 nM.

117. The anti-Vδ1 antibody or antigen-binding fragment thereof of any preceding embodiment, wherein the antibody or antigen-binding fragment thereof stimulates Vδ1 T-cell proliferation.

118. The anti-Vδ1 antibody or antigen-binding fragment thereof of any preceding embodiment, wherein the anti-Vδ1 antibody or antigen-binding fragment thereof binds human TVRD1 with a KD of less than about 100 nM.

119. The anti-Vδ1 antibody or antigen-binding fragment thereof of any preceding embodiment, wherein the anti-Vδ1 antibody or antigen-binding fragment thereof binds human TVRD1 with a KD of less than about 50 nM.

120. The anti-Vδ1 antibody or antigen-binding fragment thereof of any preceding embodiment, wherein the anti-Vδ1 antibody or antigen-binding fragment thereof binds human TRDV1 with $K_D$ of less than about 10 nM.

121. The anti-Vδ1 antibody or antigen-binding fragment thereof of any preceding embodiment, wherein the anti-Vδ1 antibody or antigen-binding fragment thereof binds human TRDV1 with $K_D$ of less than about 5 nM.

122. The anti-Vδ1 antibody or antigen-binding fragment thereof of any preceding embodiment, wherein the anti-Vδ1 antibody or antigen-binding fragment thereof binds human TRDV1 with $K_D$ of less than about 1 nM.

123. The anti-Vδ1 antibody or antigen-binding fragment thereof of any preceding embodiment, wherein the anti-Vδ1 antibody or antigen-binding fragment thereof binds cyno TRDV1 with $K_D$ of less than about 100 nM.

124. The anti-Vδ1 antibody or antigen-binding fragment thereof of any preceding embodiment, wherein the anti-Vδ1 antibody or antigen-binding fragment thereof binds cyno TRDV1 with $K_D$ of less than about 50 nM.

125. The anti-Vδ1 antibody or antigen-binding fragment thereof of any preceding embodiment, wherein the anti-Vδ1 antibody or antigen-binding fragment thereof has an IC50 for TCR downregulation of less than about 50 nM, less than about 10 nM, less than about 5 nM, less than about 1 nM or less than about 0.5 nM.

126. The anti-Vδ1 antibody or antigen-binding fragment thereof of any preceding embodiment, wherein the anti-Vδ1 antibody or antigen-binding fragment thereof has an IC90 for TCR downregulation of less than about 10 nM or less than about 5 nM 127. The anti-Vδ1 antibody or antigen-binding fragment thereof of any preceding embodiment, wherein the anti-Vδ1 antibody or antigen-binding fragment thereof has an IC50 for THP-1 cell killing of less than about 10 nM, less than about 5 nM or less than about 1 nM.

128. The anti-Vδ1 antibody or antigen-binding fragment thereof of any preceding embodiment, wherein the anti-Vδ1 antibody or antigen-binding fragment thereof has an IC90 for THP-1 cell killing of less than about 50 nM, less than about 10 nM, less than about 5 nM or less than about 1 nM.

129. The anti-Vδ1 antibody or antigen-binding fragment thereof of any preceding embodiment, wherein the anti-Vδ1 antibody or antigen-binding fragment thereof:
- a. binds to human TRDV1 (SEQ ID NOs 272 or 306) with a binding affinity ($K_D$, for example as measured by surface plasmon resonance) of less than about 100 nM (preferably less than about 50 nM);
- b. optionally binds to cyno TRDV1 (SEQ ID NO 308) with a binding affinity ($K_D$, for example as measured by surface plasmon resonance) of less than about 100 nM (preferably less than about 50 nM);
- c. has an IC50 for TCR downregulation of less than about 50 nM (preferably less than about 10 nM);
- d. has an IC50 for THP-1 cell killing of less than about 10 nM (preferably less than about 5 nM), and
- e. has an IC90 for THP-1 cell killing of less than about 50 nM.

130. The anti-Vδ1 antibody or antigen-binding fragment thereof of any preceding embodiment, wherein the anti-Vδ1 antibody or antigen-binding fragment thereof:
- a. binds to human TRDV1 with a $K_D$ of less than about 100 nM (preferably less than about 50 nM);
- b. binds to cyno TRDV1 with a $K_D$ of less than about 100 nM (preferably less than about 50 nM);
- c. has an IC50 for TCR downregulation of less than about 50 nM (preferably less than about 10 nM) and an IC90 for TCR downregulation of less than about 100 nM (less than about 50 nM);
- d. has an IC50 for THP-1 cell killing of less than about 10 nM (preferably less than about 5 nM); and
- e. has an IC90 for THP-1 cell killing of less than about 50 nM.

131. The anti-Vδ1 antibody or antigen-binding fragment thereof of any preceding embodiment, wherein the anti-Vδ1 antibody or antigen-binding fragment thereof:
- a. binds to human TRDV1 with a $K_D$ of less than about 10 nM (preferably less than about 5 nM);
- b. binds to cyno TRDV1 with a $K_D$ of less than about 100 nM (preferably less than about 50 nM);
- c. has an IC50 for TCR downregulation of less than about 1 nM (preferably less than about 0.5 nM) and an IC90 for TCR downregulation of less than about 10 nM (less than about 5 nM);
- d. has an IC50 for THP-1 cell killing of less than about 10 nM (preferably less than about 5 nM); and
- e. has an IC90 for THP-1 cell killing of less than about 50 nM.

132. The anti-Vδ1 antibody or antigen-binding fragment thereof of any preceding embodiment, wherein the anti-Vδ1 antibody or antigen-binding fragment thereof:
- a. binds to human TRDV1 with a $K_D$ of less than about 10 nM (preferably less than about 1 nM);
- b. binds to cyno TRDV1 with a $K_D$ of less than about 50 nM;
- c. has an IC50 for TCR downregulation of less than about 1 nM (preferably less than about 0.5 nM) and an IC90 for TCR downregulation of less than about 10 nM (less than about 5 nM);
d. has an IC50 for THP-1 cell killing of less than about 10 nM (preferably less than about 5 nM); and
e. has an IC90 for THP-1 cell killing of less than about 50 nM.

133. The anti-Vδ1 antibody or antigen-binding fragment thereof of any preceding embodiment, wherein the anti-Vδ1 antibody or antigen-binding fragment thereof:
a. binds to human TRDV1 with a $K_D$ of less than about 10 nM (preferably less than about 5 nM)
b. have an IC50 for TCR downregulation of less than about 50 nM (preferably less than about 10 nM);
c. have an IC50 for THP-1 cell killing of less than about 5 nM (preferably less than about 1 nM); and
d. has an IC90 for THP-1 cell killing of less than about 50 nM.

134. The anti-Vδ1 antibody or antigen-binding fragment thereof of any preceding embodiment, wherein the anti-Vδ1 antibody or antigen-binding fragment thereof:
a. binds to human TRDV1 with a $K_D$ of less than about 10 nM (preferably less than about 5 nM)
b. has an IC50 for TCR downregulation of less than about 5 nM (preferably less than about 1 nM);
c. has an IC90 for TCR downregulation of less than about 10 nM (preferably less than about 5 nM);
d. has an IC50 for THP-1 cell killing of less than about 5 nM (preferably less than about 1 nM); and
e. has an IC90 for THP-1 cell killing of less than about 10 nM (preferably less than about 5 nM).

135. The anti-Vδ1 antibody or antigen-binding fragment thereof of any preceding embodiment, wherein the antibody or antigen-binding fragment thereof is a human antibody or antigen-binding fragment thereof.

136. The anti-Vδ1 antibody or antigen-binding fragment thereof of any preceding embodiment, wherein the antibody is an scFv, Fab, Fab', F(ab')2, Fv, variable domain (e.g. VH or VL), diabody, minibody or full length antibody.

137. The anti-Vδ1 antibody or antigen-binding fragment thereof of any preceding embodiment, wherein the antibody is an scFv or a full length antibody, such as IgG1

138. The anti-Vδ1 antibody or antigen-binding fragment thereof of any preceding embodiment, wherein the antibody or antigen-binding fragment thereof is an IgA, IgD, IgE, IgG, IgM or IgY antibody.

139. The anti-Vδ1 antibody or antigen-binding fragment thereof any preceding embodiment, wherein the antibody or antigen-binding fragment thereof is an IgG antibody.

140. The anti-Vδ1 antibody or antigen-binding fragment thereof of any preceding embodiment, wherein the antibody or antigen-binding fragment thereof is an IgG1 antibody.

141. The anti-Vδ1 antibody or antigen-binding fragment thereof of any preceding embodiment, wherein the antibody is a monoclonal antibody.

142. The anti-Vδ1 antibody or antigen-binding fragment thereof of any preceding embodiment, wherein the antibody or antigen-binding fragment thereof comprises a VH and a VL, and the VH and VL region are joined by a linker, such as a polypeptide linker.

143. The anti-Vδ1 antibody or antigen-binding fragment thereof of embodiment 142, wherein the linker comprises a $(Gly_4Ser)_n$ format, where n=1 to 8.

144. The anti-Vδ1 antibody or antigen-binding fragment thereof of embodiment 142, wherein the linker comprises a $[(Gly_4Ser)_n(Gly_3AlaSer)_m]_p$ linker, where n, m and p=1 to 8.

145. The anti-Vδ1 antibody or antigen-binding fragment thereof of embodiment 142, wherein the linker comprises SEQ ID NO: 291.

146. The anti-Vδ1 antibody or antigen-binding fragment thereof of embodiment 142, wherein the linker consists of SEQ ID NO: 291.

147. The anti-Vδ1 antibody or antigen-binding fragment thereof of any preceding embodiment, wherein the antibody or antigen-binding fragment thereof only binds to an epitope in the V region of a Vδ1 chain of a γδ TCR.

148. The anti-Vδ1 antibody or antigen-binding fragment thereof of any preceding embodiment, wherein the antibody or antigen-binding fragment thereof only binds to an epitope within amino acid residues 1-90 of SEQ ID NO: 272, SEQ ID NO: 306 or SEQ ID NO: 308.

149. The anti-Vδ1 antibody or antigen-binding fragment thereof of any preceding embodiment, wherein the antibody or antigen-binding fragment thereof does not bind to an epitope found in CDR3 of a Vδ1 chain of a γδ TCR.

150. The anti-Vδ1 antibody or antigen-binding fragment thereof of any preceding embodiment, wherein the antibody or antigen-binding fragment thereof does not bind to an epitope within amino acid region 91-105 (CDR3) of SEQ ID NO: 272.

151. The anti-Vδ1 antibody or antigen-binding fragment thereof of any preceding embodiment, wherein the antibody or antigen-binding fragment thereof binds to an epitope within amino acid region
(i) 3-20 of SEQ ID NO: 272; and/or
(ii) 37-77 of SEQ ID NO: 272.

152. The anti-Vδ1 antibody or antigen-binding fragment thereof of embodiment 151, wherein the epitope bound by the antibody or antigen-binding fragment thereof comprises one or more amino acid residues within amino acid regions 37-53 and/or 59-77 of SEQ ID NO: 272.

153. The anti-Vδ1 antibody or antigen-binding fragment thereof of embodiment 151, wherein the epitope bound by the antibody or antigen-binding fragment thereof comprises amino acid residues 37, 42, 50, 53, 59, 64, 68, 69, 72, 73 and 77 of SEQ ID NO: 272.

154. The anti-Vδ1 antibody or antigen-binding fragment thereof of embodiment 151, wherein the epitope bound by the antibody or antigen-binding fragment thereof consists of amino acid residues 37, 42, 50, 53, 59, 64, 68, 69, 72, 73 and 77 of SEQ ID NO: 272.

155. The anti-Vδ1 antibody or antigen-binding fragment thereof of embodiment 151, wherein the epitope bound by the antibody or antigen-binding fragment thereof comprises one or more amino acid residues within amino acid regions 5-20 and/or 62-77 of SEQ ID NO: 272.

156. The anti-Vδ1 antibody or antigen-binding fragment thereof of embodiment 151, wherein the epitope bound by the antibody or antigen-binding fragment thereof comprises amino acid residues 5, 9, 16, 20, 62, 64, 72 and 77 of SEQ ID NO: 272.

157. The anti-Vδ1 antibody or antigen-binding fragment thereof of embodiment 151, wherein the epitope bound by the antibody or antigen-binding fragment thereof consists of amino acid residues 5, 9, 16, 20, 62, 64, 72 and 77 of SEQ ID NO: 272.

158. The anti-Vδ1 antibody or antigen-binding fragment thereof of any preceding embodiment, wherein the epitope is an activating epitope of a γδ T cell.

159. The anti-Vδ1 antibody or antigen-binding fragment thereof of embodiment 158, wherein binding of the activating epitope: (i) downregulates the γδ TCR; (ii) activates degranulation of the γδ T cell; and/or (iii) promotes γδ T cell mediated killing.

160. The anti-Vδ1 antibody or antigen-binding fragment thereof of embodiment 158 or 159, wherein binding of the activating epitope upregulates expression of CD107a, CD25, CD69 and/or Ki67.

161. The anti-Vδ1 antibody or antigen-binding fragment thereof of any preceding embodiment, wherein the antibody is a multispecific antibody that specifically binds a variable delta 1 (Vδ1) chain of a γδ T cell receptor (TCR) and a second antigen, or binds two different epitopes on a variable delta 1 (Vδ1) chain of a γδ T cell receptor (TCR).

162. The anti-Vδ1 antibody or antigen-binding fragment thereof of embodiment 161, wherein the second antigen is a cell surface protein.

163. The anti-Vδ1 antibody or antigen-binding fragment thereof of embodiment 161 or 162, wherein the second antigen is on a Vδ1+ T cell.

164. The anti-Vδ1 antibody or antigen-binding fragment thereof of embodiment 161 or 162, wherein the second antigen is not on a Vδ1 cell.

165. The anti-Vδ1 antibody or antigen-binding fragment thereof of embodiment 161 or 162 or 163, wherein the second antigen is on an immune cell.

166. The anti-Vδ1 antibody or antigen-binding fragment thereof of any one of embodiments 161 to 165, wherein the second antigen is a cancer antigen or a cancer-associated antigen.

167. The anti-Vδ1 antibody or antigen-binding fragment thereof of embodiment 166, wherein the cancer antigen or a cancer-associated antigen is a tumour associated antigen (TAA).

168. The anti-Vδ1 antibody or antigen-binding fragment thereof of embodiment 166, wherein the cancer antigen or cancer-associated antigen is selected from the group consisting of AFP, AKAP-4, ALK, alpha-fetoprotein, Androgen receptor, B7H3, BAGE, BCA225, BCAA, Bcr-abl, beta-Catenin, beta-HCG, beta-human chorionic gonadotropin, BORIS, BTAA, CA 125, CA 15-3, CA 195, CA 19-9, CA 242, CA 27.29, CA 72-4, CA-50, CAM 17.1, CAM43, Carbonic anhydrase IX, carcinoembryonic antigen, CD22, CD33/IL3Ra, CD68\P1, CDK4, CEA, chondroitin sulfate proteoglycan 4 (CSPG4), c-Met, CO-029, CSPG4, Cyclin B1, cyclophilin C-associated protein, CYP1B1, E2A-PRL, EGFR, EGFRvIII, ELF2M, EpCAM, EphA2, EphrinB2, Epstein Barr virus antigens EBVA, ERG (TMPRSS2ETS fusion gene), ETV6-AML, FAP, FGF-5, Fos-related antigen 1, Fucosyl GM1, G250, Ga733\EpCAM, GAGE-1, GAGE-2, GD2, GD3, glioma-associated antigen, GloboH, Glycolipid F77, GM3, GP 100, GP 100 (Pmel 17), H4-RET, HER-2/neu, HER-2/Neu/ErbB-2, high-molecular-weight melanoma-associated antigen (HMW-MAA), HPV E6, HPV E7, hTERT, HTgp-175, human telomerase reverse transcriptase, Idiotype, IGF-I receptor, IGF-II, IGH-IGK, insulin growth factor (IGF)-I, intestinal carboxyl esterase, K-ras, LAGE-1a, LCK, lectin-reactive AFP, Legumain, LMP2, M344, MA-50, Mac-2 binding protein, MAD-CT-1, MAD-CT-2, MAGE, MAGE A1, MAGE A3, MAGE-1, MAGE-3, MAGE-4, MAGE-5, MAGE-6, MART-1, MART-1/MelanA, M-CSF, melanoma-associated chondroitin sulfate proteoglycan (MCSP), Mesothelin, MG7-Ag, ML-IAP, MN-CA IX, MOV18, MUC1, Mum-1, hsp70-2, MYCN, MYL-RAR, NA17, NB/70K, neuron-glial antigen 2 (NG2), neutrophil elastase, nm-23H1, NuMa, NY-BR-1, NY-CO-1, NY-ESO, NY-ESO-1, NY-ESO-1, OY-TES1, p15, p16, p180erbB3, p185erbB2, p53, p53 mutant, Page4, PAX3, PAX5, PDGFR-beta, PLAC1, Polysialic Acid, prostate-carcinoma tumor antigen-1 (PCTA-1), prostate-specific antigen, prostatic acid phosphatase (PAP), Proteinase3 (PR1), PSA, PSCA, PSMA, RAGE-1, Ras, Ras-mutant, RCAS1, RGS5, RhoC, ROR1, RU1, RU2 (AS), SART3, SDCCAG16, sLe(a), Sperm protein 17, SSX2, STn, Survivin, TA-90, TAAL6, a TAG-72, telomerase, thyroglobulin, Tie 2, TLP, Tn, TPS, TRP-1, TRP-2, TRP-2, TSP-180, Tyrosinase, VEGF, VEGFR2, VISTA, WT1, XAGE 1, 43-9F, 5T4, and 791Tgp72.

169. The anti-Vδ1 antibody or antigen-binding fragment thereof of any one of embodiments 161 to 168, wherein the multispecific antibody is a T-cell engager bispecific antibody.

170. The anti-Vδ1 antibody or antigen-binding fragment thereof of any one of embodiments 161 to 169, wherein the antibody is a bispecific antibody, and the second antigen is CD19, Her2, EGFR, FAPα or MSLN.

171. The anti-Vδ1 antibody or antigen-binding fragment thereof of any one of embodiments 161 to 170, wherein the antibody is a bispecific antibody, and the second antigen is CD19.

172. The anti-Vδ1 antibody or antigen-binding fragment thereof of embodiment 171, wherein the antibody comprises a sequence selected from the group consisting of SEQ ID NO: 314, SEQ ID NO: 315, SEQ ID NO: 316, SEQ ID NO: 396 and SEQ ID NO: 397, SEQ ID NO: 421 and SEQ ID NO: 422, SEQ ID NO: 504 and SEQ ID NO: 422, SEQ ID NO: 423 and SEQ ID NO: 424.

173. The anti-Vδ1 antibody or antigen-binding fragment thereof of any one of embodiments 161 to 170, wherein the antibody is a bispecific antibody, and the second antigen is Her2 (CD340).

174. The anti-Vδ1 antibody or antigen-binding fragment thereof of embodiment 173, wherein the antibody comprises a sequence selected from the group consisting of SEQ ID NO: 393, SEQ ID NO: 394, SEQ ID NO: 395, SEQ ID NO: 398, SEQ ID NO: 414 and SEQ ID NO: 433; and SEQ ID NO: 414 and SEQ ID NO: 434; SEQ ID NO: 504 and SEQ ID NO: 433; and SEQ ID NO: 505 and SEQ ID NO: 434.

175. The anti-Vδ1 antibody or antigen-binding fragment thereof of any one of embodiments 161 to 170, wherein the antibody is a bispecific antibody, and the second antigen is EGFR.

176. The anti-Vδ1 antibody or antigen-binding fragment thereof of embodiment 175, wherein the antibody comprises SEQ ID NO: 378; SEQ ID NO: 379; SEQ ID NO: 380; SEQ ID NO: 382; SEQ ID NO: 383; SEQ ID NO: 384; SEQ ID NO: 385; SEQ ID NO: 386; SEQ ID NO: 387; SEQ ID NO: 388; SEQ ID NO: 399; SEQ ID NO: 425 and SEQ ID NO: 426; SEQ ID NO: 421 and SEQ ID NO: 437; SEQ ID NO: 504 and SEQ ID NO: 437; SEQ ID NO: 423 and SEQ ID NO: 427; SEQ ID NO: 425 and SEQ ID NO: 428; SEQ ID NO: 421 and SEQ ID NO: 429; SEQ ID NO: 504 and SEQ ID NO: 437; SEQ ID NO: 423 and SEQ ID NO: 430; SEQ ID NO: 414 and SEQ ID NO: 431; SEQ ID NO: 504 and SEQ ID NO: 431; SEQ ID NO: 505 and SEQ ID NO: 431; SEQ ID NO: 504 and SEQ ID NO: 435; SEQ ID NO: 414 and SEQ ID NO: 435 or SEQ ID NO: 414 and SEQ ID NO: 435.

177. The anti-Vδ1 antibody or antigen-binding fragment thereof of any one of embodiments 161 to 170, wherein the antibody is a bispecific antibody, and the second antigen is FAPα.

178. The anti-Vδ1 antibody or antigen-binding fragment thereof of embodiment 177, comprising
  a. a heavy chain variable region comprising a VHCDR1 comprising the amino acid sequence of SEQ ID NO: 458, a VHCDR2 comprising the amino acid sequence of SEQ ID NO: 459 and a VHCDR3 comprising the amino acid sequence of SEQ ID NO: 460; and
  b. a light chain variable region comprising a VLCDR1 comprising the amino acid sequence of SEQ ID NO: 461, a VLCDR2 comprising the amino acid sequence of SEQ ID NO: 462 and a VLCDR3 comprising the amino acid sequence of SEQ ID NO: 463;

179. The anti-Vδ1 antibody or antigen-binding fragment thereof of embodiment 178, further comprising
  a. a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 68; and
  b. a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 95;

180. The anti-Vδ1 antibody or antigen-binding fragment thereof of embodiment 177, comprising a VH comprising or consisting of the amino acid sequence of SEQ ID NO: 456 and a VL comprising or consisting of the amino acid sequence of SEQ ID NO: 457.

181. The anti-Vδ1 antibody or antigen-binding fragment thereof of embodiment 180, comprising a VH comprising or consisting of the amino acid sequence of SEQ ID NO: 15 and a VL comprising or consisting of the amino acid sequence of SEQ ID NO: 40.

182. The anti-Vδ1 antibody or antigen-binding fragment thereof of any one of embodiments 177 to 181, comprising SEQ ID NO: 402.

183. The anti-Vδ1 antibody or antigen-binding fragment thereof of any one of embodiments 177 to 182, wherein the antibody comprises SEQ ID NO: 401; or SEQ ID NO: 414 and SEQ ID NO: 415.

184. The anti-Vδ1 antibody or antigen-binding fragment thereof of any one of embodiments 161 to 170, wherein the antibody is a bispecific antibody, and the second antigen is MSLN.

185. The anti-Vδ1 antibody or antigen-binding fragment thereof of embodiment 184, comprising
  a. a heavy chain variable region comprising a VHCDR1 comprising the amino acid sequence of SEQ ID NO: 466, a VHCDR2 comprising the amino acid sequence of SEQ ID NO: 467 and a VHCDR3 comprising the amino acid sequence of SEQ ID NO: 468; and
  b. a light chain variable region comprising a VLCDR1 comprising the amino acid sequence of SEQ ID NO: 469, a VLCDR2 comprising the amino acid sequence of SEQ ID NO: 470 and a VLCDR3 comprising the amino acid sequence of SEQ ID NO: 471;

186. The anti-Vδ1 antibody or antigen-binding fragment thereof of embodiment 185, further comprising
  a. a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 68; and
  b. a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 95;

187. The anti-Vδ1 antibody or antigen-binding fragment thereof of embodiment 184, comprising a VH comprising or consisting of the amino acid sequence of SEQ ID NO: 464 and a VL comprising or consisting of the amino acid sequence of SEQ ID NO: 465.

188. The anti-Vδ1 antibody or antigen-binding fragment thereof of embodiment 187, comprising a VH comprising or consisting of the amino acid sequence of SEQ ID NO: 15 and a VL comprising or consisting of the amino acid sequence of SEQ ID NO: 40.

189. The anti-Vδ1 antibody or antigen-binding fragment thereof of any one of embodiments 184 to 188, comprising SEQ ID NO: 404.

190. The anti-Vδ1 antibody or antigen-binding fragment thereof of any one of embodiments 184 to 189, wherein the antibody comprises SEQ ID NO: 403; or SEQ ID NO: 414 and SEQ ID NO: 416.

191. The anti-Vδ1 antibody or antigen-binding fragment thereof of any one of embodiments 161 to 165, wherein the second antigen is an immunomodulatory antigen.

192. The anti-Vδ1 antibody or antigen-binding fragment thereof of embodiment 191, wherein the immunomodulatory antigen may be selected from the group consisting of B7-1 (CD80), B7-2 (CD86), B7-DC (CD273), B7-H1 (CD274), B7-H2 (CD275), B7-H3 (CD276), B7-H4 (VTCN1), B7-H5 (VISTA), BTLA (CD272), 4-1BB (CD137), CD137L, CD24, CD27, CD28, CD38, CD40, CD40L (CD154), CD54, CD59, CD70, CTLA4 (CD152), CXCL9, GITR (CD357), HVEM (CD270), ICAM-1 (CD54), ICOS (CD278), LAG-3 (CD223), OX40 (CD134), OX40L (CD252), PD-1 (CD279), PD-L1 (CD274), TIGIT, CD314, CD334, CD335, CD337, and TIM-3 (CD366).

193. The anti-Vδ1 antibody or antigen-binding fragment thereof of embodiment 191 or 192 wherein the second antigen is a stimulatory immune checkpoint molecule 194. The anti-Vδ1 antibody or antigen-binding fragment thereof of embodiment 191 or 192, wherein the second antigen is an inhibitory immune checkpoint molecule.

195. The anti-Vδ1 antibody or antigen-binding fragment thereof of embodiment 191 or 192, wherein the antibody is a bispecific antibody, and the second epitope is an epitope of PD-1, 4-1BB (CD137), OX40 or TIGIT.

196. The anti-Vδ1 antibody or antigen-binding fragment thereof of embodiment 191 or 192, wherein the antibody is a bispecific antibody, and the second epitope is an epitope of PD-1.

197. The anti-Vδ1 antibody or antigen-binding fragment thereof of embodiment 196, comprising
   a. a heavy chain variable region comprising a VHCDR1 comprising the amino acid sequence of SEQ ID NO: 474, a VHCDR2 comprising the amino acid sequence of SEQ ID NO: 475 and a VHCDR3 comprising the amino acid sequence of SEQ ID NO: 476; and
   b. a light chain variable region comprising a VLCDR1 comprising the amino acid sequence of SEQ ID NO: 477, a VLCDR2 comprising the amino acid sequence of SEQ ID NO: 478 and a VLCDR3 comprising the amino acid sequence of SEQ ID NO: 479;
198. The anti-Vδ1 antibody or antigen-binding fragment thereof of embodiment 197, further comprising
   a. a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 68; and
   b. a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 95;
199. The anti-Vδ1 antibody or antigen-binding fragment thereof of embodiment 195, comprising a VH comprising or consisting of the amino acid sequence of SEQ ID NO: 472 and a VL comprising or consisting of the amino acid sequence of SEQ ID NO: 473.
200. The anti-Vδ1 antibody or antigen-binding fragment thereof of embodiment 199, comprising a VH comprising or consisting of the amino acid sequence of SEQ ID NO: 15 and a VL comprising or consisting of the amino acid sequence of SEQ ID NO: 40.
201. The anti-Vδ1 antibody or antigen-binding fragment thereof of any one of embodiments 195 to 200, comprising SEQ ID NO: 406.
202. The anti-Vδ1 antibody or antigen-binding fragment thereof of any one of embodiments 195 to 201, wherein the antibody comprises SEQ ID NO: 405; or SEQ ID NO: 438 and SEQ ID NO: 417.
203. The anti-Vδ1 antibody or antigen-binding fragment thereof of embodiment 191 or 192, wherein the antibody is a bispecific antibody, and the second epitope is an epitope of 4-1BB (CD137).
204. The anti-Vδ1 antibody or antigen-binding fragment thereof of embodiment 203, comprising
   a. a heavy chain variable region comprising a VHCDR1 comprising the amino acid sequence of SEQ ID NO: 482, a VHCDR2 comprising the amino acid sequence of SEQ ID NO: 483 and a VHCDR3 comprising the amino acid sequence of SEQ ID NO: 484; and
   b. a light chain variable region comprising a VLCDR1 comprising the amino acid sequence of SEQ ID NO: 485, a VLCDR2 comprising the amino acid sequence of SEQ ID NO: 486 and a VLCDR3 comprising the amino acid sequence of SEQ ID NO: 487;
205. The anti-Vδ1 antibody or antigen-binding fragment thereof of embodiment 204, further comprising
   a. a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 68; and
   b. a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 95;
206. The anti-Vδ1 antibody or antigen-binding fragment thereof of embodiment 203, comprising a VH comprising or consisting of the amino acid sequence of SEQ ID NO: 480 and a VL comprising or consisting of the amino acid sequence of SEQ ID NO: 481.
207. The anti-Vδ1 antibody or antigen-binding fragment thereof of embodiment 206, comprising a VH comprising or consisting of the amino acid sequence of SEQ ID NO: 15 and a VL comprising or consisting of the amino acid sequence of SEQ ID NO: 40.
208. The anti-Vδ1 antibody or antigen-binding fragment thereof of any one of embodiments 203 to 207 comprising SEQ ID NO: 408.
209. The anti-Vδ1 antibody or antigen-binding fragment thereof of any one of embodiments 203 to 208, wherein the antibody comprises SEQ ID NO: 407; or SEQ ID NO: 414 and SEQ ID NO: 418.
210. The anti-Vδ1 antibody or antigen-binding fragment thereof of embodiment 191 or 192, wherein the antibody is a bispecific antibody, and the second epitope is an epitope of OX40.
211. The anti-Vδ1 antibody or antigen-binding fragment thereof of embodiment 210, comprising
   a. a heavy chain variable region comprising a VHCDR1 comprising the amino acid sequence of SEQ ID NO: 490, a VHCDR2 comprising the amino acid sequence of SEQ ID NO: 491 and a VHCDR3 comprising the amino acid sequence of SEQ ID NO: 492; and
   b. a light chain variable region comprising a VLCDR1 comprising the amino acid sequence of SEQ ID NO: 493, a VLCDR2 comprising the amino acid sequence of SEQ ID NO: 494 and a VLCDR3 comprising the amino acid sequence of SEQ ID NO: 495;
212. The anti-Vδ1 antibody or antigen-binding fragment thereof of embodiment 211, further comprising
   a. a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 68; and
   b. a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 95;
213. The anti-Vδ1 antibody or antigen-binding fragment thereof of embodiment 210, comprising a VH comprising or consisting of the amino acid sequence of SEQ ID NO: 488 and a VL comprising or consisting of the amino acid sequence of SEQ ID NO: 489.
214. The anti-Vδ1 antibody or antigen-binding fragment thereof of embodiment 213, comprising a VH comprising or consisting of the amino acid sequence of SEQ ID NO: 15 and a VL comprising or consisting of the amino acid sequence of SEQ ID NO: 40.
215. The anti-Vδ1 antibody or antigen-binding fragment thereof of any one of embodiments 210 to 214, comprising SEQ ID NO: 410.

216. The anti-Vδ1 antibody or antigen-binding fragment thereof of any one of embodiments 210 to 215, wherein the antibody comprises SEQ ID NO: 409; or SEQ ID NO: 414 and SEQ ID NO: 419.
217. The anti-Vδ1 antibody or antigen-binding fragment thereof of embodiment 191 or 192, wherein the antibody is a bispecific antibody, and the second epitope is an epitope of TIGIT.
218. The anti-Vδ1 antibody or antigen-binding fragment thereof of embodiment 217, comprising
   a. a heavy chain variable region comprising a VHCDR1 comprising the amino acid sequence of SEQ ID NO: 498, a VHCDR2 comprising the amino acid sequence of SEQ ID NO: 499 and a VHCDR3 comprising the amino acid sequence of SEQ ID NO: 500; and
   b. a light chain variable region comprising a VLCDR1 comprising the amino acid sequence of SEQ ID NO: 501, a VLCDR2 comprising the amino acid sequence of SEQ ID NO: 502 and a VLCDR3 comprising the amino acid sequence of SEQ ID NO: 503;
219. The anti-Vδ1 antibody or antigen-binding fragment thereof of embodiment 218, further comprising
   a. a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 68; and
   b. a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 95;
220. The anti-Vδ1 antibody or antigen-binding fragment thereof of embodiment 217, comprising a VH comprising or consisting of the amino acid sequence of SEQ ID NO: 496 and a VL comprising or consisting of the amino acid sequence of SEQ ID NO: 497.
221. The anti-Vδ1 antibody or antigen-binding fragment thereof of embodiment 220, comprising a VH comprising or consisting of the amino acid sequence of SEQ ID NO: 15 and a VL comprising or consisting of the amino acid sequence of SEQ ID NO: 40.
222. The anti-Vδ1 antibody or antigen-binding fragment thereof of any one of embodiments 217 to 221, comprising SEQ ID NO: 412.
223. The anti-Vδ1 antibody or antigen-binding fragment thereof of any one of embodiments 217 to 222, wherein the antibody comprises SEQ ID NO: 411; or SEQ ID NO: 439 and SEQ ID NO: 420.
224. The anti-Vδ1 antibody or antigen-binding fragment thereof of any one of embodiments 161 to 223, wherein the second antigen is a cluster of differentiation CD antigen. 225. The anti-Vδ1 antibody or antigen-binding fragment thereof of embodiment 224, wherein the CD antigen is selected from the group consisting of CD1a, CD1b, CD1c, CD1d, CD1e, CD2, CD3, CD3d, CD3e, CD3g, CD4, CD5, CD6, CD7, CD8, CD8a, CD8b, CD9, CD10, CD11 a, CD11 b, CD11c, CD11d, CD13, CD14, CD15, CD16, CD16a, CD16b, CD17, CD18, CD19, CD20, CD21, CD22, CD23, CD24, CD25, CD26, CD27, CD28, CD29, CD30, CD31, CD32A, CD32B, CD33, CD34, CD35, CD36, CD37, CD38, CD39, CD40, CD41, CD42, CD42a, CD42b, CD42c, CD42d, CD43, CD44, CD45, CD46, CD47, CD48, CD49a, CD49b, CD49c, CD49d, CD49e, CD49f, CD50, CD51, CD52, CD53, CD54, CD55, CD56, CD57, CD58, CD59, CD60a, CD60b, CD60c, CD61, CD62E, CD62L, CD62P, CD63, CD64a, CD65, CD65s, CD66a, CD66b, CD66c, CD66d, CD66e, CD66f, CD68, CD69, CD70, CD71, CD72, CD73, CD74, CD75, CD75s, CD77, CD79A, CD79B, CD80, CD81, CD82, CD83, CD84, CD85A, CD85B, CD85C, CD85D, CD85F, CD85G, CD85H, CD85I, CD85J, CD85K, CD85M, CD86, CD87, CD88, CD89, CD90, CD91, CD92, CD93, CD94, CD95, CD96, CD97, CD98, CD99, CD100, CD101, CD102, CD103, CD104, CD105, CD106, CD107, CD107a, CD107b, CD108, CD109, CD110, CD111, CD112, CD113, CD114, CD115, CD116, CD117, CD118, CD119, CD120, CD120a, CD120b, CD121a, CD121b, CD122, CD123, CD124, CD125, CD126, CD127, CD129, CD130, CD131, CD132, CD133, CD134, CD135, CD136, CD137, CD138, CD139, CD140A, CD140B, CD141, CD142, CD143, CD144, CDw145, CD146, CD147, CD148, CD150, CD151, CD152, CD153, CD154, CD155, CD156, CD156a, CD156b, CD156c, CD157, CD158, CD158A, CD158B1, CD158B2, CD158C, CD158D, CD158E1, CD158E2, CD158F1, CD158F2, CD158G, CD158H, CD158I, CD158J, CD158K, CD159a, CD159c, CD160, CD161, CD162, CD163, CD164, CD165, CD166, CD167a, CD167b, CD168, CD169, CD170, CD171, CD172a, CD172b, CD172g, CD173, CD174, CD175, CD175s, CD176, CD177, CD178, CD179a, CD179b, CD180, CD181, CD182, CD183, CD184, CD185, CD186, CD187, CD188, CD189, CD190, CD191, CD192, CD193, CD194, CD195, CD196, CD197, CDw198, CDw199, CD200, CD201, CD202b, CD203c, CD204, CD205, CD206, CD207, CD208, CD209, CD210, CDw210a, CDw210b, CD211, CD212, CD213a1, CD213a2, CD214, CD215, CD216, CD217, CD218a, CD218b, CD219, CD220, CD221, CD222, CD223, CD224, CD225, CD226, CD227, CD228, CD229, CD230, CD231, CD232, CD233, CD234, CD235a, CD235b, CD236, CD237, CD238, CD239, CD240CE, CD240D, CD241, CD242, CD243, CD244, CD245, CD246, CD247, CD248, CD249, CD250, CD251, CD252, CD253, CD254, CD255, CD256, CD257, CD258, CD259, CD260, CD261, CD262, CD263, CD264, CD265, CD266, CD267, CD268, CD269, CD270, CD271, CD272, CD273, CD274, CD275, CD276, CD277, CD278, CD279, CD280, CD281, CD282, CD283, CD284, CD285, CD286, CD287, CD288, CD289, CD290, CD291, CD292, CDw293, CD294, CD295, CD296, CD297, CD298, CD299, CD300A, CD300C, CD301, CD302, CD303, CD304, CD305, CD306, CD307, CD307a, CD307b, CD307c, CD307d, CD307e, CD308, CD309, CD310, CD311, CD312, CD313, CD314, CD315, CD316, CD317, CD318, CD319, CD320, CD321, CD322, CD323, CD324, CD325, CD326, CD327, CD328, CD329, CD330, CD331, CD332, CD333, CD334, CD335, CD336, CD337, CD338, CD339, CD340, CD344, CD349, CD351, CD352, CD353, CD354, CD355, CD357, CD358, CD360, CD361, CD362, CD363, CD364, CD365, CD366, CD367, CD368, CD369, CD370, and CD371.
226. The anti-Vδ1 antibody or antigen-binding fragment thereof of any one of embodiments 161 to 225, wherein the antibody is a bispecific antibody.
227. The anti-Vδ1 antibody or antigen-binding fragment thereof of any one of embodiments 161 to 226, wherein the antibody is a bispecific antibody and is selected from the group consisting of CrossMab, DAF (two-in-one), DAF (four-in-one), DutaMab, DT-IgG, Knobs-in-holes (KIH), Knobs-in-holes (common light chain), Charge pair, Fab-arm exchange, SEEDbody, Triomab, LUZ-Y, Fcab, KA-body, orthogonal Fab, DVD-IgG, IgG(H)-scFv, scFv-(H)IgG, IgG(L)-scFv, scFv-(L)IgG, IgG(L,H)-Fv, IgG(H)-V, V(H)—IgG, IgG(L)-V, V(L)-IgG, KIH IgG-scFab, 2scFv-IgG, IgG-2scFv, scFv4-Ig, Zybody, DVI-IgG(four-in-one), Nanobody, Nanoby-HAS, BiTE, Diabody, DART, TandAb, scDiabody, scDiabody-CH3, Diabody-CH3, Triple Body, Morrison formats, Miniantibody, Minibody, TriBi minibody, scFv-CH3 KIH, Fab-scFv, scFv-CH-CL-scFv, F(ab')2, F(ab)2-scFv2, scFv-KIH, Fab-scFv-Fc, Tetravalent HCAb, scDiabody-Fc, Diabody-Fc, Tandem scFv-Fc, Intrabody, Dock and Lock, ImmTAC, HSAbody, scDiabody-HAS, Tandem scFv-Toxin, IgG-IgG, ov-X-Body, duobody, mab$^2$ and scFv1-PEG-scFv2.

228. The anti-Vδ1 antibody or antigen-binding fragment thereof of any one of embodiments 161 to 227, wherein the antibody is a bispecific antibody conjugate (such as IgG2, an scFv, tandem scFv, F(ab')2, a KiH bispecific antibody, Morrison format bispecific antibody (IgG-HC-scFv), diabody, triabody, minibody or full length bispecific antibody.

229. The anti-Vδ1 antibody or antigen-binding fragment thereof of any one of embodiments 161 to 225, wherein the antibody is not a bispecific antibody.

230. The anti-Vδ1 antibody or antigen-binding fragment thereof of any preceding embodiment, wherein the multispecific antibody is larger than about 70 KDa.

231. The anti-Vδ1 antibody or antigen-binding fragment thereof of any one of embodiments 161 to 230, wherein the multispecific antibody comprises sequence selected from the group consisting of SEQ ID NO: 385, SEQ ID NO: 386, SEQ ID NO: 387, SEQ ID NO: 314, SEQ ID, SEQ ID NO: 394, SEQ ID NO: 395, SEQ ID NO: 397, SEQ ID NO: 402, SEQ ID NO: 404, SEQ ID NO: 406, SEQ ID NO: 408, SEQ ID NO: 410, SEQ ID NO: 412 and SEQ ID NO: 413.

232. The anti-Vδ1 antibody or antigen-binding fragment thereof of any one of embodiments 161 to 230, wherein the multispecific antibody comprises SEQ ID NO: 388; SEQ ID NO: 315; SEQ ID NO: 316; SEQ ID NO: 378; SEQ ID NO: 379; SEQ ID NO: 380; SEQ ID NO: 382; SEQ ID NO: 383; SEQ ID NO: 384; SEQ ID NO: 393; SEQ ID NO: 396; SEQ ID NO: 398; SEQ ID NO: 399; SEQ ID NO: 401; SEQ ID NO: 403; SEQ ID NO: 405; SEQ ID NO: 407; SEQ ID NO: 409; SEQ ID NO: 411; SEQ ID NO: 414 and SEQ ID NO: 415; SEQ ID NO: 414 and SEQ ID NO: 416; SEQ ID NO: 414 and SEQ ID NO: 419; SEQ ID NO: 414 and SEQ ID NO: 418; SEQ ID NO: 504 and SEQ ID NO: 415; SEQ ID NO: 504 and SEQ ID NO: 416; SEQ ID NO: 504 and SEQ ID NO: 419; SEQ ID NO: 504 and SEQ ID NO: 418; SEQ ID NO: 505 and SEQ ID NO: 415; SEQ ID NO: 505 and SEQ ID NO: 416; SEQ ID NO: 505 and SEQ ID NO: 419; SEQ ID NO: 505 and SEQ ID NO: 418; SEQ ID NO: 421 and SEQ ID NO: 422; SEQ ID NO: 504 and SEQ ID NO: 422; SEQ ID NO: 423 and SEQ ID NO: 424; SEQ ID NO: 425 and SEQ ID NO: 426; SEQ ID NO: 421 and SEQ ID NO: 437; SEQ ID NO: 504 and SEQ ID NO: 437; SEQ ID NO: 423 and SEQ ID NO: 427; SEQ ID NO: 425 and SEQ ID NO: 428; SEQ ID NO: 421 and SEQ ID NO: 429; SEQ ID NO: 504 and SEQ ID NO: 429; SEQ ID NO: 423 and SEQ ID NO: 430; SEQ ID NO: 414 and SEQ ID NO: 431; SEQ ID NO: 414 and SEQ ID NO: 433; SEQ ID NO: 414 and SEQ ID NO: 434; SEQ ID NO: 414 and SEQ ID NO: 435; SEQ ID NO: 504 and SEQ ID NO: 431; SEQ ID NO: 504 and SEQ ID NO: 433; SEQ ID NO: 504 and SEQ ID NO: 434; SEQ ID NO: 504 and SEQ ID NO: 435; SEQ ID NO: 505 and SEQ ID NO: 431; SEQ ID NO: 505 and SEQ ID NO: 433; SEQ ID NO: 505 and SEQ ID NO: 434; SEQ ID NO: 505 and SEQ ID NO: 435; SEQ ID NO: 438 and SEQ ID NO: 417; or SEQ ID NO: 439 and SEQ ID NO: 420.

233. A polynucleotide sequence encoding the anti-Vδ1 antibody or antigen-binding fragment thereof as defined in any preceding embodiment.

234. A polynucleotide sequence encoding the anti-Vδ1 antibody or antibody binding fragment thereof comprising a sequence having at least 70% sequence identity with SEQ ID NO: 199 to 222, 224 to 247, 249 to 259 or 261 to 271.

235. An expression vector comprising the polynucleotide sequence as defined in embodiment 233 or embodiment 234.

236. A host cell comprising the polynucleotide sequence as defined in embodiment 233 or embodiment 234 or the expression vector as defined in embodiment 235, optionally wherein the host cell is a recombinant host cell.

237. The host cell of embodiment 236, comprising a first polynucleotide sequence encoding a VH sequence, and a second polynucleotide sequence encoding a VL sequence.

238. The host cell of embodiment 236, comprising a first expression vector comprising a first polynucleotide sequence encoding a VH sequence, and a second expression vector comprising a second polynucleotide sequence encoding a VL sequence.

239. The host cell of embodiment 236, comprising an expression vector comprising a first polynucleotide sequence encoding a VH sequence and a second polynucleotide sequence encoding a VL sequence.

240. The host cell as defined in any one of embodiments 236 to 239, wherein the polynucleotide or expression vector encodes a membrane anchor or transmembrane domain fused to the antibody or antigen-binding fragment thereof, wherein the antibody or antigen-binding fragment thereof is presented on an extracellular surface of the cell 241. A method for producing any antibody or antigen-binding fragment thereof of any one of embodiments 1 to 232, comprising culturing a host cell of any one of embodiments 236 to 240 in a cell culture medium.

242. The method of embodiment 241, further comprising isolated the antibody or antigen-binding fragment thereof from the culture medium.

243. A method of mutating an antibody or antigen-binding fragment thereof, comprising providing an antibody comprising a kappa light chain having a serine at position 74 according to the IMGT numbering system, and mutating the serine to a different amino acid.

244. The method of embodiment 243, wherein the antibody is an anti-TCR delta variable 1 (anti-Vδ1) antibody or antigen-binding fragment thereof.

245. The method of embodiment 243 or embodiment 244, wherein the antibody is an antibody having a VH comprising an amino acid sequence that is at least 90% identical to SEQ ID NO: 1 and a VL comprising an amino acid sequence that is at least 90% identical to SEQ ID NO: 26 both before and after the mutation is introduced.

246. The method of any one of embodiments 243 to 244, wherein the antibody or antigen-binding fragment thereof binds a human antigen and the mutation increases the affinity of the antibody or antigen-binding fragment thereof for a homologous cynomolgus monkey antigen.

247. The method of any one of embodiments 243 to 246, wherein the antibody or antigen-binding fragment thereof is an anti-TCR delta variable 1 (anti-Vδ1) antibody or antigen-binding fragment thereof that binds to a human variable delta 1 (Vδ1) chain of a γδ T cell receptor (TCR) before and after the mutation is introduced, and the antibody has increased affinity for a cynomolgus monkey variable delta 1 (Vδ1) chain of a γδ T cell receptor (TCR) after the mutation is introduced.

248. A method of preparing a variant anti-TCR delta variable 1 (anti-Vδ1) antibody or antigen-binding fragment thereof comprising providing a parental antibody comprising:

a. a VH comprising the amino acid sequence of SEQ ID NO: 1 and a VL comprising the amino acid sequence of SEQ ID NO: 26;

b. a VH comprising the amino acid sequence of SEQ ID NO: 106 and a VL comprising the amino acid sequence of SEQ ID NO: 118;

c. a VH comprising the amino acid sequence of SEQ ID NO: 273 and a VL comprising the amino acid sequence of SEQ ID NO: 282;

d. a VH comprising the amino acid sequence of SEQ ID NO: 274 and a VL comprising the amino acid sequence of SEQ ID NO: 283;

e. a VH comprising the amino acid sequence of SEQ ID NO: 275 and a VL comprising the amino acid sequence of SEQ ID NO: 284;

f. a VH comprising the amino acid sequence of SEQ ID NO: 276 and a VL comprising the amino acid sequence of SEQ ID NO: 285;

g. a VH comprising the amino acid sequence of SEQ ID NO: 277 and a VL comprising the amino acid sequence of SEQ ID NO: 286;

h. a VH comprising the amino acid sequence of SEQ ID NO: 278 and a VL comprising the amino acid sequence of SEQ ID NO: 287;

i. a VH comprising the amino acid sequence of SEQ ID NO: 279 and a VL comprising the amino acid sequence of SEQ ID NO: 288;

j. a VH comprising the amino acid sequence of SEQ ID NO: 280 and a VL comprising the amino acid sequence of SEQ ID NO: 289;

k. a VH comprising the amino acid sequence of SEQ ID NO: 281 and a VL comprising the amino acid sequence of SEQ ID NO: 290; or l. a VH comprising the amino acid sequence of SEQ ID NO: 312 and a VL comprising the amino acid sequence of SEQ ID NO: 313;

and subjecting the antibody to affinity maturation, wherein the antibody produced has a greater affinity to a variable delta 1 (Vδ1) chain of a γδ T cell receptor (TCR) than the parental antibody.

249. The method of embodiment 248, wherein the produced antibody binds to a variable delta 1 (Vol) chain of a γδ T cell receptor (TCR) with at least 20%, at least 30%, at least 40%, more preferably at least 50%, at least 100% or more preferably at least about 1000% greater affinity than the parental antibody, for example as measured by Kd.

250. The method of embodiment 248 or embodiment 249, further comprising co-formulating the produced antibody with at least one or more pharmaceutically acceptable diluents or carriers.

251. A method of preparing a pharmaceutical composition comprising providing an antibody prepared according to a method of any one of embodiments 241 to 250 and co-formulating the antibody with at least one or more pharmaceutically acceptable diluents or carriers.

252. An anti-Vδ1 antibody or antigen binding fragment thereof prepared or preparable according to the method of any one of embodiments 241 to 250.

253. A pharmaceutical composition prepared or preparable according to the method of embodiment 251.

254. A composition comprising the antibody or antibody binding fragment thereof as defined in any one of embodiments 1 to 231 or 251.

255. A pharmaceutical composition comprising the antibody or antibody binding fragment thereof as defined in any one of embodiments 1 to 231 or 251 and a pharmaceutically acceptable diluent or carrier.

256. A kit comprising an anti-Vδ1 antibody or antibody binding fragment of any one of embodiments 1 to 229 or 249 or a pharmaceutical composition of embodiment 253 or 255.

257. The kit of embodiment 256, further comprising an additional therapeutically active agent.

258. The kit of embodiment 256 or embodiment 257, further comprising instructions for use.

259. A method of treating a disease or disorder in a subject, comprising administering to the subject an anti-Vδ1 antibody or antibody binding fragment of any one of embodiments 1 to 231 or 251, or the pharmaceutical composition of embodiment 253 or 255.

260. The method of embodiment 259, wherein the disease or disorder is cancer, an infectious disease or an inflammatory disease.

261. The method of any one of embodiments 259 to 260, further comprising administering simultaneously or sequentially in any order, a second agent to the subject.

262. A method of modulating an immune response in a subject, comprising administering to the subject an anti-Vδ1 antibody or antibody binding fragment of any one of embodiments 1 to 231 or 251, or the pharmaceutical composition of embodiment 253 or 255.

263. The method of embodiment 262, wherein the subject has cancer, an infectious disease or an inflammatory disease.

264. The method of embodiment 262 or 263, wherein modulating an immune response in a subject comprises at least one selected from the group consisting of activating γδ T cells, causing or increasing proliferation γδ T cells, causing or increasing expansion of γδ T cells, causing or increasing γδ T cell degranulation, causing or increasing γδ T cell mediated killing activity, causing or increasing γδ T cytotoxicity, causing or increasing γδ T cell mobilization, increasing survival of γδ T cells, and increasing resistance to exhaustion of γδ T cells.

265. The method of any one of embodiments 259 to 264, wherein diseased cells are killed while healthy cells are spared.

266. The anti-TCR delta variable 1 (anti-Vδ1) antibody or antigen-binding fragment thereof of any one of embodiments 1 to 231 or 251, or the pharmaceutical composition of embodiment 253 or 25, or the kit of any one of embodiments 256 to 258 for use in medicine.

267. The anti-TCR delta variable 1 (anti-Vδ1) antibody or antigen-binding fragment thereof of any one of embodiments 1 to 231 or 251, or the pharmaceutical composition of embodiment 253 or 255, or the kit of any one of embodiments 256 to 258 for use in the treatment of cancer, an infectious disease, or an inflammatory disease.
268. Use of an anti-TCR delta variable 1 (anti-Vδ1) antibody or antigen-binding fragment thereof of any one of embodiments 1 to 231 or 251 in the manufacture of a medicament.
269. Use of an anti-TCR delta variable 1 (anti-Vδ1) antibody or antigen-binding fragment thereof of any one of embodiments 1 to 231 or 251 in the manufacture of a medicament for the treatment of cancer, an infectious disease, or an inflammatory disease.
270. The anti-TCR delta variable 1 (anti-Vδ1) antibody or antigen-binding fragment thereof of any one of embodiments 103 to 110, wherein the antibody is an antibody as defined in any one of embodiments 1 to 101.

The invention claimed is:

1. An anti-TCR delta variable 1 (anti-Vδ1) antibody or antigen-binding fragment thereof comprising:

a) a variable heavy chain complementarity determining region 1 (VHCDR1), a variable heavy chain complementarity determining region 2 (VHCDR2) and a variable heavy chain complementarity determining region 3 (VHCDR3) comprising the amino acid sequences of SEQ ID NO: 51, 53 and 55, respectively, and a variable light chain complementarity determining region 1 (VLCDR1), a variable light chain complementarity determining region 2 (VLCDR2) and a variable light chain complementarity determining region 3 (VLCDR3) comprising the amino acid sequences of SEQ ID NO: 79, 80 and 82, respectively;

b) a VHCDR1, a VHCDR2 and a VHCDR3 comprising the amino acid sequences of SEQ ID NO: 51, 53 and 56, respectively, and a VLCDR1, a VLCDR2 and a VLCDR3 comprising the amino acid sequences of SEQ ID NO: 79, 80 and 83, respectively;

c) a VHCDR1, a VHCDR2 and a VHCDR3 comprising the amino acid sequences of SEQ ID NO: 51, 53 and 57, respectively, and a VLCDR1, a VLCDR2 and a VLCDR3 comprising the amino acid sequences of SEQ ID NO: 79, 80 and 84, respectively;

d) a VHCDR1, a VHCDR2 and a VHCDR3 comprising the amino acid sequences of SEQ ID NO: 51, 53 and 58, respectively, and a VLCDR1, a VLCDR2 and a VLCDR3 comprising the amino acid sequences of SEQ ID NO: 79, 80 and 85, respectively;

e) a VHCDR1, a VHCDR2 and a VHCDR3 comprising the amino acid sequences of SEQ ID NO: 51, 53 and 59, respectively, and a VLCDR1, a VLCDR2 and a VLCDR3 comprising the amino acid sequences of SEQ ID NO: 79, 80 and 86, respectively;

f) a VHCDR1, a VHCDR2 and a VHCDR3 comprising the amino acid sequences of SEQ ID NO: 51, 53 and 60, respectively, and a VLCDR1, a VLCDR2 and a VLCDR3 comprising the amino acid sequences of SEQ ID NO: 79, 80 and 87, respectively;

g) a VHCDR1, a VHCDR2 and a VHCDR3 comprising the amino acid sequences of SEQ ID NO: 52, 53 and 61, respectively, and a VLCDR1, a VLCDR2 and a VLCDR3 comprising the amino acid sequences of SEQ ID NO: 79, 80 and 88, respectively;

h) a VHCDR1, a VHCDR2 and a VHCDR3 comprising the amino acid sequences of SEQ ID NO: 51, 53 and 62, respectively, and a VLCDR1, a VLCDR2 and a VLCDR3 comprising the amino acid sequences of SEQ ID NO: 79, 80 and 89, respectively;

i) a VHCDR1, a VHCDR2 and a VHCDR3 comprising the amino acid sequences of SEQ ID NO: 51, 53 and 63, respectively, and a VLCDR1, a VLCDR2 and a VLCDR3 comprising the amino acid sequences of SEQ ID NO: 79, 80 and 90, respectively;

j) a VHCDR1, a VHCDR2 and a VHCDR3 comprising the amino acid sequences of SEQ ID NO: 51, 53 and 64, respectively, and a VLCDR1, a VLCDR2 and a VLCDR3 comprising the amino acid sequences of SEQ ID NO: 79, 80 and 91, respectively;

k) a VHCDR1, a VHCDR2 and a VHCDR3 comprising the amino acid sequences of SEQ ID NO: 51, 53 and 65, respectively, and a VLCDR1, a VLCDR2 and a VLCDR3 comprising the amino acid sequences of SEQ ID NO: 79, 80 and 92, respectively;

l) a VHCDR1, a VHCDR2 and a VHCDR3 comprising the amino acid sequences of SEQ ID NO: 52, 53 and 66, respectively, and a VLCDR1, a VLCDR2 and a VLCDR3 comprising the amino acid sequences of SEQ ID NO: 79, 80 and 93, respectively;

m) a VHCDR1, a VHCDR2 and a VHCDR3 comprising the amino acid sequences of SEQ ID NO: 51, 53 and 67, respectively, and a VLCDR1, a VLCDR2 and a VLCDR3 comprising the amino acid sequences of SEQ ID NO: 79, 80 and 94, respectively;

n) a VHCDR1, a VHCDR2 and a VHCDR3 comprising the amino acid sequences of SEQ ID NO: 51, 53 and 69, respectively, and a VLCDR1, a VLCDR2 and a VLCDR3 comprising the amino acid sequences of SEQ ID NO: 79, 80 and 96, respectively;

o) a VHCDR1, a VHCDR2 and a VHCDR3 comprising the amino acid sequences of SEQ ID NO: 51, 53 and 70, respectively, and a VLCDR1, a VLCDR2 and a VLCDR3 comprising the amino acid sequences of SEQ ID NO: 79, 80 and 97, respectively;

p) a VHCDR1, a VHCDR2 and a VHCDR3 comprising the amino acid sequences of SEQ ID NO: 51, 53 and 71, respectively, and a VLCDR1, a VLCDR2 and a VLCDR3 comprising the amino acid sequences of SEQ ID NOs: 79, 80 and 98, respectively;

q) a VHCDR1, a VHCDR2 and a VHCDR3 comprising the amino acid sequences of SEQ ID NO: 51, 53 and 72, respectively, and a VLCDR1, a VLCDR2 and a VLCDR3 comprising the amino acid sequences of SEQ ID NO: 79, 80 and 99, respectively;

r) a VHCDR1, a VHCDR2 and a VHCDR3 comprising the amino acid sequences of SEQ ID NO: 51, 53 and 73, respectively, and a VLCDR1, a VLCDR2 and a VLCDR3 comprising the amino acid sequences of SEQ ID NO: 79, 80 and 100, respectively;

s) a VHCDR1, a VHCDR2 and a VHCDR3 comprising the amino acid sequences of SEQ ID NO: 52, 53 and 74, respectively, and a VLCDR1, a VLCDR2 and a VLCDR3 comprising the amino acid sequences of SEQ ID NO: 79, 80 and 101, respectively;

t) a VHCDR1, a VHCDR2 and a VHCDR3 comprising the amino acid sequences of SEQ ID NO: 51, 53 and 75, respectively, and a VLCDR1, a VLCDR2 and a VLCDR3 comprising the amino acid sequences of SEQ ID NO: 79, 80 and 102, respectively;

u) a VHCDR1, a VHCDR2 and a VHCDR3 comprising the amino acid sequences of SEQ ID NO: 51, 53 and 76, respectively, and a VLCDR1, a VLCDR2 and a VLCDR3 comprising the amino acid sequences of SEQ ID NO: 79, 80 and 103, respectively;

V a VHCDR1, a VHCDR2 and a VHCDR3 comprising the amino acid sequences of SEQ ID NO: 51, 53 and 77, respectively, and a VLCDR1, a VLCDR2 and a VLCDR3 comprising the amino acid sequences of SEQ ID NO: 79, 80 and 104, respectively; or w) a VHCDR1, a VHCDR2 and a VHCDR3 comprising the amino acid sequences of SEQ ID NO: 51, 53 and 78, respectively, and a VLCDR1, a VLCDR2 and a VLCDR3 comprising the amino acid sequences of SEQ ID NO: 79, 80 and 105, respectively.

2. The anti-Vδ1 antibody or antigen-binding fragment thereof of claim 1, comprising:

a) a variable heavy chain (VH) comprising an amino acid sequence of SEQ ID NO: 2 and a variable light chain (VL) comprising an amino acid sequence of SEQ ID NO: 27;

b) a VH comprising an amino acid sequence of SEQ ID NO: 3 and a VL comprising an amino acid sequence of SEQ ID NO: 28;

c) a VH comprising an amino acid sequence of SEQ ID NO: 4 and a VL comprising an amino acid sequence of SEQ ID NO: 29;

d) a VH comprising an amino acid sequence of SEQ ID NO: 5 and a VL comprising an amino acid sequence of SEQ ID NO: 30;

e) a VH comprising an amino acid sequence of SEQ ID NO: 6 and a VL comprising an amino acid sequence of SEQ ID NO: 31;

f) a VH comprising an amino acid sequence of SEQ ID NO: 7 and a VL comprising an amino acid sequence of SEQ ID NO: 32;

g) a VH comprising an amino acid sequence of SEQ ID NO: 8 and a VL comprising an amino acid sequence of SEQ ID NO: 33;

h) a VH comprising an amino acid sequence of SEQ ID NO: 9 and a VL comprising an amino acid sequence of SEQ ID NO: 34;

i) a VH comprising an amino acid sequence of SEQ ID NO: 10 and a VL comprising an amino acid sequence of SEQ ID NO: 35;

j) a VH comprising an amino acid sequence of SEQ ID NO: 11 and a VL comprising an amino acid sequence of SEQ ID NO: 36;

k) a VH comprising an amino acid sequence of SEQ ID NO: 12 and a VL comprising an amino acid sequence of SEQ ID NO: 37;

l) a VH comprising an amino acid sequence of SEQ ID NO: 13 and a VL comprising an amino acid sequence of SEQ ID NO: 38;

m) a VH comprising an amino acid sequence of SEQ ID NO: 14 and a VL comprising an amino acid sequence of SEQ ID NO: 39;

n) a VH comprising an amino acid sequence of SEQ ID NO: 16 and a VL comprising an amino acid sequence of SEQ ID NO: 41;

o) a VH comprising an amino acid sequence of SEQ ID NO: 17 and a VL comprising an amino acid sequence of SEQ ID NO: 42;

p) a VH comprising an amino acid sequence of SEQ ID NO: 18 and a VL comprising an amino acid sequence of SEQ ID NO: 43;

q) a VH comprising an amino acid sequence of SEQ ID NO: 19 and a VL comprising an amino acid sequence of SEQ ID NO: 44;

r) a VH comprising an amino acid sequence of SEQ ID NO: 20 and a VL comprising an amino acid sequence of SEQ ID NO: 45;

s) a VH comprising an amino acid sequence of SEQ ID NO: 21 and a VL comprising an amino acid sequence of SEQ ID NO: 46;

t) a VH comprising an amino acid sequence of SEQ ID NO: 22 and a VL comprising an amino acid sequence of SEQ ID NO: 47;

u) a VH comprising an amino acid sequence of SEQ ID NO: 23 and a VL comprising an amino acid sequence of SEQ ID NO: 48;

v) a VH comprising an amino acid sequence of SEQ ID NO: 24 and a VL comprising an amino acid sequence of SEQ ID NO: 49; or w) a VH comprising an amino acid sequence of SEQ ID NO: 25 and a VL comprising an amino acid sequence of SEQ ID NO: 50.

3. The anti-Vδ1 antibody or antigen-binding fragment thereof of claim 1, wherein the antibody or antigen-binding fragment thereof comprises an amino acid residue other than serine at position 74 according to the IMGT kappa variable light chain sequence numbering system.

4. The anti-TCR delta variable 1 (anti-Vδ1) antibody or antigen-binding fragment thereof of claim 1, wherein the antibody or antigen-binding fragment thereof when incubated with a viable Vδ1 T+ cell population causes a depletion of less than about 30%, or less than about 20%, or less than about 10% of the viable Vδ1 T+ cell population as measured via ADCC and/or CDC.

5. The anti-TCR delta variable 1 (anti-Vδ1) antibody or antigen-binding fragment thereof of claim 1, wherein the antibody or antigen-binding fragment thereof binds to human TRVD1 with a KD of less than about 10 nM.

6. The anti-Vδ1 antibody or antigen-binding fragment thereof of claim 1, wherein the antibody or antigen-binding fragment thereof:

a) binds to human TRDV1 (SEQ ID NOs 272 or 306) with a binding affinity (KD) of less than about 100 nM as measured by surface plasmon resonance;

b) has an IC50 for TCR downregulation of less than about 50 nM;

c) has an IC50 for THP-1 cell killing of less than about 10 nM; and has an IC90 for THP-1 cell killing of less than about 50 nM.

7. The anti-Vδ1 antibody or antigen-binding fragment thereof of claim 1, wherein the epitope bound by the antibody or antigen-binding fragment thereof is an activating epitope of a γδ T cell.

8. The anti-Vδ1 antibody or antigen-binding fragment thereof of claim 1, wherein the antibody is an IgG antibody.

9. The anti-Vδ1 antibody or antigen-binding fragment thereof of claim 1, wherein the antibody is not a bispecific antibody or a multispecific antibody.

10. The anti-Vδ1 antibody or antigen-binding fragment thereof of claim 1, wherein the antibody is Fc enabled.

11. A pharmaceutical composition comprising the antibody or antibody binding fragment thereof as defined in claim 1 and a pharmaceutically acceptable diluent or carrier.

12. A method of treating a disease or disorder in a subject or a method of modulating an immune response in a subject, comprising administering to the subject an anti-Vδ1 antibody or antibody binding fragment of claim 1.

13. The method of claim 12, wherein the disease or disorder is cancer, an infectious disease or an inflammatory disease, or wherein the subject in which an immune response is modulated has cancer, an infectious disease, or an inflammatory disease or wherein modulating an immune response in a subject comprises at least one of, activating γδ T cells, causing or increasing proliferation γδ T cells, causing or increasing expansion of γδ T cells, causing or increasing γδ T cell degranulation, causing or increasing γδ T cell mediated killing activity, causing or increasing γδ T cytotoxicity, causing or increasing γδ T cell mobilization, increasing survival of γδ T cells, and increasing resistance to exhaustion of γδ T cells.

14. The method of claim 12, wherein diseased cells are killed while healthy cells are spared.

15. The anti-Vδ1 antibody or antigen-binding fragment thereof of claim 3, wherein the residue at position 74 according to the IMGT numbering system is a leucine residue.

16. An anti-TCR delta variable 1 (anti-Vδ1) antibody or antigen-binding fragment thereof comprising:

a heavy chain variable region (VH) comprising:

a VHCDR1 comprising an amino acid sequence of SEQ ID NO: 130;

a VHCDR2 comprising an amino acid sequence of: SEQ ID NO: 131; and a VHCDR3 comprising an amino acid sequence of any one of: SEQ ID NO: 133 to 143; and a light chain variable region (VL) comprising:

a VLCDR1 comprising an amino acid sequence of SEQ ID NO: 144;

a VLCDR2 comprising an amino acid sequence of SEQ ID NO: 145; and a VLCDR3 comprising an amino acid sequence of any one of: SEQ ID NO: 147 to 157.

17. The anti-Vδ1 antibody or antigen-binding fragment thereof of claim 16, wherein:

a) a VHCDR1, a VHCDR2 and a VHCDR3 comprising the amino acid sequences of SEQ ID NO: 130, 131 and 133, respectively, and a VLCDR1, a VLCDR2 and a VLCDR3 comprising the amino acid sequences of SEQ ID NO: 144, 145 and 147, respectively;

b) a VHCDR1, a VHCDR2 and a VHCDR3 comprising the amino acid sequences of SEQ ID NO: 130, 131 and 134, respectively, and a VLCDR1, a VLCDR2 and a VLCDR3 comprising the amino acid sequences of SEQ ID NO: 144, 145 and 148, respectively;

c) a VHCDR1, a VHCDR2 and a VHCDR3 comprising the amino acid sequences of SEQ ID NO: 130, 131 and 135, respectively, and a VLCDR1, a VLCDR2 and a VLCDR3 comprising the amino acid sequences of SEQ ID NO: 144, 145 and 149, respectively;

d) a VHCDR1, a VHCDR2 and a VHCDR3 comprising the amino acid sequences of SEQ ID NO: 130, 131 and 136, respectively, and a VLCDR1, a VLCDR2 and a VLCDR3 comprising the amino acid sequences of SEQ ID NO: 144, 145 and 150, respectively;

e) a VHCDR1, a VHCDR2 and a VHCDR3 comprising the amino acid sequences of SEQ ID NO: 130, 131 and 137, respectively, and a VLCDR1, a VLCDR2 and a VLCDR3 comprising the amino acid sequences of SEQ ID NO: 144, 145 and 151, respectively;

f) a VHCDR1, a VHCDR2 and a VHCDR3 comprising the amino acid sequences of SEQ ID NO: 130, 131 and 138, respectively, and a VLCDR1, a VLCDR2 and a VLCDR3 comprising the amino acid sequences of SEQ ID NO: 144, 145 and 152, respectively;

g) a VHCDR1, a VHCDR2 and a VHCDR3 comprising the amino acid sequences of SEQ ID NO: 130, 131 and 139, respectively, and a VLCDR1, a VLCDR2 and a VLCDR3 comprising the amino acid sequences of SEQ ID NO: 144, 145 and 153, respectively;

h) a VHCDR1, a VHCDR2 and a VHCDR3 comprising the amino acid sequences of SEQ ID NO: 130, 131 and 140, respectively, and a VLCDR1, a VLCDR2 and a VLCDR3 comprising the amino acid sequences of SEQ ID NO: 144, 145 and 154, respectively;

i) a VHCDR1, a VHCDR2 and a VHCDR3 comprising the amino acid sequences of SEQ ID NO: 130, 131 and 141, respectively, and a VLCDR1, a VLCDR2 and a VLCDR3 comprising the amino acid sequences of SEQ ID NO: 144, 145 and 155, respectively;

j) a VHCDR1, a VHCDR2 and a VHCDR3 comprising the amino acid sequences of SEQ ID NO: 130, 131 and 142, respectively, and a VLCDR1, a VLCDR2 and a VLCDR3 comprising the amino acid sequences of SEQ ID NO: 144, 145 and 156, respectively; or k) a VHCDR1, a VHCDR2 and a VHCDR3 comprising the amino acid sequences of SEQ ID NO: 130, 131 and 143, respectively, and a VLCDR1, a VLCDR2 and a VLCDR3 comprising the amino acid sequences of SEQ ID NO: 144, 145 and 157, respectively.

18. The anti-TCR delta variable 1 (anti-Vδ1) antibody or antigen-binding fragment thereof of claim 16, comprising: a heavy chain variable region (VH) comprising a sequence of any one of SEQ ID NO: 107 to 117; and a light chain variable region (VL) comprising a sequence of any one of SEQ ID NO: 119 to 129.

19. The anti-Vδ1 antibody or antigen-binding fragment thereof of claim 16, comprising:

a) a VH comprising an amino acid sequence of SEQ ID NO: 107 and a VL comprising an amino acid sequence of SEQ ID NO: 119;

b) a VH comprising an amino acid sequence of SEQ ID NO: 108 and a VL comprising an amino acid sequence of SEQ ID NO: 120;

c) a VH comprising an amino acid sequence of SEQ ID NO: 109 and a VL comprising an amino acid sequence of SEQ ID NO: 121;

d) a VH comprising an amino acid sequence of SEQ ID NO: 110 and a VL comprising an amino acid sequence of SEQ ID NO: 122;

e) a VH comprising an amino acid sequence of SEQ ID NO: 111 and a VL comprising an amino acid sequence of SEQ ID NO: 123;

f) a VH comprising an amino acid sequence of SEQ ID NO: 112 and a VL comprising an amino acid sequence of SEQ ID NO: 124;

g) a VH comprising an amino acid sequence of SEQ ID NO: 113 and a VL comprising an amino acid sequence of SEQ ID NO: 125;

h) a VH comprising an amino acid sequence of SEQ ID NO: 114 and a VL comprising an amino acid sequence of SEQ ID NO: 126;

i) a VH comprising an amino acid sequence of SEQ ID NO: 115 and a VL comprising an amino acid sequence of SEQ ID NO: 127;

j) a VH comprising an amino acid sequence of SEQ ID NO: 116 and a VL comprising an amino acid sequence of SEQ ID NO: 128; or k) a VH comprising an amino acid sequence of SEQ ID NO: 117 and a VL comprising an amino acid sequence of SEQ ID NO: 129.

20. A method of treating a disease or disorder in a subject or a method of modulating an immune response in a subject, comprising administering to the subject an anti-Vδ1 antibody or antibody binding fragment of claim 16.

21. The method of claim 20, wherein the disease or disorder is cancer, an infectious disease or an inflammatory disease, or wherein the subject in which an immune response is modulated has cancer, an infectious disease, or an inflammatory disease or wherein modulating an immune response in a subject comprises at least one of, activating γδ T cells, causing or increasing proliferation γδ T cells, causing or increasing expansion of γδ T cells, causing or increasing γδ T cell degranulation, causing or increasing γδ T cell mediated killing activity, causing or increasing γδ T cytotoxicity, causing or increasing γδ T cell mobilization, increasing survival of γδ T cells, and increasing resistance to exhaustion of γδ T cells.

* * * * *

SEQUENCE LISTING

```
<160> NUMBER OF SEQ ID NOS: 505

<210> SEQ ID NO 1
<211> LENGTH: 120
<212> TYPE: PRT
<213> ORGANISM: Homo Sapiens

<400> SEQUENCE: 1

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Lys
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Ser Thr Asp Tyr Ala
    50                  55                  60

Ala Ser Val Lys Ser Arg Ile Thr Ile Asn Pro Asp Thr Ser Lys Asn
65                  70                  75                  80

Gln Leu Ser Leu Gln Leu Asn Ser Val Thr Pro Glu Asp Thr Ala Val
                85                  90                  95

Tyr Tyr Cys Ala Arg Thr Trp Ser Gly Tyr Val Asp Val Trp Gly Gln
            100                 105                 110

Gly Thr Leu Val Thr Val Ser Ser
        115                 120


<210> SEQ ID NO 2
<211> LENGTH: 120
<212> TYPE: PRT
<213> ORGANISM: Homo sapiens

<400> SEQUENCE: 2

Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Lys
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Ser Thr Asp Tyr Ala
    50                  55                  60

Ala Ser Val Lys Ser Arg Ile Thr Ile Asn Pro Asp Thr Ser Lys Asn
65                  70                  75                  80

Gln Leu Ser Leu Gln Leu Asn Ser Val Thr Pro Glu Asp Thr Ala Val
                85                  90                  95

Tyr Tyr Cys Ala Arg Thr Trp Val Gly Tyr Val Asp Val Trp Gly Gln
            100                 105                 110

Gly Thr Leu Val Thr Val Ser Ser
        115                 120
```

<210> SEQ ID NO 3
<211> LENGTH: 120
<212> TYPE: PRT
<213> ORGANISM: Homo sapiens

<400> SEQUENCE: 3

```
Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Lys
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Ser Thr Asp Tyr Ala
    50                  55                  60

Ala Ser Val Lys Ser Arg Ile Thr Ile Asn Pro Asp Thr Ser Lys Asn
65                  70                  75                  80

Gln Leu Ser Leu Gln Leu Asn Ser Val Thr Pro Glu Asp Thr Ala Val
                85                  90                  95

Tyr Tyr Cys Ala Arg Thr Trp Val Gly Tyr Ala Asp Val Trp Gly Gln
            100                 105                 110

Gly Thr Leu Val Thr Val Ser Ser
        115                 120
```

<210> SEQ ID NO 4
<211> LENGTH: 120
<212> TYPE: PRT
<213> ORGANISM: Homo sapiens

<400> SEQUENCE: 4

```
Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Lys
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Ser Thr Asp Tyr Ala
    50                  55                  60

Ala Ser Val Lys Ser Arg Ile Thr Ile Asn Pro Asp Thr Ser Lys Asn
65                  70                  75                  80

Gln Leu Ser Leu Gln Leu Asn Ser Val Thr Pro Glu Asp Thr Ala Val
                85                  90                  95

Tyr Tyr Cys Ala Arg Thr Trp Val Glu Tyr Val Asp Val Trp Gly Gln
            100                 105                 110

Gly Thr Leu Val Thr Val Ser Ser
        115                 120
```

<210> SEQ ID NO 5
<211> LENGTH: 120
<212> TYPE: PRT
<213> ORGANISM: Homo sapiens

<400> SEQUENCE: 5

```
Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Lys
            20                  25                  30
```

```
Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Ser Thr Asp Tyr Ala
    50                  55                  60

Ala Ser Val Lys Ser Arg Ile Thr Ile Asn Pro Asp Thr Ser Lys Asn
65                  70                  75                  80

Gln Leu Ser Leu Gln Leu Asn Ser Val Thr Pro Glu Asp Thr Ala Val
                85                  90                  95

Tyr Tyr Cys Ala Arg Thr Trp Val Gly Tyr Val Asp Tyr Trp Gly Gln
            100                 105                 110

Gly Thr Leu Val Thr Val Ser Ser
        115                 120


<210> SEQ ID NO 6
<211> LENGTH: 120
<212> TYPE: PRT
<213> ORGANISM: Homo sapiens

<400> SEQUENCE: 6

Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Lys
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Ser Thr Asp Tyr Ala
    50                  55                  60

Ala Ser Val Lys Ser Arg Ile Thr Ile Asn Pro Asp Thr Ser Lys Asn
65                  70                  75                  80

Gln Leu Ser Leu Gln Leu Asn Ser Val Thr Pro Glu Asp Thr Ala Val
                85                  90                  95

Tyr Tyr Cys Ala Arg Thr Trp Val Gly Tyr Val Asp Val Trp Gly Gln
            100                 105                 110

Gly Thr Leu Val Thr Val Ser Ser
        115                 120


<210> SEQ ID NO 7
<211> LENGTH: 120
<212> TYPE: PRT
<213> ORGANISM: Homo sapiens

<400> SEQUENCE: 7

Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Lys
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Ser Thr Asp Tyr Ala
    50                  55                  60

Ala Ser Val Lys Ser Arg Ile Thr Ile Asn Pro Asp Thr Ser Lys Asn
65                  70                  75                  80

Gln Leu Ser Leu Gln Leu Asn Ser Val Thr Pro Glu Asp Thr Ala Val
                85                  90                  95

Tyr Tyr Cys Ala Arg Thr Trp Val Gly Tyr Val Asp Arg Trp Gly Gln
            100                 105                 110
```

```
Gly Thr Leu Val Thr Val Ser Ser
        115                 120


<210> SEQ ID NO 8
<211> LENGTH: 120
<212> TYPE: PRT
<213> ORGANISM: Homo sapiens

<400> SEQUENCE: 8

Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Lys
            20                  25                  30

Ser Val Ala Trp Asn Trp Ile Arg Gln Ser Pro Ser Arg Gly Leu Glu
        35                  40                  45

Trp Leu Gly Arg Thr Tyr Tyr Arg Ser Lys Trp Ser Thr Asp Tyr Ala
    50                  55                  60

Ala Ser Val Lys Ser Arg Ile Thr Ile Asn Pro Asp Thr Ser Lys Asn
65                  70                  75                  80

Gln Leu Ser Leu Gln Leu Asn Ser Val Thr Pro Glu Asp Thr Ala Val
                85                  90                  95

Tyr Tyr Cys Ala Arg Thr Trp Ala Asp Tyr Val Asp Val Trp Gly Gln
            100                 105                 110

Gly Thr Leu Val Thr Val Ser Ser
        115                 120


<210> SEQ ID NO 9
<211> LENGTH: 120
<212> TYPE: PRT
<213> ORGANISM: Homo sapiens

<400> SEQUENCE: 9

Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Lys
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Ser Thr Asp Tyr Ala
    50                  55                  60

Ala Ser Val Lys Ser Arg Ile Thr Ile Asn Pro Asp Thr Ser Lys Asn
65                  70                  75                  80

Gln Leu Ser Leu Gln Leu Asn Ser Val Thr Pro Glu Asp Thr Ala Val
                85                  90                  95

Tyr Tyr Cys Ala Arg Thr Trp Val Gly Tyr Ala Asp Val Trp Gly Gln
            100                 105                 110

Gly Thr Leu Val Thr Val Ser Ser
        115                 120


<210> SEQ ID NO 10
<211> LENGTH: 120
<212> TYPE: PRT
<213> ORGANISM: Homo sapiens

<400> SEQUENCE: 10

Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Lys
```

-continued

```
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Ser Thr Asp Tyr Ala
    50                  55                  60

Ala Ser Val Lys Ser Arg Ile Thr Ile Asn Pro Asp Thr Ser Lys Asn
65                  70                  75                  80

Gln Leu Ser Leu Gln Leu Asn Ser Val Thr Pro Glu Asp Thr Ala Val
                85                  90                  95

Tyr Tyr Cys Ala Arg Thr Trp Val Gly Tyr Val Asp Tyr Trp Gly Gln
            100                 105                 110

Gly Thr Leu Val Thr Val Ser Ser
        115                 120


<210> SEQ ID NO 11
<211> LENGTH: 120
<212> TYPE: PRT
<213> ORGANISM: Homo sapiens

<400> SEQUENCE: 11

Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Lys
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Ser Thr Asp Tyr Ala
    50                  55                  60

Ala Ser Val Lys Ser Arg Ile Thr Ile Asn Pro Asp Thr Ser Lys Asn
65                  70                  75                  80

Gln Leu Ser Leu Gln Leu Asn Ser Val Thr Pro Glu Asp Thr Ala Val
                85                  90                  95

Tyr Tyr Cys Ala Arg Thr Trp Val Gly Tyr Ala Asp Val Trp Gly Gln
            100                 105                 110

Gly Thr Leu Val Thr Val Ser Ser
        115                 120


<210> SEQ ID NO 12
<211> LENGTH: 120
<212> TYPE: PRT
<213> ORGANISM: Homo sapiens

<400> SEQUENCE: 12

Glu Val Gln Leu Leu Gln Ser Gly Pro Gly Leu Val Lys Pro Ser Gln
1               5                   10                  15

Thr Leu Ser Leu Thr Cys Ala Ile Ser Gly Asp Ser Val Ser Ser Lys
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Ser Thr Asp Tyr Ala
    50                  55                  60

Ala Ser Val Lys Ser Arg Ile Thr Ile Asn Pro Asp Thr Ser Lys Asn
65                  70                  75                  80

Gln Leu Ser Leu Gln Leu Asn Ser Val Thr Pro Glu Asp Thr Ala Val
                85                  90                  95

Tyr Tyr Cys Ala Arg Thr Trp Val Gly Tyr Ala Asp Val Trp Gly Gln
```

```
            100                 105                 110

Gly Thr Leu Val Thr Val Ser Ser
        115                 120


<210> SEQ ID NO 13
<211> LENGTH: 120
<212> TYPE: PRT
<213> ORGANISM: Homo sapiens

<400> SEQUENCE: 13

Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Lys
            20                  25                  30

Ser Val Ala Trp Asn Trp Ile Arg Gln Ser Pro Ser Arg Gly Leu Glu
        35                  40                  45

Trp Leu Gly Arg Thr Tyr Tyr Arg Ser Lys Trp Ser Thr Asp Tyr Ala
    50                  55                  60

Ala Ser Val Lys Ser Arg Ile Thr Ile Asn Pro Asp Thr Ser Lys Asn
65                  70                  75                  80

Gln Leu Ser Leu Gln Leu Asn Ser Val Thr Pro Glu Asp Thr Ala Val
                85                  90                  95

Tyr Tyr Cys Ala Arg Thr Trp Ala Asp Tyr Val Asp Val Trp Gly Gln
            100                 105                 110

Gly Thr Leu Val Thr Val Ser Ser
        115                 120


<210> SEQ ID NO 14
<211> LENGTH: 120
<212> TYPE: PRT
<213> ORGANISM: Homo sapiens

<400> SEQUENCE: 14

Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Lys
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Ser Thr Asp Tyr Ala
    50                  55                  60

Ala Ser Val Lys Ser Arg Ile Thr Ile Asn Pro Asp Thr Ser Lys Asn
65                  70                  75                  80

Gln Leu Ser Leu Gln Leu Asn Ser Val Thr Pro Glu Asp Thr Ala Val
                85                  90                  95

Tyr Tyr Cys Ala Arg Thr Trp Ala Gly Tyr Pro Asp Val Trp Gly Gln
            100                 105                 110

Gly Thr Leu Val Thr Val Ser Ser
        115                 120


<210> SEQ ID NO 15
<211> LENGTH: 120
<212> TYPE: PRT
<213> ORGANISM: Homo sapiens

<400> SEQUENCE: 15

Glu Val Gln Leu Gln Gln Ser Gly Pro Gly Leu Val Lys Pro Ser Gln
1               5                   10                  15
```

```
Thr Leu Ser Leu Thr Cys Ala Ile Ser Gly Asp Ser Val Ser Ser Lys
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Ser Thr Asp Tyr Ala
    50                  55                  60

Ala Ser Val Lys Ser Arg Ile Thr Ile Asn Pro Asp Thr Ser Lys Asn
65                  70                  75                  80

Gln Leu Ser Leu Gln Leu Asn Ser Val Thr Pro Glu Asp Thr Ala Val
                85                  90                  95

Tyr Tyr Cys Ala Arg Thr Trp Val Gly Tyr Val Asp Arg Trp Gly Gln
            100                 105                 110

Gly Thr Leu Val Thr Val Ser Ser
        115                 120


<210> SEQ ID NO 16
<211> LENGTH: 120
<212> TYPE: PRT
<213> ORGANISM: Homo sapiens

<400> SEQUENCE: 16

Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Lys
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Ser Thr Asp Tyr Ala
    50                  55                  60

Ala Ser Val Lys Ser Arg Ile Thr Ile Asn Pro Asp Thr Ser Lys Asn
65                  70                  75                  80

Gln Leu Ser Leu Gln Leu Asn Ser Val Thr Pro Glu Asp Thr Ala Val
                85                  90                  95

Tyr Tyr Cys Ala Arg Ser Trp Val Gly Tyr Val Asp Val Trp Gly Gln
            100                 105                 110

Gly Thr Leu Val Thr Val Ser Ser
        115                 120


<210> SEQ ID NO 17
<211> LENGTH: 120
<212> TYPE: PRT
<213> ORGANISM: Homo Sapiens

<400> SEQUENCE: 17

Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Lys
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Ser Thr Asp Tyr Ala
    50                  55                  60

Ala Ser Val Lys Ser Arg Ile Thr Ile Asn Pro Asp Thr Ser Lys Asn
65                  70                  75                  80

Gln Leu Ser Leu Gln Leu Asn Ser Val Thr Pro Glu Asp Thr Ala Val
                85                  90                  95
```

Tyr Tyr Cys Ala Arg Ser Trp Val Gly Tyr Val Asp Val Trp Gly Gln
100 105 110

Gly Thr Leu Val Thr Val Ser Ser
115 120

<210> SEQ ID NO 18
<211> LENGTH: 120
<212> TYPE: PRT
<213> ORGANISM: Homo sapiens

<400> SEQUENCE: 18

Glu Val Gln Leu Gln Gln Ser Gly Pro Gly Leu Val Lys Pro Ser Gln
1 5 10 15

Thr Leu Ser Leu Thr Cys Ala Ile Ser Gly Asp Ser Val Ser Ser Lys
20 25 30

Ser Ala Ala Trp Asn Trp Ile Arg Gln Ser Pro Ser Arg Gly Leu Glu
35 40 45

Trp Leu Gly Arg Thr Tyr Tyr Arg Ser Lys Trp Ser Thr Asp Tyr Ala
50 55 60

Ala Ser Val Lys Ser Arg Ile Thr Ile Asn Pro Asp Thr Ser Lys Asn
65 70 75 80

Gln Leu Ser Leu Gln Leu Asn Ser Val Thr Pro Glu Asp Thr Ala Val
85 90 95

Tyr Tyr Cys Ala Arg Ser Trp Val Gly Tyr Val Asp Val Trp Gly Gln
100 105 110

Gly Thr Leu Val Thr Val Ser Ser
115 120

<210> SEQ ID NO 19
<211> LENGTH: 120
<212> TYPE: PRT
<213> ORGANISM: Homo sapiens

<400> SEQUENCE: 19

Glu Val Gln Leu Gln Gln Ser Gly Pro Gly Leu Val Lys Pro Ser Gln
1 5 10 15

Thr Leu Ser Leu Thr Cys Ala Ile Ser Gly Asp Ser Val Ser Ser Lys
20 25 30

Ser Ala Ala Trp Asn Trp Ile Arg Gln Ser Pro Ser Arg Gly Leu Glu
35 40 45

Trp Leu Gly Arg Thr Tyr Tyr Arg Ser Lys Trp Ser Thr Asp Tyr Ala
50 55 60

Ala Ser Val Lys Ser Arg Ile Thr Ile Asn Pro Asp Thr Ser Lys Asn
65 70 75 80

Gln Leu Ser Leu Gln Leu Asn Ser Val Thr Pro Glu Asp Thr Ala Val
85 90 95

Tyr Tyr Cys Ala Arg Thr Trp Ala Asp Tyr Val Asp Val Trp Gly Gln
100 105 110

Gly Thr Leu Val Thr Val Ser Ser
115 120

<210> SEQ ID NO 20
<211> LENGTH: 120
<212> TYPE: PRT
<213> ORGANISM: Homo sapiens

<400> SEQUENCE: 20

Glu Val Gln Leu Gln Gln Ser Gly Pro Gly Leu Val Lys Pro Ser Gln
1 5 10 15

Thr Leu Ser Leu Thr Cys Ala Ile Ser Gly Asp Ser Val Ser Ser Lys
20 25 30

Ser Ala Ala Trp Asn Trp Ile Arg Gln Ser Pro Ser Arg Gly Leu Glu
35 40 45

Trp Leu Gly Arg Thr Tyr Tyr Arg Ser Lys Trp Ser Thr Asp Tyr Ala
50 55 60

Ala Ser Val Lys Ser Arg Ile Thr Ile Asn Pro Asp Thr Ser Lys Asn
65 70 75 80

Gln Leu Ser Leu Gln Leu Asn Ser Val Thr Pro Glu Asp Thr Ala Val
85 90 95

Tyr Tyr Cys Ala Arg Thr Trp Val Gly Tyr Ala Asp Val Trp Gly Gln
100 105 110

Gly Thr Leu Val Thr Val Ser Ser
115 120

<210> SEQ ID NO 21
<211> LENGTH: 120
<212> TYPE: PRT
<213> ORGANISM: Homo sapiens

<400> SEQUENCE: 21

Glu Val Gln Leu Gln Gln Ser Gly Pro Gly Leu Val Lys Pro Ser Gln
1 5 10 15

Thr Leu Ser Leu Thr Cys Ala Ile Ser Gly Asp Ser Val Ser Ser Lys
20 25 30

Ser Val Ala Trp Asn Trp Ile Arg Gln Ser Pro Ser Arg Gly Leu Glu
35 40 45

Trp Leu Gly Arg Thr Tyr Tyr Arg Ser Lys Trp Ser Thr Asp Tyr Ala
50 55 60

Ala Ser Val Lys Ser Arg Ile Thr Ile Asn Pro Asp Thr Ser Lys Asn
65 70 75 80

Gln Leu Ser Leu Gln Leu Asn Ser Val Thr Pro Glu Asp Thr Ala Val
85 90 95

Tyr Tyr Cys Ala Arg Thr Trp Leu Gly Asn Val Asp Val Trp Gly Gln
100 105 110

Gly Thr Leu Val Thr Val Ser Ser
115 120

<210> SEQ ID NO 22
<211> LENGTH: 120
<212> TYPE: PRT
<213> ORGANISM: Homo sapiens

<400> SEQUENCE: 22

Glu Val Gln Leu Gln Gln Ser Gly Pro Gly Leu Val Lys Pro Ser Gln
1 5 10 15

Thr Leu Ser Leu Thr Cys Ala Ile Ser Gly Asp Ser Val Ser Ser Lys
20 25 30

Ser Ala Ala Trp Asn Trp Ile Arg Gln Ser Pro Ser Arg Gly Leu Glu
35 40 45

Trp Leu Gly Arg Thr Tyr Tyr Arg Ser Lys Trp Ser Thr Asp Tyr Ala
50 55 60

Ala Ser Val Lys Ser Arg Ile Thr Ile Asn Pro Asp Thr Ser Lys Asn
65 70 75 80

```
Gln Leu Ser Leu Gln Leu Asn Ser Val Thr Pro Glu Asp Thr Ala Val
                85                  90                  95

Tyr Tyr Cys Ala Arg Thr Trp Val Gly Tyr Ala Asp Val Trp Gly Gln
            100                 105                 110

Gly Thr Leu Val Thr Val Ser Ser
        115                 120


<210> SEQ ID NO 23
<211> LENGTH: 120
<212> TYPE: PRT
<213> ORGANISM: Homo sapiens

<400> SEQUENCE: 23

Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Lys
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Ser Thr Asp Tyr Ala
    50                  55                  60

Ala Ser Val Lys Ser Arg Ile Thr Ile Asn Pro Asp Thr Ser Lys Asn
65                  70                  75                  80

Gln Leu Ser Leu Gln Leu Asn Ser Val Thr Pro Glu Asp Thr Ala Val
                85                  90                  95

Tyr Tyr Cys Ala Arg Thr Trp Val Gly Tyr Ala Asp Val Trp Gly Gln
            100                 105                 110

Gly Thr Leu Val Thr Val Ser Ser
        115                 120


<210> SEQ ID NO 24
<211> LENGTH: 120
<212> TYPE: PRT
<213> ORGANISM: Homo sapiens

<400> SEQUENCE: 24

Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Lys
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Ser Thr Asp Tyr Ala
    50                  55                  60

Ala Ser Val Lys Ser Arg Ile Thr Ile Asn Pro Asp Thr Ser Lys Asn
65                  70                  75                  80

Gln Leu Ser Leu Gln Leu Asn Ser Val Thr Pro Glu Asp Thr Ala Val
                85                  90                  95

Tyr Tyr Cys Ala Arg Thr Trp Ala Gly Tyr Pro Asp Val Trp Gly Gln
            100                 105                 110

Gly Thr Leu Val Thr Val Ser Ser
        115                 120


<210> SEQ ID NO 25
<211> LENGTH: 120
<212> TYPE: PRT
<213> ORGANISM: Homo sapiens
```

<400> SEQUENCE: 25

Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Lys
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Ser Thr Asp Tyr Ala
    50                  55                  60

Ala Ser Val Lys Ser Arg Ile Thr Ile Asn Pro Asp Thr Ser Lys Asn
65                  70                  75                  80

Gln Leu Ser Leu Gln Leu Asn Ser Val Thr Pro Glu Asp Thr Ala Val
                85                  90                  95

Tyr Tyr Cys Ala Arg Thr Trp Ala Asp Tyr Val Asp Val Trp Gly Gln
            100                 105                 110

Gly Thr Leu Val Thr Val Ser Ser
        115                 120

<210> SEQ ID NO 26
<211> LENGTH: 110
<212> TYPE: PRT
<213> ORGANISM: Homo sapiens

<400> SEQUENCE: 26

Ala Ser Asp Ile Gln Met Thr Gln Ser Pro Pro Ala Leu Ser Ala Ser
1               5                   10                  15

Val Gly Asp Arg Val Thr Ile Thr Cys Arg Ala Ser Gln Asp Ile Asn
            20                  25                  30

Asp Trp Leu Ala Trp Tyr Gln His Lys Pro Gly Lys Ala Pro Lys Leu
        35                  40                  45

Leu Ile Tyr Asp Ala Ser Ser Leu Glu Ser Gly Val Pro Ser Arg Phe
    50                  55                  60

Ser Gly Ser Gly Ser Gly Thr Glu Phe Thr Leu Thr Ile Ser Ser Leu
65                  70                  75                  80

Gln Pro Asp Asp Phe Ala Thr Tyr Tyr Cys Gln Gln Ser Tyr Ser Thr
                85                  90                  95

Pro Gln Val Thr Phe Gly Gln Gly Thr Arg Leu Glu Ile Lys
            100                 105                 110

<210> SEQ ID NO 27
<211> LENGTH: 108
<212> TYPE: PRT
<213> ORGANISM: Homo sapiens

<400> SEQUENCE: 27

Asp Ile Gln Met Thr Gln Ser Pro Pro Ala Leu Ser Ala Ser Val Gly
1               5                   10                  15

Asp Arg Val Thr Ile Thr Cys Arg Ala Ser Gln Asp Ile Asn Asp Trp
            20                  25                  30

Leu Ala Trp Tyr Gln His Lys Pro Gly Lys Ala Pro Lys Leu Leu Ile
        35                  40                  45

Tyr Asp Ala Ser Ser Leu Glu Ser Gly Val Pro Leu Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Lys Tyr Ser Thr Pro Gln

```
                85                  90                  95

Ile Thr Phe Gly Gln Gly Thr Arg Leu Glu Ile Lys
            100                 105


<210> SEQ ID NO 28
<211> LENGTH: 108
<212> TYPE: PRT
<213> ORGANISM: Homo sapiens

<400> SEQUENCE: 28

Asp Ile Gln Met Thr Gln Ser Pro Pro Ala Leu Ser Ala Ser Val Gly
1               5                   10                  15

Asp Arg Val Thr Ile Thr Cys Arg Ala Ser Gln Asp Ile Asn Asp Trp
            20                  25                  30

Leu Ala Trp Tyr Gln His Lys Pro Gly Lys Ala Pro Lys Leu Leu Ile
        35                  40                  45

Tyr Asp Ala Ser Ser Leu Glu Ser Gly Val Pro Leu Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Arg Tyr Ser Thr Pro Gln
                85                  90                  95

Ile Thr Phe Gly Gln Gly Thr Arg Leu Glu Ile Lys
            100                 105


<210> SEQ ID NO 29
<211> LENGTH: 108
<212> TYPE: PRT
<213> ORGANISM: Homo sapiens

<400> SEQUENCE: 29

Asp Ile Gln Met Thr Gln Ser Pro Pro Ala Leu Ser Ala Ser Val Gly
1               5                   10                  15

Asp Arg Val Thr Ile Thr Cys Arg Ala Ser Gln Asp Ile Asn Asp Trp
            20                  25                  30

Leu Ala Trp Tyr Gln His Lys Pro Gly Lys Ala Pro Lys Leu Leu Ile
        35                  40                  45

Tyr Asp Ala Ser Ser Leu Glu Ser Gly Val Pro Leu Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Lys Tyr Ser Thr Pro Gln
                85                  90                  95

Val Thr Phe Gly Ala Gly Thr Arg Leu Glu Ile Lys
            100                 105


<210> SEQ ID NO 30
<211> LENGTH: 108
<212> TYPE: PRT
<213> ORGANISM: Homo sapiens

<400> SEQUENCE: 30

Asp Ile Gln Met Thr Gln Ser Pro Pro Ala Leu Ser Ala Ser Val Gly
1               5                   10                  15

Asp Arg Val Thr Ile Thr Cys Arg Ala Ser Gln Asp Ile Asn Asp Trp
            20                  25                  30

Leu Ala Trp Tyr Gln His Lys Pro Gly Lys Ala Pro Lys Leu Leu Ile
        35                  40                  45
```

```
Tyr Asp Ala Ser Ser Leu Glu Ser Gly Val Pro Leu Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Lys Tyr Ser Gln Pro Gln
                85                  90                  95

Val Thr Phe Gly Gln Gly Thr Arg Leu Glu Ile Lys
            100                 105


<210> SEQ ID NO 31
<211> LENGTH: 108
<212> TYPE: PRT
<213> ORGANISM: Homo sapiens

<400> SEQUENCE: 31

Asp Ile Gln Met Thr Gln Ser Pro Pro Ala Leu Ser Ala Ser Val Gly
1               5                   10                  15

Asp Arg Val Thr Ile Thr Cys Arg Ala Ser Gln Asp Ile Asn Asp Trp
            20                  25                  30

Leu Ala Trp Tyr Gln His Lys Pro Gly Lys Ala Pro Lys Leu Leu Ile
        35                  40                  45

Tyr Asp Ala Ser Ser Leu Glu Ser Gly Val Pro Leu Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Arg Tyr Ser Thr Pro Arg
                85                  90                  95

Val Thr Phe Gly Gln Gly Thr Arg Leu Glu Ile Lys
            100                 105


<210> SEQ ID NO 32
<211> LENGTH: 108
<212> TYPE: PRT
<213> ORGANISM: Homo sapiens

<400> SEQUENCE: 32

Asp Ile Gln Met Thr Gln Ser Pro Pro Ala Leu Ser Ala Ser Val Gly
1               5                   10                  15

Asp Arg Val Thr Ile Thr Cys Arg Ala Ser Gln Asp Ile Asn Asp Trp
            20                  25                  30

Leu Ala Trp Tyr Gln His Lys Pro Gly Lys Ala Pro Lys Leu Leu Ile
        35                  40                  45

Tyr Asp Ala Ser Ser Leu Glu Ser Gly Val Pro Leu Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Lys Tyr Ser Thr Pro Lys
                85                  90                  95

Val Thr Phe Gly Gln Gly Thr Arg Leu Glu Ile Lys
            100                 105


<210> SEQ ID NO 33
<211> LENGTH: 108
<212> TYPE: PRT
<213> ORGANISM: Homo sapiens

<400> SEQUENCE: 33
```

```
Asp Ile Gln Met Thr Gln Ser Pro Pro Ala Leu Ser Ala Ser Val Gly
1               5                   10                  15

Asp Arg Val Thr Ile Thr Cys Arg Ala Ser Gln Asp Ile Asn Asp Trp
            20                  25                  30

Leu Ala Trp Tyr Gln His Lys Pro Gly Lys Ala Pro Lys Leu Leu Ile
        35                  40                  45

Tyr Asp Ala Ser Ser Leu Glu Ser Gly Val Pro Leu Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Lys Tyr Ser Thr Pro Trp
                85                  90                  95

Val Thr Phe Gly Gln Gly Thr Arg Leu Glu Ile Lys
            100                 105


<210> SEQ ID NO 34
<211> LENGTH: 108
<212> TYPE: PRT
<213> ORGANISM: Homo sapiens

<400> SEQUENCE: 34

Asp Ile Gln Met Thr Gln Ser Pro Pro Ala Leu Ser Ala Ser Val Gly
1               5                   10                  15

Asp Arg Val Thr Ile Thr Cys Arg Ala Ser Gln Asp Ile Asn Asp Trp
            20                  25                  30

Leu Ala Trp Tyr Gln His Lys Pro Gly Lys Ala Pro Lys Leu Leu Ile
        35                  40                  45

Tyr Asp Ala Ser Ser Leu Glu Ser Gly Val Pro Leu Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Arg Tyr Ser Thr Pro Pro
                85                  90                  95

Val Thr Phe Gly Gln Gly Thr Arg Leu Glu Ile Lys
            100                 105


<210> SEQ ID NO 35
<211> LENGTH: 108
<212> TYPE: PRT
<213> ORGANISM: Homo sapiens

<400> SEQUENCE: 35

Asp Ile Gln Met Thr Gln Ser Pro Pro Ala Leu Ser Ala Ser Val Gly
1               5                   10                  15

Asp Arg Val Thr Ile Thr Cys Arg Ala Ser Gln Asp Ile Asn Asp Trp
            20                  25                  30

Leu Ala Trp Tyr Gln His Lys Pro Gly Lys Ala Pro Lys Leu Leu Ile
        35                  40                  45

Tyr Asp Ala Ser Ser Leu Glu Ser Gly Val Pro Leu Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Gly Tyr Ser Thr Pro Gln
                85                  90                  95

Leu Thr Phe Gly Gln Gly Thr Arg Leu Glu Ile Lys
            100                 105
```

<210> SEQ ID NO 36
<211> LENGTH: 108
<212> TYPE: PRT
<213> ORGANISM: Homo sapiens

<400> SEQUENCE: 36

```
Asp Ile Gln Met Thr Gln Ser Pro Pro Ala Leu Ser Ala Ser Val Gly
1               5                   10                  15

Asp Arg Val Thr Ile Thr Cys Arg Ala Ser Gln Asp Ile Asn Asp Trp
            20                  25                  30

Leu Ala Trp Tyr Gln His Lys Pro Gly Lys Ala Pro Lys Leu Leu Ile
        35                  40                  45

Tyr Asp Ala Ser Ser Leu Glu Ser Gly Val Pro Leu Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Lys Tyr Ser Thr Pro Trp
                85                  90                  95

Val Thr Phe Gly Gln Gly Thr Arg Leu Glu Ile Lys
            100                 105
```

<210> SEQ ID NO 37
<211> LENGTH: 108
<212> TYPE: PRT
<213> ORGANISM: Homo sapiens

<400> SEQUENCE: 37

```
Asp Ile Gln Met Thr Gln Ser Pro Pro Ala Leu Ser Ala Ser Val Gly
1               5                   10                  15

Asp Arg Val Thr Ile Thr Cys Arg Ala Ser Gln Asp Ile Asn Asp Trp
            20                  25                  30

Leu Ala Trp Tyr Gln His Lys Pro Gly Lys Ala Pro Lys Leu Leu Ile
        35                  40                  45

Tyr Asp Ala Ser Ser Leu Glu Ser Gly Val Pro Leu Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Arg Tyr Ser Thr His Gln
                85                  90                  95

Val Thr Phe Gly Gln Gly Thr Arg Leu Val Ile Lys
            100                 105
```

<210> SEQ ID NO 38
<211> LENGTH: 108
<212> TYPE: PRT
<213> ORGANISM: Homo sapiens

<400> SEQUENCE: 38

```
Asp Ile Gln Met Thr Gln Ser Pro Pro Ala Leu Ser Ala Ser Val Gly
1               5                   10                  15

Asp Arg Val Thr Ile Thr Cys Arg Ala Ser Gln Asp Ile Asn Asp Trp
            20                  25                  30

Leu Ala Trp Tyr Gln His Lys Pro Gly Lys Ala Pro Lys Leu Leu Ile
        35                  40                  45

Tyr Asp Ala Ser Ser Leu Glu Ser Gly Val Pro Leu Arg Phe Ser Gly
    50                  55                  60

Ser Gly Ser Gly Thr Glu Phe Thr Leu Thr Ile Ser Ser Leu Gln Pro
```

```
65                  70                  75                  80

Asp Asp Phe Ala Thr Tyr Tyr Cys Gln Gln Lys Tyr Ser Thr Pro Gln
                85                  90                  95

Leu Thr Phe Gly Gln Gly Thr Arg Leu Glu Ile Lys
            100                 105


<210> SEQ ID NO 39
<211> LENGTH: 108
<212> TYPE: PRT
<213> ORGANISM: Homo sapiens

<400> SEQUENCE: 39

Asp Ile Gln Met Thr Gln Ser Pro Pro Ala Leu Ser Ala Ser Val Gly
1               5                   10                  15

Asp Arg Val Thr Ile Thr Cys Arg Ala Ser Gln Asp Ile Asn Asp Trp
            20                  25                  30

Leu Ala Trp Tyr Gln His Lys Pro Gly Lys Ala Pro Lys Leu Leu Ile
        35                  40                  45

Tyr Asp Ala Ser Ser Leu Glu Ser Gly Val Pro Leu Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Lys Tyr Ser Ala Pro Gln
                85                  90                  95

Val Thr Phe Gly Gln Gly Thr Arg Leu Glu Ile Lys
            100                 105


<210> SEQ ID NO 40
<211> LENGTH: 108
<212> TYPE: PRT
<213> ORGANISM: Homo sapiens

<400> SEQUENCE: 40

Asp Ile Gln Met Thr Gln Ser Pro Pro Ala Leu Ser Ala Ser Val Gly
1               5                   10                  15

Asp Arg Val Thr Ile Thr Cys Arg Ala Ser Gln Asp Ile Asn Asp Trp
            20                  25                  30

Leu Ala Trp Tyr Gln His Lys Pro Gly Lys Ala Pro Lys Leu Leu Ile
        35                  40                  45

Tyr Asp Ala Ser Ser Leu Glu Ser Gly Val Pro Leu Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Lys Tyr Ser Ala Pro Gln
                85                  90                  95

Val Thr Phe Gly Gln Gly Thr Arg Leu Glu Ile Lys
            100                 105


<210> SEQ ID NO 41
<211> LENGTH: 108
<212> TYPE: PRT
<213> ORGANISM: Homo sapiens

<400> SEQUENCE: 41

Asp Ile Gln Met Thr Gln Ser Pro Pro Ala Leu Ser Ala Ser Val Gly
1               5                   10                  15

Asp Arg Val Thr Ile Thr Cys Arg Ala Ser Gln Asp Ile Asn Asp Trp
            20                  25                  30
```

Leu Ala Trp Tyr Gln His Lys Pro Gly Lys Ala Pro Lys Leu Leu Ile
35 40 45

Tyr Asp Ala Ser Ser Leu Glu Ser Gly Val Pro Leu Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Lys Tyr Ser Ala Pro Gln
85 90 95

Val Thr Phe Gly Gln Gly Thr Arg Leu Glu Ile Lys
100 105

<210> SEQ ID NO 42
<211> LENGTH: 108
<212> TYPE: PRT
<213> ORGANISM: Homo sapiens

<400> SEQUENCE: 42

Asp Ile Gln Met Thr Gln Ser Pro Pro Ala Leu Ser Ala Ser Val Gly
1 5 10 15

Asp Arg Val Thr Ile Thr Cys Arg Ala Ser Gln Asp Ile Asn Asp Trp
20 25 30

Leu Ala Trp Tyr Gln His Lys Pro Gly Lys Ala Pro Lys Leu Leu Ile
35 40 45

Tyr Asp Ala Ser Ser Leu Glu Ser Gly Val Pro Leu Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Arg Tyr Ser Thr Pro Gln
85 90 95

Ile Thr Phe Gly Gln Gly Thr Arg Leu Glu Ile Lys
100 105

<210> SEQ ID NO 43
<211> LENGTH: 108
<212> TYPE: PRT
<213> ORGANISM: Homo sapiens

<400> SEQUENCE: 43

Asp Ile Gln Met Thr Gln Ser Pro Pro Ala Leu Ser Ala Ser Val Gly
1 5 10 15

Asp Arg Val Thr Ile Thr Cys Arg Ala Ser Gln Asp Ile Asn Asp Trp
20 25 30

Leu Ala Trp Tyr Gln His Lys Pro Gly Lys Ala Pro Lys Leu Leu Ile
35 40 45

Tyr Asp Ala Ser Ser Leu Glu Ser Gly Val Pro Leu Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Lys Tyr Ser Glu Pro Gln
85 90 95

Val Thr Phe Gly Gln Gly Thr Arg Leu Glu Ile Lys
100 105

<210> SEQ ID NO 44
<211> LENGTH: 108
<212> TYPE: PRT
<213> ORGANISM: Homo sapiens

<400> SEQUENCE: 44

```
Asp Ile Gln Met Thr Gln Ser Pro Pro Ala Leu Ser Ala Ser Val Gly
1               5                   10                  15

Asp Arg Val Thr Ile Thr Cys Arg Ala Ser Gln Asp Ile Asn Asp Trp
            20                  25                  30

Leu Ala Trp Tyr Gln His Lys Pro Gly Lys Ala Pro Lys Leu Leu Ile
        35                  40                  45

Tyr Asp Ala Ser Ser Leu Glu Ser Gly Val Pro Leu Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Lys Tyr Ser Thr Pro Glu
                85                  90                  95

Val Thr Phe Gly Gln Gly Thr Arg Leu Glu Ile Lys
            100                 105
```

<210> SEQ ID NO 45
<211> LENGTH: 108
<212> TYPE: PRT
<213> ORGANISM: Homo sapiens

<400> SEQUENCE: 45

```
Asp Ile Gln Met Thr Gln Ser Pro Pro Ala Leu Ser Ala Ser Val Gly
1               5                   10                  15

Asp Arg Val Thr Ile Thr Cys Arg Ala Ser Gln Asp Ile Asn Asp Trp
            20                  25                  30

Leu Ala Trp Tyr Gln His Lys Pro Gly Lys Ala Pro Lys Leu Leu Ile
        35                  40                  45

Tyr Asp Ala Ser Ser Leu Glu Ser Gly Val Pro Leu Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Lys Tyr Ser Asp Pro Gln
                85                  90                  95

Val Thr Phe Gly Gln Gly Thr Arg Leu Glu Ile Lys
            100                 105
```

<210> SEQ ID NO 46
<211> LENGTH: 108
<212> TYPE: PRT
<213> ORGANISM: Homo sapiens

<400> SEQUENCE: 46

```
Asp Ile Gln Met Thr Gln Ser Pro Pro Ala Leu Ser Ala Ser Val Gly
1               5                   10                  15

Asp Arg Val Thr Ile Thr Cys Arg Ala Ser Gln Asp Ile Asn Asp Trp
            20                  25                  30

Leu Ala Trp Tyr Gln His Lys Pro Gly Lys Ala Pro Lys Leu Leu Ile
        35                  40                  45

Tyr Asp Ala Ser Ser Leu Glu Ser Gly Val Pro Leu Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Lys Tyr Ser Glu Pro Gln
                85                  90                  95
```

```
Val Thr Phe Gly Gln Gly Thr Arg Leu Glu Ile Lys
            100                 105


<210> SEQ ID NO 47
<211> LENGTH: 108
<212> TYPE: PRT
<213> ORGANISM: Homo sapiens

<400> SEQUENCE: 47

Asp Ile Gln Met Thr Gln Ser Pro Pro Ala Leu Ser Ala Ser Val Gly
1               5                   10                  15

Asp Arg Val Thr Ile Thr Cys Arg Ala Ser Gln Asp Ile Asn Asp Trp
            20                  25                  30

Leu Ala Trp Tyr Gln His Lys Pro Gly Lys Ala Pro Lys Leu Leu Ile
        35                  40                  45

Tyr Asp Ala Ser Ser Leu Glu Ser Gly Val Pro Leu Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Lys Tyr Ser Thr Pro Gln
                85                  90                  95

Val Thr Phe Gly Ser Gly Thr Arg Leu Glu Ile Lys
            100                 105


<210> SEQ ID NO 48
<211> LENGTH: 108
<212> TYPE: PRT
<213> ORGANISM: Homo sapiens

<400> SEQUENCE: 48

Asp Ile Gln Met Thr Gln Ser Pro Pro Ala Leu Ser Ala Ser Val Gly
1               5                   10                  15

Asp Arg Val Thr Ile Thr Cys Arg Ala Ser Gln Asp Ile Asn Asp Trp
            20                  25                  30

Leu Ala Trp Tyr Gln His Lys Pro Gly Lys Ala Pro Lys Leu Leu Ile
        35                  40                  45

Tyr Asp Ala Ser Ser Leu Glu Ser Gly Val Pro Leu Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Arg Tyr Ser Thr Pro Ile
                85                  90                  95

Val Thr Phe Gly Gln Gly Thr Arg Leu Glu Ile Lys
            100                 105


<210> SEQ ID NO 49
<211> LENGTH: 108
<212> TYPE: PRT
<213> ORGANISM: Homo sapiens

<400> SEQUENCE: 49

Asp Ile Gln Met Thr Gln Ser Pro Pro Ala Leu Ser Ala Ser Val Gly
1               5                   10                  15

Asp Arg Val Thr Ile Thr Cys Arg Ala Ser Gln Asp Ile Asn Asp Trp
            20                  25                  30

Leu Ala Trp Tyr Gln His Lys Pro Gly Lys Ala Pro Lys Leu Leu Ile
        35                  40                  45

Tyr Asp Ala Ser Ser Leu Glu Ser Gly Val Pro Leu Arg Phe Ser Gly
```

```
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Lys Tyr Lys Thr Pro Gln
                85                  90                  95

Val Thr Phe Gly Gln Gly Thr Arg Leu Glu Ile Lys
            100                 105


<210> SEQ ID NO 50
<211> LENGTH: 108
<212> TYPE: PRT
<213> ORGANISM: Homo sapiens

<400> SEQUENCE: 50

Asp Ile Gln Met Thr Gln Ser Pro Pro Ala Leu Ser Ala Ser Val Gly
1               5                   10                  15

Asp Arg Val Thr Ile Thr Cys Arg Ala Ser Gln Asp Ile Asn Asp Trp
            20                  25                  30

Leu Ala Trp Tyr Gln His Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Arg Tyr Ser Thr Asp Gln
                85                  90                  95

Val Thr Phe Gly Gln Gly Thr Arg Leu Glu Ile Lys
            100                 105


<210> SEQ ID NO 51
<211> LENGTH: 10
<212> TYPE: PRT
<213> ORGANISM: Homo sapiens

<400> SEQUENCE: 51

Gly Asp Ser Val Ser Ser Lys Ser Ala Ala
1               5                   10


<210> SEQ ID NO 52
<211> LENGTH: 10
<212> TYPE: PRT
<213> ORGANISM: Homo sapiens

<400> SEQUENCE: 52

Gly Asp Ser Val Ser Ser Lys Ser Val Ala
1               5                   10


<210> SEQ ID NO 53
<211> LENGTH: 9
<212> TYPE: PRT
<213> ORGANISM: Homo sapiens

<400> SEQUENCE: 53

Thr Tyr Tyr Arg Ser Lys Trp Ser Thr
1               5


<210> SEQ ID NO 54
<211> LENGTH: 8
<212> TYPE: PRT
<213> ORGANISM: Homo sapiens
```

<400> SEQUENCE: 54

Thr Trp Ser Gly Tyr Val Asp Val
1               5

<210> SEQ ID NO 55
<211> LENGTH: 8
<212> TYPE: PRT
<213> ORGANISM: Homo sapiens

<400> SEQUENCE: 55

Thr Trp Val Gly Tyr Val Asp Val
1               5

<210> SEQ ID NO 56
<211> LENGTH: 8
<212> TYPE: PRT
<213> ORGANISM: Homo sapiens

<400> SEQUENCE: 56

Thr Trp Val Gly Tyr Ala Asp Val
1               5

<210> SEQ ID NO 57
<211> LENGTH: 8
<212> TYPE: PRT
<213> ORGANISM: Homo sapiens

<400> SEQUENCE: 57

Thr Trp Val Glu Tyr Val Asp Val
1               5

<210> SEQ ID NO 58
<211> LENGTH: 8
<212> TYPE: PRT
<213> ORGANISM: Homo sapiens

<400> SEQUENCE: 58

Thr Trp Val Gly Tyr Val Asp Tyr
1               5

<210> SEQ ID NO 59
<211> LENGTH: 8
<212> TYPE: PRT
<213> ORGANISM: Homo sapiens

<400> SEQUENCE: 59

Thr Trp Val Gly Tyr Val Asp Val
1               5

<210> SEQ ID NO 60
<211> LENGTH: 8
<212> TYPE: PRT
<213> ORGANISM: Homo sapiens

<400> SEQUENCE: 60

Thr Trp Val Gly Tyr Val Asp Arg
1               5

<210> SEQ ID NO 61
<211> LENGTH: 8
<212> TYPE: PRT
<213> ORGANISM: Homo sapiens

<400> SEQUENCE: 61

Thr Trp Ala Asp Tyr Val Asp Val
1 5

<210> SEQ ID NO 62
<211> LENGTH: 8
<212> TYPE: PRT
<213> ORGANISM: Homo sapiens

<400> SEQUENCE: 62

Thr Trp Val Gly Tyr Ala Asp Val
1 5

<210> SEQ ID NO 63
<211> LENGTH: 8
<212> TYPE: PRT
<213> ORGANISM: Homo sapiens

<400> SEQUENCE: 63

Thr Trp Val Gly Tyr Val Asp Tyr
1 5

<210> SEQ ID NO 64
<211> LENGTH: 8
<212> TYPE: PRT
<213> ORGANISM: Homo sapiens

<400> SEQUENCE: 64

Thr Trp Val Gly Tyr Ala Asp Val
1 5

<210> SEQ ID NO 65
<211> LENGTH: 8
<212> TYPE: PRT
<213> ORGANISM: Homo sapiens

<400> SEQUENCE: 65

Thr Trp Val Gly Tyr Ala Asp Val
1 5

<210> SEQ ID NO 66
<211> LENGTH: 8
<212> TYPE: PRT
<213> ORGANISM: Homo sapiens

<400> SEQUENCE: 66

Thr Trp Ala Asp Tyr Val Asp Val
1 5

<210> SEQ ID NO 67
<211> LENGTH: 8
<212> TYPE: PRT
<213> ORGANISM: Homo sapiens

<400> SEQUENCE: 67

Thr Trp Ala Gly Tyr Pro Asp Val
1 5

<210> SEQ ID NO 68
<211> LENGTH: 8
<212> TYPE: PRT
<213> ORGANISM: Homo sapiens

<400> SEQUENCE: 68

Thr Trp Val Gly Tyr Val Asp Arg
1 5

<210> SEQ ID NO 69
<211> LENGTH: 8
<212> TYPE: PRT
<213> ORGANISM: Homo sapiens

<400> SEQUENCE: 69

Thr Trp Val Gly Tyr Ala Asp Val
1 5

<210> SEQ ID NO 70
<211> LENGTH: 8
<212> TYPE: PRT
<213> ORGANISM: Homo sapiens

<400> SEQUENCE: 70

Ser Trp Val Gly Tyr Val Asp Val
1 5

<210> SEQ ID NO 71
<211> LENGTH: 8
<212> TYPE: PRT
<213> ORGANISM: Homo sapiens

<400> SEQUENCE: 71

Ser Trp Val Gly Tyr Val Asp Val
1 5

<210> SEQ ID NO 72
<211> LENGTH: 8
<212> TYPE: PRT
<213> ORGANISM: Homo sapiens

<400> SEQUENCE: 72

Thr Trp Ala Asp Tyr Val Asp Val
1 5

<210> SEQ ID NO 73
<211> LENGTH: 8
<212> TYPE: PRT
<213> ORGANISM: Homo sapiens

<400> SEQUENCE: 73

Thr Trp Val Gly Tyr Ala Asp Val
1 5

<210> SEQ ID NO 74
<211> LENGTH: 8
<212> TYPE: PRT
<213> ORGANISM: Homo sapiens

<400> SEQUENCE: 74

Thr Trp Leu Gly Asn Val Asp Val
1 5

<210> SEQ ID NO 75
<211> LENGTH: 8
<212> TYPE: PRT
<213> ORGANISM: Homo sapiens

<400> SEQUENCE: 75

Thr Trp Val Gly Tyr Ala Asp Val
1 5

<210> SEQ ID NO 76
<211> LENGTH: 8
<212> TYPE: PRT
<213> ORGANISM: Homo sapiens

<400> SEQUENCE: 76

Thr Trp Val Gly Tyr Ala Asp Val
1 5

<210> SEQ ID NO 77
<211> LENGTH: 8
<212> TYPE: PRT
<213> ORGANISM: Homo sapiens

<400> SEQUENCE: 77

Thr Trp Ala Gly Tyr Pro Asp Val
1 5

<210> SEQ ID NO 78
<211> LENGTH: 8
<212> TYPE: PRT
<213> ORGANISM: Homo sapiens

<400> SEQUENCE: 78

Thr Trp Ala Asp Tyr Val Asp Val
1 5

<210> SEQ ID NO 79
<211> LENGTH: 6
<212> TYPE: PRT
<213> ORGANISM: Homo sapiens

<400> SEQUENCE: 79

Gln Asp Ile Asn Asp Trp
1 5

<210> SEQ ID NO 80
<211> LENGTH: 3
<212> TYPE: PRT
<213> ORGANISM: Homo sapiens

<400> SEQUENCE: 80

Asp Ala Ser
1

<210> SEQ ID NO 81
<211> LENGTH: 10
<212> TYPE: PRT
<213> ORGANISM: Homo sapiens

<400> SEQUENCE: 81

Gln Gln Ser Tyr Ser Thr Pro Gln Val Thr
1 5 10

<210> SEQ ID NO 82
<211> LENGTH: 10
<212> TYPE: PRT
<213> ORGANISM: Homo sapiens

<400> SEQUENCE: 82

Gln Gln Lys Tyr Ser Thr Pro Gln Ile Thr
1 5 10

<210> SEQ ID NO 83
<211> LENGTH: 10

<212> TYPE: PRT
<213> ORGANISM: Homo sapiens

<400> SEQUENCE: 83

Gln Gln Arg Tyr Ser Thr Pro Gln Ile Thr
1 5 10

<210> SEQ ID NO 84
<211> LENGTH: 10
<212> TYPE: PRT
<213> ORGANISM: Homo sapiens

<400> SEQUENCE: 84

Gln Gln Lys Tyr Ser Thr Pro Gln Val Thr
1 5 10

<210> SEQ ID NO 85
<211> LENGTH: 10
<212> TYPE: PRT
<213> ORGANISM: Homo sapiens

<400> SEQUENCE: 85

Gln Gln Lys Tyr Ser Gln Pro Gln Val Thr
1 5 10

<210> SEQ ID NO 86
<211> LENGTH: 10
<212> TYPE: PRT
<213> ORGANISM: Homo sapiens

<400> SEQUENCE: 86

Gln Gln Arg Tyr Ser Thr Pro Arg Val Thr
1 5 10

<210> SEQ ID NO 87
<211> LENGTH: 10
<212> TYPE: PRT
<213> ORGANISM: Homo sapiens

<400> SEQUENCE: 87

Gln Gln Lys Tyr Ser Thr Pro Lys Val Thr
1 5 10

<210> SEQ ID NO 88
<211> LENGTH: 10
<212> TYPE: PRT
<213> ORGANISM: Homo sapiens

<400> SEQUENCE: 88

Gln Gln Lys Tyr Ser Thr Pro Trp Val Thr
1 5 10

<210> SEQ ID NO 89
<211> LENGTH: 10
<212> TYPE: PRT
<213> ORGANISM: Homo sapiens

<400> SEQUENCE: 89

Gln Gln Arg Tyr Ser Thr Pro Pro Val Thr
1 5 10

<210> SEQ ID NO 90
<211> LENGTH: 10
<212> TYPE: PRT
<213> ORGANISM: Homo sapiens

<400> SEQUENCE: 90

Gln Gln Gly Tyr Ser Thr Pro Gln Leu Thr
1               5                   10

<210> SEQ ID NO 91
<211> LENGTH: 10
<212> TYPE: PRT
<213> ORGANISM: Homo sapiens

<400> SEQUENCE: 91

Gln Gln Lys Tyr Ser Thr Pro Trp Val Thr
1               5                   10

<210> SEQ ID NO 92
<211> LENGTH: 10
<212> TYPE: PRT
<213> ORGANISM: Homo sapiens

<400> SEQUENCE: 92

Gln Gln Arg Tyr Ser Thr His Gln Val Thr
1               5                   10

<210> SEQ ID NO 93
<211> LENGTH: 10
<212> TYPE: PRT
<213> ORGANISM: Homo sapiens

<400> SEQUENCE: 93

Gln Gln Lys Tyr Ser Thr Pro Gln Leu Thr
1               5                   10

<210> SEQ ID NO 94
<211> LENGTH: 10
<212> TYPE: PRT
<213> ORGANISM: Homo sapiens

<400> SEQUENCE: 94

Gln Gln Lys Tyr Ser Ala Pro Gln Val Thr
1               5                   10

<210> SEQ ID NO 95
<211> LENGTH: 10
<212> TYPE: PRT
<213> ORGANISM: Homo sapiens

<400> SEQUENCE: 95

Gln Gln Lys Tyr Ser Ala Pro Gln Val Thr
1               5                   10

<210> SEQ ID NO 96
<211> LENGTH: 10
<212> TYPE: PRT
<213> ORGANISM: Homo sapiens

<400> SEQUENCE: 96

Gln Gln Lys Tyr Ser Ala Pro Gln Val Thr
1               5                   10

<210> SEQ ID NO 97
<211> LENGTH: 10
<212> TYPE: PRT
<213> ORGANISM: Homo sapiens

<400> SEQUENCE: 97

Gln Gln Arg Tyr Ser Thr Pro Gln Ile Thr
1 5 10

<210> SEQ ID NO 98
<211> LENGTH: 10
<212> TYPE: PRT
<213> ORGANISM: Homo sapiens

<400> SEQUENCE: 98

Gln Gln Lys Tyr Ser Glu Pro Gln Val Thr
1 5 10

<210> SEQ ID NO 99
<211> LENGTH: 10
<212> TYPE: PRT
<213> ORGANISM: Homo sapiens

<400> SEQUENCE: 99

Gln Gln Lys Tyr Ser Thr Pro Glu Val Thr
1 5 10

<210> SEQ ID NO 100
<211> LENGTH: 10
<212> TYPE: PRT
<213> ORGANISM: Homo sapiens

<400> SEQUENCE: 100

Gln Gln Lys Tyr Ser Asp Pro Gln Val Thr
1 5 10

<210> SEQ ID NO 101
<211> LENGTH: 10
<212> TYPE: PRT
<213> ORGANISM: Homo sapiens

<400> SEQUENCE: 101

Gln Gln Lys Tyr Ser Glu Pro Gln Val Thr
1 5 10

<210> SEQ ID NO 102
<211> LENGTH: 10
<212> TYPE: PRT
<213> ORGANISM: Homo sapiens

<400> SEQUENCE: 102

Gln Gln Lys Tyr Ser Thr Pro Gln Val Thr
1 5 10

<210> SEQ ID NO 103
<211> LENGTH: 10
<212> TYPE: PRT
<213> ORGANISM: Homo sapiens

<400> SEQUENCE: 103

Gln Gln Arg Tyr Ser Thr Pro Ile Val Thr
1 5 10

<210> SEQ ID NO 104
<211> LENGTH: 10
<212> TYPE: PRT
<213> ORGANISM: Homo sapiens

<400> SEQUENCE: 104

Gln Gln Lys Tyr Lys Thr Pro Gln Val Thr 1 5 10

<210> SEQ ID NO 105
<211> LENGTH: 10
<212> TYPE: PRT
<213> ORGANISM: Homo sapiens

<400> SEQUENCE: 105

Gln Gln Arg Tyr Ser Thr Asp Gln Val Thr
1 5 10

<210> SEQ ID NO 106
<211> LENGTH: 118
<212> TYPE: PRT
<213> ORGANISM: Homo sapiens

<400> SEQUENCE: 106

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp Tyr
20 25 30

Tyr Met Ser Trp Ile Arg Gln Ala Pro Gly Lys Gly Leu Glu Trp Val
35 40 45

Ser Tyr Ile Ser Ser Ser Gly Ser Thr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Val Asp Tyr Ala Asp Ala Phe Asp Ile Trp Gly Gln Gly Thr
100 105 110

Leu Val Thr Val Ser Ser
115

<210> SEQ ID NO 107
<211> LENGTH: 118
<212> TYPE: PRT
<213> ORGANISM: Homo sapiens

<400> SEQUENCE: 107

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp Tyr
20 25 30

Tyr Met Ser Trp Ile Arg Gln Ala Pro Gly Lys Gly Leu Glu Trp Val
35 40 45

Ser Tyr Ile Ser Ser Ser Gly Ser Thr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Asp Asp Tyr Asn Asp Ala Phe Asp Ile Trp Gly Gln Gly Thr
100 105 110

Leu Val Thr Val Ser Ser
115

<210> SEQ ID NO 108

<211> LENGTH: 118
<212> TYPE: PRT
<213> ORGANISM: Homo sapiens

<400> SEQUENCE: 108

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp Tyr
20 25 30

Tyr Met Ser Trp Ile Arg Gln Ala Pro Gly Lys Gly Leu Glu Trp Val
35 40 45

Ser Tyr Ile Ser Ser Ser Gly Ser Thr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Asp Asp Tyr Asn Asp Ala Phe Asp Ile Trp Gly Gln Gly Thr
100 105 110

Leu Val Thr Val Ser Ser
115

<210> SEQ ID NO 109
<211> LENGTH: 118
<212> TYPE: PRT
<213> ORGANISM: Homo sapiens

<400> SEQUENCE: 109

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp Tyr
20 25 30

Tyr Met Ser Trp Ile Arg Gln Ala Pro Gly Lys Gly Leu Glu Trp Val
35 40 45

Ser Tyr Ile Ser Ser Ser Gly Ser Thr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Ile Asp Tyr Glu Asp Ala Phe Asp Ile Trp Gly Gln Gly Thr
100 105 110

Leu Val Thr Val Ser Ser
115

<210> SEQ ID NO 110
<211> LENGTH: 118
<212> TYPE: PRT
<213> ORGANISM: Homo sapiens

<400> SEQUENCE: 110

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp Tyr
20 25 30

Tyr Met Ser Trp Ile Arg Gln Ala Pro Gly Lys Gly Leu Glu Trp Val
35 40 45

```
Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Ser Tyr Asp Asp Ala Phe Asp Ile Trp Gly Gln Gly Thr
            100                 105                 110

Leu Val Thr Val Ser Ser
        115


<210> SEQ ID NO 111
<211> LENGTH: 118
<212> TYPE: PRT
<213> ORGANISM: Homo sapiens

<400> SEQUENCE: 111

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ile Asp Tyr Glu Asp Ala Phe Asp Ile Trp Gly Gln Gly Thr
            100                 105                 110

Leu Val Thr Val Ser Ser
        115


<210> SEQ ID NO 112
<211> LENGTH: 118
<212> TYPE: PRT
<213> ORGANISM: Homo sapiens

<400> SEQUENCE: 112

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Asp Tyr Gln Glu Ala Phe Asp Ile Trp Gly Gln Gly Thr
            100                 105                 110

Leu Val Thr Val Ser Ser
        115
```

<210> SEQ ID NO 113
<211> LENGTH: 118
<212> TYPE: PRT
<213> ORGANISM: Homo sapiens

<400> SEQUENCE: 113

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp Tyr
20 25 30

Tyr Met Ser Trp Ile Arg Gln Ala Pro Gly Lys Gly Leu Glu Trp Val
35 40 45

Ser Tyr Ile Ser Ser Ser Gly Ser Thr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Asp Asp Tyr Asn Asp Ala Phe Asp Ile Trp Gly Gln Gly Thr
100 105 110

Leu Val Thr Val Ser Ser
115

<210> SEQ ID NO 114
<211> LENGTH: 118
<212> TYPE: PRT
<213> ORGANISM: Homo sapiens

<400> SEQUENCE: 114

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp Tyr
20 25 30

Tyr Met Ser Trp Ile Arg Gln Ala Pro Gly Lys Gly Leu Glu Trp Val
35 40 45

Ser Tyr Ile Ser Ser Ser Gly Ser Thr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Val Asp Tyr Asn Glu Ala Phe Asp Ile Trp Gly Gln Gly Thr
100 105 110

Leu Val Thr Val Ser Ser
115

<210> SEQ ID NO 115
<211> LENGTH: 118
<212> TYPE: PRT
<213> ORGANISM: Homo sapiens

<400> SEQUENCE: 115

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp Tyr
20 25 30

Tyr Met Ser Trp Ile Arg Gln Ala Pro Gly Lys Gly Leu Glu Trp Val 35 40 45

Ser Tyr Ile Ser Ser Ser Gly Ser Thr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Asp Asp Tyr Glu Asp Ala Phe Asp Ile Trp Gly Gln Gly Thr
100 105 110

Leu Val Thr Val Ser Ser
115

<210> SEQ ID NO 116
<211> LENGTH: 118
<212> TYPE: PRT
<213> ORGANISM: Homo sapiens

<400> SEQUENCE: 116

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp Tyr
20 25 30

Tyr Met Ser Trp Ile Arg Gln Ala Pro Gly Lys Gly Leu Glu Trp Val
35 40 45

Ser Tyr Ile Ser Ser Ser Gly Ser Thr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Val Ser Tyr Ala Glu Ala Phe Asp Ile Trp Gly Gln Gly Thr
100 105 110

Leu Val Thr Val Ser Ser
115

<210> SEQ ID NO 117
<211> LENGTH: 118
<212> TYPE: PRT
<213> ORGANISM: Homo sapiens

<400> SEQUENCE: 117

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp Tyr
20 25 30

Tyr Met Ser Trp Ile Arg Gln Ala Pro Gly Lys Gly Leu Glu Trp Val
35 40 45

Ser Tyr Ile Ser Ser Ser Gly Ser Thr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Asp Asp Tyr Asp Asp Ala Phe Asp Ile Trp Gly Gln Gly Thr
100 105 110

Leu Val Thr Val Ser Ser

115

<210> SEQ ID NO 118
<211> LENGTH: 109
<212> TYPE: PRT
<213> ORGANISM: Homo sapiens

<400> SEQUENCE: 118

Ala Ser Asp Ile Gln Met Thr Gln Ser Pro Ser Ser Leu Ser Ala Ser
1 5 10 15

Val Gly Asp Arg Val Thr Ile Ala Cys Arg Ala Gly Gln Ser Ile Gly
20 25 30

Thr Tyr Leu Asn Trp Tyr Gln Gln Lys Pro Gly Lys Ala Pro Lys Leu
35 40 45

Leu Ile Tyr Val Ala Ser Ser Leu Gln Ser Gly Val Pro Ser Arg Phe
50 55 60

Ser Gly Ser Gly Ser Gly Thr Glu Phe Thr Leu Thr Ile Ser Ser Leu
65 70 75 80

Gln Pro Glu Asp Phe Ala Thr Tyr Tyr Cys Gln Gln Ser Tyr Ser Thr
85 90 95

Leu Leu Thr Phe Gly Arg Gly Thr Lys Val Glu Ile Lys
100 105

<210> SEQ ID NO 119
<211> LENGTH: 107
<212> TYPE: PRT
<213> ORGANISM: Homo sapiens

<400> SEQUENCE: 119

Asp Ile Gln Met Thr Gln Ser Pro Ser Ser Leu Ser Ala Ser Val Gly
1 5 10 15

Asp Arg Val Thr Ile Ala Cys Arg Ala Gly Gln Ser Ile Gly Thr Tyr
20 25 30

Leu Asn Trp Tyr Gln Gln Lys Pro Gly Lys Ala Pro Lys Leu Leu Ile
35 40 45

Tyr Val Ala Ser Ser Leu Gln Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Gln Gln Thr Ala Ser Thr Leu Leu
85 90 95

Thr Phe Gly Arg Gly Thr Lys Val Glu Ile Lys
100 105

<210> SEQ ID NO 120
<211> LENGTH: 107
<212> TYPE: PRT
<213> ORGANISM: Homo sapiens

<400> SEQUENCE: 120

Asp Ile Gln Met Thr Gln Ser Pro Ser Ser Leu Ser Ala Ser Val Gly
1 5 10 15

Asp Arg Val Thr Ile Ala Cys Arg Ala Gly Gln Ser Ile Gly Thr Tyr
20 25 30

Leu Asn Trp Tyr Gln Gln Lys Pro Gly Lys Ala Pro Lys Leu Leu Ile
35 40 45

Tyr Val Ala Ser Ser Leu Gln Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Gln Gln Ser Ala Asp Thr Leu Leu
85 90 95

Thr Phe Gly Arg Gly Thr Lys Val Glu Ile Lys
100 105

<210> SEQ ID NO 121
<211> LENGTH: 107
<212> TYPE: PRT
<213> ORGANISM: Homo sapiens

<400> SEQUENCE: 121

Asp Ile Gln Met Thr Gln Ser Pro Ser Ser Leu Ser Ala Ser Val Gly
1 5 10 15

Asp Arg Val Thr Ile Ala Cys Arg Ala Gly Gln Ser Ile Gly Thr Tyr
20 25 30

Leu Asn Trp Tyr Gln Gln Lys Pro Gly Lys Ala Pro Lys Leu Leu Ile
35 40 45

Tyr Val Ala Ser Ser Leu Gln Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Gln Gln Ser Gly Ser Glu Leu Leu
85 90 95

Thr Phe Gly Arg Gly Thr Lys Val Glu Ile Lys
100 105

<210> SEQ ID NO 122
<211> LENGTH: 107
<212> TYPE: PRT
<213> ORGANISM: Homo sapiens

<400> SEQUENCE: 122

Asp Ile Gln Met Thr Gln Ser Pro Ser Ser Leu Ser Ala Ser Val Gly
1 5 10 15

Asp Arg Val Thr Ile Ala Cys Arg Val Gly Gln Ser Ile Gly Thr Tyr
20 25 30

Leu Asn Trp Tyr Gln Gln Lys Pro Gly Lys Ala Pro Lys Leu Leu Ile
35 40 45

Tyr Val Ala Ser Ser Leu Gln Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Gln Gln Ser Ala Ser Glu Leu Leu
85 90 95

Thr Phe Gly Arg Gly Thr Lys Val Glu Ile Lys
100 105

<210> SEQ ID NO 123
<211> LENGTH: 107
<212> TYPE: PRT
<213> ORGANISM: Homo sapiens

<400> SEQUENCE: 123

Asp Ile Gln Met Thr Gln Ser Pro Ser Ser Leu Ser Ala Ser Val Gly
1 5 10 15

```
Asp Arg Val Thr Ile Ala Cys Arg Ala Gly Gln Ser Ile Gly Thr Tyr
            20                  25                  30

Leu Asn Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ser Ala Ser Glu Leu Leu
                85                  90                  95

Thr Phe Gly Arg Gly Thr Lys Val Glu Ile Lys
            100                 105


<210> SEQ ID NO 124
<211> LENGTH: 107
<212> TYPE: PRT
<213> ORGANISM: Homo sapiens

<400> SEQUENCE: 124

Asp Ile Gln Met Thr Gln Ser Pro Ser Ser Leu Ser Ala Ser Val Gly
1               5                   10                  15

Asp Arg Val Thr Ile Ala Cys Arg Ala Gly Gln Ser Ile Gly Thr Tyr
            20                  25                  30

Leu Asn Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ser Tyr Ser Gly Leu Asp
                85                  90                  95

Thr Phe Gly Arg Gly Thr Lys Val Glu Ile Lys
            100                 105


<210> SEQ ID NO 125
<211> LENGTH: 107
<212> TYPE: PRT
<213> ORGANISM: Homo sapiens

<400> SEQUENCE: 125

Asp Ile Gln Met Thr Gln Ser Pro Ser Ser Leu Ser Ala Ser Val Gly
1               5                   10                  15

Asp Arg Val Thr Ile Ala Cys Arg Ala Gly Gln Ser Ile Gly Thr Tyr
            20                  25                  30

Leu Asn Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ser Ala Ser Glu Leu Leu
                85                  90                  95

Thr Phe Gly Arg Gly Thr Lys Val Glu Ile Lys
            100                 105


<210> SEQ ID NO 126
<211> LENGTH: 107
```

<212> TYPE: PRT
<213> ORGANISM: Homo sapiens

<400> SEQUENCE: 126

Asp Ile Gln Met Thr Gln Ser Pro Ser Ser Leu Ser Ala Ser Val Gly
1 5 10 15

Asp Arg Val Thr Ile Ala Cys Arg Ala Gly Gln Ser Ile Gly Thr Tyr
20 25 30

Leu Asn Trp Tyr Gln Gln Lys Pro Gly Lys Ala Pro Lys Leu Leu Ile
35 40 45

Tyr Val Ala Ser Ser Leu Gln Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Gln Gln Ser Tyr Ser Gly Leu Asp
85 90 95

Thr Phe Gly Arg Gly Thr Lys Val Glu Ile Lys
100 105

<210> SEQ ID NO 127
<211> LENGTH: 107
<212> TYPE: PRT
<213> ORGANISM: Homo sapiens

<400> SEQUENCE: 127

Asp Ile Gln Met Thr Gln Ser Pro Ser Ser Leu Ser Ala Ser Val Gly
1 5 10 15

Asp Arg Val Thr Ile Ala Cys Arg Ala Gly Gln Ser Ile Gly Thr Tyr
20 25 30

Leu Asn Trp Tyr Gln Gln Lys Pro Gly Lys Ala Pro Lys Leu Leu Ile
35 40 45

Tyr Val Ala Ser Ser Leu Gln Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Gln Gln Ser Ser Ser Glu Leu Leu
85 90 95

Thr Phe Gly Arg Gly Thr Lys Val Glu Ile Lys
100 105

<210> SEQ ID NO 128
<211> LENGTH: 107
<212> TYPE: PRT
<213> ORGANISM: Homo sapiens

<400> SEQUENCE: 128

Asp Ile Gln Met Thr Gln Ser Pro Ser Ser Leu Ser Ala Ser Val Gly
1 5 10 15

Asp Arg Val Thr Ile Ala Cys Arg Ala Gly Gln Ser Ile Gly Thr Tyr
20 25 30

Leu Asn Trp Tyr Gln Gln Lys Pro Gly Lys Ala Pro Lys Leu Leu Ile
35 40 45

Tyr Val Ala Ser Ser Leu Gln Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Gln Gln Ser Tyr Ser Gly Leu Asp

```
                85                  90                  95

Thr Phe Gly Arg Gly Thr Lys Val Glu Ile Lys
            100                 105


<210> SEQ ID NO 129
<211> LENGTH: 107
<212> TYPE: PRT
<213> ORGANISM: Homo sapiens

<400> SEQUENCE: 129

Asp Ile Gln Met Thr Gln Ser Pro Ser Ser Leu Ser Ala Ser Val Gly
1               5                   10                  15

Asp Arg Val Thr Ile Ala Cys Arg Ala Gly Gln Ser Ile Gly Thr Tyr
            20                  25                  30

Leu Asn Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ser Ala Ser Glu Leu Leu
                85                  90                  95

Thr Phe Gly Arg Gly Thr Lys Val Glu Ile Lys
            100                 105


<210> SEQ ID NO 130
<211> LENGTH: 8
<212> TYPE: PRT
<213> ORGANISM: Homo sapiens

<400> SEQUENCE: 130

Gly Phe Thr Phe Ser Asp Tyr Tyr
1               5


<210> SEQ ID NO 131
<211> LENGTH: 8
<212> TYPE: PRT
<213> ORGANISM: Homo sapiens )

<400> SEQUENCE: 131

Ile Ser Ser Ser Gly Ser Thr Ile
1               5


<210> SEQ ID NO 132
<211> LENGTH: 9
<212> TYPE: PRT
<213> ORGANISM: Homo sapiens

<400> SEQUENCE: 132

Val Asp Tyr Ala Asp Ala Phe Asp Ile
1               5


<210> SEQ ID NO 133
<211> LENGTH: 9
<212> TYPE: PRT
<213> ORGANISM: Homo sapiens

<400> SEQUENCE: 133

Asp Asp Tyr Asn Asp Ala Phe Asp Ile
1               5
```

<210> SEQ ID NO 134
<211> LENGTH: 9
<212> TYPE: PRT
<213> ORGANISM: Homo sapiens

<400> SEQUENCE: 134

Asp Asp Tyr Asn Asp Ala Phe Asp Ile
1 5

<210> SEQ ID NO 135
<211> LENGTH: 9
<212> TYPE: PRT
<213> ORGANISM: Homo sapiens

<400> SEQUENCE: 135

Ile Asp Tyr Glu Asp Ala Phe Asp Ile
1 5

<210> SEQ ID NO 136
<211> LENGTH: 9
<212> TYPE: PRT
<213> ORGANISM: Homo sapiens

<400> SEQUENCE: 136

Val Ser Tyr Asp Asp Ala Phe Asp Ile
1 5

<210> SEQ ID NO 137
<211> LENGTH: 9
<212> TYPE: PRT
<213> ORGANISM: Homo sapiens

<400> SEQUENCE: 137

Ile Asp Tyr Glu Asp Ala Phe Asp Ile
1 5

<210> SEQ ID NO 138
<211> LENGTH: 9
<212> TYPE: PRT
<213> ORGANISM: Homo sapiens

<400> SEQUENCE: 138

Val Asp Tyr Gln Glu Ala Phe Asp Ile
1 5

<210> SEQ ID NO 139
<211> LENGTH: 9
<212> TYPE: PRT
<213> ORGANISM: Homo sapiens

<400> SEQUENCE: 139

Asp Asp Tyr Asn Asp Ala Phe Asp Ile
1 5

<210> SEQ ID NO 140
<211> LENGTH: 9
<212> TYPE: PRT
<213> ORGANISM: Homo sapiens

<400> SEQUENCE: 140

Val Asp Tyr Asn Glu Ala Phe Asp Ile
1 5

<210> SEQ ID NO 141
<211> LENGTH: 9

<212> TYPE: PRT
<213> ORGANISM: Homo sapiens

<400> SEQUENCE: 141

Asp Asp Tyr Glu Asp Ala Phe Asp Ile
1 5

<210> SEQ ID NO 142
<211> LENGTH: 9
<212> TYPE: PRT
<213> ORGANISM: Homo sapiens

<400> SEQUENCE: 142

Val Ser Tyr Ala Glu Ala Phe Asp Ile
1 5

<210> SEQ ID NO 143
<211> LENGTH: 9
<212> TYPE: PRT
<213> ORGANISM: Homo sapiens

<400> SEQUENCE: 143

Asp Asp Tyr Asp Asp Ala Phe Asp Ile
1 5

<210> SEQ ID NO 144
<211> LENGTH: 6
<212> TYPE: PRT
<213> ORGANISM: Homo sapiens

<400> SEQUENCE: 144

Gln Ser Ile Gly Thr Tyr
1 5

<210> SEQ ID NO 145
<211> LENGTH: 3
<212> TYPE: PRT
<213> ORGANISM: Homo sapiens

<400> SEQUENCE: 145

Val Ala Ser
1

<210> SEQ ID NO 146
<211> LENGTH: 9
<212> TYPE: PRT
<213> ORGANISM: Homo sapiens

<400> SEQUENCE: 146

Gln Gln Ser Tyr Ser Thr Leu Leu Thr
1 5

<210> SEQ ID NO 147
<211> LENGTH: 9
<212> TYPE: PRT
<213> ORGANISM: Homo sapiens

<400> SEQUENCE: 147

Gln Gln Thr Ala Ser Thr Leu Leu Thr
1 5

<210> SEQ ID NO 148
<211> LENGTH: 9
<212> TYPE: PRT
<213> ORGANISM: Homo sapiens

<400> SEQUENCE: 148

Gln Gln Ser Ala Asp Thr Leu Leu Thr
1               5

<210> SEQ ID NO 149
<211> LENGTH: 9
<212> TYPE: PRT
<213> ORGANISM: Homo sapiens

<400> SEQUENCE: 149

Gln Gln Ser Gly Ser Glu Leu Leu Thr
1               5

<210> SEQ ID NO 150
<211> LENGTH: 9
<212> TYPE: PRT
<213> ORGANISM: Homo sapiens

<400> SEQUENCE: 150

Gln Gln Ser Ala Ser Glu Leu Leu Thr
1               5

<210> SEQ ID NO 151
<211> LENGTH: 9
<212> TYPE: PRT
<213> ORGANISM: Homo sapiens

<400> SEQUENCE: 151

Gln Gln Ser Ala Ser Glu Leu Leu Thr
1               5

<210> SEQ ID NO 152
<211> LENGTH: 9
<212> TYPE: PRT
<213> ORGANISM: Homo sapiens

<400> SEQUENCE: 152

Gln Gln Ser Tyr Ser Gly Leu Asp Thr
1               5

<210> SEQ ID NO 153
<211> LENGTH: 9
<212> TYPE: PRT
<213> ORGANISM: Homo sapiens

<400> SEQUENCE: 153

Gln Gln Ser Ala Ser Glu Leu Leu Thr
1               5

<210> SEQ ID NO 154
<211> LENGTH: 9
<212> TYPE: PRT
<213> ORGANISM: Homo sapiens

<400> SEQUENCE: 154

Gln Gln Ser Tyr Ser Gly Leu Asp Thr
1               5

<210> SEQ ID NO 155
<211> LENGTH: 9
<212> TYPE: PRT
<213> ORGANISM: Homo sapiens

<400> SEQUENCE: 155

```
Gln Gln Ser Ser Ser Glu Leu Leu Thr
1               5


<210> SEQ ID NO 156
<211> LENGTH: 9
<212> TYPE: PRT
<213> ORGANISM: Homo sapiens

<400> SEQUENCE: 156

Gln Gln Ser Tyr Ser Gly Leu Asp Thr
1               5


<210> SEQ ID NO 157
<211> LENGTH: 9
<212> TYPE: PRT
<213> ORGANISM: Homo sapiens

<400> SEQUENCE: 157

Gln Gln Ser Ala Ser Glu Leu Leu Thr
1               5


<210> SEQ ID NO 158
<211> LENGTH: 10
<212> TYPE: PRT
<213> ORGANISM: Homo sapiens
<220> FEATURE:
<221> NAME/KEY: misc_feature
<222> LOCATION: (9)..(9)
<223> OTHER INFORMATION: Xaa can be any naturally occurring amino acid

<400> SEQUENCE: 158

Gly Asp Ser Val Ser Ser Lys Ser Xaa Ala
1               5                   10


<210> SEQ ID NO 159
<211> LENGTH: 10
<212> TYPE: PRT
<213> ORGANISM: Homo sapiens
<220> FEATURE:
<221> NAME/KEY: misc_feature
<223> OTHER INFORMATION: X is A or V
<220> FEATURE:
<221> NAME/KEY: misc_feature
<222> LOCATION: (9)..(9)
<223> OTHER INFORMATION: Xaa can be any naturally occurring amino acid

<400> SEQUENCE: 159

Gly Asp Ser Val Ser Ser Lys Ser Xaa Ala
1               5                   10


<210> SEQ ID NO 160
<211> LENGTH: 10
<212> TYPE: PRT
<213> ORGANISM: Homo sapiens
<220> FEATURE:
<221> NAME/KEY: misc_feature
<223> OTHER INFORMATION: X is A or V
<220> FEATURE:
<221> NAME/KEY: misc_feature
<222> LOCATION: (9)..(9)
<223> OTHER INFORMATION: Xaa can be any naturally occurring amino acid

<400> SEQUENCE: 160

Gly Asp Ser Val Ser Ser Lys Ser Xaa Ala
1               5                   10


<210> SEQ ID NO 161
```

<211> LENGTH: 10
<212> TYPE: PRT
<213> ORGANISM: Homo sapiens
<220> FEATURE:
<221> NAME/KEY: misc_feature
<222> LOCATION: (9)..(9)
<223> OTHER INFORMATION: X is A or V

<400> SEQUENCE: 161

Gly Asp Ser Val Ser Ser Lys Ser Xaa Ala
1               5                   10

<210> SEQ ID NO 162
<211> LENGTH: 8
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 162

Xaa Trp Xaa Xaa Xaa Xaa Asp Xaa
1               5

<210> SEQ ID NO 163
<211> LENGTH: 8
<212> TYPE: PRT
<213> ORGANISM: Homo sapiens
<220> FEATURE:
<221> NAME/KEY: misc_feature
<222> LOCATION: (1)..(1)
<223> OTHER INFORMATION: X is S or T
<220> FEATURE:
<221> NAME/KEY: misc_feature
<222> LOCATION: (3)..(3)
<223> OTHER INFORMATION: X is V, A or L
<220> FEATURE:
<221> NAME/KEY: misc_feature
<222> LOCATION: (4)..(4)
<223> OTHER INFORMATION: X is G, E or D
<220> FEATURE:
<221> NAME/KEY: misc_feature
<222> LOCATION: (5)..(5)
<223> OTHER INFORMATION: X is Y or N
<220> FEATURE:
<221> NAME/KEY: misc_feature
<222> LOCATION: (6)..(6)
<223> OTHER INFORMATION: X is V, A or P
<220> FEATURE:
<221> NAME/KEY: misc_feature
<222> LOCATION: (8)..(8)
<223> OTHER INFORMATION: X is V, Y or R

<400> SEQUENCE: 163

Xaa Trp Xaa Xaa Xaa Xaa Asp Xaa
1               5

<210> SEQ ID NO 164
<211> LENGTH: 8
<212> TYPE: PRT
<213> ORGANISM: Homo sapiens
<220> FEATURE:
<221> NAME/KEY: misc_feature
<222> LOCATION: (1)..(1)

<223> OTHER INFORMATION: X is S or T
<220> FEATURE:
<221> NAME/KEY: misc_feature
<222> LOCATION: (3)..(3)
<223> OTHER INFORMATION: X is V, A or L
<220> FEATURE:
<221> NAME/KEY: misc_feature
<222> LOCATION: (4)..(4)
<223> OTHER INFORMATION: X is G, E or D
<220> FEATURE:
<221> NAME/KEY: misc_feature
<222> LOCATION: (5)..(5)
<223> OTHER INFORMATION: X is Y or N
<220> FEATURE:
<221> NAME/KEY: misc_feature
<222> LOCATION: (6)..(6)
<223> OTHER INFORMATION: X is V, A or P
<220> FEATURE:
<221> NAME/KEY: misc_feature
<222> LOCATION: (8)..(8)
<223> OTHER INFORMATION: X is V, Y or R

<400> SEQUENCE: 164

Xaa Trp Xaa Xaa Xaa Xaa Asp Xaa
1               5

<210> SEQ ID NO 165
<211> LENGTH: 8
<212> TYPE: PRT
<213> ORGANISM: Homo sapiens
<220> FEATURE:
<221> NAME/KEY: misc_feature
<222> LOCATION: (1)..(1)
<223> OTHER INFORMATION: X is S or T
<220> FEATURE:
<221> NAME/KEY: misc_feature
<222> LOCATION: (3)..(3)
<223> OTHER INFORMATION: X is V, A or L
<220> FEATURE:
<221> NAME/KEY: misc_feature
<222> LOCATION: (4)..(4)
<223> OTHER INFORMATION: X is G or D
<220> FEATURE:
<221> NAME/KEY: misc_feature
<222> LOCATION: (5)..(5)
<223> OTHER INFORMATION: X is Y or N
<220> FEATURE:
<221> NAME/KEY: misc_feature
<222> LOCATION: (6)..(6)
<223> OTHER INFORMATION: X is V, A or P
<220> FEATURE:
<221> NAME/KEY: misc_feature
<222> LOCATION: (8)..(8)
<223> OTHER INFORMATION: X is V, Y or R

<400> SEQUENCE: 165

Xaa Trp Xaa Xaa Xaa Xaa Asp Xaa
1               5

<210> SEQ ID NO 166
<211> LENGTH: 10
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(9)
<223> OTHER INFORMATION: Xaa can be any naturally occurring amino acid

<400> SEQUENCE: 166

Gln Gln Xaa Tyr Xaa Xaa Xaa Xaa Xaa Thr

-continued 1 5 10

<210> SEQ ID NO 167
<211> LENGTH: 10
<212> TYPE: PRT
<213> ORGANISM: Homo sapiens
<220> FEATURE:
<221> NAME/KEY: misc_feature
<222> LOCATION: (3)..(3)
<223> OTHER INFORMATION: X is K, R or G
<220> FEATURE:
<221> NAME/KEY: misc_feature
<222> LOCATION: (5)..(5)
<223> OTHER INFORMATION: X is S or K
<220> FEATURE:
<221> NAME/KEY: misc_feature
<222> LOCATION: (6)..(6)
<223> OTHER INFORMATION: X is T, Q, A, E or D
<220> FEATURE:
<221> NAME/KEY: misc_feature
<222> LOCATION: (7)..(7)
<223> OTHER INFORMATION: X is P, H or D
<220> FEATURE:
<221> NAME/KEY: misc_feature
<222> LOCATION: (8)..(8)
<223> OTHER INFORMATION: X is Q, R, K, W, P, E or I
<220> FEATURE:
<221> NAME/KEY: misc_feature
<222> LOCATION: (9)..(9)
<223> OTHER INFORMATION: X is I, V or L

<400> SEQUENCE: 167

Gln Gln Xaa Tyr Xaa Xaa Xaa Xaa Xaa Thr
1 5 10

<210> SEQ ID NO 168
<211> LENGTH: 10
<212> TYPE: PRT
<213> ORGANISM: Homo sapiens
<220> FEATURE:
<221> NAME/KEY: misc_feature
<222> LOCATION: (3)..(3)
<223> OTHER INFORMATION: X is K, R or G
<220> FEATURE:
<221> NAME/KEY: misc_feature
<222> LOCATION: (5)..(5)
<223> OTHER INFORMATION: X is S or K
<220> FEATURE:
<221> NAME/KEY: misc_feature
<222> LOCATION: (6)..(6)
<223> OTHER INFORMATION: X is T, Q, A, E or D
<220> FEATURE:
<221> NAME/KEY: misc_feature
<222> LOCATION: (7)..(7)
<223> OTHER INFORMATION: X is P or H
<220> FEATURE:
<221> NAME/KEY: misc_feature
<222> LOCATION: (8)..(8)
<223> OTHER INFORMATION: X is Q, R, K, W, P, E or I
<220> FEATURE:
<221> NAME/KEY: misc_feature
<222> LOCATION: (9)..(9)
<223> OTHER INFORMATION: X is I, V or L

<400> SEQUENCE: 168

Gln Gln Xaa Tyr Xaa Xaa Xaa Xaa Xaa Thr
1 5 10

<210> SEQ ID NO 169
<211> LENGTH: 10
<212> TYPE: PRT
<213> ORGANISM: Homo sapiens
<220> FEATURE:
<221> NAME/KEY: misc_feature

```
<222> LOCATION: (3)..(3)
<223> OTHER INFORMATION: X is K or R
<220> FEATURE:
<221> NAME/KEY: misc_feature
<222> LOCATION: (5)..(5)
<223> OTHER INFORMATION: X is S or K
<220> FEATURE:
<221> NAME/KEY: misc_feature
<222> LOCATION: (6)..(6)
<223> OTHER INFORMATION: X is T, Q, A or E
<220> FEATURE:
<221> NAME/KEY: misc_feature
<222> LOCATION: (7)..(7)
<223> OTHER INFORMATION: X is P or H
<220> FEATURE:
<221> NAME/KEY: misc_feature
<222> LOCATION: (8)..(8)
<223> OTHER INFORMATION: X is Q, K, W, P or I
<220> FEATURE:
<221> NAME/KEY: misc_feature
<222> LOCATION: (9)..(9)
<223> OTHER INFORMATION: X is V or L

<400> SEQUENCE: 169

Gln Gln Xaa Tyr Xaa Xaa Xaa Xaa Xaa Thr
1               5                   10


<210> SEQ ID NO 170
<211> LENGTH: 25
<212> TYPE: PRT
<213> ORGANISM: Homo sapiens

<400> SEQUENCE: 170

Glu Val Gln Leu Gln Gln Ser Gly Pro Gly Leu Val Lys Pro Ser Gln
1               5                   10                  15

Thr Leu Ser Leu Thr Cys Ala Ile Ser
            20                  25


<210> SEQ ID NO 171
<211> LENGTH: 25
<212> TYPE: PRT
<213> ORGANISM: Homo sapiens

<400> SEQUENCE: 171

Glu Val Gln Leu Leu Gln Ser Gly Pro Gly Leu Val Lys Pro Ser Gln
1               5                   10                  15

Thr Leu Ser Leu Thr Cys Ala Ile Ser
            20                  25


<210> SEQ ID NO 172
<211> LENGTH: 17
<212> TYPE: PRT
<213> ORGANISM: Homo sapiens

<400> SEQUENCE: 172

Trp Asn Trp Ile Arg Gln Ser Pro Ser Arg Gly Leu Glu Trp Leu Gly
1               5                   10                  15

Arg


<210> SEQ ID NO 173
<211> LENGTH: 40
<212> TYPE: PRT
<213> ORGANISM: Homo sapiens

<400> SEQUENCE: 173

Asp Tyr Ala Ala Ser Val Lys Ser Arg Ile Thr Ile Asn Pro Asp Thr
1               5                   10                  15
```

```
Ser Lys Asn Gln Leu Ser Leu Gln Leu Asn Ser Val Thr Pro Glu Asp
            20                  25                  30

Thr Ala Val Tyr Tyr Cys Ala Arg
        35                  40


<210> SEQ ID NO 174
<211> LENGTH: 11
<212> TYPE: PRT
<213> ORGANISM: Homo sapiens

<400> SEQUENCE: 174

Trp Gly Gln Gly Thr Leu Val Thr Val Ser Ser
1               5                   10


<210> SEQ ID NO 175
<211> LENGTH: 26
<212> TYPE: PRT
<213> ORGANISM: Homo sapiens

<400> SEQUENCE: 175

Asp Ile Gln Met Thr Gln Ser Pro Pro Ala Leu Ser Ala Ser Val Gly
1               5                   10                  15

Asp Arg Val Thr Ile Thr Cys Arg Ala Ser
            20                  25


<210> SEQ ID NO 176
<211> LENGTH: 17
<212> TYPE: PRT
<213> ORGANISM: Homo sapiens

<400> SEQUENCE: 176

Leu Ala Trp Tyr Gln His Lys Pro Gly Lys Ala Pro Lys Leu Leu Ile
1               5                   10                  15

Tyr


<210> SEQ ID NO 177
<211> LENGTH: 36
<212> TYPE: PRT
<213> ORGANISM: Homo sapiens

<400> SEQUENCE: 177

Ser Leu Glu Ser Gly Val Pro Leu Arg Phe Ser Gly Ser Gly Ser Gly
1               5                   10                  15

Thr Glu Phe Thr Leu Thr Ile Ser Ser Leu Gln Pro Asp Asp Phe Ala
            20                  25                  30

Thr Tyr Tyr Cys
        35


<210> SEQ ID NO 178
<211> LENGTH: 36
<212> TYPE: PRT
<213> ORGANISM: Homo sapiens

<400> SEQUENCE: 178

Ser Leu Glu Ser Gly Val Pro Ser Arg Phe Ser Gly Ser Gly Ser Gly
1               5                   10                  15

Thr Glu Phe Thr Leu Thr Ile Ser Ser Leu Gln Pro Asp Asp Phe Ala
            20                  25                  30

Thr Tyr Tyr Cys
        35
```

<210> SEQ ID NO 179
<211> LENGTH: 10
<212> TYPE: PRT
<213> ORGANISM: Homo sapiens

<400> SEQUENCE: 179

Phe Gly Gln Gly Thr Arg Leu Glu Ile Lys
1               5                   10

<210> SEQ ID NO 180
<211> LENGTH: 10
<212> TYPE: PRT
<213> ORGANISM: Homo sapiens

<400> SEQUENCE: 180

Phe Gly Ala Gly Thr Arg Leu Glu Ile Lys
1               5                   10

<210> SEQ ID NO 181
<211> LENGTH: 10
<212> TYPE: PRT
<213> ORGANISM: Homo sapiens

<400> SEQUENCE: 181

Phe Gly Gln Gly Thr Arg Leu Val Ile Lys
1               5                   10

<210> SEQ ID NO 182
<211> LENGTH: 10
<212> TYPE: PRT
<213> ORGANISM: Homo sapiens

<400> SEQUENCE: 182

Phe Gly Ser Gly Thr Arg Leu Glu Ile Lys
1               5                   10

<210> SEQ ID NO 183
<211> LENGTH: 9
<212> TYPE: PRT
<213> ORGANISM: Homo sapiens
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 183

Xaa Xaa Tyr Xaa Xaa Ala Phe Asp Ile
1               5

<210> SEQ ID NO 184
<211> LENGTH: 9
<212> TYPE: PRT
<213> ORGANISM: Homo sapiens
<220> FEATURE:
<221> NAME/KEY: misc_feature
<222> LOCATION: (1)..(1)
<223> OTHER INFORMATION: X is D, I or V
<220> FEATURE:
<221> NAME/KEY: misc_feature
<222> LOCATION: (2)..(2)
<223> OTHER INFORMATION: X is D or S
<220> FEATURE:
<221> NAME/KEY: misc_feature
<222> LOCATION: (4)..(4)

<223> OTHER INFORMATION: X is N, E, D, Q or A
<220> FEATURE:
<221> NAME/KEY: misc_feature
<222> LOCATION: (5)..(5)
<223> OTHER INFORMATION: X is D or E

<400> SEQUENCE: 184

Xaa Xaa Tyr Xaa Xaa Ala Phe Asp Ile
1               5

<210> SEQ ID NO 185
<211> LENGTH: 9
<212> TYPE: PRT
<213> ORGANISM: Homo sapiens
<220> FEATURE:
<221> NAME/KEY: misc_feature
<222> LOCATION: (1)..(1)
<223> OTHER INFORMATION: X is D or V
<220> FEATURE:
<221> NAME/KEY: misc_feature
<222> LOCATION: (2)..(2)
<223> OTHER INFORMATION: X is D or S
<220> FEATURE:
<221> NAME/KEY: misc_feature
<222> LOCATION: (4)..(4)
<223> OTHER INFORMATION: X is D, Q or A
<220> FEATURE:
<221> NAME/KEY: misc_feature
<222> LOCATION: (5)..(5)
<223> OTHER INFORMATION: X is D or E

<400> SEQUENCE: 185

Xaa Xaa Tyr Xaa Xaa Ala Phe Asp Ile
1               5

<210> SEQ ID NO 186
<211> LENGTH: 9
<212> TYPE: PRT
<213> ORGANISM: Homo sapiens
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 186

Gln Gln Xaa Xaa Xaa Xaa Leu Xaa Thr
1               5

<210> SEQ ID NO 187
<211> LENGTH: 9
<212> TYPE: PRT
<213> ORGANISM: Homo sapiens
<220> FEATURE:
<221> NAME/KEY: misc_feature
<222> LOCATION: (3)..(3)
<223> OTHER INFORMATION: X is T or S
<220> FEATURE:
<221> NAME/KEY: misc_feature
<222> LOCATION: (4)..(4)
<223> OTHER INFORMATION: X is A, G, Y or S
<220> FEATURE:
<221> NAME/KEY: misc_feature
<222> LOCATION: (5)..(5)
<223> OTHER INFORMATION: X is S or D
<220> FEATURE:
<221> NAME/KEY: misc_feature
<222> LOCATION: (6)..(6)
<223> OTHER INFORMATION: X is T, E or G
<220> FEATURE:

<221> NAME/KEY: misc_feature
<222> LOCATION: (8)..(8)
<223> OTHER INFORMATION: X is L or D

<400> SEQUENCE: 187

Gln Gln Xaa Xaa Xaa Xaa Leu Xaa Thr
1 5

<210> SEQ ID NO 188
<211> LENGTH: 9
<212> TYPE: PRT
<213> ORGANISM: Homo sapiens
<220> FEATURE:
<221> NAME/KEY: misc_feature
<222> LOCATION: (3)..(3)
<223> OTHER INFORMATION: X is S
<220> FEATURE:
<221> NAME/KEY: misc_feature
<222> LOCATION: (4)..(4)
<223> OTHER INFORMATION: X is A or Y
<220> FEATURE:
<221> NAME/KEY: misc_feature
<222> LOCATION: (5)..(5)
<223> OTHER INFORMATION: X is S
<220> FEATURE:
<221> NAME/KEY: misc_feature
<222> LOCATION: (6)..(6)
<223> OTHER INFORMATION: X is E or G
<220> FEATURE:
<221> NAME/KEY: misc_feature
<222> LOCATION: (8)..(8)
<223> OTHER INFORMATION: X is L or D

<400> SEQUENCE: 188

Gln Gln Xaa Xaa Xaa Xaa Leu Xaa Thr
1 5

<210> SEQ ID NO 189
<211> LENGTH: 25
<212> TYPE: PRT
<213> ORGANISM: Homo sapiens

<400> SEQUENCE: 189

Glu Val Gln Leu Val Glu Ser Gly Gly Gly Leu Val Lys Pro Gly Gly
1 5 10 15

Ser Leu Arg Leu Ser Cys Ala Ala Ser
20 25

<210> SEQ ID NO 190
<211> LENGTH: 17
<212> TYPE: PRT
<213> ORGANISM: Homo sapiens

<400> SEQUENCE: 190

Met Ser Trp Ile Arg Gln Ala Pro Gly Lys Gly Leu Glu Trp Val Ser
1 5 10 15

Tyr

<210> SEQ ID NO 191
<211> LENGTH: 40
<212> TYPE: PRT
<213> ORGANISM: Homo sapiens

<400> SEQUENCE: 191

Tyr Tyr Ala Asp Ser Val Lys Gly Arg Phe Thr Ile Ser Arg Asp Asn
1 5 10 15

Ala Lys Asn Ser Leu Tyr Leu Gln Met Asn Ser Leu Arg Ala Glu Asp

-continued

```
            20                  25                  30

Thr Ala Val Tyr Tyr Cys Ala Arg
        35                  40


<210> SEQ ID NO 192
<211> LENGTH: 11
<212> TYPE: PRT
<213> ORGANISM: Homo sapiens

<400> SEQUENCE: 192

Trp Gly Gln Gly Thr Leu Val Thr Val Ser Ser
1               5                   10


<210> SEQ ID NO 193
<211> LENGTH: 26
<212> TYPE: PRT
<213> ORGANISM: Homo sapiens

<400> SEQUENCE: 193

Asp Ile Gln Met Thr Gln Ser Pro Ser Ser Leu Ser Ala Ser Val Gly
1               5                   10                  15

Asp Arg Val Thr Ile Ala Cys Arg Ala Gly
            20                  25


<210> SEQ ID NO 194
<211> LENGTH: 26
<212> TYPE: PRT
<213> ORGANISM: Homo sapiens

<400> SEQUENCE: 194

Asp Ile Gln Met Thr Gln Ser Pro Ser Ser Leu Ser Ala Ser Val Gly
1               5                   10                  15

Asp Arg Val Thr Ile Ala Cys Arg Val Gly
            20                  25


<210> SEQ ID NO 195
<211> LENGTH: 17
<212> TYPE: PRT
<213> ORGANISM: Homo sapiens

<400> SEQUENCE: 195

Leu Asn Trp Tyr Gln Gln Lys Pro Gly Lys Ala Pro Lys Leu Leu Ile
1               5                   10                  15

Tyr


<210> SEQ ID NO 196
<211> LENGTH: 36
<212> TYPE: PRT
<213> ORGANISM: Homo sapiens

<400> SEQUENCE: 196

Ser Leu Gln Ser Gly Val Pro Ser Arg Phe Ser Gly Ser Gly Ser Gly
1               5                   10                  15

Thr Glu Phe Thr Leu Thr Ile Ser Ser Leu Gln Pro Glu Asp Phe Ala
            20                  25                  30

Thr Tyr Tyr Cys
        35


<210> SEQ ID NO 197
<211> LENGTH: 10
<212> TYPE: PRT
<213> ORGANISM: Homo sapiens
```

<400> SEQUENCE: 197

Phe Gly Arg Gly Thr Lys Val Glu Ile Lys
1 5 10

<210> SEQ ID NO 198
<211> LENGTH: 360
<212> TYPE: DNA
<213> ORGANISM: Homo sapiens

<400> SEQUENCE: 198
caggtacagc tgcagcagtc aggtccagga ctggtgaagc cctcgcagac cctctcactc 60
acctgtgcca tctccgggga cagtgtctcc agcaaaagtg ctgcttggaa ctggatcagg 120
cagtccccat cgagaggcct tgagtggctg ggaaggacat actacaggtc caagtggtct 180
actgattatg cagcatctgt gaaaagtcga ataaccatca acccagacac atccaagaac 240
cagctctccc tgcagttaaa ctctgtgact cccgaggaca cggctgtgta ttactgtgca 300
agaacgtgga gtggttatgt ggacgtctgg ggccaaggaa ccctggtcac cgtctcgagc 360

<210> SEQ ID NO 199
<211> LENGTH: 360
<212> TYPE: DNA
<213> ORGANISM: Homo sapiens

<400> SEQUENCE: 199
gaggtacagc tgcagcagtc aggtccagga ctggtgaagc cctcgcagac cctctcactc 60
acctgtgcca tctccgggga cagtgtctcc agcaaaagtg ctgcttggaa ctggatcagg 120
cagtccccat cgagaggcct tgagtggctg ggaaggacat actacaggtc caagtggtct 180
actgattatg cagcatctgt gaaaagtcga ataaccatca acccagacac atccaagaac 240
cagctctccc tgcagttaaa ctctgtgact cccgaggaca cggctgtgta ttactgtgca 300
agaacgtggg tgggttatgt ggacgtctgg ggccaaggaa ccctggtcac cgtctcgagc 360

<210> SEQ ID NO 200
<211> LENGTH: 360
<212> TYPE: DNA
<213> ORGANISM: Homo sapiens

<400> SEQUENCE: 200
gaggtacagc tgcagcagtc aggtccagga ctggtgaagc cctcgcagac cctctcactc 60
acctgtgcca tctccgggga cagtgtctcc agcaaaagtg ctgcttggaa ctggatcagg 120
cagtccccat cgagaggcct tgagtggctg ggaaggacat actacaggtc caagtggtct 180
actgattatg cagcatctgt gaaaagtcga ataaccatca acccagacac atccaagaac 240
cagctctccc tgcagttaaa ctctgtgact cccgaggaca cggctgtgta ttactgtgca 300
agaacgtggg tgggttatgc cgacgtctgg ggccaaggaa ccctggtcac cgtctcgagc 360

<210> SEQ ID NO 201
<211> LENGTH: 360
<212> TYPE: DNA
<213> ORGANISM: Homo sapiens

<400> SEQUENCE: 201
gaggtacagc tgcagcagtc aggtccagga ctggtgaagc cctcgcagac cctctcactc 60
acctgtgcga tctccgggga cagtgtctcc agcaaaagtg ctgcttggaa ctggatcagg 120
cagtccccat cgagaggcct tgagtggctg ggaaggacat actacaggtc caagtggtct 180
actgattatg cagcatctgt gaaaagtcga ataaccatca acccagacac atccaagaac 240
cagctctctc tgcagttaaa ctctgtgact cccgaggaca cggctgtgta ttactgtgca 300
agaacgtggg tggagtatgt ggacgtctgg ggccaaggaa ccctggtcac cgtctcgagc 360

<210> SEQ ID NO 202
<211> LENGTH: 360
<212> TYPE: DNA
<213> ORGANISM: Homo sapiens

<400> SEQUENCE: 202
gaggtacagc tgcagcagtc aggtccagga ctggtgaagc cctcgcagac cctctcactc 60
acctgtgcca tctccgggga cagtgtctcc agcaaaagtg ctgcttggaa ctggatcagg 120
cagtccccat cgagaggcct tgagtggctg ggaaggacat actacaggtc caagtggtct 180
actgattatg cagcatctgt gaaaagtcga ataaccatca acccagacac atccaagaac 240
cagctctccc tgcagttaaa ctctgtgact cccgaggaca cggctgtgta ttactgtgca 300
agaacgtggg tgggttatgt ggactactgg ggccaaggaa ccctggtcac cgtctcgagc 360

<210> SEQ ID NO 203
<211> LENGTH: 360
<212> TYPE: DNA
<213> ORGANISM: Homo sapiens

<400> SEQUENCE: 203
gaggtacagc tgcagcagtc aggtccagga ctggtgaagc cctcgcagac cctctcactc 60
acctgtgcca tctccgggga cagtgtctcc agcaaaagtg ctgcttggaa ctggatcagg 120
cagtccccat cgagaggcct tgagtggctg ggaaggacat actacaggtc caagtggtct 180
actgattatg cagcatctgt gaaaagtcga ataaccatca acccagacac atccaagaac 240
cagctctccc tgcagttaaa ctctgtgact cccgaggaca cggctgtgta ttactgtgca 300
agaacgtggg tgggttatgt ggacgtctgg ggccaaggaa ccctggtcac cgtctcgagc 360

<210> SEQ ID NO 204
<211> LENGTH: 360
<212> TYPE: DNA
<213> ORGANISM: Homo sapiens

<400> SEQUENCE: 204
gaggtacagc tgcagcagtc aggtccagga ctggtgaagc cctcgcagac cctctcactc 60
acctgtgcca tctccgggga cagtgtctcc agcaaaagtg ctgcttggaa ctggatcagg 120
cagtccccat cgagaggcct tgagtggctg ggaaggacat actacaggtc caagtggtct 180
actgattatg cagcatctgt gaaaagtcga ataaccatca acccagacac atccaagaac 240
cagctctccc tgcagttaaa ctctgtgact cccgaggaca cggctgtgta ttactgtgca 300
agaacgtggg tgggttatgt ggacaggtgg ggccaaggaa ccctggtcac cgtctcgagc 360

<210> SEQ ID NO 205
<211> LENGTH: 360
<212> TYPE: DNA
<213> ORGANISM: Homo sapiens

<400> SEQUENCE: 205
gaggtacagc tgcagcagtc aggtccagga ctggtgaagc cctcgcagac cctctcactc 60
acctgtgcca tctccgggga cagtgtctcc agcaaaagtg ttgcttggaa ctggatcagg 120
cagtccccat cgagaggcct tgagtggctg ggaaggacat actacaggtc caagtggtct 180
actgattatg cagcatctgt gaaaagtcga ataaccatca acccagacac atccaagaac 240
cagctctccc tgcagttaaa ctctgtgact cccgaggaca cggctgtgta ttactgtgca 300
agaacgtggg ccgactatgt ggacgtctgg ggccaaggaa ccctggtcac cgtctcgagc 360

<210> SEQ ID NO 206
<211> LENGTH: 360
<212> TYPE: DNA
<213> ORGANISM: Homo sapiens

<400> SEQUENCE: 206
gaggtacagc tgcagcagtc aggtccagga ctggtgaagc cctcgcagac cctctcactc 60
acctgtgcca tctccgggga cagtgtctcc agcaaaagtg ctgcttggaa ctggatcagg 120
cagtccccat cgagaggcct tgagtggctg ggaaggacat actacaggtc caagtggtct 180
actgattatg cagcatctgt gaaaagtcga ataaccatca acccagacac atccaagaac 240
cagctctccc tgcagttaaa ctctgtgact cccgaggaca cggctgtgta ttactgtgca 300
agaacgtggg tgggttatgc cgacgtctgg ggccaaggaa ccctggtcac cgtctcgagc 360

<210> SEQ ID NO 207
<211> LENGTH: 360
<212> TYPE: DNA
<213> ORGANISM: Homo sapiens

<400> SEQUENCE: 207
gaggtacagc tgcagcagtc aggtccagga ctggtgaagc cctcgcagac cctctcactc 60
acctgtgcca tctccgggga cagtgtctcc agcaaaagtg ctgcttggaa ctggatcagg 120
cagtccccat cgagaggcct tgagtggctg ggaaggacat actacaggtc caagtggtct 180
actgattatg cagcatctgt gaaaagtcga ataaccatca acccagacac atccaagaac 240
cagctctccc tgcagttaaa ctctgtgact cccgaggaca cggctgtgta ttactgtgca 300
agaacgtggg tgggttatgt ggactactgg ggccaaggaa ccctggtcac cgtctcgagc 360

<210> SEQ ID NO 208
<211> LENGTH: 360
<212> TYPE: DNA
<213> ORGANISM: Homo sapiens

<400> SEQUENCE: 208
gaggtacagc tgcagcagtc aggtccagga ctggtgaagc cctcgcagac cctctcactc 60
acctgtgcca tctccgggga cagtgtctcc agcaaaagtg ctgcttggaa ctggatcagg 120
cagtccccat cgagaggcct tgagtggctg ggaaggacat actacaggtc caagtggtct 180
actgattatg cagcatctgt gaaaagtcga ataaccatca acccagacac atccaagaac 240
cagctctccc tgcagttaaa ctctgtgact cccgaggaca cggctgtgta ttactgtgca 300
agaacgtggg tgggttatgc cgacgtctgg ggccaaggaa ccctggtcac cgtctcgagc 360

<210> SEQ ID NO 209
<211> LENGTH: 360
<212> TYPE: DNA
<213> ORGANISM: Homo sapiens

<400> SEQUENCE: 209
gaggtacagc tgctgcagtc aggtccagga ctggtgaagc cctcgcagac cctctcactc 60
acctgtgcca tctccgggga cagtgtctcc agcaaaagtg ctgcttggaa ctggatcagg 120
cagtccccat cgagaggcct tgagtggctg ggaaggacat actacaggtc caagtggtct 180
actgattatg cagcatctgt gaaaagtcga ataaccatca acccagacac atccaagaac 240
cagctctccc tgcagttaaa ctctgtgact cccgaggaca cggctgtgta ttactgtgca 300
agaacgtggg tgggttatgc cgacgtctgg ggccaaggaa ccctggtcac cgtctcgagc 360

<210> SEQ ID NO 210
<211> LENGTH: 360
<212> TYPE: DNA
<213> ORGANISM: Homo sapiens

<400> SEQUENCE: 210
gaggtacagc tgcagcagtc aggtccagga ctggtgaagc cctcgcagac cctctcactc 60
acctgtgcca tctccgggga cagtgtctcc agcaaaagtg ttgcttggaa ctggatcagg 120
cagtccccat cgagaggcct tgagtggctg ggaaggacat actacaggtc caagtggtct 180
actgattatg cagcatctgt gaaaagtcga ataaccatca acccagacac atccaagaac 240
cagctctccc tgcagttaaa ctctgtgact cccgaggaca cggctgtgta ttactgtgca 300
agaacgtggg ccgactatgt ggacgtctgg ggccaaggaa ccctggtcac cgtctcgagc 360

<210> SEQ ID NO 211
<211> LENGTH: 360
<212> TYPE: DNA
<213> ORGANISM: Homo sapiens

<400> SEQUENCE: 211
gaggtacagc tgcagcagtc aggtccagga ctggtgaagc cctcgcagac cctctcactc 60
acctgtgcca tctccgggga cagtgtctcc agcaaaagtg ctgcttggaa ctggatcagg 120
cagtccccat cgagaggcct tgagtggctg ggaaggacat actacaggtc caagtggtct 180
actgattatg cagcatctgt gaaaagtcga ataaccatca acccagacac atccaagaac 240
cagctctccc tgcagttaaa ctctgtgact cccgaggaca cggctgtgta ttactgtgca 300
agaacgtggg ccggttatcc cgacgtctgg ggccaaggaa ccctggtcac cgtctcgagc 360

<210> SEQ ID NO 212
<211> LENGTH: 360
<212> TYPE: DNA
<213> ORGANISM: Homo sapiens

<400> SEQUENCE: 212
gaggtacagc tgcagcagtc aggtccagga ctggtgaagc cctcgcagac cctctcactc 60
acctgtgcca tctccgggga cagtgtctcc agcaaaagtg ctgcttggaa ctggatcagg 120
cagtccccat cgagaggcct tgagtggctg ggaaggacat actacaggtc caagtggtct 180
actgattatg cagcatctgt gaaaagtcga ataaccatca acccagacac atccaagaac 240
cagctctccc tgcagttaaa ctctgtgact cccgaggaca cggctgtgta ttactgtgca 300
agaacgtggg tgggttatgt ggacaggtgg ggccaaggaa ccctggtcac cgtctcgagc 360

<210> SEQ ID NO 213
<211> LENGTH: 360
<212> TYPE: DNA
<213> ORGANISM: Homo sapiens

<400> SEQUENCE: 213
gaggtacagc tgcagcagtc aggtccagga ctggtgaagc cctcgcagac cctctcactc 60
acctgtgcca tctccgggga cagtgtctcc agcaaaagtg ctgcttggaa ctggatcagg 120
cagtccccat cgagaggcct tgagtggctg ggaaggacat actacaggtc caagtggtct 180
actgattatg cagcatctgt gaaaagtcga ataaccatca acccagacac atccaagaac 240
cagctctccc tgcagttaaa ctctgtgact cccgaggaca cggctgtgta ttactgtgca 300
agaacgtggg tgggttatgc cgacgtctgg ggccaaggaa ccctggtcac cgtctcgagc 360

<210> SEQ ID NO 214
<211> LENGTH: 360
<212> TYPE: DNA
<213> ORGANISM: Homo sapiens

<400> SEQUENCE: 214
gaggtacagc tgcagcagtc aggtccagga ctggtgaagc cctcgcagac cctctcactc 60
acctgtgcca tctccgggga cagtgtctcc agcaaaagtg ctgcttggaa ctggatcagg 120
cagtccccat cgagaggcct tgagtggctg ggaaggacat actacaggtc caagtggtct 180
actgattatg cagcatctgt gaaaagtcga ataaccatca acccagacac atccaagaac 240
cagctctccc tgcagttaaa ctctgtgact cccgaggaca cggctgtgta ttactgtgca 300
agaagctggg tgggttatgt ggacgtctgg ggccaaggaa ccctggtcac cgtctcgagc 360

<210> SEQ ID NO 215
<211> LENGTH: 360
<212> TYPE: DNA
<213> ORGANISM: Homo sapiens

<400> SEQUENCE: 215
gaggtacagc tgcagcagtc aggtccagga ctggtgaagc cctcgcagac cctctcactc 60
acctgtgcca tctccgggga cagtgtctcc agcaaaagtg ctgcttggaa ctggatcagg 120
cagtccccat cgagaggcct tgagtggctg ggaaggacat actacaggtc caagtggtct 180
actgattatg cagcatctgt gaaaagtcga ataaccatca acccagacac atccaagaac 240
cagctctccc tgcagttaaa ctctgtgact cccgaggaca cggctgtgta ttactgtgca 300
agaagctggg tgggttatgt ggacgtctgg ggccaaggaa ccctggtcac cgtctcgagc 360

<210> SEQ ID NO 216
<211> LENGTH: 360
<212> TYPE: DNA
<213> ORGANISM: Homo sapiens

<400> SEQUENCE: 216
gaggtacagc tgcagcagtc aggtccagga ctggtgaagc cctcgcagac cctctcactc 60
acctgtgcca tctccgggga cagtgtctcc agcaaaagtg ctgcttggaa ctggatcagg 120
cagtccccat cgagaggcct tgagtggctg ggaaggacat actacaggtc caagtggtct 180
actgattatg cagcatctgt gaaaagtcga ataaccatca acccagacac atccaagaac 240
cagctctccc tgcagttaaa ctctgtgact cccgaggaca cggctgtgta ttactgtgca 300
agaacgtggg ccgactatgt ggacgtctgg ggccaaggaa ccctggtcac cgtctcgagc 360

<210> SEQ ID NO 217
<211> LENGTH: 360
<212> TYPE: DNA
<213> ORGANISM: Homo sapiens

<400> SEQUENCE: 217
gaggtacagc tgcagcagtc aggtccagga ctggtgaagc cctcgcagac cctctcactc 60
acctgtgcca tctccgggga cagtgtctcc agcaaaagtg ctgcttggaa ctggatcagg 120
cagtccccat cgagaggcct tgagtggctg ggaaggacat actacaggtc caagtggtct 180
actgattatg cagcatctgt gaaaagtcga ataaccatca acccagacac atccaagaac 240
cagctctccc tgcagttaaa ctctgtgact cccgaggaca cggctgtgta ttactgtgca 300
agaacgtggg tgggttatgc cgacgtctgg ggccaaggaa ccctggtcac cgtctcgagc 360

<210> SEQ ID NO 218
<211> LENGTH: 360
<212> TYPE: DNA
<213> ORGANISM: Homo sapiens

<400> SEQUENCE: 218
gaggtacagc tgcagcagtc aggtccagga ctggtgaagc cctcgcagac cctctcactc 60
acctgtgcca tctccgggga cagtgtctcc agcaaaagtg ttgcttggaa ctggatcagg 120
cagtccccat cgagaggcct tgagtggctg ggaaggacat actacaggtc caagtggtct 180
actgattatg cagcatctgt gaaaagtcga ataaccatca acccagacac atccaagaac 240
cagctctccc tgcagttaaa ctctgtgact cccgaggaca cggctgtgta ttactgtgca 300
agaacgtggc tgggtaacgt ggacgtctgg ggccaaggaa ccctggtcac cgtctcgagc 360

<210> SEQ ID NO 219
<211> LENGTH: 360
<212> TYPE: DNA
<213> ORGANISM: Homo sapiens

<400> SEQUENCE: 219
gaggtacagc tgcagcagtc aggtccagga ctggtgaagc cctcgcagac cctctcactc 60
acctgtgcca tctccgggga cagtgtctcc agcaaaagtg ctgcttggaa ctggatcagg 120
cagtccccat cgagaggcct tgagtggctg ggaaggacat actacaggtc caagtggtct 180
actgattatg cagcatctgt gaaaagtcga ataaccatca acccagacac atccaagaac 240
cagctctccc tgcagttaaa ctctgtgact cccgaggaca cggctgtgta ttactgtgca 300
agaacgtggg tgggttatgc cgacgtctgg ggccaaggaa ccctggtcac cgtctcgagc 360

<210> SEQ ID NO 220
<211> LENGTH: 360
<212> TYPE: DNA
<213> ORGANISM: Homo sapiens

<400> SEQUENCE: 220
gaggtacagc tgcagcagtc aggtccagga ctggtgaagc cctcgcagac cctctcactc 60
acctgtgcca tctccgggga cagtgtctcc agcaaaagtg ctgcttggaa ctggatcagg 120
cagtccccat cgagaggcct tgagtggctg ggaaggacat actacaggtc caagtggtct 180
actgattatg cagcatctgt gaaaagtcga ataaccatca acccagacac atccaagaac 240
cagctctccc tgcagttaaa ctctgtgact cccgaggaca cggctgtgta ttactgtgca 300
agaacgtggg tgggttatgc cgacgtctgg ggccaaggaa ccctggtcac cgtctcgagc 360

<210> SEQ ID NO 221
<211> LENGTH: 360
<212> TYPE: DNA
<213> ORGANISM: Homo sapiens

<400> SEQUENCE: 221
gaggtacagc tgcagcagtc aggtccagga ctggtgaagc cctcgcagac cctctcactc 60
acctgtgcca tctccgggga cagtgtctcc agcaaaagtg ctgcttggaa ctggatcagg 120
cagtccccat cgagaggcct tgagtggctg ggaaggacat actacaggtc caagtggtct 180
actgattatg cagcatctgt gaaaagtcga ataaccatca acccagacac atccaagaac 240
cagctctccc tgcagttaaa ctctgtgact cccgaggaca cggctgtgta ttactgtgca 300
agaacgtggg ccggttatcc cgacgtctgg ggccaaggaa ccctggtcac cgtctcgagc 360

<210> SEQ ID NO 222
<211> LENGTH: 360
<212> TYPE: DNA
<213> ORGANISM: Homo sapiens

<400> SEQUENCE: 222
gaggtacagc tgcagcagtc aggtccagga ctggtgaagc cctcgcagac cctctcactc 60
acctgtgcca tctccgggga cagtgtctcc agcaaaagtg ctgcttggaa ctggatcagg 120
cagtccccat cgagaggcct tgagtggctg ggaaggacat actacaggtc caagtggtct 180
actgattatg cagcatctgt gaaaagtcga ataaccatca acccagacac atccaagaac 240
cagctctccc tgcagttaaa ctctgtgact cccgaggaca cggctgtgta ttactgtgca 300
agaacgtggg ccgactatgt ggacgtctgg ggccaaggaa ccctggtcac cgtctcgagc 360

<210> SEQ ID NO 223
<211> LENGTH: 330
<212> TYPE: DNA
<213> ORGANISM: Homo sapiens

<400> SEQUENCE: 223
gctagcgaca tccagatgac ccagtcccct cccgccctgt ctgcatctgt gggagacaga 60
gtcaccatca cttgccgggc cagtcaagat attaatgact ggttggcctg gtatcagcat 120
aaacctggga aagcccctaa gctcctgatc tatgatgcct ccagtttgga aagtggggtc 180
ccatcaaggt tcagcggcag tggatctggg acagaattca ctctcaccat cagcagcctg 240
cagcctgatg attttgcaac ttactactgt caacagagtt acagtacccc tcaggtcact 300
tttggccagg ggacacgact ggagatcaaa 330

<210> SEQ ID NO 224
<211> LENGTH: 324
<212> TYPE: DNA
<213> ORGANISM: Homo sapiens

<400> SEQUENCE: 224
gacatccaga tgacccagtc ccctcccgcc ctgtctgcat ctgtgggaga cagagtcacc 60
atcacttgcc gggccagtca agatattaat gactggttgg cctggtatca gcataaacct 120
gggaaagccc ctaagctcct gatctatgat gcctccagtt tggaaagtgg ggtcccatta 180
aggttcagcg gcagtggatc tgggacagaa ttcactctca ccatcagcag cctgcagcct 240
gatgattttg caacttacta ctgtcaacag aagtacagta cccctcagat cacttttggc 300
caggggacac gactggagat caaa 324

<210> SEQ ID NO 225
<211> LENGTH: 324
<212> TYPE: DNA
<213> ORGANISM: Homo sapiens

<400> SEQUENCE: 225
gacatccaga tgacccagtc ccctcccgcc ctgtctgcat ctgtgggaga cagagtcacc 60
atcacttgcc gggccagtca agatattaat gactggttgg cctggtatca gcataaacct 120
gggaaagccc ctaagctcct gatctatgat gcctccagtt tggaaagtgg ggtcccatta 180
aggttcagcg gcagtggatc tgggacagaa ttcactctca ccatcagcag cctgcagcct 240
gatgattttg caacttacta ctgtcaacag cgctacagta cccctcagat cacttttggc 300
caggggacac gactggagat caaa 324

<210> SEQ ID NO 226
<211> LENGTH: 324
<212> TYPE: DNA
<213> ORGANISM: Homo sapiens

<400> SEQUENCE: 226
gacatccaga tgacccagtc ccctcccgcc ctgtctgcat ctgtgggaga cagagtcacc 60
atcacttgcc gggccagtca agatattaat gactggttgg cctggtatca gcataaacct 120
gggaaagccc ctaagctcct gatctatgat gcctccagtt tggaaagtgg ggtcccatta 180
aggttcagcg gcagtggatc tgggacagaa ttcactctca ccatcagcag cctgcagcct 240
gatgattttg caacttacta ctgtcaacag aagtacagta cccctcaggt cacttttggc 300
gccgggacac gactggagat caaa 324

<210> SEQ ID NO 227
<211> LENGTH: 324
<212> TYPE: DNA
<213> ORGANISM: Homo sapiens

<400> SEQUENCE: 227
gacatccaga tgacccagtc ccctcccgcc ctgtctgcat ctgtgggaga cagagtcacc 60
atcacttgcc gggccagtca agatattaat gactggttgg cctggtatca gcataaacct 120
gggaaagccc ctaagctcct gatctatgat gcctccagtt tggaaagtgg ggtcccatta 180
aggttcagcg gcagtggatc tgggacagaa ttcactctca ccatcagcag cctgcagcct 240
gatgattttg caacttacta ctgtcaacag aagtacagtc agcctcaggt cacttttggc 300
caggggacac gactggagat caaa 324

<210> SEQ ID NO 228
<211> LENGTH: 324
<212> TYPE: DNA
<213> ORGANISM: Homo sapiens

<400> SEQUENCE: 228
gacatccaga tgacccagtc ccctcccgcc ctgtctgcat ctgtgggaga cagagtcacc 60
atcacttgcc gggccagtca agatattaat gactggttgg cctggtatca gcataaacct 120
gggaaagccc ctaagctcct gatctatgat gcctccagtt tggaaagtgg ggtcccatta 180
aggttcagcg gcagtggatc tgggacagaa ttcactctca ccatcagcag cctgcagcct 240
gatgattttg caacttacta ctgtcaacag cgctacagta cccctcgcgt cacttttggc 300
caggggacac gactggagat caaa 324

<210> SEQ ID NO 229
<211> LENGTH: 324
<212> TYPE: DNA
<213> ORGANISM: Homo sapiens

<400> SEQUENCE: 229
gacatccaga tgacccagtc ccctcccgcc ctgtctgcat ctgtgggaga cagagtcacc 60
atcacttgcc gggccagtca agatattaat gactggttgg cctggtatca gcataaacct 120
gggaaagccc ctaagctcct gatctatgat gcctccagtt tggaaagtgg ggtcccatta 180
aggttcagcg gcagtggatc tgggacagaa ttcactctca ccatcagcag cctgcagcct 240
gatgattttg caacttacta ctgtcaacag aagtacagta cccctaaggt cacttttggc 300
caggggacac gactggagat caaa 324

<210> SEQ ID NO 230
<211> LENGTH: 324
<212> TYPE: DNA
<213> ORGANISM: Homo sapiens

<400> SEQUENCE: 230
gacatccaga tgacccagtc ccctcccgcc ctgtctgcat ctgtgggaga cagagtcacc 60
atcacttgcc gggccagtca agatattaat gactggttgg cctggtatca gcataaacct 120
gggaaagccc ctaagctcct gatctatgat gcctccagtt tggaaagtgg ggtcccatta 180
aggttcagcg gcagtggatc tgggacagaa ttcactctca ccatcagcag cctgcagcct 240
gatgattttg caacttacta ctgtcaacag aagtacagta ccccttgggt cacttttggc 300
caggggacac gactggagat caaa 324

<210> SEQ ID NO 231
<211> LENGTH: 324
<212> TYPE: DNA
<213> ORGANISM: Homo sapiens

<400> SEQUENCE: 231
gacatccaga tgacccagtc ccctcccgcc ctgtctgcat ctgtgggaga cagagtcacc 60
atcacttgcc gggccagtca agatattaat gactggttgg cctggtatca gcataaacct 120
gggaaagccc ctaagctcct gatctatgat gcctccagtt tggaaagtgg ggtcccatta 180
aggttcagcg gcagtggatc tgggacagaa ttcactctca ccatcagcag cctgcagcct 240
gatgattttg caacttacta ctgtcaacag cgctacagta cccctcccgt cacttttggc 300
caggggacac gactggagat caaa 324

<210> SEQ ID NO 232
<211> LENGTH: 324
<212> TYPE: DNA
<213> ORGANISM: Homo sapiens

<400> SEQUENCE: 232
gacatccaga tgacccagtc ccctcccgcc ctgtctgcat ctgtgggaga cagagtcacc 60
atcacttgcc gggccagtca agatattaat gactggttgg cctggtatca gcataaacct 120
gggaaagccc ctaagctcct gatctatgat gcctccagtt tggaaagtgg ggtcccatta 180
aggttcagcg gcagtggatc tgggacagaa ttcactctca ccatcagcag cctgcagcct 240
gatgattttg caacttacta ctgtcaacag ggctacagta cccctcagct gacttttggc 300
caggggacac gactggagat caaa 324

<210> SEQ ID NO 233
<211> LENGTH: 324
<212> TYPE: DNA
<213> ORGANISM: Homo sapiens

<400> SEQUENCE: 233
gacatccaga tgacccagtc ccctcccgcc ctgtctgcat ctgtgggaga cagagtcacc 60
atcacttgcc gggccagtca agatattaat gactggttgg cctggtatca gcataaacct 120
gggaaagccc ctaagctcct gatctatgat gcctccagtt tggaaagtgg ggtcccatta 180
aggttcagcg gcagtggatc tgggacagaa ttcactctca ccatcagcag cctgcagcct 240
gatgattttg caacttacta ctgtcaacag aagtacagta ccccttgggt cacttttggc 300
caggggacac gactggagat caaa 324

<210> SEQ ID NO 234
<211> LENGTH: 324
<212> TYPE: DNA
<213> ORGANISM: Homo sapiens

<400> SEQUENCE: 234
gacatccaga tgacccagtc ccctcccgcc ctgtctgcat ctgtgggaga cagagtcacc 60
atcacttgcc gggccagtca agatattaat gactggttgg cctggtatca gcataaacct 120
gggaaagccc ctaagctcct gatctatgat gcctccagtt tggaaagtgg ggtcccatta 180
aggttcagcg gcagtggatc tgggacagaa ttcactctca ccatcagcag cctgcagcct 240
gatgattttg caacttacta ctgtcaacag cgctacagta cccaccaggt cacttttggc 300
caggggacac gactggtgat caaa 324

<210> SEQ ID NO 235
<211> LENGTH: 324
<212> TYPE: DNA
<213> ORGANISM: Homo sapiens

<400> SEQUENCE: 235
gacatccaga tgacccagtc ccctcccgcc ctgtctgcat ctgtgggaga cagagtcacc 60
atcacttgcc gggccagtca agatattaat gactggttgg cctggtatca gcataaacct 120
gggaaagccc ctaagctcct gatctatgat gcctccagtt tggaaagtgg ggtcccatta 180
aggttcagcg gcagtggatc tgggacagaa ttcactctca ccatcagcag cctgcagcct 240
gatgattttg caacttacta ctgtcaacag aagtacagta cccctcagct gacttttggc 300
caggggacac gactggagat caaa 324

<210> SEQ ID NO 236
<211> LENGTH: 324
<212> TYPE: DNA
<213> ORGANISM: Homo sapiens

<400> SEQUENCE: 236
gacatccaga tgacccagtc ccctcccgcc ctgtctgcat ctgtgggaga cagagtcacc 60
atcacttgcc gggccagtca agatattaat gactggttgg cctggtatca gcataaacct 120
gggaaagccc ctaagctcct gatctatgat gcctccagtt tggaaagtgg ggtcccatta 180
aggttcagcg gcagtggatc tgggacagaa ttcactctca ccatcagcag cctgcagcct 240
gatgattttg caacttacta ctgtcaacag aagtacagtg cccctcaggt cacttttggc 300
caggggacac gactggagat caaa 324

<210> SEQ ID NO 237
<211> LENGTH: 324
<212> TYPE: DNA

<213> ORGANISM: Homo sapiens

<400> SEQUENCE: 237
gacatccaga tgacccagtc ccctcccgcc ctgtctgcat ctgtgggaga cagagtcacc 60
atcacttgcc gggccagtca agatattaat gactggttgg cctggtatca gcataaacct 120
gggaaagccc ctaagctcct gatctatgat gcctccagtt tggaaagtgg ggtcccatta 180
aggttcagcg gcagtggatc tgggacagaa ttcactctca ccatcagcag cctgcagcct 240
gatgattttg caacttacta ctgtcaacag aagtacagtg cccctcaggt cacttttggc 300
caggggacac gactggagat caaa 324

<210> SEQ ID NO 238
<211> LENGTH: 324
<212> TYPE: DNA
<213> ORGANISM: Homo sapiens

<400> SEQUENCE: 238
gacatccaga tgacccagtc ccctcccgcc ctgtctgcat ctgtgggaga cagagtcacc 60
atcacttgcc gggccagtca agatattaat gactggttgg cctggtatca gcataaacct 120
gggaaagccc ctaagctcct gatctatgat gcctccagtt tggaaagtgg ggtcccatta 180
aggttcagcg gcagtggatc tgggacagaa ttcactctca ccatcagcag cctgcagcct 240
gatgattttg caacttacta ctgtcaacag aagtacagtg cccctcaggt cacttttggc 300
caggggacac gactggagat caaa 324

<210> SEQ ID NO 239
<211> LENGTH: 324
<212> TYPE: DNA
<213> ORGANISM: Homo sapiens

<400> SEQUENCE: 239
gacatccaga tgacccagtc ccctcccgcc ctgtctgcat ctgtgggaga cagagtcacc 60
atcacttgcc gggccagtca agatattaat gactggttgg cctggtatca gcataaacct 120
gggaaagccc ctaagctcct gatctatgat gcctccagtt tggaaagtgg ggtcccatta 180
aggttcagcg gcagtggatc tgggacagaa ttcactctca ccatcagcag cctgcagcct 240
gatgattttg caacttacta ctgtcaacag cgctacagta cccctcagat cacttttggc 300
caggggacac gactggagat caaa 324

<210> SEQ ID NO 240
<211> LENGTH: 324
<212> TYPE: DNA
<213> ORGANISM: Homo sapiens

<400> SEQUENCE: 240
gacatccaga tgacccagtc ccctcccgcc ctgtctgcat ctgtgggaga cagagtcacc 60
atcacttgcc gggccagtca agatattaat gactggttgg cctggtatca gcataaacct 120
gggaaagccc ctaagctcct gatctatgat gcctccagtt tggaaagtgg ggtcccatta 180
aggttcagcg gcagtggatc tgggacagaa ttcactctca ccatcagcag cctgcagcct 240
gatgattttg caacttacta ctgtcaacag aagtacagtg agcctcaggt cacttttggc 300
caggggacac gactggagat caaa 324

<210> SEQ ID NO 241
<211> LENGTH: 324

<212> TYPE: DNA
<213> ORGANISM: Homo sapiens

<400> SEQUENCE: 241
gacatccaga tgacccagtc ccctcccgcc ctgtctgcat ctgtgggaga cagagtcacc 60
atcacttgcc gggccagtca agatattaat gactggttgg cctggtatca gcataaacct 120
gggaaagccc ctaagctcct gatctatgat gcctccagtt tggaaagtgg ggtcccatta 180
aggttcagcg gcagtggatc tgggacagaa ttcactctca ccatcagcag cctgcagcct 240
gatgattttg caacttacta ctgtcaacag aagtacagta cccctgaggt cacttttggc 300
caggggacac gactggagat caaa 324

<210> SEQ ID NO 242
<211> LENGTH: 324
<212> TYPE: DNA
<213> ORGANISM: Homo sapiens

<400> SEQUENCE: 242
gacatccaga tgacccagtc ccctcccgcc ctgtctgcat ctgtgggaga cagagtcacc 60
atcacttgcc gggccagtca agatattaat gactggttgg cctggtatca gcataaacct 120
gggaaagccc ctaagctcct gatctatgat gcctccagtt tggaaagtgg ggtcccatta 180
aggttcagcg gcagtggatc tgggacagaa ttcactctca ccatcagcag cctgcagcct 240
gatgattttg caacttacta ctgtcaacag aagtacagtg accctcaggt cacttttggc 300
caggggacac gactggagat caaa 324

<210> SEQ ID NO 243
<211> LENGTH: 324
<212> TYPE: DNA
<213> ORGANISM: Homo sapiens

<400> SEQUENCE: 243
gacatccaga tgacccagtc ccctcccgcc ctgtctgcat ctgtgggaga cagagtcacc 60
atcacttgcc gggccagtca agatattaat gactggttgg cctggtatca gcataaacct 120
gggaaagccc ctaagctcct gatctatgat gcctccagtt tggaaagtgg ggtcccatta 180
aggttcagcg gcagtggatc tgggacagaa ttcactctca ccatcagcag cctgcagcct 240
gatgattttg caacttacta ctgtcaacag aagtacagtg agcctcaggt cacttttggc 300
caggggacac gactggagat caaa 324

<210> SEQ ID NO 244
<211> LENGTH: 324
<212> TYPE: DNA
<213> ORGANISM: Homo sapiens

<400> SEQUENCE: 244
gacatccaga tgacccagtc ccctcccgcc ctgtctgcat ctgtgggaga cagagtcacc 60
atcacttgcc gggccagtca agatattaat gactggttgg cctggtatca gcataaacct 120
gggaaagccc ctaagctcct gatctatgat gcctccagtt tggaaagtgg ggtcccatta 180
aggttcagcg gcagtggatc tgggacagaa ttcactctca ccatcagcag cctgcagcct 240
gatgattttg caacttacta ctgtcaacag aagtacagta cccctcaggt cacttttggc 300
agcgggacac gactggagat caaa 324

<210> SEQ ID NO 245

<211> LENGTH: 324
<212> TYPE: DNA
<213> ORGANISM: Homo sapiens

<400> SEQUENCE: 245
gacatccaga tgacccagtc ccctcccgcc ctgtctgcat ctgtgggaga cagagtcacc 60
atcacttgcc gggccagtca agatattaat gactggttgg cctggtatca gcataaacct 120
gggaaagccc ctaagctcct gatctatgat gcctccagtt tggaaagtgg ggtcccatta 180
aggttcagcg gcagtggatc tgggacagaa ttcactctca ccatcagcag cctgcagcct 240
gatgattttg caacttacta ctgtcaacag cgctacagta cccctatcgt cacttttggc 300
caggggacac gactggagat caaa 324

<210> SEQ ID NO 246
<211> LENGTH: 324
<212> TYPE: DNA
<213> ORGANISM: Homo sapiens

<400> SEQUENCE: 246
gacatccaga tgacccagtc ccctcccgcc ctgtctgcat ctgtgggaga cagagtcacc 60
atcacttgcc gggccagtca agatattaat gactggttgg cctggtatca gcataaacct 120
gggaaagccc ctaagctcct gatctatgat gcctccagtt tggaaagtgg ggtcccatta 180
aggttcagcg gcagtggatc tgggacagaa ttcactctca ccatcagcag cctgcagcct 240
gatgattttg caacttacta ctgtcaacag aagtacaaga cccctcaggt cacttttggc 300
caggggacac gactggagat caaa 324

<210> SEQ ID NO 247
<211> LENGTH: 324
<212> TYPE: DNA
<213> ORGANISM: Homo sapiens

<400> SEQUENCE: 247
gacatccaga tgacccagtc ccctcccgcc ctgtctgcat ctgtgggaga cagagtcacc 60
atcacttgcc gggccagtca agatattaat gactggttgg cctggtatca gcataaacct 120
gggaaagccc ctaagctcct gatctatgat gcctccagtt tggaaagtgg ggtcccatca 180
aggttcagcg gcagtggatc tgggacagaa ttcactctca ccatcagcag cctgcagcct 240
gatgattttg caacttacta ctgtcaacag cgctacagta ccgaccaggt cacttttggc 300
caggggacac gactggagat caaa 324

<210> SEQ ID NO 248
<211> LENGTH: 354
<212> TYPE: DNA
<213> ORGANISM: Homo sapiens

<400> SEQUENCE: 248
caggtgcagc tggtggagtc tgggggaggc ttggtcaagc ctggagggtc cctgagactc 60
tcctgtgcag cctctggatt caccttcagt gactactaca tgagctggat ccgccaggct 120
ccagggaagg ggctggagtg ggtttcatac attagtagta gtggtagtac catatactac 180
gcagactctg tgaagggccg attcaccatc tccagggaca acgccaagaa ctcactgtat 240
ctgcaaatga acagcctgag agccgaggac acggctgtgt attactgtgc aagggtggac 300
tacgctgatg catttgatat ctggggccag ggcaccctgg tcaccgtctc gagc 354

<210> SEQ ID NO 249
<211> LENGTH: 354
<212> TYPE: DNA
<213> ORGANISM: Homo sapiens

<400> SEQUENCE: 249
gaggtgcagc tggtggagtc tgggggaggc ttggtcaagc ctggagggtc cctgagactc 60
tcctgtgcag cctctggatt caccttcagt gactactaca tgagctggat ccgccaggct 120
ccagggaagg ggctggagtg ggtttcatac attagtagta gtggtagtac catatactac 180
gcagactctg tgaagggccg attcaccatc tccagggaca acgccaagaa ctcactgtat 240
ctgcaaatga acagcctgag agccgaggac acggctgtgt attactgtgc aagggacgac 300
tacaacgatg catttgatat ctggggccag ggcaccctgg tcaccgtctc gagc 354

<210> SEQ ID NO 250
<211> LENGTH: 354
<212> TYPE: DNA
<213> ORGANISM: Homo sapiens

<400> SEQUENCE: 250
gaggtgcagc tggtggagtc tgggggaggc ttggtcaagc ctggagggtc cctgagactc 60
tcctgtgcag cctctggatt caccttcagt gactactaca tgagctggat ccgccaggct 120
ccagggaagg ggctggagtg ggtttcatac attagtagta gtggtagtac catatactac 180
gcagactctg tgaagggccg attcaccatc tccagggaca acgccaagaa ctcactgtat 240
ctgcaaatga acagcctgag agccgaggac acggctgtgt attactgtgc aagggacgac 300
tacaacgatg catttgatat ctggggccag ggcaccctgg tcaccgtctc gagc 354

<210> SEQ ID NO 251
<211> LENGTH: 354
<212> TYPE: DNA
<213> ORGANISM: Homo sapiens

<400> SEQUENCE: 251
gaggtgcagc tggtggagtc tgggggaggc ttggtcaagc ctggagggtc cctgagactc 60
tcctgtgcag cctctggatt caccttcagt gactactaca tgagctggat ccgccaggct 120
ccagggaagg ggctggagtg ggtttcatac attagtagta gtggtagtac catatactac 180
gcagactctg tgaagggccg attcaccatc tccagggaca acgccaagaa ctcactgtat 240
ctgcaaatga acagcctgag agccgaggac acggctgtgt attactgtgc aaggatcgac 300
tacgaggatg catttgatat ctggggccag ggcaccctgg tcaccgtctc gagc 354

<210> SEQ ID NO 252
<211> LENGTH: 354
<212> TYPE: DNA
<213> ORGANISM: Homo sapiens

<400> SEQUENCE: 252
gaggtgcagc tggtggagtc tgggggaggc ttggtcaagc ctggagggtc cctgagactc 60
tcctgtgcag cctctggatt caccttcagt gactactaca tgagctggat ccgccaggct 120
ccagggaagg ggctggagtg ggtttcatac attagtagta gtggtagtac catatactac 180
gcagactctg tgaagggccg attcaccatc tccagggaca acgccaagaa ctcactgtat 240
ctgcaaatga acagcctgag agccgaggac acggctgtgt attactgtgc aagggtgagc 300
tacgacgatg catttgatat ctggggccag ggcaccctgg tcaccgtctc gagc 354

<210> SEQ ID NO 253
<211> LENGTH: 354
<212> TYPE: DNA
<213> ORGANISM: Homo sapiens

<400> SEQUENCE: 253
gaggtgcagc tggtggagtc tgggggaggc ttggtcaagc ctggagggtc cctgagactc 60
tcctgtgcag cctctggatt caccttcagt gactactaca tgagctggat ccgccaggct 120
ccagggaagg ggctggagtg ggtttcatac attagtagta gtggtagtac catatactac 180
gcagactctg tgaagggccg attcaccatc tccagggaca acgccaagaa ctcactgtat 240
ctgcaaatga acagcctgag agccgaggac acggctgtgt attactgtgc aaggatcgac 300
tacgaggatg catttgatat ctggggccag ggcaccctgg tcaccgtctc gagc 354

<210> SEQ ID NO 254
<211> LENGTH: 354
<212> TYPE: DNA
<213> ORGANISM: Homo sapiens

<400> SEQUENCE: 254
gaggtgcagc tggtggagtc tgggggaggc ttggtcaagc ctggagggtc cctgagactc 60
tcctgtgcag cctctggatt caccttcagt gactactaca tgagctggat ccgccaggct 120
ccagggaagg ggctggagtg ggtttcatac attagtagta gtggtagtac catatactac 180
gcagactctg tgaagggccg attcaccatc tccagggaca acgccaagaa ttcactgtat 240
ctgcaaatga acagcctgag agccgaggac acggctgtgt attactgtgc aagggtggac 300
taccaggagg catttgatat ctggggccag ggcaccctgg tcaccgtctc gagc 354

<210> SEQ ID NO 255
<211> LENGTH: 354
<212> TYPE: DNA
<213> ORGANISM: Homo sapiens

<400> SEQUENCE: 255
gaggtgcagc tggtggagtc tgggggaggc ttggtcaagc ctggagggtc cctgagactc 60
tcctgtgcag cctctggatt caccttcagt gactactaca tgagctggat ccgccaggct 120
ccagggaagg ggctggagtg ggtttcatac attagtagta gtggtagtac catatactac 180
gcagactctg tgaagggccg attcaccatc tccagggaca acgccaagaa ctcactgtat 240
ctgcaaatga acagcctgag agccgaggac acggctgtgt attactgtgc aagggacgac 300
tacaacgatg catttgatat ctggggccag ggcaccctgg tcaccgtctc gagc 354

<210> SEQ ID NO 256
<211> LENGTH: 354
<212> TYPE: DNA
<213> ORGANISM: Homo sapiens

<400> SEQUENCE: 256
gaggtgcagc tggtggagtc tgggggaggc ttggtcaagc ctggagggtc cctgagactc 60
tcctgtgcag cctctggatt caccttcagt gactactaca tgagctggat ccgccaggct 120
ccagggaagg ggctggagtg ggtttcatac attagtagta gtggtagtac catatactac 180
gcagactctg tgaagggccg attcaccatc tccagggaca acgccaagaa ctcactgtat 240
ctgcaaatga acagcctgag agccgaggac acggctgtgt attactgtgc aagggtggac 300
tacaacgagg catttgatat ctggggccag ggcaccctgg tcaccgtctc gagc 354

<210> SEQ ID NO 257
<211> LENGTH: 354
<212> TYPE: DNA
<213> ORGANISM: Homo sapiens

<400> SEQUENCE: 257
gaggtgcagc tggtggagtc tgggggaggc ttggtcaagc ctggagggtc cctgagactc 60
tcctgtgcag cctctggatt caccttcagt gactactaca tgagctggat ccgccaggct 120
ccagggaagg ggctggagtg ggtttcatac attagtagta gtggtagtac catatactac 180
gcagactctg tgaagggccg attcaccatc tccagggaca acgccaagaa ctcactgtat 240
ctgcaaatga acagcctgag agccgaggac acggctgtgt attactgtgc aagggacgac 300
tacgaggatg catttgatat ctggggccag ggcaccctgg tcaccgtctc gagc 354

<210> SEQ ID NO 258
<211> LENGTH: 354
<212> TYPE: DNA
<213> ORGANISM: Homo sapiens

<400> SEQUENCE: 258
gaggtgcagc tggtggagtc tgggggaggc ttggtcaagc ctggagggtc cctgagactc 60
tcctgtgcag cctctggatt caccttcagt gactactaca tgagctggat ccgccaggct 120
ccagggaagg ggctggagtg ggtttcatac attagtagta gtggtagtac catatactac 180
gcagactctg tgaagggccg attcaccatc tccagggaca acgccaagaa ctcactgtat 240
ctgcaaatga acagcctgag agccgaggac acggctgtgt attactgtgc aagggtgagc 300
tacgctgagg catttgatat ctggggccag ggcaccctgg tcaccgtctc gagc 354

<210> SEQ ID NO 259
<211> LENGTH: 354
<212> TYPE: DNA
<213> ORGANISM: Homo sapiens

<400> SEQUENCE: 259
gaggtgcagc tggtggagtc tgggggaggc ttggtcaagc ctggagggtc cctgagactc 60
tcctgtgcag cctctggatt caccttcagt gactactaca tgagctggat ccgccaggct 120
ccagggaagg ggctggagtg ggtttcatac attagtagta gtggtagtac catatactac 180
gcagactctg tgaagggccg attcaccatc tccagggaca acgccaagaa ctcactgtat 240
ctgcaaatga acagcctgag agccgaggac acggctgtgt attactgtgc aagggacgac 300
tacgacgatg catttgatat ctggggccag ggcaccctgg tcaccgtctc gagc 354

<210> SEQ ID NO 260
<211> LENGTH: 327
<212> TYPE: DNA
<213> ORGANISM: Homo sapiens

<400> SEQUENCE: 260
gctagcgaca tccagatgac ccagtctcca tcctccctgt ctgcatctgt aggagacaga 60
gtcaccatcg cttgccgggc aggtcagagc attggcacct atttaaattg gtatcagcag 120
aaaccaggga aagcccctaa actcctgatc tatgttgcat ccagtttgca aagtggggtc 180
ccgtcacggt tcagtggcag tggatctggg acagaattca ctctcaccat cagcagtctg 240
caacctgaag attttgcaac ttactactgt caacagagtt acagtaccct cctcactttc 300
ggcagaggga ccaaggtgga aatcaaa 327

<210> SEQ ID NO 261
<211> LENGTH: 321
<212> TYPE: DNA
<213> ORGANISM: Homo sapiens

<400> SEQUENCE: 261
gacatccaga tgacccagtc tccatcctcc ctgtctgcat ctgtaggaga cagagtcacc 60
atcgcttgcc gggcaggtca gagcattggc acctatttaa attggtatca gcagaaacca 120
gggaaagccc ctaaactcct gatctatgtt gcatccagtt tgcaaagtgg ggtcccgtca 180
cggttcagtg gcagtggatc tgggacagaa ttcactctca ccatcagcag tctgcaacct 240
gaagattttg caacttacta ctgtcaacag accgccagta ccctcctcac tttcggcaga 300
gggaccaagg tggaaatcaa a 321

<210> SEQ ID NO 262
<211> LENGTH: 321
<212> TYPE: DNA
<213> ORGANISM: Homo sapiens

<400> SEQUENCE: 262
gacatccaga tgacccagtc tccatcctcc ctgtctgcat ctgtaggaga cagagtcacc 60
atcgcttgcc gggcaggtca gagcattggc acctatttaa attggtatca gcagaaacca 120
gggaaagccc ctaaactcct gatctatgtt gcatccagtt tgcaaagtgg ggtcccgtca 180
cggttcagtg gcagtggatc tgggacagaa ttcactctca ccatcagcag tctgcaacct 240
gaagattttg caacttacta ctgtcaacag agtgccgaca ccctcctcac tttcggcaga 300
gggaccaagg tggaaatcaa a 321

<210> SEQ ID NO 263
<211> LENGTH: 321
<212> TYPE: DNA
<213> ORGANISM: Homo sapiens

<400> SEQUENCE: 263
gacatccaga tgacccagtc tccatcctcc ctgtctgcat ctgtaggaga cagagtcacc 60
atcgcttgcc gggcaggtca gagcattggc acctatttaa attggtatca gcagaaacca 120
gggaaagccc ctaaactcct gatctatgtt gcatccagtt tgcaaagtgg ggtcccgtca 180
cggttcagtg gcagtggatc tgggacagaa ttcactctca ccatcagcag tctgcaacct 240
gaagattttg caacttacta ctgtcaacag agtggcagtg agctcctcac tttcggcaga 300
gggaccaagg tggaaatcaa a 321

<210> SEQ ID NO 264
<211> LENGTH: 321
<212> TYPE: DNA
<213> ORGANISM: Homo sapiens

<400> SEQUENCE: 264
gacatccaga tgacccagtc tccatcctcc ctgtctgcat ctgtaggaga cagagtcacc 60
atcgcttgcc gggtaggtca gagcattggc acctatttaa attggtatca gcagaaacca 120
gggaaagccc ctaaactcct gatctatgtt gcatccagtt tgcaaagtgg ggtcccgtca 180
cggttcagtg gcagtggatc tgggacagaa ttcactctca ccatcagcag tctgcaacct 240
gaagattttg caacttacta ctgtcaacag agtgccagtg agctcctcac tttcggcaga 300
gggaccaagg tggaaatcaa a 321

<210> SEQ ID NO 265
<211> LENGTH: 321
<212> TYPE: DNA
<213> ORGANISM: Homo sapiens

<400> SEQUENCE: 265
gacatccaga tgacccagtc tccatcctcc ctgtctgcat ctgtaggaga cagagtcacc 60
atcgcttgcc gggcaggtca gagcattggc acctatttaa attggtatca gcagaaacca 120
gggaaagccc ctaaactcct gatctatgtt gcatccagtt tgcaaagtgg ggtcccgtca 180
cggttcagtg gcagtggatc tgggacagaa ttcactctca ccatcagcag tctgcaacct 240
gaagattttg caacttacta ctgtcaacag agtgccagtg agctcctcac tttcggcaga 300
gggaccaagg tggaaatcaa a 321

<210> SEQ ID NO 266
<211> LENGTH: 321
<212> TYPE: DNA
<213> ORGANISM: Homo sapiens

<400> SEQUENCE: 266
gacatccaga tgacccagtc tccatcctcc ctgtctgcat ctgtaggaga cagagtcacc 60
atcgcttgcc gggcaggtca gagcattggc acctatttaa attggtatca gcagaaacca 120
gggaaagccc ctaaactcct gatctatgtt gcatccagtt tgcaaagtgg ggtcccgtca 180
cggttcagtg gcagtggatc tgggacagaa ttcactctca ccatcagcag tctgcaacct 240
gaagattttg caacttacta ctgtcaacag agttacagtg gcctcgacac tttcggcaga 300
gggaccaagg tggaaatcaa a 321

<210> SEQ ID NO 267
<211> LENGTH: 321
<212> TYPE: DNA
<213> ORGANISM: Homo sapiens

<400> SEQUENCE: 267
gacatccaga tgacccagtc tccatcctcc ctgtctgcat ctgtaggaga cagagtcacc 60
atcgcttgcc gggcaggtca gagcattggc acctatttaa attggtatca gcagaaacca 120
gggaaagccc ctaaactcct gatctatgtt gcatccagtt tgcaaagtgg ggtcccgtca 180
cggttcagtg gcagtggatc tgggacagaa ttcactctca ccatcagcag tctgcaacct 240
gaagattttg caacttacta ctgtcaacag agtgccagtg agctcctcac tttcggcaga 300
gggaccaagg tggaaatcaa a 321

<210> SEQ ID NO 268
<211> LENGTH: 321
<212> TYPE: DNA
<213> ORGANISM: Homo sapiens

<400> SEQUENCE: 268
gacatccaga tgacccagtc tccatcctcc ctgtctgcat ctgtaggaga cagagtcacc 60
atcgcttgcc gggcaggtca gagcattggc acctatttaa attggtatca gcagaaacca 120
gggaaagccc ctaaactcct gatctatgtt gcatccagtt tgcaaagtgg ggtcccgtca 180
cggttcagtg gcagtggatc tgggacagaa ttcactctca ccatcagcag tctgcaacct 240
gaagattttg caacttacta ctgtcaacag agttacagtg gcctcgacac tttcggcaga 300
gggaccaagg tggaaatcaa a 321

<210> SEQ ID NO 269
<211> LENGTH: 321
<212> TYPE: DNA
<213> ORGANISM: Homo sapiens

<400> SEQUENCE: 269
gacatccaga tgacccagtc tccatcctcc ctgtctgcat ctgtaggaga cagagtcacc 60
atcgcttgcc gggcaggtca gagcattggc acctatttaa attggtatca gcagaaacca 120
gggaaagccc ctaaactcct gatctatgtt gcatccagtt tgcaaagtgg ggtcccgtca 180
cggttcagtg gcagtggatc tgggacagaa ttcactctca ccatcagcag tctgcaacct 240
gaagattttg caacttacta ctgtcaacag agtagcagtg agctcctcac tttcggcaga 300
gggaccaagg tggaaatcaa a 321

<210> SEQ ID NO 270
<211> LENGTH: 321
<212> TYPE: DNA
<213> ORGANISM: Homo sapiens

<400> SEQUENCE: 270
gacatccaga tgacccagtc tccatcctcc ctgtctgcat ctgtaggaga cagagtcacc 60
atcgcttgcc gggcaggtca gagcattggc acctatttaa attggtatca gcagaaacca 120
gggaaagccc ctaaactcct gatctatgtt gcatccagtt tgcaaagtgg ggtcccgtca 180
cggttcagtg gcagtggatc tgggacagaa ttcactctca ccatcagcag tctgcaacct 240
gaagattttg caacttacta ctgtcaacag agttacagtg gcctcgacac tttcggcaga 300
gggaccaagg tggaaatcaa a 321

<210> SEQ ID NO 271
<211> LENGTH: 321
<212> TYPE: DNA
<213> ORGANISM: Homo sapiens

<400> SEQUENCE: 271
gacatccaga tgacccagtc tccatcctcc ctgtctgcat ctgtaggaga cagagtcacc 60
atcgcttgcc gggcaggtca gagcattggc acctatttaa attggtatca gcagaaacca 120
gggaaagccc ctaaactcct gatctatgtt gcatccagtt tgcaaagtgg ggtcccgtca 180
cggttcagtg gcagtggatc tgggacagaa ttcactctca ccatcagcag tctgcaacct 240
gaagattttg caacttacta ctgtcaacag agtgccagtg agctcctcac tttcggcaga 300
gggaccaagg tggaaatcaa a 321

<210> SEQ ID NO 272
<211> LENGTH: 209
<212> TYPE: PRT
<213> ORGANISM: Homo sapiens

<400> SEQUENCE: 272

Ala Gln Lys Val Thr Gln Ala Gln Ser Ser Val Ser Met Pro Val Arg
1 5 10 15

Lys Ala Val Thr Leu Asn Cys Leu Tyr Glu Thr Ser Trp Trp Ser Tyr
20 25 30

Tyr Ile Phe Trp Tyr Lys Gln Leu Pro Ser Lys Glu Met Ile Phe Leu

```
        35                  40                  45

Ile Arg Gln Gly Ser Asp Glu Gln Asn Ala Lys Ser Gly Arg Tyr Ser
    50                  55                  60

Val Asn Phe Lys Lys Ala Ala Lys Ser Val Ala Leu Thr Ile Ser Ala
65                  70                  75                  80

Leu Gln Leu Glu Asp Ser Ala Lys Tyr Phe Cys Ala Leu Gly Glu Ser
                85                  90                  95

Leu Thr Arg Ala Asp Lys Leu Ile Phe Gly Lys Gly Thr Arg Val Thr
            100                 105                 110

Val Glu Pro Asn Ile Gln Asn Pro Asp Pro Ala Val Tyr Gln Leu Arg
        115                 120                 125

Asp Ser Lys Ser Ser Asp Lys Ser Val Cys Leu Phe Thr Asp Phe Asp
    130                 135                 140

Ser Gln Thr Asn Val Ser Gln Ser Lys Asp Ser Asp Val Tyr Ile Thr
145                 150                 155                 160

Asp Lys Thr Val Leu Asp Met Arg Ser Met Asp Phe Lys Ser Asn Ser
                165                 170                 175

Ala Val Ala Trp Ser Asn Lys Ser Asp Phe Ala Cys Ala Asn Ala Phe
            180                 185                 190

Asn Asn Ser Ile Ile Pro Glu Asp Thr Phe Phe Pro Ser Pro Glu Ser
        195                 200                 205

Ser


<210> SEQ ID NO 273
<211> LENGTH: 117
<212> TYPE: PRT
<213> ORGANISM: Homo sapiens

<400> SEQUENCE: 273

Glu Val Gln Leu Leu Glu Ser Gly Gly Gly Leu Val Gln Pro Gly Arg
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ser Pro Ile Glu Leu Gly Ala Phe Asp Ile Trp Gly Gln Gly Thr Leu
            100                 105                 110

Val Thr Val Ser Ser
        115


<210> SEQ ID NO 274
<211> LENGTH: 118
<212> TYPE: PRT
<213> ORGANISM: Homo sapiens

<400> SEQUENCE: 274

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30
```

```
Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asn Tyr Leu Asn Ala Phe Asp Ile Trp Gly Arg Gly Thr
            100                 105                 110

Leu Val Thr Val Ser Ser
        115


<210> SEQ ID NO 275
<211> LENGTH: 117
<212> TYPE: PRT
<213> ORGANISM: Homo sapiens

<400> SEQUENCE: 275

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Gly Gly Gly Thr Thr Tyr Ser Ser Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Gly Val Ala Phe Asp Ile Trp Gly Gln Gly Thr Leu
            100                 105                 110

Val Thr Val Ser Ser
        115


<210> SEQ ID NO 276
<211> LENGTH: 120
<212> TYPE: PRT
<213> ORGANISM: Homo sapiens

<400> SEQUENCE: 276

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Arg Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Ser Trp Asn Asp Ala Phe Asp Ile Trp Gly Gln
            100                 105                 110
```

```
Gly Thr Thr Val Thr Val Ser Ser
        115                 120


<210> SEQ ID NO 277
<211> LENGTH: 120
<212> TYPE: PRT
<213> ORGANISM: Homo sapiens

<400> SEQUENCE: 277

Gln Val Gln Leu Gln Gln Ser Gly Pro Gly Leu Val Lys Pro Ser Gln
1               5                   10                  15

Thr Leu Ser Leu Thr Cys Val Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Tyr Tyr Tyr Ser Met Asp Val Trp Gly Gln
            100                 105                 110

Gly Thr Met Val Thr Val Ser Ser
        115                 120


<210> SEQ ID NO 278
<211> LENGTH: 118
<212> TYPE: PRT
<213> ORGANISM: Homo sapiens

<400> SEQUENCE: 278

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ser Trp Asn Asp Ala Phe Asp Val Trp Gly Gln Gly Thr
            100                 105                 110

Leu Val Thr Val Ser Ser
        115


<210> SEQ ID NO 279
<211> LENGTH: 120
<212> TYPE: PRT
<213> ORGANISM: Homo sapiens

<400> SEQUENCE: 279

Gln Val Gln Leu Gln Gln Ser Gly Pro Gly Leu Val Lys Pro Ser Gln
1               5                   10                  15
```

```
Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Gly Ser Lys Trp Tyr Asn Glu Tyr Ala
    50                  55                  60

Leu Ser Val Lys Ser Arg Ile Ile Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Tyr Tyr Tyr Ser Met Asp Val Trp Gly Gln
            100                 105                 110

Gly Thr Leu Val Thr Val Ser Ser
        115                 120


<210> SEQ ID NO 280
<211> LENGTH: 118
<212> TYPE: PRT
<213> ORGANISM: Homo sapiens

<400> SEQUENCE: 280

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ser Trp Ser Asp Ala Phe Asp Ile Trp Gly Gln Gly Thr
            100                 105                 110

Leu Val Thr Val Ser Ser
        115


<210> SEQ ID NO 281
<211> LENGTH: 118
<212> TYPE: PRT
<213> ORGANISM: Homo sapiens

<400> SEQUENCE: 281

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95
```

Ala Arg His Ser Trp Asn Asp Ala Phe Asp Ile Trp Gly Arg Gly Thr
100 105 110

Leu Val Thr Val Ser Ser
115

<210> SEQ ID NO 282
<211> LENGTH: 110
<212> TYPE: PRT
<213> ORGANISM: Homo sapiens

<400> SEQUENCE: 282

Ala Ser Ser Tyr Glu Leu Thr Gln Pro Pro Ser Val Ser Val Ala Pro
1 5 10 15

Gly Lys Thr Ala Arg Ile Thr Cys Gly Gly Asn Asn Ile Gly Ser Gln
20 25 30

Ser Val His Trp Tyr Gln Gln Lys Pro Gly Gln Ala Pro Met Leu Val
35 40 45

Ile Tyr Tyr Asp Ser Asp Arg Pro Ser Gly Ile Pro Glu Arg Phe Ser
50 55 60

Gly Ser Asn Ser Gly Asn Thr Ala Thr Leu Thr Ile Ser Arg Val Glu
65 70 75 80

Ala Gly Asp Glu Ala Asp Tyr Tyr Cys Gln Val Trp Asp Ser Ser Ser
85 90 95

Asp His Val Val Phe Gly Gly Gly Thr Lys Leu Thr Val Leu
100 105 110

<210> SEQ ID NO 283
<211> LENGTH: 109
<212> TYPE: PRT
<213> ORGANISM: Homo sapiens

<400> SEQUENCE: 283

Ala Ser Asp Ile Gln Met Thr Gln Ser Pro Ser Ser Leu Ser Ala Ser
1 5 10 15

Val Gly Asp Arg Val Thr Ile Thr Cys Arg Thr Ser Gln Ser Leu Ser
20 25 30

Asn Tyr Leu Asn Trp Tyr Gln Gln Lys Pro Gly Lys Ala Pro Lys Leu
35 40 45

Leu Ile Tyr Ala Ala Ser Ser Leu Gln Ser Gly Val Pro Ser Arg Phe
50 55 60

Ser Gly Ser Gly Ser Gly Thr Asp Phe Thr Leu Thr Ile Ser Ser Leu
65 70 75 80

Gln Pro Glu Asp Phe Ala Thr Tyr Tyr Cys Gln Gln Ser Tyr Ser Thr
85 90 95

Pro Leu Thr Phe Gly Gly Gly Thr Lys Leu Glu Ile Lys
100 105

<210> SEQ ID NO 284
<211> LENGTH: 109
<212> TYPE: PRT
<213> ORGANISM: Homo sapiens

<400> SEQUENCE: 284

Ala Ser Asp Ile Gln Met Thr Gln Ser Pro Ser Phe Leu Ser Ala Ser
1 5 10 15

Val Gly Asp Arg Val Thr Ile Thr Cys Arg Ala Ser Gln Asn Ile Arg
20 25 30

Thr Trp Leu Ala Trp Tyr Gln Gln Lys Pro Gly Arg Ala Pro Lys Leu

```
        35                  40                  45

Leu Ile Tyr Asp Ala Ser Ser Leu Glu Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Phe Lys Arg Tyr
                85                  90                  95

Pro Pro Thr Phe Gly Leu Gly Thr Lys Val Glu Ile Lys
            100                 105


<210> SEQ ID NO 285
<211> LENGTH: 109
<212> TYPE: PRT
<213> ORGANISM: Homo sapiens

<400> SEQUENCE: 285

Ala Ser Asp Ile Val Met Thr Gln Ser Pro Ser Thr Leu Ser Ala Ser
1               5                   10                  15

Ile Gly Asp Arg Val Thr Ile Thr Cys Arg Ala Gly Gln Ser Ile Ser
            20                  25                  30

Thr Trp Leu Ala Trp Tyr Gln Gln Lys Pro Gly Lys Ala Pro Lys Leu
        35                  40                  45

Leu Ile Tyr Asp Ala Ser Ser Leu Glu Ser Gly Val Pro Leu Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Ser Thr
                85                  90                  95

Pro Leu Thr Phe Gly Gly Gly Thr Lys Val Glu Ile Lys
            100                 105


<210> SEQ ID NO 286
<211> LENGTH: 109
<212> TYPE: PRT
<213> ORGANISM: Homo sapiens

<400> SEQUENCE: 286

Ala Ser Asp Ile Gln Met Thr Gln Ser Pro Ser Thr Leu Ser Ala Ser
1               5                   10                  15

Val Gly Asp Arg Val Thr Ile Thr Cys Arg Ala Ser Gln Ser Ile Ser
            20                  25                  30

Ser Trp Leu Ala Trp Tyr Gln Gln Lys Pro Gly Lys Ala Pro Lys Leu
        35                  40                  45

Leu Ile Tyr Asp Ala Ser Ser Leu Glu Ser Gly Val Pro Leu Arg Phe
    50                  55                  60

Ser Gly Ser Gly Ser Gly Thr Glu Phe Thr Leu Thr Ile Ser Ser Leu
65                  70                  75                  80

Gln Pro Asp Asp Phe Ala Thr Tyr Tyr Cys Gln Gln Ser His Ser His
                85                  90                  95

Pro Pro Thr Phe Gly Pro Gly Thr Lys Val Asp Ile Lys
            100                 105


<210> SEQ ID NO 287
<211> LENGTH: 109
<212> TYPE: PRT
<213> ORGANISM: Homo sapiens

<400> SEQUENCE: 287
```

Ala Ser Asp Ile Gln Met Thr Gln Ser Pro Ser Ser Leu Ser Ala Ser
1 5 10 15

Val Gly Asp Arg Val Ser Ile Thr Cys Arg Ala Ser Gln Ser Ile Ser
20 25 30

Ser Tyr Leu Asn Trp Tyr Gln Gln Lys Pro Gly Lys Ala Pro Lys Leu
35 40 45

Leu Ile Tyr Ala Ala Ser Ser Leu Gln Ser Gly Val Pro Ser Arg Phe
50 55 60

Ser Gly Ser Gly Ser Gly Thr Asp Phe Thr Leu Thr Ile Ser Ser Leu
65 70 75 80

Gln Pro Glu Asp Phe Ala Thr Tyr Tyr Cys Gln Gln Ser Tyr Ser Thr
85 90 95

Pro Asp Thr Phe Gly Gly Gly Thr Lys Val Glu Ile Lys
100 105

<210> SEQ ID NO 288
<211> LENGTH: 109
<212> TYPE: PRT
<213> ORGANISM: Homo sapiens

<400> SEQUENCE: 288

Ala Ser Asp Ile Val Met Thr Gln Ser Pro Ser Thr Leu Ser Ala Ser
1 5 10 15

Ile Gly Asp Arg Val Thr Ile Thr Cys Arg Ala Gly Gln Ser Ile Ser
20 25 30

Thr Trp Leu Ala Trp Tyr Gln Gln Lys Pro Gly Lys Ala Pro Lys Leu
35 40 45

Leu Ile Tyr Asp Ala Ser Ser Leu Glu Ser Gly Val Pro Leu Arg Phe
50 55 60

Ser Gly Ser Gly Ser Gly Thr Glu Phe Thr Leu Ala Ile Ser Ser Leu
65 70 75 80

Gln Pro Asp Asp Phe Ala Thr Tyr Tyr Cys Gln Gln Ser Tyr Ser Thr
85 90 95

Pro Val Thr Phe Gly Gln Gly Thr Lys Val Glu Ile Lys
100 105

<210> SEQ ID NO 289
<211> LENGTH: 109
<212> TYPE: PRT
<213> ORGANISM: Homo sapiens

<400> SEQUENCE: 289

Ala Ser Asp Ile Gln Met Thr Gln Ser Pro Ser Ser Leu Ser Ala Ser
1 5 10 15

Val Gly Asp Arg Val Thr Ile Thr Cys Gln Ala Ser Gln Asp Ile Ser
20 25 30

Asn Tyr Leu Asn Trp Tyr Gln Gln Lys Pro Gly Lys Ala Pro Lys Leu
35 40 45

Leu Ile Tyr Asp Ala Ser Asn Leu Glu Thr Gly Val Pro Ser Arg Phe
50 55 60

Ser Gly Ser Gly Ser Gly Thr Asp Phe Thr Leu Thr Ile Ser Ser Leu
65 70 75 80

Gln Pro Glu Asp Phe Ala Thr Tyr Tyr Cys Gln Gln Ser Tyr Ser Thr
85 90 95

Pro Leu Thr Phe Gly Gly Gly Thr Lys Val Glu Ile Lys
100 105

<210> SEQ ID NO 290
<211> LENGTH: 109
<212> TYPE: PRT
<213> ORGANISM: Homo sapiens

<400> SEQUENCE: 290

```
Ala Ser Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Ser Ile Ser
            20                  25                  30

Ser His Leu Asn Trp Tyr Gln Gln Lys Pro Gly Lys Ala Pro Lys Leu
        35                  40                  45

Leu Ile Tyr Ala Ala Ser Ser Leu Gln Ser Gly Val Pro Ser Arg Phe
    50                  55                  60

Ser Ala Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Ser Thr
                85                  90                  95

Leu Leu Thr Phe Gly Gly Gly Thr Lys Val Glu Ile Lys
            100                 105
```

<210> SEQ ID NO 291
<211> LENGTH: 13
<212> TYPE: PRT
<213> ORGANISM: Artificial Sequence
<220> FEATURE:
<223> OTHER INFORMATION: Synthetic, VH-VL linker

<400> SEQUENCE: 291

```
Gly Gly Gly Gly Ser Gly Gly Gly Gly Ser Gly Gly Gly
1               5                   10
```

<210> SEQ ID NO 292
<211> LENGTH: 12
<212> TYPE: PRT
<213> ORGANISM: Artificial Sequence
<220> FEATURE:
<223> OTHER INFORMATION: Synthetic, Optional scFv tag sequence (kappa
      sequence + His tag)

<400> SEQUENCE: 292

```
Arg Thr Ala Ala Ala Ser Ala His His His His His
1               5                   10
```

<210> SEQ ID NO 293
<211> LENGTH: 37
<212> TYPE: PRT
<213> ORGANISM: Artificial Sequence
<220> FEATURE:
<223> OTHER INFORMATION: Synthetic, Optional scFv tag sequence (kappa
      sequence + His and FLAG tag)

<400> SEQUENCE: 293

```
Arg Thr Ala Ala Ala Ser Ala His His His His His His Lys Leu Asp
1               5                   10                  15

Tyr Lys Asp His Asp Gly Asp Tyr Lys Asp His Asp Ile Asp Tyr Lys
            20                  25                  30

Asp Asp Asp Asp Lys
        35
```

<210> SEQ ID NO 294

<211> LENGTH: 13
<212> TYPE: PRT
<213> ORGANISM: Artificial Sequence
<220> FEATURE:
<223> OTHER INFORMATION: Synthetic, Optional scFv tag sequence (lambda sequence + His tag)

<400> SEQUENCE: 294

Gly Gln Pro Ala Ala Ala Ser Ala His His His His His
1 5 10

<210> SEQ ID NO 295
<211> LENGTH: 38
<212> TYPE: PRT
<213> ORGANISM: Artificial Sequence
<220> FEATURE:
<223> OTHER INFORMATION: Synthetic, Optional scFv tag sequence (lambda sequence + His and FLAG tag)

<400> SEQUENCE: 295

Gly Gln Pro Ala Ala Ala Ser Ala His His His His His His Lys Leu
1 5 10 15

Asp Tyr Lys Asp His Asp Gly Asp Tyr Lys Asp His Asp Ile Asp Tyr
20 25 30

Lys Asp Asp Asp Asp Lys
35

<210> SEQ ID NO 296
<211> LENGTH: 107
<212> TYPE: PRT
<213> ORGANISM: Homo sapiens

<400> SEQUENCE: 296

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Asp Ser Lys Asp Ser
50 55 60

Thr Tyr Ser Leu Ser Ser Thr Leu Thr Leu Ser Lys Ala Asp Tyr Glu
65 70 75 80

Lys His Lys Val Tyr Ala Cys Glu Val Thr His Gln Gly Leu Ser Ser
85 90 95

Pro Val Thr Lys Ser Phe Asn Arg Gly Glu Cys
100 105

<210> SEQ ID NO 297
<211> LENGTH: 330
<212> TYPE: PRT
<213> ORGANISM: Homo sapiens

<400> SEQUENCE: 297

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser

```
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 298
<211> LENGTH: 330
<212> TYPE: PRT
<213> ORGANISM: Homo sapiens

<400> SEQUENCE: 298

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

```
Lys Val Glu Pro Lys Ser Cys Asp Lys Thr His Thr Cys Pro Pro Cys
            100                 105                 110

Pro Ala Pro Glu Leu Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 299
<211> LENGTH: 20
<212> TYPE: PRT
<213> ORGANISM: Homo sapiens

<400> SEQUENCE: 299

Met Leu Phe Ser Ser Leu Leu Cys Val Phe Val Ala Phe Ser Tyr Ser
1               5                   10                  15

Gly Ser Ser Val
            20


<210> SEQ ID NO 300
<211> LENGTH: 95
<212> TYPE: PRT
<213> ORGANISM: Homo sapiens

<400> SEQUENCE: 300

Ala Gln Lys Val Thr Gln Ala Gln Ser Ser Val Ser Met Pro Val Arg
1               5                   10                  15

Lys Ala Val Thr Leu Asn Cys Leu Tyr Glu Thr Ser Trp Trp Ser Tyr
            20                  25                  30

Tyr Ile Phe Trp Tyr Lys Gln Leu Pro Ser Lys Glu Met Ile Phe Leu
        35                  40                  45

Ile Arg Gln Gly Ser Asp Glu Gln Asn Ala Lys Ser Gly Arg Tyr Ser
    50                  55                  60
```

Val Asn Phe Lys Lys Ala Ala Lys Ser Val Ala Leu Thr Ile Ser Ala
65 70 75 80

Leu Gln Leu Glu Asp Ser Ala Lys Tyr Phe Cys Ala Leu Gly Glu
85 90 95

<210> SEQ ID NO 301
<211> LENGTH: 16
<212> TYPE: PRT
<213> ORGANISM: Homo sapiens

<400> SEQUENCE: 301

Thr Asp Lys Leu Ile Phe Gly Lys Gly Thr Arg Val Thr Val Glu Pro
1 5 10 15

<210> SEQ ID NO 302
<211> LENGTH: 17
<212> TYPE: PRT
<213> ORGANISM: Homo sapiens

<400> SEQUENCE: 302

Leu Thr Ala Gln Leu Phe Phe Gly Lys Gly Thr Gln Leu Ile Val Glu
1 5 10 15

Pro

<210> SEQ ID NO 303
<211> LENGTH: 19
<212> TYPE: PRT
<213> ORGANISM: Homo sapiens

<400> SEQUENCE: 303

Ser Trp Asp Thr Arg Gln Met Phe Phe Gly Thr Gly Ile Lys Leu Phe
1 5 10 15

Val Glu Pro

<210> SEQ ID NO 304
<211> LENGTH: 15
<212> TYPE: PRT
<213> ORGANISM: Homo sapiens

<400> SEQUENCE: 304

Arg Pro Leu Ile Phe Gly Lys Gly Thr Tyr Leu Glu Val Gln Gln
1 5 10 15

<210> SEQ ID NO 305
<211> LENGTH: 153
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 305

Xaa Ser Gln Pro His Thr Lys Pro Ser Val Phe Val Met Lys Asn Gly
1 5 10 15

Thr Asn Val Ala Cys Leu Val Lys Glu Phe Tyr Pro Lys Asp Ile Arg
20 25 30

Ile Asn Leu Val Ser Ser Lys Lys Ile Thr Glu Phe Asp Pro Ala Ile
35 40 45

Val Ile Ser Pro Ser Gly Lys Tyr Asn Ala Val Lys Leu Gly Lys Tyr
50 55 60

Glu Ser Asn Ser Val Thr Cys Ser Val Gln His Asp Asn Lys Thr Val 65 70 75 80

His Ser Thr Asp Phe Glu Val Lys Thr Asp Ser Thr Asp His Val Lys
85 90 95

Pro Lys Glu Thr Glu Asn Thr Lys Gln Pro Ser Lys Ser Cys His Lys
100 105 110

Pro Lys Ala Ile Val His Thr Glu Lys Val Asn Met Met Ser Leu Thr
115 120 125

Val Leu Gly Leu Arg Met Leu Phe Ala Lys Thr Val Ala Val Asn Phe
130 135 140

Leu Leu Thr Ala Lys Leu Phe Phe Leu
145 150

<210> SEQ ID NO 306
<211> LENGTH: 254
<212> TYPE: PRT
<213> ORGANISM: Homo sapiens

<400> SEQUENCE: 306

Ala Gln Lys Val Thr Gln Ala Gln Ser Ser Val Ser Met Pro Val Arg
1 5 10 15

Lys Ala Val Thr Leu Asn Cys Leu Tyr Glu Thr Ser Trp Trp Ser Tyr
20 25 30

Tyr Ile Phe Trp Tyr Lys Gln Leu Pro Ser Lys Glu Met Ile Phe Leu
35 40 45

Ile Arg Gln Gly Ser Asp Glu Gln Asn Ala Lys Ser Gly Arg Tyr Ser
50 55 60

Val Asn Phe Lys Lys Ala Val Lys Ser Val Ala Leu Thr Ile Ser Ala
65 70 75 80

Leu Gln Leu Glu Asp Ser Ala Lys Tyr Phe Cys Ala Leu Gly Glu Ser
85 90 95

Leu Thr Arg Ala Asp Lys Leu Ile Phe Gly Lys Gly Thr Arg Val Thr
100 105 110

Val Glu Pro Asn Ile Gln Asn Pro Asp Pro Ala Val Tyr Gln Leu Arg
115 120 125

Asp Ser Lys Ser Ser Asp Lys Ser Val Cys Leu Phe Thr Asp Phe Asp
130 135 140

Ser Gln Thr Asn Val Ser Gln Ser Lys Asp Ser Asp Val Tyr Ile Thr
145 150 155 160

Asp Lys Thr Val Leu Asp Met Arg Ser Met Asp Phe Lys Ser Asn Ser
165 170 175

Ala Val Ala Trp Ser Asn Lys Ser Asp Phe Ala Cys Ala Asn Ala Phe
180 185 190

Asn Asn Ser Ile Ile Pro Glu Asp Thr Phe Phe Pro Ser Pro Glu Ser
195 200 205

Ser Cys Thr Thr Ala Pro Ser Ala Gln Leu Lys Lys Lys Leu Gln Ala
210 215 220

Leu Lys Lys Lys Asn Ala Gln Leu Lys Trp Lys Leu Gln Ala Leu Lys
225 230 235 240

Lys Lys Leu Ala Gln Gly Ser Gly His His His His His His
245 250

<210> SEQ ID NO 307
<211> LENGTH: 107
<212> TYPE: PRT
<213> ORGANISM: Homo sapiens

<400> SEQUENCE: 307

```
Arg Thr Ala Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 308
<211> LENGTH: 92
<212> TYPE: PRT
<213> ORGANISM: Homo sapiens

<400> SEQUENCE: 308

```
Ala Gln Lys Val Thr Gln Ala Gln Ser Ser Val Ser Met Pro Val Glu
1               5                   10                  15

Lys Ala Val Thr Leu Asn Cys Gln Tyr Glu Thr Ser Ser Trp Ser Tyr
            20                  25                  30

Asp Leu Phe Trp Tyr Lys Gln Leu Pro Gly Lys Glu Met Ile Phe Leu
        35                  40                  45

Ile His Gln Gly Ser Ser Gln Gln Asn Ala Arg Asn Gly Arg Tyr Ser
    50                  55                  60

Val Asn Phe Gln Lys Ala Ala Ser Ser Ile Thr Leu Thr Ile Ser Ala
65                  70                  75                  80

Leu Gln Leu Glu Asp Ser Ala Thr Tyr Phe Cys Ala
                85                  90
```

<210> SEQ ID NO 309
<211> LENGTH: 101
<212> TYPE: PRT
<213> ORGANISM: Homo sapiens

<400> SEQUENCE: 309

```
Lys Ser Ser Asn Leu Glu Gly Arg Thr Lys Ser Val Ile Arg Gln Thr
1               5                   10                  15

Gly Ser Ser Ala Glu Ile Thr Cys Asp Leu Ala Glu Gly Ser Thr Gly
            20                  25                  30

Tyr Ile His Trp Tyr Leu His Gln Glu Gly Lys Ala Pro Gln Arg Leu
        35                  40                  45

Leu Tyr Tyr Asp Ser Tyr Thr Ser Ser Val Val Leu Glu Ser Gly Ile
    50                  55                  60

Ser Pro Gly Lys Tyr Asp Thr Tyr Gly Ser Thr Arg Lys Asn Leu Arg
65                  70                  75                  80

Met Ile Leu Arg Asn Leu Ile Glu Asn Asp Ser Gly Val Tyr Tyr Cys
                85                  90                  95

Ala Thr Trp Asp Gly
            100
```

<210> SEQ ID NO 310
<211> LENGTH: 96
<212> TYPE: PRT
<213> ORGANISM: Homo sapiens

<400> SEQUENCE: 310

```
Ala Ile Glu Leu Val Pro Glu His Gln Thr Val Pro Val Ser Ile Gly
1               5                   10                  15

Val Pro Ala Thr Leu Arg Cys Ser Met Lys Gly Glu Ala Ile Gly Asn
            20                  25                  30

Tyr Tyr Ile Asn Trp Tyr Arg Lys Thr Gln Gly Asn Thr Met Thr Phe
        35                  40                  45

Ile Tyr Arg Glu Lys Asp Ile Tyr Gly Pro Gly Phe Lys Asp Asn Phe
    50                  55                  60

Gln Gly Asp Ile Asp Ile Ala Lys Asn Leu Ala Val Leu Lys Ile Leu
65                  70                  75                  80

Ala Pro Ser Glu Arg Asp Glu Gly Ser Tyr Tyr Cys Ala Cys Asp Thr
                85                  90                  95
```

<210> SEQ ID NO 311
<211> LENGTH: 95
<212> TYPE: PRT
<213> ORGANISM: Homo sapiens

<400> SEQUENCE: 311

```
Asp Lys Val Thr Gln Ser Ser Pro Asp Gln Thr Val Ala Ser Gly Ser
1               5                   10                  15

Glu Val Val Leu Leu Cys Thr Tyr Asp Thr Val Tyr Ser Asn Pro Asp
            20                  25                  30

Leu Phe Trp Tyr Arg Ile Arg Pro Asp Tyr Ser Phe Gln Phe Val Phe
        35                  40                  45

Tyr Gly Asp Asn Ser Arg Ser Glu Gly Ala Asp Phe Thr Gln Gly Arg
    50                  55                  60

Phe Ser Val Lys His Ile Leu Thr Gln Lys Ala Phe His Leu Val Ile
65                  70                  75                  80

Ser Pro Val Arg Thr Glu Asp Ser Ala Thr Tyr Tyr Cys Ala Phe
                85                  90                  95
```

<210> SEQ ID NO 312
<211> LENGTH: 119
<212> TYPE: PRT
<213> ORGANISM: Homo sapiens

<400> SEQUENCE: 312

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gln Val Asp Thr Arg Thr Ala Asp Tyr Trp Gly Gln Gly
            100                 105                 110
```

Thr Leu Val Thr Val Ser Ser
        115

<210> SEQ ID NO 313
<211> LENGTH: 112
<212> TYPE: PRT
<213> ORGANISM: Homo sapiens

<400> SEQUENCE: 313

Ala Ser Gln Ser Ala Leu Thr Gln Pro Ala Ser Val Ser Gly Ser Pro
1               5                   10                  15

Gly Gln Ser Val Thr Ile Ser Cys Thr Gly Thr Arg Ser Asp Val Gly
            20                  25                  30

Gly Tyr Asn Tyr Val Ser Trp Tyr Gln His His Pro Gly Lys Ala Pro
        35                  40                  45

Lys Leu Met Ile Tyr Glu Val Ser Asn Arg Pro Ser Gly Val Ser Asn
    50                  55                  60

Arg Phe Ser Gly Ser Lys Ser Gly Asn Thr Ala Ser Leu Thr Ile Ser
65                  70                  75                  80

Gly Leu Gln Ala Glu Asp Glu Ala Asp Tyr Tyr Cys Ser Ser Tyr Thr
                85                  90                  95

Ser Thr Ser Thr Leu Val Phe Gly Gly Gly Thr Lys Leu Thr Val Leu
            100                 105                 110

<210> SEQ ID NO 314
<211> LENGTH: 250
<212> TYPE: PRT
<213> ORGANISM: Homo sapiens

<400> SEQUENCE: 314

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Gly Gly Gly Gly
        115                 120                 125

Ser Gly Gly Gly Gly Ser Gly Gly Gly Gly Ser Asp Ile Gln Leu Thr
    130                 135                 140

Gln Ser Pro Ala Ser Leu Ala Val Ser Leu Gly Gln Arg Ala Thr Ile
145                 150                 155                 160

Ser Cys Lys Ala Ser Gln Ser Val Asp Tyr Asp Gly Asp Ser Tyr Leu
                165                 170                 175

Asn Trp Tyr Gln Gln Ile Pro Gly Gln Pro Pro Lys Leu Leu Ile Tyr
            180                 185                 190

Asp Ala Ser Asn Leu Val Ser Gly Ile Pro Pro Arg Phe Ser Gly Ser
        195                 200                 205

```
Gly Ser Gly Thr Asp Phe Thr Leu Asn Ile His Pro Val Glu Lys Val
    210                 215                 220

Asp Ala Ala Thr Tyr His Cys Gln Gln Ser Thr Glu Asp Pro Trp Thr
225                 230                 235                 240

Phe Gly Gly Gly Thr Lys Leu Glu Ile Lys
                245                 250


<210> SEQ ID NO 315
<211> LENGTH: 931
<212> TYPE: PRT
<213> ORGANISM: Homo sapiens

<400> SEQUENCE: 315

Ala Ser Asp Ile Gln Met Thr Gln Ser Pro Pro Ala Leu Ser Ala Ser
1               5                   10                  15

Val Gly Asp Arg Val Thr Ile Thr Cys Arg Ala Ser Gln Asp Ile Asn
            20                  25                  30

Asp Trp Leu Ala Trp Tyr Gln His Lys Pro Gly Lys Ala Pro Lys Leu
        35                  40                  45

Leu Ile Tyr Asp Ala Ser Ser Leu Glu Ser Gly Val Pro Ser Arg Phe
    50                  55                  60

Ser Gly Ser Gly Ser Gly Thr Glu Phe Thr Leu Thr Ile Ser Ser Leu
65                  70                  75                  80

Gln Pro Asp Asp Phe Ala Thr Tyr Tyr Cys Gln Gln Ser Tyr Ser Thr
                85                  90                  95

Pro Gln Val Thr Phe Gly Gln Gly Thr Arg Leu Glu Ile Lys Arg Thr
            100                 105                 110

Ala Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Leu Tyr Ala Cys Glu Val Thr His Gln Gly Leu Ser Ser Pro Val
        195                 200                 205

Thr Lys Ser Phe Asn Arg Gly Glu Cys Gln Val Gln Leu Gln Gln Ser
    210                 215                 220

Gly Pro Gly Leu Val Lys Pro Ser Gln Thr Leu Ser Leu Thr Cys Ala
225                 230                 235                 240

Ile Ser Gly Asp Ser Val Ser Ser Lys Ser Ala Ala Trp Asn Trp Ile
                245                 250                 255

Arg Gln Ser Pro Ser Arg Gly Leu Glu Trp Leu Gly Arg Thr Tyr Tyr
            260                 265                 270

Arg Ser Lys Trp Ser Thr Asp Tyr Ala Ala Ser Val Lys Ser Arg Ile
        275                 280                 285

Thr Ile Asn Pro Asp Thr Ser Lys Asn Gln Leu Ser Leu Gln Leu Asn
    290                 295                 300

Ser Val Thr Pro Glu Asp Thr Ala Val Tyr Tyr Cys Ala Arg Thr Trp
305                 310                 315                 320

Ser Gly Tyr Val Asp Val Trp Gly Gln Gly Thr Leu Val Thr Val Ser
```

```
                325                 330                 335

Ser Ala Ser Thr Lys Gly Pro Ser Val Phe Pro Leu Ala Pro Ser Ser
            340                 345                 350

Lys Ser Thr Ser Gly Gly Thr Ala Ala Leu Gly Cys Leu Val Lys Asp
        355                 360                 365

Tyr Phe Pro Glu Pro Val Thr Val Ser Trp Asn Ser Gly Ala Leu Thr
    370                 375                 380

Ser Gly Val His Thr Phe Pro Ala Val Leu Gln Ser Ser Gly Leu Tyr
385                 390                 395                 400

Ser Leu Ser Ser Val Val Thr Val Pro Ser Ser Ser Leu Gly Thr Gln
                405                 410                 415

Thr Tyr Ile Cys Asn Val Asn His Lys Pro Ser Asn Thr Lys Val Asp
            420                 425                 430

Lys Lys Val Glu Pro Lys Ser Cys Asp Lys Thr His Thr Cys Pro Pro
        435                 440                 445

Cys Pro Ala Pro Glu Leu Ala Gly Ala Pro Ser Val Phe Leu Phe Pro
    450                 455                 460

Pro Lys Pro Lys Asp Thr Leu Met Ile Ser Arg Thr Pro Glu Val Thr
465                 470                 475                 480

Cys Val Val Val Asp Val Ser His Glu Asp Pro Glu Val Lys Phe Asn
                485                 490                 495

Trp Tyr Val Asp Gly Val Glu Val His Asn Ala Lys Thr Lys Pro Arg
            500                 505                 510

Glu Glu Gln Tyr Asn Ser Thr Tyr Arg Val Val Ser Val Leu Thr Val
        515                 520                 525

Leu His Gln Asp Trp Leu Asn Gly Lys Glu Tyr Lys Cys Lys Val Ser
    530                 535                 540

Asn Lys Ala Leu Pro Ala Pro Ile Glu Lys Thr Ile Ser Lys Ala Lys
545                 550                 555                 560

Gly Gln Pro Arg Glu Pro Gln Val Tyr Thr Leu Pro Pro Ser Arg Asp
                565                 570                 575

Glu Leu Thr Lys Asn Gln Val Ser Leu Thr Cys Leu Val Lys Gly Phe
            580                 585                 590

Tyr Pro Ser Asp Ile Ala Val Glu Trp Glu Ser Asn Gly Gln Pro Glu
        595                 600                 605

Asn Asn Tyr Lys Thr Thr Pro Pro Val Leu Asp Ser Asp Gly Ser Phe
    610                 615                 620

Phe Leu Tyr Ser Lys Leu Thr Val Asp Lys Ser Arg Trp Gln Gln Gly
625                 630                 635                 640

Asn Val Phe Ser Cys Ser Val Met His Glu Ala Leu His Asn His Tyr
                645                 650                 655

Thr Gln Lys Ser Leu Ser Leu Ser Pro Gly Gly Gly Gly Gly Ser Gly
            660                 665                 670

Gly Gly Gly Ser Gly Gly Gly Gly Ser Gln Val Gln Leu Gln Gln Ser
        675                 680                 685

Gly Ala Glu Leu Val Arg Pro Gly Ser Ser Val Lys Ile Ser Cys Lys
    690                 695                 700

Ala Ser Gly Tyr Ala Phe Ser Ser Tyr Trp Met Asn Trp Val Lys Gln
705                 710                 715                 720

Arg Pro Gly Gln Gly Leu Glu Trp Ile Gly Gln Ile Trp Pro Gly Asp
                725                 730                 735

Gly Asp Thr Asn Tyr Asn Gly Lys Phe Lys Gly Lys Ala Thr Leu Thr
            740                 745                 750
```

Ala Asp Glu Ser Ser Ser Thr Ala Tyr Met Gln Leu Ser Ser Leu Ala
755 760 765

Ser Glu Asp Ser Ala Val Tyr Phe Cys Ala Arg Arg Glu Thr Thr Thr
770 775 780

Val Gly Arg Tyr Tyr Tyr Ala Met Asp Tyr Trp Gly Gln Gly Thr Thr
785 790 795 800

Val Thr Val Ser Ser Gly Gly Gly Gly Ser Gly Gly Gly Gly Ser Gly
805 810 815

Gly Gly Gly Ser Asp Ile Gln Leu Thr Gln Ser Pro Ala Ser Leu Ala
820 825 830

Val Ser Leu Gly Gln Arg Ala Thr Ile Ser Cys Lys Ala Ser Gln Ser
835 840 845

Val Asp Tyr Asp Gly Asp Ser Tyr Leu Asn Trp Tyr Gln Gln Ile Pro
850 855 860

Gly Gln Pro Pro Lys Leu Leu Ile Tyr Asp Ala Ser Asn Leu Val Ser
865 870 875 880

Gly Ile Pro Pro Arg Phe Ser Gly Ser Gly Ser Gly Thr Asp Phe Thr
885 890 895

Leu Asn Ile His Pro Val Glu Lys Val Asp Ala Ala Thr Tyr His Cys
900 905 910

Gln Gln Ser Thr Glu Asp Pro Trp Thr Phe Gly Gly Gly Thr Lys Leu
915 920 925

Glu Ile Lys
930

<210> SEQ ID NO 316
<211> LENGTH: 928
<212> TYPE: PRT
<213> ORGANISM: Homo sapiens

<400> SEQUENCE: 316

Ala Ser Asp Ile Gln Met Thr Gln Ser Pro Ser Ser Leu Ser Ala Ser
1 5 10 15

Val Gly Asp Arg Val Thr Ile Ala Cys Arg Ala Gly Gln Ser Ile Gly
20 25 30

Thr Tyr Leu Asn Trp Tyr Gln Gln Lys Pro Gly Lys Ala Pro Lys Leu
35 40 45

Leu Ile Tyr Val Ala Ser Ser Leu Gln Ser Gly Val Pro Ser Arg Phe
50 55 60

Ser Gly Ser Gly Ser Gly Thr Glu Phe Thr Leu Thr Ile Ser Ser Leu
65 70 75 80

Gln Pro Glu Asp Phe Ala Thr Tyr Tyr Cys Gln Gln Ser Tyr Ser Thr
85 90 95

Leu Leu Thr Phe Gly Arg Gly Thr Lys Val Glu Ile Lys Arg Thr Ala
100 105 110

Ala Ala Pro Ser Val Phe Ile Phe Pro Pro Ser Asp Glu Gln Leu Lys
115 120 125

Ser Gly Thr Ala Ser Val Val Cys Leu Leu Asn Asn Phe Tyr Pro Arg
130 135 140

Glu Ala Lys Val Gln Trp Lys Val Asp Asn Ala Leu Gln Ser Gly Asn
145 150 155 160

Ser Gln Glu Ser Val Thr Glu Gln Asp Ser Lys Asp Ser Thr Tyr Ser
165 170 175

Leu Ser Ser Thr Leu Thr Leu Ser Lys Ala Asp Tyr Glu Lys His Lys

-continued

```
            180                 185                 190

Leu Tyr Ala Cys Glu Val Thr His Gln Gly Leu Ser Ser Pro Val Thr
        195                 200                 205

Lys Ser Phe Asn Arg Gly Glu Cys Gln Val Gln Leu Val Glu Ser Gly
    210                 215                 220

Gly Gly Leu Val Lys Pro Gly Gly Ser Leu Arg Leu Ser Cys Ala Ala
225                 230                 235                 240

Ser Gly Phe Thr Phe Ser Asp Tyr Tyr Met Ser Trp Ile Arg Gln Ala
                245                 250                 255

Pro Gly Lys Gly Leu Glu Trp Val Ser Tyr Ile Ser Ser Ser Gly Ser
            260                 265                 270

Thr Ile Tyr Tyr Ala Asp Ser Val Lys Gly Arg Phe Thr Ile Ser Arg
        275                 280                 285

Asp Asn Ala Lys Asn Ser Leu Tyr Leu Gln Met Asn Ser Leu Arg Ala
    290                 295                 300

Glu Asp Thr Ala Val Tyr Tyr Cys Ala Arg Val Asp Tyr Ala Asp Ala
305                 310                 315                 320

Phe Asp Ile Trp Gly Gln Gly Thr Leu Val Thr Val Ser Ser Ala Ser
                325                 330                 335

Thr Lys Gly Pro Ser Val Phe Pro Leu Ala Pro Ser Ser Lys Ser Thr
            340                 345                 350

Ser Gly Gly Thr Ala Ala Leu Gly Cys Leu Val Lys Asp Tyr Phe Pro
        355                 360                 365

Glu Pro Val Thr Val Ser Trp Asn Ser Gly Ala Leu Thr Ser Gly Val
    370                 375                 380

His Thr Phe Pro Ala Val Leu Gln Ser Ser Gly Leu Tyr Ser Leu Ser
385                 390                 395                 400

Ser Val Val Thr Val Pro Ser Ser Ser Leu Gly Thr Gln Thr Tyr Ile
                405                 410                 415

Cys Asn Val Asn His Lys Pro Ser Asn Thr Lys Val Asp Lys Lys Val
            420                 425                 430

Glu Pro Lys Ser Cys Asp Lys Thr His Thr Cys Pro Pro Cys Pro Ala
        435                 440                 445

Pro Glu Leu Ala Gly Ala Pro Ser Val Phe Leu Phe Pro Pro Lys Pro
    450                 455                 460

Lys Asp Thr Leu Met Ile Ser Arg Thr Pro Glu Val Thr Cys Val Val
465                 470                 475                 480

Val Asp Val Ser His Glu Asp Pro Glu Val Lys Phe Asn Trp Tyr Val
                485                 490                 495

Asp Gly Val Glu Val His Asn Ala Lys Thr Lys Pro Arg Glu Glu Gln
            500                 505                 510

Tyr Asn Ser Thr Tyr Arg Val Val Ser Val Leu Thr Val Leu His Gln
        515                 520                 525

Asp Trp Leu Asn Gly Lys Glu Tyr Lys Cys Lys Val Ser Asn Lys Ala
    530                 535                 540

Leu Pro Ala Pro Ile Glu Lys Thr Ile Ser Lys Ala Lys Gly Gln Pro
545                 550                 555                 560

Arg Glu Pro Gln Val Tyr Thr Leu Pro Pro Ser Arg Asp Glu Leu Thr
                565                 570                 575

Lys Asn Gln Val Ser Leu Thr Cys Leu Val Lys Gly Phe Tyr Pro Ser
            580                 585                 590

Asp Ile Ala Val Glu Trp Glu Ser Asn Gly Gln Pro Glu Asn Asn Tyr
        595                 600                 605
```

```
Lys Thr Thr Pro Pro Val Leu Asp Ser Asp Gly Ser Phe Phe Leu Tyr
    610                 615                 620

Ser Lys Leu Thr Val Asp Lys Ser Arg Trp Gln Gln Gly Asn Val Phe
625                 630                 635                 640

Ser Cys Ser Val Met His Glu Ala Leu His Asn His Tyr Thr Gln Lys
                645                 650                 655

Ser Leu Ser Leu Ser Pro Gly Gly Gly Gly Gly Ser Gly Gly Gly Gly
            660                 665                 670

Ser Gly Gly Gly Gly Ser Gln Val Gln Leu Gln Gln Ser Gly Ala Glu
        675                 680                 685

Leu Val Arg Pro Gly Ser Ser Val Lys Ile Ser Cys Lys Ala Ser Gly
    690                 695                 700

Tyr Ala Phe Ser Ser Tyr Trp Met Asn Trp Val Lys Gln Arg Pro Gly
705                 710                 715                 720

Gln Gly Leu Glu Trp Ile Gly Gln Ile Trp Pro Gly Asp Gly Asp Thr
                725                 730                 735

Asn Tyr Asn Gly Lys Phe Lys Gly Lys Ala Thr Leu Thr Ala Asp Glu
            740                 745                 750

Ser Ser Ser Thr Ala Tyr Met Gln Leu Ser Ser Leu Ala Ser Glu Asp
        755                 760                 765

Ser Ala Val Tyr Phe Cys Ala Arg Arg Glu Thr Thr Thr Val Gly Arg
    770                 775                 780

Tyr Tyr Tyr Ala Met Asp Tyr Trp Gly Gln Gly Thr Thr Val Thr Val
785                 790                 795                 800

Ser Ser Gly Gly Gly Gly Ser Gly Gly Gly Gly Ser Gly Gly Gly Gly
                805                 810                 815

Ser Asp Ile Gln Leu Thr Gln Ser Pro Ala Ser Leu Ala Val Ser Leu
            820                 825                 830

Gly Gln Arg Ala Thr Ile Ser Cys Lys Ala Ser Gln Ser Val Asp Tyr
        835                 840                 845

Asp Gly Asp Ser Tyr Leu Asn Trp Tyr Gln Gln Ile Pro Gly Gln Pro
    850                 855                 860

Pro Lys Leu Leu Ile Tyr Asp Ala Ser Asn Leu Val Ser Gly Ile Pro
865                 870                 875                 880

Pro Arg Phe Ser Gly Ser Gly Ser Gly Thr Asp Phe Thr Leu Asn Ile
                885                 890                 895

His Pro Val Glu Lys Val Asp Ala Ala Thr Tyr His Cys Gln Gln Ser
            900                 905                 910

Thr Glu Asp Pro Trp Thr Phe Gly Gly Gly Thr Lys Leu Glu Ile Lys
        915                 920                 925


<210> SEQ ID NO 317
<211> LENGTH: 8
<212> TYPE: PRT
<213> ORGANISM: Homo sapiens

<400> SEQUENCE: 317

Gly Phe Thr Val Ser Ser Asn Tyr
1               5


<210> SEQ ID NO 318
<211> LENGTH: 7
<212> TYPE: PRT
<213> ORGANISM: Homo sapiens

<400> SEQUENCE: 318
```

Ile Tyr Ser Gly Gly Ser Thr
1 5

<210> SEQ ID NO 319
<211> LENGTH: 9
<212> TYPE: PRT
<213> ORGANISM: Homo sapiens

<400> SEQUENCE: 319

Pro Ile Glu Leu Gly Ala Phe Asp Ile
1 5

<210> SEQ ID NO 320
<211> LENGTH: 8
<212> TYPE: PRT
<213> ORGANISM: Homo sapiens

<400> SEQUENCE: 320

Gly Phe Thr Phe Ser Asp Tyr Tyr
1 5

<210> SEQ ID NO 321
<211> LENGTH: 8
<212> TYPE: PRT
<213> ORGANISM: Homo sapiens

<400> SEQUENCE: 321

Ile Ser Ser Ser Gly Ser Thr Ile
1 5

<210> SEQ ID NO 322
<211> LENGTH: 9
<212> TYPE: PRT
<213> ORGANISM: Homo sapiens

<400> SEQUENCE: 322

Glu Asn Tyr Leu Asn Ala Phe Asp Ile
1 5

<210> SEQ ID NO 323
<211> LENGTH: 8
<212> TYPE: PRT
<213> ORGANISM: Homo sapiens

<400> SEQUENCE: 323

Gly Phe Thr Phe Ser Ser Tyr Ala
1 5

<210> SEQ ID NO 324
<211> LENGTH: 8
<212> TYPE: PRT
<213> ORGANISM: Homo sapiens

<400> SEQUENCE: 324

Ile Ser Gly Gly Gly Gly Thr Thr
1 5

<210> SEQ ID NO 325
<211> LENGTH: 8
<212> TYPE: PRT
<213> ORGANISM: Homo sapiens

<400> SEQUENCE: 325

Asp Ser Gly Val Ala Phe Asp Ile 1 5

<210> SEQ ID NO 326
<211> LENGTH: 10
<212> TYPE: PRT
<213> ORGANISM: Homo sapiens

<400> SEQUENCE: 326

Gly Asp Ser Val Ser Ser Asn Ser Ala Ala
1 5 10

<210> SEQ ID NO 327
<211> LENGTH: 9
<212> TYPE: PRT
<213> ORGANISM: Homo sapiens

<400> SEQUENCE: 327

Thr Tyr Tyr Arg Ser Lys Trp Tyr Asn
1 5

<210> SEQ ID NO 328
<211> LENGTH: 8
<212> TYPE: PRT
<213> ORGANISM: Homo sapiens

<400> SEQUENCE: 328

Ser Trp Asn Asp Ala Phe Asp Ile
1 5

<210> SEQ ID NO 329
<211> LENGTH: 10
<212> TYPE: PRT
<213> ORGANISM: Homo sapiens

<400> SEQUENCE: 329

Gly Asp Ser Val Ser Ser Asn Ser Ala Ala
1 5 10

<210> SEQ ID NO 330
<211> LENGTH: 9
<212> TYPE: PRT
<213> ORGANISM: Homo sapiens

<400> SEQUENCE: 330

Thr Tyr Tyr Arg Ser Lys Trp Tyr Asn
1 5

<210> SEQ ID NO 331
<211> LENGTH: 8
<212> TYPE: PRT
<213> ORGANISM: Homo sapiens

<400> SEQUENCE: 331

Asp Tyr Tyr Tyr Ser Met Asp Val
1 5

<210> SEQ ID NO 332
<211> LENGTH: 8
<212> TYPE: PRT
<213> ORGANISM: Homo sapiens

<400> SEQUENCE: 332

Gly Phe Thr Phe Ser Asp Tyr Tyr
1 5

<210> SEQ ID NO 333
<211> LENGTH: 8
<212> TYPE: PRT
<213> ORGANISM: Homo sapiens

<400> SEQUENCE: 333

Ile Ser Ser Ser Gly Ser Thr Ile
1               5

<210> SEQ ID NO 334
<211> LENGTH: 9
<212> TYPE: PRT
<213> ORGANISM: Homo sapiens

<400> SEQUENCE: 334

His Ser Trp Asn Asp Ala Phe Asp Val
1               5

<210> SEQ ID NO 335
<211> LENGTH: 10
<212> TYPE: PRT
<213> ORGANISM: Homo sapiens

<400> SEQUENCE: 335

Gly Asp Ser Val Ser Ser Asn Ser Ala Ala
1               5                   10

<210> SEQ ID NO 336
<211> LENGTH: 9
<212> TYPE: PRT
<213> ORGANISM: Homo sapiens

<400> SEQUENCE: 336

Thr Tyr Tyr Gly Ser Lys Trp Tyr Asn
1               5

<210> SEQ ID NO 337
<211> LENGTH: 8
<212> TYPE: PRT
<213> ORGANISM: Homo sapiens

<400> SEQUENCE: 337

Asp Tyr Tyr Tyr Ser Met Asp Val
1               5

<210> SEQ ID NO 338
<211> LENGTH: 8
<212> TYPE: PRT
<213> ORGANISM: Homo sapiens

<400> SEQUENCE: 338

Gly Phe Thr Phe Ser Asp Tyr Tyr
1               5

<210> SEQ ID NO 339
<211> LENGTH: 8
<212> TYPE: PRT
<213> ORGANISM: Homo sapiens

<400> SEQUENCE: 339

Ile Ser Ser Ser Gly Ser Thr Ile
1               5

<210> SEQ ID NO 340

<211> LENGTH: 9
<212> TYPE: PRT
<213> ORGANISM: Homo sapiens

<400> SEQUENCE: 340

His Ser Trp Ser Asp Ala Phe Asp Ile
1 5

<210> SEQ ID NO 341
<211> LENGTH: 8
<212> TYPE: PRT
<213> ORGANISM: Homo sapiens

<400> SEQUENCE: 341

Gly Phe Thr Phe Ser Asp Tyr Tyr
1 5

<210> SEQ ID NO 342
<211> LENGTH: 8
<212> TYPE: PRT
<213> ORGANISM: Homo sapiens

<400> SEQUENCE: 342

Ile Ser Ser Ser Gly Ser Thr Ile
1 5

<210> SEQ ID NO 343
<211> LENGTH: 9
<212> TYPE: PRT
<213> ORGANISM: Homo sapiens

<400> SEQUENCE: 343

His Ser Trp Asn Asp Ala Phe Asp Ile
1 5

<210> SEQ ID NO 344
<211> LENGTH: 8
<212> TYPE: PRT
<213> ORGANISM: Homo sapiens

<400> SEQUENCE: 344

Gly Tyr Ser Phe Thr Ser Tyr Trp
1 5

<210> SEQ ID NO 345
<211> LENGTH: 8
<212> TYPE: PRT
<213> ORGANISM: Homo sapiens

<400> SEQUENCE: 345

Ile Tyr Pro Gly Asp Ser Asp Thr
1 5

<210> SEQ ID NO 346
<211> LENGTH: 10
<212> TYPE: PRT
<213> ORGANISM: Homo sapiens

<400> SEQUENCE: 346

His Gln Val Asp Thr Arg Thr Ala Asp Tyr
1 5 10

<210> SEQ ID NO 347
<211> LENGTH: 6
<212> TYPE: PRT

<213> ORGANISM: Homo sapiens

<400> SEQUENCE: 347

Asn Ile Gly Ser Gln Ser
1 5

<210> SEQ ID NO 348
<211> LENGTH: 3
<212> TYPE: PRT
<213> ORGANISM: Homo sapiens

<400> SEQUENCE: 348

Tyr Asp Ser
1

<210> SEQ ID NO 349
<211> LENGTH: 11
<212> TYPE: PRT
<213> ORGANISM: Homo sapiens

<400> SEQUENCE: 349

Gln Val Trp Asp Ser Ser Ser Asp His Val Val
1 5 10

<210> SEQ ID NO 350
<211> LENGTH: 6
<212> TYPE: PRT
<213> ORGANISM: Homo sapiens

<400> SEQUENCE: 350

Gln Ser Leu Ser Asn Tyr
1 5

<210> SEQ ID NO 351
<211> LENGTH: 3
<212> TYPE: PRT
<213> ORGANISM: Homo sapiens

<400> SEQUENCE: 351

Ala Ala Ser
1

<210> SEQ ID NO 352
<211> LENGTH: 9
<212> TYPE: PRT
<213> ORGANISM: Homo sapiens

<400> SEQUENCE: 352

Gln Gln Ser Tyr Ser Thr Pro Leu Thr
1 5

<210> SEQ ID NO 353
<211> LENGTH: 6
<212> TYPE: PRT
<213> ORGANISM: Homo sapiens

<400> SEQUENCE: 353

Gln Asn Ile Arg Thr Trp
1 5

<210> SEQ ID NO 354
<211> LENGTH: 3
<212> TYPE: PRT
<213> ORGANISM: Homo sapiens

<400> SEQUENCE: 354

Asp Ala Ser
1

<210> SEQ ID NO 355
<211> LENGTH: 9
<212> TYPE: PRT
<213> ORGANISM: Homo sapiens

<400> SEQUENCE: 355

Gln Gln Phe Lys Arg Tyr Pro Pro Thr
1               5

<210> SEQ ID NO 356
<211> LENGTH: 6
<212> TYPE: PRT
<213> ORGANISM: Homo sapiens

<400> SEQUENCE: 356

Gln Ser Ile Ser Thr Trp
1               5

<210> SEQ ID NO 357
<211> LENGTH: 3
<212> TYPE: PRT
<213> ORGANISM: Homo sapiens

<400> SEQUENCE: 357

Asp Ala Ser
1

<210> SEQ ID NO 358
<211> LENGTH: 9
<212> TYPE: PRT
<213> ORGANISM: Homo sapiens

<400> SEQUENCE: 358

Gln Gln Ser Tyr Ser Thr Pro Leu Thr
1               5

<210> SEQ ID NO 359
<211> LENGTH: 6
<212> TYPE: PRT
<213> ORGANISM: Homo sapiens

<400> SEQUENCE: 359

Gln Ser Ile Ser Ser Trp
1               5

<210> SEQ ID NO 360
<211> LENGTH: 3
<212> TYPE: PRT
<213> ORGANISM: Homo sapiens

<400> SEQUENCE: 360

Asp Ala Ser
1

<210> SEQ ID NO 361
<211> LENGTH: 9
<212> TYPE: PRT
<213> ORGANISM: Homo sapiens

<400> SEQUENCE: 361

Gln Gln Ser His Ser His Pro Pro Thr
1 5

<210> SEQ ID NO 362
<211> LENGTH: 6
<212> TYPE: PRT
<213> ORGANISM: Homo sapiens

<400> SEQUENCE: 362

Gln Ser Ile Ser Ser Tyr
1 5

<210> SEQ ID NO 363
<211> LENGTH: 3
<212> TYPE: PRT
<213> ORGANISM: Homo sapiens

<400> SEQUENCE: 363

Ala Ala Ser
1

<210> SEQ ID NO 364
<211> LENGTH: 9
<212> TYPE: PRT
<213> ORGANISM: Homo sapiens

<400> SEQUENCE: 364

Gln Gln Ser Tyr Ser Thr Pro Asp Thr
1 5

<210> SEQ ID NO 365
<211> LENGTH: 6
<212> TYPE: PRT
<213> ORGANISM: Homo sapiens

<400> SEQUENCE: 365

Gln Ser Ile Ser Thr Trp
1 5

<210> SEQ ID NO 366
<211> LENGTH: 3
<212> TYPE: PRT
<213> ORGANISM: Homo sapiens

<400> SEQUENCE: 366

Asp Ala Ser
1

<210> SEQ ID NO 367
<211> LENGTH: 9
<212> TYPE: PRT
<213> ORGANISM: Homo sapiens

<400> SEQUENCE: 367

Gln Gln Ser Tyr Ser Thr Pro Val Thr
1 5

<210> SEQ ID NO 368
<211> LENGTH: 6
<212> TYPE: PRT
<213> ORGANISM: Homo sapiens

<400> SEQUENCE: 368

Gln Asp Ile Ser Asn Tyr
1 5

<210> SEQ ID NO 369
<211> LENGTH: 3
<212> TYPE: PRT
<213> ORGANISM: Homo sapiens

<400> SEQUENCE: 369

Asp Ala Ser
1

<210> SEQ ID NO 370
<211> LENGTH: 9
<212> TYPE: PRT
<213> ORGANISM: Homo sapiens

<400> SEQUENCE: 370

Gln Gln Ser Tyr Ser Thr Pro Leu Thr
1 5

<210> SEQ ID NO 371
<211> LENGTH: 6
<212> TYPE: PRT
<213> ORGANISM: Homo sapiens

<400> SEQUENCE: 371

Gln Ser Ile Ser Ser His
1 5

<210> SEQ ID NO 372
<211> LENGTH: 3
<212> TYPE: PRT
<213> ORGANISM: Homo sapiens

<400> SEQUENCE: 372

Ala Ala Ser
1

<210> SEQ ID NO 373
<211> LENGTH: 9
<212> TYPE: PRT
<213> ORGANISM: Homo sapiens

<400> SEQUENCE: 373

Gln Gln Ser Tyr Ser Thr Leu Leu Thr
1 5

<210> SEQ ID NO 374
<211> LENGTH: 9
<212> TYPE: PRT
<213> ORGANISM: Homo sapiens

<400> SEQUENCE: 374

Arg Ser Asp Val Gly Gly Tyr Asn Tyr
1 5

<210> SEQ ID NO 375
<211> LENGTH: 3
<212> TYPE: PRT
<213> ORGANISM: Homo sapiens

<400> SEQUENCE: 375

Glu Val Ser
1

<210> SEQ ID NO 376
<211> LENGTH: 10
<212> TYPE: PRT
<213> ORGANISM: Homo sapiens

<400> SEQUENCE: 376

Ser Ser Tyr Thr Ser Thr Ser Thr Leu Val
1               5                   10

<210> SEQ ID NO 377
<211> LENGTH: 661
<212> TYPE: PRT
<213> ORGANISM: Artificial Sequence
<220> FEATURE:
<223> OTHER INFORMATION: Synthetic, Anti-Chick Lysozyme x FS1-67 Fcab
      (EGFR binding domain)

<400> SEQUENCE: 377

Ala Ser Asp Ile Gln Met Thr Gln Ser Pro Ser Ser Leu Ser Ala Ser
1               5                   10                  15

Val Gly Asp Arg Val Thr Ile Thr Cys Arg Ala Ser Gly Asn Ile His
            20                  25                  30

Asn Tyr Leu Ala Trp Tyr Gln Gln Lys Pro Gly Lys Ala Pro Lys Leu
        35                  40                  45

Leu Ile Tyr Tyr Thr Thr Thr Leu Ala Asp Gly Val Pro Ser Arg Phe
    50                  55                  60

Ser Gly Ser Gly Ser Gly Thr Asp Tyr Thr Phe Thr Ile Ser Ser Leu
65                  70                  75                  80

Gln Pro Glu Asp Ile Ala Thr Tyr Tyr Cys Gln His Phe Trp Ser Thr
                85                  90                  95

Pro Arg Thr Phe Gly Gln Gly Thr Lys Val Glu Ile Lys Arg Thr Ala
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Leu Tyr Ala Cys Glu Val Thr His Gln Gly Leu Ser Ser Pro Val Thr
        195                 200                 205

Lys Ser Phe Asn Arg Gly Glu Cys Gln Val Gln Leu Gln Glu Ser Gly
    210                 215                 220

Pro Gly Leu Val Arg Pro Ser Gln Thr Leu Ser Leu Thr Cys Thr Val
225                 230                 235                 240

Ser Gly Ser Thr Phe Ser Gly Tyr Gly Val Asn Trp Val Arg Gln Pro
                245                 250                 255

Pro Gly Arg Gly Leu Glu Trp Ile Gly Met Ile Trp Gly Asp Gly Asn
            260                 265                 270

Thr Asp Tyr Asn Ser Ala Leu Lys Ser Arg Val Thr Met Leu Val Asp
        275                 280                 285

Thr Ser Lys Asn Gln Phe Ser Leu Arg Leu Ser Ser Val Thr Ala Ala
    290                 295                 300

Asp Thr Ala Val Tyr Tyr Cys Ala Arg Glu Arg Asp Tyr Arg Leu Asp

-continued

```
305                 310                 315                 320

Tyr Trp Gly Gln Gly Ser Leu Val Thr Val Ser Ser Ala Ser Thr Lys
                325                 330                 335

Gly Pro Ser Val Phe Pro Leu Ala Pro Ser Ser Lys Ser Thr Ser Gly
            340                 345                 350

Gly Thr Ala Ala Leu Gly Cys Leu Val Lys Asp Tyr Phe Pro Glu Pro
        355                 360                 365

Val Thr Val Ser Trp Asn Ser Gly Ala Leu Thr Ser Gly Val His Thr
    370                 375                 380

Phe Pro Ala Val Leu Gln Ser Ser Gly Leu Tyr Ser Leu Ser Ser Val
385                 390                 395                 400

Val Thr Val Pro Ser Ser Ser Leu Gly Thr Gln Thr Tyr Ile Cys Asn
                405                 410                 415

Val Asn His Lys Pro Ser Asn Thr Lys Val Asp Lys Lys Val Glu Pro
            420                 425                 430

Lys Ser Cys Asp Lys Thr His Thr Cys Pro Pro Cys Pro Ala Pro Glu
        435                 440                 445

Leu Ala Gly Ala Pro Ser Val Phe Leu Phe Pro Pro Lys Pro Lys Asp
    450                 455                 460

Thr Leu Met Ile Ser Arg Thr Pro Glu Val Thr Cys Val Val Val Asp
465                 470                 475                 480

Val Ser His Glu Asp Pro Glu Val Lys Phe Asn Trp Tyr Val Asp Gly
                485                 490                 495

Val Glu Val His Asn Ala Lys Thr Lys Pro Arg Glu Glu Gln Tyr Asn
            500                 505                 510

Ser Thr Tyr Arg Val Val Ser Val Leu Thr Val Leu His Gln Asp Trp
        515                 520                 525

Leu Asn Gly Lys Glu Tyr Lys Cys Lys Val Ser Asn Lys Ala Leu Pro
    530                 535                 540

Ala Pro Ile Glu Lys Thr Ile Ser Lys Ala Lys Gly Gln Pro Arg Glu
545                 550                 555                 560

Pro Gln Val Tyr Thr Leu Pro Pro Ser Arg Asp Glu Thr Asp Asp Gly
                565                 570                 575

Pro Val Ser Leu Thr Cys Leu Val Lys Gly Phe Tyr Pro Ser Asp Ile
            580                 585                 590

Ala Val Glu Trp Glu Ser Thr Tyr Gly Pro Glu Asn Asn Tyr Lys Thr
        595                 600                 605

Thr Pro Pro Val Leu Asp Ser Asp Gly Ser Phe Phe Leu Tyr Ser Lys
    610                 615                 620

Leu Thr Val Ser Tyr Trp Arg Trp Tyr Lys Gly Asn Val Phe Ser Cys
625                 630                 635                 640

Ser Val Met His Glu Ala Leu His Asn His Tyr Thr Gln Lys Ser Leu
                645                 650                 655

Ser Leu Ser Pro Gly
            660


<210> SEQ ID NO 378
<211> LENGTH: 662
<212> TYPE: PRT
<213> ORGANISM: Homo sapiens

<400> SEQUENCE: 378

Ala Ser Ser Tyr Glu Leu Thr Gln Pro Pro Ser Val Ser Val Ala Pro
1               5                   10                  15
```

-continued

```
Gly Lys Thr Ala Arg Ile Thr Cys Gly Gly Asn Asn Ile Gly Ser Gln
            20                  25                  30

Ser Val His Trp Tyr Gln Gln Lys Pro Gly Gln Ala Pro Met Leu Val
        35                  40                  45

Ile Tyr Tyr Asp Ser Asp Arg Pro Ser Gly Ile Pro Glu Arg Phe Ser
    50                  55                  60

Gly Ser Asn Ser Gly Asn Thr Ala Thr Leu Thr Ile Ser Arg Val Glu
65                  70                  75                  80

Ala Gly Asp Glu Ala Asp Tyr Tyr Cys Gln Val Trp Asp Ser Ser Ser
                85                  90                  95

Asp His Val Val Phe Gly Gly Gly Thr Lys Leu Thr Val Leu Gly Gln
            100                 105                 110

Pro Ala Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser Glu Val Gln Leu Leu Glu Ser Gly
    210                 215                 220

Gly Gly Leu Val Gln Pro Gly Arg Ser Leu Arg Leu Ser Cys Ala Ala
225                 230                 235                 240

Ser Gly Phe Thr Val Ser Ser Asn Tyr Met Ser Trp Val Arg Gln Ala
                245                 250                 255

Pro Gly Lys Gly Leu Glu Trp Val Ser Val Ile Tyr Ser Gly Gly Ser
            260                 265                 270

Thr Tyr Tyr Ala Asp Ser Val Lys Gly Arg Phe Thr Ile Ser Arg Asp
        275                 280                 285

Asn Ser Lys Asn Thr Leu Tyr Leu Gln Met Asn Ser Leu Arg Ala Glu
    290                 295                 300

Asp Thr Ala Val Tyr Tyr Cys Ala Ser Pro Ile Glu Leu Gly Ala Phe
305                 310                 315                 320

Asp Ile Trp Gly Gln Gly Thr Leu Val Thr Val Ser Ser Ala Ser Thr
                325                 330                 335

Lys Gly Pro Ser Val Phe Pro Leu Ala Pro Ser Ser Lys Ser Thr Ser
            340                 345                 350

Gly Gly Thr Ala Ala Leu Gly Cys Leu Val Lys Asp Tyr Phe Pro Glu
        355                 360                 365

Pro Val Thr Val Ser Trp Asn Ser Gly Ala Leu Thr Ser Gly Val His
    370                 375                 380

Thr Phe Pro Ala Val Leu Gln Ser Ser Gly Leu Tyr Ser Leu Ser Ser
385                 390                 395                 400

Val Val Thr Val Pro Ser Ser Ser Leu Gly Thr Gln Thr Tyr Ile Cys
                405                 410                 415

Asn Val Asn His Lys Pro Ser Asn Thr Lys Val Asp Lys Lys Val Glu
            420                 425                 430

Pro Lys Ser Cys Asp Lys Thr His Thr Cys Pro Pro Cys Pro Ala Pro
```

```
        435                 440                 445

Glu Leu Ala Gly Ala Pro Ser Val Phe Leu Phe Pro Pro Lys Pro Lys
    450                 455                 460

Asp Thr Leu Met Ile Ser Arg Thr Pro Glu Val Thr Cys Val Val Val
465                 470                 475                 480

Asp Val Ser His Glu Asp Pro Glu Val Lys Phe Asn Trp Tyr Val Asp
                485                 490                 495

Gly Val Glu Val His Asn Ala Lys Thr Lys Pro Arg Glu Glu Gln Tyr
            500                 505                 510

Asn Ser Thr Tyr Arg Val Val Ser Val Leu Thr Val Leu His Gln Asp
        515                 520                 525

Trp Leu Asn Gly Lys Glu Tyr Lys Cys Lys Val Ser Asn Lys Ala Leu
    530                 535                 540

Pro Ala Pro Ile Glu Lys Thr Ile Ser Lys Ala Lys Gly Gln Pro Arg
545                 550                 555                 560

Glu Pro Gln Val Tyr Thr Leu Pro Pro Ser Arg Asp Glu Thr Asp Asp
                565                 570                 575

Gly Pro Val Ser Leu Thr Cys Leu Val Lys Gly Phe Tyr Pro Ser Asp
            580                 585                 590

Ile Ala Val Glu Trp Glu Ser Thr Tyr Gly Pro Glu Asn Asn Tyr Lys
        595                 600                 605

Thr Thr Pro Pro Val Leu Asp Ser Asp Gly Ser Phe Phe Leu Tyr Ser
    610                 615                 620

Lys Leu Thr Val Ser Tyr Trp Arg Trp Tyr Lys Gly Asn Val Phe Ser
625                 630                 635                 640

Cys Ser Val Met His Glu Ala Leu His Asn His Tyr Thr Gln Lys Ser
                645                 650                 655

Leu Ser Leu Ser Pro Gly
            660


<210> SEQ ID NO 379
<211> LENGTH: 666
<212> TYPE: PRT
<213> ORGANISM: Homo sapiens

<400> SEQUENCE: 379

Ala Ser Asp Ile Gln Met Thr Gln Ser Pro Pro Ala Leu Ser Ala Ser
1               5                   10                  15

Val Gly Asp Arg Val Thr Ile Thr Cys Arg Ala Ser Gln Asp Ile Asn
            20                  25                  30

Asp Trp Leu Ala Trp Tyr Gln His Lys Pro Gly Lys Ala Pro Lys Leu
        35                  40                  45

Leu Ile Tyr Asp Ala Ser Ser Leu Glu Ser Gly Val Pro Ser Arg Phe
    50                  55                  60

Ser Gly Ser Gly Ser Gly Thr Glu Phe Thr Leu Thr Ile Ser Ser Leu
65                  70                  75                  80

Gln Pro Asp Asp Phe Ala Thr Tyr Tyr Cys Gln Gln Ser Tyr Ser Thr
                85                  90                  95

Pro Gln Val Thr Phe Gly Gln Gly Thr Arg Leu Glu Ile Lys Arg Thr
            100                 105                 110

Ala Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140
```

-continued

```
Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Leu Tyr Ala Cys Glu Val Thr His Gln Gly Leu Ser Ser Pro Val
        195                 200                 205

Thr Lys Ser Phe Asn Arg Gly Glu Cys Gln Val Gln Leu Gln Gln Ser
    210                 215                 220

Gly Pro Gly Leu Val Lys Pro Ser Gln Thr Leu Ser Leu Thr Cys Ala
225                 230                 235                 240

Ile Ser Gly Asp Ser Val Ser Ser Lys Ser Ala Ala Trp Asn Trp Ile
                245                 250                 255

Arg Gln Ser Pro Ser Arg Gly Leu Glu Trp Leu Gly Arg Thr Tyr Tyr
            260                 265                 270

Arg Ser Lys Trp Ser Thr Asp Tyr Ala Ala Ser Val Lys Ser Arg Ile
        275                 280                 285

Thr Ile Asn Pro Asp Thr Ser Lys Asn Gln Leu Ser Leu Gln Leu Asn
    290                 295                 300

Ser Val Thr Pro Glu Asp Thr Ala Val Tyr Tyr Cys Ala Arg Thr Trp
305                 310                 315                 320

Ser Gly Tyr Val Asp Val Trp Gly Gln Gly Thr Leu Val Thr Val Ser
                325                 330                 335

Ser Ala Ser Thr Lys Gly Pro Ser Val Phe Pro Leu Ala Pro Ser Ser
            340                 345                 350

Lys Ser Thr Ser Gly Gly Thr Ala Ala Leu Gly Cys Leu Val Lys Asp
        355                 360                 365

Tyr Phe Pro Glu Pro Val Thr Val Ser Trp Asn Ser Gly Ala Leu Thr
    370                 375                 380

Ser Gly Val His Thr Phe Pro Ala Val Leu Gln Ser Ser Gly Leu Tyr
385                 390                 395                 400

Ser Leu Ser Ser Val Val Thr Val Pro Ser Ser Ser Leu Gly Thr Gln
                405                 410                 415

Thr Tyr Ile Cys Asn Val Asn His Lys Pro Ser Asn Thr Lys Val Asp
            420                 425                 430

Lys Lys Val Glu Pro Lys Ser Cys Asp Lys Thr His Thr Cys Pro Pro
        435                 440                 445

Cys Pro Ala Pro Glu Leu Ala Gly Ala Pro Ser Val Phe Leu Phe Pro
    450                 455                 460

Pro Lys Pro Lys Asp Thr Leu Met Ile Ser Arg Thr Pro Glu Val Thr
465                 470                 475                 480

Cys Val Val Val Asp Val Ser His Glu Asp Pro Glu Val Lys Phe Asn
                485                 490                 495

Trp Tyr Val Asp Gly Val Glu Val His Asn Ala Lys Thr Lys Pro Arg
            500                 505                 510

Glu Glu Gln Tyr Asn Ser Thr Tyr Arg Val Val Ser Val Leu Thr Val
        515                 520                 525

Leu His Gln Asp Trp Leu Asn Gly Lys Glu Tyr Lys Cys Lys Val Ser
    530                 535                 540

Asn Lys Ala Leu Pro Ala Pro Ile Glu Lys Thr Ile Ser Lys Ala Lys
545                 550                 555                 560

Gly Gln Pro Arg Glu Pro Gln Val Tyr Thr Leu Pro Pro Ser Arg Asp
```

-continued

```
                565                 570                 575

Glu Thr Asp Asp Gly Pro Val Ser Leu Thr Cys Leu Val Lys Gly Phe
            580                 585                 590

Tyr Pro Ser Asp Ile Ala Val Glu Trp Glu Ser Thr Tyr Gly Pro Glu
        595                 600                 605

Asn Asn Tyr Lys Thr Thr Pro Pro Val Leu Asp Ser Asp Gly Ser Phe
    610                 615                 620

Phe Leu Tyr Ser Lys Leu Thr Val Ser Tyr Trp Arg Trp Tyr Lys Gly
625                 630                 635                 640

Asn Val Phe Ser Cys Ser Val Met His Glu Ala Leu His Asn His Tyr
                645                 650                 655

Thr Gln Lys Ser Leu Ser Leu Ser Pro Gly
            660                 665


<210> SEQ ID NO 380
<211> LENGTH: 663
<212> TYPE: PRT
<213> ORGANISM: Homo sapiens

<400> SEQUENCE: 380

Ala Ser Asp Ile Gln Met Thr Gln Ser Pro Ser Ser Leu Ser Ala Ser
1               5                   10                  15

Val Gly Asp Arg Val Thr Ile Ala Cys Arg Ala Gly Gln Ser Ile Gly
            20                  25                  30

Thr Tyr Leu Asn Trp Tyr Gln Gln Lys Pro Gly Lys Ala Pro Lys Leu
        35                  40                  45

Leu Ile Tyr Val Ala Ser Ser Leu Gln Ser Gly Val Pro Ser Arg Phe
    50                  55                  60

Ser Gly Ser Gly Ser Gly Thr Glu Phe Thr Leu Thr Ile Ser Ser Leu
65                  70                  75                  80

Gln Pro Glu Asp Phe Ala Thr Tyr Tyr Cys Gln Gln Ser Tyr Ser Thr
                85                  90                  95

Leu Leu Thr Phe Gly Arg Gly Thr Lys Val Glu Ile Lys Arg Thr Ala
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Leu Tyr Ala Cys Glu Val Thr His Gln Gly Leu Ser Ser Pro Val Thr
        195                 200                 205

Lys Ser Phe Asn Arg Gly Glu Cys Gln Val Gln Leu Val Glu Ser Gly
    210                 215                 220

Gly Gly Leu Val Lys Pro Gly Gly Ser Leu Arg Leu Ser Cys Ala Ala
225                 230                 235                 240

Ser Gly Phe Thr Phe Ser Asp Tyr Tyr Met Ser Trp Ile Arg Gln Ala
                245                 250                 255

Pro Gly Lys Gly Leu Glu Trp Val Ser Tyr Ile Ser Ser Ser Gly Ser
            260                 265                 270
```

```
Thr Ile Tyr Tyr Ala Asp Ser Val Lys Gly Arg Phe Thr Ile Ser Arg
        275                 280                 285

Asp Asn Ala Lys Asn Ser Leu Tyr Leu Gln Met Asn Ser Leu Arg Ala
    290                 295                 300

Glu Asp Thr Ala Val Tyr Tyr Cys Ala Arg Val Asp Tyr Ala Asp Ala
305                 310                 315                 320

Phe Asp Ile Trp Gly Gln Gly Thr Leu Val Thr Val Ser Ser Ala Ser
                325                 330                 335

Thr Lys Gly Pro Ser Val Phe Pro Leu Ala Pro Ser Ser Lys Ser Thr
            340                 345                 350

Ser Gly Gly Thr Ala Ala Leu Gly Cys Leu Val Lys Asp Tyr Phe Pro
        355                 360                 365

Glu Pro Val Thr Val Ser Trp Asn Ser Gly Ala Leu Thr Ser Gly Val
    370                 375                 380

His Thr Phe Pro Ala Val Leu Gln Ser Ser Gly Leu Tyr Ser Leu Ser
385                 390                 395                 400

Ser Val Val Thr Val Pro Ser Ser Ser Leu Gly Thr Gln Thr Tyr Ile
                405                 410                 415

Cys Asn Val Asn His Lys Pro Ser Asn Thr Lys Val Asp Lys Lys Val
            420                 425                 430

Glu Pro Lys Ser Cys Asp Lys Thr His Thr Cys Pro Pro Cys Pro Ala
        435                 440                 445

Pro Glu Leu Ala Gly Ala Pro Ser Val Phe Leu Phe Pro Pro Lys Pro
    450                 455                 460

Lys Asp Thr Leu Met Ile Ser Arg Thr Pro Glu Val Thr Cys Val Val
465                 470                 475                 480

Val Asp Val Ser His Glu Asp Pro Glu Val Lys Phe Asn Trp Tyr Val
                485                 490                 495

Asp Gly Val Glu Val His Asn Ala Lys Thr Lys Pro Arg Glu Glu Gln
            500                 505                 510

Tyr Asn Ser Thr Tyr Arg Val Val Ser Val Leu Thr Val Leu His Gln
        515                 520                 525

Asp Trp Leu Asn Gly Lys Glu Tyr Lys Cys Lys Val Ser Asn Lys Ala
    530                 535                 540

Leu Pro Ala Pro Ile Glu Lys Thr Ile Ser Lys Ala Lys Gly Gln Pro
545                 550                 555                 560

Arg Glu Pro Gln Val Tyr Thr Leu Pro Pro Ser Arg Asp Glu Thr Asp
                565                 570                 575

Asp Gly Pro Val Ser Leu Thr Cys Leu Val Lys Gly Phe Tyr Pro Ser
            580                 585                 590

Asp Ile Ala Val Glu Trp Glu Ser Thr Tyr Gly Pro Glu Asn Asn Tyr
        595                 600                 605

Lys Thr Thr Pro Pro Val Leu Asp Ser Asp Gly Ser Phe Phe Leu Tyr
    610                 615                 620

Ser Lys Leu Thr Val Ser Tyr Trp Arg Trp Tyr Lys Gly Asn Val Phe
625                 630                 635                 640

Ser Cys Ser Val Met His Glu Ala Leu His Asn His Tyr Thr Gln Lys
                645                 650                 655

Ser Leu Ser Leu Ser Pro Gly
            660
```

<210> SEQ ID NO 381
<211> LENGTH: 917
<212> TYPE: PRT

<213> ORGANISM: Artificial Sequence
<220> FEATURE:
<223> OTHER INFORMATION: Synthetic, Anti-Chick Lysozyme x linker
Cetuximav scFV (EGFR binding domain as a Morrison body at C-term
of CH3)

<400> SEQUENCE: 381

```
Ala Ser Asp Ile Gln Met Thr Gln Ser Pro Ser Ser Leu Ser Ala Ser
1               5                   10                  15

Val Gly Asp Arg Val Thr Ile Thr Cys Arg Ala Ser Gly Asn Ile His
            20                  25                  30

Asn Tyr Leu Ala Trp Tyr Gln Gln Lys Pro Gly Lys Ala Pro Lys Leu
        35                  40                  45

Leu Ile Tyr Tyr Thr Thr Thr Leu Ala Asp Gly Val Pro Ser Arg Phe
    50                  55                  60

Ser Gly Ser Gly Ser Gly Thr Asp Tyr Thr Phe Thr Ile Ser Ser Leu
65                  70                  75                  80

Gln Pro Glu Asp Ile Ala Thr Tyr Tyr Cys Gln His Phe Trp Ser Thr
                85                  90                  95

Pro Arg Thr Phe Gly Gln Gly Thr Lys Val Glu Ile Lys Arg Thr Ala
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Leu Tyr Ala Cys Glu Val Thr His Gln Gly Leu Ser Ser Pro Val Thr
        195                 200                 205

Lys Ser Phe Asn Arg Gly Glu Cys Gln Val Gln Leu Gln Glu Ser Gly
    210                 215                 220

Pro Gly Leu Val Arg Pro Ser Gln Thr Leu Ser Leu Thr Cys Thr Val
225                 230                 235                 240

Ser Gly Ser Thr Phe Ser Gly Tyr Gly Val Asn Trp Val Arg Gln Pro
                245                 250                 255

Pro Gly Arg Gly Leu Glu Trp Ile Gly Met Ile Trp Gly Asp Gly Asn
            260                 265                 270

Thr Asp Tyr Asn Ser Ala Leu Lys Ser Arg Val Thr Met Leu Val Asp
        275                 280                 285

Thr Ser Lys Asn Gln Phe Ser Leu Arg Leu Ser Ser Val Thr Ala Ala
    290                 295                 300

Asp Thr Ala Val Tyr Tyr Cys Ala Arg Glu Arg Asp Tyr Arg Leu Asp
305                 310                 315                 320

Tyr Trp Gly Gln Gly Ser Leu Val Thr Val Ser Ser Ala Ser Thr Lys
                325                 330                 335

Gly Pro Ser Val Phe Pro Leu Ala Pro Ser Ser Lys Ser Thr Ser Gly
            340                 345                 350

Gly Thr Ala Ala Leu Gly Cys Leu Val Lys Asp Tyr Phe Pro Glu Pro
        355                 360                 365

Val Thr Val Ser Trp Asn Ser Gly Ala Leu Thr Ser Gly Val His Thr
    370                 375                 380
```

-continued

```
Phe Pro Ala Val Leu Gln Ser Ser Gly Leu Tyr Ser Leu Ser Ser Val
385                 390                 395                 400

Val Thr Val Pro Ser Ser Ser Leu Gly Thr Gln Thr Tyr Ile Cys Asn
                405                 410                 415

Val Asn His Lys Pro Ser Asn Thr Lys Val Asp Lys Lys Val Glu Pro
            420                 425                 430

Lys Ser Cys Asp Lys Thr His Thr Cys Pro Pro Cys Pro Ala Pro Glu
        435                 440                 445

Leu Ala Gly Ala Pro Ser Val Phe Leu Phe Pro Pro Lys Pro Lys Asp
    450                 455                 460

Thr Leu Met Ile Ser Arg Thr Pro Glu Val Thr Cys Val Val Val Asp
465                 470                 475                 480

Val Ser His Glu Asp Pro Glu Val Lys Phe Asn Trp Tyr Val Asp Gly
                485                 490                 495

Val Glu Val His Asn Ala Lys Thr Lys Pro Arg Glu Glu Gln Tyr Asn
            500                 505                 510

Ser Thr Tyr Arg Val Val Ser Val Leu Thr Val Leu His Gln Asp Trp
        515                 520                 525

Leu Asn Gly Lys Glu Tyr Lys Cys Lys Val Ser Asn Lys Ala Leu Pro
    530                 535                 540

Ala Pro Ile Glu Lys Thr Ile Ser Lys Ala Lys Gly Gln Pro Arg Glu
545                 550                 555                 560

Pro Gln Val Tyr Thr Leu Pro Pro Ser Arg Asp Glu Leu Thr Lys Asn
                565                 570                 575

Gln Val Ser Leu Thr Cys Leu Val Lys Gly Phe Tyr Pro Ser Asp Ile
            580                 585                 590

Ala Val Glu Trp Glu Ser Asn Gly Gln Pro Glu Asn Asn Tyr Lys Thr
        595                 600                 605

Thr Pro Pro Val Leu Asp Ser Asp Gly Ser Phe Phe Leu Tyr Ser Lys
    610                 615                 620

Leu Thr Val Asp Lys Ser Arg Trp Gln Gln Gly Asn Val Phe Ser Cys
625                 630                 635                 640

Ser Val Met His Glu Ala Leu His Asn His Tyr Thr Gln Lys Ser Leu
                645                 650                 655

Ser Leu Ser Pro Gly Gly Gly Gly Gly Ser Gly Gly Gly Gly Ser Gly
            660                 665                 670

Gly Gly Gly Ser Gln Val Gln Leu Lys Gln Ser Gly Pro Gly Leu Val
        675                 680                 685

Gln Pro Ser Gln Ser Leu Ser Ile Thr Cys Thr Val Ser Gly Phe Ser
    690                 695                 700

Leu Thr Asn Tyr Gly Val His Trp Val Arg Gln Ser Pro Gly Lys Gly
705                 710                 715                 720

Leu Glu Trp Leu Gly Val Ile Trp Ser Gly Gly Asn Thr Asp Tyr Asn
                725                 730                 735

Thr Pro Phe Thr Ser Arg Leu Ser Ile Asn Lys Asp Asn Ser Lys Ser
            740                 745                 750

Gln Val Phe Phe Lys Met Asn Ser Leu Gln Ser Asn Asp Thr Ala Ile
        755                 760                 765

Tyr Tyr Cys Ala Arg Ala Leu Thr Tyr Tyr Asp Tyr Glu Phe Ala Tyr
    770                 775                 780

Trp Gly Gln Gly Thr Leu Val Thr Val Ser Ala Gly Gly Gly Gly Ser
785                 790                 795                 800
```

```
Gly Gly Gly Gly Ser Gly Gly Gly Gly Ser Asp Ile Leu Leu Thr Gln
                805                 810                 815

Ser Pro Val Ile Leu Ser Val Ser Pro Gly Glu Arg Val Ser Phe Ser
            820                 825                 830

Cys Arg Ala Ser Gln Ser Ile Gly Thr Asn Ile His Trp Tyr Gln Gln
        835                 840                 845

Arg Thr Asn Gly Ser Pro Arg Leu Leu Ile Lys Tyr Ala Ser Glu Ser
    850                 855                 860

Ile Ser Gly Ile Pro Ser Arg Phe Ser Gly Ser Gly Ser Gly Thr Asp
865                 870                 875                 880

Phe Thr Leu Ser Ile Asn Ser Val Glu Ser Glu Asp Ile Ala Asp Tyr
                885                 890                 895

Tyr Cys Gln Gln Asn Asn Asn Trp Pro Thr Thr Phe Gly Ala Gly Thr
            900                 905                 910

Lys Leu Glu Leu Lys
        915


<210> SEQ ID NO 382
<211> LENGTH: 918
<212> TYPE: PRT
<213> ORGANISM: Homo sapiens

<400> SEQUENCE: 382

Ala Ser Ser Tyr Glu Leu Thr Gln Pro Pro Ser Val Ser Val Ala Pro
1               5                   10                  15

Gly Lys Thr Ala Arg Ile Thr Cys Gly Gly Asn Asn Ile Gly Ser Gln
            20                  25                  30

Ser Val His Trp Tyr Gln Gln Lys Pro Gly Gln Ala Pro Met Leu Val
        35                  40                  45

Ile Tyr Tyr Asp Ser Asp Arg Pro Ser Gly Ile Pro Glu Arg Phe Ser
    50                  55                  60

Gly Ser Asn Ser Gly Asn Thr Ala Thr Leu Thr Ile Ser Arg Val Glu
65                  70                  75                  80

Ala Gly Asp Glu Ala Asp Tyr Tyr Cys Gln Val Trp Asp Ser Ser Ser
                85                  90                  95

Asp His Val Val Phe Gly Gly Gly Thr Lys Leu Thr Val Leu Gly Gln
            100                 105                 110

Pro Ala Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser Glu Val Gln Leu Leu Glu Ser Gly
    210                 215                 220

Gly Gly Leu Val Gln Pro Gly Arg Ser Leu Arg Leu Ser Cys Ala Ala
225                 230                 235                 240

Ser Gly Phe Thr Val Ser Ser Asn Tyr Met Ser Trp Val Arg Gln Ala
                245                 250                 255
```

```
Pro Gly Lys Gly Leu Glu Trp Val Ser Val Ile Tyr Ser Gly Gly Ser
            260                 265                 270

Thr Tyr Tyr Ala Asp Ser Val Lys Gly Arg Phe Thr Ile Ser Arg Asp
        275                 280                 285

Asn Ser Lys Asn Thr Leu Tyr Leu Gln Met Asn Ser Leu Arg Ala Glu
    290                 295                 300

Asp Thr Ala Val Tyr Tyr Cys Ala Ser Pro Ile Glu Leu Gly Ala Phe
305                 310                 315                 320

Asp Ile Trp Gly Gln Gly Thr Leu Val Thr Val Ser Ser Ala Ser Thr
                325                 330                 335

Lys Gly Pro Ser Val Phe Pro Leu Ala Pro Ser Ser Lys Ser Thr Ser
            340                 345                 350

Gly Gly Thr Ala Ala Leu Gly Cys Leu Val Lys Asp Tyr Phe Pro Glu
        355                 360                 365

Pro Val Thr Val Ser Trp Asn Ser Gly Ala Leu Thr Ser Gly Val His
    370                 375                 380

Thr Phe Pro Ala Val Leu Gln Ser Ser Gly Leu Tyr Ser Leu Ser Ser
385                 390                 395                 400

Val Val Thr Val Pro Ser Ser Ser Leu Gly Thr Gln Thr Tyr Ile Cys
                405                 410                 415

Asn Val Asn His Lys Pro Ser Asn Thr Lys Val Asp Lys Lys Val Glu
            420                 425                 430

Pro Lys Ser Cys Asp Lys Thr His Thr Cys Pro Pro Cys Pro Ala Pro
        435                 440                 445

Glu Leu Ala Gly Ala Pro Ser Val Phe Leu Phe Pro Pro Lys Pro Lys
    450                 455                 460

Asp Thr Leu Met Ile Ser Arg Thr Pro Glu Val Thr Cys Val Val Val
465                 470                 475                 480

Asp Val Ser His Glu Asp Pro Glu Val Lys Phe Asn Trp Tyr Val Asp
                485                 490                 495

Gly Val Glu Val His Asn Ala Lys Thr Lys Pro Arg Glu Glu Gln Tyr
            500                 505                 510

Asn Ser Thr Tyr Arg Val Val Ser Val Leu Thr Val Leu His Gln Asp
        515                 520                 525

Trp Leu Asn Gly Lys Glu Tyr Lys Cys Lys Val Ser Asn Lys Ala Leu
    530                 535                 540

Pro Ala Pro Ile Glu Lys Thr Ile Ser Lys Ala Lys Gly Gln Pro Arg
545                 550                 555                 560

Glu Pro Gln Val Tyr Thr Leu Pro Pro Ser Arg Asp Glu Leu Thr Lys
                565                 570                 575

Asn Gln Val Ser Leu Thr Cys Leu Val Lys Gly Phe Tyr Pro Ser Asp
            580                 585                 590

Ile Ala Val Glu Trp Glu Ser Asn Gly Gln Pro Glu Asn Asn Tyr Lys
        595                 600                 605

Thr Thr Pro Pro Val Leu Asp Ser Asp Gly Ser Phe Phe Leu Tyr Ser
    610                 615                 620

Lys Leu Thr Val Asp Lys Ser Arg Trp Gln Gln Gly Asn Val Phe Ser
625                 630                 635                 640

Cys Ser Val Met His Glu Ala Leu His Asn His Tyr Thr Gln Lys Ser
                645                 650                 655

Leu Ser Leu Ser Pro Gly Gly Gly Gly Gly Ser Gly Gly Gly Gly Ser
            660                 665                 670
```

Gly Gly Gly Gly Ser Gln Val Gln Leu Lys Gln Ser Gly Pro Gly Leu
675 680 685

Val Gln Pro Ser Gln Ser Leu Ser Ile Thr Cys Thr Val Ser Gly Phe
690 695 700

Ser Leu Thr Asn Tyr Gly Val His Trp Val Arg Gln Ser Pro Gly Lys
705 710 715 720

Gly Leu Glu Trp Leu Gly Val Ile Trp Ser Gly Gly Asn Thr Asp Tyr
725 730 735

Asn Thr Pro Phe Thr Ser Arg Leu Ser Ile Asn Lys Asp Asn Ser Lys
740 745 750

Ser Gln Val Phe Phe Lys Met Asn Ser Leu Gln Ser Asn Asp Thr Ala
755 760 765

Ile Tyr Tyr Cys Ala Arg Ala Leu Thr Tyr Tyr Asp Tyr Glu Phe Ala
770 775 780

Tyr Trp Gly Gln Gly Thr Leu Val Thr Val Ser Ala Gly Gly Gly Gly
785 790 795 800

Ser Gly Gly Gly Gly Ser Gly Gly Gly Gly Ser Asp Ile Leu Leu Thr
805 810 815

Gln Ser Pro Val Ile Leu Ser Val Ser Pro Gly Glu Arg Val Ser Phe
820 825 830

Ser Cys Arg Ala Ser Gln Ser Ile Gly Thr Asn Ile His Trp Tyr Gln
835 840 845

Gln Arg Thr Asn Gly Ser Pro Arg Leu Leu Ile Lys Tyr Ala Ser Glu
850 855 860

Ser Ile Ser Gly Ile Pro Ser Arg Phe Ser Gly Ser Gly Ser Gly Thr
865 870 875 880

Asp Phe Thr Leu Ser Ile Asn Ser Val Glu Ser Glu Asp Ile Ala Asp
885 890 895

Tyr Tyr Cys Gln Gln Asn Asn Asn Trp Pro Thr Thr Phe Gly Ala Gly
900 905 910

Thr Lys Leu Glu Leu Lys
915

<210> SEQ ID NO 383
<211> LENGTH: 922
<212> TYPE: PRT
<213> ORGANISM: Homo sapiens

<400> SEQUENCE: 383

Ala Ser Asp Ile Gln Met Thr Gln Ser Pro Pro Ala Leu Ser Ala Ser
1 5 10 15

Val Gly Asp Arg Val Thr Ile Thr Cys Arg Ala Ser Gln Asp Ile Asn
20 25 30

Asp Trp Leu Ala Trp Tyr Gln His Lys Pro Gly Lys Ala Pro Lys Leu
35 40 45

Leu Ile Tyr Asp Ala Ser Ser Leu Glu Ser Gly Val Pro Ser Arg Phe
50 55 60

Ser Gly Ser Gly Ser Gly Thr Glu Phe Thr Leu Thr Ile Ser Ser Leu
65 70 75 80

Gln Pro Asp Asp Phe Ala Thr Tyr Tyr Cys Gln Gln Ser Tyr Ser Thr
85 90 95

Pro Gln Val Thr Phe Gly Gln Gly Thr Arg Leu Glu Ile Lys Arg Thr
100 105 110

Ala Ala Ala Pro Ser Val Phe Ile Phe Pro Pro Ser Asp Glu Gln Leu
115 120 125

-continued

```
Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Leu Tyr Ala Cys Glu Val Thr His Gln Gly Leu Ser Ser Pro Val
        195                 200                 205

Thr Lys Ser Phe Asn Arg Gly Glu Cys Gln Val Gln Leu Gln Gln Ser
    210                 215                 220

Gly Pro Gly Leu Val Lys Pro Ser Gln Thr Leu Ser Leu Thr Cys Ala
225                 230                 235                 240

Ile Ser Gly Asp Ser Val Ser Ser Lys Ser Ala Ala Trp Asn Trp Ile
                245                 250                 255

Arg Gln Ser Pro Ser Arg Gly Leu Glu Trp Leu Gly Arg Thr Tyr Tyr
            260                 265                 270

Arg Ser Lys Trp Ser Thr Asp Tyr Ala Ala Ser Val Lys Ser Arg Ile
        275                 280                 285

Thr Ile Asn Pro Asp Thr Ser Lys Asn Gln Leu Ser Leu Gln Leu Asn
    290                 295                 300

Ser Val Thr Pro Glu Asp Thr Ala Val Tyr Tyr Cys Ala Arg Thr Trp
305                 310                 315                 320

Ser Gly Tyr Val Asp Val Trp Gly Gln Gly Thr Leu Val Thr Val Ser
                325                 330                 335

Ser Ala Ser Thr Lys Gly Pro Ser Val Phe Pro Leu Ala Pro Ser Ser
            340                 345                 350

Lys Ser Thr Ser Gly Gly Thr Ala Ala Leu Gly Cys Leu Val Lys Asp
        355                 360                 365

Tyr Phe Pro Glu Pro Val Thr Val Ser Trp Asn Ser Gly Ala Leu Thr
    370                 375                 380

Ser Gly Val His Thr Phe Pro Ala Val Leu Gln Ser Ser Gly Leu Tyr
385                 390                 395                 400

Ser Leu Ser Ser Val Val Thr Val Pro Ser Ser Ser Leu Gly Thr Gln
                405                 410                 415

Thr Tyr Ile Cys Asn Val Asn His Lys Pro Ser Asn Thr Lys Val Asp
            420                 425                 430

Lys Lys Val Glu Pro Lys Ser Cys Asp Lys Thr His Thr Cys Pro Pro
        435                 440                 445

Cys Pro Ala Pro Glu Leu Ala Gly Ala Pro Ser Val Phe Leu Phe Pro
    450                 455                 460

Pro Lys Pro Lys Asp Thr Leu Met Ile Ser Arg Thr Pro Glu Val Thr
465                 470                 475                 480

Cys Val Val Val Asp Val Ser His Glu Asp Pro Glu Val Lys Phe Asn
                485                 490                 495

Trp Tyr Val Asp Gly Val Glu Val His Asn Ala Lys Thr Lys Pro Arg
            500                 505                 510

Glu Glu Gln Tyr Asn Ser Thr Tyr Arg Val Val Ser Val Leu Thr Val
        515                 520                 525

Leu His Gln Asp Trp Leu Asn Gly Lys Glu Tyr Lys Cys Lys Val Ser
    530                 535                 540
```

-continued

Asn Lys Ala Leu Pro Ala Pro Ile Glu Lys Thr Ile Ser Lys Ala Lys
545 550 555 560

Gly Gln Pro Arg Glu Pro Gln Val Tyr Thr Leu Pro Pro Ser Arg Asp
565 570 575

Glu Leu Thr Lys Asn Gln Val Ser Leu Thr Cys Leu Val Lys Gly Phe
580 585 590

Tyr Pro Ser Asp Ile Ala Val Glu Trp Glu Ser Asn Gly Gln Pro Glu
595 600 605

Asn Asn Tyr Lys Thr Thr Pro Pro Val Leu Asp Ser Asp Gly Ser Phe
610 615 620

Phe Leu Tyr Ser Lys Leu Thr Val Asp Lys Ser Arg Trp Gln Gln Gly
625 630 635 640

Asn Val Phe Ser Cys Ser Val Met His Glu Ala Leu His Asn His Tyr
645 650 655

Thr Gln Lys Ser Leu Ser Leu Ser Pro Gly Gly Gly Gly Gly Ser Gly
660 665 670

Gly Gly Gly Ser Gly Gly Gly Gly Ser Gln Val Gln Leu Lys Gln Ser
675 680 685

Gly Pro Gly Leu Val Gln Pro Ser Gln Ser Leu Ser Ile Thr Cys Thr
690 695 700

Val Ser Gly Phe Ser Leu Thr Asn Tyr Gly Val His Trp Val Arg Gln
705 710 715 720

Ser Pro Gly Lys Gly Leu Glu Trp Leu Gly Val Ile Trp Ser Gly Gly
725 730 735

Asn Thr Asp Tyr Asn Thr Pro Phe Thr Ser Arg Leu Ser Ile Asn Lys
740 745 750

Asp Asn Ser Lys Ser Gln Val Phe Phe Lys Met Asn Ser Leu Gln Ser
755 760 765

Asn Asp Thr Ala Ile Tyr Tyr Cys Ala Arg Ala Leu Thr Tyr Tyr Asp
770 775 780

Tyr Glu Phe Ala Tyr Trp Gly Gln Gly Thr Leu Val Thr Val Ser Ala
785 790 795 800

Gly Gly Gly Gly Ser Gly Gly Gly Gly Ser Gly Gly Gly Gly Ser Asp
805 810 815

Ile Leu Leu Thr Gln Ser Pro Val Ile Leu Ser Val Ser Pro Gly Glu
820 825 830

Arg Val Ser Phe Ser Cys Arg Ala Ser Gln Ser Ile Gly Thr Asn Ile
835 840 845

His Trp Tyr Gln Gln Arg Thr Asn Gly Ser Pro Arg Leu Leu Ile Lys
850 855 860

Tyr Ala Ser Glu Ser Ile Ser Gly Ile Pro Ser Arg Phe Ser Gly Ser
865 870 875 880

Gly Ser Gly Thr Asp Phe Thr Leu Ser Ile Asn Ser Val Glu Ser Glu
885 890 895

Asp Ile Ala Asp Tyr Tyr Cys Gln Gln Asn Asn Asn Trp Pro Thr Thr
900 905 910

Phe Gly Ala Gly Thr Lys Leu Glu Leu Lys
915 920

<210> SEQ ID NO 384
<211> LENGTH: 919
<212> TYPE: PRT
<213> ORGANISM: Homo sapiens

<400> SEQUENCE: 384

-continued

```
Ala Ser Asp Ile Gln Met Thr Gln Ser Pro Ser Ser Leu Ser Ala Ser
1               5                   10                  15

Val Gly Asp Arg Val Thr Ile Ala Cys Arg Ala Gly Gln Ser Ile Gly
            20                  25                  30

Thr Tyr Leu Asn Trp Tyr Gln Gln Lys Pro Gly Lys Ala Pro Lys Leu
        35                  40                  45

Leu Ile Tyr Val Ala Ser Ser Leu Gln Ser Gly Val Pro Ser Arg Phe
    50                  55                  60

Ser Gly Ser Gly Ser Gly Thr Glu Phe Thr Leu Thr Ile Ser Ser Leu
65                  70                  75                  80

Gln Pro Glu Asp Phe Ala Thr Tyr Tyr Cys Gln Gln Ser Tyr Ser Thr
                85                  90                  95

Leu Leu Thr Phe Gly Arg Gly Thr Lys Val Glu Ile Lys Arg Thr Ala
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Leu Tyr Ala Cys Glu Val Thr His Gln Gly Leu Ser Ser Pro Val Thr
        195                 200                 205

Lys Ser Phe Asn Arg Gly Glu Cys Gln Val Gln Leu Val Glu Ser Gly
    210                 215                 220

Gly Gly Leu Val Lys Pro Gly Gly Ser Leu Arg Leu Ser Cys Ala Ala
225                 230                 235                 240

Ser Gly Phe Thr Phe Ser Asp Tyr Tyr Met Ser Trp Ile Arg Gln Ala
                245                 250                 255

Pro Gly Lys Gly Leu Glu Trp Val Ser Tyr Ile Ser Ser Ser Gly Ser
            260                 265                 270

Thr Ile Tyr Tyr Ala Asp Ser Val Lys Gly Arg Phe Thr Ile Ser Arg
        275                 280                 285

Asp Asn Ala Lys Asn Ser Leu Tyr Leu Gln Met Asn Ser Leu Arg Ala
    290                 295                 300

Glu Asp Thr Ala Val Tyr Tyr Cys Ala Arg Val Asp Tyr Ala Asp Ala
305                 310                 315                 320

Phe Asp Ile Trp Gly Gln Gly Thr Leu Val Thr Val Ser Ser Ala Ser
                325                 330                 335

Thr Lys Gly Pro Ser Val Phe Pro Leu Ala Pro Ser Ser Lys Ser Thr
            340                 345                 350

Ser Gly Gly Thr Ala Ala Leu Gly Cys Leu Val Lys Asp Tyr Phe Pro
        355                 360                 365

Glu Pro Val Thr Val Ser Trp Asn Ser Gly Ala Leu Thr Ser Gly Val
    370                 375                 380

His Thr Phe Pro Ala Val Leu Gln Ser Ser Gly Leu Tyr Ser Leu Ser
385                 390                 395                 400

Ser Val Val Thr Val Pro Ser Ser Ser Leu Gly Thr Gln Thr Tyr Ile
                405                 410                 415
```

Cys Asn Val Asn His Lys Pro Ser Asn Thr Lys Val Asp Lys Lys Val
420 425 430

Glu Pro Lys Ser Cys Asp Lys Thr His Thr Cys Pro Pro Cys Pro Ala
435 440 445

Pro Glu Leu Ala Gly Ala Pro Ser Val Phe Leu Phe Pro Pro Lys Pro
450 455 460

Lys Asp Thr Leu Met Ile Ser Arg Thr Pro Glu Val Thr Cys Val Val
465 470 475 480

Val Asp Val Ser His Glu Asp Pro Glu Val Lys Phe Asn Trp Tyr Val
485 490 495

Asp Gly Val Glu Val His Asn Ala Lys Thr Lys Pro Arg Glu Glu Gln
500 505 510

Tyr Asn Ser Thr Tyr Arg Val Val Ser Val Leu Thr Val Leu His Gln
515 520 525

Asp Trp Leu Asn Gly Lys Glu Tyr Lys Cys Lys Val Ser Asn Lys Ala
530 535 540

Leu Pro Ala Pro Ile Glu Lys Thr Ile Ser Lys Ala Lys Gly Gln Pro
545 550 555 560

Arg Glu Pro Gln Val Tyr Thr Leu Pro Pro Ser Arg Asp Glu Leu Thr
565 570 575

Lys Asn Gln Val Ser Leu Thr Cys Leu Val Lys Gly Phe Tyr Pro Ser
580 585 590

Asp Ile Ala Val Glu Trp Glu Ser Asn Gly Gln Pro Glu Asn Asn Tyr
595 600 605

Lys Thr Thr Pro Pro Val Leu Asp Ser Asp Gly Ser Phe Phe Leu Tyr
610 615 620

Ser Lys Leu Thr Val Asp Lys Ser Arg Trp Gln Gln Gly Asn Val Phe
625 630 635 640

Ser Cys Ser Val Met His Glu Ala Leu His Asn His Tyr Thr Gln Lys
645 650 655

Ser Leu Ser Leu Ser Pro Gly Gly Gly Gly Gly Ser Gly Gly Gly Gly
660 665 670

Ser Gly Gly Gly Gly Ser Gln Val Gln Leu Lys Gln Ser Gly Pro Gly
675 680 685

Leu Val Gln Pro Ser Gln Ser Leu Ser Ile Thr Cys Thr Val Ser Gly
690 695 700

Phe Ser Leu Thr Asn Tyr Gly Val His Trp Val Arg Gln Ser Pro Gly
705 710 715 720

Lys Gly Leu Glu Trp Leu Gly Val Ile Trp Ser Gly Gly Asn Thr Asp
725 730 735

Tyr Asn Thr Pro Phe Thr Ser Arg Leu Ser Ile Asn Lys Asp Asn Ser
740 745 750

Lys Ser Gln Val Phe Phe Lys Met Asn Ser Leu Gln Ser Asn Asp Thr
755 760 765

Ala Ile Tyr Tyr Cys Ala Arg Ala Leu Thr Tyr Tyr Asp Tyr Glu Phe
770 775 780

Ala Tyr Trp Gly Gln Gly Thr Leu Val Thr Val Ser Ala Gly Gly Gly
785 790 795 800

Gly Ser Gly Gly Gly Gly Ser Gly Gly Gly Gly Ser Asp Ile Leu Leu
805 810 815

Thr Gln Ser Pro Val Ile Leu Ser Val Ser Pro Gly Glu Arg Val Ser
820 825 830

Phe Ser Cys Arg Ala Ser Gln Ser Ile Gly Thr Asn Ile His Trp Tyr

-continued 835 840 845

Gln Gln Arg Thr Asn Gly Ser Pro Arg Leu Leu Ile Lys Tyr Ala Ser
850 855 860

Glu Ser Ile Ser Gly Ile Pro Ser Arg Phe Ser Gly Ser Gly Ser Gly
865 870 875 880

Thr Asp Phe Thr Leu Ser Ile Asn Ser Val Glu Ser Glu Asp Ile Ala
885 890 895

Asp Tyr Tyr Cys Gln Gln Asn Asn Asn Trp Pro Thr Thr Phe Gly Ala
900 905 910

Gly Thr Lys Leu Glu Leu Lys
915

<210> SEQ ID NO 385
<211> LENGTH: 329
<212> TYPE: PRT
<213> ORGANISM: Homo sapiens

<400> SEQUENCE: 385

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Asp Glu
225 230 235 240

Thr Asp Asp Gly Pro Val Ser Leu Thr Cys Leu Val Lys Gly Phe Tyr
245 250 255

Pro Ser Asp Ile Ala Val Glu Trp Glu Ser Thr Tyr Gly Pro Glu Asn
260 265 270

Asn Tyr Lys Thr Thr Pro Pro Val Leu Asp Ser Asp Gly Ser Phe Phe
275 280 285

-continued

Leu Tyr Ser Lys Leu Thr Val Ser Tyr Trp Arg Trp Tyr Lys Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 386
<211> LENGTH: 329
<212> TYPE: PRT
<213> ORGANISM: Homo sapiens

<400> SEQUENCE: 386

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Thr Asp Asp Gly Pro Val Ser Leu Thr Cys Leu Val Lys Gly Phe Tyr
                245                 250                 255

Pro Ser Asp Ile Ala Val Glu Trp Glu Ser Thr Tyr Gly Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Ser Tyr Trp Arg Trp Tyr Lys Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 387
<211> LENGTH: 241
<212> TYPE: PRT
<213> ORGANISM: Homo sapiens

<400> SEQUENCE: 387

Gln Val Gln Leu Lys Gln Ser Gly Pro Gly Leu Val Gln Pro Ser Gln
1 5 10 15

Ser Leu Ser Ile Thr Cys Thr Val Ser Gly Phe Ser Leu Thr Asn Tyr
20 25 30

Gly Val His Trp Val Arg Gln Ser Pro Gly Lys Gly Leu Glu Trp Leu
35 40 45

Gly Val Ile Trp Ser Gly Gly Asn Thr Asp Tyr Asn Thr Pro Phe Thr
50 55 60

Ser Arg Leu Ser Ile Asn Lys Asp Asn Ser Lys Ser Gln Val Phe Phe
65 70 75 80

Lys Met Asn Ser Leu Gln Ser Asn Asp Thr Ala Ile Tyr Tyr Cys Ala
85 90 95

Arg Ala Leu Thr Tyr Tyr Asp Tyr Glu Phe Ala Tyr Trp Gly Gln Gly
100 105 110

Thr Leu Val Thr Val Ser Ala Gly Gly Gly Gly Ser Gly Gly Gly Gly
115 120 125

Ser Gly Gly Gly Gly Ser Asp Ile Leu Leu Thr Gln Ser Pro Val Ile
130 135 140

Leu Ser Val Ser Pro Gly Glu Arg Val Ser Phe Ser Cys Arg Ala Ser
145 150 155 160

Gln Ser Ile Gly Thr Asn Ile His Trp Tyr Gln Gln Arg Thr Asn Gly
165 170 175

Ser Pro Arg Leu Leu Ile Lys Tyr Ala Ser Glu Ser Ile Ser Gly Ile
180 185 190

Pro Ser Arg Phe Ser Gly Ser Gly Ser Gly Thr Asp Phe Thr Leu Ser
195 200 205

Ile Asn Ser Val Glu Ser Glu Asp Ile Ala Asp Tyr Tyr Cys Gln Gln
210 215 220

Asn Asn Asn Trp Pro Thr Thr Phe Gly Ala Gly Thr Lys Leu Glu Leu
225 230 235 240

Lys

<210> SEQ ID NO 388
<211> LENGTH: 664
<212> TYPE: PRT
<213> ORGANISM: Homo sapiens

<400> SEQUENCE: 388

Asp Ile Gln Met Thr Gln Ser Pro Pro Ala Leu Ser Ala Ser Val Gly
1 5 10 15

Asp Arg Val Thr Ile Thr Cys Arg Ala Ser Gln Asp Ile Asn Asp Trp
20 25 30

Leu Ala Trp Tyr Gln His Lys Pro Gly Lys Ala Pro Lys Leu Leu Ile
35 40 45

Tyr Asp Ala Ser Ser Leu Glu Ser Gly Val Pro Leu Arg Phe Ser Gly
50 55 60

Ser Gly Ser Gly Thr Glu Phe Thr Leu Thr Ile Ser Ser Leu Gln Pro
65 70 75 80

-continued

```
Asp Asp Phe Ala Thr Tyr Tyr Cys Gln Gln Lys Tyr Ser Ala Pro Gln
                85                  90                  95

Val Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Glu Val Gln Leu Gln Gln Ser Gly Pro
    210                 215                 220

Gly Leu Val Lys Pro Ser Gln Thr Leu Ser Leu Thr Cys Ala Ile Ser
225                 230                 235                 240

Gly Asp Ser Val Ser Ser Lys Ser Ala Ala Trp Asn Trp Ile Arg Gln
                245                 250                 255

Ser Pro Ser Arg Gly Leu Glu Trp Leu Gly Arg Thr Tyr Tyr Arg Ser
            260                 265                 270

Lys Trp Ser Thr Asp Tyr Ala Ala Ser Val Lys Ser Arg Ile Thr Ile
        275                 280                 285

Asn Pro Asp Thr Ser Lys Asn Gln Leu Ser Leu Gln Leu Asn Ser Val
    290                 295                 300

Thr Pro Glu Asp Thr Ala Val Tyr Tyr Cys Ala Arg Thr Trp Val Gly
305                 310                 315                 320

Tyr Val Asp Arg Trp Gly Gln Gly Thr Leu Val Thr Val Ser Ser Ala
                325                 330                 335

Ser Thr Lys Gly Pro Ser Val Phe Pro Leu Ala Pro Ser Ser Lys Ser
            340                 345                 350

Thr Ser Gly Gly Thr Ala Ala Leu Gly Cys Leu Val Lys Asp Tyr Phe
        355                 360                 365

Pro Glu Pro Val Thr Val Ser Trp Asn Ser Gly Ala Leu Thr Ser Gly
    370                 375                 380

Val His Thr Phe Pro Ala Val Leu Gln Ser Ser Gly Leu Tyr Ser Leu
385                 390                 395                 400

Ser Ser Val Val Thr Val Pro Ser Ser Ser Leu Gly Thr Gln Thr Tyr
                405                 410                 415

Ile Cys Asn Val Asn His Lys Pro Ser Asn Thr Lys Val Asp Lys Lys
            420                 425                 430

Val Glu Pro Lys Ser Cys Asp Lys Thr His Thr Cys Pro Pro Cys Pro
        435                 440                 445

Ala Pro Glu Leu Ala Gly Ala Pro Ser Val Phe Leu Phe Pro Pro Lys
    450                 455                 460

Pro Lys Asp Thr Leu Met Ile Ser Arg Thr Pro Glu Val Thr Cys Val
465                 470                 475                 480

Val Val Asp Val Ser His Glu Asp Pro Glu Val Lys Phe Asn Trp Tyr
                485                 490                 495

Val Asp Gly Val Glu Val His Asn Ala Lys Thr Lys Pro Arg Glu Glu
```

500 505 510

Gln Tyr Asn Ser Thr Tyr Arg Val Val Ser Val Leu Thr Val Leu His
515 520 525

Gln Asp Trp Leu Asn Gly Lys Glu Tyr Lys Cys Lys Val Ser Asn Lys
530 535 540

Ala Leu Pro Ala Pro Ile Glu Lys Thr Ile Ser Lys Ala Lys Gly Gln
545 550 555 560

Pro Arg Glu Pro Gln Val Tyr Thr Leu Pro Pro Ser Arg Asp Glu Thr
565 570 575

Asp Asp Gly Pro Val Ser Leu Thr Cys Leu Val Lys Gly Phe Tyr Pro
580 585 590

Ser Asp Ile Ala Val Glu Trp Glu Ser Thr Tyr Gly Pro Glu Asn Asn
595 600 605

Tyr Lys Thr Thr Pro Pro Val Leu Asp Ser Asp Gly Ser Phe Phe Leu
610 615 620

Tyr Ser Lys Leu Thr Val Ser Tyr Trp Arg Trp Tyr Lys Gly Asn Val
625 630 635 640

Phe Ser Cys Ser Val Met His Glu Ala Leu His Asn His Tyr Thr Gln
645 650 655

Lys Ser Leu Ser Leu Ser Pro Gly
660

<210> SEQ ID NO 389
<211> LENGTH: 664
<212> TYPE: PRT
<213> ORGANISM: Homo sapiens

<400> SEQUENCE: 389

Asp Ile Gln Met Thr Gln Ser Pro Pro Ala Leu Ser Ala Ser Val Gly
1 5 10 15

Asp Arg Val Thr Ile Thr Cys Arg Ala Ser Gln Asp Ile Asn Asp Trp
20 25 30

Leu Ala Trp Tyr Gln His Lys Pro Gly Lys Ala Pro Lys Leu Leu Ile
35 40 45

Tyr Asp Ala Ser Ser Leu Glu Ser Gly Val Pro Leu Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Lys Tyr Ser Ala Pro Gln
85 90 95

Val Thr Phe Gly Gln Gly Thr Arg Leu Glu Ile Lys Arg Thr Val Ala
100 105 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu
130 135 140

Ala Lys Val Gln Trp Lys Val Asp Asn Ala Leu Gln Ser Gly Asn Ser
145 150 155 160

Gln Glu Ser Val Thr Glu Gln Asp Ser Lys Asp Ser Thr Tyr Ser Leu
165 170 175

Ser Ser Thr Leu Thr Leu Ser Lys Ala Asp Tyr Glu Lys His Lys Val
180 185 190

Tyr Ala Cys Glu Val Thr His Gln Gly Leu Ser Ser Pro Val Thr Lys
195 200 205

-continued

```
Ser Phe Asn Arg Gly Glu Cys Glu Val Gln Leu Gln Gln Ser Gly Pro
    210                 215                 220

Gly Leu Val Lys Pro Ser Gln Thr Leu Ser Leu Thr Cys Ala Ile Ser
225                 230                 235                 240

Gly Asp Ser Val Ser Ser Lys Ser Ala Ala Trp Asn Trp Ile Arg Gln
                245                 250                 255

Ser Pro Ser Arg Gly Leu Glu Trp Leu Gly Arg Thr Tyr Tyr Arg Ser
            260                 265                 270

Lys Trp Ser Thr Asp Tyr Ala Ala Ser Val Lys Ser Arg Ile Thr Ile
        275                 280                 285

Asn Pro Asp Thr Ser Lys Asn Gln Leu Ser Leu Gln Leu Asn Ser Val
    290                 295                 300

Thr Pro Glu Asp Thr Ala Val Tyr Tyr Cys Ala Arg Thr Trp Val Gly
305                 310                 315                 320

Tyr Val Asp Arg Trp Gly Gln Gly Thr Leu Val Thr Val Ser Ser Ala
                325                 330                 335

Ser Thr Lys Gly Pro Ser Val Phe Pro Leu Ala Pro Ser Ser Lys Ser
            340                 345                 350

Thr Ser Gly Gly Thr Ala Ala Leu Gly Cys Leu Val Lys Asp Tyr Phe
        355                 360                 365

Pro Glu Pro Val Thr Val Ser Trp Asn Ser Gly Ala Leu Thr Ser Gly
    370                 375                 380

Val His Thr Phe Pro Ala Val Leu Gln Ser Ser Gly Leu Tyr Ser Leu
385                 390                 395                 400

Ser Ser Val Val Thr Val Pro Ser Ser Ser Leu Gly Thr Gln Thr Tyr
                405                 410                 415

Ile Cys Asn Val Asn His Lys Pro Ser Asn Thr Lys Val Asp Lys Lys
            420                 425                 430

Val Glu Pro Lys Ser Cys Asp Lys Thr His Thr Cys Pro Pro Cys Pro
        435                 440                 445

Ala Pro Glu Leu Ala Gly Ala Pro Ser Val Phe Leu Phe Pro Pro Lys
    450                 455                 460

Pro Lys Asp Thr Leu Met Ile Ser Arg Thr Pro Glu Val Thr Cys Val
465                 470                 475                 480

Val Val Asp Val Ser His Glu Asp Pro Glu Val Lys Phe Asn Trp Tyr
                485                 490                 495

Val Asp Gly Val Glu Val His Asn Ala Lys Thr Lys Pro Arg Glu Glu
            500                 505                 510

Gln Tyr Asn Ser Thr Tyr Arg Val Val Ser Val Leu Thr Val Leu His
        515                 520                 525

Gln Asp Trp Leu Asn Gly Lys Glu Tyr Lys Cys Lys Val Ser Asn Lys
    530                 535                 540

Ala Leu Pro Ala Pro Ile Glu Lys Thr Ile Ser Lys Ala Lys Gly Gln
545                 550                 555                 560

Pro Arg Glu Pro Gln Val Tyr Thr Leu Pro Pro Ser Arg Asp Glu Leu
                565                 570                 575

Glu Glu Gly Pro Val Ser Leu Thr Cys Leu Val Lys Gly Phe Tyr Pro
            580                 585                 590

Ser Asp Ile Ala Val Glu Trp Glu Ser Thr Tyr Gly Pro Glu Asn Asn
        595                 600                 605

Tyr Lys Thr Thr Pro Pro Val Leu Asp Ser Asp Gly Ser Phe Phe Leu
    610                 615                 620

Tyr Ser Lys Leu Thr Val Ser Tyr Trp Arg Trp Tyr Lys Gly Asn Val
```

-continued

```
625                 630                 635                 640

Phe Ser Cys Ser Val Met His Glu Ala Leu His Asn His Tyr Thr Gln
                645                 650                 655

Lys Ser Leu Ser Leu Ser Pro Gly
            660


<210> SEQ ID NO 390
<211> LENGTH: 257
<212> TYPE: PRT
<213> ORGANISM: Homo sapiens

<400> SEQUENCE: 390

Met Ala Gln Arg Met Thr Thr Gln Leu Leu Leu Leu Leu Val Trp Val
1               5                   10                  15

Ala Val Val Gly Glu Ala Gln Thr Arg Ile Ala Trp Ala Arg Thr Glu
            20                  25                  30

Leu Leu Asn Val Cys Met Asn Ala Lys His His Lys Glu Lys Pro Gly
        35                  40                  45

Pro Glu Asp Lys Leu His Glu Gln Cys Arg Pro Trp Arg Lys Asn Ala
    50                  55                  60

Cys Cys Ser Thr Asn Thr Ser Gln Glu Ala His Lys Asp Val Ser Tyr
65                  70                  75                  80

Leu Tyr Arg Phe Asn Trp Asn His Cys Gly Glu Met Ala Pro Ala Cys
                85                  90                  95

Lys Arg His Phe Ile Gln Asp Thr Cys Leu Tyr Glu Cys Ser Pro Asn
            100                 105                 110

Leu Gly Pro Trp Ile Gln Gln Val Asp Gln Ser Trp Arg Lys Glu Arg
        115                 120                 125

Val Leu Asn Val Pro Leu Cys Lys Glu Asp Cys Glu Gln Trp Trp Glu
    130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
            180                 185                 190

Trp Thr His Ser Tyr Lys Val Ser Asn Tyr Ser Arg Gly Ser Gly Arg
        195                 200                 205

Cys Ile Gln Met Trp Phe Asp Pro Ala Gln Gly Asn Pro Asn Glu Glu
    210                 215                 220

Val Ala Arg Phe Tyr Ala Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                245                 250                 255

Ser


<210> SEQ ID NO 391
<211> LENGTH: 329
<212> TYPE: PRT
<213> ORGANISM: Homo sapiens

<400> SEQUENCE: 391

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Glu Glu Gly Pro Val Ser Leu Thr Cys Leu Val Lys Gly Phe Tyr
                245                 250                 255

Pro Ser Asp Ile Ala Val Glu Trp Glu Ser Thr Tyr Gly Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Ser Tyr Trp Arg Trp Tyr Lys Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325


<210> SEQ ID NO 392
<211> LENGTH: 329
<212> TYPE: PRT
<213> ORGANISM: Homo sapiens

<400> SEQUENCE: 392

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
```

-continued 65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Asp Glu
225 230 235 240

Leu Glu Glu Gly Pro Val Ser Leu Thr Cys Leu Val Lys Gly Phe Tyr
245 250 255

Pro Ser Asp Ile Ala Val Glu Trp Glu Ser Thr Tyr Gly Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Ser Tyr Trp Arg Trp Tyr Lys Gly Asn
290 295 300

Val Phe Ser Cys Ser Val Met His Glu Ala Leu His Asn His Tyr Thr
305 310 315 320

Gln Lys Ser Leu Ser Leu Ser Pro Gly
325

<210> SEQ ID NO 393
<211> LENGTH: 664
<212> TYPE: PRT
<213> ORGANISM: Homo sapiens

<400> SEQUENCE: 393

Asp Ile Gln Met Thr Gln Ser Pro Pro Ala Leu Ser Ala Ser Val Gly
1 5 10 15

Asp Arg Val Thr Ile Thr Cys Arg Ala Ser Gln Asp Ile Asn Asp Trp
20 25 30

Leu Ala Trp Tyr Gln His Lys Pro Gly Lys Ala Pro Lys Leu Leu Ile
35 40 45

Tyr Asp Ala Ser Ser Leu Glu Ser Gly Val Pro Leu Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Lys Tyr Ser Ala Pro Gln
85 90 95

Val Thr Phe Gly Gln Gly Thr Arg Leu Glu Ile Lys Arg Thr Val Ala
100 105 110

-continued

```
Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Glu Val Gln Leu Gln Gln Ser Gly Pro
    210                 215                 220

Gly Leu Val Lys Pro Ser Gln Thr Leu Ser Leu Thr Cys Ala Ile Ser
225                 230                 235                 240

Gly Asp Ser Val Ser Ser Lys Ser Ala Ala Trp Asn Trp Ile Arg Gln
                245                 250                 255

Ser Pro Ser Arg Gly Leu Glu Trp Leu Gly Arg Thr Tyr Tyr Arg Ser
            260                 265                 270

Lys Trp Ser Thr Asp Tyr Ala Ala Ser Val Lys Ser Arg Ile Thr Ile
        275                 280                 285

Asn Pro Asp Thr Ser Lys Asn Gln Leu Ser Leu Gln Leu Asn Ser Val
    290                 295                 300

Thr Pro Glu Asp Thr Ala Val Tyr Tyr Cys Ala Arg Thr Trp Val Gly
305                 310                 315                 320

Tyr Val Asp Arg Trp Gly Gln Gly Thr Leu Val Thr Val Ser Ser Ala
                325                 330                 335

Ser Thr Lys Gly Pro Ser Val Phe Pro Leu Ala Pro Ser Ser Lys Ser
            340                 345                 350

Thr Ser Gly Gly Thr Ala Ala Leu Gly Cys Leu Val Lys Asp Tyr Phe
        355                 360                 365

Pro Glu Pro Val Thr Val Ser Trp Asn Ser Gly Ala Leu Thr Ser Gly
    370                 375                 380

Val His Thr Phe Pro Ala Val Leu Gln Ser Ser Gly Leu Tyr Ser Leu
385                 390                 395                 400

Ser Ser Val Val Thr Val Pro Ser Ser Ser Leu Gly Thr Gln Thr Tyr
                405                 410                 415

Ile Cys Asn Val Asn His Lys Pro Ser Asn Thr Lys Val Asp Lys Lys
            420                 425                 430

Val Glu Pro Lys Ser Cys Asp Lys Thr His Thr Cys Pro Pro Cys Pro
        435                 440                 445

Ala Pro Glu Leu Ala Gly Ala Pro Ser Val Phe Leu Phe Pro Pro Lys
    450                 455                 460

Pro Lys Asp Thr Leu Met Ile Ser Arg Thr Pro Glu Val Thr Cys Val
465                 470                 475                 480

Val Val Asp Val Ser His Glu Asp Pro Glu Val Lys Phe Asn Trp Tyr
                485                 490                 495

Val Asp Gly Val Glu Val His Asn Ala Lys Thr Lys Pro Arg Glu Glu
            500                 505                 510

Gln Tyr Asn Ser Thr Tyr Arg Val Val Ser Val Leu Thr Val Leu His
        515                 520                 525

Gln Asp Trp Leu Asn Gly Lys Glu Tyr Lys Cys Lys Val Ser Asn Lys
```

530 535 540

Ala Leu Pro Ala Pro Ile Glu Lys Thr Ile Ser Lys Ala Lys Gly Gln
545 550 555 560

Pro Arg Glu Pro Gln Val Tyr Thr Leu Pro Pro Ser Arg Asp Glu Phe
565 570 575

Phe Thr Tyr Trp Val Ser Leu Thr Cys Leu Val Lys Gly Phe Tyr Pro
580 585 590

Ser Asp Ile Ala Val Glu Trp Glu Ser Asn Gly Gln Pro Glu Asn Asn
595 600 605

Tyr Lys Thr Thr Pro Pro Val Leu Asp Ser Asp Gly Ser Phe Phe Leu
610 615 620

Tyr Ser Lys Leu Thr Val Asp Arg Arg Arg Trp Thr Ala Gly Asn Val
625 630 635 640

Phe Ser Cys Ser Val Met His Glu Ala Leu His Asn His Tyr Thr Gln
645 650 655

Lys Ser Leu Ser Leu Ser Pro Gly
660

<210> SEQ ID NO 394
<211> LENGTH: 329
<212> TYPE: PRT
<213> ORGANISM: Homo sapiens

<400> SEQUENCE: 394

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Ala Gly Ala Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Asp Glu
225 230 235 240

Phe Phe Thr Tyr Trp Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Arg Arg Arg Trp Thr Ala Gly Asn
290 295 300

Val Phe Ser Cys Ser Val Met His Glu Ala Leu His Asn His Tyr Thr
305 310 315 320

Gln Lys Ser Leu Ser Leu Ser Pro Gly
325

<210> SEQ ID NO 395
<211> LENGTH: 329
<212> TYPE: PRT
<213> ORGANISM: Homo sapiens

<400> SEQUENCE: 395

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Asp Glu
225 230 235 240

Phe Phe Thr Tyr Trp Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

```
Leu Tyr Ser Lys Leu Thr Val Asp Arg Arg Arg Trp Thr Ala Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325


<210> SEQ ID NO 396
<211> LENGTH: 498
<212> TYPE: PRT
<213> ORGANISM: Homo sapiens

<400> SEQUENCE: 396

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Gln
                245                 250                 255

Val Gln Leu Gln Gln Ser Gly Pro Gly Leu Val Lys Pro Ser Gln Thr
            260                 265                 270

Leu Ser Leu Thr Cys Ala Ile Ser Gly Asp Ser Val Ser Ser Lys Ser
        275                 280                 285

Ala Ala Trp Asn Trp Ile Arg Gln Ser Pro Ser Arg Gly Leu Glu Trp
    290                 295                 300

Leu Gly Arg Thr Tyr Tyr Arg Ser Lys Trp Ser Thr Asp Tyr Ala Ala
305                 310                 315                 320

Ser Val Lys Ser Arg Ile Thr Ile Asn Pro Asp Thr Ser Lys Asn Gln
```

```
                325                 330                 335

Leu Ser Leu Gln Leu Asn Ser Val Thr Pro Glu Asp Thr Ala Val Tyr
            340                 345                 350

Tyr Cys Ala Arg Thr Trp Val Gly Tyr Val Asp Arg Trp Gly Gln Gly
        355                 360                 365

Thr Leu Val Thr Val Ser Ser Gly Gly Gly Gly Ser Gly Gly Gly Gly
    370                 375                 380

Ser Gly Gly Gly Gly Ser Asp Ile Gln Met Thr Gln Ser Pro Pro Ala
385                 390                 395                 400

Leu Ser Ala Ser Val Gly Asp Arg Val Thr Ile Thr Cys Arg Ala Ser
                405                 410                 415

Gln Asp Ile Asn Asp Trp Leu Ala Trp Tyr Gln His Lys Pro Gly Lys
            420                 425                 430

Ala Pro Lys Leu Leu Ile Tyr Asp Ala Ser Ser Leu Glu Ser Gly Val
        435                 440                 445

Pro Leu Arg Phe Ser Gly Ser Gly Ser Gly Thr Glu Phe Thr Leu Thr
    450                 455                 460

Ile Ser Ser Leu Gln Pro Asp Asp Phe Ala Thr Tyr Tyr Cys Gln Gln
465                 470                 475                 480

Lys Tyr Ser Ala Pro Gln Val Thr Phe Gly Gln Gly Thr Arg Leu Glu
                485                 490                 495

Ile Lys


<210> SEQ ID NO 397
<211> LENGTH: 250
<212> TYPE: PRT
<213> ORGANISM: Homo sapiens

<400> SEQUENCE: 397

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
```

-continued

```
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser
                245                 250


<210> SEQ ID NO 398
<211> LENGTH: 664
<212> TYPE: PRT
<213> ORGANISM: Homo sapiens

<400> SEQUENCE: 398

Asp Ile Gln Met Thr Gln Ser Pro Pro Ala Leu Ser Ala Ser Val Gly
1               5                   10                  15

Asp Arg Val Thr Ile Thr Cys Arg Ala Ser Gln Asp Ile Asn Asp Trp
            20                  25                  30

Leu Ala Trp Tyr Gln His Lys Pro Gly Lys Ala Pro Lys Leu Leu Ile
        35                  40                  45

Tyr Asp Ala Ser Ser Leu Glu Ser Gly Val Pro Leu Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Lys Tyr Ser Ala Pro Gln
                85                  90                  95

Val Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Glu Val Gln Leu Gln Gln Ser Gly Pro
    210                 215                 220

Gly Leu Val Lys Pro Ser Gln Thr Leu Ser Leu Thr Cys Ala Ile Ser
225                 230                 235                 240

Gly Asp Ser Val Ser Ser Lys Ser Ala Ala Trp Asn Trp Ile Arg Gln
                245                 250                 255

Ser Pro Ser Arg Gly Leu Glu Trp Leu Gly Arg Thr Tyr Tyr Arg Ser
            260                 265                 270

Lys Trp Ser Thr Asp Tyr Ala Ala Ser Val Lys Ser Arg Ile Thr Ile
        275                 280                 285

Asn Pro Asp Thr Ser Lys Asn Gln Leu Ser Leu Gln Leu Asn Ser Val
    290                 295                 300

Thr Pro Glu Asp Thr Ala Val Tyr Tyr Cys Ala Arg Thr Trp Val Gly
305                 310                 315                 320
```

Tyr Val Asp Arg Trp Gly Gln Gly Thr Leu Val Thr Val Ser Ser Ala
325 330 335

Ser Thr Lys Gly Pro Ser Val Phe Pro Leu Ala Pro Ser Ser Lys Ser
340 345 350

Thr Ser Gly Gly Thr Ala Ala Leu Gly Cys Leu Val Lys Asp Tyr Phe
355 360 365

Pro Glu Pro Val Thr Val Ser Trp Asn Ser Gly Ala Leu Thr Ser Gly
370 375 380

Val His Thr Phe Pro Ala Val Leu Gln Ser Ser Gly Leu Tyr Ser Leu
385 390 395 400

Ser Ser Val Val Thr Val Pro Ser Ser Ser Leu Gly Thr Gln Thr Tyr
405 410 415

Ile Cys Asn Val Asn His Lys Pro Ser Asn Thr Lys Val Asp Lys Lys
420 425 430

Val Glu Pro Lys Ser Cys Asp Lys Thr His Thr Cys Pro Pro Cys Pro
435 440 445

Ala Pro Glu Leu Leu Gly Gly Pro Ser Val Phe Leu Phe Pro Pro Lys
450 455 460

Pro Lys Asp Thr Leu Met Ile Ser Arg Thr Pro Glu Val Thr Cys Val
465 470 475 480

Val Val Asp Val Ser His Glu Asp Pro Glu Val Lys Phe Asn Trp Tyr
485 490 495

Val Asp Gly Val Glu Val His Asn Ala Lys Thr Lys Pro Arg Glu Glu
500 505 510

Gln Tyr Asn Ser Thr Tyr Arg Val Val Ser Val Leu Thr Val Leu His
515 520 525

Gln Asp Trp Leu Asn Gly Lys Glu Tyr Lys Cys Lys Val Ser Asn Lys
530 535 540

Ala Leu Pro Ala Pro Ile Glu Lys Thr Ile Ser Lys Ala Lys Gly Gln
545 550 555 560

Pro Arg Glu Pro Gln Val Tyr Thr Leu Pro Pro Ser Arg Asp Glu Phe
565 570 575

Phe Thr Tyr Trp Val Ser Leu Thr Cys Leu Val Lys Gly Phe Tyr Pro
580 585 590

Ser Asp Ile Ala Val Glu Trp Glu Ser Asn Gly Gln Pro Glu Asn Asn
595 600 605

Tyr Lys Thr Thr Pro Pro Val Leu Asp Ser Asp Gly Ser Phe Phe Leu
610 615 620

Tyr Ser Lys Leu Thr Val Asp Arg Arg Arg Trp Thr Ala Gly Asn Val
625 630 635 640

Phe Ser Cys Ser Val Met His Glu Ala Leu His Asn His Tyr Thr Gln
645 650 655

Lys Ser Leu Ser Leu Ser Pro Gly
660

<210> SEQ ID NO 399
<211> LENGTH: 664
<212> TYPE: PRT
<213> ORGANISM: Homo sapiens

<400> SEQUENCE: 399

Asp Ile Gln Met Thr Gln Ser Pro Pro Ala Leu Ser Ala Ser Val Gly
1 5 10 15

Asp Arg Val Thr Ile Thr Cys Arg Ala Ser Gln Asp Ile Asn Asp Trp
20 25 30

-continued

Leu Ala Trp Tyr Gln His Lys Pro Gly Lys Ala Pro Lys Leu Leu Ile
35 40 45

Tyr Asp Ala Ser Ser Leu Glu Ser Gly Val Pro Leu Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Lys Tyr Ser Ala Pro Gln
85 90 95

Val Thr Phe Gly Gln Gly Thr Arg Leu Glu Ile Lys Arg Thr Val Ala
100 105 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu
130 135 140

Ala Lys Val Gln Trp Lys Val Asp Asn Ala Leu Gln Ser Gly Asn Ser
145 150 155 160

Gln Glu Ser Val Thr Glu Gln Asp Ser Lys Asp Ser Thr Tyr Ser Leu
165 170 175

Ser Ser Thr Leu Thr Leu Ser Lys Ala Asp Tyr Glu Lys His Lys Val
180 185 190

Tyr Ala Cys Glu Val Thr His Gln Gly Leu Ser Ser Pro Val Thr Lys
195 200 205

Ser Phe Asn Arg Gly Glu Cys Glu Val Gln Leu Gln Gln Ser Gly Pro
210 215 220

Gly Leu Val Lys Pro Ser Gln Thr Leu Ser Leu Thr Cys Ala Ile Ser
225 230 235 240

Gly Asp Ser Val Ser Ser Lys Ser Ala Ala Trp Asn Trp Ile Arg Gln
245 250 255

Ser Pro Ser Arg Gly Leu Glu Trp Leu Gly Arg Thr Tyr Tyr Arg Ser
260 265 270

Lys Trp Ser Thr Asp Tyr Ala Ala Ser Val Lys Ser Arg Ile Thr Ile
275 280 285

Asn Pro Asp Thr Ser Lys Asn Gln Leu Ser Leu Gln Leu Asn Ser Val
290 295 300

Thr Pro Glu Asp Thr Ala Val Tyr Tyr Cys Ala Arg Thr Trp Val Gly
305 310 315 320

Tyr Val Asp Arg Trp Gly Gln Gly Thr Leu Val Thr Val Ser Ser Ala
325 330 335

Ser Thr Lys Gly Pro Ser Val Phe Pro Leu Ala Pro Ser Ser Lys Ser
340 345 350

Thr Ser Gly Gly Thr Ala Ala Leu Gly Cys Leu Val Lys Asp Tyr Phe
355 360 365

Pro Glu Pro Val Thr Val Ser Trp Asn Ser Gly Ala Leu Thr Ser Gly
370 375 380

Val His Thr Phe Pro Ala Val Leu Gln Ser Ser Gly Leu Tyr Ser Leu
385 390 395 400

Ser Ser Val Val Thr Val Pro Ser Ser Ser Leu Gly Thr Gln Thr Tyr
405 410 415

Ile Cys Asn Val Asn His Lys Pro Ser Asn Thr Lys Val Asp Lys Lys
420 425 430

Val Glu Pro Lys Ser Cys Asp Lys Thr His Thr Cys Pro Pro Cys Pro
435 440 445

Ala Pro Glu Leu Leu Gly Gly Pro Ser Val Phe Leu Phe Pro Pro Lys
450 455 460

Pro Lys Asp Thr Leu Met Ile Ser Arg Thr Pro Glu Val Thr Cys Val
465 470 475 480

Val Val Asp Val Ser His Glu Asp Pro Glu Val Lys Phe Asn Trp Tyr
485 490 495

Val Asp Gly Val Glu Val His Asn Ala Lys Thr Lys Pro Arg Glu Glu
500 505 510

Gln Tyr Asn Ser Thr Tyr Arg Val Val Ser Val Leu Thr Val Leu His
515 520 525

Gln Asp Trp Leu Asn Gly Lys Glu Tyr Lys Cys Lys Val Ser Asn Lys
530 535 540

Ala Leu Pro Ala Pro Ile Glu Lys Thr Ile Ser Lys Ala Lys Gly Gln
545 550 555 560

Pro Arg Glu Pro Gln Val Tyr Thr Leu Pro Pro Ser Arg Asp Glu Thr
565 570 575

Asp Asp Gly Pro Val Ser Leu Thr Cys Leu Val Lys Gly Phe Tyr Pro
580 585 590

Ser Asp Ile Ala Val Glu Trp Glu Ser Thr Tyr Gly Pro Glu Asn Asn
595 600 605

Tyr Lys Thr Thr Pro Pro Val Leu Asp Ser Asp Gly Ser Phe Phe Leu
610 615 620

Tyr Ser Lys Leu Thr Val Ser Tyr Trp Arg Trp Tyr Lys Gly Asn Val
625 630 635 640

Phe Ser Cys Ser Val Met His Glu Ala Leu His Asn His Tyr Thr Gln
645 650 655

Lys Ser Leu Ser Leu Ser Pro Gly
660

<210> SEQ ID NO 400
<211> LENGTH: 664
<212> TYPE: PRT
<213> ORGANISM: Homo sapiens

<400> SEQUENCE: 400

Asp Ile Gln Met Thr Gln Ser Pro Pro Ala Leu Ser Ala Ser Val Gly
1 5 10 15

Asp Arg Val Thr Ile Thr Cys Arg Ala Ser Gln Asp Ile Asn Asp Trp
20 25 30

Leu Ala Trp Tyr Gln His Lys Pro Gly Lys Ala Pro Lys Leu Leu Ile
35 40 45

Tyr Asp Ala Ser Ser Leu Glu Ser Gly Val Pro Leu Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Lys Tyr Ser Ala Pro Gln
85 90 95

Val Thr Phe Gly Gln Gly Thr Arg Leu Glu Ile Lys Arg Thr Val Ala
100 105 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu
130 135 140

Ala Lys Val Gln Trp Lys Val Asp Asn Ala Leu Gln Ser Gly Asn Ser
145 150 155 160

```
Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Glu Val Gln Leu Gln Gln Ser Gly Pro
    210                 215                 220

Gly Leu Val Lys Pro Ser Gln Thr Leu Ser Leu Thr Cys Ala Ile Ser
225                 230                 235                 240

Gly Asp Ser Val Ser Ser Lys Ser Ala Ala Trp Asn Trp Ile Arg Gln
                245                 250                 255

Ser Pro Ser Arg Gly Leu Glu Trp Leu Gly Arg Thr Tyr Tyr Arg Ser
            260                 265                 270

Lys Trp Ser Thr Asp Tyr Ala Ala Ser Val Lys Ser Arg Ile Thr Ile
        275                 280                 285

Asn Pro Asp Thr Ser Lys Asn Gln Leu Ser Leu Gln Leu Asn Ser Val
    290                 295                 300

Thr Pro Glu Asp Thr Ala Val Tyr Tyr Cys Ala Arg Thr Trp Val Gly
305                 310                 315                 320

Tyr Val Asp Arg Trp Gly Gln Gly Thr Leu Val Thr Val Ser Ser Ala
                325                 330                 335

Ser Thr Lys Gly Pro Ser Val Phe Pro Leu Ala Pro Ser Ser Lys Ser
            340                 345                 350

Thr Ser Gly Gly Thr Ala Ala Leu Gly Cys Leu Val Lys Asp Tyr Phe
        355                 360                 365

Pro Glu Pro Val Thr Val Ser Trp Asn Ser Gly Ala Leu Thr Ser Gly
    370                 375                 380

Val His Thr Phe Pro Ala Val Leu Gln Ser Ser Gly Leu Tyr Ser Leu
385                 390                 395                 400

Ser Ser Val Val Thr Val Pro Ser Ser Ser Leu Gly Thr Gln Thr Tyr
                405                 410                 415

Ile Cys Asn Val Asn His Lys Pro Ser Asn Thr Lys Val Asp Lys Lys
            420                 425                 430

Val Glu Pro Lys Ser Cys Asp Lys Thr His Thr Cys Pro Pro Cys Pro
        435                 440                 445

Ala Pro Glu Leu Leu Gly Gly Pro Ser Val Phe Leu Phe Pro Pro Lys
    450                 455                 460

Pro Lys Asp Thr Leu Met Ile Ser Arg Thr Pro Glu Val Thr Cys Val
465                 470                 475                 480

Val Val Asp Val Ser His Glu Asp Pro Glu Val Lys Phe Asn Trp Tyr
                485                 490                 495

Val Asp Gly Val Glu Val His Asn Ala Lys Thr Lys Pro Arg Glu Glu
            500                 505                 510

Gln Tyr Asn Ser Thr Tyr Arg Val Val Ser Val Leu Thr Val Leu His
        515                 520                 525

Gln Asp Trp Leu Asn Gly Lys Glu Tyr Lys Cys Lys Val Ser Asn Lys
    530                 535                 540

Ala Leu Pro Ala Pro Ile Glu Lys Thr Ile Ser Lys Ala Lys Gly Gln
545                 550                 555                 560

Pro Arg Glu Pro Gln Val Tyr Thr Leu Pro Pro Ser Arg Asp Glu Leu
                565                 570                 575
```

```
Glu Glu Gly Pro Val Ser Leu Thr Cys Leu Val Lys Gly Phe Tyr Pro
            580                 585                 590

Ser Asp Ile Ala Val Glu Trp Glu Ser Thr Tyr Gly Pro Glu Asn Asn
        595                 600                 605

Tyr Lys Thr Thr Pro Pro Val Leu Asp Ser Asp Gly Ser Phe Phe Leu
    610                 615                 620

Tyr Ser Lys Leu Thr Val Ser Tyr Trp Arg Trp Tyr Lys Gly Asn Val
625                 630                 635                 640

Phe Ser Cys Ser Val Met His Glu Ala Leu His Asn His Tyr Thr Gln
                645                 650                 655

Lys Ser Leu Ser Leu Ser Pro Gly
            660


<210> SEQ ID NO 401
<211> LENGTH: 931
<212> TYPE: PRT
<213> ORGANISM: Homo sapiens

<400> SEQUENCE: 401

Asp Ile Gln Met Thr Gln Ser Pro Pro Ala Leu Ser Ala Ser Val Gly
1               5                   10                  15

Asp Arg Val Thr Ile Thr Cys Arg Ala Ser Gln Asp Ile Asn Asp Trp
            20                  25                  30

Leu Ala Trp Tyr Gln His Lys Pro Gly Lys Ala Pro Lys Leu Leu Ile
        35                  40                  45

Tyr Asp Ala Ser Ser Leu Glu Ser Gly Val Pro Leu Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Lys Tyr Ser Ala Pro Gln
                85                  90                  95

Val Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Glu Val Gln Leu Gln Gln Ser Gly Pro
    210                 215                 220

Gly Leu Val Lys Pro Ser Gln Thr Leu Ser Leu Thr Cys Ala Ile Ser
225                 230                 235                 240

Gly Asp Ser Val Ser Ser Lys Ser Ala Ala Trp Asn Trp Ile Arg Gln
                245                 250                 255

Ser Pro Ser Arg Gly Leu Glu Trp Leu Gly Arg Thr Tyr Tyr Arg Ser
            260                 265                 270

Lys Trp Ser Thr Asp Tyr Ala Ala Ser Val Lys Ser Arg Ile Thr Ile
        275                 280                 285
```

-continued

```
Asn Pro Asp Thr Ser Lys Asn Gln Leu Ser Leu Gln Leu Asn Ser Val
    290                 295                 300

Thr Pro Glu Asp Thr Ala Val Tyr Tyr Cys Ala Arg Thr Trp Val Gly
305                 310                 315                 320

Tyr Val Asp Arg Trp Gly Gln Gly Thr Leu Val Thr Val Ser Ser Ala
                325                 330                 335

Ser Thr Lys Gly Pro Ser Val Phe Pro Leu Ala Pro Ser Ser Lys Ser
            340                 345                 350

Thr Ser Gly Gly Thr Ala Ala Leu Gly Cys Leu Val Lys Asp Tyr Phe
        355                 360                 365

Pro Glu Pro Val Thr Val Ser Trp Asn Ser Gly Ala Leu Thr Ser Gly
    370                 375                 380

Val His Thr Phe Pro Ala Val Leu Gln Ser Ser Gly Leu Tyr Ser Leu
385                 390                 395                 400

Ser Ser Val Val Thr Val Pro Ser Ser Ser Leu Gly Thr Gln Thr Tyr
                405                 410                 415

Ile Cys Asn Val Asn His Lys Pro Ser Asn Thr Lys Val Asp Lys Lys
            420                 425                 430

Val Glu Pro Lys Ser Cys Asp Lys Thr His Thr Cys Pro Pro Cys Pro
        435                 440                 445

Ala Pro Glu Leu Leu Gly Gly Pro Ser Val Phe Leu Phe Pro Pro Lys
    450                 455                 460

Pro Lys Asp Thr Leu Met Ile Ser Arg Thr Pro Glu Val Thr Cys Val
465                 470                 475                 480

Val Val Asp Val Ser His Glu Asp Pro Glu Val Lys Phe Asn Trp Tyr
                485                 490                 495

Val Asp Gly Val Glu Val His Asn Ala Lys Thr Lys Pro Arg Glu Glu
            500                 505                 510

Gln Tyr Asn Ser Thr Tyr Arg Val Val Ser Val Leu Thr Val Leu His
        515                 520                 525

Gln Asp Trp Leu Asn Gly Lys Glu Tyr Lys Cys Lys Val Ser Asn Lys
    530                 535                 540

Ala Leu Pro Ala Pro Ile Glu Lys Thr Ile Ser Lys Ala Lys Gly Gln
545                 550                 555                 560

Pro Arg Glu Pro Gln Val Tyr Thr Leu Pro Pro Ser Arg Asp Glu Leu
                565                 570                 575

Thr Lys Asn Gln Val Ser Leu Thr Cys Leu Val Lys Gly Phe Tyr Pro
            580                 585                 590

Ser Asp Ile Ala Val Glu Trp Glu Ser Asn Gly Gln Pro Glu Asn Asn
        595                 600                 605

Tyr Lys Thr Thr Pro Pro Val Leu Asp Ser Asp Gly Ser Phe Phe Leu
    610                 615                 620

Tyr Ser Lys Leu Thr Val Asp Lys Ser Arg Trp Gln Gln Gly Asn Val
625                 630                 635                 640

Phe Ser Cys Ser Val Met His Glu Ala Leu His Asn His Tyr Thr Gln
                645                 650                 655

Lys Ser Leu Ser Leu Ser Pro Gly Gly Gly Gly Gly Ser Gly Gly Gly
            660                 665                 670

Gly Ser Gly Gly Gly Gly Ser Gln Val Gln Leu Val Gln Ser Gly Ala
        675                 680                 685

Glu Val Lys Lys Pro Gly Ala Ser Val Lys Val Ser Cys Lys Thr Ser
    690                 695                 700
```

-continued

Arg Tyr Thr Phe Thr Glu Tyr Thr Ile His Trp Val Arg Gln Ala Pro
705 710 715 720

Gly Gln Arg Leu Glu Trp Ile Gly Gly Ile Asn Pro Asn Asn Gly Ile
725 730 735

Pro Asn Tyr Asn Gln Lys Phe Lys Gly Arg Val Thr Ile Thr Val Asp
740 745 750

Thr Ser Ala Ser Thr Ala Tyr Met Glu Leu Ser Ser Leu Arg Ser Glu
755 760 765

Asp Thr Ala Val Tyr Tyr Cys Ala Arg Arg Arg Ile Ala Tyr Gly Tyr
770 775 780

Asp Glu Gly His Ala Met Asp Tyr Trp Gly Gln Gly Thr Leu Val Thr
785 790 795 800

Val Ser Ser Gly Gly Gly Gly Ser Gly Gly Gly Gly Ser Gly Gly Gly
805 810 815

Gly Ser Asp Ile Val Met Thr Gln Ser Pro Asp Ser Leu Ala Val Ser
820 825 830

Leu Gly Glu Arg Ala Thr Ile Asn Cys Lys Ser Ser Gln Ser Leu Leu
835 840 845

Tyr Ser Arg Asn Gln Lys Asn Tyr Leu Ala Trp Tyr Gln Gln Lys Pro
850 855 860

Gly Gln Pro Pro Lys Leu Leu Ile Phe Trp Ala Ser Thr Arg Glu Ser
865 870 875 880

Gly Val Pro Asp Arg Phe Ser Gly Ser Gly Phe Gly Thr Asp Phe Thr
885 890 895

Leu Thr Ile Ser Ser Leu Gln Ala Glu Asp Val Ala Val Tyr Tyr Cys
900 905 910

Gln Gln Tyr Phe Ser Tyr Pro Leu Thr Phe Gly Gln Gly Thr Lys Val
915 920 925

Glu Ile Lys
930

<210> SEQ ID NO 402
<211> LENGTH: 252
<212> TYPE: PRT
<213> ORGANISM: Homo sapiens

<400> SEQUENCE: 402

Gln Val Gln Leu Val Gln Ser Gly Ala Glu Val Lys Lys Pro Gly Ala
1 5 10 15

Ser Val Lys Val Ser Cys Lys Thr Ser Arg Tyr Thr Phe Thr Glu Tyr
20 25 30

Thr Ile His Trp Val Arg Gln Ala Pro Gly Gln Arg Leu Glu Trp Ile
35 40 45

Gly Gly Ile Asn Pro Asn Asn Gly Ile Pro Asn Tyr Asn Gln Lys Phe
50 55 60

Lys Gly Arg Val Thr Ile Thr Val Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Arg Arg Ile Ala Tyr Gly Tyr Asp Glu Gly His Ala Met Asp
100 105 110

Tyr Trp Gly Gln Gly Thr Leu Val Thr Val Ser Ser Gly Gly Gly Gly
115 120 125

Ser Gly Gly Gly Gly Ser Gly Gly Gly Gly Ser Asp Ile Val Met Thr
130 135 140

Gln Ser Pro Asp Ser Leu Ala Val Ser Leu Gly Glu Arg Ala Thr Ile
145 150 155 160

Asn Cys Lys Ser Ser Gln Ser Leu Leu Tyr Ser Arg Asn Gln Lys Asn
165 170 175

Tyr Leu Ala Trp Tyr Gln Gln Lys Pro Gly Gln Pro Pro Lys Leu Leu
180 185 190

Ile Phe Trp Ala Ser Thr Arg Glu Ser Gly Val Pro Asp Arg Phe Ser
195 200 205

Gly Ser Gly Phe Gly Thr Asp Phe Thr Leu Thr Ile Ser Ser Leu Gln
210 215 220

Ala Glu Asp Val Ala Val Tyr Tyr Cys Gln Gln Tyr Phe Ser Tyr Pro
225 230 235 240

Leu Thr Phe Gly Gln Gly Thr Lys Val Glu Ile Lys
245 250

<210> SEQ ID NO 403
<211> LENGTH: 919
<212> TYPE: PRT
<213> ORGANISM: Homo sapiens

<400> SEQUENCE: 403

Asp Ile Gln Met Thr Gln Ser Pro Pro Ala Leu Ser Ala Ser Val Gly
1 5 10 15

Asp Arg Val Thr Ile Thr Cys Arg Ala Ser Gln Asp Ile Asn Asp Trp
20 25 30

Leu Ala Trp Tyr Gln His Lys Pro Gly Lys Ala Pro Lys Leu Leu Ile
35 40 45

Tyr Asp Ala Ser Ser Leu Glu Ser Gly Val Pro Leu Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Lys Tyr Ser Ala Pro Gln
85 90 95

Val Thr Phe Gly Gln Gly Thr Arg Leu Glu Ile Lys Arg Thr Val Ala
100 105 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu
130 135 140

Ala Lys Val Gln Trp Lys Val Asp Asn Ala Leu Gln Ser Gly Asn Ser
145 150 155 160

Gln Glu Ser Val Thr Glu Gln Asp Ser Lys Asp Ser Thr Tyr Ser Leu
165 170 175

Ser Ser Thr Leu Thr Leu Ser Lys Ala Asp Tyr Glu Lys His Lys Val
180 185 190

Tyr Ala Cys Glu Val Thr His Gln Gly Leu Ser Ser Pro Val Thr Lys
195 200 205

Ser Phe Asn Arg Gly Glu Cys Glu Val Gln Leu Gln Gln Ser Gly Pro
210 215 220

Gly Leu Val Lys Pro Ser Gln Thr Leu Ser Leu Thr Cys Ala Ile Ser
225 230 235 240

Gly Asp Ser Val Ser Ser Lys Ser Ala Ala Trp Asn Trp Ile Arg Gln
245 250 255

Ser Pro Ser Arg Gly Leu Glu Trp Leu Gly Arg Thr Tyr Tyr Arg Ser

-continued

```
            260                 265                 270

Lys Trp Ser Thr Asp Tyr Ala Ala Ser Val Lys Ser Arg Ile Thr Ile
        275                 280                 285

Asn Pro Asp Thr Ser Lys Asn Gln Leu Ser Leu Gln Leu Asn Ser Val
    290                 295                 300

Thr Pro Glu Asp Thr Ala Val Tyr Tyr Cys Ala Arg Thr Trp Val Gly
305                 310                 315                 320

Tyr Val Asp Arg Trp Gly Gln Gly Thr Leu Val Thr Val Ser Ser Ala
                325                 330                 335

Ser Thr Lys Gly Pro Ser Val Phe Pro Leu Ala Pro Ser Ser Lys Ser
            340                 345                 350

Thr Ser Gly Gly Thr Ala Ala Leu Gly Cys Leu Val Lys Asp Tyr Phe
        355                 360                 365

Pro Glu Pro Val Thr Val Ser Trp Asn Ser Gly Ala Leu Thr Ser Gly
    370                 375                 380

Val His Thr Phe Pro Ala Val Leu Gln Ser Ser Gly Leu Tyr Ser Leu
385                 390                 395                 400

Ser Ser Val Val Thr Val Pro Ser Ser Ser Leu Gly Thr Gln Thr Tyr
                405                 410                 415

Ile Cys Asn Val Asn His Lys Pro Ser Asn Thr Lys Val Asp Lys Lys
            420                 425                 430

Val Glu Pro Lys Ser Cys Asp Lys Thr His Thr Cys Pro Pro Cys Pro
        435                 440                 445

Ala Pro Glu Leu Leu Gly Gly Pro Ser Val Phe Leu Phe Pro Pro Lys
    450                 455                 460

Pro Lys Asp Thr Leu Met Ile Ser Arg Thr Pro Glu Val Thr Cys Val
465                 470                 475                 480

Val Val Asp Val Ser His Glu Asp Pro Glu Val Lys Phe Asn Trp Tyr
                485                 490                 495

Val Asp Gly Val Glu Val His Asn Ala Lys Thr Lys Pro Arg Glu Glu
            500                 505                 510

Gln Tyr Asn Ser Thr Tyr Arg Val Val Ser Val Leu Thr Val Leu His
        515                 520                 525

Gln Asp Trp Leu Asn Gly Lys Glu Tyr Lys Cys Lys Val Ser Asn Lys
    530                 535                 540

Ala Leu Pro Ala Pro Ile Glu Lys Thr Ile Ser Lys Ala Lys Gly Gln
545                 550                 555                 560

Pro Arg Glu Pro Gln Val Tyr Thr Leu Pro Pro Ser Arg Asp Glu Leu
                565                 570                 575

Thr Lys Asn Gln Val Ser Leu Thr Cys Leu Val Lys Gly Phe Tyr Pro
            580                 585                 590

Ser Asp Ile Ala Val Glu Trp Glu Ser Asn Gly Gln Pro Glu Asn Asn
        595                 600                 605

Tyr Lys Thr Thr Pro Pro Val Leu Asp Ser Asp Gly Ser Phe Phe Leu
    610                 615                 620

Tyr Ser Lys Leu Thr Val Asp Lys Ser Arg Trp Gln Gln Gly Asn Val
625                 630                 635                 640

Phe Ser Cys Ser Val Met His Glu Ala Leu His Asn His Tyr Thr Gln
                645                 650                 655

Lys Ser Leu Ser Leu Ser Pro Gly Gly Gly Gly Gly Ser Gly Gly Gly
            660                 665                 670

Gly Ser Gly Gly Gly Gly Ser Gln Val Gln Leu Gln Glu Ser Gly Pro
        675                 680                 685
```

```
Gly Leu Val Lys Pro Ser Gln Thr Leu Ser Leu Thr Cys Thr Val Ser
    690                 695                 700

Gly Gly Ser Ile Asn Asn Asn Asn Tyr Tyr Trp Thr Trp Ile Arg Gln
705                 710                 715                 720

His Pro Gly Lys Gly Leu Glu Trp Ile Gly Tyr Ile Tyr Tyr Ser Gly
                725                 730                 735

Ser Thr Phe Tyr Asn Pro Ser Leu Lys Ser Arg Val Thr Ile Ser Val
            740                 745                 750

Asp Thr Ser Lys Thr Gln Phe Ser Leu Lys Leu Ser Ser Val Thr Ala
        755                 760                 765

Ala Asp Thr Ala Val Tyr Tyr Cys Ala Arg Glu Asp Thr Met Thr Gly
    770                 775                 780

Leu Asp Val Trp Gly Gln Gly Thr Thr Val Thr Val Ser Ser Gly Gly
785                 790                 795                 800

Gly Gly Ser Gly Gly Gly Gly Ser Gly Gly Gly Gly Ser Asp Ile Gln
                805                 810                 815

Met Thr Gln Ser Pro Ser Ser Leu Ser Ala Ser Val Gly Asp Arg Val
            820                 825                 830

Thr Ile Thr Cys Arg Ala Ser Gln Ser Ile Asn Asn Tyr Leu Asn Trp
        835                 840                 845

Tyr Gln Gln Lys Pro Gly Lys Ala Pro Thr Leu Leu Ile Tyr Ala Ala
    850                 855                 860

Ser Ser Leu Gln Ser Gly Val Pro Ser Arg Phe Ser Gly Ser Arg Ser
865                 870                 875                 880

Gly Thr Asp Phe Thr Leu Thr Ile Ser Ser Leu Gln Pro Glu Asp Phe
                885                 890                 895

Ala Ala Tyr Phe Cys Gln Gln Thr Tyr Ser Asn Pro Thr Phe Gly Gln
            900                 905                 910

Gly Thr Lys Val Glu Val Lys
        915
```

<210> SEQ ID NO 404
<211> LENGTH: 240
<212> TYPE: PRT
<213> ORGANISM: Homo sapiens

<400> SEQUENCE: 404

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Asn Asn Asn
            20                  25                  30

Asn Tyr Tyr Trp Thr Trp Ile Arg Gln His Pro Gly Lys Gly Leu Glu
        35                  40                  45

Trp Ile Gly Tyr Ile Tyr Tyr Ser Gly Ser Thr Phe Tyr Asn Pro Ser
    50                  55                  60

Leu Lys Ser Arg Val Thr Ile Ser Val Asp Thr Ser Lys Thr Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asp Thr Met Thr Gly Leu Asp Val Trp Gly Gln Gly
            100                 105                 110

Thr Thr Val Thr Val Ser Ser Gly Gly Gly Gly Ser Gly Gly Gly Gly
        115                 120                 125

Ser Gly Gly Gly Gly Ser Asp Ile Gln Met Thr Gln Ser Pro Ser Ser
```

```
    130                 135                 140

Leu Ser Ala Ser Val Gly Asp Arg Val Thr Ile Thr Cys Arg Ala Ser
145                 150                 155                 160

Gln Ser Ile Asn Asn Tyr Leu Asn Trp Tyr Gln Gln Lys Pro Gly Lys
                165                 170                 175

Ala Pro Thr Leu Leu Ile Tyr Ala Ala Ser Ser Leu Gln Ser Gly Val
            180                 185                 190

Pro Ser Arg Phe Ser Gly Ser Arg Ser Gly Thr Asp Phe Thr Leu Thr
        195                 200                 205

Ile Ser Ser Leu Gln Pro Glu Asp Phe Ala Ala Tyr Phe Cys Gln Gln
    210                 215                 220

Thr Tyr Ser Asn Pro Thr Phe Gly Gln Gly Thr Lys Val Glu Val Lys
225                 230                 235                 240


<210> SEQ ID NO 405
<211> LENGTH: 926
<212> TYPE: PRT
<213> ORGANISM: Homo sapiens

<400> SEQUENCE: 405

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Gln Val Gln Leu Val Gln
    210                 215                 220

Ser Gly Val Glu Val Lys Lys Pro Gly Ala Ser Val Lys Val Ser Cys
225                 230                 235                 240

Lys Ala Ser Gly Tyr Thr Phe Thr Asn Tyr Tyr Met Tyr Trp Val Arg
                245                 250                 255

Gln Ala Pro Gly Gln Gly Leu Glu Trp Met Gly Gly Ile Asn Pro Ser
            260                 265                 270
```

-continued

```
Asn Gly Gly Thr Asn Phe Asn Glu Lys Phe Lys Asn Arg Val Thr Leu
        275                 280                 285

Thr Thr Asp Ser Ser Thr Thr Thr Ala Tyr Met Glu Leu Lys Ser Leu
    290                 295                 300

Gln Phe Asp Asp Thr Ala Val Tyr Tyr Cys Ala Arg Arg Asp Tyr Arg
305                 310                 315                 320

Phe Asp Met Gly Phe Asp Tyr Trp Gly Gln Gly Thr Thr Val Thr Val
                325                 330                 335

Ser Ser Ala Ser Thr Lys Gly Pro Ser Val Phe Pro Leu Ala Pro Ser
            340                 345                 350

Ser Lys Ser Thr Ser Gly Gly Thr Ala Ala Leu Gly Cys Leu Val Lys
        355                 360                 365

Asp Tyr Phe Pro Glu Pro Val Thr Val Ser Trp Asn Ser Gly Ala Leu
    370                 375                 380

Thr Ser Gly Val His Thr Phe Pro Ala Val Leu Gln Ser Ser Gly Leu
385                 390                 395                 400

Tyr Ser Leu Ser Ser Val Val Thr Val Pro Ser Ser Ser Leu Gly Thr
                405                 410                 415

Gln Thr Tyr Ile Cys Asn Val Asn His Lys Pro Ser Asn Thr Lys Val
            420                 425                 430

Asp Lys Lys Val Glu Pro Lys Ser Cys Asp Lys Thr His Thr Cys Pro
        435                 440                 445

Pro Cys Pro Ala Pro Glu Leu Ala Gly Ala Pro Ser Val Phe Leu Phe
    450                 455                 460

Pro Pro Lys Pro Lys Asp Thr Leu Met Ile Ser Arg Thr Pro Glu Val
465                 470                 475                 480

Thr Cys Val Val Val Asp Val Ser His Glu Asp Pro Glu Val Lys Phe
                485                 490                 495

Asn Trp Tyr Val Asp Gly Val Glu Val His Asn Ala Lys Thr Lys Pro
            500                 505                 510

Arg Glu Glu Gln Tyr Asn Ser Thr Tyr Arg Val Val Ser Val Leu Thr
        515                 520                 525

Val Leu His Gln Asp Trp Leu Asn Gly Lys Glu Tyr Lys Cys Lys Val
    530                 535                 540

Ser Asn Lys Ala Leu Pro Ala Pro Ile Glu Lys Thr Ile Ser Lys Ala
545                 550                 555                 560

Lys Gly Gln Pro Arg Glu Pro Gln Val Tyr Thr Leu Pro Pro Ser Arg
                565                 570                 575

Asp Glu Leu Thr Lys Asn Gln Val Ser Leu Thr Cys Leu Val Lys Gly
            580                 585                 590

Phe Tyr Pro Ser Asp Ile Ala Val Glu Trp Glu Ser Asn Gly Gln Pro
        595                 600                 605

Glu Asn Asn Tyr Lys Thr Thr Pro Pro Val Leu Asp Ser Asp Gly Ser
    610                 615                 620

Phe Phe Leu Tyr Ser Lys Leu Thr Val Asp Lys Ser Arg Trp Gln Gln
625                 630                 635                 640

Gly Asn Val Phe Ser Cys Ser Val Met His Glu Ala Leu His Asn His
                645                 650                 655

Tyr Thr Gln Lys Ser Leu Ser Leu Ser Pro Gly Gly Gly Gly Gly Gly
            660                 665                 670

Ser Gly Gly Gly Gly Ser Gly Gly Gly Gly Ser Glu Val Gln Leu Gln
        675                 680                 685

Gln Ser Gly Pro Gly Leu Val Lys Pro Ser Gln Thr Leu Ser Leu Thr
```

```
    690                 695                 700

Cys Ala Ile Ser Gly Asp Ser Val Ser Ser Lys Ser Ala Ala Trp Asn
705                 710                 715                 720

Trp Ile Arg Gln Ser Pro Ser Arg Gly Leu Glu Trp Leu Gly Arg Thr
                725                 730                 735

Tyr Tyr Arg Ser Lys Trp Ser Thr Asp Tyr Ala Ala Ser Val Lys Ser
            740                 745                 750

Arg Ile Thr Ile Asn Pro Asp Thr Ser Lys Asn Gln Leu Ser Leu Gln
        755                 760                 765

Leu Asn Ser Val Thr Pro Glu Asp Thr Ala Val Tyr Tyr Cys Ala Arg
    770                 775                 780

Thr Trp Val Gly Tyr Val Asp Arg Trp Gly Gln Gly Thr Leu Val Thr
785                 790                 795                 800

Val Ser Ser Gly Gly Gly Gly Ser Gly Gly Gly Gly Ser Gly Gly Gly
                805                 810                 815

Gly Ser Asp Ile Gln Met Thr Gln Ser Pro Pro Ala Leu Ser Ala Ser
            820                 825                 830

Val Gly Asp Arg Val Thr Ile Thr Cys Arg Ala Ser Gln Asp Ile Asn
        835                 840                 845

Asp Trp Leu Ala Trp Tyr Gln His Lys Pro Gly Lys Ala Pro Lys Leu
    850                 855                 860

Leu Ile Tyr Asp Ala Ser Ser Leu Glu Ser Gly Val Pro Leu Arg Phe
865                 870                 875                 880

Ser Gly Ser Gly Ser Gly Thr Glu Phe Thr Leu Thr Ile Ser Ser Leu
                885                 890                 895

Gln Pro Asp Asp Phe Ala Thr Tyr Tyr Cys Gln Gln Lys Tyr Ser Ala
            900                 905                 910

Pro Gln Val Thr Phe Gly Gln Gly Thr Arg Leu Glu Ile Lys
        915                 920                 925


<210> SEQ ID NO 406
<211> LENGTH: 246
<212> TYPE: PRT
<213> ORGANISM: Homo sapiens

<400> SEQUENCE: 406

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Glu Ile Val Leu Thr Gln Ser Pro Ala
    130                 135                 140
```

Thr Leu Ser Leu Ser Pro Gly Glu Arg Ala Thr Leu Ser Cys Arg Ala
145 150 155 160

Ser Lys Gly Val Ser Thr Ser Gly Tyr Ser Tyr Leu His Trp Tyr Gln
165 170 175

Gln Lys Pro Gly Gln Ala Pro Arg Leu Leu Ile Tyr Leu Ala Ser Tyr
180 185 190

Leu Glu Ser Gly Val Pro Ala Arg Phe Ser Gly Ser Gly Ser Gly Thr
195 200 205

Asp Phe Thr Leu Thr Ile Ser Ser Leu Glu Pro Glu Asp Phe Ala Val
210 215 220

Tyr Tyr Cys Gln His Ser Arg Asp Leu Pro Leu Thr Phe Gly Gly Gly
225 230 235 240

Thr Lys Val Glu Ile Lys
245

<210> SEQ ID NO 407
<211> LENGTH: 918
<212> TYPE: PRT
<213> ORGANISM: Homo sapiens

<400> SEQUENCE: 407

Asp Ile Gln Met Thr Gln Ser Pro Pro Ala Leu Ser Ala Ser Val Gly
1 5 10 15

Asp Arg Val Thr Ile Thr Cys Arg Ala Ser Gln Asp Ile Asn Asp Trp
20 25 30

Leu Ala Trp Tyr Gln His Lys Pro Gly Lys Ala Pro Lys Leu Leu Ile
35 40 45

Tyr Asp Ala Ser Ser Leu Glu Ser Gly Val Pro Leu Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Lys Tyr Ser Ala Pro Gln
85 90 95

Val Thr Phe Gly Gln Gly Thr Arg Leu Glu Ile Lys Arg Thr Val Ala
100 105 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu
130 135 140

Ala Lys Val Gln Trp Lys Val Asp Asn Ala Leu Gln Ser Gly Asn Ser
145 150 155 160

Gln Glu Ser Val Thr Glu Gln Asp Ser Lys Asp Ser Thr Tyr Ser Leu
165 170 175

Ser Ser Thr Leu Thr Leu Ser Lys Ala Asp Tyr Glu Lys His Lys Val
180 185 190

Tyr Ala Cys Glu Val Thr His Gln Gly Leu Ser Ser Pro Val Thr Lys
195 200 205

Ser Phe Asn Arg Gly Glu Cys Glu Val Gln Leu Gln Gln Ser Gly Pro
210 215 220

Gly Leu Val Lys Pro Ser Gln Thr Leu Ser Leu Thr Cys Ala Ile Ser
225 230 235 240

Gly Asp Ser Val Ser Ser Lys Ser Ala Ala Trp Asn Trp Ile Arg Gln
245 250 255

Ser Pro Ser Arg Gly Leu Glu Trp Leu Gly Arg Thr Tyr Tyr Arg Ser
260 265 270

Lys Trp Ser Thr Asp Tyr Ala Ala Ser Val Lys Ser Arg Ile Thr Ile
275 280 285

Asn Pro Asp Thr Ser Lys Asn Gln Leu Ser Leu Gln Leu Asn Ser Val
290 295 300

Thr Pro Glu Asp Thr Ala Val Tyr Tyr Cys Ala Arg Thr Trp Val Gly
305 310 315 320

Tyr Val Asp Arg Trp Gly Gln Gly Thr Leu Val Thr Val Ser Ser Ala
325 330 335

Ser Thr Lys Gly Pro Ser Val Phe Pro Leu Ala Pro Ser Ser Lys Ser
340 345 350

Thr Ser Gly Gly Thr Ala Ala Leu Gly Cys Leu Val Lys Asp Tyr Phe
355 360 365

Pro Glu Pro Val Thr Val Ser Trp Asn Ser Gly Ala Leu Thr Ser Gly
370 375 380

Val His Thr Phe Pro Ala Val Leu Gln Ser Ser Gly Leu Tyr Ser Leu
385 390 395 400

Ser Ser Val Val Thr Val Pro Ser Ser Ser Leu Gly Thr Gln Thr Tyr
405 410 415

Ile Cys Asn Val Asn His Lys Pro Ser Asn Thr Lys Val Asp Lys Lys
420 425 430

Val Glu Pro Lys Ser Cys Asp Lys Thr His Thr Cys Pro Pro Cys Pro
435 440 445

Ala Pro Glu Leu Ala Gly Ala Pro Ser Val Phe Leu Phe Pro Pro Lys
450 455 460

Pro Lys Asp Thr Leu Met Ile Ser Arg Thr Pro Glu Val Thr Cys Val
465 470 475 480

Val Val Asp Val Ser His Glu Asp Pro Glu Val Lys Phe Asn Trp Tyr
485 490 495

Val Asp Gly Val Glu Val His Asn Ala Lys Thr Lys Pro Arg Glu Glu
500 505 510

Gln Tyr Asn Ser Thr Tyr Arg Val Val Ser Val Leu Thr Val Leu His
515 520 525

Gln Asp Trp Leu Asn Gly Lys Glu Tyr Lys Cys Lys Val Ser Asn Lys
530 535 540

Ala Leu Pro Ala Pro Ile Glu Lys Thr Ile Ser Lys Ala Lys Gly Gln
545 550 555 560

Pro Arg Glu Pro Gln Val Tyr Thr Leu Pro Pro Ser Arg Asp Glu Leu
565 570 575

Thr Lys Asn Gln Val Ser Leu Thr Cys Leu Val Lys Gly Phe Tyr Pro
580 585 590

Ser Asp Ile Ala Val Glu Trp Glu Ser Asn Gly Gln Pro Glu Asn Asn
595 600 605

Tyr Lys Thr Thr Pro Pro Val Leu Asp Ser Asp Gly Ser Phe Phe Leu
610 615 620

Tyr Ser Lys Leu Thr Val Asp Lys Ser Arg Trp Gln Gln Gly Asn Val
625 630 635 640

Phe Ser Cys Ser Val Met His Glu Ala Leu His Asn His Tyr Thr Gln
645 650 655

Lys Ser Leu Ser Leu Ser Pro Gly Gly Gly Gly Gly Ser Gly Gly Gly
660 665 670

Gly Ser Gly Gly Gly Gly Ser Glu Val Gln Leu Val Gln Ser Gly Ala
675 680 685

```
Glu Val Lys Lys Pro Gly Glu Ser Leu Arg Ile Ser Cys Lys Gly Ser
    690                 695                 700

Gly Tyr Ser Phe Ser Thr Tyr Trp Ile Ser Trp Val Arg Gln Met Pro
705                 710                 715                 720

Gly Lys Gly Leu Glu Trp Met Gly Lys Ile Tyr Pro Gly Asp Ser Tyr
                725                 730                 735

Thr Asn Tyr Ser Pro Ser Phe Gln Gly Gln Val Thr Ile Ser Ala Asp
            740                 745                 750

Lys Ser Ile Ser Thr Ala Tyr Leu Gln Trp Ser Ser Leu Lys Ala Ser
        755                 760                 765

Asp Thr Ala Met Tyr Tyr Cys Ala Arg Gly Tyr Gly Ile Phe Asp Tyr
    770                 775                 780

Trp Gly Gln Gly Thr Leu Val Thr Val Ser Ser Gly Gly Gly Gly Ser
785                 790                 795                 800

Gly Gly Gly Gly Ser Gly Gly Gly Gly Ser Ser Tyr Glu Leu Thr Gln
                805                 810                 815

Pro Pro Ser Val Ser Val Ser Pro Gly Gln Thr Ala Ser Ile Thr Cys
            820                 825                 830

Ser Gly Asp Asn Ile Gly Asp Gln Tyr Ala His Trp Tyr Gln Gln Lys
        835                 840                 845

Pro Gly Gln Ser Pro Val Leu Val Ile Tyr Gln Asp Lys Asn Arg Pro
    850                 855                 860

Ser Gly Ile Pro Glu Arg Phe Ser Gly Ser Asn Ser Gly Asn Thr Ala
865                 870                 875                 880

Thr Leu Thr Ile Ser Gly Thr Gln Ala Met Asp Glu Ala Asp Tyr Tyr
                885                 890                 895

Cys Ala Thr Tyr Thr Gly Phe Gly Ser Leu Ala Val Phe Gly Gly Gly
            900                 905                 910

Thr Lys Leu Thr Val Leu
        915


<210> SEQ ID NO 408
<211> LENGTH: 239
<212> TYPE: PRT
<213> ORGANISM: Homo sapiens

<400> SEQUENCE: 408

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Tyr
            20                  25                  30

Trp Ile Ser Trp Val Arg Gln Met Pro Gly Lys Gly Leu Glu Trp Met
        35                  40                  45

Gly Lys Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Gly Ile Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Ser Tyr Glu Leu Thr Gln Pro Pro Ser Val Ser Val Ser
    130                 135                 140
```

```
Pro Gly Gln Thr Ala Ser Ile Thr Cys Ser Gly Asp Asn Ile Gly Asp
145                 150                 155                 160

Gln Tyr Ala His Trp Tyr Gln Gln Lys Pro Gly Gln Ser Pro Val Leu
                165                 170                 175

Val Ile Tyr Gln Asp Lys Asn Arg Pro Ser Gly Ile Pro Glu Arg Phe
            180                 185                 190

Ser Gly Ser Asn Ser Gly Asn Thr Ala Thr Leu Thr Ile Ser Gly Thr
        195                 200                 205

Gln Ala Met Asp Glu Ala Asp Tyr Tyr Cys Ala Thr Tyr Thr Gly Phe
    210                 215                 220

Gly Ser Leu Ala Val Phe Gly Gly Gly Thr Lys Leu Thr Val Leu
225                 230                 235


<210> SEQ ID NO 409
<211> LENGTH: 918
<212> TYPE: PRT
<213> ORGANISM: Homo sapiens

<400> SEQUENCE: 409

Asp Ile Gln Met Thr Gln Ser Pro Pro Ala Leu Ser Ala Ser Val Gly
1               5                   10                  15

Asp Arg Val Thr Ile Thr Cys Arg Ala Ser Gln Asp Ile Asn Asp Trp
            20                  25                  30

Leu Ala Trp Tyr Gln His Lys Pro Gly Lys Ala Pro Lys Leu Leu Ile
        35                  40                  45

Tyr Asp Ala Ser Ser Leu Glu Ser Gly Val Pro Leu Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Lys Tyr Ser Ala Pro Gln
                85                  90                  95

Val Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Glu Val Gln Leu Gln Gln Ser Gly Pro
    210                 215                 220

Gly Leu Val Lys Pro Ser Gln Thr Leu Ser Leu Thr Cys Ala Ile Ser
225                 230                 235                 240

Gly Asp Ser Val Ser Ser Lys Ser Ala Ala Trp Asn Trp Ile Arg Gln
                245                 250                 255

Ser Pro Ser Arg Gly Leu Glu Trp Leu Gly Arg Thr Tyr Tyr Arg Ser
            260                 265                 270

Lys Trp Ser Thr Asp Tyr Ala Ala Ser Val Lys Ser Arg Ile Thr Ile
```

-continued

```
        275                 280                 285

Asn Pro Asp Thr Ser Lys Asn Gln Leu Ser Leu Gln Leu Asn Ser Val
    290                 295                 300

Thr Pro Glu Asp Thr Ala Val Tyr Tyr Cys Ala Arg Thr Trp Val Gly
305                 310                 315                 320

Tyr Val Asp Arg Trp Gly Gln Gly Thr Leu Val Thr Val Ser Ser Ala
                325                 330                 335

Ser Thr Lys Gly Pro Ser Val Phe Pro Leu Ala Pro Ser Ser Lys Ser
            340                 345                 350

Thr Ser Gly Gly Thr Ala Ala Leu Gly Cys Leu Val Lys Asp Tyr Phe
        355                 360                 365

Pro Glu Pro Val Thr Val Ser Trp Asn Ser Gly Ala Leu Thr Ser Gly
    370                 375                 380

Val His Thr Phe Pro Ala Val Leu Gln Ser Ser Gly Leu Tyr Ser Leu
385                 390                 395                 400

Ser Ser Val Val Thr Val Pro Ser Ser Ser Leu Gly Thr Gln Thr Tyr
                405                 410                 415

Ile Cys Asn Val Asn His Lys Pro Ser Asn Thr Lys Val Asp Lys Lys
            420                 425                 430

Val Glu Pro Lys Ser Cys Asp Lys Thr His Thr Cys Pro Pro Cys Pro
        435                 440                 445

Ala Pro Glu Leu Ala Gly Ala Pro Ser Val Phe Leu Phe Pro Pro Lys
    450                 455                 460

Pro Lys Asp Thr Leu Met Ile Ser Arg Thr Pro Glu Val Thr Cys Val
465                 470                 475                 480

Val Val Asp Val Ser His Glu Asp Pro Glu Val Lys Phe Asn Trp Tyr
                485                 490                 495

Val Asp Gly Val Glu Val His Asn Ala Lys Thr Lys Pro Arg Glu Glu
            500                 505                 510

Gln Tyr Asn Ser Thr Tyr Arg Val Val Ser Val Leu Thr Val Leu His
        515                 520                 525

Gln Asp Trp Leu Asn Gly Lys Glu Tyr Lys Cys Lys Val Ser Asn Lys
    530                 535                 540

Ala Leu Pro Ala Pro Ile Glu Lys Thr Ile Ser Lys Ala Lys Gly Gln
545                 550                 555                 560

Pro Arg Glu Pro Gln Val Tyr Thr Leu Pro Pro Ser Arg Asp Glu Leu
                565                 570                 575

Thr Lys Asn Gln Val Ser Leu Thr Cys Leu Val Lys Gly Phe Tyr Pro
            580                 585                 590

Ser Asp Ile Ala Val Glu Trp Glu Ser Asn Gly Gln Pro Glu Asn Asn
        595                 600                 605

Tyr Lys Thr Thr Pro Pro Val Leu Asp Ser Asp Gly Ser Phe Phe Leu
    610                 615                 620

Tyr Ser Lys Leu Thr Val Asp Lys Ser Arg Trp Gln Gln Gly Asn Val
625                 630                 635                 640

Phe Ser Cys Ser Val Met His Glu Ala Leu His Asn His Tyr Thr Gln
                645                 650                 655

Lys Ser Leu Ser Leu Ser Pro Gly Gly Gly Gly Gly Ser Gly Gly Gly
            660                 665                 670

Gly Ser Gly Gly Gly Gly Ser Glu Val Gln Leu Val Gln Ser Gly Ala
        675                 680                 685

Glu Val Lys Lys Pro Gly Ala Ser Val Lys Val Ser Cys Lys Ala Ser
    690                 695                 700
```

Gly Tyr Thr Phe Thr Asp Ser Tyr Met Ser Trp Val Arg Gln Ala Pro
705 710 715 720

Gly Gln Gly Leu Glu Trp Ile Gly Asp Met Tyr Pro Asp Asn Gly Asp
725 730 735

Ser Ser Tyr Asn Gln Lys Phe Arg Glu Arg Val Thr Ile Thr Arg Asp
740 745 750

Thr Ser Thr Ser Thr Ala Tyr Leu Glu Leu Ser Ser Leu Arg Ser Glu
755 760 765

Asp Thr Ala Val Tyr Tyr Cys Val Leu Ala Pro Arg Trp Tyr Phe Ser
770 775 780

Val Trp Gly Gln Gly Thr Leu Val Thr Val Ser Ser Gly Gly Gly Gly
785 790 795 800

Ser Gly Gly Gly Gly Ser Gly Gly Gly Gly Ser Asp Ile Gln Met Thr
805 810 815

Gln Ser Pro Ser Ser Leu Ser Ala Ser Val Gly Asp Arg Val Thr Ile
820 825 830

Thr Cys Arg Ala Ser Gln Asp Ile Ser Asn Tyr Leu Asn Trp Tyr Gln
835 840 845

Gln Lys Pro Gly Lys Ala Pro Lys Leu Leu Ile Tyr Tyr Thr Ser Arg
850 855 860

Leu Arg Ser Gly Val Pro Ser Arg Phe Ser Gly Ser Gly Ser Gly Thr
865 870 875 880

Asp Phe Thr Leu Thr Ile Ser Ser Leu Gln Pro Glu Asp Phe Ala Thr
885 890 895

Tyr Tyr Cys Gln Gln Gly His Thr Leu Pro Pro Thr Phe Gly Gln Gly
900 905 910

Thr Lys Val Glu Ile Lys
915

<210> SEQ ID NO 410
<211> LENGTH: 239
<212> TYPE: PRT
<213> ORGANISM: Homo sapiens

<400> SEQUENCE: 410

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asp Ser
20 25 30

Tyr Met Ser Trp Val Arg Gln Ala Pro Gly Gln Gly Leu Glu Trp Ile
35 40 45

Gly Asp Met Tyr Pro Asp Asn Gly Asp Ser Ser Tyr Asn Gln Lys Phe
50 55 60

Arg Glu Arg Val Thr Ile Thr Arg Asp Thr Ser Thr Ser Thr Ala Tyr
65 70 75 80

Leu Glu Leu Ser Ser Leu Arg Ser Glu Asp Thr Ala Val Tyr Tyr Cys
85 90 95

Val Leu Ala Pro Arg Trp Tyr Phe Ser Val Trp Gly Gln Gly Thr Leu
100 105 110

Val Thr Val Ser Ser Gly Gly Gly Gly Ser Gly Gly Gly Gly Ser Gly
115 120 125

Gly Gly Gly Ser Asp Ile Gln Met Thr Gln Ser Pro Ser Ser Leu Ser
130 135 140

Ala Ser Val Gly Asp Arg Val Thr Ile Thr Cys Arg Ala Ser Gln Asp 145 150 155 160

Ile Ser Asn Tyr Leu Asn Trp Tyr Gln Gln Lys Pro Gly Lys Ala Pro
165 170 175

Lys Leu Leu Ile Tyr Tyr Thr Ser Arg Leu Arg Ser Gly Val Pro Ser
180 185 190

Arg Phe Ser Gly Ser Gly Ser Gly Thr Asp Phe Thr Leu Thr Ile Ser
195 200 205

Ser Leu Gln Pro Glu Asp Phe Ala Thr Tyr Tyr Cys Gln Gln Gly His
210 215 220

Thr Leu Pro Pro Thr Phe Gly Gln Gly Thr Lys Val Glu Ile Lys
225 230 235

<210> SEQ ID NO 411
<211> LENGTH: 934
<212> TYPE: PRT
<213> ORGANISM: Homo sapiens

<400> SEQUENCE: 411

Asp Ile Val Met Thr Gln Ser Pro Asp Ser Leu Ala Val Ser Leu Gly
1 5 10 15

Glu Arg Ala Thr Ile Asn Cys Lys Ser Ser Gln Thr Val Leu Tyr Ser
20 25 30

Ser Asn Asn Lys Lys Tyr Leu Ala Trp Tyr Gln Gln Lys Pro Gly Gln
35 40 45

Pro Pro Asn Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Gln
85 90 95

Tyr Tyr Ser Thr Pro Phe Thr Phe Gly Pro Gly Thr Lys Val Glu Ile
100 105 110

Lys Arg Thr Val Ala Ala Pro Ser Val Phe Ile Phe Pro Pro Ser Asp
115 120 125

Glu Gln Leu Lys Ser Gly Thr Ala Ser Val Val Cys Leu Leu Asn Asn
130 135 140

Phe Tyr Pro Arg Glu Ala Lys Val Gln Trp Lys Val Asp Asn Ala Leu
145 150 155 160

Gln Ser Gly Asn Ser Gln Glu Ser Val Thr Glu Gln Asp Ser Lys Asp
165 170 175

Ser Thr Tyr Ser Leu Ser Ser Thr Leu Thr Leu Ser Lys Ala Asp Tyr
180 185 190

Glu Lys His Lys Val Tyr Ala Cys Glu Val Thr His Gln Gly Leu Ser
195 200 205

Ser Pro Val Thr Lys Ser Phe Asn Arg Gly Glu Cys Glu Val Gln Leu
210 215 220

Gln Gln Ser Gly Pro Gly Leu Val Lys Pro Ser Gln Thr Leu Ser Leu
225 230 235 240

Thr Cys Ala Ile Ser Gly Asp Ser Val Ser Ser Asn Ser Ala Ala Trp
245 250 255

Asn Trp Ile Arg Gln Ser Pro Ser Arg Gly Leu Glu Trp Leu Gly Lys
260 265 270

Thr Tyr Tyr Arg Phe Lys Trp Tyr Ser Asp Tyr Ala Val Ser Val Lys
275 280 285

-continued

```
Gly Arg Ile Thr Ile Asn Pro Asp Thr Ser Lys Asn Gln Phe Ser Leu
    290                 295                 300

Gln Leu Asn Ser Val Thr Pro Glu Asp Thr Ala Val Phe Tyr Cys Thr
305                 310                 315                 320

Arg Glu Ser Thr Thr Tyr Asp Leu Leu Ala Gly Pro Phe Asp Tyr Trp
                325                 330                 335

Gly Gln Gly Thr Leu Val Thr Val Ser Ser Ala Ser Thr Lys Gly Pro
            340                 345                 350

Ser Val Phe Pro Leu Ala Pro Ser Ser Lys Ser Thr Ser Gly Gly Thr
        355                 360                 365

Ala Ala Leu Gly Cys Leu Val Lys Asp Tyr Phe Pro Glu Pro Val Thr
    370                 375                 380

Val Ser Trp Asn Ser Gly Ala Leu Thr Ser Gly Val His Thr Phe Pro
385                 390                 395                 400

Ala Val Leu Gln Ser Ser Gly Leu Tyr Ser Leu Ser Ser Val Val Thr
                405                 410                 415

Val Pro Ser Ser Ser Leu Gly Thr Gln Thr Tyr Ile Cys Asn Val Asn
            420                 425                 430

His Lys Pro Ser Asn Thr Lys Val Asp Lys Lys Val Glu Pro Lys Ser
        435                 440                 445

Cys Asp Lys Thr His Thr Cys Pro Pro Cys Pro Ala Pro Glu Leu Ala
    450                 455                 460

Gly Ala Pro Ser Val Phe Leu Phe Pro Pro Lys Pro Lys Asp Thr Leu
465                 470                 475                 480

Met Ile Ser Arg Thr Pro Glu Val Thr Cys Val Val Val Asp Val Ser
                485                 490                 495

His Glu Asp Pro Glu Val Lys Phe Asn Trp Tyr Val Asp Gly Val Glu
            500                 505                 510

Val His Asn Ala Lys Thr Lys Pro Arg Glu Glu Gln Tyr Asn Ser Thr
        515                 520                 525

Tyr Arg Val Val Ser Val Leu Thr Val Leu His Gln Asp Trp Leu Asn
    530                 535                 540

Gly Lys Glu Tyr Lys Cys Lys Val Ser Asn Lys Ala Leu Pro Ala Pro
545                 550                 555                 560

Ile Glu Lys Thr Ile Ser Lys Ala Lys Gly Gln Pro Arg Glu Pro Gln
                565                 570                 575

Val Tyr Thr Leu Pro Pro Ser Arg Asp Glu Leu Thr Lys Asn Gln Val
            580                 585                 590

Ser Leu Thr Cys Leu Val Lys Gly Phe Tyr Pro Ser Asp Ile Ala Val
        595                 600                 605

Glu Trp Glu Ser Asn Gly Gln Pro Glu Asn Asn Tyr Lys Thr Thr Pro
    610                 615                 620

Pro Val Leu Asp Ser Asp Gly Ser Phe Phe Leu Tyr Ser Lys Leu Thr
625                 630                 635                 640

Val Asp Lys Ser Arg Trp Gln Gln Gly Asn Val Phe Ser Cys Ser Val
                645                 650                 655

Met His Glu Ala Leu His Asn His Tyr Thr Gln Lys Ser Leu Ser Leu
            660                 665                 670

Ser Pro Gly Gly Gly Gly Gly Gly Ser Gly Gly Gly Gly Ser Gly Gly
        675                 680                 685

Gly Gly Ser Glu Val Gln Leu Gln Gln Ser Gly Pro Gly Leu Val Lys
    690                 695                 700

Pro Ser Gln Thr Leu Ser Leu Thr Cys Ala Ile Ser Gly Asp Ser Val
```

705 710 715 720

Ser Ser Lys Ser Ala Ala Trp Asn Trp Ile Arg Gln Ser Pro Ser Arg
725 730 735

Gly Leu Glu Trp Leu Gly Arg Thr Tyr Tyr Arg Ser Lys Trp Ser Thr
740 745 750

Asp Tyr Ala Ala Ser Val Lys Ser Arg Ile Thr Ile Asn Pro Asp Thr
755 760 765

Ser Lys Asn Gln Leu Ser Leu Gln Leu Asn Ser Val Thr Pro Glu Asp
770 775 780

Thr Ala Val Tyr Tyr Cys Ala Arg Thr Trp Val Gly Tyr Val Asp Arg
785 790 795 800

Trp Gly Gln Gly Thr Leu Val Thr Val Ser Ser Gly Gly Gly Gly Ser
805 810 815

Gly Gly Gly Gly Ser Gly Gly Gly Gly Ser Asp Ile Gln Met Thr Gln
820 825 830

Ser Pro Pro Ala Leu Ser Ala Ser Val Gly Asp Arg Val Thr Ile Thr
835 840 845

Cys Arg Ala Ser Gln Asp Ile Asn Asp Trp Leu Ala Trp Tyr Gln His
850 855 860

Lys Pro Gly Lys Ala Pro Lys Leu Leu Ile Tyr Asp Ala Ser Ser Leu
865 870 875 880

Glu Ser Gly Val Pro Leu Arg Phe Ser Gly Ser Gly Ser Gly Thr Glu
885 890 895

Phe Thr Leu Thr Ile Ser Ser Leu Gln Pro Asp Asp Phe Ala Thr Tyr
900 905 910

Tyr Cys Gln Gln Lys Tyr Ser Ala Pro Gln Val Thr Phe Gly Gln Gly
915 920 925

Thr Arg Leu Glu Ile Lys
930

<210> SEQ ID NO 412
<211> LENGTH: 255
<212> TYPE: PRT
<213> ORGANISM: Homo sapiens

<400> SEQUENCE: 412

Glu Val Gln Leu Gln Gln Ser Gly Pro Gly Leu Val Lys Pro Ser Gln
1 5 10 15

Thr Leu Ser Leu Thr Cys Ala Ile Ser Gly Asp Ser Val Ser Ser Asn
20 25 30

Ser Ala Ala Trp Asn Trp Ile Arg Gln Ser Pro Ser Arg Gly Leu Glu
35 40 45

Trp Leu Gly Lys Thr Tyr Tyr Arg Phe Lys Trp Tyr Ser Asp Tyr Ala
50 55 60

Val Ser Val Lys Gly Arg Ile Thr Ile Asn Pro Asp Thr Ser Lys Asn
65 70 75 80

Gln Phe Ser Leu Gln Leu Asn Ser Val Thr Pro Glu Asp Thr Ala Val
85 90 95

Phe Tyr Cys Thr Arg Glu Ser Thr Thr Tyr Asp Leu Leu Ala Gly Pro
100 105 110

Phe Asp Tyr Trp Gly Gln Gly Thr Leu Val Thr Val Ser Ser Gly Gly
115 120 125

Gly Gly Gly Ser Gly Gly Gly Gly Ser Gly Gly Gly Gly Ser Asp Ile
130 135 140

```
Val Met Thr Gln Ser Pro Asp Ser Leu Ala Val Ser Leu Gly Glu Arg
145                 150                 155                 160

Ala Thr Ile Asn Cys Lys Ser Ser Gln Thr Val Leu Tyr Ser Ser Asn
                165                 170                 175

Asn Lys Lys Tyr Leu Ala Trp Tyr Gln Gln Lys Pro Gly Gln Pro Pro
            180                 185                 190

Asn Leu Leu Ile Tyr Trp Ala Ser Thr Arg Glu Ser Gly Val Pro Asp
        195                 200                 205

Arg Phe Ser Gly Ser Gly Ser Gly Thr Asp Phe Thr Leu Thr Ile Ser
    210                 215                 220

Ser Leu Gln Ala Glu Asp Val Ala Val Tyr Tyr Cys Gln Gln Tyr Tyr
225                 230                 235                 240

Ser Thr Pro Phe Thr Phe Gly Pro Gly Thr Lys Val Glu Ile Lys
                245                 250                 255


<210> SEQ ID NO 413
<211> LENGTH: 243
<212> TYPE: PRT
<213> ORGANISM: Homo sapiens

<400> SEQUENCE: 413

Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Lys
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Ser Thr Asp Tyr Ala
    50                  55                  60

Ala Ser Val Lys Ser Arg Ile Thr Ile Asn Pro Asp Thr Ser Lys Asn
65                  70                  75                  80

Gln Leu Ser Leu Gln Leu Asn Ser Val Thr Pro Glu Asp Thr Ala Val
                85                  90                  95

Tyr Tyr Cys Ala Arg Thr Trp Val Gly Tyr Val Asp Arg Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Pro
    130                 135                 140

Ala Leu Ser Ala Ser Val Gly Asp Arg Val Thr Ile Thr Cys Arg Ala
145                 150                 155                 160

Ser Gln Asp Ile Asn Asp Trp Leu Ala Trp Tyr Gln His Lys Pro Gly
                165                 170                 175

Lys Ala Pro Lys Leu Leu Ile Tyr Asp Ala Ser Ser Leu Glu Ser Gly
            180                 185                 190

Val Pro Leu Arg Phe Ser Gly Ser Gly Ser Gly Thr Glu Phe Thr Leu
        195                 200                 205

Thr Ile Ser Ser Leu Gln Pro Asp Asp Phe Ala Thr Tyr Tyr Cys Gln
    210                 215                 220

Gln Lys Tyr Ser Ala Pro Gln Val Thr Phe Gly Gln Gly Thr Arg Leu
225                 230                 235                 240

Glu Ile Lys


<210> SEQ ID NO 414
<211> LENGTH: 215
```

<212> TYPE: PRT
<213> ORGANISM: Homo sapiens

<400> SEQUENCE: 414

Asp Ile Gln Met Thr Gln Ser Pro Pro Ala Leu Ser Ala Ser Val Gly
1 5 10 15

Asp Arg Val Thr Ile Thr Cys Arg Ala Ser Gln Asp Ile Asn Asp Trp
20 25 30

Leu Ala Trp Tyr Gln His Lys Pro Gly Lys Ala Pro Lys Leu Leu Ile
35 40 45

Tyr Asp Ala Ser Ser Leu Glu Ser Gly Val Pro Leu Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Lys Tyr Ser Ala Pro Gln
85 90 95

Val Thr Phe Gly Gln Gly Thr Arg Leu Glu Ile Lys Arg Thr Val Ala
100 105 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu
130 135 140

Ala Lys Val Gln Trp Lys Val Asp Asn Ala Leu Gln Ser Gly Asn Ser
145 150 155 160

Gln Glu Ser Val Thr Glu Gln Asp Ser Lys Asp Ser Thr Tyr Ser Leu
165 170 175

Ser Ser Thr Leu Thr Leu Ser Lys Ala Asp Tyr Glu Lys His Lys Val
180 185 190

Tyr Ala Cys Glu Val Thr His Gln Gly Leu Ser Ser Pro Val Thr Lys
195 200 205

Ser Phe Asn Arg Gly Glu Cys
210 215

<210> SEQ ID NO 415
<211> LENGTH: 716
<212> TYPE: PRT
<213> ORGANISM: Homo sapiens

<400> SEQUENCE: 415

Glu Val Gln Leu Gln Gln Ser Gly Pro Gly Leu Val Lys Pro Ser Gln
1 5 10 15

Thr Leu Ser Leu Thr Cys Ala Ile Ser Gly Asp Ser Val Ser Ser Lys
20 25 30

Ser Ala Ala Trp Asn Trp Ile Arg Gln Ser Pro Ser Arg Gly Leu Glu
35 40 45

Trp Leu Gly Arg Thr Tyr Tyr Arg Ser Lys Trp Ser Thr Asp Tyr Ala
50 55 60

Ala Ser Val Lys Ser Arg Ile Thr Ile Asn Pro Asp Thr Ser Lys Asn
65 70 75 80

Gln Leu Ser Leu Gln Leu Asn Ser Val Thr Pro Glu Asp Thr Ala Val
85 90 95

Tyr Tyr Cys Ala Arg Thr Trp Val Gly Tyr Val Asp Arg Trp Gly Gln
100 105 110

Gly Thr Leu Val Thr Val Ser Ser Ala Ser Thr Lys Gly Pro Ser Val
115 120 125

-continued

```
Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Gly Gly Gly Gly Ser Gly Gly Gly Gly Ser Gly Gly Gly Gly Ser
    450                 455                 460

Gln Val Gln Leu Val Gln Ser Gly Ala Glu Val Lys Lys Pro Gly Ala
465                 470                 475                 480

Ser Val Lys Val Ser Cys Lys Thr Ser Arg Tyr Thr Phe Thr Glu Tyr
                485                 490                 495

Thr Ile His Trp Val Arg Gln Ala Pro Gly Gln Arg Leu Glu Trp Ile
            500                 505                 510

Gly Gly Ile Asn Pro Asn Asn Gly Ile Pro Asn Tyr Asn Gln Lys Phe
        515                 520                 525

Lys Gly Arg Val Thr Ile Thr Val Asp Thr Ser Ala Ser Thr Ala Tyr
    530                 535                 540

Met Glu Leu Ser Ser Leu Arg Ser Glu Asp Thr Ala Val Tyr Tyr Cys
```

-continued 545 550 555 560

Ala Arg Arg Arg Ile Ala Tyr Gly Tyr Asp Glu Gly His Ala Met Asp
565 570 575

Tyr Trp Gly Gln Gly Thr Leu Val Thr Val Ser Ser Gly Gly Gly Gly
580 585 590

Ser Gly Gly Gly Gly Ser Gly Gly Gly Gly Ser Asp Ile Val Met Thr
595 600 605

Gln Ser Pro Asp Ser Leu Ala Val Ser Leu Gly Glu Arg Ala Thr Ile
610 615 620

Asn Cys Lys Ser Ser Gln Ser Leu Leu Tyr Ser Arg Asn Gln Lys Asn
625 630 635 640

Tyr Leu Ala Trp Tyr Gln Gln Lys Pro Gly Gln Pro Pro Lys Leu Leu
645 650 655

Ile Phe Trp Ala Ser Thr Arg Glu Ser Gly Val Pro Asp Arg Phe Ser
660 665 670

Gly Ser Gly Phe Gly Thr Asp Phe Thr Leu Thr Ile Ser Ser Leu Gln
675 680 685

Ala Glu Asp Val Ala Val Tyr Tyr Cys Gln Gln Tyr Phe Ser Tyr Pro
690 695 700

Leu Thr Phe Gly Gln Gly Thr Lys Val Glu Ile Lys
705 710 715

<210> SEQ ID NO 416
<211> LENGTH: 704
<212> TYPE: PRT
<213> ORGANISM: Homo sapiens

<400> SEQUENCE: 416

Glu Val Gln Leu Gln Gln Ser Gly Pro Gly Leu Val Lys Pro Ser Gln
1 5 10 15

Thr Leu Ser Leu Thr Cys Ala Ile Ser Gly Asp Ser Val Ser Ser Lys
20 25 30

Ser Ala Ala Trp Asn Trp Ile Arg Gln Ser Pro Ser Arg Gly Leu Glu
35 40 45

Trp Leu Gly Arg Thr Tyr Tyr Arg Ser Lys Trp Ser Thr Asp Tyr Ala
50 55 60

Ala Ser Val Lys Ser Arg Ile Thr Ile Asn Pro Asp Thr Ser Lys Asn
65 70 75 80

Gln Leu Ser Leu Gln Leu Asn Ser Val Thr Pro Glu Asp Thr Ala Val
85 90 95

Tyr Tyr Cys Ala Arg Thr Trp Val Gly Tyr Val Asp Arg Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

-continued

```
Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Gly Gly Gly Gly Ser Gly Gly Gly Gly Ser Gly Gly Gly Gly Ser
    450                 455                 460

Gln Val Gln Leu Gln Glu Ser Gly Pro Gly Leu Val Lys Pro Ser Gln
465                 470                 475                 480

Thr Leu Ser Leu Thr Cys Thr Val Ser Gly Gly Ser Ile Asn Asn Asn
                485                 490                 495

Asn Tyr Tyr Trp Thr Trp Ile Arg Gln His Pro Gly Lys Gly Leu Glu
            500                 505                 510

Trp Ile Gly Tyr Ile Tyr Tyr Ser Gly Ser Thr Phe Tyr Asn Pro Ser
        515                 520                 525

Leu Lys Ser Arg Val Thr Ile Ser Val Asp Thr Ser Lys Thr Gln Phe
    530                 535                 540

Ser Leu Lys Leu Ser Ser Val Thr Ala Ala Asp Thr Ala Val Tyr Tyr
545                 550                 555                 560

Cys Ala Arg Glu Asp Thr Met Thr Gly Leu Asp Val Trp Gly Gln Gly
                565                 570                 575

Thr Thr Val Thr Val Ser Ser Gly Gly Gly Gly Ser Gly Gly Gly Gly
            580                 585                 590

Ser Gly Gly Gly Gly Ser Asp Ile Gln Met Thr Gln Ser Pro Ser Ser
        595                 600                 605

Leu Ser Ala Ser Val Gly Asp Arg Val Thr Ile Thr Cys Arg Ala Ser
    610                 615                 620

Gln Ser Ile Asn Asn Tyr Leu Asn Trp Tyr Gln Gln Lys Pro Gly Lys
```

```
625                 630                 635                 640

Ala Pro Thr Leu Leu Ile Tyr Ala Ala Ser Ser Leu Gln Ser Gly Val
                645                 650                 655

Pro Ser Arg Phe Ser Gly Ser Arg Ser Gly Thr Asp Phe Thr Leu Thr
            660                 665                 670

Ile Ser Ser Leu Gln Pro Glu Asp Phe Ala Ala Tyr Phe Cys Gln Gln
        675                 680                 685

Thr Tyr Ser Asn Pro Thr Phe Gly Gln Gly Thr Lys Val Glu Val Lys
    690                 695                 700


<210> SEQ ID NO 417
<211> LENGTH: 708
<212> TYPE: PRT
<213> ORGANISM: Homo sapiens

<400> SEQUENCE: 417

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300
```

```
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Gly Gly Gly Gly Gly Ser Gly Gly Gly Gly Ser Gly Gly Gly Gly
    450                 455                 460

Ser Glu Val Gln Leu Gln Gln Ser Gly Pro Gly Leu Val Lys Pro Ser
465                 470                 475                 480

Gln Thr Leu Ser Leu Thr Cys Ala Ile Ser Gly Asp Ser Val Ser Ser
                485                 490                 495

Lys Ser Ala Ala Trp Asn Trp Ile Arg Gln Ser Pro Ser Arg Gly Leu
            500                 505                 510

Glu Trp Leu Gly Arg Thr Tyr Tyr Arg Ser Lys Trp Ser Thr Asp Tyr
        515                 520                 525

Ala Ala Ser Val Lys Ser Arg Ile Thr Ile Asn Pro Asp Thr Ser Lys
    530                 535                 540

Asn Gln Leu Ser Leu Gln Leu Asn Ser Val Thr Pro Glu Asp Thr Ala
545                 550                 555                 560

Val Tyr Tyr Cys Ala Arg Thr Trp Val Gly Tyr Val Asp Arg Trp Gly
                565                 570                 575

Gln Gly Thr Leu Val Thr Val Ser Ser Gly Gly Gly Gly Ser Gly Gly
            580                 585                 590

Gly Gly Ser Gly Gly Gly Gly Ser Asp Ile Gln Met Thr Gln Ser Pro
        595                 600                 605

Pro Ala Leu Ser Ala Ser Val Gly Asp Arg Val Thr Ile Thr Cys Arg
    610                 615                 620

Ala Ser Gln Asp Ile Asn Asp Trp Leu Ala Trp Tyr Gln His Lys Pro
625                 630                 635                 640

Gly Lys Ala Pro Lys Leu Leu Ile Tyr Asp Ala Ser Ser Leu Glu Ser
                645                 650                 655

Gly Val Pro Leu Arg Phe Ser Gly Ser Gly Ser Gly Thr Glu Phe Thr
            660                 665                 670

Leu Thr Ile Ser Ser Leu Gln Pro Asp Asp Phe Ala Thr Tyr Tyr Cys
        675                 680                 685

Gln Gln Lys Tyr Ser Ala Pro Gln Val Thr Phe Gly Gln Gly Thr Arg
    690                 695                 700

Leu Glu Ile Lys
705
```

<210> SEQ ID NO 418
<211> LENGTH: 703
<212> TYPE: PRT
<213> ORGANISM: Homo sapiens

<400> SEQUENCE: 418

```
Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Lys
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Ser Thr Asp Tyr Ala
    50                  55                  60

Ala Ser Val Lys Ser Arg Ile Thr Ile Asn Pro Asp Thr Ser Lys Asn
65                  70                  75                  80

Gln Leu Ser Leu Gln Leu Asn Ser Val Thr Pro Glu Asp Thr Ala Val
                85                  90                  95

Tyr Tyr Cys Ala Arg Thr Trp Val Gly Tyr Val Asp Arg Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380
```

-continued

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Gly Gly Gly Gly Ser Gly Gly Gly Gly Ser Gly Gly Gly Gly Ser
    450                 455                 460

Glu Val Gln Leu Val Gln Ser Gly Ala Glu Val Lys Lys Pro Gly Glu
465                 470                 475                 480

Ser Leu Arg Ile Ser Cys Lys Gly Ser Gly Tyr Ser Phe Ser Thr Tyr
                485                 490                 495

Trp Ile Ser Trp Val Arg Gln Met Pro Gly Lys Gly Leu Glu Trp Met
            500                 505                 510

Gly Lys Ile Tyr Pro Gly Asp Ser Tyr Thr Asn Tyr Ser Pro Ser Phe
        515                 520                 525

Gln Gly Gln Val Thr Ile Ser Ala Asp Lys Ser Ile Ser Thr Ala Tyr
    530                 535                 540

Leu Gln Trp Ser Ser Leu Lys Ala Ser Asp Thr Ala Met Tyr Tyr Cys
545                 550                 555                 560

Ala Arg Gly Tyr Gly Ile Phe Asp Tyr Trp Gly Gln Gly Thr Leu Val
                565                 570                 575

Thr Val Ser Ser Gly Gly Gly Gly Ser Gly Gly Gly Gly Ser Gly Gly
            580                 585                 590

Gly Gly Ser Ser Tyr Glu Leu Thr Gln Pro Pro Ser Val Ser Val Ser
        595                 600                 605

Pro Gly Gln Thr Ala Ser Ile Thr Cys Ser Gly Asp Asn Ile Gly Asp
    610                 615                 620

Gln Tyr Ala His Trp Tyr Gln Gln Lys Pro Gly Gln Ser Pro Val Leu
625                 630                 635                 640

Val Ile Tyr Gln Asp Lys Asn Arg Pro Ser Gly Ile Pro Glu Arg Phe
                645                 650                 655

Ser Gly Ser Asn Ser Gly Asn Thr Ala Thr Leu Thr Ile Ser Gly Thr
            660                 665                 670

Gln Ala Met Asp Glu Ala Asp Tyr Tyr Cys Ala Thr Tyr Thr Gly Phe
        675                 680                 685

Gly Ser Leu Ala Val Phe Gly Gly Gly Thr Lys Leu Thr Val Leu
    690                 695                 700
```

<210> SEQ ID NO 419
<211> LENGTH: 703
<212> TYPE: PRT
<213> ORGANISM: Homo sapiens

<400> SEQUENCE: 419

```
Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Lys
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Ser Thr Asp Tyr Ala
    50                  55                  60
```

Ala Ser Val Lys Ser Arg Ile Thr Ile Asn Pro Asp Thr Ser Lys Asn
65 70 75 80

Gln Leu Ser Leu Gln Leu Asn Ser Val Thr Pro Glu Asp Thr Ala Val
85 90 95

Tyr Tyr Cys Ala Arg Thr Trp Val Gly Tyr Val Asp Arg Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Leu Ala Gly Ala
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Asp Glu Leu Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly Gly Gly Gly Gly Ser Gly Gly Gly Gly Ser Gly Gly Gly Gly Ser
450 455 460

Glu Val Gln Leu Val Gln Ser Gly Ala Glu Val Lys Lys Pro Gly Ala
465 470 475 480

-continued

Ser Val Lys Val Ser Cys Lys Ala Ser Gly Tyr Thr Phe Thr Asp Ser
485 490 495

Tyr Met Ser Trp Val Arg Gln Ala Pro Gly Gln Gly Leu Glu Trp Ile
500 505 510

Gly Asp Met Tyr Pro Asp Asn Gly Asp Ser Ser Tyr Asn Gln Lys Phe
515 520 525

Arg Glu Arg Val Thr Ile Thr Arg Asp Thr Ser Thr Ser Thr Ala Tyr
530 535 540

Leu Glu Leu Ser Ser Leu Arg Ser Glu Asp Thr Ala Val Tyr Tyr Cys
545 550 555 560

Val Leu Ala Pro Arg Trp Tyr Phe Ser Val Trp Gly Gln Gly Thr Leu
565 570 575

Val Thr Val Ser Ser Gly Gly Gly Gly Ser Gly Gly Gly Gly Ser Gly
580 585 590

Gly Gly Gly Ser Asp Ile Gln Met Thr Gln Ser Pro Ser Ser Leu Ser
595 600 605

Ala Ser Val Gly Asp Arg Val Thr Ile Thr Cys Arg Ala Ser Gln Asp
610 615 620

Ile Ser Asn Tyr Leu Asn Trp Tyr Gln Gln Lys Pro Gly Lys Ala Pro
625 630 635 640

Lys Leu Leu Ile Tyr Tyr Thr Ser Arg Leu Arg Ser Gly Val Pro Ser
645 650 655

Arg Phe Ser Gly Ser Gly Ser Gly Thr Asp Phe Thr Leu Thr Ile Ser
660 665 670

Ser Leu Gln Pro Glu Asp Phe Ala Thr Tyr Tyr Cys Gln Gln Gly His
675 680 685

Thr Leu Pro Pro Thr Phe Gly Gln Gly Thr Lys Val Glu Ile Lys
690 695 700

<210> SEQ ID NO 420
<211> LENGTH: 714
<212> TYPE: PRT
<213> ORGANISM: Homo sapiens

<400> SEQUENCE: 420

Glu Val Gln Leu Gln Gln Ser Gly Pro Gly Leu Val Lys Pro Ser Gln
1 5 10 15

Thr Leu Ser Leu Thr Cys Ala Ile Ser Gly Asp Ser Val Ser Ser Asn
20 25 30

Ser Ala Ala Trp Asn Trp Ile Arg Gln Ser Pro Ser Arg Gly Leu Glu
35 40 45

Trp Leu Gly Lys Thr Tyr Tyr Arg Phe Lys Trp Tyr Ser Asp Tyr Ala
50 55 60

Val Ser Val Lys Gly Arg Ile Thr Ile Asn Pro Asp Thr Ser Lys Asn
65 70 75 80

Gln Phe Ser Leu Gln Leu Asn Ser Val Thr Pro Glu Asp Thr Ala Val
85 90 95

Phe Tyr Cys Thr Arg Glu Ser Thr Thr Tyr Asp Leu Leu Ala Gly Pro
100 105 110

Phe Asp Tyr Trp Gly Gln Gly Thr Leu Val Thr Val Ser Ser Ala Ser
115 120 125

Thr Lys Gly Pro Ser Val Phe Pro Leu Ala Pro Ser Ser Lys Ser Thr
130 135 140

Ser Gly Gly Thr Ala Ala Leu Gly Cys Leu Val Lys Asp Tyr Phe Pro
145 150 155 160

```
Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Ala Gly Ala Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Gly Gly Gly Gly Gly Ser Gly Gly Gly
    450                 455                 460

Gly Ser Gly Gly Gly Gly Ser Glu Val Gln Leu Gln Gln Ser Gly Pro
465                 470                 475                 480

Gly Leu Val Lys Pro Ser Gln Thr Leu Ser Leu Thr Cys Ala Ile Ser
                485                 490                 495

Gly Asp Ser Val Ser Ser Lys Ser Ala Ala Trp Asn Trp Ile Arg Gln
            500                 505                 510

Ser Pro Ser Arg Gly Leu Glu Trp Leu Gly Arg Thr Tyr Tyr Arg Ser
        515                 520                 525

Lys Trp Ser Thr Asp Tyr Ala Ala Ser Val Lys Ser Arg Ile Thr Ile
    530                 535                 540

Asn Pro Asp Thr Ser Lys Asn Gln Leu Ser Leu Gln Leu Asn Ser Val
545                 550                 555                 560

Thr Pro Glu Asp Thr Ala Val Tyr Tyr Cys Ala Arg Thr Trp Val Gly
                565                 570                 575
```

-continued

```
Tyr Val Asp Arg Trp Gly Gln Gly Thr Leu Val Thr Val Ser Ser Gly
            580                 585                 590

Gly Gly Gly Ser Gly Gly Gly Gly Ser Gly Gly Gly Gly Ser Asp Ile
        595                 600                 605

Gln Met Thr Gln Ser Pro Pro Ala Leu Ser Ala Ser Val Gly Asp Arg
    610                 615                 620

Val Thr Ile Thr Cys Arg Ala Ser Gln Asp Ile Asn Asp Trp Leu Ala
625                 630                 635                 640

Trp Tyr Gln His Lys Pro Gly Lys Ala Pro Lys Leu Leu Ile Tyr Asp
                645                 650                 655

Ala Ser Ser Leu Glu Ser Gly Val Pro Leu Arg Phe Ser Gly Ser Gly
            660                 665                 670

Ser Gly Thr Glu Phe Thr Leu Thr Ile Ser Ser Leu Gln Pro Asp Asp
        675                 680                 685

Phe Ala Thr Tyr Tyr Cys Gln Gln Lys Tyr Ser Ala Pro Gln Val Thr
    690                 695                 700

Phe Gly Gln Gly Thr Arg Leu Glu Ile Lys
705                 710


<210> SEQ ID NO 421
<211> LENGTH: 217
<212> TYPE: PRT
<213> ORGANISM: Homo sapiens

<400> SEQUENCE: 421

Ala Ser Asp Ile Gln Met Thr Gln Ser Pro Pro Ala Leu Ser Ala Ser
1               5                   10                  15

Val Gly Asp Arg Val Thr Ile Thr Cys Arg Ala Ser Gln Asp Ile Asn
            20                  25                  30

Asp Trp Leu Ala Trp Tyr Gln His Lys Pro Gly Lys Ala Pro Lys Leu
        35                  40                  45

Leu Ile Tyr Asp Ala Ser Ser Leu Glu Ser Gly Val Pro Ser Arg Phe
    50                  55                  60

Ser Gly Ser Gly Ser Gly Thr Glu Phe Thr Leu Thr Ile Ser Ser Leu
65                  70                  75                  80

Gln Pro Asp Asp Phe Ala Thr Tyr Tyr Cys Gln Gln Ser Tyr Ser Thr
                85                  90                  95

Pro Gln Val Thr Phe Gly Gln Gly Thr Arg Leu Glu Ile Lys Arg Thr
            100                 105                 110

Ala Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Leu Tyr Ala Cys Glu Val Thr His Gln Gly Leu Ser Ser Pro Val
        195                 200                 205

Thr Lys Ser Phe Asn Arg Gly Glu Cys
    210                 215


<210> SEQ ID NO 422
```

<211> LENGTH: 714
<212> TYPE: PRT
<213> ORGANISM: Homo sapiens

<400> SEQUENCE: 422

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Lys
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Ser Thr Asp Tyr Ala
    50                  55                  60

Ala Ser Val Lys Ser Arg Ile Thr Ile Asn Pro Asp Thr Ser Lys Asn
65                  70                  75                  80

Gln Leu Ser Leu Gln Leu Asn Ser Val Thr Pro Glu Asp Thr Ala Val
                85                  90                  95

Tyr Tyr Cys Ala Arg Thr Trp Ser Gly Tyr Val Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val

-continued 385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly Gly Gly Gly Gly Ser Gly Gly Gly Gly Ser Gly Gly Gly Gly Ser
450 455 460

Gln Val Gln Leu Gln Gln Ser Gly Ala Glu Leu Val Arg Pro Gly Ser
465 470 475 480

Ser Val Lys Ile Ser Cys Lys Ala Ser Gly Tyr Ala Phe Ser Ser Tyr
485 490 495

Trp Met Asn Trp Val Lys Gln Arg Pro Gly Gln Gly Leu Glu Trp Ile
500 505 510

Gly Gln Ile Trp Pro Gly Asp Gly Asp Thr Asn Tyr Asn Gly Lys Phe
515 520 525

Lys Gly Lys Ala Thr Leu Thr Ala Asp Glu Ser Ser Ser Thr Ala Tyr
530 535 540

Met Gln Leu Ser Ser Leu Ala Ser Glu Asp Ser Ala Val Tyr Phe Cys
545 550 555 560

Ala Arg Arg Glu Thr Thr Thr Val Gly Arg Tyr Tyr Tyr Ala Met Asp
565 570 575

Tyr Trp Gly Gln Gly Thr Thr Val Thr Val Ser Ser Gly Gly Gly Gly
580 585 590

Ser Gly Gly Gly Gly Ser Gly Gly Gly Gly Ser Asp Ile Gln Leu Thr
595 600 605

Gln Ser Pro Ala Ser Leu Ala Val Ser Leu Gly Gln Arg Ala Thr Ile
610 615 620

Ser Cys Lys Ala Ser Gln Ser Val Asp Tyr Asp Gly Asp Ser Tyr Leu
625 630 635 640

Asn Trp Tyr Gln Gln Ile Pro Gly Gln Pro Pro Lys Leu Leu Ile Tyr
645 650 655

Asp Ala Ser Asn Leu Val Ser Gly Ile Pro Pro Arg Phe Ser Gly Ser
660 665 670

Gly Ser Gly Thr Asp Phe Thr Leu Asn Ile His Pro Val Glu Lys Val
675 680 685

Asp Ala Ala Thr Tyr His Cys Gln Gln Ser Thr Glu Asp Pro Trp Thr
690 695 700

Phe Gly Gly Gly Thr Lys Leu Glu Ile Lys
705 710

<210> SEQ ID NO 423
<211> LENGTH: 216
<212> TYPE: PRT
<213> ORGANISM: Homo sapiens

<400> SEQUENCE: 423

Ala Ser Asp Ile Gln Met Thr Gln Ser Pro Ser Ser Leu Ser Ala Ser
1 5 10 15

Val Gly Asp Arg Val Thr Ile Ala Cys Arg Ala Gly Gln Ser Ile Gly
20 25 30

Thr Tyr Leu Asn Trp Tyr Gln Gln Lys Pro Gly Lys Ala Pro Lys Leu
35 40 45

-continued

```
Leu Ile Tyr Val Ala Ser Ser Leu Gln Ser Gly Val Pro Ser Arg Phe
    50                  55                  60

Ser Gly Ser Gly Ser Gly Thr Glu Phe Thr Leu Thr Ile Ser Ser Leu
65                  70                  75                  80

Gln Pro Glu Asp Phe Ala Thr Tyr Tyr Cys Gln Gln Ser Tyr Ser Thr
                85                  90                  95

Leu Leu Thr Phe Gly Arg Gly Thr Lys Val Glu Ile Lys Arg Thr Ala
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Leu Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 424
<211> LENGTH: 712
<212> TYPE: PRT
<213> ORGANISM: Homo sapiens

<400> SEQUENCE: 424

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Asp Tyr Ala Asp Ala Phe Asp Ile Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205
```

```
Asn Thr Lys Val Asp Lys Lys Val Glu Pro Lys Ser Cys Asp Lys Thr
    210                 215                 220

His Thr Cys Pro Pro Cys Pro Ala Pro Glu Leu Ala Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Gly
        435                 440                 445

Gly Gly Gly Ser Gly Gly Gly Gly Ser Gly Gly Gly Gly Ser Gln Val
    450                 455                 460

Gln Leu Gln Gln Ser Gly Ala Glu Leu Val Arg Pro Gly Ser Ser Val
465                 470                 475                 480

Lys Ile Ser Cys Lys Ala Ser Gly Tyr Ala Phe Ser Ser Tyr Trp Met
                485                 490                 495

Asn Trp Val Lys Gln Arg Pro Gly Gln Gly Leu Glu Trp Ile Gly Gln
            500                 505                 510

Ile Trp Pro Gly Asp Gly Asp Thr Asn Tyr Asn Gly Lys Phe Lys Gly
        515                 520                 525

Lys Ala Thr Leu Thr Ala Asp Glu Ser Ser Ser Thr Ala Tyr Met Gln
    530                 535                 540

Leu Ser Ser Leu Ala Ser Glu Asp Ser Ala Val Tyr Phe Cys Ala Arg
545                 550                 555                 560

Arg Glu Thr Thr Thr Val Gly Arg Tyr Tyr Tyr Ala Met Asp Tyr Trp
                565                 570                 575

Gly Gln Gly Thr Thr Val Thr Val Ser Ser Gly Gly Gly Gly Ser Gly
            580                 585                 590

Gly Gly Gly Ser Gly Gly Gly Gly Ser Asp Ile Gln Leu Thr Gln Ser
        595                 600                 605

Pro Ala Ser Leu Ala Val Ser Leu Gly Gln Arg Ala Thr Ile Ser Cys
    610                 615                 620
```

```
Lys Ala Ser Gln Ser Val Asp Tyr Asp Gly Asp Ser Tyr Leu Asn Trp
625                 630                 635                 640

Tyr Gln Gln Ile Pro Gly Gln Pro Pro Lys Leu Leu Ile Tyr Asp Ala
                645                 650                 655

Ser Asn Leu Val Ser Gly Ile Pro Pro Arg Phe Ser Gly Ser Gly Ser
            660                 665                 670

Gly Thr Asp Phe Thr Leu Asn Ile His Pro Val Glu Lys Val Asp Ala
        675                 680                 685

Ala Thr Tyr His Cys Gln Gln Ser Thr Glu Asp Pro Trp Thr Phe Gly
    690                 695                 700

Gly Gly Thr Lys Leu Glu Ile Lys
705                 710


<210> SEQ ID NO 425
<211> LENGTH: 216
<212> TYPE: PRT
<213> ORGANISM: Homo sapiens

<400> SEQUENCE: 425

Ala Ser Ser Tyr Glu Leu Thr Gln Pro Pro Ser Val Ser Val Ala Pro
1               5                   10                  15

Gly Lys Thr Ala Arg Ile Thr Cys Gly Gly Asn Asn Ile Gly Ser Gln
            20                  25                  30

Ser Val His Trp Tyr Gln Gln Lys Pro Gly Gln Ala Pro Met Leu Val
        35                  40                  45

Ile Tyr Tyr Asp Ser Asp Arg Pro Ser Gly Ile Pro Glu Arg Phe Ser
    50                  55                  60

Gly Ser Asn Ser Gly Asn Thr Ala Thr Leu Thr Ile Ser Arg Val Glu
65                  70                  75                  80

Ala Gly Asp Glu Ala Asp Tyr Tyr Cys Gln Val Trp Asp Ser Ser Ser
                85                  90                  95

Asp His Val Val Phe Gly Gly Gly Thr Lys Leu Thr Val Leu Gly Gln
            100                 105                 110

Pro Ala Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215


<210> SEQ ID NO 426
<211> LENGTH: 446
<212> TYPE: PRT
<213> ORGANISM: Homo sapiens

<400> SEQUENCE: 426

Glu Val Gln Leu Leu Glu Ser Gly Gly Gly Leu Val Gln Pro Gly Arg
1               5                   10                  15
```

-continued

```
Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ser Pro Ile Glu Leu Gly Ala Phe Asp Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Ala Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Thr Asp Asp Gly Pro Val Ser Leu Thr Cys Leu
        355                 360                 365

Val Lys Gly Phe Tyr Pro Ser Asp Ile Ala Val Glu Trp Glu Ser Thr
    370                 375                 380

Tyr Gly Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Ser Tyr Trp Arg
                405                 410                 415

Trp Tyr Lys Gly Asn Val Phe Ser Cys Ser Val Met His Glu Ala Leu
            420                 425                 430

His Asn His Tyr Thr Gln Lys Ser Leu Ser Leu Ser Pro Gly
```

435 440 445

<210> SEQ ID NO 427
<211> LENGTH: 447
<212> TYPE: PRT
<213> ORGANISM: Homo sapiens

<400> SEQUENCE: 427

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp Tyr
20 25 30

Tyr Met Ser Trp Ile Arg Gln Ala Pro Gly Lys Gly Leu Glu Trp Val
35 40 45

Ser Tyr Ile Ser Ser Ser Gly Ser Thr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Val Asp Tyr Ala Asp Ala Phe Asp Ile Trp Gly Gln Gly Thr
100 105 110

Leu Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Lys Val Glu Pro Lys Ser Cys Asp Lys Thr
210 215 220

His Thr Cys Pro Pro Cys Pro Ala Pro Glu Leu Ala Gly Ala Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Asp Glu Thr Asp Asp Gly Pro Val Ser Leu Thr Cys
355 360 365

-continued

Leu Val Lys Gly Phe Tyr Pro Ser Asp Ile Ala Val Glu Trp Glu Ser
370 375 380

Thr Tyr Gly Pro Glu Asn Asn Tyr Lys Thr Thr Pro Pro Val Leu Asp
385 390 395 400

Ser Asp Gly Ser Phe Phe Leu Tyr Ser Lys Leu Thr Val Ser Tyr Trp
405 410 415

Arg Trp Tyr Lys Gly Asn Val Phe Ser Cys Ser Val Met His Glu Ala
420 425 430

Leu His Asn His Tyr Thr Gln Lys Ser Leu Ser Leu Ser Pro Gly
435 440 445

<210> SEQ ID NO 428
<211> LENGTH: 702
<212> TYPE: PRT
<213> ORGANISM: Homo sapiens

<400> SEQUENCE: 428

Glu Val Gln Leu Leu Glu Ser Gly Gly Gly Leu Val Gln Pro Gly Arg
1 5 10 15

Ser Leu Arg Leu Ser Cys Ala Ala Ser Gly Phe Thr Val Ser Ser Asn
20 25 30

Tyr Met Ser Trp Val Arg Gln Ala Pro Gly Lys Gly Leu Glu Trp Val
35 40 45

Ser Val Ile Tyr Ser Gly Gly Ser Thr Tyr Tyr Ala Asp Ser Val Lys
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Ser Pro Ile Glu Leu Gly Ala Phe Asp Ile Trp Gly Gln Gly Thr Leu
100 105 110

Val Thr Val Ser Ser Ala Ser Thr Lys Gly Pro Ser Val Phe Pro Leu
115 120 125

Ala Pro Ser Ser Lys Ser Thr Ser Gly Gly Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Gln Thr Tyr Ile Cys Asn Val Asn His Lys Pro Ser Asn
195 200 205

Thr Lys Val Asp Lys Lys Val Glu Pro Lys Ser Cys Asp Lys Thr His
210 215 220

Thr Cys Pro Pro Cys Pro Ala Pro Glu Leu Ala Gly Ala Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser His Glu Asp Pro Glu
260 265 270

Val Lys Phe Asn Trp Tyr Val Asp Gly Val Glu Val His Asn Ala Lys
275 280 285

Thr Lys Pro Arg Glu Glu Gln Tyr Asn Ser Thr Tyr Arg Val Val Ser
290 295 300

```
Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
        435                 440                 445

Gly Gly Ser Gly Gly Gly Gly Ser Gly Gly Gly Gly Ser Gln Val Gln
    450                 455                 460

Leu Lys Gln Ser Gly Pro Gly Leu Val Gln Pro Ser Gln Ser Leu Ser
465                 470                 475                 480

Ile Thr Cys Thr Val Ser Gly Phe Ser Leu Thr Asn Tyr Gly Val His
                485                 490                 495

Trp Val Arg Gln Ser Pro Gly Lys Gly Leu Glu Trp Leu Gly Val Ile
            500                 505                 510

Trp Ser Gly Gly Asn Thr Asp Tyr Asn Thr Pro Phe Thr Ser Arg Leu
        515                 520                 525

Ser Ile Asn Lys Asp Asn Ser Lys Ser Gln Val Phe Phe Lys Met Asn
    530                 535                 540

Ser Leu Gln Ser Asn Asp Thr Ala Ile Tyr Tyr Cys Ala Arg Ala Leu
545                 550                 555                 560

Thr Tyr Tyr Asp Tyr Glu Phe Ala Tyr Trp Gly Gln Gly Thr Leu Val
                565                 570                 575

Thr Val Ser Ala Gly Gly Gly Gly Ser Gly Gly Gly Gly Ser Gly Gly
            580                 585                 590

Gly Gly Ser Asp Ile Leu Leu Thr Gln Ser Pro Val Ile Leu Ser Val
        595                 600                 605

Ser Pro Gly Glu Arg Val Ser Phe Ser Cys Arg Ala Ser Gln Ser Ile
    610                 615                 620

Gly Thr Asn Ile His Trp Tyr Gln Gln Arg Thr Asn Gly Ser Pro Arg
625                 630                 635                 640

Leu Leu Ile Lys Tyr Ala Ser Glu Ser Ile Ser Gly Ile Pro Ser Arg
                645                 650                 655

Phe Ser Gly Ser Gly Ser Gly Thr Asp Phe Thr Leu Ser Ile Asn Ser
            660                 665                 670

Val Glu Ser Glu Asp Ile Ala Asp Tyr Tyr Cys Gln Gln Asn Asn Asn
        675                 680                 685

Trp Pro Thr Thr Phe Gly Ala Gly Thr Lys Leu Glu Leu Lys
    690                 695                 700
```

<210> SEQ ID NO 429
<211> LENGTH: 705

-continued

<212> TYPE: PRT
<213> ORGANISM: Homo sapiens

<400> SEQUENCE: 429

Gln Val Gln Leu Gln Gln Ser Gly Pro Gly Leu Val Lys Pro Ser Gln
1 5 10 15

Thr Leu Ser Leu Thr Cys Ala Ile Ser Gly Asp Ser Val Ser Ser Lys
20 25 30

Ser Ala Ala Trp Asn Trp Ile Arg Gln Ser Pro Ser Arg Gly Leu Glu
35 40 45

Trp Leu Gly Arg Thr Tyr Tyr Arg Ser Lys Trp Ser Thr Asp Tyr Ala
50 55 60

Ala Ser Val Lys Ser Arg Ile Thr Ile Asn Pro Asp Thr Ser Lys Asn
65 70 75 80

Gln Leu Ser Leu Gln Leu Asn Ser Val Thr Pro Glu Asp Thr Ala Val
85 90 95

Tyr Tyr Cys Ala Arg Thr Trp Ser Gly Tyr Val Asp Val Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Leu Ala Gly Ala
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Asp Glu Leu Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly Gly Gly Gly Gly Ser Gly Gly Gly Gly Ser Gly Gly Gly Gly Ser
450 455 460

Gln Val Gln Leu Lys Gln Ser Gly Pro Gly Leu Val Gln Pro Ser Gln
465 470 475 480

Ser Leu Ser Ile Thr Cys Thr Val Ser Gly Phe Ser Leu Thr Asn Tyr
485 490 495

Gly Val His Trp Val Arg Gln Ser Pro Gly Lys Gly Leu Glu Trp Leu
500 505 510

Gly Val Ile Trp Ser Gly Gly Asn Thr Asp Tyr Asn Thr Pro Phe Thr
515 520 525

Ser Arg Leu Ser Ile Asn Lys Asp Asn Ser Lys Ser Gln Val Phe Phe
530 535 540

Lys Met Asn Ser Leu Gln Ser Asn Asp Thr Ala Ile Tyr Tyr Cys Ala
545 550 555 560

Arg Ala Leu Thr Tyr Tyr Asp Tyr Glu Phe Ala Tyr Trp Gly Gln Gly
565 570 575

Thr Leu Val Thr Val Ser Ala Gly Gly Gly Gly Ser Gly Gly Gly Gly
580 585 590

Ser Gly Gly Gly Gly Ser Asp Ile Leu Leu Thr Gln Ser Pro Val Ile
595 600 605

Leu Ser Val Ser Pro Gly Glu Arg Val Ser Phe Ser Cys Arg Ala Ser
610 615 620

Gln Ser Ile Gly Thr Asn Ile His Trp Tyr Gln Gln Arg Thr Asn Gly
625 630 635 640

Ser Pro Arg Leu Leu Ile Lys Tyr Ala Ser Glu Ser Ile Ser Gly Ile
645 650 655

Pro Ser Arg Phe Ser Gly Ser Gly Ser Gly Thr Asp Phe Thr Leu Ser
660 665 670

Ile Asn Ser Val Glu Ser Glu Asp Ile Ala Asp Tyr Tyr Cys Gln Gln
675 680 685

Asn Asn Asn Trp Pro Thr Thr Phe Gly Ala Gly Thr Lys Leu Glu Leu
690 695 700

Lys
705

<210> SEQ ID NO 430
<211> LENGTH: 703
<212> TYPE: PRT
<213> ORGANISM: Homo sapiens

<400> SEQUENCE: 430

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp Tyr
20 25 30

Tyr Met Ser Trp Ile Arg Gln Ala Pro Gly Lys Gly Leu Glu Trp Val
35 40 45

Ser Tyr Ile Ser Ser Ser Gly Ser Thr Ile Tyr Tyr Ala Asp Ser Val

-continued

```
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Asp Tyr Ala Asp Ala Phe Asp Ile Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Ala Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Gly
        435                 440                 445

Gly Gly Gly Ser Gly Gly Gly Gly Ser Gly Gly Gly Gly Ser Gln Val
    450                 455                 460

Gln Leu Lys Gln Ser Gly Pro Gly Leu Val Gln Pro Ser Gln Ser Leu
465                 470                 475                 480
```

```
Ser Ile Thr Cys Thr Val Ser Gly Phe Ser Leu Thr Asn Tyr Gly Val
                485                 490                 495

His Trp Val Arg Gln Ser Pro Gly Lys Gly Leu Glu Trp Leu Gly Val
            500                 505                 510

Ile Trp Ser Gly Gly Asn Thr Asp Tyr Asn Thr Pro Phe Thr Ser Arg
        515                 520                 525

Leu Ser Ile Asn Lys Asp Asn Ser Lys Ser Gln Val Phe Phe Lys Met
    530                 535                 540

Asn Ser Leu Gln Ser Asn Asp Thr Ala Ile Tyr Tyr Cys Ala Arg Ala
545                 550                 555                 560

Leu Thr Tyr Tyr Asp Tyr Glu Phe Ala Tyr Trp Gly Gln Gly Thr Leu
                565                 570                 575

Val Thr Val Ser Ala Gly Gly Gly Gly Ser Gly Gly Gly Gly Ser Gly
            580                 585                 590

Gly Gly Gly Ser Asp Ile Leu Leu Thr Gln Ser Pro Val Ile Leu Ser
        595                 600                 605

Val Ser Pro Gly Glu Arg Val Ser Phe Ser Cys Arg Ala Ser Gln Ser
    610                 615                 620

Ile Gly Thr Asn Ile His Trp Tyr Gln Gln Arg Thr Asn Gly Ser Pro
625                 630                 635                 640

Arg Leu Leu Ile Lys Tyr Ala Ser Glu Ser Ile Ser Gly Ile Pro Ser
                645                 650                 655

Arg Phe Ser Gly Ser Gly Ser Gly Thr Asp Phe Thr Leu Ser Ile Asn
            660                 665                 670

Ser Val Glu Ser Glu Asp Ile Ala Asp Tyr Tyr Cys Gln Gln Asn Asn
        675                 680                 685

Asn Trp Pro Thr Thr Phe Gly Ala Gly Thr Lys Leu Glu Leu Lys
    690                 695                 700
```

<210> SEQ ID NO 431
<211> LENGTH: 449
<212> TYPE: PRT
<213> ORGANISM: Homo sapiens

<400> SEQUENCE: 431

```
Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Lys
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Ser Thr Asp Tyr Ala
    50                  55                  60

Ala Ser Val Lys Ser Arg Ile Thr Ile Asn Pro Asp Thr Ser Lys Asn
65                  70                  75                  80

Gln Leu Ser Leu Gln Leu Asn Ser Val Thr Pro Glu Asp Thr Ala Val
                85                  90                  95

Tyr Tyr Cys Ala Arg Thr Trp Val Gly Tyr Val Asp Arg Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
```

```
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Thr Asp Asp Gly Pro Val Ser Leu
        355                 360                 365

Thr Cys Leu Val Lys Gly Phe Tyr Pro Ser Asp Ile Ala Val Glu Trp
    370                 375                 380

Glu Ser Thr Tyr Gly Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Ser
                405                 410                 415

Tyr Trp Arg Trp Tyr Lys Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 432
<211> LENGTH: 449
<212> TYPE: PRT
<213> ORGANISM: Homo sapiens

<400> SEQUENCE: 432

Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Lys
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Ser Thr Asp Tyr Ala
    50                  55                  60

Ala Ser Val Lys Ser Arg Ile Thr Ile Asn Pro Asp Thr Ser Lys Asn
```

65 70 75 80

Gln Leu Ser Leu Gln Leu Asn Ser Val Thr Pro Glu Asp Thr Ala Val
85 90 95

Tyr Tyr Cys Ala Arg Thr Trp Val Gly Tyr Val Asp Arg Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Leu Ala Gly Ala
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Asp Glu Leu Glu Glu Gly Pro Val Ser Leu
355 360 365

Thr Cys Leu Val Lys Gly Phe Tyr Pro Ser Asp Ile Ala Val Glu Trp
370 375 380

Glu Ser Thr Tyr Gly Pro Glu Asn Asn Tyr Lys Thr Thr Pro Pro Val
385 390 395 400

Leu Asp Ser Asp Gly Ser Phe Phe Leu Tyr Ser Lys Leu Thr Val Ser
405 410 415

Tyr Trp Arg Trp Tyr Lys Gly Asn Val Phe Ser Cys Ser Val Met His
420 425 430

Glu Ala Leu His Asn His Tyr Thr Gln Lys Ser Leu Ser Leu Ser Pro
435 440 445

Gly

<210> SEQ ID NO 433
<211> LENGTH: 449
<212> TYPE: PRT
<213> ORGANISM: Homo sapiens

<400> SEQUENCE: 433

```
Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Lys
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Ser Thr Asp Tyr Ala
    50                  55                  60

Ala Ser Val Lys Ser Arg Ile Thr Ile Asn Pro Asp Thr Ser Lys Asn
65                  70                  75                  80

Gln Leu Ser Leu Gln Leu Asn Ser Val Thr Pro Glu Asp Thr Ala Val
                85                  90                  95

Tyr Tyr Cys Ala Arg Thr Trp Val Gly Tyr Val Asp Arg Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Phe Phe Thr Tyr Trp Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415
```

Arg Arg Arg Trp Thr Ala Gly Asn Val Phe Ser Cys Ser Val Met His
420 425 430

Glu Ala Leu His Asn His Tyr Thr Gln Lys Ser Leu Ser Leu Ser Pro
435 440 445

Gly

<210> SEQ ID NO 434
<211> LENGTH: 449
<212> TYPE: PRT
<213> ORGANISM: Homo sapiens

<400> SEQUENCE: 434

Glu Val Gln Leu Gln Gln Ser Gly Pro Gly Leu Val Lys Pro Ser Gln
1 5 10 15

Thr Leu Ser Leu Thr Cys Ala Ile Ser Gly Asp Ser Val Ser Ser Lys
20 25 30

Ser Ala Ala Trp Asn Trp Ile Arg Gln Ser Pro Ser Arg Gly Leu Glu
35 40 45

Trp Leu Gly Arg Thr Tyr Tyr Arg Ser Lys Trp Ser Thr Asp Tyr Ala
50 55 60

Ala Ser Val Lys Ser Arg Ile Thr Ile Asn Pro Asp Thr Ser Lys Asn
65 70 75 80

Gln Leu Ser Leu Gln Leu Asn Ser Val Thr Pro Glu Asp Thr Ala Val
85 90 95

Tyr Tyr Cys Ala Arg Thr Trp Val Gly Tyr Val Asp Arg Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

```
Lys Thr Ile Ser Lys Ala Lys Gly Gln Pro Arg Glu Pro Gln Val Tyr
            340                 345                 350

Thr Leu Pro Pro Ser Arg Asp Glu Phe Phe Thr Tyr Trp Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Arg Arg Arg Trp Thr Ala Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 435
<211> LENGTH: 449
<212> TYPE: PRT
<213> ORGANISM: Homo sapiens

<400> SEQUENCE: 435

Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Lys
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Ser Thr Asp Tyr Ala
    50                  55                  60

Ala Ser Val Lys Ser Arg Ile Thr Ile Asn Pro Asp Thr Ser Lys Asn
65                  70                  75                  80

Gln Leu Ser Leu Gln Leu Asn Ser Val Thr Pro Glu Asp Thr Ala Val
                85                  90                  95

Tyr Tyr Cys Ala Arg Thr Trp Val Gly Tyr Val Asp Arg Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255
```

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Asp Glu Thr Asp Asp Gly Pro Val Ser Leu
355 360 365

Thr Cys Leu Val Lys Gly Phe Tyr Pro Ser Asp Ile Ala Val Glu Trp
370 375 380

Glu Ser Thr Tyr Gly Pro Glu Asn Asn Tyr Lys Thr Thr Pro Pro Val
385 390 395 400

Leu Asp Ser Asp Gly Ser Phe Phe Leu Tyr Ser Lys Leu Thr Val Ser
405 410 415

Tyr Trp Arg Trp Tyr Lys Gly Asn Val Phe Ser Cys Ser Val Met His
420 425 430

Glu Ala Leu His Asn His Tyr Thr Gln Lys Ser Leu Ser Leu Ser Pro
435 440 445

Gly

<210> SEQ ID NO 436
<211> LENGTH: 449
<212> TYPE: PRT
<213> ORGANISM: Homo sapiens

<400> SEQUENCE: 436

Glu Val Gln Leu Gln Gln Ser Gly Pro Gly Leu Val Lys Pro Ser Gln
1 5 10 15

Thr Leu Ser Leu Thr Cys Ala Ile Ser Gly Asp Ser Val Ser Ser Lys
20 25 30

Ser Ala Ala Trp Asn Trp Ile Arg Gln Ser Pro Ser Arg Gly Leu Glu
35 40 45

Trp Leu Gly Arg Thr Tyr Tyr Arg Ser Lys Trp Ser Thr Asp Tyr Ala
50 55 60

Ala Ser Val Lys Ser Arg Ile Thr Ile Asn Pro Asp Thr Ser Lys Asn
65 70 75 80

Gln Leu Ser Leu Gln Leu Asn Ser Val Thr Pro Glu Asp Thr Ala Val
85 90 95

Tyr Tyr Cys Ala Arg Thr Trp Val Gly Tyr Val Asp Arg Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

```
Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Glu Glu Gly Pro Val Ser Leu
        355                 360                 365

Thr Cys Leu Val Lys Gly Phe Tyr Pro Ser Asp Ile Ala Val Glu Trp
    370                 375                 380

Glu Ser Thr Tyr Gly Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Ser
                405                 410                 415

Tyr Trp Arg Trp Tyr Lys Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly
```

<210> SEQ ID NO 437
<211> LENGTH: 449
<212> TYPE: PRT
<213> ORGANISM: Homo sapiens

<400> SEQUENCE: 437

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Lys
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Ser Thr Asp Tyr Ala
    50                  55                  60

Ala Ser Val Lys Ser Arg Ile Thr Ile Asn Pro Asp Thr Ser Lys Asn
65                  70                  75                  80

Gln Leu Ser Leu Gln Leu Asn Ser Val Thr Pro Glu Asp Thr Ala Val
                85                  90                  95
```

-continued

```
Tyr Tyr Cys Ala Arg Thr Trp Ser Gly Tyr Val Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Thr Asp Asp Gly Pro Val Ser Leu
        355                 360                 365

Thr Cys Leu Val Lys Gly Phe Tyr Pro Ser Asp Ile Ala Val Glu Trp
    370                 375                 380

Glu Ser Thr Tyr Gly Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Ser
                405                 410                 415

Tyr Trp Arg Trp Tyr Lys Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 438
<211> LENGTH: 218
<212> TYPE: PRT
<213> ORGANISM: Homo sapiens

<400> SEQUENCE: 438

Glu Ile Val Leu Thr Gln Ser Pro Ala Thr Leu Ser Leu Ser Pro Gly
1               5                   10                  15
```

```
Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 439
<211> LENGTH: 220
<212> TYPE: PRT
<213> ORGANISM: Homo sapiens

<400> SEQUENCE: 439

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Val Leu Tyr Ser
            20                  25                  30

Ser Asn Asn Lys Lys Tyr Leu Ala Trp Tyr Gln Gln Lys Pro Gly Gln
        35                  40                  45

Pro Pro Asn Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Phe Thr Phe Gly Pro Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
```

```
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 440
<211> LENGTH: 124
<212> TYPE: PRT
<213> ORGANISM: Homo sapiens

<400> SEQUENCE: 440

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
        115                 120


<210> SEQ ID NO 441
<211> LENGTH: 111
<212> TYPE: PRT
<213> ORGANISM: Homo sapiens

<400> SEQUENCE: 441

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys
            100                 105                 110


<210> SEQ ID NO 442
<211> LENGTH: 8
<212> TYPE: PRT
<213> ORGANISM: Homo sapiens

<400> SEQUENCE: 442
```

Gly Tyr Ala Phe Ser Ser Tyr Trp
1 5

<210> SEQ ID NO 443
<211> LENGTH: 8
<212> TYPE: PRT
<213> ORGANISM: Homo sapiens

<400> SEQUENCE: 443

Ile Trp Pro Gly Asp Gly Asp Thr
1 5

<210> SEQ ID NO 444
<211> LENGTH: 17
<212> TYPE: PRT
<213> ORGANISM: Homo sapiens

<400> SEQUENCE: 444

Ala Arg Arg Glu Thr Thr Thr Val Gly Arg Tyr Tyr Tyr Ala Met Asp
1 5 10 15

Tyr

<210> SEQ ID NO 445
<211> LENGTH: 10
<212> TYPE: PRT
<213> ORGANISM: Homo sapiens

<400> SEQUENCE: 445

Gln Ser Val Asp Tyr Asp Gly Asp Ser Tyr
1 5 10

<210> SEQ ID NO 446
<211> LENGTH: 2
<212> TYPE: PRT
<213> ORGANISM: Homo sapiens

<400> SEQUENCE: 446

Asp Ala
1

<210> SEQ ID NO 447
<211> LENGTH: 9
<212> TYPE: PRT
<213> ORGANISM: Homo sapiens

<400> SEQUENCE: 447

Gln Gln Ser Thr Glu Asp Pro Trp Thr
1 5

<210> SEQ ID NO 448
<211> LENGTH: 118
<212> TYPE: PRT
<213> ORGANISM: Homo sapiens

<400> SEQUENCE: 448

Gln Val Gln Leu Lys Gln Ser Gly Pro Gly Leu Val Gln Pro Ser Gln
1 5 10 15

Ser Leu Ser Ile Thr Cys Thr Val Ser Gly Phe Ser Leu Thr Asn Tyr
20 25 30

Gly Val His Trp Val Arg Gln Ser Pro Gly Lys Gly Leu Glu Trp Leu
35 40 45

Gly Val Ile Trp Ser Gly Gly Asn Thr Asp Tyr Asn Thr Pro Phe Thr

```
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser
        115


<210> SEQ ID NO 449
<211> LENGTH: 107
<212> TYPE: PRT
<213> ORGANISM: Homo sapiens

<400> SEQUENCE: 449

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys
            100                 105


<210> SEQ ID NO 450
<211> LENGTH: 8
<212> TYPE: PRT
<213> ORGANISM: Homo sapiens

<400> SEQUENCE: 450

Gly Phe Ser Leu Thr Asn Tyr Gly
1               5


<210> SEQ ID NO 451
<211> LENGTH: 7
<212> TYPE: PRT
<213> ORGANISM: Homo sapiens

<400> SEQUENCE: 451

Ile Trp Ser Gly Gly Asn Thr
1               5


<210> SEQ ID NO 452
<211> LENGTH: 13
<212> TYPE: PRT
<213> ORGANISM: Homo sapiens

<400> SEQUENCE: 452

Ala Arg Ala Leu Thr Tyr Tyr Asp Tyr Glu Phe Ala Tyr
1               5                   10


<210> SEQ ID NO 453
<211> LENGTH: 11
```

<212> TYPE: PRT
<213> ORGANISM: Homo sapiens

<400> SEQUENCE: 453

Arg Ala Ser Gln Ser Ile Gly Thr Asn Ile His
1 5 10

<210> SEQ ID NO 454
<211> LENGTH: 7
<212> TYPE: PRT
<213> ORGANISM: Homo sapiens

<400> SEQUENCE: 454

Tyr Ala Ser Glu Ser Ile Ser
1 5

<210> SEQ ID NO 455
<211> LENGTH: 9
<212> TYPE: PRT
<213> ORGANISM: Homo sapiens

<400> SEQUENCE: 455

Gln Gln Asn Asn Asn Trp Pro Thr Thr
1 5

<210> SEQ ID NO 456
<211> LENGTH: 124
<212> TYPE: PRT
<213> ORGANISM: Homo sapiens

<400> SEQUENCE: 456

Gln Val Gln Leu Val Gln Ser Gly Ala Glu Val Lys Lys Pro Gly Ala
1 5 10 15

Ser Val Lys Val Ser Cys Lys Thr Ser Arg Tyr Thr Phe Thr Glu Tyr
20 25 30

Thr Ile His Trp Val Arg Gln Ala Pro Gly Gln Arg Leu Glu Trp Ile
35 40 45

Gly Gly Ile Asn Pro Asn Asn Gly Ile Pro Asn Tyr Asn Gln Lys Phe
50 55 60

Lys Gly Arg Val Thr Ile Thr Val Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Arg Arg Ile Ala Tyr Gly Tyr Asp Glu Gly His Ala Met Asp
100 105 110

Tyr Trp Gly Gln Gly Thr Leu Val Thr Val Ser Ser
115 120

<210> SEQ ID NO 457
<211> LENGTH: 113
<212> TYPE: PRT
<213> ORGANISM: Homo sapiens

<400> SEQUENCE: 457

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Leu Leu Tyr Ser
20 25 30

Arg Asn Gln Lys Asn Tyr Leu Ala Trp Tyr Gln Gln Lys Pro Gly Gln
35 40 45

```
Pro Pro Lys Leu Leu Ile Phe Trp Ala Ser Thr Arg Glu Ser Gly Val
    50                  55                  60

Pro Asp Arg Phe Ser Gly Ser Gly Phe Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Phe Ser Tyr Pro Leu Thr Phe Gly Gln Gly Thr Lys Val Glu Ile
            100                 105                 110

Lys


<210> SEQ ID NO 458
<211> LENGTH: 8
<212> TYPE: PRT
<213> ORGANISM: Homo sapiens

<400> SEQUENCE: 458

Arg Tyr Thr Phe Thr Glu Tyr Thr
1               5


<210> SEQ ID NO 459
<211> LENGTH: 8
<212> TYPE: PRT
<213> ORGANISM: Homo sapiens

<400> SEQUENCE: 459

Ile Asn Pro Asn Asn Gly Ile Pro
1               5


<210> SEQ ID NO 460
<211> LENGTH: 17
<212> TYPE: PRT
<213> ORGANISM: Homo sapiens

<400> SEQUENCE: 460

Ala Arg Arg Arg Ile Ala Tyr Gly Tyr Asp Glu Gly His Ala Met Asp
1               5                   10                  15

Tyr


<210> SEQ ID NO 461
<211> LENGTH: 17
<212> TYPE: PRT
<213> ORGANISM: Homo sapiens

<400> SEQUENCE: 461

Lys Ser Ser Gln Ser Leu Leu Tyr Ser Arg Asn Gln Lys Asn Tyr Leu
1               5                   10                  15

Ala


<210> SEQ ID NO 462
<211> LENGTH: 7
<212> TYPE: PRT
<213> ORGANISM: Homo sapiens

<400> SEQUENCE: 462

Trp Ala Ser Thr Arg Glu Ser
1               5


<210> SEQ ID NO 463
<211> LENGTH: 9
<212> TYPE: PRT
<213> ORGANISM: Homo sapiens
```

<400> SEQUENCE: 463

Gln Gln Tyr Phe Ser Tyr Pro Leu Thr
1 5

<210> SEQ ID NO 464
<211> LENGTH: 119
<212> TYPE: PRT
<213> ORGANISM: Homo sapiens

<400> SEQUENCE: 464

Gln Val Gln Leu Gln Glu Ser Gly Pro Gly Leu Val Lys Pro Ser Gln
1 5 10 15

Thr Leu Ser Leu Thr Cys Thr Val Ser Gly Gly Ser Ile Asn Asn Asn
20 25 30

Asn Tyr Tyr Trp Thr Trp Ile Arg Gln His Pro Gly Lys Gly Leu Glu
35 40 45

Trp Ile Gly Tyr Ile Tyr Tyr Ser Gly Ser Thr Phe Tyr Asn Pro Ser
50 55 60

Leu Lys Ser Arg Val Thr Ile Ser Val Asp Thr Ser Lys Thr Gln Phe
65 70 75 80

Ser Leu Lys Leu Ser Ser Val Thr Ala Ala Asp Thr Ala Val Tyr Tyr
85 90 95

Cys Ala Arg Glu Asp Thr Met Thr Gly Leu Asp Val Trp Gly Gln Gly
100 105 110

Thr Thr Val Thr Val Ser Ser
115

<210> SEQ ID NO 465
<211> LENGTH: 106
<212> TYPE: PRT
<213> ORGANISM: Homo sapiens

<400> SEQUENCE: 465

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Asn Asn Tyr
20 25 30

Leu Asn Trp Tyr Gln Gln Lys Pro Gly Lys Ala Pro Thr Leu Leu Ile
35 40 45

Tyr Ala Ala Ser Ser Leu Gln Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Phe Ala Ala Tyr Phe Cys Gln Gln Thr Tyr Ser Asn Pro Thr
85 90 95

Phe Gly Gln Gly Thr Lys Val Glu Val Lys
100 105

<210> SEQ ID NO 466
<211> LENGTH: 10
<212> TYPE: PRT
<213> ORGANISM: Homo sapiens

<400> SEQUENCE: 466

Gly Gly Ser Ile Asn Asn Asn Asn Tyr Tyr
1 5 10

<210> SEQ ID NO 467

<211> LENGTH: 7
<212> TYPE: PRT
<213> ORGANISM: Homo sapiens

<400> SEQUENCE: 467

Ile Tyr Tyr Ser Gly Ser Thr
1 5

<210> SEQ ID NO 468
<211> LENGTH: 11
<212> TYPE: PRT
<213> ORGANISM: Homo sapiens

<400> SEQUENCE: 468

Ala Arg Glu Asp Thr Met Thr Gly Leu Asp Val
1 5 10

<210> SEQ ID NO 469
<211> LENGTH: 6
<212> TYPE: PRT
<213> ORGANISM: Homo sapiens

<400> SEQUENCE: 469

Gln Ser Ile Asn Asn Tyr
1 5

<210> SEQ ID NO 470
<211> LENGTH: 2
<212> TYPE: PRT
<213> ORGANISM: Homo sapiens

<400> SEQUENCE: 470

Ala Ala
1

<210> SEQ ID NO 471
<211> LENGTH: 8
<212> TYPE: PRT
<213> ORGANISM: Homo sapiens

<400> SEQUENCE: 471

Gln Gln Thr Tyr Ser Asn Pro Thr
1 5

<210> SEQ ID NO 472
<211> LENGTH: 120
<212> TYPE: PRT
<213> ORGANISM: Homo sapiens

<400> SEQUENCE: 472

Gln Val Gln Leu Val Gln Ser Gly Val Glu Val Lys Lys Pro Gly Ala
1 5 10 15

Ser Val Lys Val Ser Cys Lys Ala Ser Gly Tyr Thr Phe Thr Asn Tyr
20 25 30

Tyr Met Tyr Trp Val Arg Gln Ala Pro Gly Gln Gly Leu Glu Trp Met
35 40 45

Gly Gly Ile Asn Pro Ser Asn Gly Gly Thr Asn Phe Asn Glu Lys Phe
50 55 60

Lys Asn Arg Val Thr Leu Thr Thr Asp Ser Ser Thr Thr Thr Ala Tyr
65 70 75 80

Met Glu Leu Lys Ser Leu Gln Phe Asp Asp Thr Ala Val Tyr Tyr Cys
85 90 95

-continued

```
Ala Arg Arg Asp Tyr Arg Phe Asp Met Gly Phe Asp Tyr Trp Gly Gln
            100                 105                 110

Gly Thr Thr Val Thr Val Ser Ser
        115                 120


<210> SEQ ID NO 473
<211> LENGTH: 111
<212> TYPE: PRT
<213> ORGANISM: Homo sapiens

<400> SEQUENCE: 473

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110


<210> SEQ ID NO 474
<211> LENGTH: 8
<212> TYPE: PRT
<213> ORGANISM: Homo sapiens

<400> SEQUENCE: 474

Gly Tyr Thr Phe Thr Asn Tyr Tyr
1               5


<210> SEQ ID NO 475
<211> LENGTH: 8
<212> TYPE: PRT
<213> ORGANISM: Homo sapiens

<400> SEQUENCE: 475

Ile Asn Pro Ser Asn Gly Gly Thr
1               5


<210> SEQ ID NO 476
<211> LENGTH: 13
<212> TYPE: PRT
<213> ORGANISM: Homo sapiens

<400> SEQUENCE: 476

Ala Arg Arg Asp Tyr Arg Phe Asp Met Gly Phe Asp Tyr
1               5                   10


<210> SEQ ID NO 477
<211> LENGTH: 10
<212> TYPE: PRT
<213> ORGANISM: Homo sapiens

<400> SEQUENCE: 477

Lys Gly Val Ser Thr Ser Gly Tyr Ser Tyr
1               5                   10
```

<210> SEQ ID NO 478
<211> LENGTH: 2
<212> TYPE: PRT
<213> ORGANISM: Homo sapiens

<400> SEQUENCE: 478

Leu Ala
1

<210> SEQ ID NO 479
<211> LENGTH: 9
<212> TYPE: PRT
<213> ORGANISM: Homo sapiens

<400> SEQUENCE: 479

Gln His Ser Arg Asp Leu Pro Leu Thr
1 5

<210> SEQ ID NO 480
<211> LENGTH: 116
<212> TYPE: PRT
<213> ORGANISM: Homo sapiens

<400> SEQUENCE: 480

Glu Val Gln Leu Val Gln Ser Gly Ala Glu Val Lys Lys Pro Gly Glu
1 5 10 15

Ser Leu Arg Ile Ser Cys Lys Gly Ser Gly Tyr Ser Phe Ser Thr Tyr
20 25 30

Trp Ile Ser Trp Val Arg Gln Met Pro Gly Lys Gly Leu Glu Trp Met
35 40 45

Gly Lys Ile Tyr Pro Gly Asp Ser Tyr Thr Asn Tyr Ser Pro Ser Phe
50 55 60

Gln Gly Gln Val Thr Ile Ser Ala Asp Lys Ser Ile Ser Thr Ala Tyr
65 70 75 80

Leu Gln Trp Ser Ser Leu Lys Ala Ser Asp Thr Ala Met Tyr Tyr Cys
85 90 95

Ala Arg Gly Tyr Gly Ile Phe Asp Tyr Trp Gly Gln Gly Thr Leu Val
100 105 110

Thr Val Ser Ser
115

<210> SEQ ID NO 481
<211> LENGTH: 107
<212> TYPE: PRT
<213> ORGANISM: Homo sapiens

<400> SEQUENCE: 481

Tyr Glu Leu Thr Gln Pro Pro Ser Val Ser Val Ser Pro Gly Gln Thr
1 5 10 15

Ala Ser Ile Thr Cys Ser Gly Asp Asn Ile Gly Asp Gln Tyr Ala His
20 25 30

Trp Tyr Gln Gln Lys Pro Gly Gln Ser Pro Val Leu Val Ile Tyr Gln
35 40 45

Asp Lys Asn Arg Pro Ser Gly Ile Pro Glu Arg Phe Ser Gly Ser Asn
50 55 60

Ser Gly Asn Thr Ala Thr Leu Thr Ile Ser Gly Thr Gln Ala Met Asp
65 70 75 80

Glu Ala Asp Tyr Tyr Cys Ala Thr Tyr Thr Gly Phe Gly Ser Leu Ala
85 90 95

```
Val Phe Gly Gly Gly Thr Lys Leu Thr Val Leu
            100                 105


<210> SEQ ID NO 482
<211> LENGTH: 8
<212> TYPE: PRT
<213> ORGANISM: Homo sapiens

<400> SEQUENCE: 482

Gly Tyr Ser Phe Ser Thr Tyr Trp
1               5


<210> SEQ ID NO 483
<211> LENGTH: 8
<212> TYPE: PRT
<213> ORGANISM: Homo sapiens

<400> SEQUENCE: 483

Ile Tyr Pro Gly Asp Ser Tyr Thr
1               5


<210> SEQ ID NO 484
<211> LENGTH: 9
<212> TYPE: PRT
<213> ORGANISM: Homo sapiens

<400> SEQUENCE: 484

Ala Arg Gly Tyr Gly Ile Phe Asp Tyr
1               5


<210> SEQ ID NO 485
<211> LENGTH: 11
<212> TYPE: PRT
<213> ORGANISM: Homo sapiens

<400> SEQUENCE: 485

Ser Gly Asp Asn Ile Gly Asp Gln Tyr Ala His
1               5                   10


<210> SEQ ID NO 486
<211> LENGTH: 7
<212> TYPE: PRT
<213> ORGANISM: Homo sapiens

<400> SEQUENCE: 486

Gln Asp Lys Asn Arg Pro Ser
1               5


<210> SEQ ID NO 487
<211> LENGTH: 11
<212> TYPE: PRT
<213> ORGANISM: Homo sapiens

<400> SEQUENCE: 487

Ala Thr Tyr Thr Gly Phe Gly Ser Leu Ala Val
1               5                   10


<210> SEQ ID NO 488
<211> LENGTH: 117
<212> TYPE: PRT
<213> ORGANISM: Homo sapiens

<400> SEQUENCE: 488

Glu Val Gln Leu Val Gln Ser Gly Ala Glu Val Lys Lys Pro Gly Ala
```

```
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115


<210> SEQ ID NO 489
<211> LENGTH: 107
<212> TYPE: PRT
<213> ORGANISM: Homo sapiens

<400> SEQUENCE: 489

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105


<210> SEQ ID NO 490
<211> LENGTH: 8
<212> TYPE: PRT
<213> ORGANISM: Homo sapiens

<400> SEQUENCE: 490

Gly Tyr Thr Phe Thr Asp Ser Tyr
1               5


<210> SEQ ID NO 491
<211> LENGTH: 8
<212> TYPE: PRT
<213> ORGANISM: Homo sapiens

<400> SEQUENCE: 491

Met Tyr Pro Asp Asn Gly Asp Ser
1               5


<210> SEQ ID NO 492
<211> LENGTH: 10
<212> TYPE: PRT
<213> ORGANISM: Homo sapiens
```

<400> SEQUENCE: 492

Val Leu Ala Pro Arg Trp Tyr Phe Ser Val
1 5 10

<210> SEQ ID NO 493
<211> LENGTH: 6
<212> TYPE: PRT
<213> ORGANISM: Homo sapiens

<400> SEQUENCE: 493

Gln Asp Ile Ser Asn Tyr
1 5

<210> SEQ ID NO 494
<211> LENGTH: 2
<212> TYPE: PRT
<213> ORGANISM: Homo sapiens

<400> SEQUENCE: 494

Tyr Thr
1

<210> SEQ ID NO 495
<211> LENGTH: 9
<212> TYPE: PRT
<213> ORGANISM: Homo sapiens

<400> SEQUENCE: 495

Gln Gln Gly His Thr Leu Pro Pro Thr
1 5

<210> SEQ ID NO 496
<211> LENGTH: 126
<212> TYPE: PRT
<213> ORGANISM: Homo sapiens

<400> SEQUENCE: 496

Glu Val Gln Leu Gln Gln Ser Gly Pro Gly Leu Val Lys Pro Ser Gln
1 5 10 15

Thr Leu Ser Leu Thr Cys Ala Ile Ser Gly Asp Ser Val Ser Ser Asn
20 25 30

Ser Ala Ala Trp Asn Trp Ile Arg Gln Ser Pro Ser Arg Gly Leu Glu
35 40 45

Trp Leu Gly Lys Thr Tyr Tyr Arg Phe Lys Trp Tyr Ser Asp Tyr Ala
50 55 60

Val Ser Val Lys Gly Arg Ile Thr Ile Asn Pro Asp Thr Ser Lys Asn
65 70 75 80

Gln Phe Ser Leu Gln Leu Asn Ser Val Thr Pro Glu Asp Thr Ala Val
85 90 95

Phe Tyr Cys Thr Arg Glu Ser Thr Thr Tyr Asp Leu Leu Ala Gly Pro
100 105 110

Phe Asp Tyr Trp Gly Gln Gly Thr Leu Val Thr Val Ser Ser
115 120 125

<210> SEQ ID NO 497
<211> LENGTH: 113
<212> TYPE: PRT
<213> ORGANISM: Homo sapiens

<400> SEQUENCE: 497

Asp Ile Val Met Thr Gln Ser Pro Asp Ser Leu Ala Val Ser Leu Gly
1 5 10 15

Glu Arg Ala Thr Ile Asn Cys Lys Ser Ser Gln Thr Val Leu Tyr Ser
20 25 30

Ser Asn Asn Lys Lys Tyr Leu Ala Trp Tyr Gln Gln Lys Pro Gly Gln
35 40 45

Pro Pro Asn Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Gln
85 90 95

Tyr Tyr Ser Thr Pro Phe Thr Phe Gly Pro Gly Thr Lys Val Glu Ile
100 105 110

Lys

<210> SEQ ID NO 498
<211> LENGTH: 10
<212> TYPE: PRT
<213> ORGANISM: Homo sapiens

<400> SEQUENCE: 498

Gly Asp Ser Val Ser Ser Asn Ser Ala Ala
1 5 10

<210> SEQ ID NO 499
<211> LENGTH: 9
<212> TYPE: PRT
<213> ORGANISM: Homo sapiens

<400> SEQUENCE: 499

Thr Tyr Tyr Arg Phe Lys Trp Tyr Ser
1 5

<210> SEQ ID NO 500
<211> LENGTH: 16
<212> TYPE: PRT
<213> ORGANISM: Homo sapiens

<400> SEQUENCE: 500

Thr Arg Glu Ser Thr Thr Tyr Asp Leu Leu Ala Gly Pro Phe Asp Tyr
1 5 10 15

<210> SEQ ID NO 501
<211> LENGTH: 12
<212> TYPE: PRT
<213> ORGANISM: Homo sapiens

<400> SEQUENCE: 501

Gln Thr Val Leu Tyr Ser Ser Asn Asn Lys Lys Tyr
1 5 10

<210> SEQ ID NO 502
<211> LENGTH: 2
<212> TYPE: PRT
<213> ORGANISM: Homo sapiens

<400> SEQUENCE: 502

Trp Ala
1

-continued

<210> SEQ ID NO 503
<211> LENGTH: 9
<212> TYPE: PRT
<213> ORGANISM: Homo sapiens

<400> SEQUENCE: 503

Gln Gln Tyr Tyr Ser Thr Pro Phe Thr
1 5

<210> SEQ ID NO 504
<211> LENGTH: 215
<212> TYPE: PRT
<213> ORGANISM: Homo sapiens

<400> SEQUENCE: 504

Asp Ile Gln Met Thr Gln Ser Pro Pro Ala Leu Ser Ala Ser Val Gly
1 5 10 15

Asp Arg Val Thr Ile Thr Cys Arg Ala Ser Gln Asp Ile Asn Asp Trp
20 25 30

Leu Ala Trp Tyr Gln His Lys Pro Gly Lys Ala Pro Lys Leu Leu Ile
35 40 45

Tyr Asp Ala Ser Ser Leu Glu Ser Gly Val Pro Leu Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Ser Tyr Ser Thr Pro Gln
85 90 95

Val Thr Phe Gly Gln Gly Thr Arg Leu Glu Ile Lys Arg Thr Val Ala
100 105 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu
130 135 140

Ala Lys Val Gln Trp Lys Val Asp Asn Ala Leu Gln Ser Gly Asn Ser
145 150 155 160

Gln Glu Ser Val Thr Glu Gln Asp Ser Lys Asp Ser Thr Tyr Ser Leu
165 170 175

Ser Ser Thr Leu Thr Leu Ser Lys Ala Asp Tyr Glu Lys His Lys Val
180 185 190

Tyr Ala Cys Glu Val Thr His Gln Gly Leu Ser Ser Pro Val Thr Lys
195 200 205

Ser Phe Asn Arg Gly Glu Cys
210 215

<210> SEQ ID NO 505
<211> LENGTH: 215
<212> TYPE: PRT
<213> ORGANISM: Homo sapiens

<400> SEQUENCE: 505

Asp Ile Gln Met Thr Gln Ser Pro Pro Ala Leu Ser Ala Ser Val Gly
1 5 10 15

Asp Arg Val Thr Ile Thr Cys Arg Ala Ser Gln Asp Ile Asn Asp Trp
20 25 30

Leu Ala Trp Tyr Gln His Lys Pro Gly Lys Ala Pro Lys Leu Leu Ile
35 40 45

Tyr Asp Ala Ser Ser Leu Glu Ser Gly Val Pro Ser Arg Phe Ser Gly
50 55 60

-continued

```
Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Lys Tyr Ser Ala Pro Gln
                85                  90                  95

Val Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```